United States Patent
Anderson et al.

(10) Patent No.: US 7,101,878 B1
(45) Date of Patent: Sep. 5, 2006

(54) NON-PEPTIDE GNRH AGENTS, METHODS AND INTERMEDIATES FOR THEIR PREPARATION

(75) Inventors: Mark Brian Anderson, Orinda, CA (US); Haresh N. Vazir, San Diego, CA (US); David Robert Luthin, Encinitas, CA (US); Genevieve DeGuzman Paderes, San Diego, CA (US); Ved P. Pathak, San Diego, CA (US); Lance Christopher Christie, Vista, CA (US); Yufeng Hong, San Diego, CA (US); Eileen Valenzuela Tompkins, Escondido, CA (US); Haitao Li, San Diego, CA (US); James Faust, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/763,216

(22) PCT Filed: Aug. 20, 1999

(86) PCT No.: PCT/US99/18790

§ 371 (c)(1),
(2), (4) Date: Feb. 20, 2001

(87) PCT Pub. No.: WO00/20358

PCT Pub. Date: Apr. 13, 2000

Related U.S. Application Data

(60) Provisional application No. 60/097,520, filed on Aug. 20, 1998.

(51) Int. Cl.
C07D 405/12 (2006.01)
C07D 307/68 (2006.01)
A61K 31/34 (2006.01)
A61K 31/505 (2006.01)
A61P 5/04 (2006.01)

(52) U.S. Cl. .................. 514/231.5; 549/487; 549/488; 514/461; 514/370; 514/336; 514/444; 514/255.05; 514/394; 548/195; 548/304.7; 544/152; 544/405; 546/233; 546/284.7; 546/60

(58) Field of Classification Search ............... 549/487, 549/488; 514/461, 370, 231.5, 336, 444, 514/255.05, 394; 548/195, 3.47; 544/152, 544/405, 333; 546/233, 284.7, 60
See application file for complete search history.

(56) References Cited

U.S. PATENT DOCUMENTS 3,907,700 A    9/1975   Grier ........................ 252/589

(Continued)

FOREIGN PATENT DOCUMENTS

| GB | 1 267 583 | 3/1972 |
|----|-----------|--------|
| GB | 1 491 776 | 11/1977 |
| WO | WO 97/21707 | 6/1997 |
| WO | WO 97/44339 | 11/1997 |

OTHER PUBLICATIONS

Parce et al., Science, 1989, 246:243–247.
B.E. Howland et al., Experentia, 1974, 1223–1225.

(Continued)

*Primary Examiner*—Richard Raymond
*Assistant Examiner*—Hong Liu
(74) *Attorney, Agent, or Firm*—Keith D. Hutchinson; Bryan C. Zielinski; Peter C. Richardson

(57) ABSTRACT

Non-peptide GnRH agents capable of inhibiting the effect of gonadotropin-releasing hormone are described. Such compounds and their pharmaceutically acceptable salts, multimers, prodrugs, and active metabolites are suitable for treating mammalian reproductive disorders and steroid hormone-dependent tumors as well as for regulating fertility, where suppression of gonadotropin release is indicated. Methods for synthesizing the compounds and intermediates useful in their preparation are also described.

8 Claims, 15 Drawing Sheets

U.S. PATENT DOCUMENTS

| | | |
|---|---|---|
| 3,932,444 A | 1/1976 | Ellis .................... 260/309 |
| 4,013,647 A | 3/1977 | Sellstedt et al. ......... 260/247.2 |
| 4,076,718 A | 2/1978 | Sellstedt et al. ............ 260/295 |
| 5,236,928 A | 8/1993 | Chakravarty et al. ....... 514/275 |
| 5,780,393 A | 7/1998 | Newton .................. 504/271 |
| 5,834,482 A | 11/1998 | Lundbeck et al. .......... 514/292 |
| 5,981,521 A | 11/1999 | Haviv et al. ................ 514/213 |

OTHER PUBLICATIONS

Bernatowicz et al., J. Org. Chem., 1992, 57:2497–2502.

Mndzhoyan et al., Chem., Abstr., 1962, vol. 57, No. 9, 11137.

Goulet, M.T., Ann. Reports Med. Chem., 1995, vol. 30, Chap. 18, 169–177.

Abdel–Magid et al., J. Org. Chem. 1996, 61:3849–3862.

Owicki et al., Ann. Rev. Biophys. Biomol. Struc., 1994, 23:87–113.

Pitchford et al., Am. J. Physiol., 1995, 268, (Cell Physiol. 37), C936–C943.

Parlow, Tetrahedron, 1993, vol. 49 (13), 2577–2588.

Drake et al., Synth., 1994, 579–582.

Marelli et al., Arch. Ital. Urol., 1997, 69 (4), 257–263.

Jungwirth et al., Prostrate, 1997, 32 (3), 164–172.

Sralovic et al., Int. J. Oncol., 1998, 12 (3), 489–498.

Kottler et al., Int. J. Cancer, 1997, 71 (4), 595–599.

Bowers et al., Endocrinology, 1980, 106 (3):674–683.

Corbin et al., Endocr. Res. Commun., 1975, 2 (1):1–23.

Still et al., J. Org. Chem., 1978, 43:2923–2925.

Cheng et al., Biochemical Pharmacology, 1973, 22:3099–3108.

Mndzhoyan et al., Khim.–Farm. Zh., 1988, vol. 22, No. 9, 1091–1094.

Mndzhoyan et al., Khim.–Farm. Zh., 1986, vol. 20, No. 4, 446–450.

Figure 2:
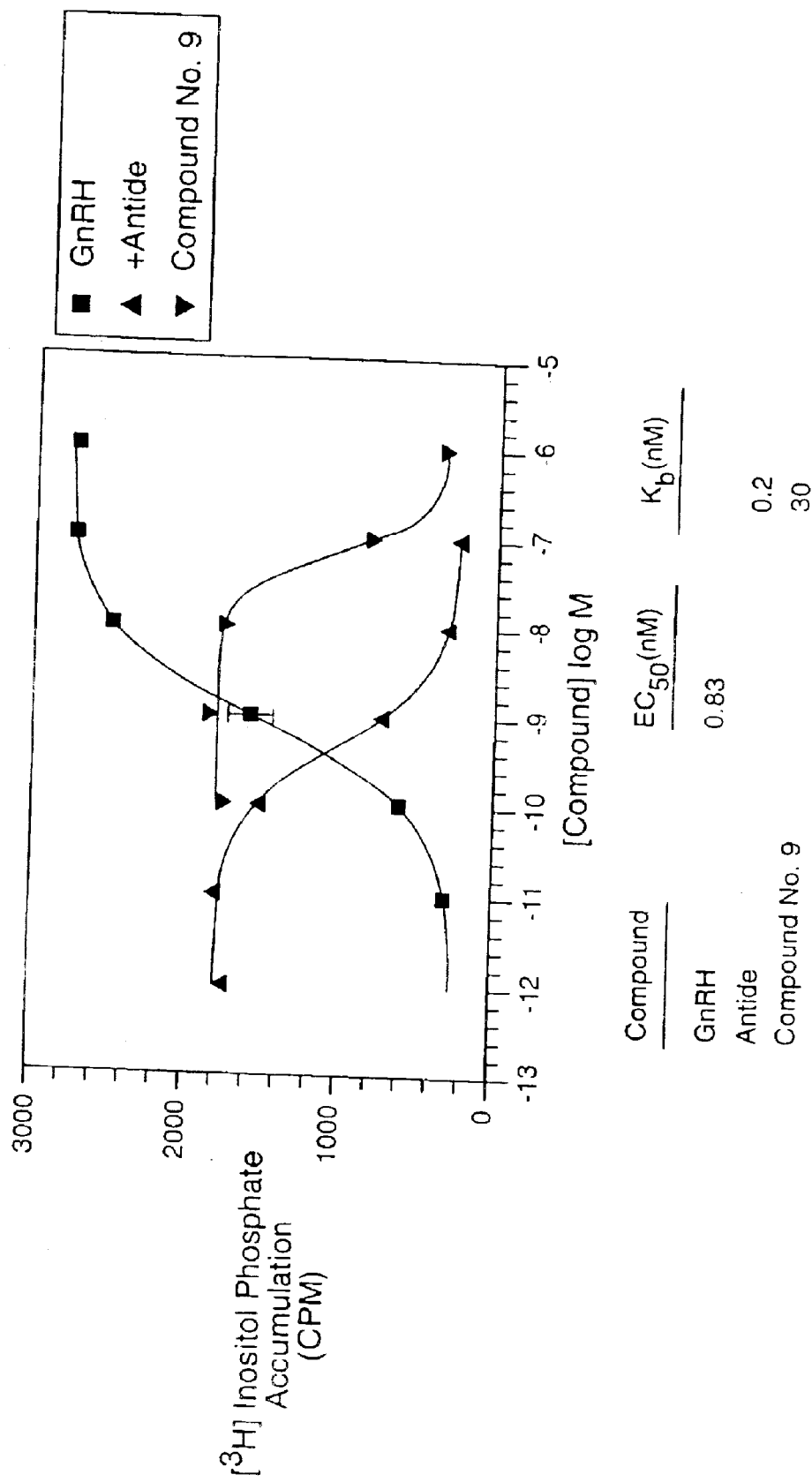

FIG. 2 Effects of Compounds on GnRH-stimulated (1 nM) total inositol phosphate accumulation in 293 cells expressing the hGnRH receptor

NON-PEPTIDE GNRH AGENTS, METHODS AND INTERMEDIATES FOR THEIR PREPARATION

This application claims the benefit of U.S. Provisional Application No. 60/097,530, filed on Aug. 20, 1998.

TECHNICAL FIELD AND INDUSTRIAL APPLICABILITY OF THE INVENTION

This invention relates generally to compounds that affect the action of human gonadotropin-releasing hormone (GnRH). More particularly, it relates to non-peptide GnRH antagonists or agonists and to their preparation. These non-peptide GnRH agents have advantageous physical, chemical and biological properties, and are useful medicaments for diseases or conditions mediated by modulation of the pituitary-gonadal axis. The compounds of the invention avoid the degradation and biodistribution problems of peptide agents.

BACKGROUND OF THE INVENTION

Gonadotropin-Releasing Hormone (GnRH), also known as luteinizing hormone-releasing hormone (LH-RH), plays a central role in the biology of reproduction. A large variety of analogs have been used for an increasing number of clinical indications. The GnRH decapeptide (pyro-Glu-His-Trp-Ser-Tyr-Gly-Leu-Arg-Pro-Gly-$NH_2$ or p-EHWSYGLRPG-$NH_2$) is produced in neurons of the medial basal hypothalamus from a larger precursor by enzymatic processing. The decapeptide is released in a pulsatile manner into the pituitary portal circulation system where GnRH interacts with high-affinity receptors (7-Transmembrane G-Protein Coupled Receptors) in the anterior pituitary gland located at the base of the brain. In the pituitary, GnRH triggers the release of two gonadotropic hormones (gonadotropins): luteinizing hormone (LH) and follicle-stimulating hormone (FSH). In testes and ovaries, LH stimulates the production of testosterone and estradiol, respectively. FSH stimulates follicle growth in women and sperm formation in men. When correctly functioning, the pulse-timed release and concentration levels of GnRH are critical for the maintenance of gonadal steroidogenesis and for normal functions of reproduction related to growth and sexual development.

The pituitary response to GnRH varies greatly throughout life. GnRH and the gonadotropins first appear in the fetus at about ten weeks of gestation. The sensitivity to GnRH declines, after a brief rise during the first three months after birth, until the onset of puberty. Before puberty, the FSH response to GnRH is greater than that of LH. Once puberty begins, sensitivity to GnRH increases, and pulsatile LH secretion ensues. Later in puberty and throughout the reproductive years, pulsatile release of GnRH occurs throughout the day, with LH responsiveness being greater than that of FSH. Pulsatile GnRH release results in pulsatile LH and FSH release and hence testosterone and estradiol release from the gonads. After menopause, FSH and LH concentrations rise, and post-menopausal FSH levels are higher than those of LH.

Chronic administration of GnRH agonists and antagonists to animals or to man results in decreased circulating levels of both LH and FSH. GnRH agonists are compounds that mimic endogenous GnRH to stimulate receptors on the pituitary gland, resulting in release of LH and FSH. After a transient rise in gonadal hormone production or "flare" response, chronic administration of GnRH agonists results in a down-regulation of GnRH receptors. GnRH receptor down-regulation and desensitization of the pituitary results in a decrease of circulating levels of LH and FSH. In spite of the symptom-exacerbating hormonal flare experienced, GnRH agonists have been the treatment of choice for sex-steroid-dependent pathophysiologies. For example, GnRH agonists have been used to reduce testosterone production, thereby reducing prostate volume in benign prostatic hyperplasia (BPH) and slowing tumor growth in prostate cancer. These compounds have also been used to treat breast and ovarian cancers.

Recently, GnRH antagonists have become available for clinical evaluation. GnRH antagonists have an immediate effect on the pituitary without the observed flare associated with agonists. Use of GnRH antagonists (usually decapeptides) has been reported in the literature for treatment of breast, ovarian, and prostatic cancers. Other uses of antagonists, like agonists, include endometriosis (including endometriosis with pain), uterine myoma, ovarian and mammary cystic diseases (including polycystic ovarian disease), prostatic hypertrophy, amenorrhea (e.g., secondary amenorrhea), and precocious puberty. These compounds may also be useful in the symptomatic relief of premenstrual syndrome (PMS). Furthermore, antagonists may be useful to regulate the secretion of gonadotropins in male mammals to arrest spermatogenesis (e.g., as male contraceptives), and for treatment of male sex offenders. Importantly, GnRH antagonists (and agonists) have found utility in treatments where a reversible suppression of the pituitary-gonadal axis is desired.

The presence of GnRH receptors on anterior pituitary cells and several tumor cell types offers the opportunity to develop drugs that act upon these receptors to treat both hormone-dependent and hormone-independent cancers.

For over 50 years, androgen deprivation has been the most effective systematic therapy for the treatment of metastatic carcinoma of the prostate. The rationale is simple—the prostate gland requires androgens for proper growth, maintenance, and function. Yet, prostate cancer and benign prostate hyperplasia are common in men and develop in an environment of continuous androgen exposure. Thus, utilizing a GnRH antagonist to interrupt the pituitary-gonadal axis reduces androgen production and results in tumor growth modulation. Furthermore, GnRH antagonists may have a direct effect on tumor growth by blocking receptors on the tumor cells. For those cancer types that respond both to sex hormones and to GnRH directly, antagonists should be effective in slowing tumor growth by two mechanisms. Since GnRH receptors are present on many prostate and breast cancer cells, it has recently been speculated that GnRH antagonists may also be effective in treating non-hormone-dependent tumors. Recent literature examples indicate that GnRH receptors are present on a number of cancer cell lines, including:

Prostate Cancer: GnRH agonists exert both in vitro, and in vivo, a direct inhibitory action on the growth of both androgen-dependent (LNCaP) and androgen-independent (DU 145) human prostatic cancer cell lines. Montagnani et al, *Arch. Ital. Urol. Androl.* 1997, 69(4), 257–263. GnRH antagonist inhibit the growth of androgen-independent PC-3 prostate cancer in nude mice. Jungwirth et al., *Prostate* 1997, 32(3), 164–172.

Ovarian Cancer: The demonstration of GnRH receptors in human ovarian cancers provides a rationale for the use of therapeutic approaches based on GnRH analogues in this malignancy. Srkalovic et al., *Int. J. Oncol.* 1998, 12(3), 489–498.

Breast Cancer: Breast cancer is the most common type of cancer in women over the age of 40 and is the leading cause of cancer-related death in women. Systematic endocrine intervention represents a major treatment option for the management of advanced breast cancer, especially with estrogen-dependent cancers. The genes for gonadotropin-releasing hormone and its receptor are expressed in human breast with fibrocystic disease and cancer. Kottler et al., *Int. J. Cancer* 1997, 71(4), 595–599.

Heretofore, available GnRH antagonists have primarily been peptide analogs of GnRH. See, e.g., International Publication No. WO 93/03058. Peptide antagonists of peptide hormones are often quite potent; however, the use of peptide antagonists is typically associated with problems because peptides are degraded by physiological enzymes and often poorly distributed within the organism being treated. Thus, they have limited effectiveness as drugs. Consequently, there presently exists a need for non-peptide antagonists of the peptide hormone GnRH.

SUMMARY OF THE INVENTION

An object of the invention is to develop small-molecule non-peptide GnRH antagonists that exploit both of the above-described mechanisms of action. Non-peptide GnRH agents have advantageous physical, chemical and biological properties compared to peptides, and will be useful medicaments for diseases mediated via the pituitary-gonadal axis and by directly targeting the receptor on tumor cells. There is a need to develop drugs that act upon these receptors to treat both hormone-dependent and hormone-independent cancers.

Another object of the invention is to provide non-peptide compounds that are GnRH agents (agonists or antagonists) that bind to GnRH receptors and thus modulate activity, especially those that are potent GnRH antagonists. Another object of the invention is to provide effective therapies for individuals needing therapeutic regulation of GnRH and to provide methods for treating diseases and conditions mediated by GnRH regulation.

Such objects have been achieved by the non-peptide GnRH compounds of the invention; which are useful as pharmaceuticals for indications mediated by GnRH regulation. The inventive compounds are pharmaceutically advantageous over peptide compounds since they provide better biodistribution and tolerance to degradation by physiological enzymes. The invention further provides methods of synthesizing the compounds as well as intermediate compounds useful for making the compounds.

The invention is directed to compounds of the general Formula I:

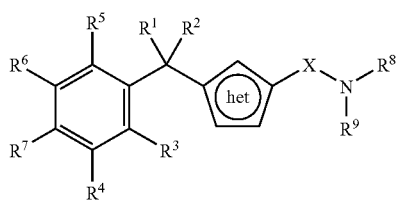

where:
X is selected from C=O, C=S, S=O, and S(O)$_2$;

is a 5-membered heterocyclic ring containing from 1 to 4, preferably 2 or 3, heteroatoms selected from N, O, and S, wherein the ring may be saturated, partially unsaturated, or fully unsaturated, and may be aromatic;

$R^1$ and $R^2$ are independently selected from H and lower alkyl;

$R^3$ is selected from H, halogen, and substituted and unsubstituted alkyl, alkenyl, alkynyl, cycloalkyl, heterocycle, aryl, heteroaryl, CH, OR, OR, and C(O)OR, where R is selected from substituted and unsubstituted alkyl, alkenyl, alkynyl, cycloalkyl, heterocycle, aryl, and heteroaryl, and where the total number of carbon atoms present (not including any optional substituents) ranges from 1 to 12;

$R^4$ and $R^5$ are independently selected from H, halogen, and substituted and unsubstituted alkyl, alkenyl, alkynyl, cycloalkyl, heterocycle, aryl, heteroaryl, CH$_2$OR, OR, and C(O)OR, where R is as defined above; and where the total number of carbon atoms present (not including any optional substituents) ranges from 1 to 12;

$R^6$ and $R^7$ are independently selected from H, halogen and substituted and unsubstituted alkyl, alkenyl, alkynyl, cycloalkyl, heterocycle, aryl, heteroaryl, CH$_2$OR, OR, and C(O)OR; where R is as defined above, and where the total number of carbon atoms present (not including any optional substituents) ranges from 1 to 12; or $R^6$ and $R^7$ taken together with the atoms to which they are bonded form an optionally substituted 5- or 6-membered ring optionally having up to four heteroatoms selected from O, N, and S;

$R^8$ is a lipophilic moiety selected from substituted and unsubstituted alkyl, alkenyl, alkynyl, cycloalkyl, heterocycle, aryl, heteroaryl, CH$_2$OR, OR, and C(O)OR, where R is as defined above, and where the total number of carbon atoms present (not including any optional substituents) ranges from 6 to 20; and $R^9$ is selected from H and substituted and unsubstituted alkyl, preferably lower alkyl.

In some embodiments, $R^1$ or $R^2$ can be —OH or =O; and/or $R^8$ can also be hydrogen;

and/or R can be COR or hydrogen; and/or R8 can have any desired number of carbon atoms;

and/or $R^8$ ad $R^9$ can also form a ring; and/or any adjacent R groups, such as $R^5$ and $R^6$ or $R^3$ and $R^4$ can form a ring, such as those described for $R^6$ and $R^7$;

and/or $R^6$ can be COR; and/or the (het) group can be substituted or unsubstituted.

Also, in another embodiment $R^8$ and/or $R^9$ can be selected from heterocyclic groups or any compound that forms an amide bond with the nitrogen of Formula I. That is, $R^8$ and $R^9$ can be any groups starting with a carbon bonded to the nitrogen of general Formula I.

Preferred compounds of the invention are of the general formula II:

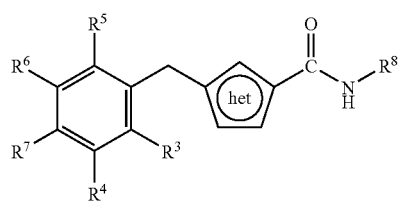

where the variables in the formula are as defined above. Especially preferred compounds have the formula III:

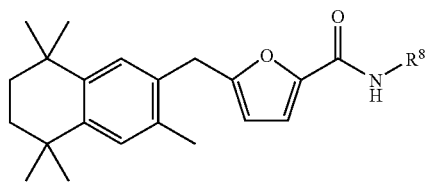

where $R^8$ is defined above. Preferred $R^8$ groups include: aryl, —$CH_2$-aryl, —$CH_2$-heteroaryl, —$CH_2$-cycloalkyl, and —$(CH_2)_n$—O-aryl where n is an integer of from 1 to 4.

Preferred compounds of the invention include:

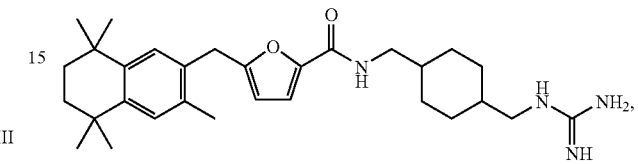

including both cis- and trans-isomers at the cyclohexyl substituent;

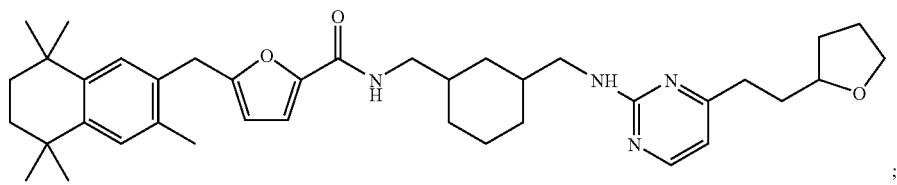

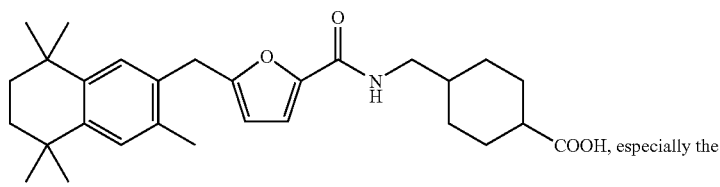

COOH, especially the

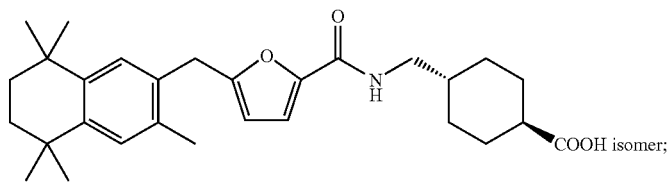

COOH isomer;

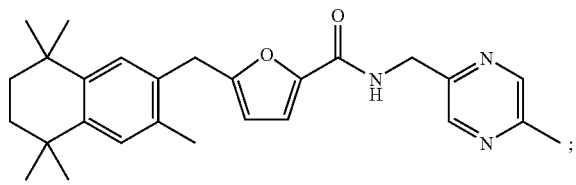

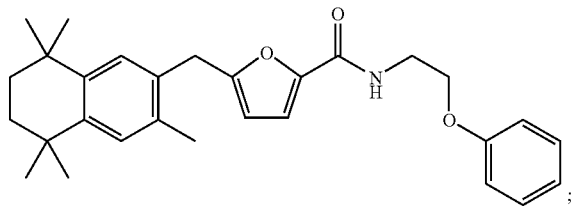

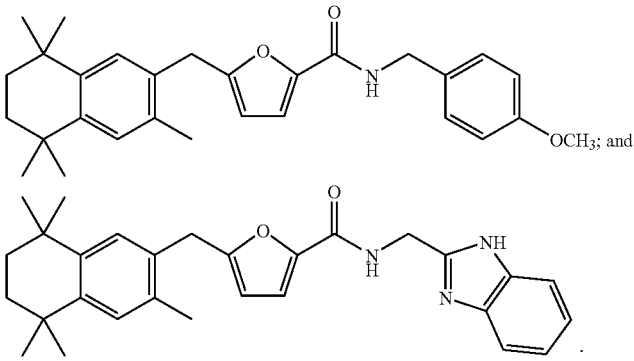

In addition to compounds of the above formulae, GnRH agents of the invention include pharmaceutically acceptable salts, multimeric forms, prodrugs, and active metabolites of such compounds. Such non-peptide agents are pharmaceutically advantageous over peptide agents since they provide better biodistribution and tolerance to degradation by physiological enzymes.

The invention also relates to pharmaceutical compositions comprising a therapeutically effective amount of a GnRH agent of the invention in combination with a pharmaceutically acceptable carrier or diluent. Moreover, the invention relates to methods for regulating the secretion of gonadotropins in mammals, comprising administering therapeutically effective amounts of GnRH agents of the invention.

The invention also relates to methods and intermediates useful for making compounds of the Formula I.

Other features, objects, and advantages of the invention will become apparent from the following detailed description of the invention and its preferred embodiments.

DETAILED DESCRIPTION OF INVENTION AND PREFERRED EMBODIMENTS

Some of the compounds of the invention contain one or more centers of asymmetry, and may thus give rise to enantiomers, diastereoisomers, and other stereoisomeric forms. The invention is meant to include all such possible stereoisomers as well as their racemic and optically pure forms. When the compounds described herein contain olefinic double bonds, they are intended to encompass both E and Z geometric isomers.

The chemical formulae referred to herein may exhibit the phenomenon of tautomerism. As the structural formulae shown in this specification only depict one of the possible tautomeric forms, it should be understood that the invention nonetheless encompasses all tautomeric forms.

The term "alkyl" refers to straight- and branched-chain alkyl groups having one to twelve carbon atoms. Exemplary alkyl groups include methyl (Me), ethyl, n-propyl, isopropyl, butyl, isobutyl, sec-butyl, tert-butyl (tBu), pentyl, isopentyl, tert-pentyl, hexyl, isohexyl, and the like. The term "lower alkyl" designates an alkyl having from 1 to 8 carbon atoms (a $C_{1-8}$-alkyl). Suitable substituted alkyls include fluoromethyl, difluoromethyl, trifluoromethyl, 2-fluoroethyl, 3-fluoropropyl, hydroxymethyl, 2-hydroxyethyl, 3-hydroxypropyl, and the like.

The term "alkenyl" refers to straight- and branched-chain alkenyl groups having from 2 to 12 carbon atoms. Illustrative alkenyl groups include prop-2-enyl, but-2-enyl, but-3-enyl, 2-methylprop-2-enyl, hex-2-enyl, and the like.

The term "alkynyl" refers to straight- and branched-chain alkynyl groups having from 2 to 12 carbons atoms. Exemplary alkynyls include prop-2-ynyl, 3-methylpent-4-ynyl, hex-2-ynyl, and the like.

The term "carbocycle" refers to a monocyclic or polycyclic carbon ring structure (with no heteroatoms) having from 3 to 7 carbon atoms in each ring, which may be saturated, partially saturated, or unsaturated. Exemplary carbocycles include cycloalkyls and aryls.

The term "heterocycle" refers to a monocyclic or polycyclic ring structure with one or more heteroatoms selected from N, O, and S, and having from 3 to 7 atoms (carbon atoms plus any heteroatom(s)) in each ring, which may be saturated, partially saturated, or unsaturated Exemplary heterocycles include tetrahydrofuranyl, tetrahydropyranyl, azetidinyl, pyrrolidinyl, piperidinyl, piperazinyl, and the like.

The term "cycloalkyls" as used herein refers to saturated carbocycles having 3 to 12 carbons, including bicyclic and tricyclic cycloalkyl structures. Suitable cycloalkyls include cyclopropyl, cyclobutyl, cyclopentyl, cyclohexyl, cycloheptyl, and the like.

The terms "aryls" and "heteroaryls" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indoly, quinolinyl, benzofuranyl, benzothiophenyl (thianaphthenyl), and the like. Such moieties may be optionally substituted by one or more suitable substituents, for example, a substituent selected from a halogen (F, Cl, Br or I); lower alkyl; OH; $NO_2$; CN; $CO_2H$; O-lower alkyl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O.

The term "aryl-lower alkyl" means a lower alkyl bearing an aryl. Examples include benzyl, phenethyl, pyridylmethyl, naphthylmethyl, and the like. The aryl-lower alkyl may be optionally substituted.

In general, the various moieties or functional groups for variables in Formula I may be optionally substituted by one or more suitable substituents. Exemplary substituents include a halogen (F, Cl, Br, or I), lower alkyl, —OH, —$NO_2$, —CN, —$CO_2H$, —O-lower alkyl, -aryl, -aryl-lower alkyl, —$CO_2CH_3$, —$CONH_2$, —$OCH_2CONH_2$, —$NH_2$, —$SO_2NH_2$, haloalkyl (e.g., —$CF_3$, —$CH_2CF_3$), —O-haloalkyl (e.g., —$OCF_3$, —$OCHF_2$), and the like.

In addition to compounds of the Formula I, GnRH agents of the invention include pharmaceutically acceptable salts, multimeric forms, prodrugs, and active metabolites of compounds of the Formula I. Such non-peptide agents are pharmaceutically advantageous over peptide agents since they provide better biodistribution and tolerance to degradation by physiological enzymes.

Additionally, Formula I is intended to cover, where applicable, solvated as well as unsolvated forms of the compounds. Thus, Formula I includes compounds having the indicated structure, including the hydrated as well as the non-hydrated forms.

As indicated above, GnRH agents in accordance with the invention also include active tautomeric and stereoisomeric forms of the compounds of the Formula I, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

GnRH agents further include multivalent or multimeric forms of active forms of the compounds of the Formula I. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding (see, for example, Lee et al., *Biochem.*, 1984, 23:4255). The artisan may control the multivalency and spacing by selection of a suitable carrier moiety or linker units. Useful moieties include molecular supports containing a multiplicity of functional groups that can be reacted with functional groups associated with the active compounds of the invention. A variety of carrier moieties may be used to build highly active multimers, including proteins such as BSA (bovine serum albumin) or HAS, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

Additionally, GnRH agents of the invention include pharmaceutically acceptable salts of compounds of the Formula I. The term "pharmaceutically acceptable" refers to salt forms that are pharmacologically acceptable and substantially non-toxic to the subject being administered the GnRH agent Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from organic bases such as amines, benzylamines, piperidines, and pyrrolidines.

The term "prodrug" refers to a metabolic precursor of a compound of the Formula I (or a salt thereof) that is pharmaceutically acceptable. A prodrug may be inactive when administered to a subject but is converted in viva to an active compound of the Formula I. The term "active metabolite" refers to a metabolic product of a compound of the Formula I that is pharmaceutically acceptable and effective. Prodrugs and active metabolites of compounds of the Formula I may be determined using techniques known in the art.

A variety of known assays and techniques may be employed to determine the level of activity of various forms of the compounds in the GnRH system. Ligand-binding assays are used to determine interaction with the receptor of interest. Where binding is of interest, a labeled receptor may be used, where the label is a fluorescer, enzyme, radioisotope, or the like, which registers a quantifiable change upon the binding of the receptor. Alternatively, the artisan may provide for an antibody to the receptor, where the antibody is labeled, which may allow for amplification of the signal. Binding may also be determined by competitive displacement of a ligand bound to the receptor, where the ligand is labeled with a detectable label. Where agonist and/or antagonist activity is of interest, an intact organism or cell may be studied, and the change in an organismic or cellular function in response to the binding of the compound of interest may be measured. Various devices are available for detecting cellular response, such as a microphysiometer available from Molecular-Device, Redwood City, Calif. In vitro and in vivo assays useful in measuring GnRH antagonist activity are known in the art. See, e.g., Bowers et al., "LH suppression in cultured rat pituitary cells treated with 1 ng of LHRH," *Endocrinology*, 1980, 106:675–683 (in vitro,) and Corbin et al., "Antiovulatory activity (AOA) in rats," *Endocr. Res. Commun.* 1975, 2:1–23 (in vivo). Particular test protocols that may be used are described below.

For example, GnRH-receptor antagonists may be functionally assessed by measurement of change in extracellular acidification rates as follows. The ability of compounds to block the extracellular rate of acidification mediated by GnRH in HEK 293 cells expressing human GnRH receptors is determined as a measure of the compound's antagonist activity in vitro. Approximately 100,000 cells/chamber are immobilized in agarose suspension medium (Molecular Devices) and perfused with unbuffered MEM media utilizing the Cytosensor® Microphysiometer (Molecular Devices). Cells are allowed to equilibrate until the basal acidification rate remains stable (approximately one hour). Control dose-response curves are performed to GnRH ($10^{-11}$M to $10^{-7}$ M). Compounds are allowed to incubate 15 minutes prior to stimulation with GnRH, and are assessed for antagonist activity. After incubation with test compounds, repeat dose-response curves to GnRH in the presence or absence of various concentrations of the test compounds are obtained. Schild regression analysis is performed on compounds to determine whether compounds antagonize GnRH-mediated increases in extracellular acidification rates through a competitive interaction with the GnRH receptor.

In another test, accumulation of total inositol phosphates may be measured by formic acid extraction from cells, followed by separation of the phosphates on Dowex columns. Cells are split using trypsin into two 12-well plates and pre-labeled with $^3$H-myoinositol (0.5 Ci–2 mCi per mL) for 16–18 hours in inositol-free medium. The medium is then aspirated and the cells rinsed with either 1×HBSS, 20 mM HEPES (pH 7.5), or serum-free DMEM, 1×HBSS, 20 mM HEPES (pH 7.5) containing agonist, and 20 mM LiCl is then added and the cells are incubated for the desired time. The medium is aspirated and the reaction stopped by addition of ice-cold 10 mM formic acid, which also serves to extract cellular lipids. Inositol phosphates are separated by ion-exchange chromatography on Dowex columns, which are then washed with 5 mL of 10 mM myoinositol and 10 mM formic acid. The columns are then washed with 10 mL of 6 mL sodium formate and 5 mM borax, and total inositol phosphates are eluted with 4.5 mL 1M ammonium formate, 0.1M formic acid.

Preferred GnRH agents of the invention include those having a K, value of about 10 μM or less. Especially preferred GnRH agents are those having a K, value in the nanomolar range.

Preferred compounds of the inventions are shown in the following table:

| COMPOUND NO. | STRUCTURAL FORMULA | mol. weight |
|---|---|---|
| 9 | | 492.704 |
| 10 | | 492.704 |
| 11 | | 627.869 |
| 12 | | 465.63 |

-continued
| COMPOUND NO. | STRUCTURAL FORMULA | mol. weight |
|---|---|---|
| 13 | 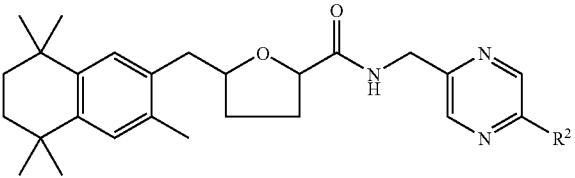 | 431.577 |
| 14 | 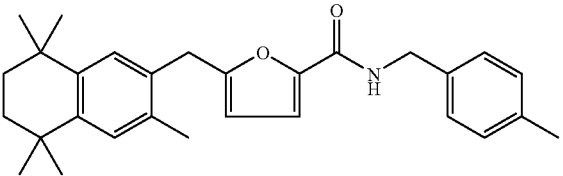 | 429.6 |
| 15 | 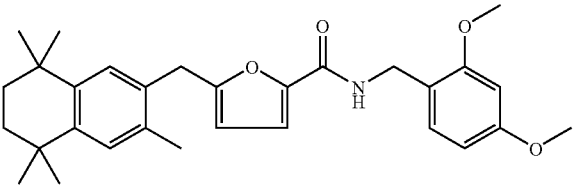 | 475.625 |
| 16 | 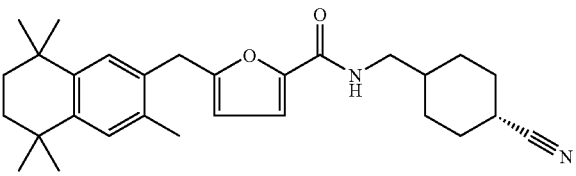 | 446.631 |
| 17 | 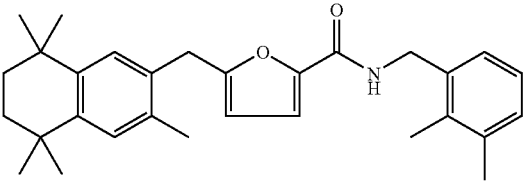 | 443.627 |
| 18 | 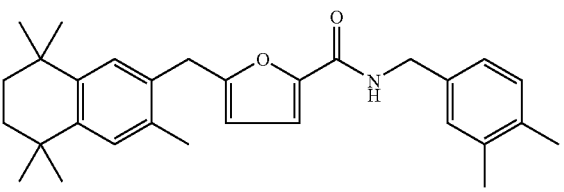 | 443.627 |
| 19 | 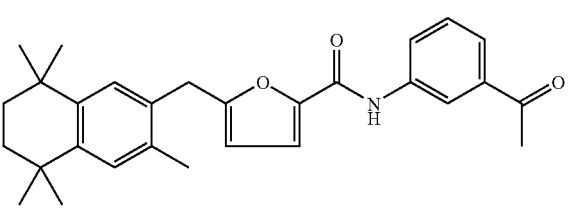 | 443.584 |

-continued

| COMPOUND NO. | STRUCTURAL FORMULA | mol. weight |
|---|---|---|
| 20 | 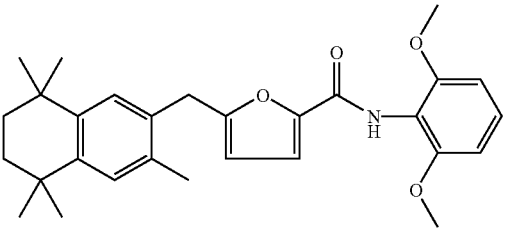 | 461.599 |

Pharmaceutical compositions according to the invention comprise an effective GnRH-suppressing amount of at least one GnRH agent according to the invention and an inert or pharmaceutically acceptable carrier or diluent. These compositions may be prepared in a unit-dosage form appropriate for the desired mode of administration, e.g., parenteral or oral.

To treat diseases or conditions mediated by GnRH agonism or antagonism, a pharmaceutical composition of the invention is administered in a suitable formulation prepared by combining a therapeutically effective amount (i.e., a GnRH-modulating amount effective to achieve therapeutic efficacy) of at least one GnRH agent of the invention (as an active ingredient) with one or more pharmaceutically suitable carriers or diluents. Such formulations may be prepared according to conventional procedures, e.g., by appropriately mixing, granulating, and compressing or dissolving the ingredients in known manners. Optionally, one or more different active ingredients, such as different GnRH antagonists, may be employed in a pharmaceutical composition.

The pharmaceutical carrier may be either a solid or liquid. Exemplary solid carriers include lactose, sucrose, talc, gelatin, agar, pectin, acacia, magnesium stearate, stearic acid, and the like. Illustrative of liquid carriers are syrup, peanut oil, olive oil, water, and the like. Similarly, the carrier or diluent may include time-delay or time-release materials known in the art, such as glyceryl monostearate or glyceryl distearate, alone or in combination with a wax, ethylcellulose, hydroxypropylmethylcellulose, methylmethacrylate, or the like.

A variety of pharmaceutical forms can be employed. For example, if a solid carrier is used, the preparation may be in the form of a tablet, hard-gelatin capsule, powder, pellet, troche, or lozenge. The amount of solid carrier may vary widely, with an exemplary amount ranging from about 25 mg to about 1 g. If a liquid carrier is used, the preparation may be in the form of a syrup, emulsion, soft-gelatin capsule, sterile injectable solution, suspension in an ampoule or vial, or non-aqueous liquid suspension.

To obtain a stable, water-soluble dosage form, a pharmaceutically acceptable salt of a compound of Formula I may be dissolved in an aqueous solution of an organic or inorganic acid, such as 0.3M solution of succinic acid or, more preferably, citric acid. If a soluble salt form is not available, the agent may be dissolved in one or more suitable cosolvents. Examples of suitable cosolvents include alcohol, propylene glycol, polyethylene glycol 300, polysorbate 80, gylcerin, and the like in concentrations ranging from 0% to 60% of the total volume. In an exemplary embodiment, a compound of Formula I is dissolved in DMSO and diluted with water. The composition may also be in the form of a solution of a salt form of a compound of the Formula I in an appropriate aqueous vehicle, such as water, or isotonic saline or dextrose solutions.

The pharmaceutical compositions of the present invention may be manufactured using conventional techniques, e.g., mixing, dissolving, granulating, dragee-making, levigating, emulsifiying, encapsulating, entrapping, or lyophilizing processes. Pharmaceutical compositions may be formulated in a conventional manner using one or more physiologically acceptable carriers comprising excipients or auxiliaries selected to facilitate processing of the active compounds into pharmaceutical preparations. An appropriate formulation is selected in view of the route of administration chosen.

For preparing injectable preparations, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation and may be selected from those known in the art.

For oral administration, the agents may be formulated readily by combining the active ingredient(s) with pharmaceutically acceptable carriers known in the art. Such carriers enable the compounds of the invention to be formulated as tablets, pills, dragees, capsules, liquids, gels, syrups, slurries, suspensions, and the like, for oral ingestion by a patient to be treated. Pharmaceutical preparations for oral use can be obtained by combining one or more agents with a solid excipient, optionally grinding the resulting mixture into granules, and processing the mixture of granules after adding suitable auxiliaries, if desired, to obtain tablets or dragee cores. Suitable excipients include fillers such as sugars (e.g., lactose, sucrose, mannitol, or sorbitol) and cellulose preparations (e.g., maize starch, wheat starch, rice starch, potato starch, gelatin, gum, methyl cellulose, hydroxypropylmethylcellulose, sodium carboxymethylcellulose, and/or polyvinylpyrrolidone (PVP)). If desired, disintegrating agents may be added, such as crosslinked PVP, agar, or alginic acid or a salt thereof such as sodium alginate.

Dragee cores are provided with suitable coatings. For this purpose, concentrated sugar solutions may be used, which may optionally contain guru arabic, PVP, Carbopol™ gel, polyethylene glycol, titanium dioxide, lacquer solutions, and/or one or more suitable organic solvents. Dyestuffs or pigments may be added to the tablets or dragee coatings for identification or to characterize different combinations of active compound doses.

Pharmaceutical forms that are suitable for oral administration include push-ft capsules made of gelatin, as well as soft, sealed capsules made of gelatin and a plasticizer, such as glycerol or sorbitol. The push-fit capsules may contain the active ingredient(s) in admixture with one or more fillers such as lactose, binders such as starches, and/or lubricants such as talc or magnesium stearate, and, optionally, stabilizers. In soft capsules, the active compound may be dissolved or suspended in a suitable liquid, such as fatty oil, liquid paraffin, or liquid polyethylene glycol. In addition, stabilizers may be added. For buccal administration, the compositions may take the form of tablets or lozenges formulated in a conventional manner.

For administration by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetafluoroethane, carbon dioxide, or another suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the agent and a suitable powder base such as lactose or starch.

The agents may be formulated for parenteral administration by injection, e.g., by bolus injection or continuous infusion. Formulations for injection may be prepared in unit-dosage form, e.g., in ampoules, or in multi-dose containers, with an added preservative. The compositions may take such forms as suspensions, solutions, or emulsions in oily or aqueous vehicles, and may contain formulatory agents such as suspending, stabilizing, and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters such as ethyl oleate or triglycerides, or liposomes. Aqueous injectable suspensions may contain substances increasing the viscosity of the suspension, such as sodium carboxymethyl cellulose, sorbitol, or dextran. Optionally, the suspension may also contain suitable stabilizers or agents increasing the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated as rectal compositions, such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system (VPD is a solution of 3% w/v benzyl alcohol, 8% w/v of the nonpolar surfactant polysorbate 80, and 65% w/v polyethylene glycol 300, made up to volume in absolute ethanol). The VPD co-solvent system (VPD:5W) is comprised of VPD diluted 1:1 with a 5% dextrose-in-water solution. This co-solvent system dissolves hydrophobic compounds well, and the resulting formulation produces low toxicity upon systemic administration. As will be apparent, the proportions of a suitable co-solvent system may be varied in light of the solubility and toxicity characteristics. Furthermore, the identity of the co-solvent components may be varied: for example, other low-toxicity nonpolar surfactants may be used instead of polysorbate 80; the fraction size of polyethylene glycol may be varied; one or more other biocompatible polymers (e.g., PVP) may be added or replace polyethylene glycol; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs and may be used to formulate suitable preparations. Certain organic solvents such as dimethylsulfoxide also may be employed, although this may cause an increase in toxicity. Additionally, delivery may be achieved using a sustained-release system, such as semipermeable matrices of solid hydrophobic polymers containing the therapeutic agent. Various sustained-release materials are available and known to those skilled in the art. Sustained-release capsules may, depending on their chemical nature, release the compounds for a period lasting from a few weeks or up to over 100 days. Depending on the chemical nature and the biological stability of the therapeutic agent, additional techniques for protein stabilization may be readily employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter-ions. Pharmaceutically acceptable salts may be formed with many acids, including hydrochloric, sulfuric, acetic, lactic, tartaric, malic, succinic, and like acids. Salts tend to be more soluble in aqueous or other protonic solvents than are the corresponding free-base forms.

It will be appreciated that the actual dosages of the agents used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of the experimental data for a given compound. For oral administration, an exemplary daily dose generally employed will be from about 0.001 to about 1000 mg/kg of body weight, with courses of treatment repeated at appropriate intervals. Administration of prodrugs may be dosed at weight levels that are chemically equivalent to the weight levels of the fully active compounds.

Examples of specific pharmaceutical preparations in accordance with the invention are provided below.

Parenteral Composition: To prepare a pharmaceutical composition of this invention suitable for administration by injection, 100 mg of a pharmaceutically acceptable water-soluble salt of a compound of Formula I is dissolved in DMSO and then mixed with 10 mL of 0.9% sterile saline. The resulting mixture is incorporated into a unit-dosage form suitable for administration by injection.

Oral Composition: To prepare an orally administerable pharmaceutical composition, 100 mg of a compound of Formula I is mixed with 750 mg of lactose. The resulting mixture is incorporated into a unit-dosage form suitable for oral administration, such as a hard-gelatin capsule.

Synthesis of GnRH Reagents and Compounds

A. Building Block Example:

Naphthalene-Based Building Blocks: A useful acylating agent is prepared by sequential Friedel-Crafts alkylations and is shown below:

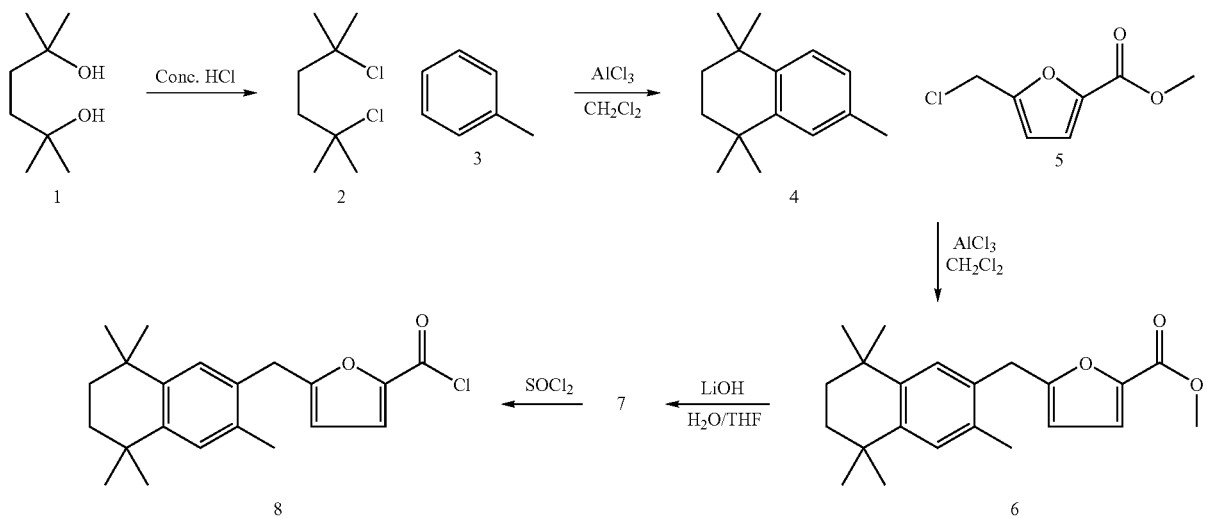

Compound 2 can be prepared as follows:

2,5-Dimethyl-2,5-hexanediol (200 grams, 1.37 mole) was added as a solid portion wise to 3 liters of concentrated hydrochloric acid in a large Erlenmeyer flask. The diol quickly dissolved in the hydrochloric acid and the desired product 2,5-dichloro-2,5-dimethylhexane precipitated out of solution as it was formed. The reaction was stirred at room temperature for 4 hours. One liter of 50% ethyl acetate in hexanes were added and the organic later separated and washed several times with water (until neutral by pH paper). The organic solvents were removed in vacuo at room temperature. The crude 2,5-dichloro-2,5-dimethylhexane was dissolved in hexanes and plugged through a pad of silica gel (10:1 ratio) and eluted with hexanes. This final filtration step gives a white solid after removal of the organic solvent in vacuo. Recovery of pure 2,5-dichloro-2,5-dimethylhexane was 230 grams 92% yield. 1H NMR (CDCl$_3$, delta): 1.96 (4H, s); 1.61 (12H, s).

Using a similar procedure 2,4-dimethyl-2,4-pentanediol was converted to 2,4-dichloro-2,4-dimethylpentane. 1H NMR (CDCl$_3$, delta): 2.42 (2H, s); 1.73 (12H, s).

1,1,4,4,6-pentamethyl-1,2,3,4-tetrahydronaphtalene 4. To a solution of 2.5 dichloro-2,5 dimethylhexane 2 (10 g, 54.7 mmol) in toluene (270 Ml, 0.2 M) is slowly added aluminum trichloride (5.47 g, 41 mmol) as a solid over a 15-minute period. The reaction is complete after 10 minutes as assayed by tlc in hexanes. The unreacted aluminum trichloride is quenched slowly with water over 10 minutes. Additional toluene (250 mL) is added to extract the product from the aqueous layer. The organic layer is passed through a pad of silica gel (40 g) and eluted with toluene. The organic layer is evaporated in vacuo to dryness to yield 1,1,4,4,6-pentamethyl-1,2,3,4-tetrahydronaphtalene 4 (11 g, 97% yield). NMR 1.29 (s, 6H), 1.28 (s, 6H), 1.69 (s, 4H), 2.32 (s, 3H), 7.22 (d, 1H), 7.12 (s, 1H), 6.97 (dd, 1H).

Methyl 5-[(3,5,5,8,8-pentamethyl-5,6,7,8-tetrahydro-2-naphthalenyl)methyl]-2-furoate 6: To a solution containing 1,1,4,4,6-pentamethyl-1,2,3,4-tetrahydronaphtalene 4 (20 g, 99 mmol) and methyl 5-(chloromethyl)-2-furoate 5 (17.28 g, 99 mmol) in methylene chloride (500 mL, 0.2 M), aluminum trichloride (16.46 g, 124 mmol) is added slowly as a solid at the reflux temperature of methylene chloride. The solution is refluxed for an additional two hours. The reaction is monitored by tlc in 10% ethyl acetate/hexanes solution. The reaction is cooled to room temperature and the unreacted aluminum trichloride is quenched with water over 15 minutes. The crude product is extracted with methylene chloride and passed through silica gel (80 g) and eluted with methylene chloride. The solvent is evaporated in vacuo to syrup. The crude product us purified with silica gel (300 g) via a plug filtration column. Methyl 5-[(3,5,5,8,8-pentamethyl-5,6,7,8-tetrahydro-2-naphthalenyl)methyl]-2-furoate 6 is eluted with 2% ethyl acetate/hexanes to afford 15.4 g (46% yield). NMR 1.25 (s, 6H), 1.28 (s, 6H), 1.67 (s, 4H), 2.23 (s, 3H), 3.89 (s, 3H), 3.97 (s, 2H), 5.95 (d, 1H), 7.09 (m, 3H).

5-[(3,5,5,8,8-pentamethyl-5,6,7,8-tetrahydro-2-naphthalenyl)methyl]-2-furoic acid 7: To a solution containing methyl 5-[(3,5,5,8,8-pentamethyl-5,6,7,8-tetrahydro-2-naphthalenyl) methyl]-2-furoate 6 (15.1 g, 44 mmol) in MeOH (175 mL) and water (175 mL), a solution of NaOH (3.53 g, 88.3 mmol) in water (29 mL) is added. The reaction mixture is stirred overnight. After completion as judged by tlc, the solution is acidified with 1M HCl to pH 2. The crude product is extracted into organic layer using ethyl acetate, and concentrated to afford 5-[(3,5,5,8,8-pentamethyl-5,6,7,8-tetrahydro-2-naphthalenyl)methyl]-2-furoic acid 7 (15.0 g, 99% yield). NMR 1.26 (s, 6H), 1.28 (s, 6H), 1.68 (s, 4H), 2.24 (s, 3H), 4.00 (s, 2H), 6.01 (d, 1H), 7.10 (s, 21), 7.23 (d, 1H).

5-[(3,5,5,8,8-pentamethyl-5,6,7,8-tetrahydro-2-naphthalenyl)methyl]-2-furoyl chloride 8: To a solution containing 5-[(3,5,5,8,8-pentamethyl-5,6,7,8-tetrahydro-2-naphthalenyl)methyl]-2-furoic acid 7 (20.15 g, 61.77 mmol) in methylene chloride (310 mL), thionyl chloride (45 mL, 617 mmol) is added. The reaction is refluxed for 5 hours and another batch of thionyl chloride (45 mL, 617 mmol) is added. The reaction is stirred overnight at room temperature. The solution is concentrated to a syrup and passed through a pad of silica gel (50 g), washed with 3% hexanes, and concentrated in vacuo to afford 5-[(3,5,5,8,8-pentamethyl-5,6,7,8-tetrahydro-2-naphthalenyl)methyl]-2-furoyl chloride 8 (17 g, 80% yield). NMR 1.26 (s, 6H), 1.28 (s, 6H), 1.68 (s, 4H), 2.25 (s, 3H), 4.00 (s, 2H), 6.11 (d, 1H), 7.10 (s, 1H), 7.11 (s, 1H), 7.41 (d, 1H).

Additional building blocks can be prepared under these reaction conditions which contain a variety of functional groups contained in the general formula shown above.

B. Acylation Examples:

The next scheme shows several examples which can use the general synthetic procedure for acylations given below.

REAGENT EXAMPLES COUPLING TO Y

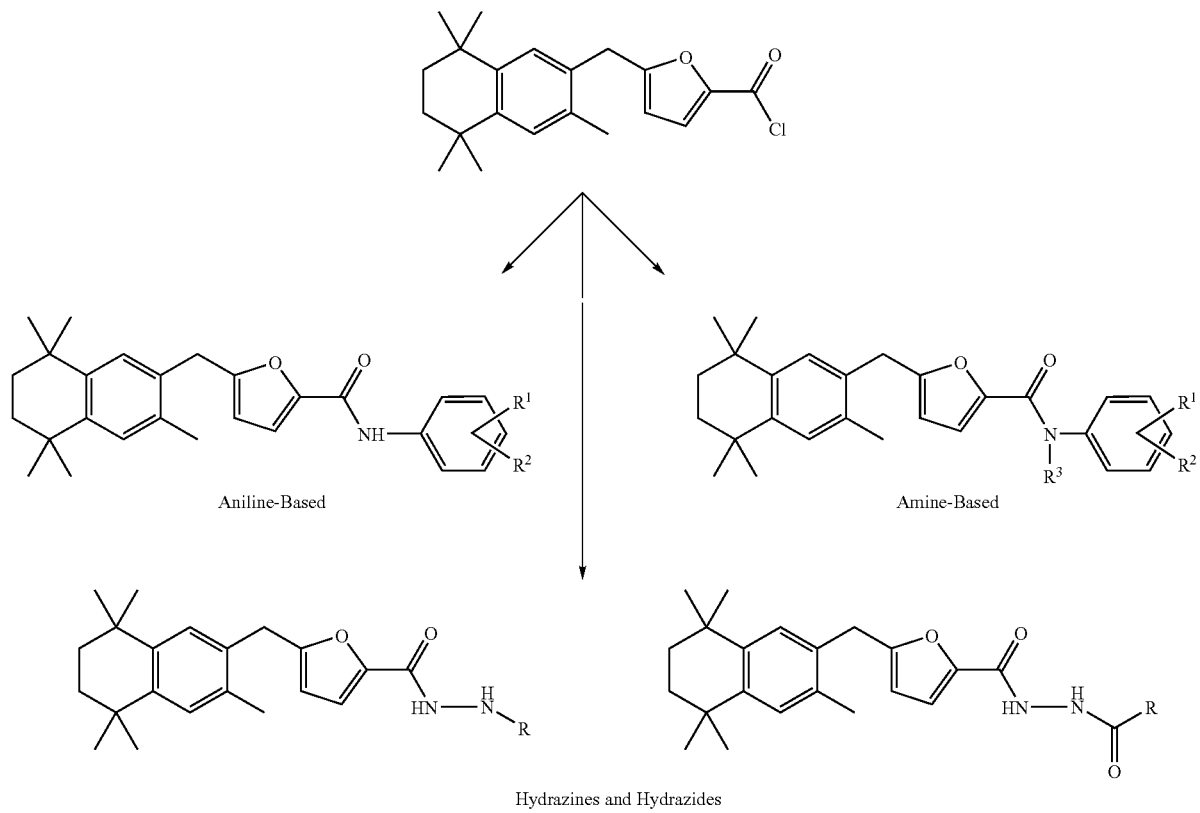

Hydrazines and Hydrazides

Amines are dissolved or suspended in dichloromethane, dichloroethane, ethyl acetate, acetonitrile, or the like (0.2M concentration) followed by the addition of the acid chloride reagent (1.00 mmol. equiv.). To the mixture is added triethyl amine (5.00 mmol. equiv.) and the reaction stirred at room temperature for 12–48 hours. The solvents are removed in vacuo. The product is purified by column chromatography on silica gel and eluted with an appropriate elution solvent (e.g., 3:1 hexanes:ethyl acetate). The solvents are removed in vacuo to yield the acylated product.

As an alternative, the reaction mixture is diluted with dichloromethane (five times the amount of dichloromethane used) and washed with saturated sodium bicarbonate. The organic layer is dried over magnesium sulfate and filtered. The product is purified by column chromatography on silica gel and eluted with an appropriate elution solvent (e.g., 3:1 hexanes:ethyl acetate). The solvents are removed in vacuo to yield the acylated product.

Using the general reaction protocol, large numbers of compounds can be readily prepared and assayed for their activities either as pure or impure materials. The reaction protocol works well on anilines, amines, benzyl amines, hydrazines, hydrazides, alcohols and the like.

Specific examples showing a variety of structures acylated according to a general procedure are shown below:

| COMPOUND NO. | STRUCTURE | mol. weight |
|---|---|---|
| 9 | 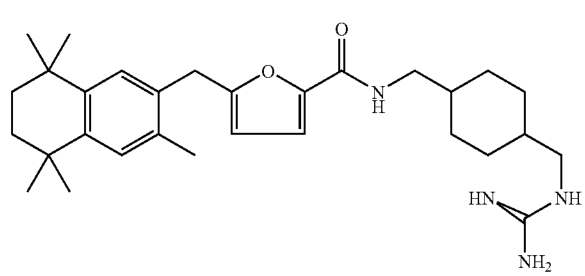 | 492.704 |

-continued

| COMPOUND NO. | STRUCTURE | mol. weight |
|---|---|---|
| 10 | 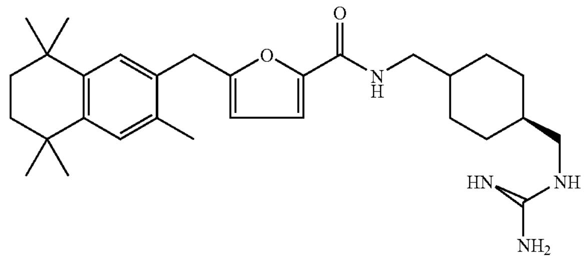 | 492.704 |
| 11 | 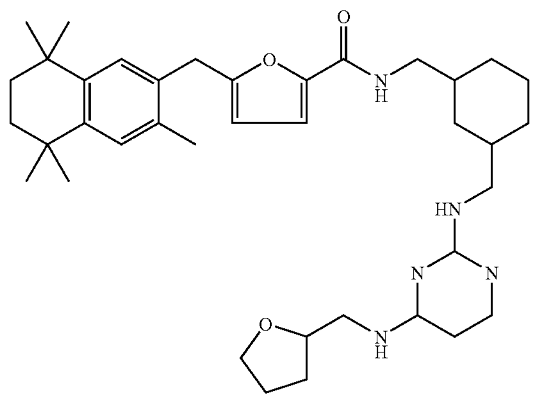 | 627.869 |
| 12 | 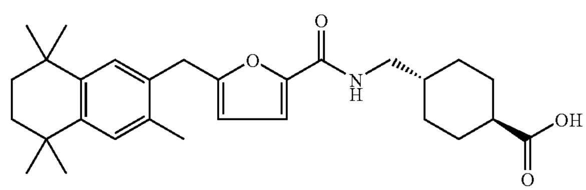 | 465.63 |
| 13 | 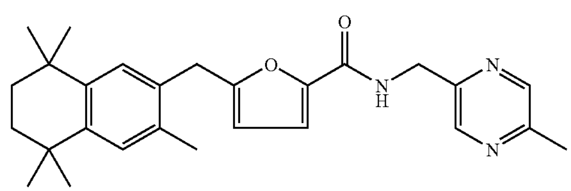 | 431.577 |
| 14 | 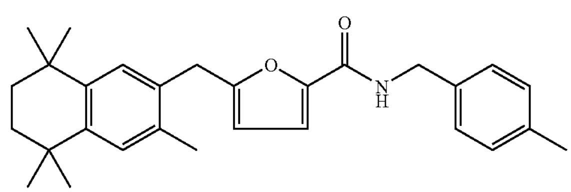 | 429.6 |
| 15 | 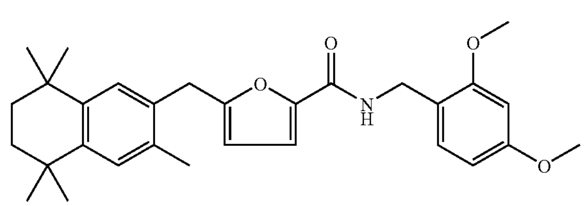 | 475.625 |

-continued
| COMPOUND NO. | STRUCTURE | mol. weight |
|---|---|---|
| 16 | 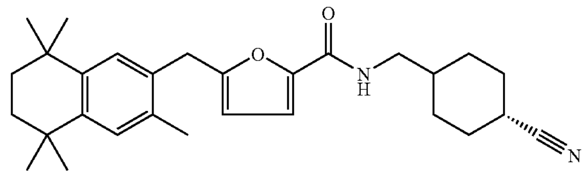 | 446.631 |
| 17 | 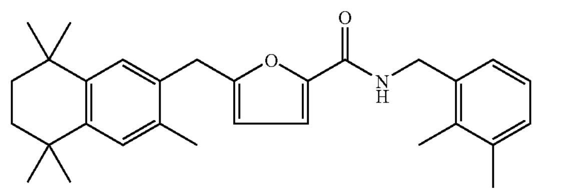 | 443.627 |
| 18 | 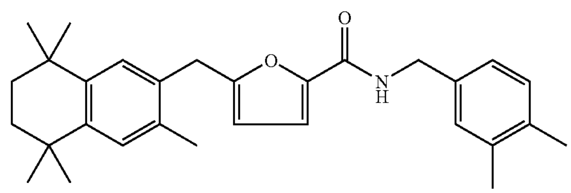 | 443.627 |
| 19 | 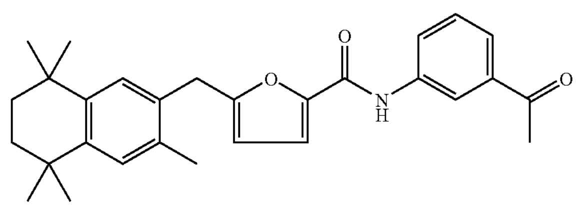 | 443.584 |
| 20 | 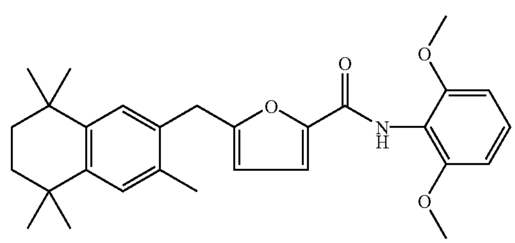 | 461.599 |
C. Synthesis and Acylation of Guanidine-Containing Compounds:
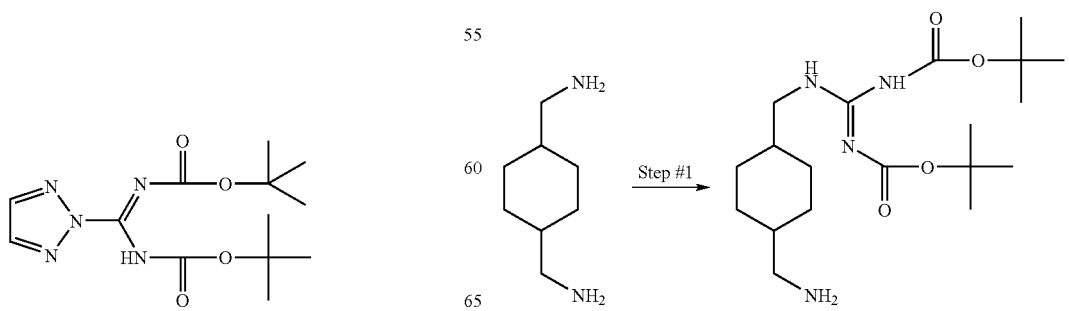

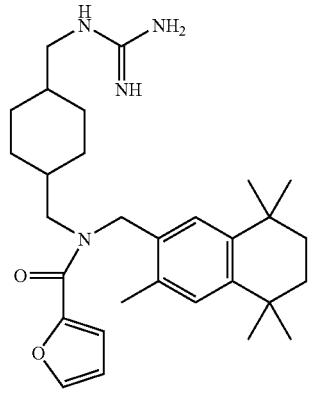

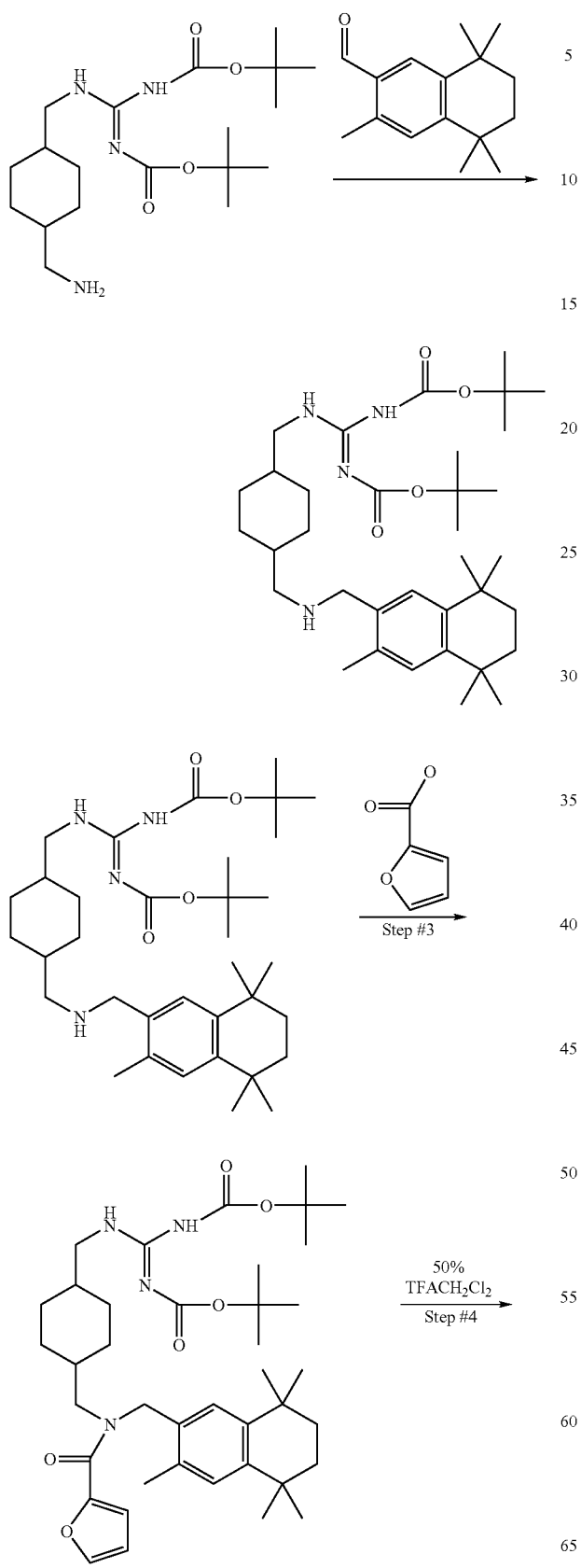

Step 1—Preparation of Protected Compound by 1-(N,N'-diBoc)-guanidinomethylation: Alternative Steps 1(A) and 1(B) below provide two general 1-(N,N'-diBoc)-guanidinomethylation procedures.

Step 1(A): To a solution of diamine (2.00 mmol equiv.) in THF (0.7 M) is added a solution of 1-H-pyrazole-1-(N,N-bis(tert-butoxycarbonyl)carboxamidine) (1.00 mmol equiv.) in THF (0.7M). The solution is stirred at room temperature for 3 hours (h), or until DO further transformation can be observed by tlc (thin-layer chromatography). The solvent is removed under reduced pressure to give a syrupy residue, which is taken up in ethyl acetate (~1.5 times the volume amount of THF used in the reaction or the volume of solvent needed to dissolve the amount of residue obtained) and washed with water until neutral pH. The organic layer is washed with brine, dried over MgSO$_4$, and concentrated. The product is purified by column chromatography on silica gel and eluted with an appropriate elution solvent (which may be readily determined, e.g., using 5% MeOH in dichloromethane as a starting point). The solvents are removed in vacuo to afford the 1-(N,N'-diBoc)-guanidinomethyl-linked-amine. In addition other reagents can be used to place a protected N,N'-diBoc-guanidine unit on diamines, such as 1,3-bis(tert-butoxycarbonyl)-2-methyl-2-thiopseudourea (CAS No. 107819-90-0). Alternatively, the 1-H-pyrazole-1-(N,N-bis(tert-butoxycarbonyl)carboxamidine) can be added directly as a solid, rather than as a solution as described above.

Step 1(B): To a solution of diamine (1.00 mmol equiv.) in THF (0.07M) is added portionwise as a solid (over a 10-minute time period) 1-H-pyrazole-1-(N,N-bis(tert-butoxy-carbonyl)carboxamidine) (1.00 mmol equiv.). The solution is stirred at room temperature for 0.5 hour. The solvent is removed under reduced pressure to give a syrupy residue, which is taken up in ethyl acetate (0.5 times the volume amount of THF used in the reaction, or the volume of solvent needed to dissolve the amount of residue obtained) and washed twice with water. The layers are separated, and the product is purified by column chromatography on silica gel and eluted with 100% ethyl acetate to remove any non-polar impurities and then with 100% isopropyl alcohol to give the pure product. The solvents are removed in vacuo to afford the desired product. Typical TLC conditions are 15:85:0.1 methanol/chloroform/acetic acid. Typical yields range from 40% to 44% of the desired protected compound.

Step 2—Reductive Amination (optional): Reductive amination may be accomplished in a suitable manner. For reductive amination of aldehydes and ketones with sodium triacetoxyborohydride, see generally, Abdel-Magid et al., *J. Org. Chem.*, 1996, 61:3849. Two alternate reductive-aminations procedures are described below.

Step 2(A): 3,5,5,8,8-Pentamethyl-5,6,7,8-tetrahydro-2-naphth-aldehyde (1.00 mmol equiv.) and 1-N,N'-diBoc)-guanidinomethyl-linked-amine (1.00 mmol equiv.) are dissolved in methanol (0.09M). Then, 1% glacial acetic acid in methanol solution (10% of the volume of methanol used) is added followed by NaCNBH$_3$ (1.00 mmol equiv.), and the reaction contents are stirred overnight. The reaction is assayed by TLC to reveal three components (aldehyde, desired product, and starting guanidine derivative). The reaction is terminated by adding water (50% of the volume of methanol used), extracted with dichloromethane (10 times the volume of methanol used), and washed with saturated sodium bicarbonate. The organic layer is dried over magnesium sulfate, filtered, and concentrated. The product is purified by column chromatography on silica gel and eluted with an appropriate elution solvent (e.g., 3:1 ethyl acetate in hexanes to remove the unreacted aldehyde, followed by elution with 1:1 ethyl acetate in hexanes), obtaining the desired reductive amination product. In some cases, warming to reflux for 2 hours will facilitate the imine formation reaction. See also, Abdel-Magid et al., *J. Org. Chem.*, 1996, 61:3849, which describes the reductive amination of aldehydes and ketones with sodium triacetoxyborohydride.

Step 2(B): 3,5,5,8,8-Pentamethyl-5,6,7,8-tetrahydro-2-naphth-aldehyde (1.00 mmol equiv.) and 1-(N,N'-diBoc)-guanidinomethyl-linked-amine (1.00 mmol equiv.) are dissolved in methanol (0.09M). Then, NaBH$_4$ (1.00 mmol equiv.) is added (in ethanol via the additional small-scale procedures given below, or carefully as a solid) and the reaction contents are stirred overnight. The reaction is assayed by TLC to reveal three components (aldehyde, desired product and starting guanidine derivative). The reaction is terminated by the addition of water (50% of the volume of methanol used), extracted with dichloromethane (10 times the volume of methanol used), and washed with saturated sodium bicarbonate. The organic layer is dried over magnesium sulfate, filtered, and concentrated. The product is purified by column chromatography on silica gel and eluted with an appropriate elution solvent (as can be readily determined by the skilled artisan or, for example, with 3:1 ethyl acetate in hexanes to remove the unreacted aldehyde followed by elution with 1:1 ethyl acetate in hexanes) to obtain the desired reductive-amination product. In some cases, warming to reflux for 2 hours should facilitate the imine-formation reaction.

Step 3— Acylation: The products from the reductive amination (1.00 mmol equiv.) are dissolved in dichloromethane (~0.2 to 0.05M, depending on solubilities of the substrates), followed by the addition of triethylamine (2.00 mmol equiv.) and 2-furoyl chloride reagent 8 (1.00 mmol equiv.). The reaction contents are stirred overnight at room temperature (RT). The reaction mixture is diluted with dichloromethane (5 times the amount of dichloromethane used) and washed with saturated sodium bicarbonate. The organic layer is dried over magnesium sulfate and filtered. The product is purified by column chromatography on silica gel and eluted with an appropriate elution solvent (e.g., 3:1 hexanes:ethyl acetate). The solvents are removed in vacuo to yield the acylated product.

Step 4— Basic Group Deprotection: The product from the acylation step (1.00 mmol equiv.) is dissolved in a solution of 25–50% TFA in dichloromethane (0.02M), and the reaction contents are stirred at room temperature (15–20 minutes; solution becomes slight reddish-orange). The reaction contents are stirred for an additional 1 hour and 20 minutes or until the BOC deprotection is complete. The reaction is terminated by concentration in vacuo, followed by the addition of water/acetonitrile (0.006M) and lyophilization overnight. The final compound is purified by high-performance liquid chromatography (HPLC) methodology. The solvents are removed in vacuo (yields range from 30% to 50%) to give the product.

An alternate procedure for removing of N,N'-bis-BOC guanidines using tin tetrachloride, which can give the corresponding guanidinium chloride salts, is described in Miel et al., *Tetrahedron Letters*, 1997, 38:7865–7866.

Compound 9 may be prepared according to the steps shown above with the exclusion of step #2, as shown in the following scheme:

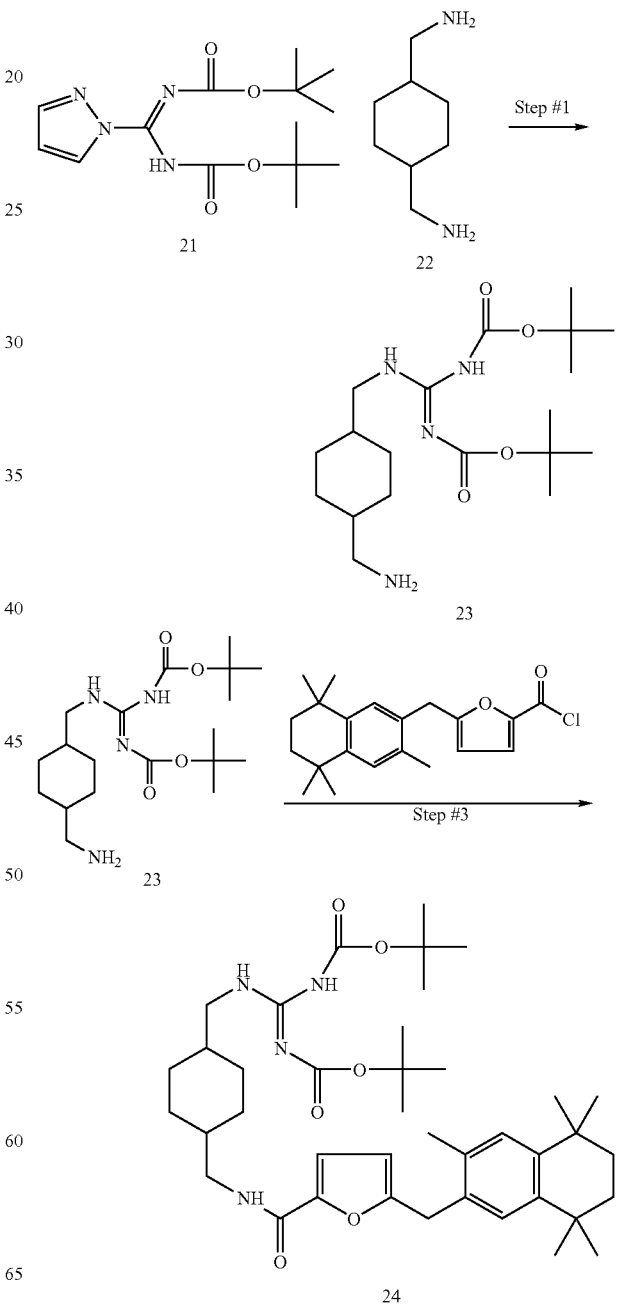

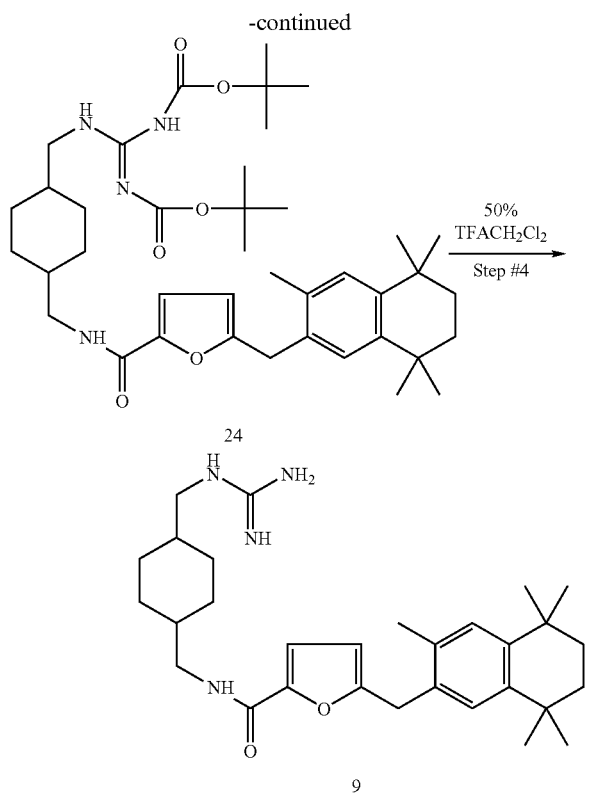

Preparation of Reagents: Reagents useful for synthesizing compounds may be obtained or prepared according to techniques known in the art. For example, the preparation of free amines from common salt forms and stock reagent solutions can be useful for small-scale reactions. See also Abdel-Magid et al., "Reductive amination of aldehydes and ketones with sodium triacetoxyborohydride," *J. Org. Chem.*, 1996, 61:3849.

Methanolic solutions of the free bases can be prepared from hydrochloride, dihydrochloride, hydrobromide, or other salts when the free base is soluble in methanol. In this procedure, once the sodium methoxide is added, care should be taken to prevent exposure to air, since amine free bases, particularly primary amines, absorb carbon dioxide from the air to form salts. A 10-mL quantity of a 0.1M solution of a free base in methanol may be prepared as follows. Weigh 1.0 mmol of a monohydrochloride salt into a tared Erlenmeyer flask containing a stirring bar, and add 7 mL of methanol. To the stirred slurry, add 229 mL (1.0 mmol, 1 equiv.) of sodium methoxide in methanol (25 wt %, 4.37M), stopper the flask, and stir the mixture vigorously for 2 hours. The slurry will sometimes change in appearance as a finer, milky precipitate of sodium chloride is formed. Filter the slurry through a 15-mL medium fritted glass funnel, wash the filter case with 1–2 mL methanol, transfer the filtrate to a 20-mL vial, and dilute to 10 mL with methanol. The theoretical yield of sodium chloride is nearly 59 mg, but the recovery is usually not quantitative, owing to a slight solubility in methanol. For a dihydrochloride salt, a second equivalent of sodium methoxide is required (458 mL).

A 0.5M solution of sodium borohydride in ethanol may be prepared as follows. Sodium borohydride (520 mg, 13.8 mmol) is stirred in pure (non-denatured) anhydrous ethanol (25 mL) for ~2–3 minutes. The suspension is filtered through a medium fritted glass funnel to remove a small amount of undissolved solid (typically about 5% of the total mass of borohydride, or 25 mg). The filtrate should appears as a colorless solution that evolves only a little hydrogen. This solution should be used immediately, as it decomposes significantly over a period of a few hours, resulting in the formation of a gelatinous precipitate. Sodium borohydride is hygroscopic, so avoid exposure to air by making the solution at once after weighing the solid. Sodium borohydride has a solubility of about 4% in ethanol at room temperature. This corresponds to a little over 0.8M. However, sometimes a small percentage of the solid remains undissolved regardless of the concentration being prepared, even after stirring for >5 minutes.

To perform small-scale synthesis of compounds of the Formula I, the reactions described below may be performed to prepare various reactants useful in the reaction scheme described above. As with the rest of the specification, all temperatures in the following description are in degrees Celsius and all parts and percentages are by weight, unless indicated otherwise.

Various starting materials and other reagents may be purchased from commercial suppliers, such as Aldrich Chemical Company or Lancaster Synthesis Ltd., and used without further purification, unless otherwise indicated. Tetrahydrofuran (THF) and N,N-dimethylformamide (DMF) are purchased from Aldrich in SureSeal® bottles and used as received. All solvents are purified by using standard methods in the art, unless otherwise indicated.

The reactions set forth below are performed under a positive pressure of nitrogen or with a drying tube, at ambient temperature (unless otherwise stated), in anhydrous solvents, and the reaction flasks are fitted with rubber septa for the introduction of substrates and reagents via syringe. Glassware is oven-dried and/or heat-dried. Analytical thin-layer chromatography is performed on glass-backed silica gel 60° F. 254 plates (Analtech (0.25 mm)) and eluted with the appropriate solvent ratios (v/v). The reactions are assayed by TLC and terminated as judged by the so consumption of starting material.

The tip plates are visualized with a p-anisaldehyde spray reagent or phosphomolybdic acid reagent (Aldrich Chemical, 20 wt % in ethanol) and activated with heat. Work-ups are typically done by doubling the reaction volume with the reaction solvent or extraction solvent and then washing with the indicated aqueous solutions using 25% by volume of the extraction volume (unless otherwise indicated). Product solutions are dried over anhydrous $Na_2SO_4$ prior to filtration, and evaporation of the solvents is under reduced pressure on a rotary evaporator and noted as solvents removed in vacuo. Flash column chromatography (Still et al., *A.J. Org. Chem.*, 1978, 43;2923) is conducted using Baker-grade flash silica gel (47–61 mm) and a silica gel:crude material ratio of about 20:1 to 50:1, unless otherwise stated. Hydrogenolysis is done at the pressure indicated or at ambient pressure.

$^1$H-NMR spectra are recorded on a Bruker instrument operating at 300 MHz, and $^{13}$C-NMR spectra are recorded operating at 75 MHz. NM spectra are obtained as $CDCl_3$ solutions (reported in ppm), using chloroform as the reference standard (7.25 ppm and 77.00 ppm) or $CD_3OD$ (3.4 and 4.8 ppm and 49.3 ppm), or an internal tetramethylsilane standard (0.00 ppm) when appropriate. Other NMR solvents are used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra are recorded on a Perkin-Elmer FT-IR Spectrometer as neat oils, as KBr pellets, or as CDCl$_3$ solutions, and when reported are in wave numbers (cm$^{-1}$). The mass spectra are obtained using LSIMS or electrospray. All melting points are uncorrected.

Preparation of the Building Block 1-H-pyrazole-1-carboxamidine:

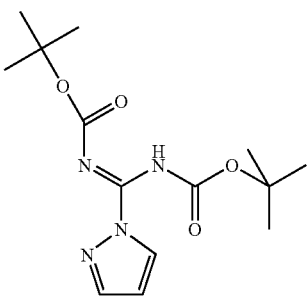

1-H-pyrazole-1-carboxamidine is prepared according to Bernatowicz et al., *J. Org. Chem.*, 1992, 57:2497–2502 (and references therein), and protected with di-tert-butyldicarbonate to give 1-H-pyrazole-1-(N,N-bis(tert-butoxycarbonyl)carboxamidine) according to Drake et al., *Synth.*, 1994, 579–582.

Preparation of 1-(N,N'-diBoc)-guanidinomethyl-4-aminomethylcyclohexane:

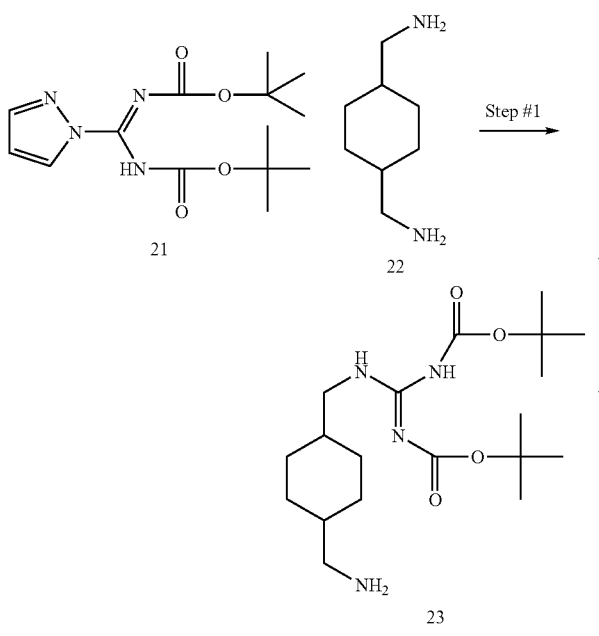

To a solution of 1,4-bis-aminomethyl-cyclohexane 22 (20 g, 0.14 mol) in THF (200 mL) is added a solution of 1-H-pyrazole-1-(N,N-bis(tert-butoxycarbonyl) carboxamidine) 21 (22.0 g, 0.07 mol) in THF (100 mL). (Note that 1-H-pyrazole-1-(N,N-bis(tert-butoxycarbonyl)carboxamidine) does not need to be dissolved in THF; rather it may be added neat as a solid to the process.) The solution is stirred at room temperature for 3 hours. The solvent is removed under reduced pressure to give a syrupy residue, which is taken up in ethyl acetate (500 mL) and washed with water until neutral pH. The organic layer is washed with brine, dried over MgSO$_4$, and concentrated. The product is purified by column chromatography on silica gel and eluted with 5% MeOH in dichloromethane. The solvents are removed in vacuo to afford 11.6 g (43% yield) of 1-(N,N'-diBoc)-guanidinomethyl-4-aminomethyl cyclohexane (Compound 23). $^1$H NMR (CDCl$_3$) δ 11.5 (br s, 1H), 8.35 (br s, 1H), 3.26 (dt, 2H), 2.52 (dd, 2H), 1.82–0.97 (m, 28H, with singlet at 1.5).

An alternate preparation of 1-(N,N'-diBoc)-guanidinomethyl-3-aminomethylcyclohexane is as follows. To a solution of cis/trans 1,4-bis-aminomethyl-cyclohexane (9.0 g, 63.3 mmol) in THF (903 mL, 0.07M) is added portionwise as a solid (over a 10 minute period) 1-H-Pyrazole-1-(N,N-bis(tert-butoxycarbonyl)carboxamidine) (19.6 g, 63.3 mmol). The solution is stirred at room temperature for 0.5 hour. The solvent is removed under reduced pressure to give a syrupy residue, which is taken up in ethyl acetate (500 mL) and washed twice with water. The layers are separated and the product is purified by column chromatography on silica gel and eluted with 100% ethyl acetate to remove any non-polar impurities, followed by elution with 100% isopropyl alcohol, to give the pure product. The solvents are removed in vacuo to afford 10.2 g (42% yield) of 1-(N,N'-diBoc)-guanidinomethyl-4-aminomethylcyclohexane. $^1$H NMR (CDCl$_3$) δ 11.5 (br s, 1H), 8.35 (br s, 1H), 3.26 (dt, 2H), 2.52 (dd, 2H), 1.82–0.97 (m, 28H, with singlet at 1.5).

Reductive Amination.

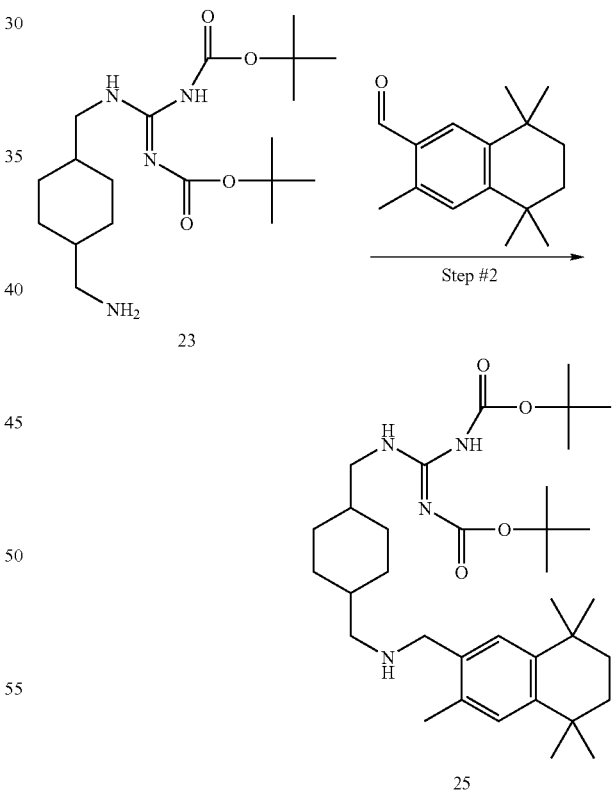

3,5,5,8,8-Pentamethyl-5,6,7,8-tetrahydro-2-naphthaldehyde (0.2021 g, 0.88 mmol) and 1-(N,N'-diBoc)-guanidinomethyl-4-aminomethylcyclohexane (Compound 23, 0.337 g, 0.88 mmol) are dissolved in methanol (10 mL). Then, 1% glacial acetic acid in methanol (100 μL) solution is added followed by NaCNBH$_3$ (55.4 mg, 0.88 mmol, 1.0 equiv.), and the reaction contents are stirred overnight. The reaction is assayed by TLC to reveal three components (aldehyde, desired product, and starting guanidine derivative). The reaction is terminated by the addition of water (~5 mL), extracted with dichloromethane (~100 mL), and washed with saturated sodium bicarbonate. The organic layer is dried over magnesium sulfate, filtered, concentrated, and subjected to column chromatography eluting with 3:1 ethyl acetate in hexanes to remove the unreacted aldehyde, followed by eluting with 1:1 ethyl acetate in hexanes, yielding the desired product (Compound 25, cyclohexyl, cis/trans mixture). The solvents are removed in vacuo (typical general yields range from 50 to 80%).

Preparation of the Acylated Derivative Followed by Deprotection of Guanidine:

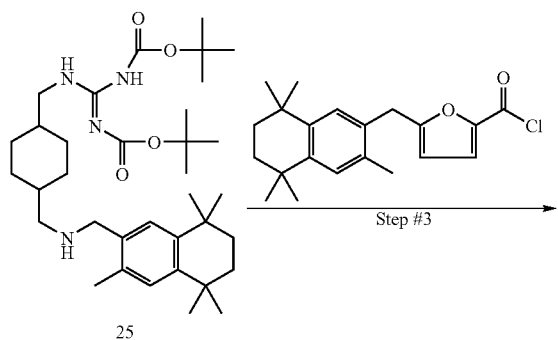

25

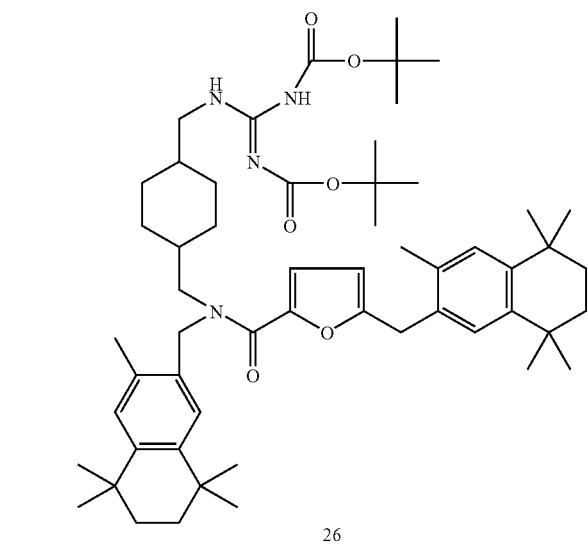

26

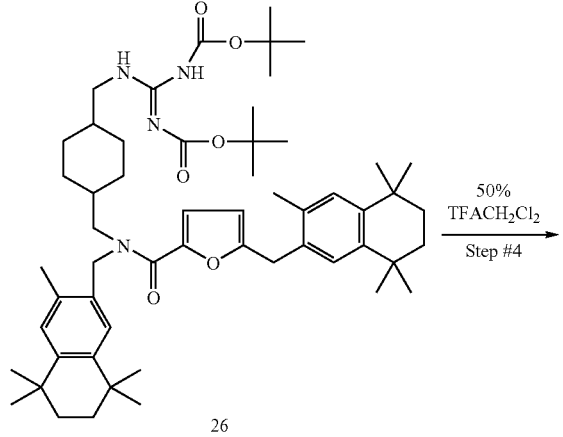

26

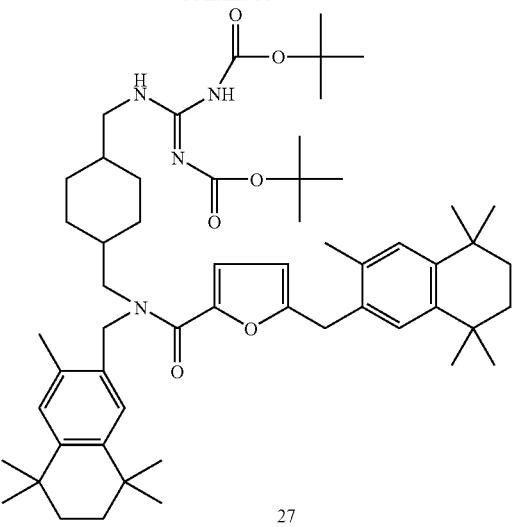

27

The product from the reductive amination 25 (1.0 equiv.) is dissolved in dichloromethane (10–15 mL), followed by the addition of triethylamine (2 equiv.), and 2-furoyl chloride reagent (1.0 equiv.). The reaction contents are stirred overnight at room temperature. The reaction is diluted with dichloromethane (50 mL) and washed with saturated sodium bicarbonate. The organic layer is dried over magnesium sulfate, filtered, and purified by column chromatography and eluted using 3:1 hexanes in ethyl acetate. The solvents are removed in vacuo to give Compound 26.

The product from the acylation reaction 26 (1.0 equiv.) is dissolved in a solution of 50% TFA in dichloromethane (20–25 mL), and the reaction contents are stirred at room temperature (15–20 minutes; solution becomes slight reddish-orange). The reaction contents are stirred for an additional 1 hour and 20 minutes until the deprotection is complete. The reaction is terminated by concentration in vacuo, followed by the addition of water/acetonitrile (~50 mL) and lyophilization overnight. The final compound is purified by HPLC methods. The solvents are removed in vacuo to give Compound 27.

The following discussion relates to the preparation of exemplary Compounds (e)–(k). Compounds (e)–(k) may be used as described above to produce the corresponding deprotected (free guanidinyl) compounds, through hydrolysis under acid conditions.

Preparation of 1-(N,N'-diBoc)-guanidinomethyl-3-aminomethylcyclohexane:

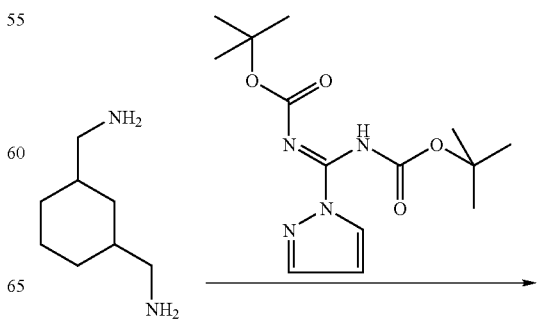

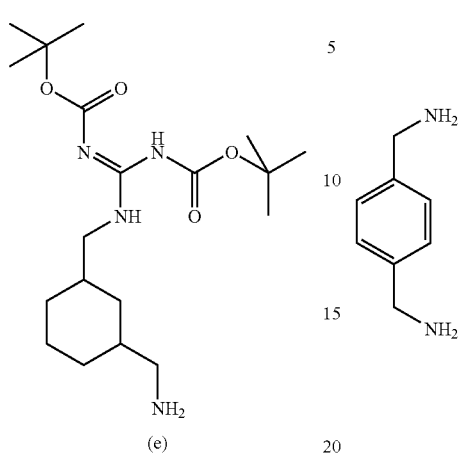

(e)

To a solution of cis/trans-1,3-bis-aminomethylcyclohexane (7.5 g, 52.8 mmol) in THF (30 mL) is added a solution of 1,3-bis(tert-butoxycarbonyl)$_2$-methyl-2-thiopseudourea (7.65 g, 26.3 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 2.2 g (22% yield) of 1-(N,N'-diBoc)-guanidinomethyl-3-aminomethylcyclohexane (Compound (e)). $^1$H NMR (CDCl$_3$) δ 11.53 (br s, 1H), 8.40 (br s, 1H), 3.28–3.30 (m, 2H), 2.54–2.61 (m, 2H), 1.81 (br s, 2H), 1.27–1.58 (m, 26H), 0.89 (m, 1H), 0.65 (m, 1H).

Alternatively, Compound (e) may be prepared as follows. To a solution of cis/trans 1,3-bis-aminomethylcyclohexane (10.0 g, 70.3 mmol) in THF (1000 mL, 0.07M) is added portionwise as a solid (over a 10-minute period) 1-H-Pyrazole-1-(N,N-bis(tert-butoxycarbonyl)carboxamidine) (21.8 g, 70.3 mmol). The solution is stirred at room temperature for 0.5 hour. The solvent is removed under reduced pressure to give a syrupy residue, which is taken up in ethyl acetate (500 mL) and washed twice with water. The layers are separated, and the product is purified by column chromatography on silica gel and eluted with 100% ethyl acetate to remove any non-polar impurities, followed by elution with 100% isopropyl alcohol to give the pure product. The solvents are removed in vacuo to afford 11.4 g (41% yield) of 1-(N,N'-diBoc)-guanidinomethyl-3-aminomethylcyclohexane. $^1$H NMR (CDCl$_3$) δ 11.53 (br s, 1H), 8.40 (br s, 1H), 3.28–3.30 (m, 2H), 2.54–2.61 (m, 2H), 1.81 (br s, 2H), 1.27–1.58 (m, 26H), 0.89 (m, 1H), 0.65 (m, 1H).

Preparation of 1-(N,N'-diBoc)-guanidinomethyl-4-aminomethylbenzene:

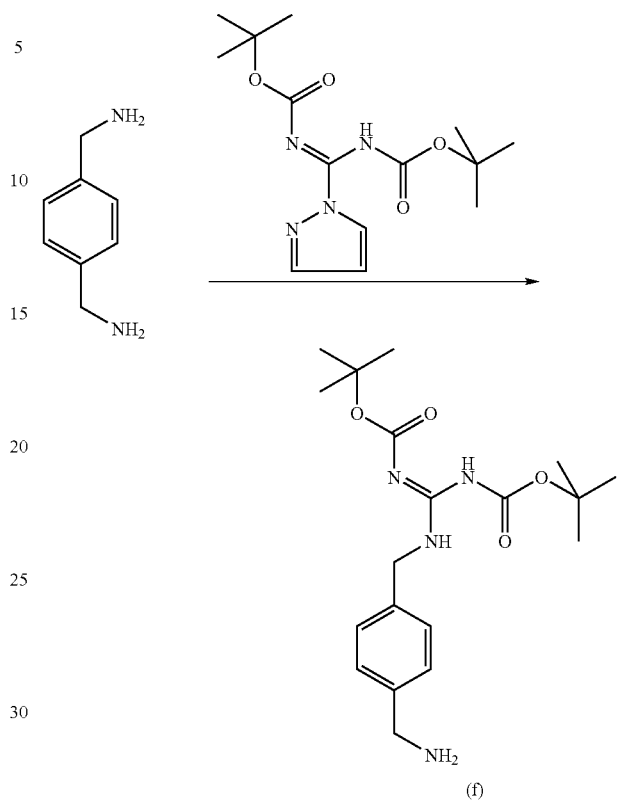

(f)

To a solution of p-xylylenediamine (6.44 g, 47.4 mmol) in THF (30 mL) is added a solution of 1,3-bis(tert-butoxycarbonyl)-2-methyl-2-thiopseudourea (6.63 g, 22.9 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 8.0 g (92% yield) of 1-(N,N'-diBoc)-guanidinomethyl-4-aminomethyl benzene (Compound (f)). $^1$H NMR (CDCl$_3$) δ 11.54 (br s, 1H), 8.56 (br s, 1H), 7.29 (s, 4H), 4.60 (d, 2H), 3.86 (s, 2H), 1.64 (br s, 2H), 1.52 (s, 9H), 1.48 (s, 9H).

Preparation of 1-(N,N'-diBoc)-guanidinomethyl-3-aminomethylbenzene:

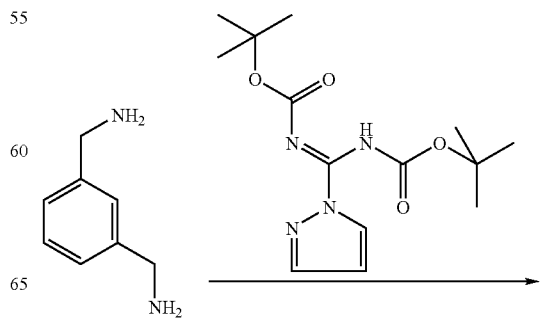

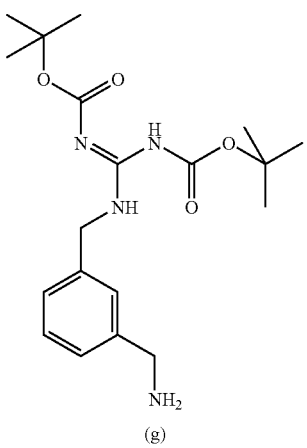

To a solution of m-xylylenediamine (7.14 g, 52.5 mmol) in THF (30 mL) is added a solution of 1,3-bis(tert-butoxycarbonyl)-2-methyl-2-thiopseudourea (7.57 g, 26.1 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 7.9 g (80% yield) of 1-(N,N'-diBoc)-guanidinomethyl-3-aminomethylbenzene (Compound (g)). $^1$H NMR(CDCl$_3$) δ 11.54 (br s, 1H), 8.58 (br s, 1H), 7.19–7.34 (m, 4H), 4.62 (d, 2H), 3.86 (s, 2H), 1.83 (br s, 2H), 1.52 (s, 9H), 1.48 (s, 9H).

Preparation of 1-(N,N'-diBoc)-guanidine-4-aminobutane:

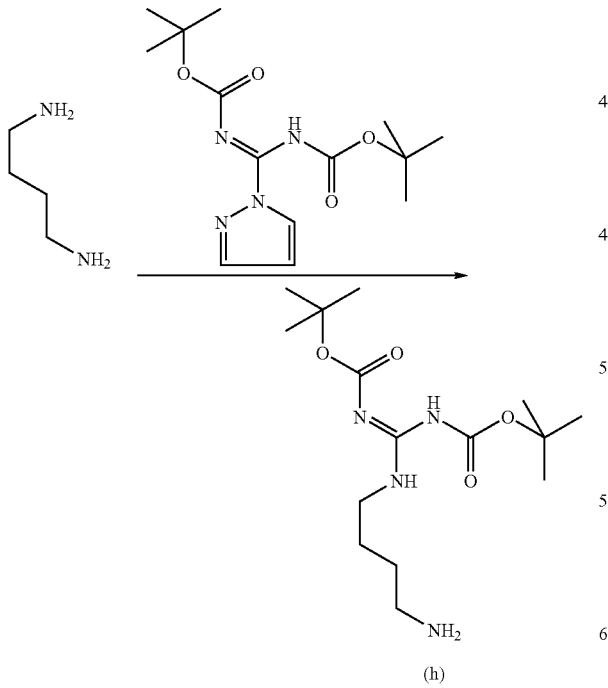

To a solution of 1,4-diaminobutane (4.15 g, 47.1 mmol) in THF (30 mL) is added a solution of 1,3-bis(tert-butoxycarbonyl)-2-methyl-2-thiopseudourea (6.83 g, 23.6 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 3.0 g (40% yield) of 1-(N,N'-diBoc)-guanidino-4-aminobutane (Compound (h)). $^1$H NMR (CDCl$_3$) δ 11.49 (br s, 1H), 8.35 (br s, 1H), 3.42–3.47 (m, 2H), 2.72–2.76 (t, 2H), 0.86–1.65 (m, 24H).

An alternate procedure for preparing Compound (h) is as follows. To a solution of 1,4-diaminobutane (6.0 g, 68.1 mmol) in TH (972 mL, 0.07M) is added portionwise as a solid (over a 10-minute period) 1-H-pyrazole-1-(N,N-bis(tert-butoxycarbonyl)carboxamidine) (21.5 g, 68.1 mmol). The solution is stirred at room temperature for 0.5 hour. The solvent is removed under reduced pressure to give a syrupy residue, which is taken up in ethyl acetate (500 mL) and washed twice with water. The layers are separated and the product is purified by column chromatography on silica gel and eluted with 100% ethyl acetate to remove any non-polar impurities and then with 100% isopropyl alcohol to give the pure product. The solvents are removed in vacuo to afford 10.0 g (44% yield) of 1-(N,N'-diBoc)-guanidino-4-aminobutane. $^1$H NMR (CDCl$_3$) δ 11.49 (br s, 1H), 8.35 (br s, 1H), 3.42–3.47 (m, 2H), 2.72–2.76 (t, 2H), 0.86–1.65 (m, 24H).

Preparation of 1-N,N-dimethylaminomethyl-4-aminomethylbenzene:

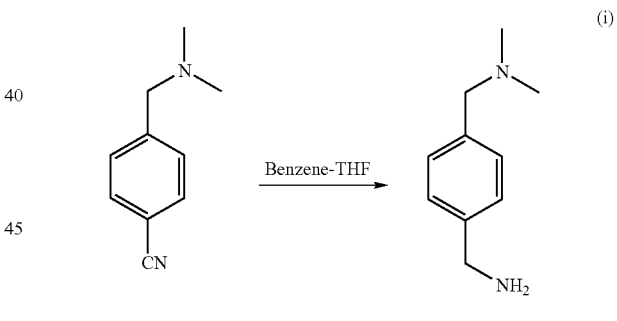

To a solution of 1-N,N-dimethyl aminomethyl-4-carbonitrile benzene (4.8 g, 30 mmol) in THF is added a solution of 1 M borane tetrahydrofuran complex (90 mL). The mixture is heated at reflux temperature for 16 hours under nitrogen. After cooling to room temperature, a 1M solution of HCl in methanol (100 mL) is added. The reaction mixture is heated at reflux for 3 hours. The product, which precipitates, is collected by filtration, washed with diethyl ether, and dried in vacuo to give 5.9 g (83% yield) of the product as the hydrochloride salt (Compound (i)): $^1$H NMR (DMSO-d) δ 8.65 (br s, 3H), 7.55 (dd, 4H), 4.25 (s, 2H), 3.98 (s, 2H), 2.62 (s, 6H).

Preparation of 1-(N,N'-diBoc)-guanidinomethyl-2-aminomethylbenzene:

Preparation of 1-(N,N'-diBoc)-guanidinomethyl-2-aminomethylcyclohexane:

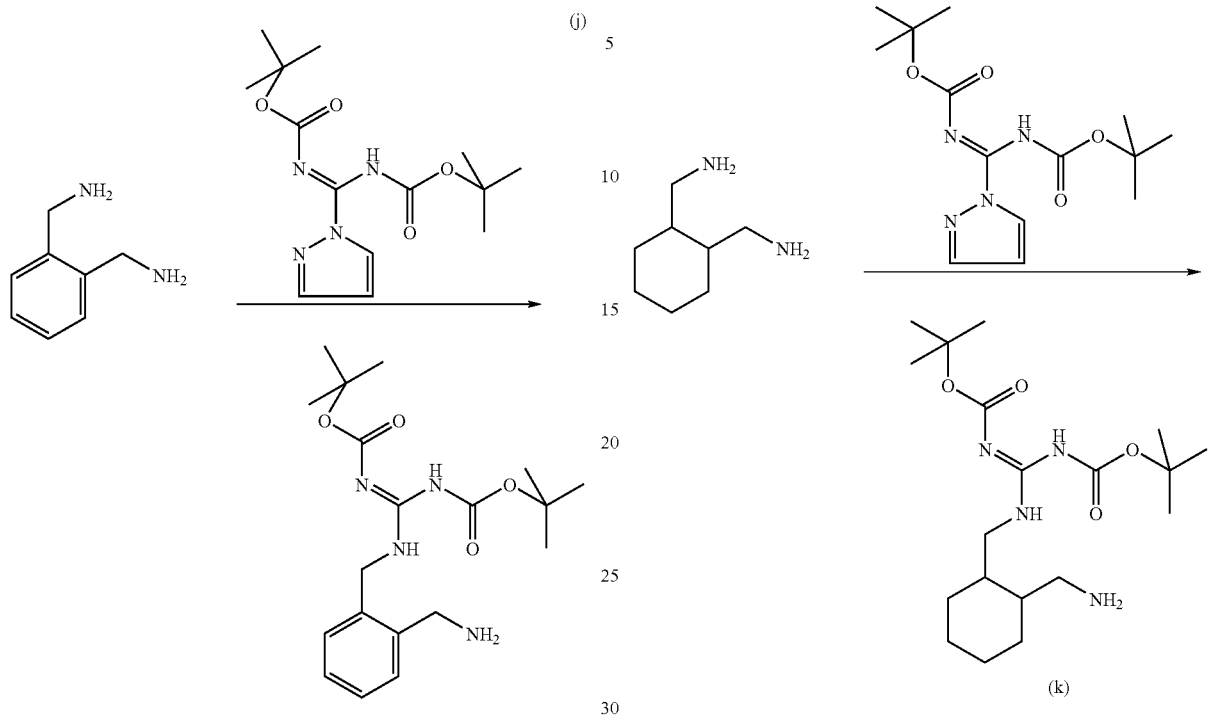

To a solution of o-xylylenediamine (7.14 g, 52.5 mmol) in THF (30 mL) is added a solution of 1,3-bis(tert-butoxycarbonyl)-2-methyl-2-thiopseudourea (7.57 g, 26.1 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 1-(N,N'-diBoc)-guanidinomethyl-3-aminomethyl benzene (Compound (j)).

Alternatively, Compound (j) may be prepared in a manner analogous to the alternative preparation described above for Compound (e).

To a solution of cis/trans-1,2-bis-aminomethylcyclohexane (7.5 g, 52.8 mmol) in THF (30 mL) is added a solution of 1,3-bis(tert-butoxycarbonyl)-2-methyl-2-thiopseudourea (7.65 g, 26.3 mmol) in THF (40 mL) within 0.5 hour. The solution is stirred at room temperature for 5 hours. The solvent is removed under reduced pressure, and the product is purified by column chromatography on silica gel using a mixture of methylene chloride/methanol as the eluant, to afford 1-(N,N'-diBoc)-guanidinomethyl-2-aminomethylcyclohexane (Compound (k)).

Alternatively, Compound (k) may be prepared in a manner analogous to the alternative preparation described above for Compound (e).

D. Pyrimidine Compounds

Pyrimidines can be utilized according to the following procedures:

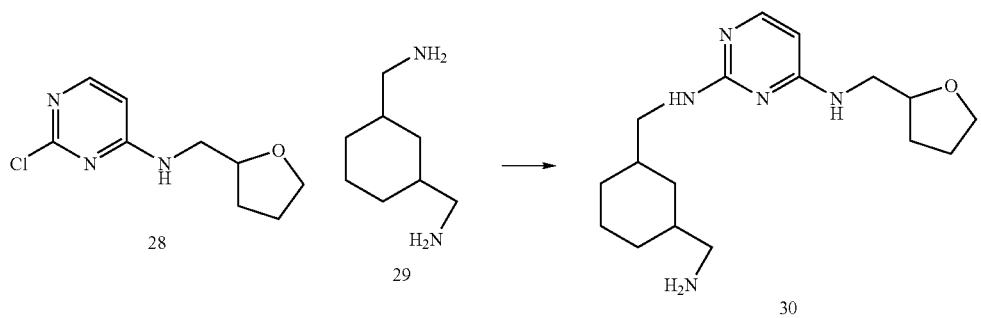

-continued

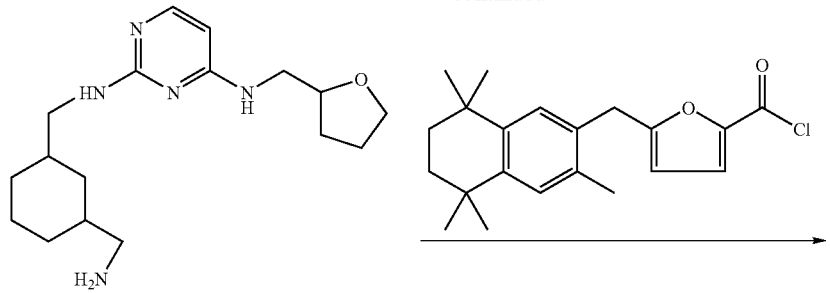

31

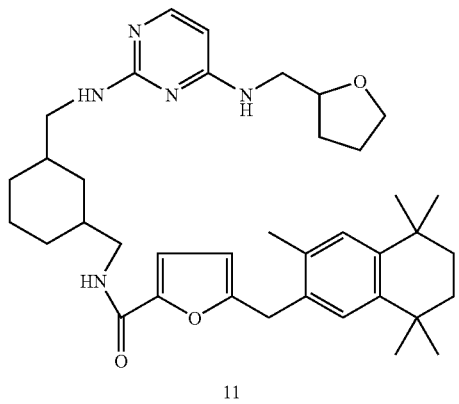

11

30

A general procedure for the preparation of pyrimidine containing compounds is as follows. To a solution of 1.3 diamine 29 in THF is added 28 and the contents refluxed for 12 hours. The solvents are removed in vacuo and the desired adduct purified by column chromatography. Pure 31 is acylated according to the general procedure given above to give 11.

As skilled artisans will appreciate, a variety of compounds according to the invention may be prepared based on the above teachings. The chemical reactions described above have general applicability to the preparation of the GnRH agents of the invention. Thus, other GnRH agents may be similarly prepared by suitable modification as will be readily appreciated by those skilled in the art, e.g., by protection of interfering groups, by adapting for use with other conventional reagents, and/or by routine modifications of reaction conditions.

In Vitro Pharmacology Radioligand Binding.

Cell membranes prepared from human embryonic kidney 293 cells stably transfected with cDNA for the human GnRH receptor were suspended in binding assay buffer containing: 50 mM HEPES, 1 mM EDTA, 2.5 mM $MgCl_2$, and 0.1% bovine serum albumin. Membranes (5–50 µg total protein per well containing approximately 10–100 fmol of GnRH receptor) were incubated in duplicate in 96-well plates in 200 µl total volume with $^{125}$I-GnRH-A (approximately 0.05 nM) and test compounds for one hour at room temperature. All compounds were diluted in 1% DMSO (final assay concentration) in binding assay buffer. Nonspecific binding was determined in the presence of 100 nM GnRH. Reactions were terminated by rapid filtration onto 96-well Packard GF/C filters soaked in 0.1% polyethyleneimine. Filters were washed three times with PBS buffer, dried and counted on a Packard Topcount by liquid scintillation counting.

Figure 1:
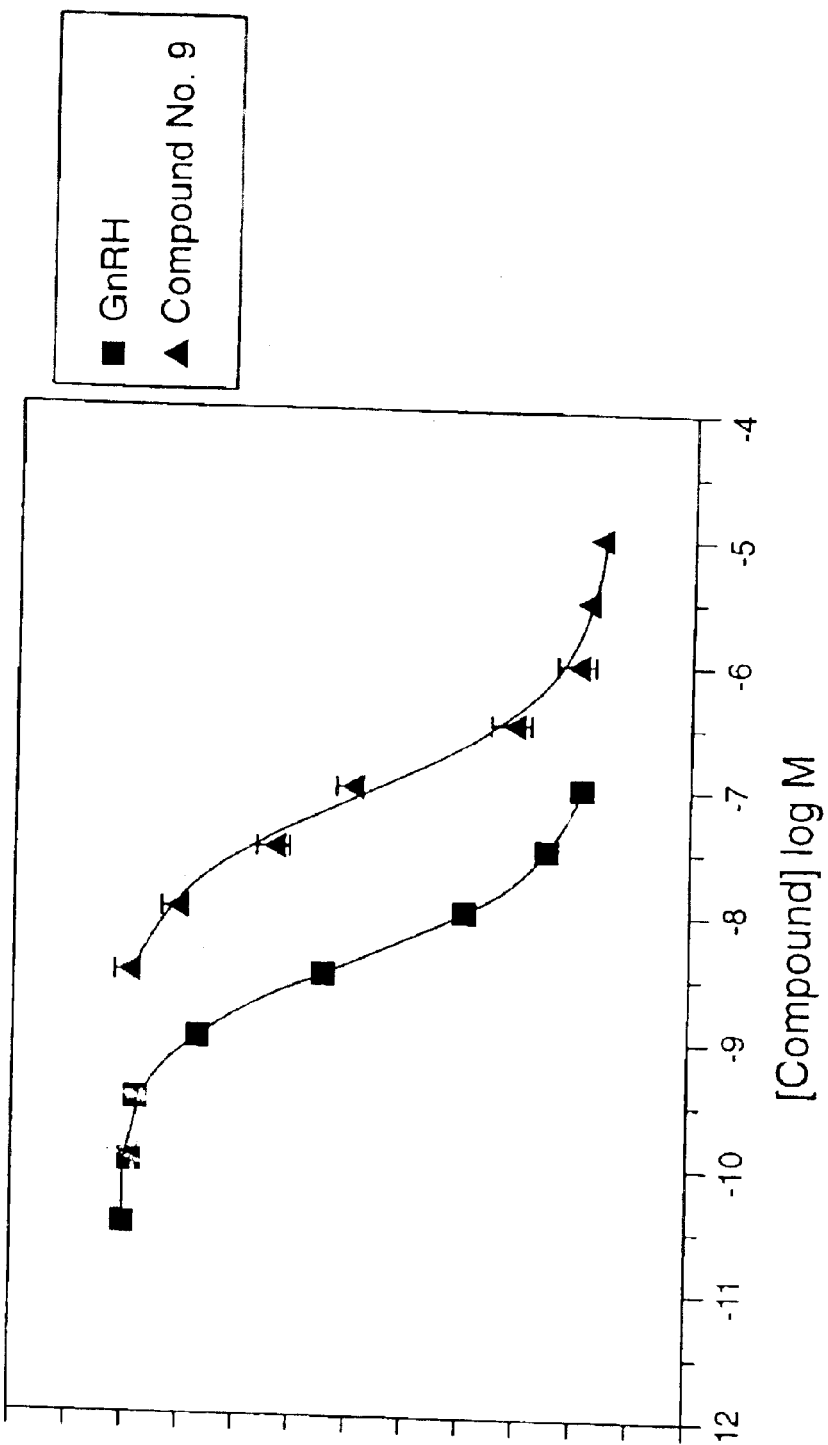

Assay conditions were identical for assessing compound activities at other species. A similar number of GnRH receptors was utilized for each species assay. For rat GnRH receptor-binding, membranes were prepared from rat pituitary and approximately 25–30 µg/well of total membrane protein were utilized. For bovine GnRH receptor binding, membranes were prepared from bovine pituitary and utilized at 40–50 µg/well. For mouse GnRH receptor binding, membranes were prepared from 293 cells stably expressing mouse GnRH receptors and were utilized at approximately 25–30 µg/well. $IC_{50}$ values for control peptides and test compounds were calculated utilizing GraphPad Prism™ software. The result of a radioligand binding experiment is shown in FIG. 1. Table 1 shows mean values from multiple experiments of the affinities of various peptide and non-peptide compounds at GnRH receptors from four species.

FIG. 1. Effects of compounds on $^{125}$I-GnRH-A binding to hGnRH receptors expressed in HEK-293 cells. The ability of GnRH (squares) and 9 (triangles) to displace $^{125}$I-GnRH-A (approximately 0.05 nM) binding to hGnRH receptors was examined. Values shown are from one representative experiment performed in duplicate.

Various compounds of the Formula I were synthesized according to the general reaction scheme generally described above. Crude compounds were tested using the competitive radioligand binding assay described above. Results of the GnRH competitive binding assay are shown in the table (each compound tested at 1 or 10 µM).

TABLE 1

| Compound | Human $IC_{50}$ (nM) | Bovine $IC_{50}$ (nM) | Rat $IC_{50}$ (nM) | Mouse $IC_{50}$ (nM) |
| --- | --- | --- | --- | --- |
| GnRH | 7.2 ± 1.5 | 13 ± 2 | 33 ± 1.9 | 11 ± 2 |
| GnRH-A | 0.34 ± 0.06 | 0.3 ± 0.05 | 0.49 ± 0.1 | 0.22 ± 0.03 |
| Antide | 0.67 ± 0.09 | 0.15 ± 0.02 | 0.19 ± 0.04 | 0.25 ± 0.05 |
| 9 | 220 ± 33 | 3800 ± 220 | 680 ± 120 | 2300 ± 460 |
| 10 | 130 ± 24 | 1500 ± 480 | 390 ± 10 | 1400 ± 440 |

TABLE 1-continued

| Compound | Human IC$_{50}$ (nM) | Bovine IC$_{50}$ (nM) | Rat IC$_{50}$ (nM) | Mouse IC$_{50}$ (nM) |
|---|---|---|---|---|
| 11 | 190 ± 40 | 320 ± 10 | 9.0 ± 0.3 | 50 ± 10 |
| 12 | 230 ± 37 | 10400 ± 3000 | 3080 ± 630 | 7130 ± 1350 |
| 13 | 110 ± 20 | 530 ± 100 | 60 ± 8 | 120 ± 20 |
| 14 | 80 ± 4 | 1050 ± 30 | 60 ± 15 | 290 ± 70 |
| 15 | 100 ± 17 | 1000 ± 240 | 70 ± 16 | 220 ± 50 |
| 16 | 30 ± 6 | 4380 ± 510 | 560 ± 50 | 1290 ± 210 |
| 17 | 80 ± 20 | 670 ± 120 | 30 ± 4 | 80 ± 20 |
| 18 | 55 ± 11 | 460 ± 90 | 40 ± 3 | 115 ± 25 |
| 19 | 50 ± 3 | ND | ND | ND |
| 20 | 8.0 ± 0.9 | ND | ND | ND |

Values are means ± SE of at least three experiments performed in duplicate.
ND = not determined.

Total Inositol Phosphates Measurement.

To assess the activity of the compounds as agonists or antagonists, an assay measuring accumulation of total inositol phosphates was employed. 293 cells containing the hGnRH receptor were plated onto 24-well plates (approximately 200,000 cells/well) using DMEM media. The following day, cells were loaded with [$^3$H]myoinositol (0.5 Ci/ml) for 16–18 hours in inositol-free medium. The medium was aspirated and the cells rinsed with serum-free DMEM. The medium was aspirated and the cells were then treated with test compounds or vehicle for 30 minutes at 37° C. A half-maximal concentration of GnRH (1 nM) or vehicle was then added to the cells and allowed to equilibrate at 37° C. for 45 minutes. The media was replaced with ice-cold 10 mM formic acid, which stopped the reaction and also served to extract cellular lipids. Inositol phosphates were separated by ion-exchange chromatography on Dowex columns, which were washed with 2.5 mL of 10 mM myoinositol and 10 mM formic acid. The columns were then washed with 5 mL of 60 mM sodium formate and mM borax, and total inositol phosphates were eluted with 5 mL 1M ammonium formate, 0.1 M formic acid. The column eluates were added to liquid scintillation vials containing 15 ml of scintillation cocktail and were counted by liquid scintillation counting. The result of a typical experiment is shown in FIG. 2.

FIG. 2. Effects of compounds on GnRH-stimulated total inositol phosphate accumulation in HEK-293 cells expressing the hGnRH receptor. The ability of the peptide antagonist, Antide, and non-peptide compound 9 to block GnRH-stimulated increases in [$^3$H]inositol phosphates was examined. Neither compound alone stimulated an increase in total [$^3$H]inositol phosphates (not shown), but both compounds were able to inhibit the stimulation mediated by a half-maximal concentration of GnRH peptide. GnRH alone dose-dependently increased [$^3$H]inositol phosphate accumulation with an EC$_{50}$ of approximately 0.8 nM. In the experiment shown, the K$_b$ values of Antide and compound 9 were determined by the method of Cheng and Prusoff (*Biochem. Pharmacol.* 22:3099–3108, 1973). Values shown are from one experiment performed in duplicate.

Vivo Pharmacology Animal Efficacy Studies

Experimental Protocol: Male Sprague-Dawley (225–250 g) rats were castrated and allowed 10 days postoperative recovery. Ten days post castration animals were instrumented with indwelling femoral venous and arterial catheters to facilitate remote infusions and blood sampling. On the day of the experiment, animals were allowed to acclimate to the procedure room while residing in their home cage. Basal blood samples were drawn from all animals. Following basal sampling, either vehicle (10% DMSO, 10% cremophor/saline), Antide (1.0 µg) or compound 11 (10 mg/kg) was administered intravenously. Blood samples were drawn 10, 60, 90, 120, 180, 240 minutes after injections. Blood was centrifuged, serum collected and stored in −70° freezer until assayed. Serum samples were analyzed using DSL-4600 ACTIVE LH coated-tube immunoradiometric assay kit from Diagnostic Systems Laboratories, Inc.

Figure 3:
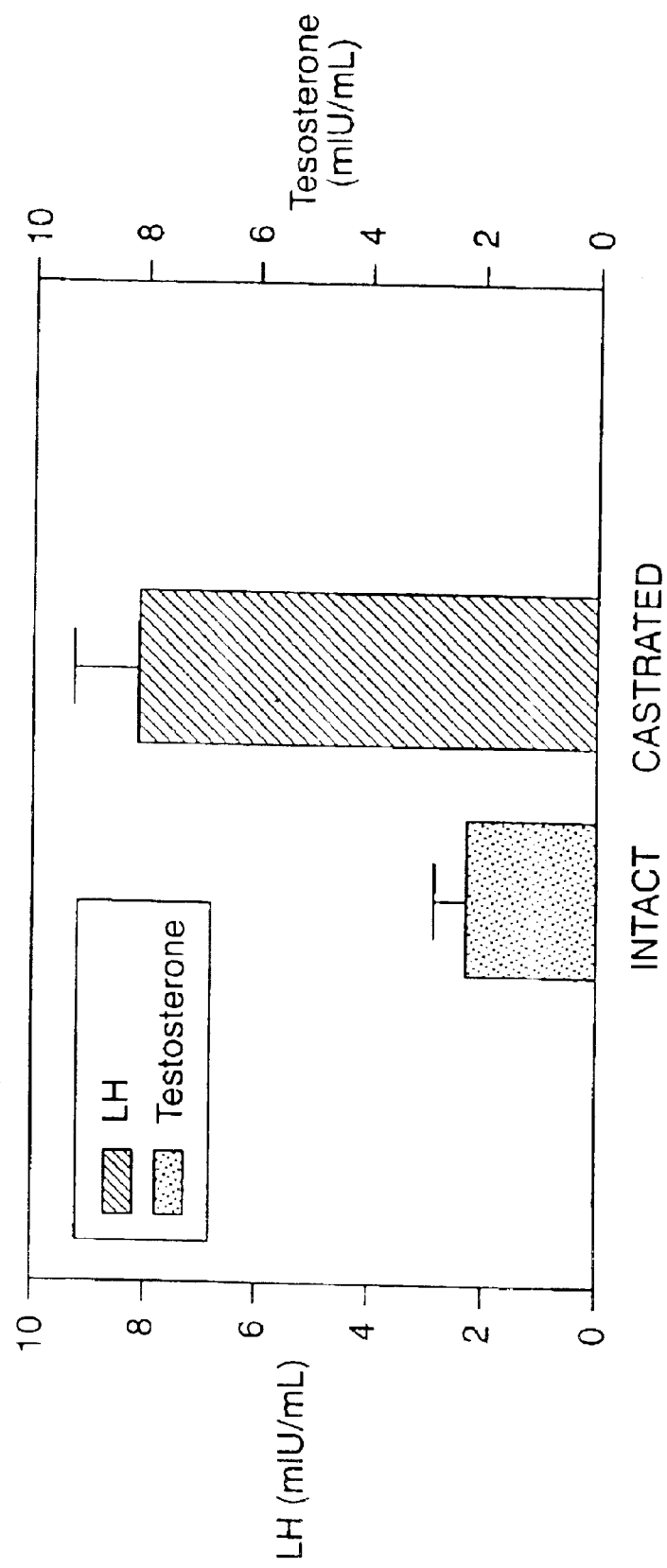
Figure 4A:
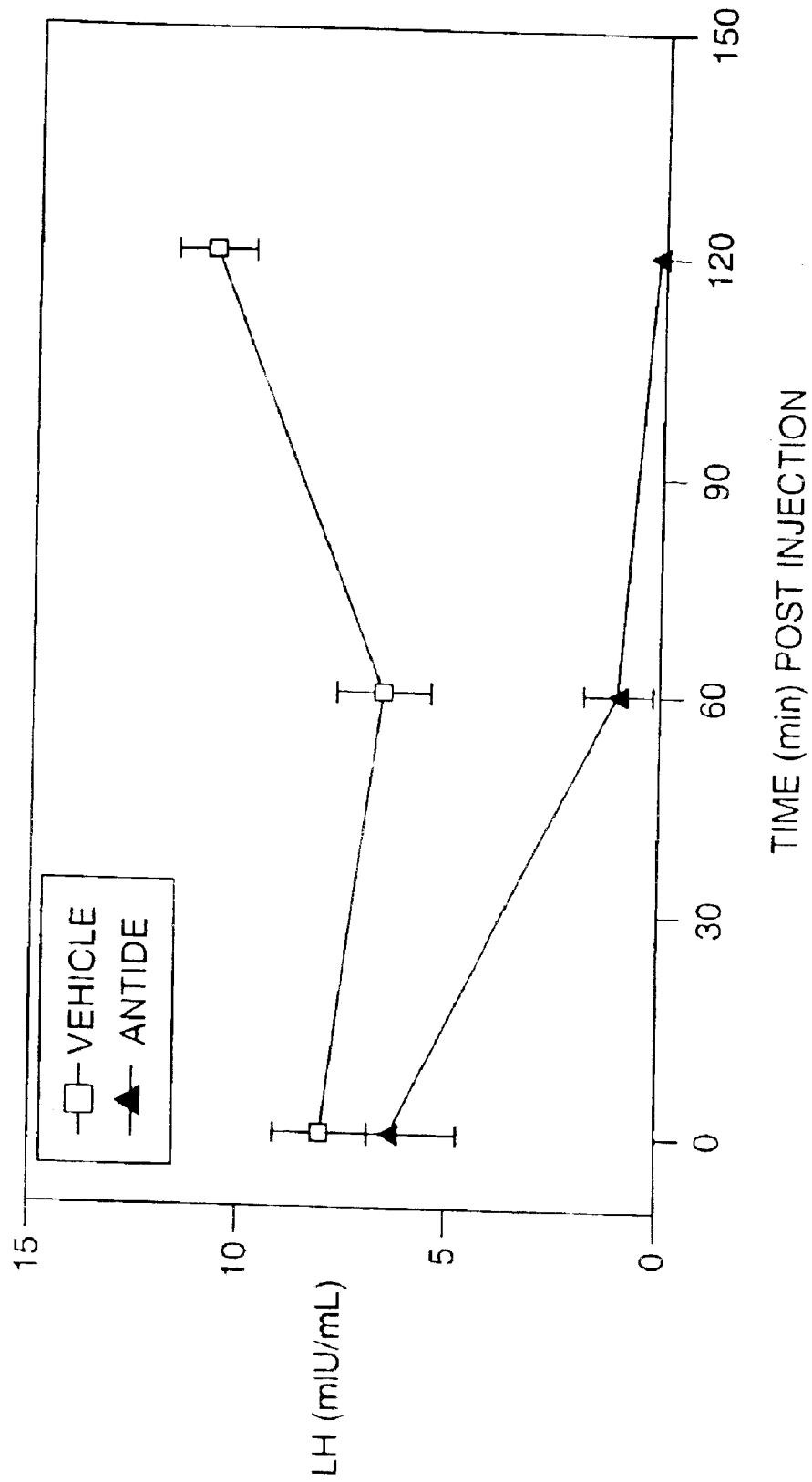
Figure 4B:
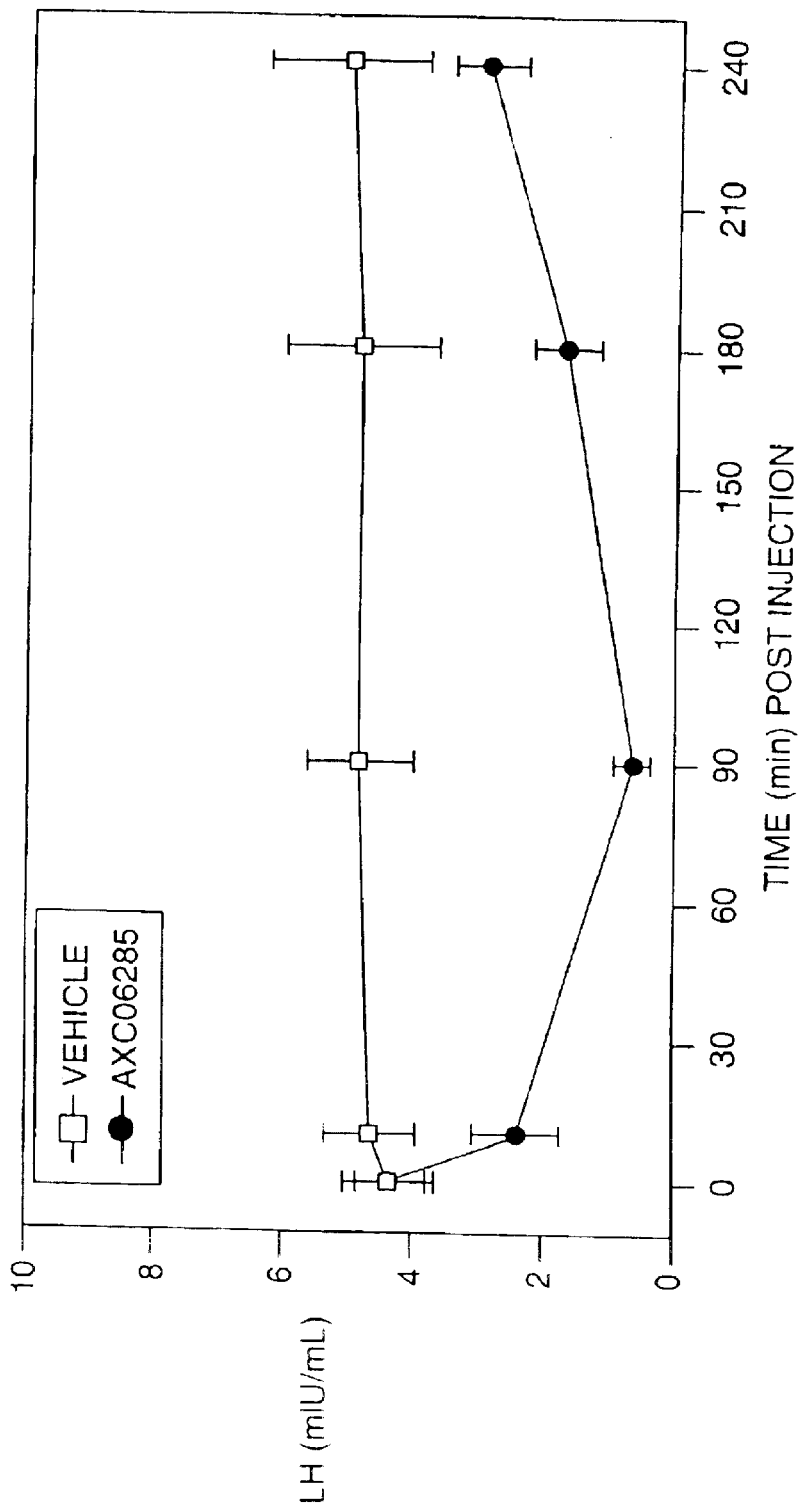

Results and discussion: Removal of the gonads eliminates the negative feedback of testosterone on the hypothalamus, resulting in elevated GnRH and consequently elevated LH. FIG. 3 illustrates the plasma levels of both LH and testosterone in control and castrated rats 10 days after surgery. In these rats, a GnRH antagonist would be expected to reduce GnRH mediated elevations of LH levels. Antide, a peptide GnRH antagonist, reduces LH in the castrated rat model (FIG. 4). Compound 11, a small-molecule GnRH antagonist, also suppresses LH in the castrated rat model (FIG. 4).

Pharmacokinetic Studies

Experimental protocol: Rats were prepared with intravenous catheters inserted in the superior vena cava through the incision in the right external jugular vein and allowed to recover. Drugs were dissolved in a mixture of 10% DMSO, 10% cremaphor, and 80% saline and administered i.v. at a dose of 10 mg/kg. Blood samples were taken at the times indicated, and the compounds were extracted from 0.2 mL of plasma with butyl chloride containing an internal standard. Samples were analyzed by HPLC on a Beta-Basic C18 4×50 mm column using a gradient of 40–80% acetonitrile in 10 mM ammonium phosphate buffer at a flow rate of 1 ml/min. Sample detection was by UV absorbance at 260 nm.

Figure 5:
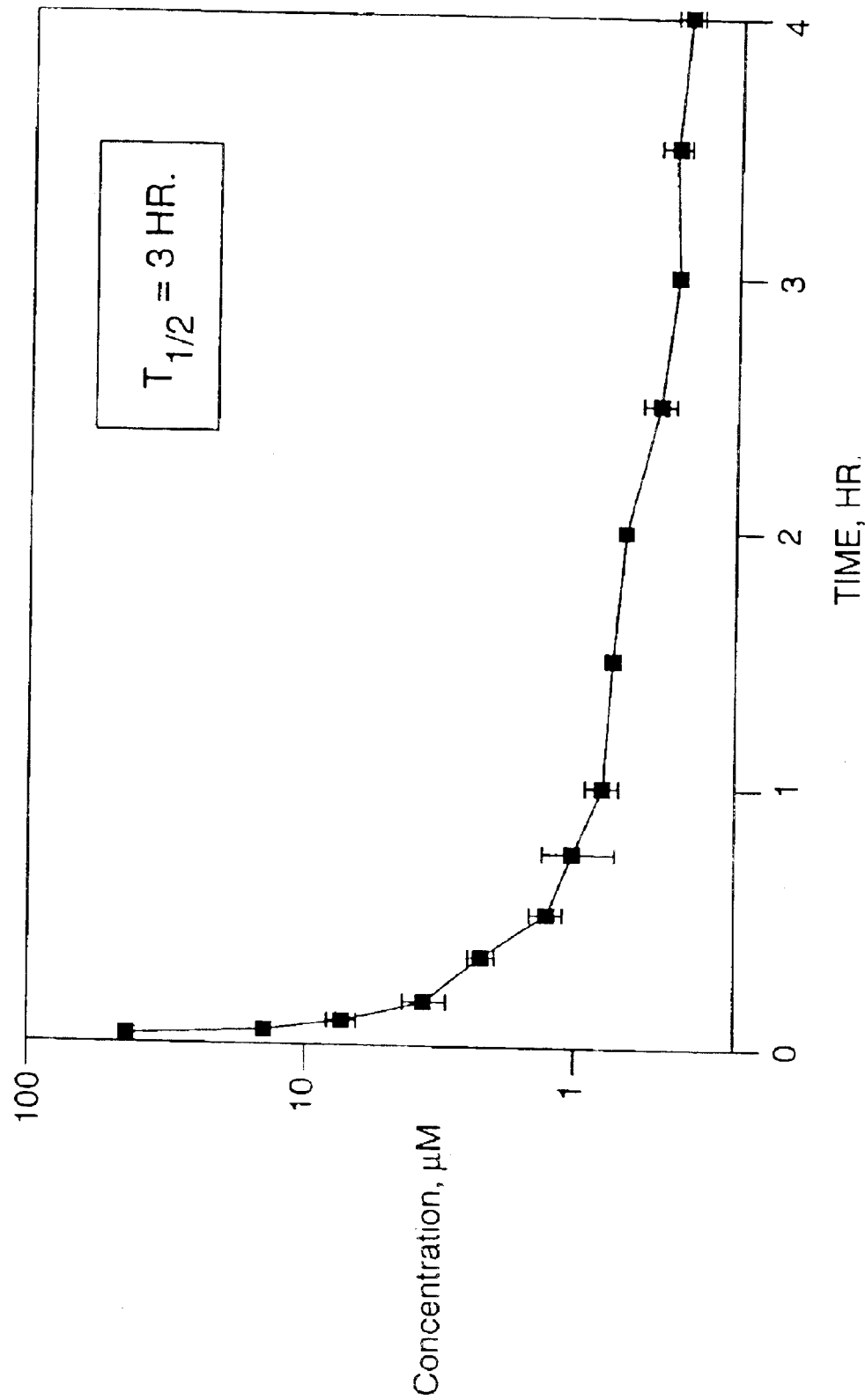

Results and Discussion: Compound 11, which has excellent affinity at the rat GnRH receptor, had a half life in rat plasma of approximately three hours and had a concentration in plasma of 100–200 nM four hours after i.v. injection (FIG. 5).

Binding of the reference peptides to rat, mouse, bovine and human GnRH receptors are in good agreement with those reported in the literature. Non-peptide compounds of the invention show marked species differences in their binding profile. Several of these compounds exhibit high affinity (<100 nM) at the human GnRH receptor. Functionally, all of these non-peptide compounds assessed for activity in an inositol phosphate assay act as antagonists of GnRH-stimulated total inositol phosphate accumulation in cells containing recombinant human GnRH receptors. Intravenous administration of compound 11 reduced plasma levels of LH in castrated male rats, a model for chronically elevated plasma LH levels. This compound has a half life of three hours, and the plasma concentration correlated with efficacy. Taken together, these data suggest that these non-peptide compounds should have utility as GnRH receptor antagonists.

Peptide Agonists and Antagonists Used as Reference Compounds:
[D-ALA6, DES-GLY 10]-LH-RH-ETHYLAMIDE
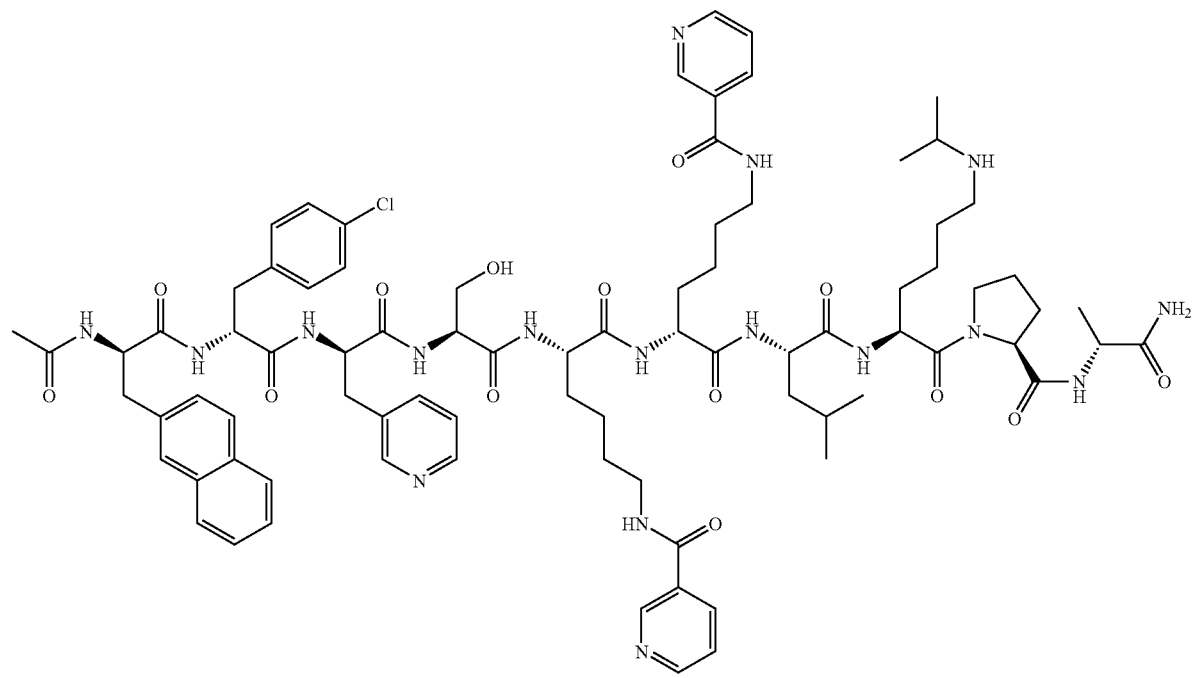
Antide
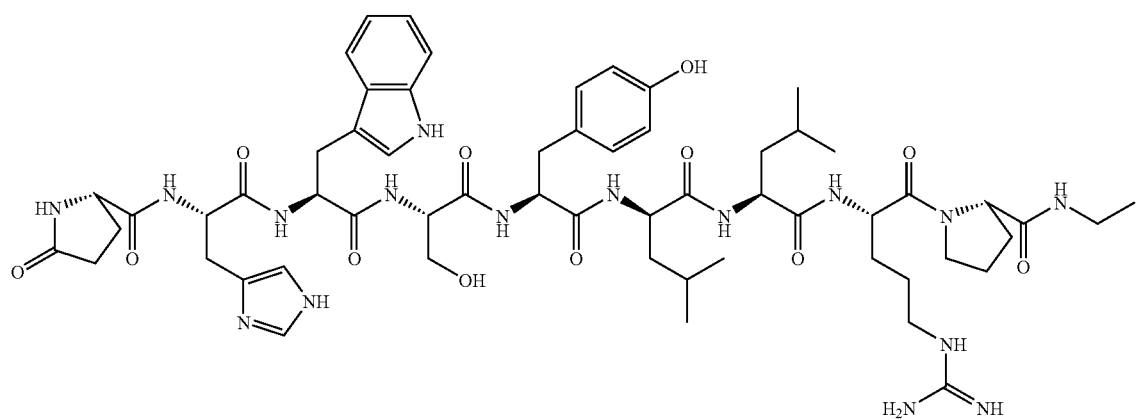
Leuprolide
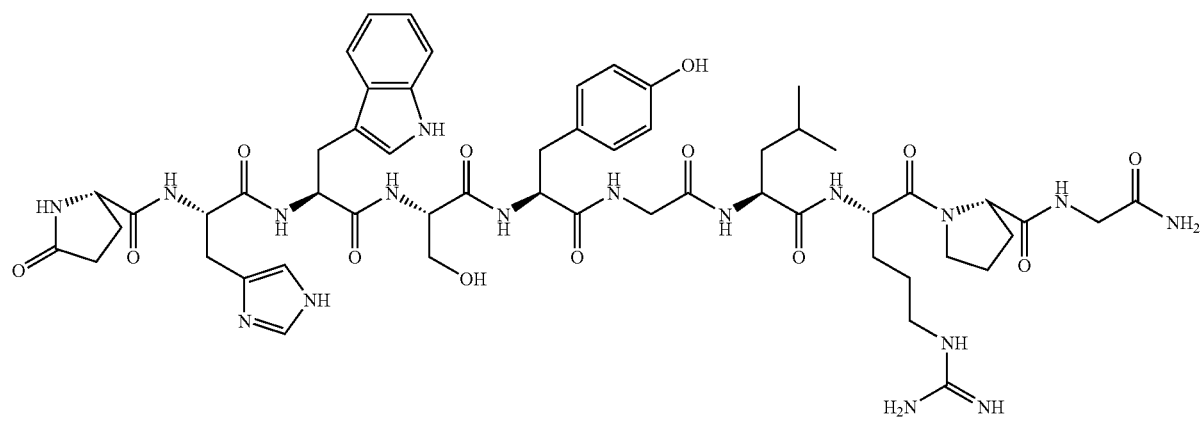
Human GnRH -continued GnRH-A

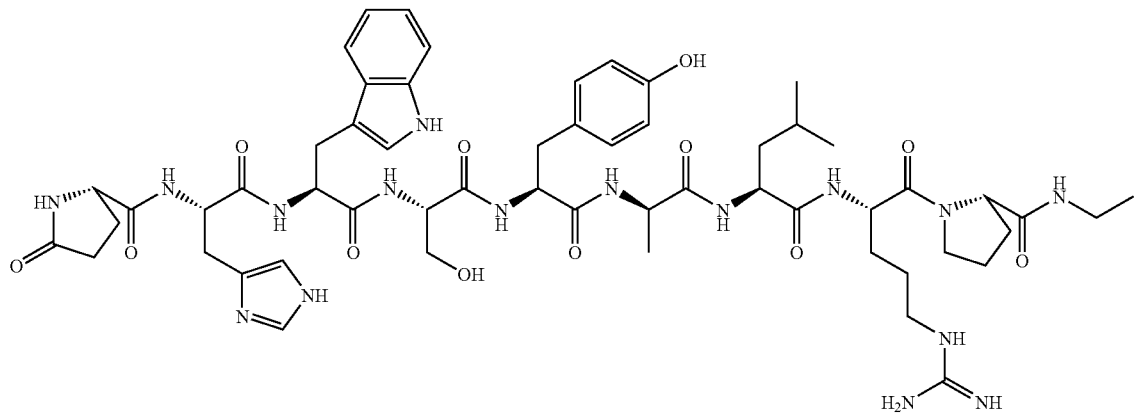

[D-ALA6, DES-GLY10]-LH-RH ETHYLAMIDE

The data on the compounds to follow was obtained as follows:

Cell Culture $GH_3$ cells stably transfected with the rat GnRH receptor ($GGH_3$) were provided by Dr. William Chin (Harvard Medical School, Boston, Mass.). These cells have been extensively characterized previously (Kaiser et al., 1997). These cells were grown in low glucose Dulbecco's modified Eagle's medium (DMEM) containing: 100U/mL penicillin/streptomycin, 0.6 g/L G418 and 10% beat-inactivated fetal bovine serum The cDNA for the human GnRH receptor was cloned into the plasmid expression vector, pcDNA 3 (In Vitrogen), and stably transfected into HEK 293 cells (hGnRH-R/293). This cell line was provided by Dr. Stuart Sealfon, Mount Sinai Medical School New York, N.Y. These cells were grown in DMEM supplemented with 0.2 g/L G418 100 U/ml penicillin/streptomycin and 10% FBS. Both $GGH_3$ and hGnRH-R/293 cells were utilized for both for both total inositol phosphate measurement and for microphysiometry assessment of compound efficacy.

Radioligand Preparation

The radioiodinated agonist analog of GnRH, [des-Gly[10], D-Ala[6]]GnRH ethylamide ([125]I-GnRH-A) was used as the radioligand. One µg of GnRH-A diluted in 0.1M acetic acid was added to an Iodogeno®-coated borosilicate glass tube (Pierce) containing 35 µl of 0.05 M phospate buffer (pH 7.4–7.6) and 1 mCi of Na[125]I]. The reaction mixture was vortexed and incubated for 1 min at room temperature. After one min, the mixture was vortexed and allowed to incubate for an additional minute. 2 ml of 0.5 M acetic acid/1% BSA was added to the reaction tube and the mixture was added to a C18 Sep-Pak cartridge. The cartridge was washed with subsequent washes of 5 ml $H_2O$ and 5 ml 0.5M acetic acid and then eluted with 5×1 ml of 60% $CH_3CN$/40% 0.5M acetic acid. The eluate was diluted with 3× volume of HPLC buffer A (0.1% TFA in $H_2O$) and loaded onto a C18 column. The iodinated product was eluted over 20–25 min with a gradient of 25–100% $CH_3CN$ containing 0.1% TFA. The radioactive fractions (750 ed/fraction) are collected into clean polypropylene tubes containing 100 µl of 10% BSA. Fractions were assessed for biological activity by radioligand binding. Specific Activity of the radioligand was approximately 2200 Ci/mmol.

Microphysiometry.

The Cytosensor®Microphysiometer (Molecular Devices, Sunnyvale, Calif.) is a real-time, noninvasive, nonradioactive semiconductor-based system for monitoring the cellular responses to various stimuli. It is based on a pH-sensitive silicon sensor, the light-addressable potentiometric sensor which forms part of a microvolume flow chamber in which cultured cells are immobilized (Pitchford et al., 1995; Parce et al., 1989; Owicki, et al. 1994).

ADDITIONAL REFERENCES

Owicki, J. C., L. J. Bousse, D. G. Hafeman, G. L. Kirk, J. D. Olson, H. G. Wada, and J. W. Parce. The light-addressable potentiometric sensor: principles and biological applications. *Ann. Rev. Biophys. Biomol. Struc.* 23:87–113, 1994.

Parce, J. W., J. C. Owicki, K. M. Kercso, G. B. Sigal, H. G. Wada, V. C. Muir, L. J. Bousse, K. L. Ross, B. I. Sikic, H. M. McConnell. Detection of cell-affecting agents with a silicon biosensor. *Science* 246:243–247, 1989.

Pitchford, S. K. DeMoor, and B. S. Glaeser. Nerve growth factor stimulates rapid metabolic responses in PC12 cells. *Am. J. Physiol.* 268(*Cell Physiol.* 37): C936–C943, 1995.

$GGH_3$ cells were seeded in low-buffered minimal essential media (MEM, Sigma) containing 25 mM NaCl and 0.1% BSA at a density of 500,000 cells/capsule onto the polycarbonate membrane (3 µm porosity) of cell capsule cups (Molecular Devices, Sunnyvale, Calif.). Capsule cups were transferred to sensor chambers where cells were held in close apposition to a silicon sensor within a sensor chamber, which measures small changes in pH in the microvolume of the sensor chamber. Low-buffered medium was pumped continuously across the cells at a rate of approximately 100 µl/min from one of two fluid reservoirs. A selection valve determined which reservoir from which fluid was perifused onto the cells.

The Cytosensor®Microphysiometer generates a voltage signal, which is a linear function of pH, every second. In order to measure acidification rates, flow to the sensor chamber containing the cells was periodically interrupted, allowing for excreted acidic metabolites to build up in the extracellular fluid of the cells. In these experiments, cells were maintained at 37° C. on a two minute flow cycle with cells being perfused with media for 80 seconds followed by 40 seconds in which the flow of media was stopped. During this 40 second interval, acidification rates were measured for a 30 sec interval. In this fashion, a single acidification rate was calculated every two min. The Cytosensor®Microphysiometer device contains eight such sensor units, allowing for eight simultaneous experiments to be performed. Each unit was individually programmed utilizing a computer linked to the system.

GGH$_3$ cells were initially equilibrated in the low-buffered MEM media for a period of 30–60 min in which basal acidification rates (measured as μV/sec), in the absence of any stimuli, were monitored. When the basal rate of acidification changed by less than ten percent over a period of twenty minutes, experiments were initiated. Time course experiments were performed to determine the optimal time for agonist exposure prior to acidification rate measurement and the duration of exposure needed to obtain peak acidification responses to various agonists. From these time course experiments, it was determined that cells should be exposed to GnRH peptide agonists at least one minute prior to collection of acidification rate data. Peak acidification rates usually occurred in the first two-minute exposure cycle. In order to capture the peak response to GnRH, cells were exposed to the agonist for a total of four minutes. Cells were exposed to compounds for 20–60 min prior to a four-minute stimulation with GnRH (1.0 nM–10 μM) alone or in combination with the various test concentration of each compound. All compounds were tested in a final concentration of 1% DMSO in low-buffered MEM media described above.

Selectivity Profile

In order to determine the specificity of binding of compounds to GnRH receptors, compounds were tested in various binding and functional assays for activity. Table 2 below shows the activity of Compound 20 in other assays.

TABLE 2

Binding Affinity or Functional Assessment of Compound 20 in Various Assays

| Assay | K$_i$ (nM)* |
|---|---|
| Adenosine (non-selective) | >1000 |
| Alpha1 adrenergic (non-selective) | >1000 |
| Alpha2 adrenergic (non-selective) | >1000 |
| Beta adrenergic (non-selective) | >1000 |
| Dopamine (non-selective) | >1000 |
| D2 Dopamine | >3200 |
| H1 Histamine | >1000 |
| H2 Histamine | ≈1000 |
| H3 Histamine | >1000 |
| M2 Muscarinic | >1000 |
| Muscarinic (non-selective) peripheral | >1000 |
| Opiate (non-selective) | >1000 |
| Serotonin Transporter | >1000 |
| Serotonin (non-selective) | >1000 |
| 5-HT$_{2a}$ | 2350 |
| 5-HT$_7$ | >4400 |

TABLE 2-continued

Binding Affinity or Functional Assessment of Compound 20 in Various Assays

| Assay | K$_i$ (nM)* |
|---|---|
| Estrogen | >1000 |
| Testosterone | >1000 |
| L-type Ca2+ Channel | >1000 |
| N-type Ca2+ Channel | >1000 |
| ATP-sens. K+ Channel | >1000 |
| Ca2+-Activated K+ Channel | >1000 |
| Na+ Channel (site 1) | >1000 |
| Na+ Channel (site 2) | >1000 |
| LTB4 | >1000 |
| LTD4 | >1000 |
| TXA2 | >1000 |
| PAF | ≈3000–5000 |
| TRH | >1000 |
| Oxytocin | >1000 |
| AT1 Angiotensin | ≈3000–5000 |
| Bradykinin 2 | >1000 |
| CCKA | >1000 |
| ET-A | >1000 |
| Galanin | >1000 |
| NK1 | >1000 |
| NK2 | >1000 |
| NK3 | ≈1000–5000 |
| VIP (non-selective) | >1000 |
| AchE | >1000 |
| Choline Acetyltransferase | >1000 |
| MAO-A | >1000 |
| MAO-B | >1000 |
| ILRA (CXCR-1) | >10000 |
| GLP-1 | >10000 |
| Glucagon | 6700 |
| NPY Y1 | >10000 |
| CYP3A4 Cytochrome P450 IC50 | 1700 |
| Basal Histamine Release (rat mast cells) EC50 | >10000 |
| RARγ Retinoid | >10000 |
| RXRα Retinoid | >10000 |
| Vasopressin1 | >1000 |

*EC$_{50}$ for Basal Histamine Release Assay

Figure 6:
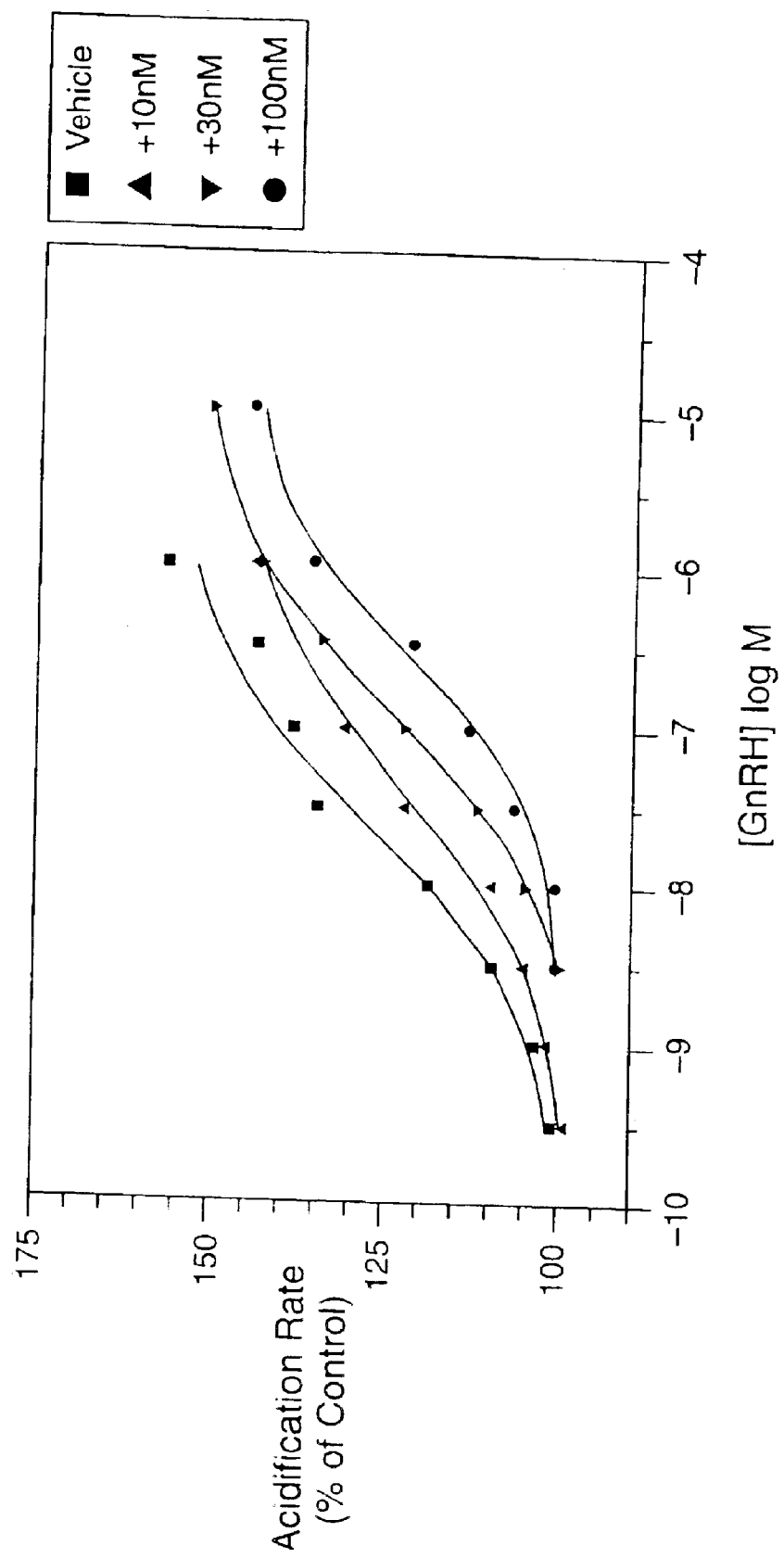

FIG. 6 shows the effect of Compound 136 on GnRH-stimulated increases in extracellular acidification rate in GGH$_3$ cells. GnRH produced a dose-dependent increase in the extracellular acidification rate of GGH$_3$ cells. Compound 136 caused a rightward shift in the dose-response curves to GnRH without decreasing the maximum response to GnRH. This suggests that this compound is a competitive receptor antagonist of GnRH at this receptor. Values shown are from one experiment.

An example of preparation methods for compounds according to the invention is as follows:

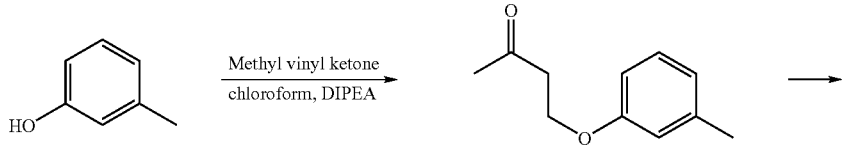

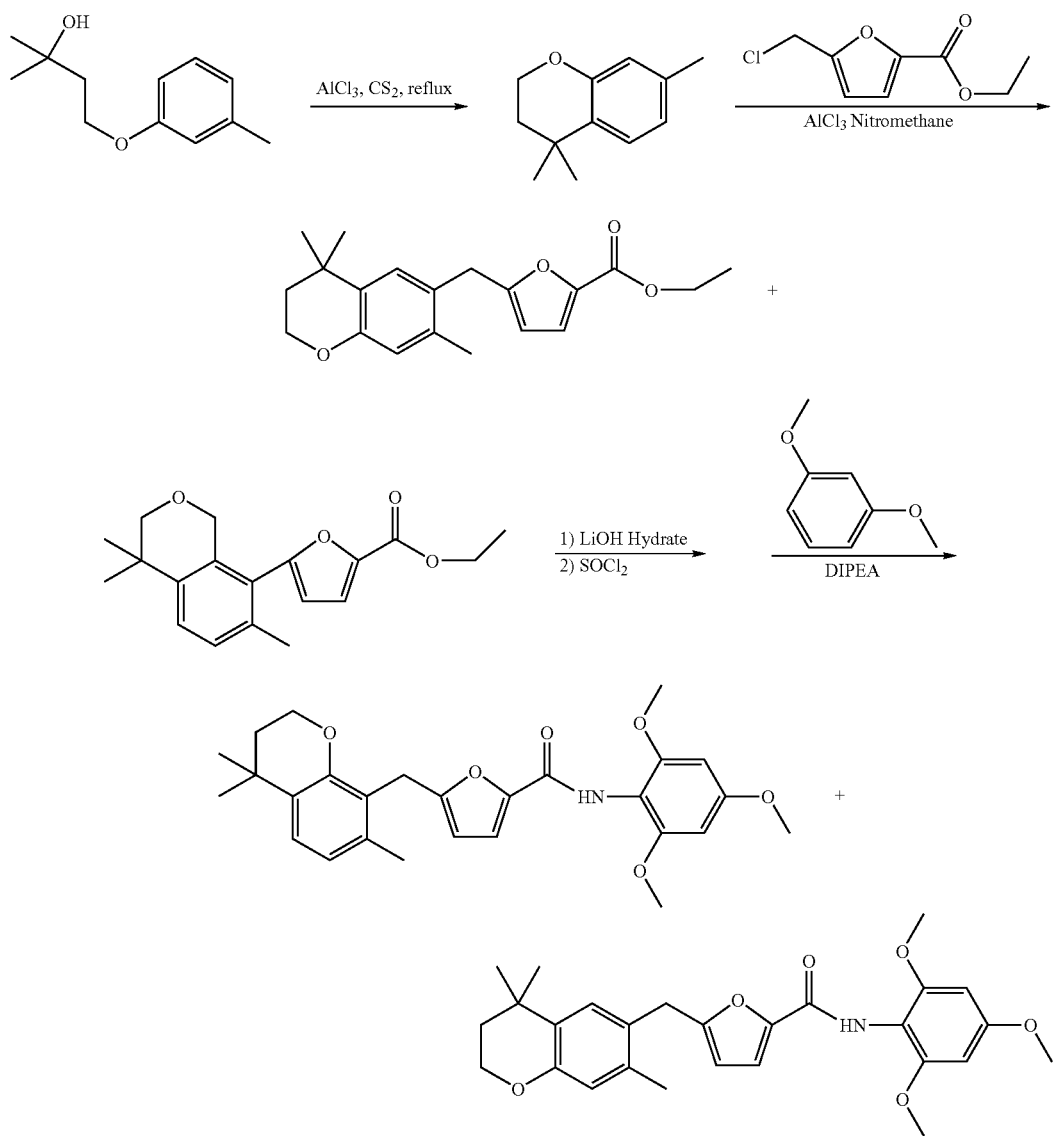

4-(3-methylphenoxy)-2-butanone:

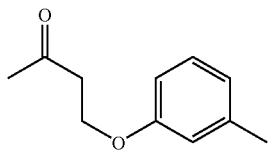

2-Methyl-4(3-methylphenoxy)-2-butanol:

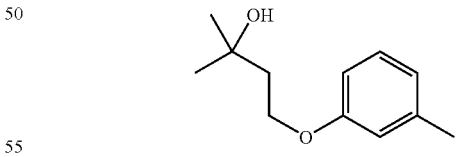

To m-Cresol (4.0 g, 37 mmol), methyl vinyl ketone (3.2 mL, 37 mmol) in chloroform (25 mL), added diisopropyl ethyl amine. The mixture was heated at reflux for 16 h, allowed to cool to room temperature and evaporated. The residue has 50% product and 50% starting material starting material. The starting, material was separated as t-butyldimethyl silyl ether. The product was isolated through plug filteration. Yield 4.5 g (68%).

To a solution of methyl magnesium bromide in ether (50 mL), prepared from Mg (572 mg, 23.56 mmol) and MeI (3.34 g, 23.56 mmol), was added 4-(3-methylphenoxy)-2-butanone (2.1 g, 11.78 mmol) in 10 mL ether. The solution was stirred at room temperature for 30 minutes, after which quenched with water and dil. Hydrochloric acid. The organic layer was separated, dried over sodium sulfate, filtered through a silica plug. Colorless syrup 1.91 g (83%).

4,4,7-trimethyl chroman:

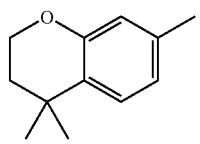

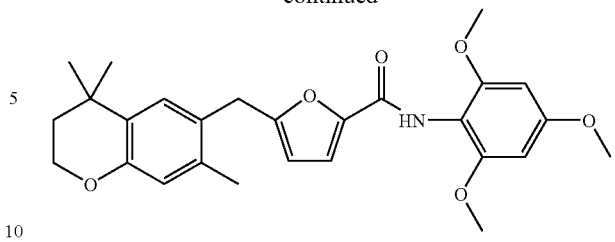

To aluminium chloride (1.3 g, 9.79 mmol) in 40 mL carbon disulfide, added 2-methyl-4(3-methylphenoxy)-2-butanol (1.9 g, 9.79 mmol) in 10 mL carbon disulfide. The mixture was heated at reflux for 2 h. Solvent evaporated, the residue diluted with 50 mL of ethyl acetate, and 10 mL of water. The organic layer separated, dried over sodium sulfate, and purified thorugh a quick column. Light yellow syrup 1.5 g (87%).

Ethyl-5-[(4,4,7-trimethyl-3,4-dihydro-2H-chromen-6-yl)methyl]-2-furoate, and ethyl-5-[(4,4,7-trimethyl-3,4-dihydro-2H-chromen-8-yl)methyl]-2-furoate:

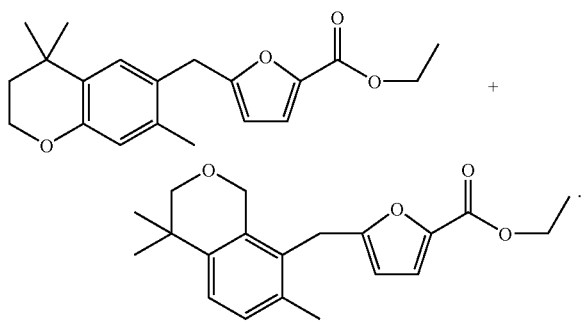

To zinc chloride (950 mg, 6.97 mmol) in nitromethane (20 mL), was added a mixture of 4,4,7-trimethyl chroman (1.23 g, 6.97 mmol) and ethyl-5-chloromethyl-2-furoate (656 mg, 3.48 mmol) in nitromethane (15 mL). The mixture was stirred at room temperature for 16 h. Evaporated to dryness and triturated with ethyl acetate-water (1:1, 100 mL). The organic layer on usual work up, and plug filtration using hexane:ethyl acetate (9:1) gave mixture of these two compounds. 1.34 g (46% based on chroman).

N-(2,4,6-trimethoxyphenyl)-5-[(4,4,7-trimethyl-3,4-dihydro-2H-chromen-6-yl)methyl]-2-furamide and N-(2,4,6-trimethoxyphenyl)-5-[(4,4,7-trimethyl-3,4-dihydro-2H-chromen-8-yl)methyl]-2-furamide:

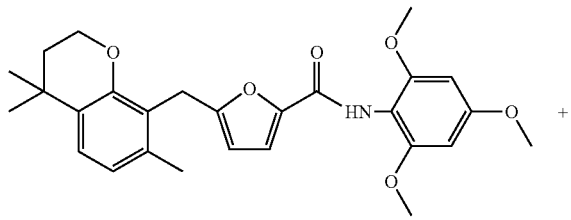

To a mixture of ethyl-5-[(4,4,7-trimethyl-3,4-dihydro-2H-chromen-6-yl)methyl]-2-furoate, and ethyl-5-[(4,4,7-trimethyl-3,4-dihydro-2H-chromen-8-yl)methyl]-2-furoate (1.34 g, 3.74 mmol) in THF-MeOH—H2O (7:5:5, 20 mL) was added lithium hydroxide monohydride (784 mg, 18.7 mmol). The mixture was stirred for 4 h at room temperature. The mixture evaporated to dryness, diluted with 30 mL, ethyl acetate and 50 mL, of water. After acidification with diluted HCl, ethyl acetate layer separated, dried and evaporated to give mixture of corresponding acids, 1.03 (quantitative). The acids could not be separated using column chromatography or crystallization.

To the mixture of acids (200 mg, 0.66 mmol) in dichloromethane (30 mL) was added thionyl chloride (392 mg, 3.3 mmol). The mixture was refluxed for 1 h and evaporated. The residue was dissolved in hexane-ethyl aceatate (9:1, 20 mL) and filtered through a silica gel plug (0.5 cm×1.0 cm).

To the residue in 10 mL ethyl acetate, was added 2,4,6-trimethoxyphenyl amine hydrochloride (145 mg, 0.66 mmol) followed by diisopropyl ethyl amine (256 mg, 1.98 mmol). The mixture was stirred at room temperature for 16 h. The reaction was quenched with water (10 mL), ethyl acetate layer separated. The combination and column and HPLC purification gave 15 mg and 21 mg of two components (12%).

Bioavailability of compounds of the invention are shown in the following Table.

In vivo pharmacology of some compounds of the invention was tested as follows:

In viva experiments: general.

Adult male Sprague-Dawley rats were purchased from Harlan Sprague Dawley (San Diego). Animals were housed two per cage and maintained in a temperature-controlled room (22±2° C.) with a photoperiod of 12 hr light/12 hr dark (lights on at 0600 h). Rat chow (Teklad rat diet) and tap water were provided ad libitum.

Figure 8:
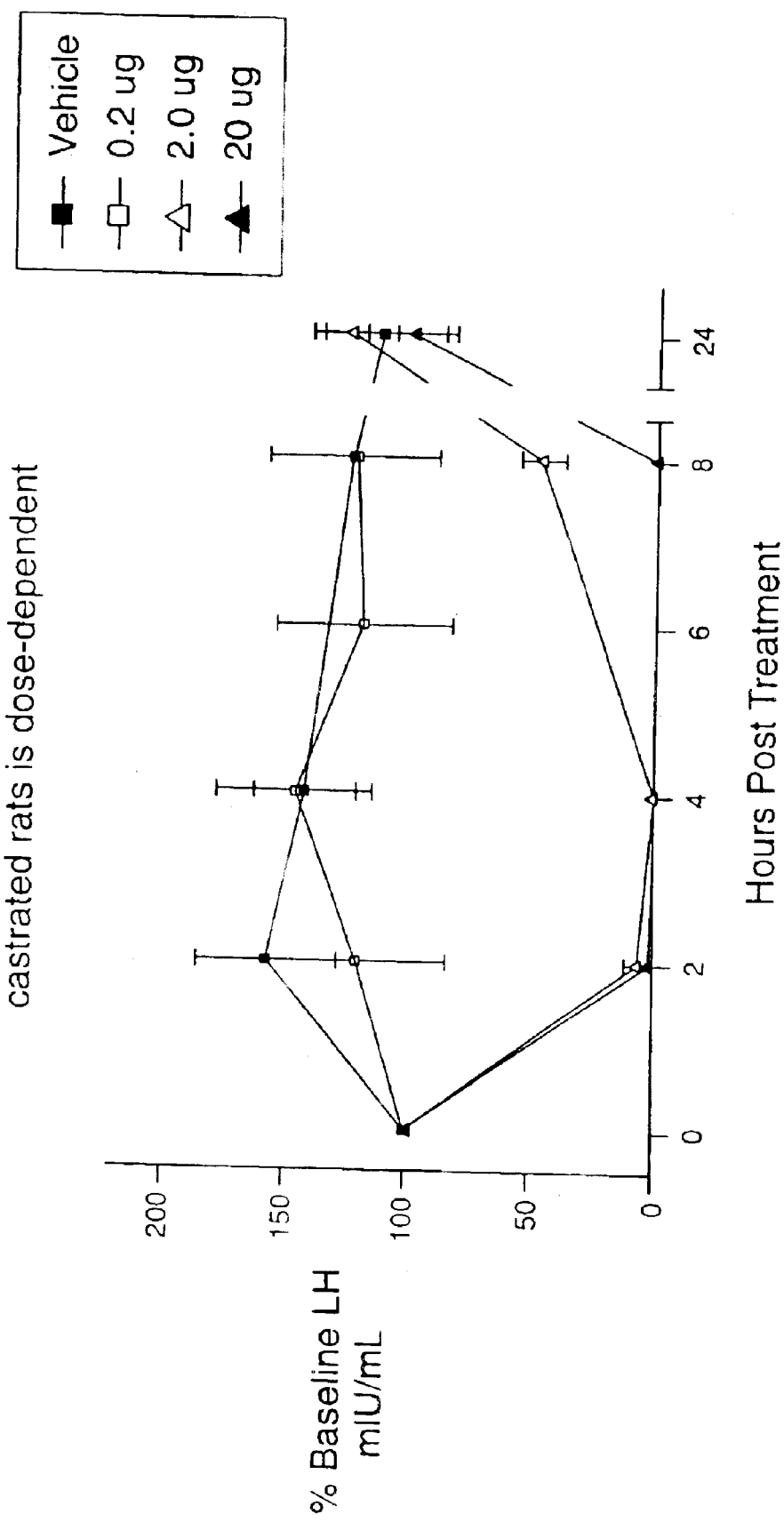

Animal Models to Access Activity of GnRH Antagonists:
Castrated Male Rat Model
Rationale:

Surgical removal of the gonads removes circulating testosterone and eliminates the negative feedback of testosterone on the hypothalamus. As a result GnRH is elevated and consequently elevates LH (FIG. 1). A GnRH antagonist would be expected to reduce GnRH mediated elevations of LH levels. Antide, a GnRH peptide antagonist reduces LH levels in castrated rats (FIG. 8). This model seems suitable for evaluating small molecule GnRH antagonists.

Protocol:

Male Sprague-Dawley (2000–225 g) rats were castrated via the scrotal approach under halothane anesthesia. Animals were allowed 14 days post operative recovery prior to study. Thirteen days following castration, animals were anesthetized with halothane and instrumented with indwelling jugular vein cannula. Details of the cannulation procedure have been described previously {Harms and Ojeda, 1974)}. On study day, animals were allowed to acclimate to the procedure room while residing in their home cage. Basal blood samples were drawn from all animals. Immediately following basal sampling, vehicle or test compounds were administered by various routes. The routes of administration employed were intravenous (iv), intramuscular (im), intraperitoneal (ip), subcutaneous (sc) and oral (po). Blood samples were drawn into heparin containing tubes at multiple time points post treatment. Blood was centrifuged immediately, plasma collected and stored in −20° freezer until assayed. Plasma samples were analyzed using DSL-4600 ACTIVE LH coated-tube immunoradiometric assay kit from Diagnostic Systems Laboratories, Inc.

Compound Formulations:

Formulation #1 (denoted with superscript 1): 10% DMSO, 10% Cremophor EL and 80% physiological saline.

Formulation #2 (denoted with superscript 2): 10% Cremophor EL and 90% physiological saline.

Results

Figure 9:
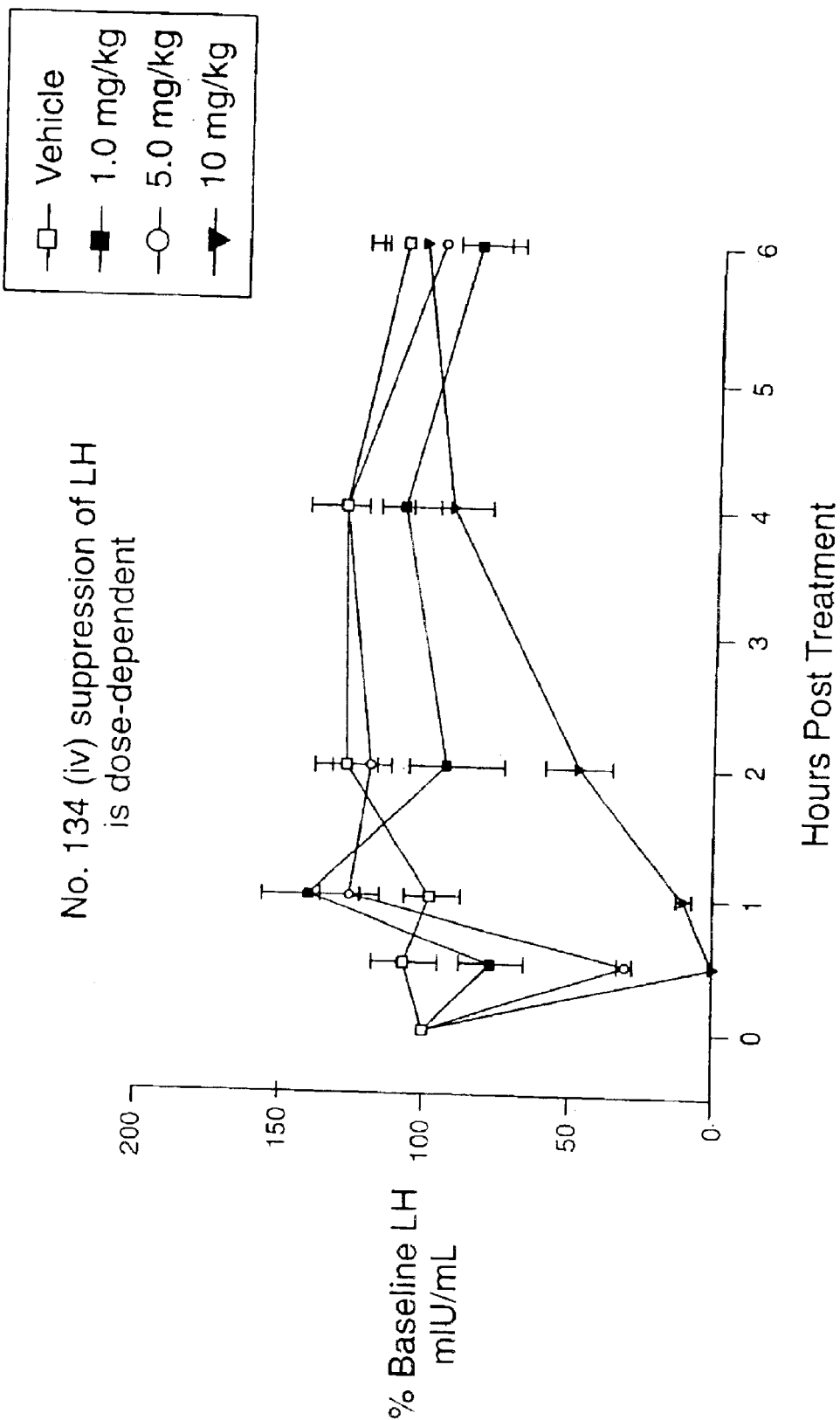
Figure 10:
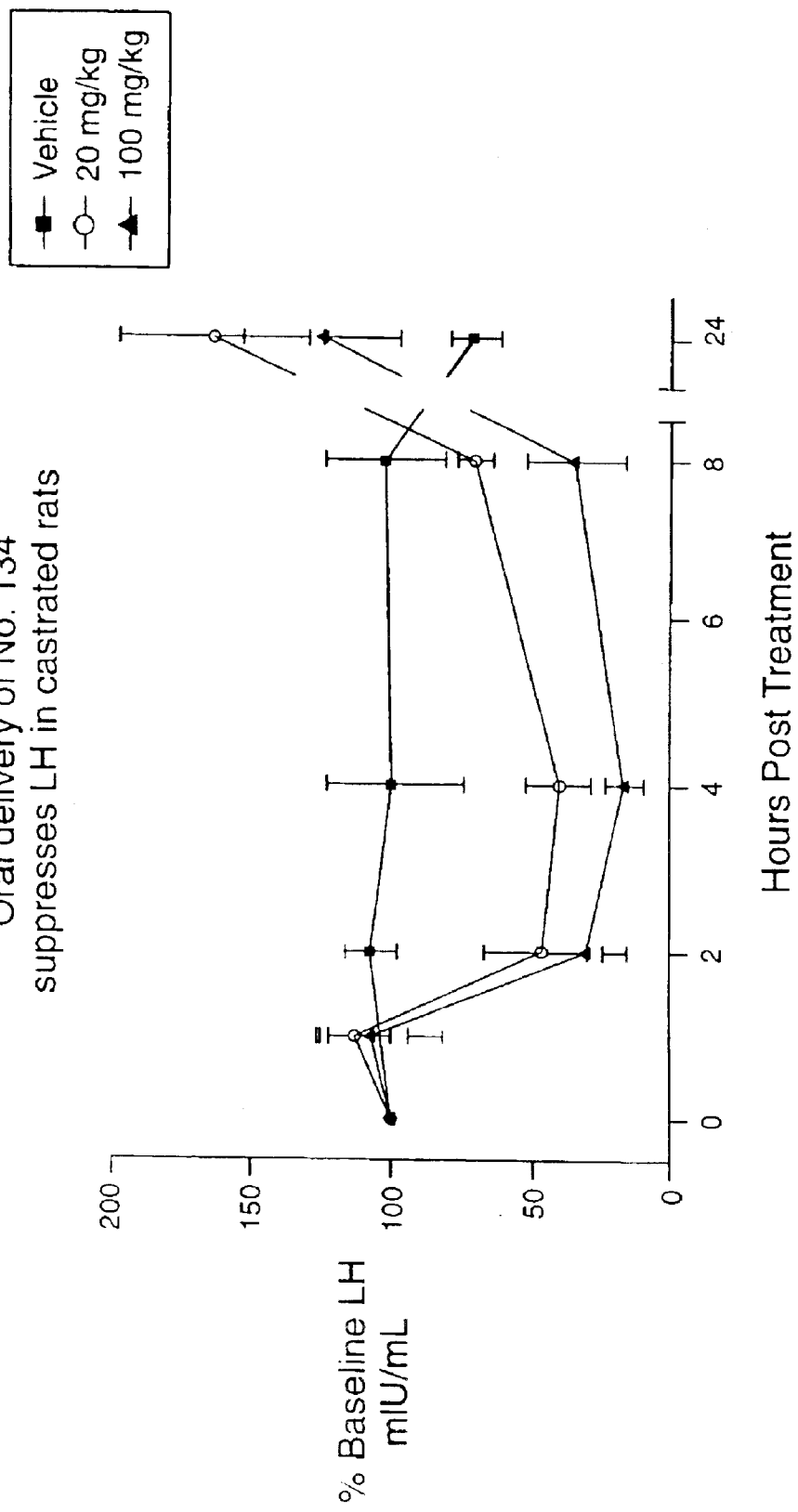
Figure 11:
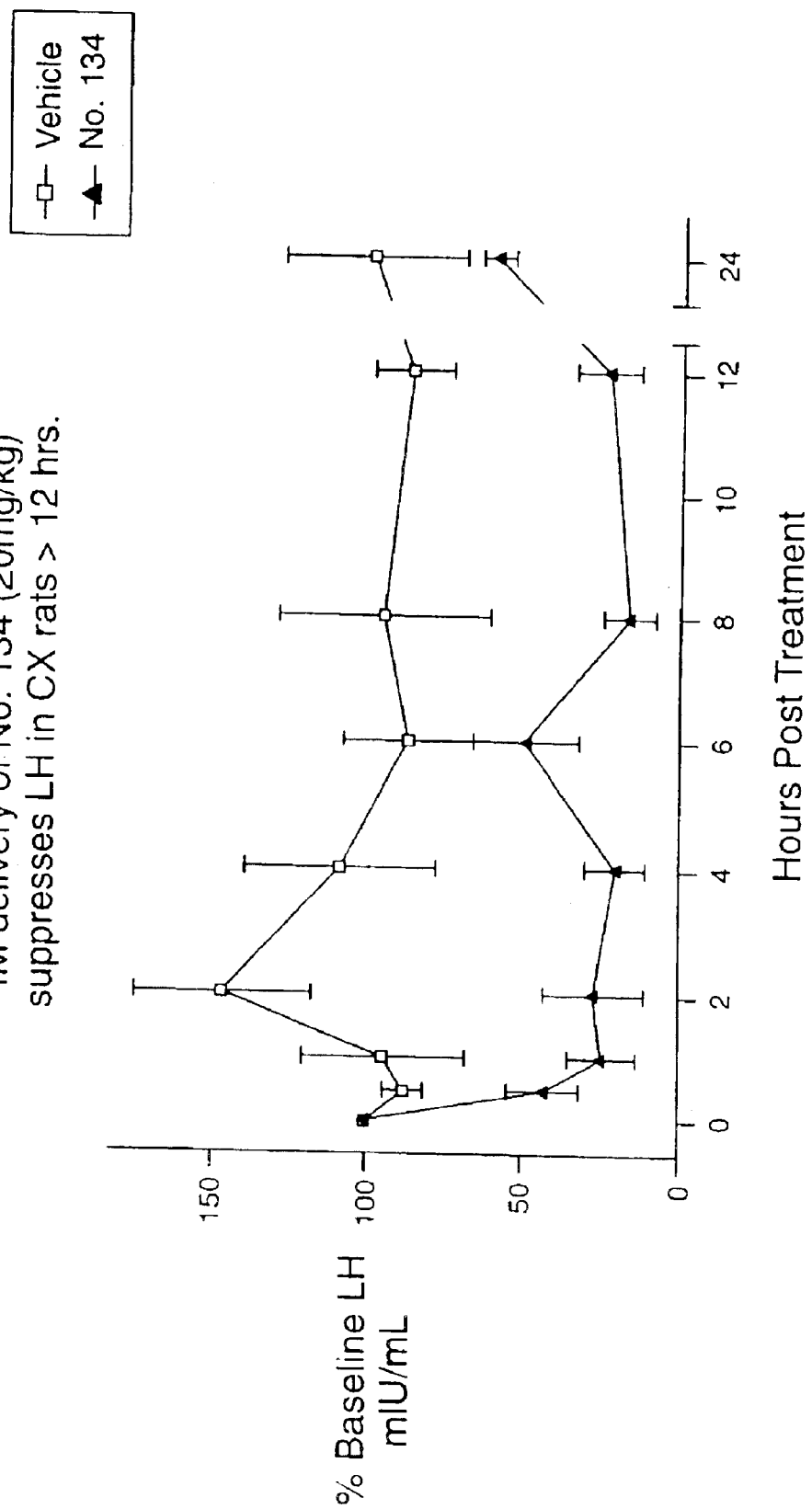

See FIGS. 9–11 and Table.

Intact Male Rat

Rationale:

Testosterone is a hormone regulated by the hypothalamic-pituitary-gonadal axis. GnRH is secreted in pulses from the hypothalamus and stimulates the anterior pituitary gland to release gonadotropic hormones LH and FSH. Testosterone is produced when the testes are stimulated by LH. The quantity of testosterone secreted increases approximately in direct proportion to the amount of LH available (Guyton, 1986). A GnRH antagonist is expected to reduce testosterone level by inhibiting LH.

Protocol 1:

Male Sprague-Dawley (250–275 g) rats were single-housed and allowed to acclimate for 1 week prior to study. On study day animals were dosed with vehicle or test compound by various routes of administration, including ip, sc, or po. Blood samples were obtained via cardiac puncture under halothane anesthesia from individual animals at predetermined time points post treatment. Blood samples were drawn into heparin containing tubes. Blood was centrifuged immediately, plasma collected and stored in −20° freezer until assayed. Plasma samples were analyzed using DSL-4000 ACTIVE Testosterone coated-tube raduioimmunoassay kit from Diagnostic Systems Laboratories, Inc.

Protocol 2:

Male Sprague-Dawley (250–275 g) rats were single-housed and allowed to acclimate for 1 week prior to study. We developed a technique to allow for repeated sampling from the jugular vein by using microrenathane (MRE) catheters implanted 7 days prior to study. Details of the surgical procedure have been described previously {Harms and Ojeda, 1974}. On study day, animals were allowed to acclimate to the procedure room while residing in their home cage. Basal blood samples were drawn from all animals. Immediately following basal sampling, vehicle or test compounds were administered by various routes. The routes of administration employed were intravenous (iv), intramuscular (im), and oral (po). Blood samples were drawn into heparin containing tubes at multiple time points post treatment. Blood was centrifuged immediately, plasma collected and stored in −20° freezer until assayed. Plasma samples were analyzed using DSL-4000 ACTIVE Testosterone coated-tube raduioimmunoassay kit from Diagnostic Systems Laboratories, Inc.

Protocol 3: Repeated Dosing Study Compound No. 134

Male Sprague-Dawley (250–275 g) rats were double-housed and allowed to acclimate for 1 week prior to study. Daily vehicle treatments were administered either, im, sc, or po between 8:00 and 9:00 am for seven days. On day 8 between 8:00 and 9:00 am, blood samples were drawn via cardiac puncture under halothane anesthesia. The procedure was complete in 45–60 seconds. Over the next 7 days one groups of animals continued to receive vehicle treatments while another group of animals received no treatment. Samples were collected as described above following the 7$^{th}$ day of this treatment regimen. Testosterone levels were not different between vehicle treated animals and untreated animals.

Daily im dosing of Compound 134 (100 mg/kg) or vehicle was performed between 8:00 and 9:00 am for seven days. Samples were collected as described above following the 7$^{th}$ day of treatment.

All blood samples were collected in heparin containing tubes. Blood was centrifuged immediately, plasma collected and stored in −20° freezer until assayed the next day. Plasma samples were analyzed using DSL-4000 ACTIVE Testosterone coated-tube raduioimmunoassay kit from Diagnostic Systems Laboratories, Inc.

Results

Figure 12:
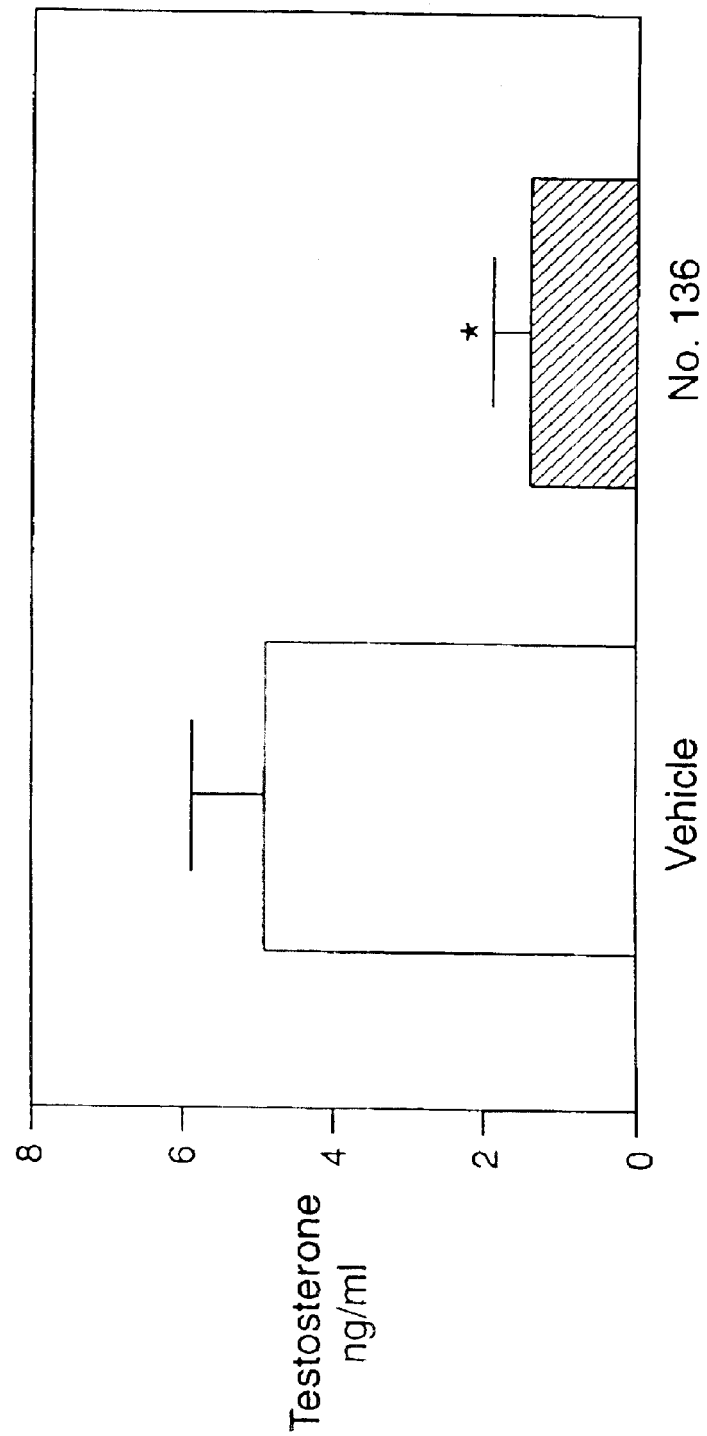
Figure 13:
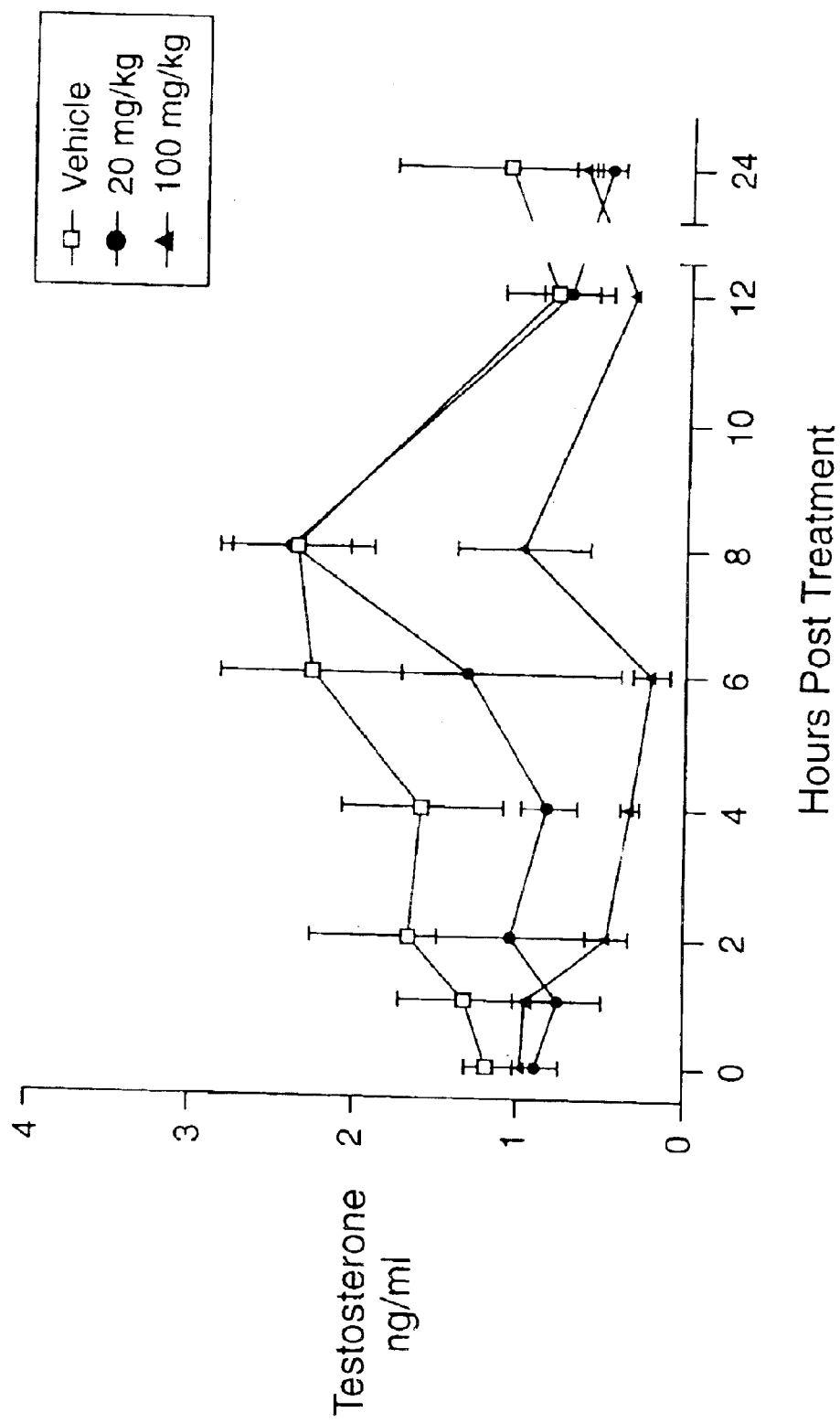
Figure 14:
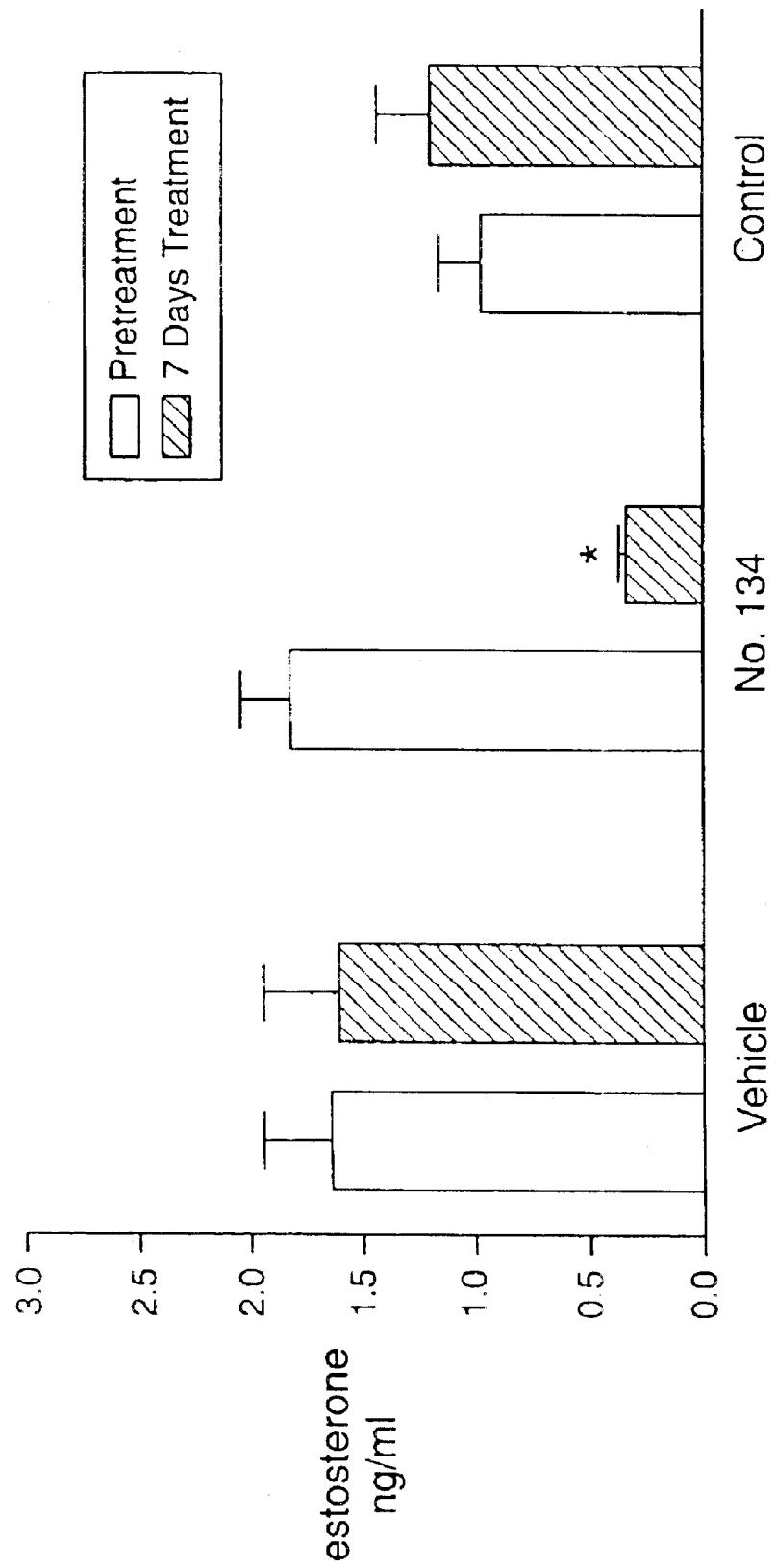

See Table 2 and FIGS. 12–14.

Figure Legends

Figure 7:
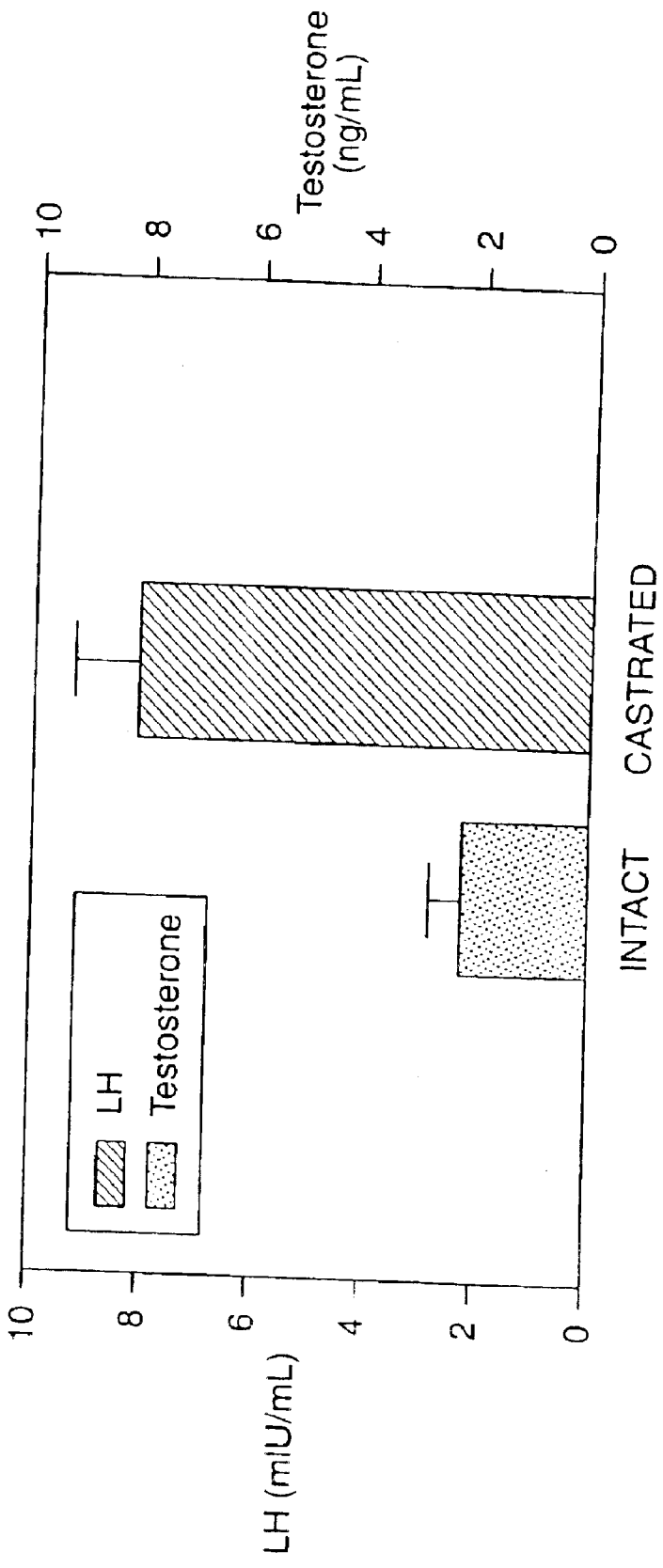

FIG. 7: Bar graph shows basal LH and testosterone levels in castrated (CX) and intact rats. LH is elevated in CX rats. Testosterone is absent in CX rats.

FIG. 8: Line plot shows LH levels expressed as a percentage of basal LH in vehicle and Antide treated animals. Antide (2.0 and 20 ug;sc) suppresses LH in CX rats.

FIG. 9: Line plot shows LH levels expressed as a percentage of basal LH in vehicle and compound treated animals. Compound 134 (1.0, 5.0 & 10 mg/kg;iv) produces dose-dependent suppression of LH in CX rats.

FIG. 10: Line plot shows LH levels expressed as a percentage of basal LH in vehicle and compound treated animals. Compound 134 (20 or 100 mg/kg;ip) suppresses LH in CX rats.

FIG. 11: Line plot shows LH levels expressed as a percentage of basal LH in vehicle and compound treated animals. Compound 134 (20 mg/kg;im) suppresses LH in CX rats.

TABLE 1

GnRH Compounds in Castrated Rat Model

| Compound | Dose mg/kg Route | % Max LH Suppression | ≥50% Suppression Duration | Range of Plasma Conc. µM |
|---|---|---|---|---|
| No. 9 | 1.0/iv | 40 @ 0.5 hr | NS | ND |
| No. 11 | 10/iv | 85 @ 0.75 hr | 3 hr | ND |
|  | 10/ip | 50 @ 0.5 hr | <1 hr |  |
|  | 20/po | NS | NS |  |
| No. 13 | 20/iv | 63 @ 0.5 hr | <1 hr | ND |
| No. 48 | 10/iv | 75 @ 0.5 hr | <1 hr |  |
|  | 20/iv | 51 @ 1 hr | 1 hr | 35.7–3.49 |
| No. 20 | 10/iv | 78 @ 0.5 hr | 0.5 hr | ND |
|  | 20/iv | 72 @ 1 hr | 1.0 hr |  |
|  | 50/im | 65 @ 1 hr | 2 hr |  |
|  | 50/po | 59 @ 1 hr | 2 hr |  |
|  | 100/po | 43 @ 2 hr | NS |  |
| No. 136 | 5.0/iv | 48 @ 1 hr | 1.0 hr | 3.0–0.3 |
|  | 10/iv | 74 @ 2 hr | 6 hr | 3.7–0.28 |
|  | 20/iv | 98 @ 4 hr | ≥6 hr | 8.9–0.7 |
|  | 20/ip |  |  |  |
|  | 20/po | NS | NS | 0.29 |
|  | 40/po | NS | NS | 0.72 |

TABLE 1-continued

GnRH Compounds in Castrated Rat Model

| Compound | Dose mg/kg Route | % Max LH Suppression | ≧50% Suppression Duration | Range of Plasma Conc. μM |
|---|---|---|---|---|
| No. 134 | 1.0/iv | 24 @ 0.5 hr | | 0.53–0.20 |
| | 5.0/iv | 70 @ 0.5 hr | | 3.2–0.11 |
| | 10/iv | 100 @ 0.5 hr | 2 hr | 4.8–0.16 |
| | 20/po | 62 @ 4 hr | 4 hr | 0.94–0.3 |
| | 100/po | 84 @ 4 hr | 8 hr | 1.27–0.7 |
| | 20/ip | 80 @ 2 hr | 4 hr | 1.7–0.45 |
| | 100/ip | 98 @ 4 hr | 8 hr | 1.7–0.32 |
| | 20/sc | 53 @ 8 hr | only @ 8 hr | 0.6–0.3 |
| | 100/sc | 80 @ 6 hr | 8 hr | 0.39–.15 |
| | 20/im | 73 @ 2 hr | 8 hr | 1.3–0.12 |
| | 100/im | 98 @ 2–24 hr | 24 hr | 10.8–0.5 |
| No. 119 | 5.0/iv | 63 @ 1 hr | 1 hr | 3.1–0.8 |
| | 10/iv | 61 @ 1 hr | 1 hr | 8.13–0.35 |
| | 20/po | 63 @ 2 hr | 2 hr | 0.1 |
| | 20/ip | 79 @ 2 hr | 2 hr | 0.6–0.1 |
| | 20/sc | NS | NS | 0.2 |
| No. 183 | 10/iv | 92 @ 1 hr | 8 hr | 1.5–0.89 |
| | 50/po | 60 @ 2 hr | 8 hr | 0.65–.13 |
| | 10/im | 58 @ 2 hr | NS | 0.18–.08 |
| No. 206 | 10/iv | 51 @ 1 hr | NS | 0.2–0.06 |
| | 20/po | NS | NS | 0.1–0.05 |

NS = No suppression
ND = Not determined

Figure Legends
Representation of Protocol 1:

FIG. 12: Bar graph shows testosterone levels in vehicle and compound treated animals 6 hours post ip injection. Compound 136 suppressed testosterone levels compared to vehicle treated animals *=p<0.05, t-test.

Representative of Protocol 2:

FIG. 13: Line plot shows testosterone levels over a 12 hour time course and 24 hour time point in vehicle and compound 134 treated rats. Vehicle and compound 134 was delivered by oral gavage. The highest dose of compound 134 suppressed testosterone throughout the course of the study.

Representative of Protocol 3:

FIG. 14: Bar graph shows testosterone levels for vehicle, compound 134 and control treated animals. Open bars represent pretreatment testosterone levels and solid bars represent testosterone levels following 7 days of repeated treatment. Compound 134 significantly suppressed testosterone levels compared to pretreatment, vehicle and control-treated animals. *=p<0.05, t-test.

TABLE 2

GnRH Compounds in Intact Male Rat

| Compound | Dose mg/kg Route | % Testosterone suppression | Suppression Duration | Range of Plasma Conc. μM |
|---|---|---|---|---|
| No. 134 | 20/ip | 36 @ 4 hr | 4 hr | 0.2 |
| | 100/sc | 60 @ 24 hr | 24 hr | 0.13 |
| | 20/po | NS @ 2 or 4 hr | NS | 0.15 @ 2 hr 0.17 @ 4 hr |
| | 100/im* 7 days | 80 @ 12 hr | 12 hr | 1.3 |
| | 20/po | NS | NS | 1.1 @ 1 hr |
| | 50/po | 75 @ 4 hr | 8 hr | 2.5–0.22 |
| | 100/po | 80 @ 6 hr | 12 hr | 2.4–0.25 |
| No. 136 | 20/ip | 72 @ 6 hr | 6 hr | 0.4 |
| | 40/po | 46 @ 4 hr | 4 hr | 0.34 |

NS = No suppression
ND = Not determined

Procedural Notes

It has been documented that some of the procedures commonly used in endocrine studies on animals, such as anesthesia, fasting, surgery may affect the hormone levels being studied (B. E. Howland, et al., Experentia, 1974.) Luteinizing hormone and testosterone are sensitive to stressors. Numerous reports are conflicting about the effects of stressors on the HPG axis even when the same species and stressors are utilized. For example, male rats that are subjected to restraint or immobilization have been reported to have low, (Kruhlich et al., 1974; DuRuisseau et al., 1978), normal (Tache et al., 1980; Charpenet et al., 1982; Collu et al., 1984), or elevated LH concentrations (Briski et al, 1984). Similarly, plasma testosterone levels have been reported to change following exposure to stressful situations, but again the data appear contradictory and therefore difficult to interpret. For example, during intense physical exercise plasma testosterone levels have been reported to increase (Dessypris et al., 1976), decrease (Sutton et al., 1973) or remain unchanged (Lamb, 1975). The effects of immobilization on testosterone concentrations have been more consistent with most investigations reporting a decline in circulating values (Tache et al., 1980; Charpenet et al., 1982; Collu et al., 1984). It is, however, accepted that stressors do elicit changes in circulating testosterone and the type of stress used, duration and severity cause different stress-induced changes in testosterone concentrations. Considering the susceptibility of LH and testosterone to stress, we have optimized protocols to evaluate LH and testosterone under conditions which minimize stress.

Compounds according to the invention that have been prepared are shown in the attached Tables.

Compounds can be prepared with the general experimentals provided above. Specific examples are given below.

Pyrimidine-Containing Compounds

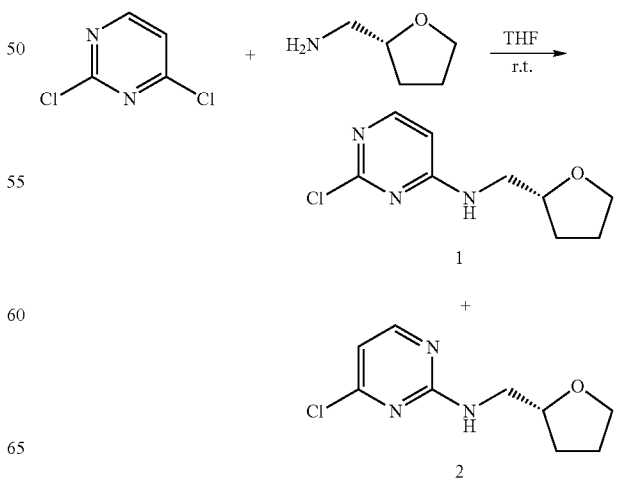

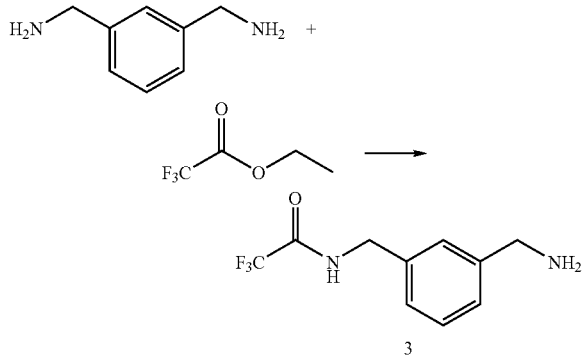

Preparation of 2-chloro-N-[(2R)-tetrahydro-2-furanmethyl]-4-pyrimidinamine 1 and 4-chloro-N-[(2R)-tetrahydro-2-furanmethyl]-2-pyrimidinamine 2:

To a 250 mL round bottom flask was placed 2,4-dichloropyrimidine (5.0 g, 33.56 mmol) and 200 mL THF. To this solution was added triethylamine (14.0 mL, 100.68 mmol) and [R]-tetrahydrofurfurylamine. The solution was stirred overnight. The reaction mixture was poured into water and extracted with methylene chloride. The separated organic layer was washed with brine, dried over magnesium sulfate, and concentrated on a rotary evaporator. The crude compound was purified by silica gel chromatography with hexane/ethyl acetate (4:1 v/v to 1:1 v/v) to yield 2 (1.3 g) and 1 (3.98 g).

Preparation of N-[3-(aminomethyl)benzyl]-2,2,2-trifluoroacetamide 3.

To a solution of m-xylene diamine (28.76 g, 211.15 mmol) in THF (300 mL, 0.7M) was added dropwise a solution of ethyl trifluoroacetate (10 g, 70.38 mmol) in THY (50 mL, 1.4M). The solution was stirred at room temperature overnight. The reaction was monitored by TLC. The solvent was concentrated and residue was acidified to pH 2 with 4N HCl and dissolved in water and washed with ethyl acetate. The separated aqueous layer was basified to pH 11 using $NH_4OH$ and compound was extracted with dichloromethane. The separated organic layer was wash with water/brine, dried over magnesium sulfate and concentrated to yield 3 (8.71 g, 53% yield).

Synthesis of 5-[(3,5,5,8,8-pentamethyl-5,6,7,8-tetrahydro-2-naphthalenyl)methyl]-N-(3-{[(2-{[(2R)-tetrahydro-2-furanylmethyl]amino}-4-pyrimidinyl) amino]methyl}benzyl)-2-furamide 9.

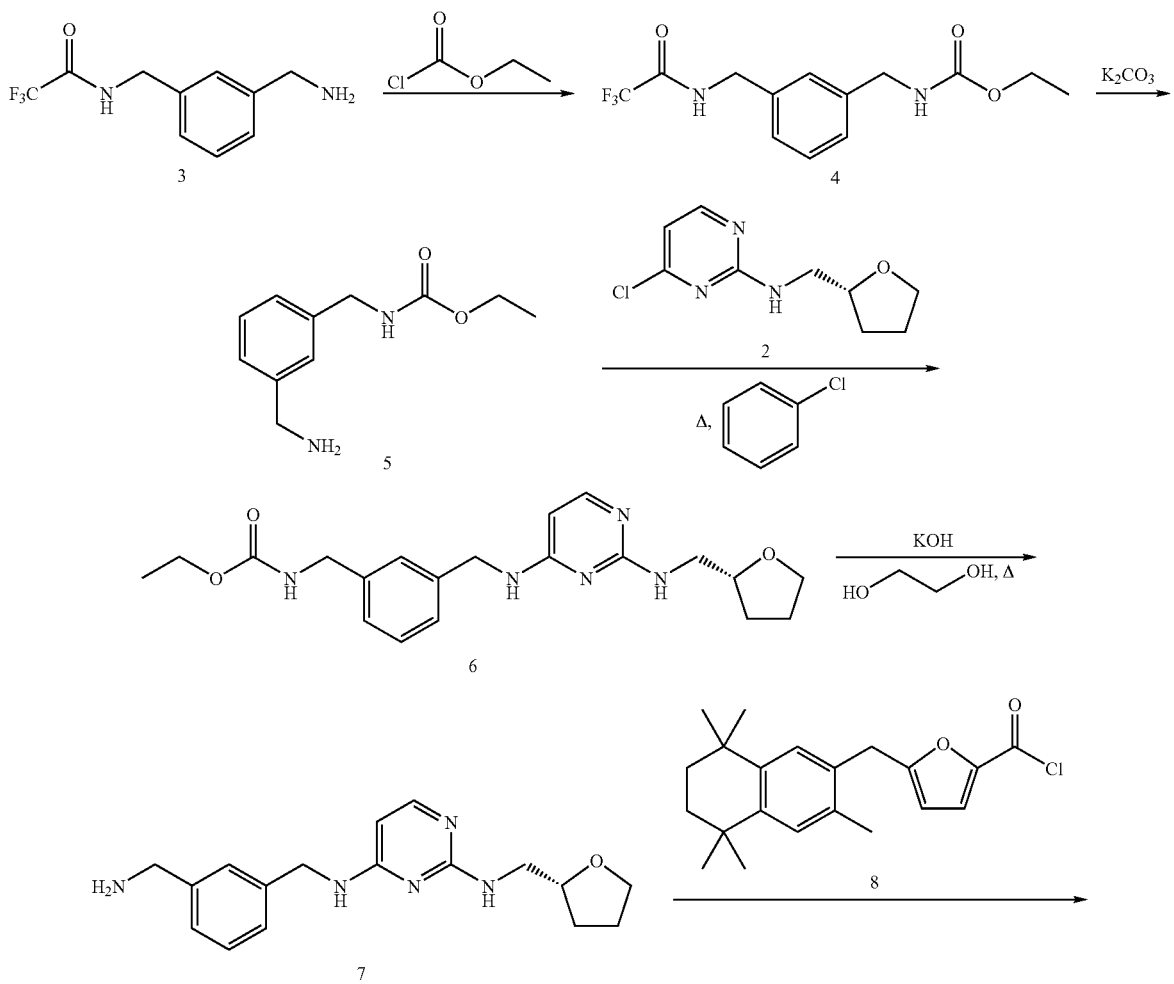

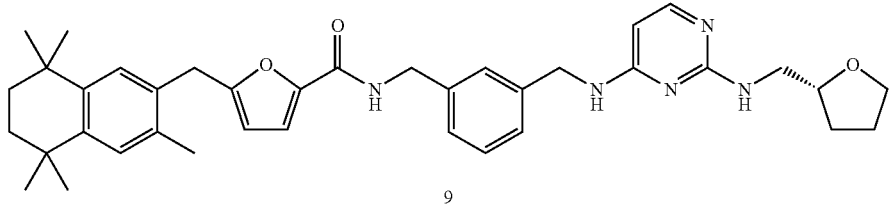

9

Preparation of ethyl 3-(aminomethyl)benzylcarbamate 5.

To a solution of N-[3-(aminomethyl)benzyl]-2,2,2-trifluoroacetamide 3 (10.6 g, 43.1 mmol) was added ethyl chloroformate (1 eq.) followed by triethylamine. Reaction was stirred at room temperature for 30 min. Crude product was extracted with methylene chloride and concentrated to give ethyl 3-{[(trifluoroacetyl)amino]methyl} benzylcarbamate 4. This crude product was dissolved in methanol (100 mL) and 2 $K_2CO_3$ (100 mL) and stirred overnight. Reaction mixture was basified to pH 14 with 20% NaOH, extracted with methylene chloride, wash with brine and dried over magnesium sulfate to yield 5 (5.2 g)

Preparation of ethyl 3-{[(2-{[(2R)-tetrahydro-2-furanylmethyl]amino}-4-pyrimidinyl)amino]methyl}benzylcarbamate 6

To a solution of ethyl 3-(aminomethyl)benzylcarbamate 5 yield 4-chloro-N-[(2R)-tetrahydro-2-furanmethyl]-2-pyrimidinamine 2 in chlorobenzene was added triethylamine. Reaction mixture was reflux overnight. The solution was cooled to room temperature and loaded on a silica gel column and eluted with hexane/ethyl acetate (1:1 v/v) to yield ethyl 3-{[(2-{[(2R)-tetrahydro-2-furanylmethyl]amino}4-pyrimidinayl)amino]methyl}benzylcarbamate 6 (73% yield).

Ethyl 3-{[(2-{[(2R)-tetrahydro-2-furanylmethyl]amino}4-pyrimidinyl) amino]methyl}benzylcarbamate 6 was dissolved in ethylene glycol and potassium hydroxide (1:1 v/v). The solution was heated to 100° C. overnight. The mixture was cooled to room temperature and extracted with chloroform, washed with brine, and dried over magnesium sulfate to yield $N^4$-[3-aminomethyl0benzyl]-$N^2$-[(2R)-tetrahydro-2-furanylmethyl]-2,4-pyrimidinediamine 7 (82% yield).

Preparation of 5-[(3,5,5,8,8-pentamethyl-5,6,7,8-tetrahydro-2-naphthalenyl)methyl]-N-(3-{[(2-{[(2R)-tetrahydro-2-furanylmethyl]amino})-4-pyrimidinyl)amino]methyl}benzyl)-2-furamide 9.

Ethyl 3-{[(2-{[(2R)-tetrahydro-2-furanylmethyl]amino}-4-pyrimidinyl amino]methyl}benzylcarbamate 6 was dissolved in ethylene glycol and potassium hydroxide (1:1 v/v). The solution was heated to 100° C. overnight. The mixture was cooled to room temperature and extracted with chloroform, washed with brine, and dried over magnesium sulfate to yield N'-[3-(aminomethyl0benzyl]-N'-[(2R)-tetrahydro-2-furanylmethyl]-2,4-pyrimidinediamine 7 (82% yield). This product, 7, (182 mg, 0.580 mmol) and 2-furoyl chloride reagent 8 was dissolved dichloromethane followed by triethylamine. Reaction was stirred at room temperature overnight. Crude compound was purified on silica gel column and eluted ethyl acetate/hexane (4:1 v/v) to yield S-[(3,5,5,8,8-pentamethyl-5,6,7,8-tetrahydro-2-naphthalenyl)methyl]-N-(3-{[(2-{[(2R)-tetrahydro-2-furanylmethyl]amino}-4-pyrimidinyl) amino]methyl}benzyl)-2-furamide 9 (159.1 mg). $^1$H NMR (CDCl$_3$): 61.19 (s, 6H), 1.26 (s, 6H), 1.65 (m, 5H), 1.92 (m, 3H), 2.23 (s, 3H), 3.45 (m, 1H), 3.5 (m, 1H), 3.7 (m, 1H), 3.9 (m, 3H), 4.05 (m, 1H), 4.50 (d, 2H), 4.58 (d, 2H), 5.01 (brd, 1H), 5.30 (brd, 1H), 5.71 (d, 1 h), 6.03 (d, 1H), 6.61 (t, 1H), 6.99 (s, 1H), 7.06 (s, 1H), 7.07 (s, 1H), 7.28 (m, 4H), 7.80 (d, 1H). MS: 622.4 (M+1).

Synthesis of 5-[(3,5,5,8,8-pentamethyl-5,6,7,8-tetrahydro-2naphthalenzyl) methyl]-N-(3-{[(4-{[(2S)-tetrahydro-2-furanylmethyl]amino}-2-pyrimidinyl)amino]methyl}benzyl)-2-furamide 12.

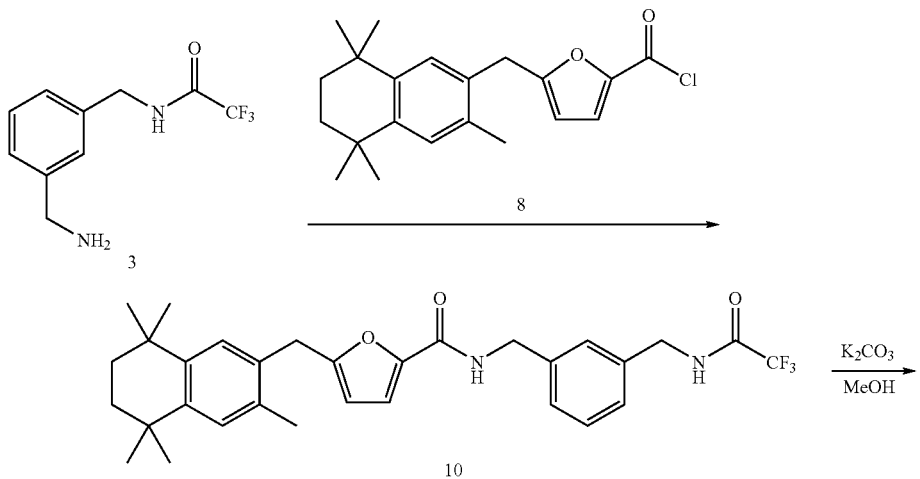

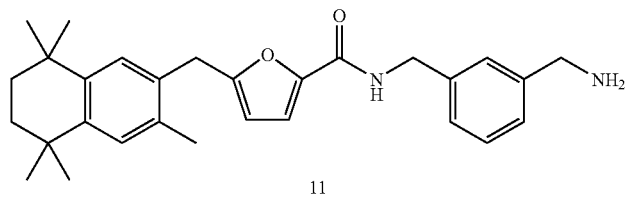

11

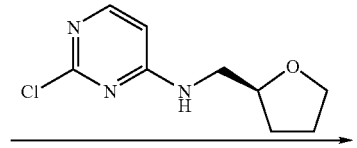

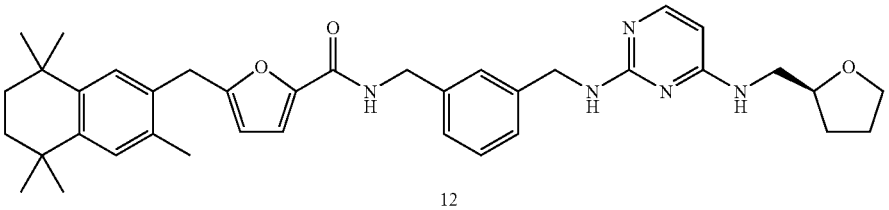

12

Preparation of N-[3-(aminomethyl) benzyl]-5-[(3,5,5,8,8-pentamethyl-5,6,7,8-tetrahydro-2-naphthalenyl)methyl]-2-furamide 11.

To a solution of N-[3-(aminomethyl)benzyl]-2,2,2-trifluoroacetamide 3 and 2-furoyl chloride reagent 8 was added triethylamine. Reaction mixture was stirred at room temperature for 1 hour. Crude mixture was purified by silica gel chromatography eluting with hexane/ethyl acetate (4:1 v/v) to yield 5-[(3,5,5,8,8-pentamethyl-5,6,7,8-tetrahydro-2-naphthalenyl)methyl]-N-(3-{[(trifluoroacetyl)amino]methyl}benzyl)-2-furamide 10. The purified compound was dissolve in methanol (100 mL) and potassium carbonate in water (2M, 100 mL). Reaction was heated to 70° C. overnight. The solution was cooled to room temperature, basified with 20% NaOH to pH 14, extract with methylene chloride, washed with brine, and dried over magnesium sulfate to yield N-[3-(aminomethyl) benzyl]-5-[(3,5,5,8,8-pentamethyl-5,6,7,8-tetrahydro-2naphthalenyl)methyl]-2-furamide 11 (4.97 g, 85.1% yield).

Preparation of 5-[(3,5,5,8,8-pentamethyl-5,6,7,8-tetrahydro-2-naphthalenzyl) methyl]-N-(3-{[(4-{[(2S)-tetrahydro-2furanylmethyl]amino}-2-pyrimidinyl)amino]methyl}benzyl)$_2$-furamide 12.

To a solution of N-[3-(aminomethyl) benzyl]-5-[(3,5,5,8,8-pentamethyl-5,6,7,8-tetrahydro-2-naphthalenyl)methyl]-2-furamide 11 in chlorobenzene was added and 2-chloro-N-[(2S)-tetrahydro-2-furanmethyl]4-pyrimidinamine and triethylamine. Reaction mixture was reflux overnight. The cooled mixture was then purified by silica gel chromatography followed by HPLC. To yield of 5-[(3,5,5,8,8-pentamethyl-, 5,6,7,8-tetrahydro-2naphthalenzyl) methyl]-N-(3-{[(4-{[(2S)-tetrahydro-2furanylmethyl]amino}-2-pyrimidinyl)amino]methyl}benzyl)-2-furamide 12. $^1$H NMR (CDCl$_3$): δ 1.01 (s, 6H), 1.25 (s, 6H), 1.43 (m, 1H), 1.56 (s, 4H), 1.70–1.98 (m, 3H), 2.13 (s, 3H), 3.24 (m, 1H), 3.61 (m, 1H), 3.63–3.80 (m, 2H), 3.82 (s, 2H), 3.87 4.06 (m, 1H), 4.37–4.60 4.37 (d, 2H), 4.60 (d, 2H), 5.73 (d, 1H), 5.92 (d, 1H), 6.3 (brd, 1H), 6.75 (brd, 1H), 6.92 (s, 1H), 6.98 (d, 1H), 7.0 (s, 1H), 7.09–7.26 (m, 4H), 7.4 (s, 1H), 9.5 (brd, 1H). MS (APCI): 622.3 (M+1).

EXAMPLES OF HETEROCYCLIC-CONTAINING COMPOUNDS

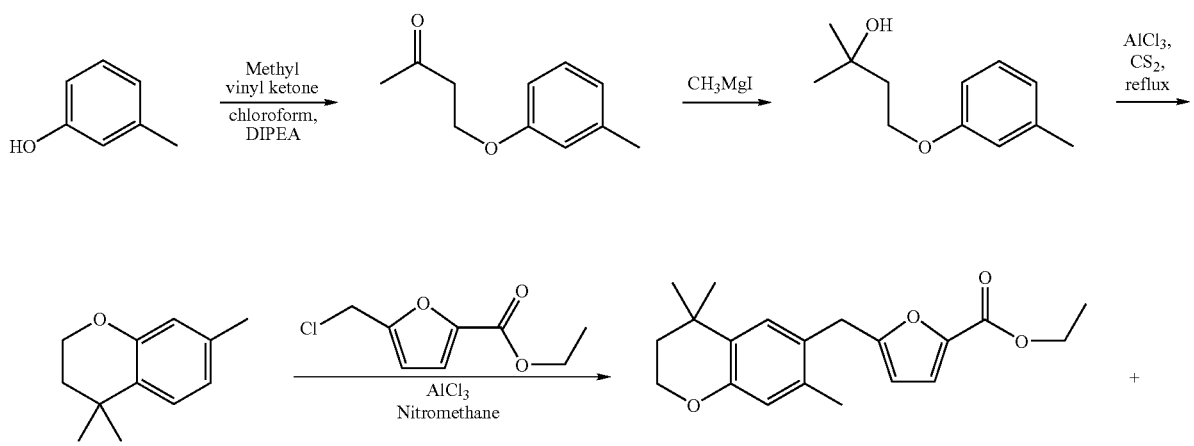

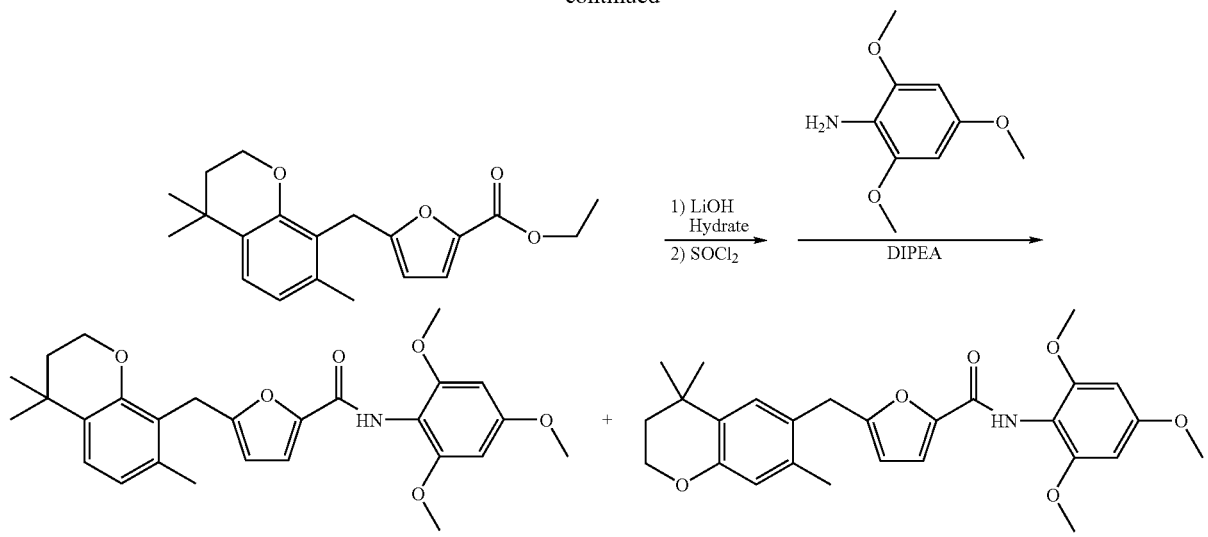

4-(3-methylphenoxy)-2-butanone:

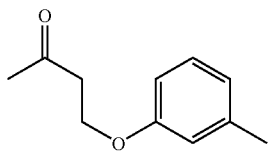

To m-Cresol (4.0 g, 37 mmol), methyl vinyl ketone (3.2 mL, 37 mmol) in chloroform (25 mL), was added diisopropyl ethyl amine. The mixture was heated at reflux for 16 h, allowed to cool to room temperature and evaporated. The residue has 50% product and 50% starting material. The starting material was separated as t-butyldimethyl silyl ether. The product was isolated via plug filteration using silica gel 50% hexane/ethyl acetate. Yield 4.5 g (68%). As an alternative purification procedure, the crude reaction mixture was evaporated, dissolved in DMF (0.2M) and 0.5 equivalents of imidazole and 0.5 equivalents of tBDMSCI were added. The reaction was stirred for 3 hr at room temperature and then the solvents were removed in vacuo. To the residue was added 75 mL ethyl acetate and 75 mL water (ratio of 1/1). The ethyl acetate layer was separated and dried over Na$_2$SO$_4$. The solvents were removed in vacuo. The crude material was placed on a pad of silical gel and the silylated m-cresol was removed with hexanes. The product was obtained by eluting with 5–10% ethyl acetate in hexanes. The solvents were removed in vacuo to give the desired product. $^1$H(CDCl$_3$):7.15 (t, 1H), 6.65–6.80(m, 2H), 4.25 (t, 2H), 2.75 (t, 2H), 2.25 and 2.35 (2 s, 3H each).

2-Methyl-4(3-methylphenoxy)-2-butanol:

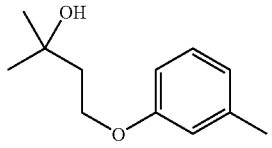

To a solution of methyl magnesium bromide in ether (50 mL), prepared from Mg (572 mg, 23.56 mmol) and MeI (3.34 g, 23.56 mmol), was added 4(3-methylphenoxy)-2-butanone (2.1 g, 11.78 mmol) in 10 mL ether. The solution was stirred at room temperature for 30 minutes, after which it was quenched with water and dilute Hydrochloric acid. The organic layer was separated, dried over sodium sulfate, filtered through a silica plug to give a colorless syrup 1.91 g (83%) mass spectral analysis using APCI+ve 177 (M+—OH).

4,4,7-trimethyl chroman:

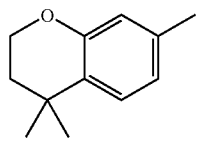

To aluminium chloride (1.3 g, 9.79 mmol) in 40 mL carbon disulfide, was added 2-methyl-4(3-methylphenoxy-2-butanol (1.9 g, 9.79 mmol) in 10 mL carbon disulfide. The mixture was heated at reflux for 2 h. Solvent evaporated, the residue diluted with 50 mL of ethyl acetate, and 10 mL of water. The organic layer was separated, dried over sodium sulfate, and purified via column chromatography to give a light yellow syrup 1.5 g (87%). $^1$H(CDCl$_3$): 7.05(br d, 1H), 6.87 (dd, 1H), 6.69 (d, 1H), 4.20 (t, 2H), 2.35 (s, 3H), 1.80 (t, 2H), 1.40 (s, 6H).

Ethyl-5[(4,4,7-trimethyl-3,4-dihydro-2H-chromen-6-yl) methyl]-2-furoate, and ethyl-5-[(4,4,7-trimethyl-3,4-dihydro-2H-chromen-8-yl)methyl]-2-furoate:

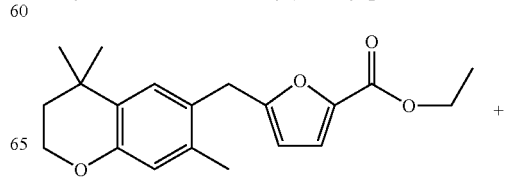

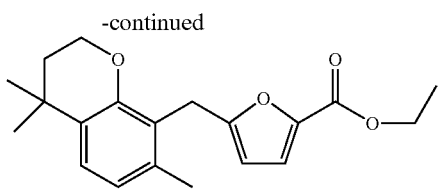

To zinc chloride (950 mg, 6.97 mmol) in nitromethane (20 mL), was added a mixture of 4,4,7-trimethyl chroman (1.23 g, 6.97 mmol) and ethyl-5-chloromethyl-2-furoate (656 mg, 3.48 mmol) in nitromethane (15 mL). The mixture was stirred at room temperature for 16 h. The reaction was evaporated to dryness and triturated with ethyl acetate-water (1:1, 100 mL). The organic layer on usual work up, and plug filtration using hexanes in ethyl acetate (9:1) gave mixture of these two compounds. 1.34 g (46% based on chroman). N-(2,4,6-trimethoxyphenyl)-5-[(4,4,7-trimethyl-3,4-dihydro-2H-chromen-6-yl)methyl]-2-furamide and N-(2,4,6-trimethoxyphenyl)-5-[(4,4,7-trimethyl-3,4-dihydro-2H-chromen-8-yl)methyl]-2-furamide:

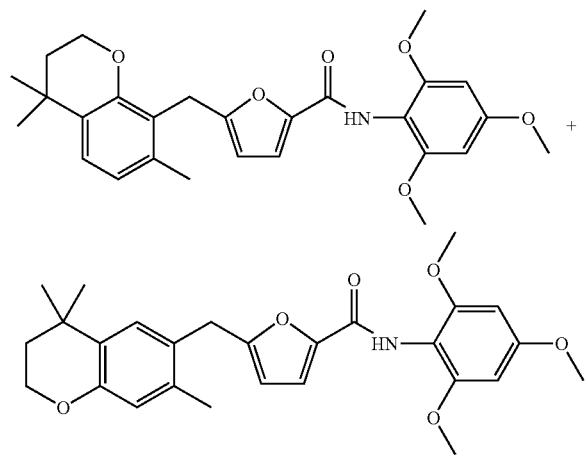

To a mixture of ethyl-5-[(4,4,7-trimethyl-3,4-dihydro-2H-chromen-6-yl)methyl]-2-furoate, and ethyl-5-[(4,4,7-trimethyl-3,4-dihydro-2H-chromen-8-yl)methyl]-2-furoate (1.34 g, 3.74 mmol) in THF-MeOH—H2O (7:5:5, 20 mL) was added lithium hydroxide monohydrate (784 mg, 18.7 mmol). The mixture was stirred for 4 h at room temperature. The mixture evaporated to dryness, diluted with 30 mL ethyl acetate and 50 mL of water. After acidification with diluted HCl, ethyl acetate layer was separated, dried and evaporated in vacuo to give a mixture of corresponding acids, 1.03 g (quantitative). These acids were not separable using typical column chromatography or crystallization. To the mixture of the acids (200 mg, 0.66 mmol) in dichloromethane (30 mL) was added thionyl chloride (392 mg, 3.3 mmol). The mixture was refluxed for 1 h and evaporated. The residue was dissolved in hexane-ethyl aceatate (9:1, 20 mL) and filtered through a silica gel plug (0.5 cm×1.0 cm). To the residue in 10 mL ethyl acetate, was added 2,4,6-trimethoxyphenyl amine hydrochloride (145 mg, 0.66 mmol) followed by diisopropyl ethyl amine (256 mg, 1.98 mmol). The mixture was stirred at room temperature for 16 h. The reaction was quenched with water (10 mL), ethyl acetate layer separated. The combination and column and HPLC purification gave 15 mg and 21 mg of two components (12%). The isomers were separated using reverse phase HPLC chromatography.

Linear isomer: 1H(CDCl$_3$):7.46(br s, 1H), 7.23 (br s, 1H), 7.14 (br s, 1H), 7.02 (s, 2H), 6.63 (s, 1H), 6.15 (s, 2H), 6.0(d, 1H), 4.17 (t, 2H), 3.93 (s, 3H), 3.81, 3.80 (2 s, 3H each), 2.21 (s, 3H), 1.81 (t, 2H), 1.29 (s, 6H). M+ at 466.2. Angular isomer: AXC07302: 7.25 (br s, 1H), 6.91 (d, 1H), 6.88 (d, hidden, 1H), 6.53 (d, 1H), 5.95 (s, 2H), 5.72 (d, 1H), 3.96 (t, 2H), 3.8 (s, 3H), 3.6 (s, 6H), 2.07 (s, 3H), 1.59 (t, 2H), 1.11 (s, 6H). M+ at 466.1

EXAMPLES OF AROMATIC COMPOUNDS

Compound A

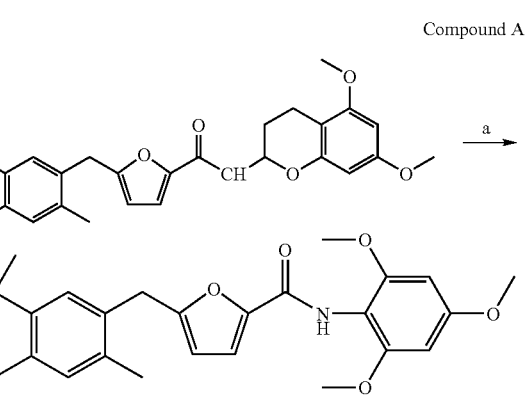

a. Ethyl Acetate, triethyl amine, overnight

Compound B

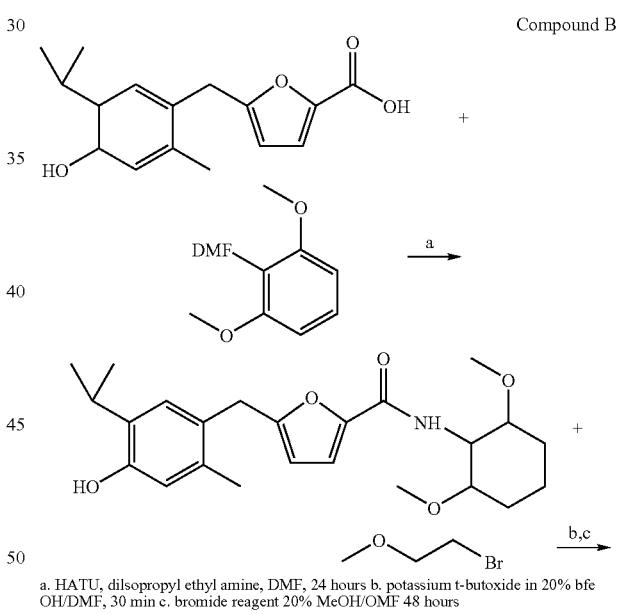

a. HATU, diisopropyl ethyl amine, DMF, 24 hours b. potassium t-butoxide in 20% bfe OH/DMF, 30 min c. bromide reagent 20% MeOH/OMF 48 hours

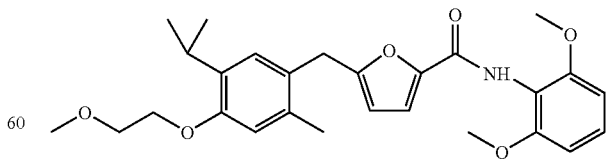

Compound 183

Thymol (1.0 eq, 33.3 mmol) and methyl 5-(chloromethyl)-2-furoate (1.0 eq, 33.3 mmol) were dissolved in nitromethane (120 mL, 0.2M). Aluminum trichloride (1.0 eq, 33.3 mmol) dissolved in 25 mL nitromethane was added to the above solution under nitrogen and heated to slow reflux over 10 min. The heat was turned off and left under nitrogen overnight. The reaction was quenched with 100 mL of water and extracted with dichloromethane. The crude mixture was evaporated to dryness and loaded onto plug chromatography column (1 g crude/100 g silica gel ratio). The column was eluted with 7 and 11% ethyl acetate/hexanes to yield the desired product (2.9 g, 30%). The ester was hydrolyzed to acid by lithium hydroxide in THF/MeOH/H$_2$O (35/25/25).

To a solution containing the 5-(4-hydorxy-5-isopropyl-2-methylbenzyl)-2-furoic acid (10 eq, 3.6 mmol, 0.5M), and 2,6-dimethoxyaniline (10 eq, 3.6 mmol) were dissolved in DMF. To this mixture, HATU (1.0 eq, 3.6 mmol) and di-isopropyl ethyl amine (1.0 eq, 3.6 mmol) were added and stirred overnight. The mixture was heated for 10 min at 45° C. The solution was placed into ethyl acetate (3× volume) and washed with water. The organic layer was evaporated to syrup and eluted on plug column chromatography (1:100 g crude/g silicagel) with 30 and 50% ethyl acetate/hexane to yield: N-(2,6-dimethoxyphenyl)-5-(4-hydroxy-5-isopropyl-2-methylbenzyl)-2furamide (820 mgs, 55% yield). $^1$HNMR (CDCl$_3$) 7.22 ppm (1H, t, J=8.68 Hz), 7.08 ppm (1H, d, J=3.40 Hz), 6.99 ppm (1H, s), 6.64 ppm (2H, d, J=8.68 Hz), 6.61 ppm (1H, s), 5.97 ppm (1H, d, k=3.40 Hz), 3.95 ppm, (2H, s), 3.85 ppm, (6H, s), 3.17 ppm, (1H, pentet, J=6.8 Hz) 2.23 ppm, (3H, s), 1.25 ppm (3H, s), and 1.23 ppm (3H, s).

Potassium t-butoxide was dissolved (1.05 eq, 0.128 mmol) in MeOH (24 μL). To the solution of above furamide (1.0 eq, 0.122 mmol, 1M) in DMF, t-butoxide solution was added and stirred for 30 min. The 2-Bromoethyl methyl ether (10 eq, 0.122 mmol) was added (20% MeOH/DMF, 1M) and stirred at room temperature for 48 hours and purified by reverse phase HPLC (method: 35–75% 90 min acetonitrile in 0.1% aqueous TFA) to yield (8.5 mgs, 15% yield). $^1$H NMR (CDCl$_3$): 7.04 ppm (1H, J=8.31 Hz, t), 6.85 ppm (1H, J=3.40, d), 6.80 ppm (1H, s), 6.53 ppm (1H, s), 6.48 (2H, J=8.31 Hz, d), 5.76 (1H, J=3.40 Hz, d), 3.88 (2H, J=3.40/4.53 Hz, dd), 3.78 (2H, s), 3.58 (6H, s), 3.54 (2H, J=3.40/4.54 Hz, dd), 3.20 (3H, s), 3.07(1H, 3=7.2 Hz, pentet), 2.04 (3H, s), 0.97 (3H, s), 0.95(3H, s).

Compound A 1,1,6-trimethyl-1,2,3,4-tetrahydronaphtalene was synthesized from reference: John J. Parlow *Tetrahedron* Vol 49 (13) 2577. It was then connected with methyl 5-(chloromethyl)-2-furoate by Friedles-Crafts reaction as previously stated to yield two major regio-isomers. The desired isomer was separated after hydrolysis using three to five succesive recrystalization from 10% acetone/heptane (1 g/10 mL) system. The acid was then converted to acid chloride with thionyl chloride as previously stated.

To a solution of 5-[(3,8,8-trimethyl-5,6,7,8-tetrahydro-2-naphthalenyl)methyl]-2-furoyl chloride (10 eq, 0.32 mmol, 0.2M) in 2 mL ethyl acetate, the 2,4,6 trimethoxy aniline mono HCl salt (10 eq, 0.32 mmol) was added. Triethyl amine (excess) was added to this mixture and stirred overnight. The crude product was dried under vacuo and purified through plug column chromatography (1:100 crude mass/silicagel ratio) by eluting with 20 and 30 percent ethyl acetate/hexane solution. In some cases, the regio-isomers were separated by recrystallization in twenty five percent ethyl acetate/hexanes (1 g/75 mL compound/volume) to yield N-(2,4,6-trimethoxylphenyl)-5-[(3,8,8-trimethyl-5,6,7,8-tetrahydro-2-naphthalenyl)methyl]-2-furamide (120 mgs, 82% yield). $^1$H NMR (CDCl$_3$) 7.28 ppm (1H, broad), 7.12 (1H, s), 7.08 (1H, 3=3.40 Hz, d), 6.89 (1H, s), 6.19 (2H, s), 6.00 (1H, J=3.40 Hz, d), 3.97 (2H, s), 3.83 (3H, s), 3.82 (6H, s) 2.73 (2H, J=6.05 Hz, t), 2.25 (3H, s), 1.84–1.76(2H, multiplet), 1.69–1.63 (2H, multiplet), 1.59 (3H, s), 1.26(6H, s) elemental: expected C(72.55), H(7.18), N(3.02); actual C(72.67), H(7.22), N(2.98).

Compound 228

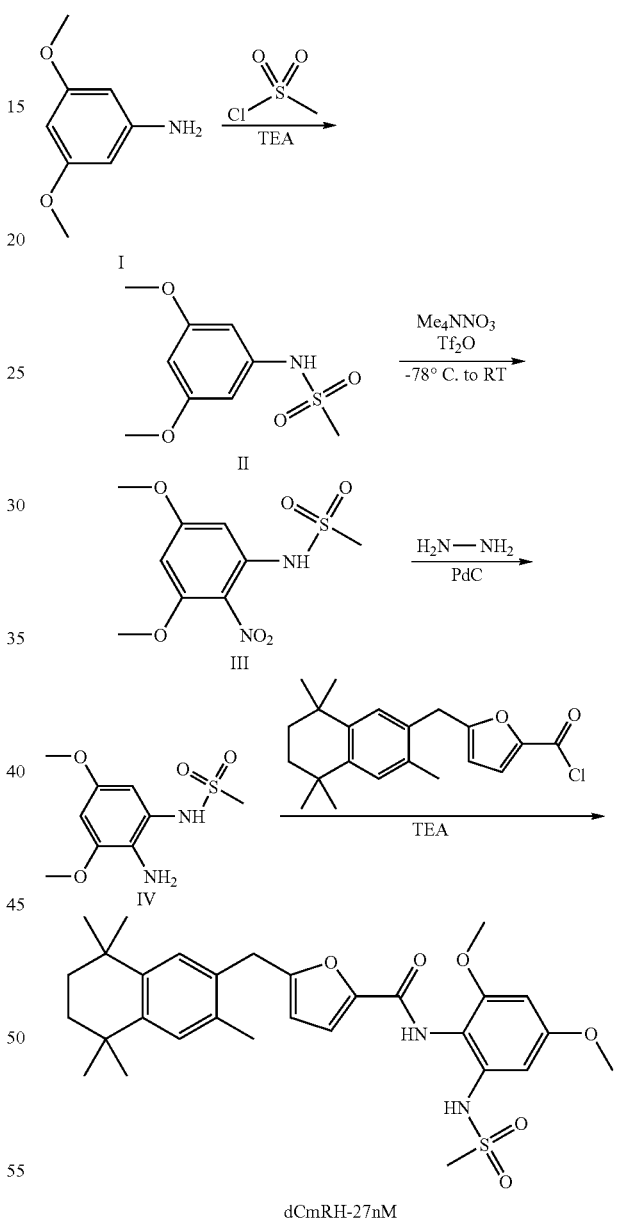

dCmRH-27nM

Compound II To a solution of 3,5-dimethoxyaniline (Compound I, 1.53 g, 10 mmol) in DCM (20 ml) was added methanesulfonyl chloride (0.88 mL, 10 mmol). TEA (1.4 mL, 10 mmol) was added dropwise. The reaction mixture was stirred at rt for 15 h. The crude product was taken to dryness and purified by flash chromatography (30% ethyl acetate/hexanes), yielding compound II (2.10 g, 91%) as a white solid. $^1$H NMR δ(300 Hz, CDCl$_3$) 2.96(s, 3H), 3.71 (s, 6H), 6.20 (d, 1H, J=3 Hz), 6.34 (d, 2H, J=3 Hz), 6.76 (s, 1H). APCI-MS m/z 232 (M+H)⁺.

Compound III To a solution of (CH₃)₄NNO, (1.12 g, 7.89 mmol) in DCM (10 mL) was added triflic anhydride dropwise. The reaction mixture was stirred at 0° C. for 1.5 h. In a dropping funnel was placed the compound II (1.75 g, 7.51 mmol) in 10 mL of DCM and the solution was added to the nitronium triflate reaction mixture at −78° C. The reaction mixture was kept in −78° C. for 30 min and gradually warmed to rt. It was stirred for 15 h. The reaction was quenched with 5% NaHCO₃ (5 mL), the mixture was stirred for 30 min. The aqueous layer was extracted with DCM (3×20 mL). Combined DCM layer was dried over Na₂SO₄. The crude product was purified by HPLC, yielding compound III (250 mg, 11%) as a white solid. ¹H NMR δ (300 Hz, CDCl₃) 3.03(s, 3H), 3.87 (s, 3H), 3.90 (s, 3H), 6.32 (d, 1H, J=3 Hz), 6.88 (d, 1H, J=3 Hz), 8.31 (s, 1H). APCI-MS m/z 275(M−H)⁻.

Compound IV To a solution of compound III (106 mg, 0.38 mmol) in EtOH (2 mL) was added 20 mg Pd/C and NH₂NH₂ (1 mL). The reaction mixture was refluxed for 9 h. The reaction mixture passes through a celite pad. The solution was taken to dryness to afford compound IV as a brown solid (90 mg, 95%). This compound was used directly in the next step.

Compound 228

To a solution of compound IV (39 mg, 0.16 mmol), 5-[(3,5,5,8,8-pentamethyl-5,6,7,8-tetrahydro-2-naphthalenyl]-2-furoyl chloride (60 mg, 0.174 mmol) in DCM (1 mL) was added TEA (44 µL, 0.31 mmol). The reaction mixture was stirred at rt for overnight. Flash chromatography (30% ethyl acetate/hexanes) yields Compound 228 (65 mg, 74%) as a white solid. ¹H NMR δ (300 Hz, CDCl₃) 1.04 (m, 12H), 1.45 (m, 4H), 2.09 (s, 3H), 2.71(s, 3H), 3.60 (s, 3H), 3.63 (s, 3H), 3.78 (s, 2H), 5.89 (d, 1H, J=3 Hz), 6.17 (d, 1H, J=3 Hz), 6.58 (d, 1H, J=3 Hz), 6.85 (s, 1H), 6.90 (s, 1H), 6.96 (d, 1H, J=3 Hz), 7.90 (s, 1H), 8.24 (s, 1H). APCI-MS m/z 556 (M+H)⁺.

ADDITIONAL EXAMPLES (NMR) OF SOME COMPOUNDS ARE SHOWN BELOW

Compound 20
¹H NMR δ (300 Hz, CDCl₃) 1.26 (m, 12H), 1.66 (m, 4H), 2.28 (s, 3H), 3.82 (s, 6H), 3.96 (s, 2H), 6.04 (d, 1H, J-6 Hz), 6.60 (s, 1H), 6.62 (s, 1H), 7.05 (m, 3H), 7.23 (t, 1H, 6 Hz), 7.44 (s, 1H). APCI-MS m/z 462 (M+H)⁺.

Compound 126
¹H NMR δ (300 Hz, DMSO) 2.20 (s, 3H), 2.27 (s, 6H), 3.71 (s, 6H), 3.98 (s, 2H), 5.93 (d, 1H, J=3 Hz), 6.68 (s, 1H), 6.69 (s, 1H), 6.86 (d, 2H, J=3 Hz), 7.10 (d, 1H, J=3 Hz), 7.23 (t, 1H, J=7 Hz), 9.04 (s, 1H). APCI-MS m/z 379 (M+H)⁺.

Compound 140
¹H NMR δ (300 Hz, DMSO) 2.28 (s, 3H), 2.32 (s, 3H), 2.42 (s, 3H), 3.72 (s, 6H), 4.10 (s, 2H), 6.00 (d, 1H, J=3 Hz), 6.60 (s, 1H), 6.68 (s, 1H), 6.71 (s, 1H), 7.10 (m, 2H), 7.24 (t, 1H, J=6 Hz), 9.04 (s, 1H). APCI-MS m/z 458 (M+H)⁻.

Compound 211
¹H NMR δ (300 Hz, CDCl₃) 3.76–3.83 (m, 15H), 4.07 (s, 2H), 5.95 (d, 1H, J=3 Hz), 6.60 (s, 1H), 6.57–6.62 (m, 3H), 6.78 (d, 1H, J=9 Hz), 7.03 (d, 1H, J=3 Hz), 7.19 (t, 1H, J=6 Hz), 7.46 (s, 1H). APCI-MS m/z 428 (M+H)⁺.

Compound 220
¹H NMR δ (300 Hz, CDCl₃) 3.72–3.77 (m, 15H), 3.90 (s, 2H), 5.78 (d, 1H, J=3 Hz), 6.08 (s, 2H), 6.52–6.55 (m, 2H), 6.94 (d, 1H, J=9 Hz), 7.12 (t, 1H, J=9 Hz), 7.39 (s, 1H). APCI-MS m/z 428 (M+H)⁺.

Compound 226
¹H NMR δ (300 Hz, CD₃OD) 2.33–2.48 (m, 12H), 3.84 (s, 6H), 4.19 (s, 2H), 5.81 (d, 1H, J=3 Hz), 6.73 (d, 2H, J=9 Hz), 7.06 (d, 1H, J=3 Hz), 7.29 (t, 1H, J=9 Hz). APCI-MS m/z 472 (M+H)⁺.

Compound 231
¹H NMR δ (300 Hz, CDCl₃) 0.67 (t, 3H, J=6 Hz), 1.27 (m, 6H), 1.70 (m, 2H), 3.62 (s, 3H), 3.80–3.83 (m, 6H), 4.02 (s, 2H), 6.02 (d, 1H, J=3 Hz), 6.60 (d, 2H, J=9 Hz), 6.83 (d, 1H, J=3 Hz), 7.07–7.19(m, 4H), 7.43 (s, 1H), APCI-MS m/z 438 (M+H)⁺.

Compound 232
¹H NMR δ (300 Hz, CDCl₃) 0.66 (t, 3H, J=6 Hz), 1.23 (m, 6H), 1.54–1.62 (m, 2H), 3.80–3.81 (m, 12H), 4.01 (s, 2H), 6.00 (d, 1H, J=3 Hz), 6.81 (d, 2H, J=9 Hz), 6.82 (d, 1H, J=3 Hz), 7.06–7.28 (m, 4H). APCI-MS m/z 468 (M+H)⁺.

EXAMPLES OF OTHER AROMATIC CONTAINING COMPOUNDS

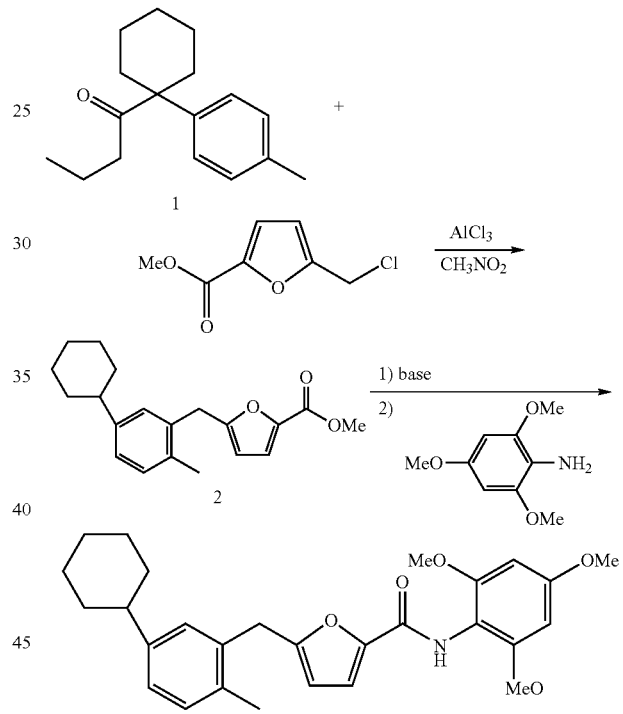

Synthesis of 5-(5-cyclohexyl-2-methylbenzyl)-N-(2,4,6-trimethoxyphenyl)-2-furamide.

To a mixture of compounds 1 (5.0 g, 20.3 µmol) and the methyl furoate (3.5 g, 20.3 mmol) in 100 ml of nitromethane was added a solution of AlCl₃ (5.4 g, 40.6 mol) in CH₂NO₂ (50 ml) at room temperature. The solution was heated to 70~75° C. overnight. The dark brown mixture was cooled to room temperature and slowly poured into 300 ml of ice water. The mixture was extracted with ethylacetate. The concentrated organic layer was purified by silica gel chromatography and eluted with hexane/ethyl acetate (15:1 to 9:1 v/v) to yield 920 mg of compound 2, which was then hydrolyzed and coupled with the trimethoxyaniline according to the general procedure to give the compound in a good yield. ¹HNMR(CDCl₃): a 1.23–1.48 (m, 5H), 1.73–1.86 (m, 5H), 2.31 (s, 3H), 2.51 (m, 1H), 3.83 (s, 1H), 4.02 (s, 2H), 6.03 (s, 1H), 7.44 (s, 1H) MS (APCI): 464.2 (M+1)

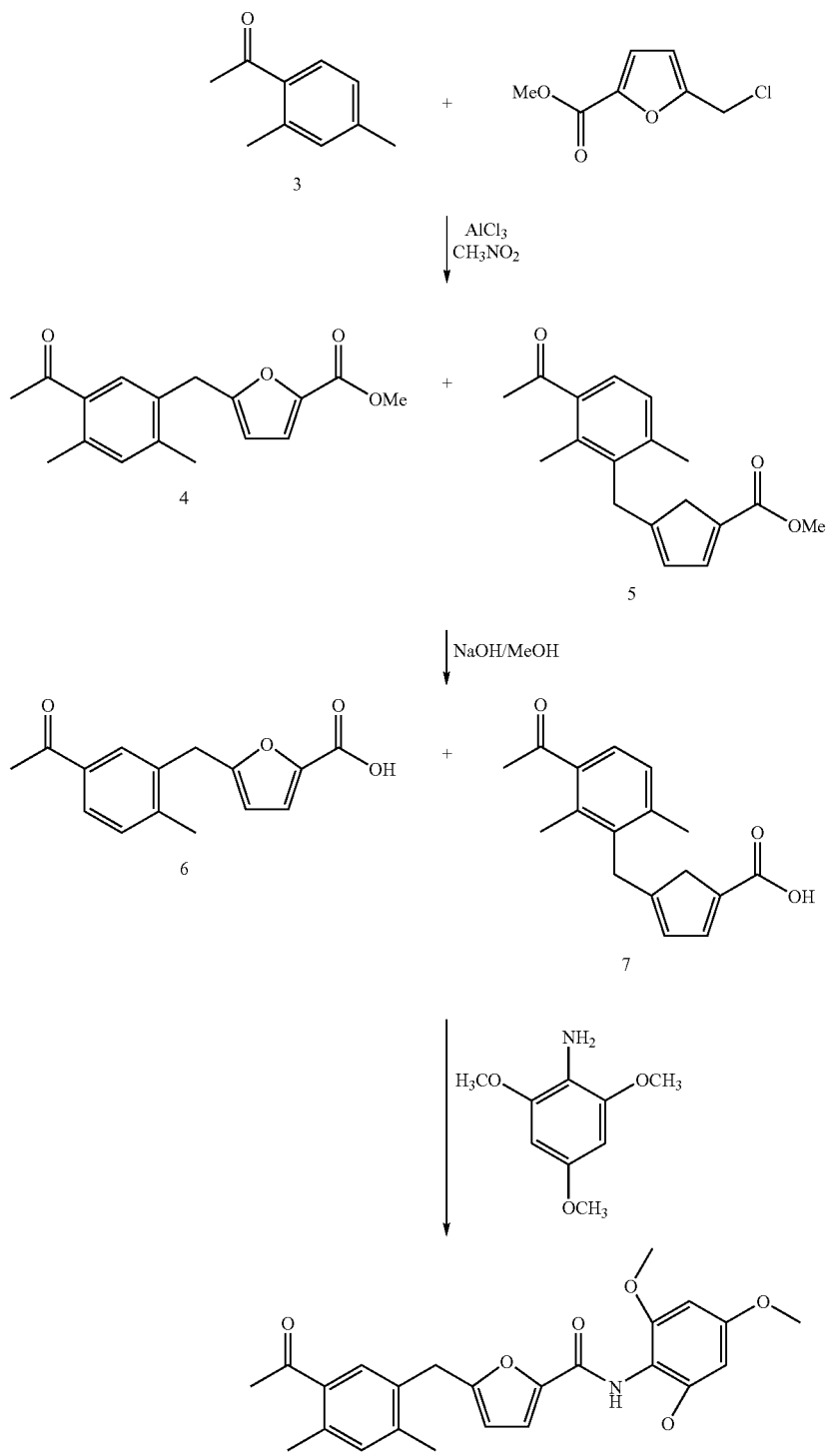

Synthesis of 5(5-acetyl-2,4-dimethylbenzyl)-N-(2,4,6-trimethoxyphenyl)-2-furamide.

A mixture of compound 3 (14 g, 94.4 mmol), methyl furoate (16.4 g, 94.4 mmol) and AlCl$_3$ (25 g, 189 mmol) in 200 mL of nitromethane was stirred and heated to 80° C. overnight. The mixture was worked up and purified by silica gel column, eluted with hexane/ethyl acetate (9:1 v/v) to give a mixture of 4 and 5 (3:1, total 16.2 g). The mixture of 4 and 5 (2.0 g) was hydrolyzed in 2N NaOH/MeOH (1:1 v/v) at room temperature to give a mixture of 6 and 7, which was recrystallized in acetone and heptane to afford 6 (460 mg).

Compound 6 (150 mg, 0.55 mmol) was treated with thionyl chloride and coupled with trimethoxy aniline to give AXC07485 (124 mg). $^1$HNMR (CDCl$_3$): σ 2.31 (s, 3H), 2.50 (s, 3H), 2.54 (s, 3H), 3.80 (s, 9H), 4.02 (s, 2H), 6.00 (d, 1 h), 6.16 (s, 2 h), 7.08 (s, 1H), 7.35 (s, 1H), 7.52 (s, 1H), MS (APCI): 438.7 (M+1)

Synthesis of 5-(5-isopropenyl-2,4-dimethylbenzyl)-N-(2,4,6-trimethoxyphenyl)-2-furamide

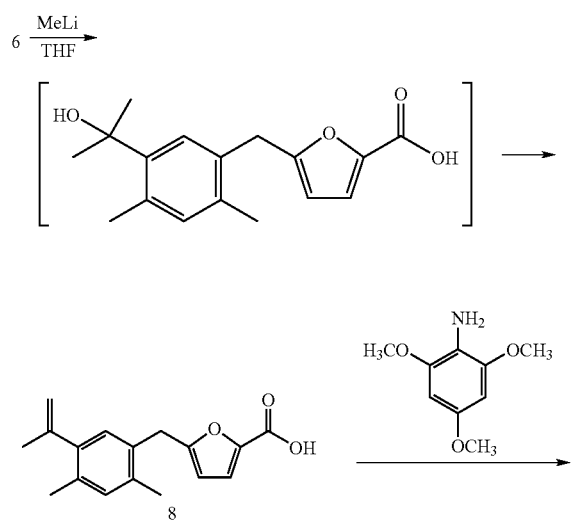

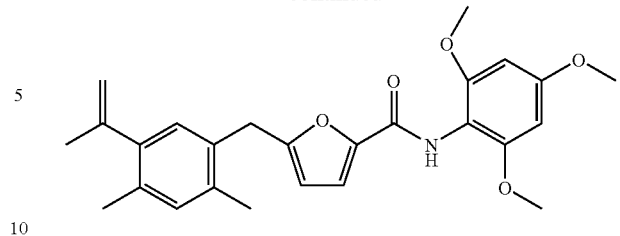

To a solution of compound 6 (250 mg, 0.92 mmol) in 5 mL dry THF at 0° C. under $N_2$ was added methyl lithium (1.4M in hexanes, 3 eq.). The solution was stirred at 0° C. for 3 hours, quench with water and extracted with ethyl acetate. The organic layer was dried over magnesium sulfate and concentrated under reduced pressure. The crude compound was treated with $SOCl_2$ and coupled with trimethoxy aniline to give AXC 07499 (36 mg). $^1$HNMR ($CDCl_3$): σ 1.80 (s, 3H), 2.06 (s, 3 h), 2.11 (s, 3 h0, 3.59 (s, 9H), 3.75 (s, 2H), 4.60 (d, 1H), 4.95 (d, 1H), 5.81 (d, 1H), 5.95 (s, 2H), 6.71 (s, 1H), 6.79 (s, 1H), 6.89 (d, 1H), 7.18 (s, 1H). MS (APCI): 436.2 (M+1).

Synthesis of 5-[(4,6-dimethyl[1,1'-biphenyl]-3-yl)methyl]-N-(2,4,6-trimethoxyphenyl)-2-furamide.

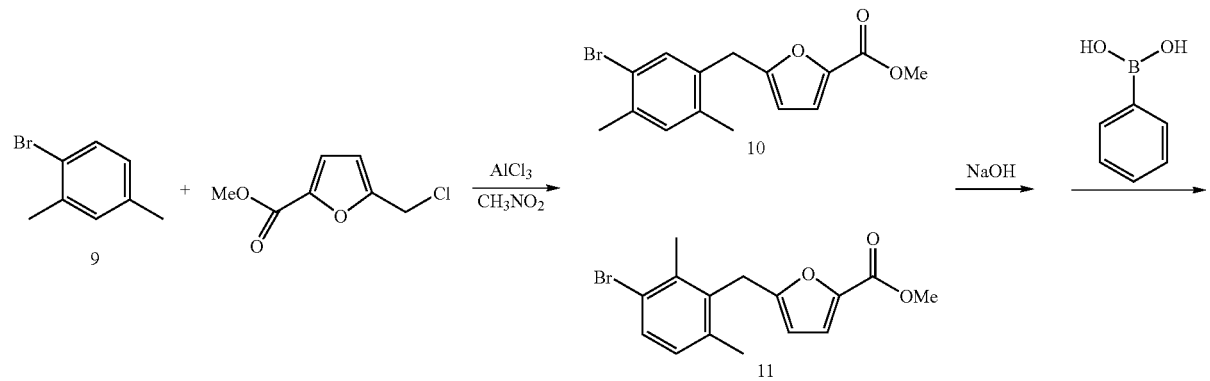

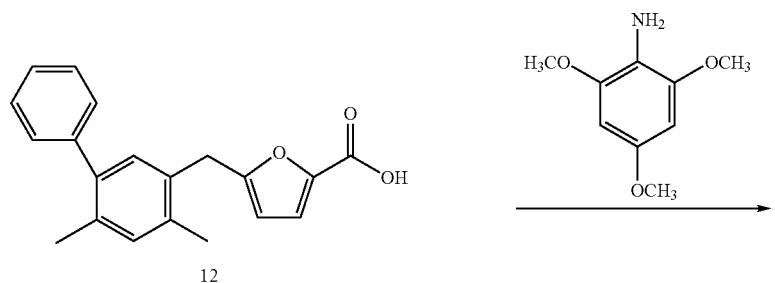

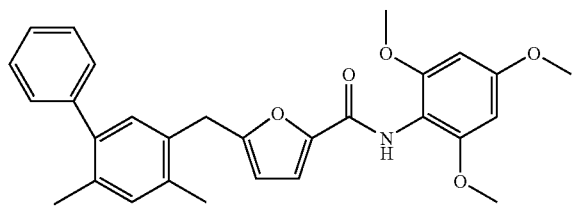

Friedal Crafts reaction of compound 9 (10 g, 57.3 mmol), methyl furoate (12.7 g, 68.7 mmol) and AlCl₃ (9.1 g, 68.7 mmol) was carried out in nitromethane at 80° C. for 2 hours. The solution was poured in 200 mL ice water and extracted with ethyl acetate. The organic layer was concentrated and purified by silica gel column eluted with hexane/ethyl acetate (9:1 v/v) to give a mixture of regioisomers 10 and 11 (15.5 g) with a ratio of 2:1.

The mixture was hydrolyzed in 2N NaOH/MeOH (1:1 v/v) to give the mixture of acid analogs.

The acid mixture (2.3 g, 7.4 mmol), benzene boronic acid (1.1 g, 8.9 mmol), [P(Ph)₃]₄Pd, and potassium carbonate (2N, 11 mL) in DMF (20 mL) was heated to 80° C. overnight. After aqueous work up the residue was passed through a silica gel column and eluted with a mixture of solvent hexane/ethyl acetate/acetic acid (7:3:1 v/v/v) to yield a mixture of 2 regioisomers with was recrystallized in hexane and ethyl acetate to give 12 (610 mg). The compound 12 was coupled with trimethoxyaniline through standard procedure to give AXC07468 in good yield. ¹HNMR (CDCl₃): σ 2.24 (d, 3H), 2.33 (d, 3H), 3.82 (s, 6H), 3.84 (s, 3H), 4.02 (s, 2H), 6.03 (d, 1H), 6.18 (s, 2H), 7.06 (s, 2H), 7.12 (s, 1H), 7.29–7.40 (m, 5H). MS (APCI): 472.1 (M+1).

Synthesis of 5-[5-(2,2-dimethylpropanoyl)-2,4-dimethoxybenzyl]-N-(2,4,6-trimethoxyphenyl)-2-furamide

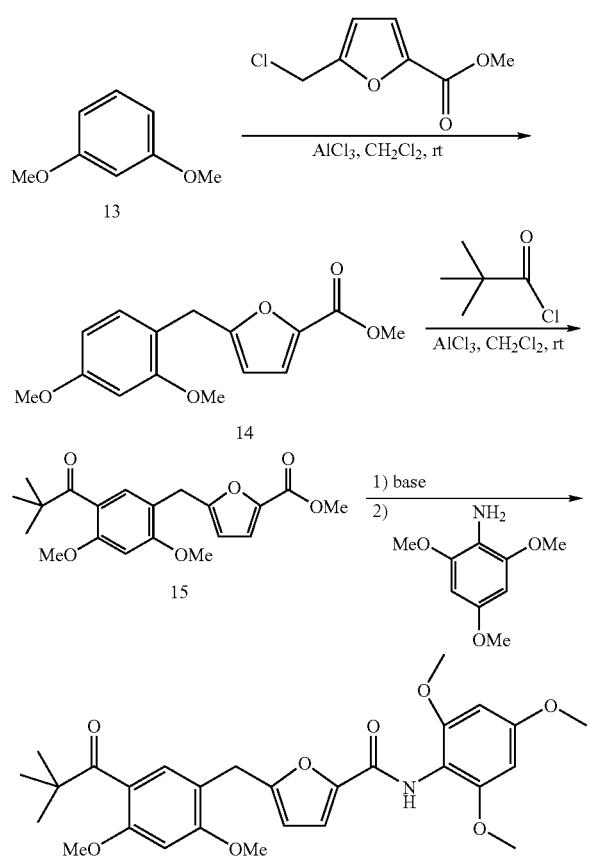

Compound 15 was prepared in two steps of Friedal Crafts reaction (see general procedure) from compound 13 in moderate yield with good regio selectivity. Compound 15 was hydrolyzed and coupled with trimethoxyaniline to give the compound. ¹HNMR(CDCl₃): a 1.18(s, 9H), 3.79 (s, 3H), 3.81 (s, 6H), 3.85 (s, 6H), 3.93 (s, 2H), 6.03 (d, 1H), 6.15 (s, 2H), 6.45 (s, 1H), 6.86 (s, 114), 7.11 (s, 1H), 7.40 (s, 1H). Ms (APCI) 512.1 (M+1).

Synthesis of 5-[(3,5,5,8,8-pentamethyl-5,6,7,8-tetrahydro-2-naphthalenyl)carbonyl]-N-(2,4,6-trimethlxyphenyl-2-furamide and 5-[hydroxy(3,5,5,8,8-pentamethyl-5,6,7,8-tetrahydro-2-naphthalenyl)methyl]-N-(2,4,6-trimethoxyphenyl)-2-furamide

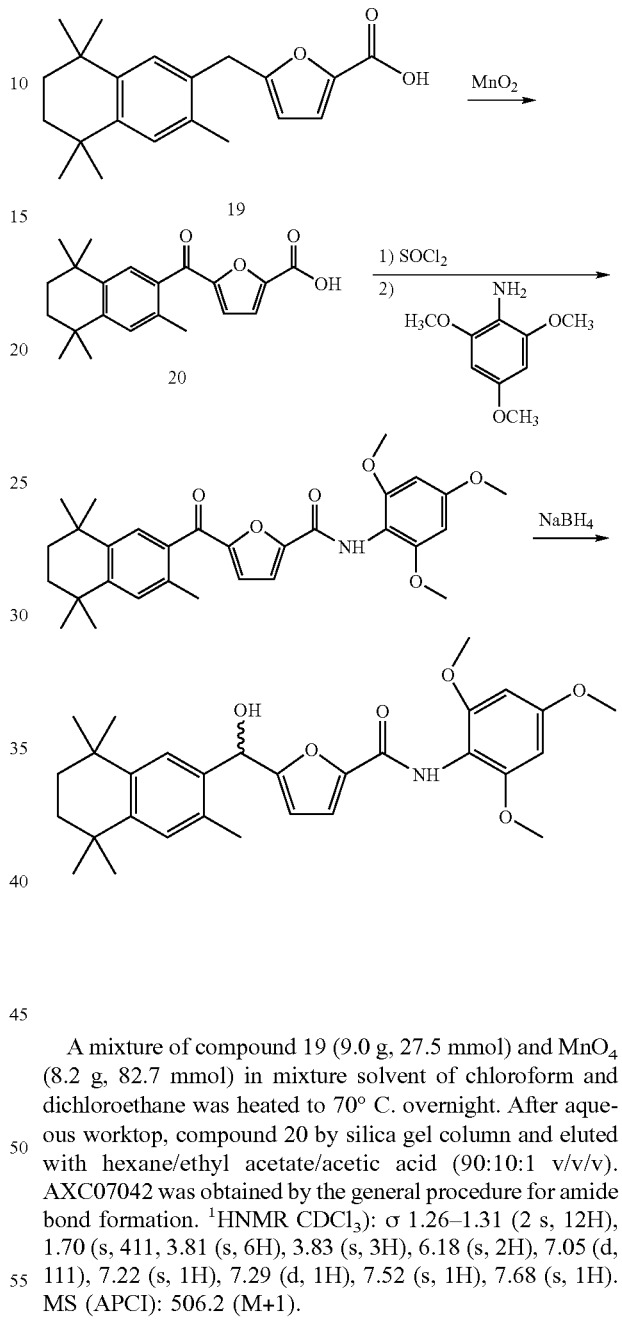

A mixture of compound 19 (9.0 g, 27.5 mmol) and MnO₄ (8.2 g, 82.7 mmol) in mixture solvent of chloroform and dichloroethane was heated to 70° C. overnight. After aqueous worktop, compound 20 by silica gel column and eluted with hexane/ethyl acetate/acetic acid (90:10:1 v/v/v). AXC07042 was obtained by the general procedure for amide bond formation. ¹HNMR CDCl₃): σ 1.26–1.31 (2 s, 12H), 1.70 (s, 411, 3.81 (s, 6H), 3.83 (s, 3H), 6.18 (s, 2H), 7.05 (d, 111), 7.22 (s, 1H), 7.29 (d, 1H), 7.52 (s, 1H), 7.68 (s, 1H). MS (APCI): 506.2 (M+1).

The compound (50 mg) was treated with NaBH₄ (1.5 eq) in ethanol (2 mL) and diethyl ether (0.5 mL). The solution was stirred at room temperature for 1.5 hours, quenched with water, and extracted with ethyl acetate. The organic layer was concentrated to give the compound as a white solid. ¹HNMR (CDCl₃) σ 1.24, 1.28, 1.29 (3 s, 12H), 1.66, 1.67 (2 s, 4H), 2.29 (s, 3H), 2.55 (d, 1H), 3.80 (s, 6H), 3.82 (s, 3H), 5.98 (d, 1H), 6.17 (s, 2H), 7.08, 7.10 (2 s, 2H), 7.38 (s, 1H), 7.41 (s, 1H). MS (APCI): 508.2 (M+1).

Synthesis of 5-(5-{1-[(ethylamino)carbonyl]cyclpropyl}-2-methylbenzyl)-N-(2,4,6-trimethoxyphenyl)-2-furamide

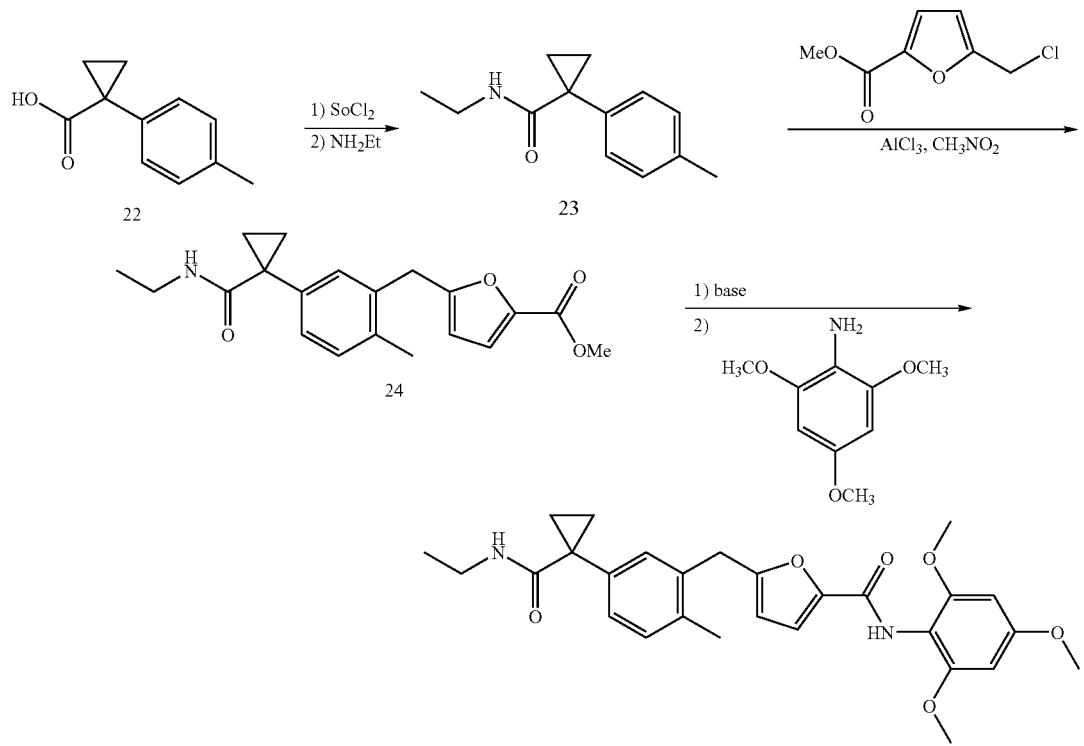

A solution of 22 (2.0 g, 11.3 mmol) in thionyl chloride (8 mL) was heated to reflux for 3 minutes. The unreacted thionyl chloride was remove by rotary evaporator. The concentrated residue was dissolved in $CH_2Cl_2$. To this solution ethylamine (excess) was added to give compound 23 (1.3 g). The compound was converted to AXC07555 by 3 steps (Friedal Crafts reaction, hydrolysis, and amide bond formation) as described in general procedures. $^1$HNMR ($CDCl_3$): σ 0.94–1.02 (m, 5H), 1.59 (m, 2H), 2.34 (s, 3H), 3.17 (q, 2 h), 3.80, 3.81 (2 s, 9H), 4.01 (s, 2H), 5.39 (brd, 1H), 6.01 (d, 1H), 6.17 9 s, 2H), 7.11 (d, 1H), 7.21 (m, 2H), 7.31 9 s, 1H). MS (APCI): 493.2 (M+1).

ADDITIONAL EXAMPLES

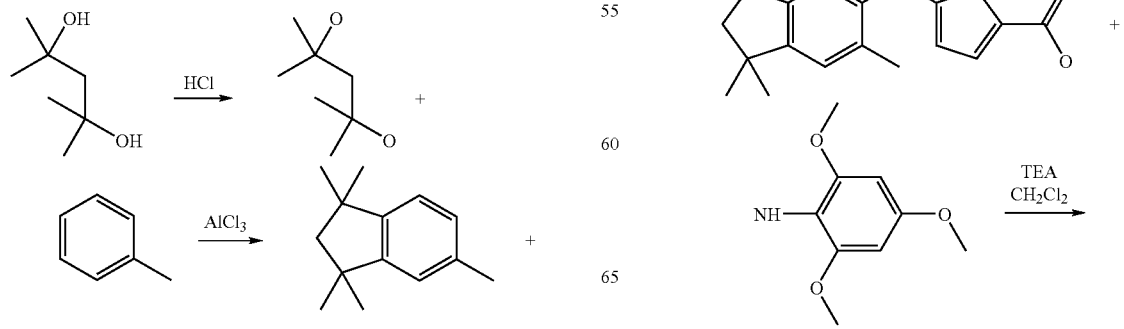

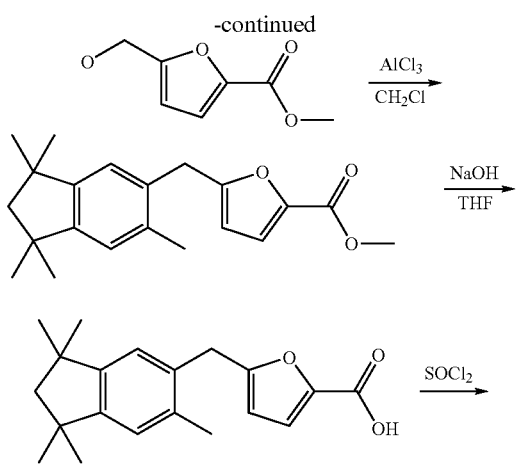

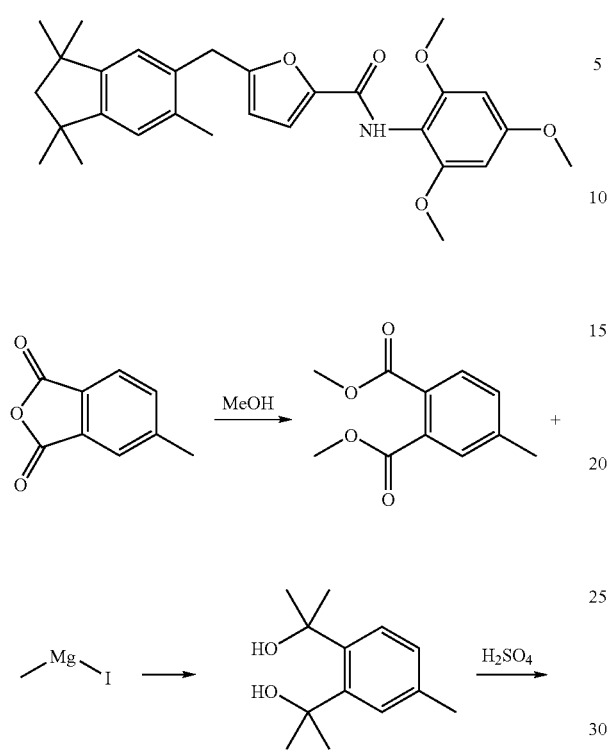

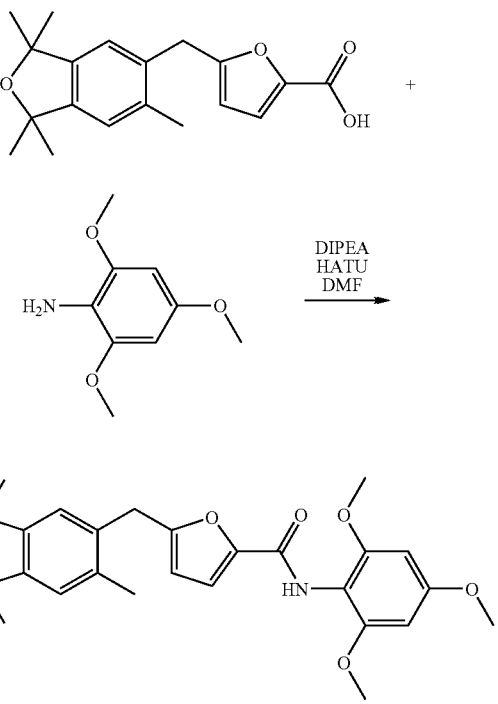

A useful intermediate can be prepared as follows:
Preparation of methyl-5-(chloromethyl)-2-furoate

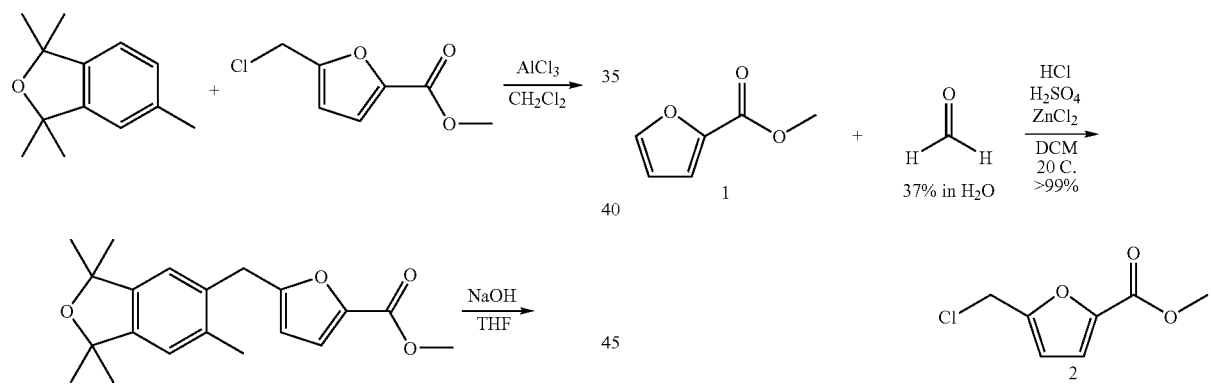

| Required Materials | | | | | | | |
|---|---|---|---|---|---|---|---|
| Materials | Conc. | Molecular Weight | Amount | Number of Moles | Number of Equivalents | Density | CAS |
| Methyl 2-furoate | 97% | 126.11 | 0.371 kg | 2.88 | 1 | 1.179 | [611-13-2] |
| Formaldehyde$_{(aq)}$ | 37% | 30.03 | 0.371 L | 4.95 | 1.72 | 1.083 | [50-00-0] |
| HCl | 37% | 36.46 | 2.2 L | 22.3 | 7.74 | 1.19 | [7647-01-0] |
| H$_2$SO$_4$ | 95–98% | 98.08 | 1.1 L | 11 | 3.82 | 1.84 | [7664-93-9] |
| Dichloromethane | Reagent | 84.93 | 2.2 L | — | — | 1.325 | [75-09-2] |
| ZnCl$_2$ | 98% | 136.28 | 0.520 kg | 3.7 | 1.3 | — | [7646-85-7] |
| Dichloromethane | Reagent | 84.93 | ******L | — | — | 1.325 | [75-09-2] |
| NaHCO$_{3(aq)}$ | Saturated | — | *****L | — | — | — | [144-55-8] |
| Silica Gel | — | — | 0.600 kg | — | — | — | — |
| Na$_2$SO$_4$ | 98% | — | as necessary | — | — | — | [7757-82-6] |

Itemized Procedure for a 2.88 Mole Scale Batch of Methyl 5-(chloro-methyl)-2-furoate (2)

- A 12L 3-neck round bottom flask (r.b.) is equipped with an addition funnel; over-head electric stirrer; thermocouple; and an ice bath. (a nitrogen blanket is recommended, but may not necessarily be required)
- Charge 2.2 L DCM to r.b. followed by 2.2 L conc. Hcl. (no significant exothermic reaction observed; two layers formed)
- Begin agitation. (ensure adequate mixing of both phases)
- Charge 1.1 L $H_2SO_4$ to the addition funnel as space permits. Cool reactor to 0–10° C. Begin addition of sulfuric acid drop-wise initially until the exothermic reaction subsides (approximately ½ addition), and then increase addition rate to a light stream. (maintain temperature below 20° C. for safety purposes)
- Change cooling bath to water at room temperature. (this will act as a heat-sink for the subsequent additions without slowing reaction rates significantly)
- Charge 0.371 kg methyl 2-furoate to r.b. in one portion. (no the exothermic reaction noticed, green/brown solution)
- Charge 0.520 kg $ZnCl_2$ in many portions. (some bubbling—suspect HCl gas; the exothermic reaction controlled by water bath)
- Charge 0.371 L formaldehyde to rinsed addition funnel. Add to reactor over 2.5–3.5 hours. (temperature is maintained at room temperature by water bath; slow addition results in fewer polymerization reactions between 'free' formaldehyde)
- Stir overnight at room temperature.
- When reaction is complete by TLC (see below) drop aqueous layer. Filter organic layer through a 0.550 kg silica plug (dry packed, approx. 10 cm thick). Elute with approximately 4 L DCM until no further product comes off a sindicated by TLC. (ensure this step is performed with proper ventilation, as some acid vapors are still present, even in the filtrate)
- Concentrate to give an oil ranging in color from yellow to brown (approximately 0.5 L)
- Charge an equal amount DCM, about 0.5 L. Wash with 2×0.2 L distilled water. Then wash organic layer with 0.05 L sat $NaHCO_3$ in 0.15 L distilled water. (ensure pH 7–10, no significant product lost in aqueous layer)
- Drop aqueous layer, and dry organic with $Na_2SO_4$. Filter through 0.05 kg silica (about 5 cm thick). Elute with DCM until no further product comes off.
- Concentrate by rotovap using house vacuum. Then place oil on high vacuum pump overnight. (yellow to light brown oil)

Yield range: 95–100%

Purity range: 95–98% (HPLC A%)

Further Comments

- Visual: The reaction is followed by TLC (254 nm) using 30% EtOAc/Hexanes (r.f. starting material—0.52, r.f product—0.40).
- HPLC: TFA method (method and spectra attached). Starting material rt=12.67 min., product rt=17.37 min.
- NMR: $^1H$ ($CDCl_3$) (spectra attached) 3.93 (s, 3H), 4.63 (s, 2H), 6.52 (d, 1H), 7.18 (d, 1H).

If the reaction has not gone to completion, 10% of the original volume of formaldehyde can be added every 4 hours. Temperature effects have not been extensively studied, but it has been convenient to maintain pot temperatures in the ranges specified for each step. Acid vapors present in the organic layer even after filtration make handling outside of the fume hood problematic, so care should be taken when transferring material outside of the hood until the pH is neutralized. If the addition rate of formaldehyde is increased, polymer formation will prevent the reaction from going to completion due to the consumption of formaldehyde. Arrangements with the safety department should be made prior to the start of this process so that arrangements to accommodate the large volumes of acid being discharged in the aqueous layer can be made. Neutralization of the aqueous acid layer requires large volumes of base, produces a considerable exotherm, and requires a prolonged addition period, and is therefor not recommended. The final product should be kept cool, as no stability data of this product is available. Keeping te product in a Nalgene container at −20° C. causes the product to crystallize, slightly darkening the material, but appears to have no effect on later reactions using this material.

The compounds of the present invention should be useful in treating:

1. hormone dependent cancers/tumors
2. hormone independent cancers/tumors by direct interactions
3. use in other mechanisms of action It is believed that Applicants' invention includes many other embodiments which are not herein specifically described, accordingly this disclosure should not be read as being limited to the foregoing examples or preferred embodiments.

The following compounds have been made as discussed above. Certain properties of some of the compounds have also been measured using techniques discussed earlier. S%R is the substrate remaining. The closer S%R is to zero, the closer to 100% inhibition.

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 9 | | 220 (40*) | 3800 | 680 | 2300 | Antagonist | 30 | | | | | | | |
| 10 | | 130 (20*) | 1500 | 390 | 1400 | Antagonist | 95 | 1270 | 1200 | 550 | 6400 | 9700 | 6600 | |
| 21 | | 920 | 3340 | 540 | 1200 | Antagonist | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 11 | | 190 (80*) | 320 | 9 | 50 | Antagonist | | 1800 | | 150 | >10000 | 2550 | 3200 | >10000 |
| 22 | | 540 | 1710 | 310 | 1100 | | | | | | | | | |
| 23 | | 220 (40*) | 2830 | 730 | 2100 | Antagonist | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 24 | | 550 | 760 | 150 | 560 | | | | | | | | | |
| 25 | | 410 | 940 | 260 | 950 | | | | | | | | | |
| 26 | | 1010 | | | | | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 27 | | >10000 | | | | | | | | | | | | |
| 28 | | >10000 | | | | | | | | | | | | |
| 29 | | 1420 | | | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 30 | | 1350 | | | | | | | | | | | | |
| 30.5 | | 5030 | | | | | | | | | | | | |
| 12 | | 230 (210*) | 10400 | 3080 | 7130 | Antagonist | 170 | >4500 | >4000 | 1400 | >10000 | >10000 | 10000 | |
| 31 | | 140 | 8900 | 2800 | 1880 | Antagonist | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 32 | | 3800 | | | | | | | | | | | | |
| 33 | | 5300 | | | | | | | | | | | | |
| 13 | | 110 (40*) | 530 | 60 | 120 | Antagonist | 85 | >4400 | | >3200 | >10000 | >10000 | 7900 | >10000 |
| 34 | | >10000 | | | | | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 35 | | 1200 | | | | | | | | | | | | |
| 36 | | 215 | 12500 | 2900 | 3800 | Antagonist | | | | | | | | |
| 37 | | 2100 | | | | | | | | | | | | |
| 37.5 | | 7800 | | | | | | | | | | | | |
| 38 | | 370 | | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 38.5 | China | >10000 | | | | | | | | | | | | |
| 39 | | 190 | 2340 | 220 | 830 | | | | | | | | | |
| 40 | | 530 | | | | | | | | | | | | |
| 41 | | 140 | 1400 | 210 | 490 | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 42 | | 75 (65*) | 1780 | 100 | 280 | | | | | | | | | |
| 43 | | 320 (130*) | 4000 | 330 | 630 | | | | | | | | | |
| 44 | | 390 (120*) | 4440 | 510 | 610 | | | | | | | | | |
| 45 | | >10000 | | | | | | | | | | | | |
| 46 | | 330* | 8700 | 900 | 1880 | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 47 | | 230 (80*) | 1920 | 130 | 240 | | | | | | | | | |
| 48 | | 50 (40*) | 490 | 6 | 10 | Antagonist | | >4400 | | >3200 | >10000 | >10000 | 6300 | >10000 |
| 14 | | 80 | 1050 | 60 | 290 | | | | | | | | | |
| 49 | | 3700 | | | | | | | | | | | | |
| 50 | | 230 | 1520 | 150 | 370 | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 51 | | 150 | 1930 | 120 | 400 | | | | | | | | | |
| 52 | | 280 | 2900 | 270 | 660 | | | | | | | | | |
| 53 | | 250 | 2930 | 270 | 630 | | | | | | | | | |
| 54 | | 680 | | | | | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 15 | | 290 | | | | | | | | | | | | |
| 55 | | 570 | | | | | | | | | | | | |
| 56 | | 100 | 1000 | 70 | 220 | | | | | | | | | |
| 16 | | 30 | 4380 | 560 | 1290 | | | | | | | | | |

-continued

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 57 | Chiral | 830 | | | | | | | | | | | | |
| 58 | Chiral | 205 | | | | | | | | | | | | |
| 59 | | 980 | | | | | | | | | | | | |
| 60 | | 4200 | | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 17 | | 80 | 670 | 30 | 80 | | | | | | | | | |
| 18 | | 55 | 460 | 40 | 115 | | | | | | | | | |
| 19 | | 50 | 605 | 60 | 160 | | | | | | | | | |
| 61 | | 760 | | | | | | | | | | | | |

-continued

| COM-POUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 62 | | >10000 | | | | | | | | | | | | |
| 20 | | 8 | 130 | 5 | 20 | Antagonist (rat) | 9 (rat) | >4400 | | | >3200 | >10000 | >10000 | >10000 |
| 63 | | 2500 | | | | | | | | | | | 6700 | >10000 |

-continued

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 64 | | 125 | 380 | 60 | 34 | | | | | | | | | |
| 65 | | 710 | | | | | | | | | | | | |
| 66 | | 3500 | | 1160 | | | | | | | | | | |
| 67 | | | | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 68 | | 90 | | 890 | 1010 | | | | | | | | | |
| 69 | | 1410 | | | | | | | | | | | | |
| 70 | | 50 | 43 | 6 | 6 | Antagonist (rat) | 8 (rat) | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 71 | | 2000 | | | | | | | | | | | | |
| 72 | | 130 | 1440 | 84 | 85 | | | | | | | | | |
| 73 | | 580 | | | | | | | | | | | | |
| 73 | | 180 | 2140 | 2940 | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 75 | | 115 | | 740 | 710 | | | | | | | | | |
| 76 | | 880 | | 5300 | | | | | | | | | | |
| 77 | | >10000 | | 8450 | | | | | | | | | | |
| 78 | | >1000 (<10000) | | 1300 | | | | | | | | | | |
| 79 | | 250 | | 370 | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 80 | | 10000 | | 5610 | | | | | | | | | | |
| 81 | | 12000 | | 8080 | | | | | | | | | | |
| 82 | | 10000 | | 9200 | | | | | | | | | | |
| 83 | | 620 | | 1740 | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 84 | | 8000 | | 770 | | | | | | | | | | |
| 85 | | 12000 | | >10000 | | | | | | | | | | |
| 86 | | 8000 | | 510 | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 86.5 | | 2570 | | 2050 | | | | | | | | | | |
| 87 | | 270 | | 3310 | | | | | | | | | | |
| 88 | | 1000 | | 2340 | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 89 | | 250 | | 2730 | | | | | | | | | | |
| 90 | | 560 | | 1260 | | | | | | | | | | |
| 91 | | 120 | | 950 | 790 | | | | | | | | | |
| 92 | | 80 | | 27 | 42 | | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 93 | | 8000 | | 5470 | | | | | | | | | | |
| 94 | | 315 | | 1490 | 1300 | | | | | | | | | |
| 94.2 | | 3000 | | 1580 | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func- tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca- gon IC50 (nM) | GLP-1 IC50 (nM) |
|---|---|---|---|---|---|---|---|---|---|---|---|---|---|---|
| 94.5 | | >1000 (<10000) | | 4830 | | | | | | | | | | |
| 95 | | 31 | | 60 | 21 | | | | | | | | | |
| 96 | | 40 | | 90 | 130 | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 Ki (nM) | DA (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|---|
| 97 | | 1700 | | 1690 | | | | | | | | | | | |
| 98 | | 80 | | 220 | 84 | | | | | | | | | | |
| 99 | | 56 | | 108 | 105 | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 100 | | 585 | | 6000 | | | | | | | | | | |
| 101 | | >10000 | | >10000 | | | | | | | | | | |
| 102 | | 1180 | | 970 | | | | | | | | | | |
| 103 | | 360 | | 3460 | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 104 | | >1000 (<10000) | | 1260 | | | | | | | | | | |
| 105 | | 22 | | 250 | 200 | | | | | | | | | |
| 106 | | 2000 | | 510 | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 107 | | >20000 | >10000 | | | | | | | | | | | |
| 108 | | 1000 | 2740 | | | | | | | | | | | |
| 109 | | 75 | 140 | 140 | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 110 | | 12000 | >10000 | | | | | | | | | | | |
| 111 | | 630 | 1740 | | | | | | | | | | | |
| 112 | | 12000 | 7780 | | | | | | | | | | | |
| 113 | | 340 | 300 | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 114 | | 10000 | | 7000 | | | | | | | | | | |
| 115 | | 6000 | | 5130 | | | | | | | | | | |
| 116 | | 1170 | | 390 | | | | | | | | | | |

-continued
| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 117 | 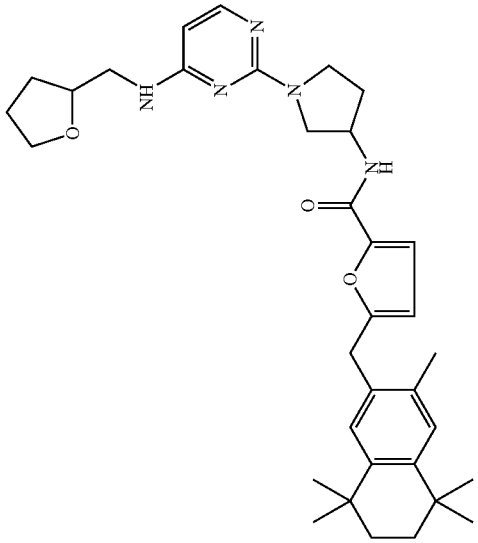 | 1810 | 3000 | | | | | | | | | | | |
| 118 | 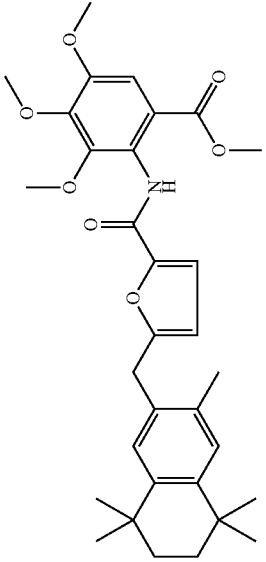 | 380 | 430 | | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 119 | | 12000 | | 1300 | | | | | | | | | | |
| 120 | | >10000 | | >10000 | | | | | | | | | | |
| 121 | | 1100 | | | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 122 | | 730 | | 1260 | | | | | | | | | | |
| 123 | | 510 | | | | | | | | | | | | |
| 124 | | 1000 | | 750 | | | | | | | | | | |
| 125 | | 135 | | 560 | 1050 | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 Ki (nM) | DA (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|---|
| 126 | | 128** | | 325** | 684** | | | | | | | | | | |
| 127 | | 510 | | 910 | | | | | | | | | | | |
| 128 | | 220 | | 170 | 220 | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 129 | | 12000 | | 1390 | | | | | | | | | | |
| 130 | | 3000 | | 590 | | | | | | | | | | |
| 131 | | 600 | | | | | | | | | | | | |
| 132 | | 640 | | | | | | | | | | | | |
| 133 | | 490 | | | | | | | | | | | | |

-continued

| COM-POUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 134 | | 6 | | 3 | 3 | Antagonist | 13 (rpH) 13 (hPI) | >4400 | 3720 | 2400 | | | | |
| 135 | | 1440 | | | | | | | | | | | | |
| 136 | | China 9.4 | | 4.7 | 8.6 | Antagonist | 6.3 & 8 rat PI, p | 2400 | | 160 | | | | |
| 137 | | 200 | | 400 | 360 | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 138 | | 200 | | 1630 | 1570 | | | | | | | | | |
| 139 | | 110 | | 113 | 150 | | | | | | | | | |
| 140 | | 110 | | 530 | 320 | | | >4400 | | 2300 | | | | |

| COM-POUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 Ki (nM) | DA (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|---|
| 141 | | 150 | | 35 | 64 | | | | | | | | | | |
| 142 | | 3000 (solubility?) | | | | | | | | | | | | | |
| 143 | | 1870 | | | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 144 | | 230 | | | | | | | | | | | | |
| 145 | | 200 | | | | | | | | | | | | |
| 146 | | >10000 | | | | | | | | | | | | |
| 147 | | China 60 | 3 | 5 | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 148 | | Chira 12 | | 1.6 | 1.3 | | | | | | | | | |
| 149 | | 360 | | | | | | | | | | | | |
| 150 | | 80 | | 8 | 13 | | | | | | | | | |
| 151 | | 65 | | 7.2 | 5.2 | | | | | | | | | |
| 152 | | 700 | | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 153 | | 120 | | 11 | 21 | | | | | | | | | |
| 154 | | 150 | | 22 | 36 | | | | | | | | | |
| 155 | | 210 | | 270 | 400 | | | | | | | | | |
| 156 | | 24 | | | | | | | | | | | | |
| 157 | | 620 | | | | | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 158 | | 1090 | | | | | | | | | | | | |
| 159 | | 45 | | 5 | 16 | | | | | | | | | |
| 160 | | 390 | | | | | | | | | | | | |
| 161 | | 300 | | | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 162 | | >10000 | | | | | | | | | | | | |
| 163 | | 1960 | | | | | | | | | | | | |
| 164 | | 1970 | | | | | | | | | | | | |
| 165 | | >10000 (solu-bility?) | | | | | | | | | | | | |
| 166 | | 260 | | | | | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 167 | | 7640 | | | | | | | | | | | | |
| 168 | | 230 | | 130 | 130 | | | | | | | | | |
| 169 | | 12 | | 7 | 5 | Antagonist | 17 (rat) | | 2710 | 3400 | | | | |
| 170 | | 50 | | 30 | 22 | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 171 |  | 1140 | | | | | | | | | | | | |
| 172 |  | 3200 | | | | | | | | | | | | |
| 173 |  | 2800 | | | | | | | | | | | | |
| 174 |  | Chiral 220 | 385 | 570 | | | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 175 | | >10000 | | | | | | | | | | | | |
| 176 | | 54 | | 3 | 4 | | | | | | | | | |
| 177 | | 7.4 | | 5.7 | 7.3 | Antagonist | 9 (rat) | | | | | | | |
| 178 | | 185 | | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 179 | | 190 | | | | | | | | | | | | |
| 180 | | 350 | | | | | | | | | | | | |
| 181 | | 190 | | | | | | | | | | | | |
| 182 | | 430 | | | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 183 | | 6.8 | | 2.5 | 2.7 | Antagonist | 11.0 (rat) | | | | | | | |
| 184 | | 560 | | | | | | | | | | | | |
| 185 | | 120 | | 250 | 270 | | | | | | | | | |
| 186 | | 7310 | | | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func- tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca- gon IC50 (nM) | GLP-1 IC50 (nM) |
|---|---|---|---|---|---|---|---|---|---|---|---|---|---|---|
| 187 | | 9000 | | | | | | | | | | | | |
| 188 | | 290 | | | | | | | | | | | | |
| 189 | | 940 | | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 190 | | 420 | | | | | | | | | | | | |
| 190.5 | | 350 | | | | | | | | | | | | |
| 191 | | 4240 | | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 192 | | 235 | | | | | | | | | | | | |
| 193 | | >10000 | | | | | | | | | | | | |
| 194 | | 18 | 35 | 14 | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 195 | | 320 (Insol. >3 uM) | | | | | | | | | | | | |
| 196 | | 760 | | | | | | | | | | | | |
| 197 | | 1040 | | | | | | | | | | | | |
| 198 | | 780 (Insol. >3 uM) | | | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 199 | | 92 | | 9.6 | 15 | | | | | | | | | |
| 200 | | 42 | | 2.8 | 13 | Antag-onist | 0.9 nM (rat) | | | | | | | |
| 200.5 | | 1230 | | | | | | | | | | | | |
| 201 | | 380 | | | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 202 | | 1425 | | | | | | | | | | | | |
| 203 | | 130 | | 58 | 62 | | | | | | | | | |
| 204 | | 1270 | | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 205 | | >10000 | | | | | | | | | | | | |
| 206 | | 52 | | 23 | 83 | | | | | | | | | |
| 207 | | 200 | | | | | | | | | | | | |
| 208 | | 8620 | | | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func- tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca- gon IC50 (nM) | GLP-1 IC50 (nM) |
|---|---|---|---|---|---|---|---|---|---|---|---|---|---|---|
| 209 | | 4380 | | | | | | | | | | | | |
| 210 | | 12000 | | | | | | | | | | | | |
| 211 | | 1320 | | | | | | | | | | | | |
| 212 | | 80 | 12 | 62 | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 213 | | >10000 | | | | | | | | | | | | |
| 214 | | >10000 | | | | | | | | | | | | |
| 215 | | 7800 | | | | | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 216 | | 4400 | | | | | | | | | | | | |
| 217 | | 29 | | 21 | 11 | | | | | | | | | |
| 218 | | 6460 | | | | | | | | | | | | |
| 219 | | 875 | | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 220 | | 630 | | | | | | | | | | | | |
| 221 | | 15 | | 11 | 9.2 | | | | | | | | | |
| 222 | | 110 | | 78 | 65 | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 223 | | 1660 | | | | | | | | | | | | |
| 224 | | >10000 | | | | | | | | | | | | |
| 225 | | 174 | 1510 | 850 | | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 226 | | 240 | | 2130 | 720 | | | | | | | | | |
| 227 | | >10000 | | | | | | | | | | | | |
| 228 | | 27 | | 57 | 14 | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH func-tional | GnRH Kb (nM) | 5-HT7 Ki (nM) | 5-HT2a Ki (nM) | D2 DA Ki (nM) | IL8 IC50 (nM) | NPY Y1 IC50 (nM) | Gluca-gon IC50 (nM) | GLP-1 IC50 (nM) |
|---|---|---|---|---|---|---|---|---|---|---|---|---|---|---|
| 229 | | 250 | | | | | | | | | | | | |
| 230 | | 580 | | | | | | | | | | | | |
| 231 | | 5 | | 51 | 24 | | | | | | | | | |
| 232 | | 19 | | 5.7 | 9 | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 233 | | 60 | 51 | | 68 | | | | | | | | | |
| 234 | | >10000 | | | | | | | | | | | | |
| 235 | | 3720 | | | | | | | | | | | | |
| 236 | | 903 | | | | | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 237 | | >10000 | | | | | | | | | | | | |
| 238 | | 7830 | | | | | | | | | | | | |
| 299 | | 80 | | 290 | 105 | | | | | | | | | |
| 300 | | 3.2 | | | 3.1 | | | | | | | | | |

| COM-POUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| 301 | | 45 | | | 38 | | | | | | | | | |
| 302 | | 167 | | 220 | 119 | | | | | | | | | |
| 303 | | 320 | | | | | | | | | | | | |
| 304 | | 303 | | | | | | | | | | | | |

-continued

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| AXC-07047 | | 1410 | | | | | | | | | | | | |
| AXC-06675 | | 2000 | 2800 | | | | | | | | | | | |
| AXC-07450 | | >10000 | | | | | | | | | | | | |

| COMPOUND NO. | MOLSTRUCTURE | hGnRH IC50 (nM) | bGnRH IC50 (nM) | rGnRH IC50 (nM) | mGnRH IC50 (nM) | GnRH functional | GnRH Kb (nM) | 5-HT7 Ki (nM) | 5-HT2a Ki (nM) | D2 DA Ki (nM) | IL8 IC50 (nM) | NPY Y1 IC50 (nM) | Glucagon IC50 (nM) | GLP-1 IC50 (nM) |
|---|---|---|---|---|---|---|---|---|---|---|---|---|---|---|
| AXC-07350 | | >10000 | | | | | | | | | | | | |

This Table shows bioavailability of compound according to the invention. The properties were determined using the methods described previously. The Table is in two parts.

| No. | Compound | Human pmol/min/mg 1 µM | pmol/min/mg 1 µM | T₁/₂ | Rat male C$_{max}$ µM | T$_{max}$ | F$_{p.o.}$ |
|---|---|---|---|---|---|---|---|
| 11 | | 231 | 741 | 3 hr | 0.15 | 1.5–3.5 hr | 10% (10 mg/kg) |
| 23 | | 263 | 141 | 48 min | | | |
| 12 | | 418 | 450 | 36 min | | | |

-continued

| | | | |
|---|---|---|---|
| 13 | [structure: tetramethyltetrahydronaphthalene-methyl-furan-C(O)NH-CH2-(5-methylpyrazine)] | 462 | 1236 | 1.5 hr |
| 38 | [structure: tetramethyltetrahydronaphthalene-methyl-furan-C(O)NH-(CH2)4-C(O)NH-methyl] | 2776 | | |
| 41 | [structure: tetramethyltetrahydronaphthalene-methyl-furan-C(O)NH-CH2-(3-methylphenyl)] | 185 | 1606 | |
| 42 | [structure: tetramethyltetrahydronaphthalene-methyl-furan-C(O)NH-CH2-(4-methoxyphenyl)] | 361 | 1387 | 58 min |
| 44 | [structure: tetramethyltetrahydronaphthalene-methyl-furan-C(O)NH-CH2-(2-thienyl)] | 459 | 1759 | 55 min |

-continued
| | | | | | |
|---|---|---|---|---|---|
| 46 | 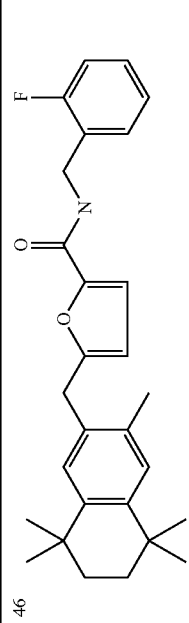 | 485 | 1781 | 55 min | |
| 47 | 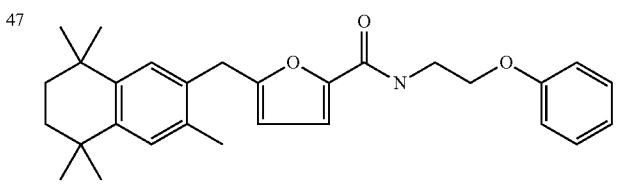 | 392 | 2198 | 1.5 hr | |
| 48 | 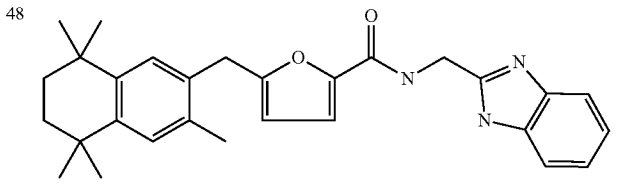 | 289 | 2869 | 1.1 hr | 0.33 | 1.5 hr | 4% (20 mg/kg)[1] |
| 14 | 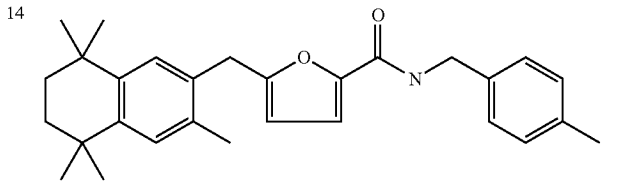 | 329 | 1626 | 1.4 hr | 1.6 | 1 hr | (10 mg/kg)[8] |
| 51 | 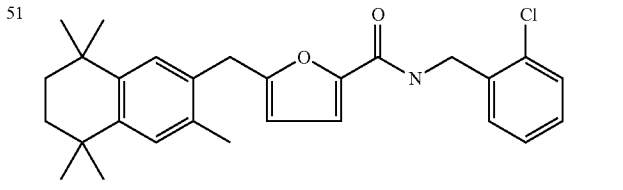 | 392 | 1877 | | |

-continued

| | | | | |
|---|---|---|---|---|
| 56 | [structure: furan carboxamide with 2,4-dimethoxybenzyl and tetramethyltetrahydronaphthalene] | 392 | 3412 | 2.6 hr |
| 16 | [structure: furan carboxamide with cyanocyclohexylmethyl and tetramethyltetrahydronaphthalene] | 691 | 2602 | 40 min |
| 17 | [structure: furan carboxamide with 2,3-dimethylbenzyl and tetramethyltetrahydronaphthalene] | 699 | 2282 | 2.2 hr |
| 18 | [structure: furan carboxamide with 3,4-dimethylbenzyl and tetramethyltetrahydronaphthalene] | 320 | 1648 | 55 min |
| 19 | [structure: furan carboxamide with 3-acetylphenyl and tetramethyltetrahydronaphthalene] | 457 | 4510 | 43 min |

| | | | | | | |
|---|---|---|---|---|---|---|
| 20 | 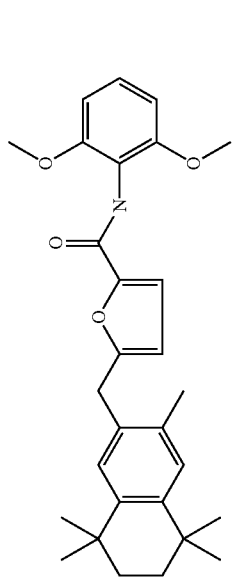 | 620 | 3908 | 52 min | 0.2 | 1 hr | 3% (20 mg/kg)[3] |
| 68 | 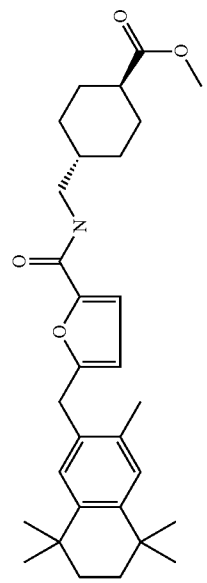 | 2716 | 8125 | | | | |
| 70 | 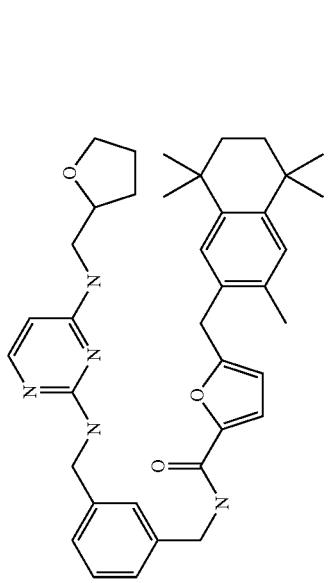 | 311 | 2393 | 58 min | | | |
| 72 | 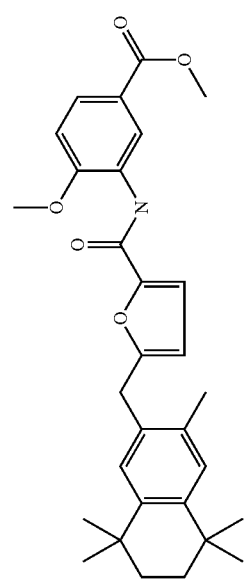 | 278 | 4226 | | | | |

| | | | |
|---|---|---|---|
| 92 | 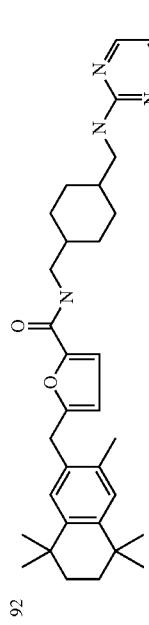 | 241 | 1282 |
| 95 | 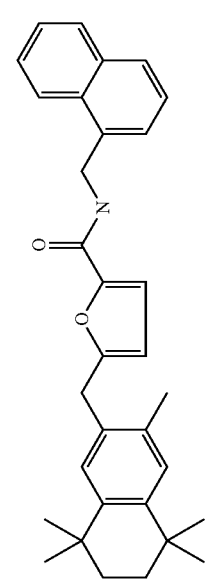 | 283 | 3356 |
| 96 | 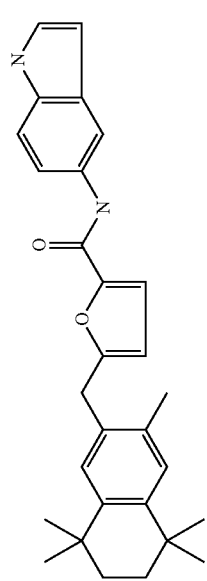 | 182 | 1692 |
| 99 | 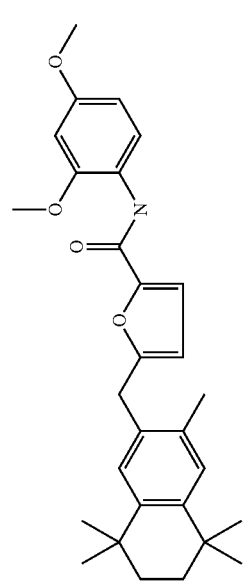 | 353 | 2549 |

-continued
| | | | | | |
|---|---|---|---|---|---|
| 109 | 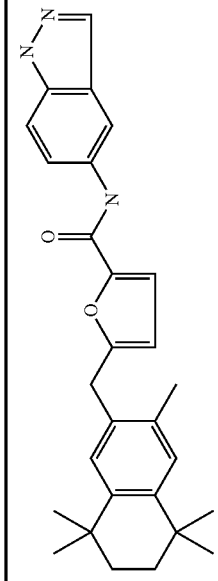 | 130 | 1055 | | |
| 126 | 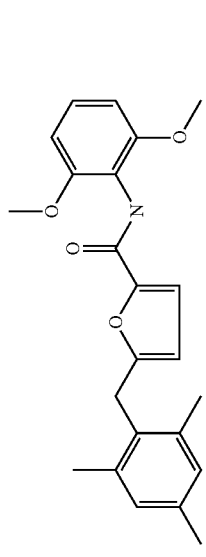 | 544 | | | |
| 134 | 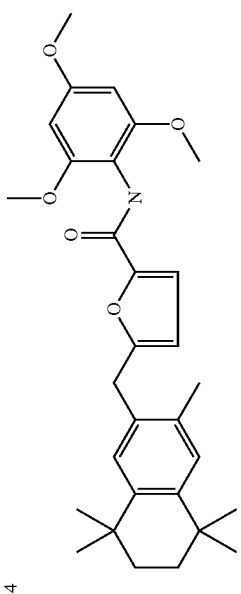 | 630 | 3909 | 1.4 hr 0.61 1 hr | 8% (20 mg/kg)[5] |
| 136 | 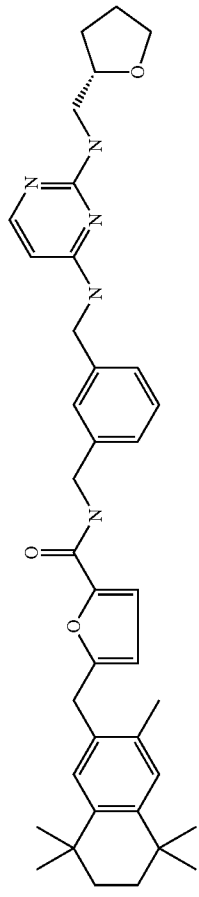 Chiral | 191 | 4437 | 2 hr 0.24 2 hr | 6% (20 mg/kg)[4] |

| | | | | | |
|---|---|---|---|---|---|
| 137 | 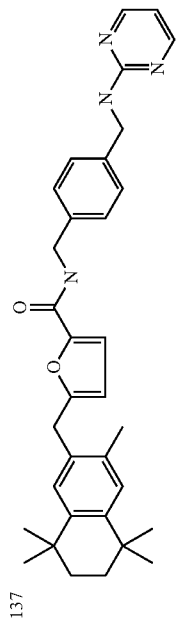 | 594 | | | |
| 140 | 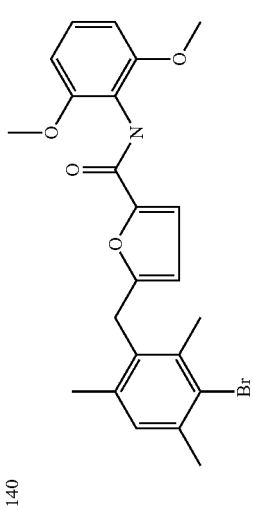 | 497 | 2521 | | |
| 147 | 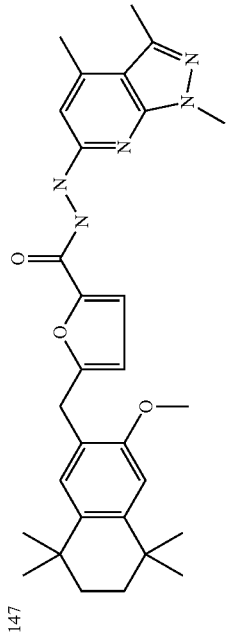 | 523 | 3524 | 1 hr | |
| 148 | 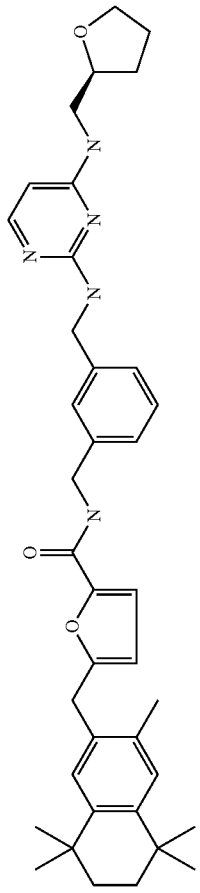 Chiral | 248 | 1414 | 1.1 hr | 0.03 | 2 hr | 3% (20 mg/kg)[1] |

| | | |
|---|---|---|
| 150 | 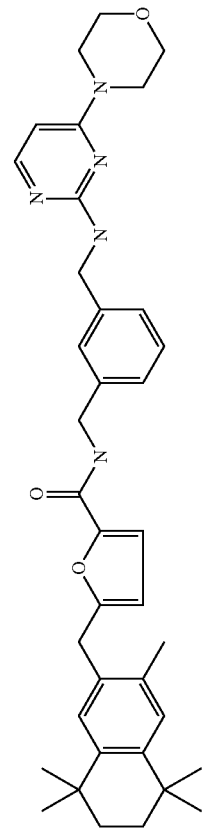 | 655 3334 |
| 151 | 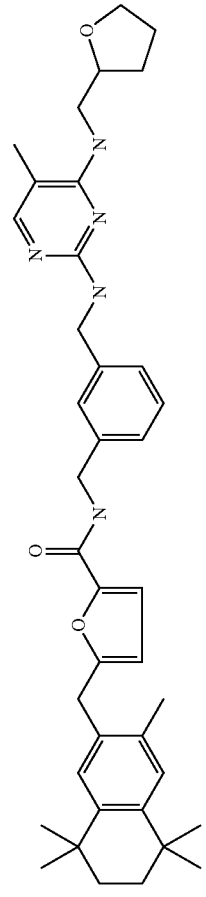 | 225 3043 |
| 154 | 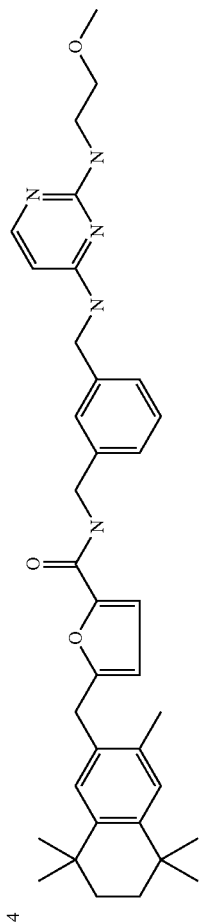 | 241 4481 |
| 156 | 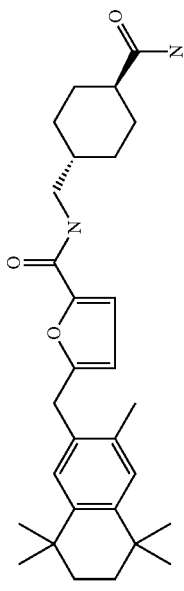 | 867 2995 |
| 159 | 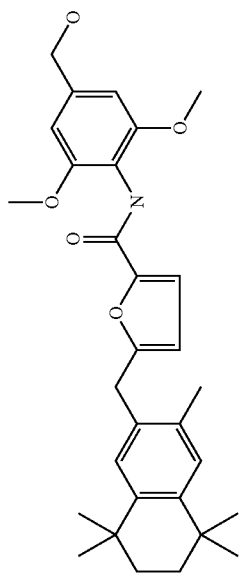 | 793 6642 |

| # | Structure | | | | | |
|---|---|---|---|---|---|---|
| 168 | (2,4,6-trimethoxyphenyl furan amide with mesityl methyl) | 407 | 1087 | 1.8 hr | 0.3 | 1 hr | 1% (20 mg/kg)[6] |
| 169 | (2,4,6-trimethoxyphenyl furan amide with methoxy-tetramethyltetralin) | 589 | 3320 | 1.5 hr | 0.97 | 1 hr | 27% (20 mg/kg)[1] |
| 170 | (acetyl-dimethoxyphenyl furan amide with tetramethyltetralin) | | | toxic | | | 0 (20 mg/kg)[7] |
| 176 | Chiral (tetrahydrofuran-methyl-aminopyrimidine benzyl furan amide with tetramethyltetralin) | 273 | 2341 | 2.8 hr | | | |

-continued
| | | | | | | | |
|---|---|---|---|---|---|---|---|
| 177 | 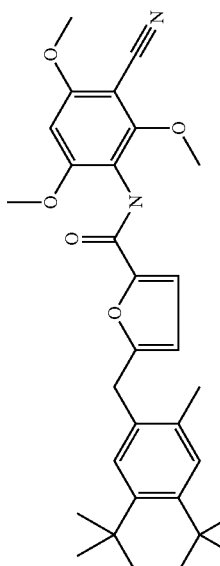 | 876 | 2930 | 2.2 hr | | | 0 (20 mg/kg)[9] |
| 181 | 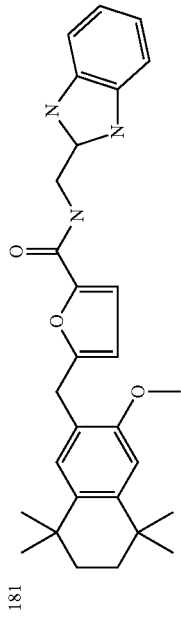 | 514 | 1589 | 1.1 hr | 2.43 | 2.5 hr | 28% (20 mg/kg)[1] |
| 182 | 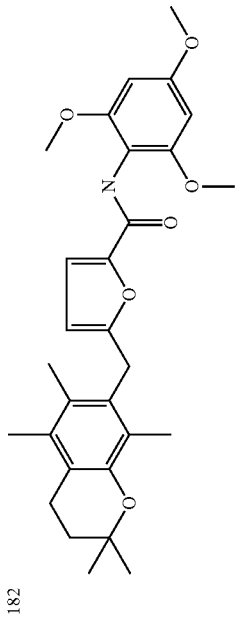 | 326 | | | | | |
| 183 | 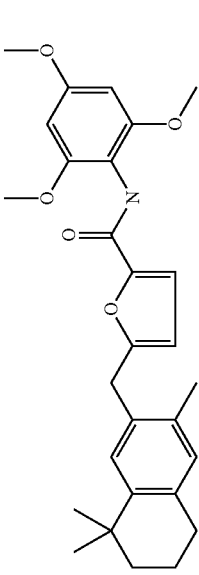 | 238 | 1246 | 4.1 hr | 0.35 | 1 hr | 29% (10 mg/kg)[10] |

| | | |
|---|---|---|
| 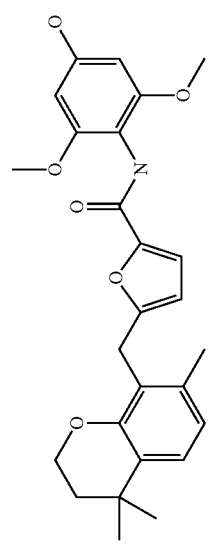 | 524 | |
| 188 | | |
| 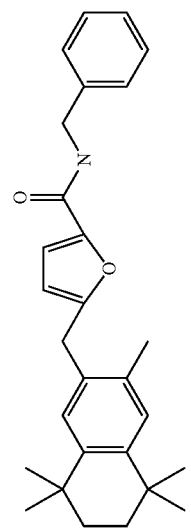 | 646 | 3713 |
| 185 | | |
| 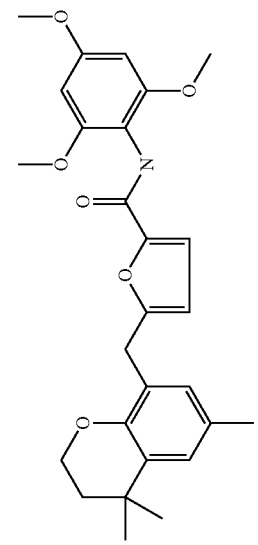 | 1124 | |
| 190.5 | | |
| 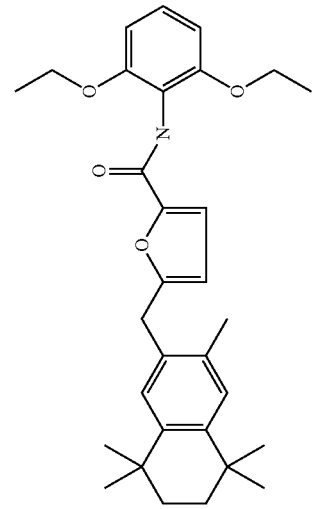 | 750 | 5978 |
| 194 | | |

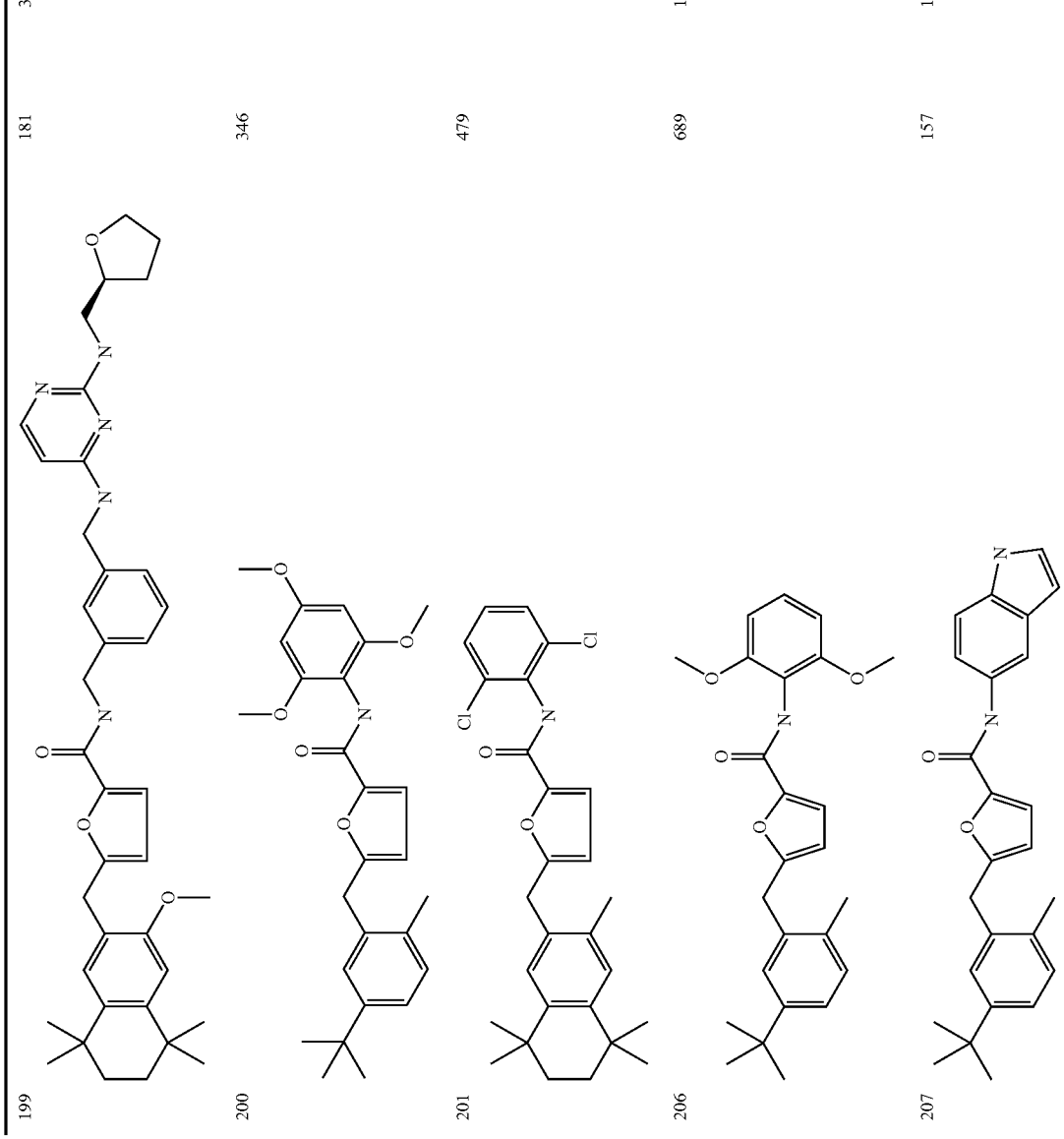

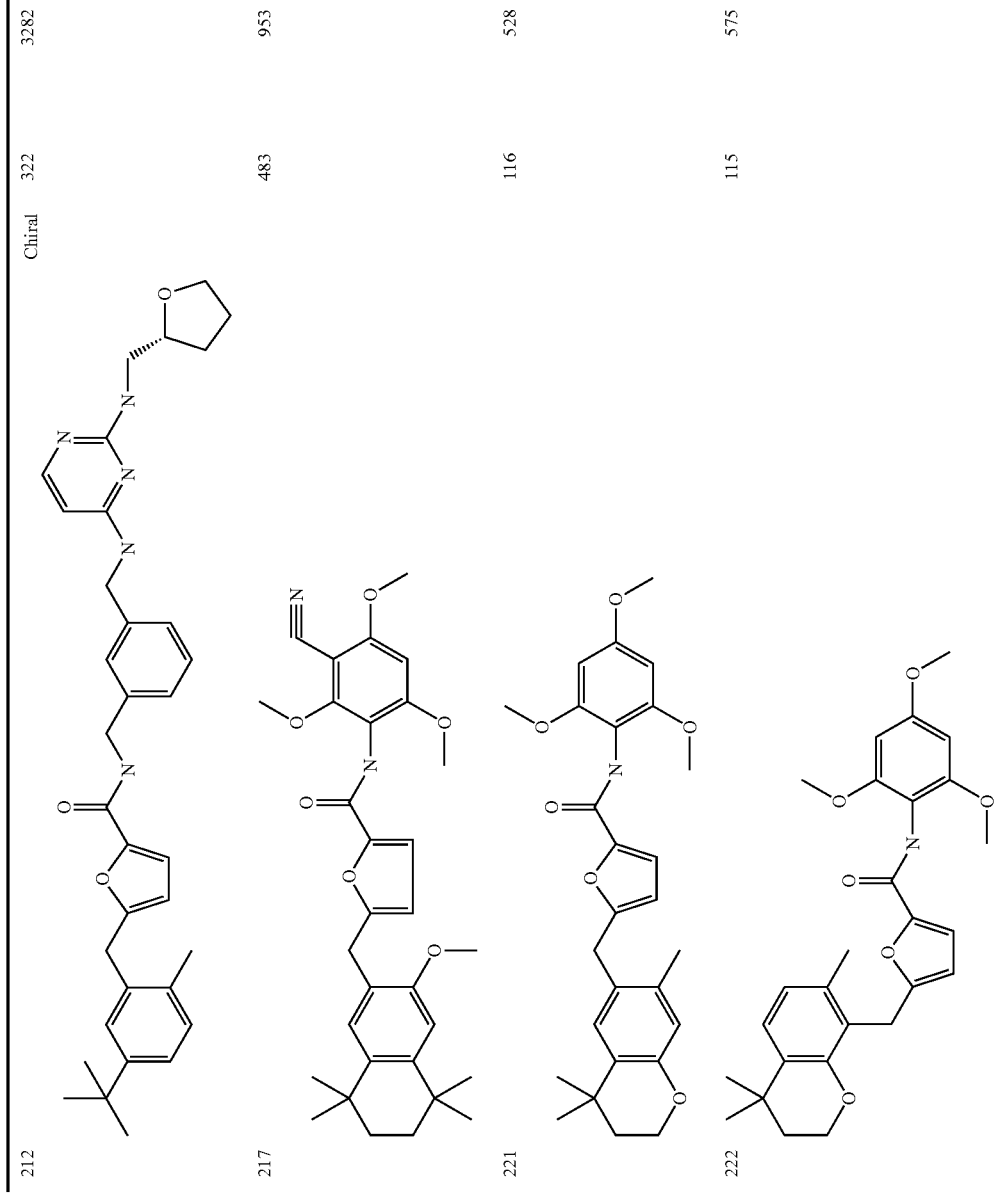

| | | | |
|---|---|---|---|
| 225 | 450 | 2180 | |
| 226 | 369 | 990 | |
| 228 | 641 | 320 | |
| 233 | 773 | 2988 | |
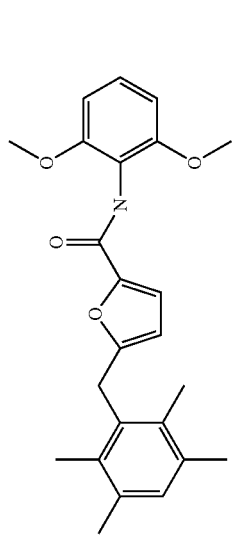
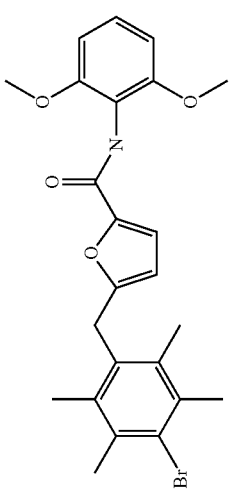
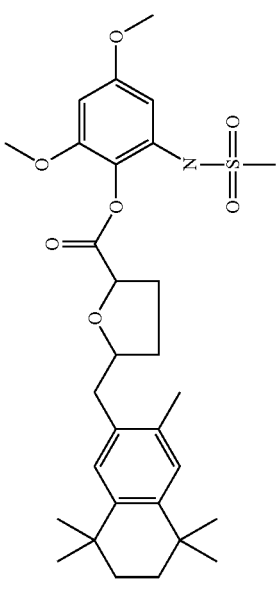
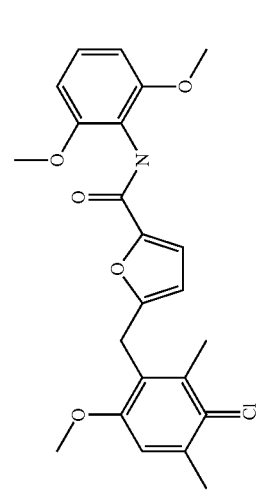

| | | | | | |
|---|---|---|---|---|---|
| | | | | Rat female | Dog | Monkey |
| 299 | 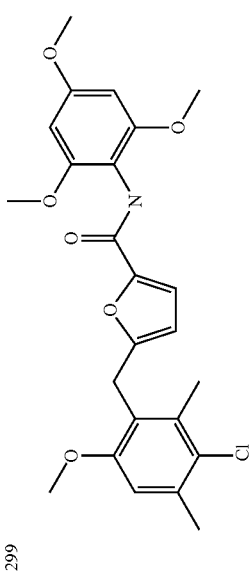 | | | | | |
| 300 | 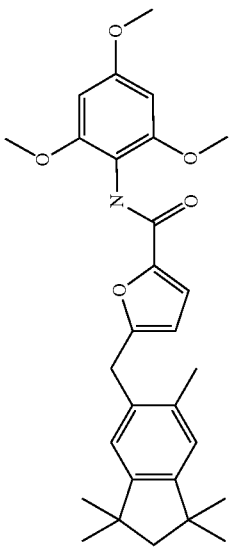 | | | | | |
| | Castrated male rats: | | | | | |
| 134 | 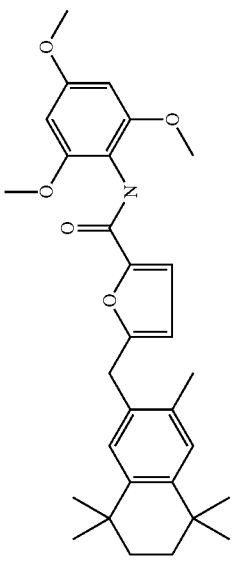 | 1.7 hr | 1.98 | 1.5 hr | 23% (20 mg/kg)[1] | |
| | Bioavailability after i.p. dosing: | | | | | |
| 134 | 38% (20 mg/kg) | | | | | |
| 169 | 70% (20 mg/kg) | | | | | |
| 177 | 8% (20 mg/kg) | | | | | |
| | Portal vein infusion: | | | | | |
| 136 | 36% bioavailable (20 mg/kg) Metabolism by CYP3A4: | | | | | |
| 20 | 3.4 pmol/min/pmol | | | | | |

| No. | Compound | pmol/min/mg 1 μM | $T_{1/2}$ | $C_{max}$ μM | $T_{max}$ | $F_{p.o.}$ | pmol/min/mg 1 μM | pmol/min/mg 1 μM |
|---|---|---|---|---|---|---|---|---|
| 11 | | | | | | | | |
| 23 | | | | | | | | |
| 12 | | | | | | | | |

-continued
| | | 1.9 hr |
|---|---|---|
| 13 | 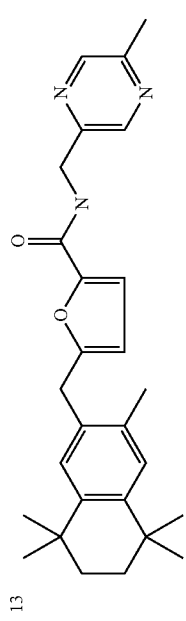 | |
| 38 | 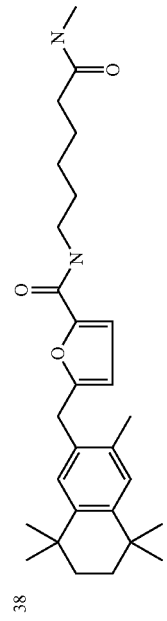 | |
| 41 | 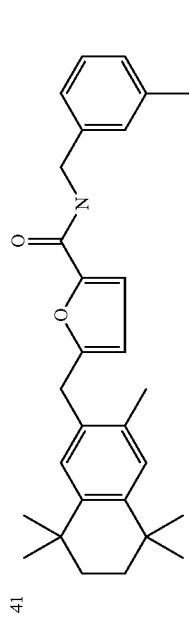 | |
| 42 | 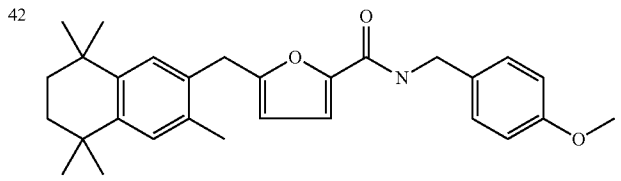 | |
| 44 |  | |

-continued
| | |
|---|---|
| 46 | 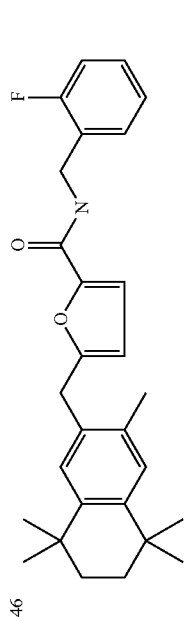 |
| 47 | 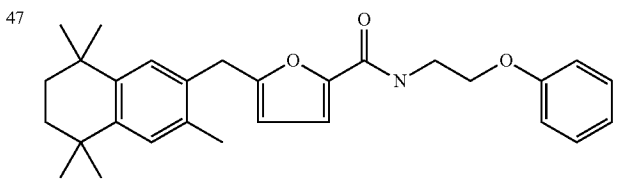 |
| 48 | 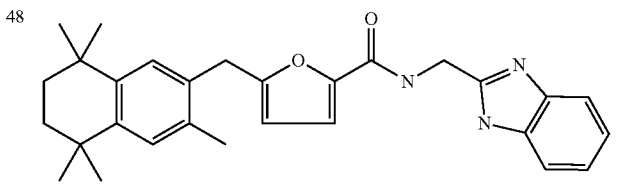 |
| 14 | 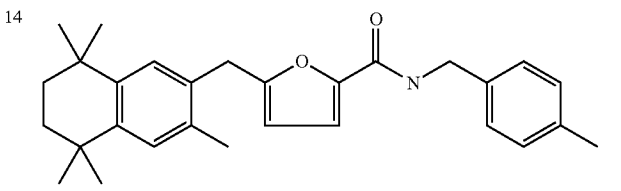 |
| 51 | 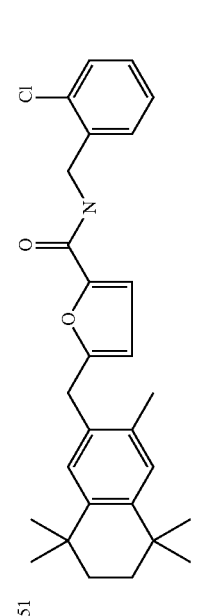 |

-continued
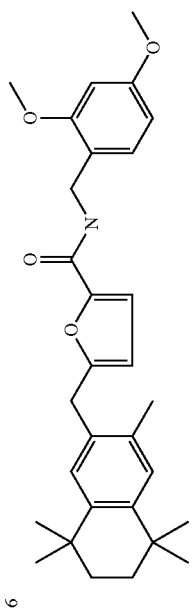
56
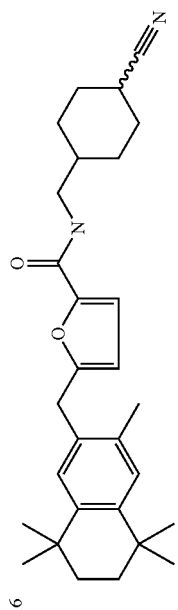
16
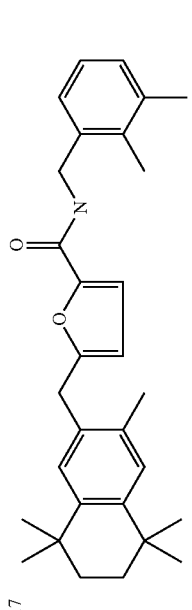
17
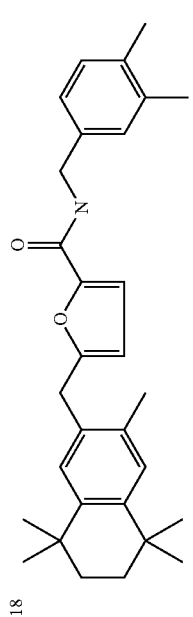
18
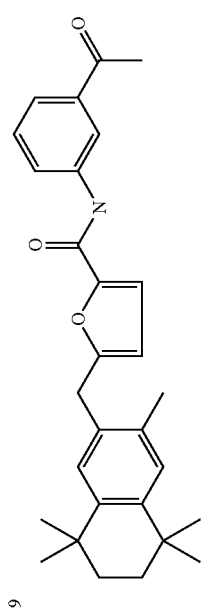
19

| | | |
|---|---|---|
| 20 | 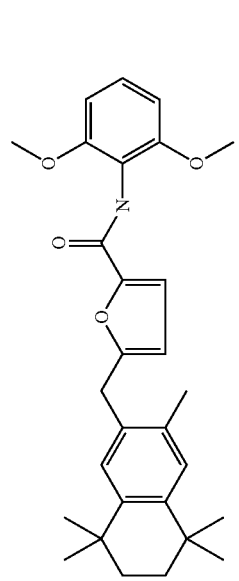 | 2520 |
| 68 | 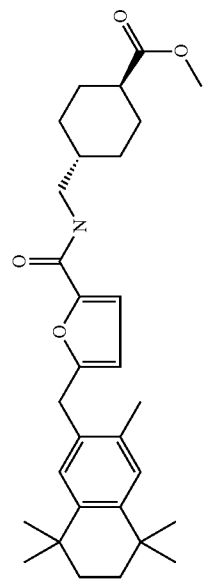 | 7366 |
| 70 | 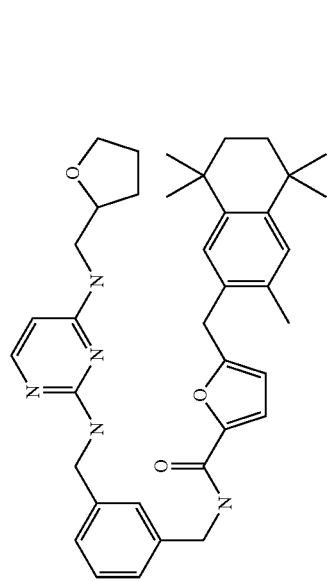 | |
| 72 | 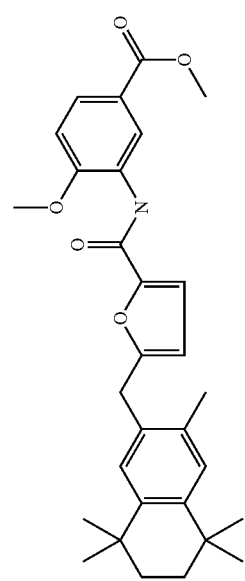 | |

-continued
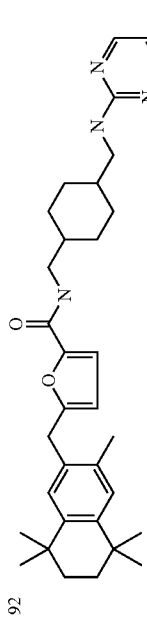
92
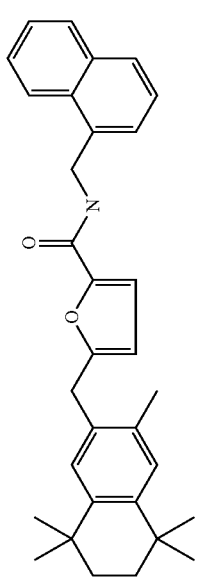
95
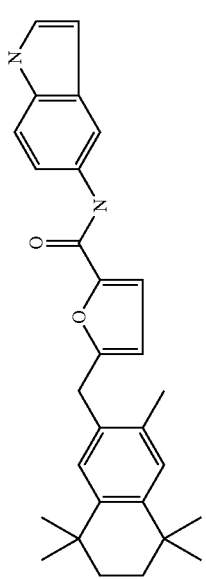
96
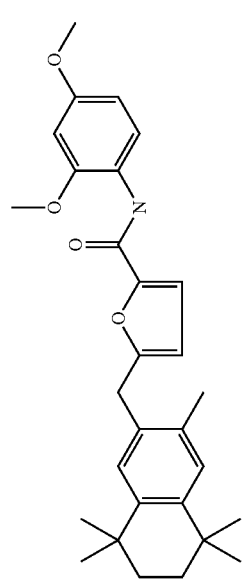
99

-continued
| | | | | | | | |
|---|---|---|---|---|---|---|---|
| 109 | 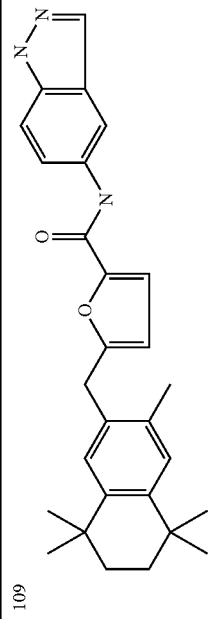 | | | | | | |
| 126 | 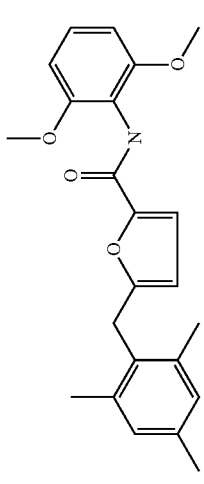 | 94 | 1.9 hr | 0.02 | 30 min | 2% (10 mg/kg)[10] | 2159 | 9277 |
| 134 | 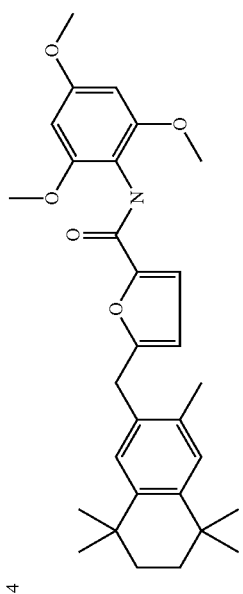 | | 1.7 hr | 2.31 | 1 hr | 24% (20 mg/kg)[1] | | |
| 136 | 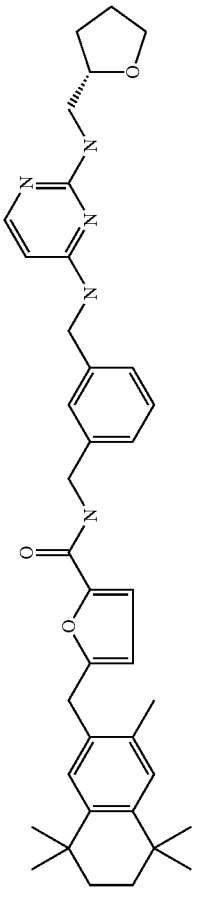 Chiral | 271 | 3.2 hr | 0.24 | 2.5 hr | 8% (20 mg/kg)[1] | 3071 | 5959 |

-continued

| | | | | | | |
|---|---|---|---|---|---|---|
| 137 | 182 | 7.9 hr | 0.23 | 1 hr | 1% (10 mg/kg)[10] | |
| 140 | | 4.6 hr | 0.44 | 1 hr | 59% (10 mg/kg)[10] | |
| 147 | | | | | | |
| 148 | 133 | | | | 1960 | 5019 |

-continued
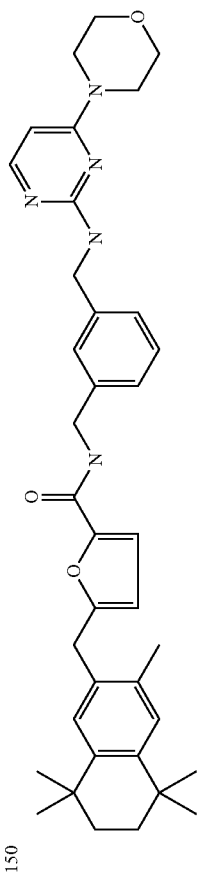
150
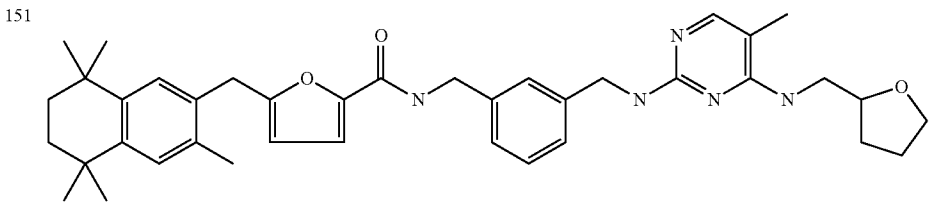
151
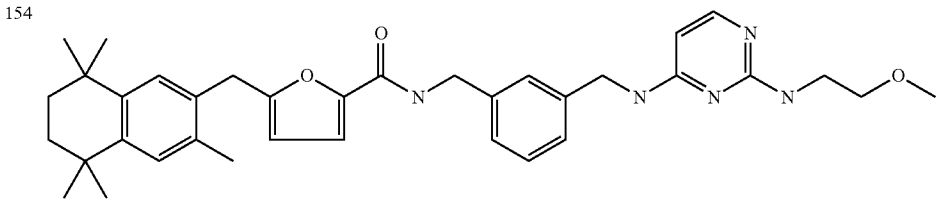
154
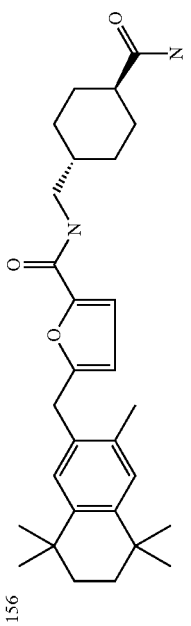
156
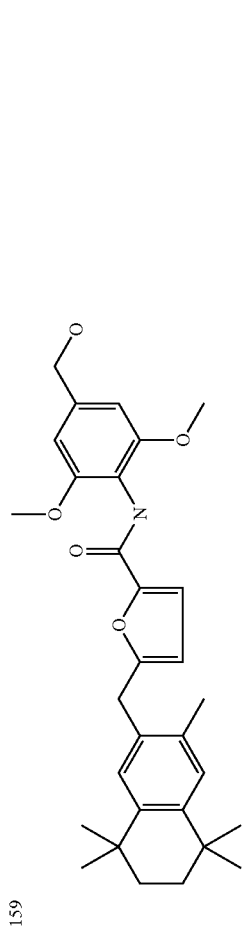
159

-continued
| | |
|---|---|
| 168 | 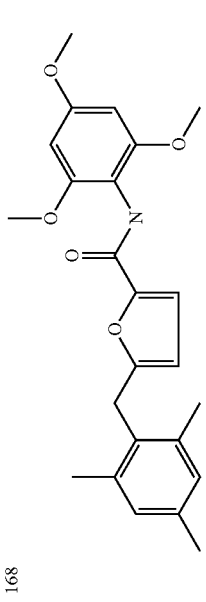 |
| 169 | 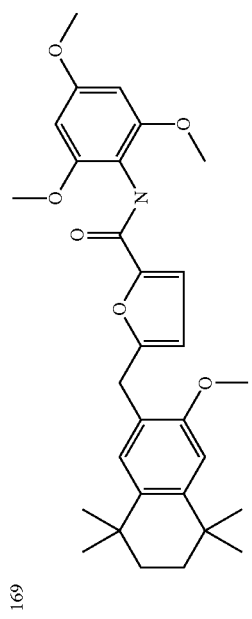 |
| 170 | 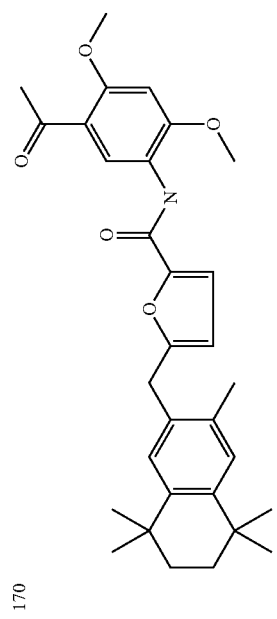 |
| 176 | 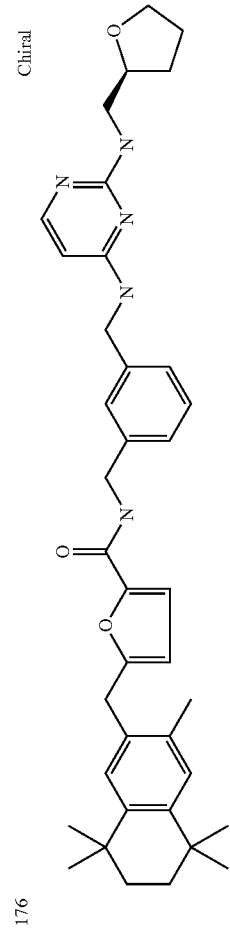 |

-continued
| | | | | | |
|---|---|---|---|---|---|
| 177 | 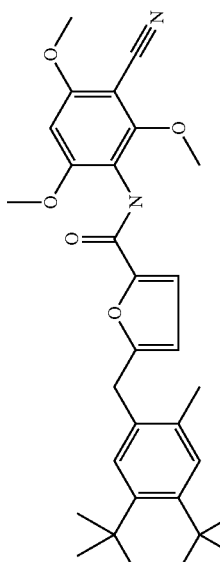 | | | | 2456 3120 |
| 181 | 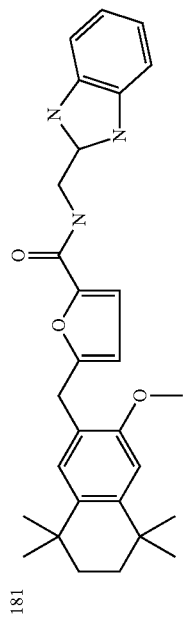 | 139 | 1.9 hr 3.64 | 4 hr 59% (20 mg/kg)[1] | |
| 182 | 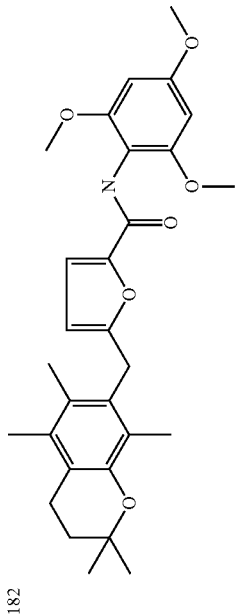 | | 3.2 hr 1.1 | 1.5 hr 33% (10 mg/kg)[10] | |
| 183 | 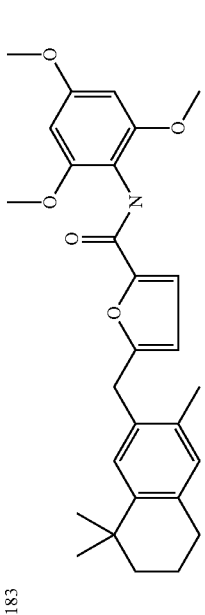 | 64 | 3.6 hr 0.51 | 1 hr 37% (10 mg/kg)[10] | |

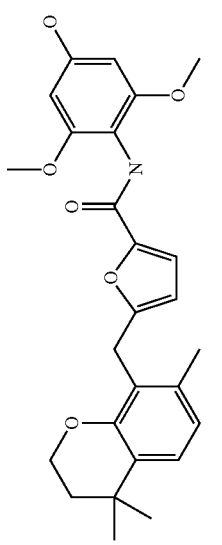 188 224
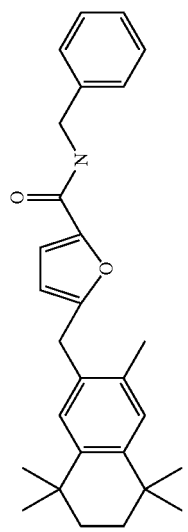 185
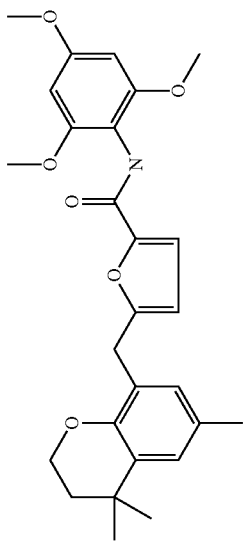 190.5 205
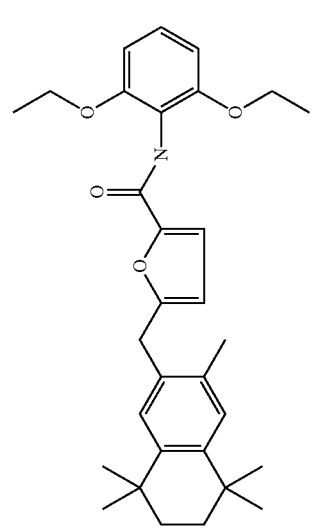 194

281

-continued

| | | | | | |
|---|---|---|---|---|---|
| 199 | [structure] | 181 | 1.5 hr 0.08 | 4 hr | 10% (10 mg/kg)[10] |
| 200 | [structure] | 86 | 2.0 hr 0.96 | 1.5 hr | 33% (10 mg/kg)[10] |
| 201 | [structure] | 330 | 2.5 hr 1.9 | 30 min | 21% (10 mg/kg)[10] |
| 206 | [structure] | | | | |
| 207 | [structure] | 159 | 1.6 hr 2.81 | 1 hr | 41% (10 mg/kg)[10] |

-continued
| | | | | | | |
|---|---|---|---|---|---|---|
| 212 | 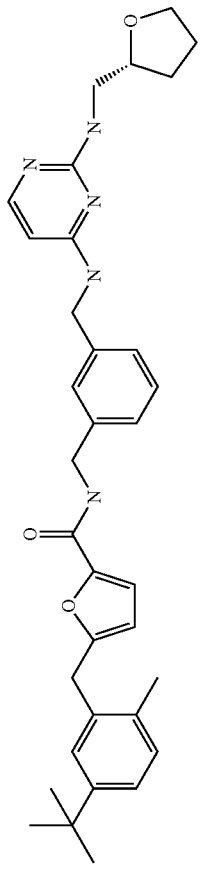 | Chiral | 430 | 1.6 hr | 0.05 | 1 hr | 1% (10 mg/kg)[10] |
| 217 | 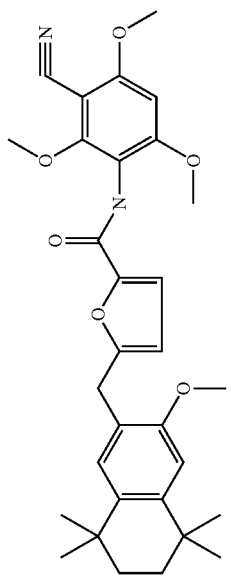 | | 203 | 3.8 hr | 0.1 | 1 hr | 16% (10 mg/kg)[10] |
| 221 | 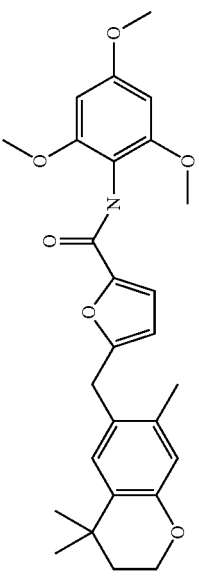 | | 223 | 3 hr | 0.34 | 1 hr | 41% (10 mg/kg)[10] |
| 222 | 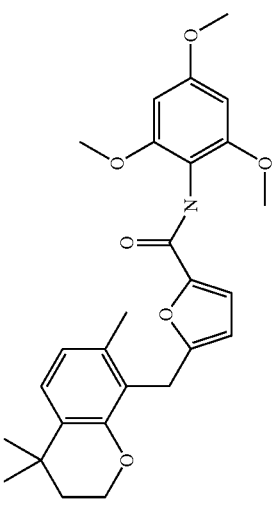 | | 167 | 3.2 | 0.81 | 1.5 | 54% (10 mg/kg)[10] |

| | | | | | |
|---|---|---|---|---|---|
| 225 | [structure] | 330 | 1.1 hr | 0.34 | 1 hr | 24% (10 mg/kg)[10] |
| 226 | [structure] | 173 | 4.6 hr | 0.42 | 1–5 hr | 34% (10 mg/kg)[10] |
| 228 | [structure] | 227 | 2.4 hr | 0.07 | 0.5 hr | 2% (10 mg/kg)[10] |
| 233 | [structure] | 338 | 1.4 hr | 0.34 | 1 hr | 34% (10 mg/kg)[10] |

-continued

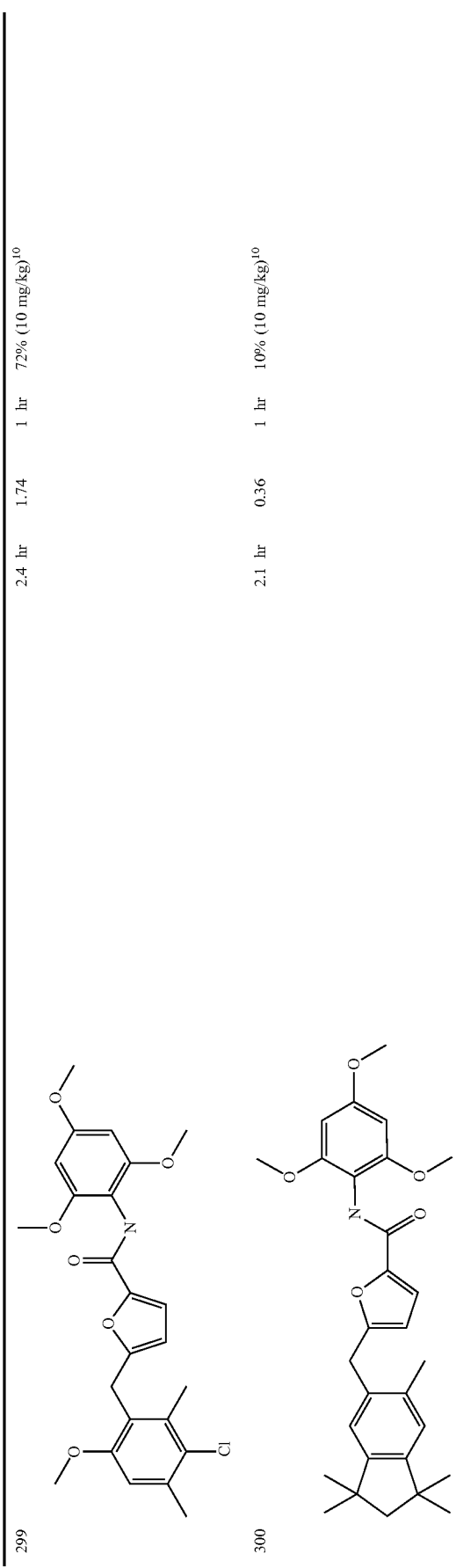

| 299 | | 2.4 hr | 1.74 | 1 hr | 72% (10 mg/kg)[10] |
| 300 | | 2.1 hr | 0.36 | 1 hr | 10% (10 mg/kg)[10] |

[1]10 mg/ml solution in 10% DMSO 10% cremophor 80% saline
[2]10 mg/ml solution in 10% DMSO 10% cremophor 80% saline (when given as 40 mg/ml in PEG400 or PG, $F_{p.o.}$ was 0%)
[3]10 mg/ml solution in 10% DMSO 10% cremophor 80% saline; or 40 mg/ml in PEG400 ($T_{max}$ = 4 hr); or PG ($T_{max}$ = 3.5 hr)
[4]10 mg/ml solution in 10% DMSO 10% cremophor 80% saline; or 40 mg/ml in PEG400 ($C_{max}$ = 0.23 plateau 2–4 hr)
[5]40 mg/ml solution in 50% DMSO 50% cremophor
[6]10 mg/ml suspention in 10% DMSO 20% cremophor 70% saline
[7]5 mg/ml suspension in 10% DMSO 10% cremophor 80% saline
[8]10 mg/ml suspension in 10% DMSO 10% cremophor 80% saline
[9]5 mg/ml solution in 10% DMSO 10% cremophor 80% saline
[10]

The following compounds have been made and tested using the procedures previously discussed. The data is in two parts and shows the binding of a compound to a receptor.
| Compound | MOLSTRUCTURE | S%R 10 uM hGnRHR |
|---|---|---|
| 320 | 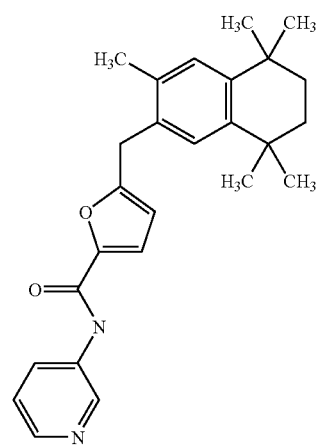 | 9 |
| 321 | 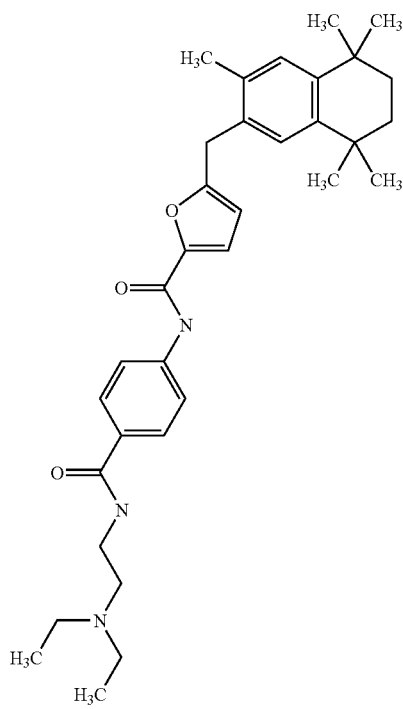 | 55 |

-continued
| | | |
|---|---|---|
| 322 | 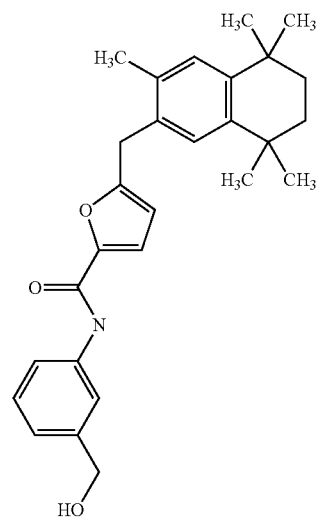 | 4 |
| 323 | 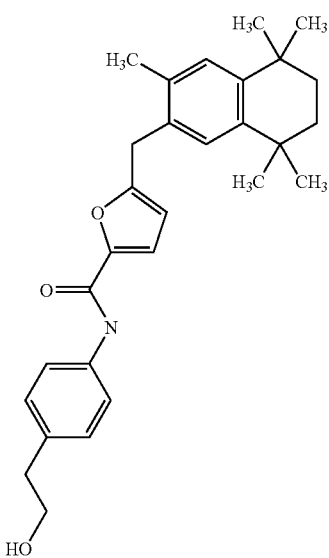 | 1 |
| 324 | 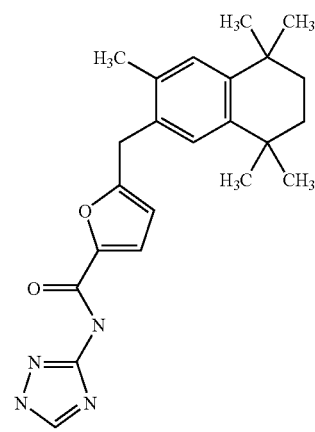 | 27 |

-continued
| 325 | 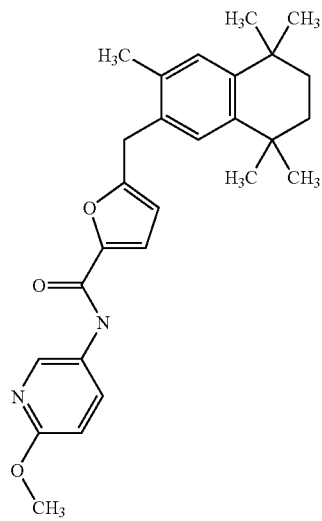 | 3 |
| 326 | 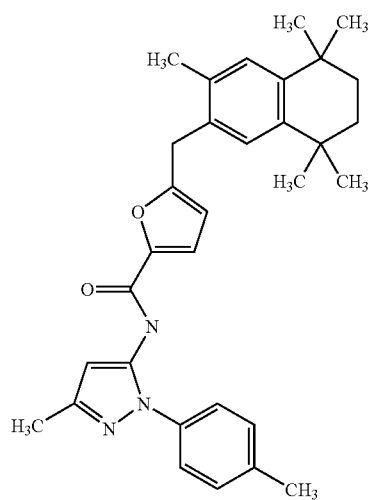 | 51 |
| 327 | 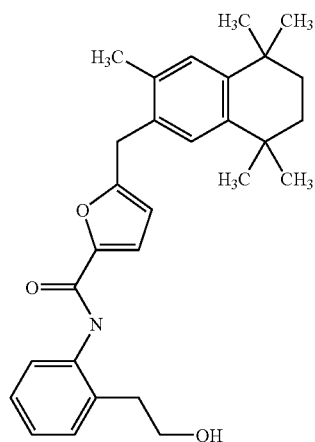 | 0 |

-continued
328
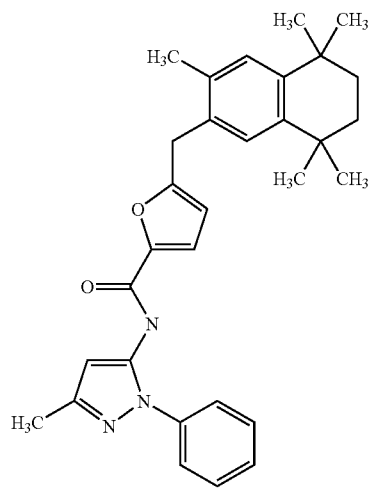
33
329
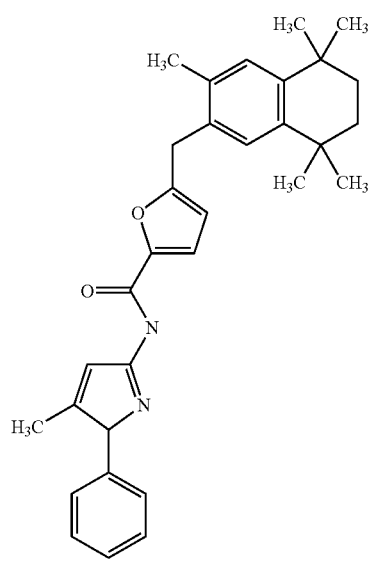
31
330
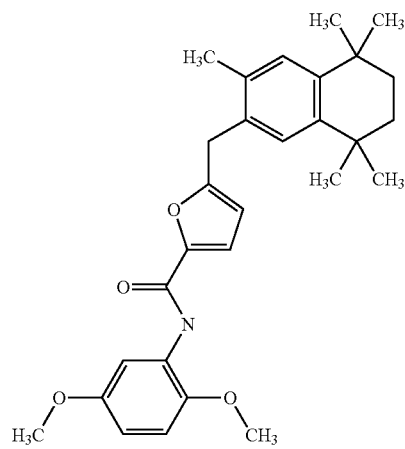
10

331 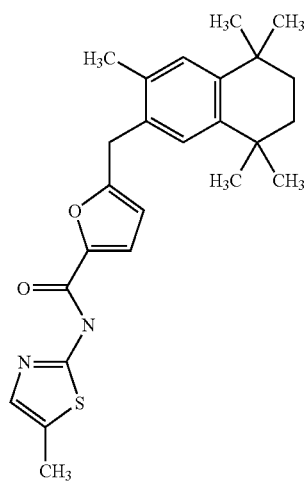 49
332 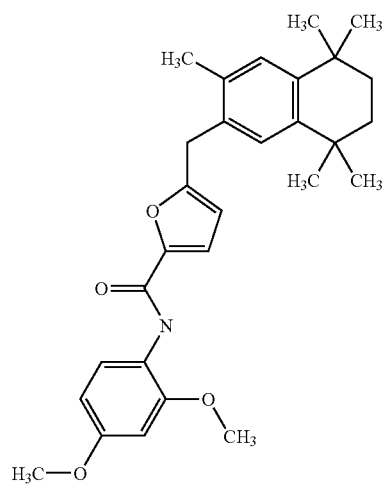 1
333 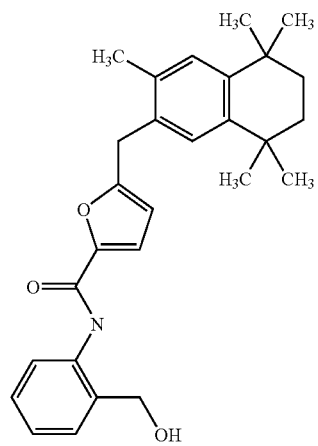 28

| 334 | 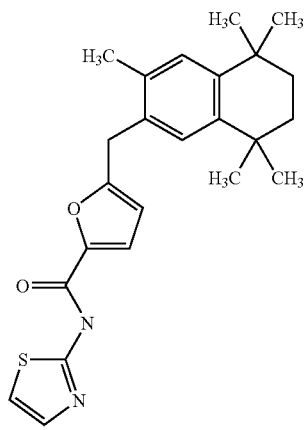 | 34 |
| 335 | 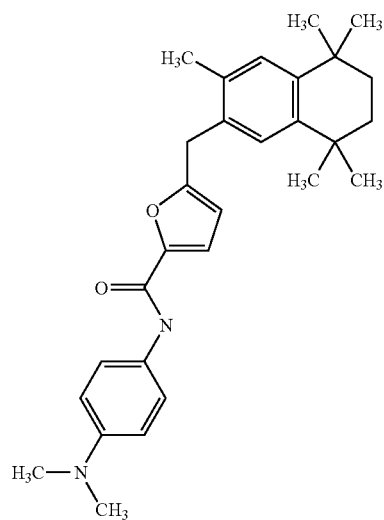 | 2 |
| 336 | 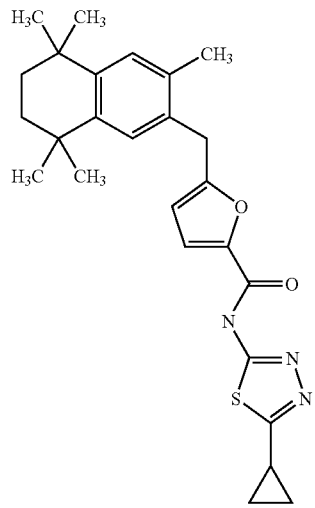 | 57 |

-continued
| | | |
|---|---|---|
| 337 | 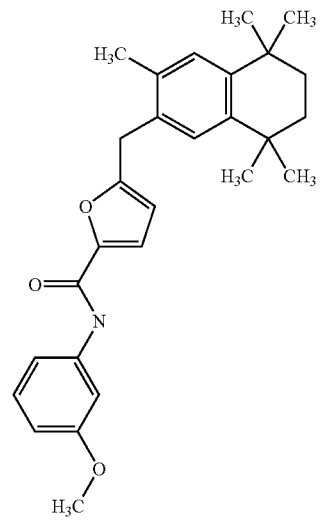 | 6 |
| 338 | 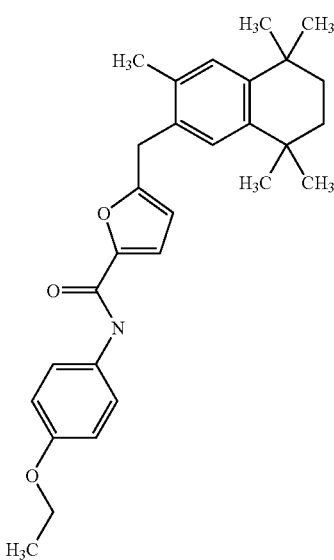 | 26 |
| 339 | 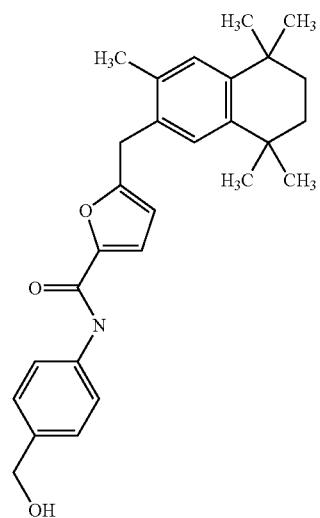 | 17 |

| 340 | 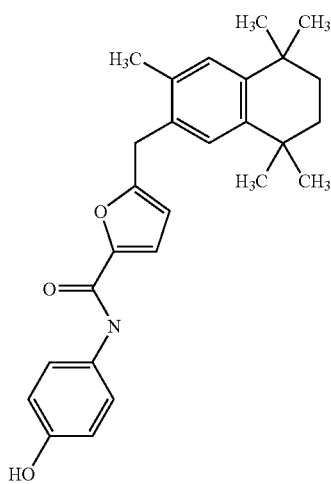 | 28 |
| 341 | 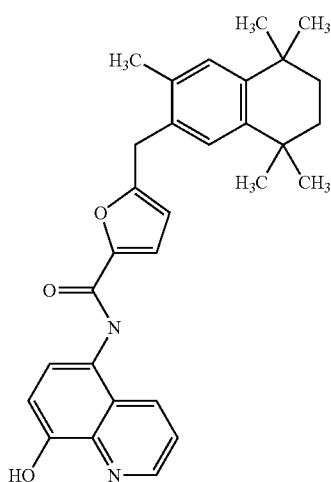 | 20 |
| 342 | 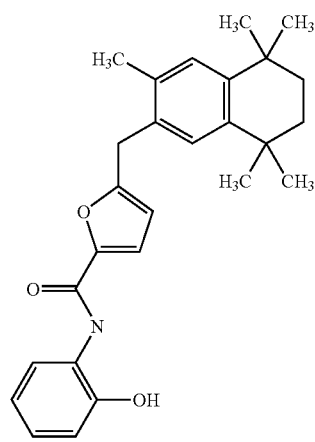 | 45 |

-continued
343
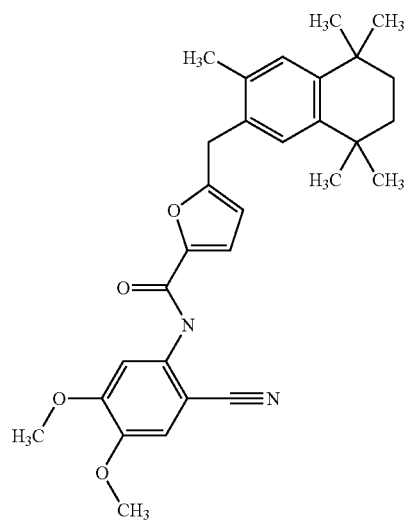
33
344
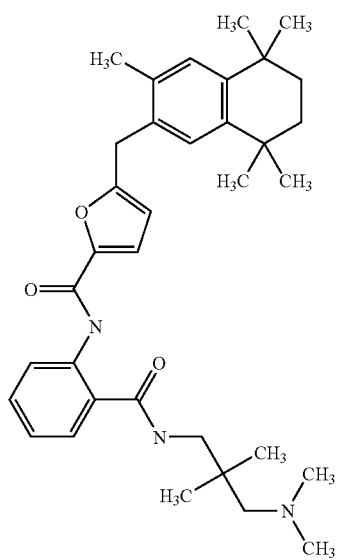
57
345
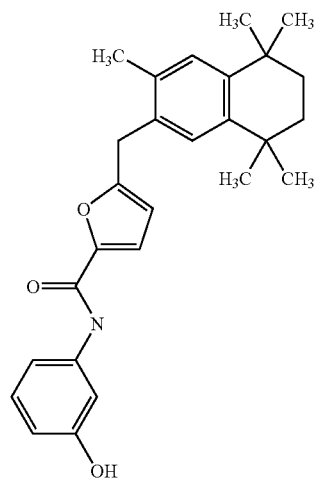
40

-continued
| 346 | 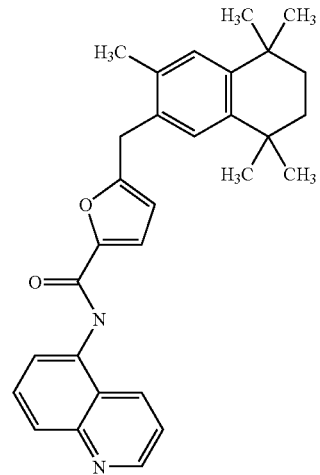 | −14 |
| 347 | 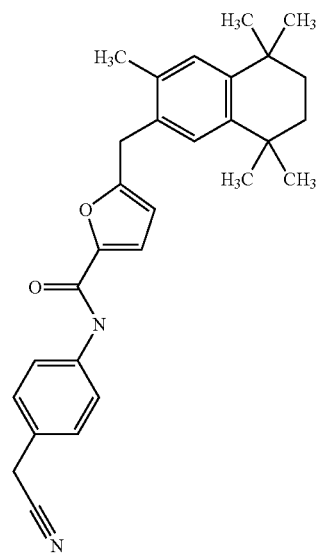 | 2 |
| 348 | 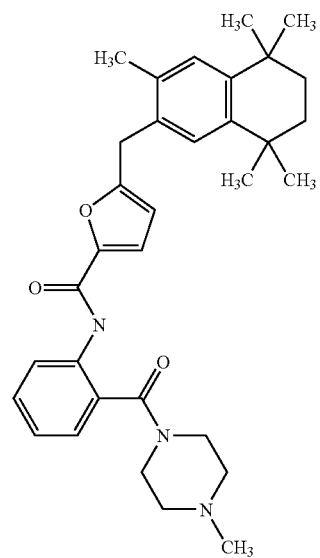 | 49 |

-continued
| | | |
|---|---|---|
| 349 | 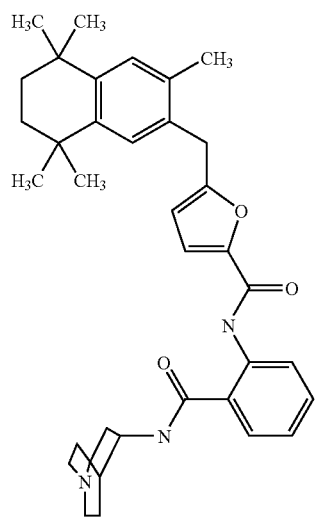 | 47 |
| 350 | 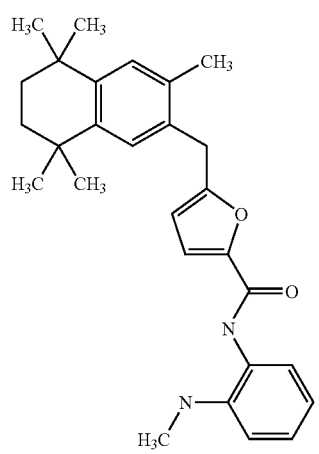 | 10 |
| 351 | 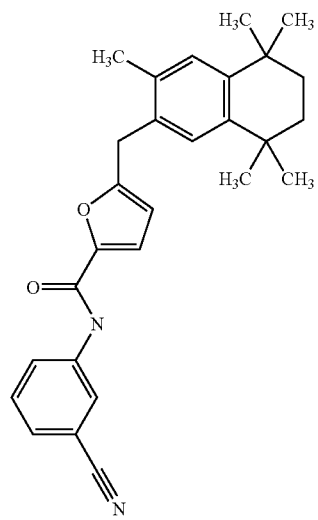 | 24 |

-continued
| 352 | 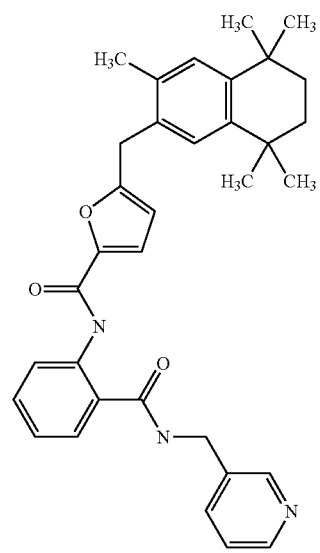 | 51 |
| 353 | 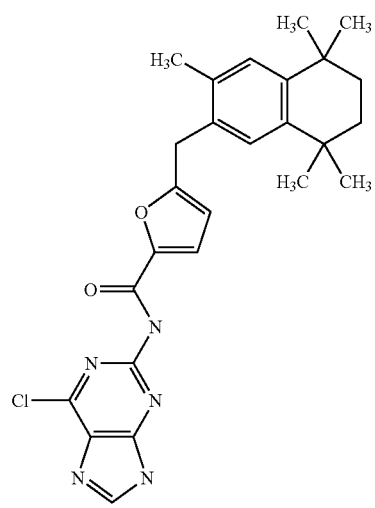 | −4 |
| 354 | 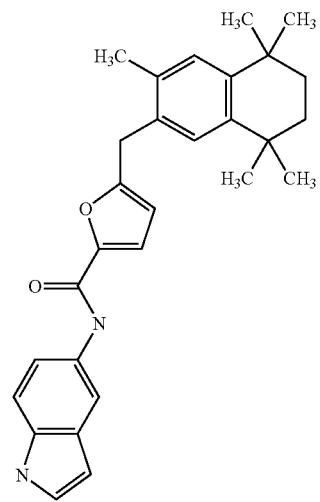 | −5 |

| | | |
|---|---|---|
| 355 | 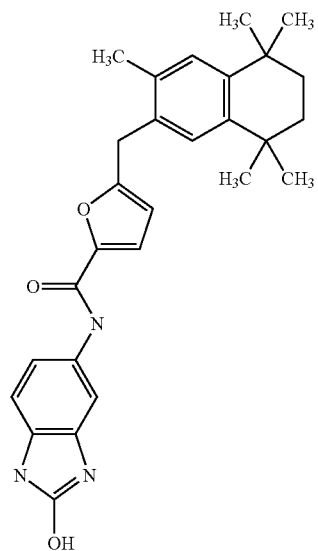 | 20 |
| 356 | 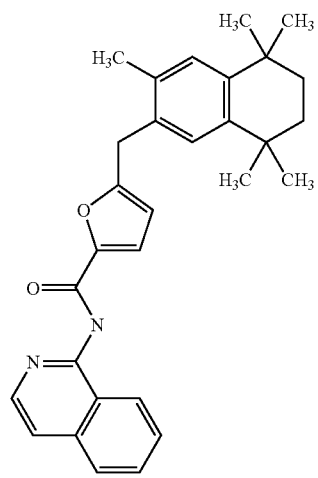 | 17 |
| 357 | 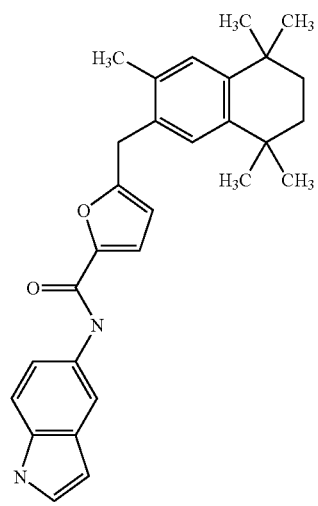 | −2 |

| | | |
|---|---|---|
| 358 | 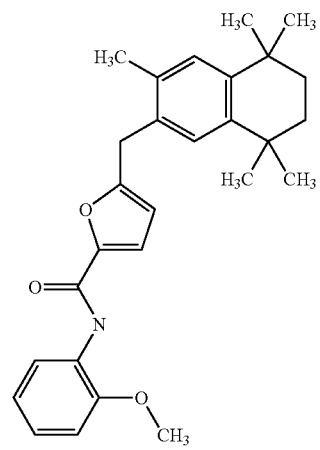 | 9 |
| 359 | 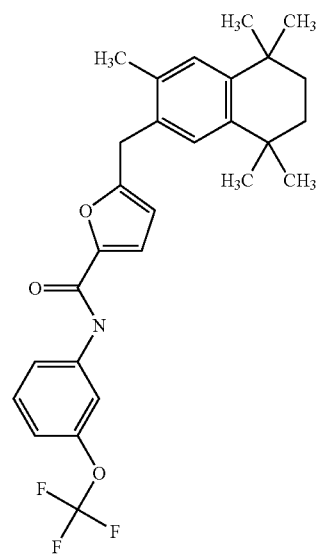 | 55 |
| 360 | 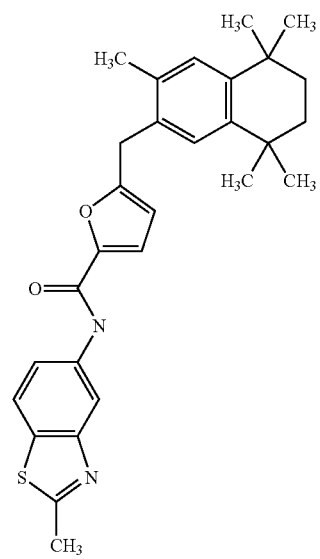 | 4 |

-continued
| 361 | 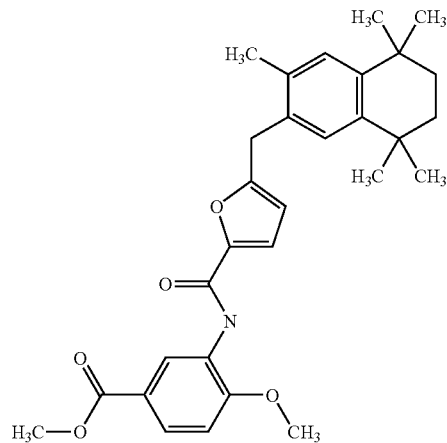 | 4 |
| 362 | 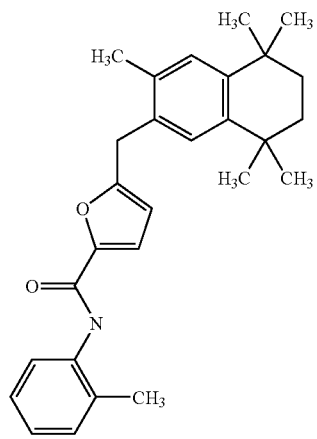 | 1 |
| 363 | 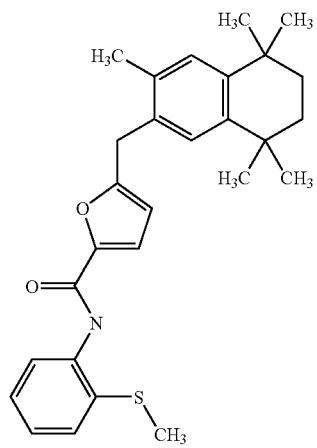 | 14 |

-continued
| | | |
|---|---|---|
| 364 | 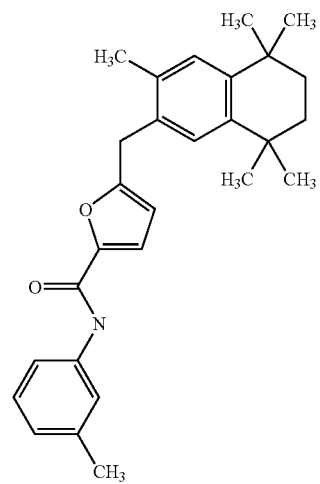 | 21 |
| 365 | 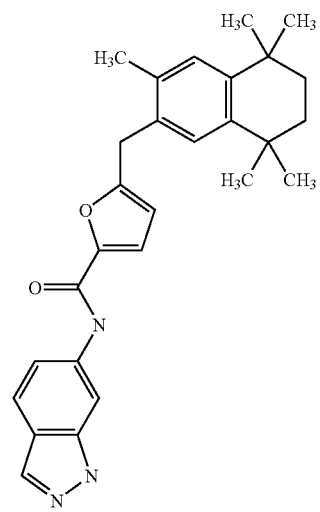 | 47 |
| 366 | 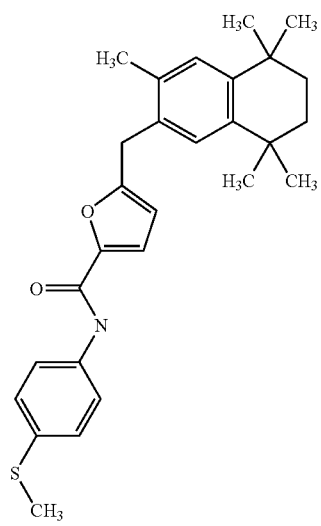 | 37 |

-continued
367
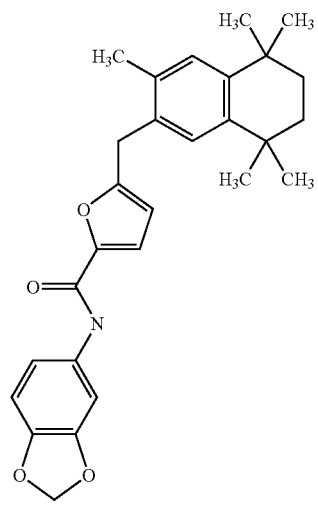
15
368
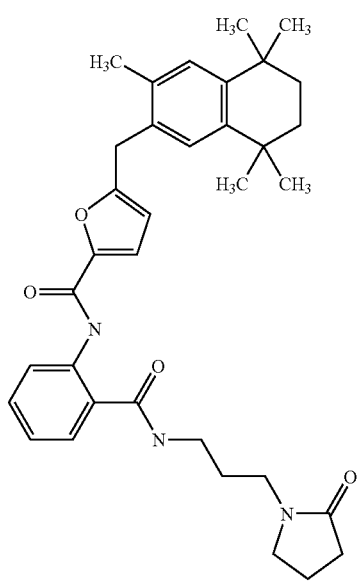
56
369
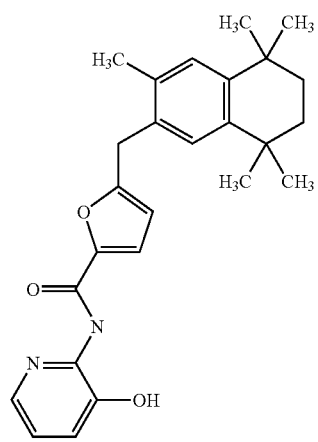
11

| | | |
|---|---|---|
| 370 | 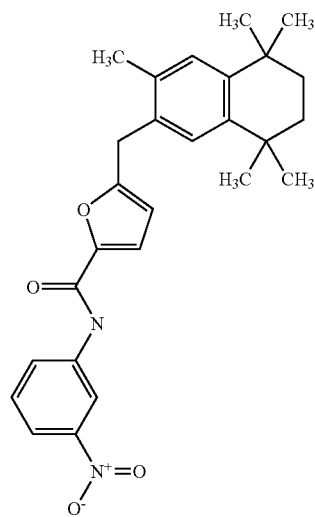 | 37 |
| 371 | 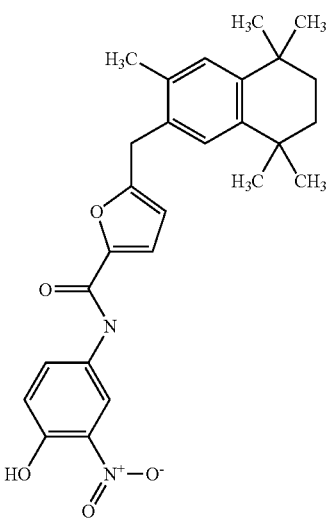 | 55 |
| 372 | 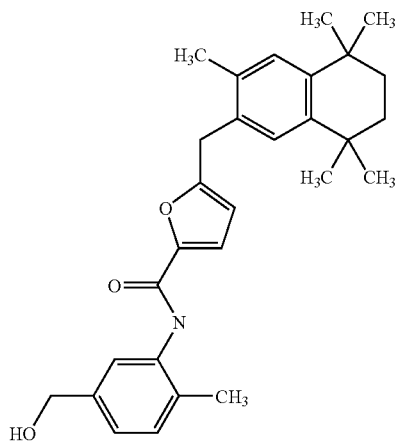 | 1 |

-continued
| | |
|---|---|
| 373 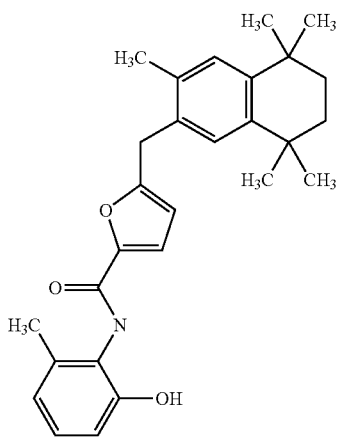 | 19 |
| 374 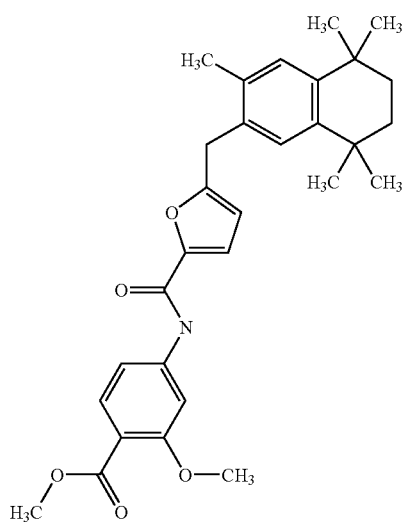 | 13 |
| 375 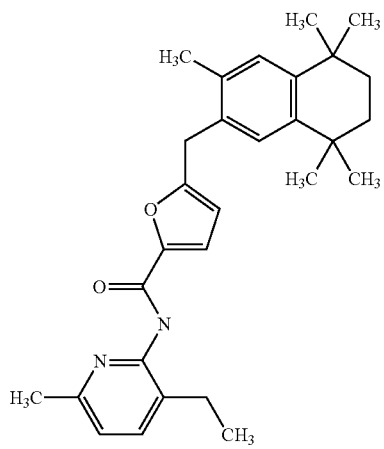 | 16 |

-continued
| | | |
|---|---|---|
| 376 | 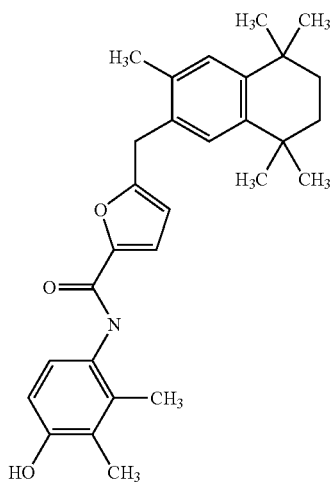 | 50 |
| 377 | 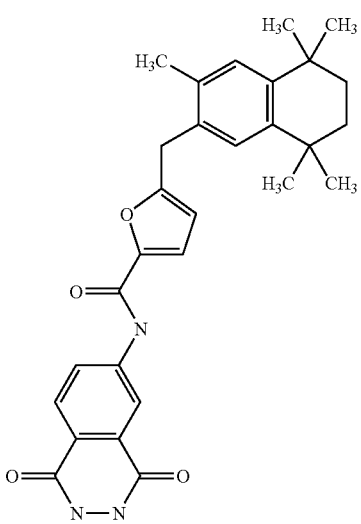 | 39 |
| 378 | 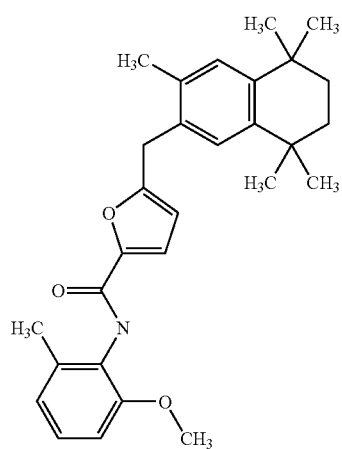 | −4 |

-continued
| | | |
|---|---|---|
| 379 | 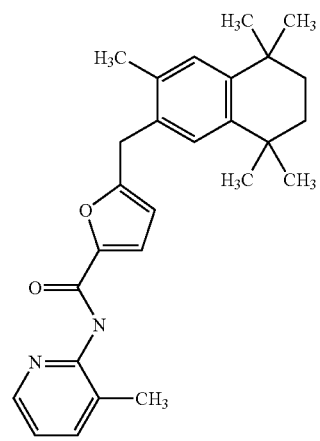 | 4 |
| 380 | 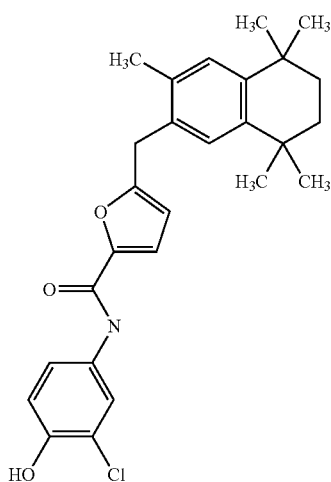 | 29 |
| 381 | 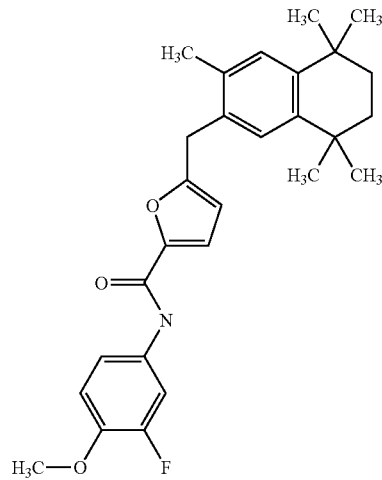 | 34 |

-continued
| | | |
|---|---|---|
| 382 | 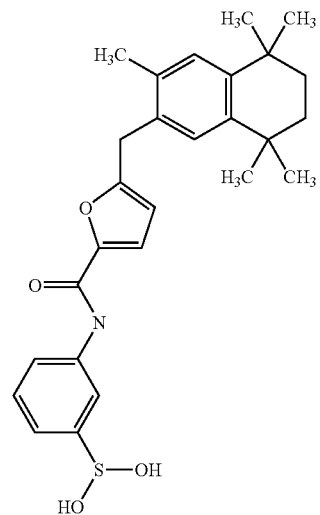 | 8 |
| 383 | 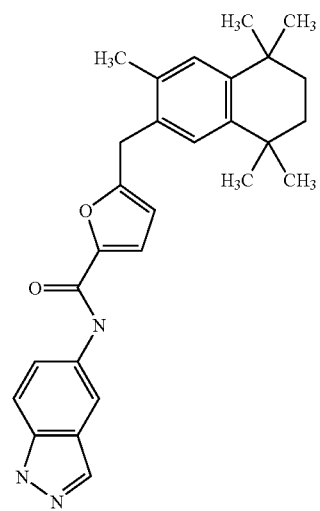 | 7 |
| 384 | 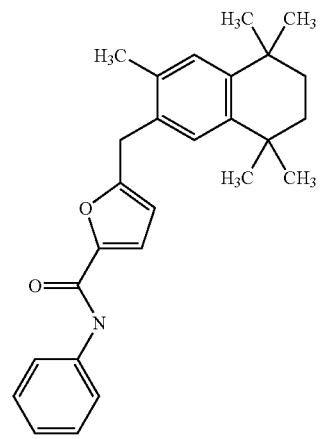 | 21 |

-continued
| | | |
|---|---|---|
| 385 | 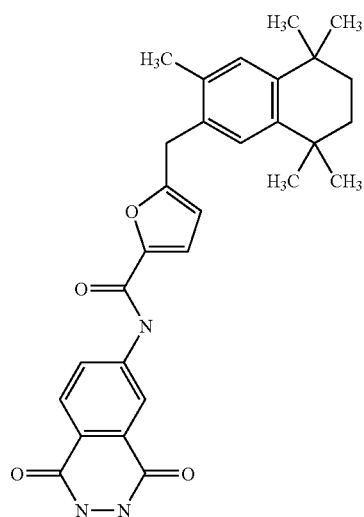 | 41 |
| 386 | 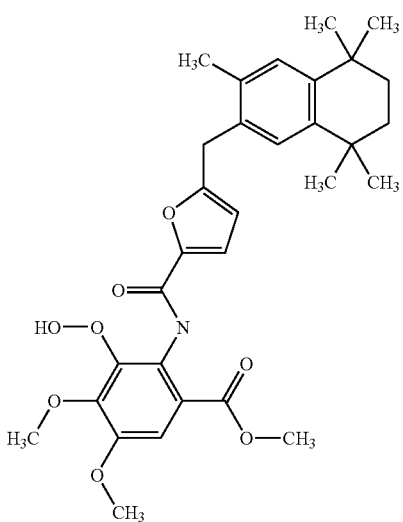 | 27 |
| 387 | 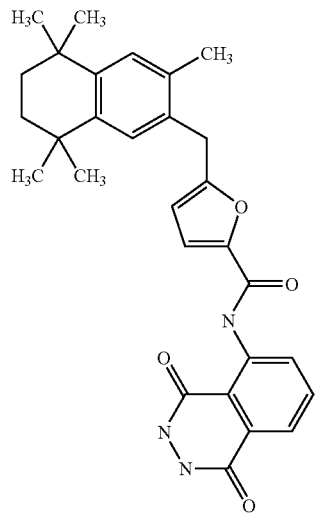 | 52 |

-continued
| | | |
|---|---|---|
| 388 | 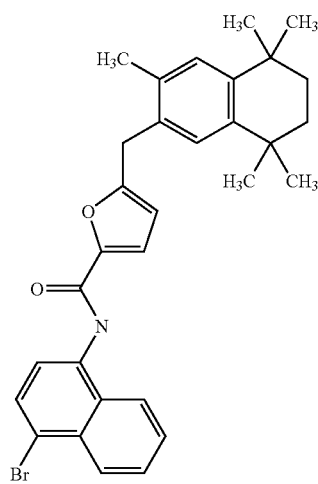 | 30 |
| 389 | 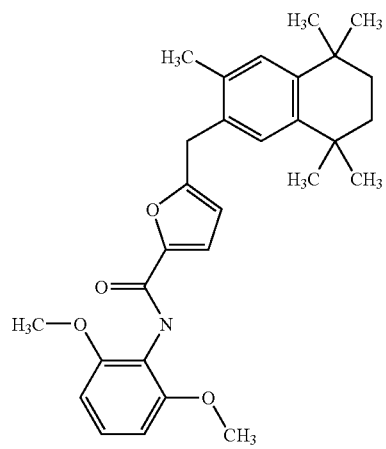 | 3 |
| 390 | 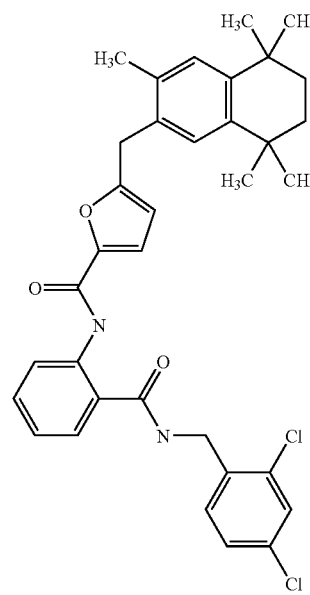 | 55 |

-continued
| 391 | 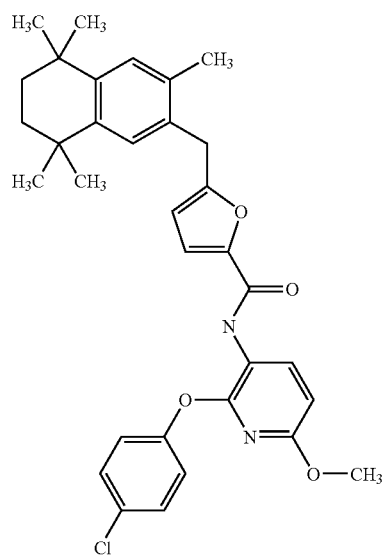 | 48 |
| 392 | 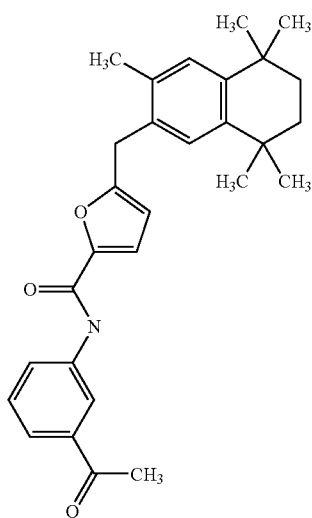 | 0 |
| 393 | 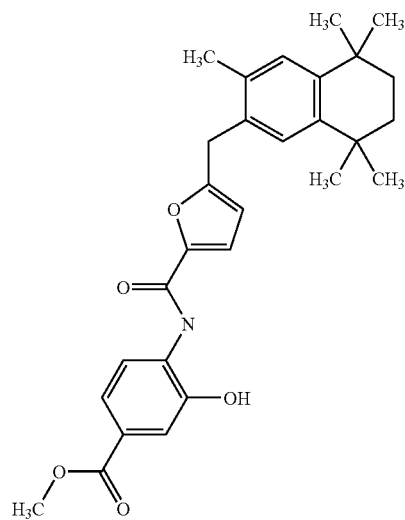 | 44 |

-continued
| | | |
|---|---|---|
| 394 | 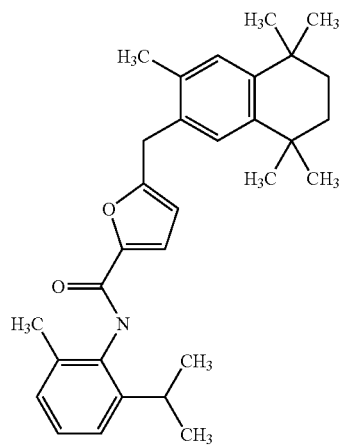 | 57 |
| 395 | 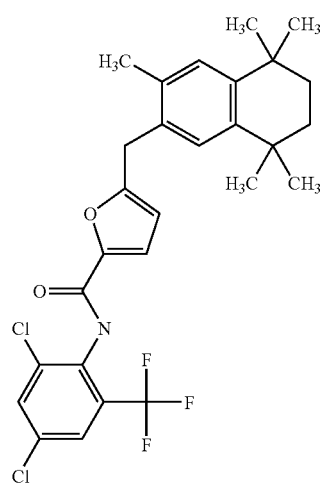 | 40 |
| 396 | 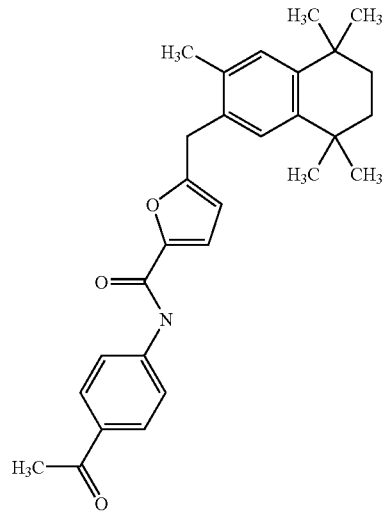 | 55 |

-continued
397 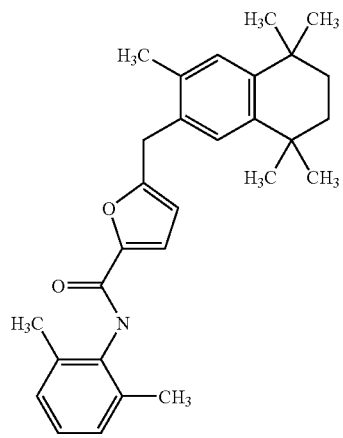 43
390 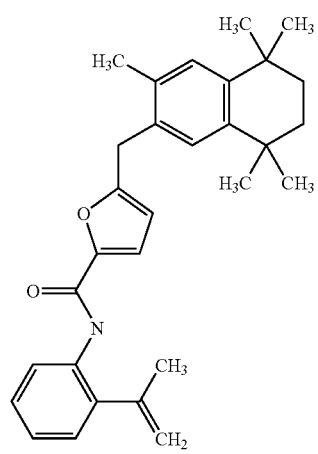 44
399 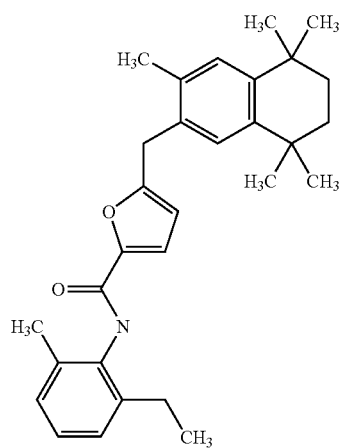 41

-continued
| COMPOUND | MOLSTRUCTURE | S%R 1 uM hGnRHR |
|---|---|---|
| 400 | 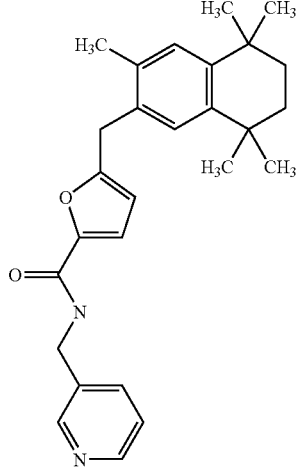 | 28 |
| 401 | 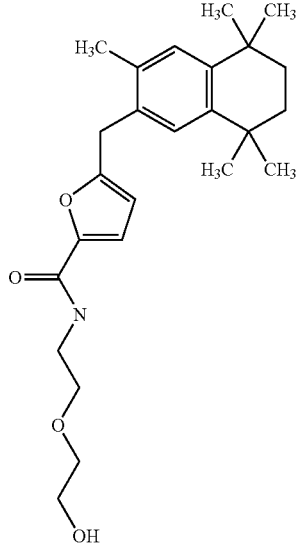 | 32 |
| 402 | 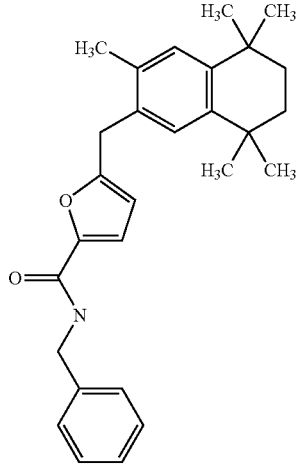 | 18 |

-continued
403
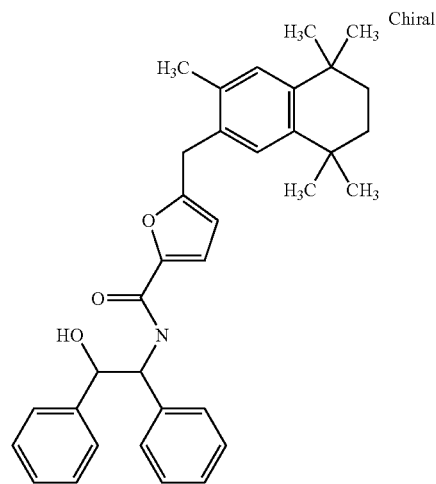
44
404
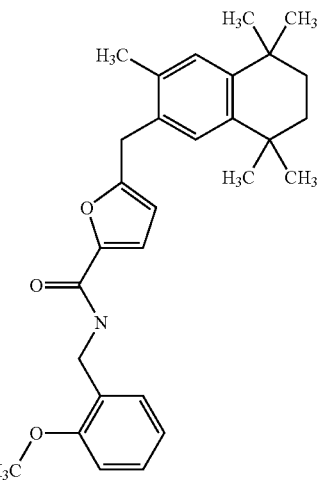
13
405
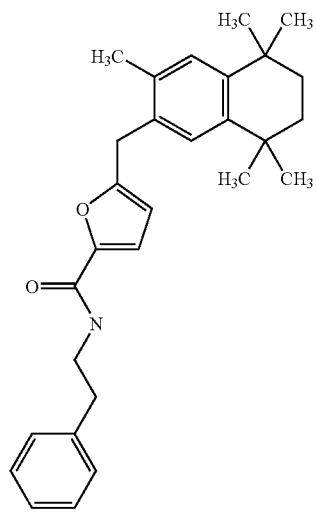
40

-continued
| | | |
|---|---|---|
| 406 | 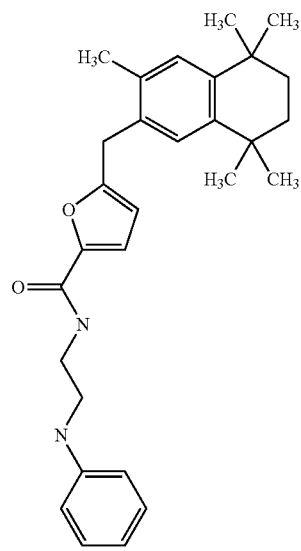 | 30 |
| 407 | 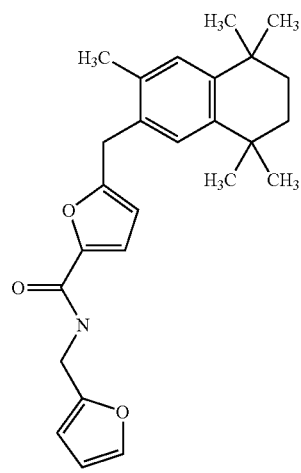 | 20 |
| 408 | 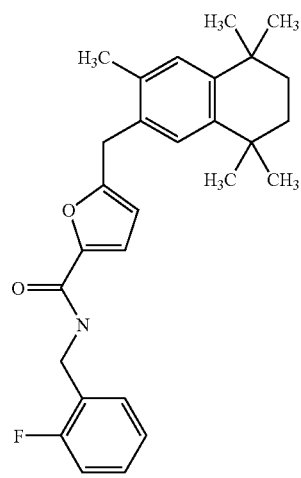 | 16 |

-continued
| | | |
|---|---|---|
| 409 | 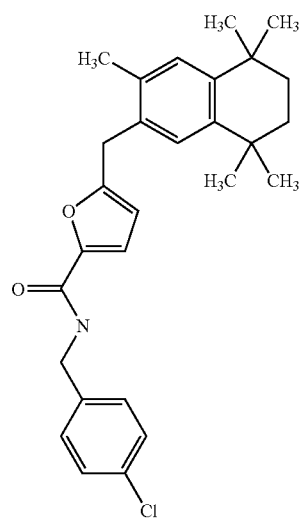 | 32 |
| 410 | 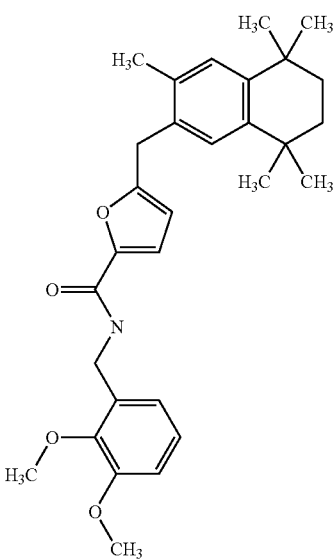 | 21 |
| 411 | 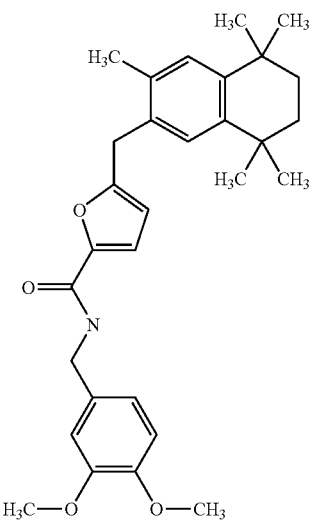 | 28 |

-continued
| | | |
|---|---|---|
| 412 | 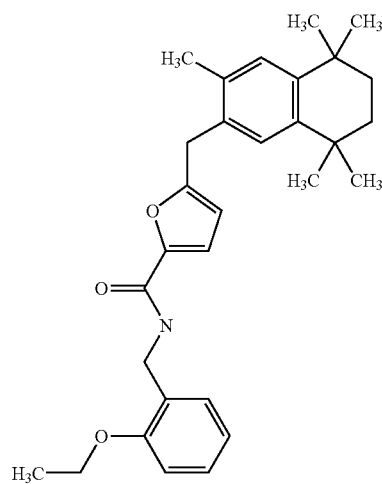 | 49 |
| 413 | 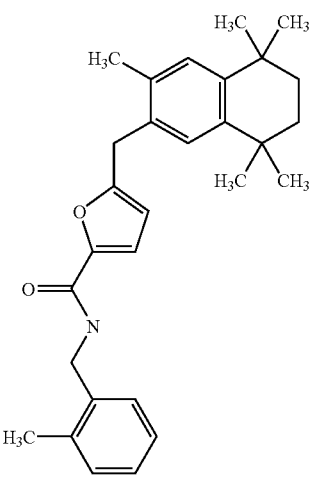 | 16 |
| 414 | 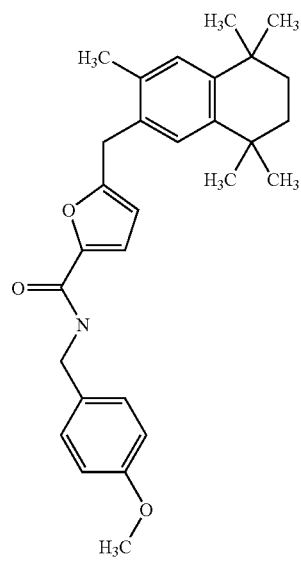 | 10 |

-continued
| | | |
|---|---|---|
| 415 | 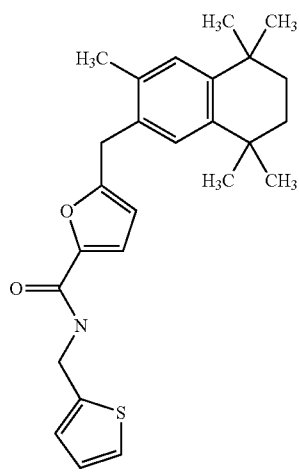 | 18 |
| 416 | 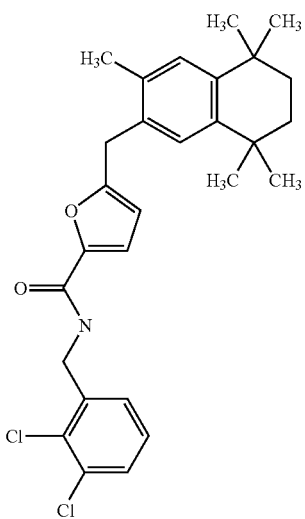 | 34 |
| 417 | 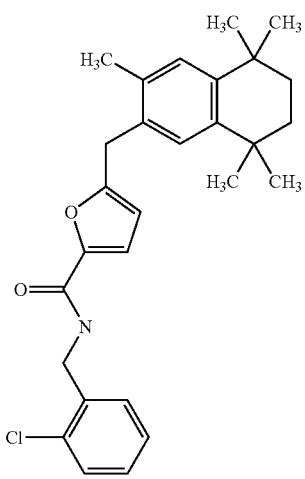 | 20 |

| 418 | 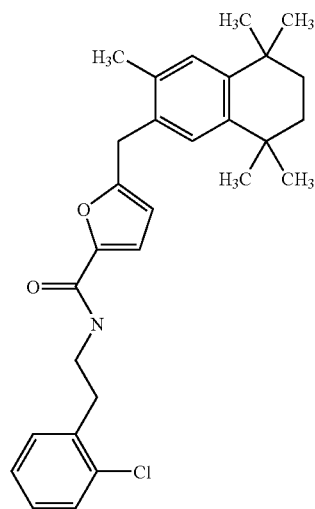 | 42 |
| 419 | 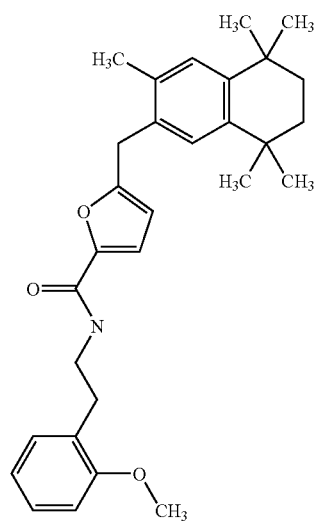 | 36 |
| 420 | 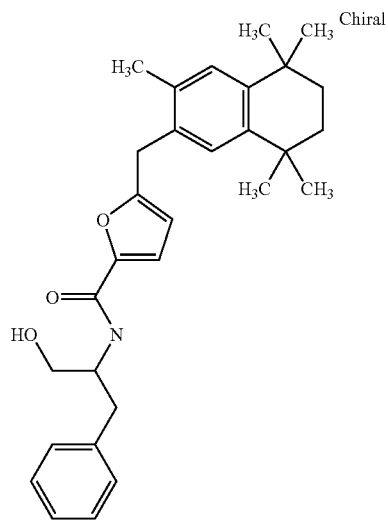 | 28 |

-continued
| | | |
|---|---|---|
| 421 | 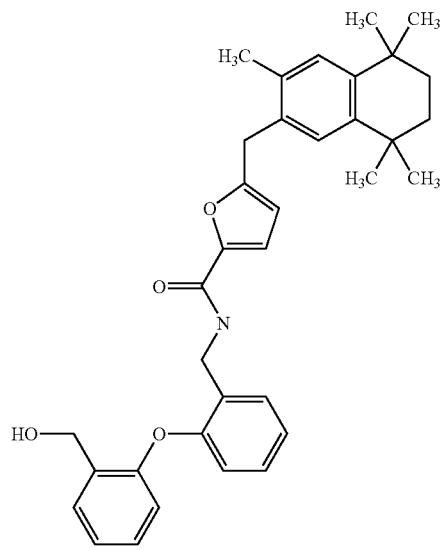 | 48 |
| 422 | 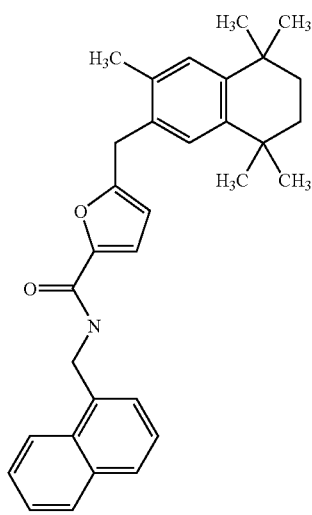 | 34 |
| 423 | 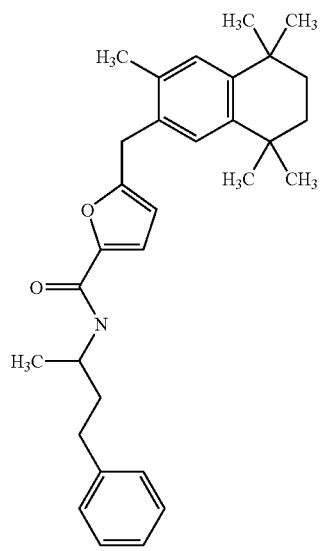 | 49 |

-continued
| 424 | 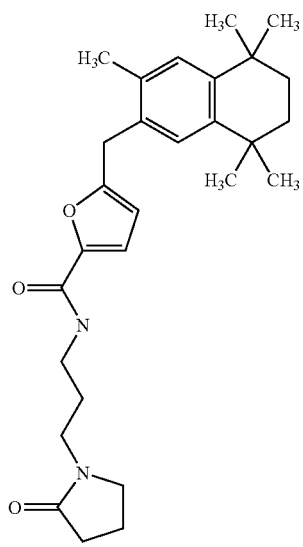 | 31 |
| 425 | 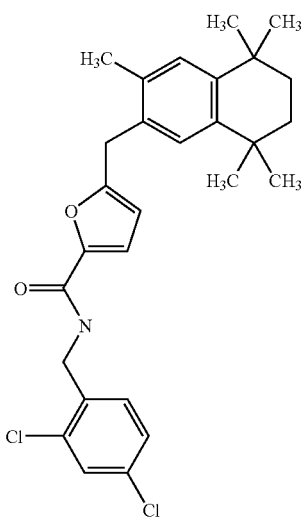 | 42 |
| 426 | 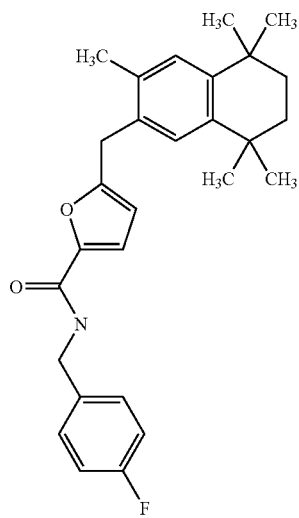 | 30 |

-continued
| | | |
|---|---|---|
| 427 | 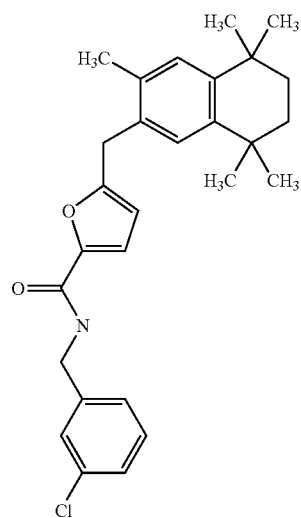 | 20 |
| 428 | 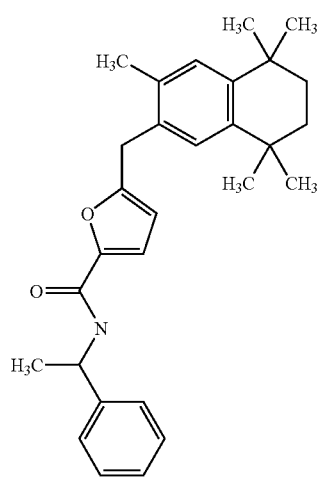 | 46 |
| 429 | 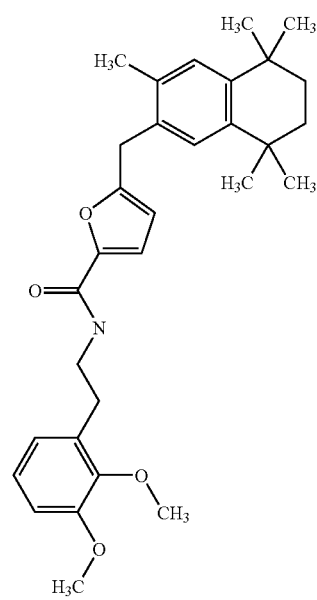 | 40 |

-continued
| | | |
|---|---|---|
| 430 | 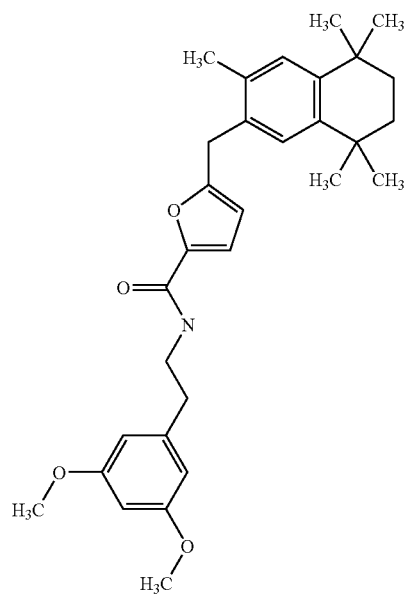 | 55 |
| 431 | 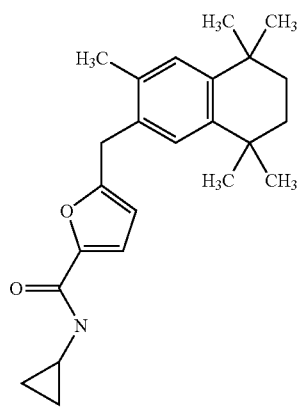 | 47 |
| 432 | 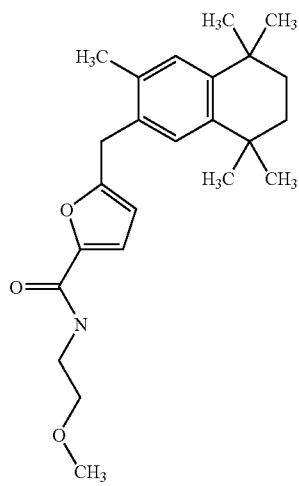 | 42 |

-continued
| | |
|---|---|
| 433 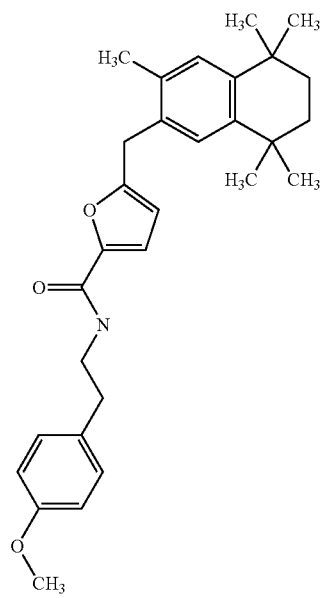 | 54 |
| 434 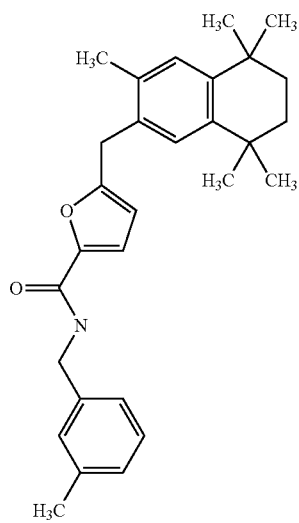 | 6 |
| 435 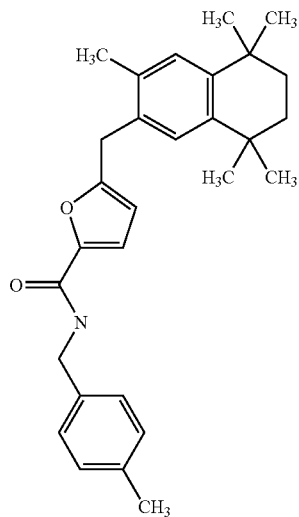 | 12 |

-continued
| | | |
|---|---|---|
| 436 | 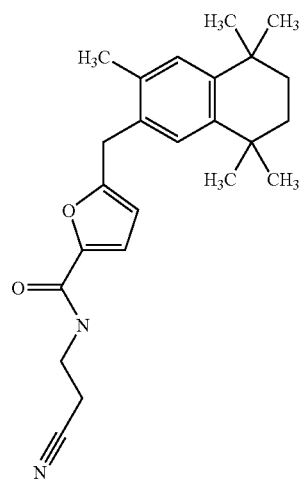 | 58 |
| 437 | 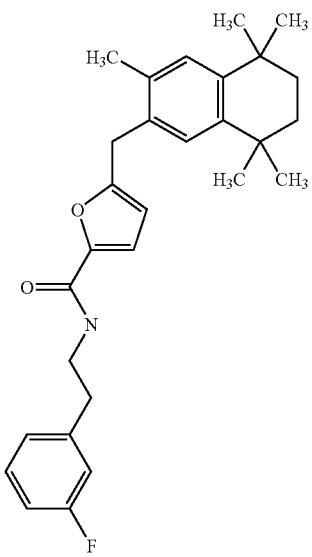 | 40 |
| 438 | 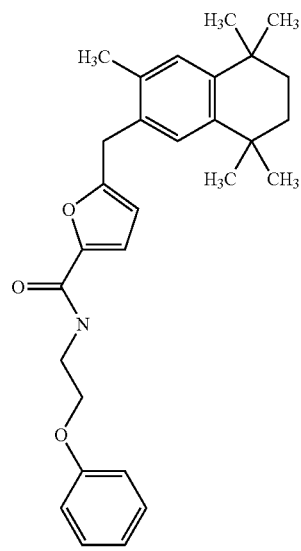 | 7 |

-continued
| 439 | 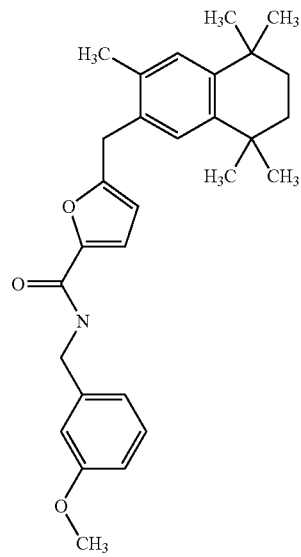 | 23 |
| 440 | 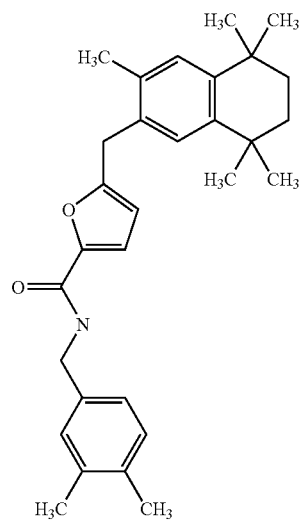 | 22 |
| 441 | 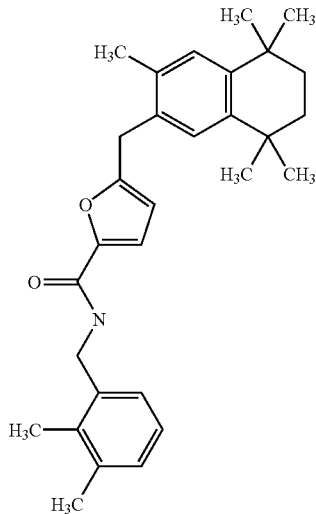 | 17 |

-continued
442 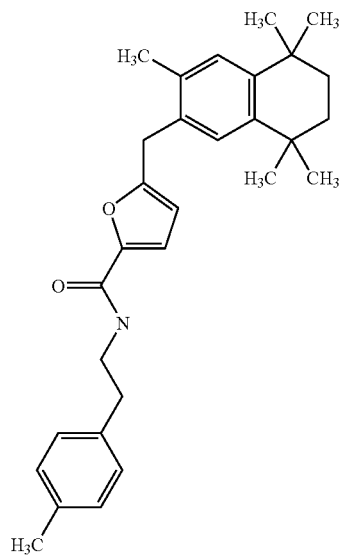 50
443 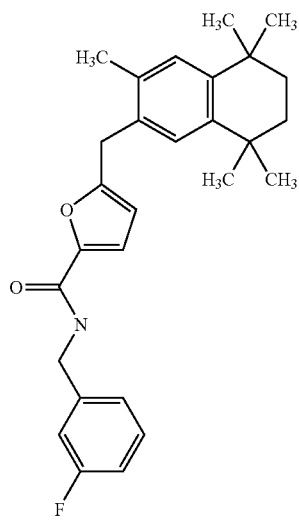 19
444 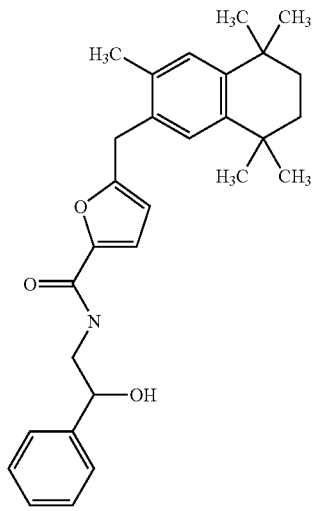 32

-continued
| 445 | 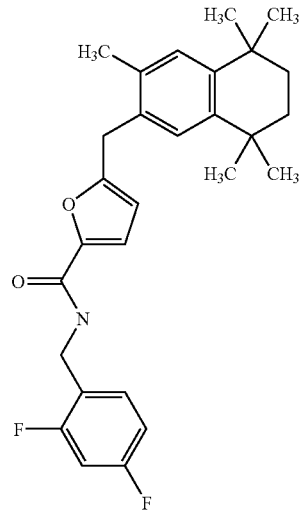 | 22 |
| 446 | 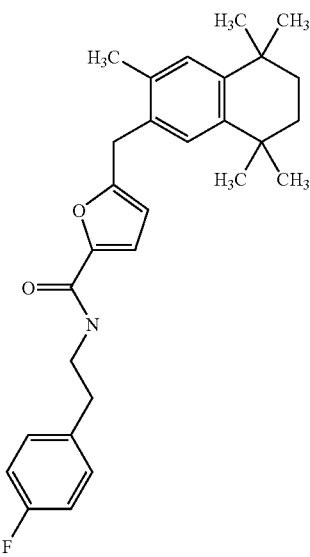 | 55 |
| 447 | 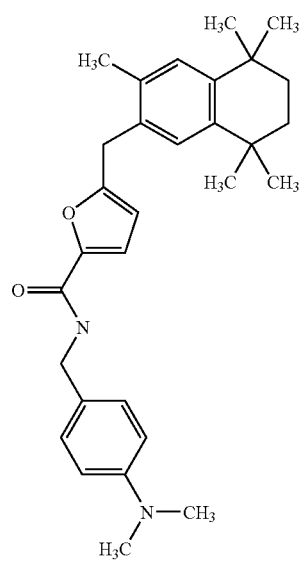 | 18 |

-continued
448 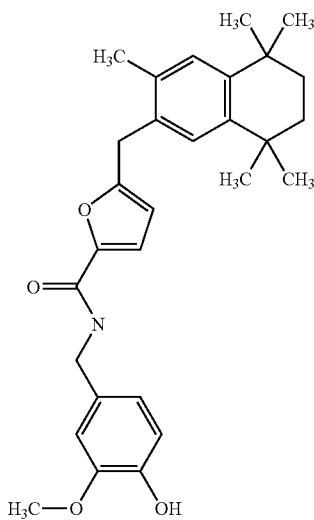 46
449 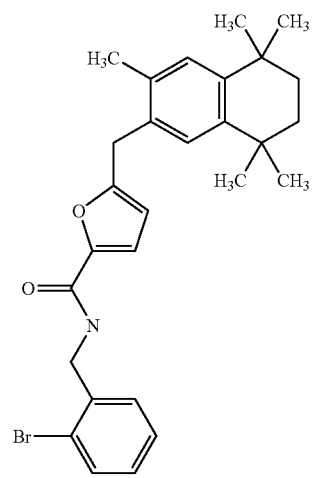 42
450 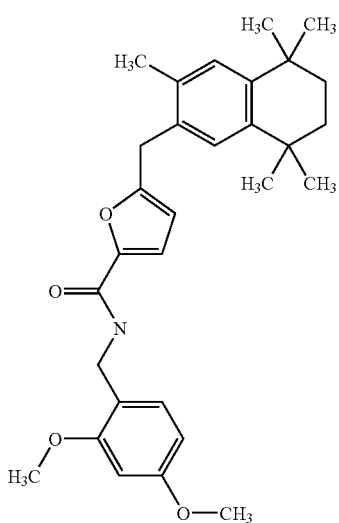 6

| | | |
|---|---|---|
| 451 | 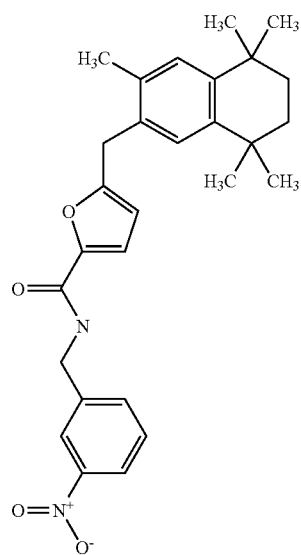 | 24 |
| 452 | 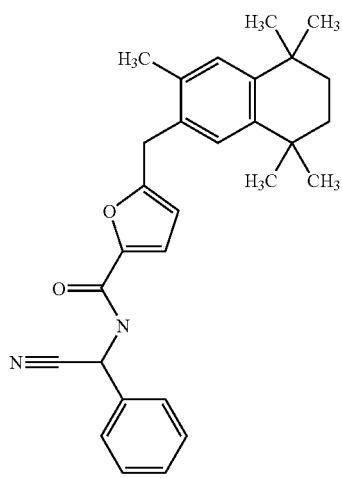 | 55 |
| 453 | 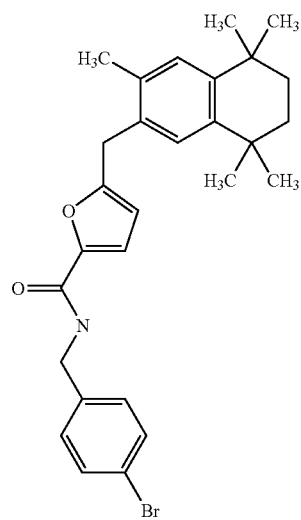 | 50 |

| 454 | 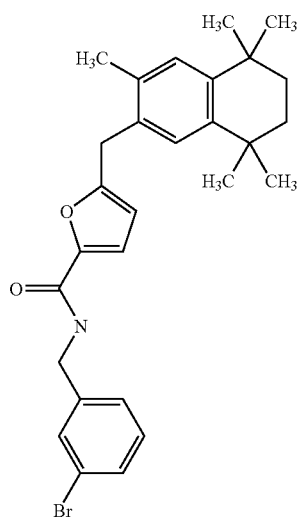 | 36 |
| 455 | 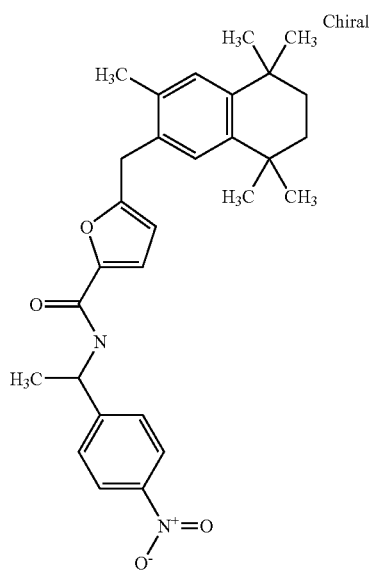 | 58 |

-continued
| COMPOUND | MOLSTRUCTURE | S%R 10 uM mGnRHR |
|---|---|---|
| 456 | 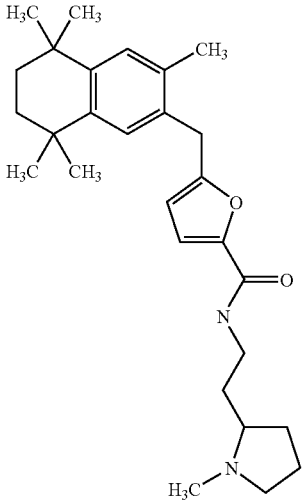 | −12 |
| 457 | 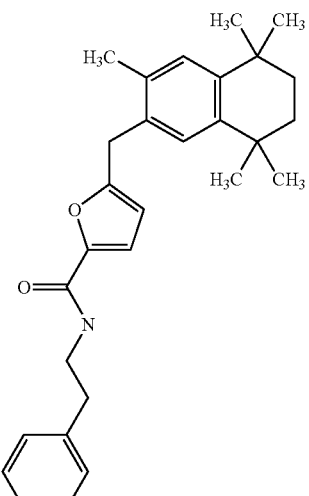 | −3 |

| 458 | 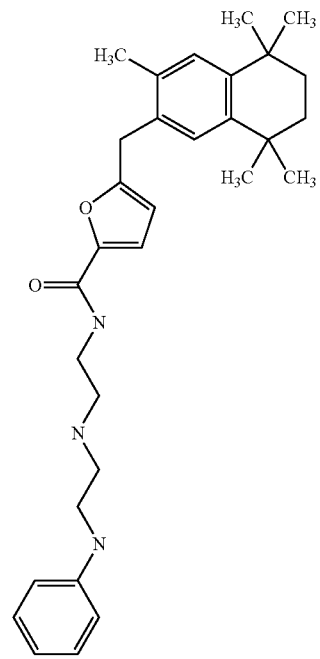 | 29 |
| --- | --- | --- |
| 459 | 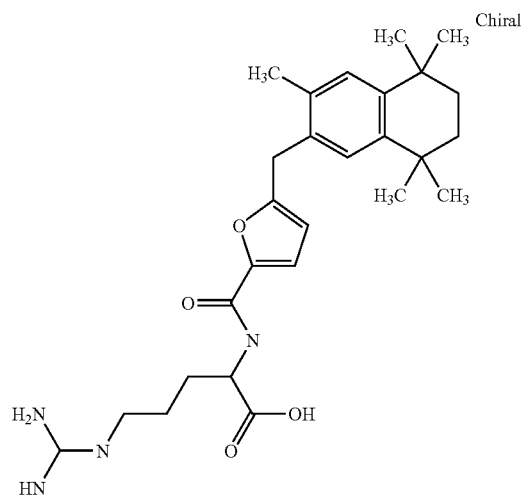 | 53 |
| --- | --- | --- |

-continued
| | | |
|---|---|---|
| 460 | 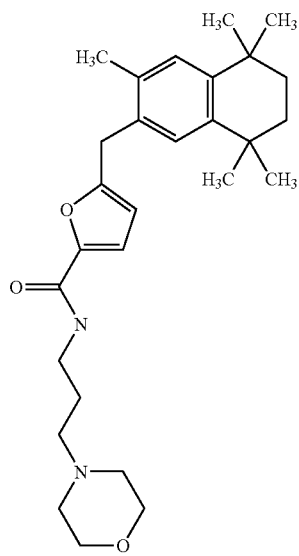 | -4 |
| 461 | 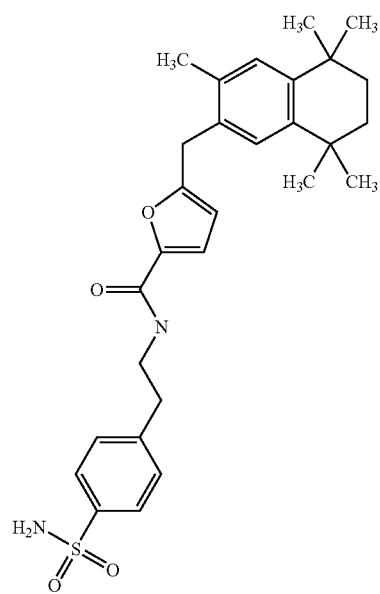 | 53 |

| 462 | 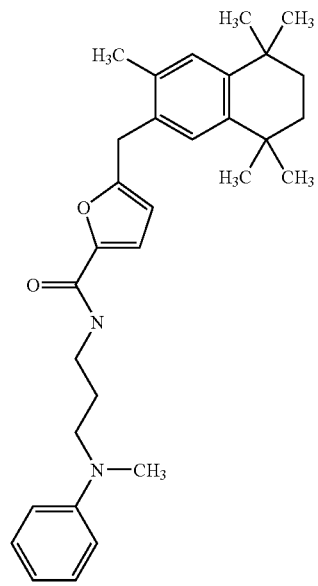 | 0 |
| --- | --- | --- |
| 463 | 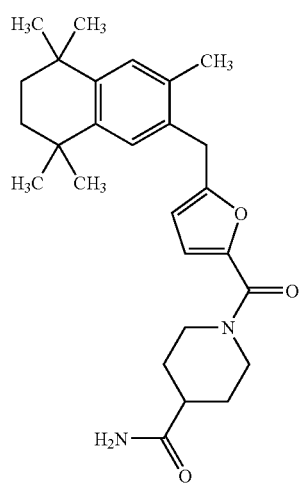 | −5 |

-continued
| | | |
|---|---|---|
| 464 | 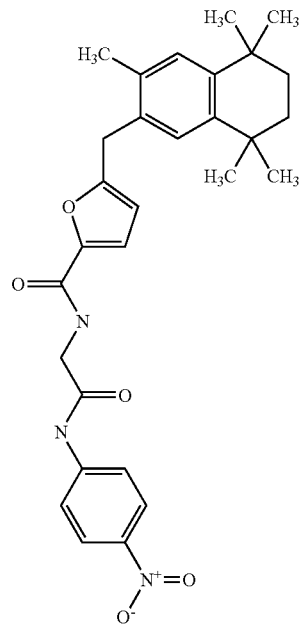 | 7 |
| 465 | 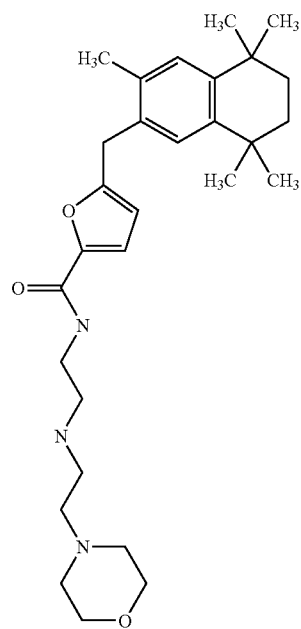 | 32 |

| 466 | 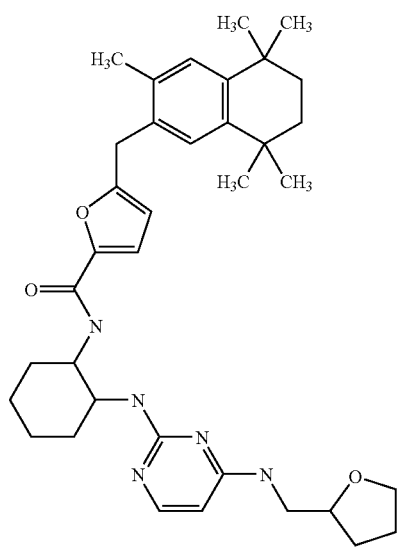 | 30 |
| 467 | 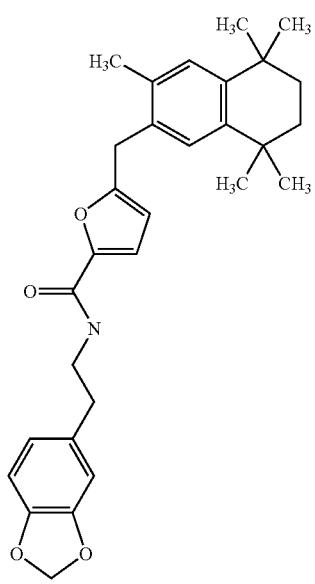 | −1 |

-continued
| 468 | 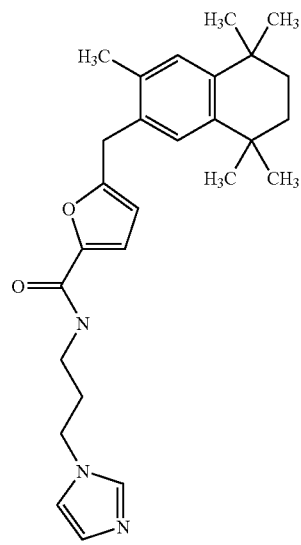 | −10 |
| 469 | 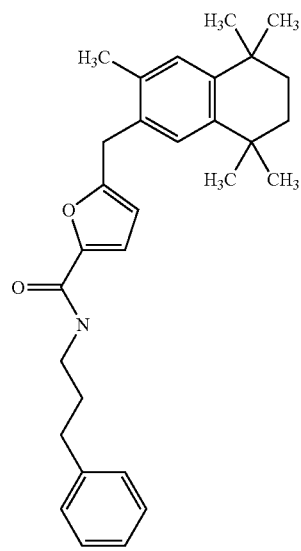 | −9 |
| 470 | 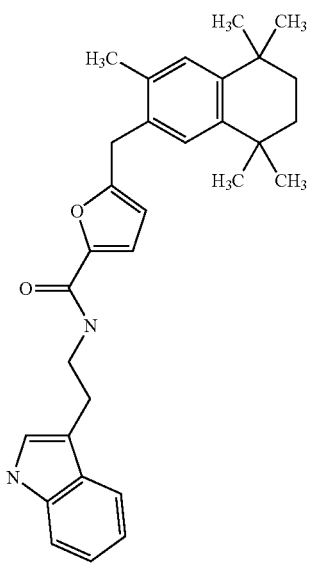 | 6 |

471 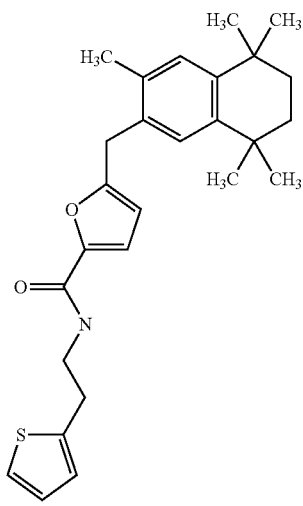 -4
472 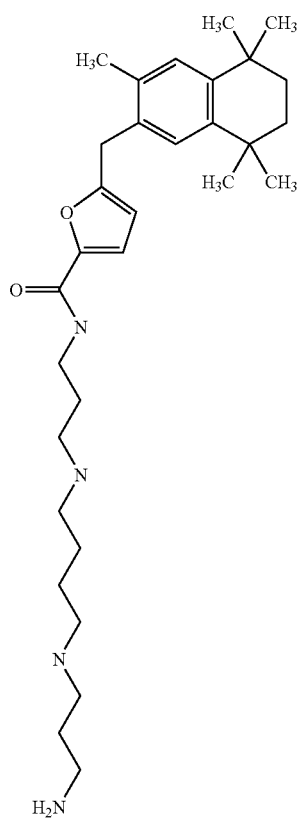 42

-continued
473
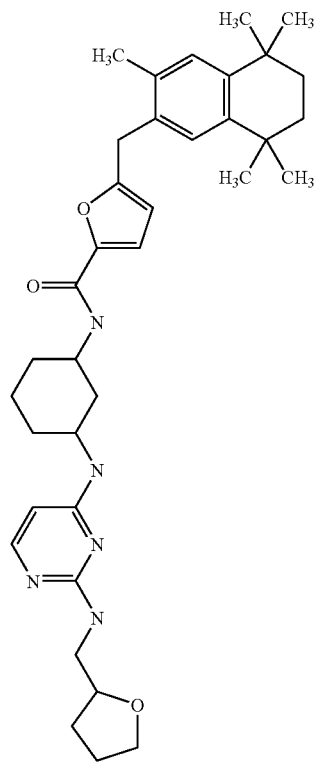
−14
474
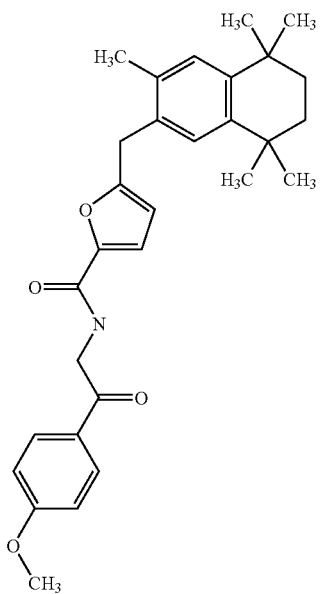
39

475 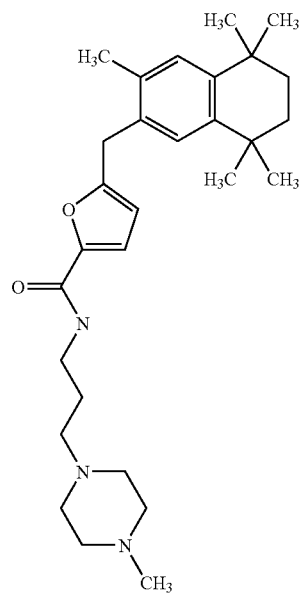 −3
476 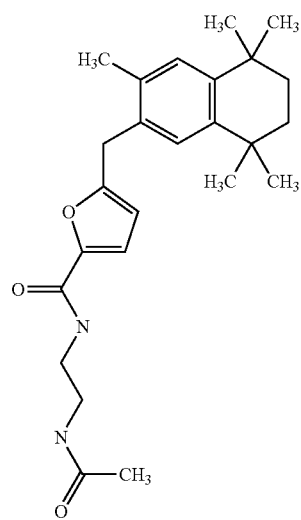 20

-continued
| 477 | 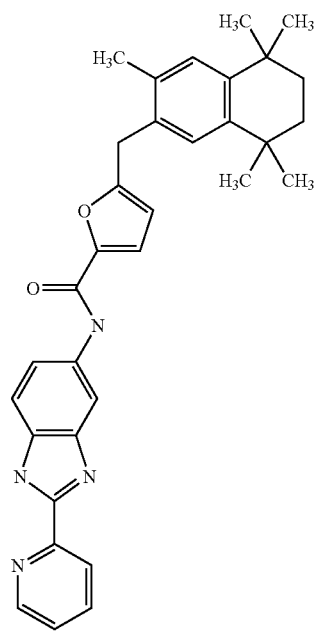 | 47 |
| 478 | 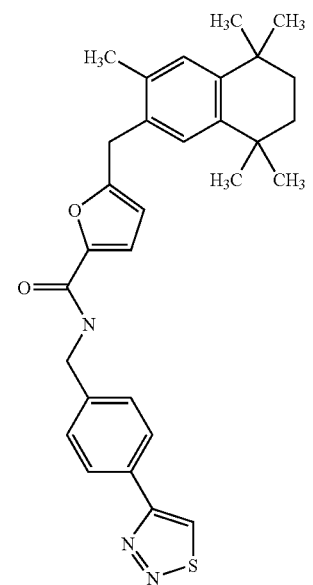 | 3 |

-continued
| | | |
|---|---|---|
| 479 | 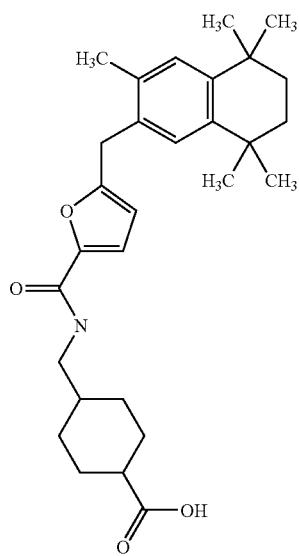 | −3 |
| 480 | 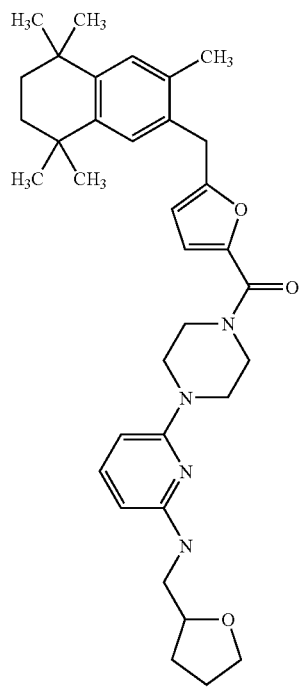 | −2 |

-continued
481 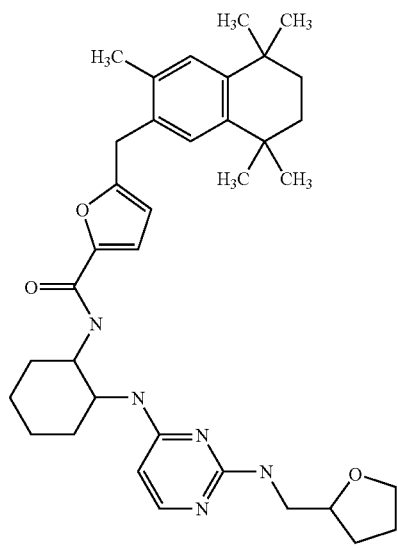 5
482 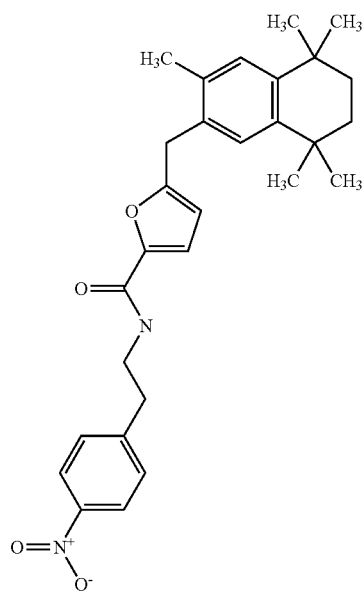 34
483 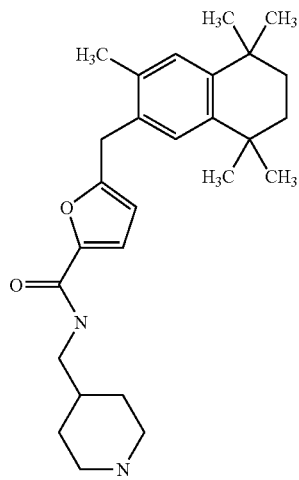 10

484 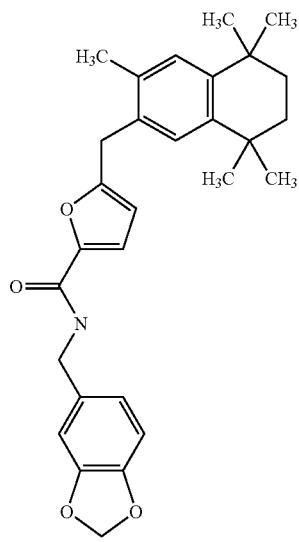 -1
485 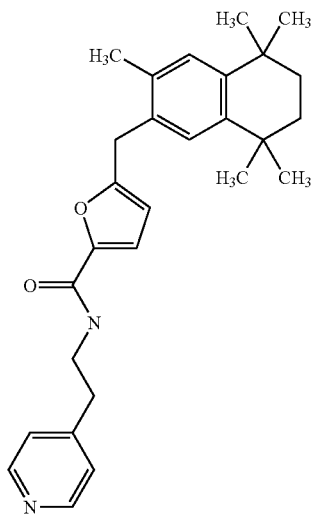 -5

-continued
| 486 | 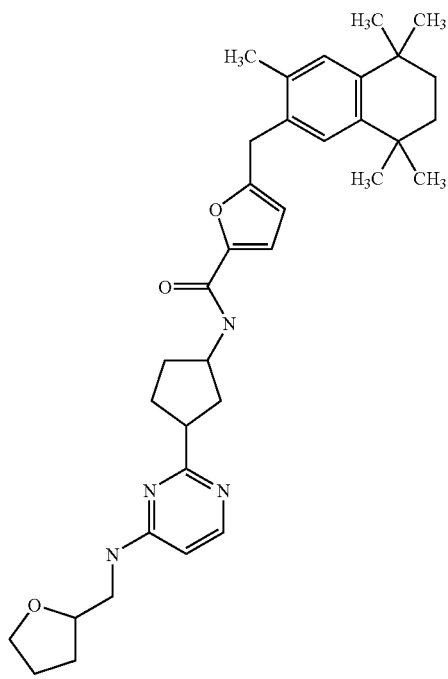 | 33 |
| 487 | 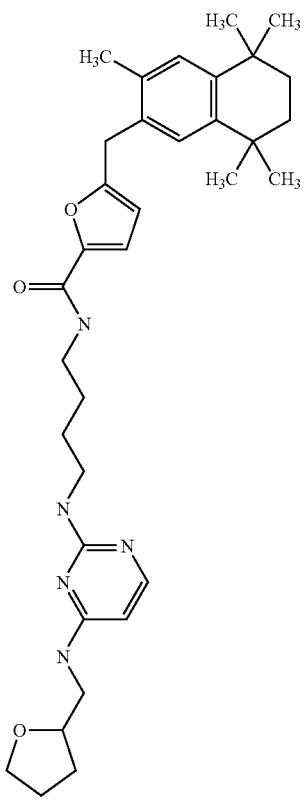 | 3 |

-continued
| 488 | 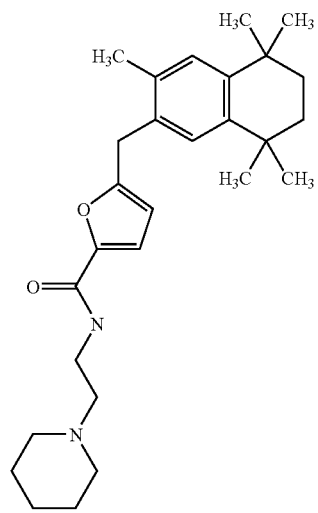 | −3 |
| 489 | 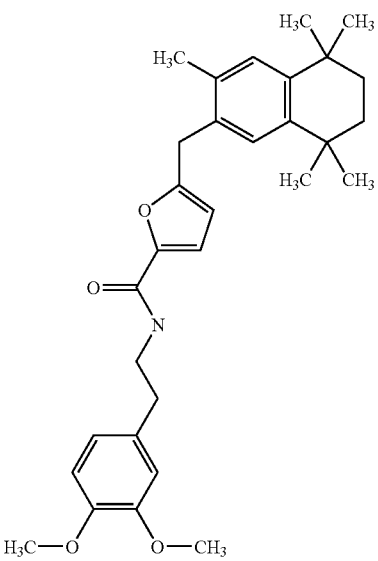 | −1 |
| 490 | 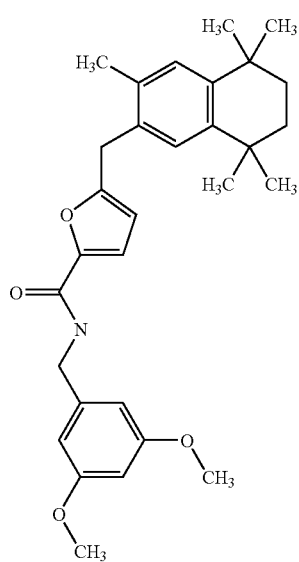 | 4 |

| 491 | 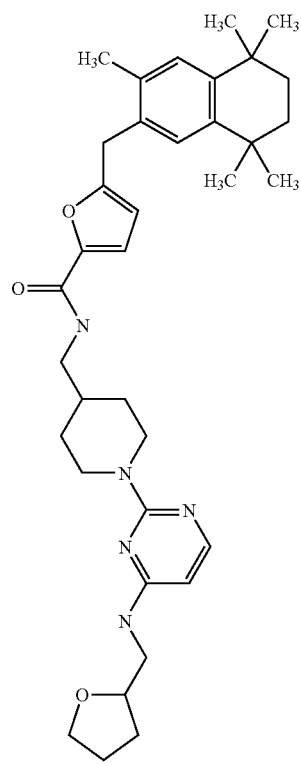 | 9 |
| 492 | 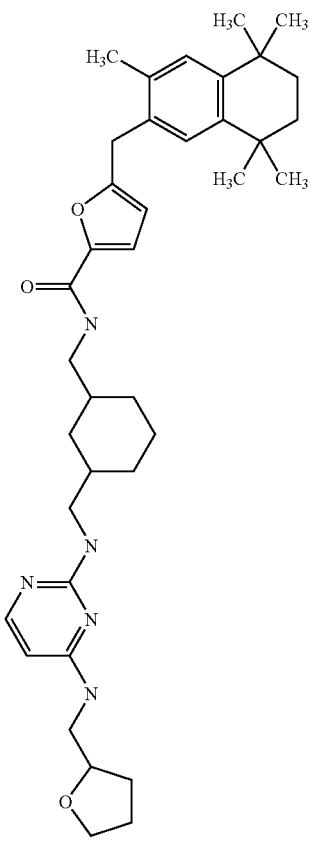 | −7 |

-continued
493
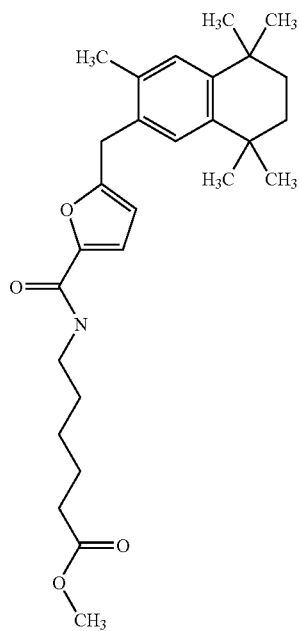
-6
494
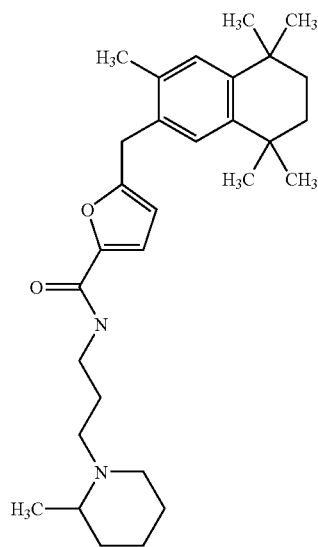
-7

495
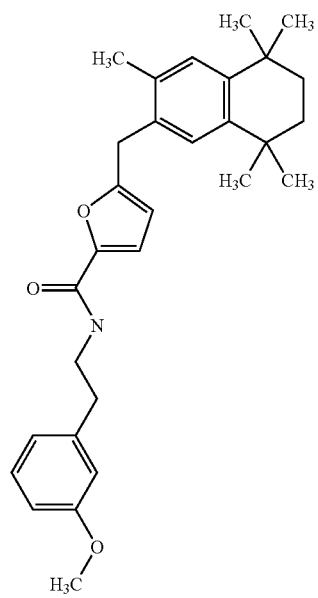
496
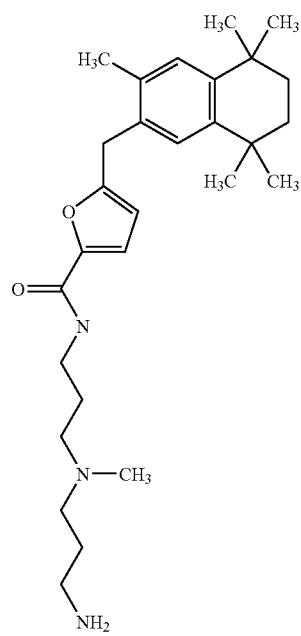

-continued
497 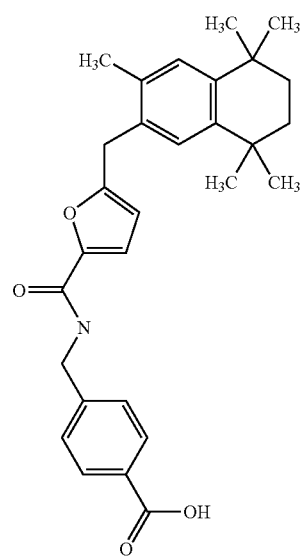 2
498 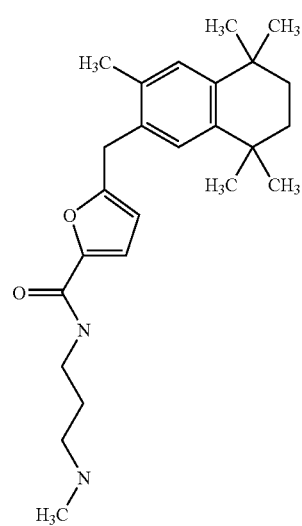 58

-continued
| | | |
|---|---|---|
| 499 | 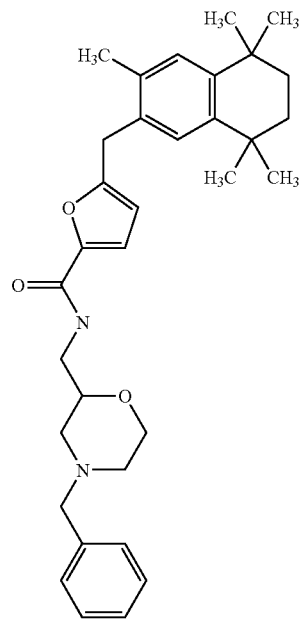 | 1 |
| 500 | 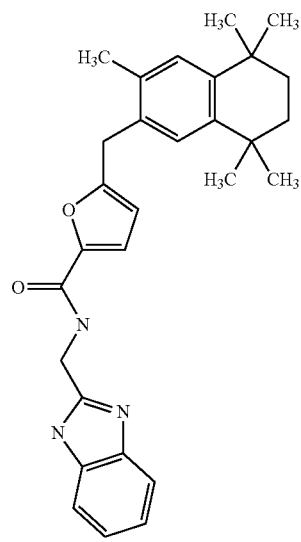 | −4 |
| 501 | 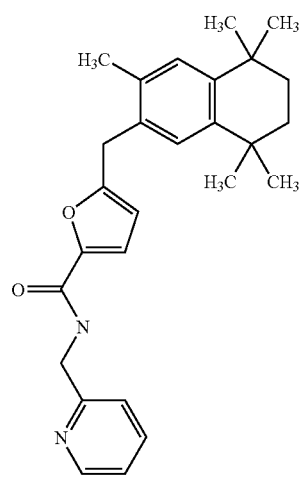 | −3 |

502 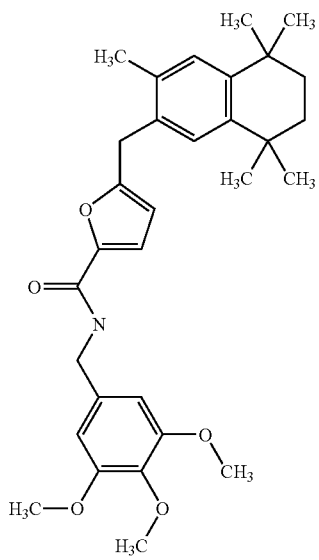 -2
503 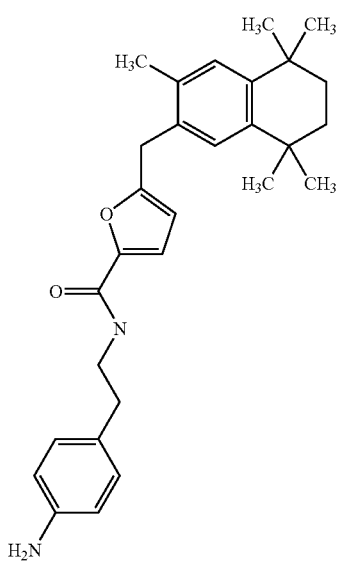 -3

-continued
504
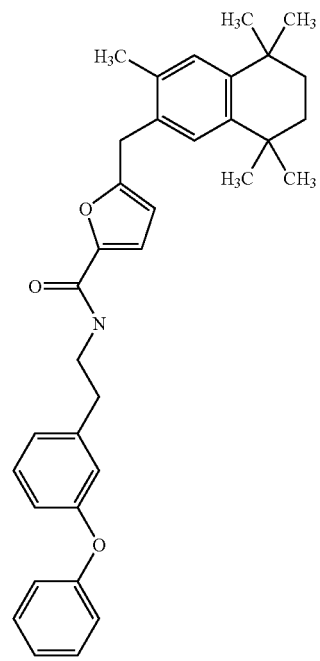
505
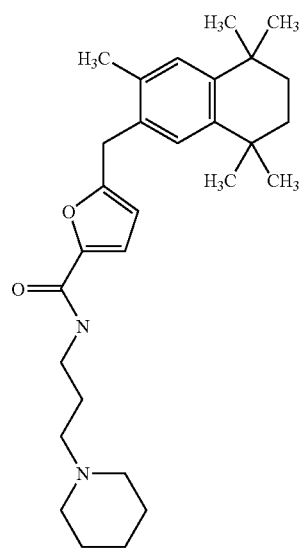

-continued
| | | |
|---|---|---|
| 506 | 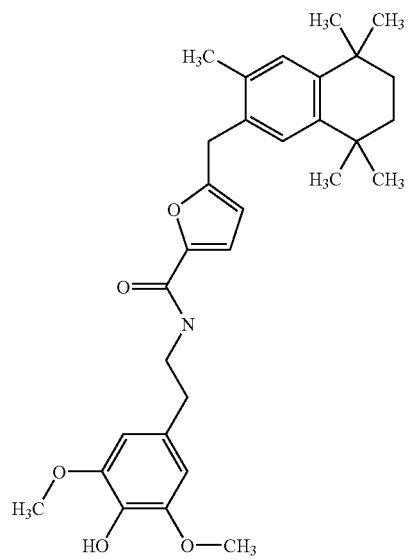 | 3 |
| 507 | 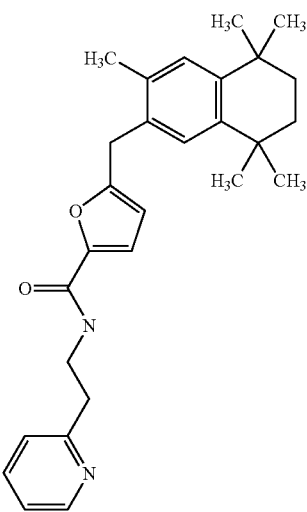 | −4 |
| 508 | 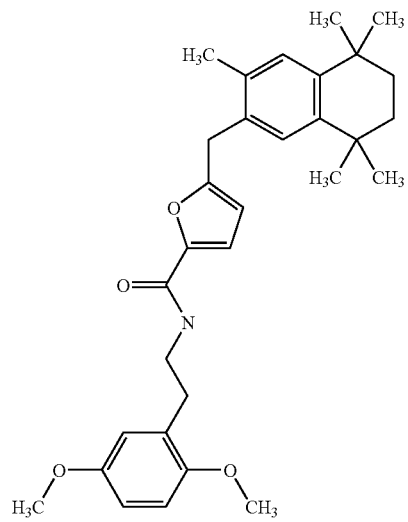 | 7 |

509
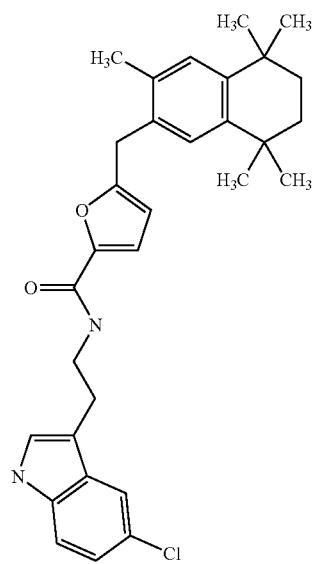
16
510
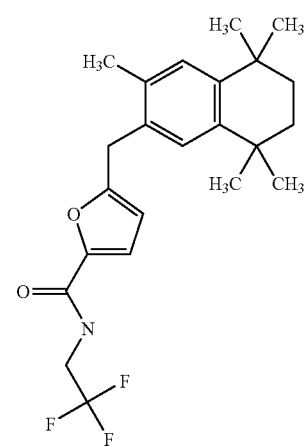
23

-continued
511
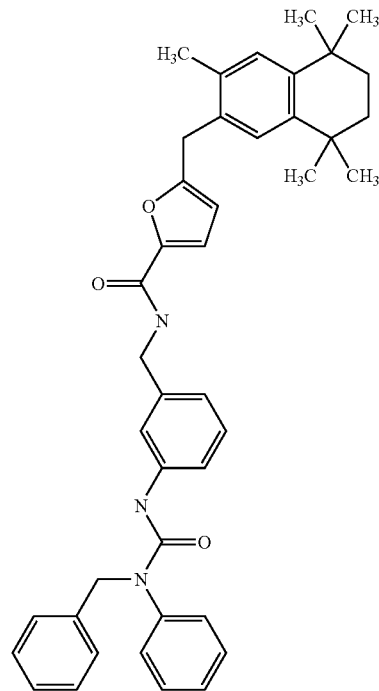
47
512
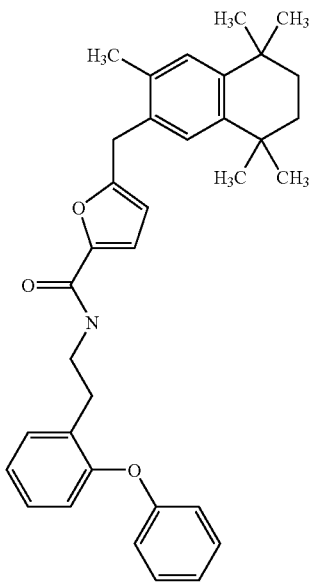
51

| | | |
|---|---|---|
| 513 | 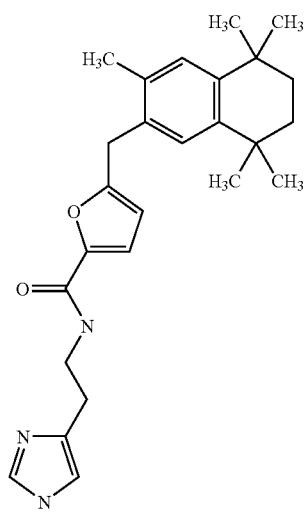 | 9 |
| 514 | 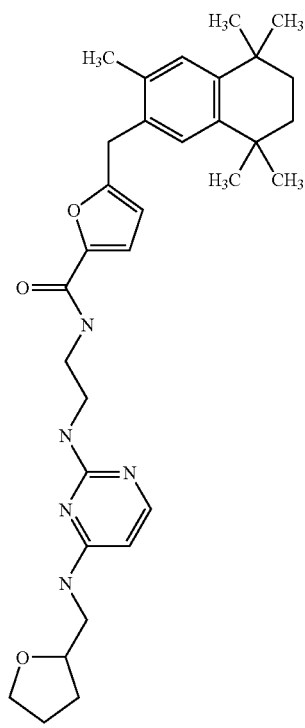 | 2 |

-continued
515 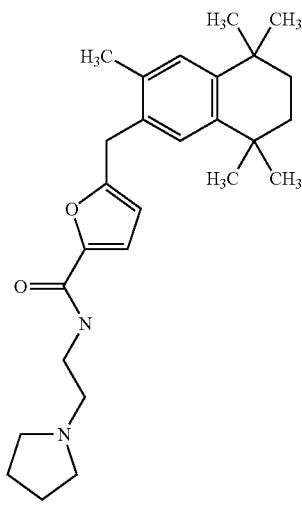 11
516 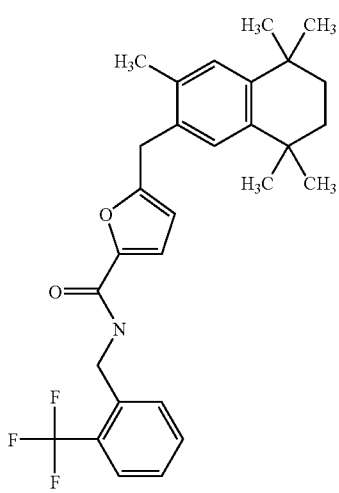 21
517 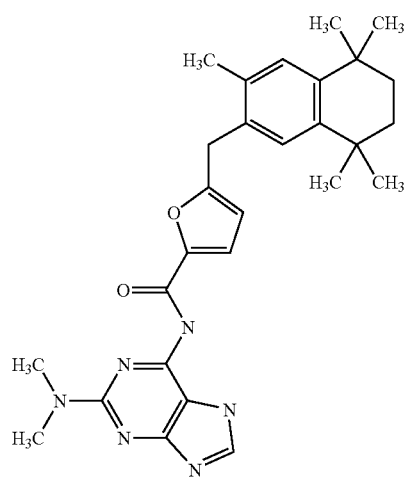 34

| | | |
|---|---|---|
| 518 | 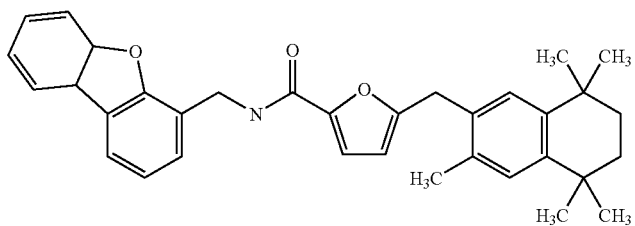 | 56 |
| 519 | 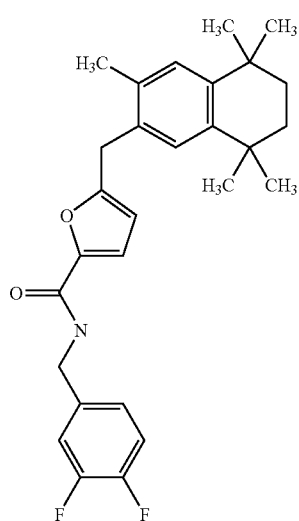 | 0 |
| 520 | 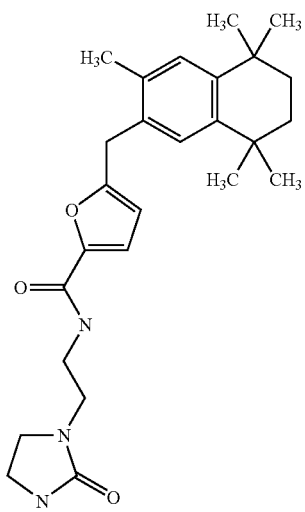 | −3 |

-continued
| | | |
|---|---|---|
| 521 | 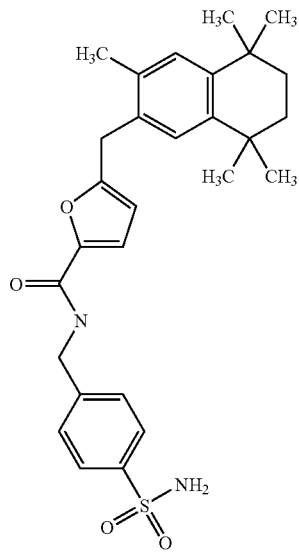 | 51 |
| 522 | 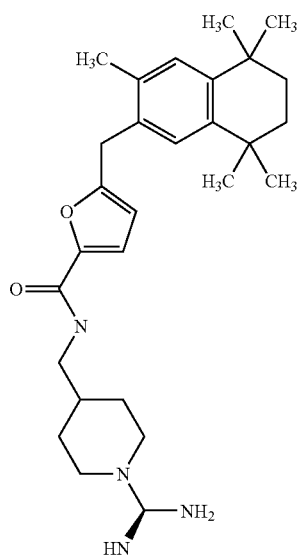 | 9 |
| 523 | 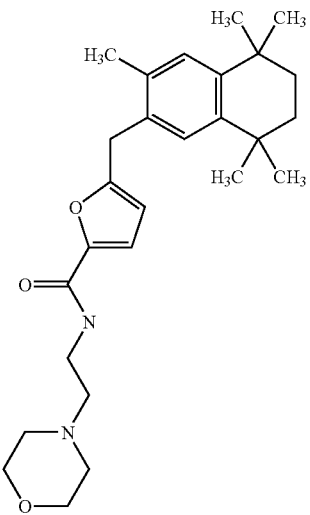 | −4 |

524
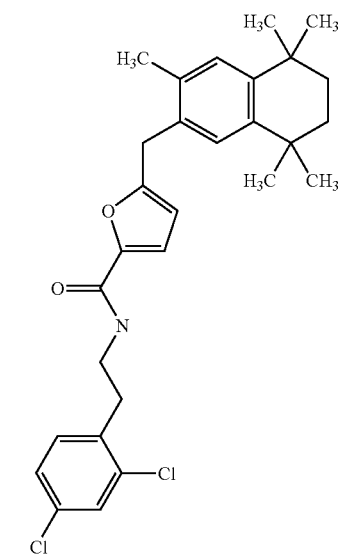
35
525
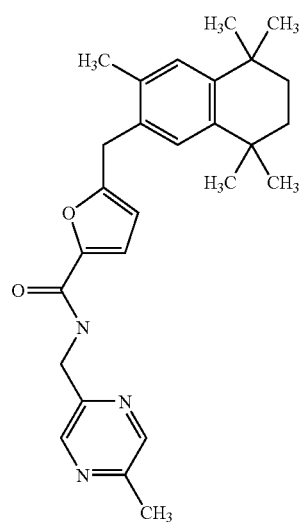
-9

-continued
| 526 | 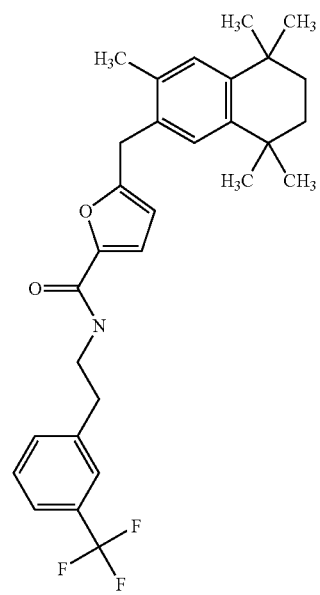 | 9 |
| 527 | 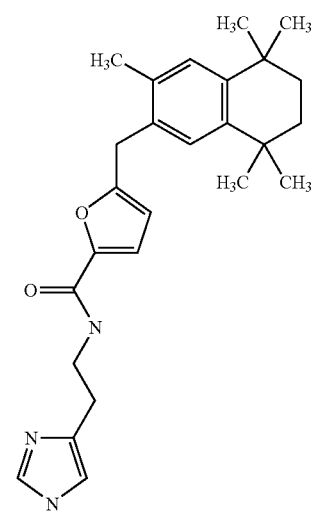 | 10 |

| 528 | 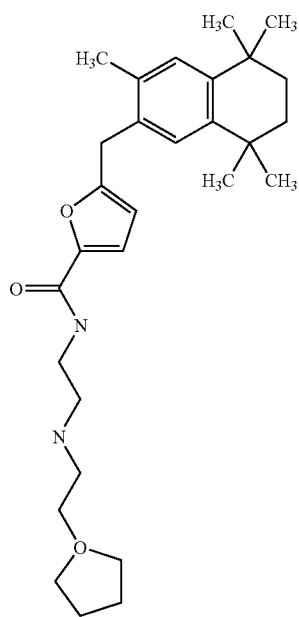 | 22 |
| --- | --- | --- |
| 529 | 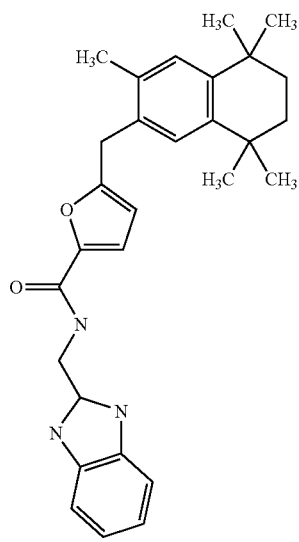 | −3 |

-continued
| 530 | 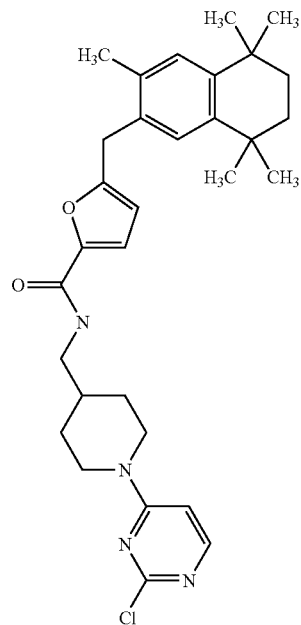 | −4 |
| 531 | 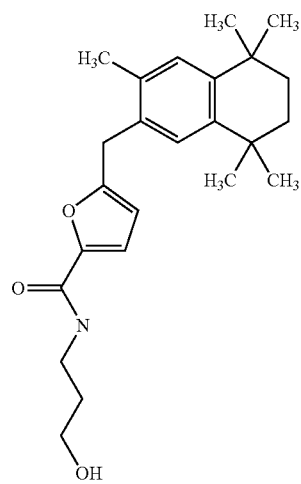 | 4 |
| 532 | 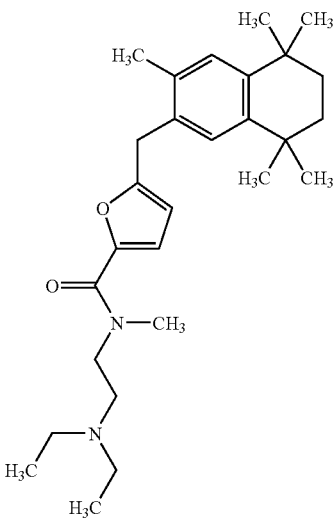 | 12 |

| | |
|---|---|
| 533 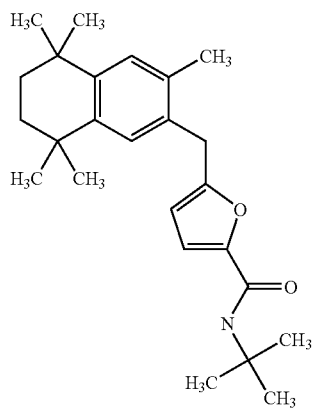 | 29 |
| 534 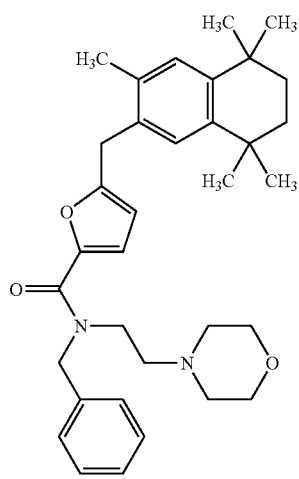 | 9 |
| 535 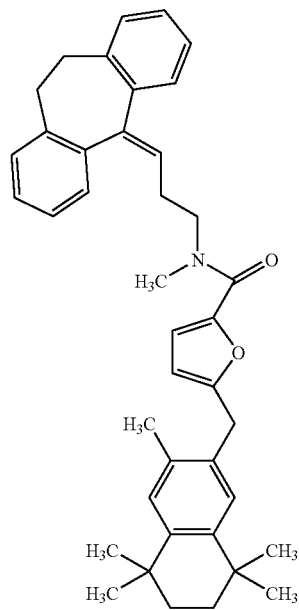 | 43 |

-continued
| 536 | 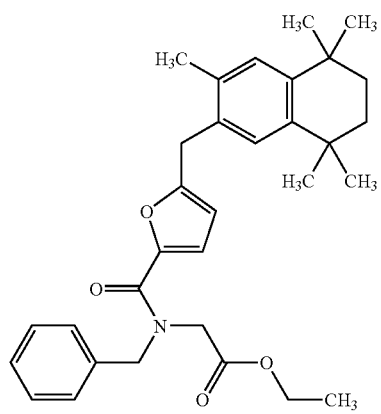 | 38 |
| 537 | 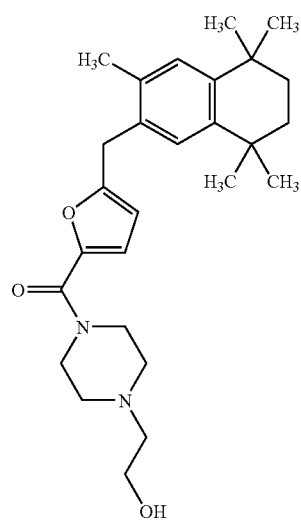 | 32 |
| 538 | 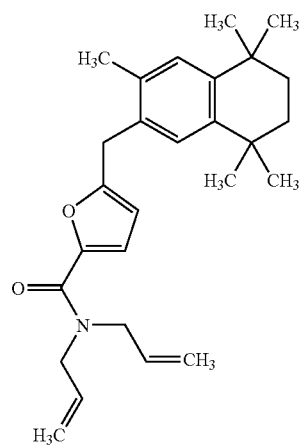 | 17 |

-continued
| 539 | 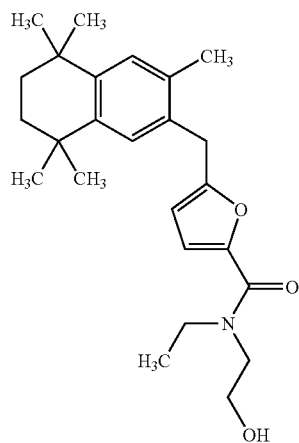 | 19 |
| 540 | 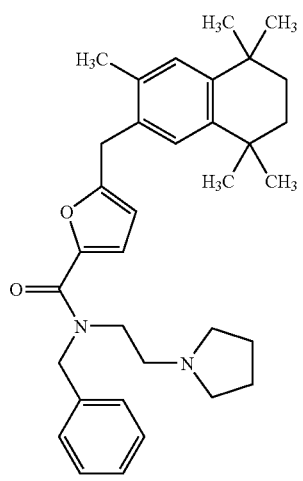 | 0 |
| 541 | 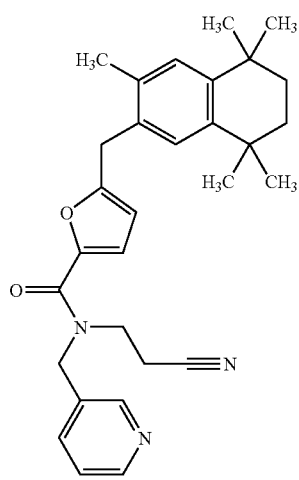 | 9 |

-continued
| | | |
|---|---|---|
| 542 | 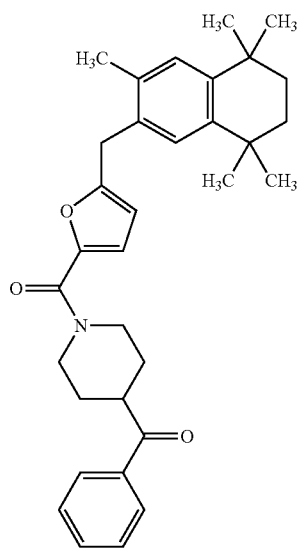 | 42 |
| 543 | 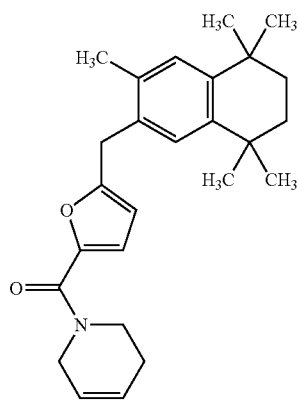 | 31 |
| 544 | 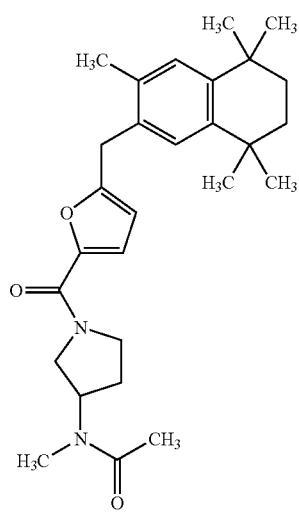 | 27 |

-continued
| | | |
|---|---|---|
| 545 | 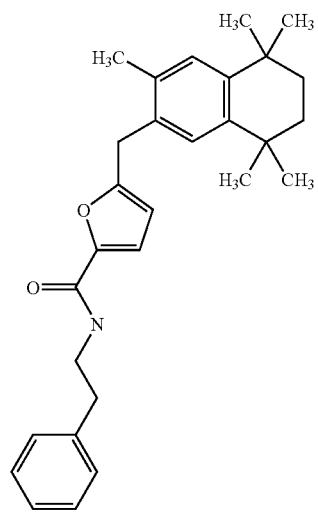 | 28 |
| 546 |  | 29 |
| 547 | 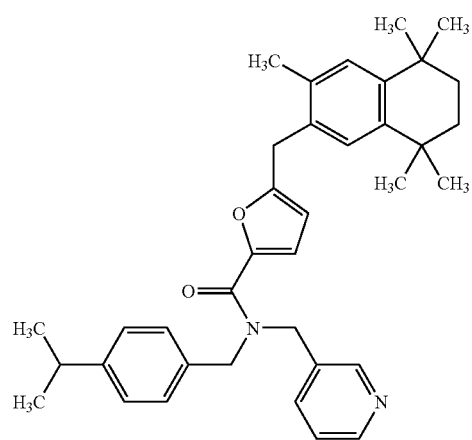 | 24 |

-continued
| | | |
|---|---|---|
| 548 | 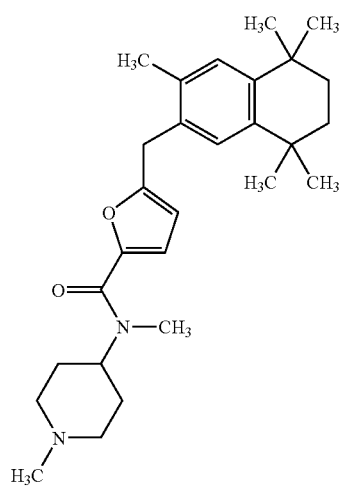 | 12 |
| 549 | 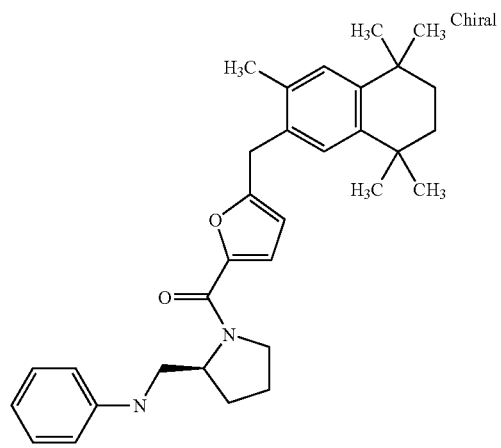 | 48 |
| 550 | 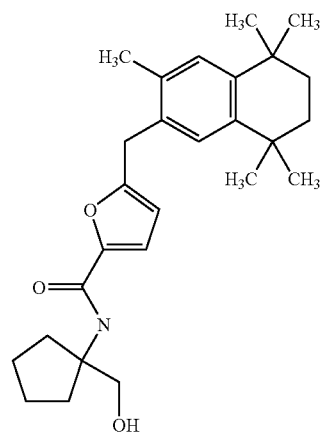 | 3 |

-continued
| | | |
|---|---|---|
| 551 | 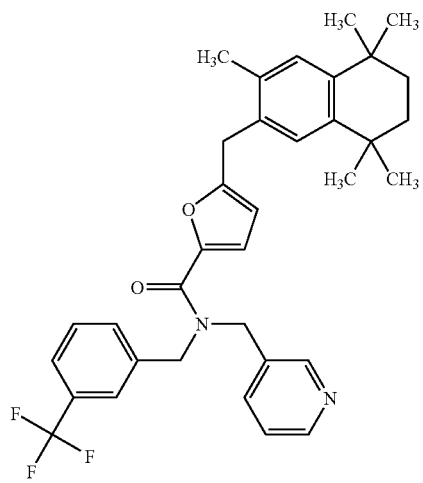 | 21 |
| 552 | 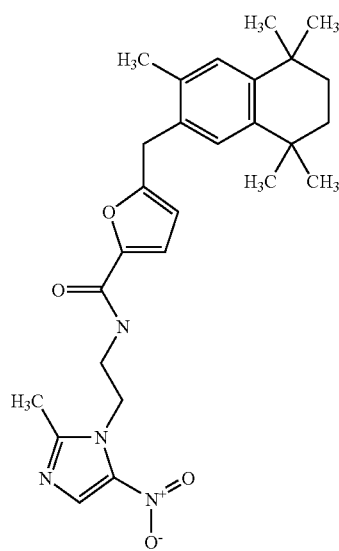 | 58 |
| 553 | 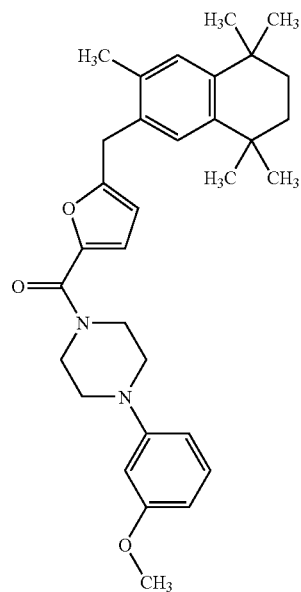 | 34 |

| | | |
|---|---|---|
| 554 | 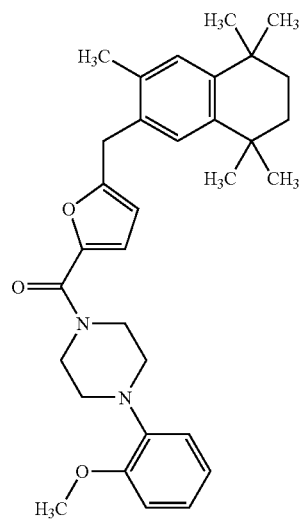 | 27 |
| 555 | 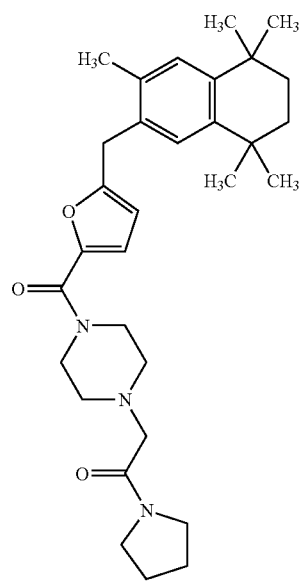 | 21 |
| 556 | 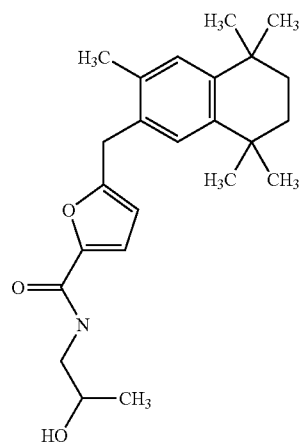 | 10 |

-continued
557 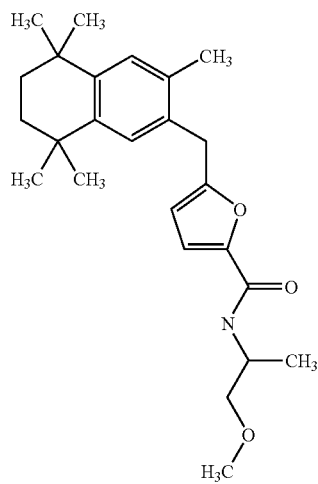 10
558 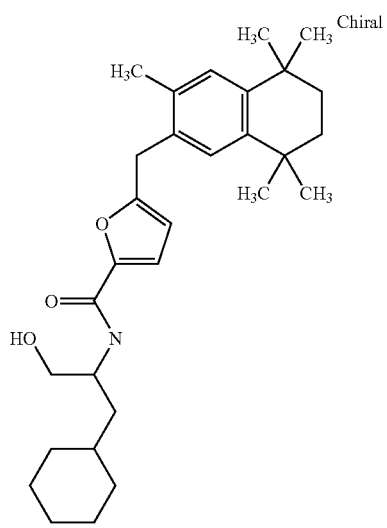 24
559 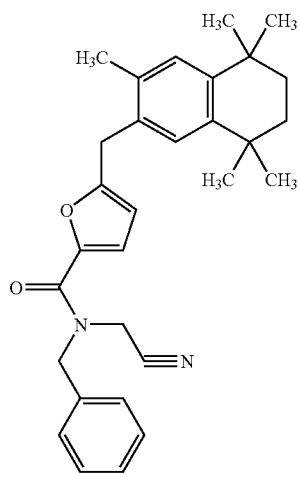 26

-continued
560 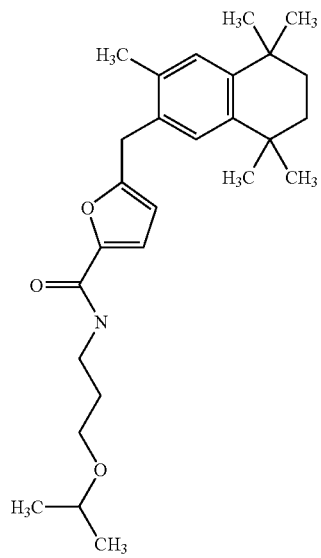 7
561 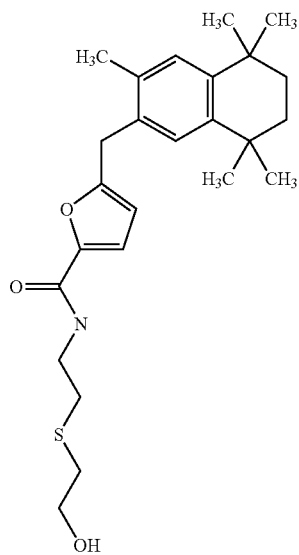 0
562 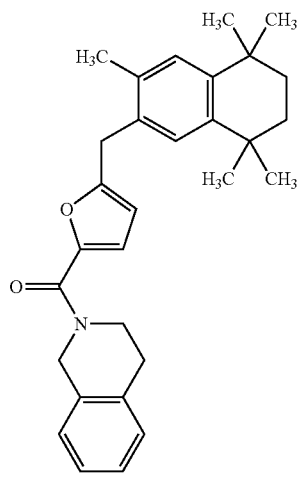 30

-continued
| | | |
|---|---|---|
| 563 | 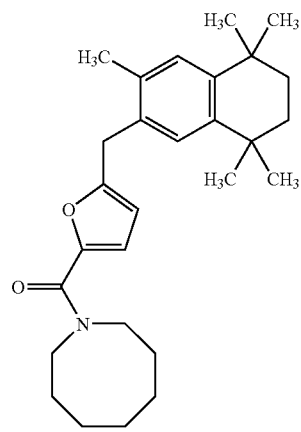 | 13 |
| 564 | 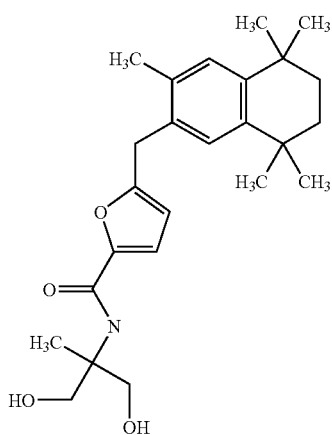 | 45 |
| 565 | 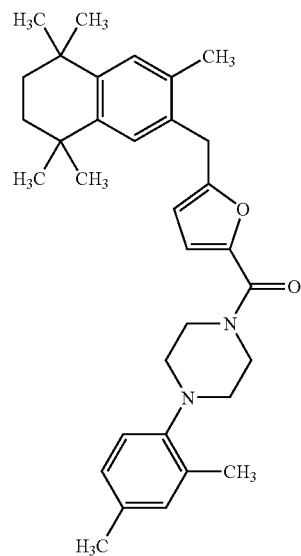 | 48 |

-continued
| | | |
|---|---|---|
| 566 | 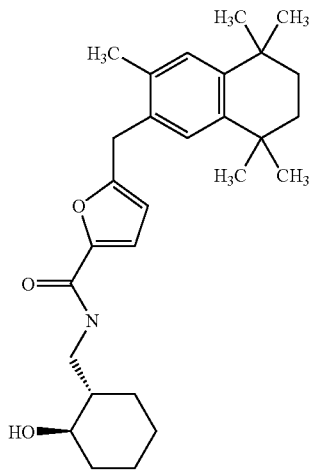 | 3 |
| 567 | 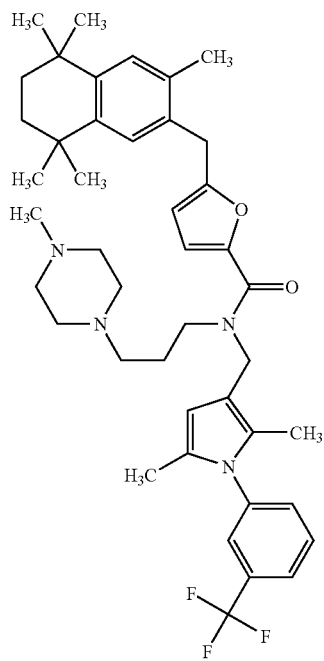 | −1 |
| 568 | 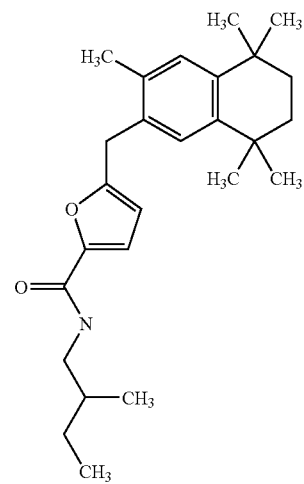 | 28 |

-continued
| | |
|---|---|
| 569 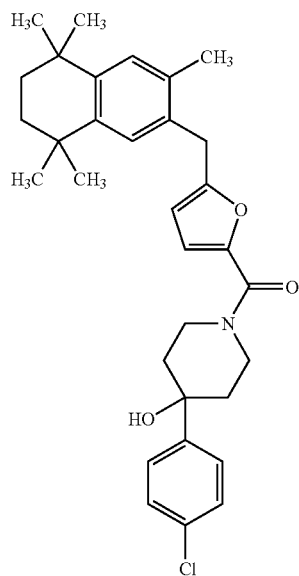 | 58 |
| 570 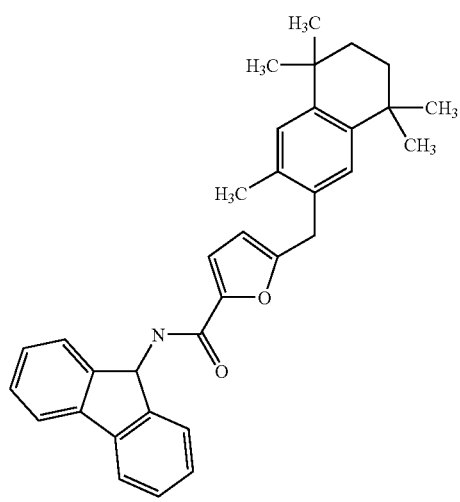 | 48 |
| 571 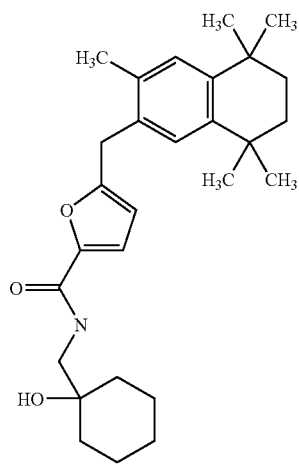 | 36 |

| | | |
|---|---|---|
| 572 | 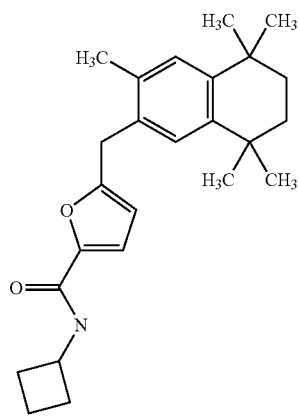 | 41 |
| 573 | 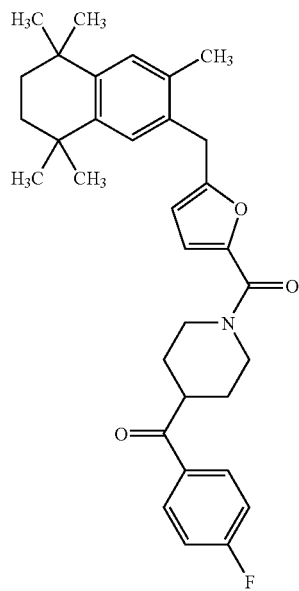 | 37 |
| 574 | 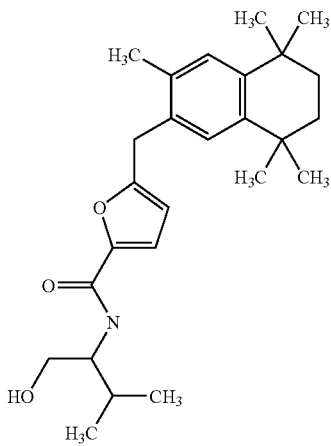 | 13 |

-continued
| | | |
|---|---|---|
| 575 | 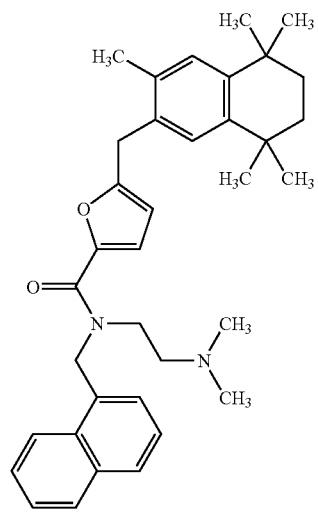 | −3 |
| 576 | 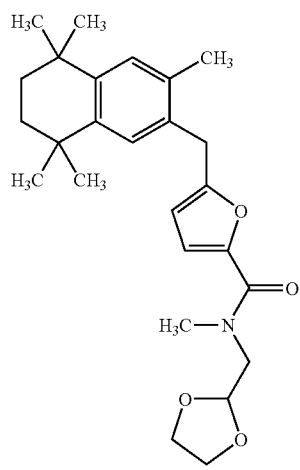 | 15 |
| 577 | 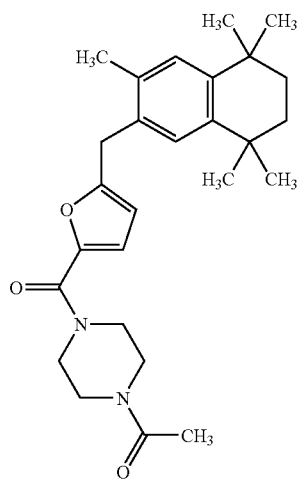 | 30 |

-continued
| | | |
|---|---|---|
| 578 | 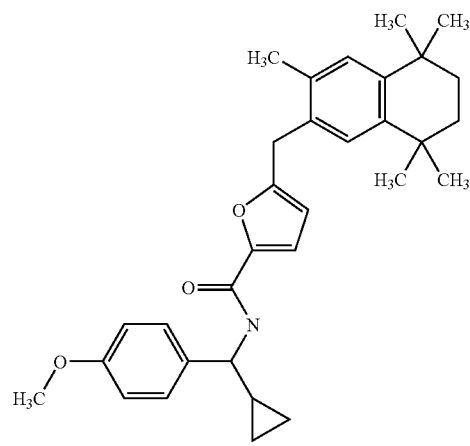 | 17 |
| 579 | 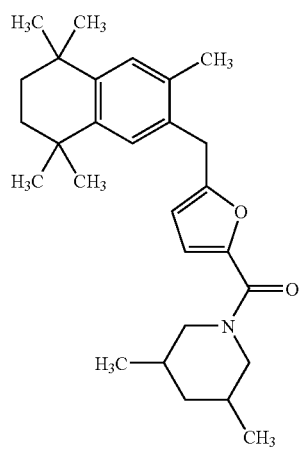 | 10 |
| 580 | 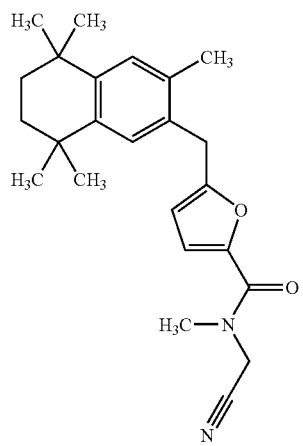 | 18 |

-continued
581 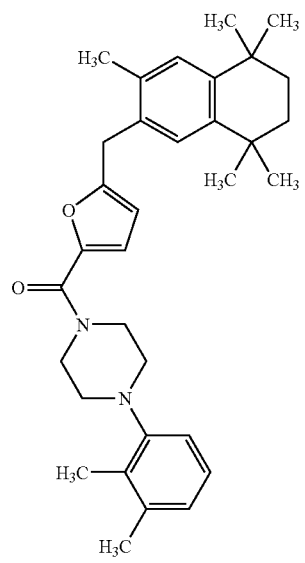 43
582 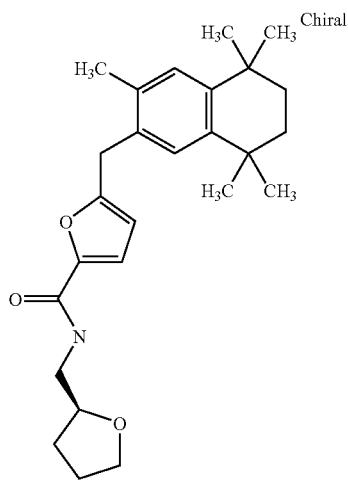 −2
583 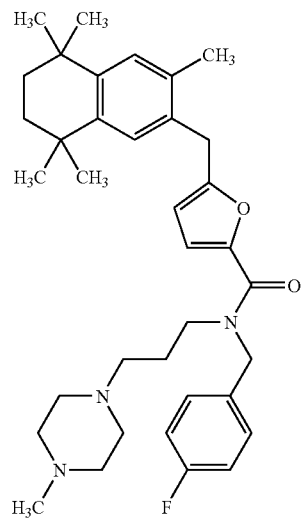 −3

584 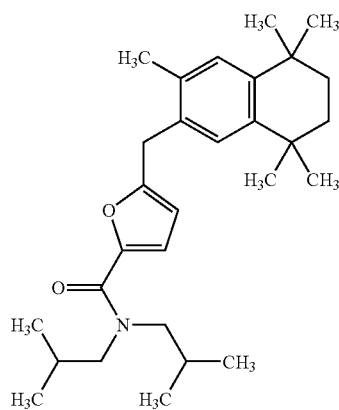 15
585 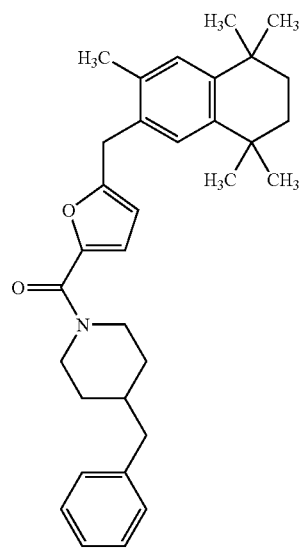 52
586 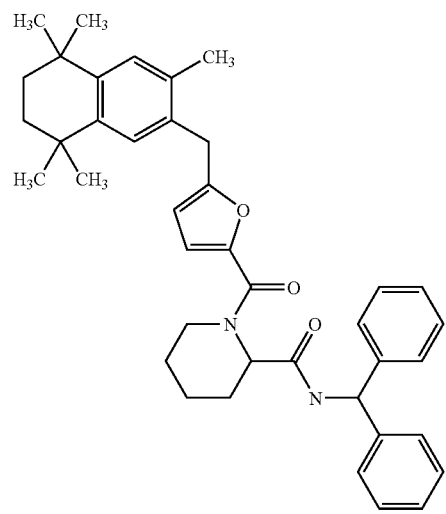 57

-continued
| | | |
|---|---|---|
| 587 | 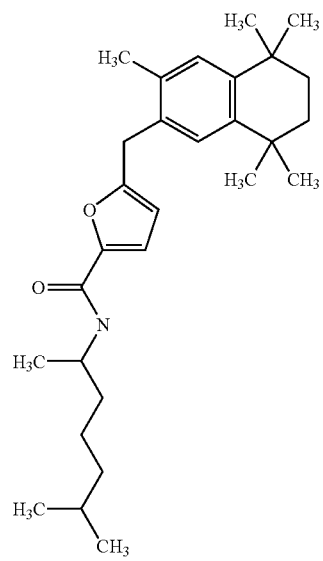 | 29 |
| 588 | 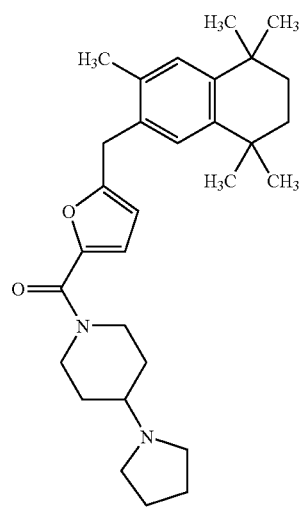 | 4 |
| 589 | 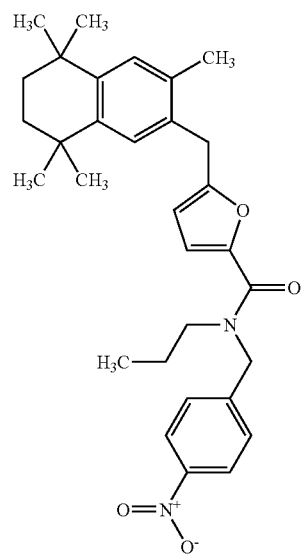 | 35 |

-continued
| | | | |
|---|---|---|---|
| 590 | 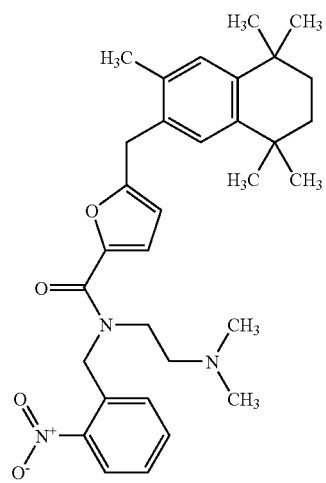 | | −2 |
| 591 | 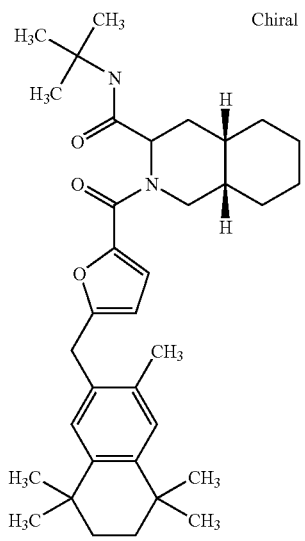 | Chiral | 48 |
| 592 | 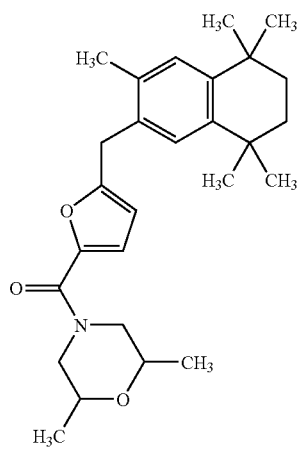 | | 17 |

-continued
593 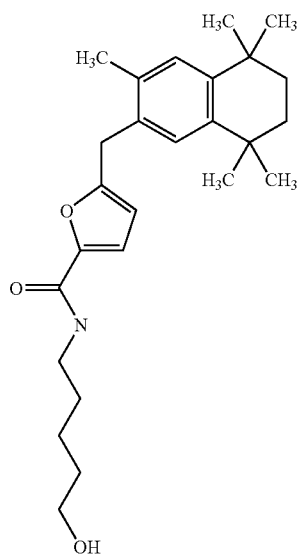 2
594 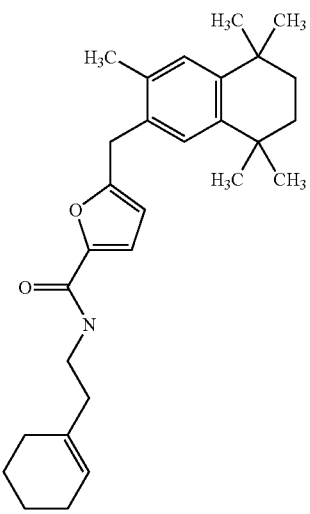 16
595 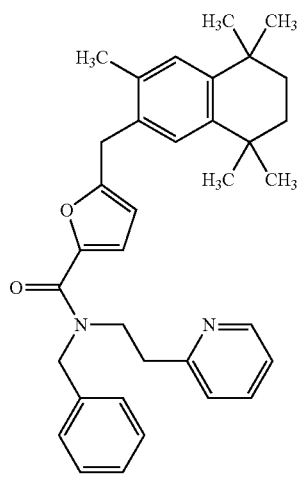 24

-continued
| | | |
|---|---|---|
| 596 | 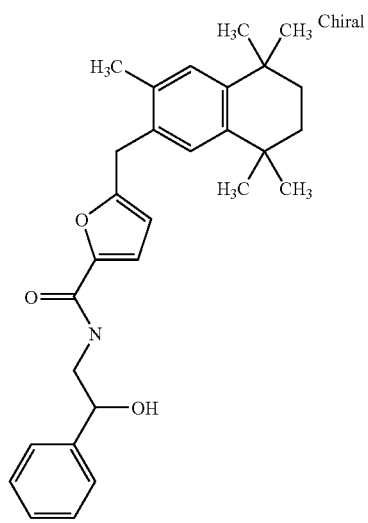 | −1 |
| 597 | 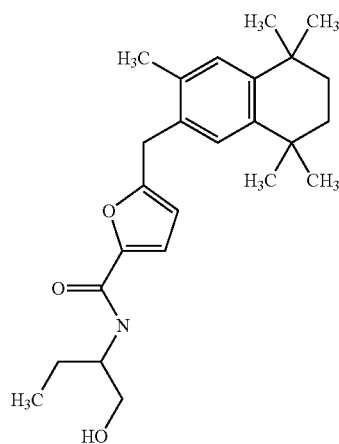 | 11 |
| 598 | 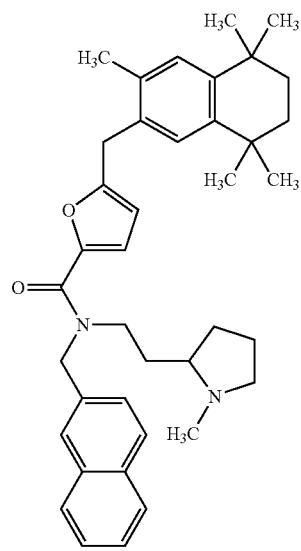 | −4 |

599 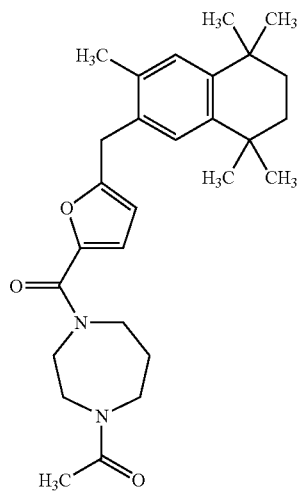 28
600 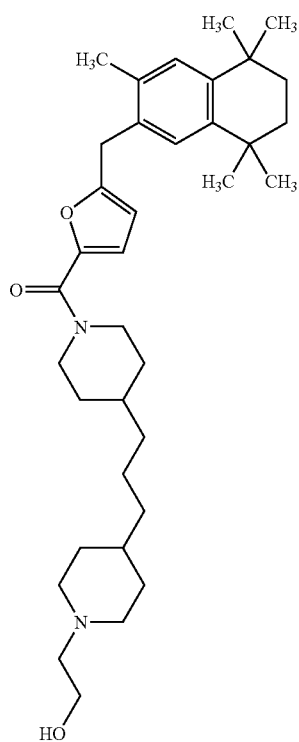 −4

-continued
601 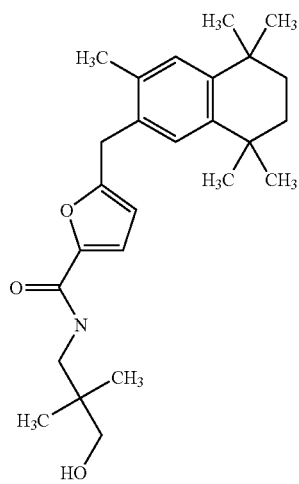 17
602 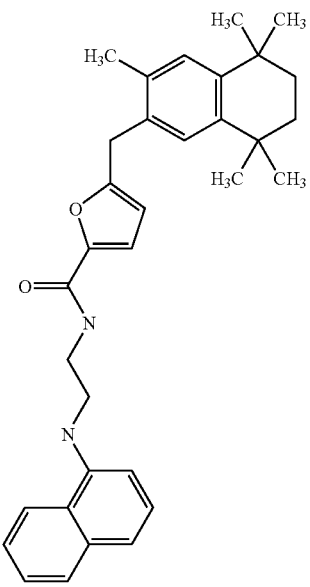 44
603 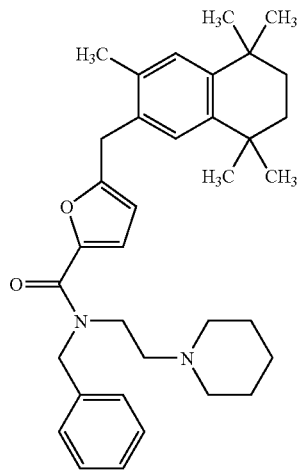 −4

| | | |
|---|---|---|
| 604 | 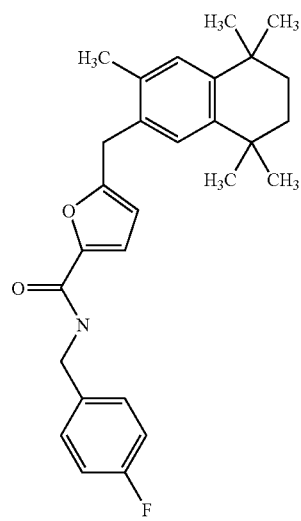 | 4 |
| 605 | 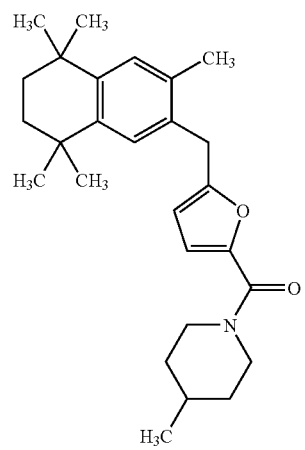 | 19 |
| 606 | 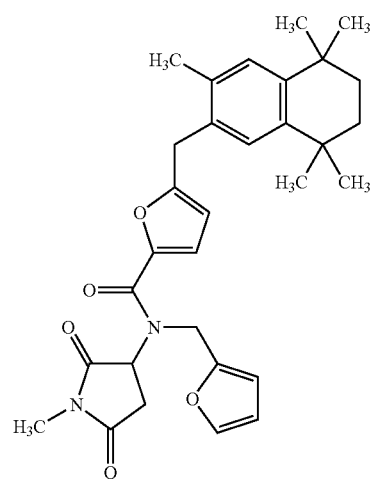 | 32 |

| | | |
|---|---|---|
| 607 | 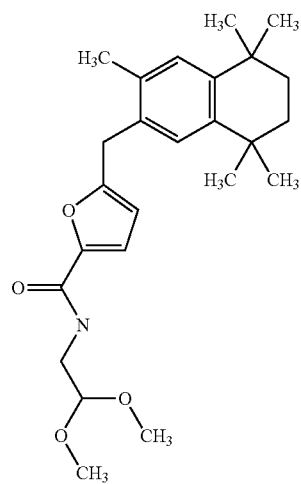 | -2 |
| 608 | 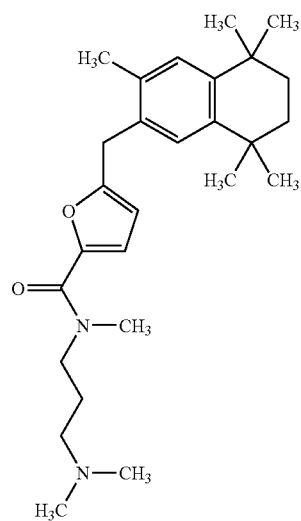 | 8 |
| 609 | 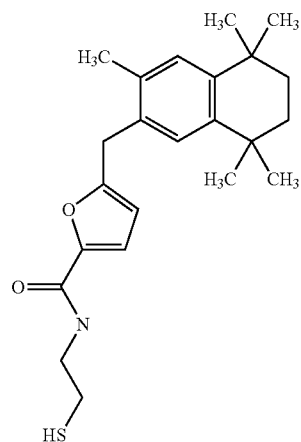 | 47 |

-continued
| | | |
|---|---|---|
| 610 | 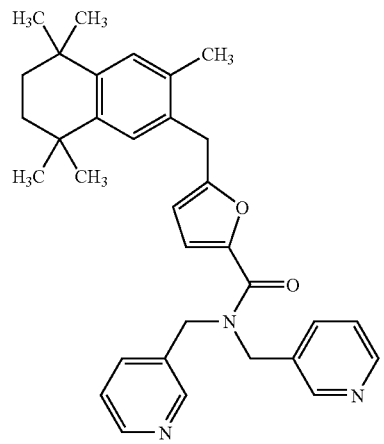 | 0 |
| 611 | 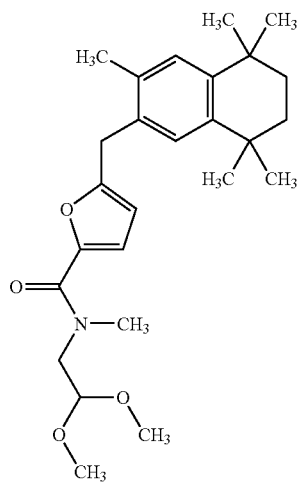 | 11 |
| 612 | 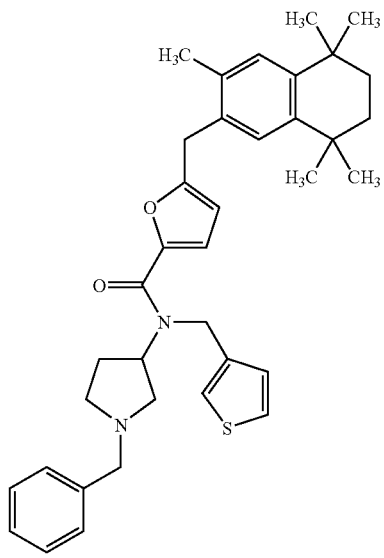 | 9 |

-continued
| | |
|---|---|
| 613 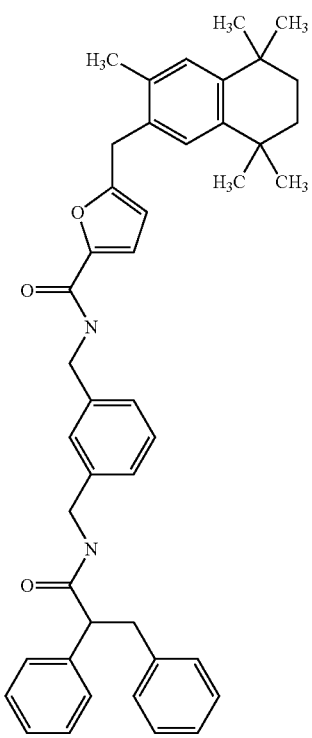 | 53 |
| 614 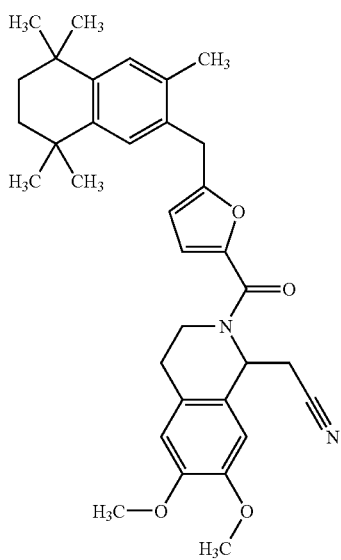 | 48 |

-continued
| | | |
|---|---|---|
| 615 | 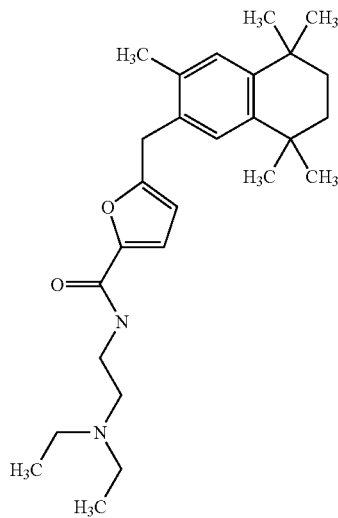 | 7 |
| 616 | 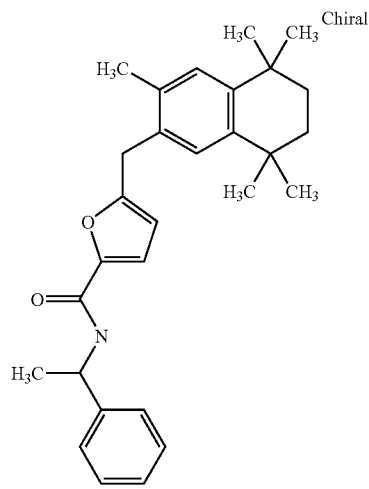 | 29 |
| 617 | 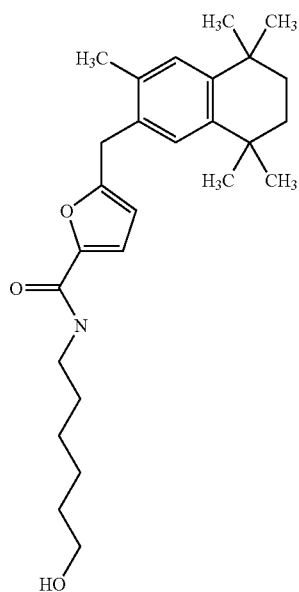 | −2 |

-continued
618 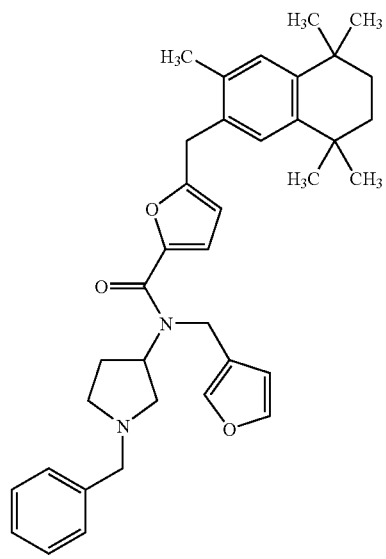 9
619 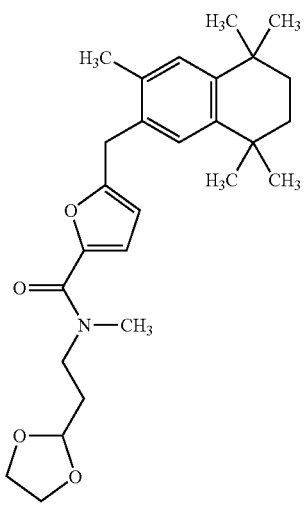 5
620 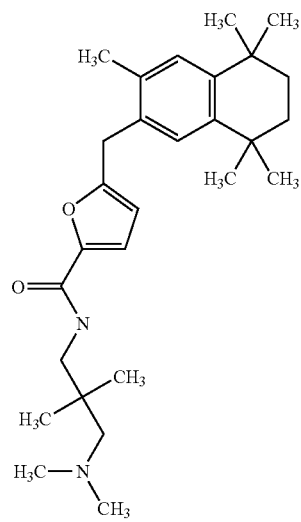 3

-continued
| | | | |
|---|---|---|---|
| 621 | 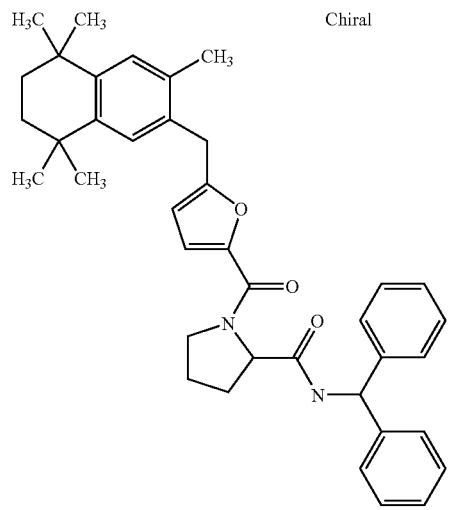 | Chiral | 43 |
| 622 | 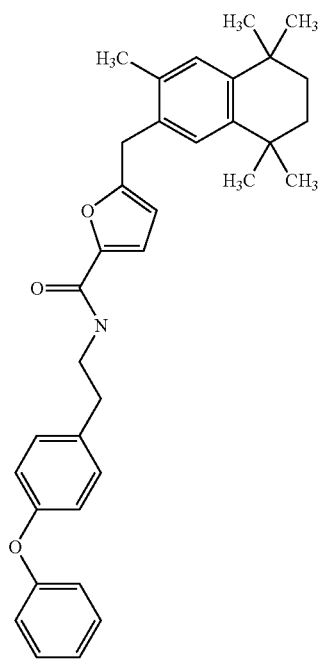 | | 43 |

-continued
| | | |
|---|---|---|
| 623 | 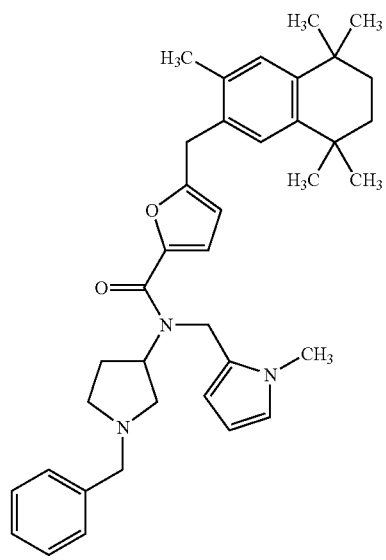 | 2 |
| 624 | 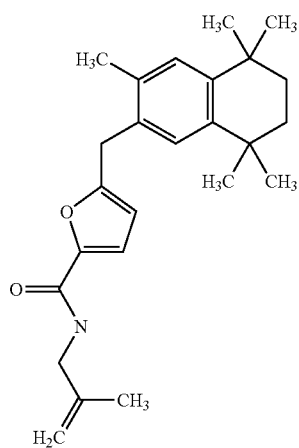 | 8 |
| 625 | 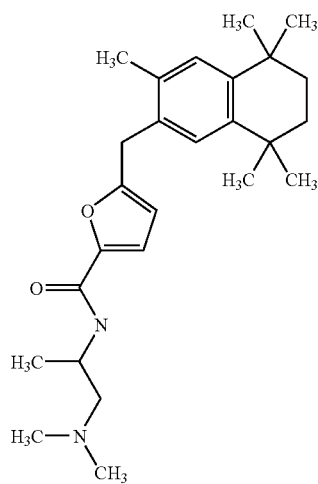 | 8 |

-continued
626
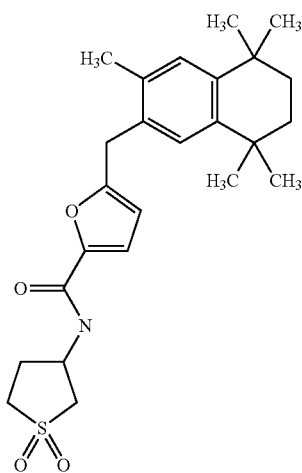
627
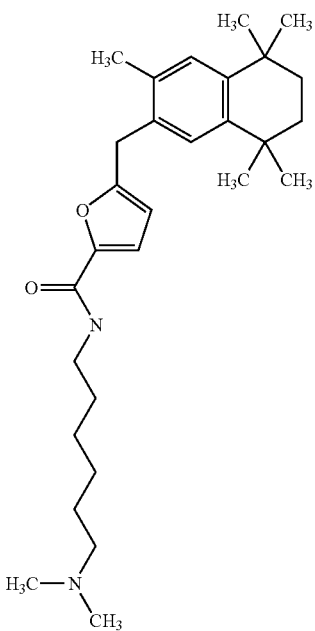

| 628 | 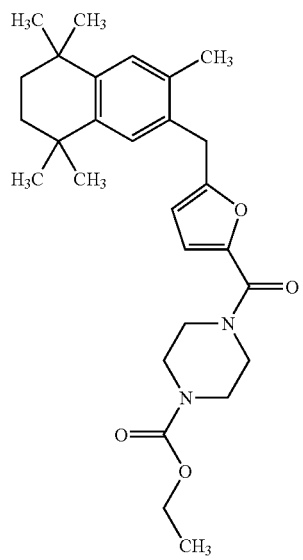 | 35 |
| 629 | 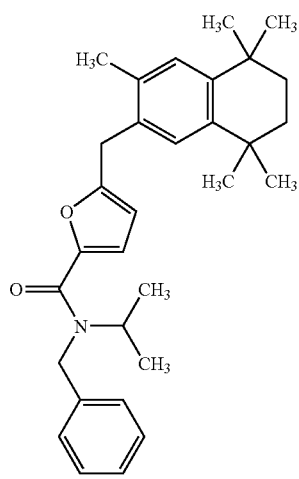 | 17 |
| 630 | 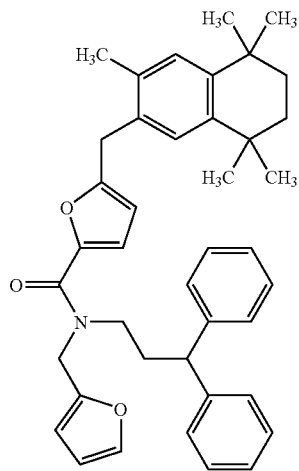 | 58 |

-continued
| | | |
|---|---|---|
| 631 | 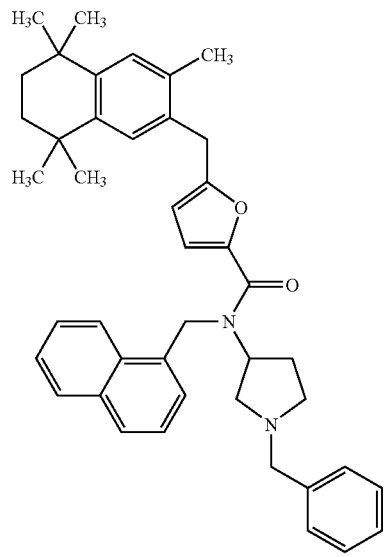 | 43 |
| 632 | 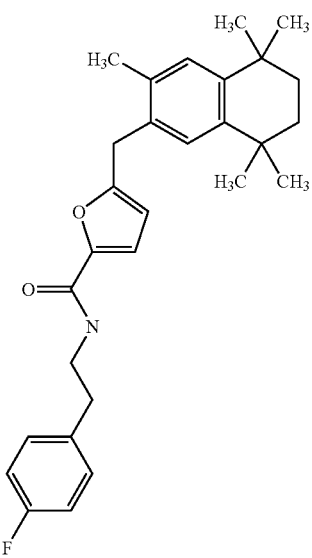 | 21 |
| 633 | 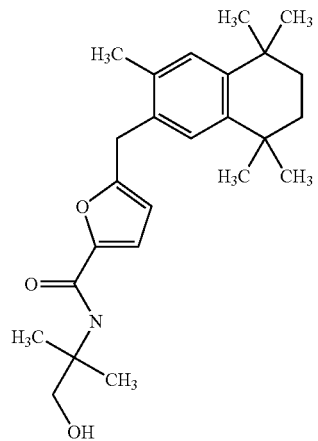 | 10 |

-continued
| | | |
|---|---|---|
| 634 | 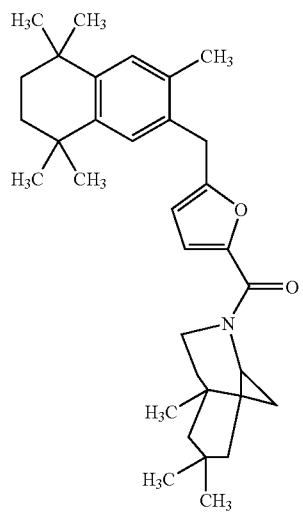 | 1 |
| 635 | 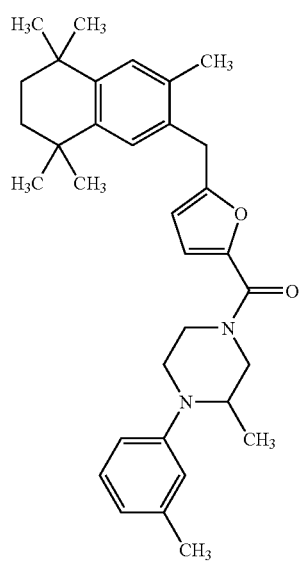 | 27 |
| 636 | 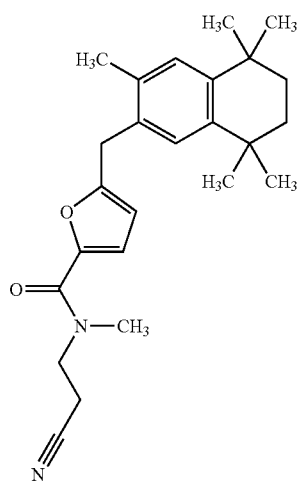 | 17 |

-continued
| | | |
|---|---|---|
| 637 | 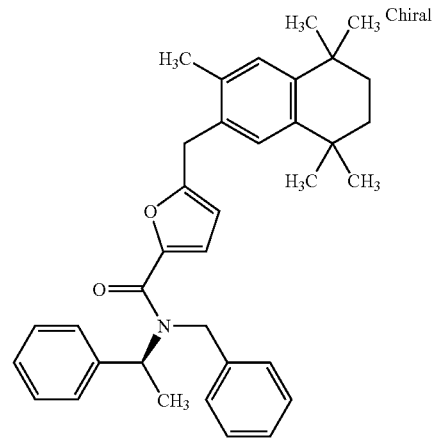 | 55 |
| 638 | 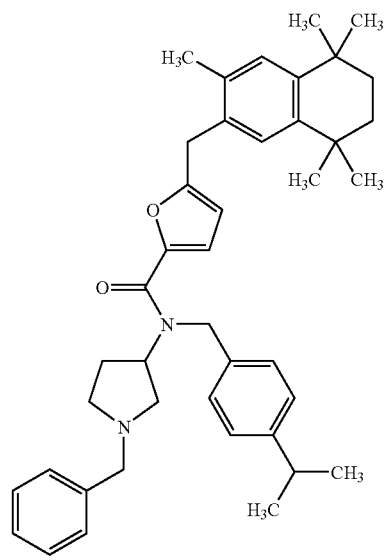 | 53 |
| 639 | 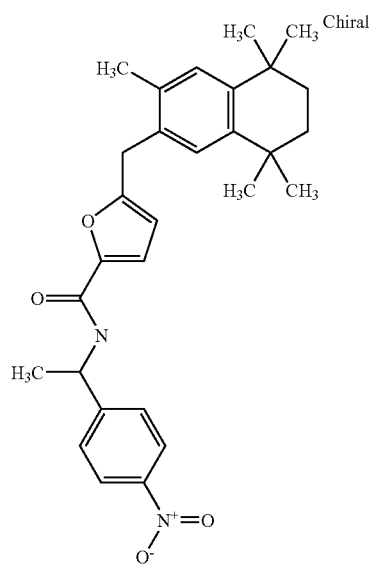 | 57 |

-continued
| | | |
|---|---|---|
| 640 | 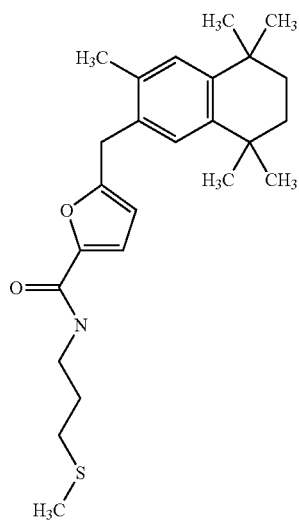 | 2 |
| 641 | 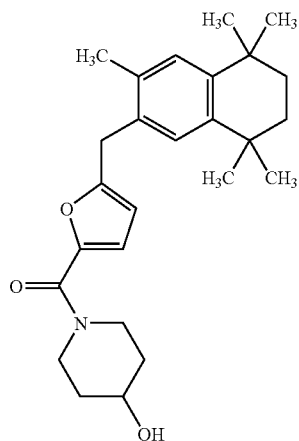 | 23 |
| 642 | 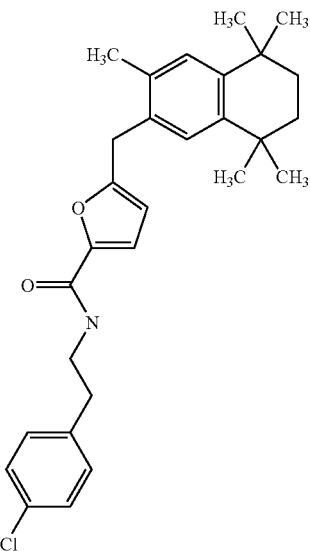 | 19 |

-continued
| | | |
|---|---|---|
| 643 | 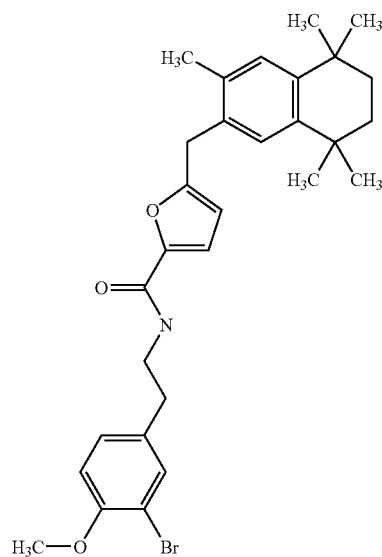 | 23 |
| 644 | 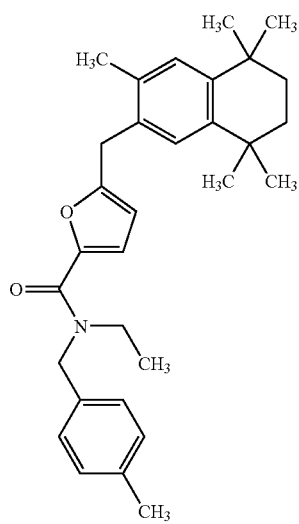 | 22 |
| 645 | 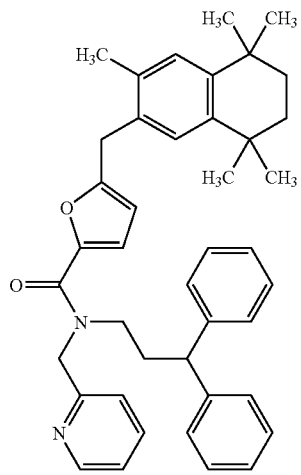 | 51 |

-continued
646
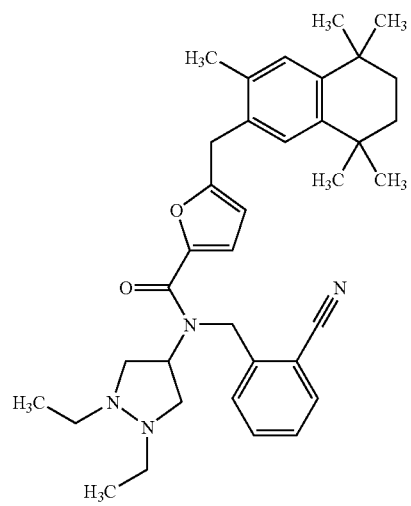
647
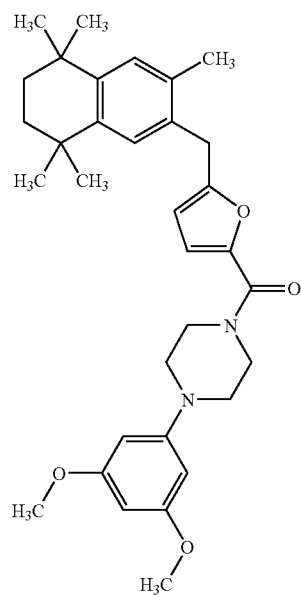
648
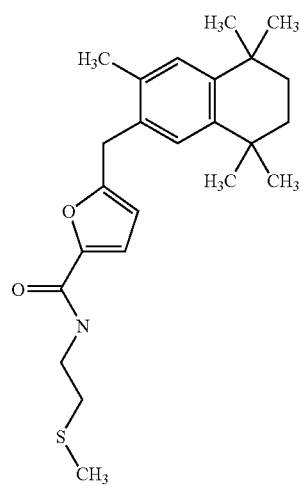

649 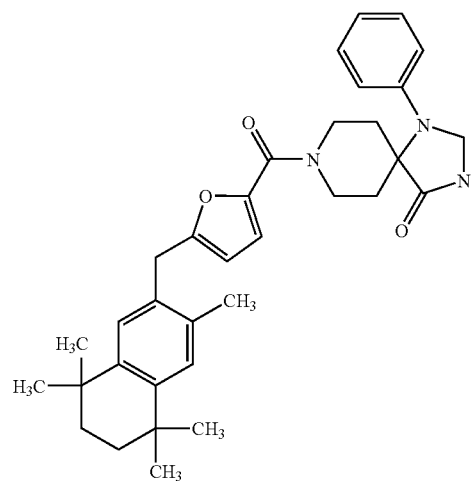 28
650 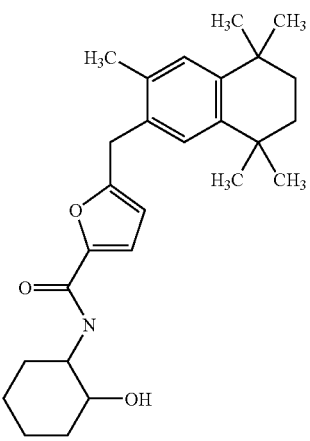 4
651 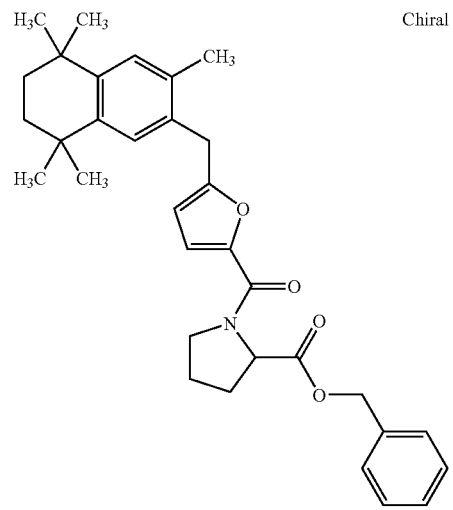 Chiral 15

-continued
| | | |
|---|---|---|
| 652 | 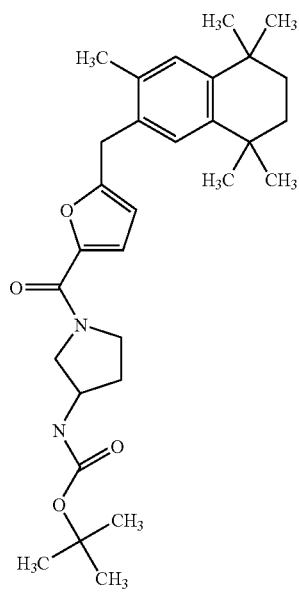 | 19 |
| 653 | 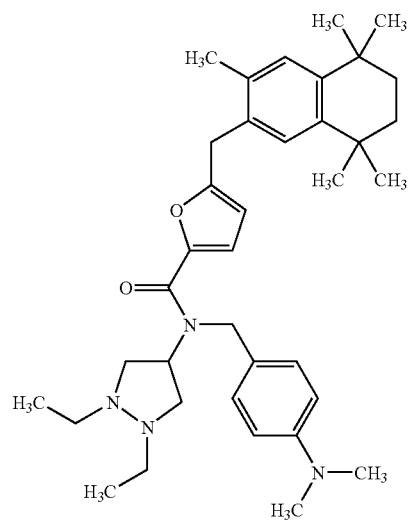 | 6 |
| 654 | 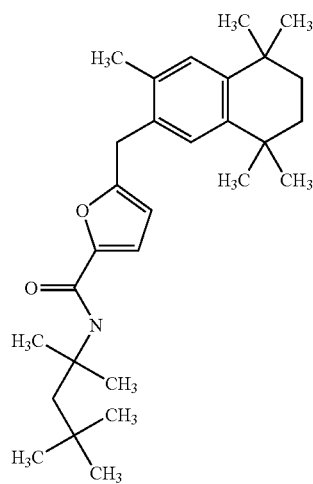 | 34 |

-continued
655 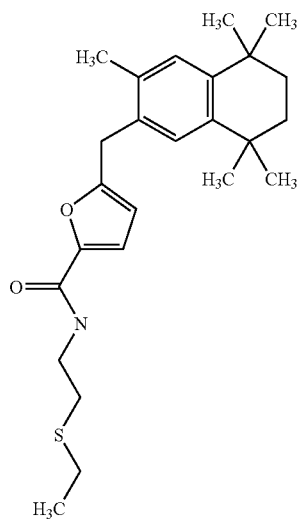 2
656 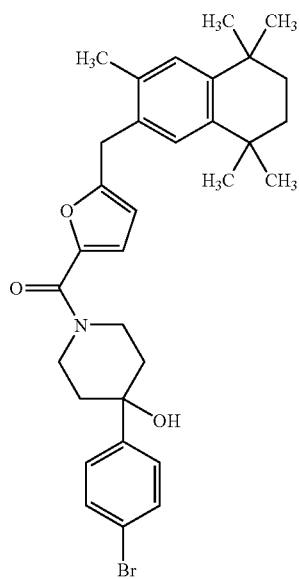 52
657 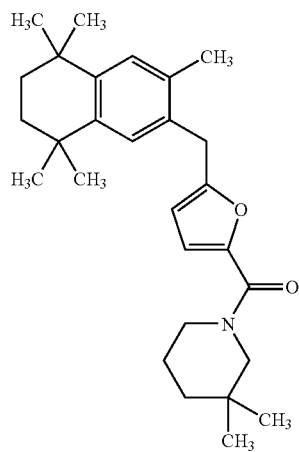 3

-continued
| 658 | 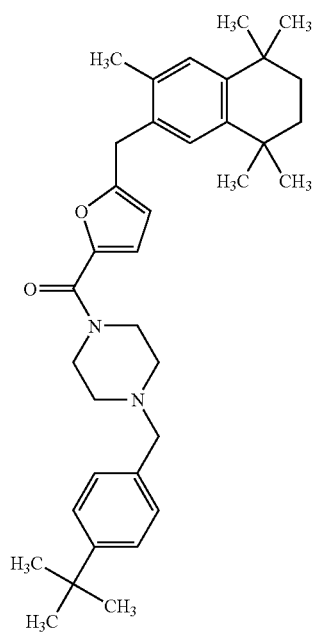 | 35 |
| 659 | 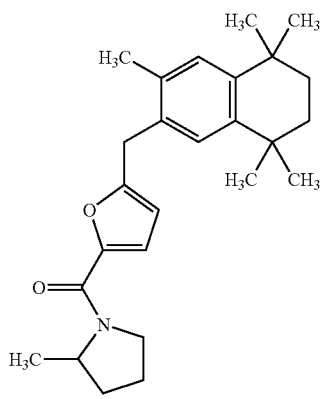 | −2 |
| 660 | 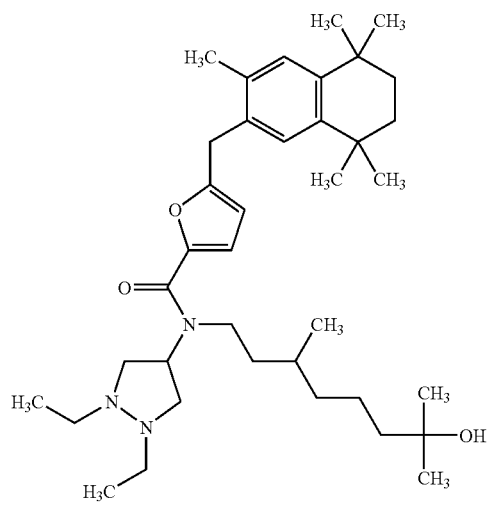 | −4 |

-continued
| | | |
|---|---|---|
| 661 | 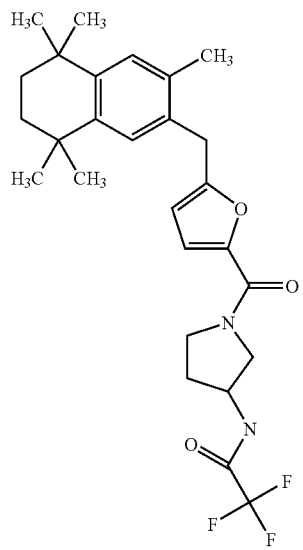 | 41 |
| 662 | 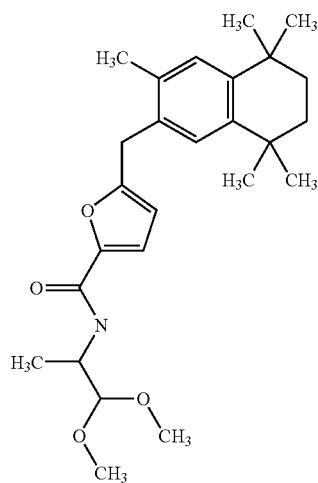 | 3 |
| 663 | 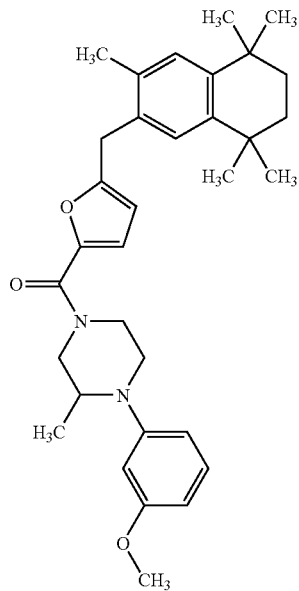 | 25 |

-continued
664 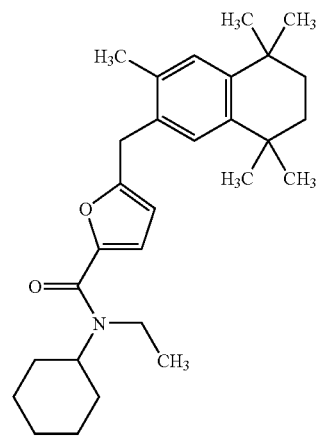 1
665 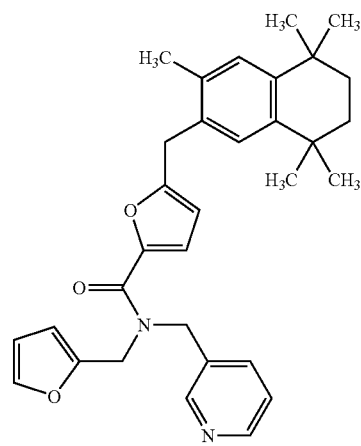 12
666 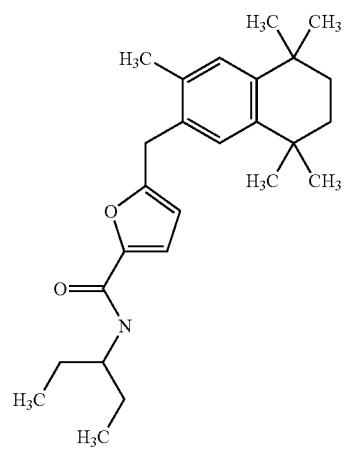 24

-continued
| | | |
|---|---|---|
| 667 | 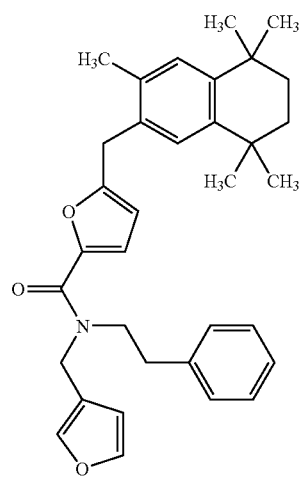 | 39 |
| 668 | 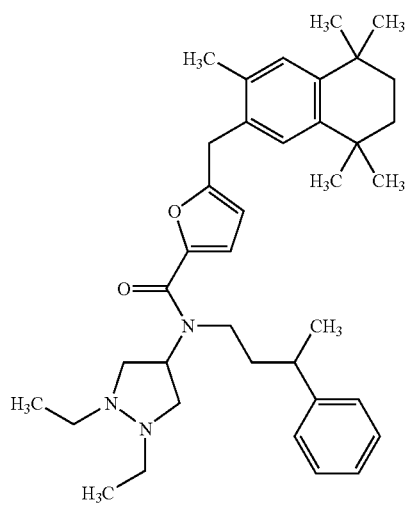 | 6 |
| 669 | 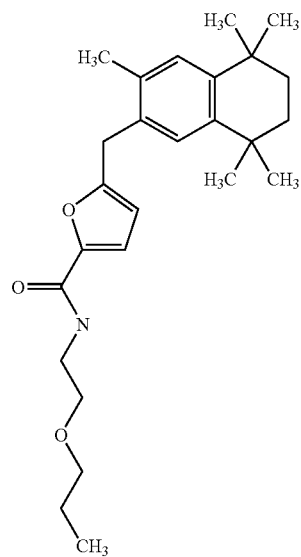 | −3 |

-continued
| | | |
|---|---|---|
| 670 | 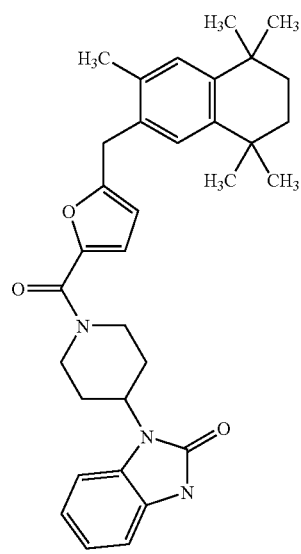 | 16 |
| 671 | 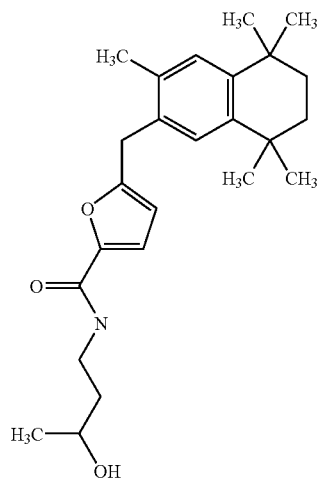 | 12 |
| 672 | 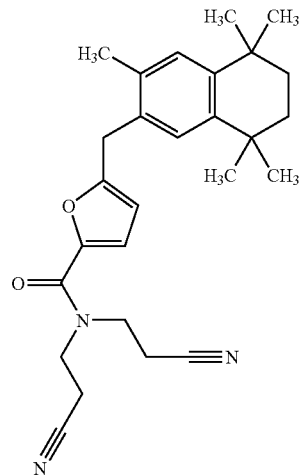 | 23 |

-continued
| 673 | 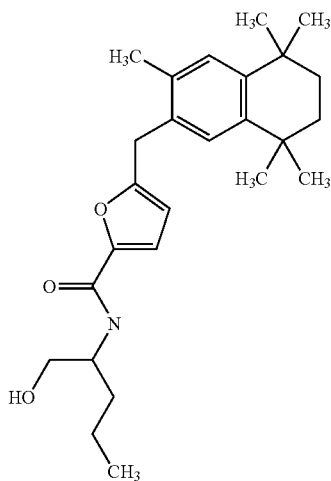 | 2 |
| 674 | 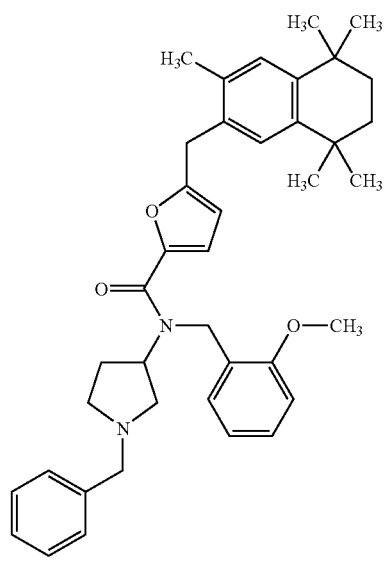 | 10 |
| 675 | 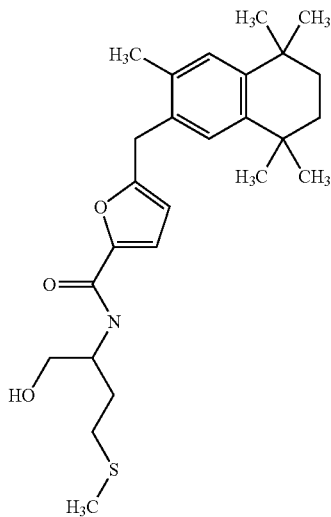 | −5 |

-continued
| 676 | 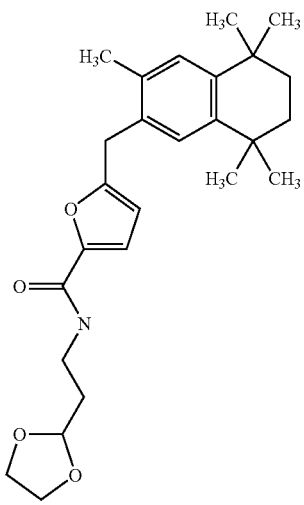 | −4 |
| 677 | 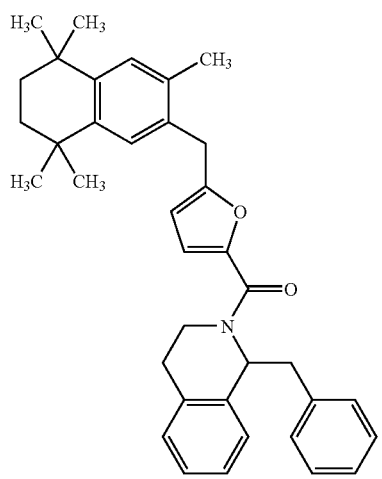 | 54 |
| 678 | 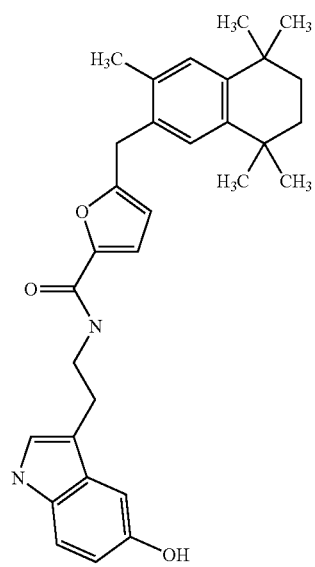 | 17 |

| | | |
|---|---|---|
| 679 | 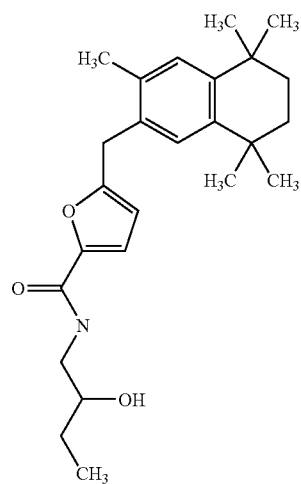 | 1 |
| 680 | 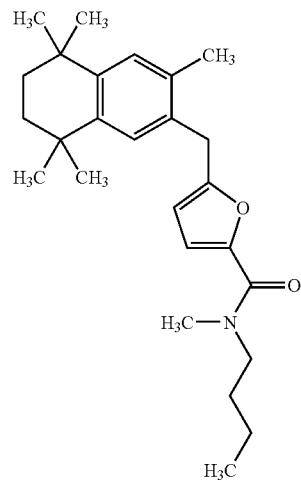 | 0 |
| 681 | 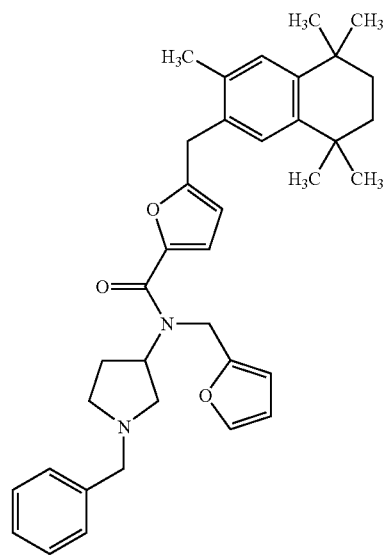 | 6 |

-continued
682 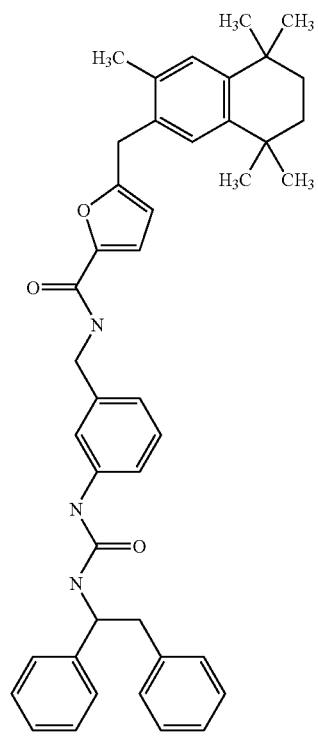 59
683 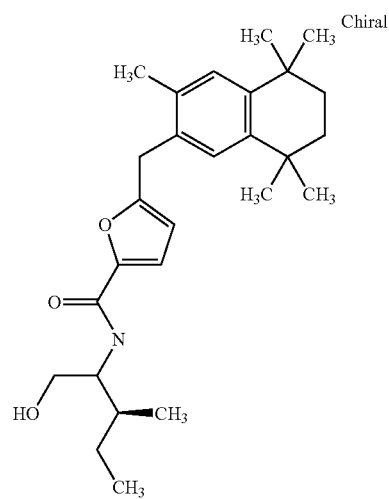 23

-continued
| | | |
|---|---|---|
| 684 | 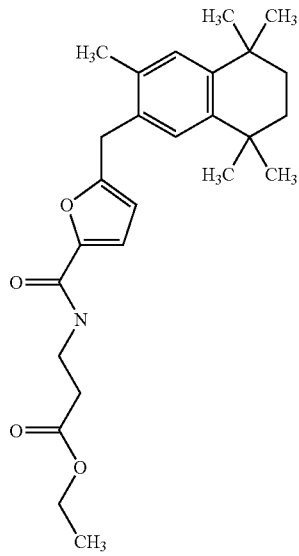 | 2 |
| 685 | 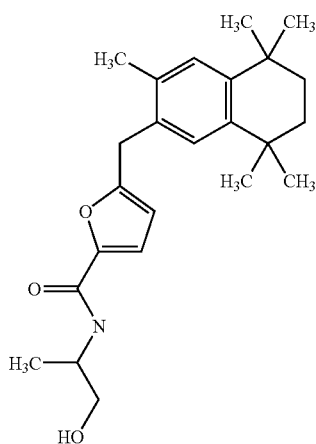 | 19 |
| 686 | 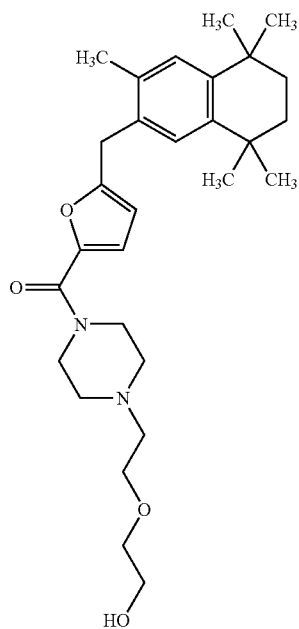 | 37 |

| | | |
|---|---|---|
| 687 | 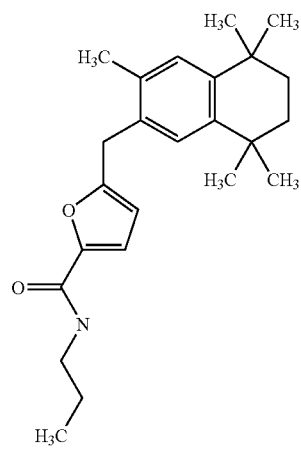 | 7 |
| 688 | 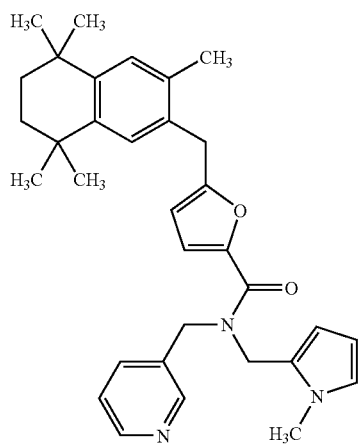 | 0 |
| 689 | 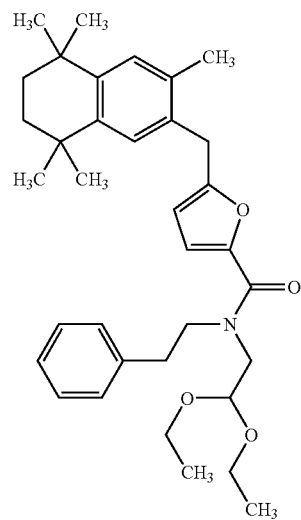 | 34 |

-continued
| 690 | 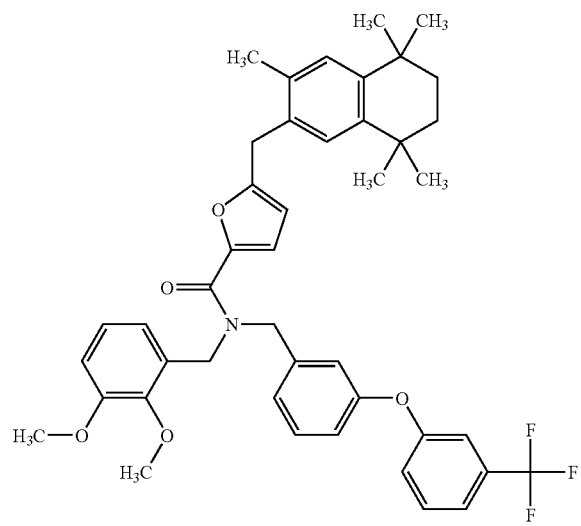 | 25 |
| 691 | 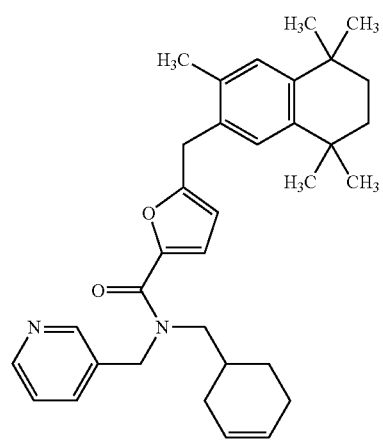 | 7 |
| 692 | 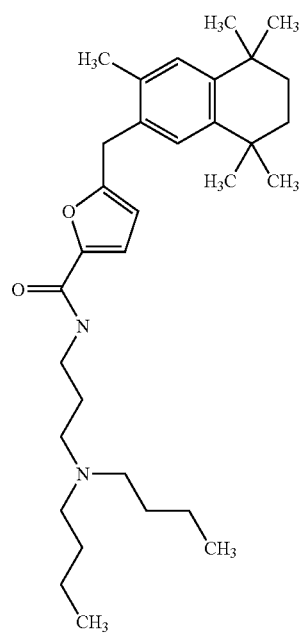 | −2 |

-continued
| 693 | 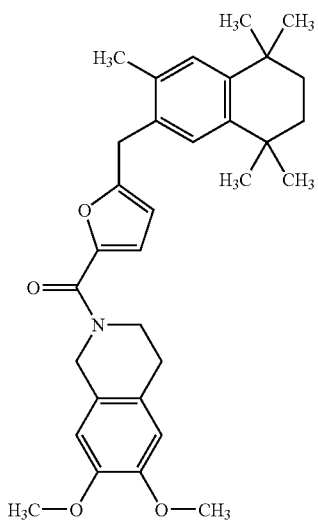 | 55 |
| 694 | 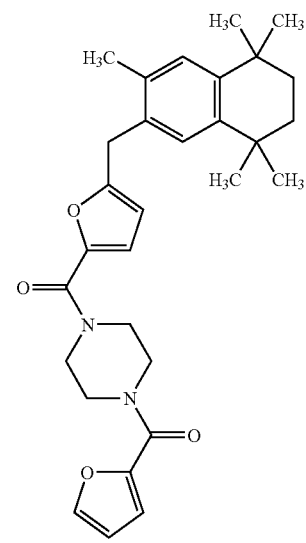 | 11 |
| 695 | 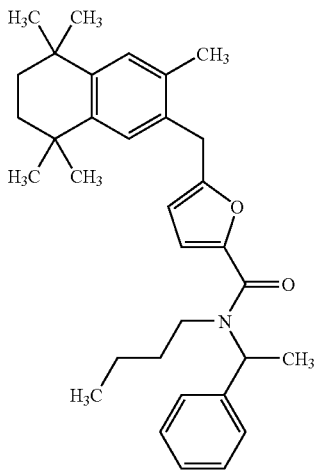 | 35 |

-continued
| | | |
|---|---|---|
| 696 | 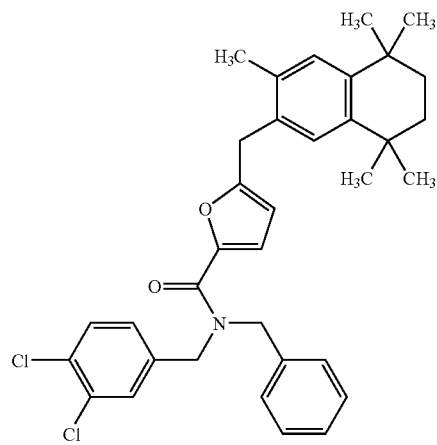 | 21 |
| 697 | 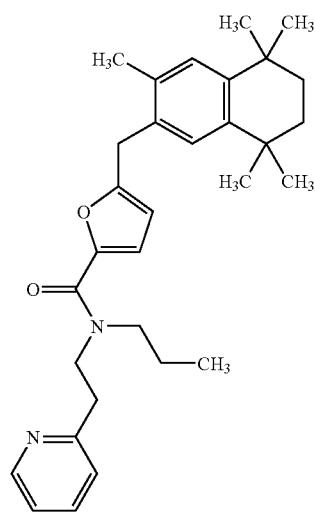 | 1 |
| 698 | 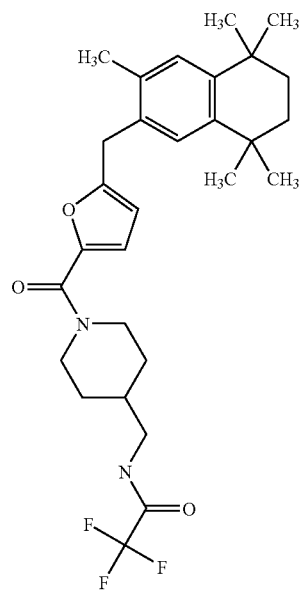 | 59 |

-continued
| 699 | 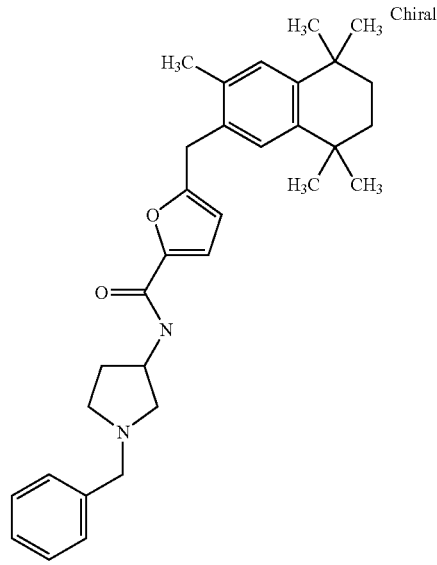 | −1 |
| 700 | 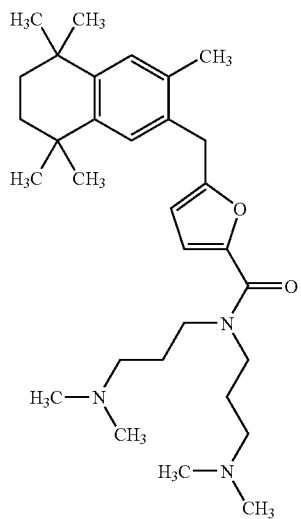 | 30 |
| 701 | 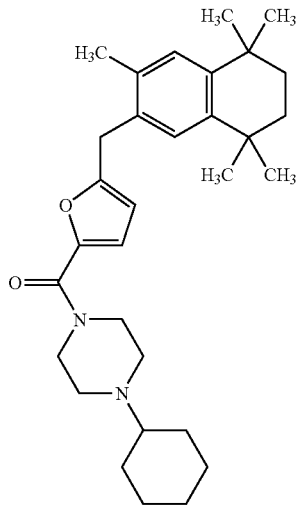 | −1 |

| | | |
|---|---|---|
| 702 | 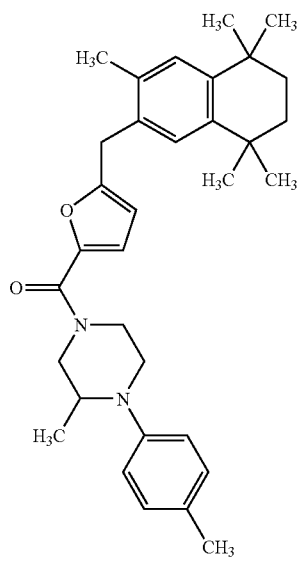 | 28 |
| 703 | 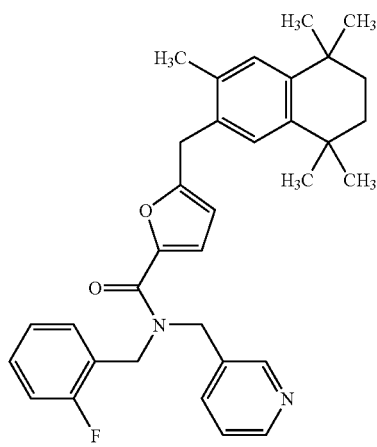 | 5 |
| 704 | 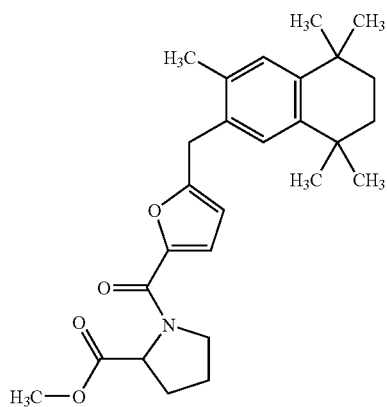 | 4 |

-continued
| | | |
|---|---|---|
| 705 | 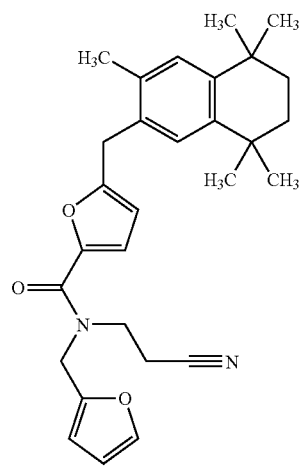 | 23 |
| 706 | 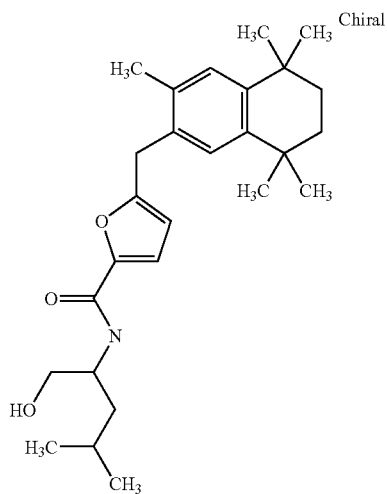 | 3 |
| 707 | 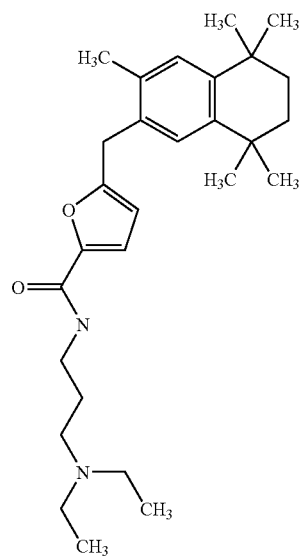 | 0 |

-continued
| 708 | 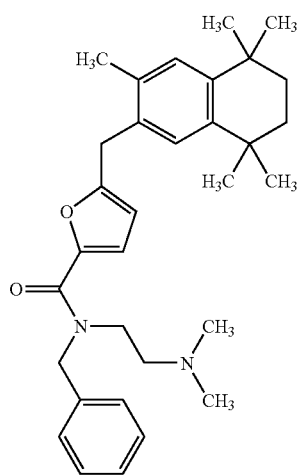 | −4 |
| --- | --- | --- |
| 709 | 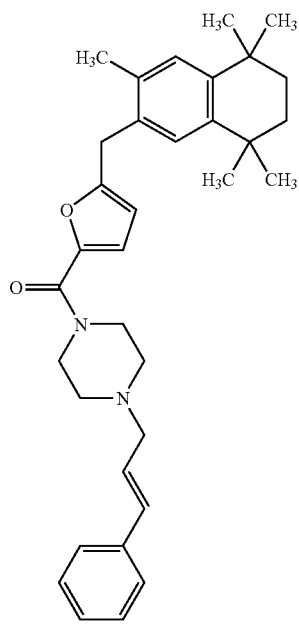 | 15 |
| 710 | 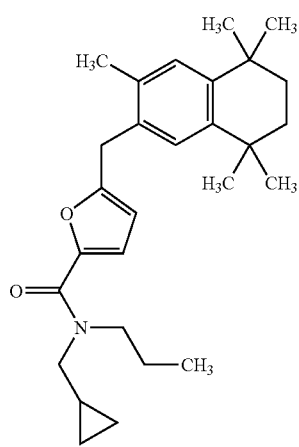 | 4 |

-continued
| 711 | 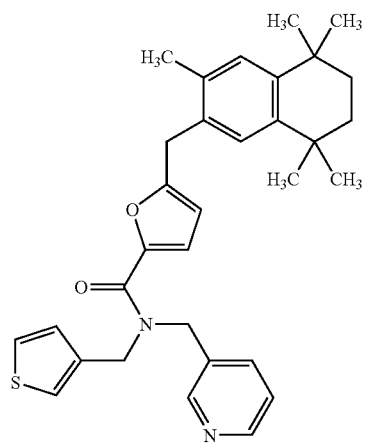 | 2 |
| 712 | 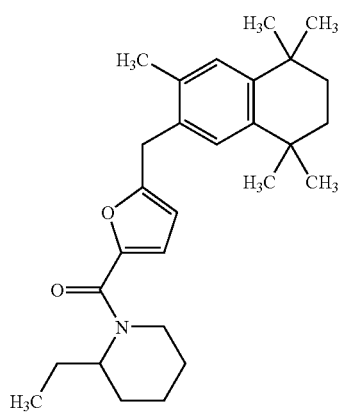 | 1 |
| 713 | 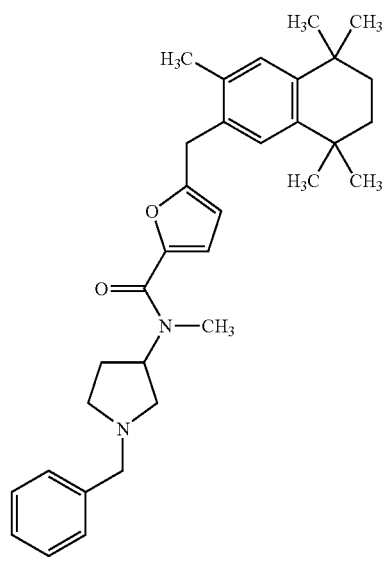 | 2 |

-continued
| 714 | 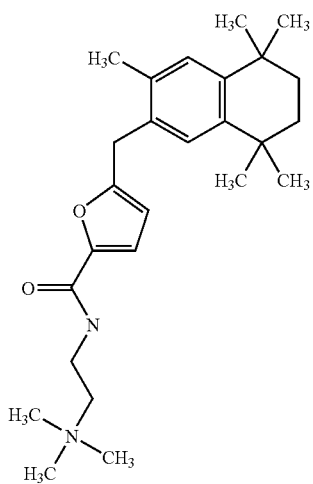 | 52 |
| 715 | 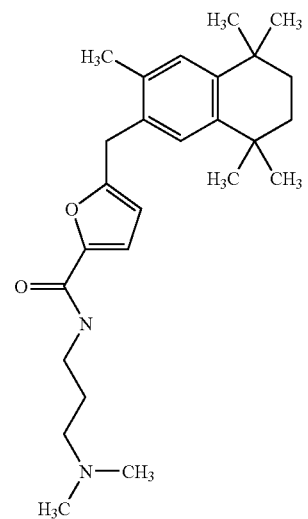 | 1 |
| 716 | 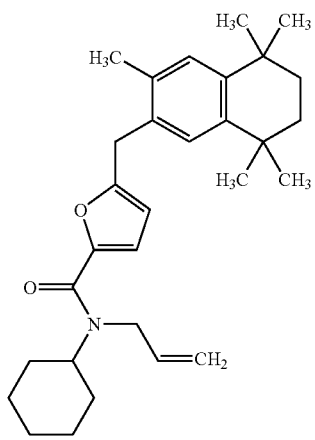 | 35 |

-continued
| | | |
|---|---|---|
| 717 | 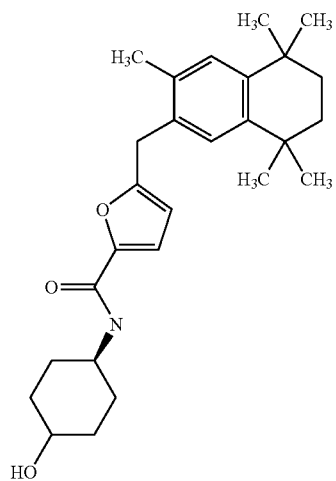 | 19 |
| 718 | 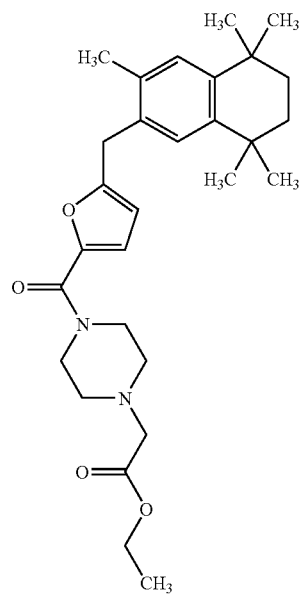 | 34 |
| 719 | 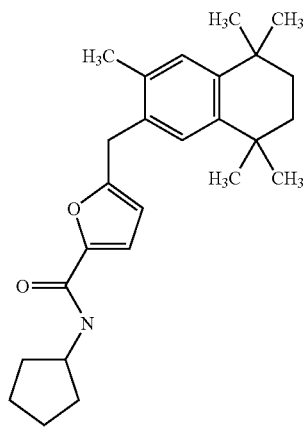 | 28 |

-continued
720 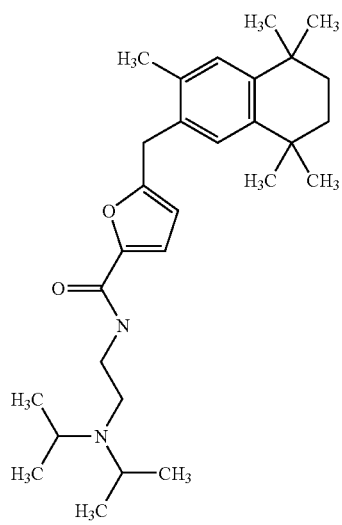 -1
721 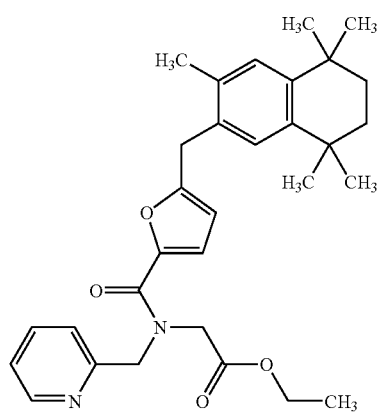 2
722 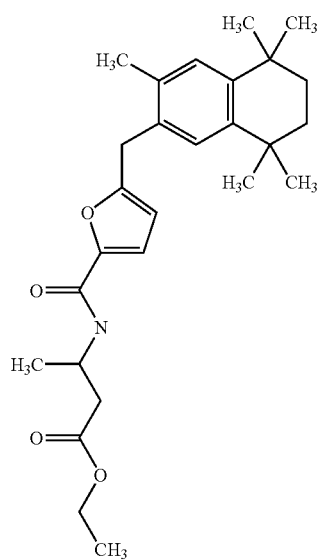 12

| | | |
|---|---|---|
| 723 | 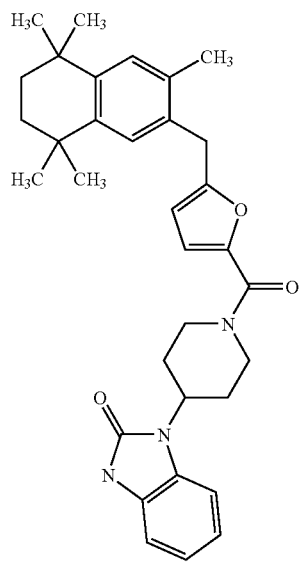 | 20 |
| 724 | 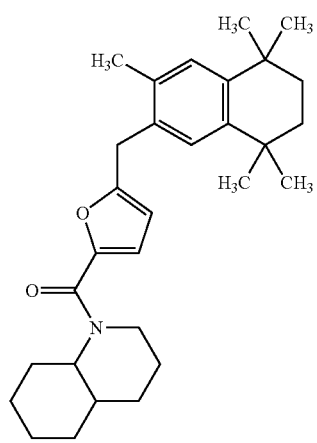 | 6 |
| 725 | 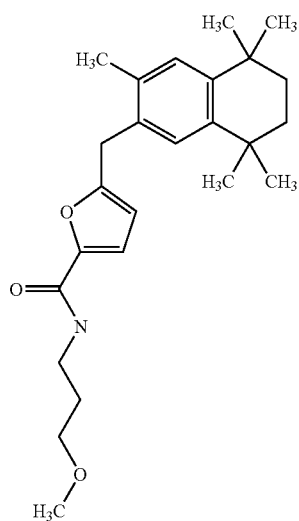 | −1 |

-continued
| | | |
|---|---|---|
| 726 | 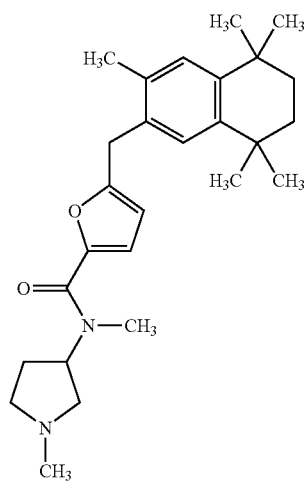 | 11 |
| 727 | 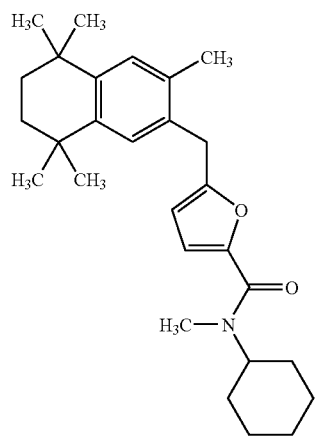 | 3 |
| 728 | 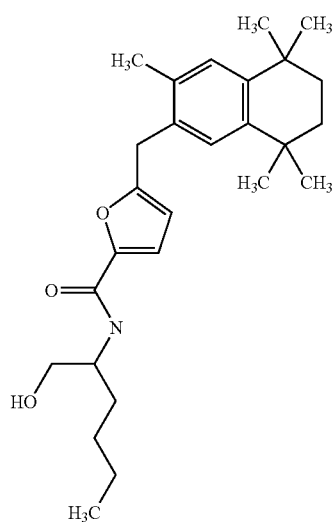 | 0 |

-continued
| | | |
|---|---|---|
| 729 | 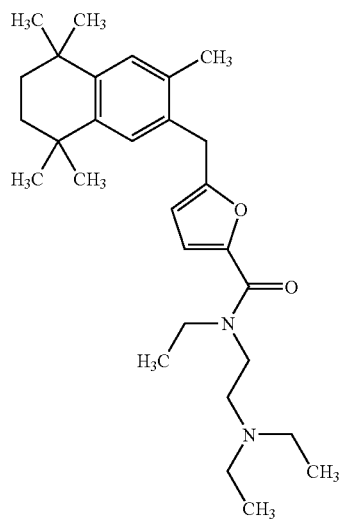 | 2 |
| 730 | 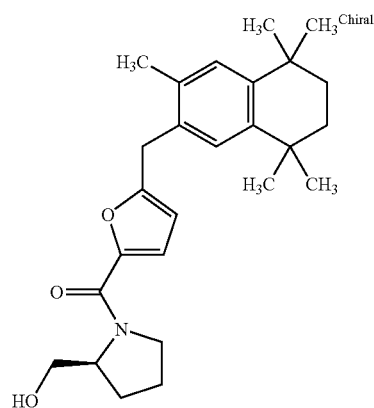 | 8 |
| 731 | 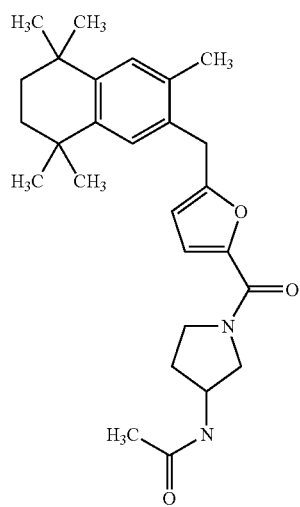 | 37 |

-continued
| | | |
|---|---|---|
| 732 | 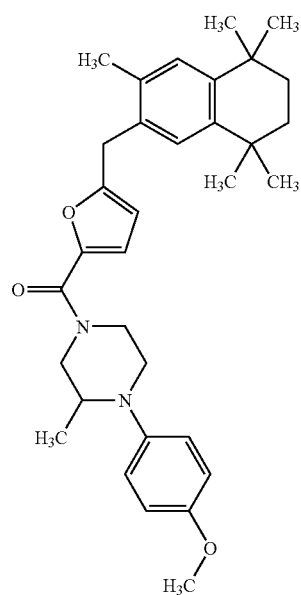 | 28 |
| 733 | 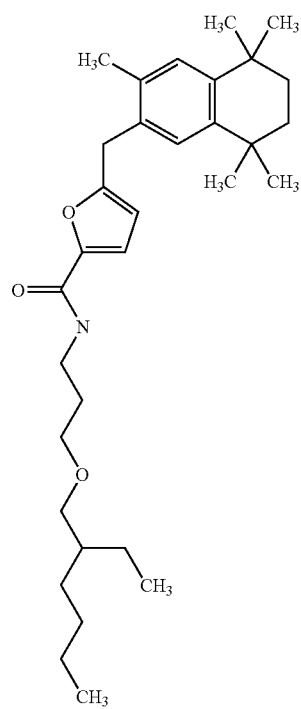 | 42 |

| | | |
|---|---|---|
| 734 | 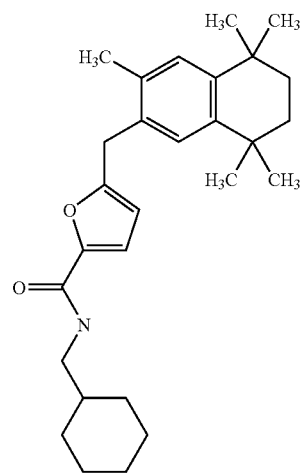 | 28 |
| 735 | 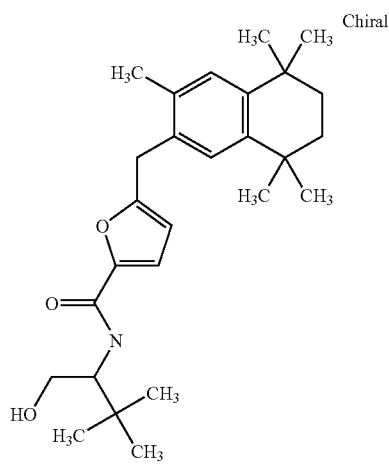 Chiral | −1 |
| 736 | 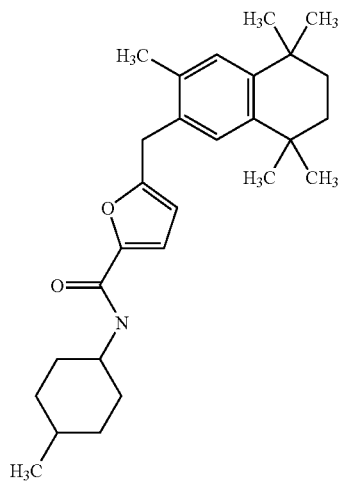 | 37 |

-continued
737 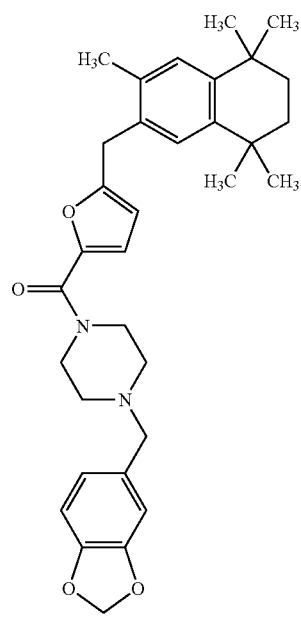 36
738 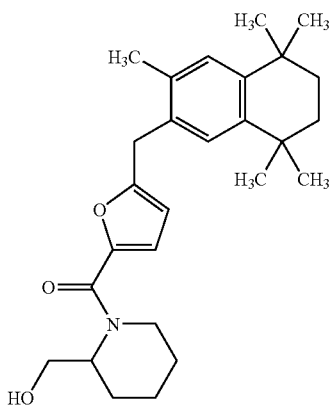 16
739 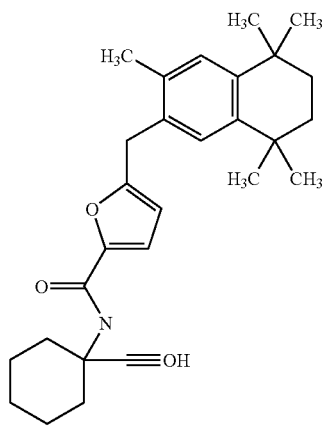 42

-continued
| | | |
|---|---|---|
| 740 | 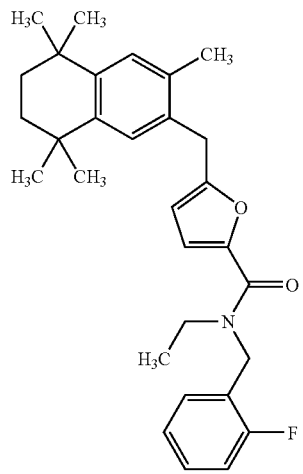 | 15 |
| 741 | 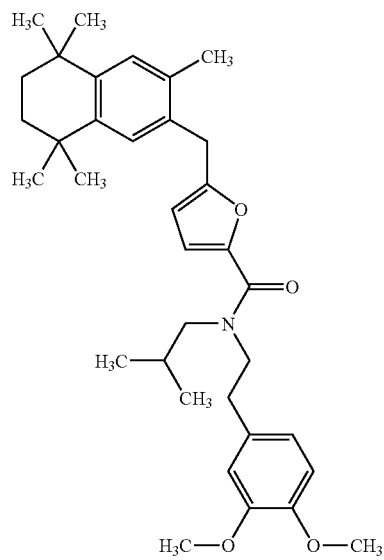 | 11 |
| 742 | 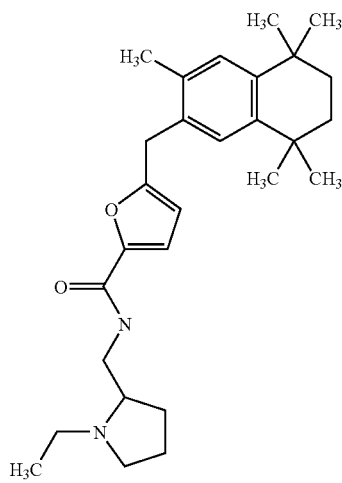 | 5 |

-continued
743 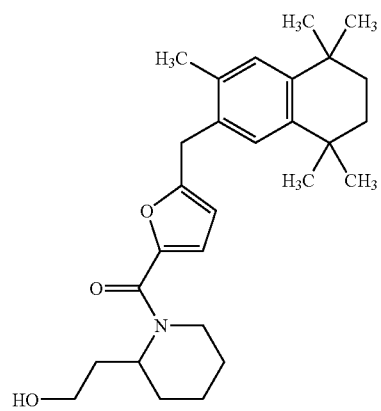 0
744 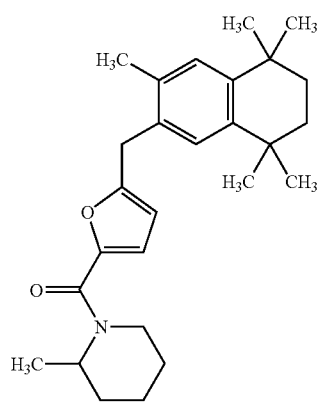 0
745 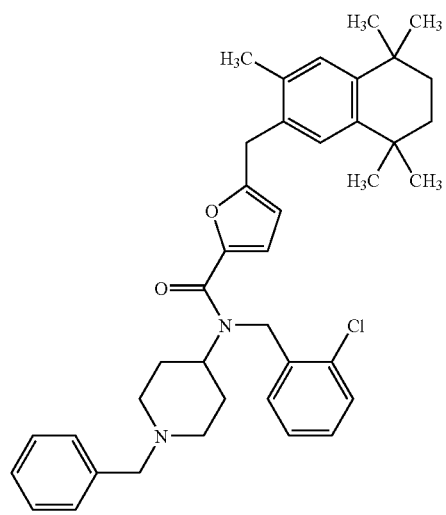 58

-continued
746 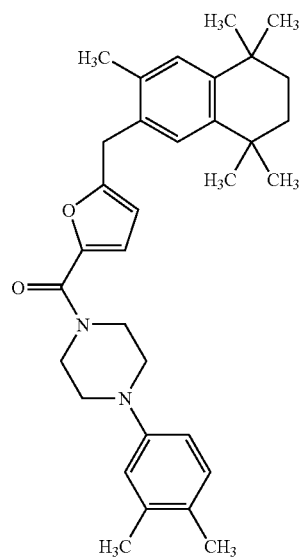 25
747 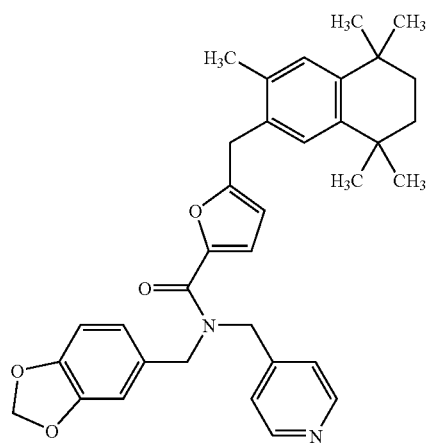 10
748 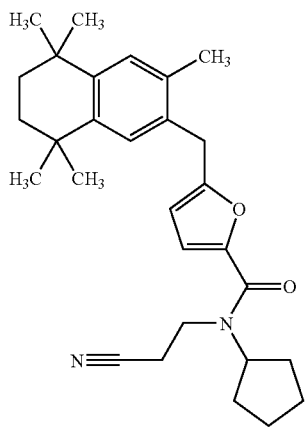 12

749 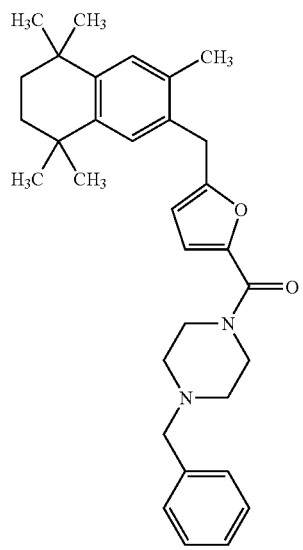 17
750 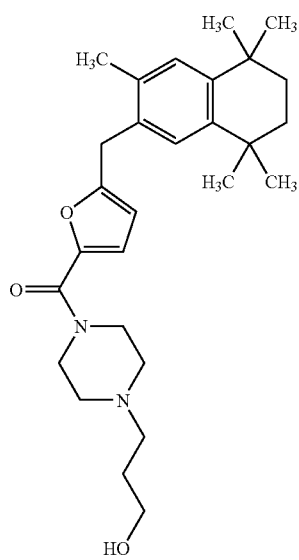 34

751 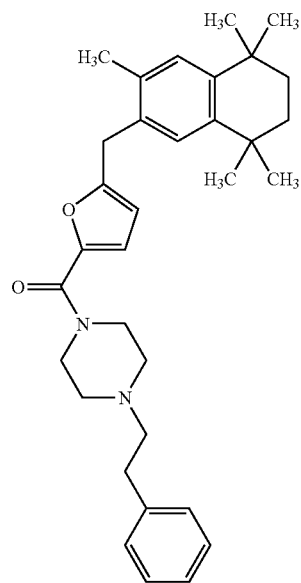 4
752 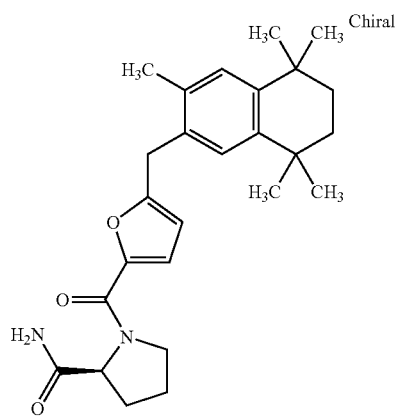 27

-continued
| | |
|---|---|
| 753 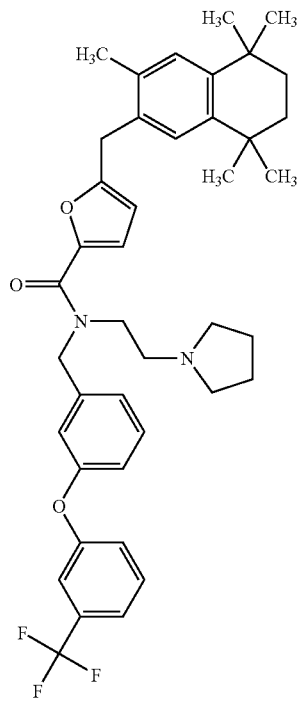 | 1 |
| 754 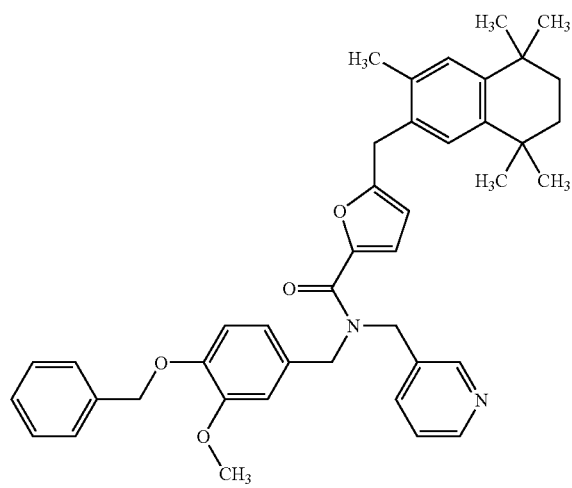 | 37 |
| 755 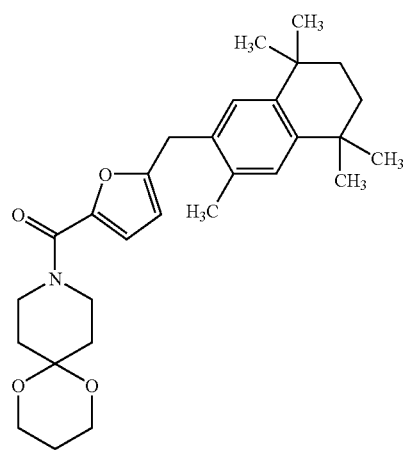 | 2 |

-continued
| | | |
|---|---|---|
| 756 | 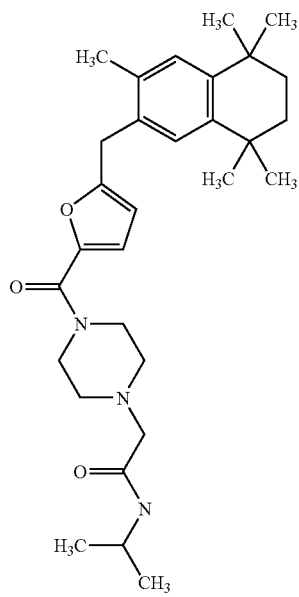 | 38 |
| 757 | 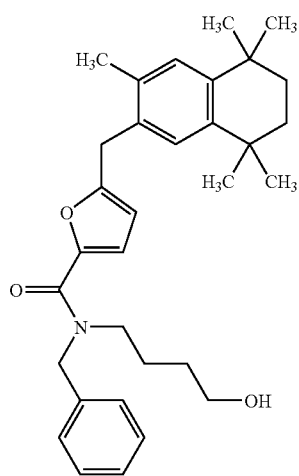 | 1 |
| 758 | 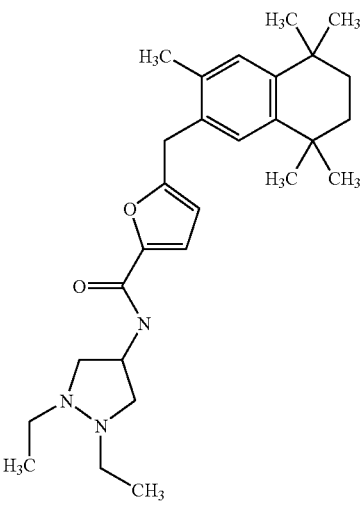 | 9 |

-continued
759
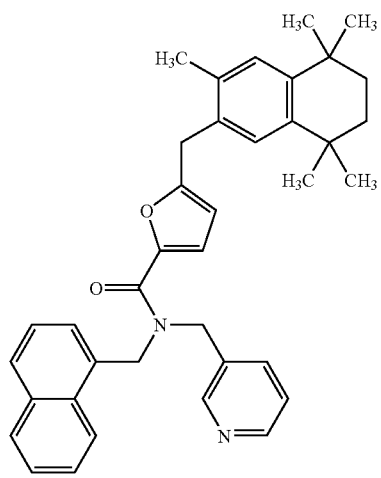
21
760
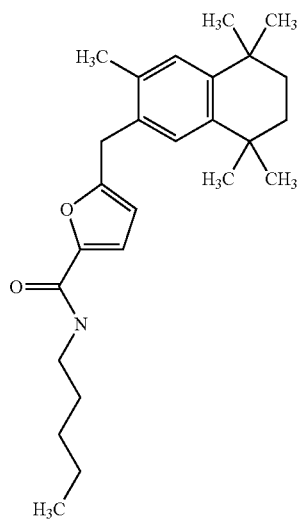
10
761
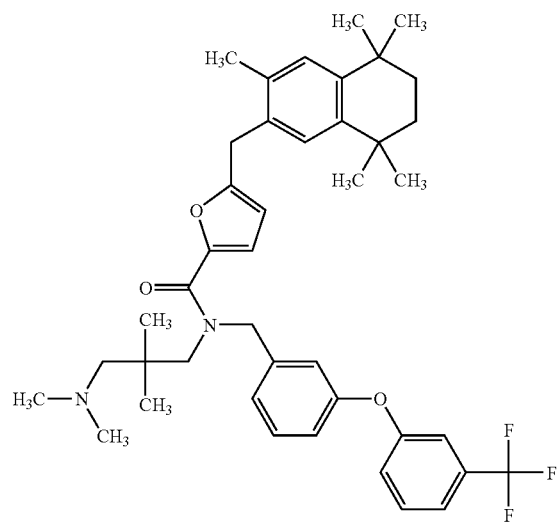
12

-continued
| 762 | 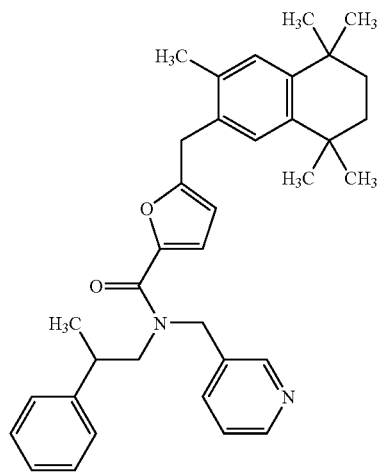 | 3 |
| 763 | 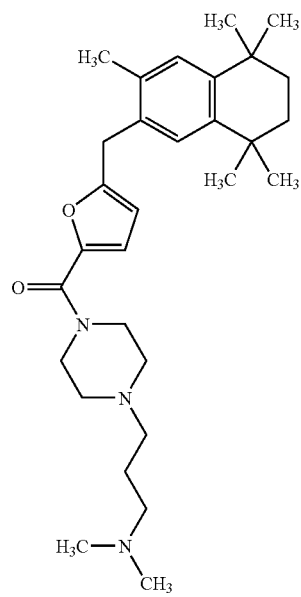 | 5 |
| 764 | 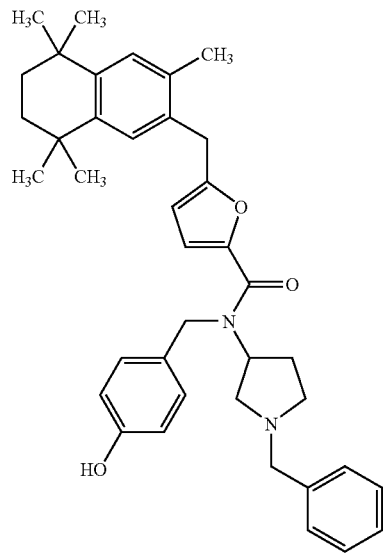 | 18 |

-continued
| | | |
|---|---|---|
| 765 | 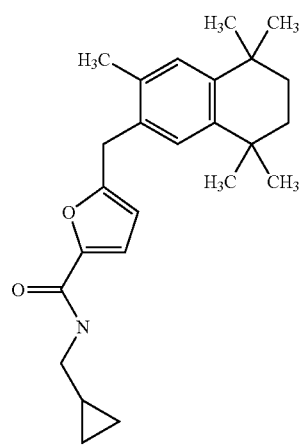 | 15 |
| 766 | 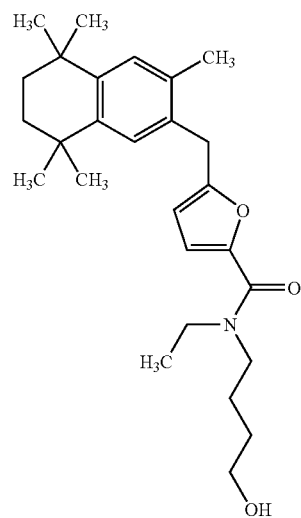 | 6 |
| 767 | 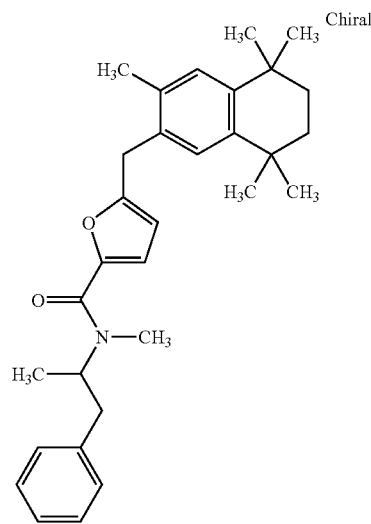 | 42 |

-continued
| 768 | 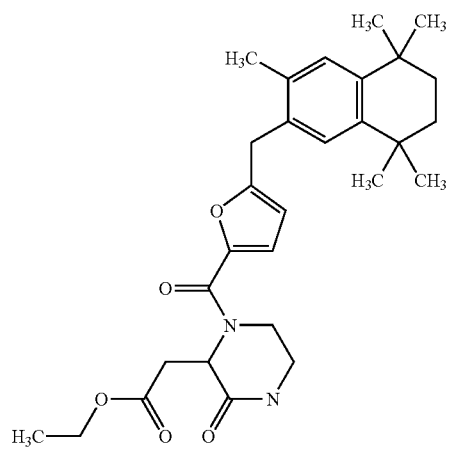 | 3 |
| 769 | 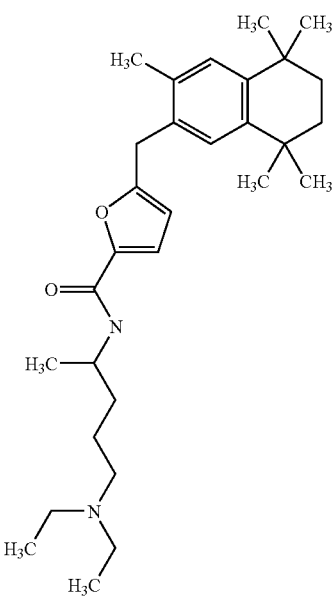 | 2 |
| 770 | 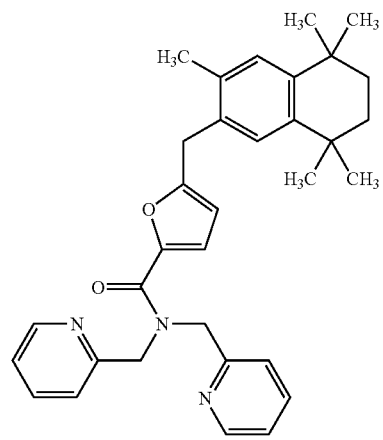 | 3 |

| 771 | 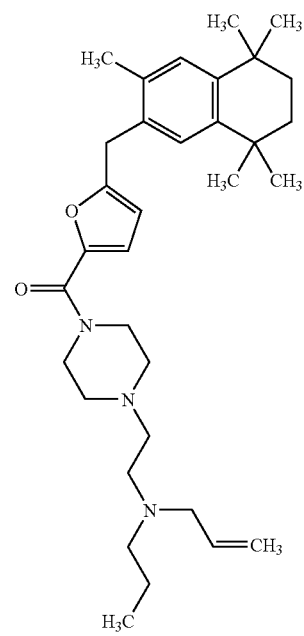 | 0 |
| --- | --- | --- |
| 772 | 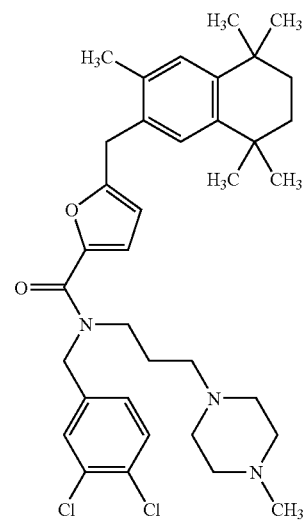 | −4 |
| --- | --- | --- |

-continued
773 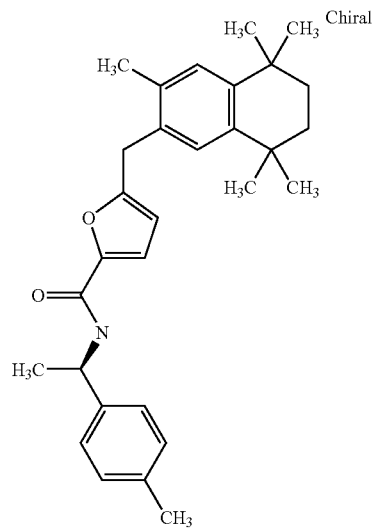 3
774 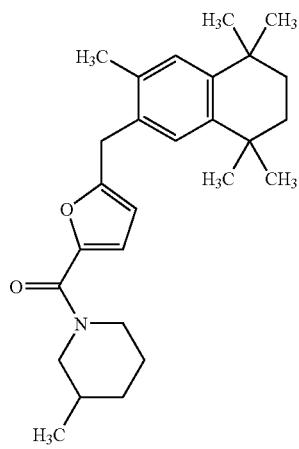 3
775 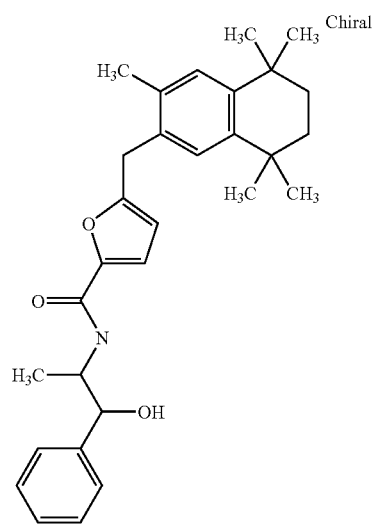 38

-continued
776 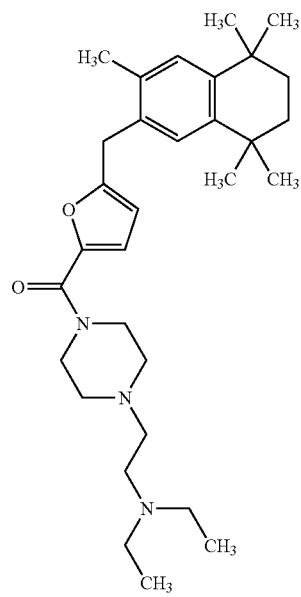 3
777 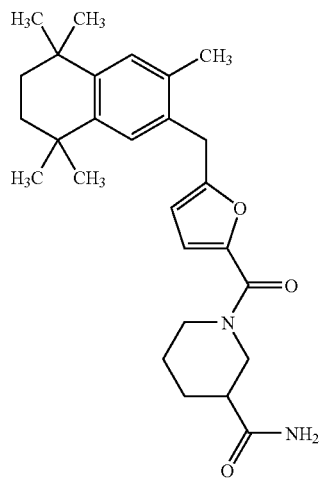 31
778 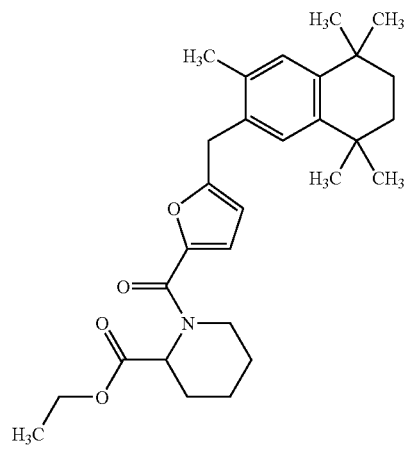 6

-continued
779 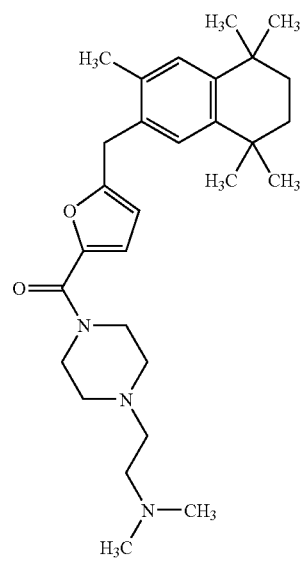 2
780 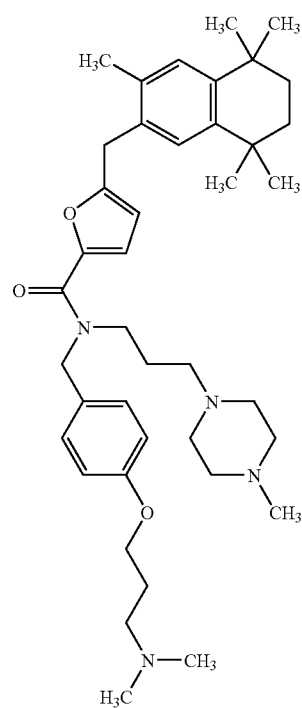 1

-continued
| | | |
|---|---|---|
| 781 | 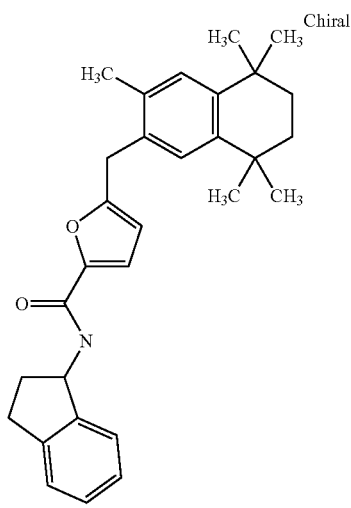 | 44 |
| 782 | 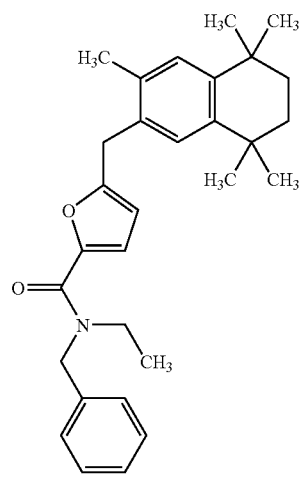 | 15 |
| 783 | 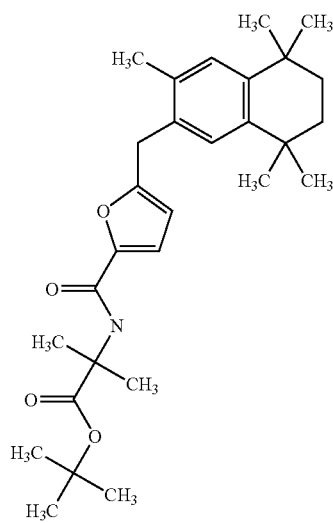 | 25 |

-continued
| | | |
|---|---|---|
| 784 | 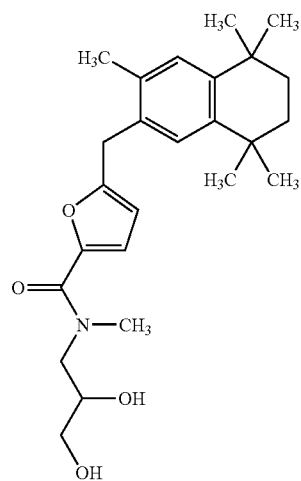 | 31 |
| 785 | 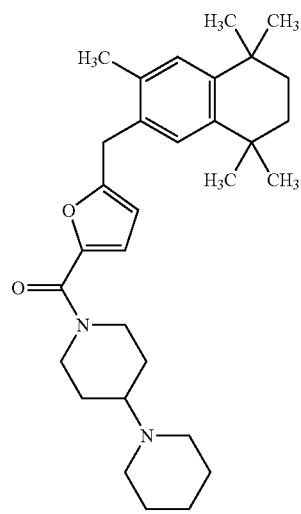 | 9 |
| 786 | 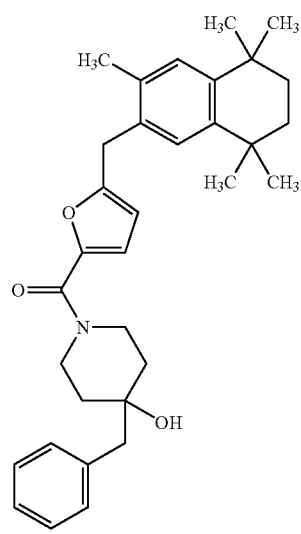 | 34 |

-continued
| | | |
|---|---|---|
| 787 | 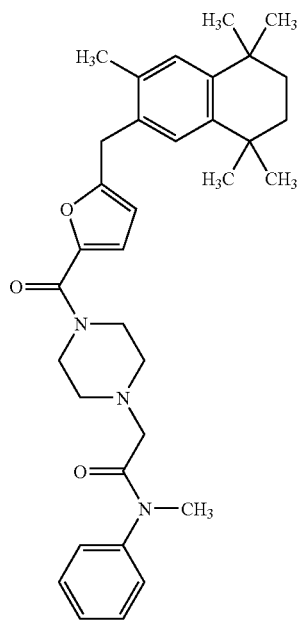 | −3 |
| 788 | 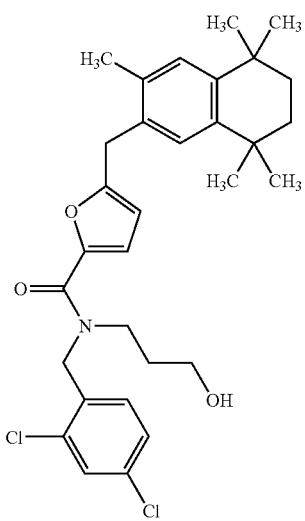 | 6 |
| 789 | 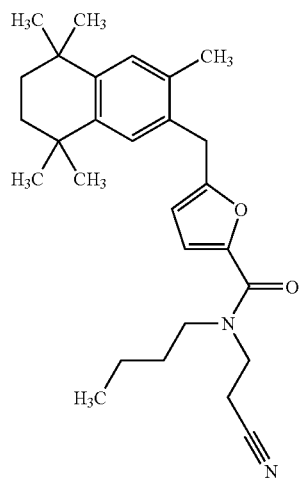 | 14 |

-continued
790 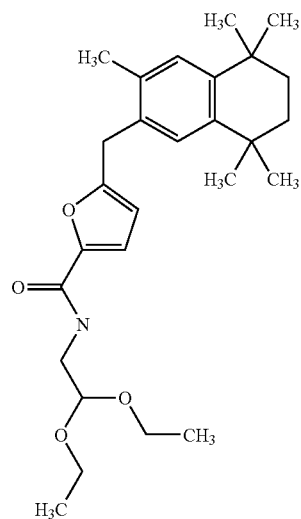 0
791 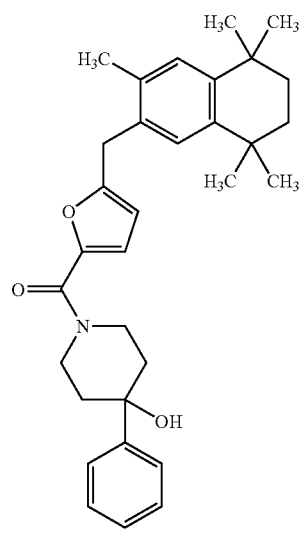 29
792 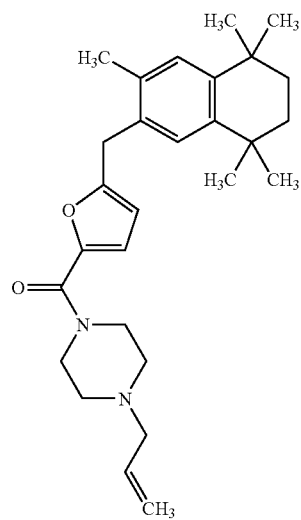 5

-continued
| | | |
|---|---|---|
| 793 | 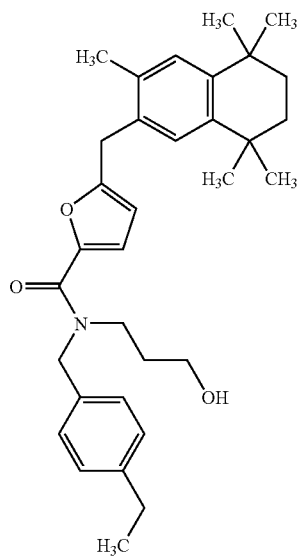 | 13 |
| 794 | 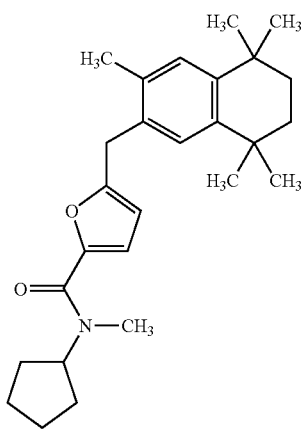 | 0 |
| 795 | 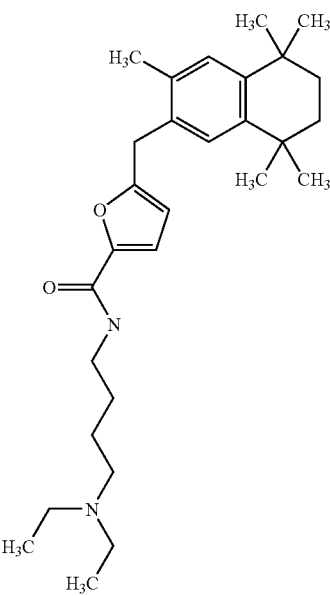 | 0 |

| | | |
|---|---|---|
| 796 | 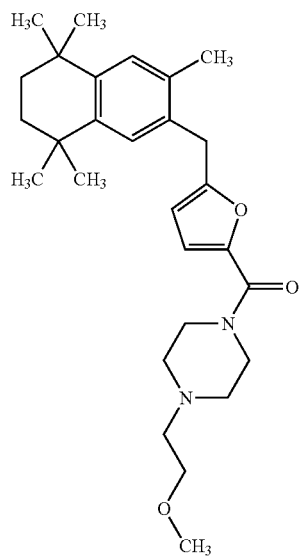 | 19 |
| 797 | 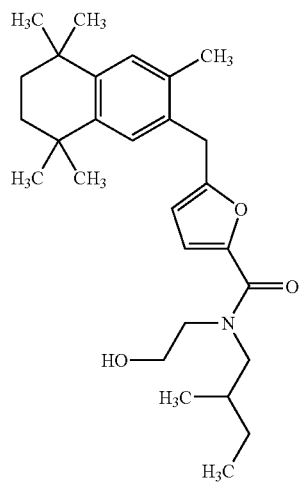 | −1 |
| 798 | 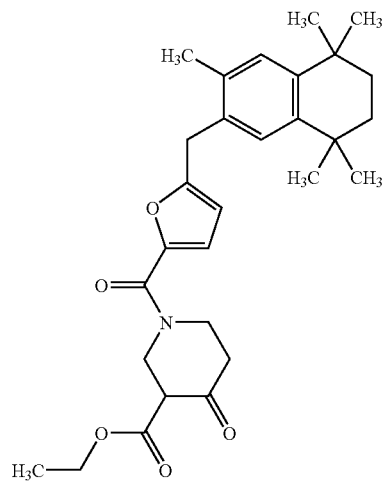 | 29 |

-continued
| | | |
|---|---|---|
| 799 | 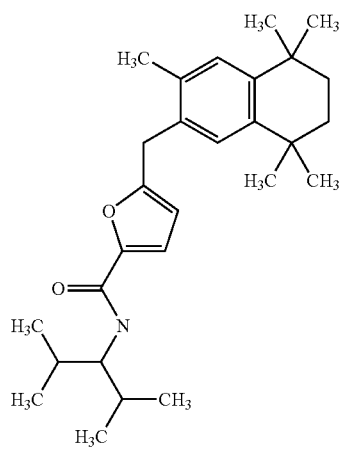 | 42 |
| 800 | 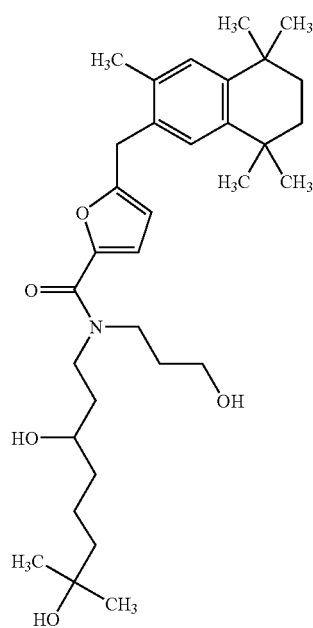 | 1 |
| 801 | 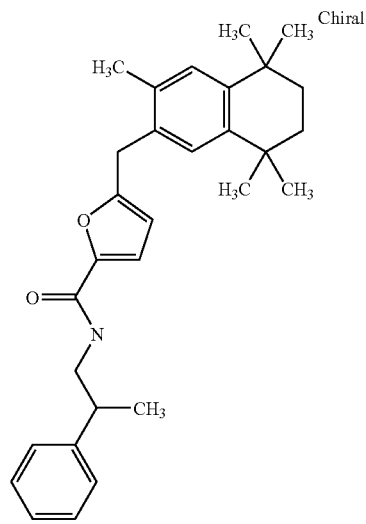 | 31 |

-continued
802 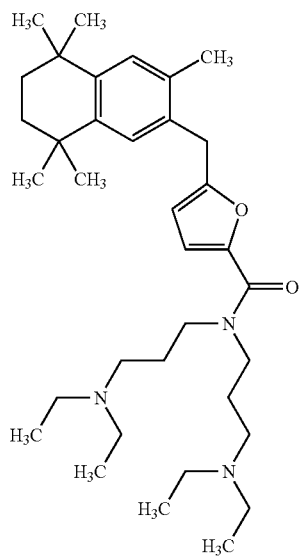 31
803 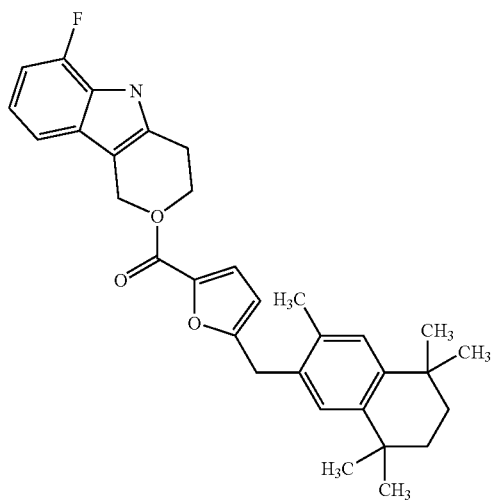 54
804 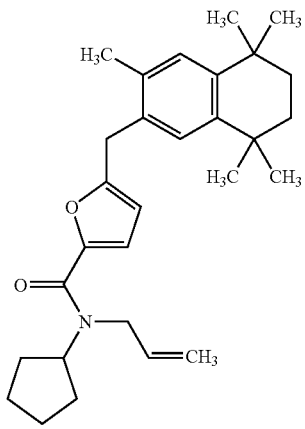 5

| | | |
|---|---|---|
| 805 | 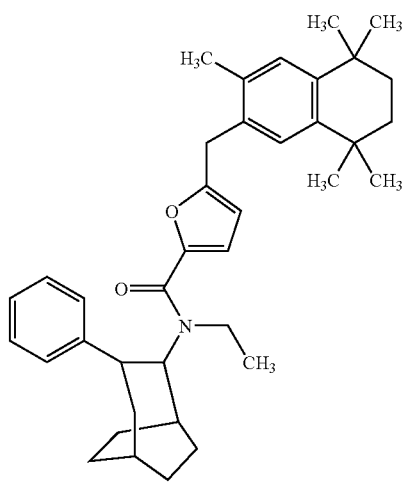 | 51 |
| 806 | 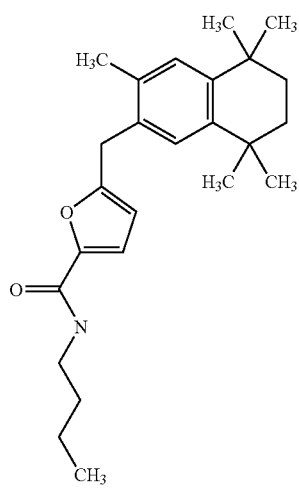 | 10 |
| 807 | 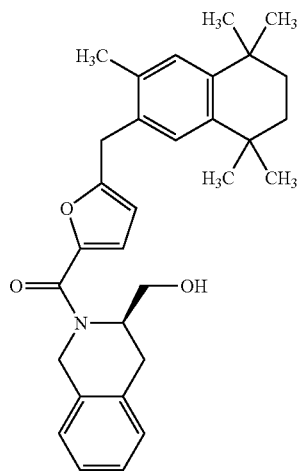 | 39 |

-continued
808 9
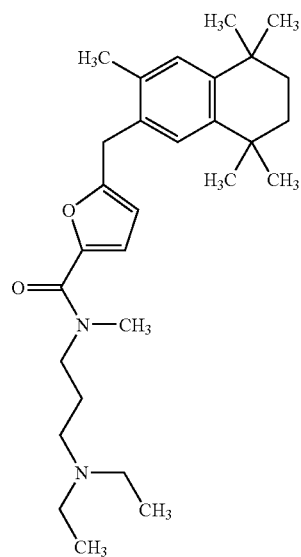
809 38
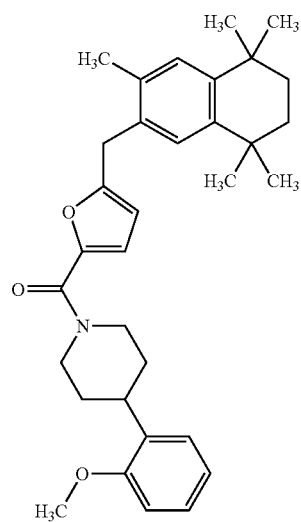

810
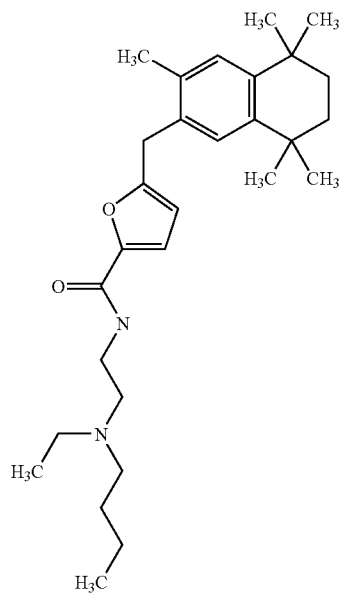
811
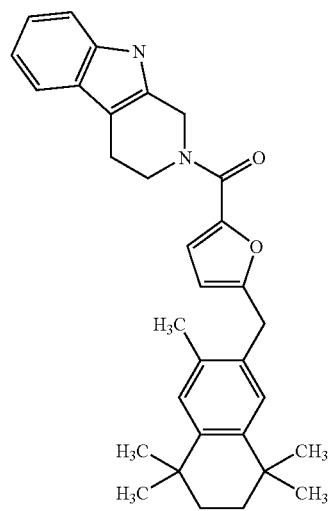

| | | |
|---|---|---|
| 812 | 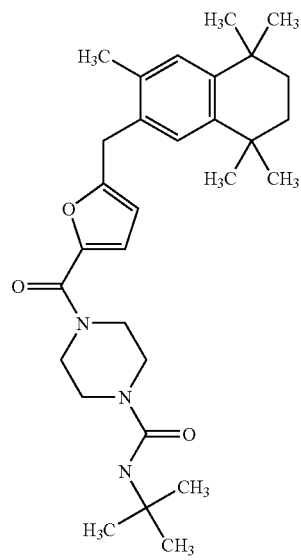 | 10 |
| 813 | 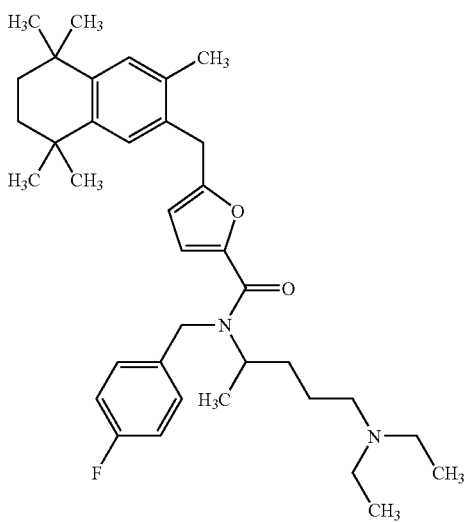 | −2 |
| 814 | 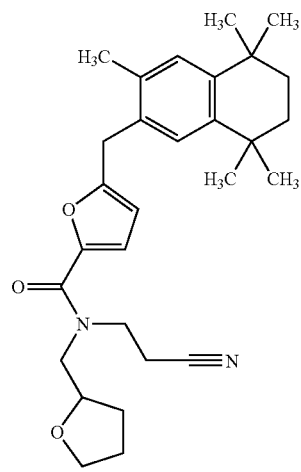 | 6 |

-continued
815 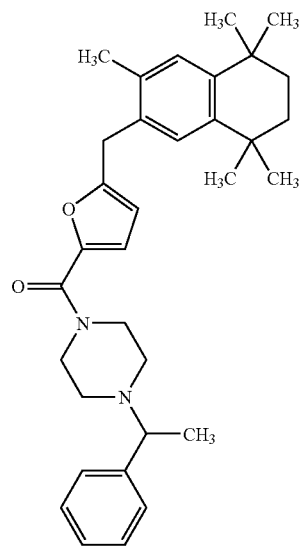 9
816 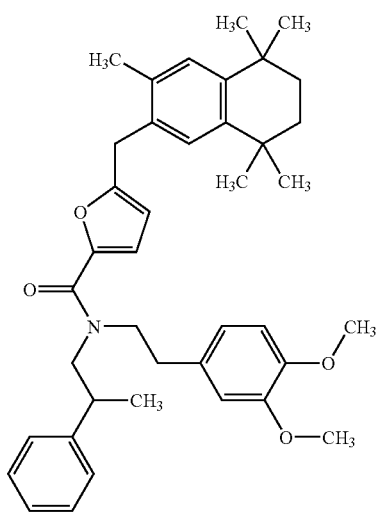 29
817 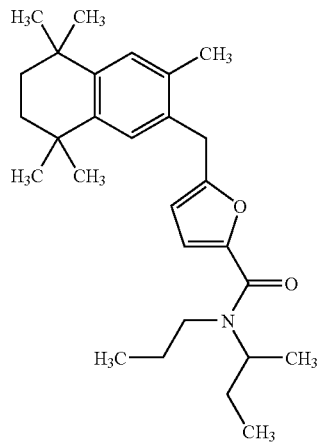 7

-continued
| 818 | 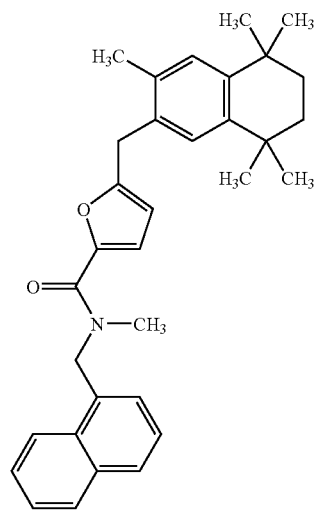 | 50 |
| 819 | 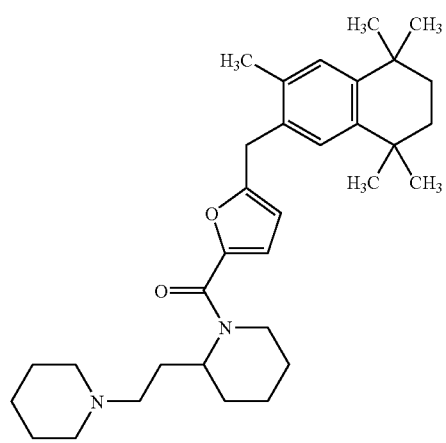 | −2 |
| 820 | 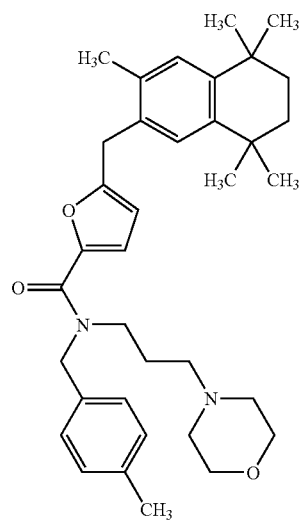 | −2 |

| | | |
|---|---|---|
| 821 | 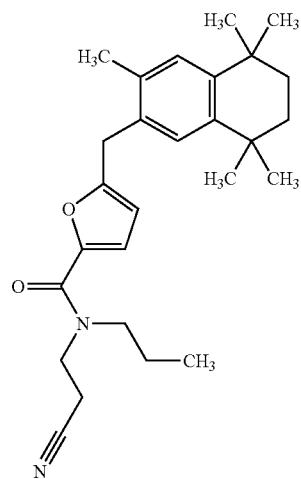 | 7 |
| 822 | 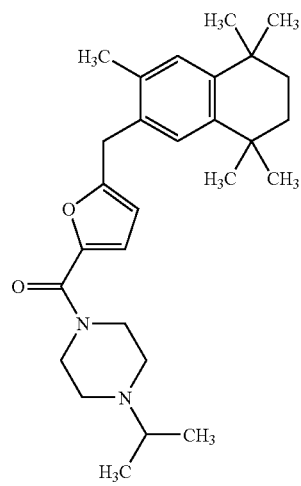 | 0 |
| 823 | 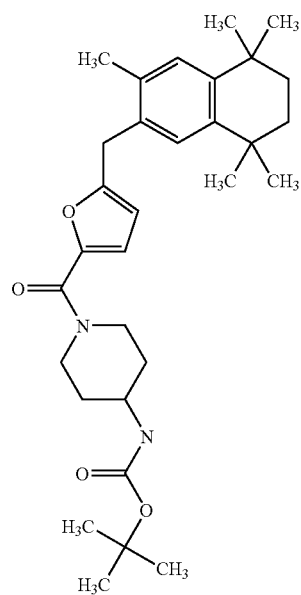 | 33 |

-continued
| | | |
|---|---|---|
| 824 | 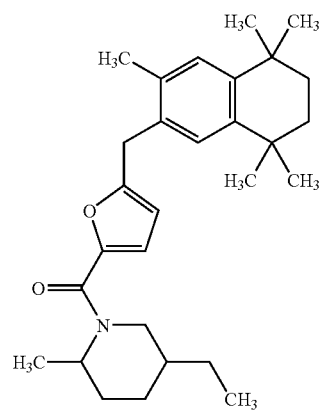 | 6 |
| 825 | 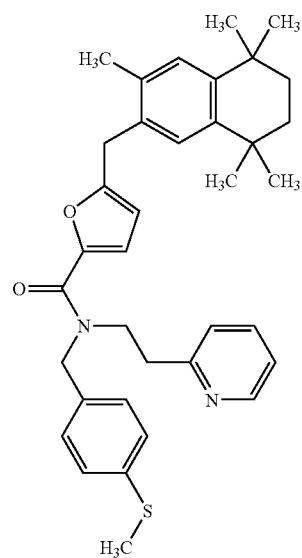 | 26 |
| 826 | 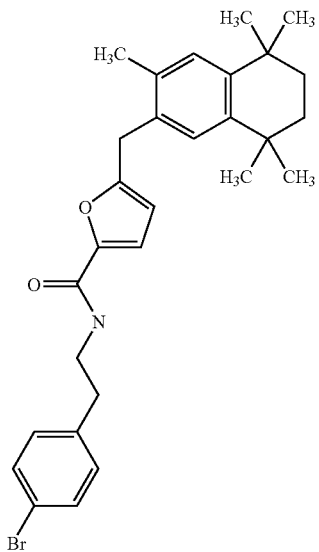 | 53 |

-continued
827
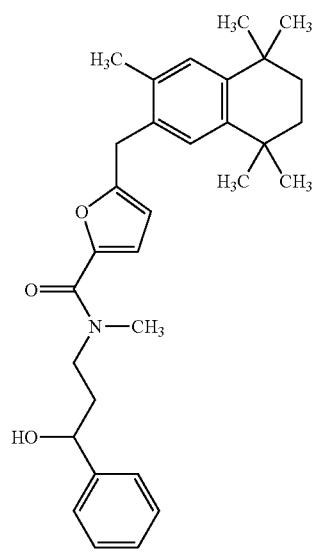
1
828
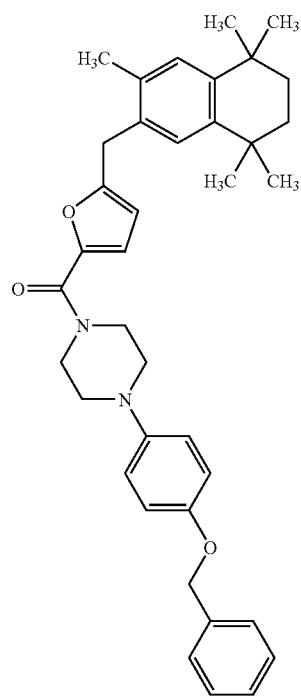
56

829 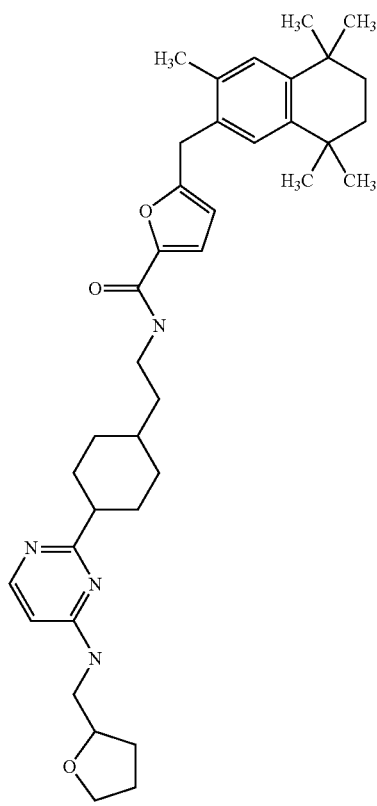 4
830 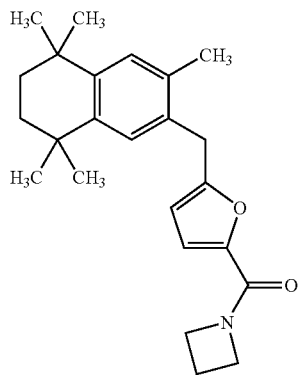 38

-continued
| | | |
|---|---|---|
| 831 | 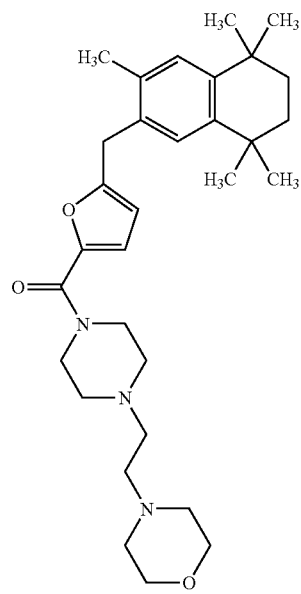 | 27 |
| 832 |  | 2 |
| 833 | 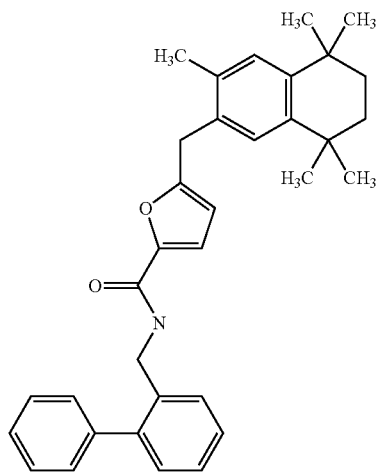 | 26 |

-continued
| | | |
|---|---|---|
| 834 | 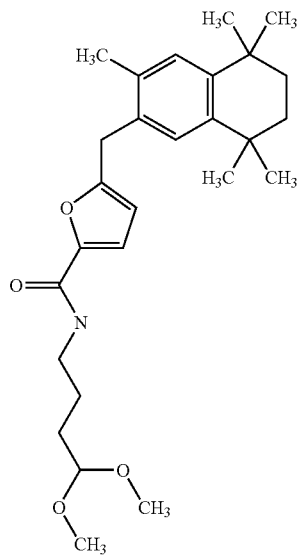 | 0 |
| 835 | 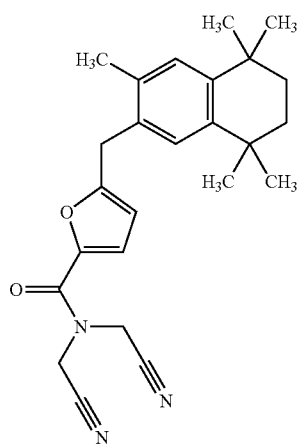 | 36 |
| MOLSTRUCTURE | % Inhib. @ 1 uM hGnRH | Repeats @ 1 uM hGnRH |
|---|---|---|
| 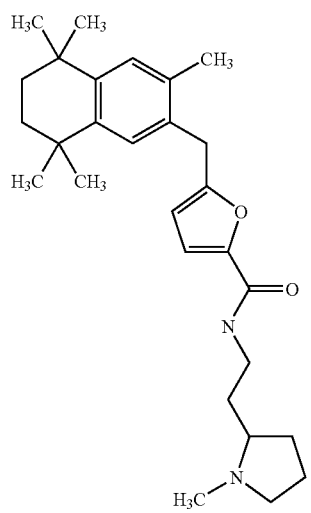 | 40 | 49 |

-continued
| | 57 | 58 |
|---|---|---|
| 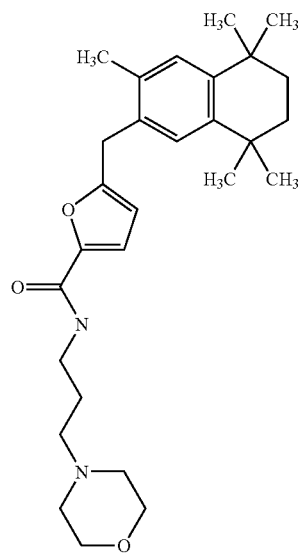 | | |
| | 86 | 93 |
| 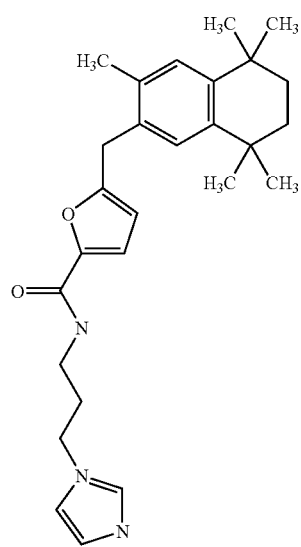 | | |

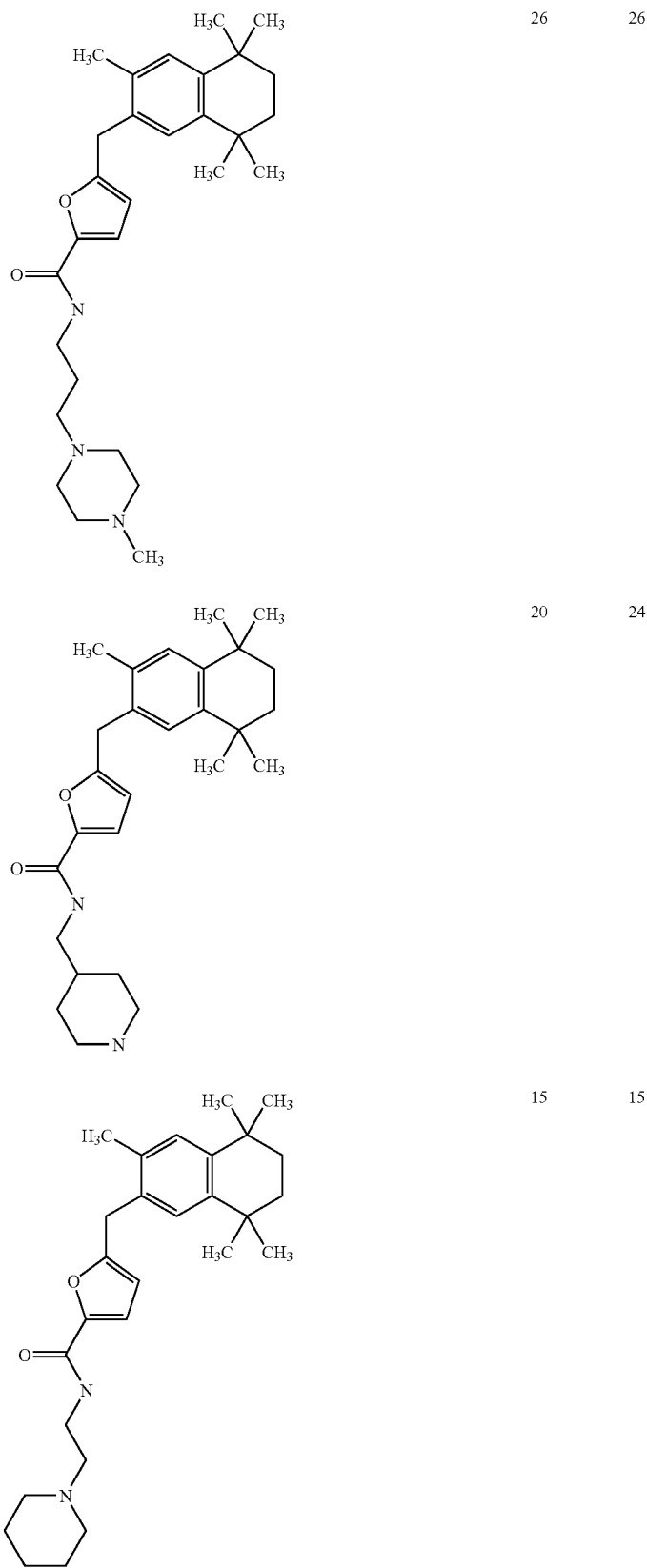

-continued
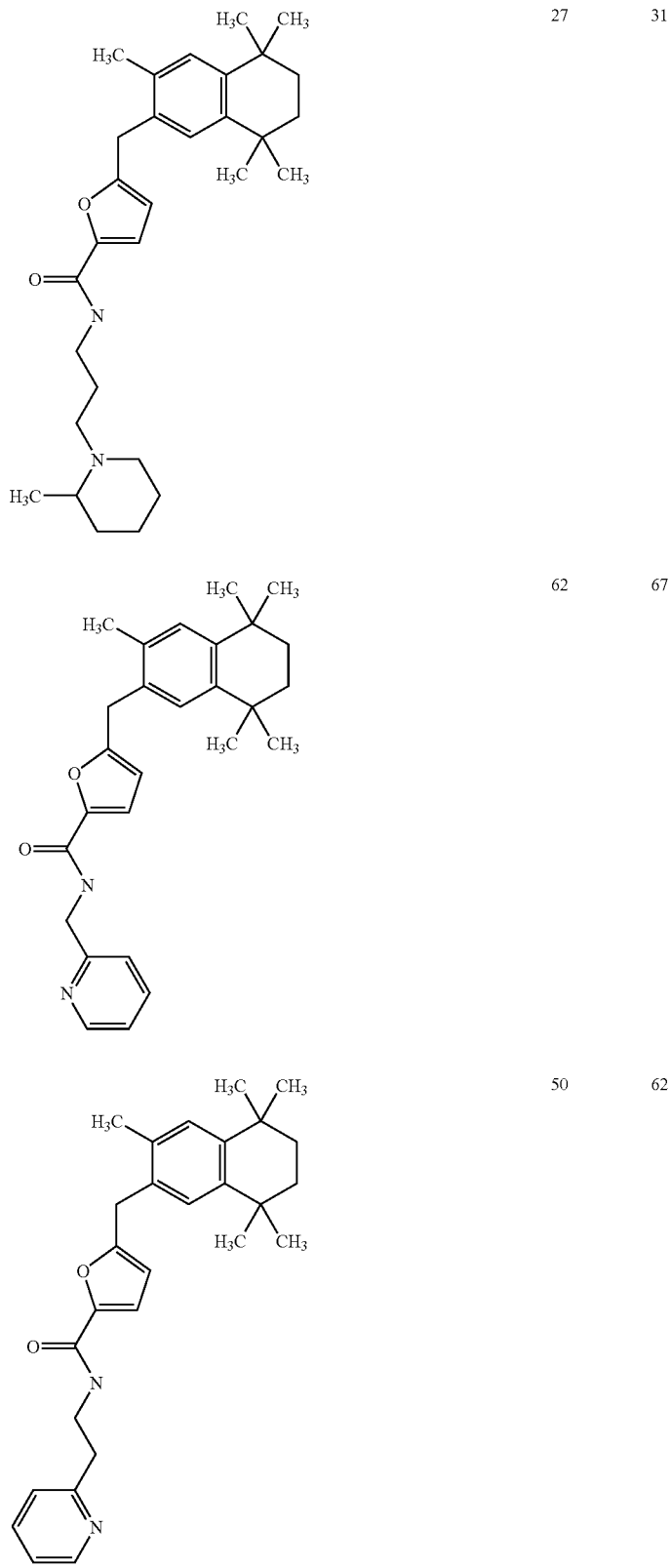
| | |
|---|---|
| 27 | 31 |
| 62 | 67 |
| 50 | 62 |

-continued
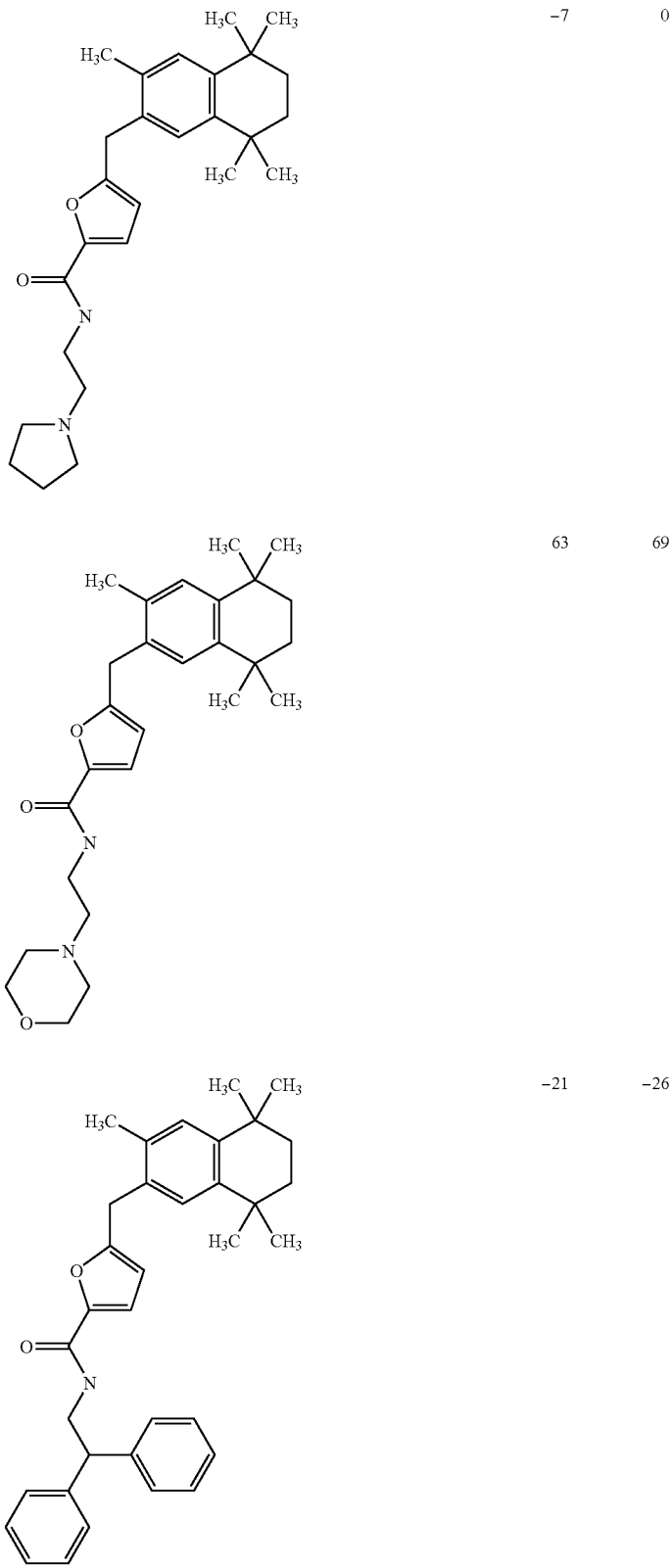

-continued
| | | |
|---|---|---|
| 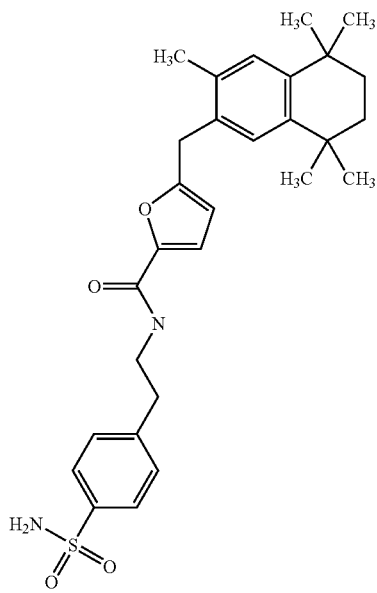 | 38 | 41 |
| 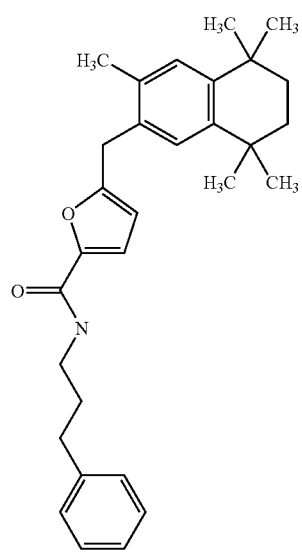 | 86 | 90 |
| 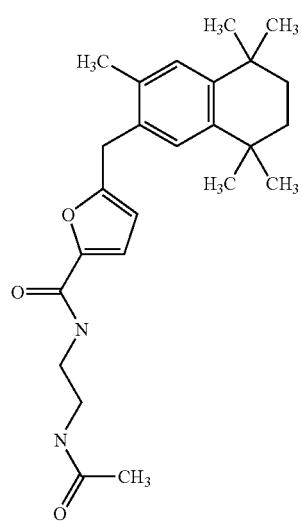 | 52 | 54 |

-continued
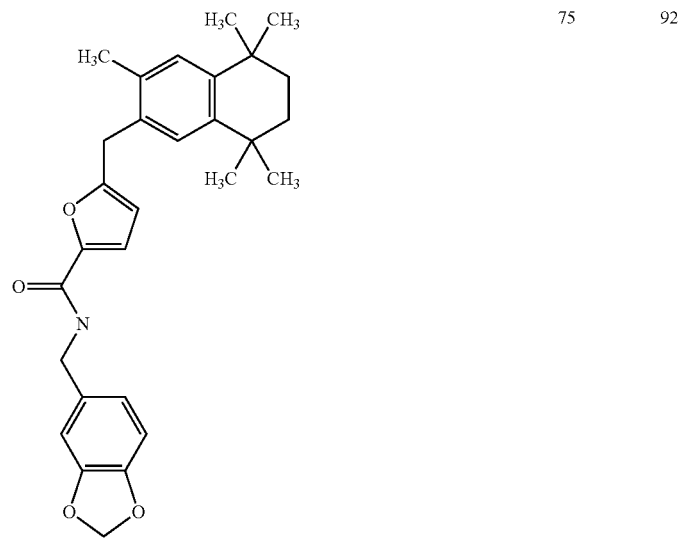
75  92
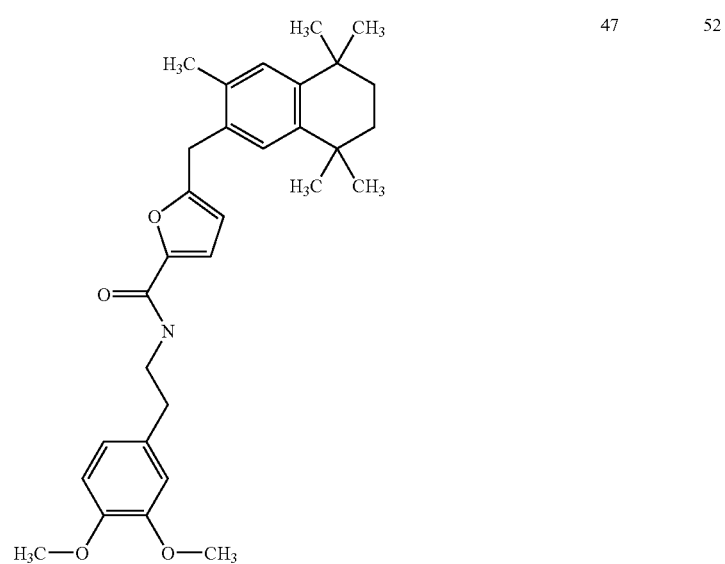
47  52

-continued
| | 49 | 50 |
|---|---|---|
| 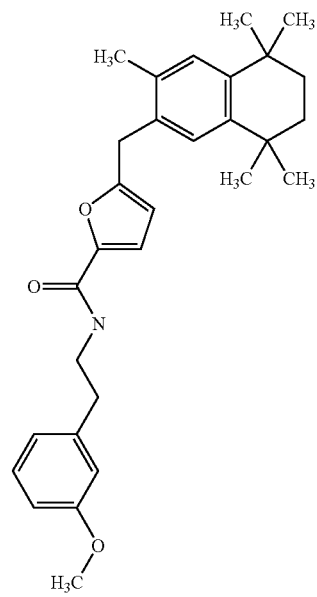 | | |
| | 60 | 62 |
|---|---|---|
| 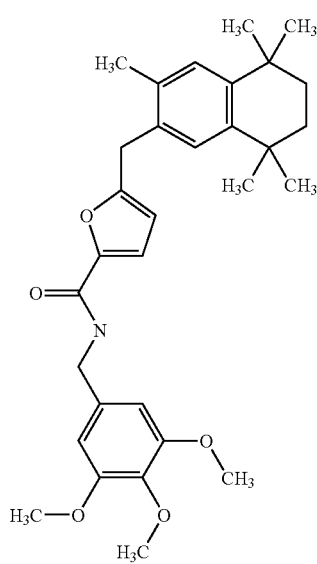 | | |

-continued
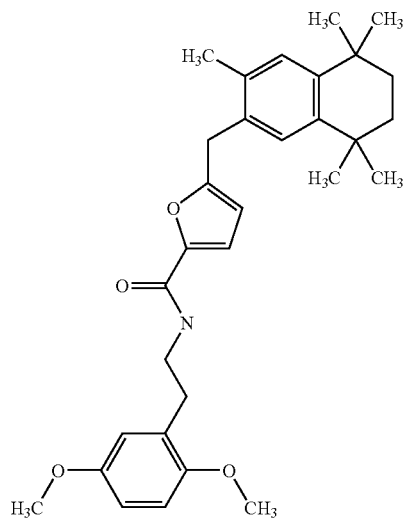
23 36
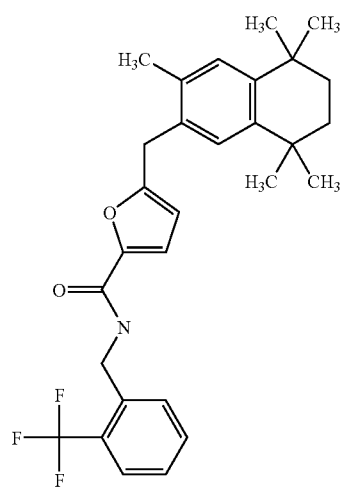
11 6
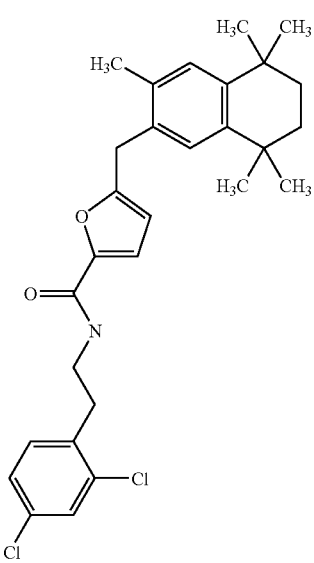
16 23

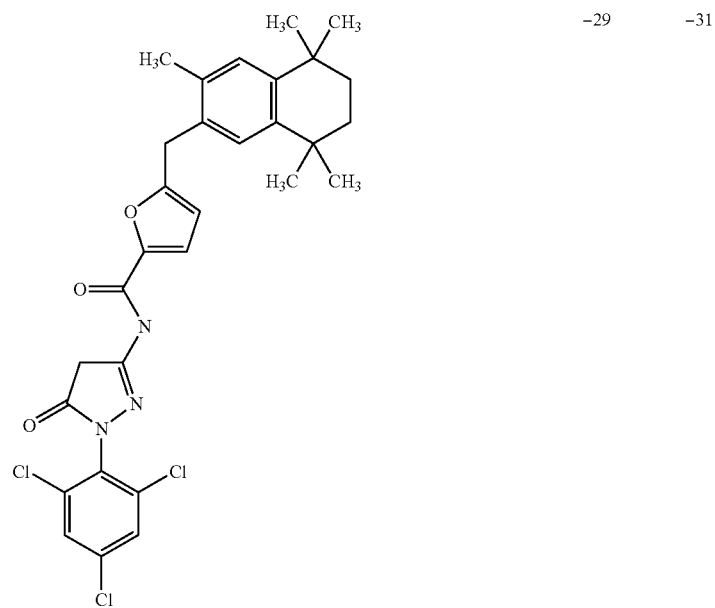
-29  -31
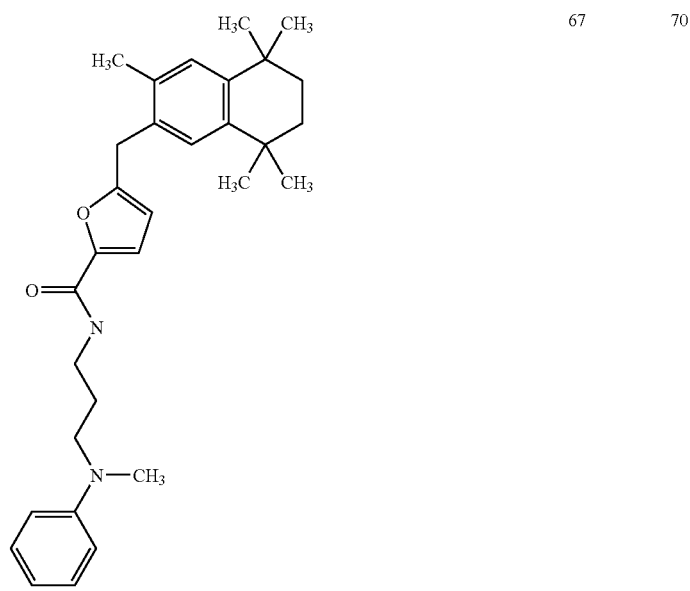
67  70

-continued
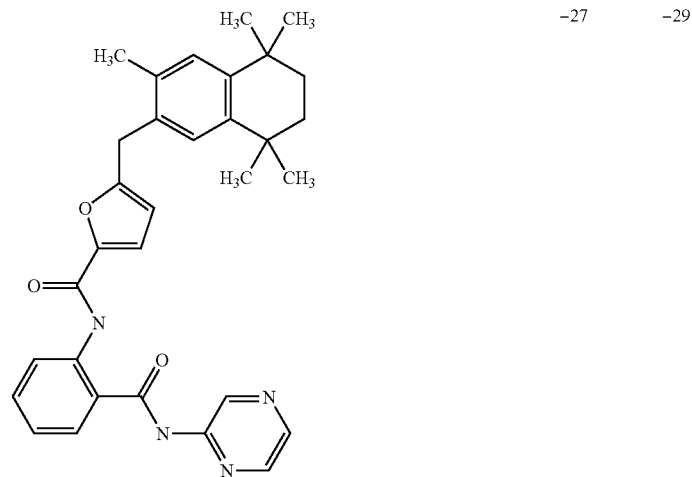
−27  −29
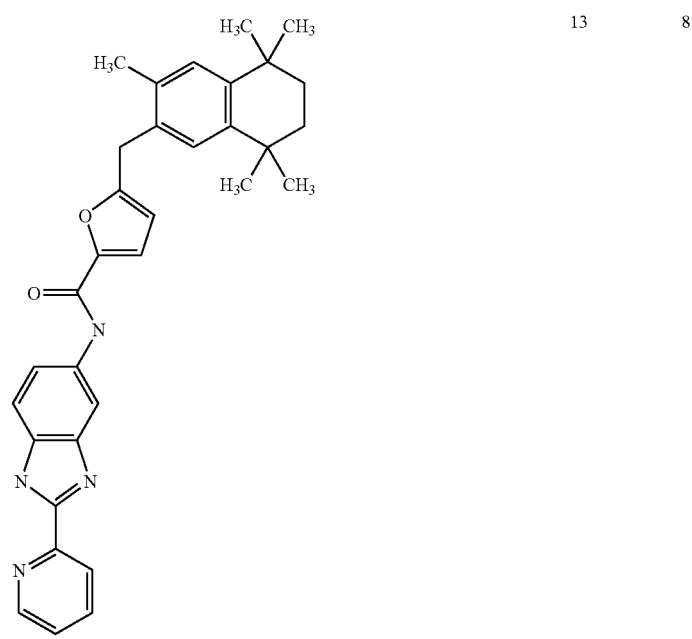
13  8

-continued
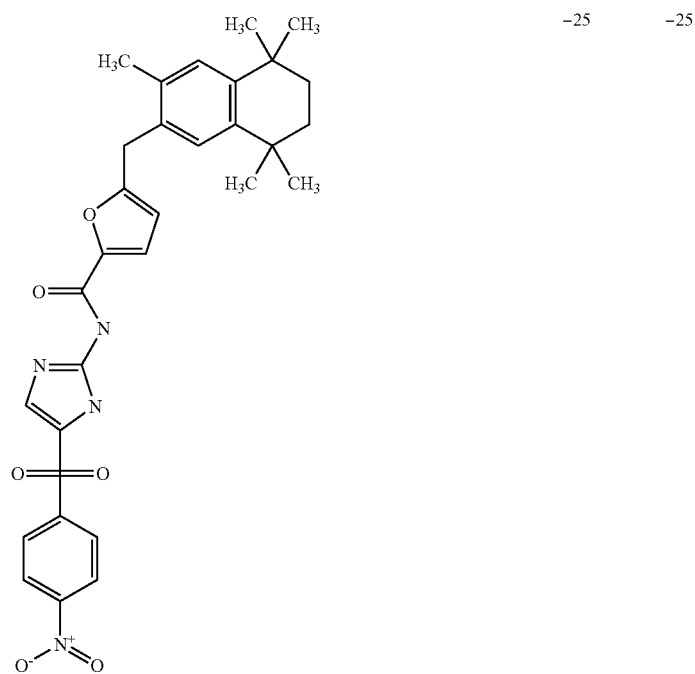
-25  -25

-36  -37

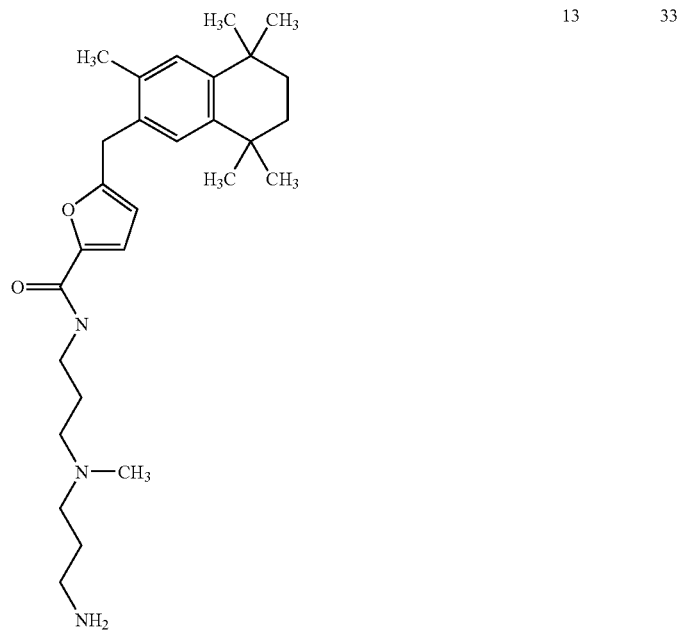
13 33
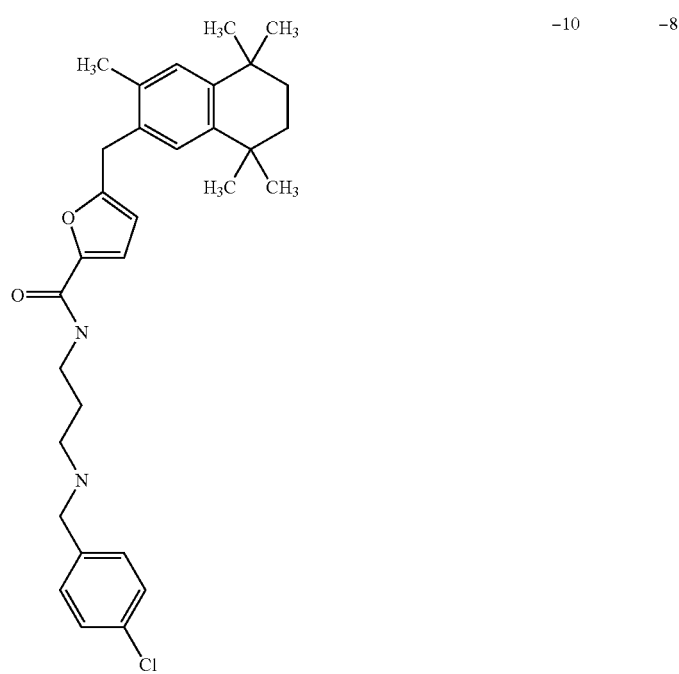
−10 −8

-continued
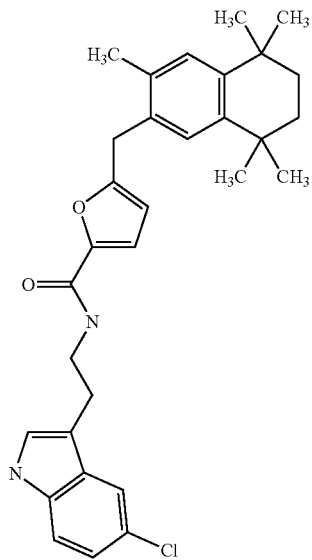
31 45
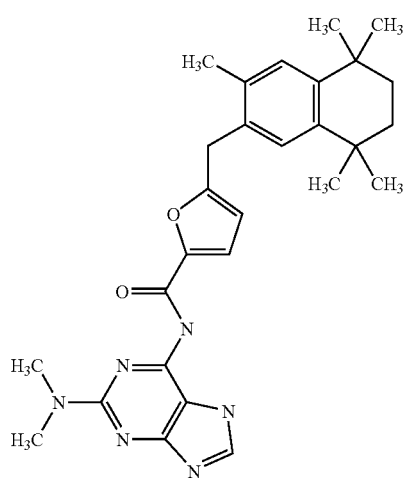
−13 −9
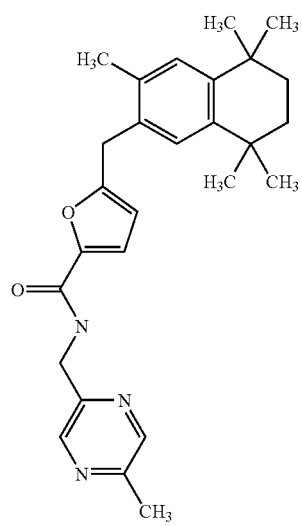
102 107

-continued
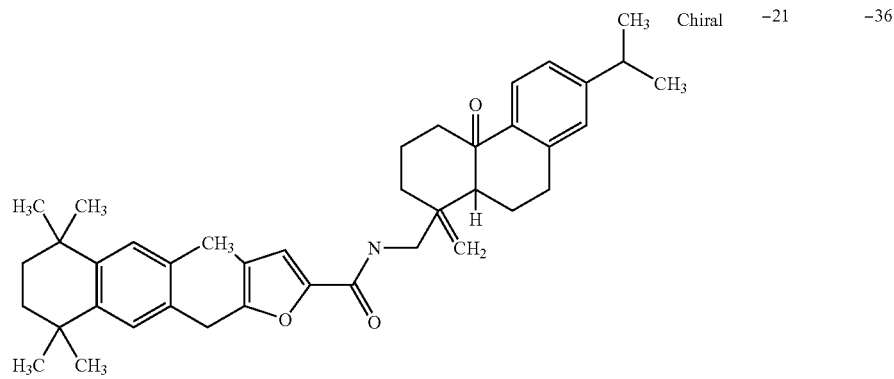
Chiral   −21   −36
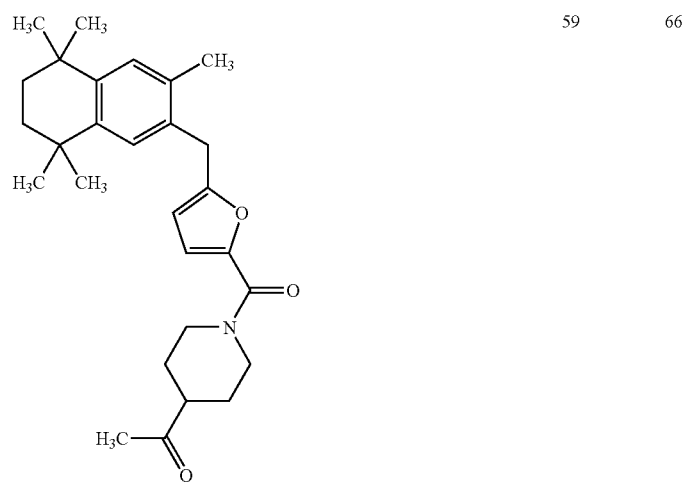
59   66
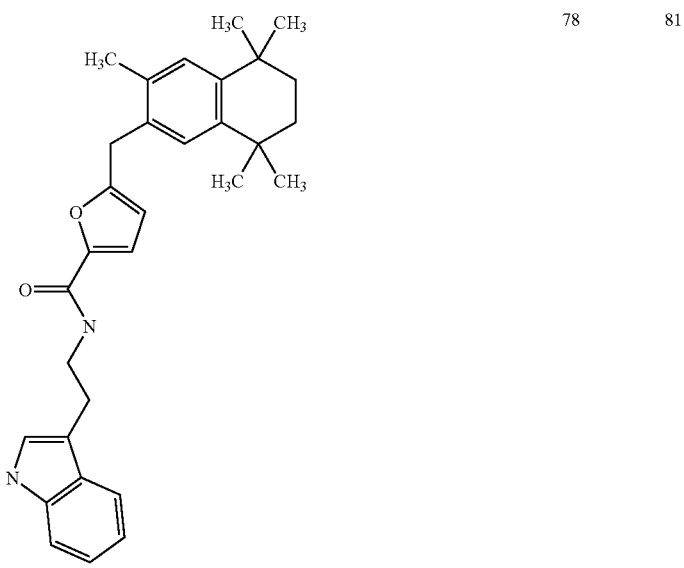
78   81

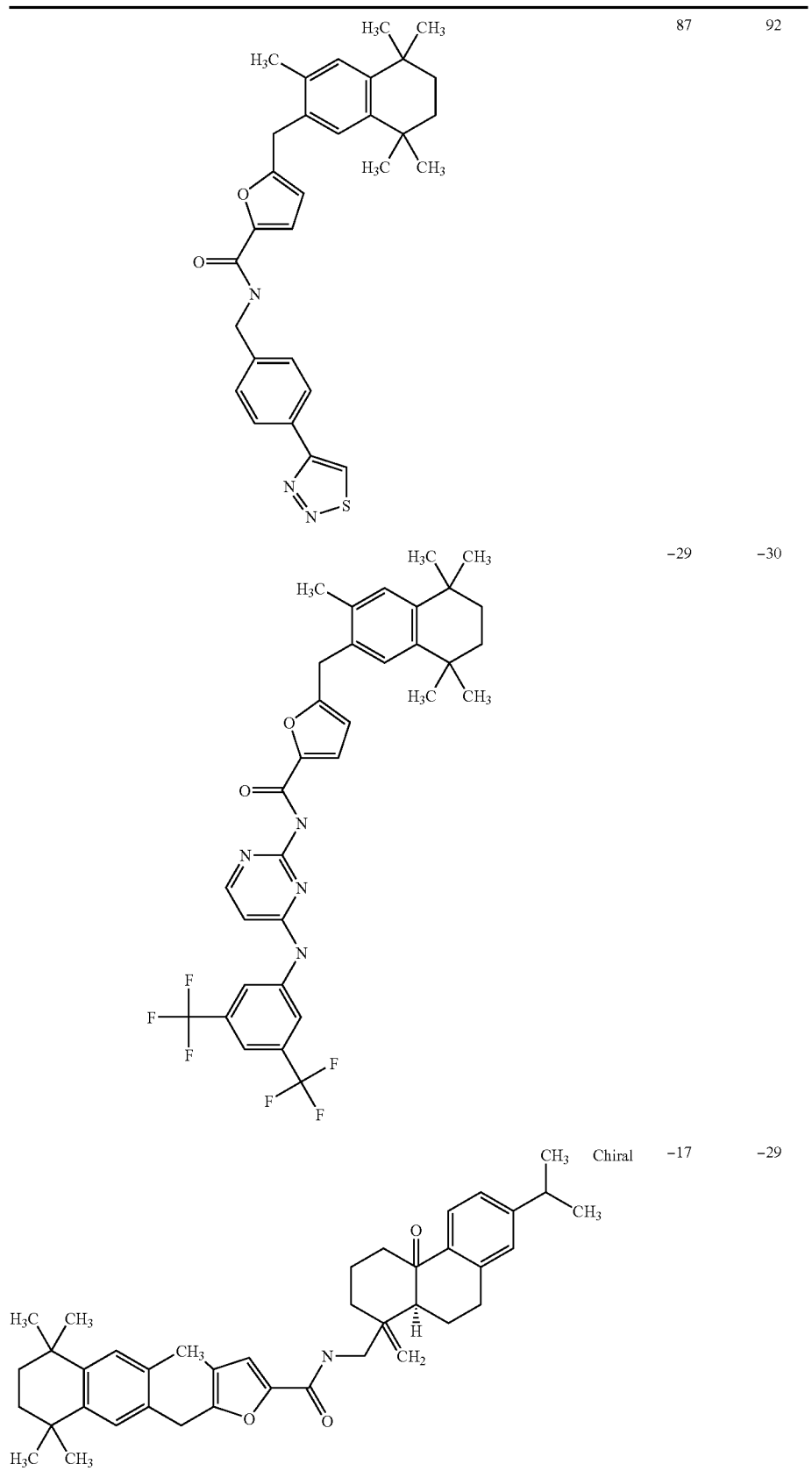

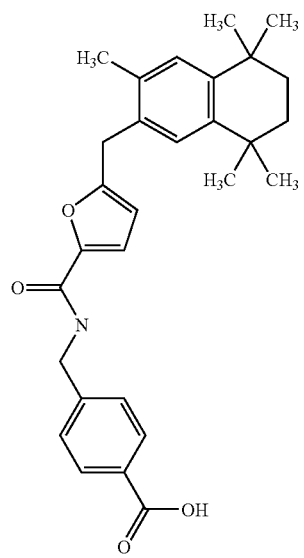 44 45
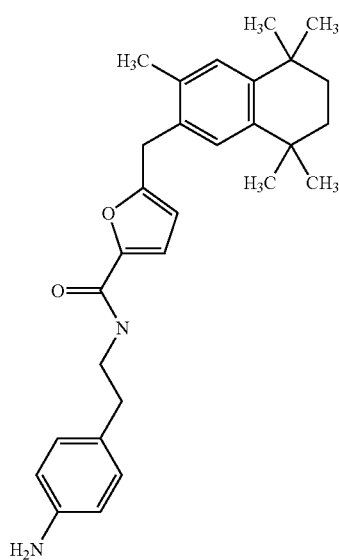 57 64
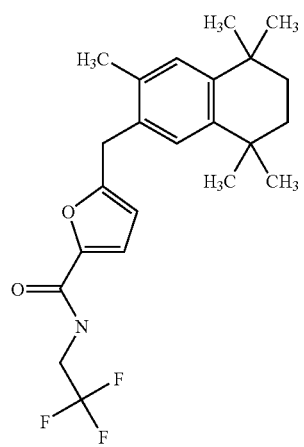 18 9

-continued
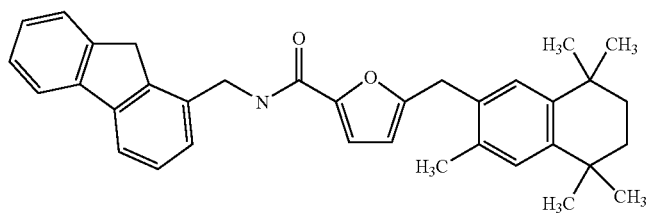 −21 −23
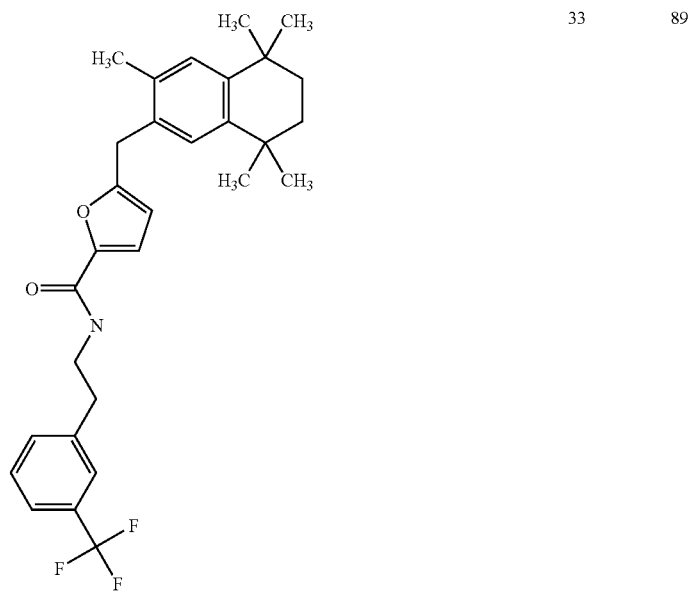 33 89
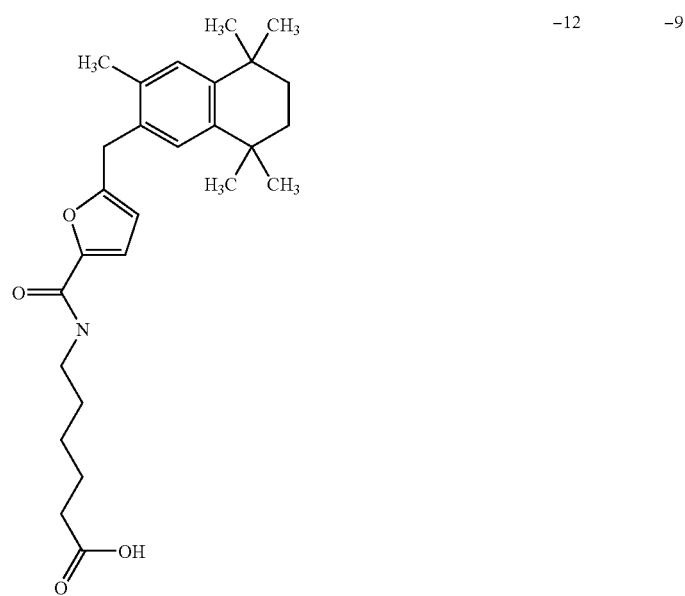 −12 −9

| | 83 | 86 |
|---|---|---|
| 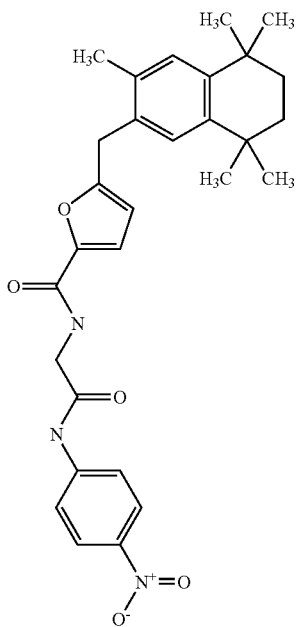 | | |
| | 63 | 64 |
|---|---|---|
| 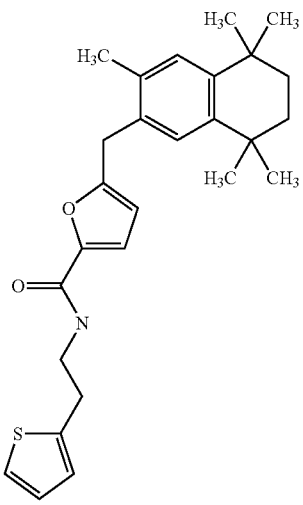 | | |

-continued
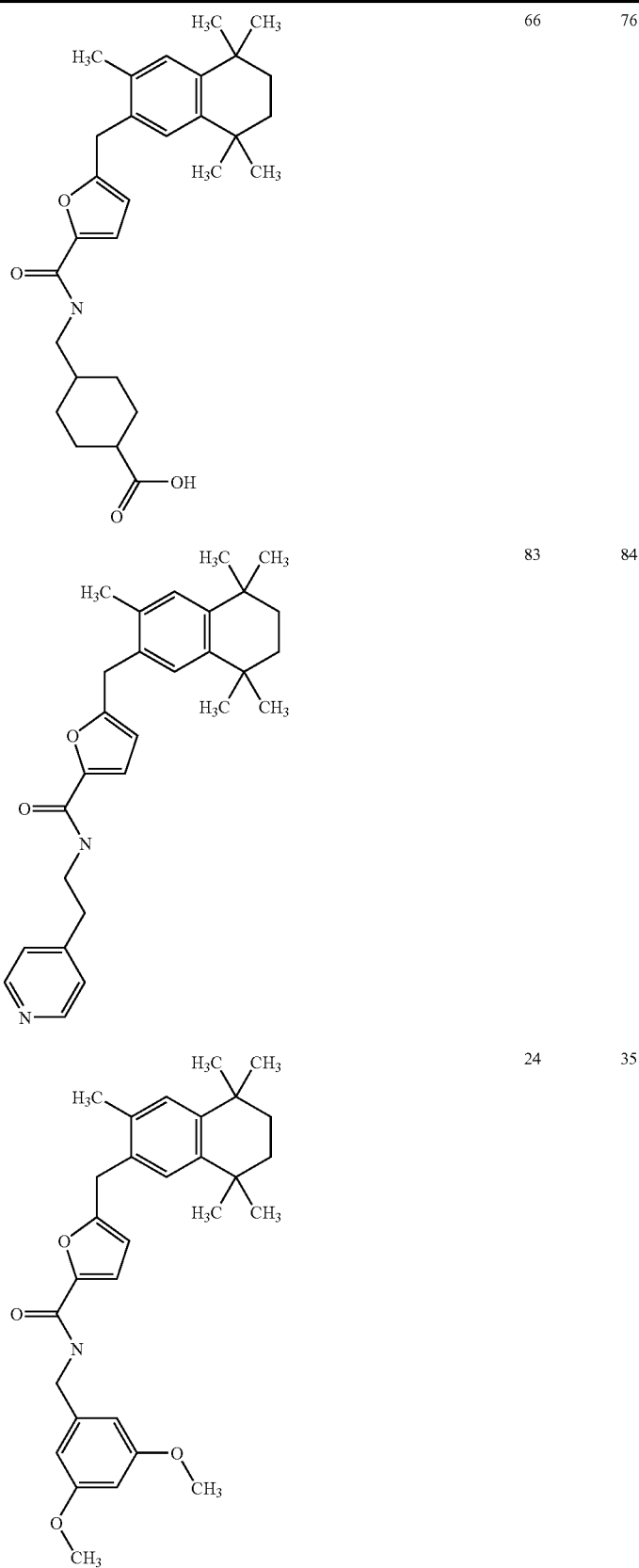
| | 66 | 76 |
| | 83 | 84 |
| | 24 | 35 |

-continued
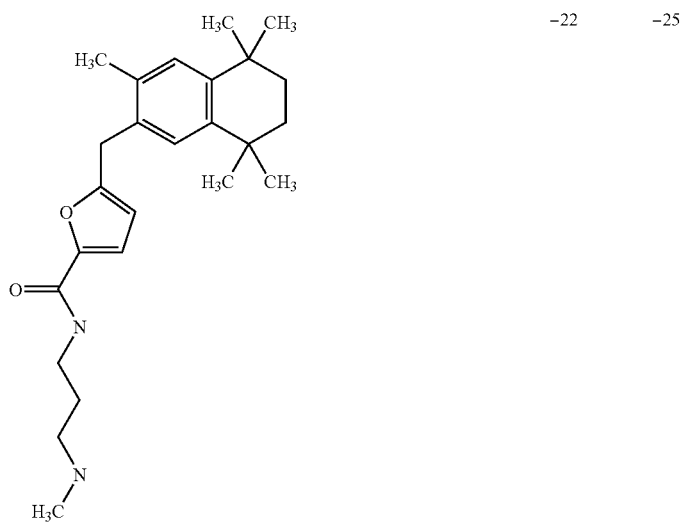
−22 −25
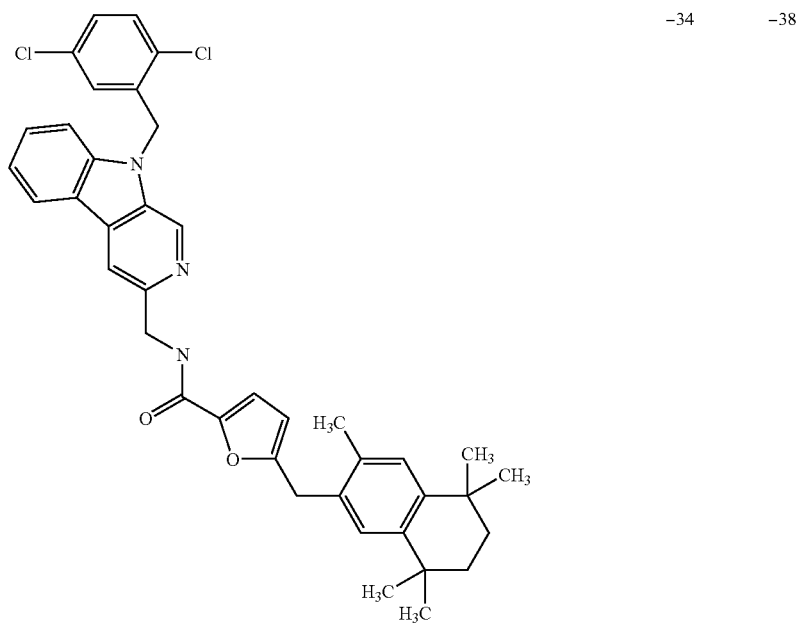
−34 −38

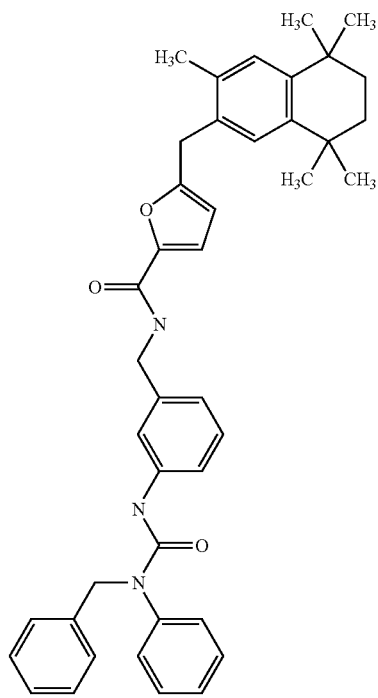
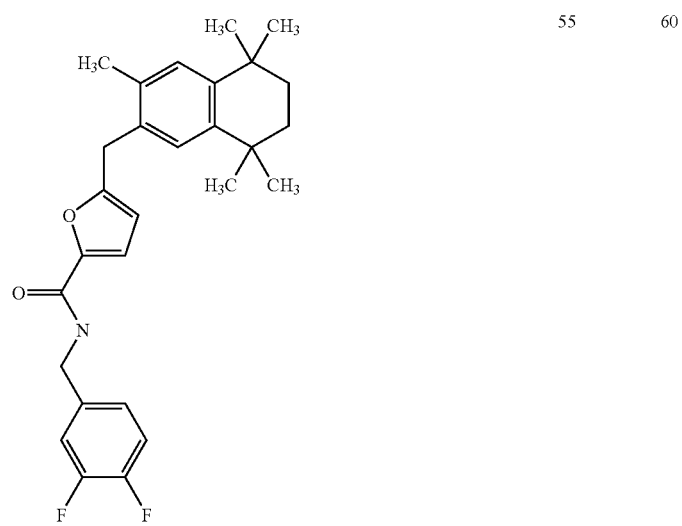

-continued
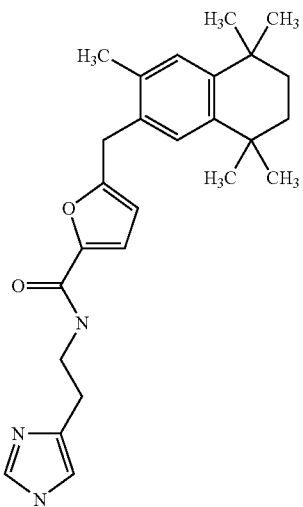
22  28
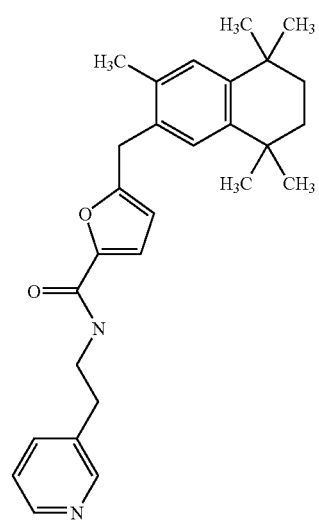
80  90

-continued
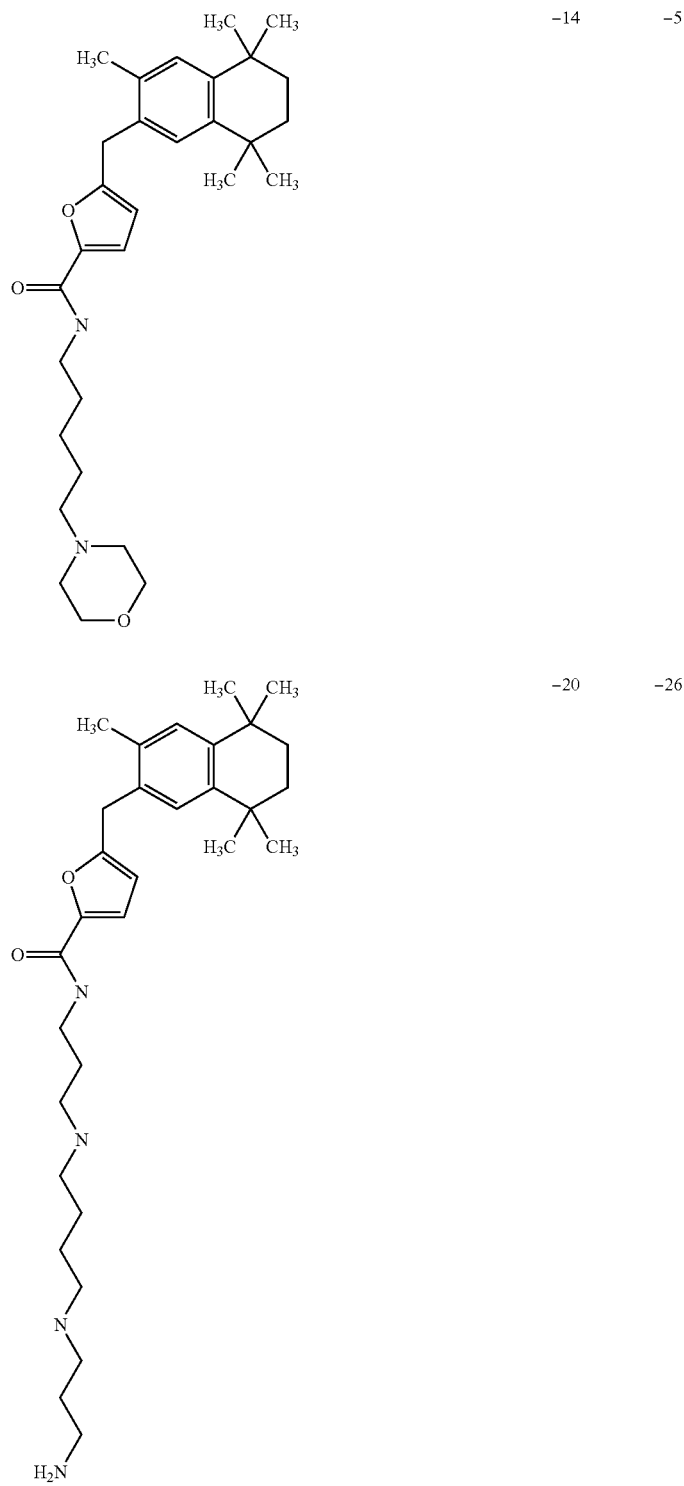
| | |
|---|---|
| −14 | −5 |
| −20 | −26 |

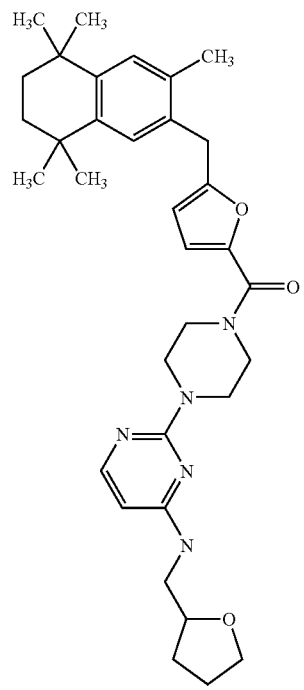
22 25
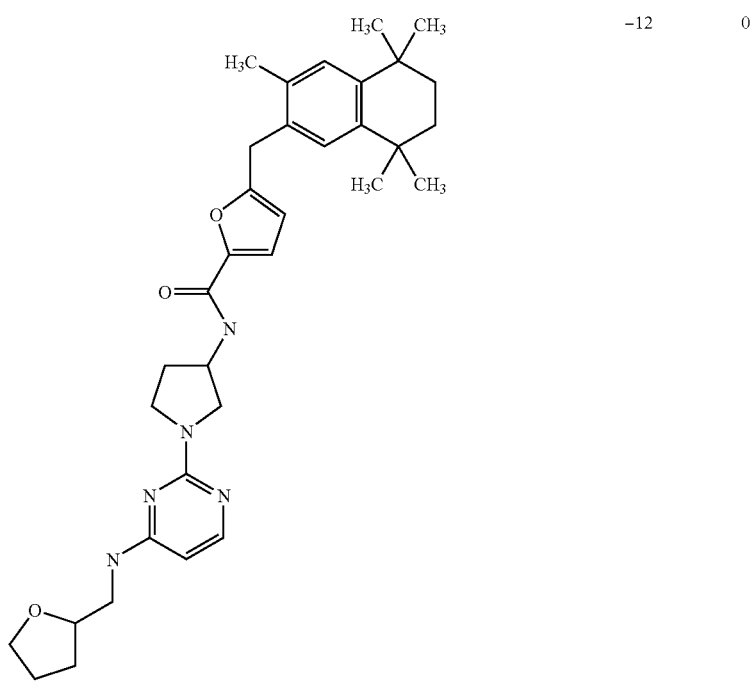
−12 0

-continued
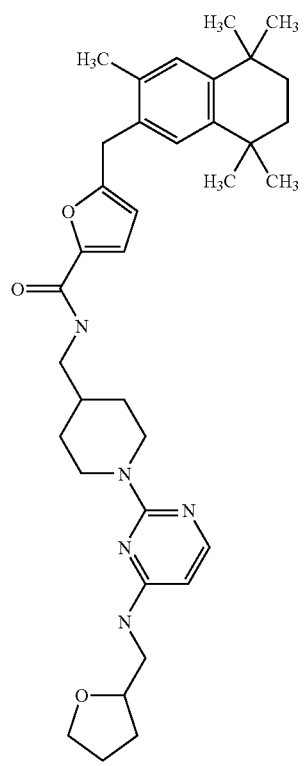
35　35
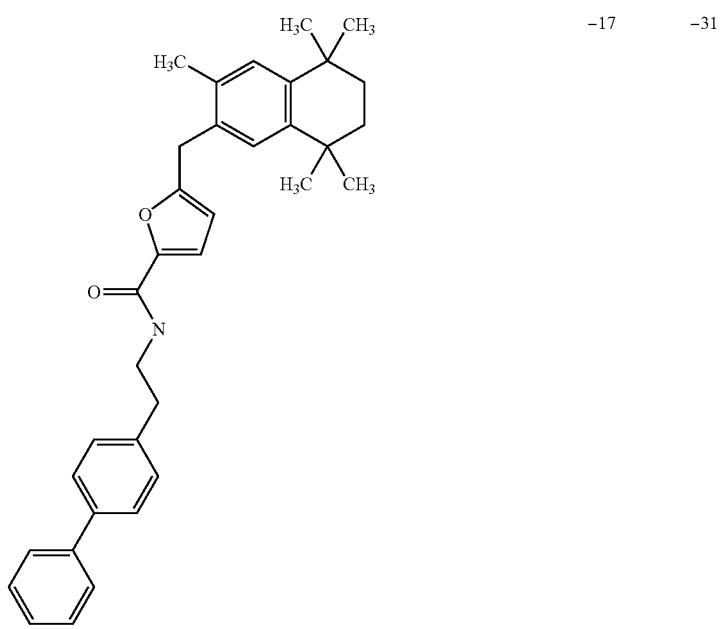
−17　−31

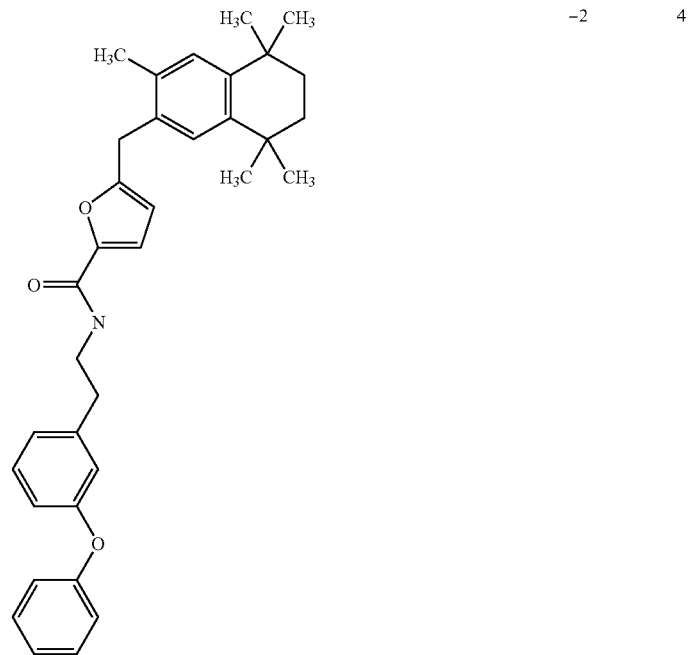
−2    4
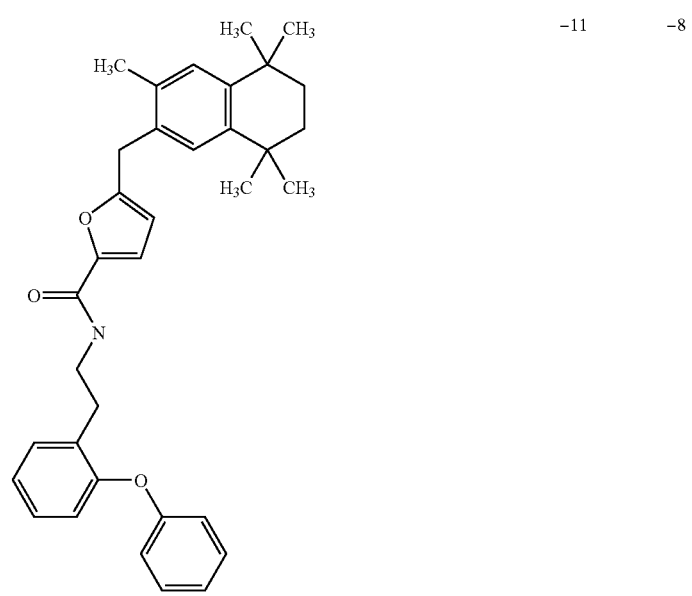
−11   −8

-continued
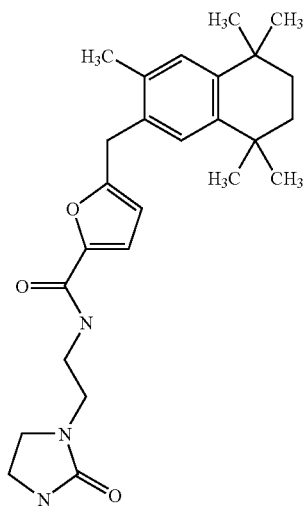
32 44
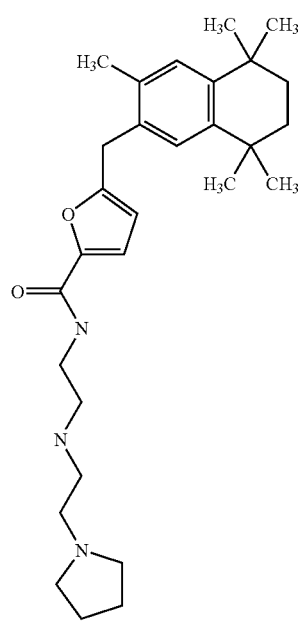
−5 0

-continued
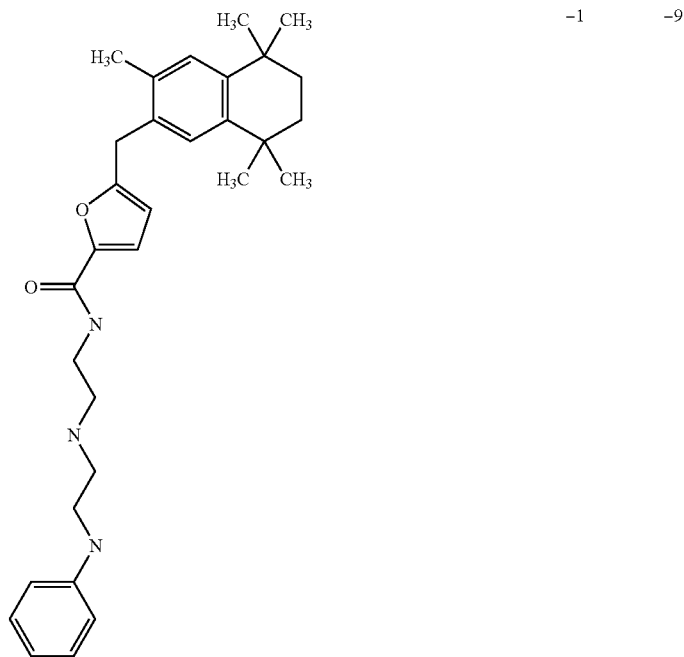
-1  -9
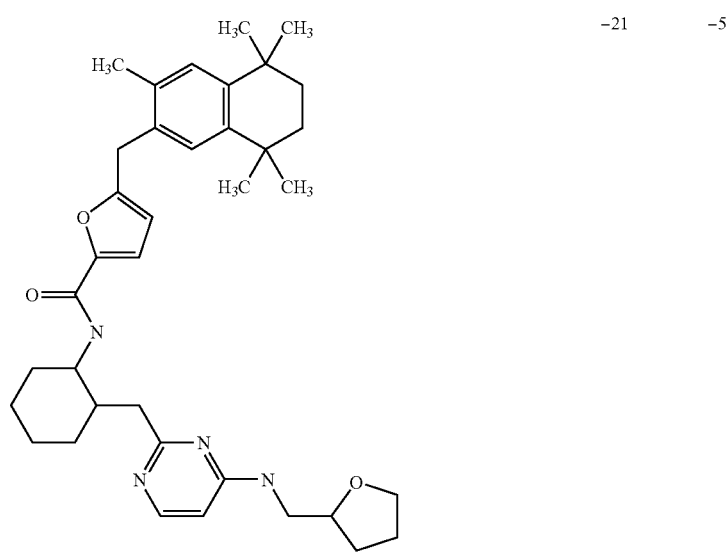
-21  -5

| | 17 | 25 |
|---|---|---|
| 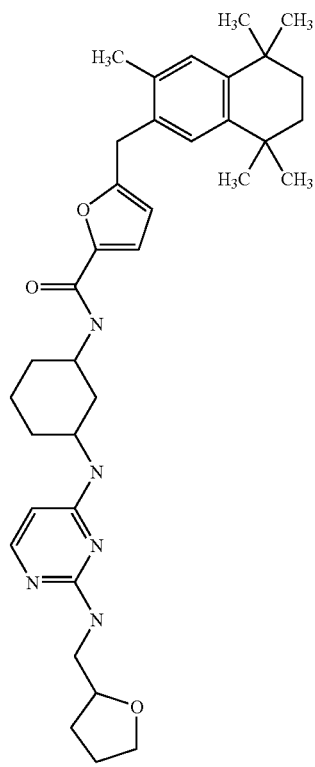 | | |
| | 11 | 13 |
|---|---|---|
| 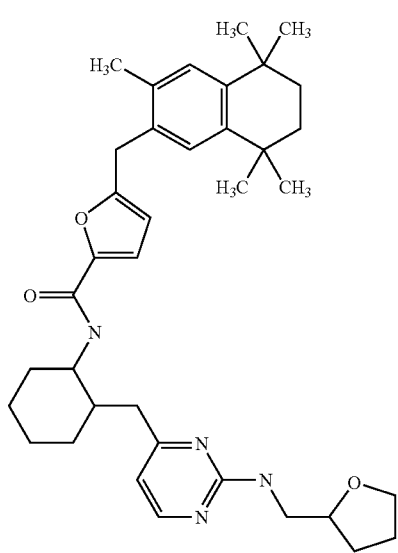 | | |

-continued
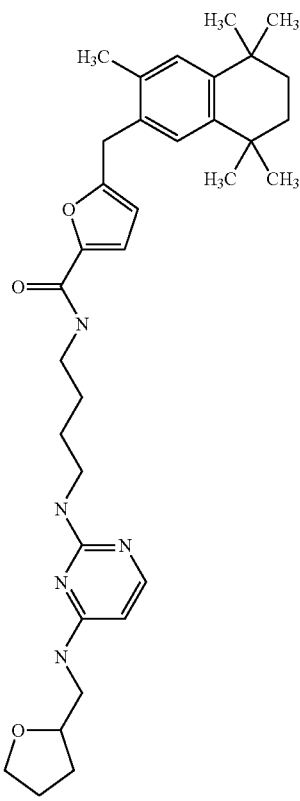
27 38
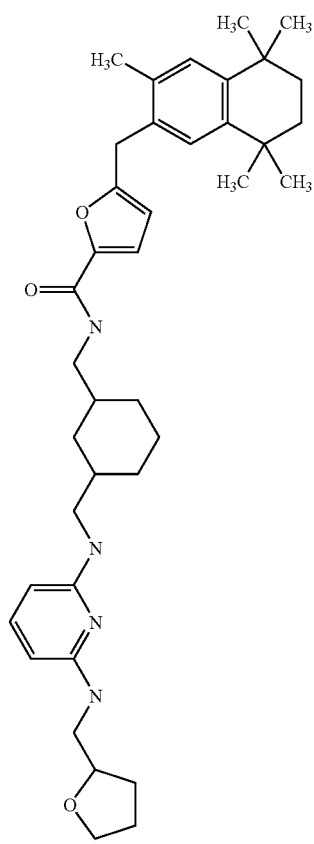
84 89

-continued
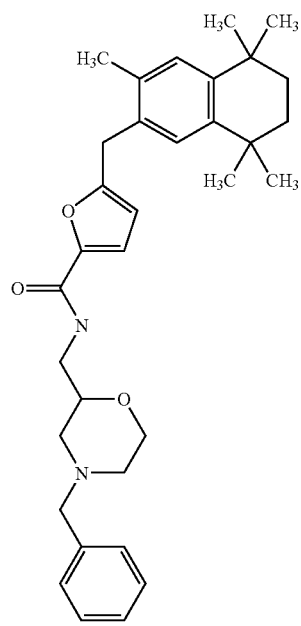
35 42
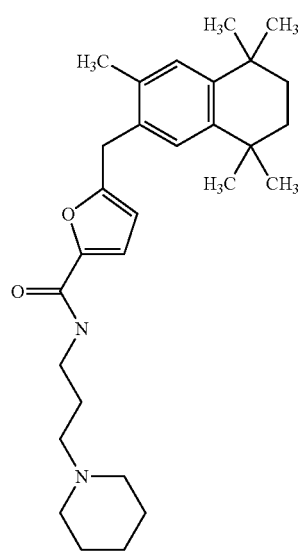
−3 8

-continued
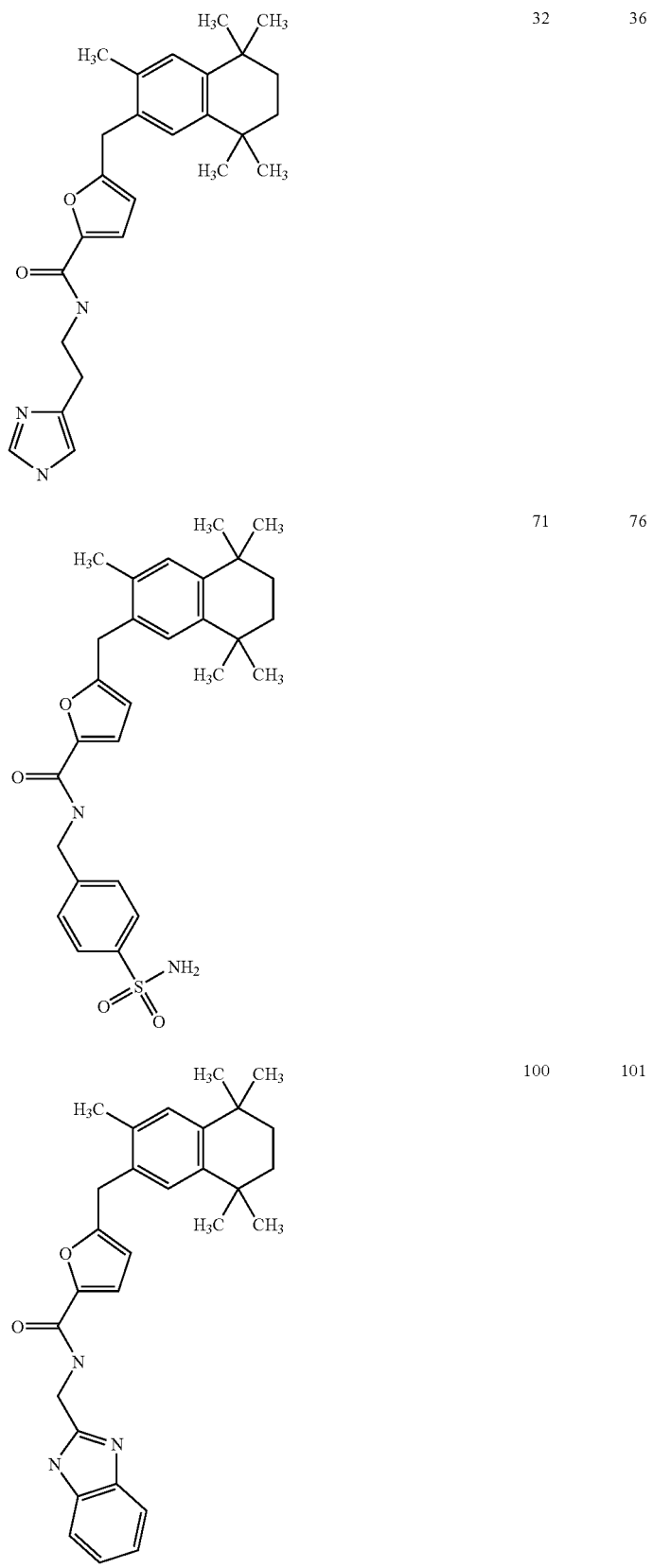
| | 32 | 36 |
| | 71 | 76 |
| | 100 | 101 |

-continued
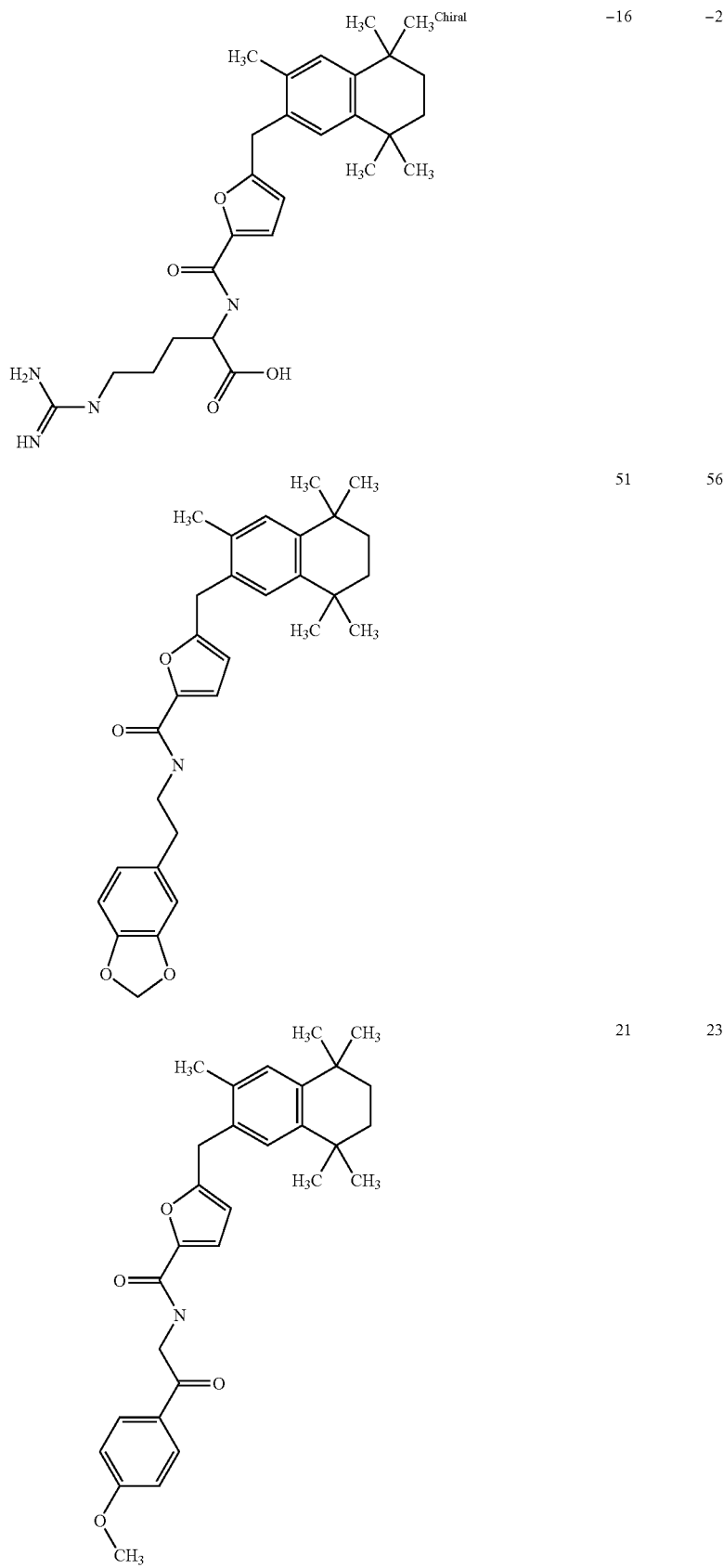

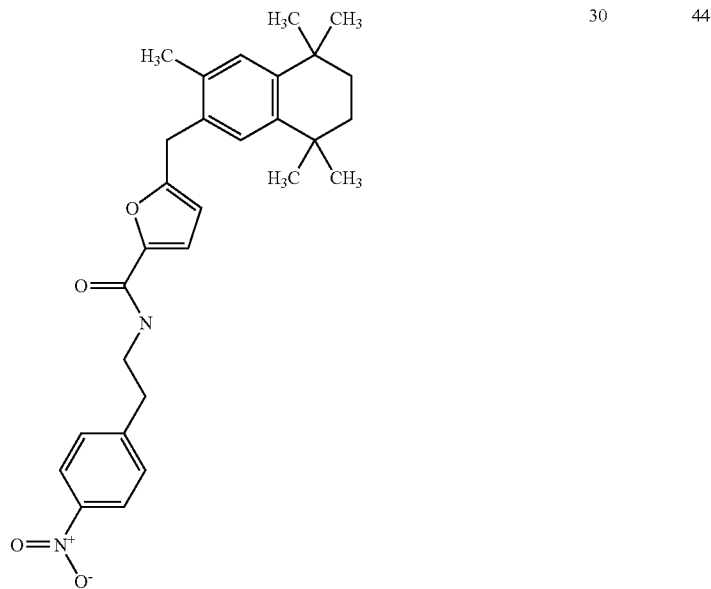
30    44
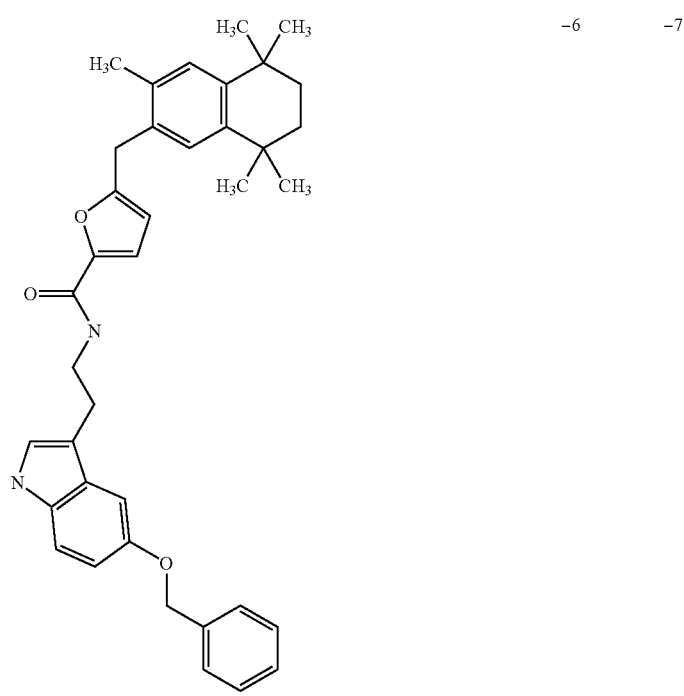
−6    −7

-continued
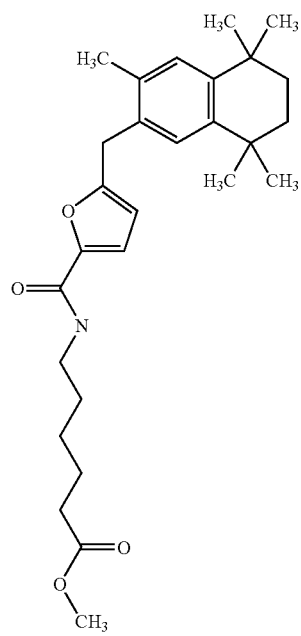
85 85
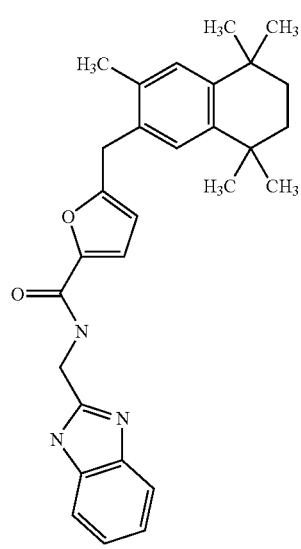
101 99

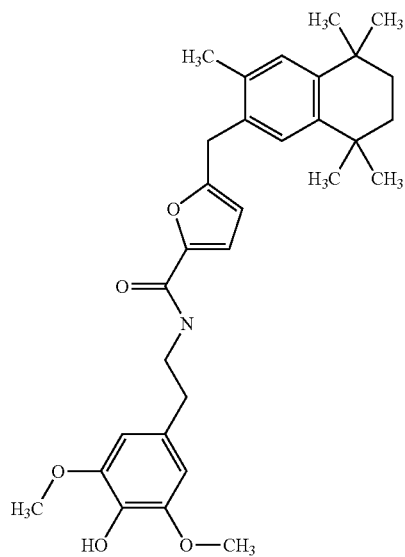
44 49
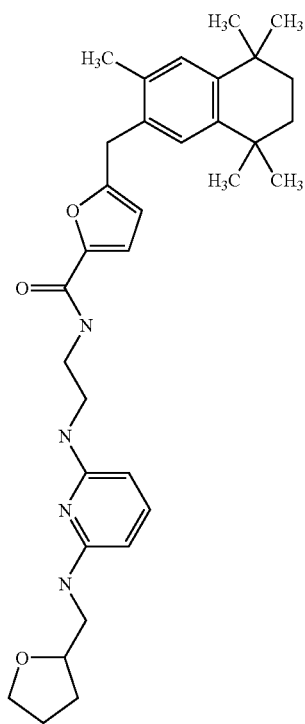
18 22

-continued
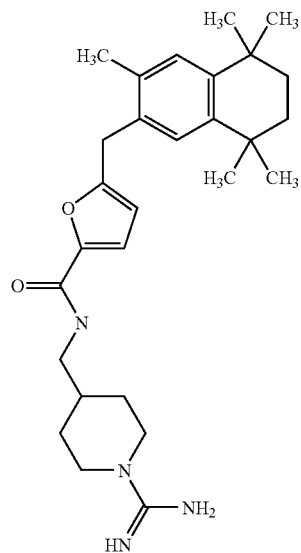 26 87
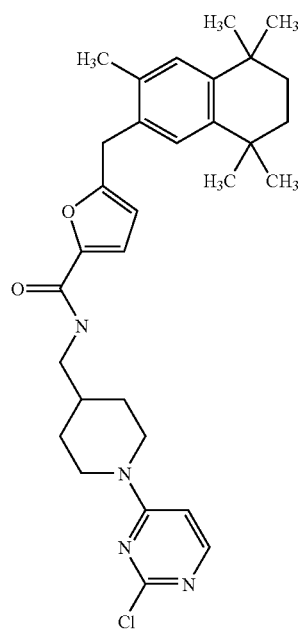 79 91

-continued
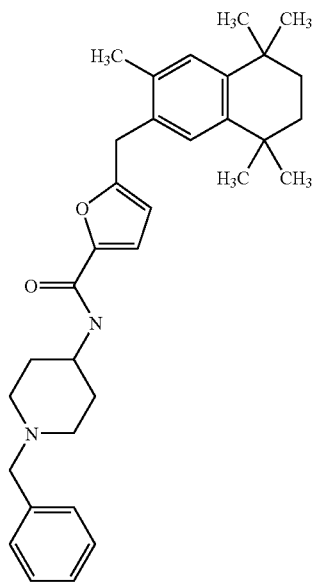 −12 14
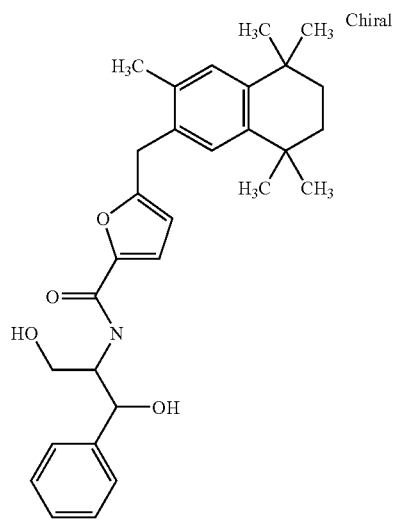 −1 12
Chiral
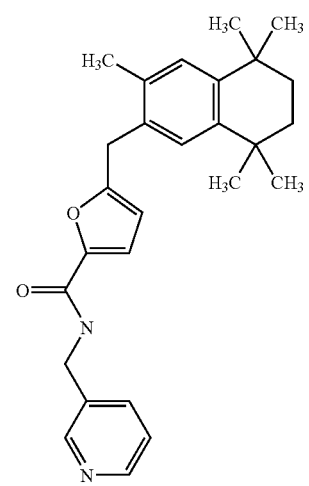 69 74

-continued
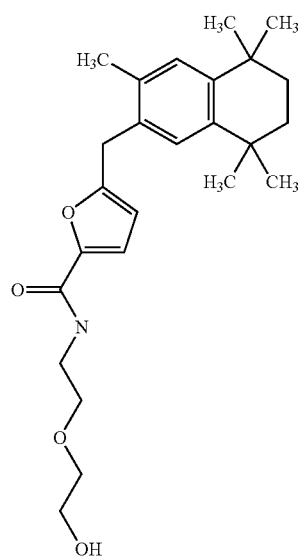
67    69
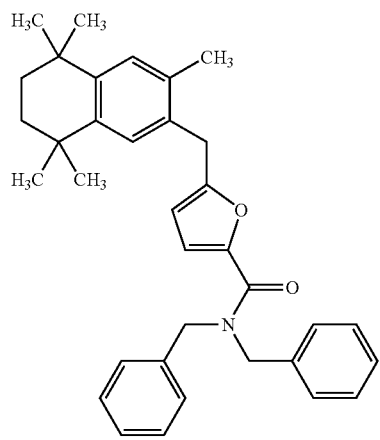
−2    3
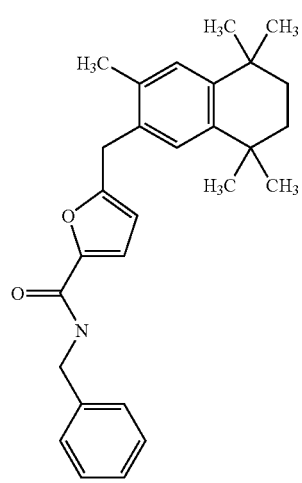
82    85

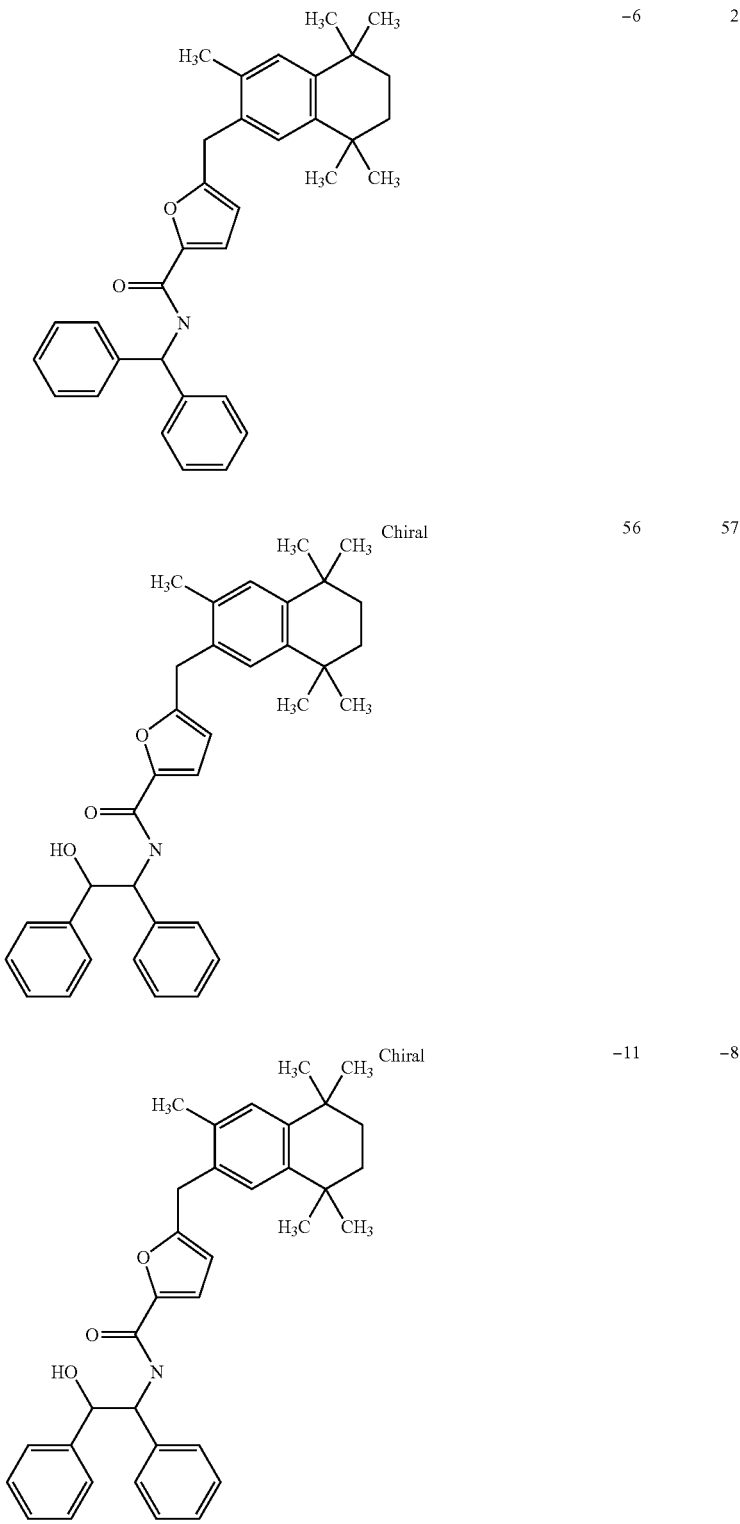

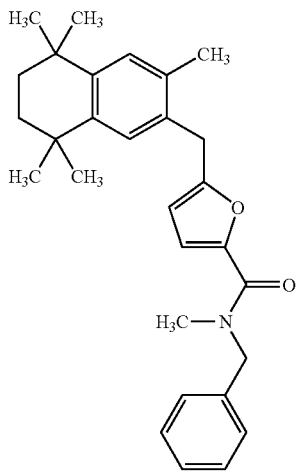 −7 4
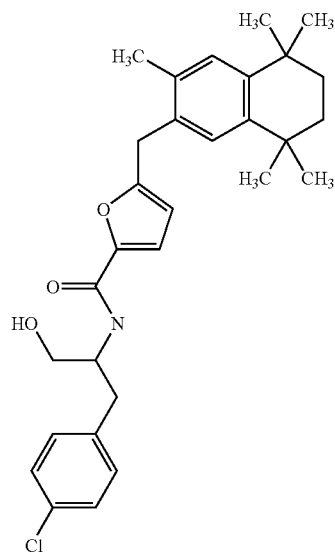 16 3
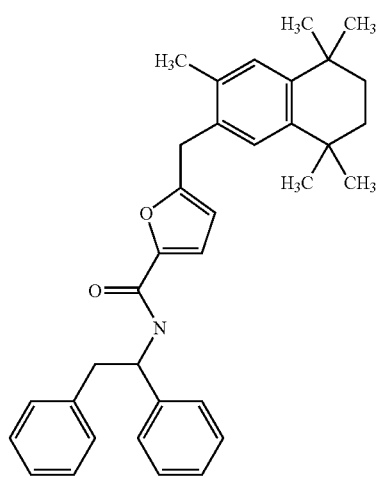 13 19

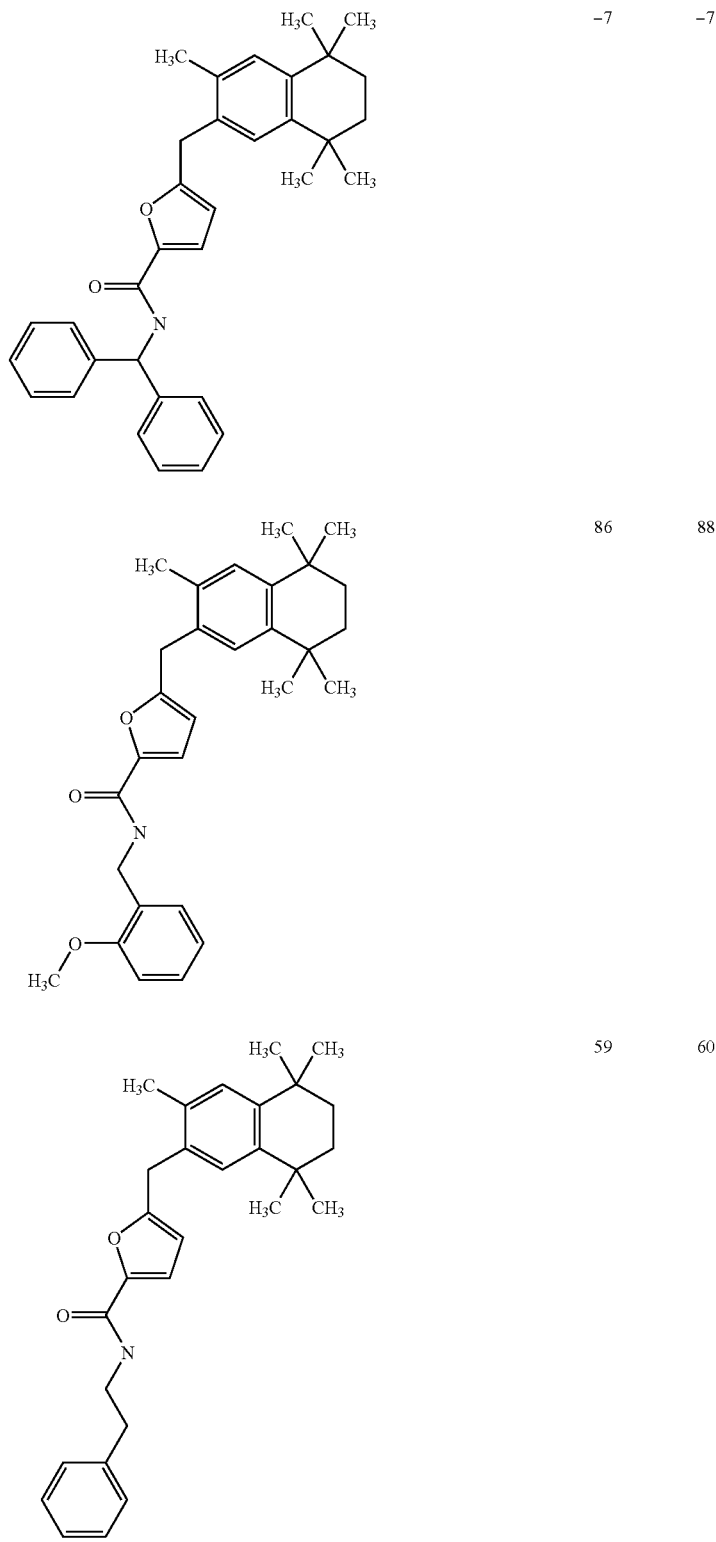

-continued
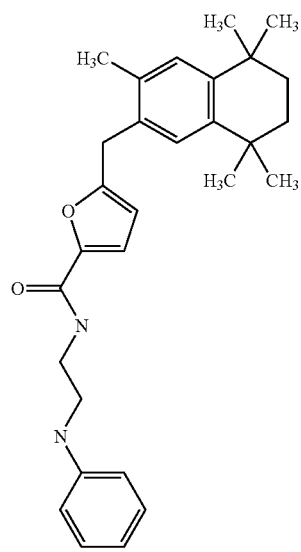 70 72
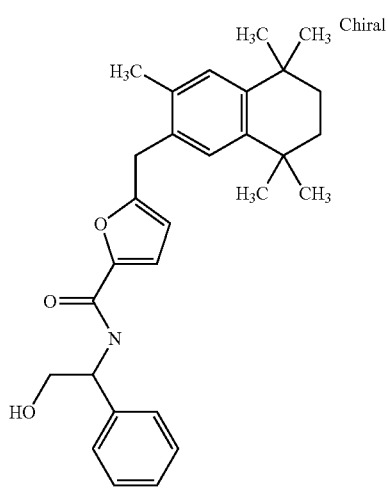 17 26 Chiral
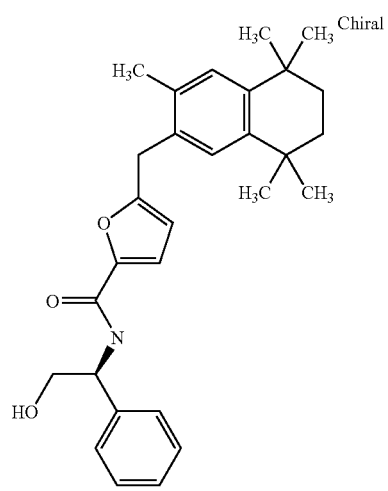 15 26 Chiral

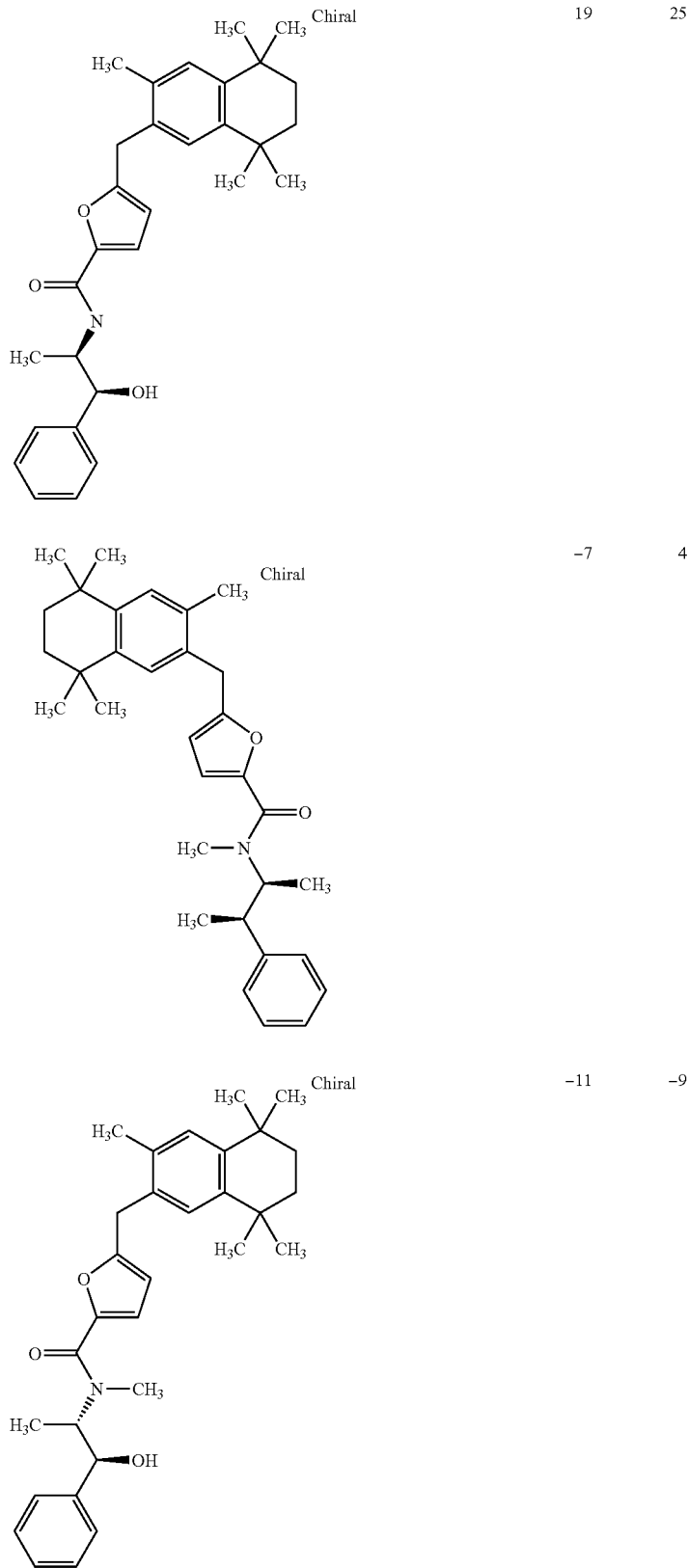

-continued
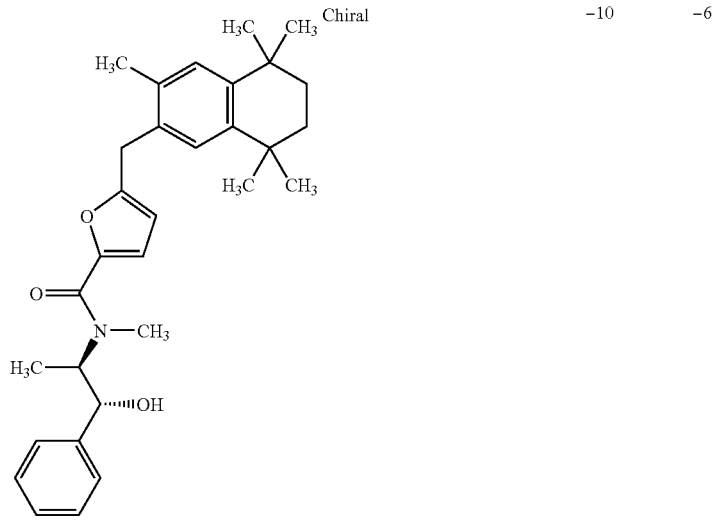
−10   −6
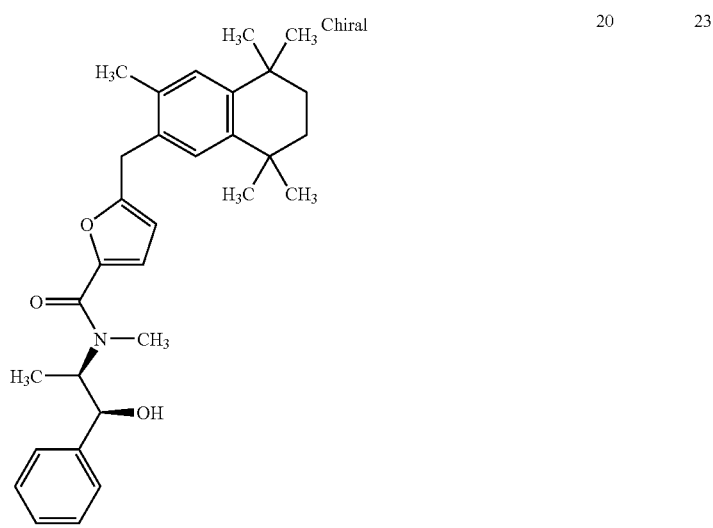
20   23
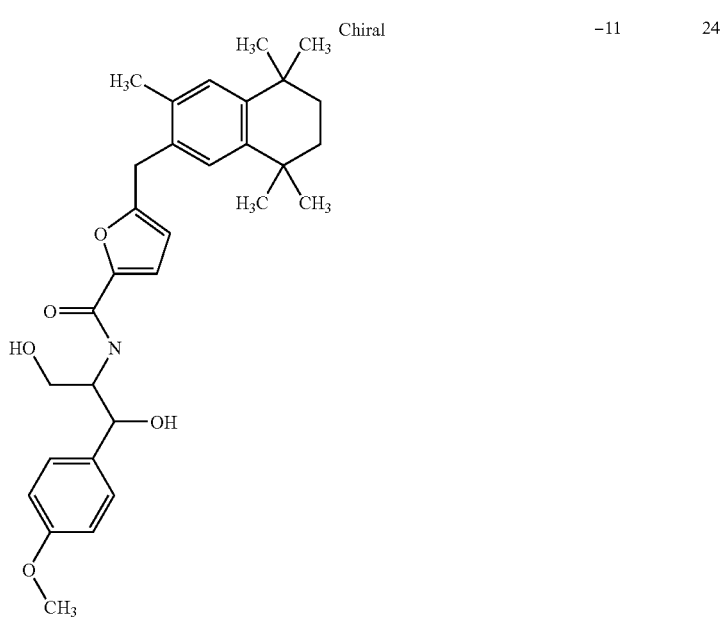
−11   24

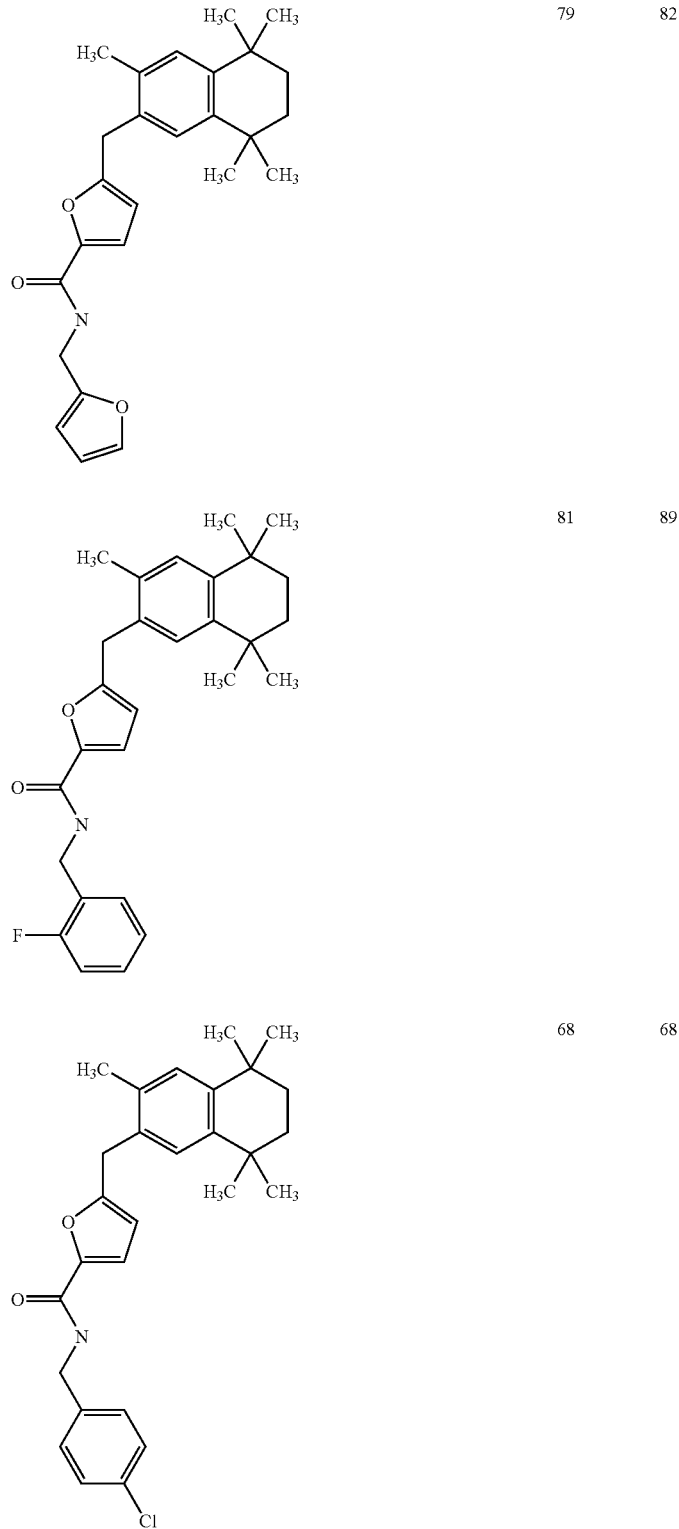

-continued
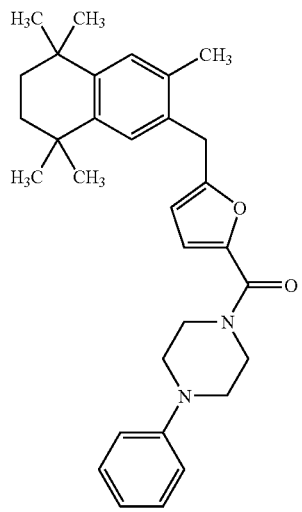  −1  6
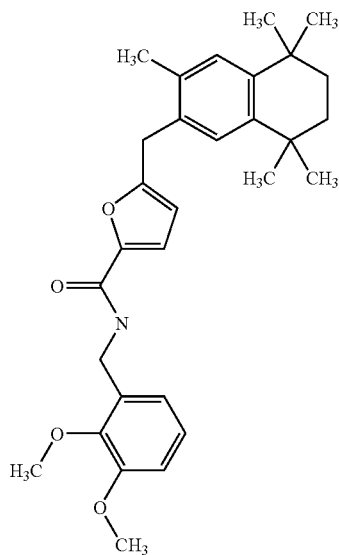  76  83
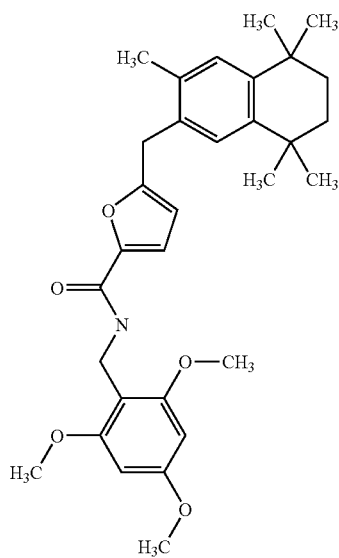  −10  13

-continued
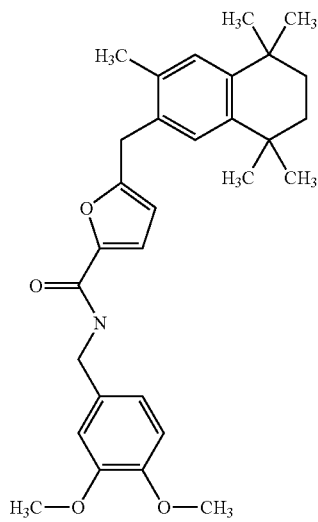 69 75
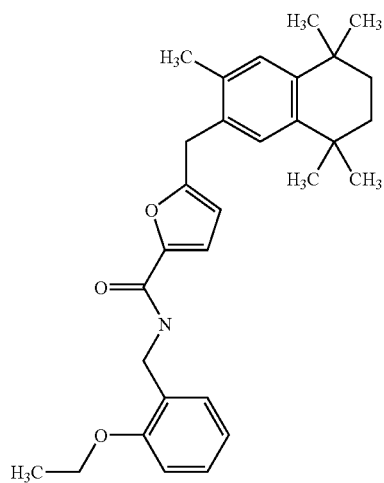 48 55
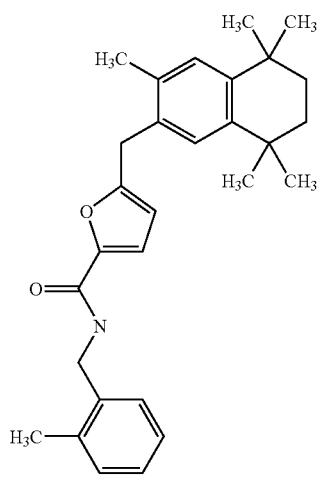 84 86

-continued
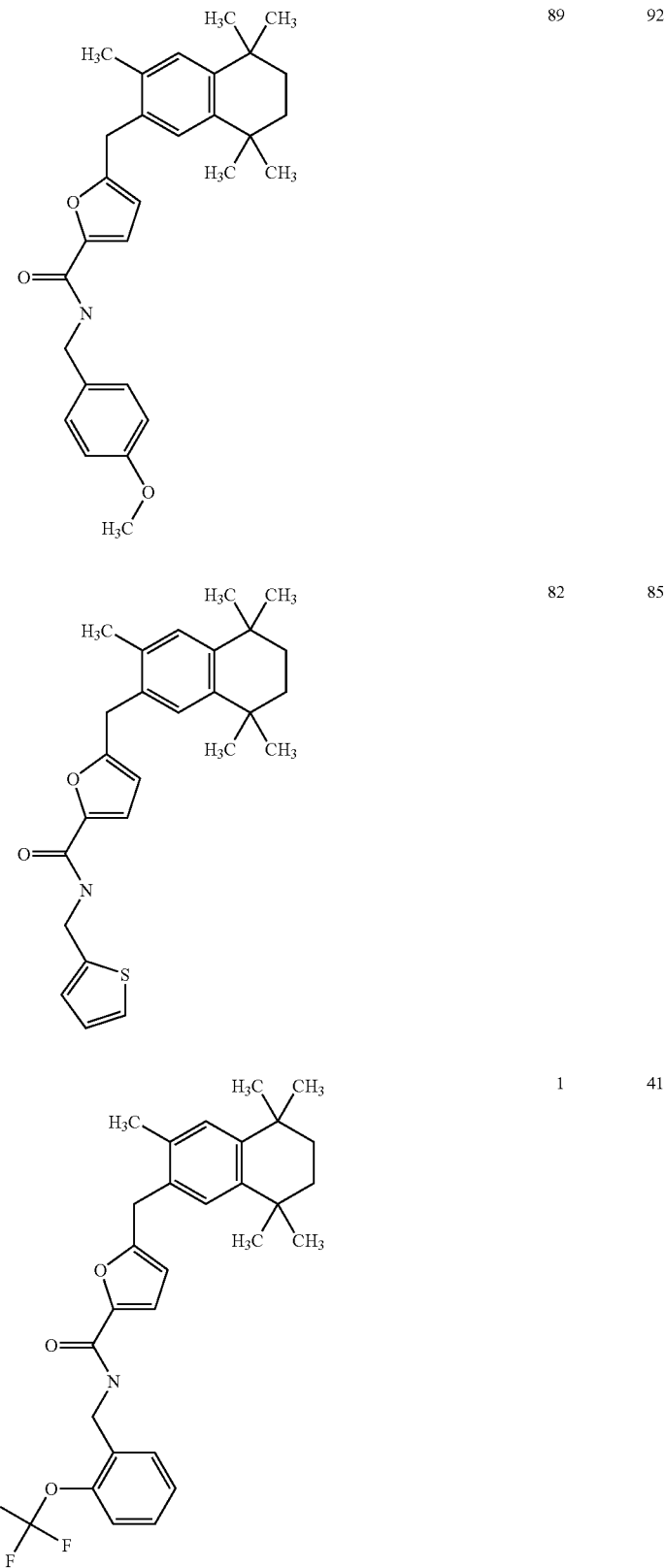
| | |
|---|---|
| 89 | 92 |
| 82 | 85 |
| 1 | 41 |

-continued
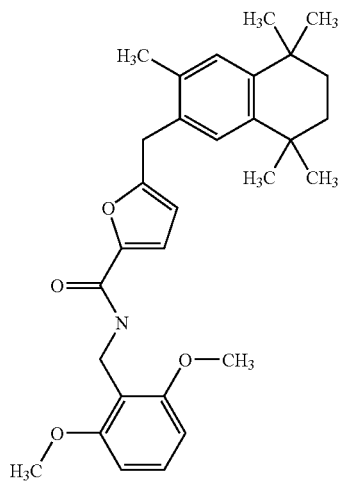
−3   2
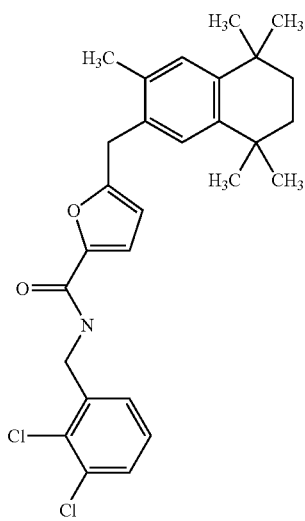
62   69
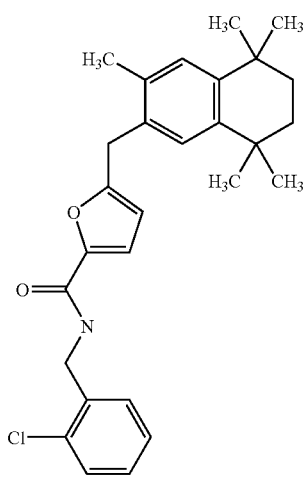
77   84

-continued
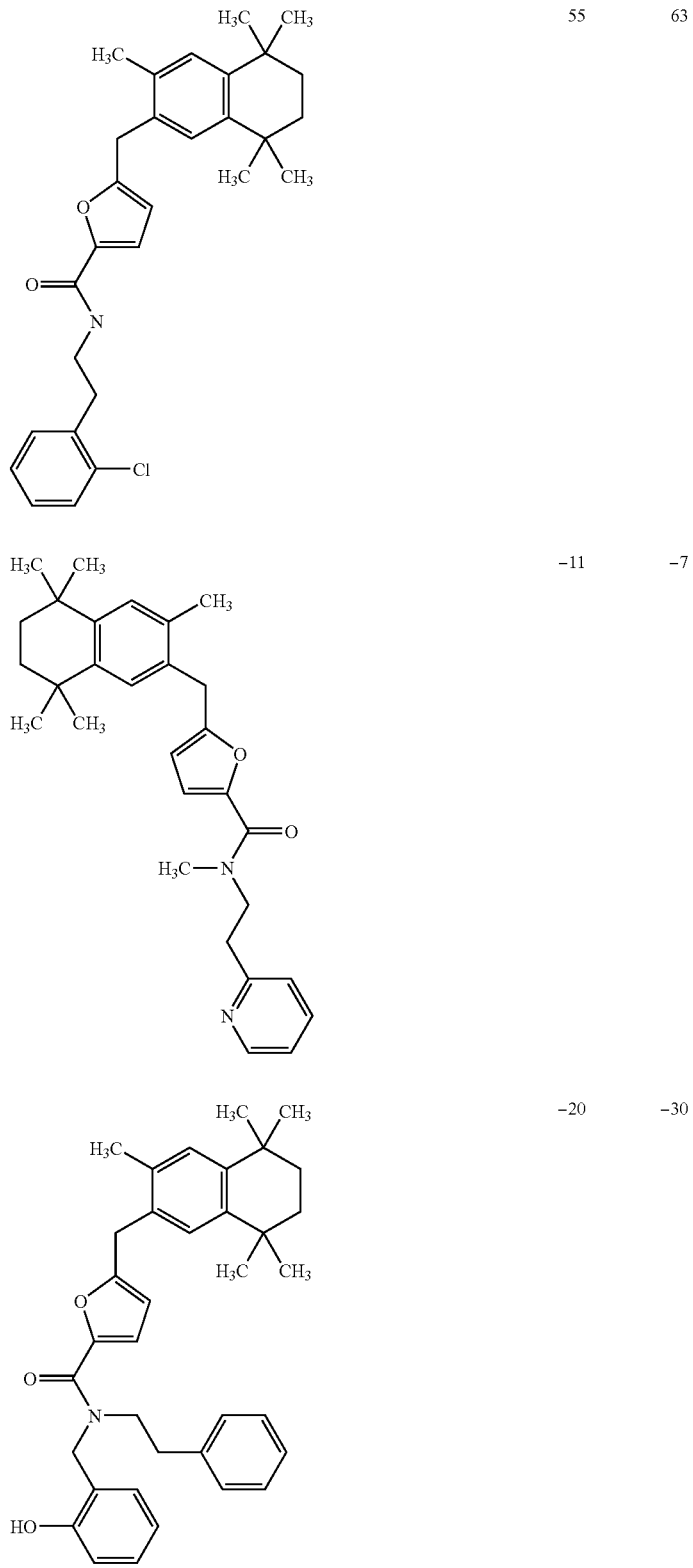

-continued
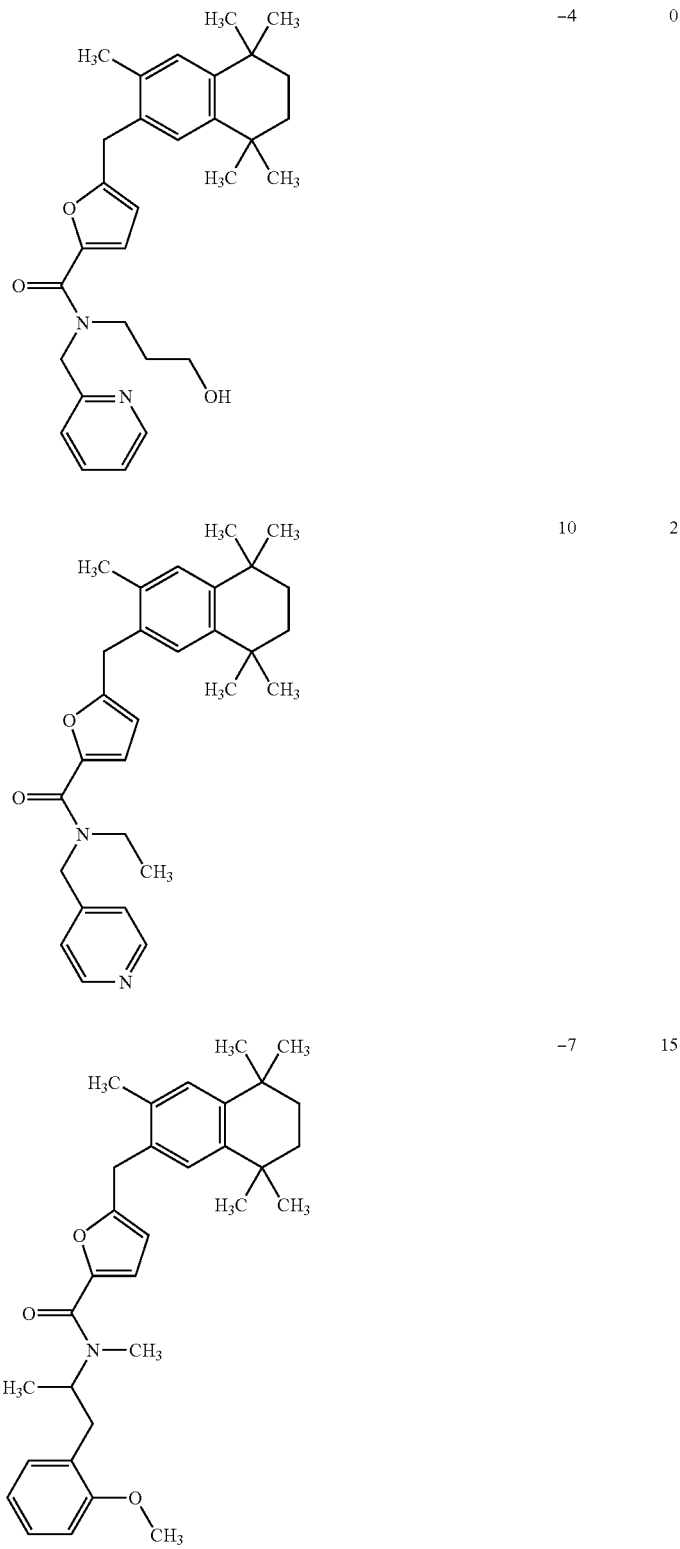
| | |
|---|---|
| −4 | 0 |
| 10 | 2 |
| −7 | 15 |

-continued
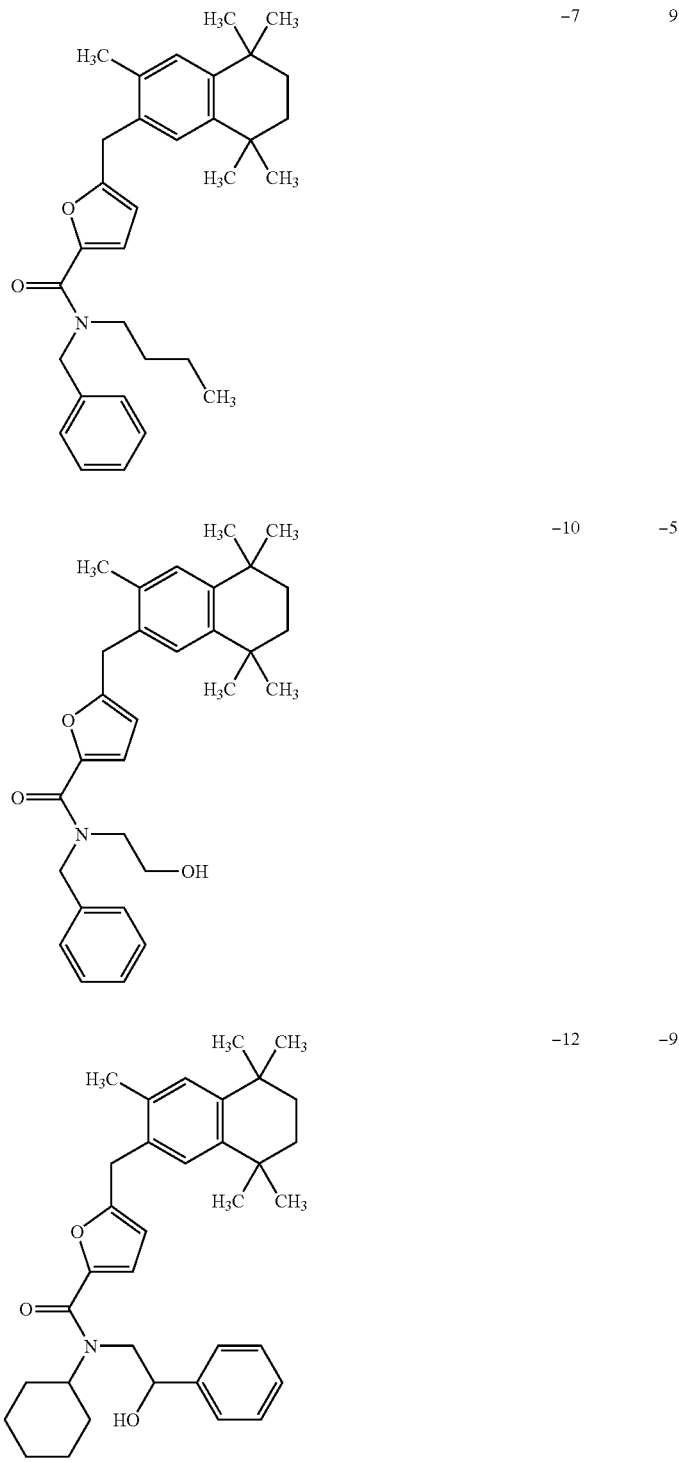

-continued
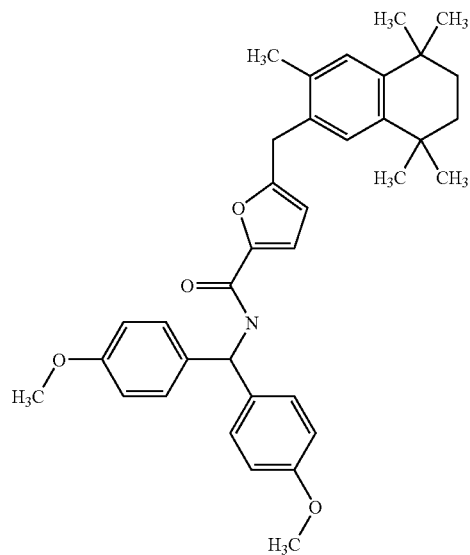 31 42
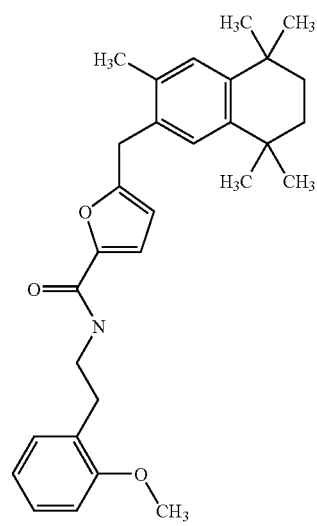 61 70

-continued
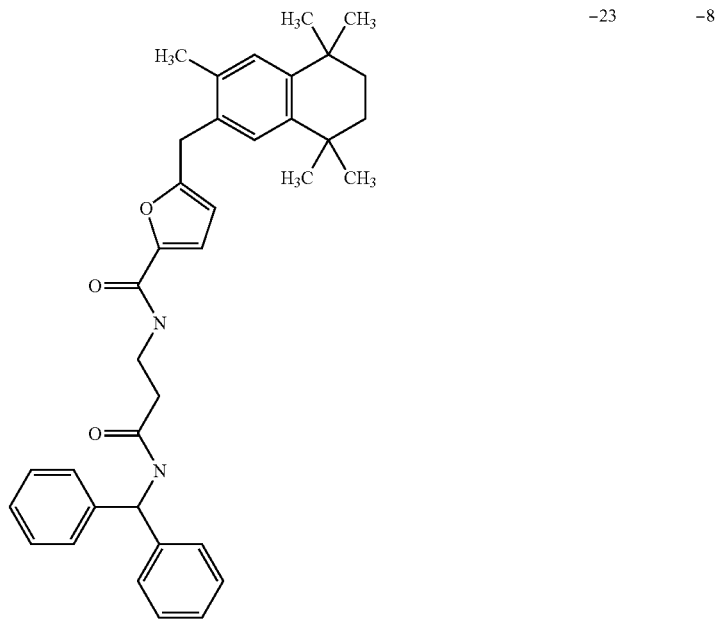 −23 −8
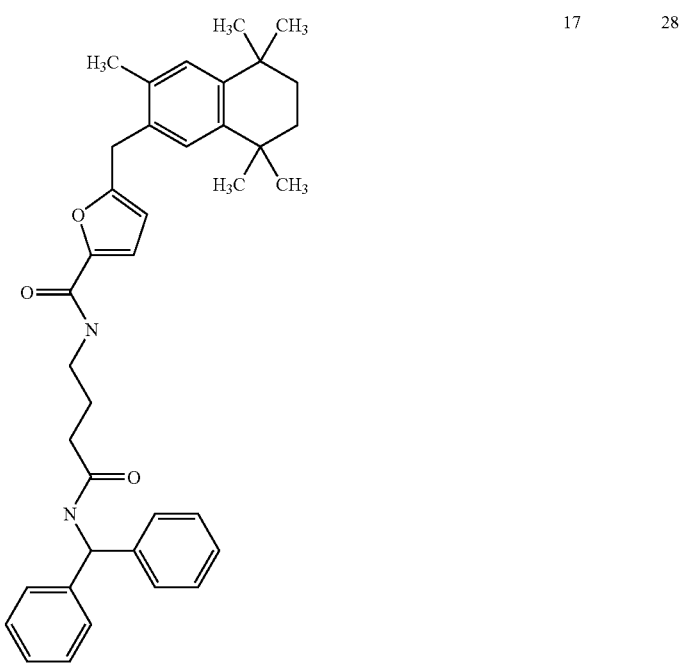 17 28

-continued
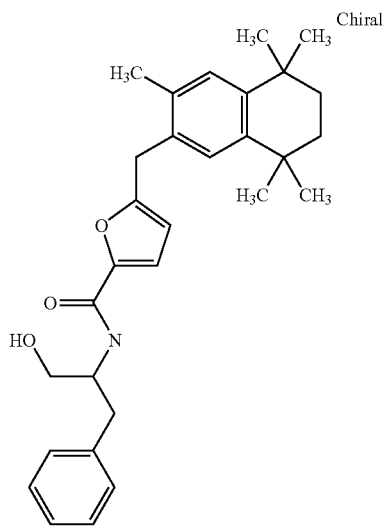 72 72
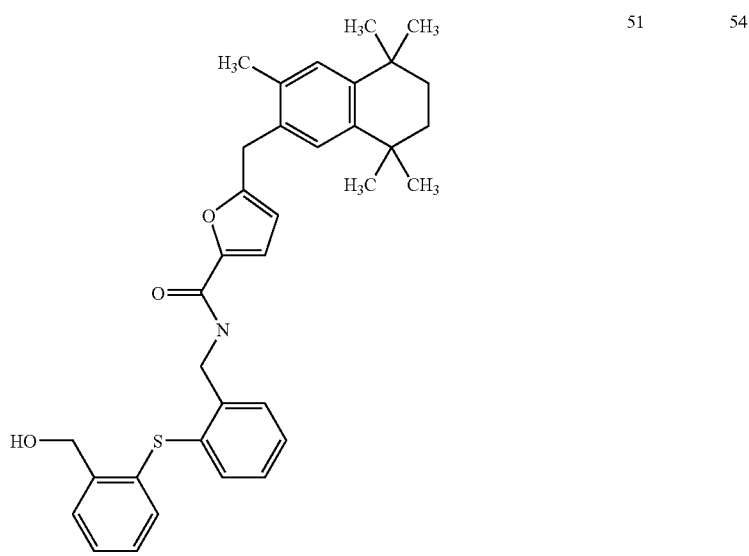 51 54

-continued
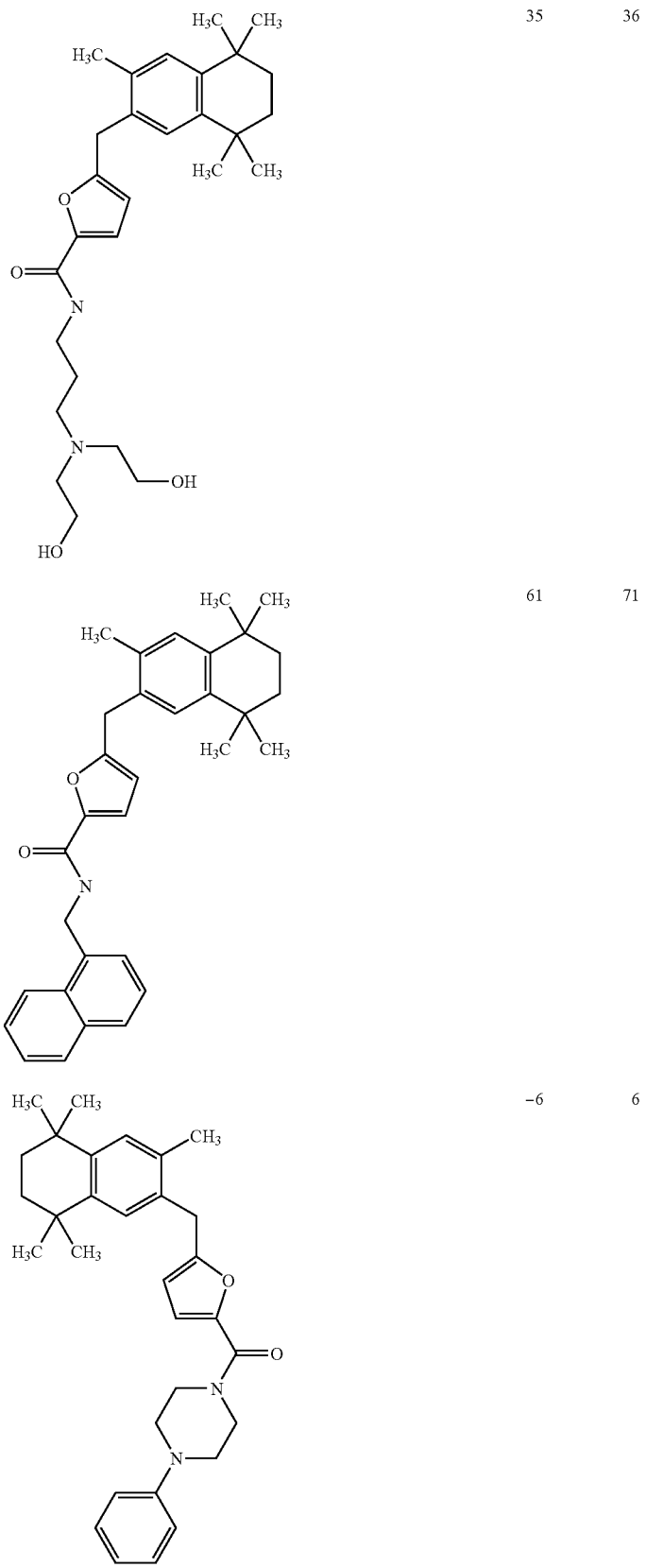
| | |
|---|---|
| 35 | 36 |
| 61 | 71 |
| −6 | 6 |

-continued
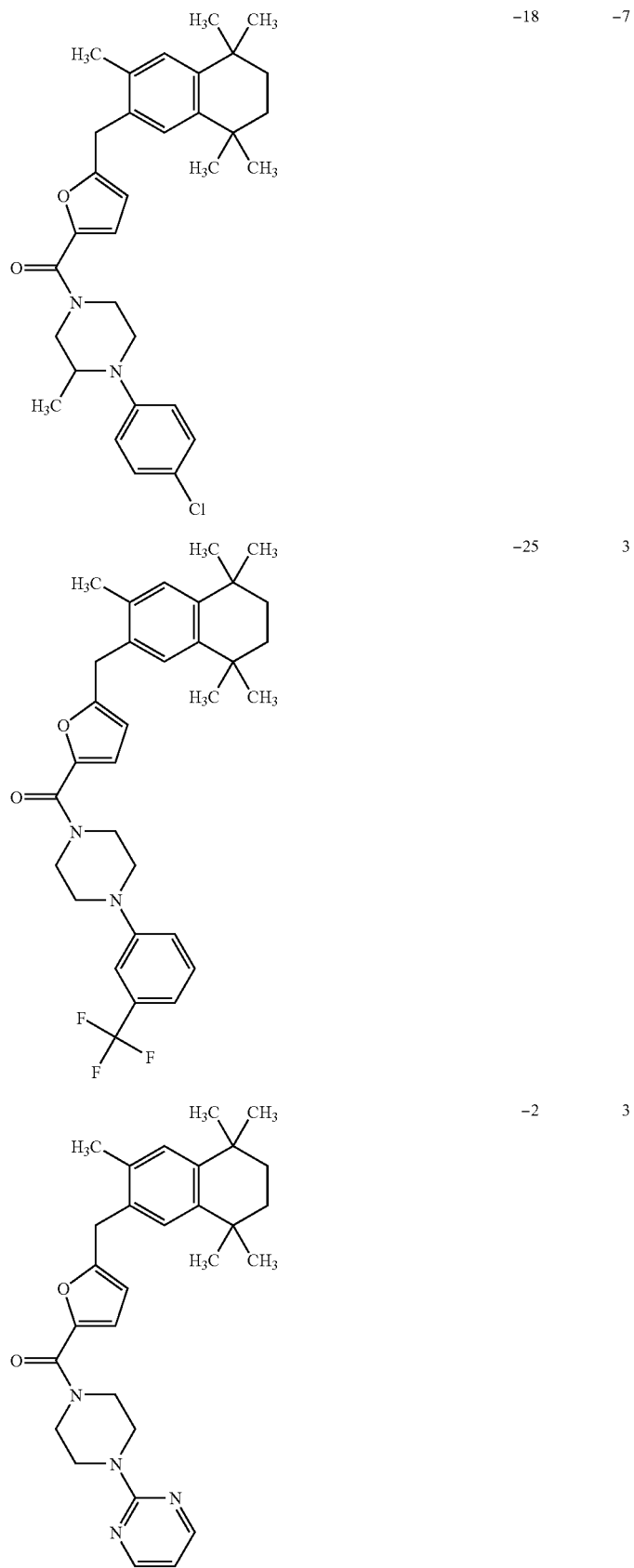
| | |
|---|---|
| −18 | −7 |
| −25 | 3 |
| −2 | 3 |

-continued
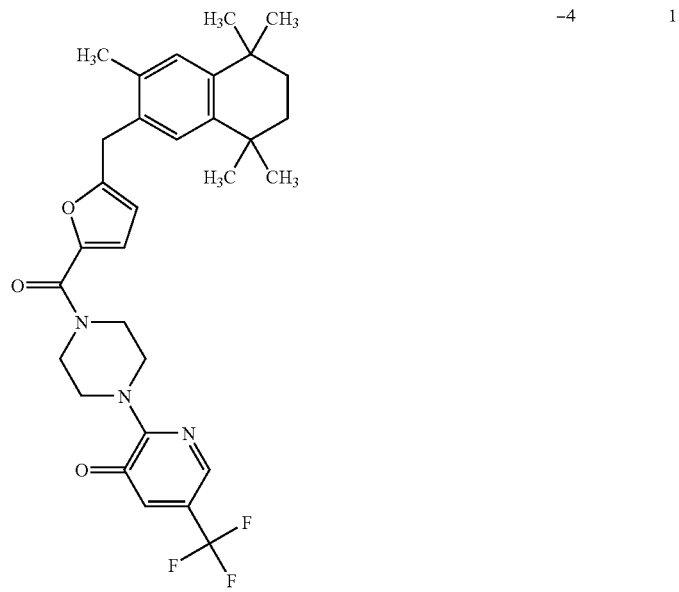
-4 1
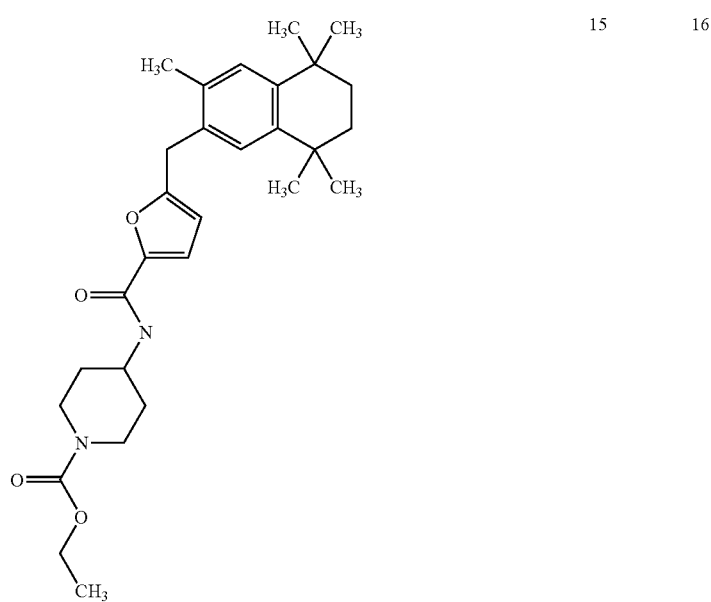
15 16

-continued
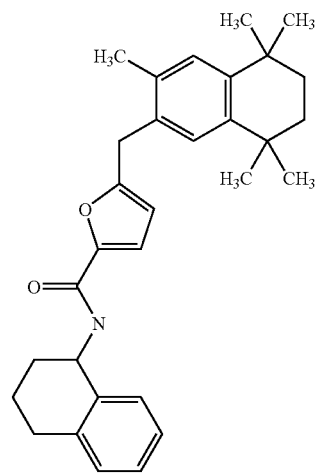 14 27
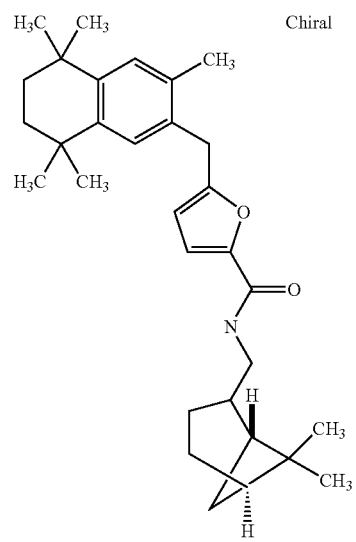 Chiral −3 −5
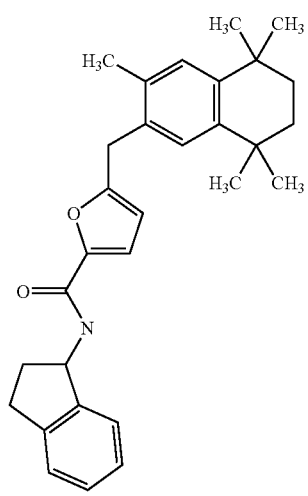 38 45

-continued
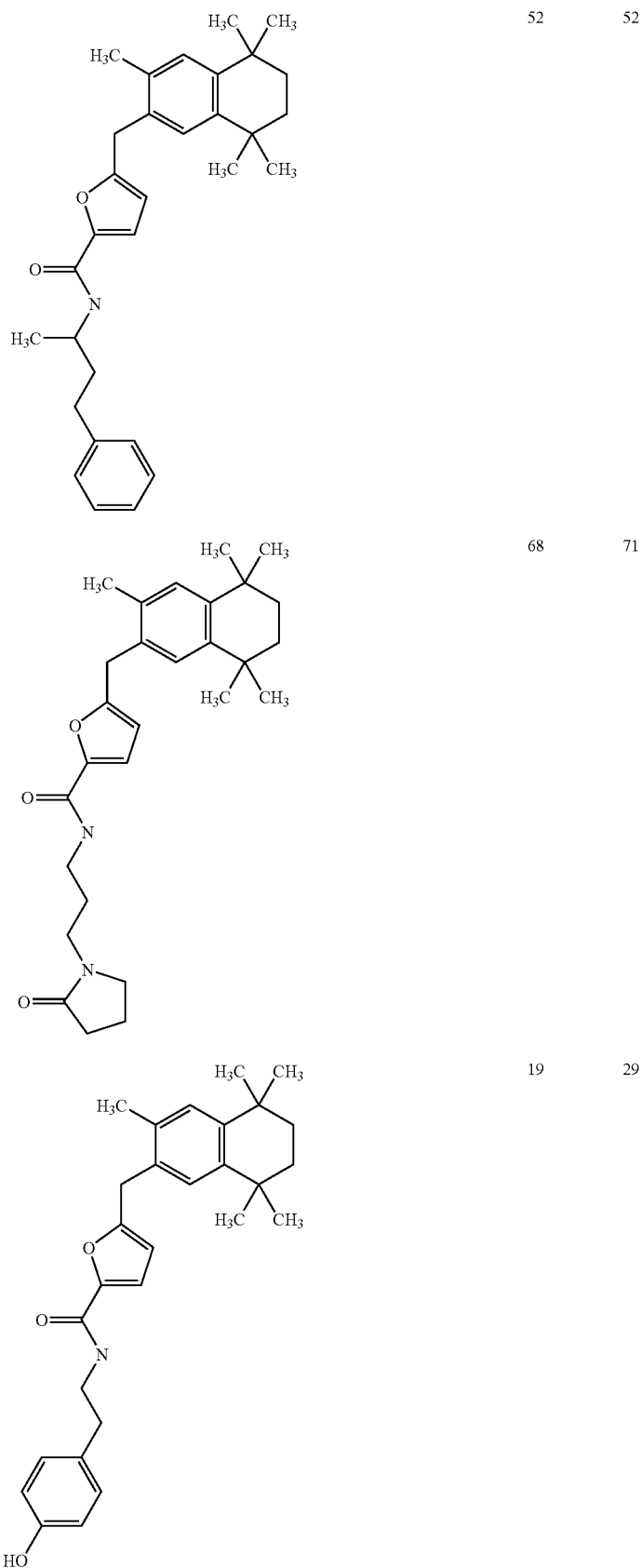
| | |
|---|---|
| 52 | 52 |
| 68 | 71 |
| 19 | 29 |

-continued
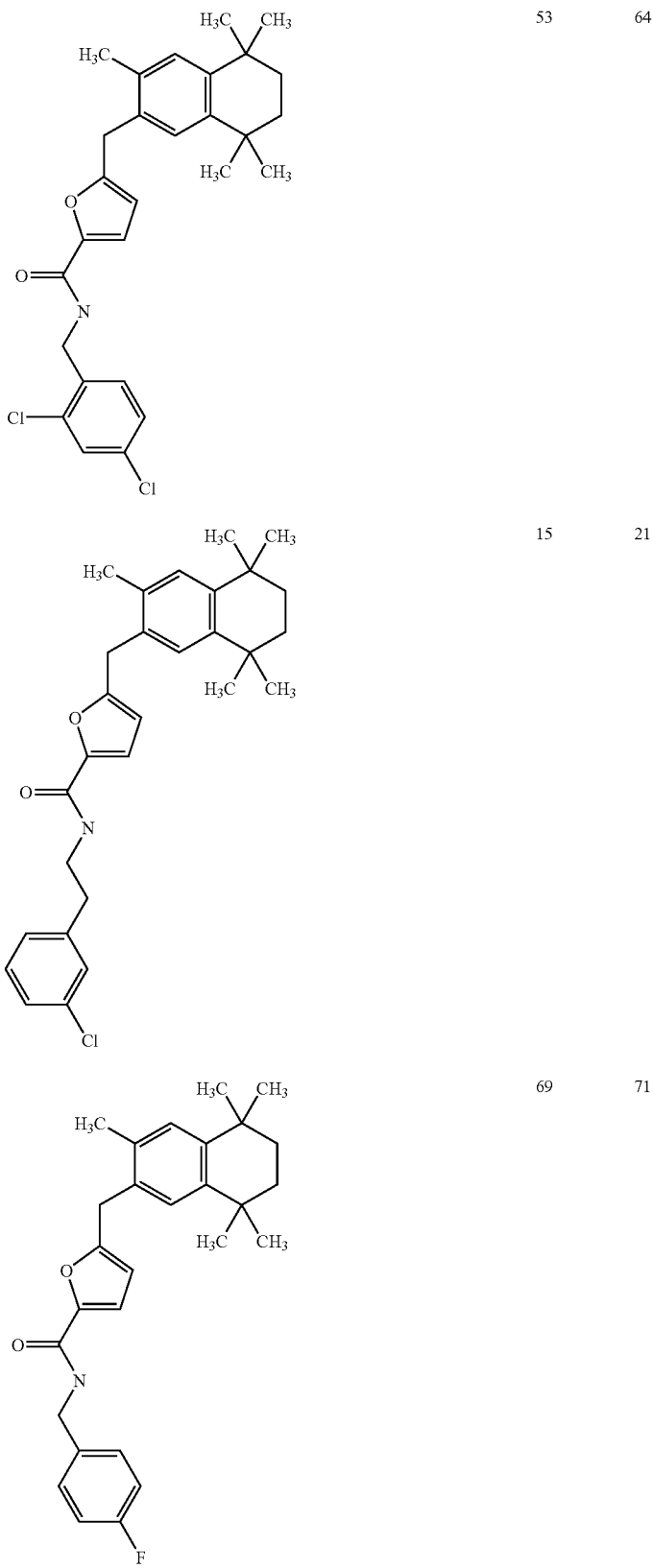
| | |
|---|---|
| 53 | 64 |
| 15 | 21 |
| 69 | 71 |

| | | |
|---|---|---|
| 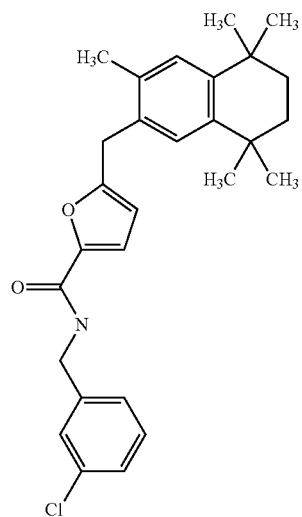 | 78 | 84 |
| 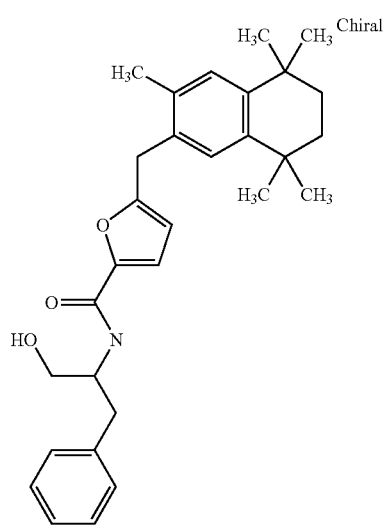 Chiral | 17 | 20 |
| 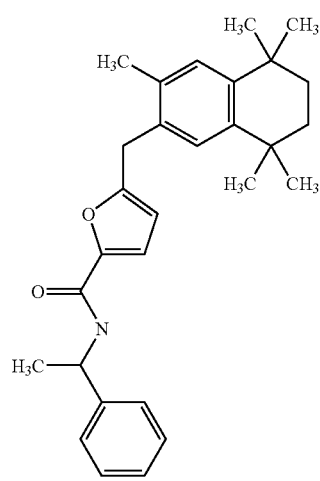 | 53 | 58 |

-continued
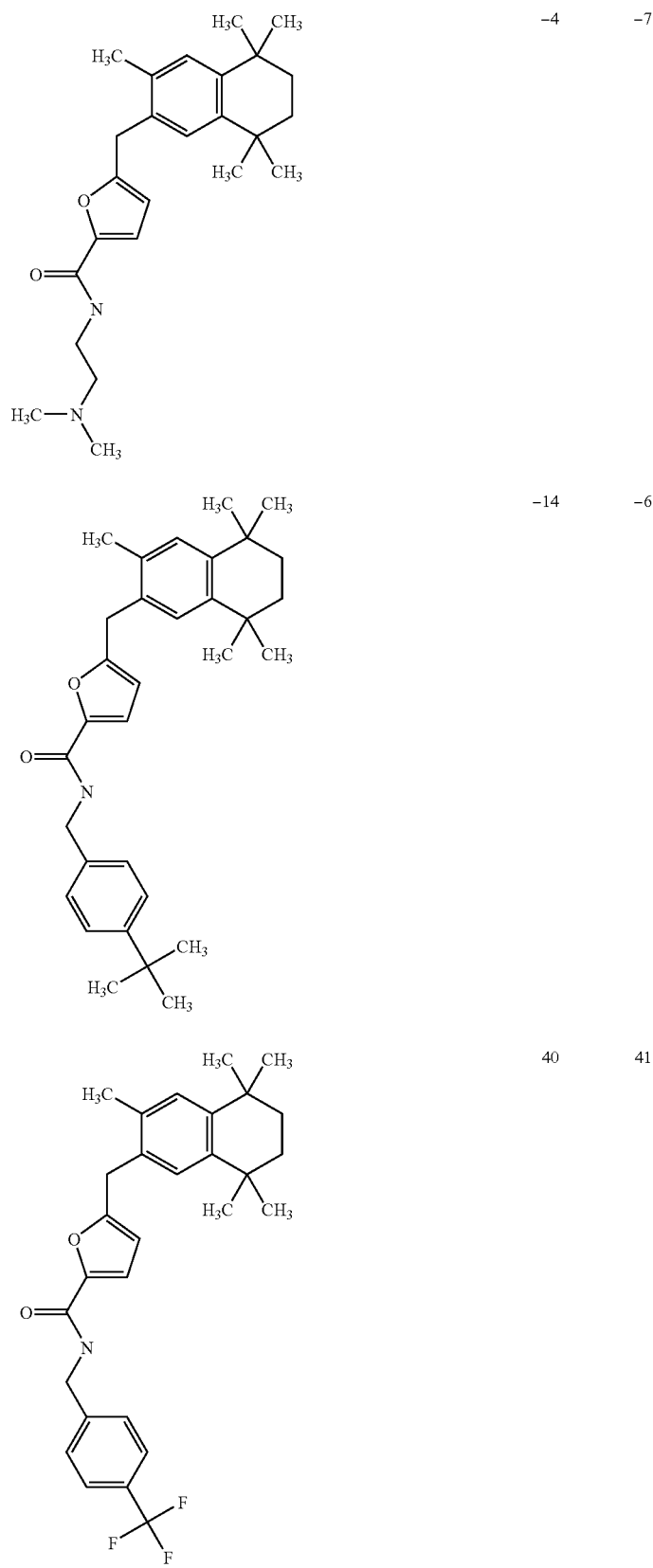
| | |
|---|---|
| −4 | −7 |
| −14 | −6 |
| 40 | 41 |

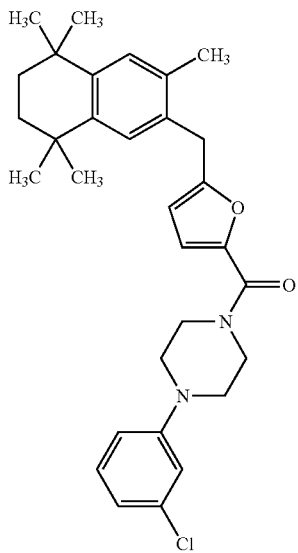 −22 9
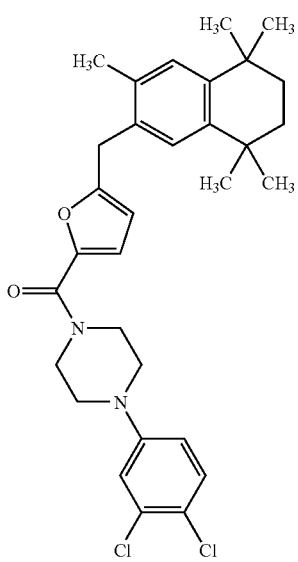 −20 −7

-continued
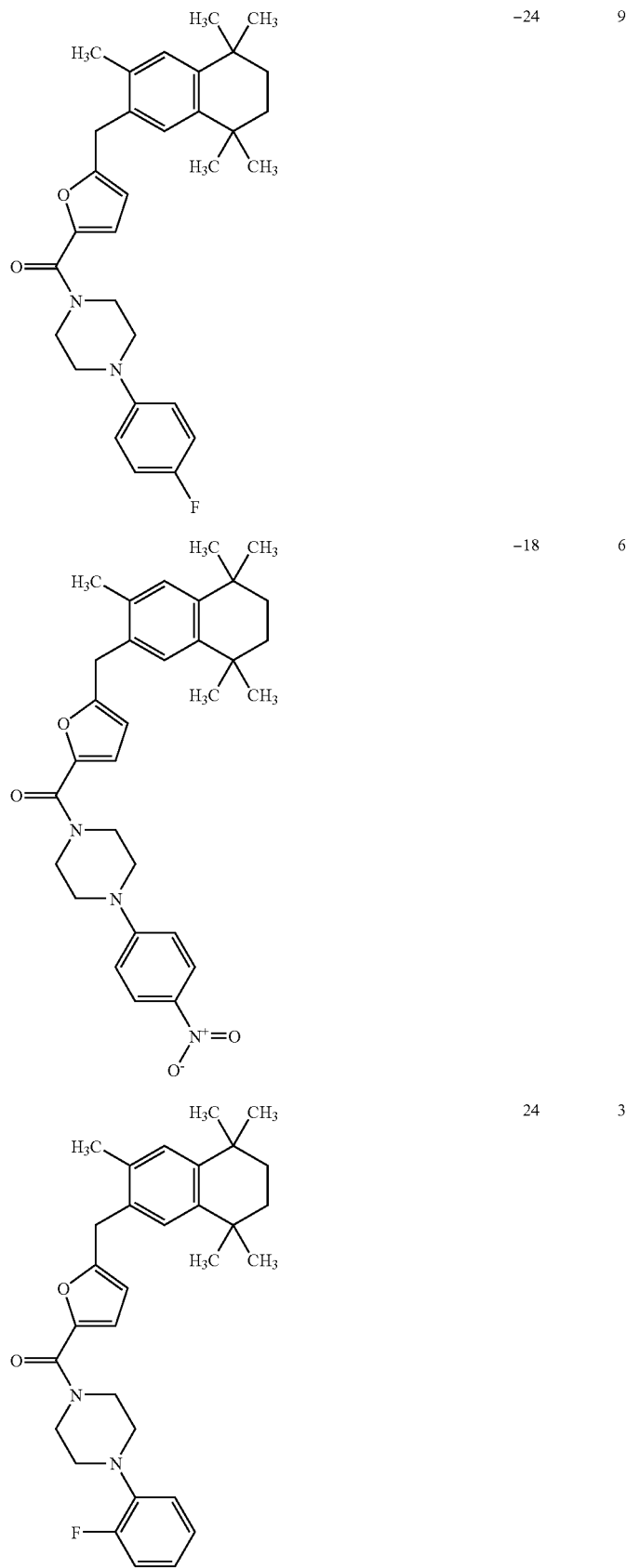
| | |
|---|---|
| −24 | 9 |
| −18 | 6 |
| 24 | 3 |

-continued
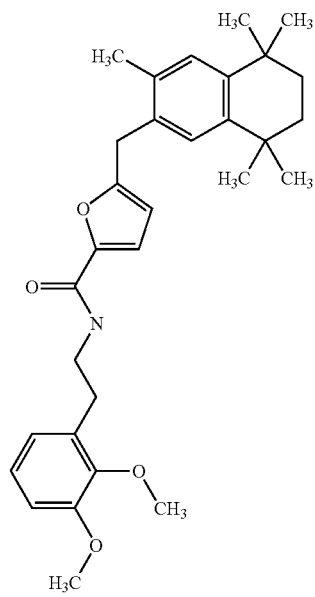 58 63
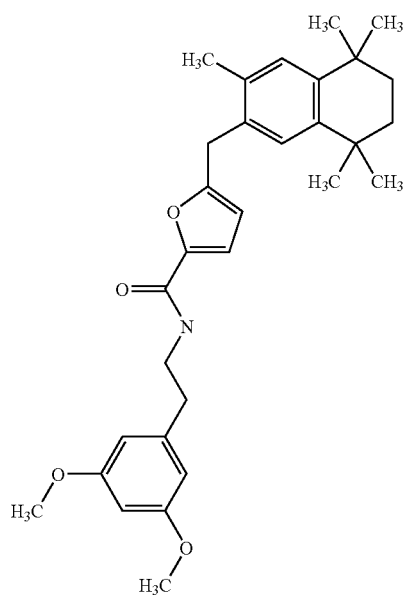 44 48
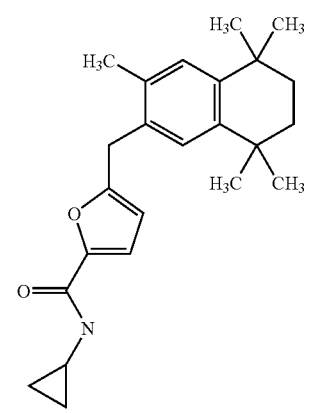 49 58

-continued
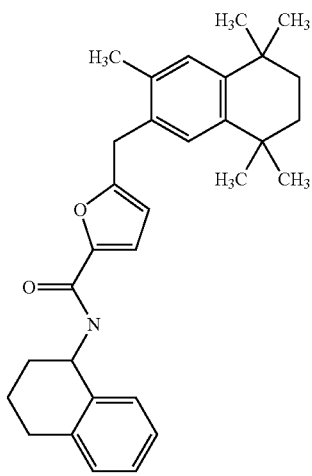 16 32
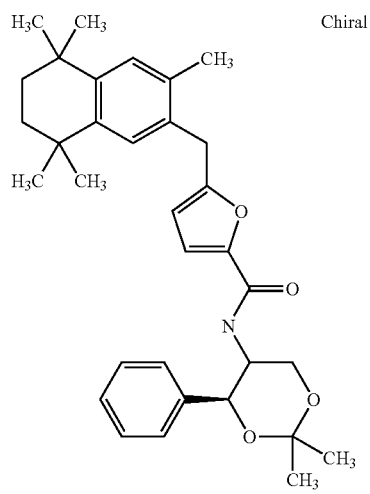 Chiral −6 0
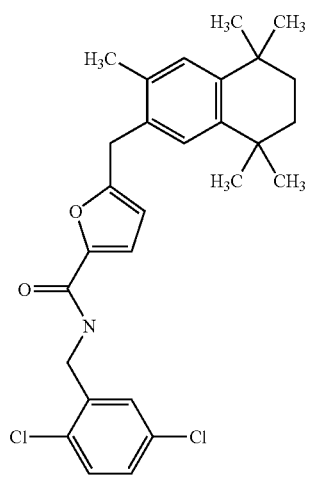 26 34

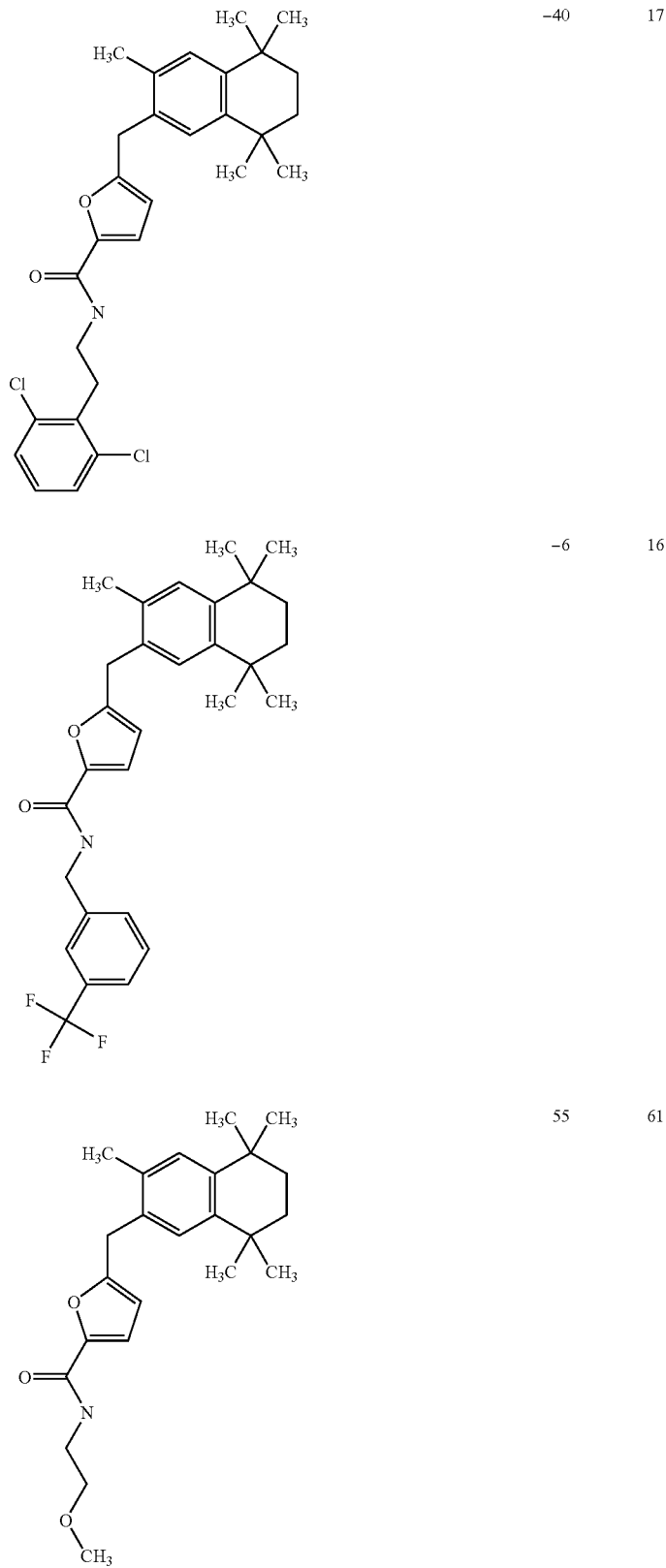

-continued
| | | |
|---|---|---|
| 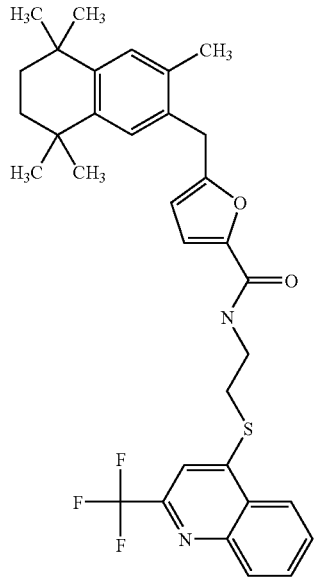 | −18 | 5 |
| 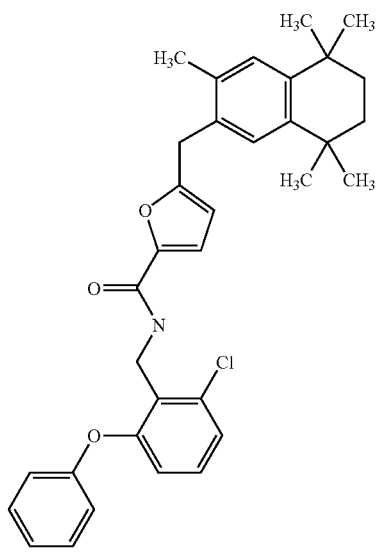 | −10 | −15 |
| 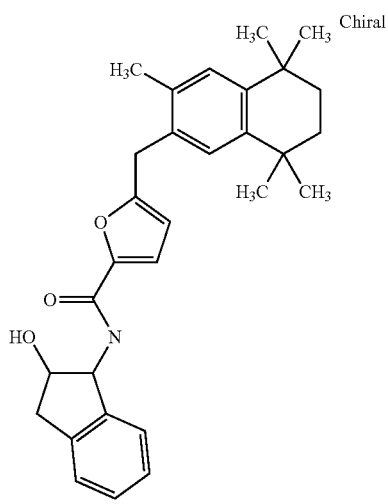 | −11 | −29 |

-continued
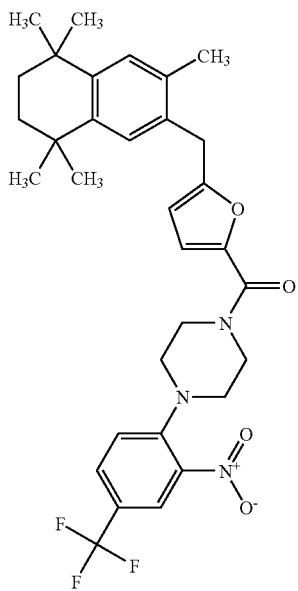
-20  -21
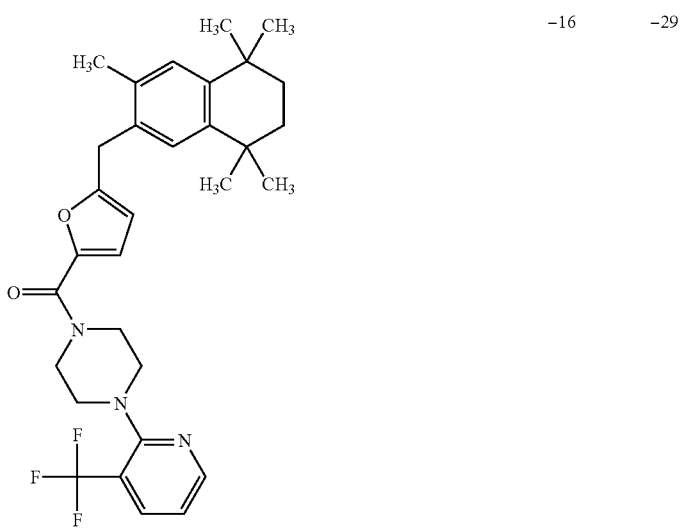
-16  -29

-continued
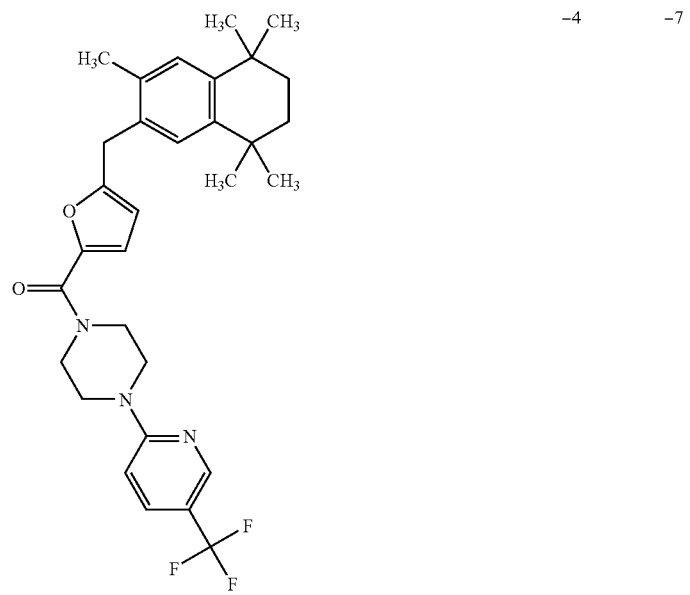
−4 −7
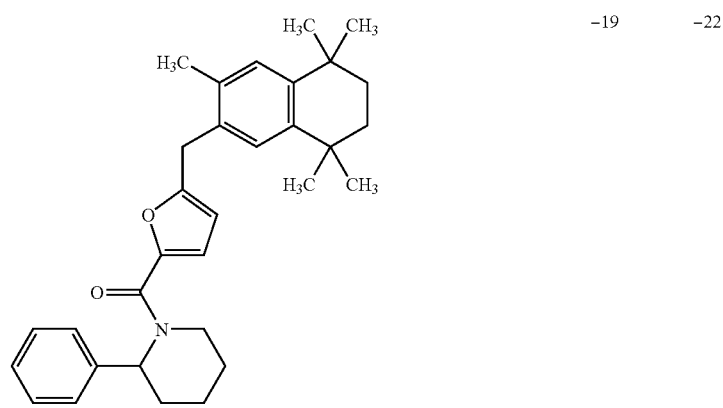
−19 −22
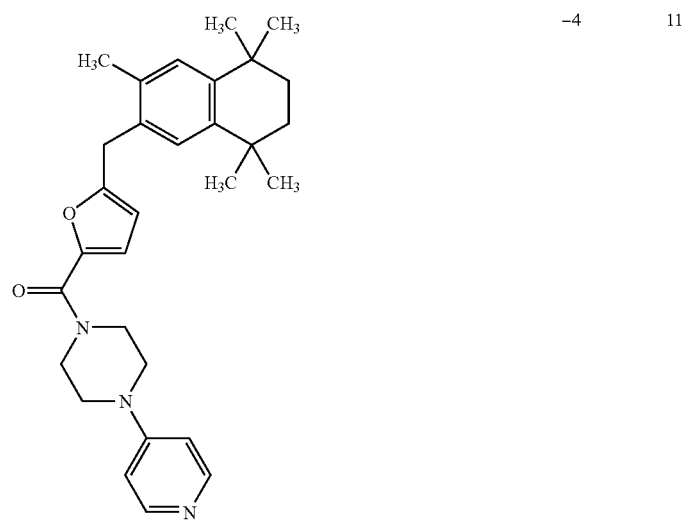
−4 11

-continued
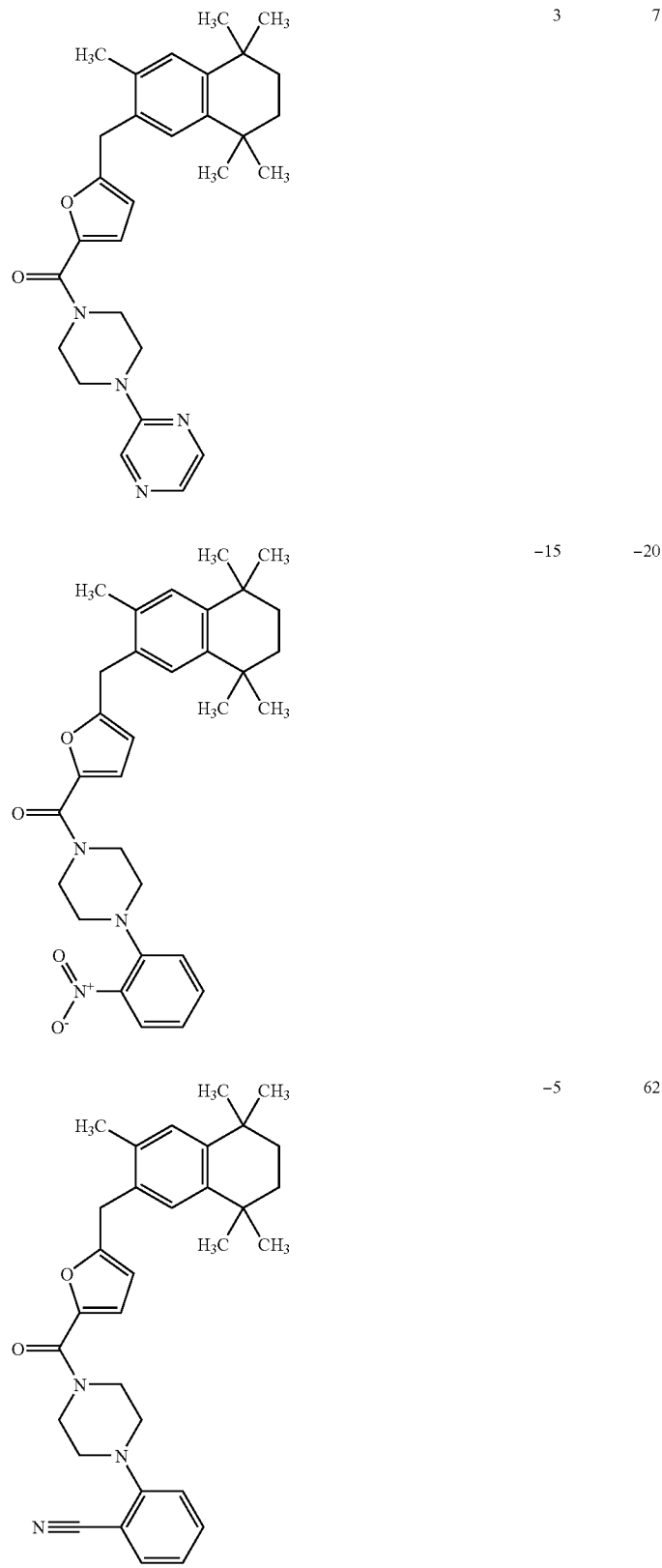
| | |
|---|---|
| 3 | 7 |
| −15 | −20 |
| −5 | 62 |

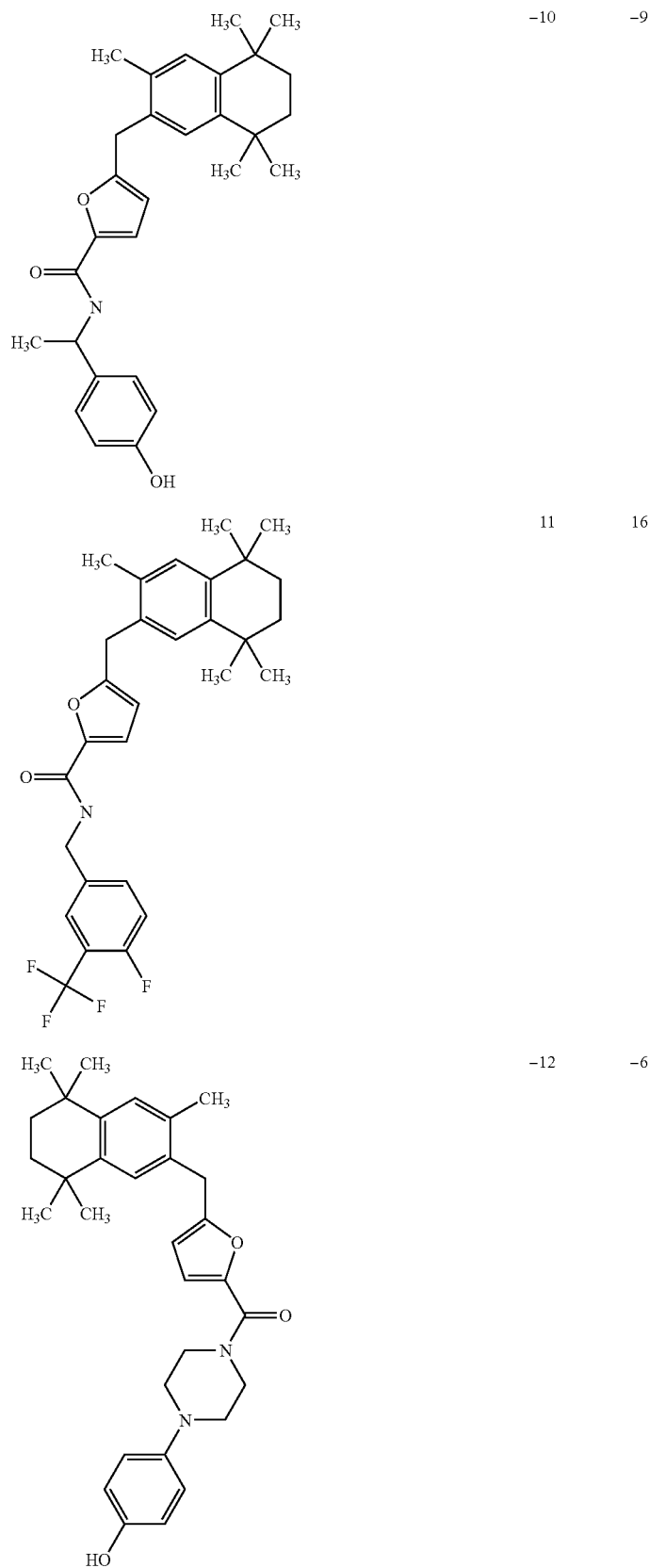

-continued
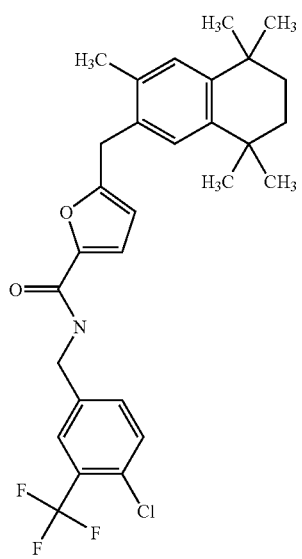
15 19
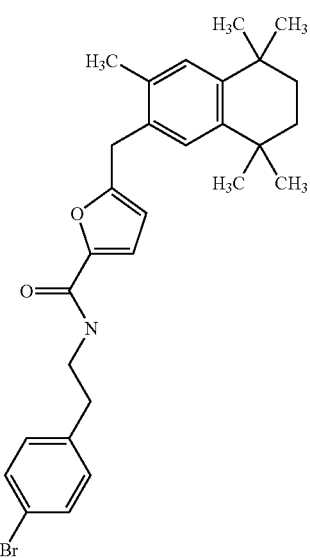
16 24
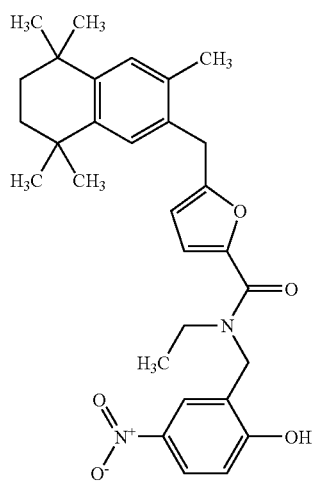
−11 −5

-continued
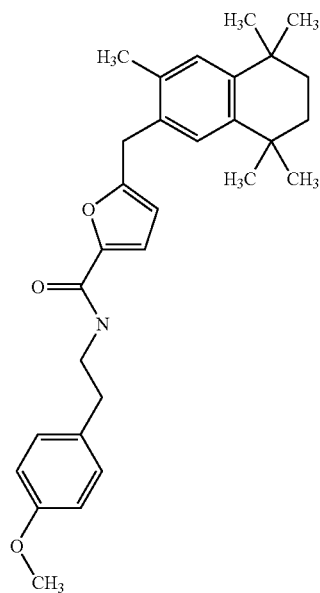
42 53
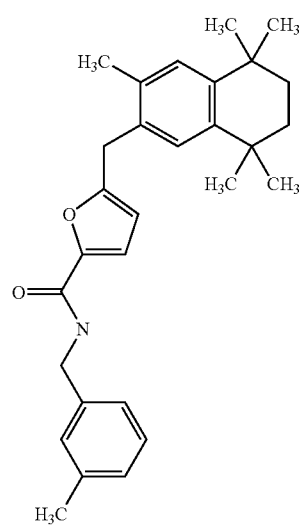
93 95
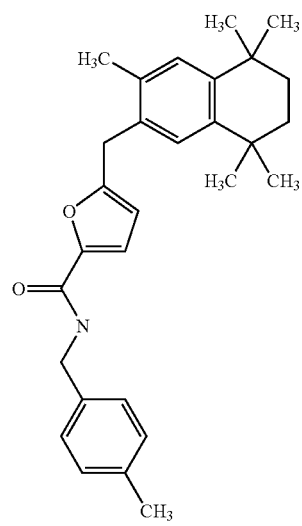
87 90

-continued
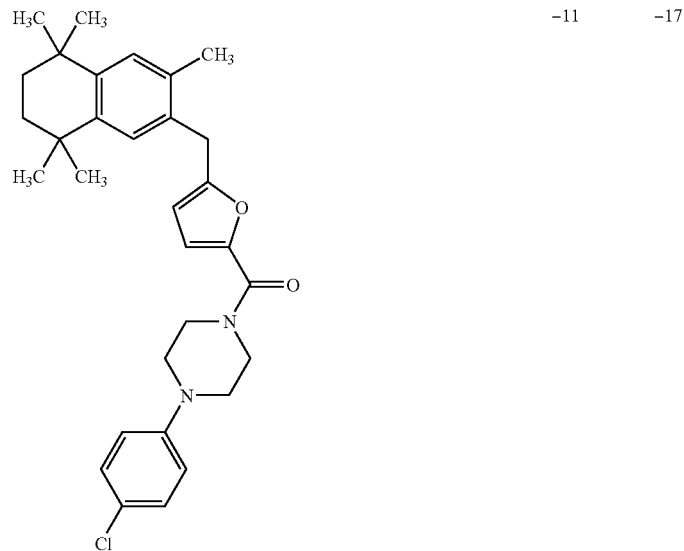
−11  −17
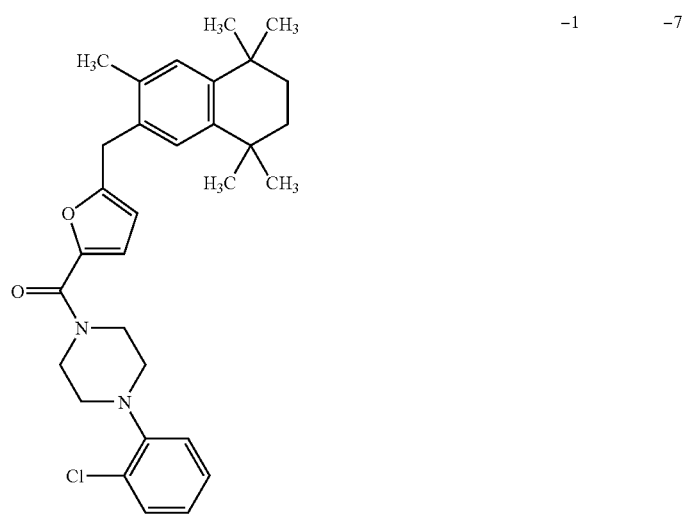
−1  −7
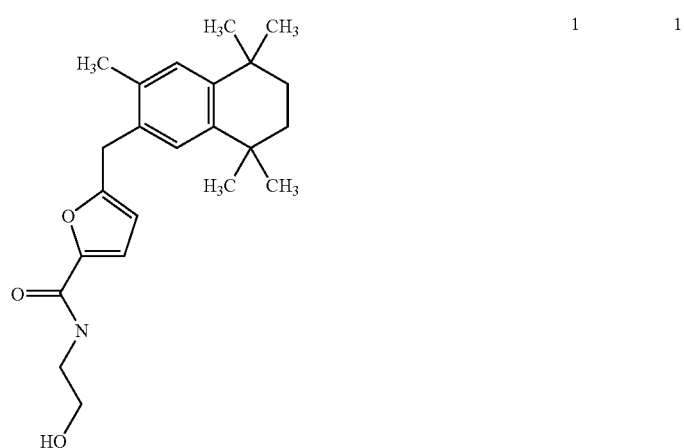
1  1

-continued
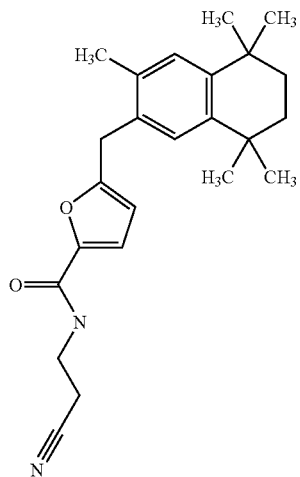
42 44
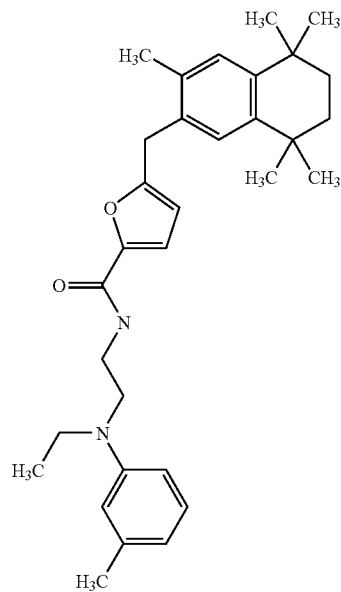
2 21
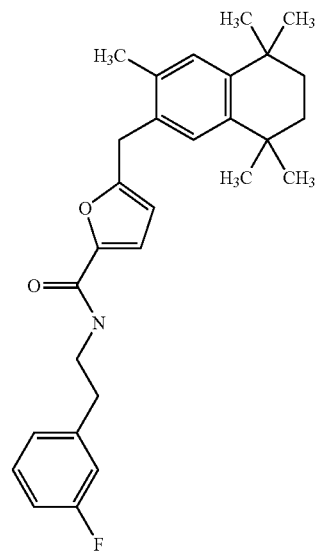
59 62

| | | |
|---|---|---|
| 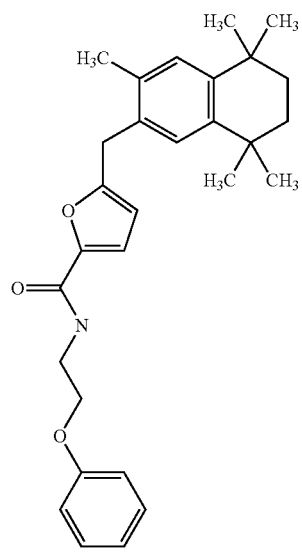 | 93 | 95 |
| 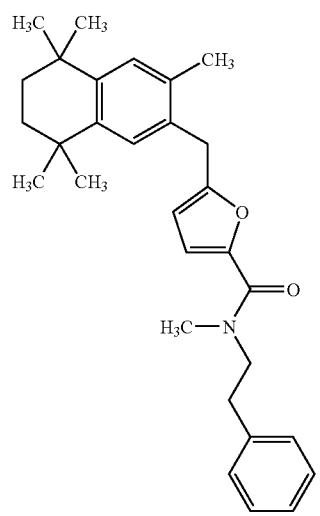 | 10 | 9 |
| 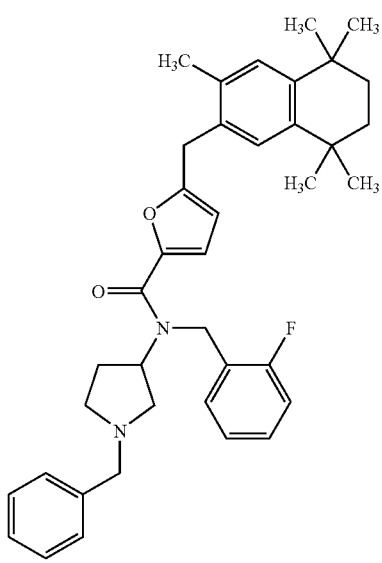 | 7 | 9 |

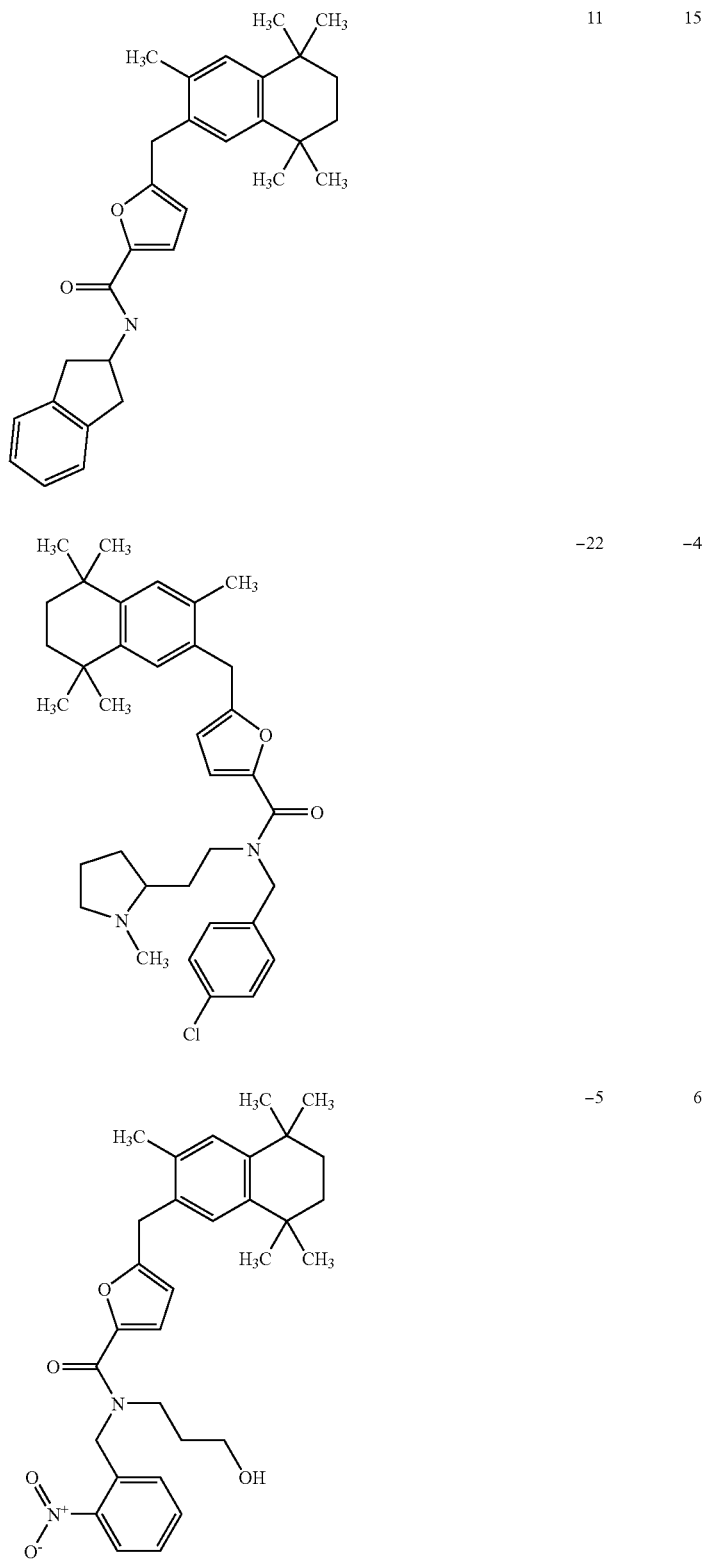

-continued
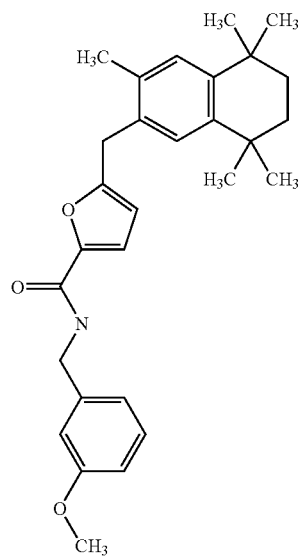   76   79
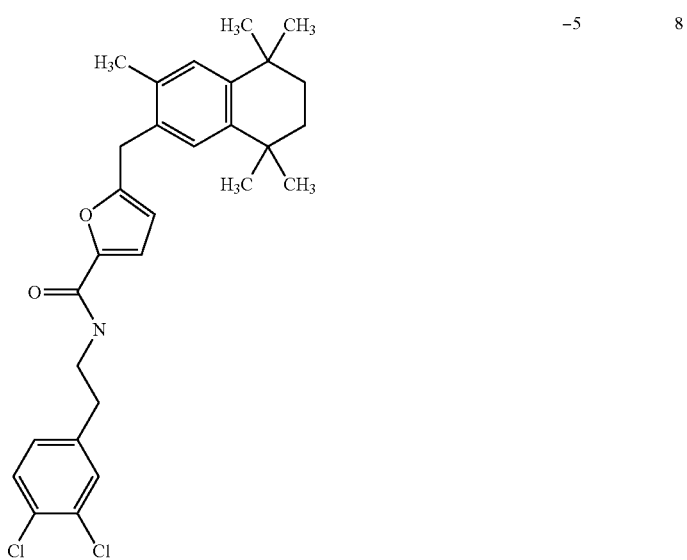   −5   8

-continued
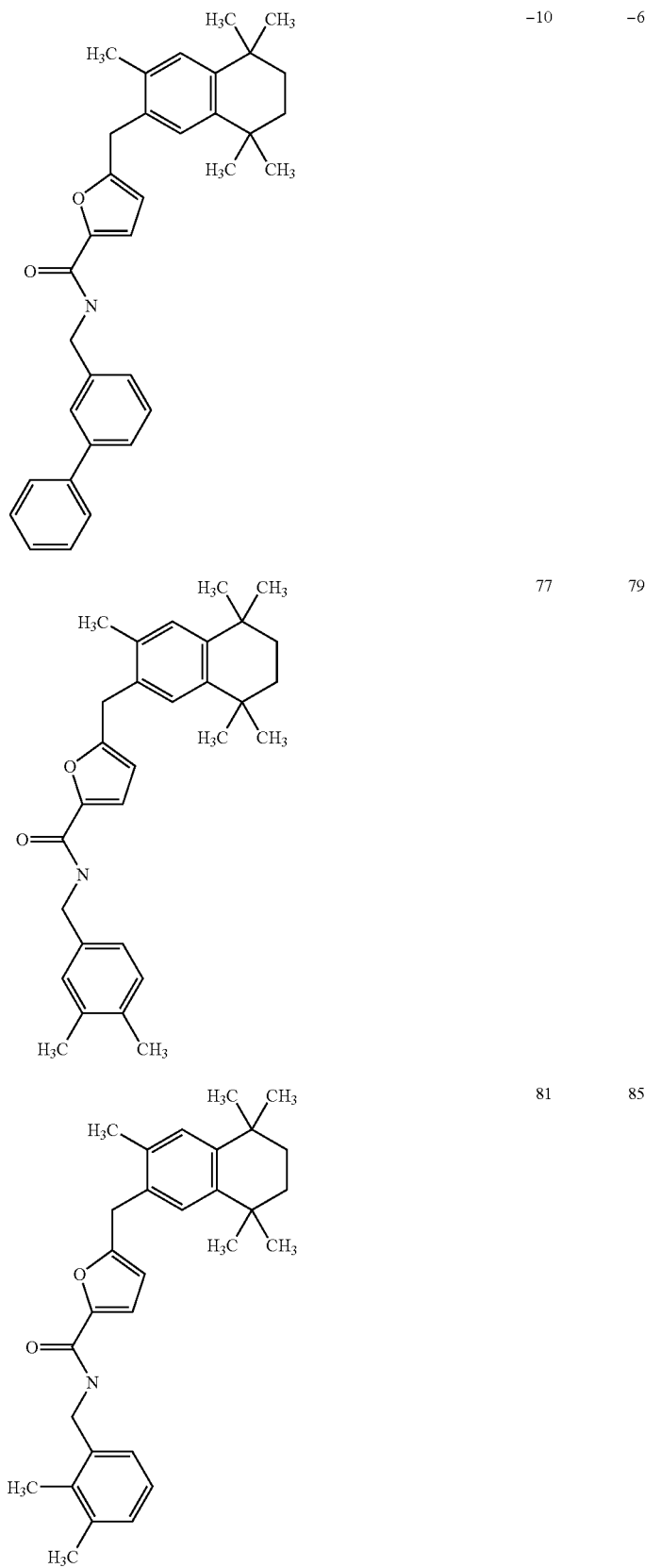
| | |
|---|---|
| −10 | −6 |
| 77 | 79 |
| 81 | 85 |

-continued
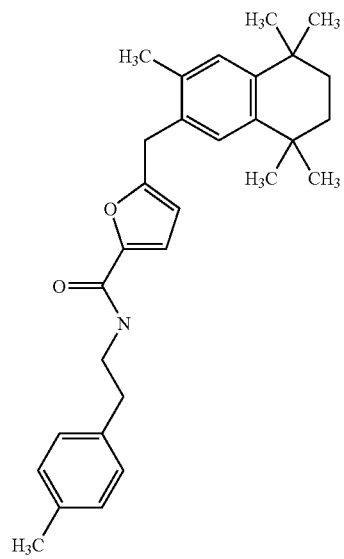
48 52
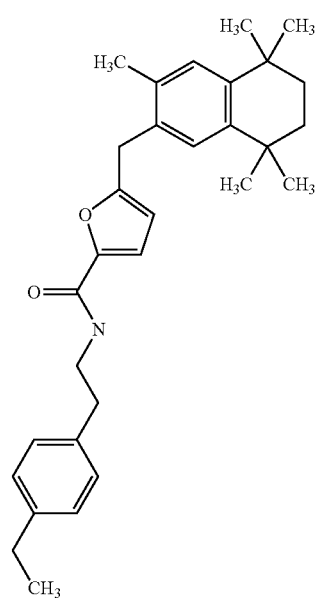
29 32

-continued
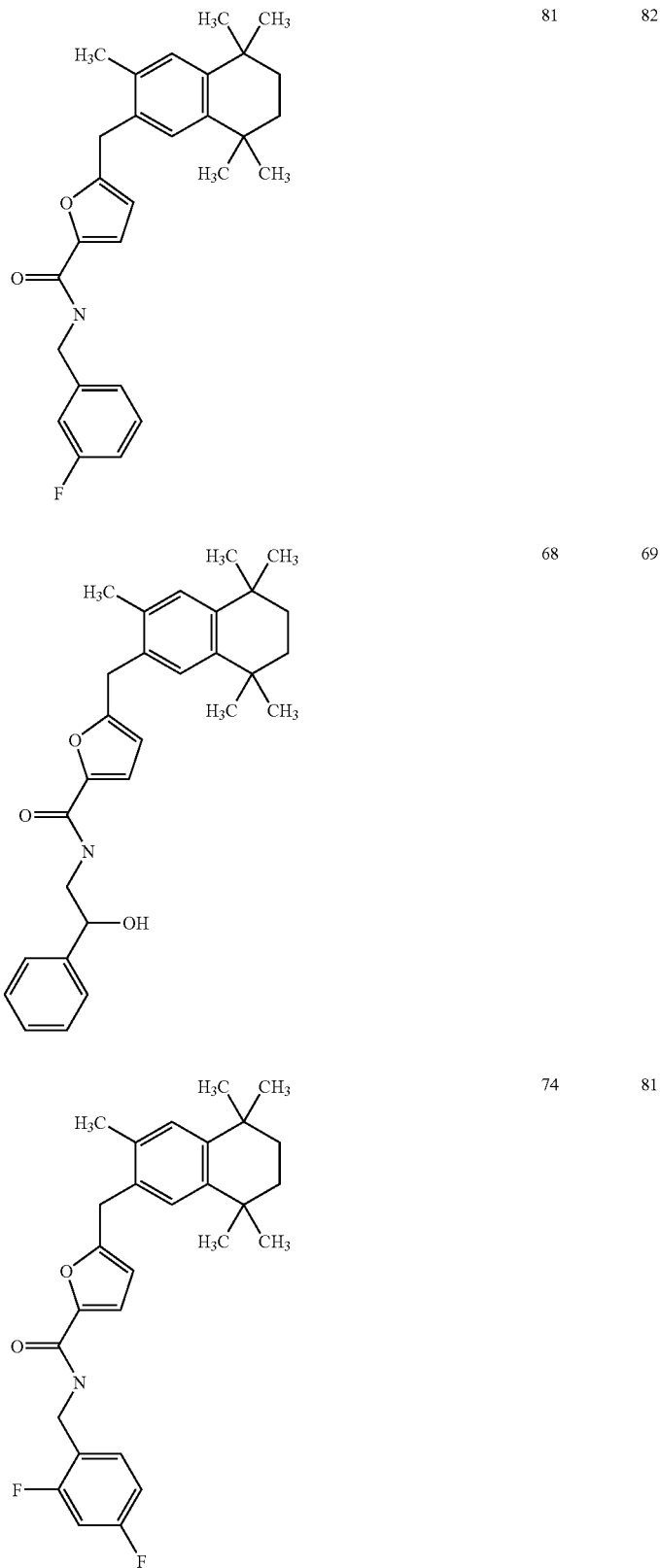
| | | |
|---|---|---|
| 81 | 82 | |
| 68 | 69 | |
| 74 | 81 | |

| | | |
|---|---|---|
| 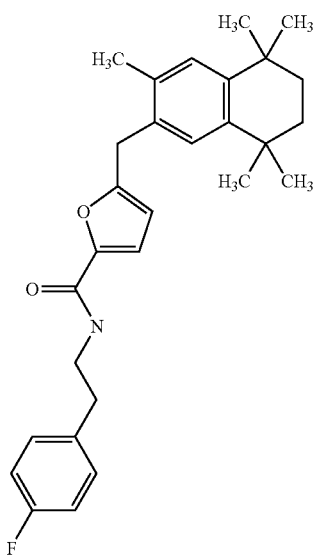 | 45 | 45 |
| 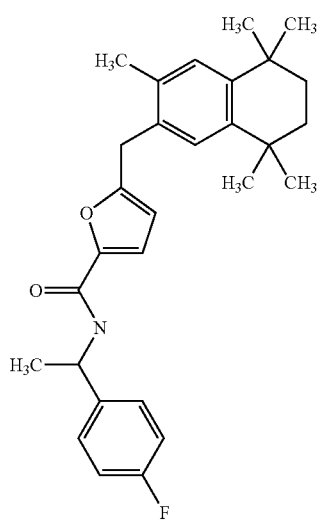 | 28 | 35 |
| 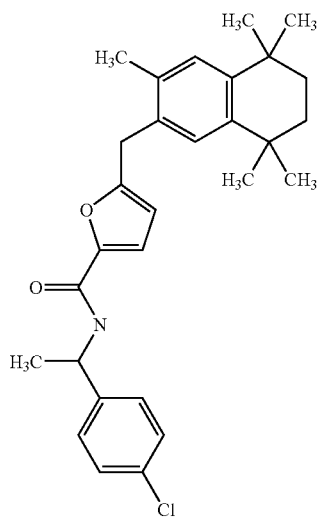 | 20 | 28 |

| | | |
|---|---|---|
| 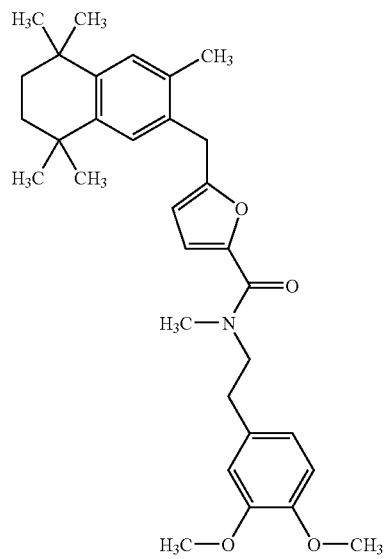 | 13 | 7 |
| 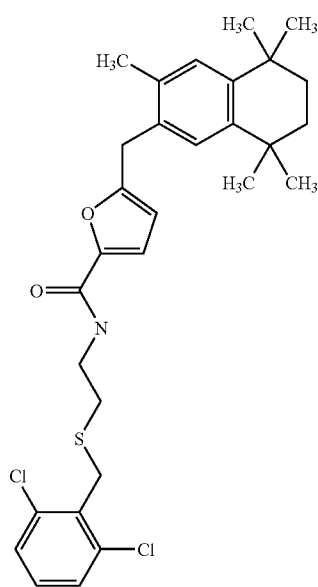 | 14 | 20 |
| 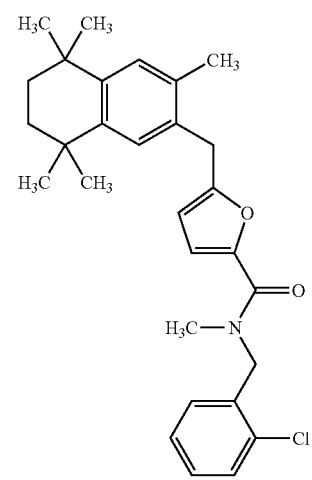 | 14 | 21 |

-continued
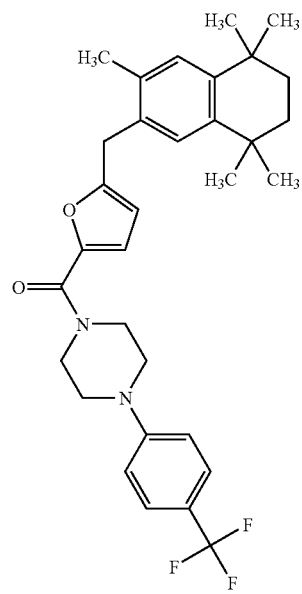 −12 1
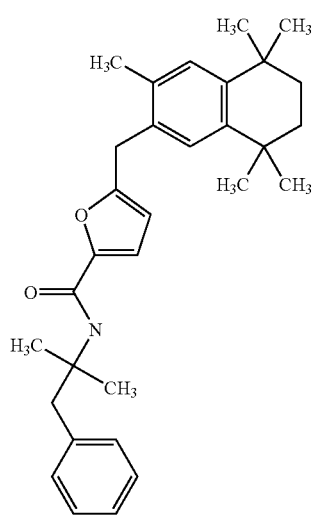 38 39
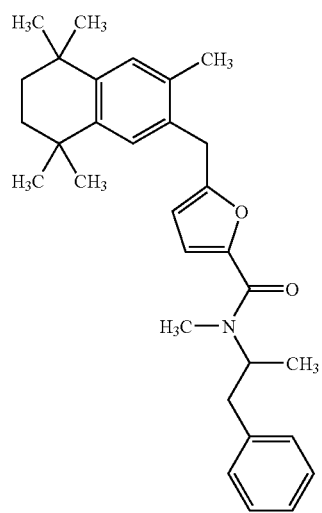 15 17

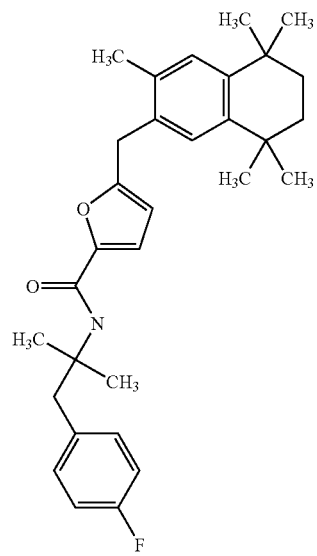 21 22
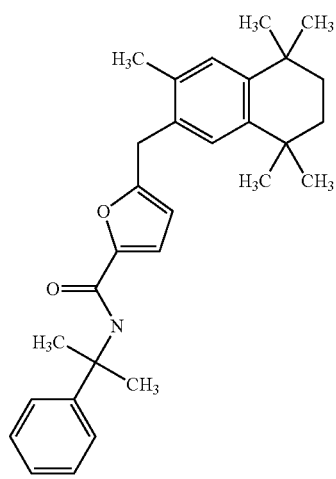 28 45
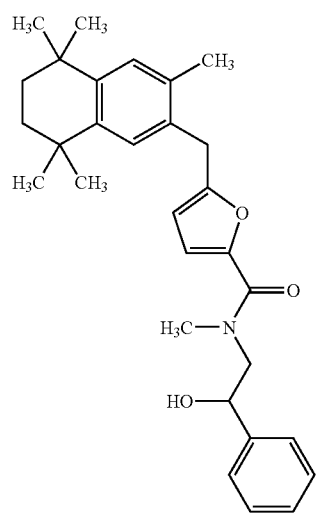 20 22

-continued
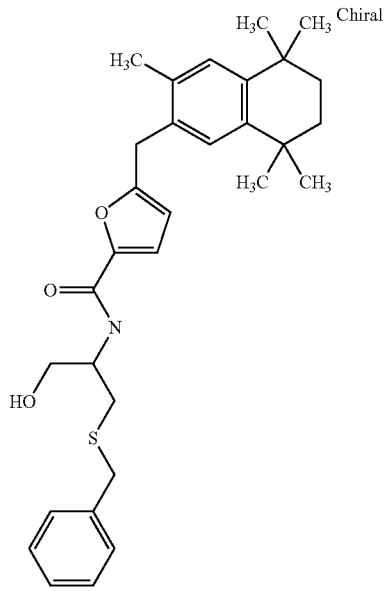
16 7
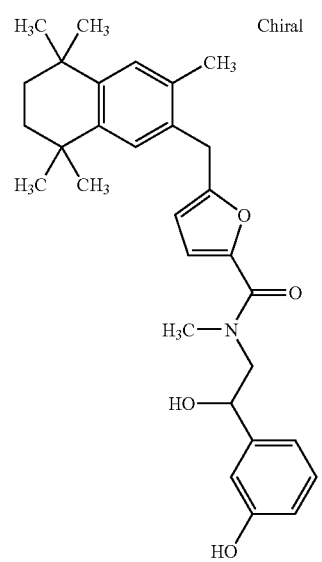
−2 9

-continued
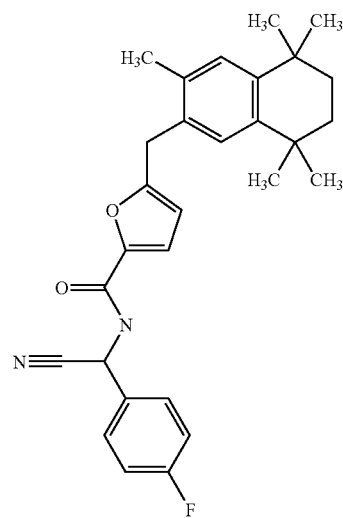  2  4
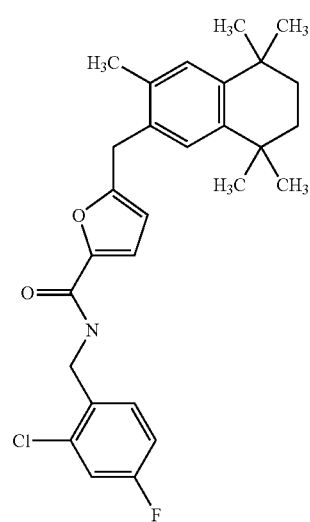  27  48
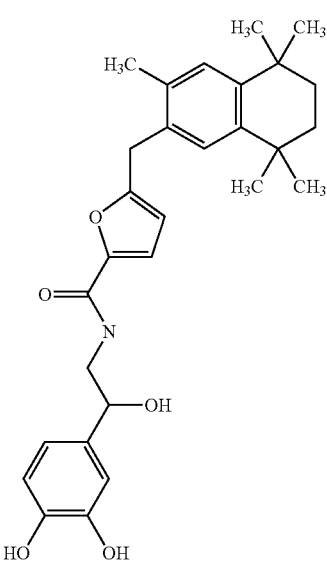  −26  11

-continued
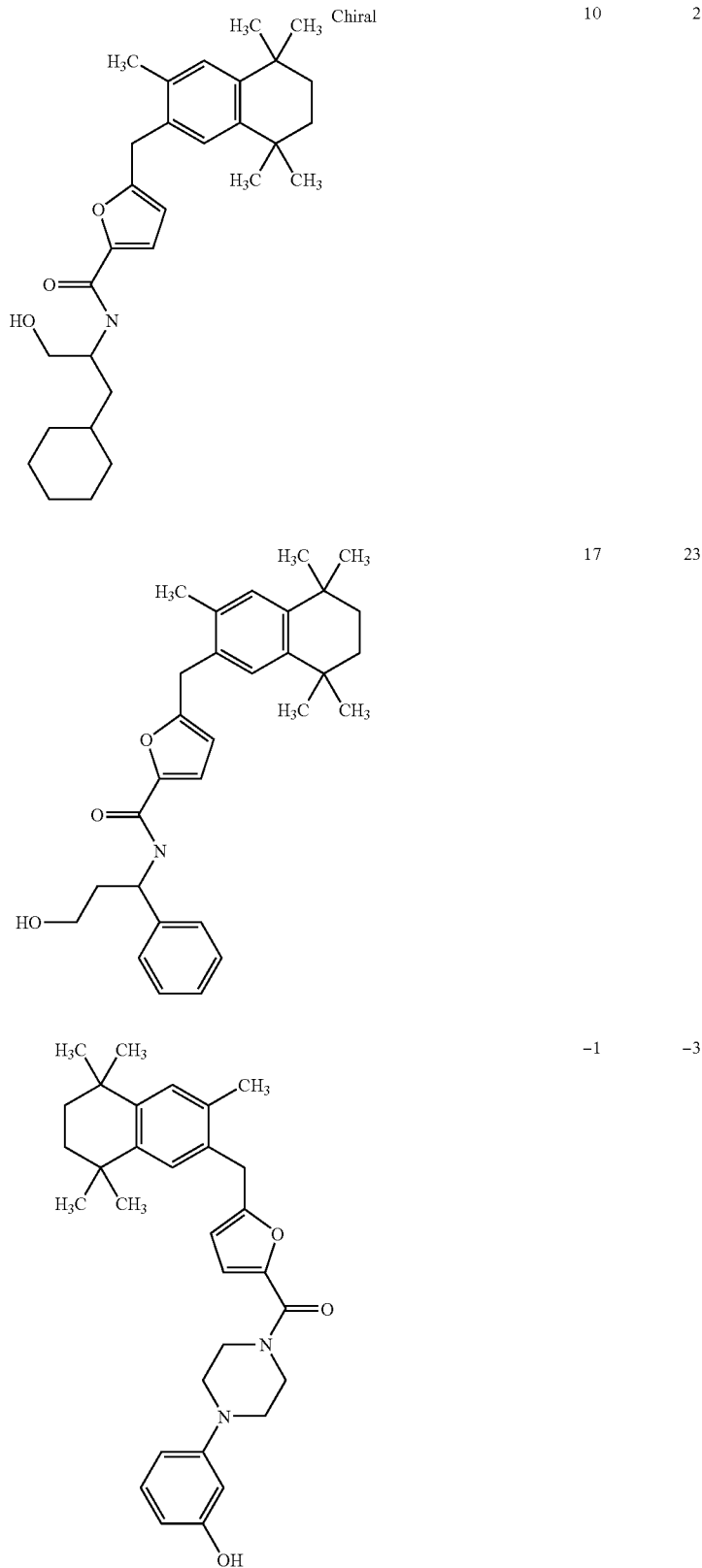

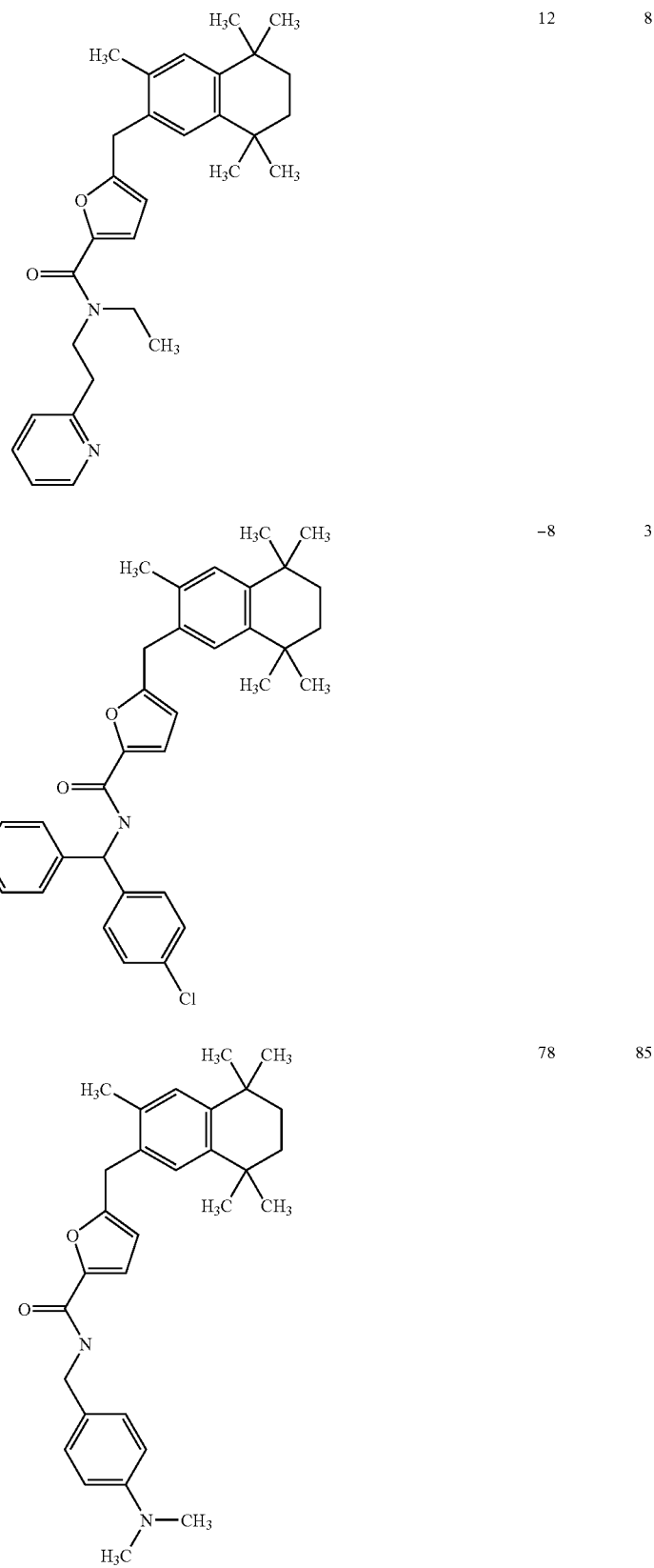

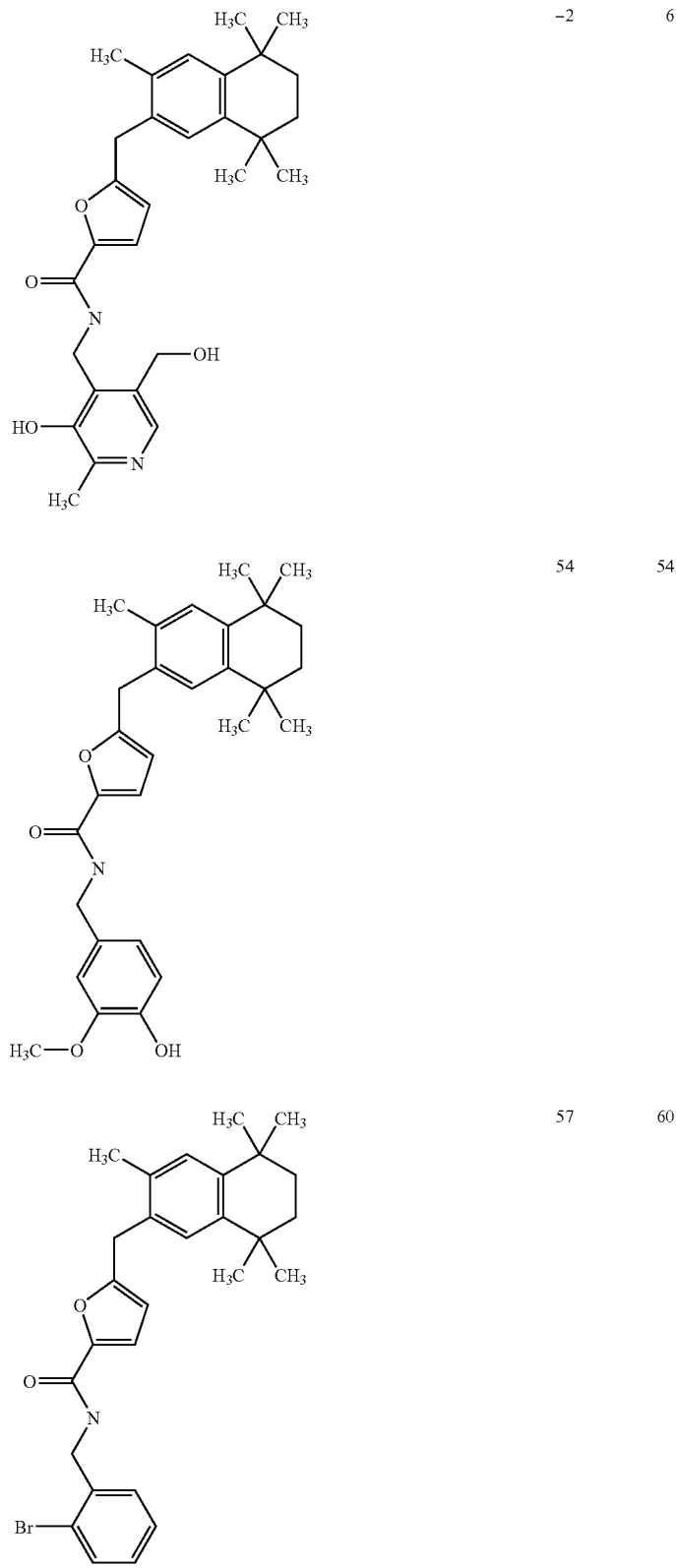

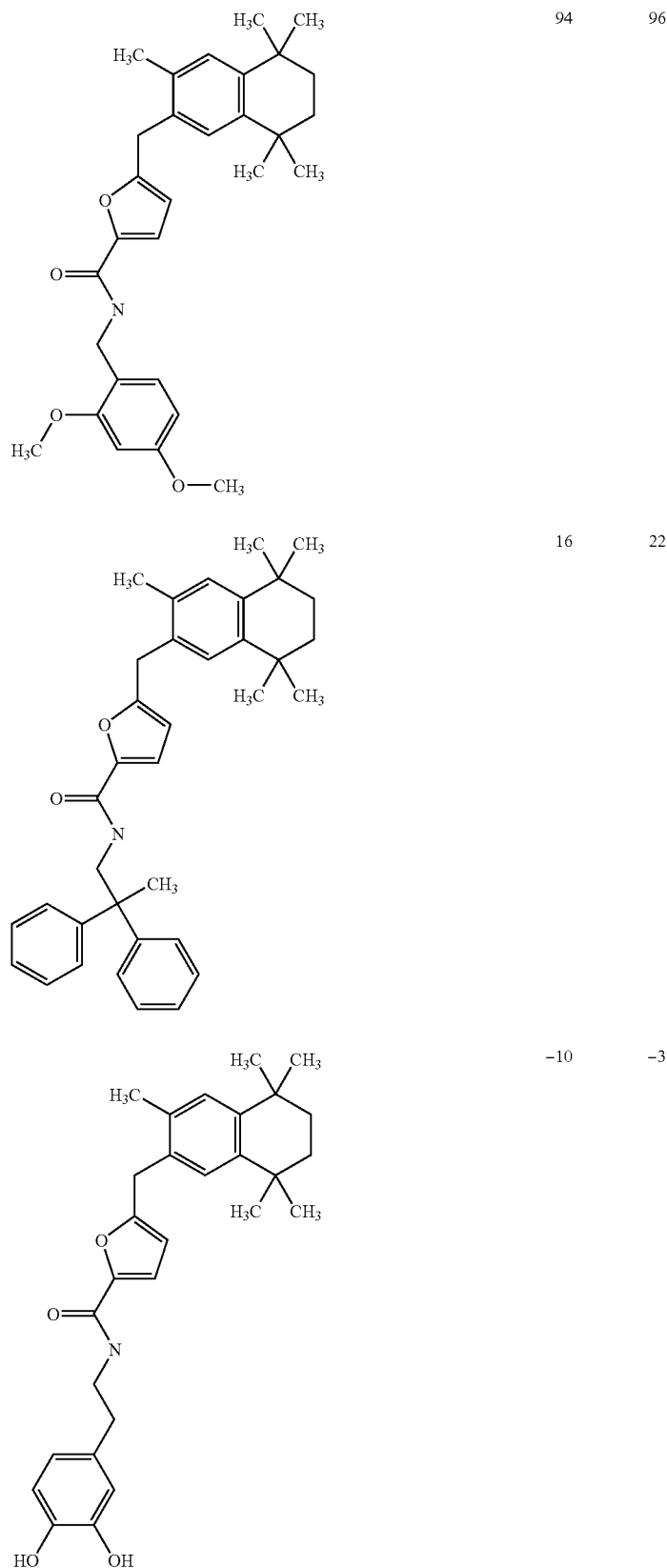

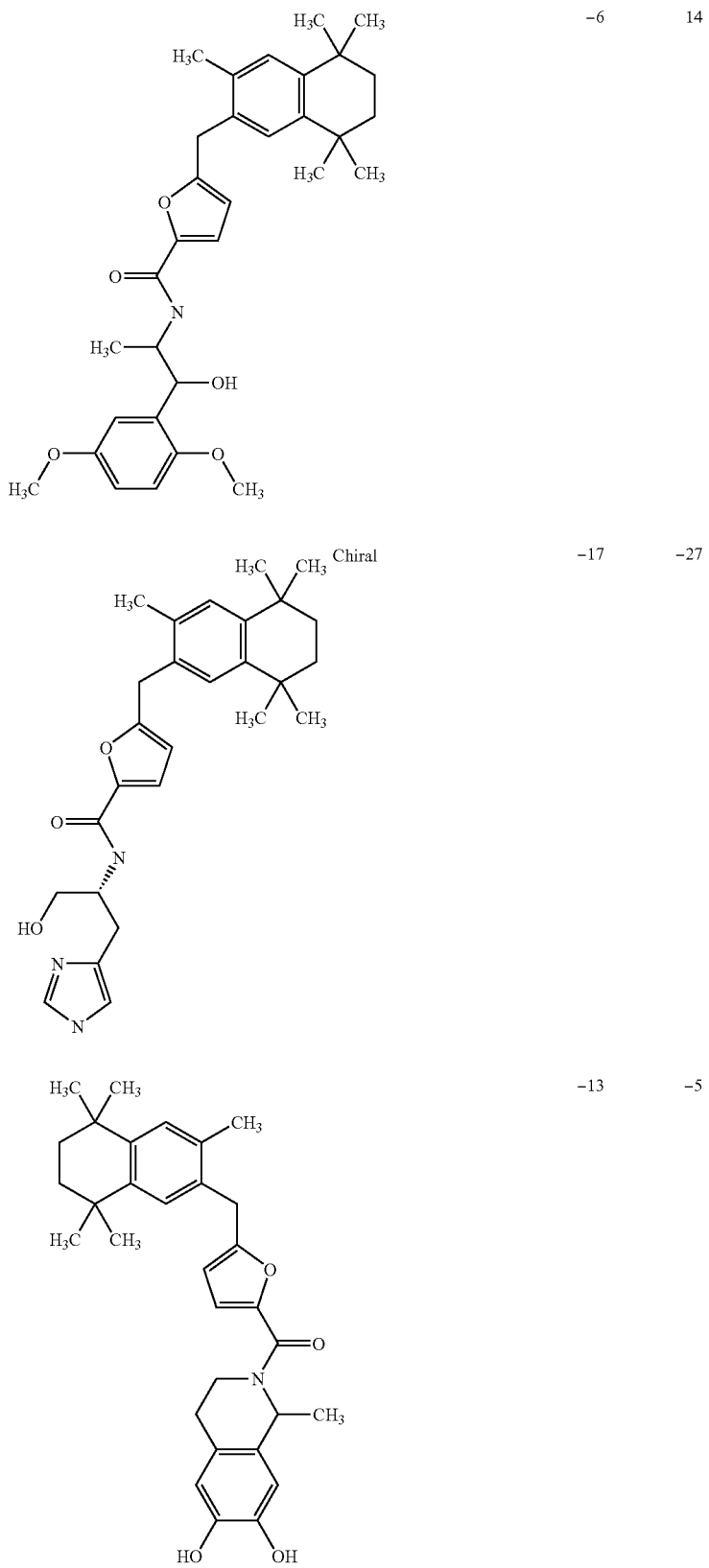

-continued
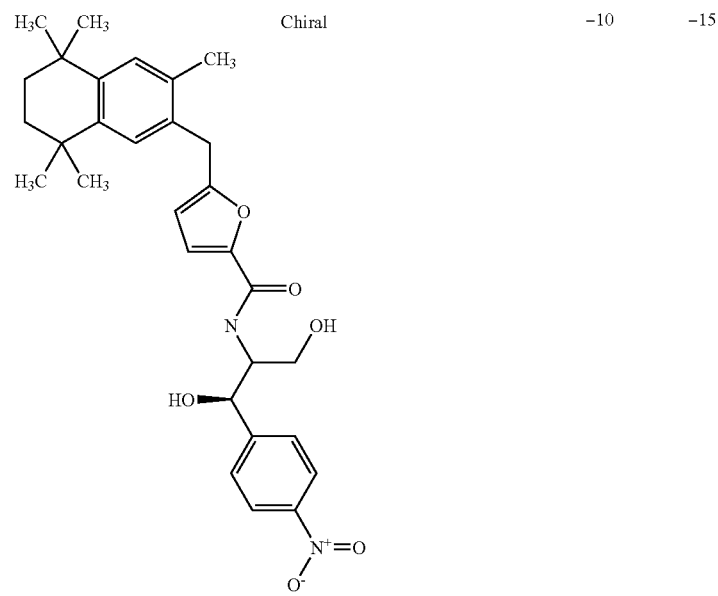
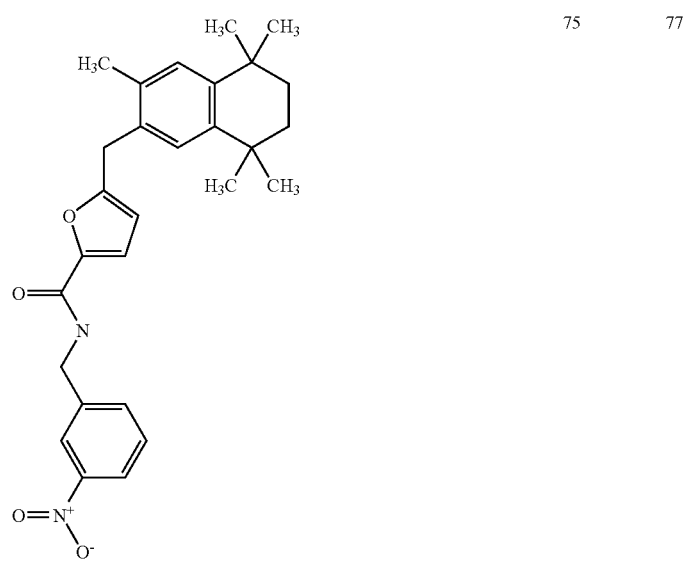

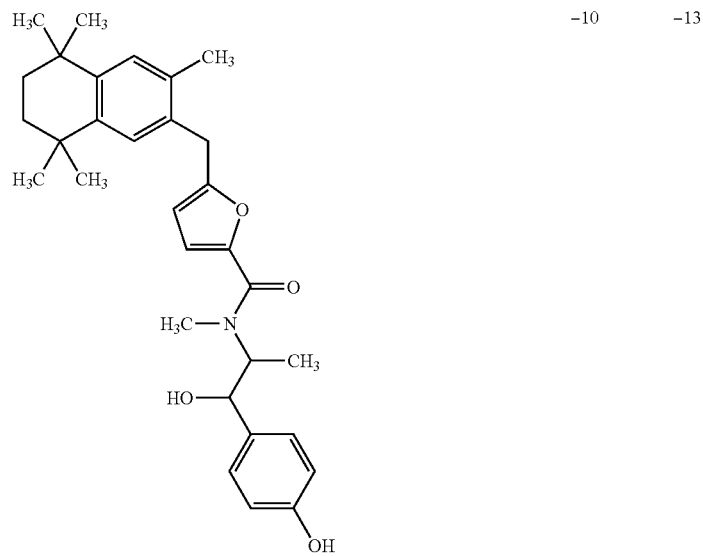 −10 −13
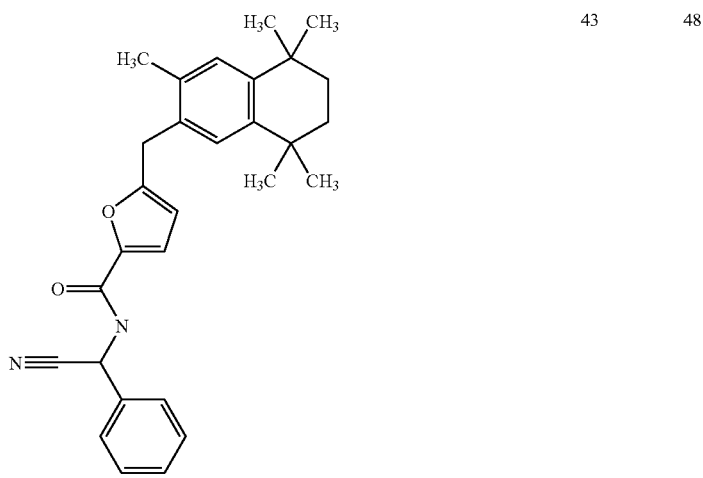 43 48
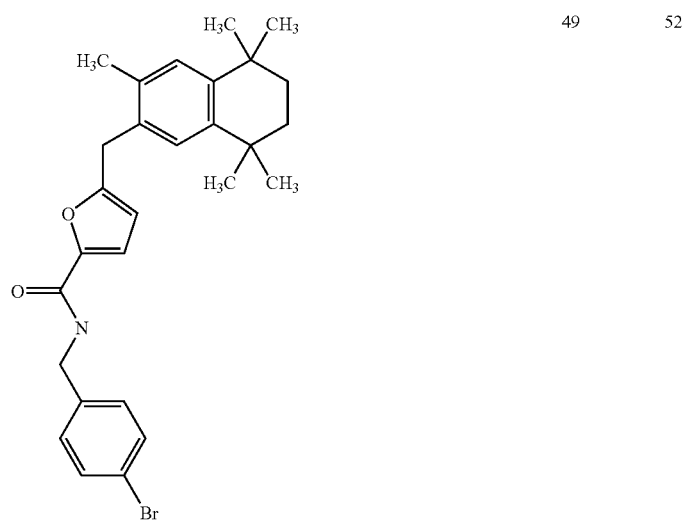 49 52

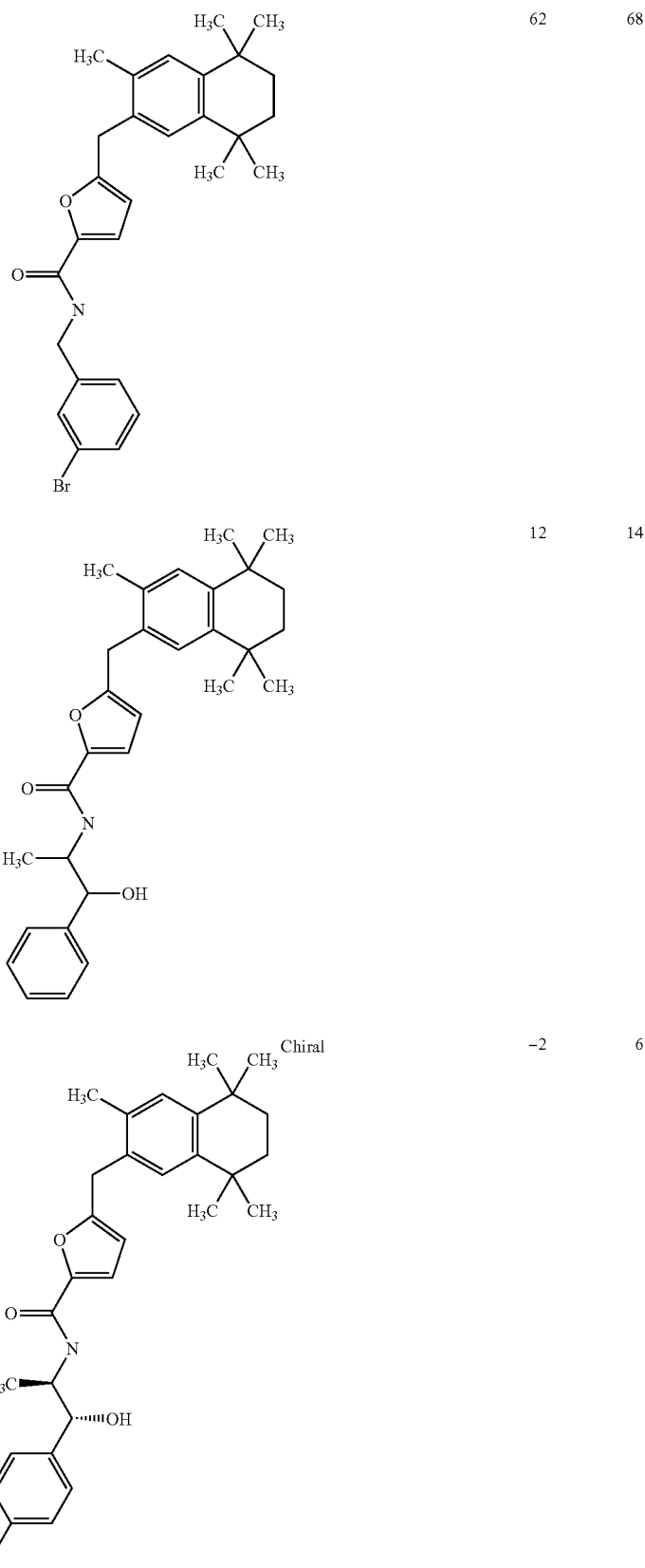

| | 41 | 44 |
|---|---|---|
| 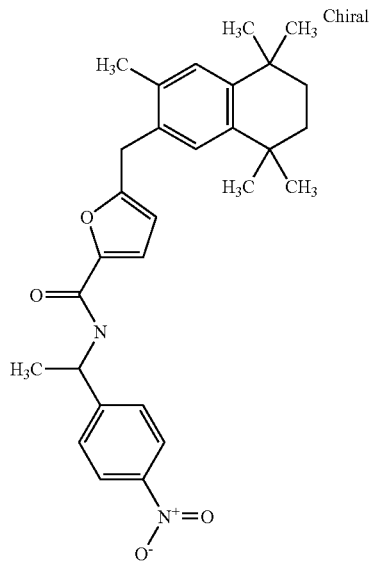 | | |
| 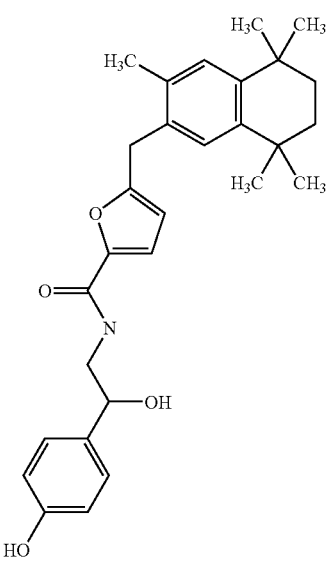 | 25 | 28 |

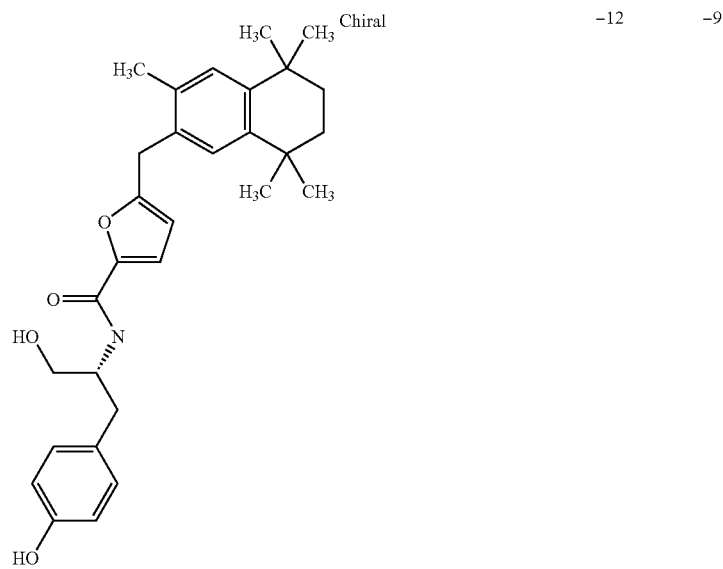
| MOLSTRUCTURE | % Inhib. @ 10 uM mGnRH |
|---|---|
| 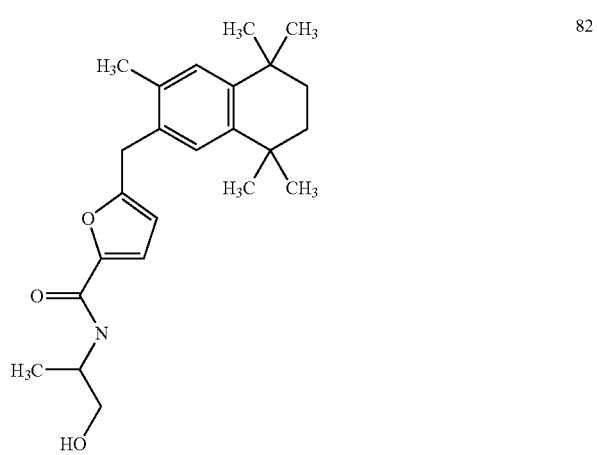 | 82 |

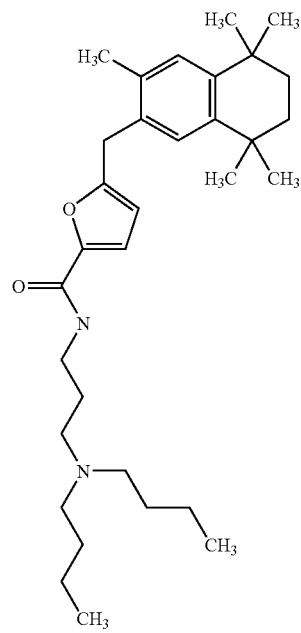
103
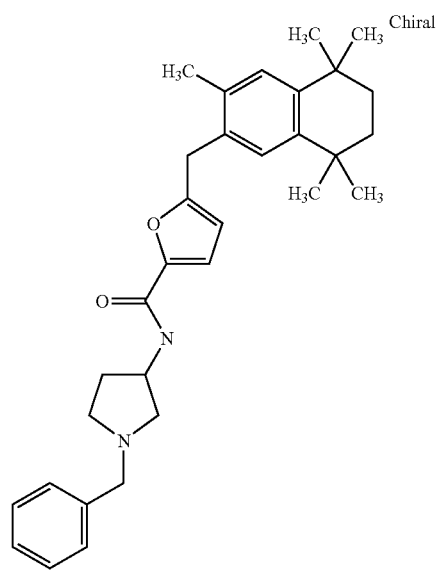
101

-continued
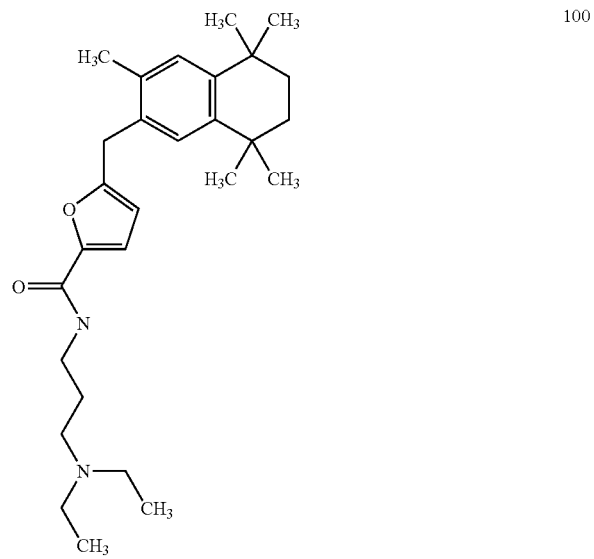
100
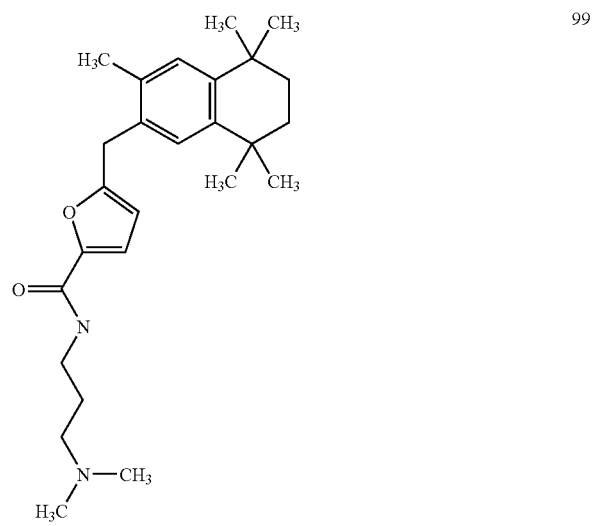
99
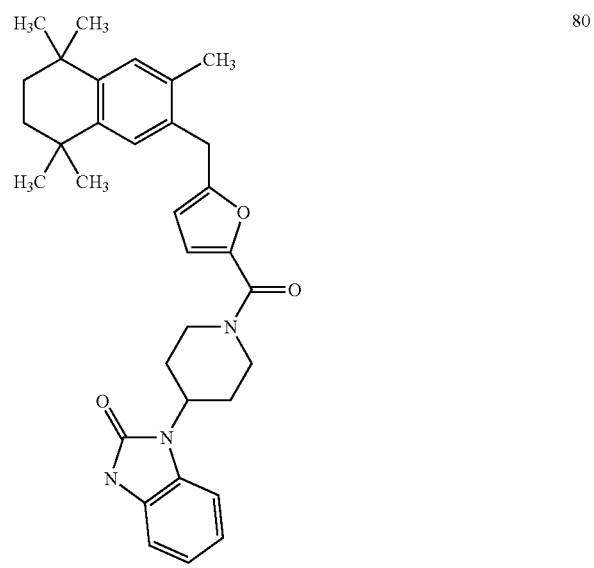
80

-continued
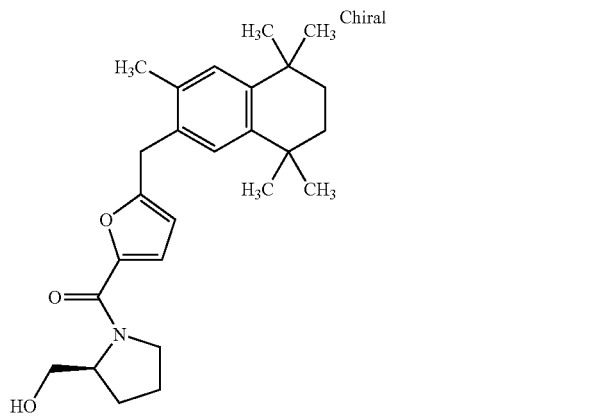
93
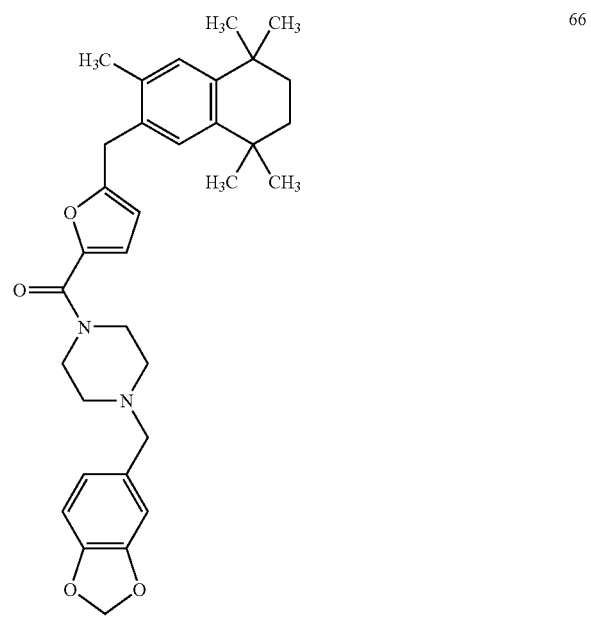
66
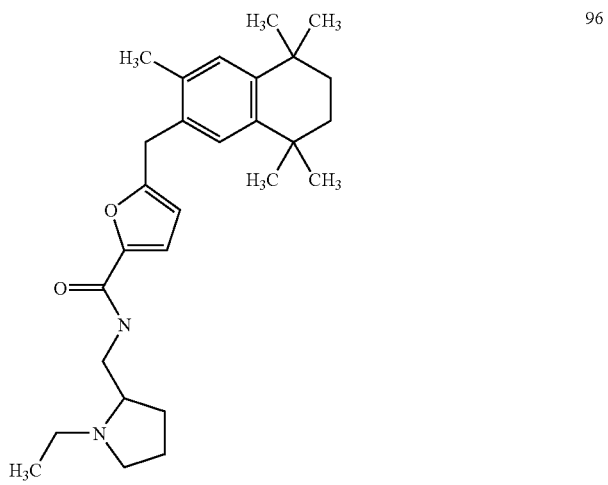
96

-continued
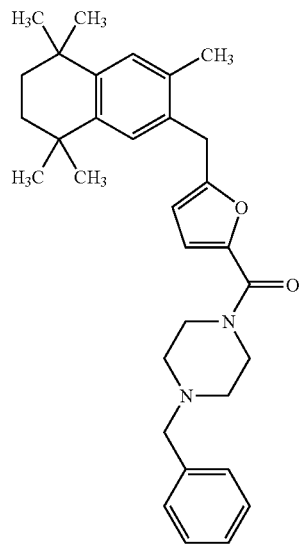
83
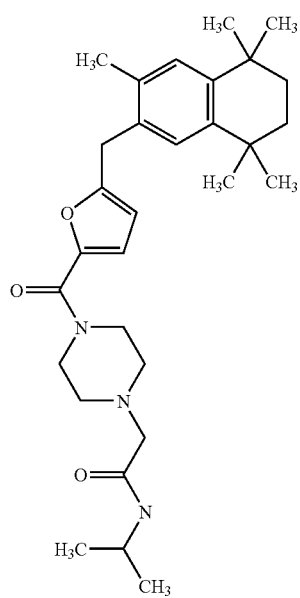
63

-continued
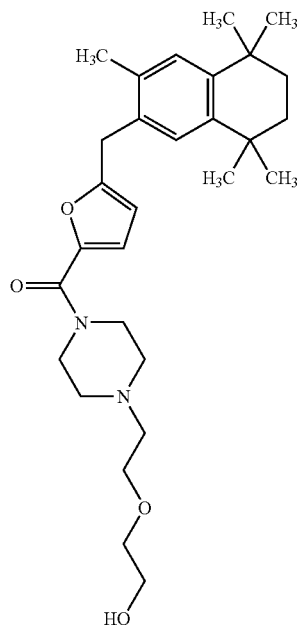
63
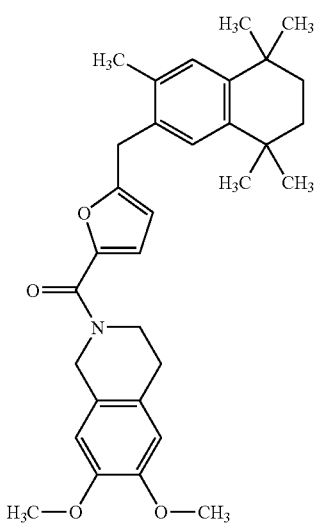
46

-continued
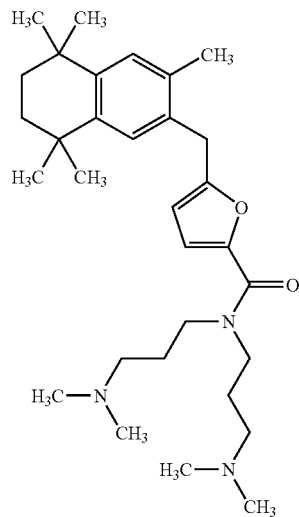
71
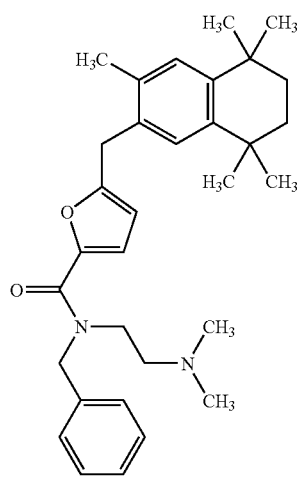
104
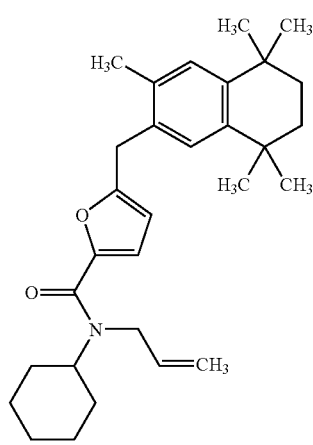
65

-continued
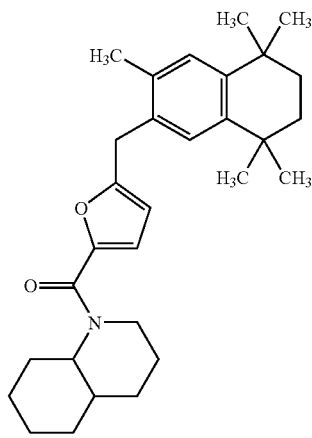 94
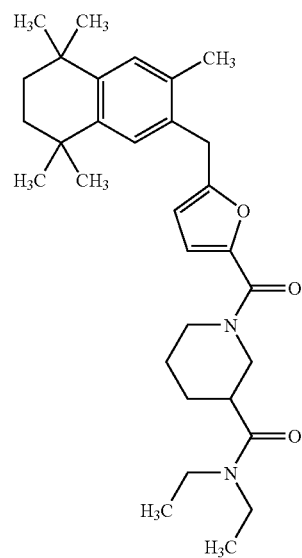 21
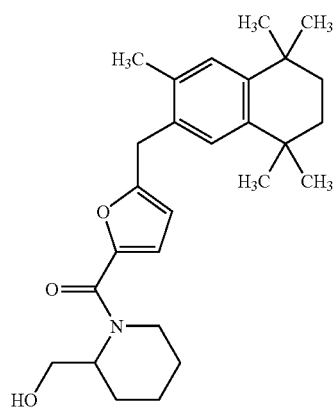 84

-continued
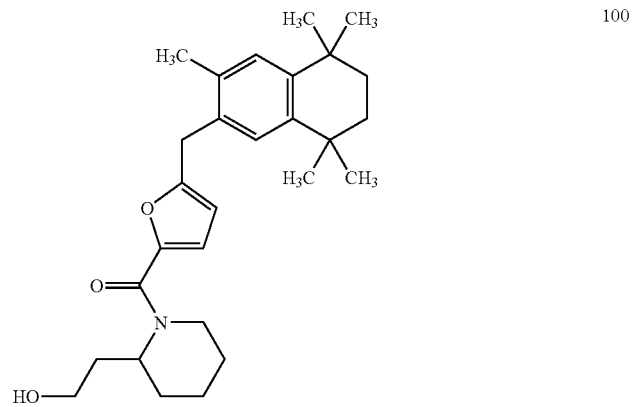
100
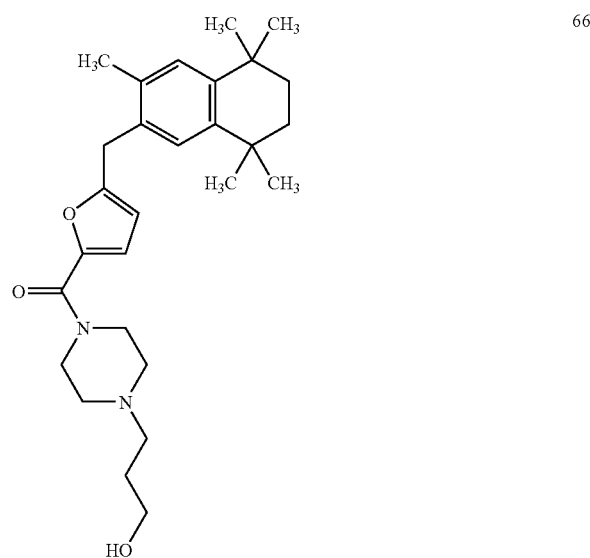
66
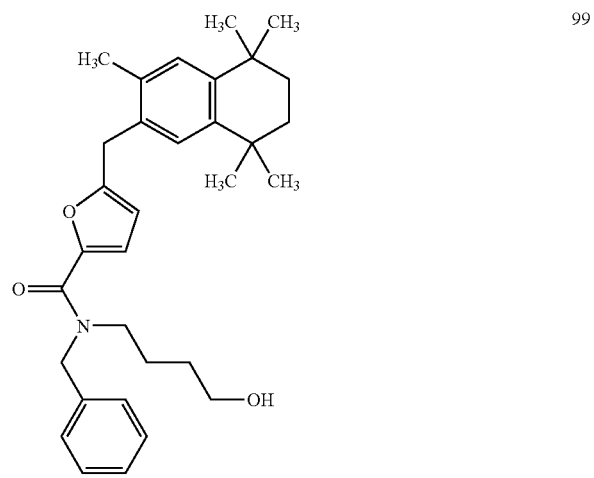
99

-continued
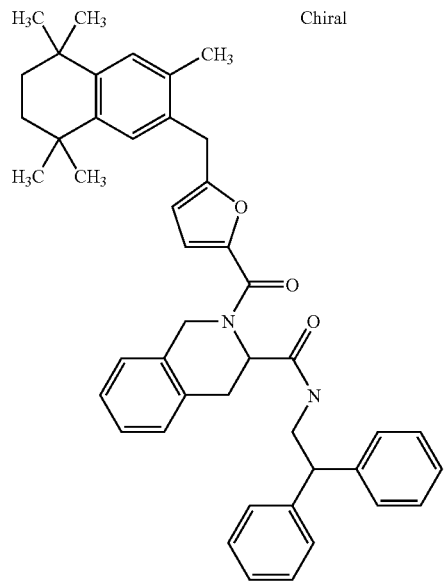
9 Chiral
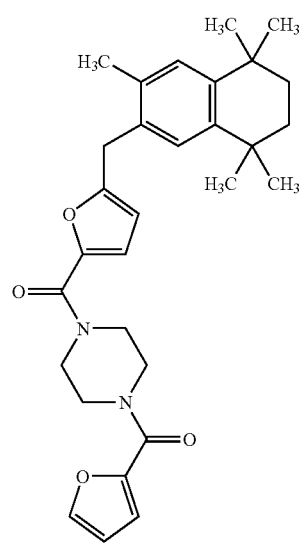
89
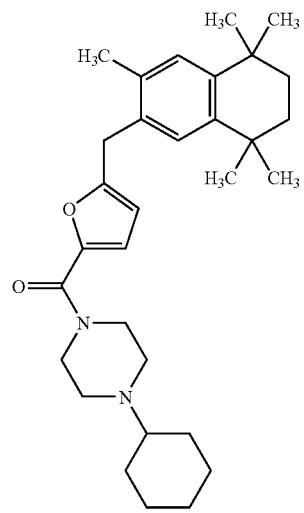
102

-continued
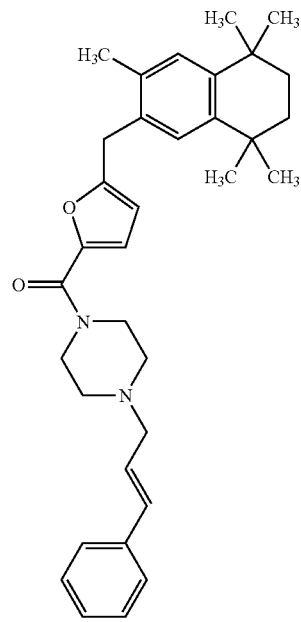
86
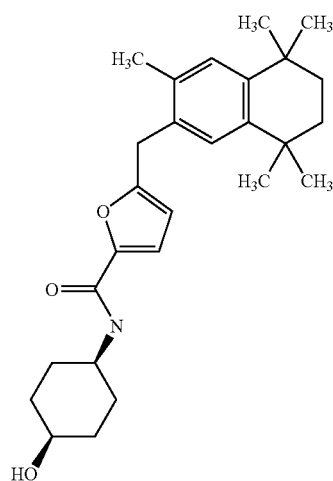
82
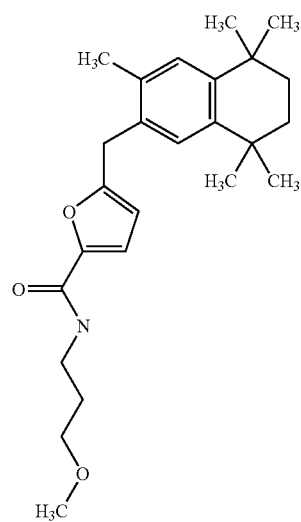
101

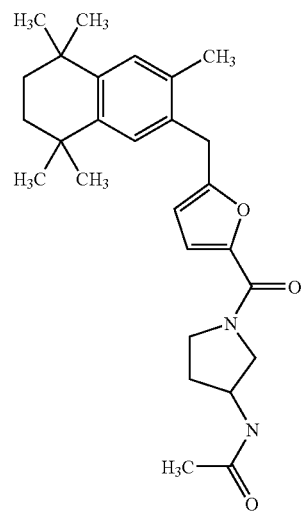
63
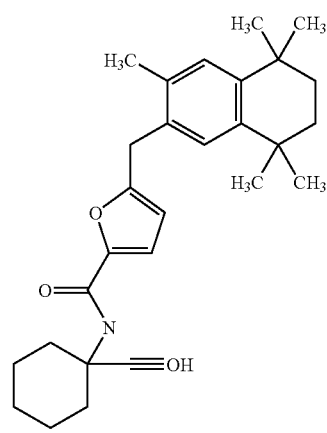
59
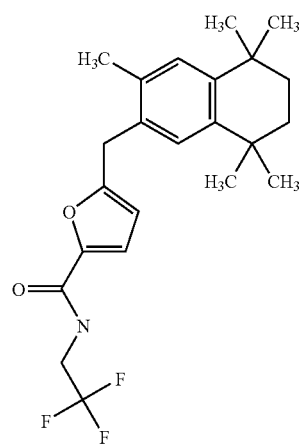
26

-continued
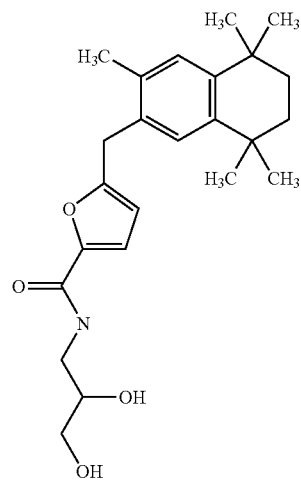
14
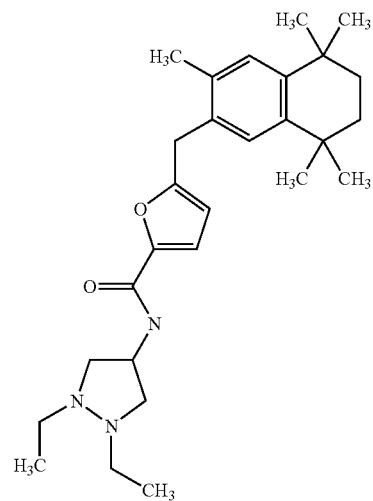
91
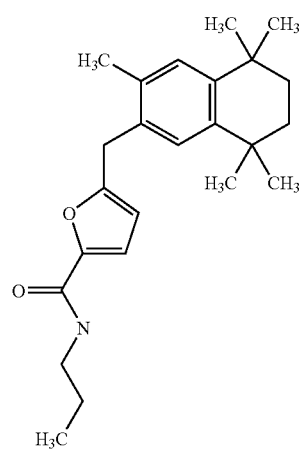
93

| | |
|---|---|
| 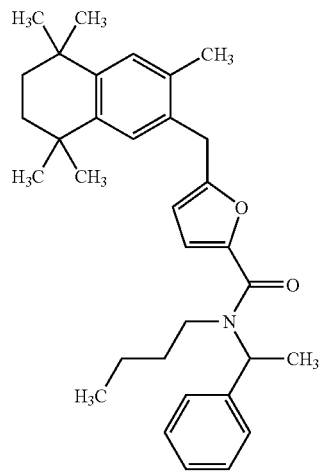 | 65 |
| 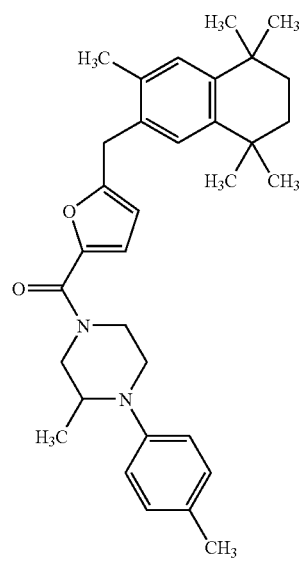 | 73 |
| 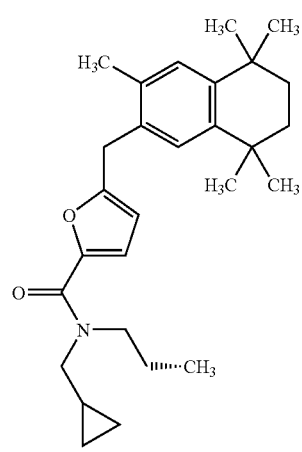 | 96 |

-continued
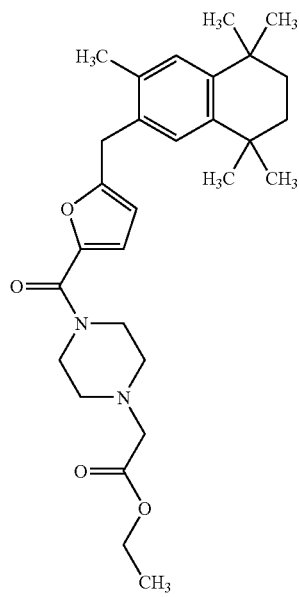
66
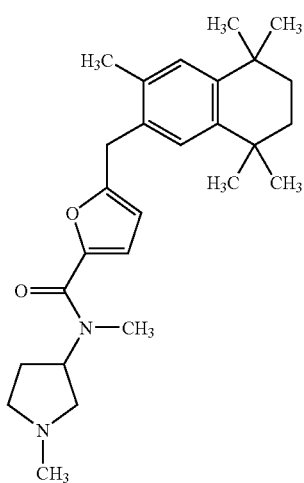
89

-continued
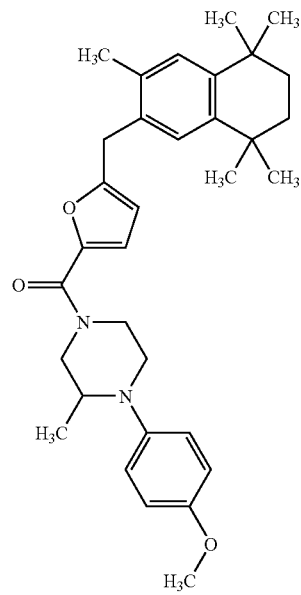
73
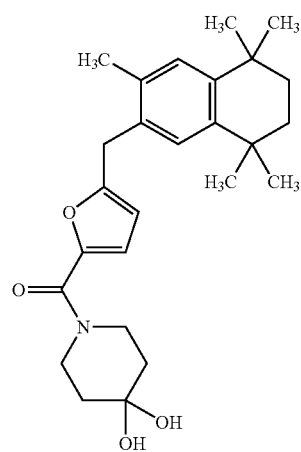
22
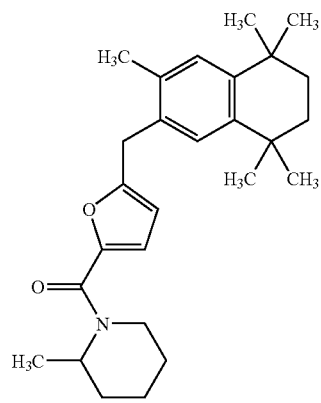
100

-continued
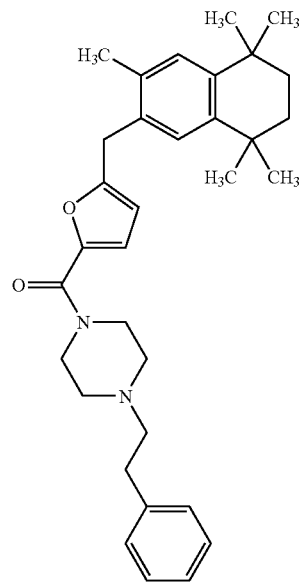
97
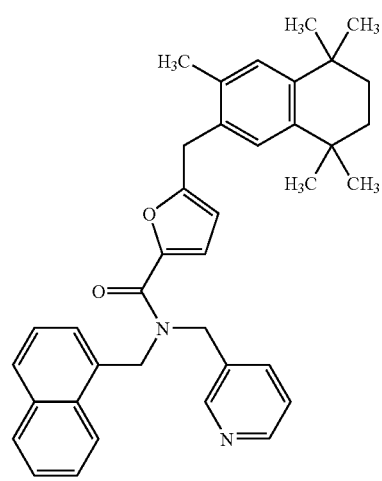
79
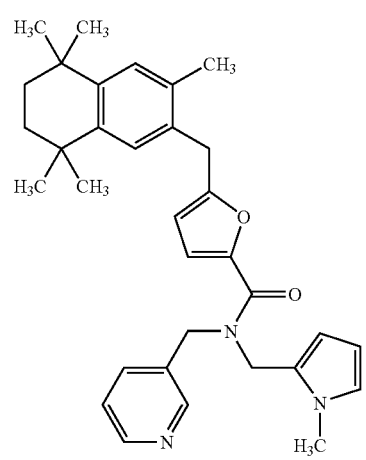
100

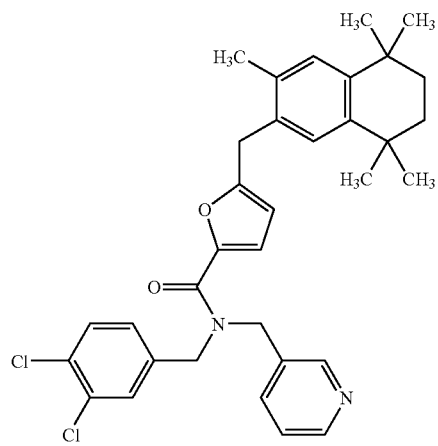
79
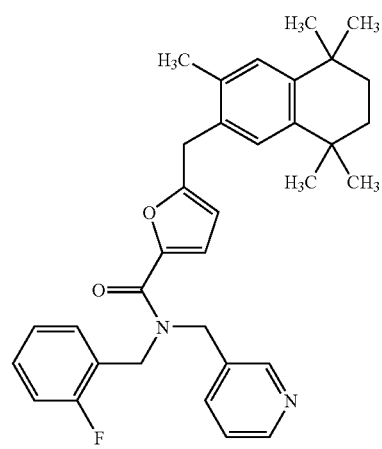
95
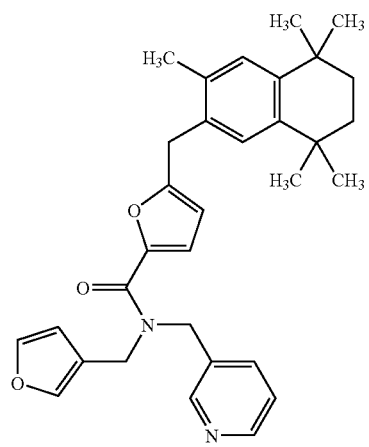
99

-continued
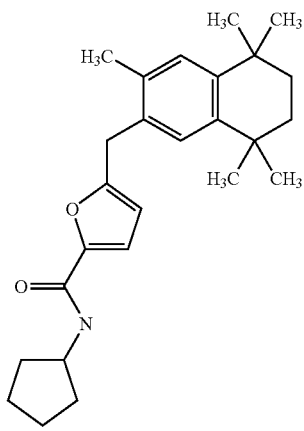
73
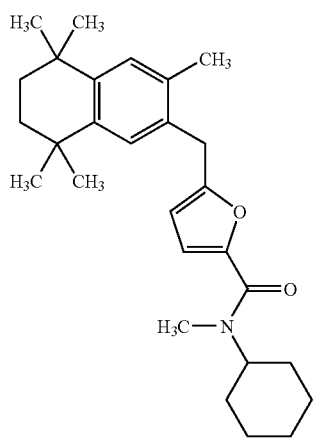
97
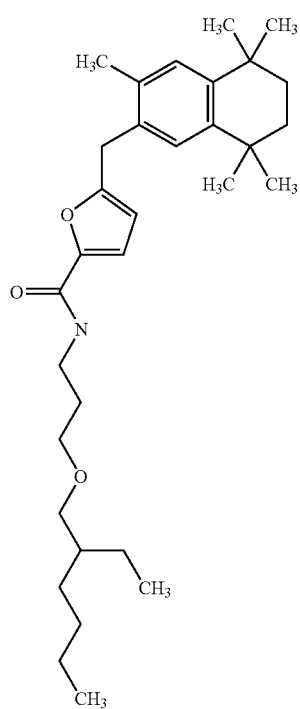
58

-continued
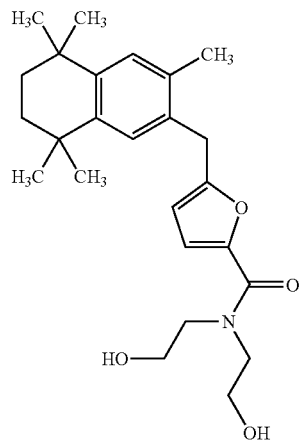
34
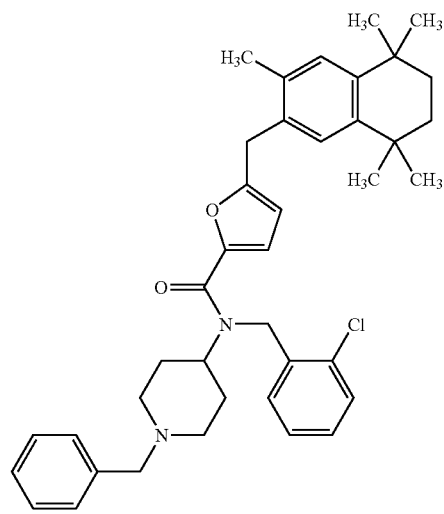
43
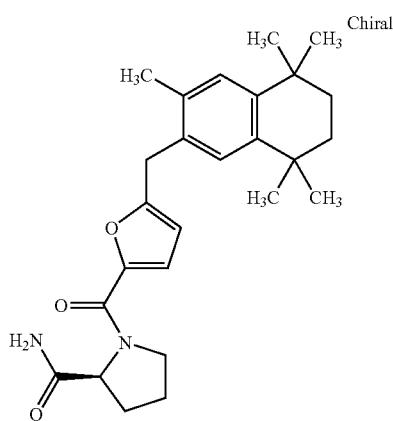
74

-continued
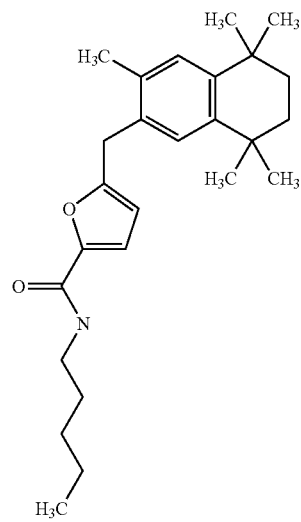
91
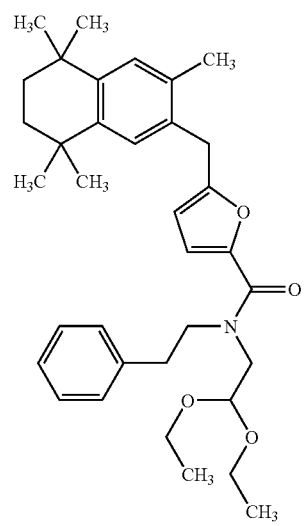
66
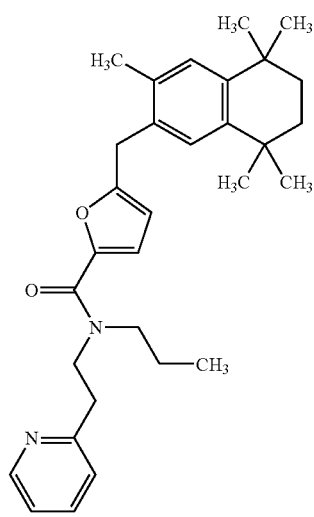
100

-continued
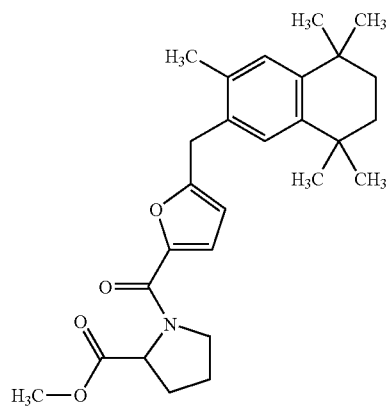
97
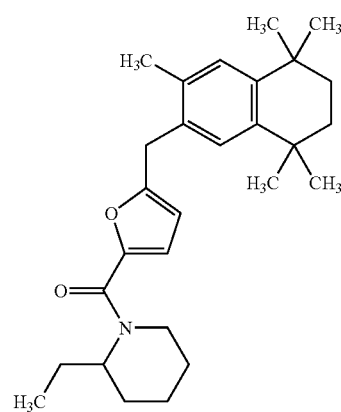
100
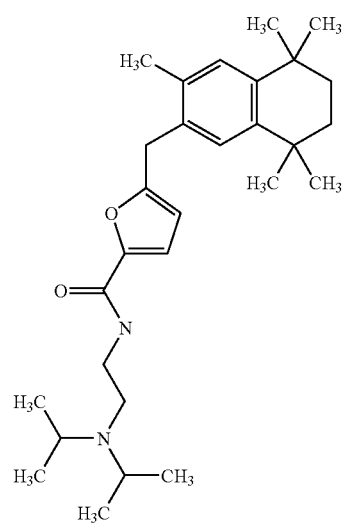
102

-continued
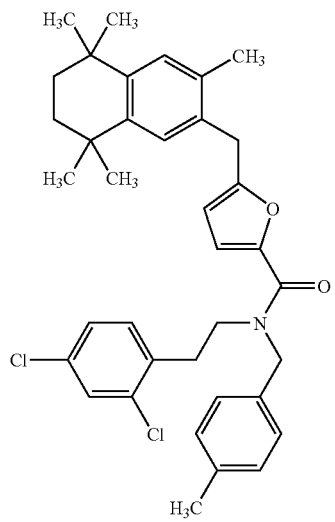
23
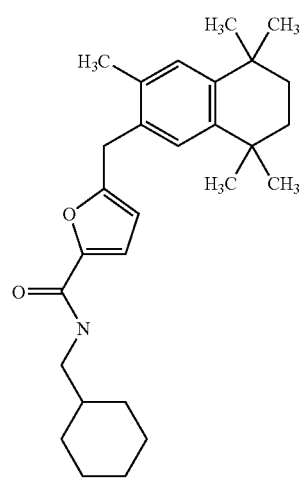
72
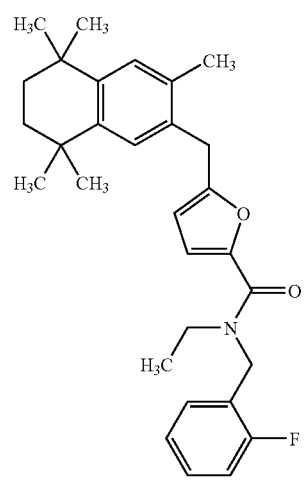
86

-continued
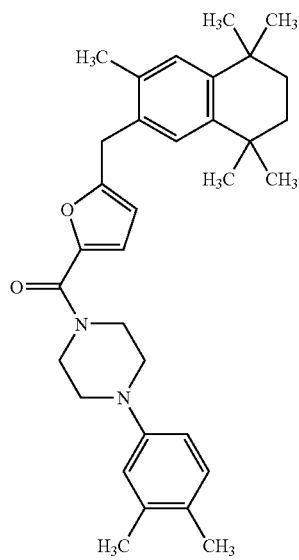
75
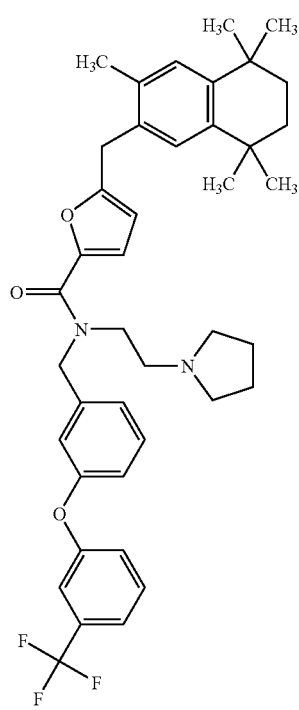
99

-continued
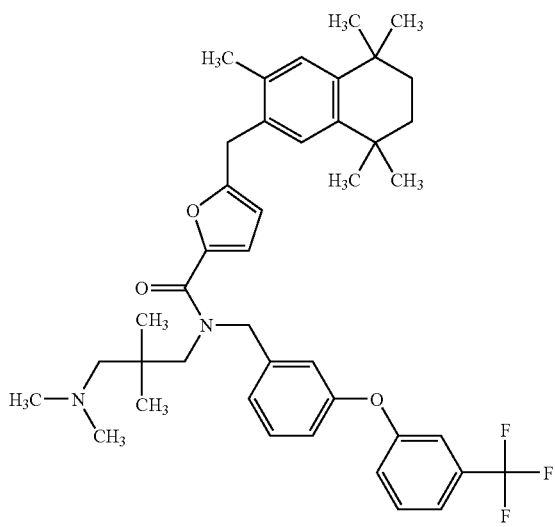 89
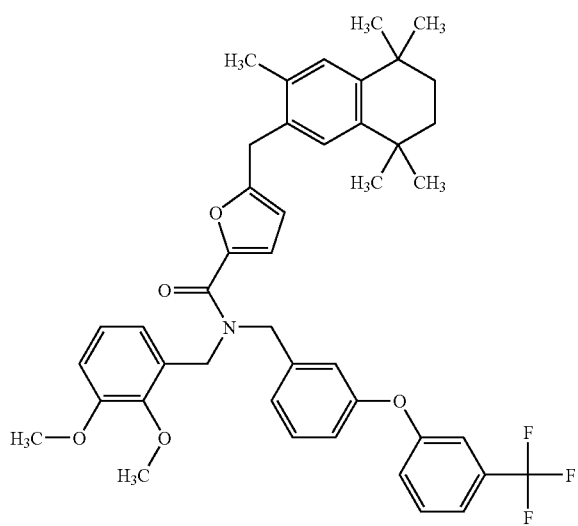 75
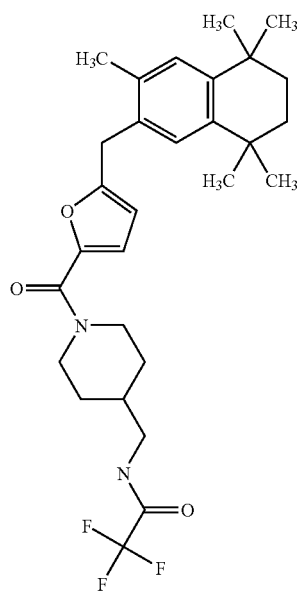 41

-continued
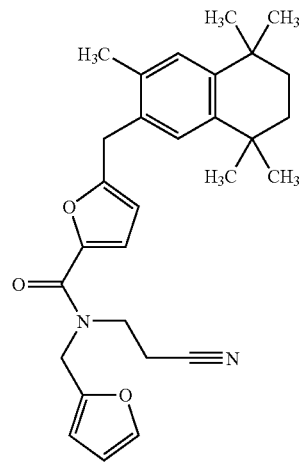
77
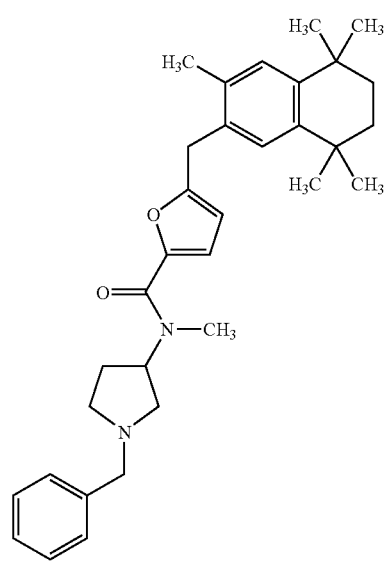
98
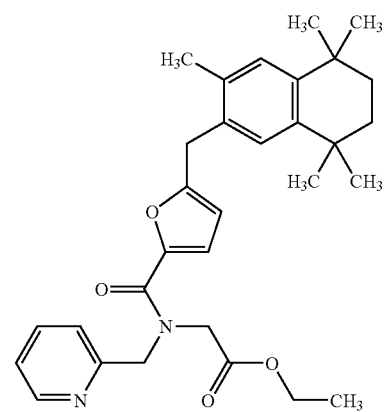

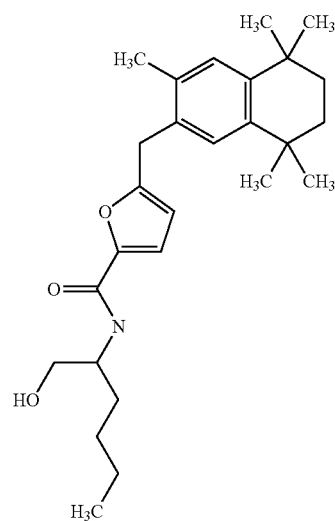
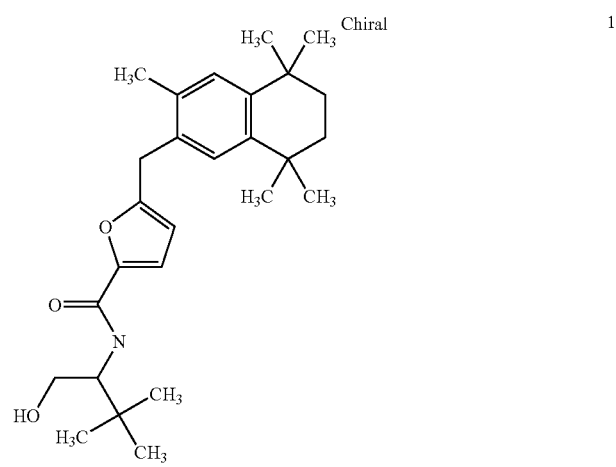
101
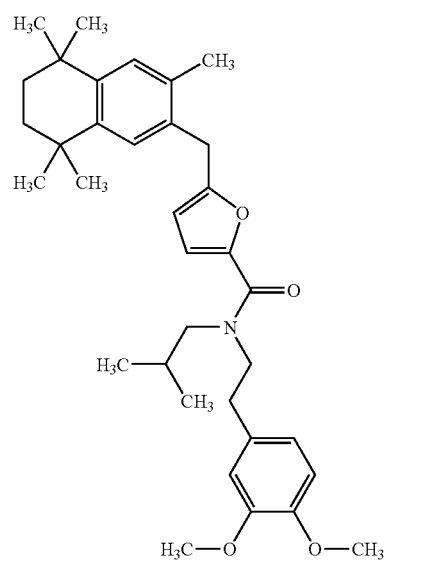
90

-continued
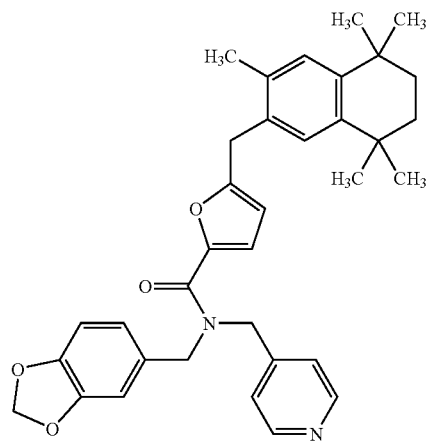
91
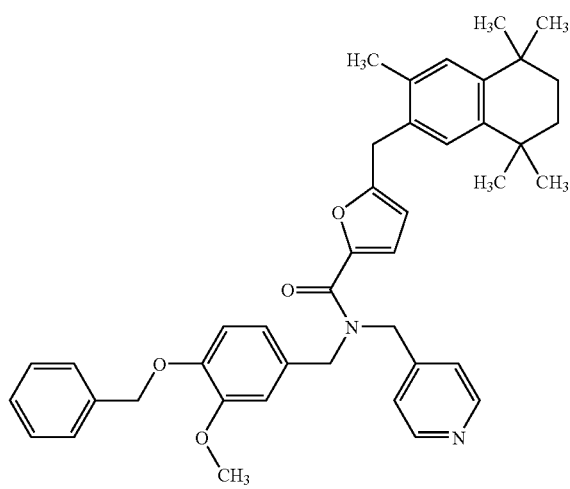
64
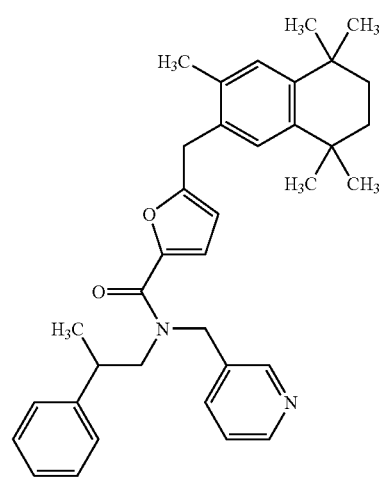
97

-continued
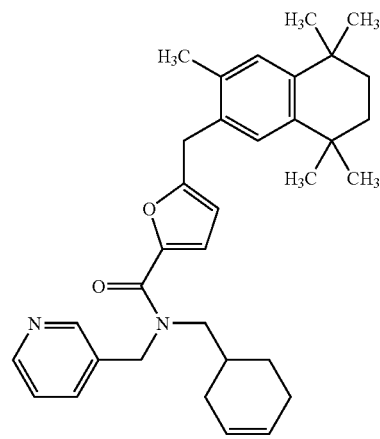
94
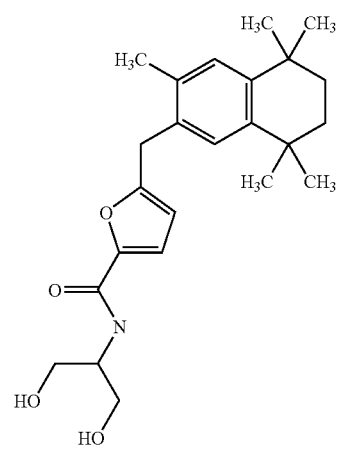
22
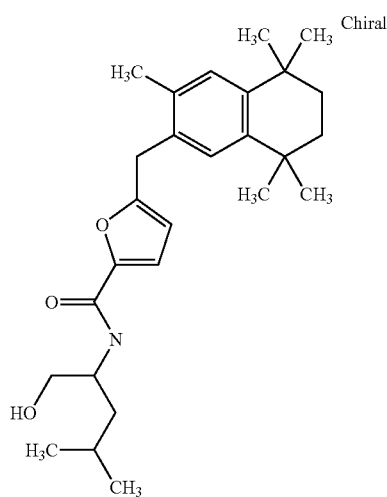
98

-continued
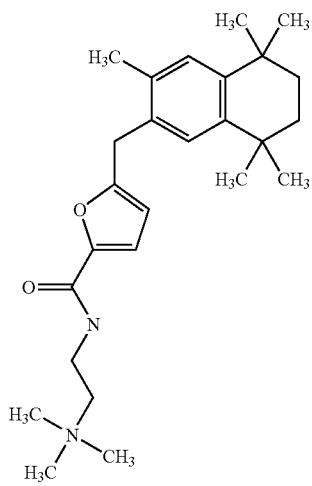
49
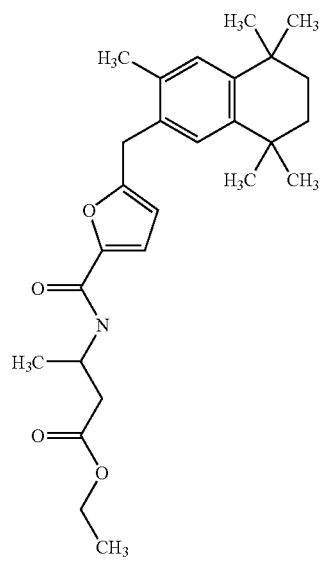
88
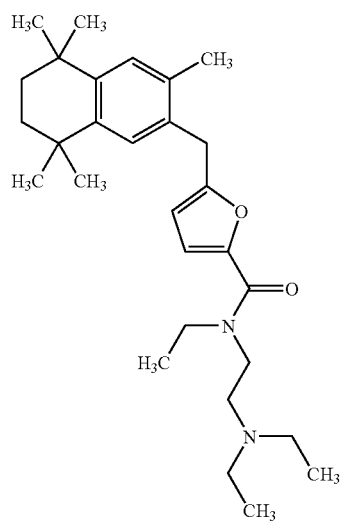
98

-continued
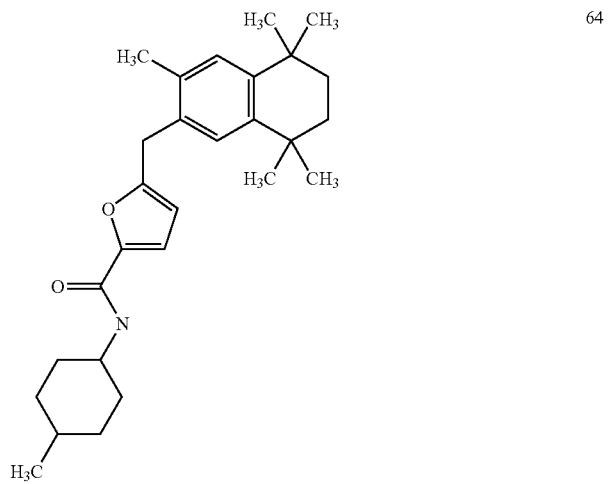
64
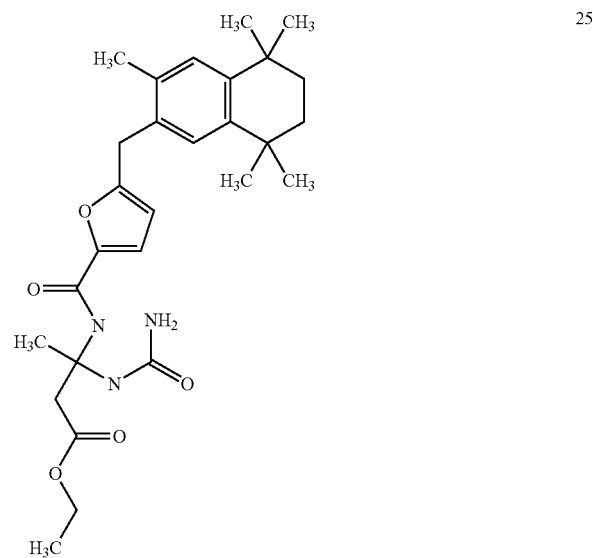
25
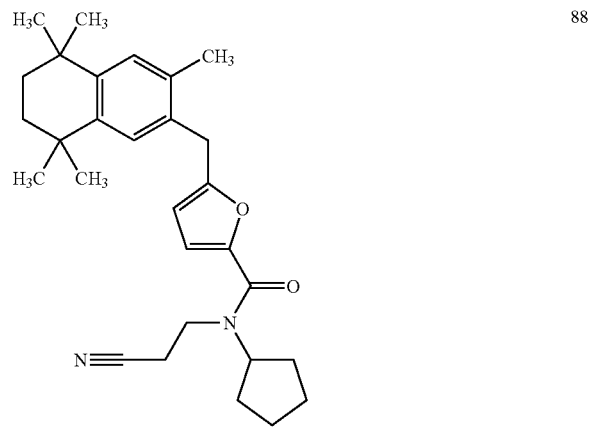
88

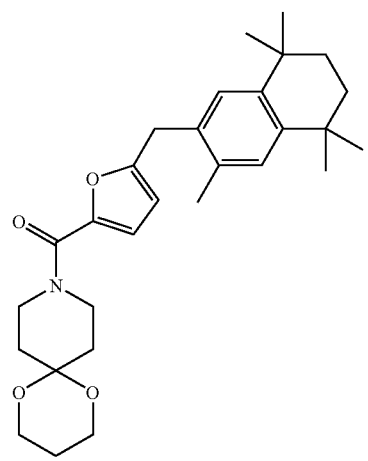
99
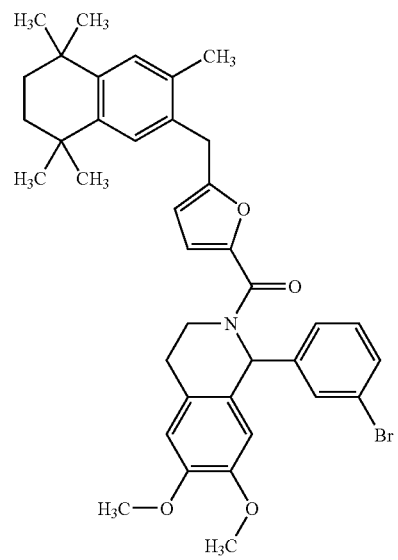
−23
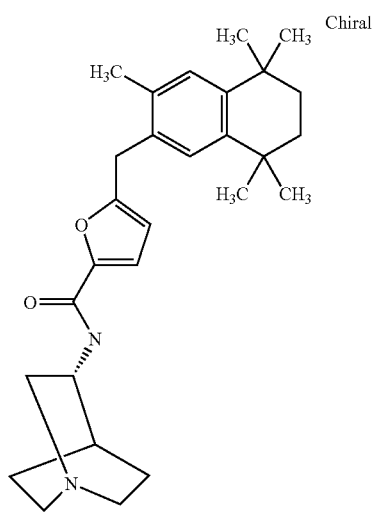
12

-continued
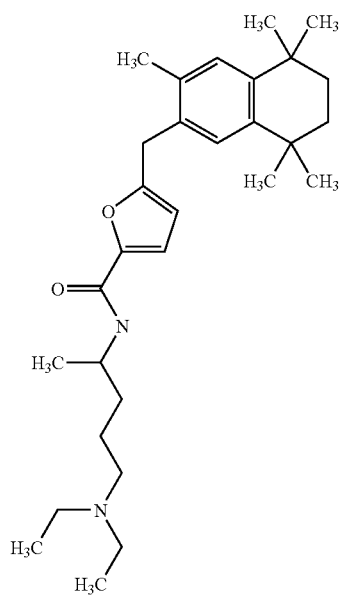
99
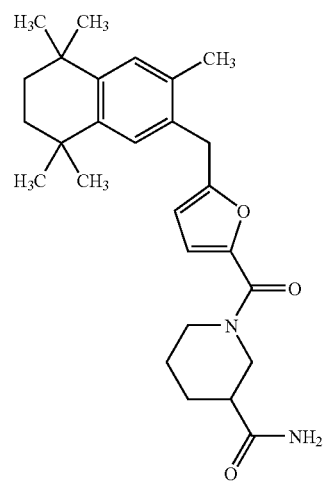
69
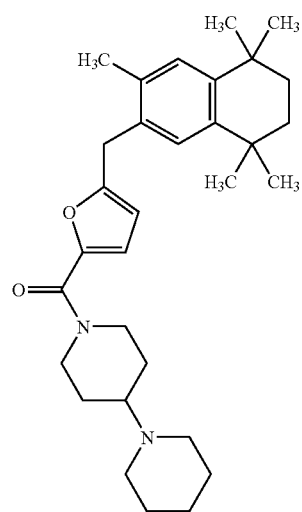
92

-continued
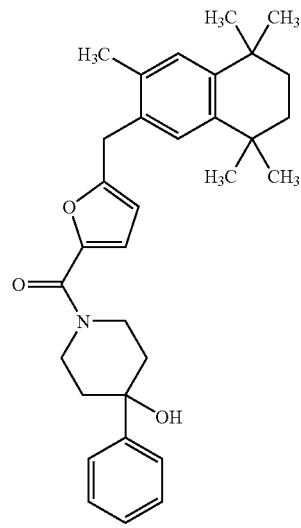
72
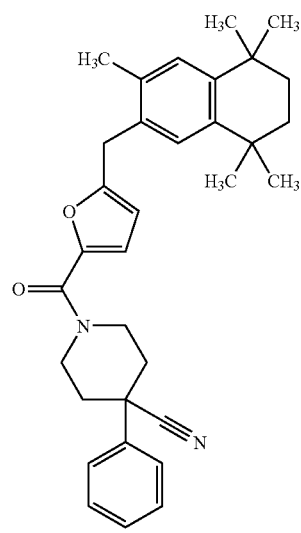
40
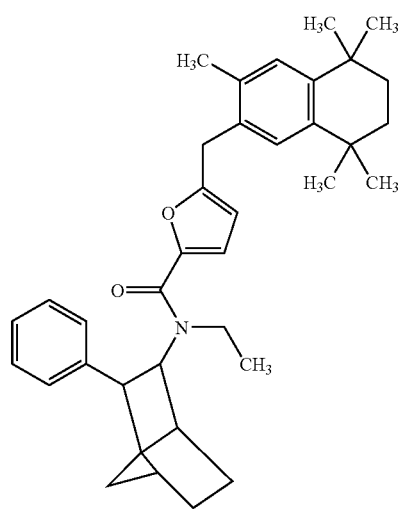
49

-continued
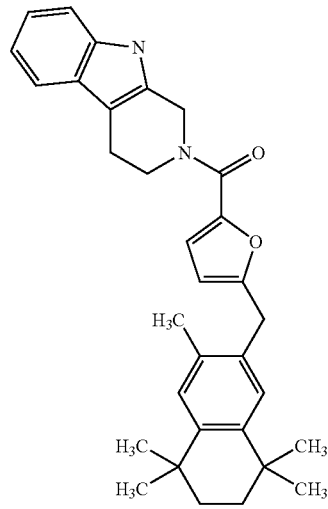
44
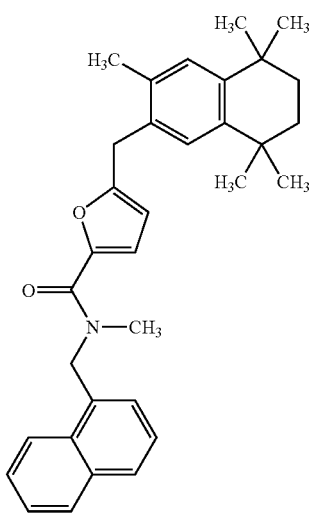
51
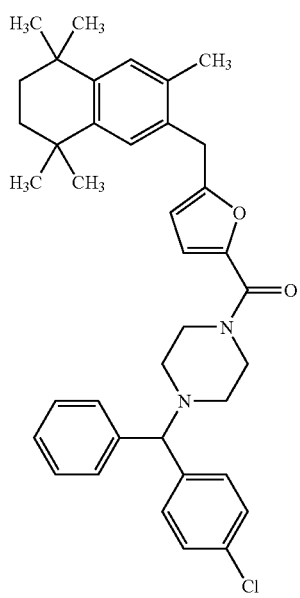
4

-continued
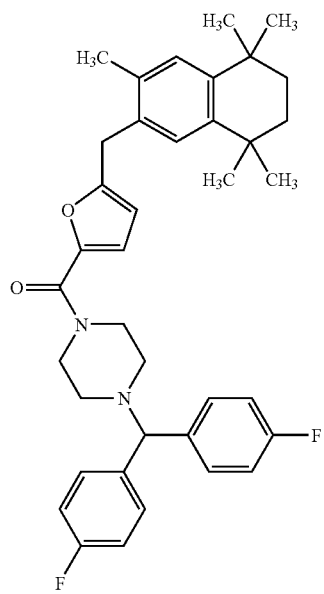
16
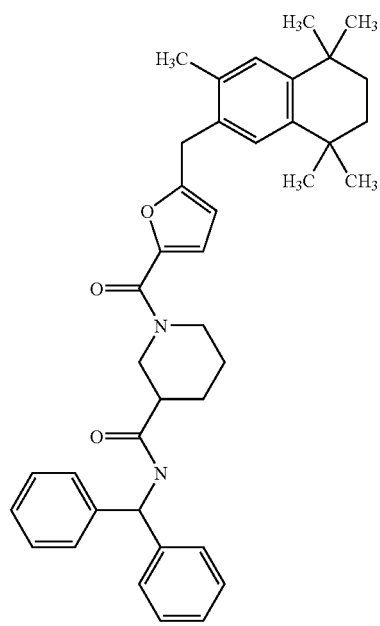
9
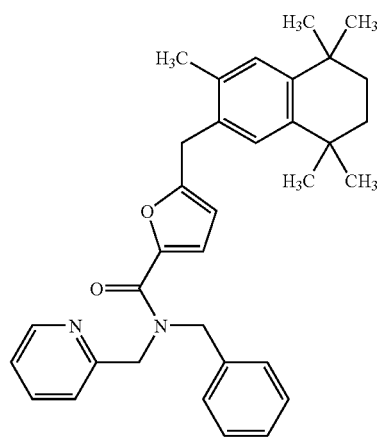
98

-continued
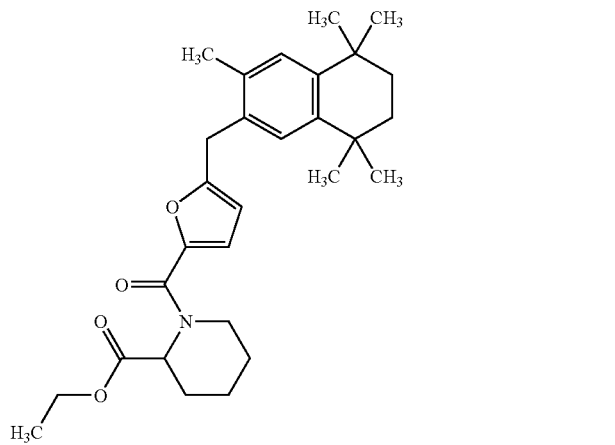
94
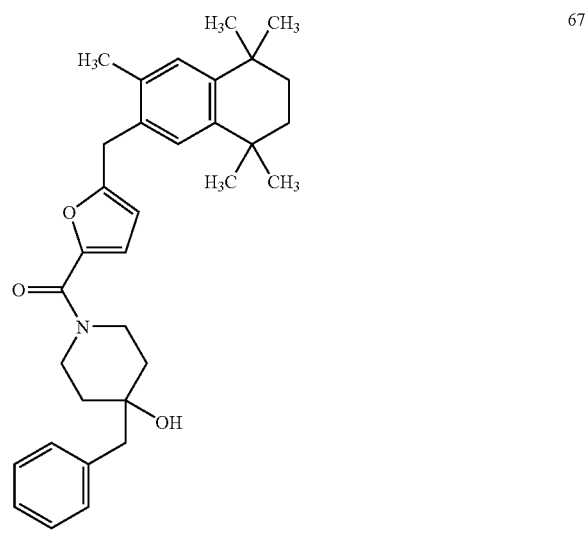
67
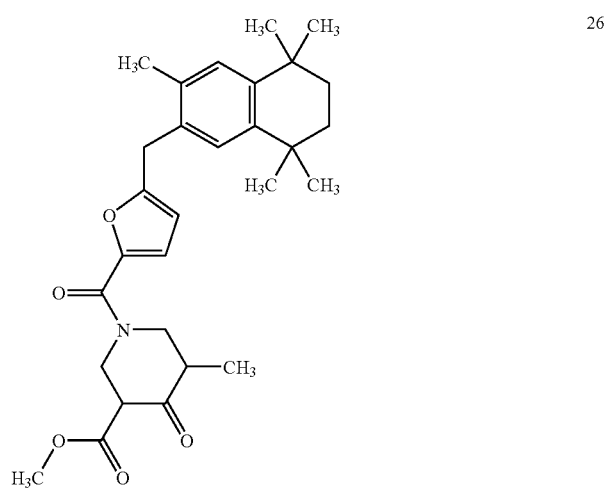
26

-continued
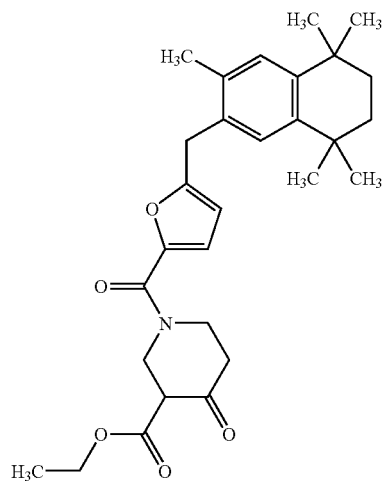
71
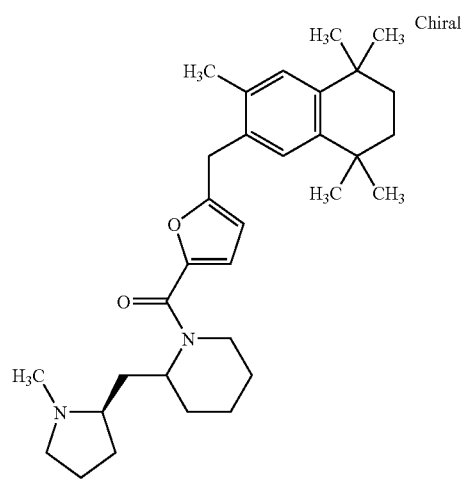
28
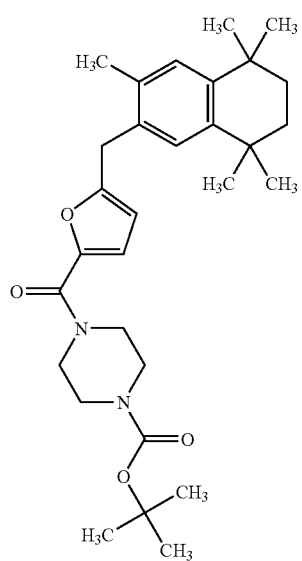
90

-continued
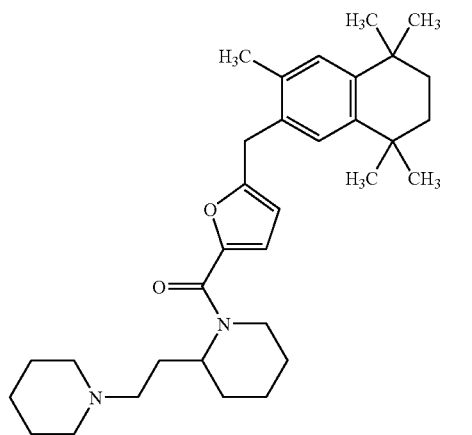
103
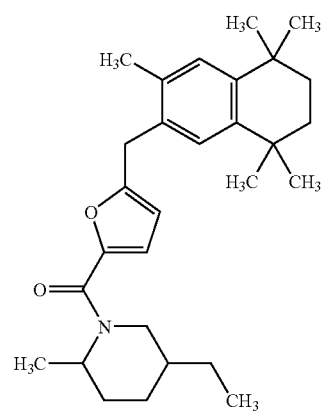
95
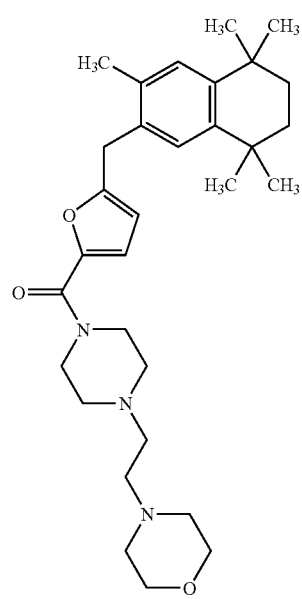
73

-continued
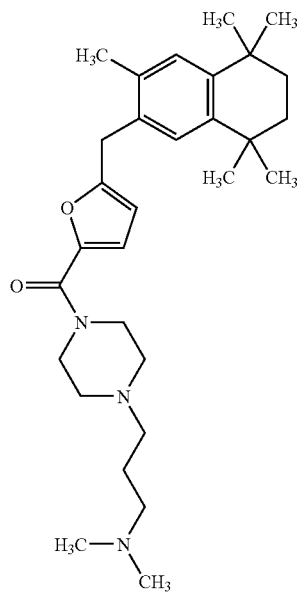
96
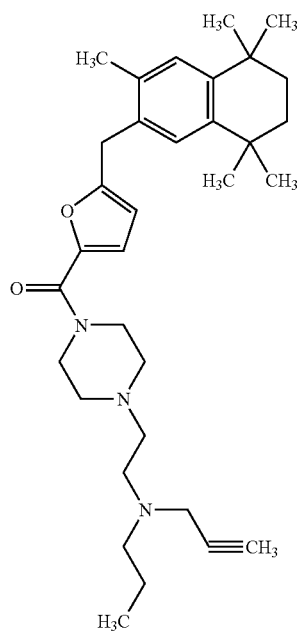
101

-continued
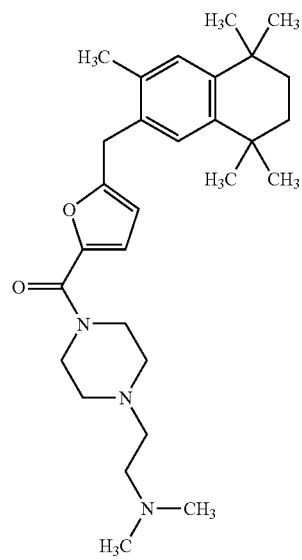
98
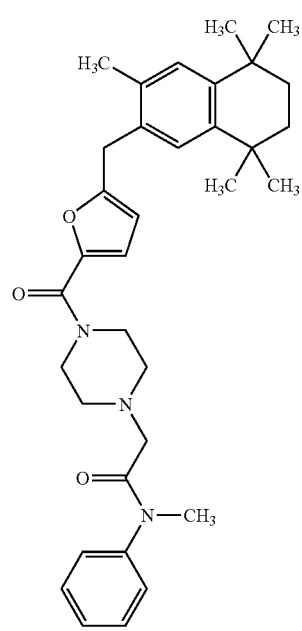
103

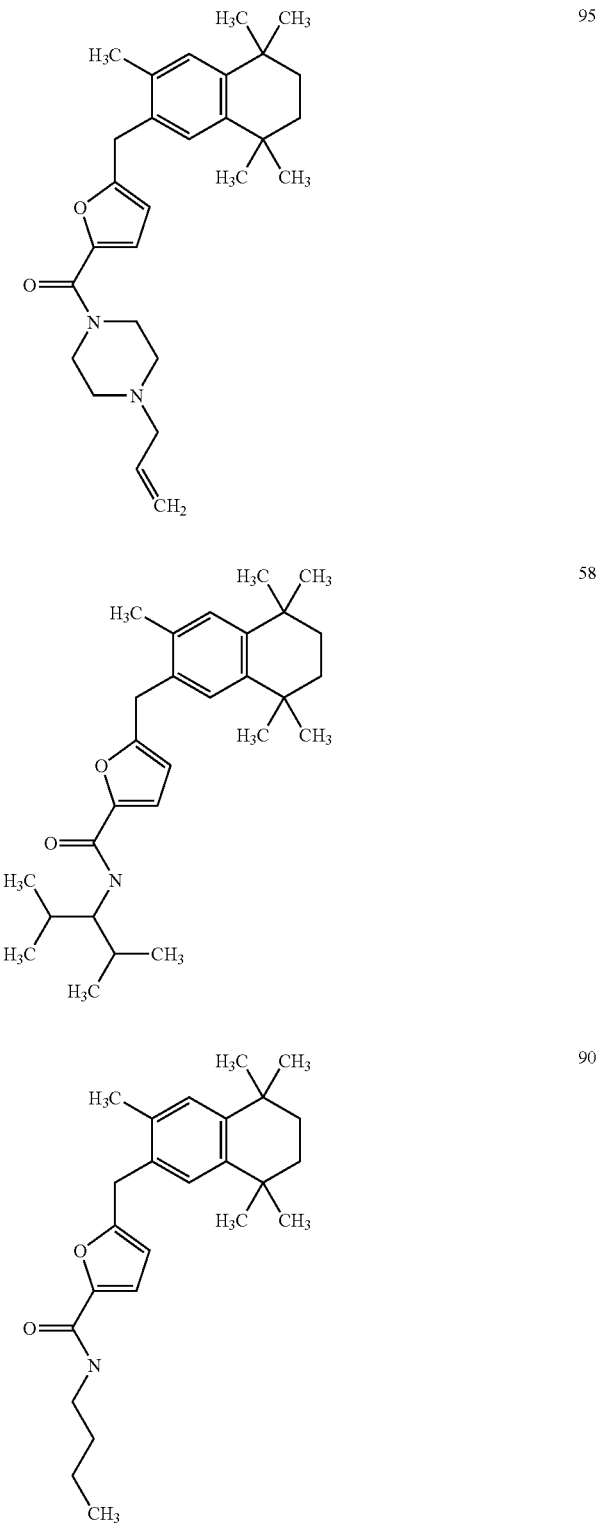

-continued
| | |
|---|---|
| 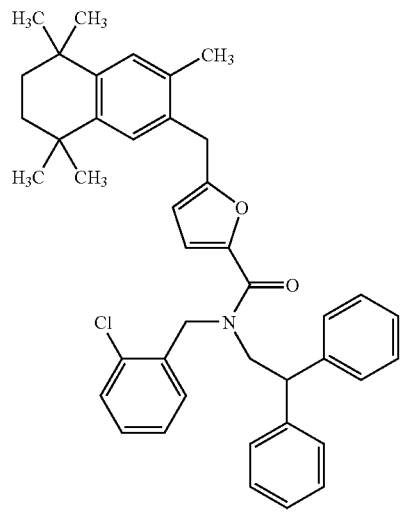 | 8 |
| 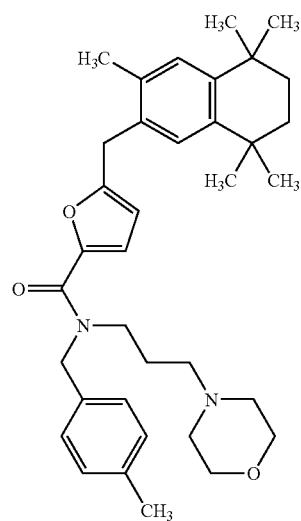 | 103 |
| 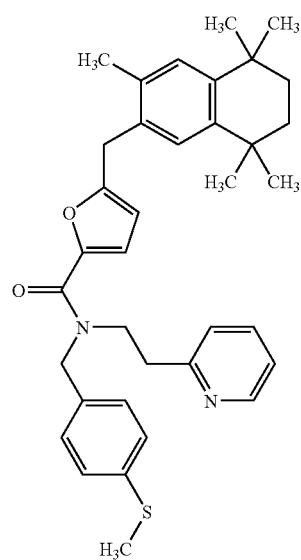 | 75 |

-continued
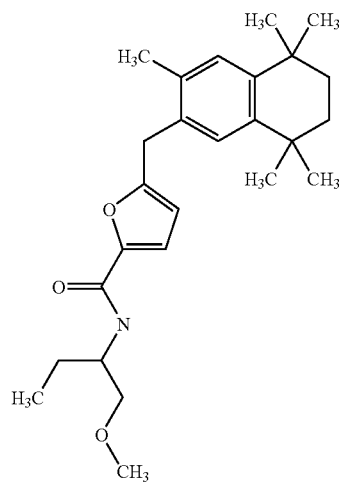
98
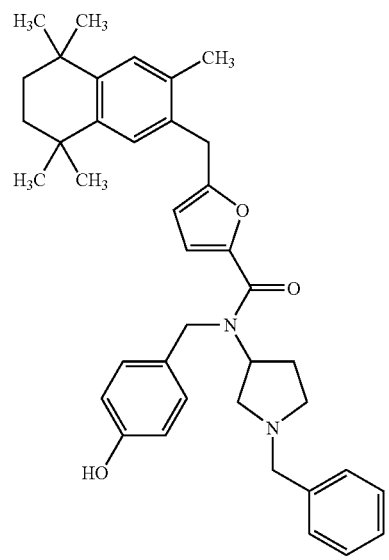
82
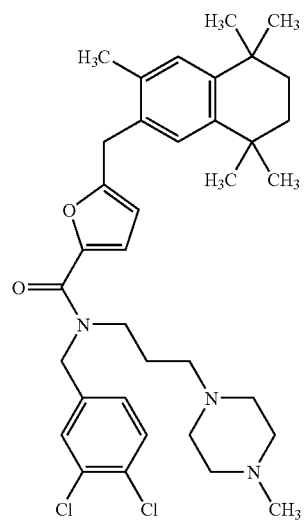
104

-continued
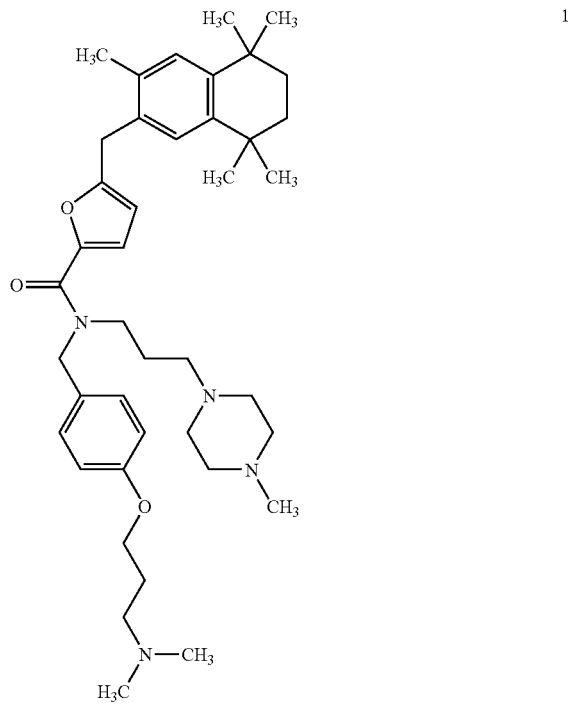
100
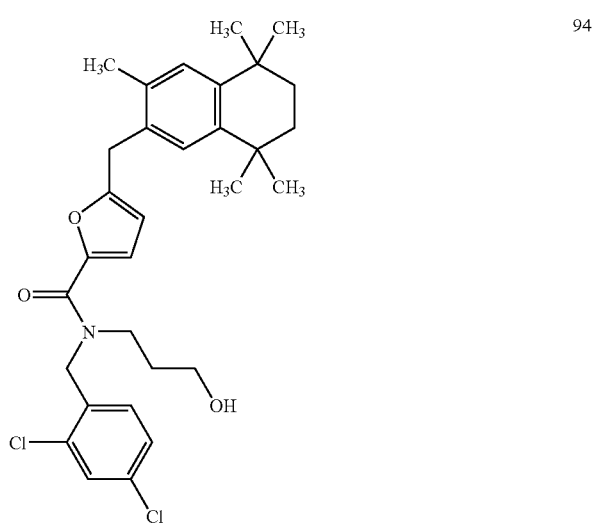
94

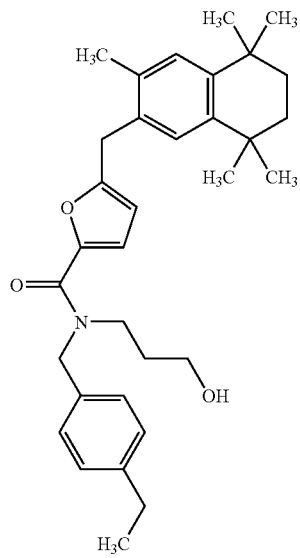
88
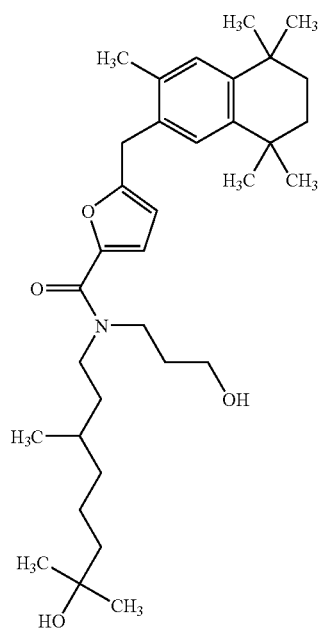
99

-continued
61
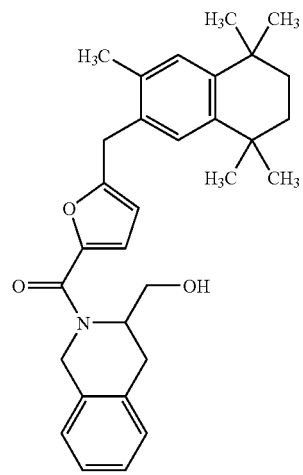
102
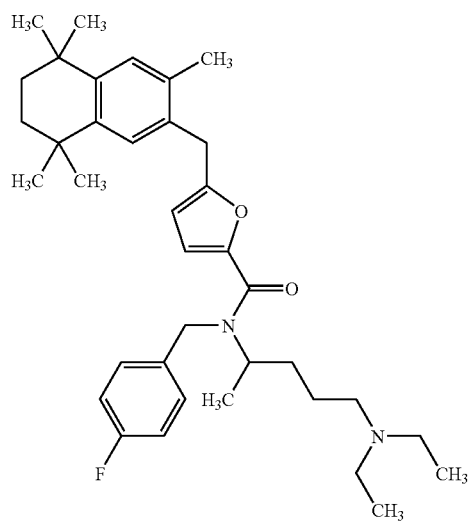
17
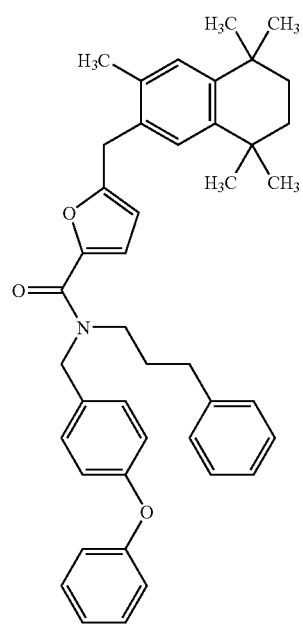

-continued
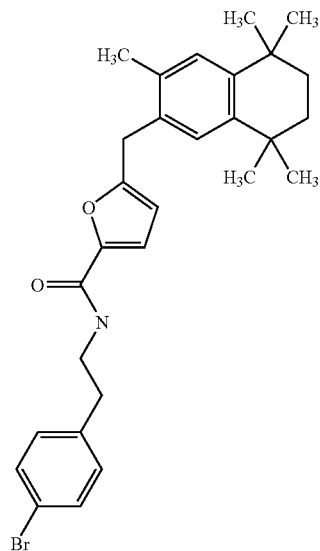
47
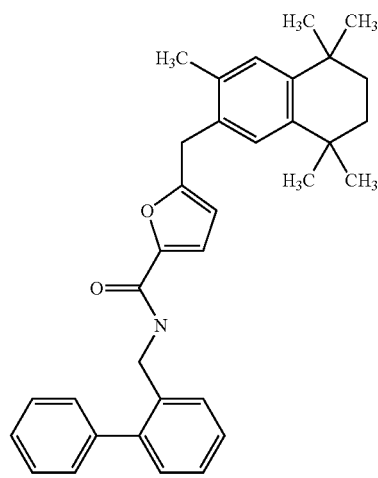
74
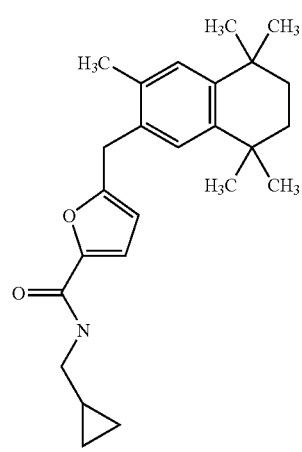
86

-continued
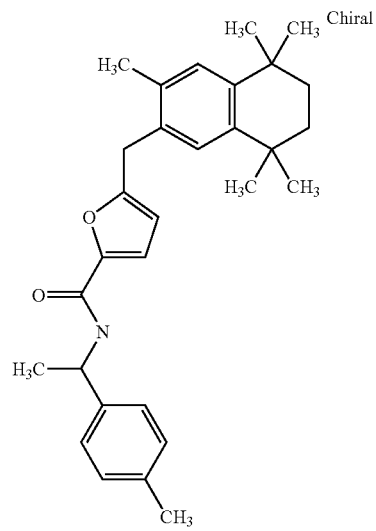
97
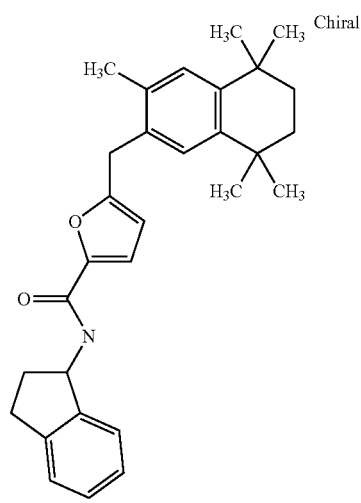
57
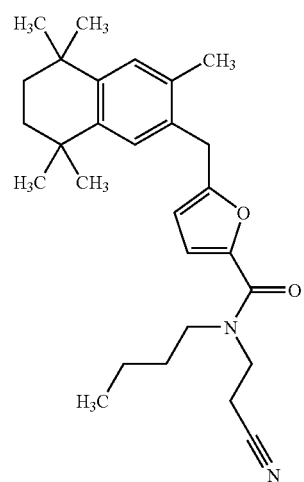
87

-continued
| | |
|---|---|
| 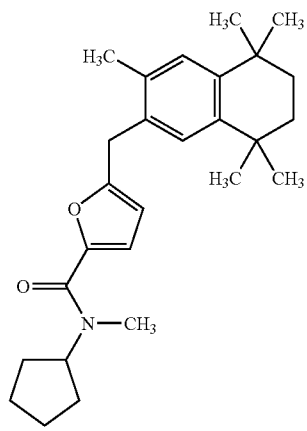 | 100 |
| 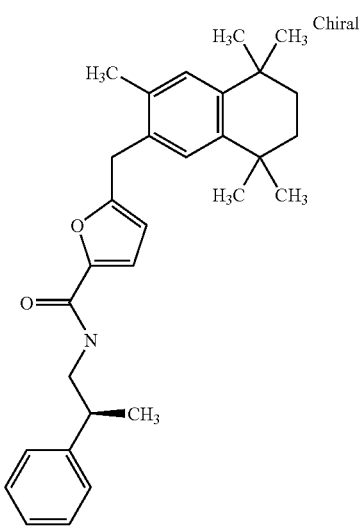 | 70 |
| 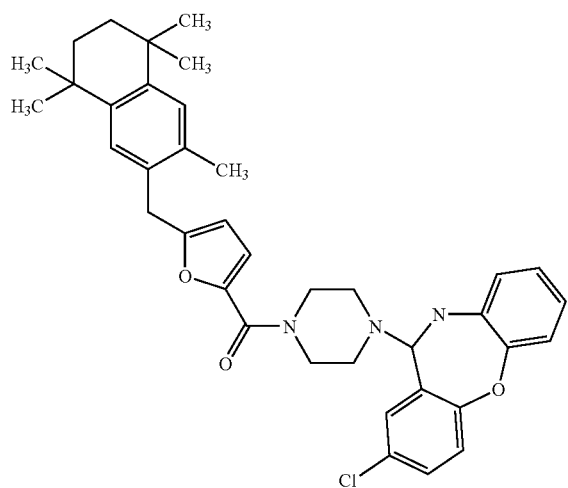 | 5 |

-continued
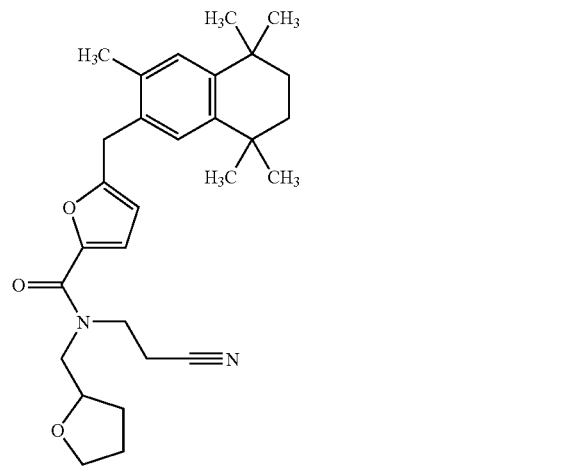
95
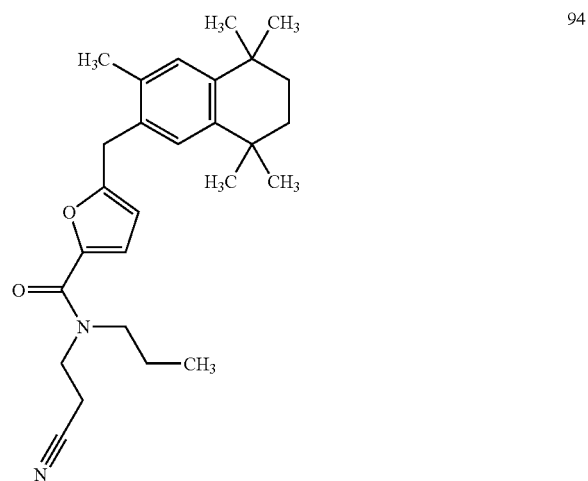
94
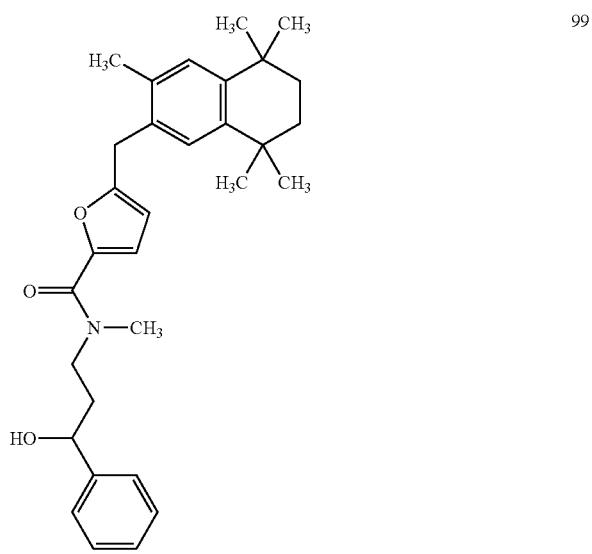
99

-continued
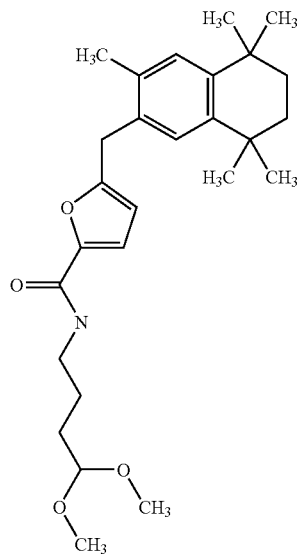
101
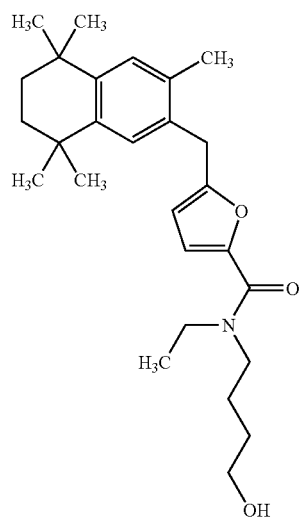
94
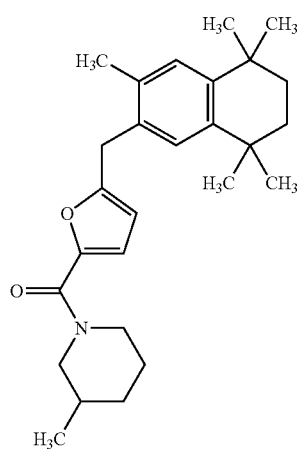
97

-continued
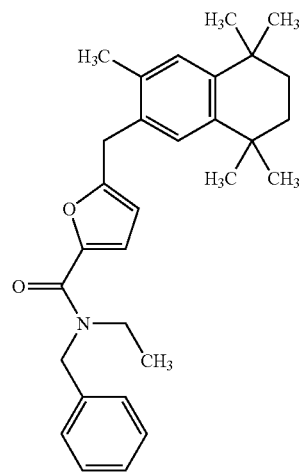
86
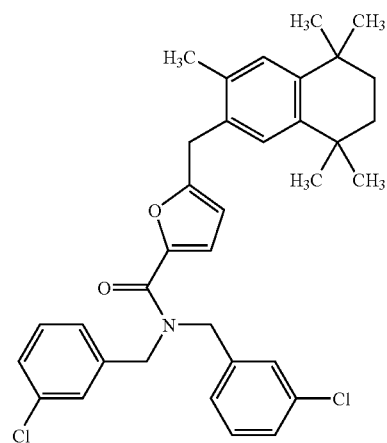
17
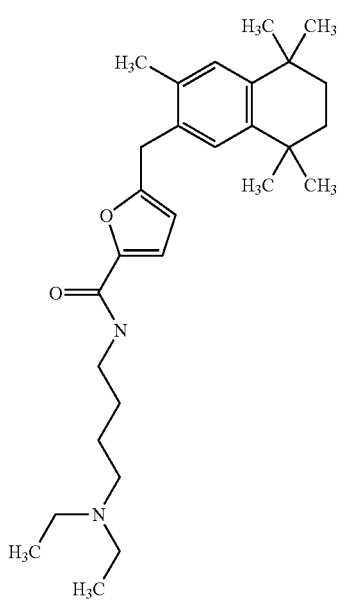
101

-continued
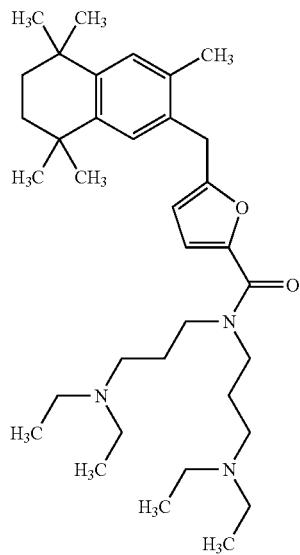
69
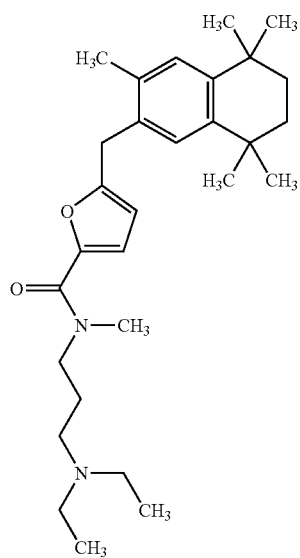
92

-continued
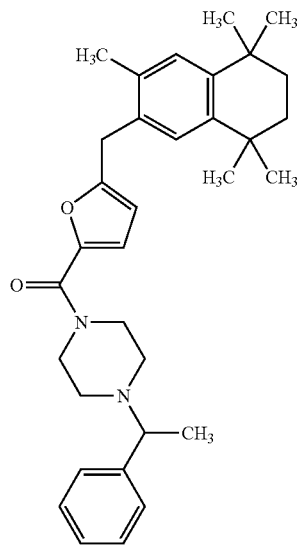
91
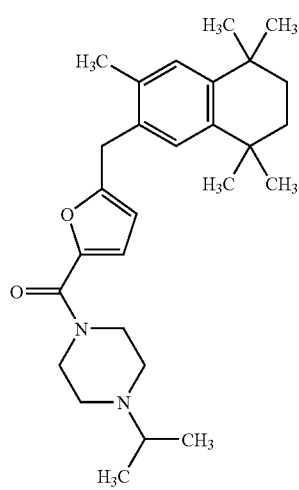
100

-continued
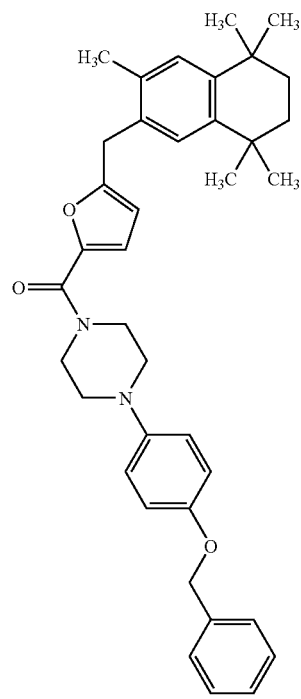
44
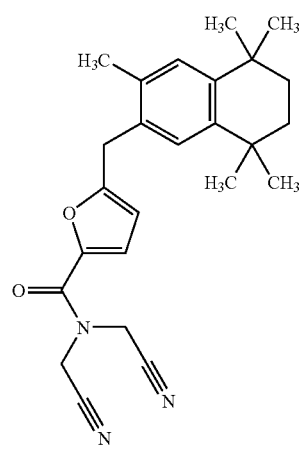
64

-continued
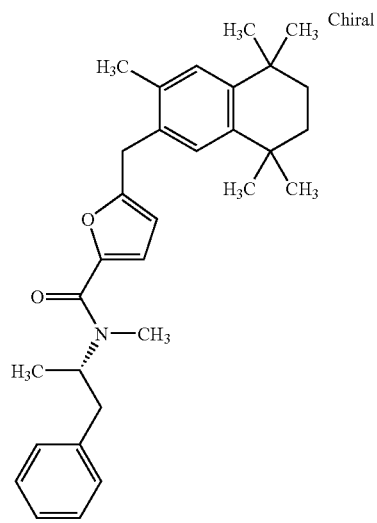
59
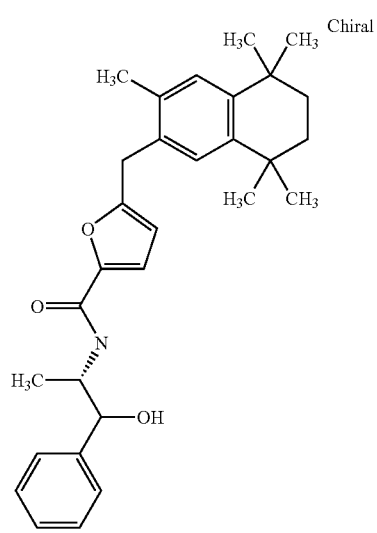
63
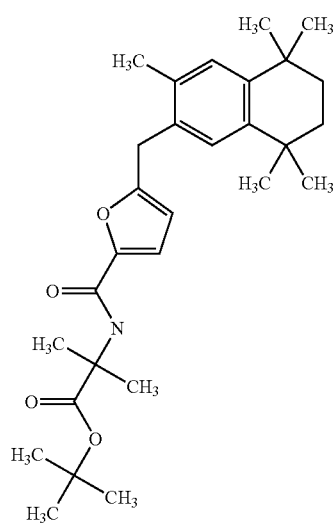
75

-continued
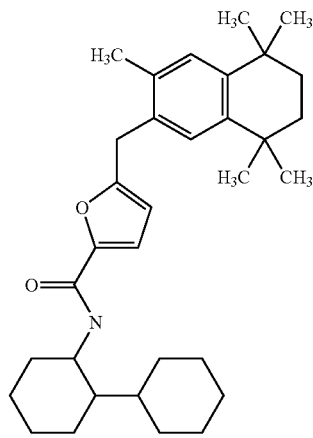
13
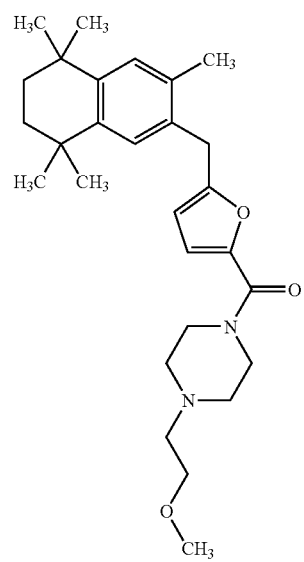
81
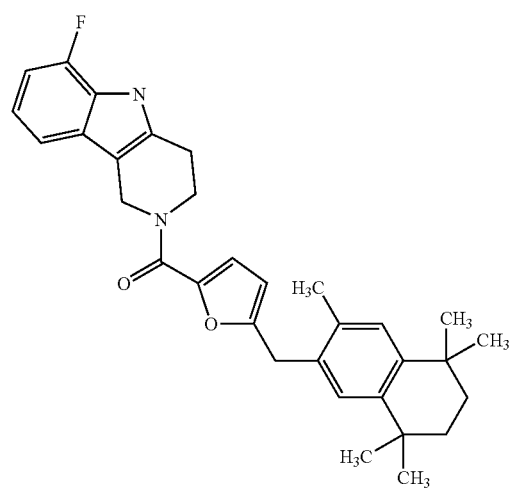
46

-continued
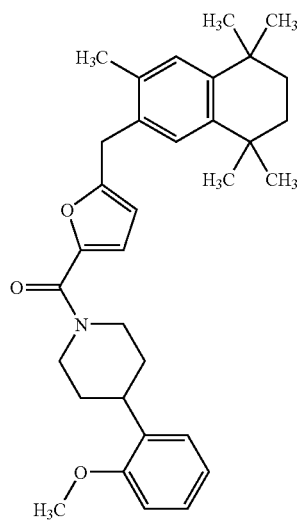
63
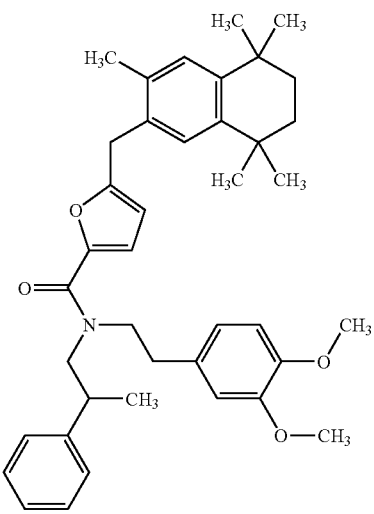
72
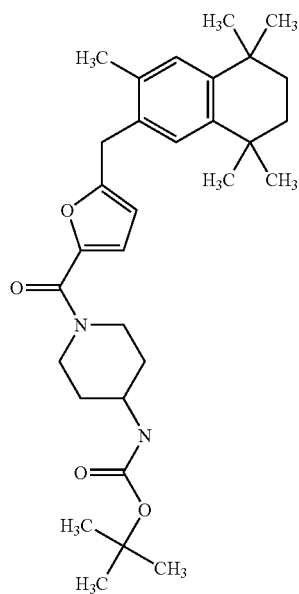
67

-continued
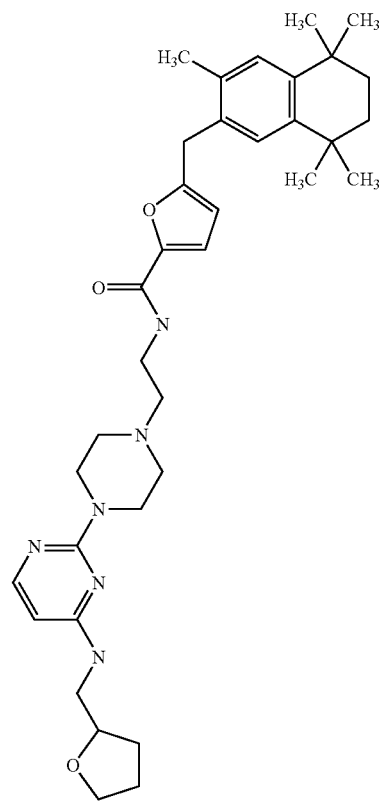
96
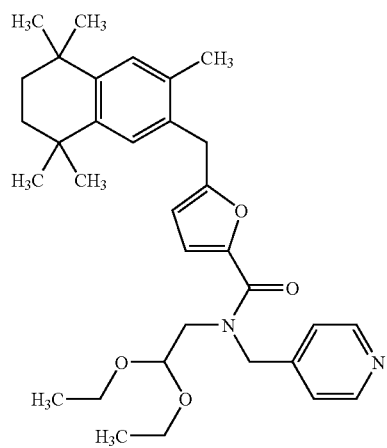
31

-continued
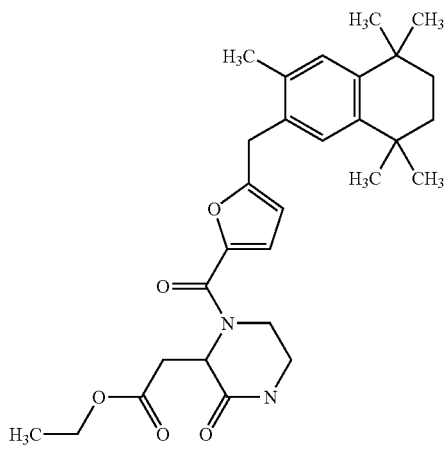
98
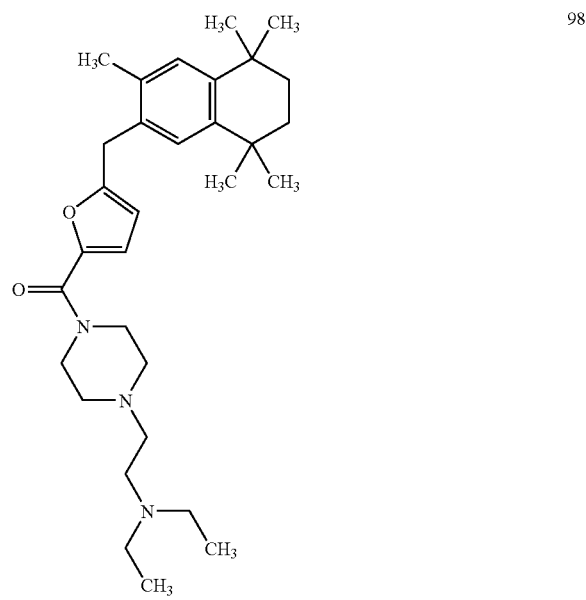
98
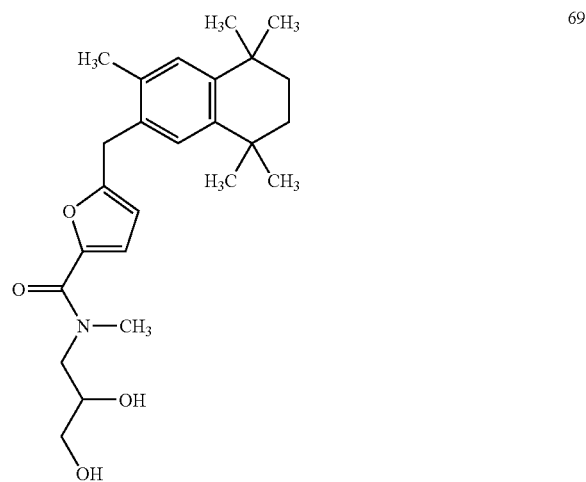
69

-continued
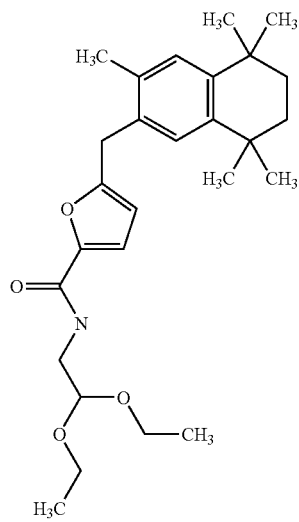
100
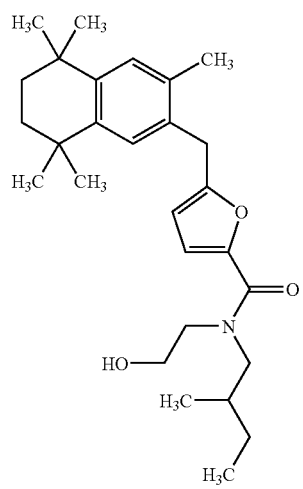
101
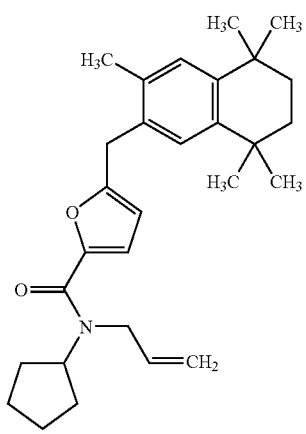
95

-continued
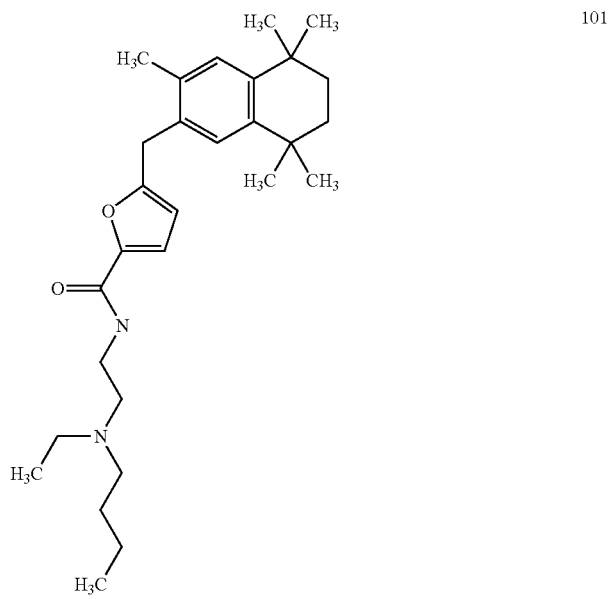
101
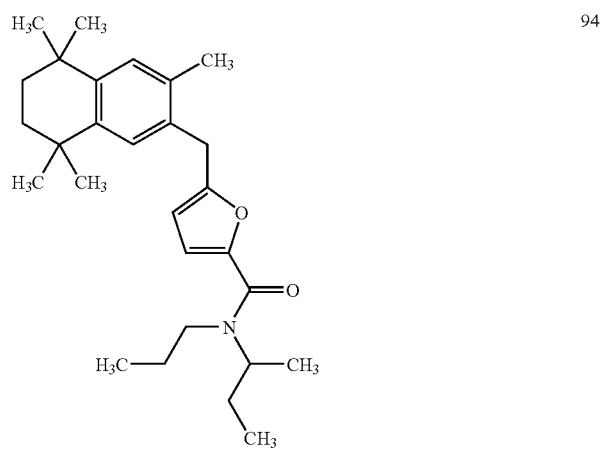
94
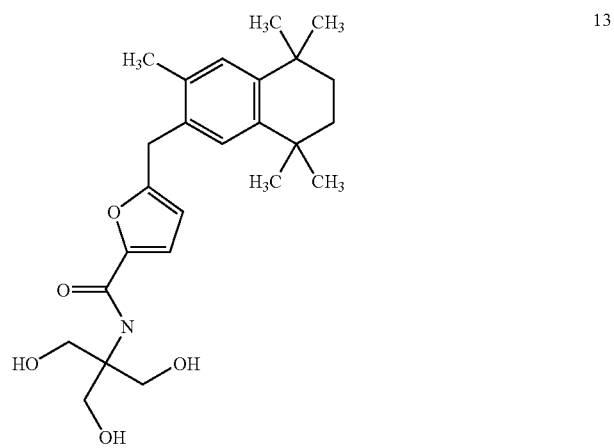
13

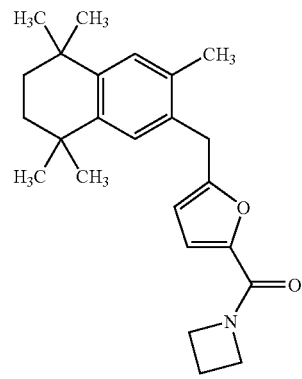
63
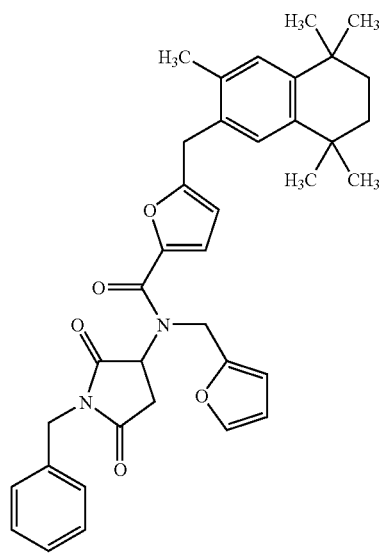
20
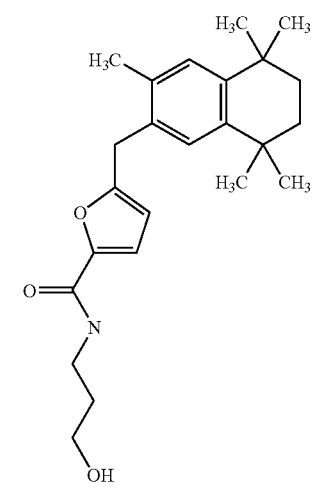
96

-continued
| | |
|---|---|
| 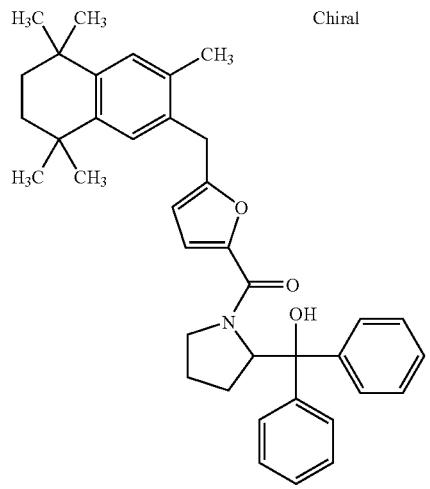 Chiral | 31 |
| 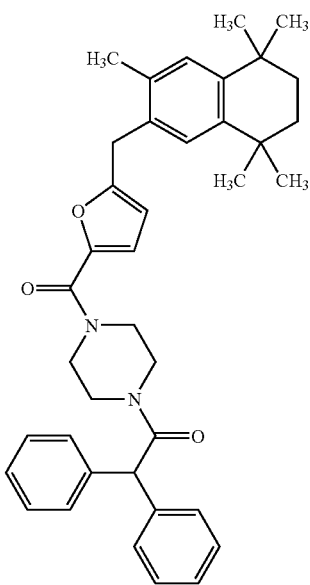 | 36 |
| 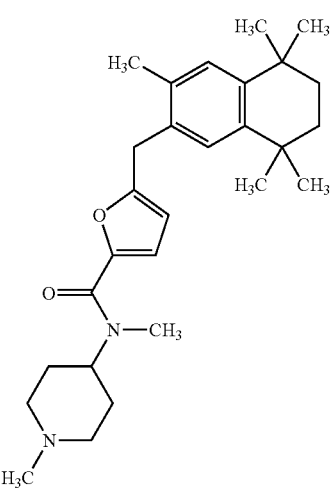 | 89 |

-continued
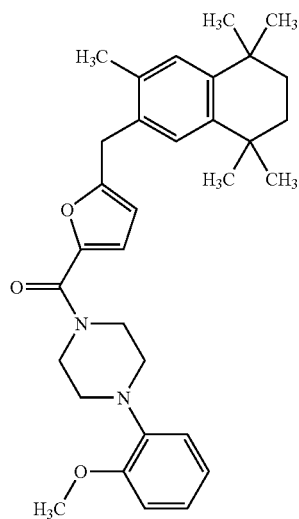
73
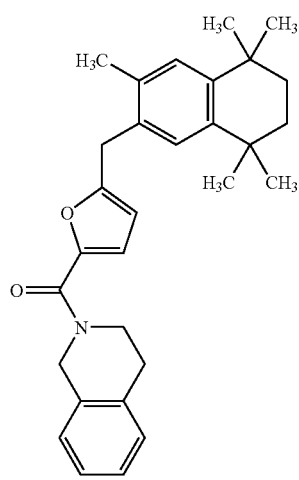
70
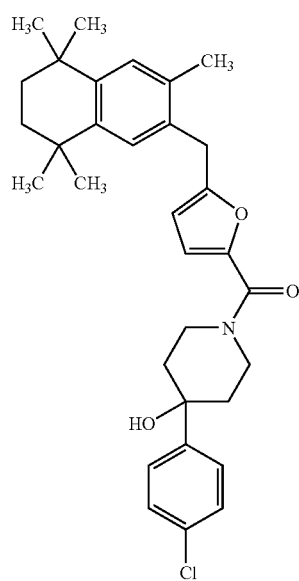
43

-continued
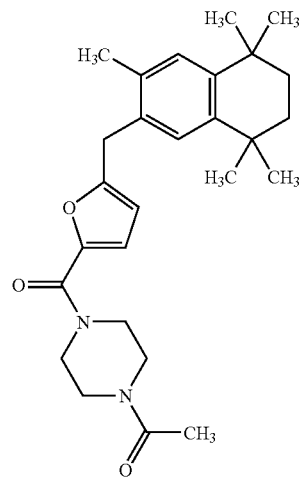
71
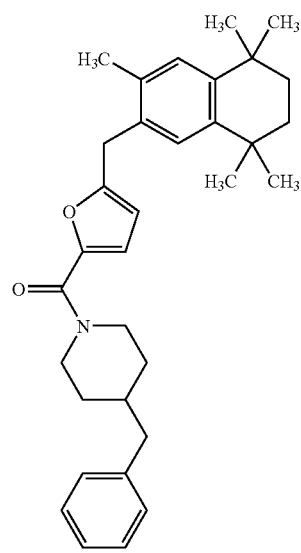
48
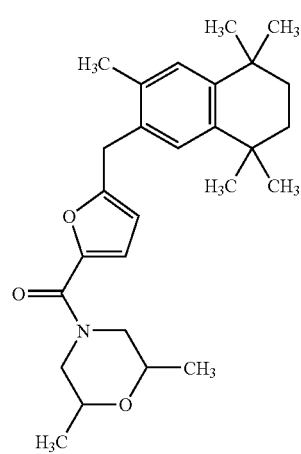
84

-continued
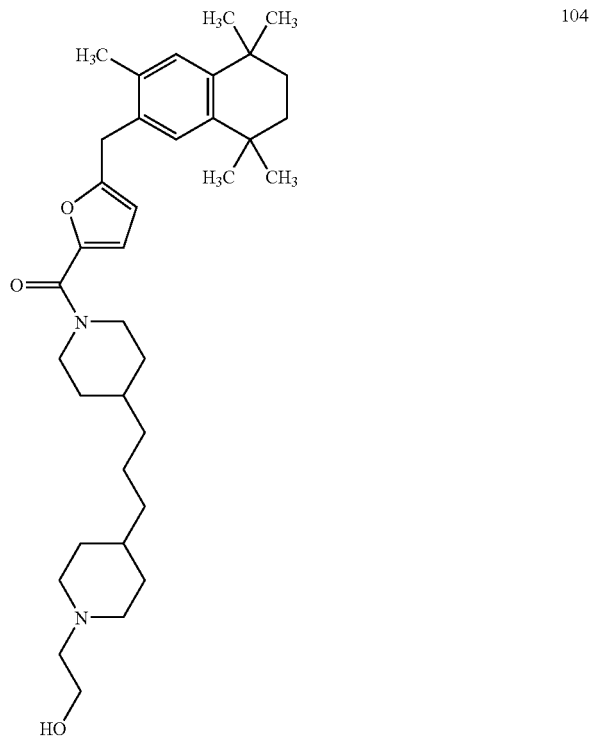
104
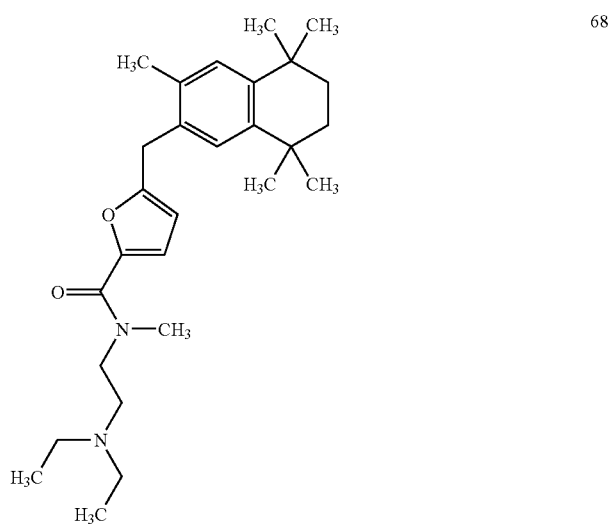
68

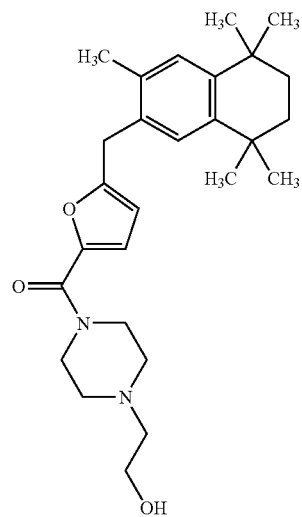 69
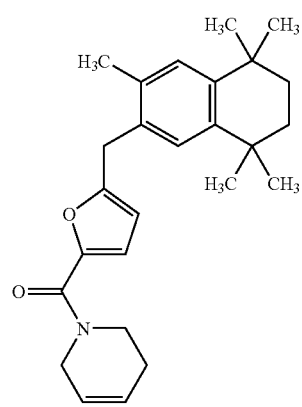 69
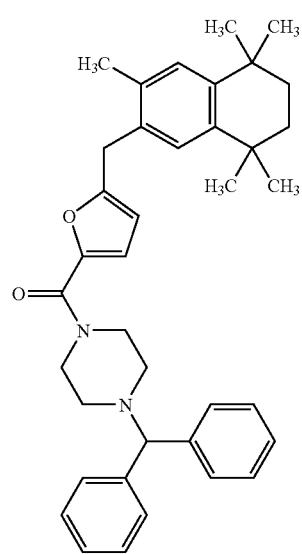 33

-continued
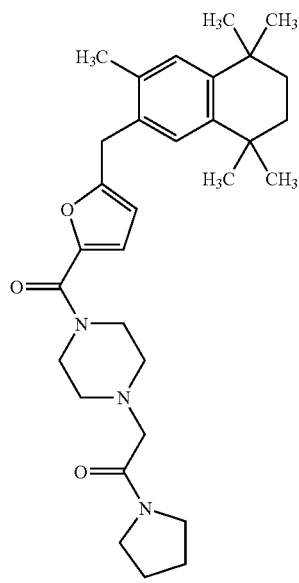
79
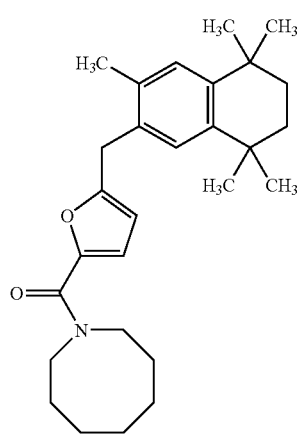
88
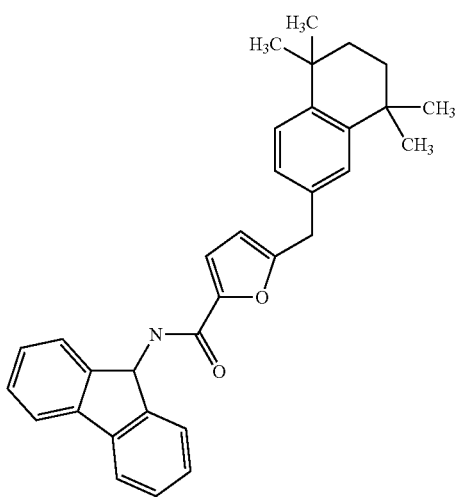
53

-continued
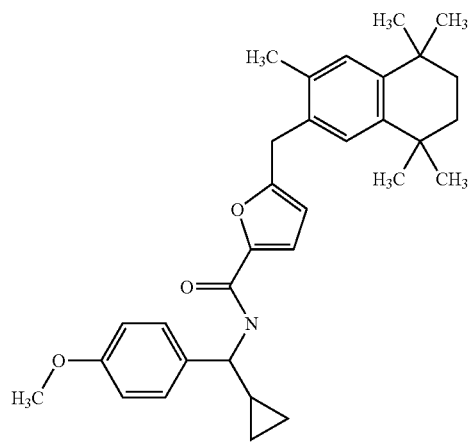
83
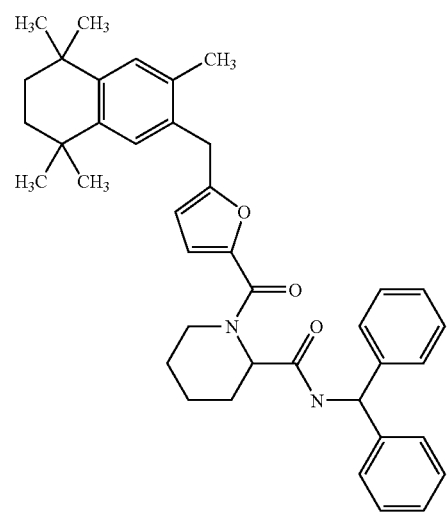
43
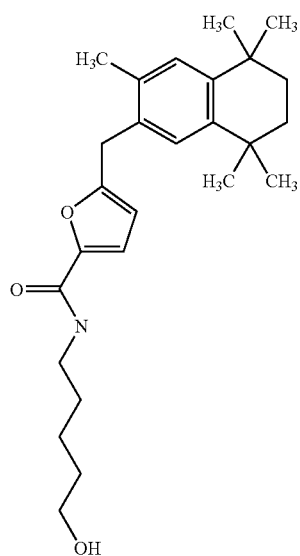
99

-continued
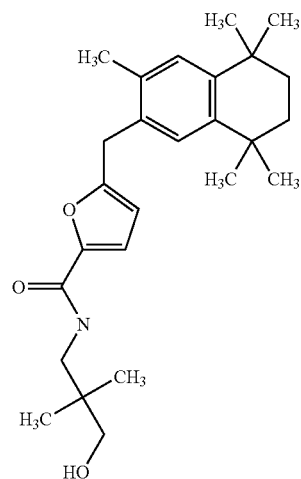
84
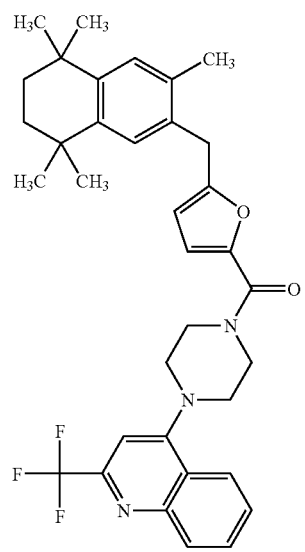
28
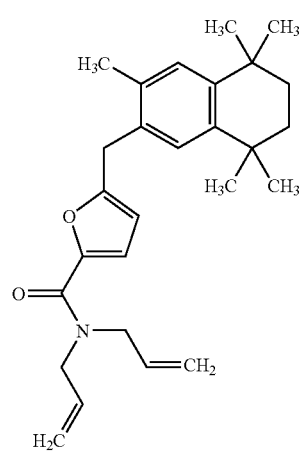
83

-continued
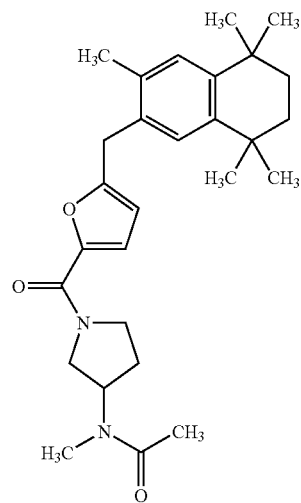
74
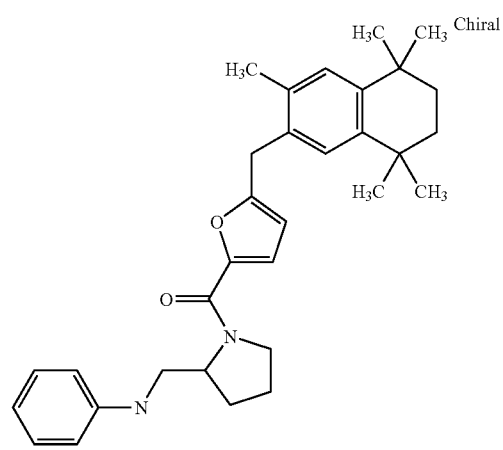
53
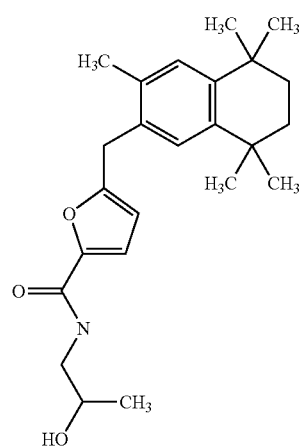
90

-continued
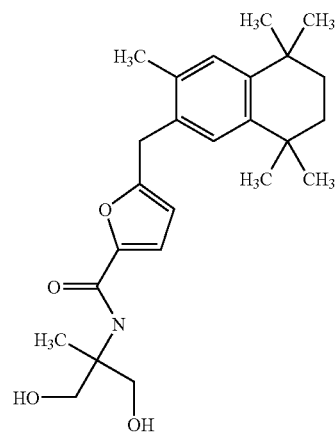
55
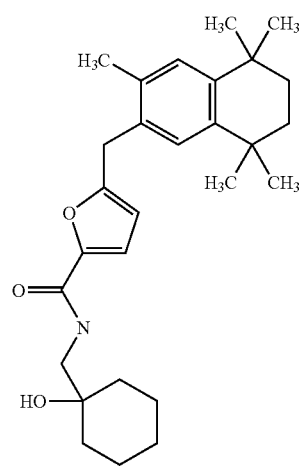
65
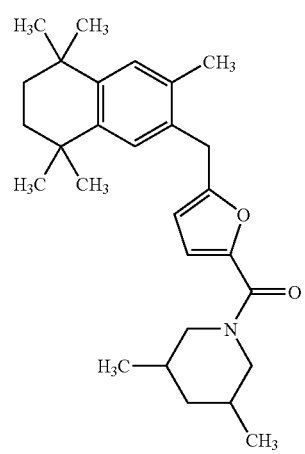
90

-continued
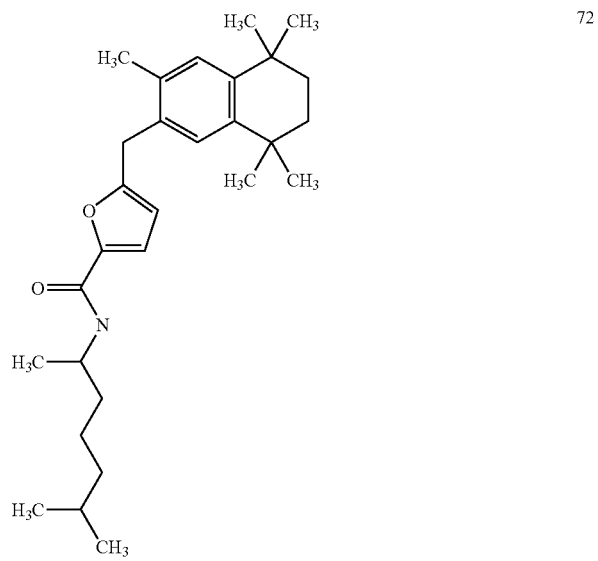
72
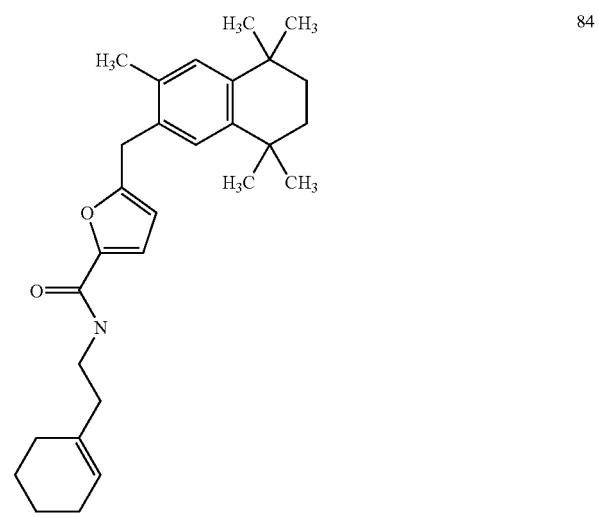
84
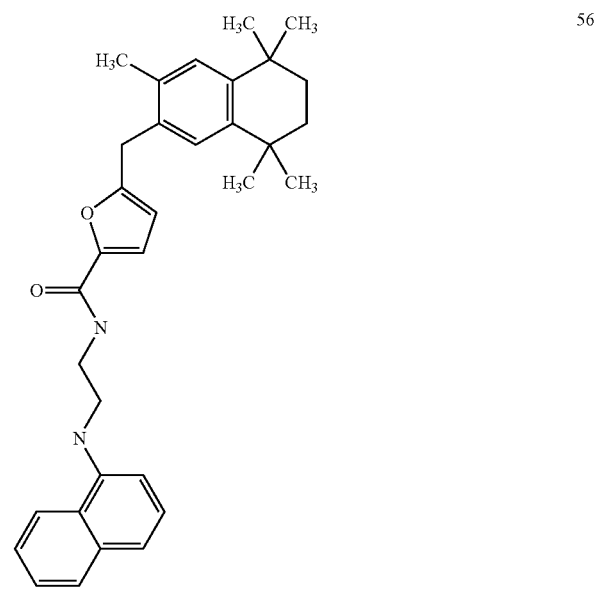
56

-continued
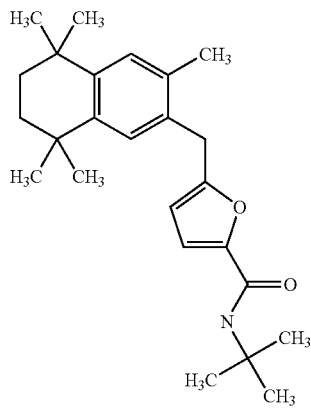
72
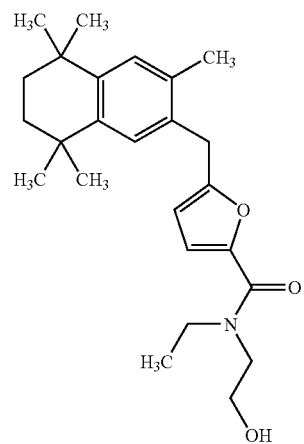
81
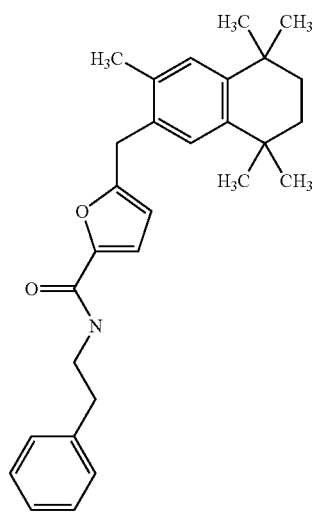
73

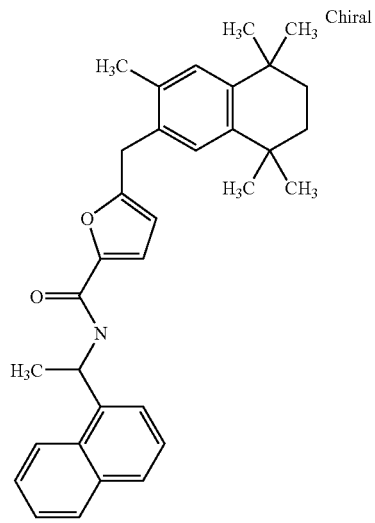
28
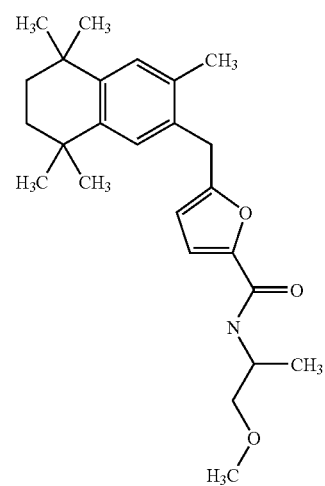
91
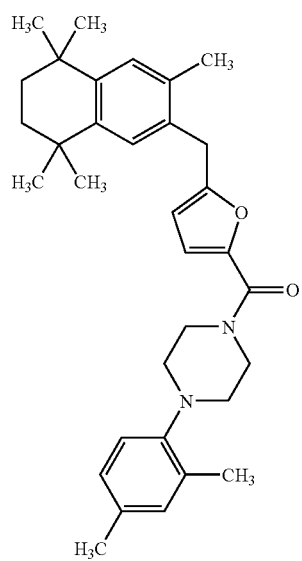
52

-continued
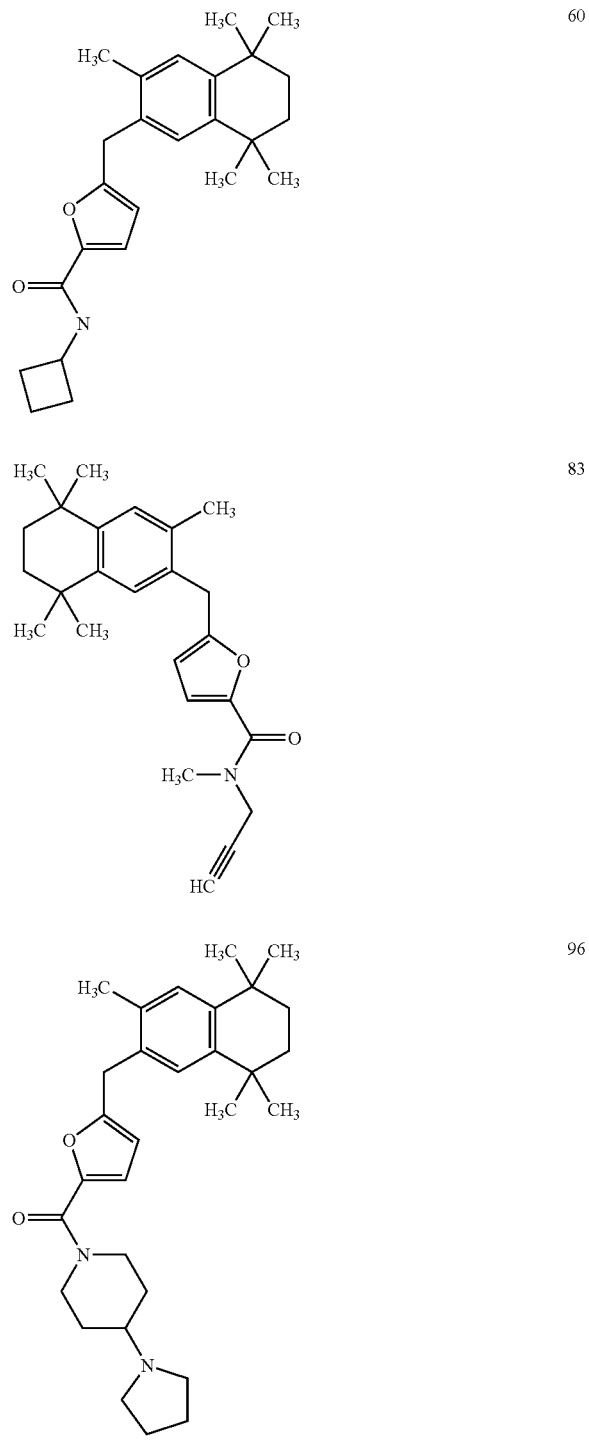
60
83
96

-continued
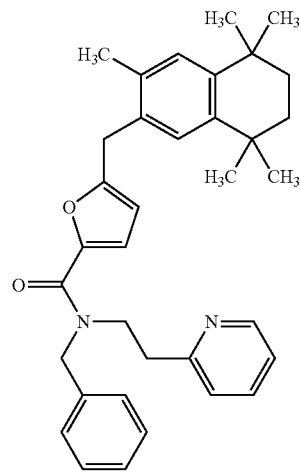
76
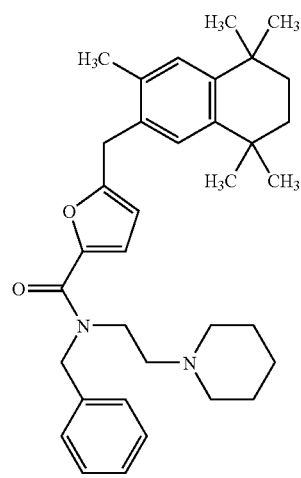
104
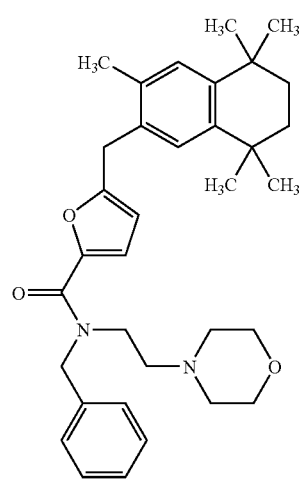
91

-continued
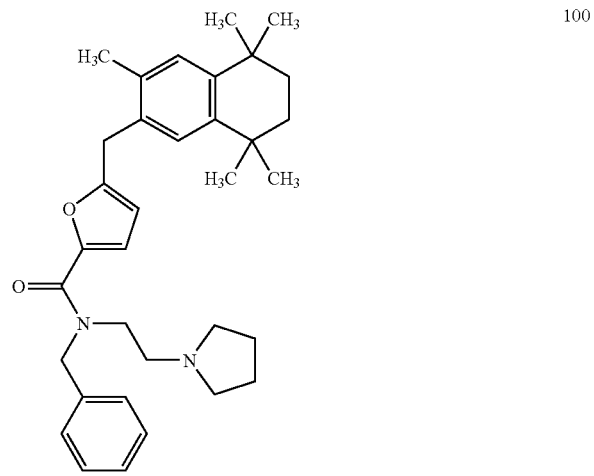
100
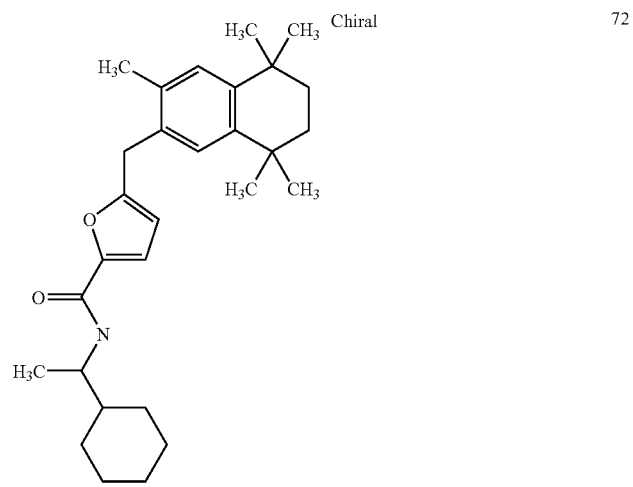
72
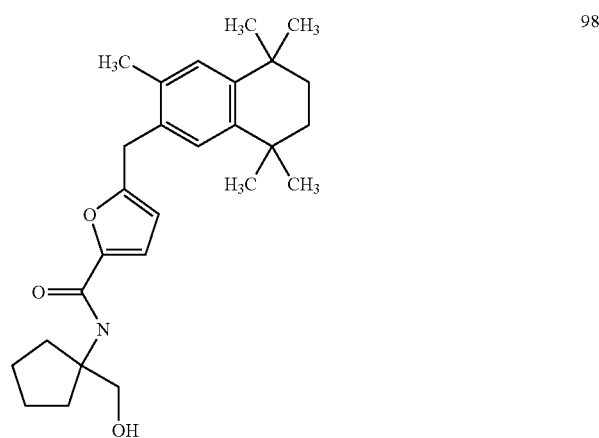
98

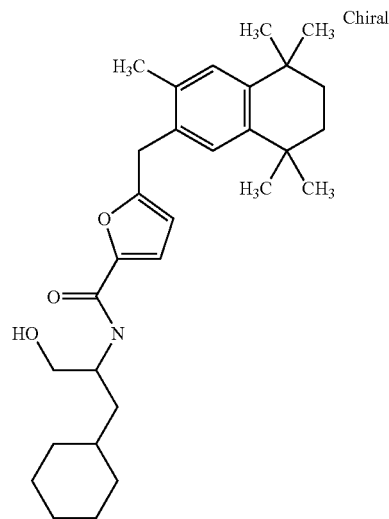
76
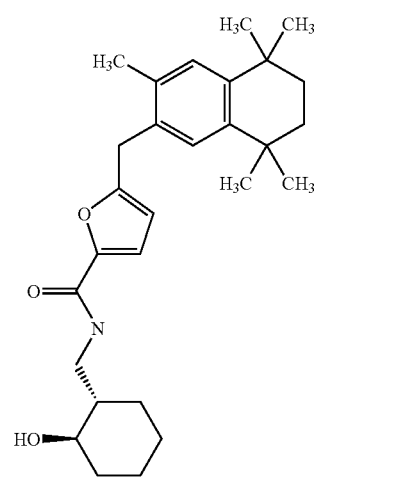
97
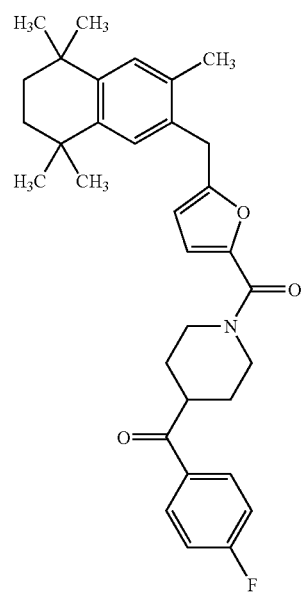
63

-continued
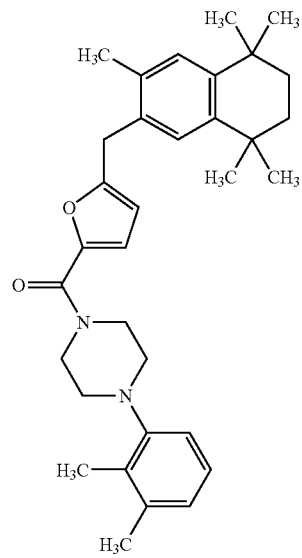
58
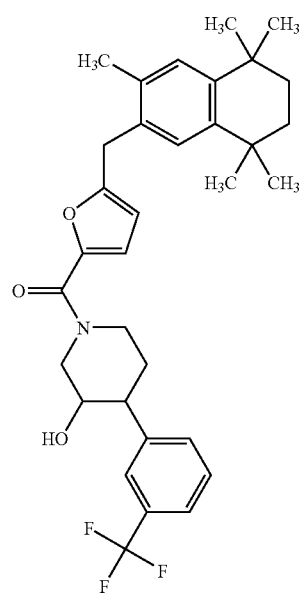
35

-continued
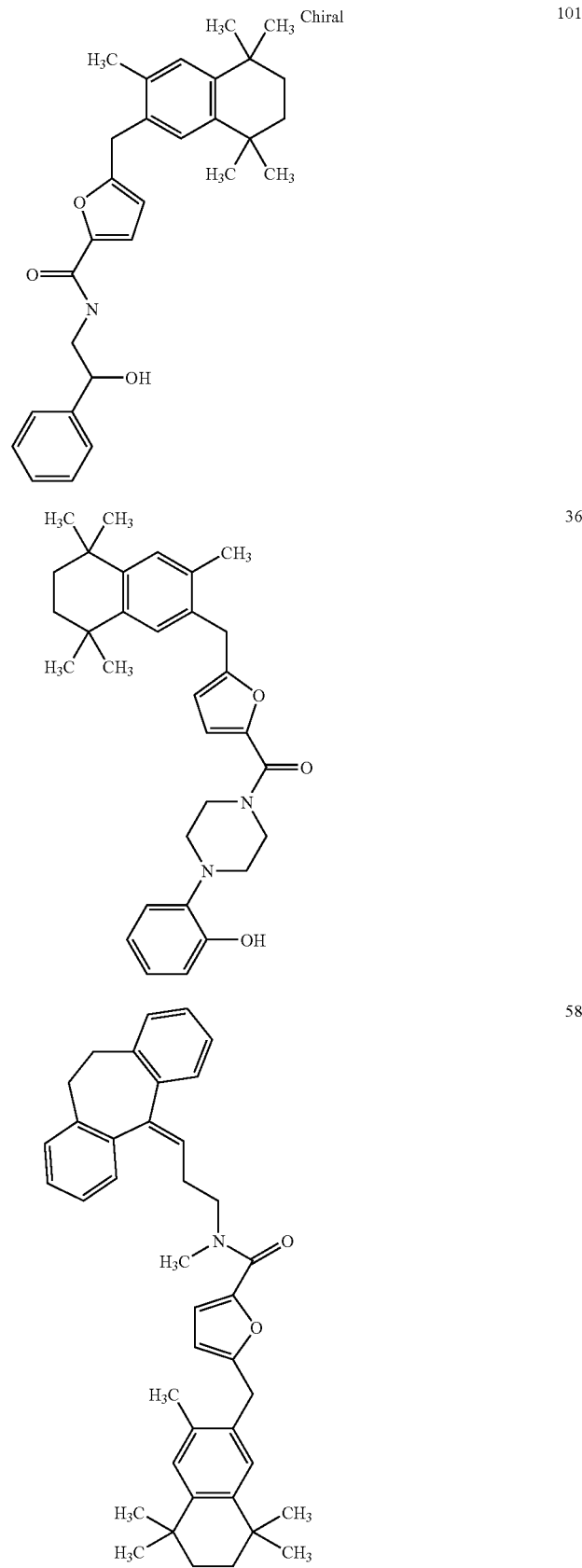

-continued
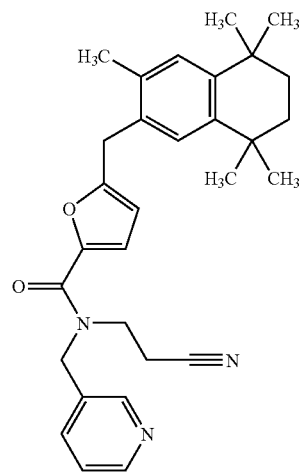
91
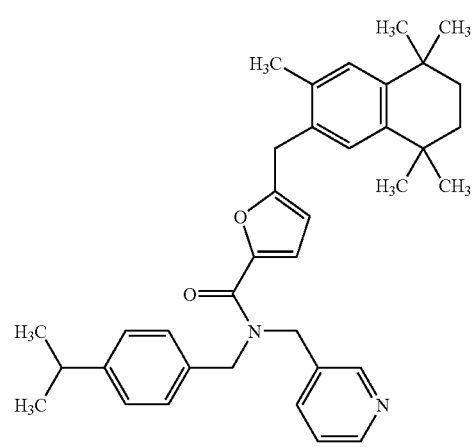
76
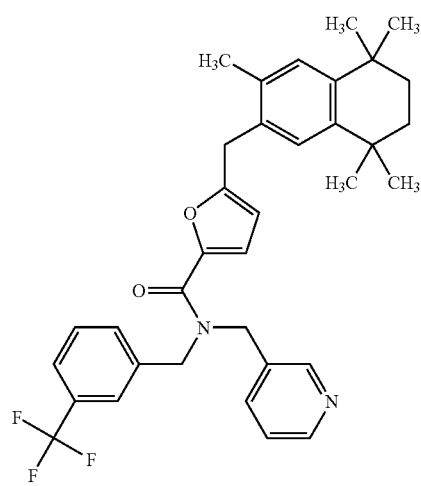
80

-continued
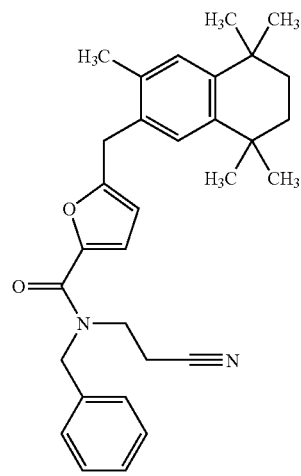
74
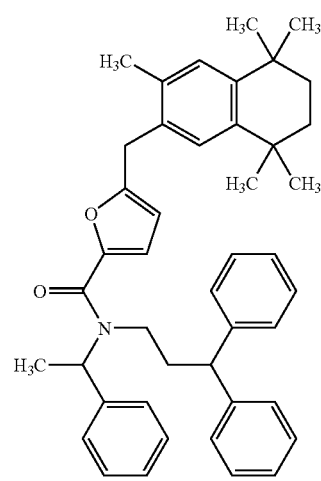
30
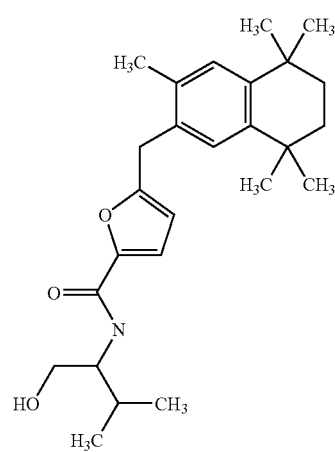
87

-continued
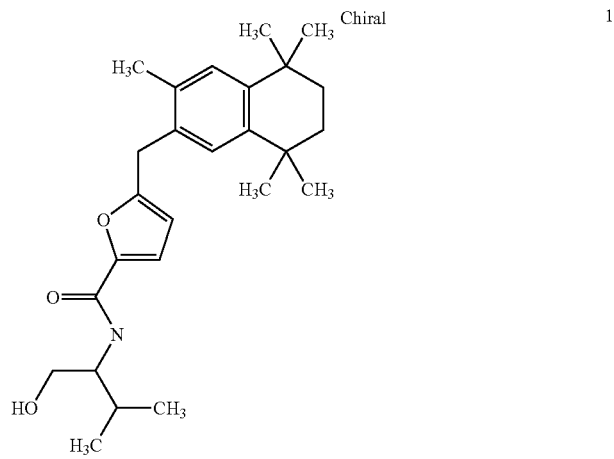
103
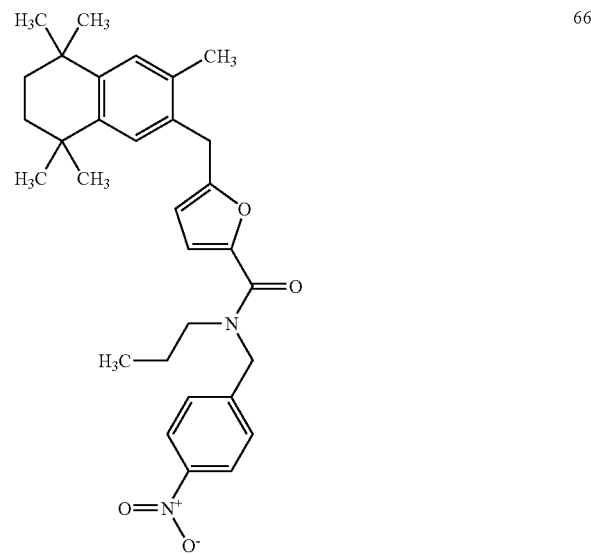
66
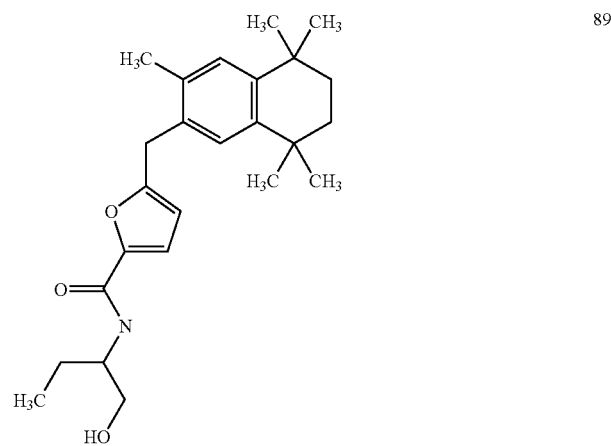
89

-continued
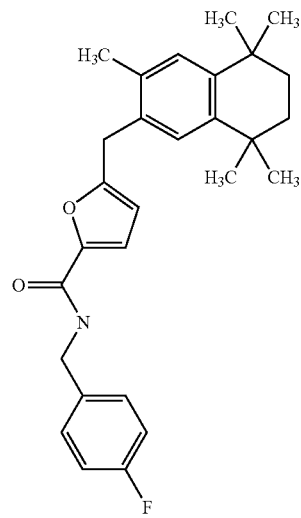
97
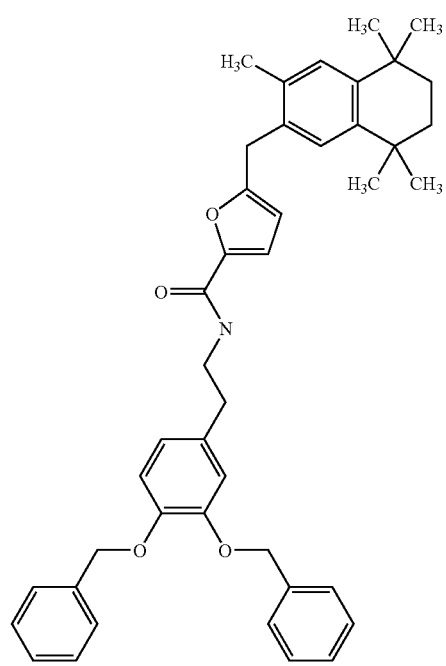
20

-continued
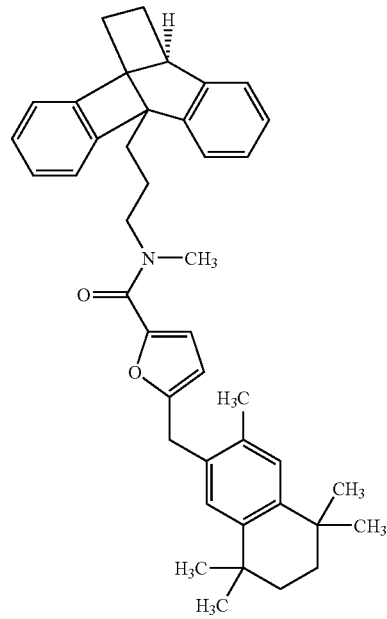
14
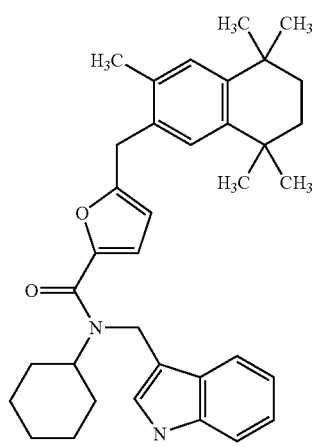
27
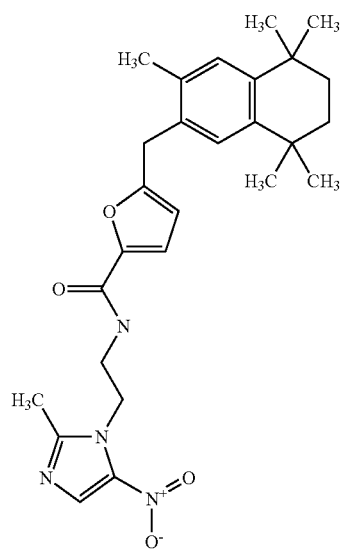
42

-continued
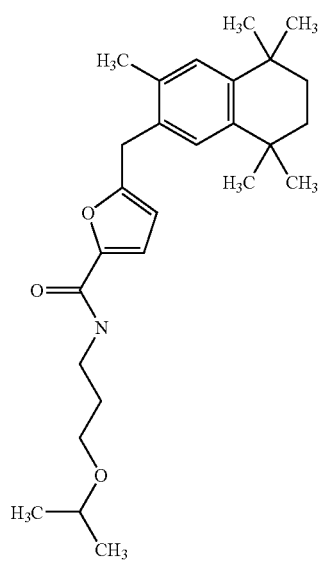
93
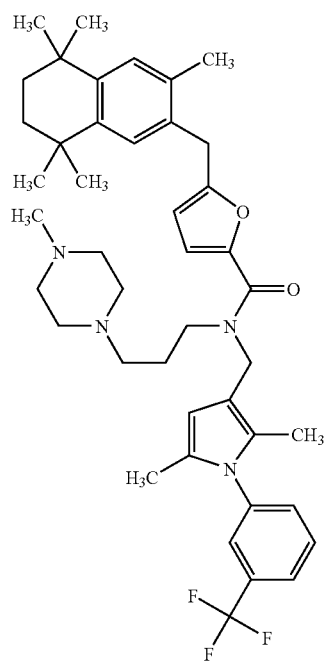
102

-continued
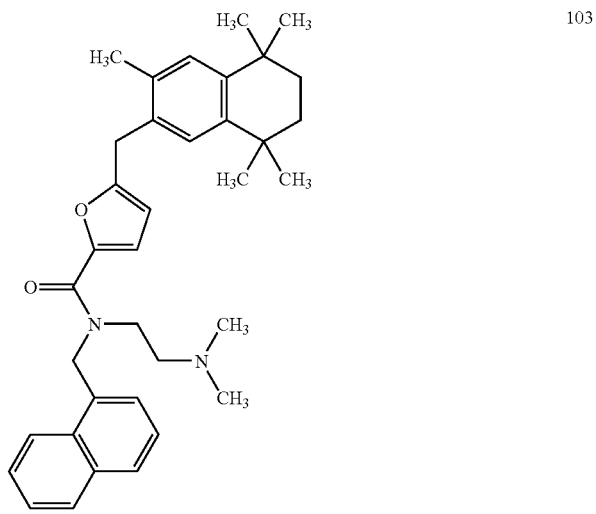
103
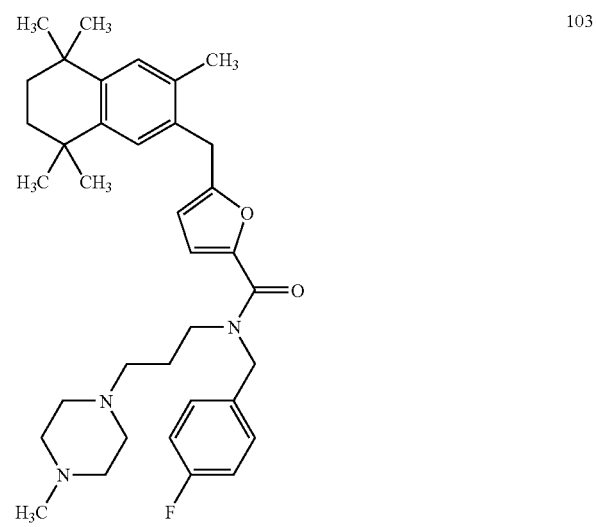
103
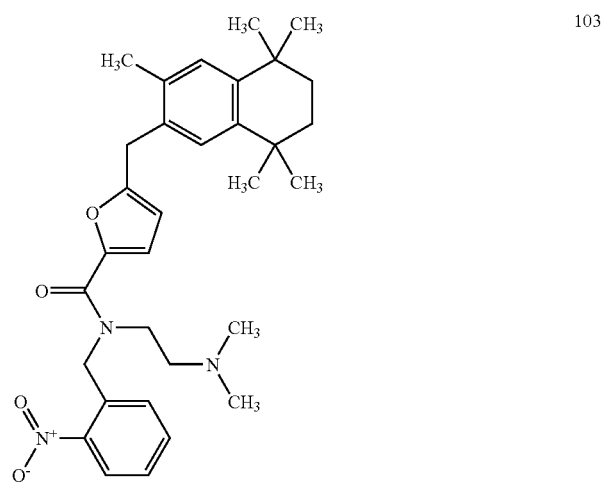
103

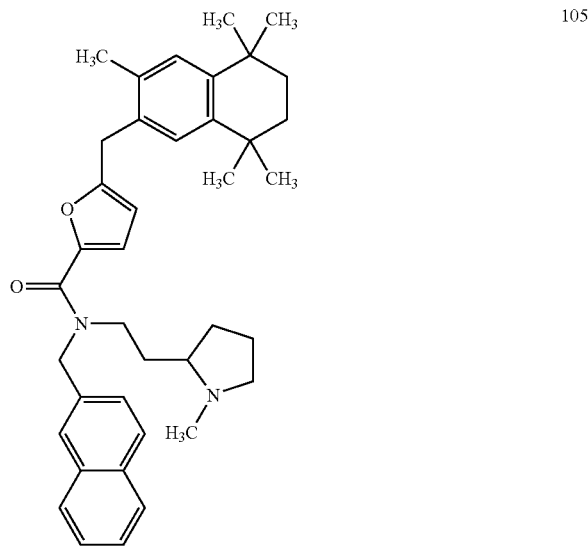
105
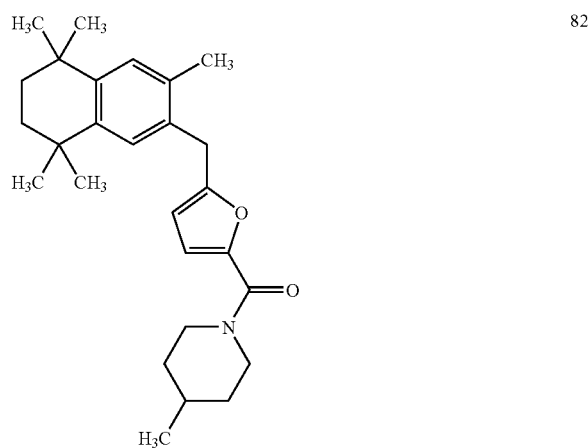
82
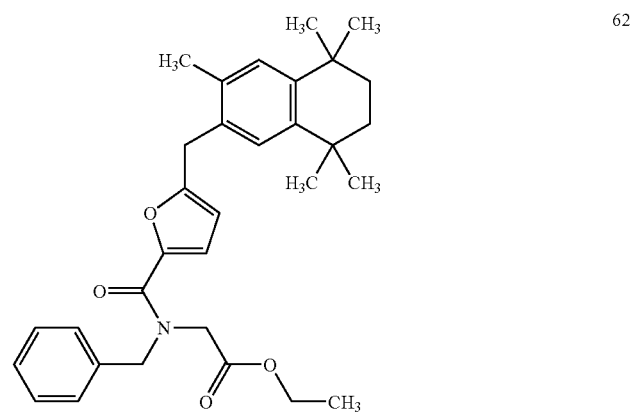
62

-continued
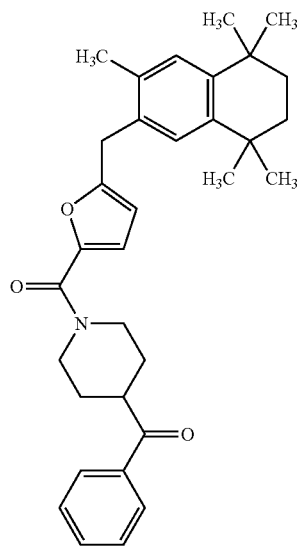
59
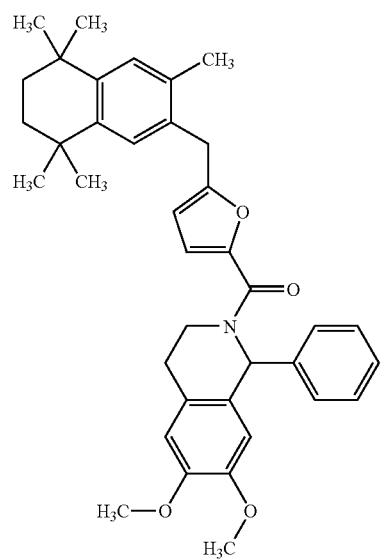
29

-continued
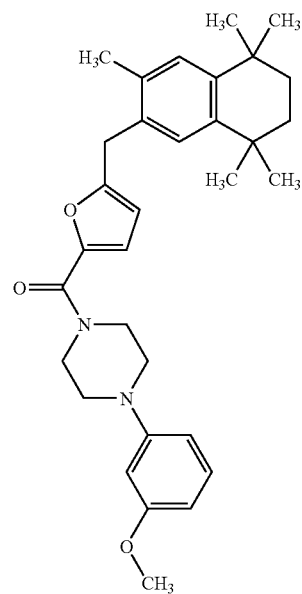
67
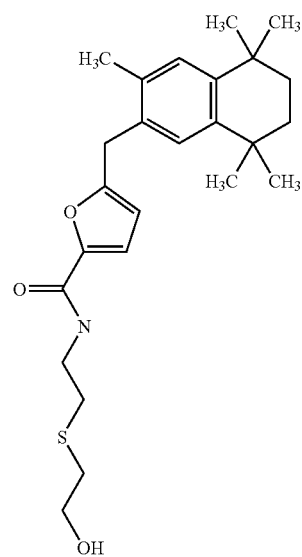
101
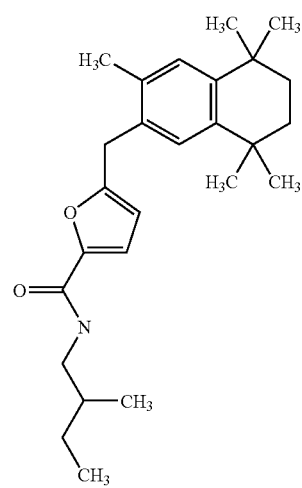
73

-continued
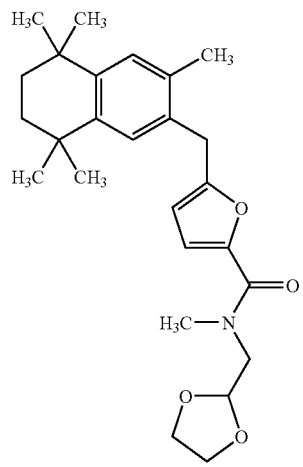
86
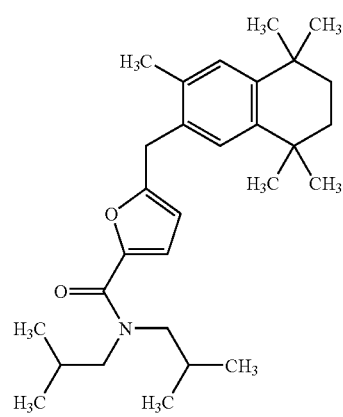
85
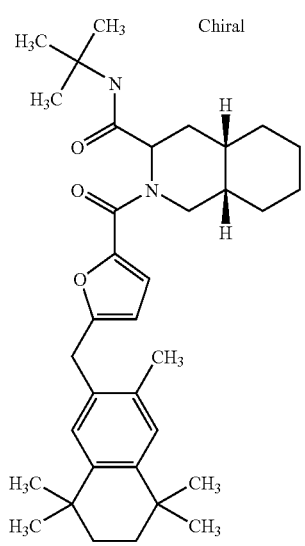
52

-continued
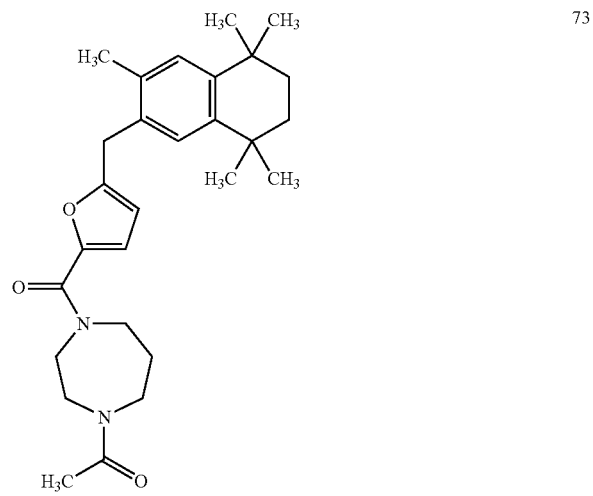
73
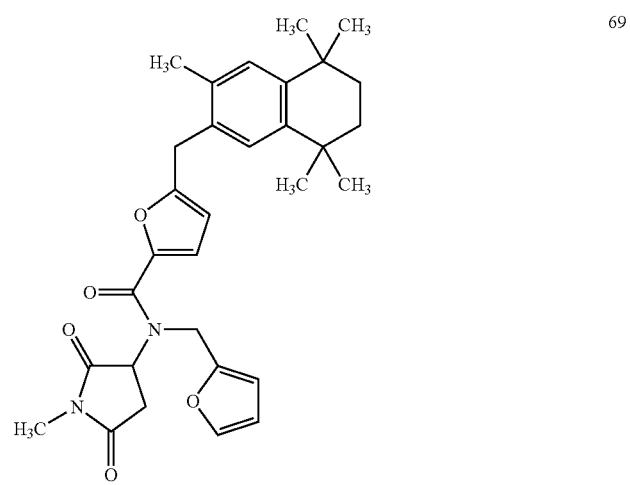
69
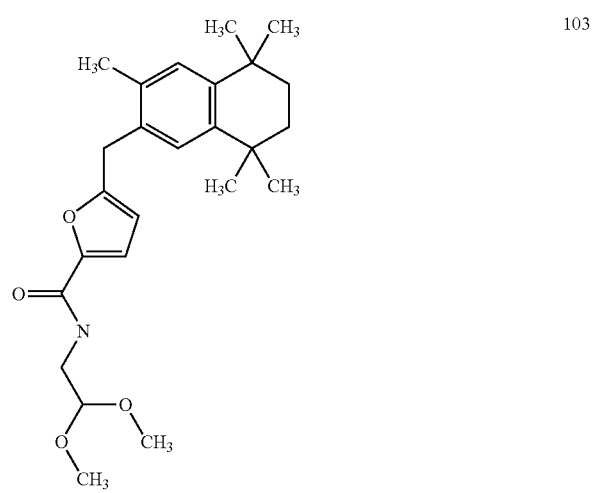
103

-continued
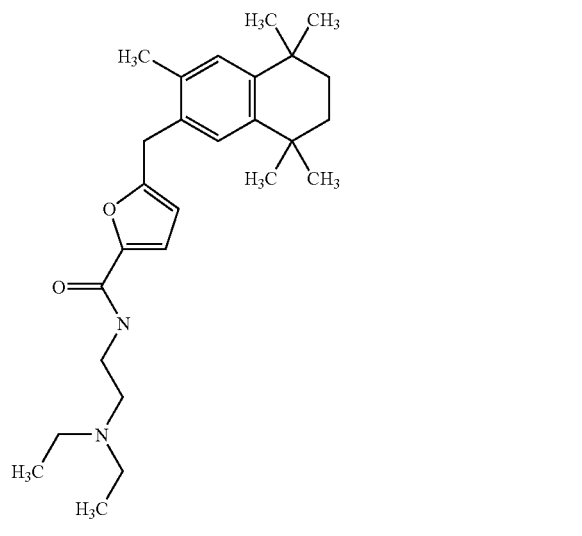
94
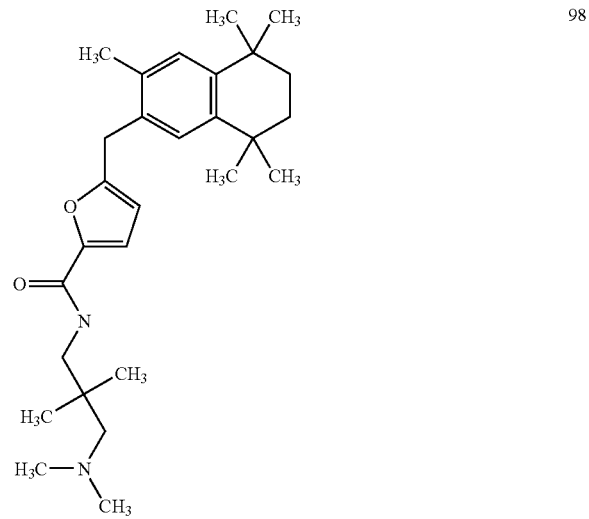
98
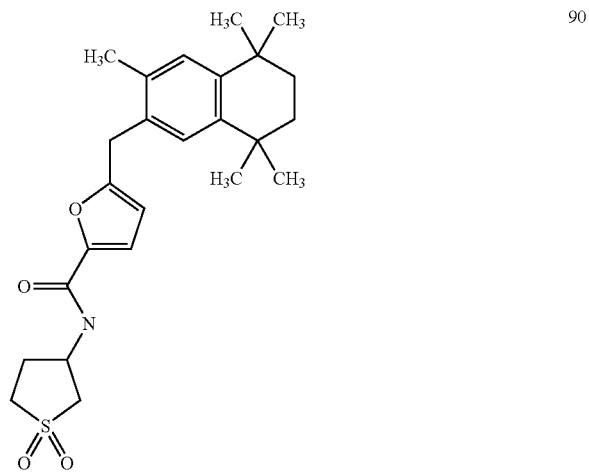
90

-continued
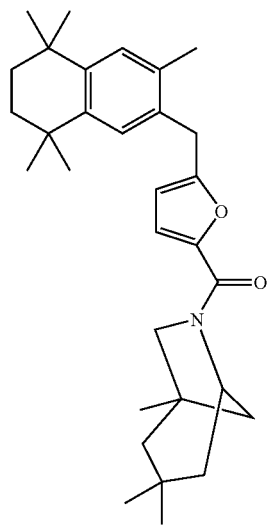
100
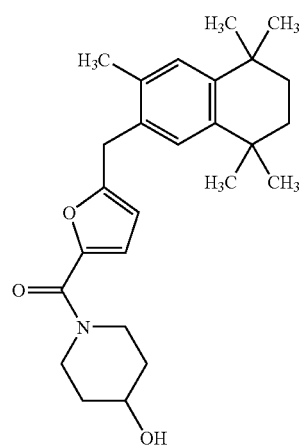
77
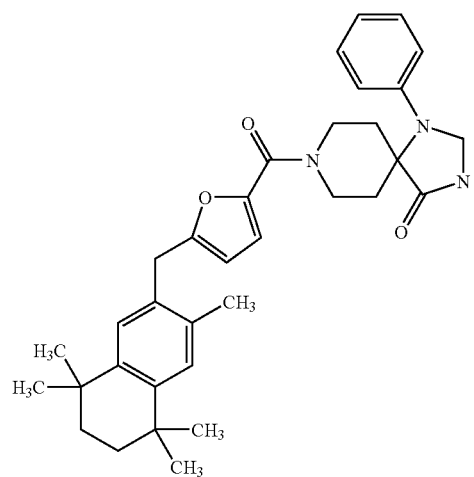
72

-continued
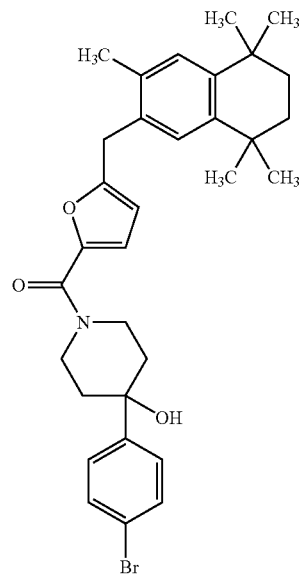
49
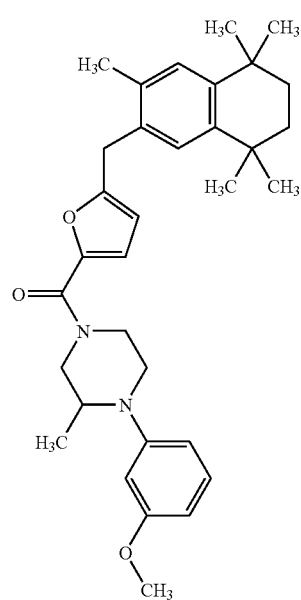
76

-continued
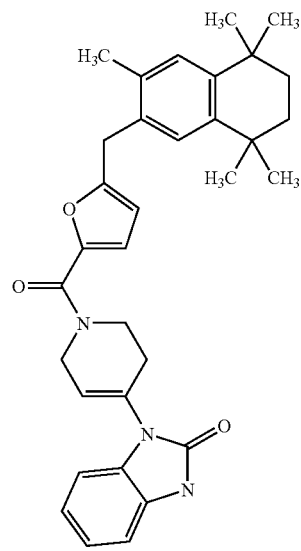
85
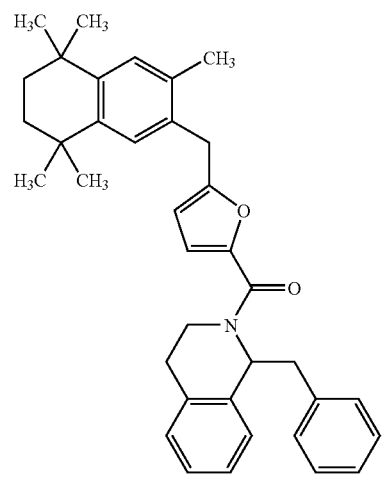
46
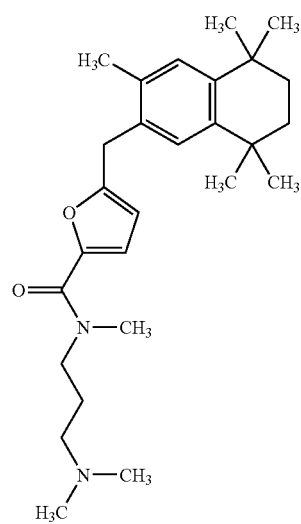
92

-continued
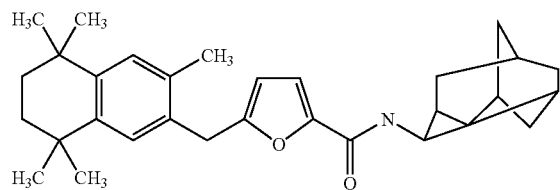
37
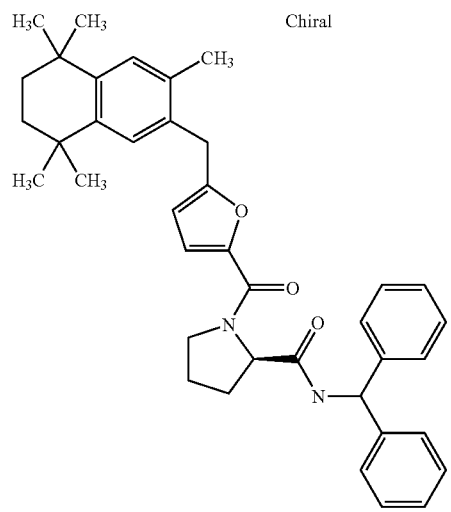
Chiral 58
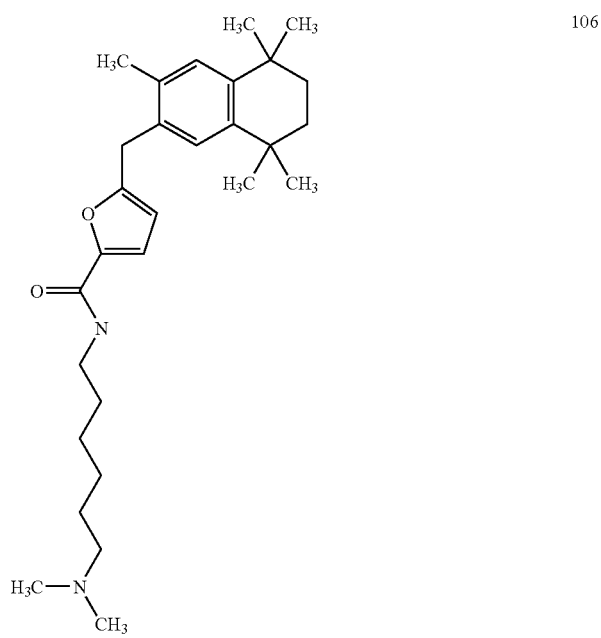
106

-continued
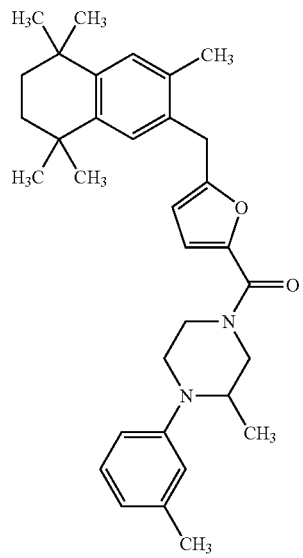 73
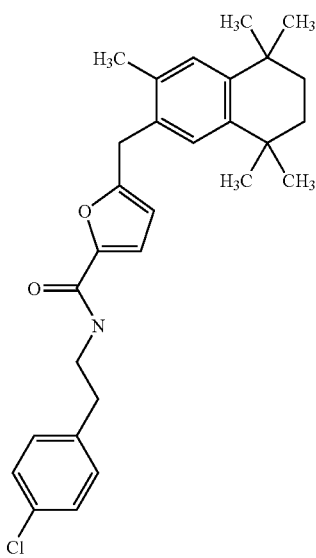 81
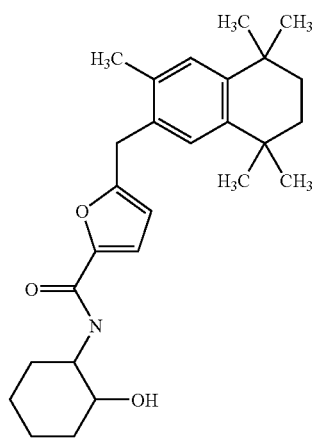 97

-continued
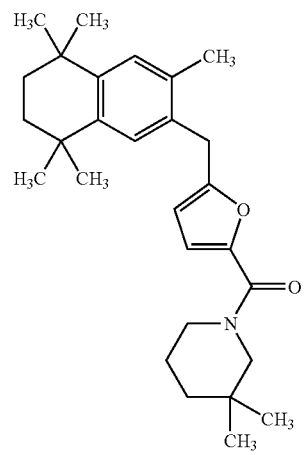
98
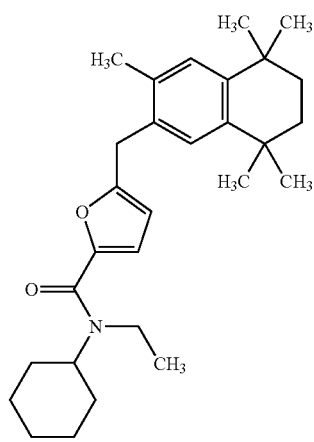
100
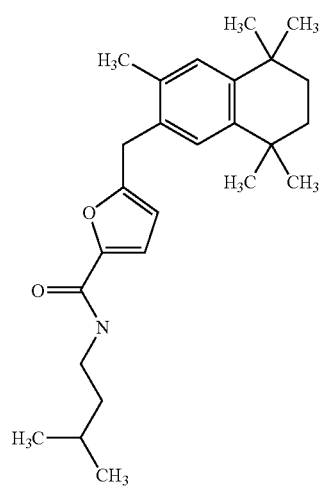
88

-continued
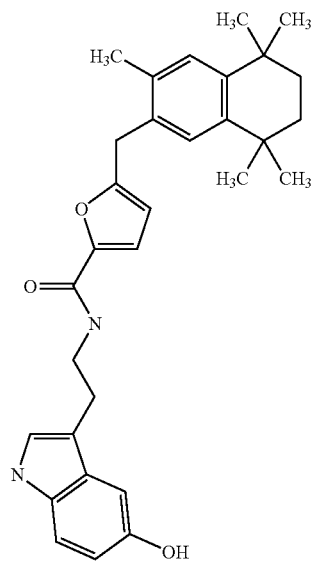
84
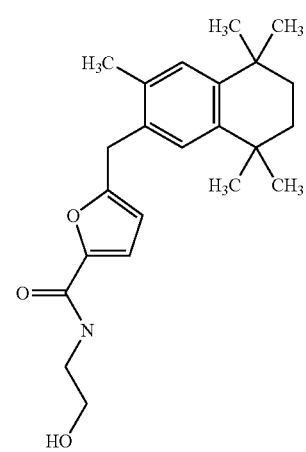
53
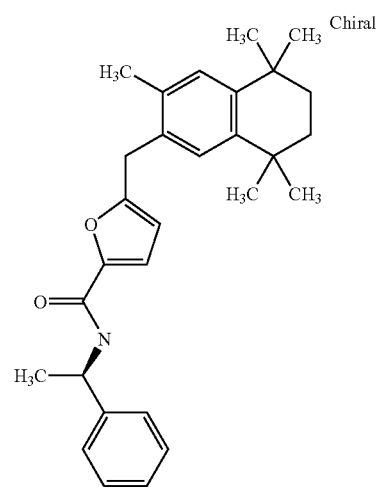
72

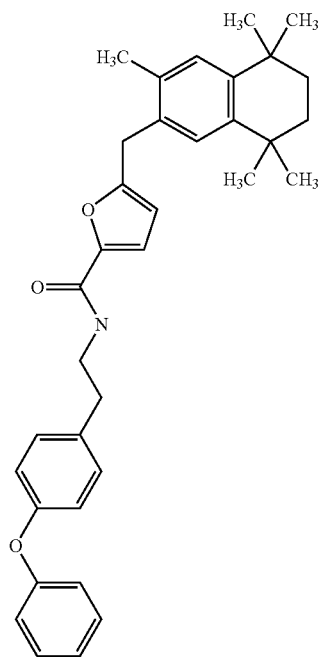
57
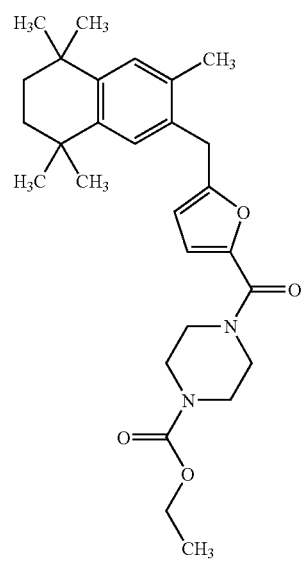
65

-continued
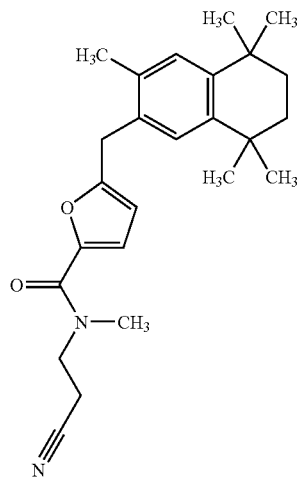
83
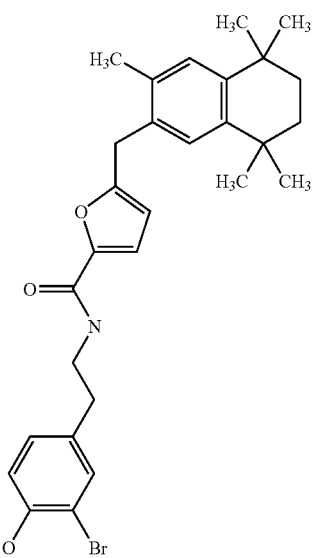
78
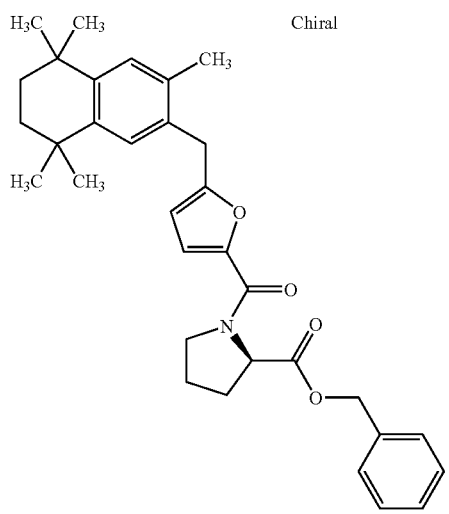
Chiral 86

-continued
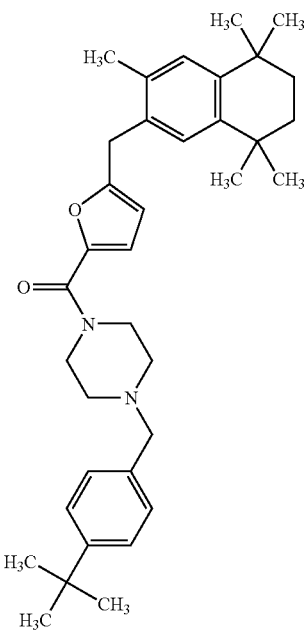
65
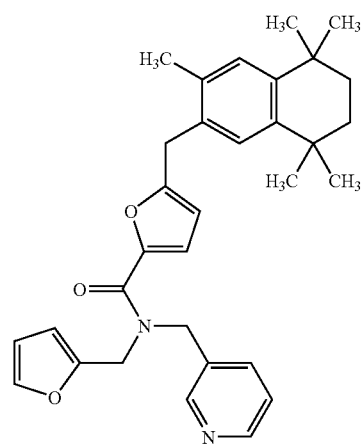
89
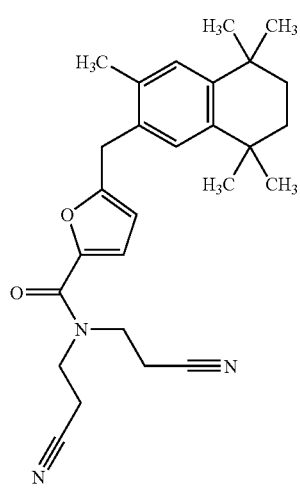
77

-continued
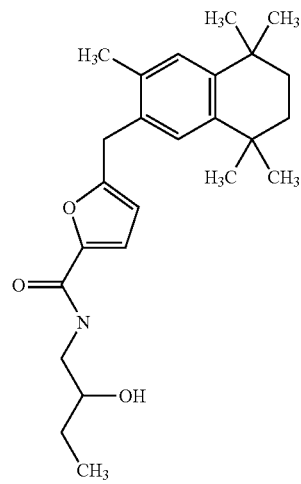
99
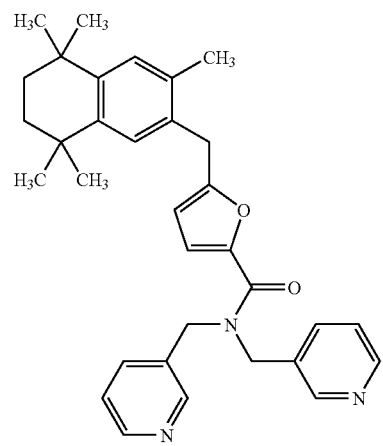
101
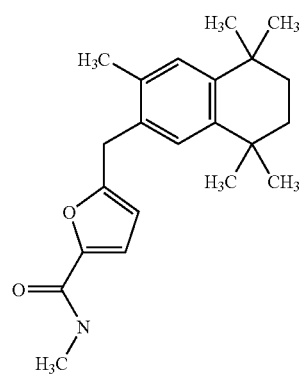
23

-continued
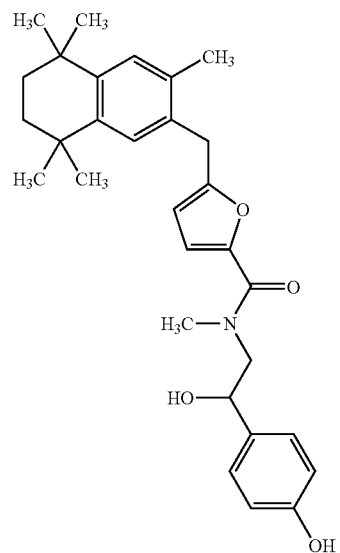
34
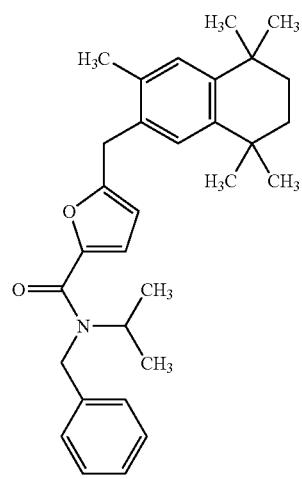
84
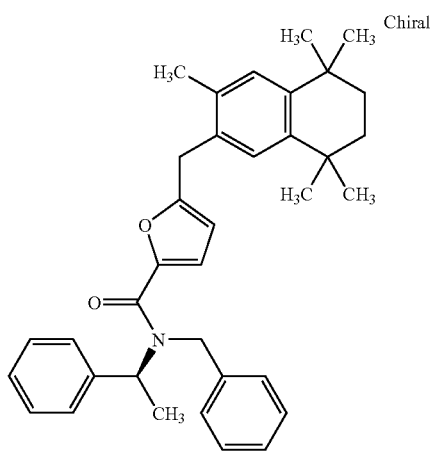
46

-continued
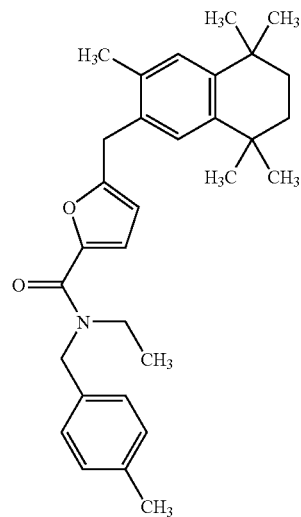
79
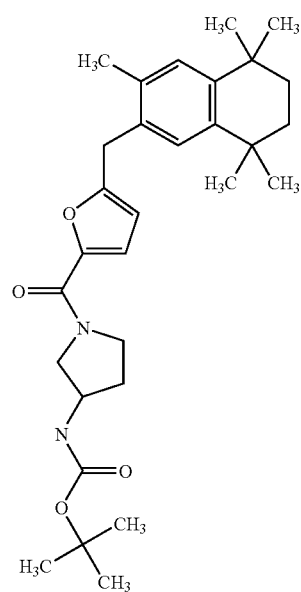
82
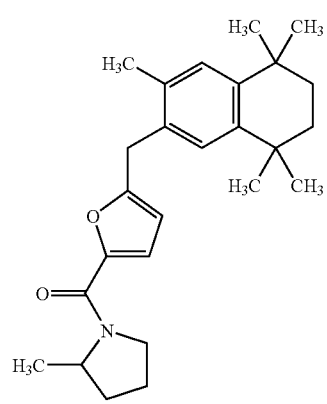
102

-continued
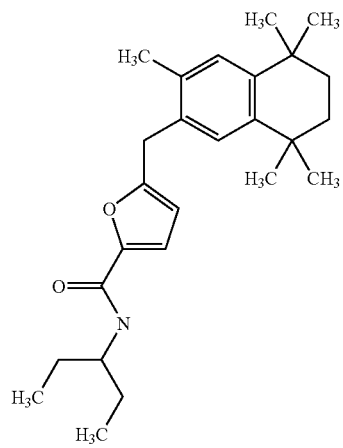
76
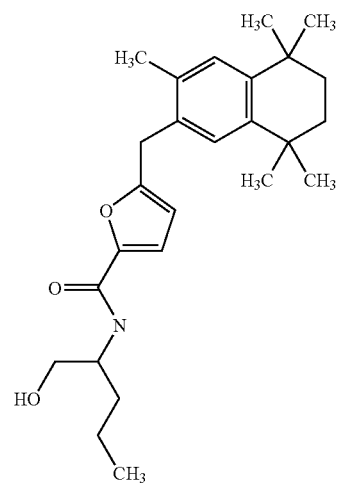
99
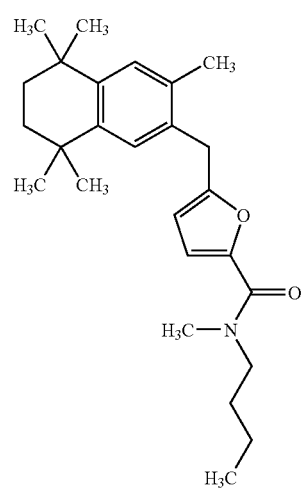
100

-continued
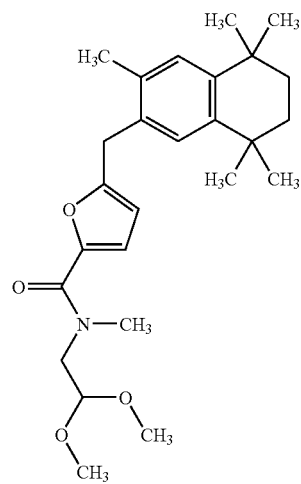
90
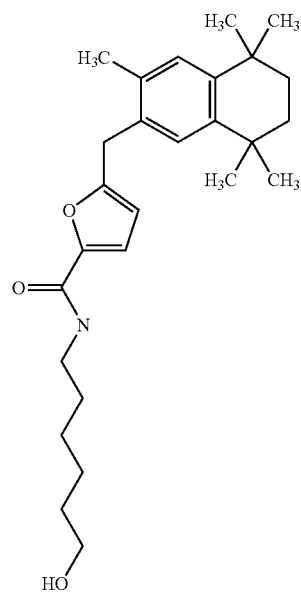
103
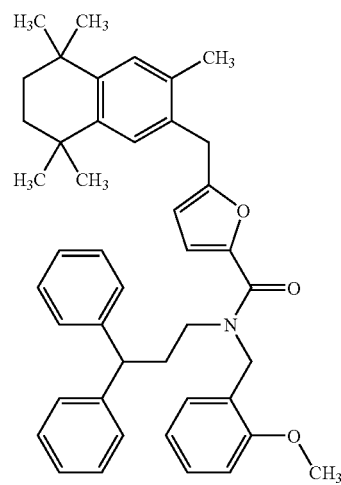
21

-continued
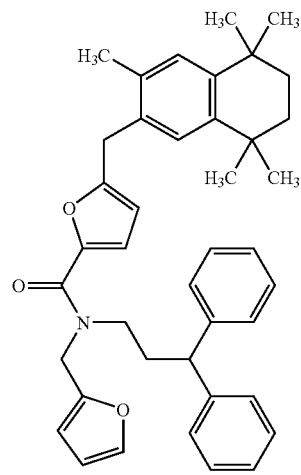
43
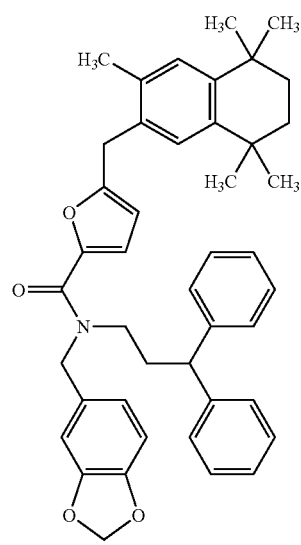
25
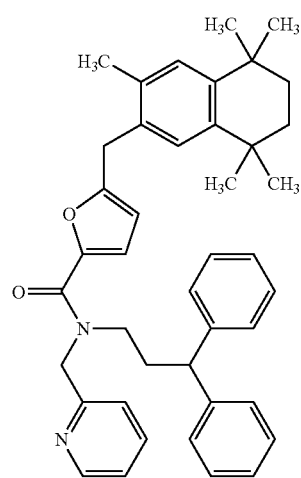
50

-continued
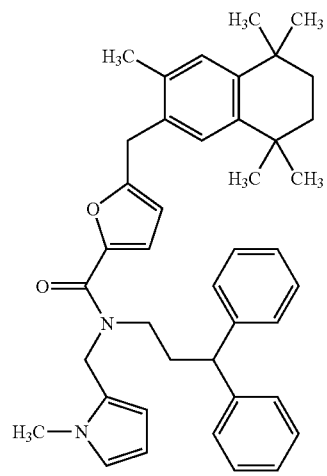
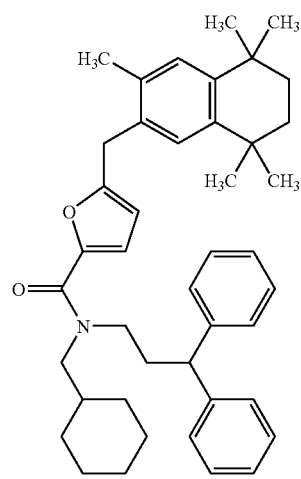
31
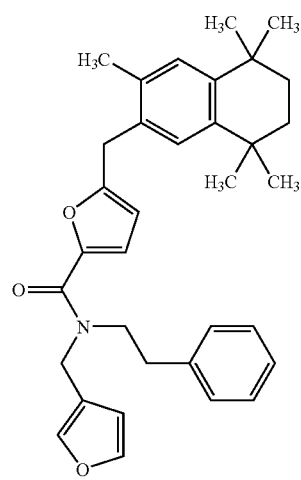
61

-continued
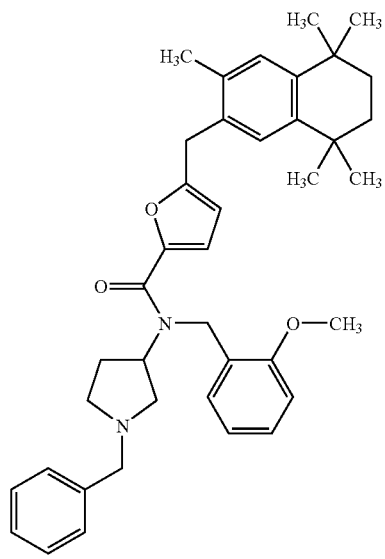
91
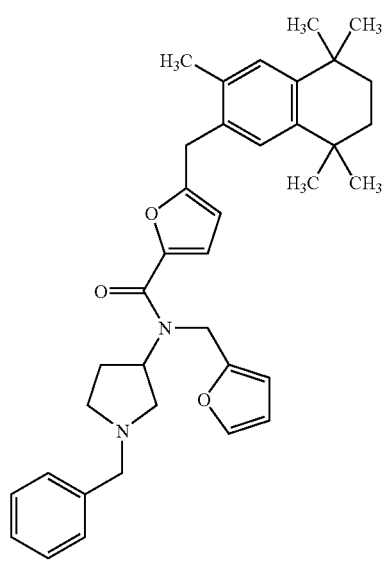
94

-continued
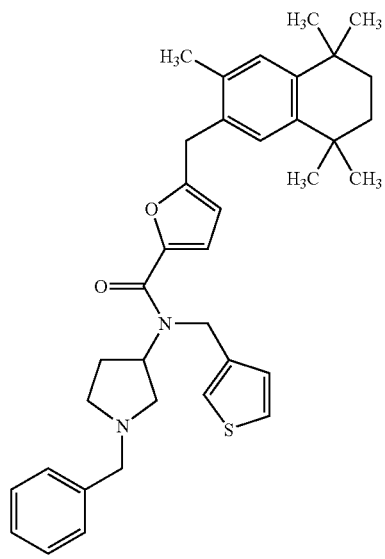
91
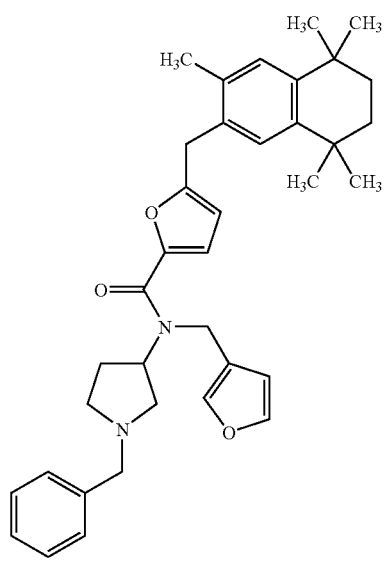
91

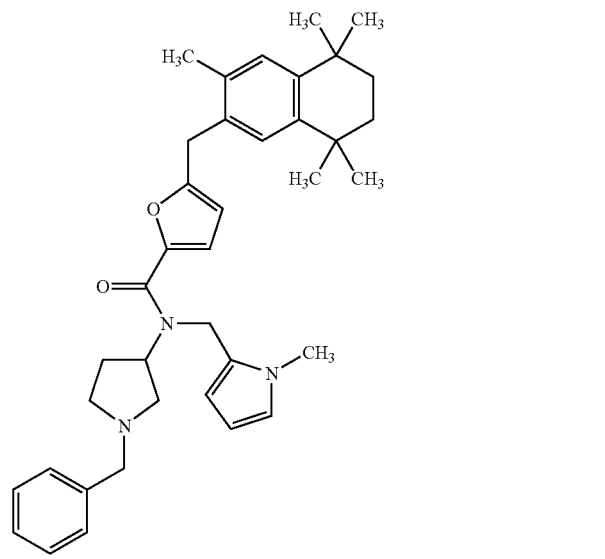
98
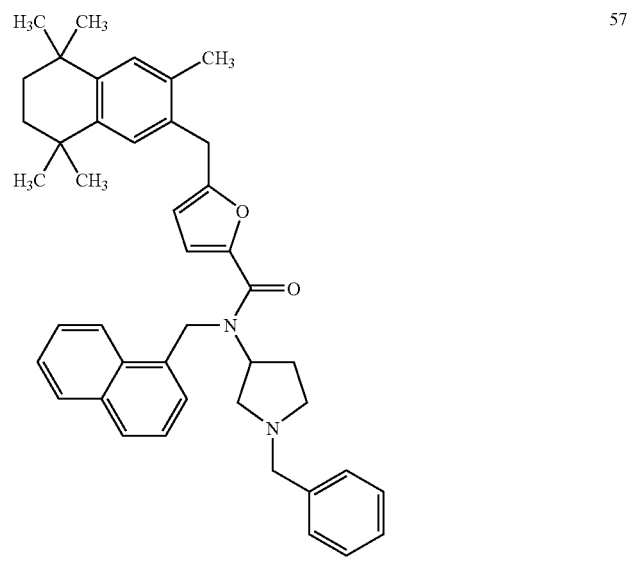
57

-continued
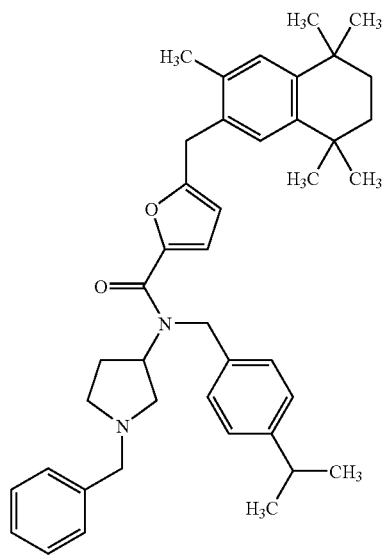
48
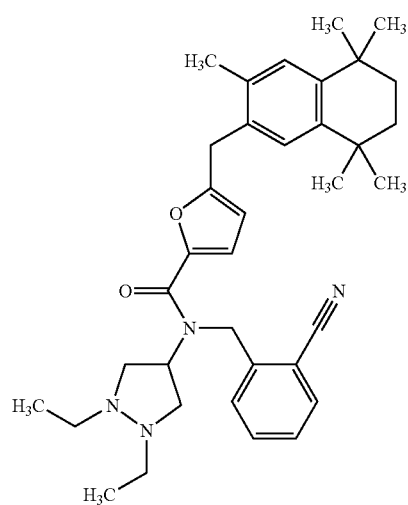
101
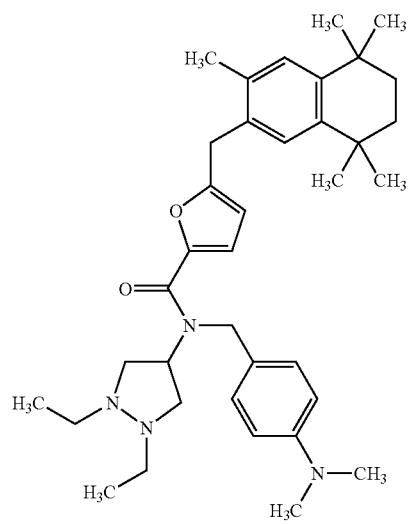
95

-continued
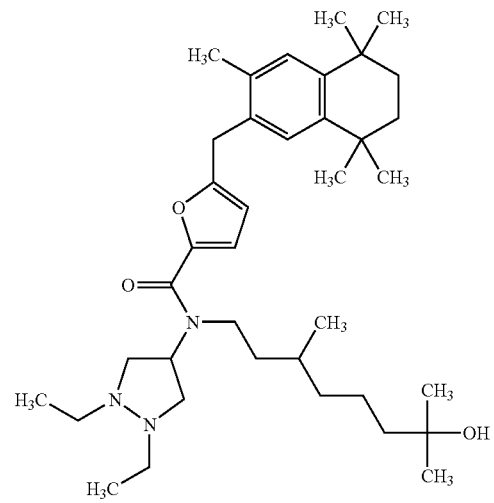
104
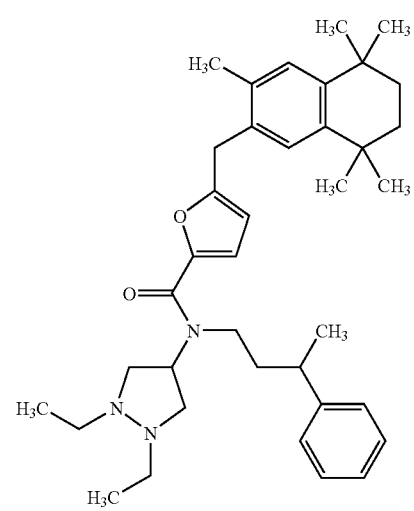
95
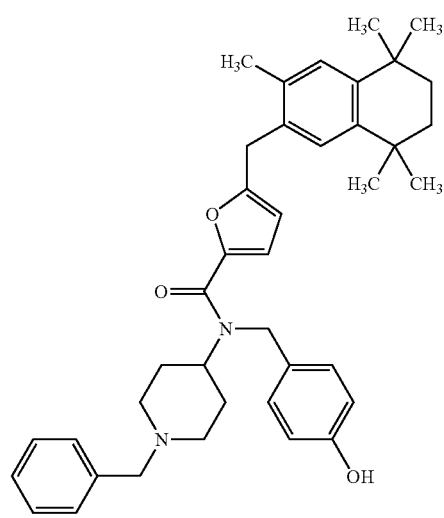
28

-continued
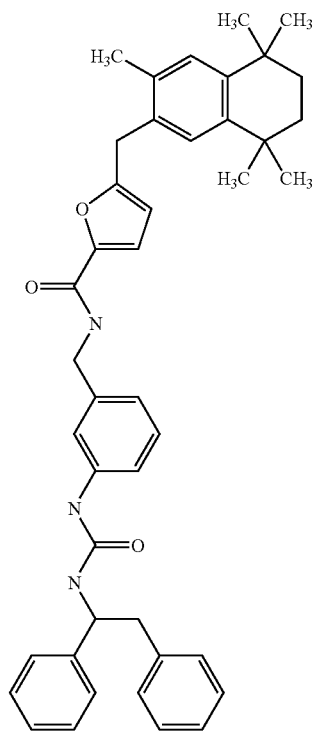
42
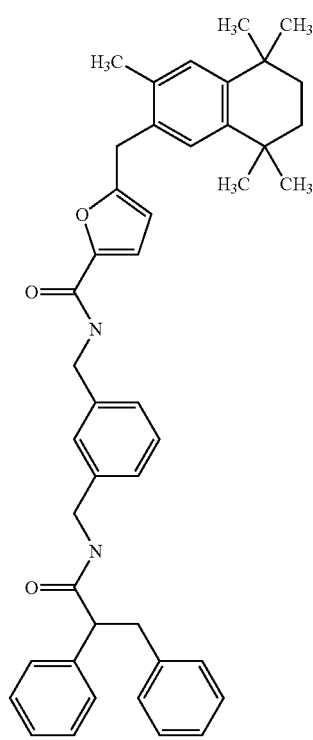
47

-continued
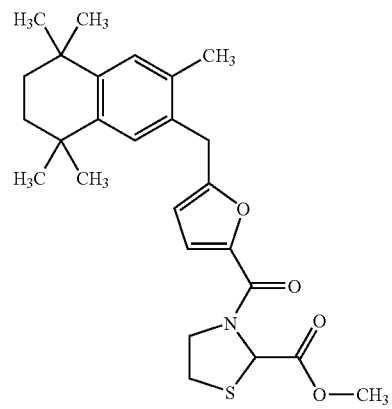
39
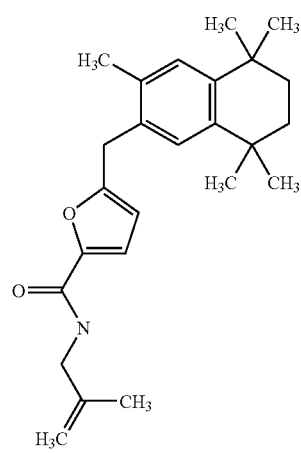
93
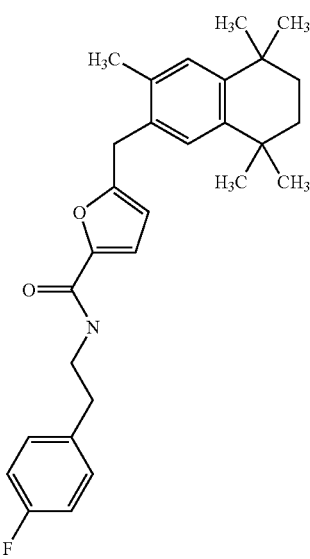
79

-continued
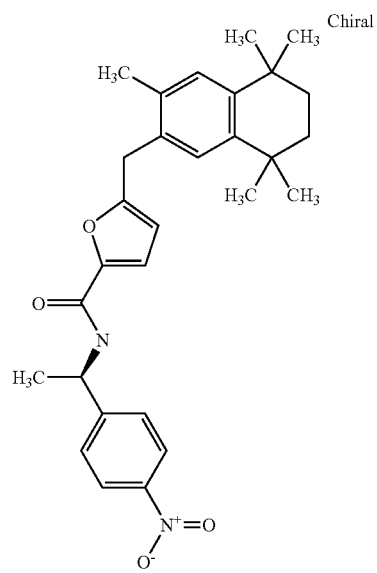
44
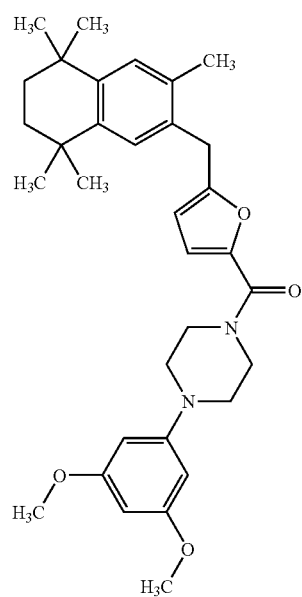
65
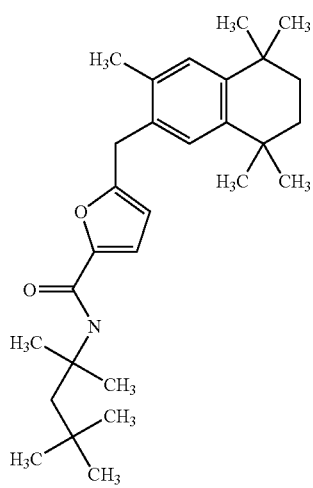
66

-continued
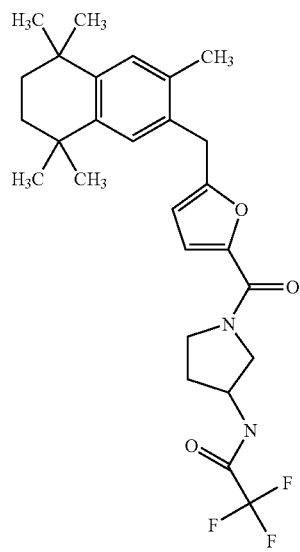
60
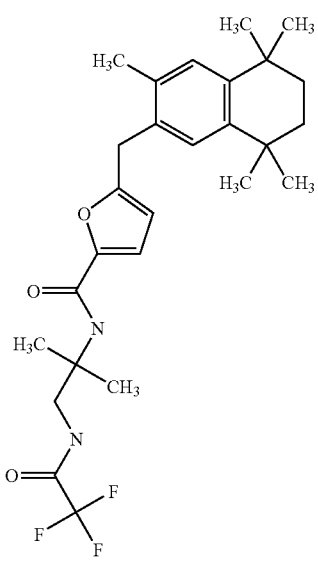
37
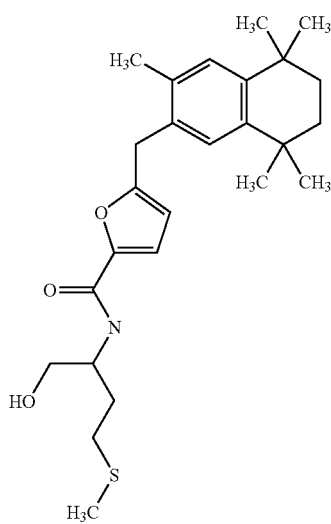
105

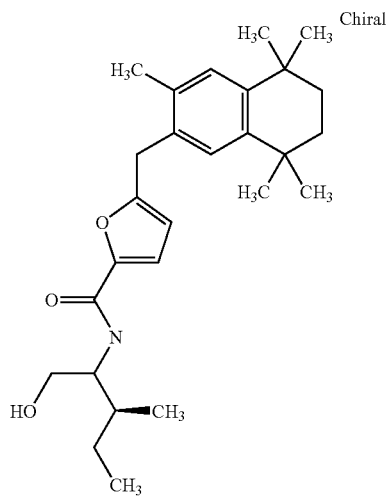
77
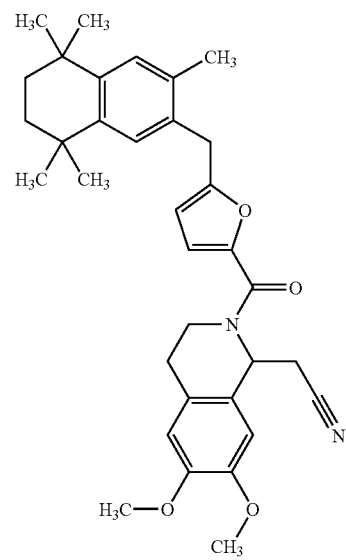
52
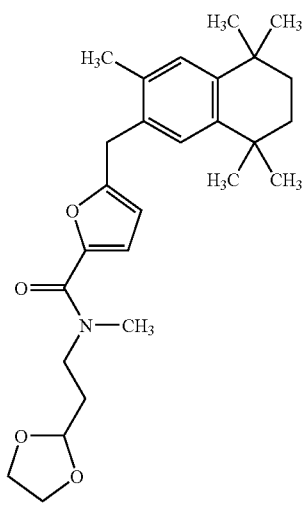
96

| | |
|---|---|
| 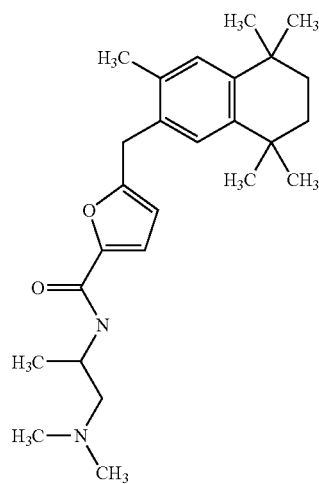 | 92 |
| 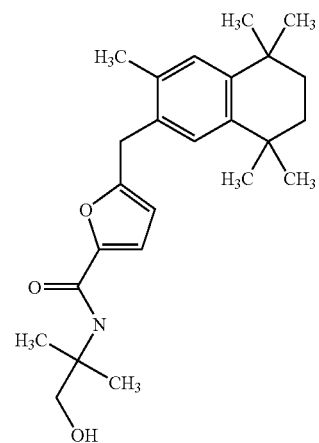 | 90 |
| 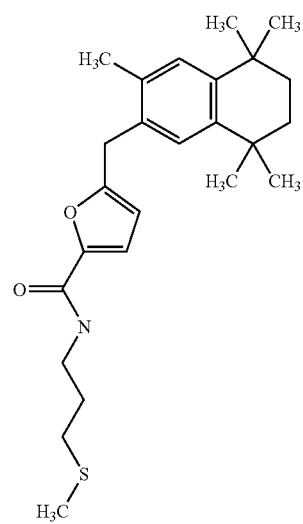 | 99 |

-continued
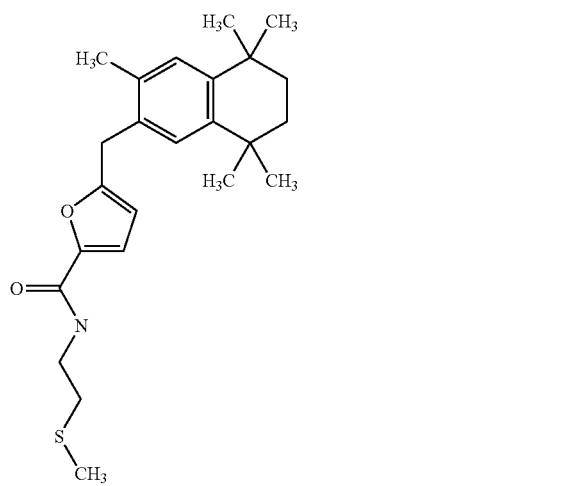
97
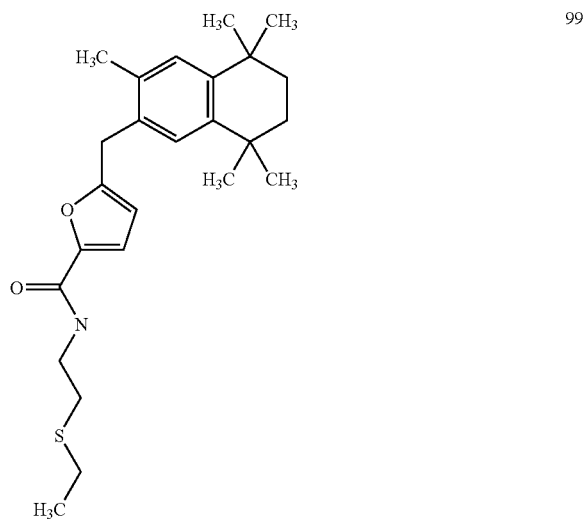
99
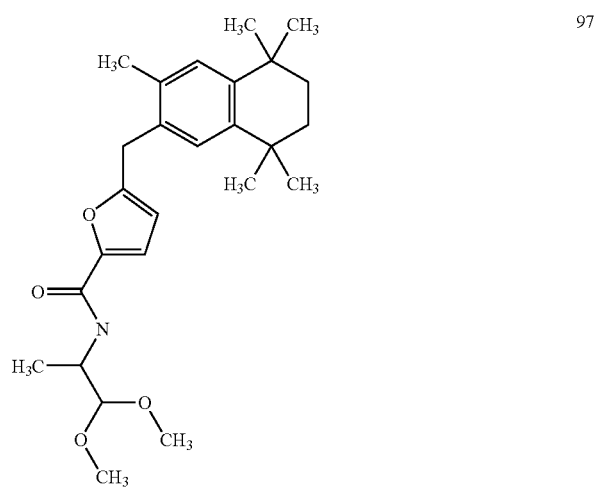
97

-continued
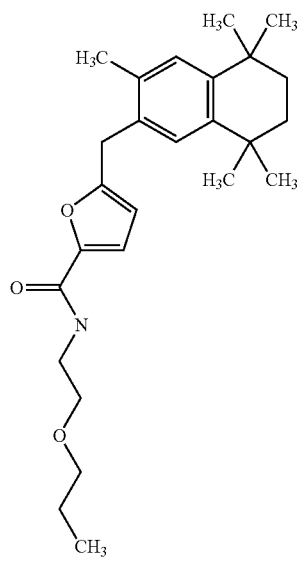
103
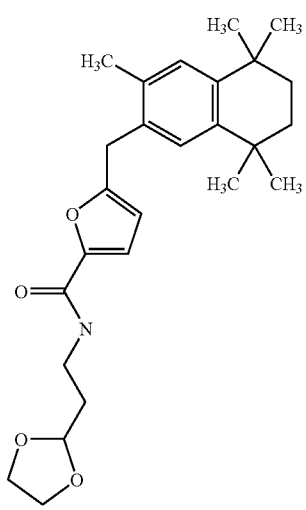
104
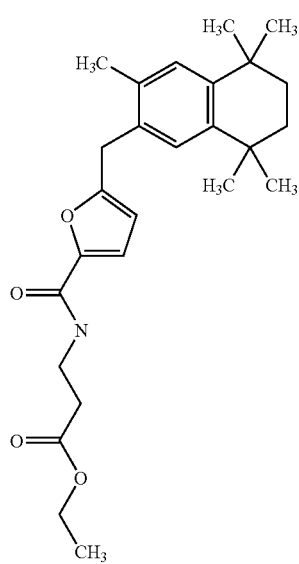
99

| MOLSTRUCTURE | % inhib. @ 10 uM hGnRH | Repeats @ 10 uM hGnRH |
|---|---|---|
| 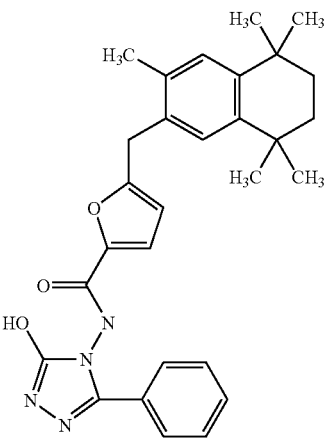 | −25 | −25 |
| 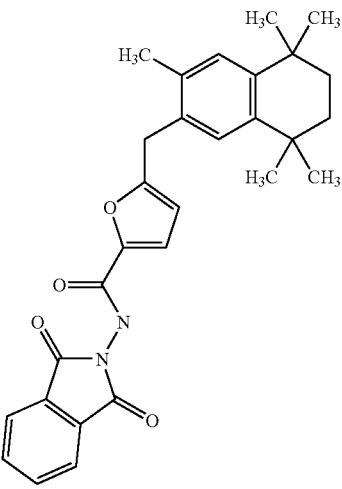 | −15 | −20 |
| 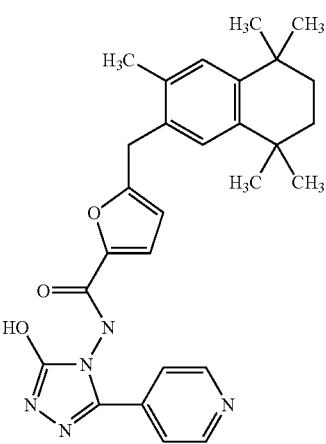 | −17 | −28 |
-continued
| MOLSTRUCTURE | % inhib. @ 10 uM hGnRH | Repeats @ 10 uM hGnRH |
|---|---|---|
| 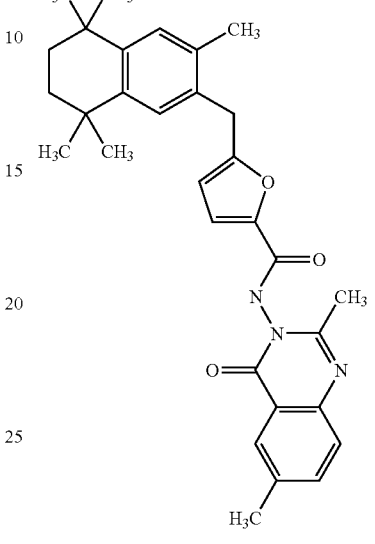 | −4 | −4 |
| 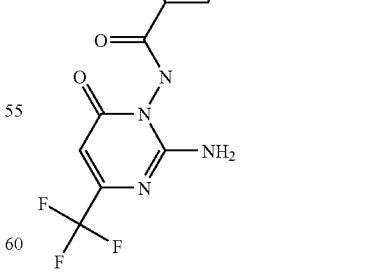 | −10 | −5 |

| MOLSTRUCTURE |
|---|
| 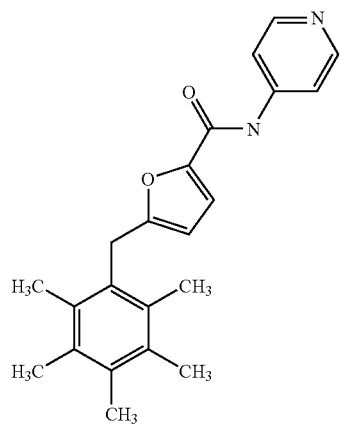 |
| 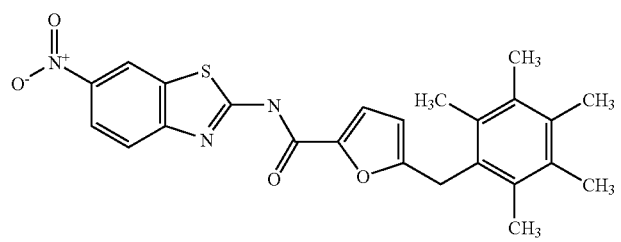 |
| 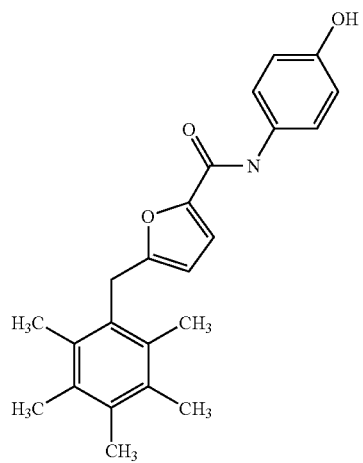 |

| MOLSTRUCTURE |
| --- |
| 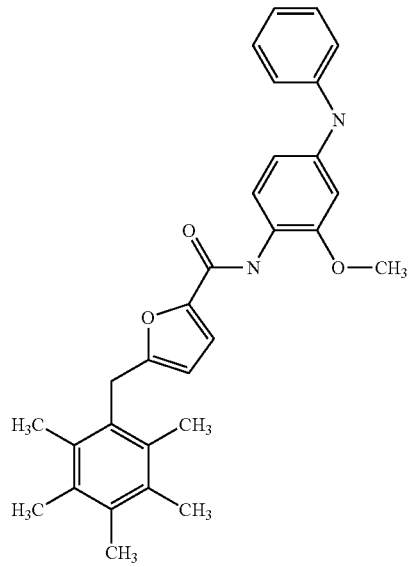 |
| 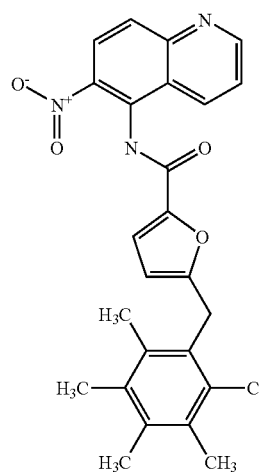 |
| 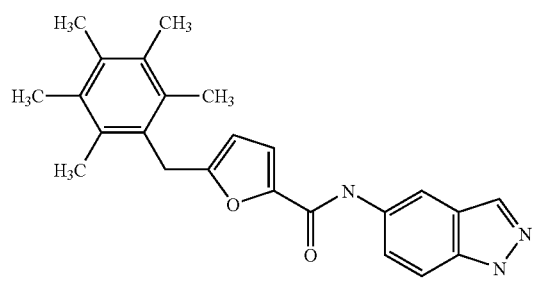 |

-continued
MOLSTRUCTURE
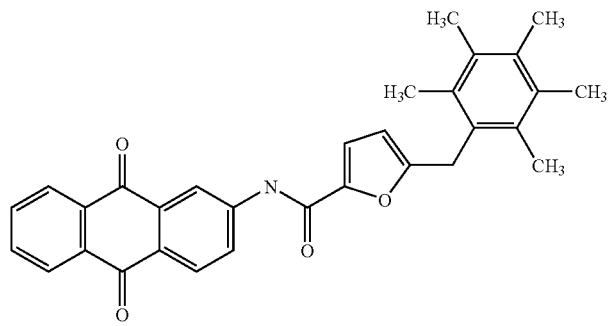
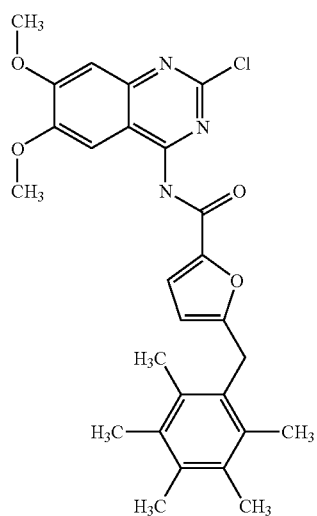
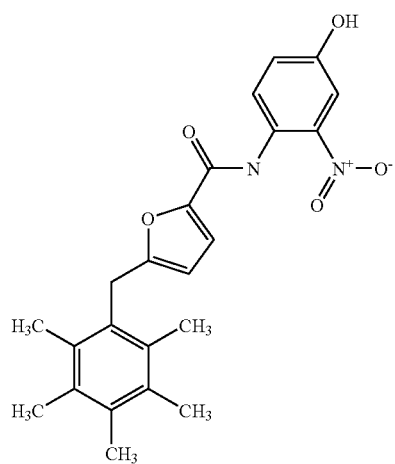

-continued
MOLSTRUCTURE
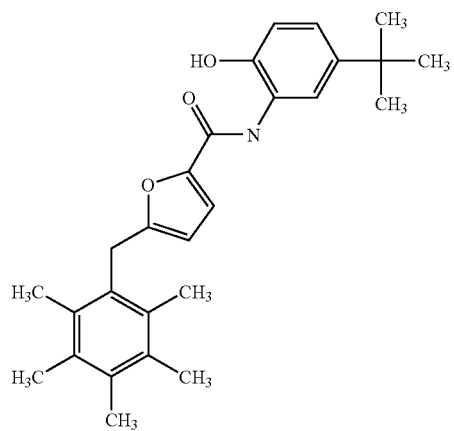
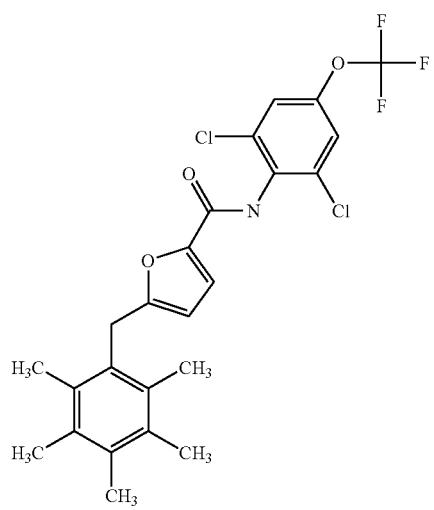
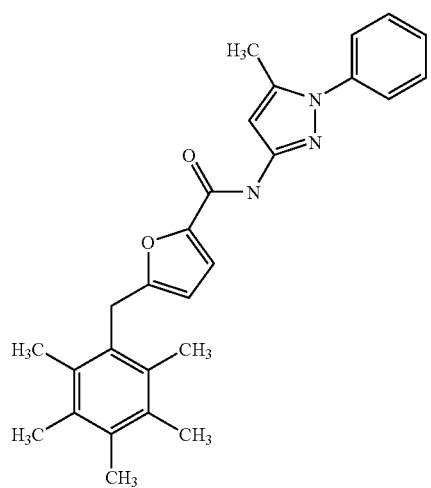

-continued
MOLSTRUCTURE
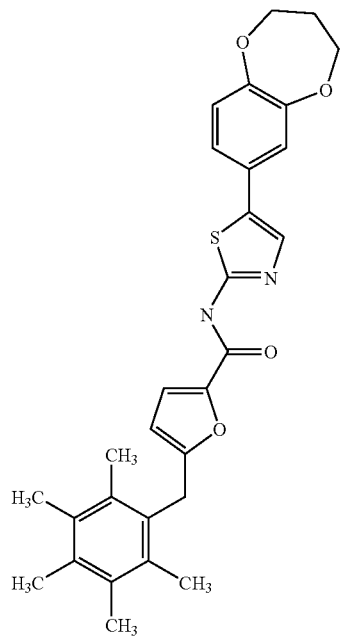
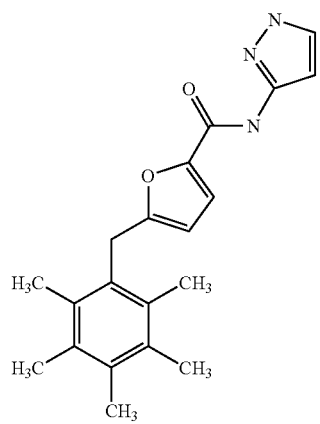
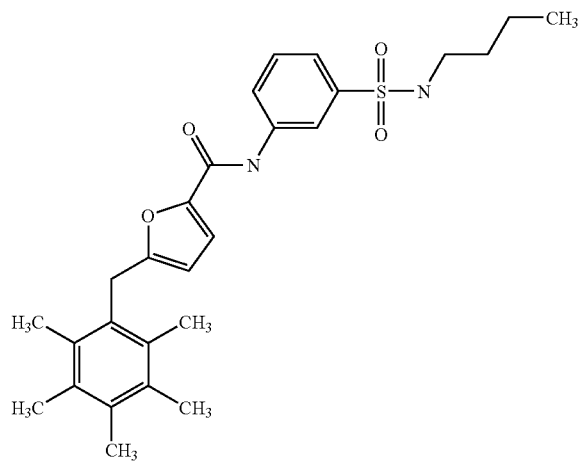

-continued
MOLSTRUCTURE
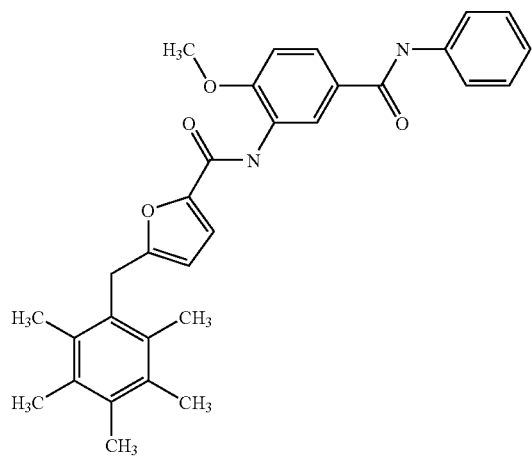
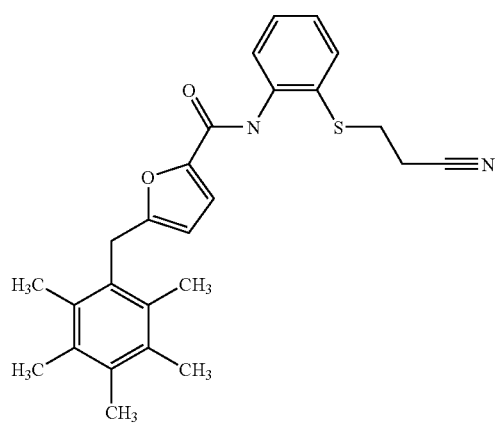
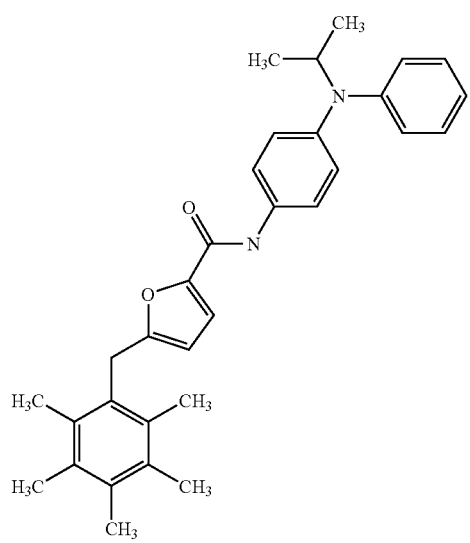

-continued
| MOLSTRUCTURE |
|---|
| 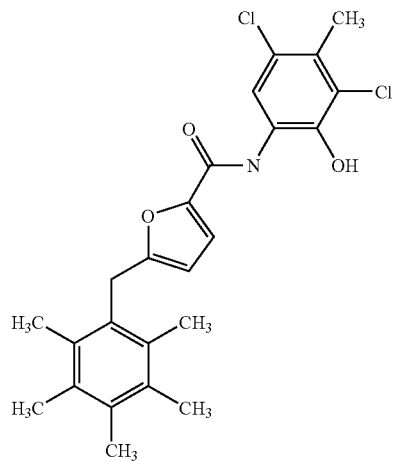 |
| 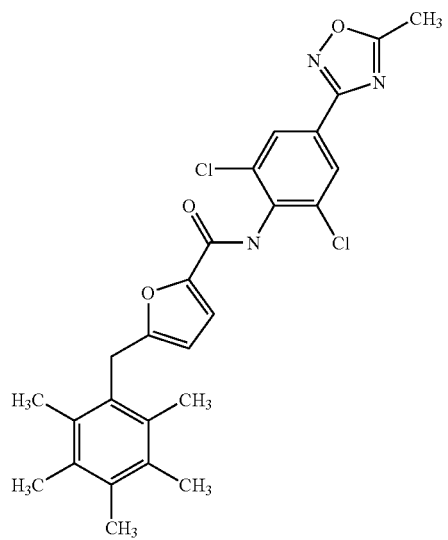 |
| 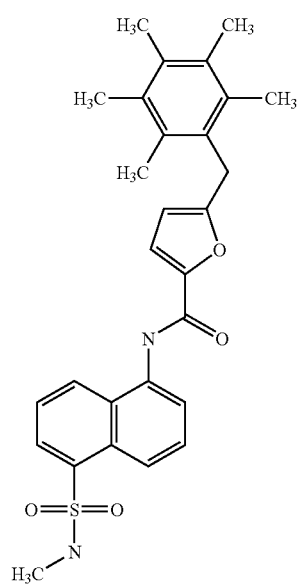 |

| MOLSTRUCTURE |
| --- |
| 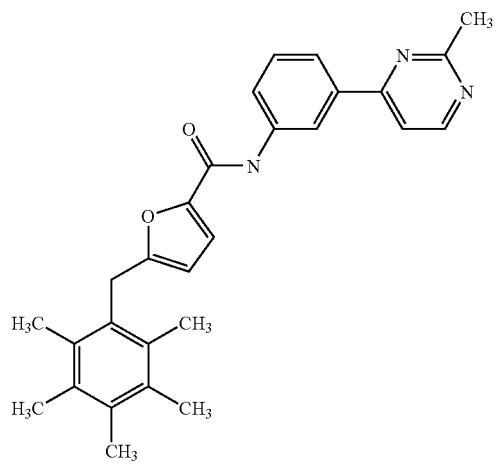 |
| 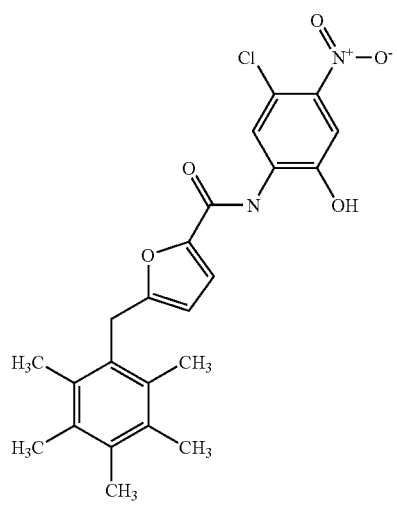 |
| 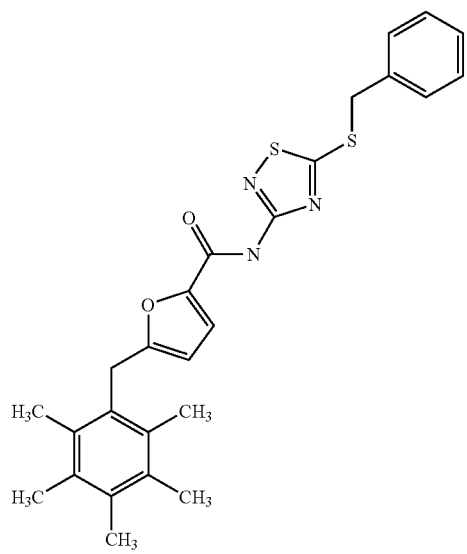 |

-continued
MOLSTRUCTURE
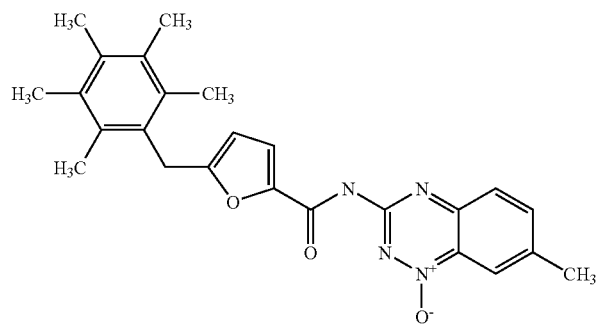
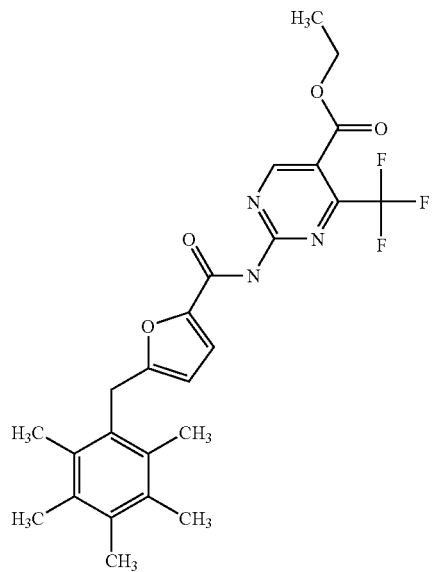
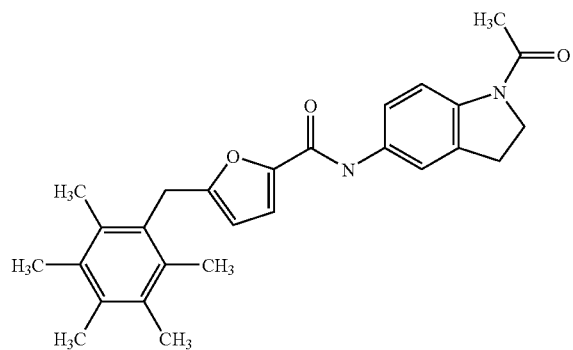

-continued
| MOLSTRUCTURE |
|---|
| 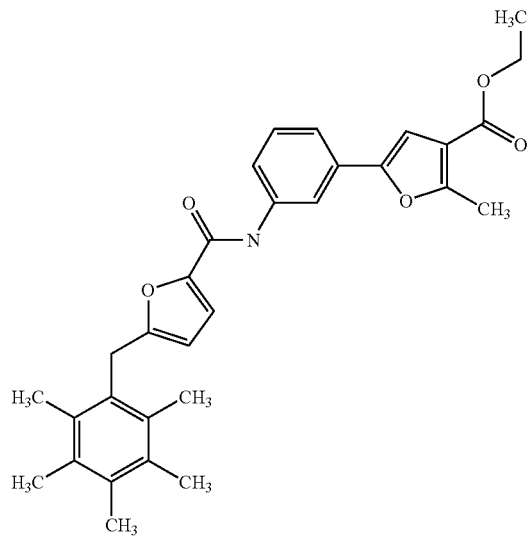 |
| 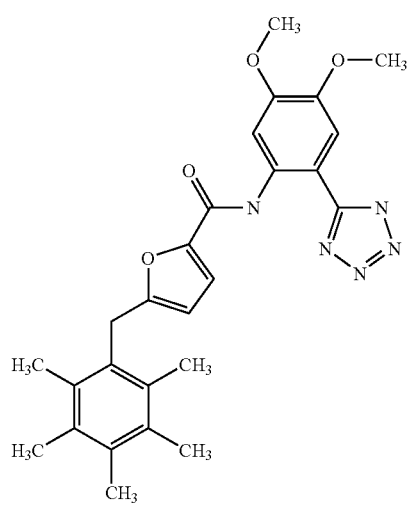 |
| 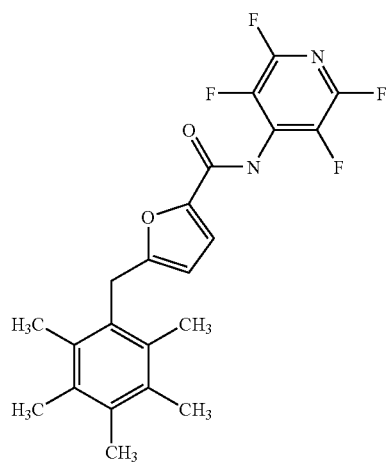 |

| MOLSTRUCTURE |
| --- |
| 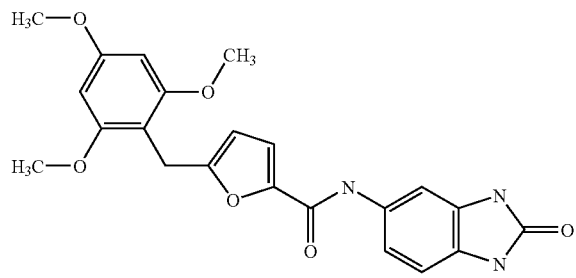 |
| 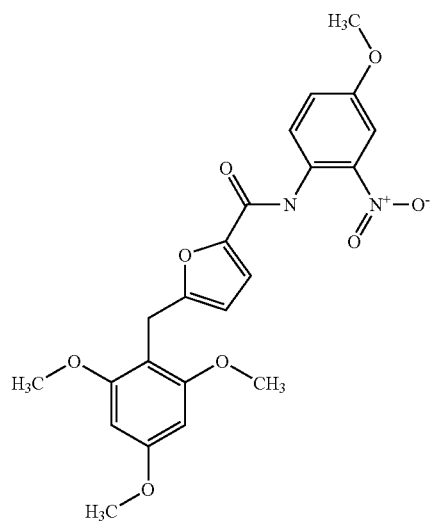 |
| 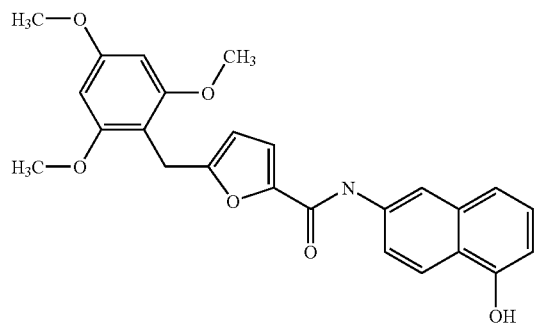 |

-continued
| MOLSTRUCTURE |
|---|
| 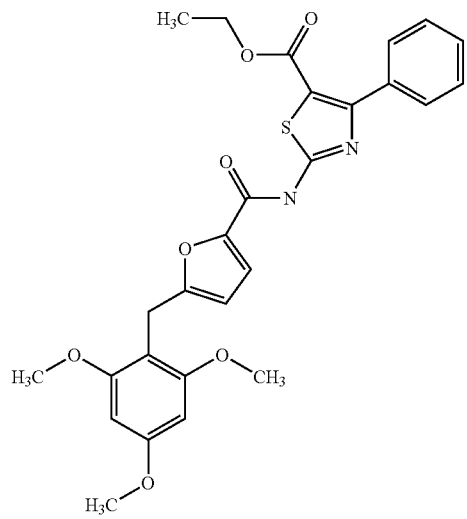 |
| 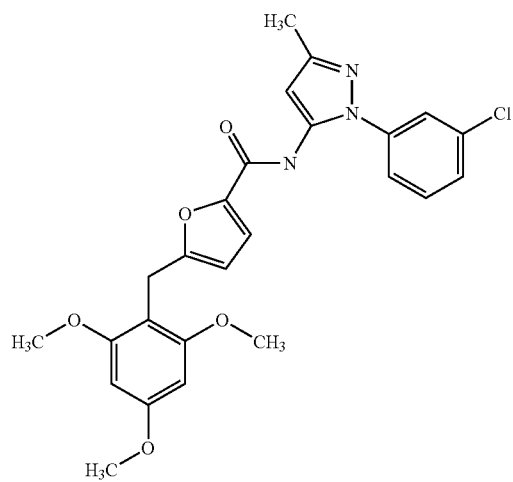 |
| 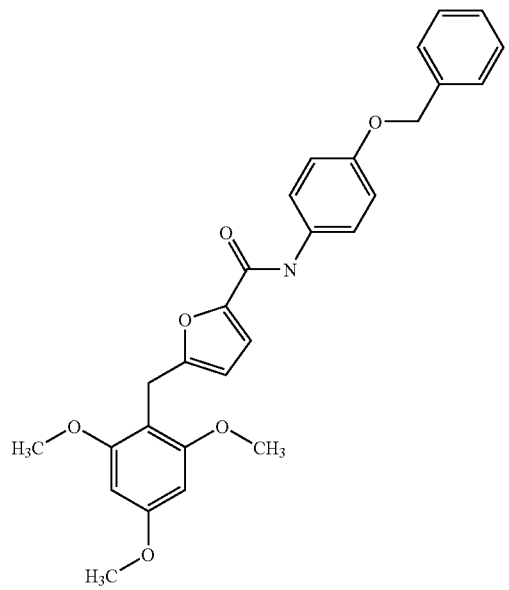 |

-continued
| MOLSTRUCTURE |
|---|
| 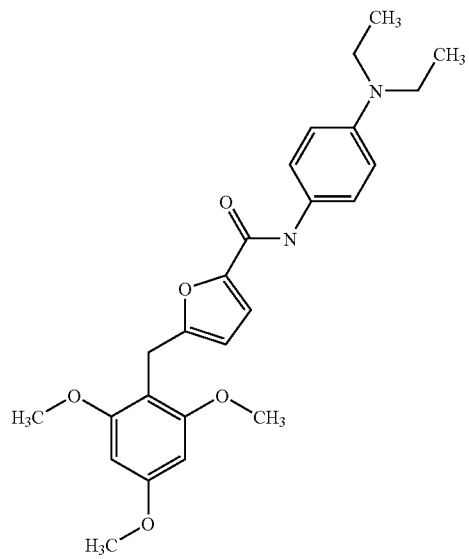 |
| 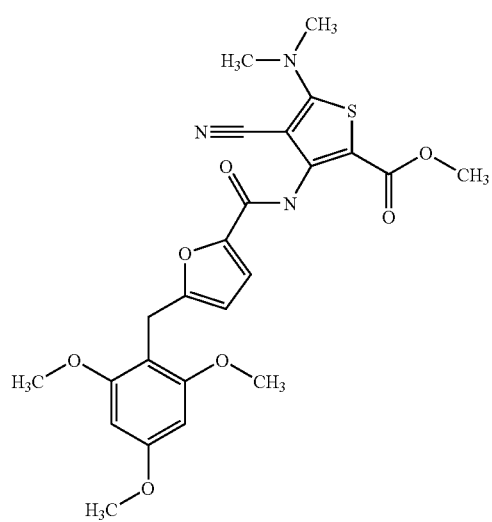 |
| 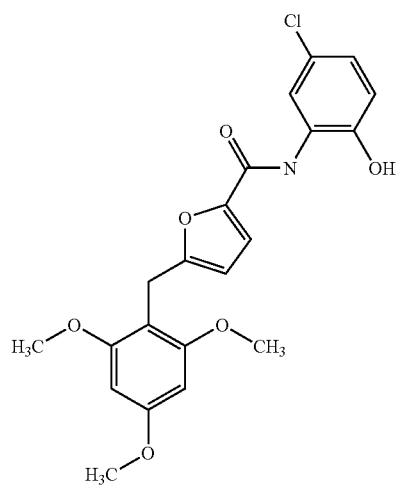 |

| MOLSTRUCTURE |
|---|
| 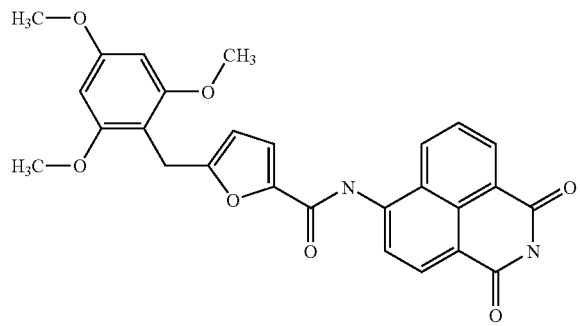 |
| 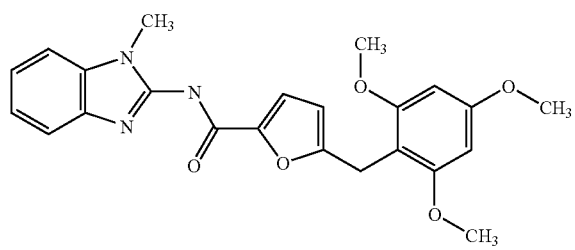 |
| 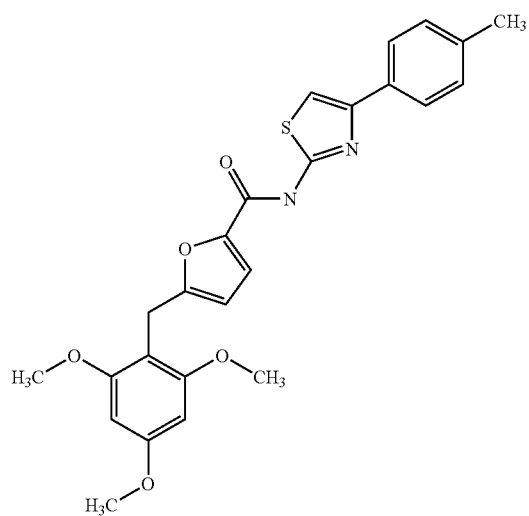 |
| 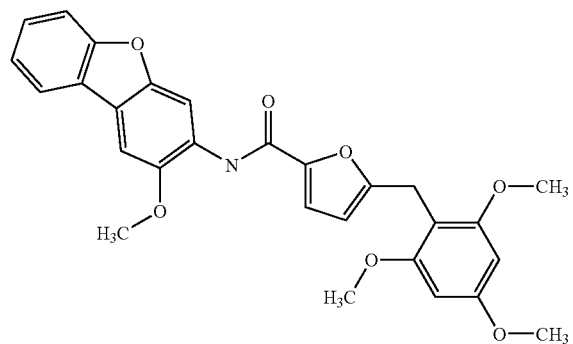 |

| MOLSTRUCTURE |
|---|
| 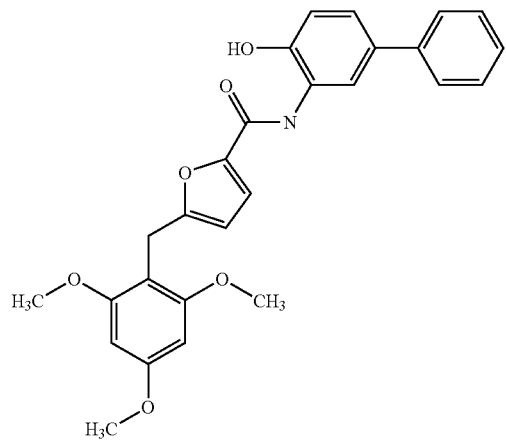 |
| 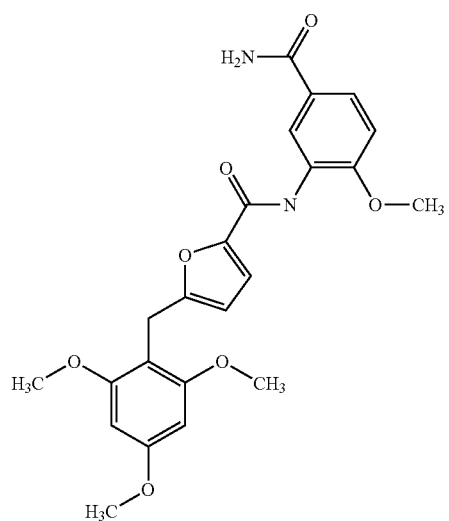 |
| 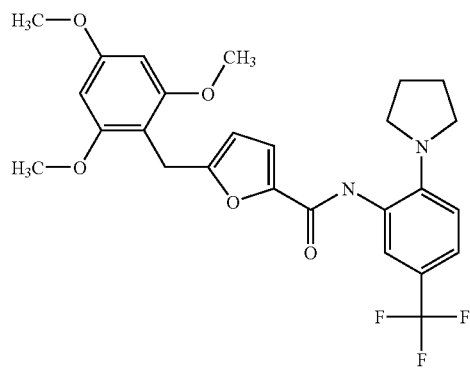 |

-continued
| MOLSTRUCTURE |
| --- |
| 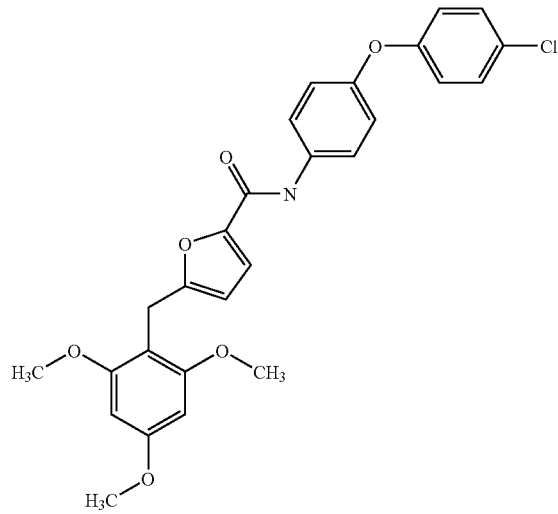 |
| 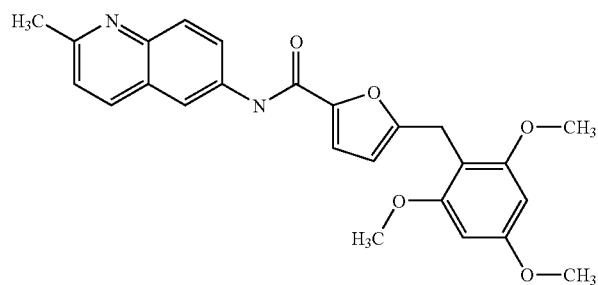 |
| 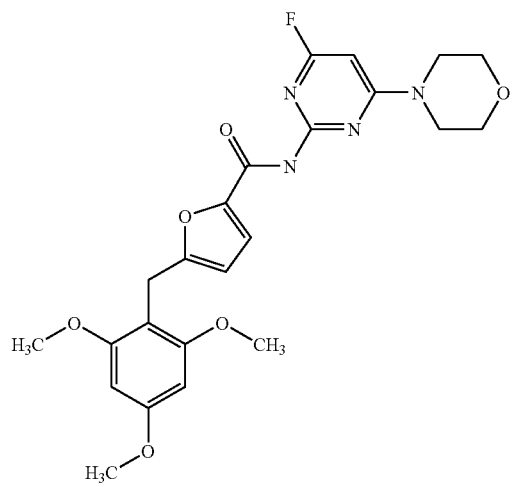 |
| 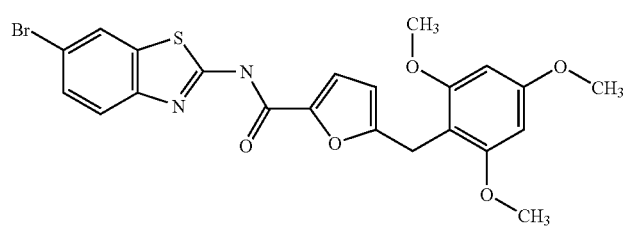 |

-continued
MOLSTRUCTURE
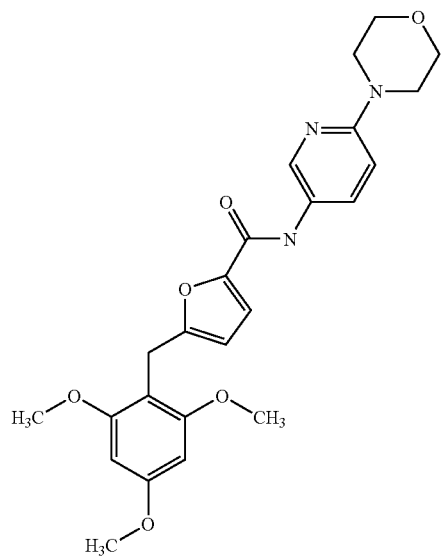
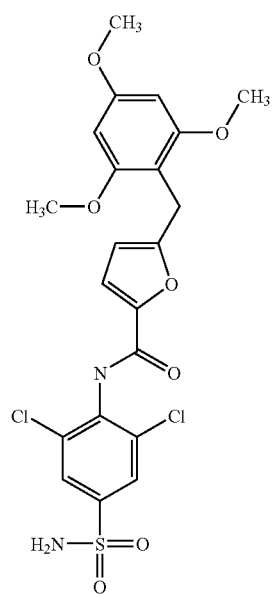

| MOLSTRUCTURE |
|---|
| 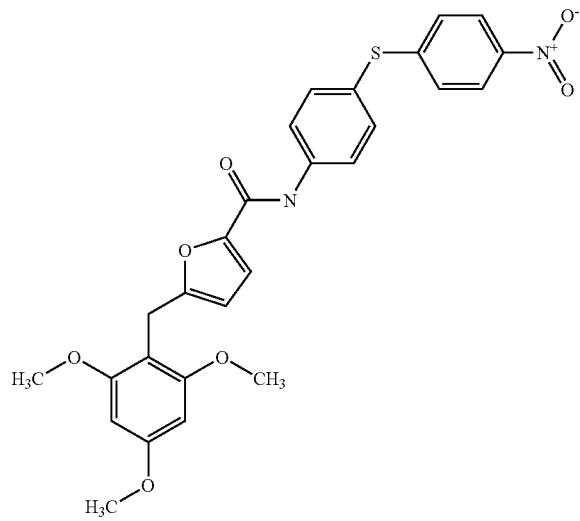 |
| 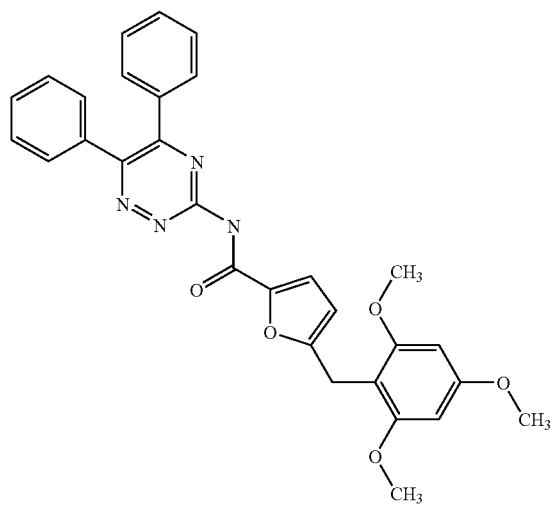 |
| 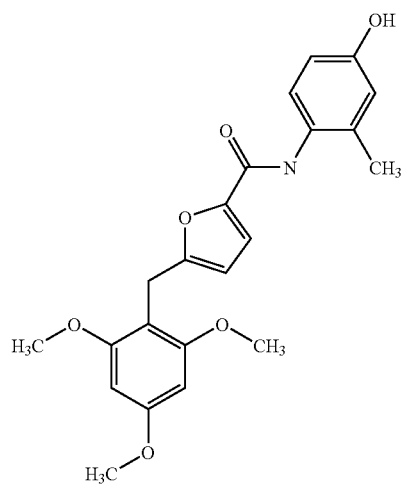 |

MOLSTRUCTURE
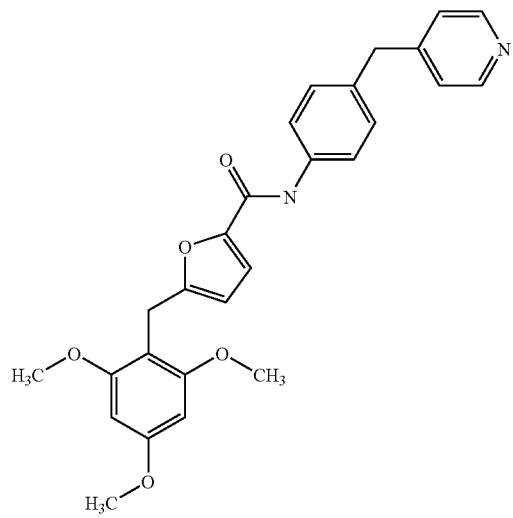
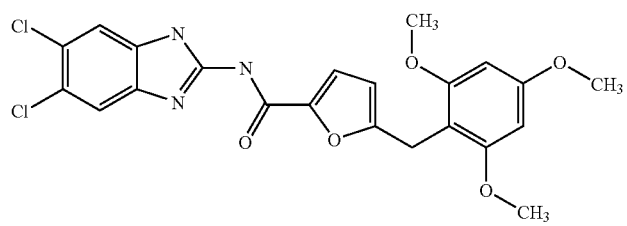
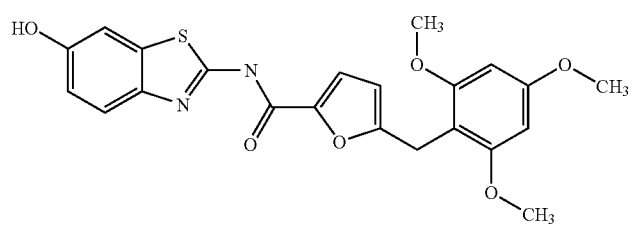
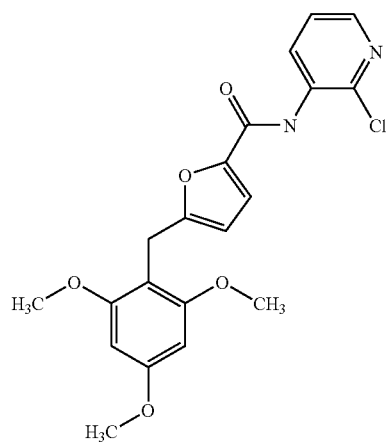

| MOLSTRUCTURE |
|---|
| 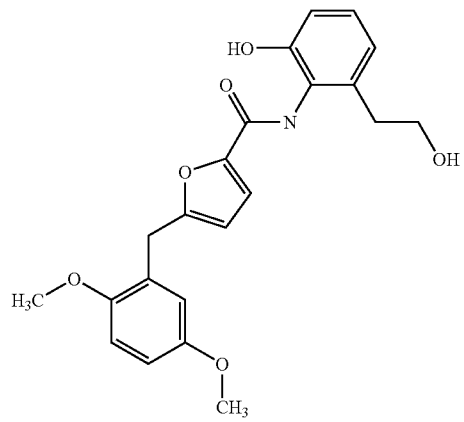 |
| 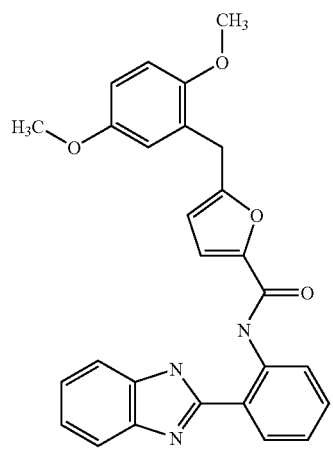 |
| 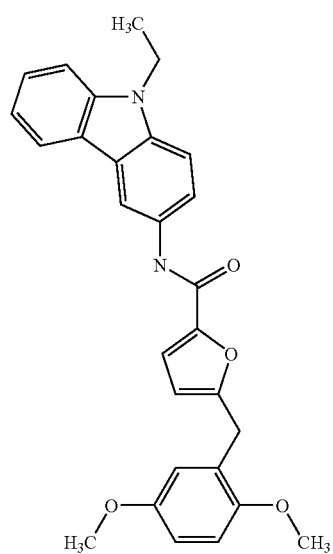 |

-continued
MOLSTRUCTURE
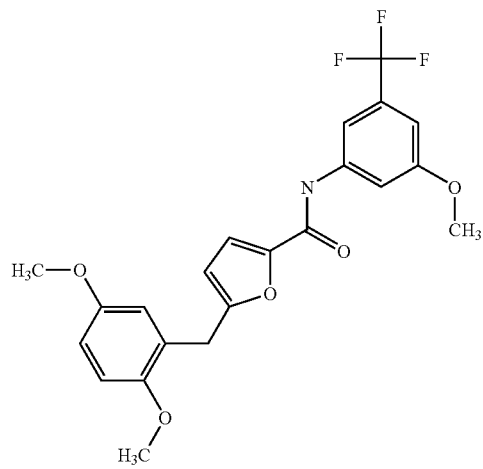
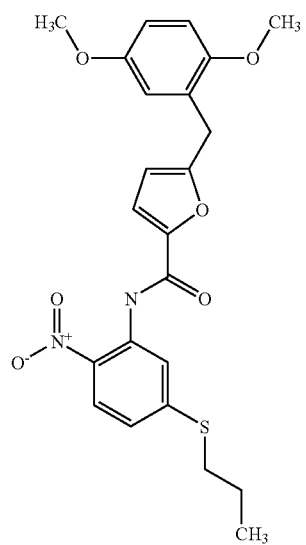
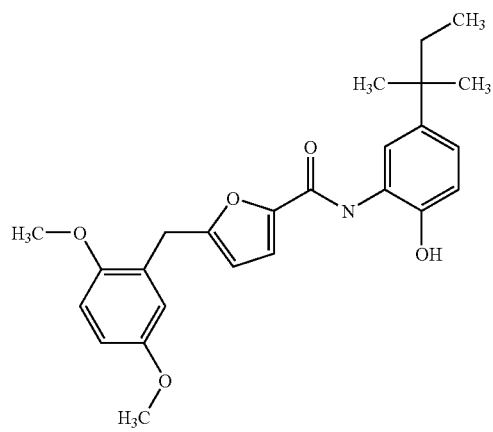

-continued
MOLSTRUCTURE
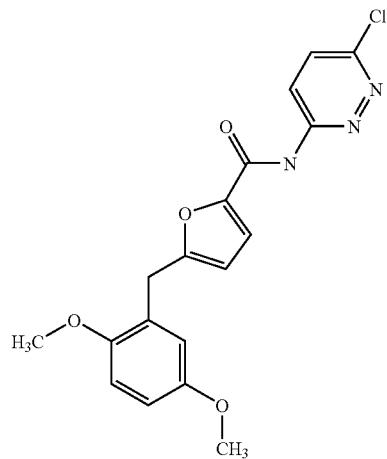
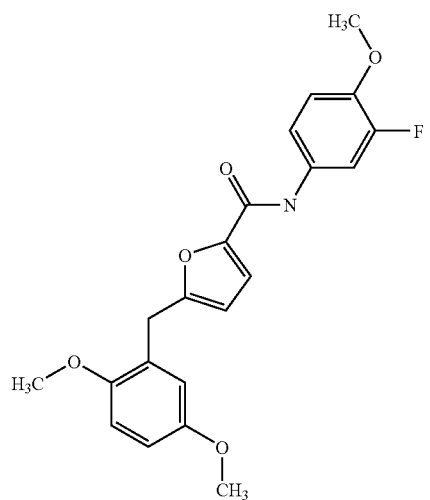
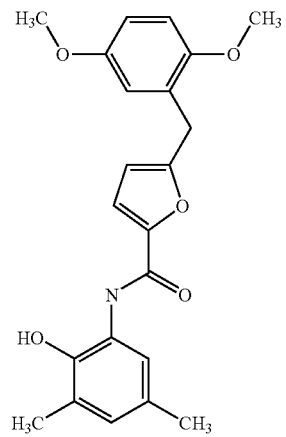

-continued
MOLSTRUCTURE
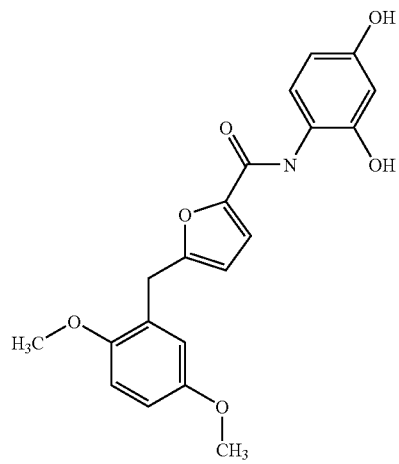
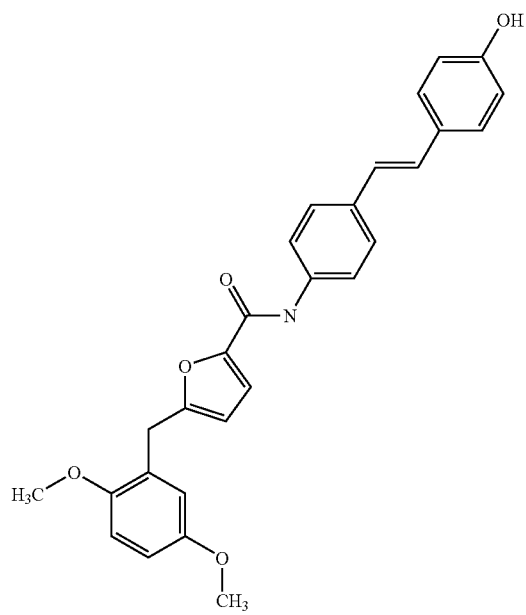
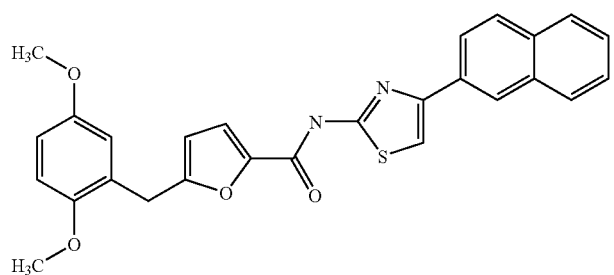

-continued
MOLSTRUCTURE
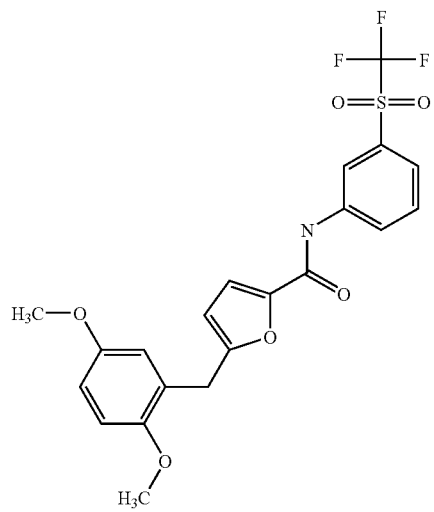
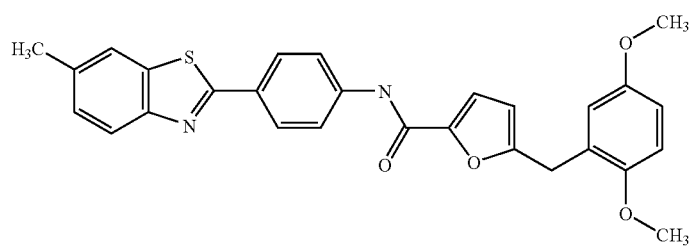
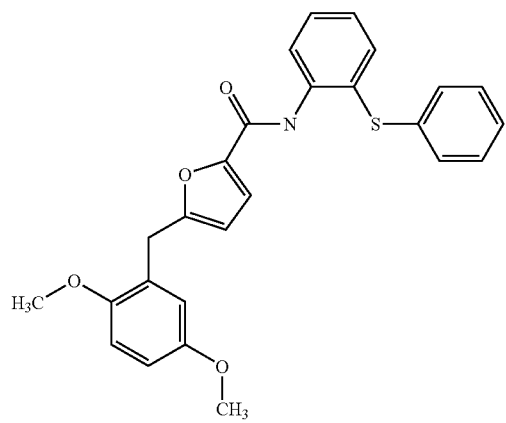

| MOLSTRUCTURE |
|---|
| 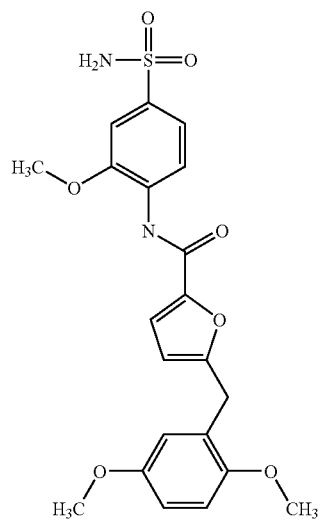 |
| 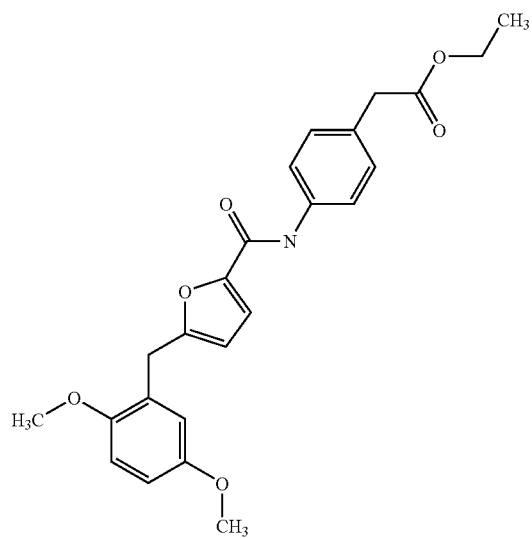 |
| 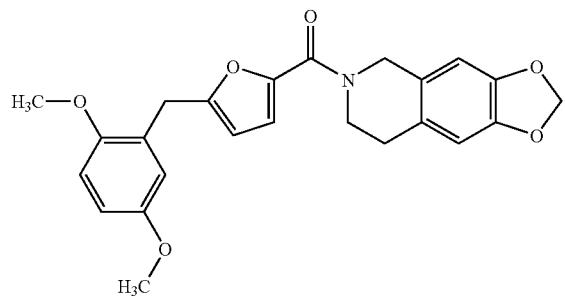 |

| MOLSTRUCTURE |
|---|
| 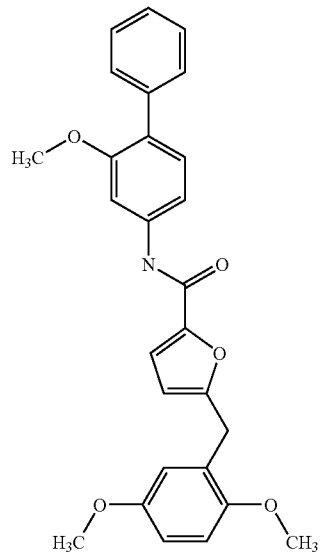 |
| 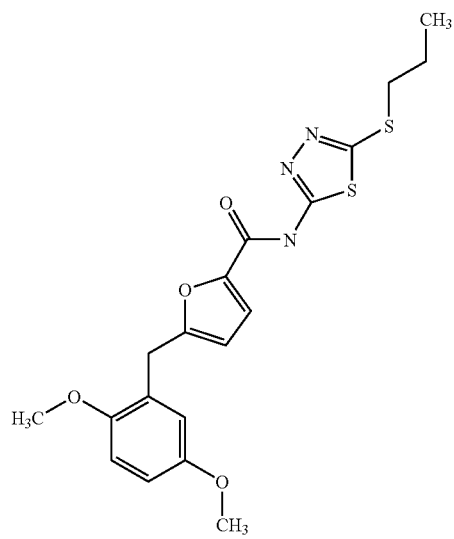 |

| MOLSTRUCTURE |
|---|
| 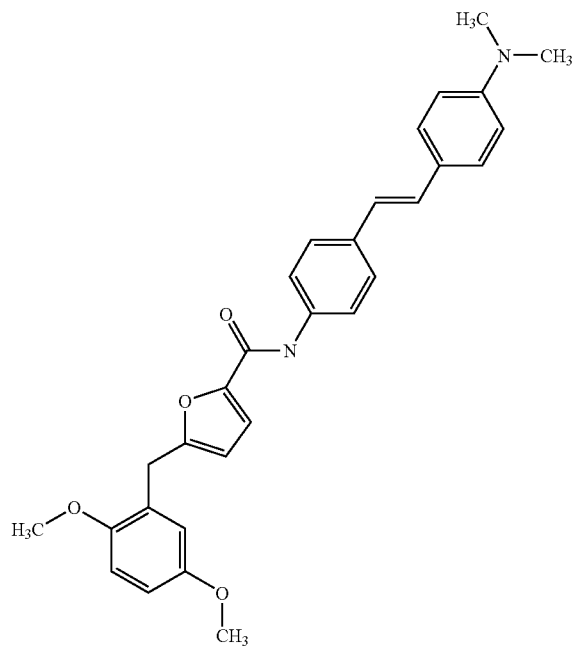 |
| 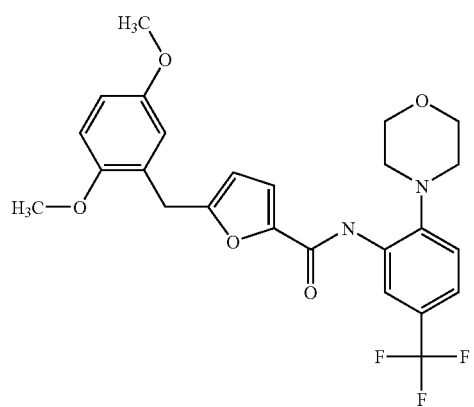 |

-continued
MOLSTRUCTURE
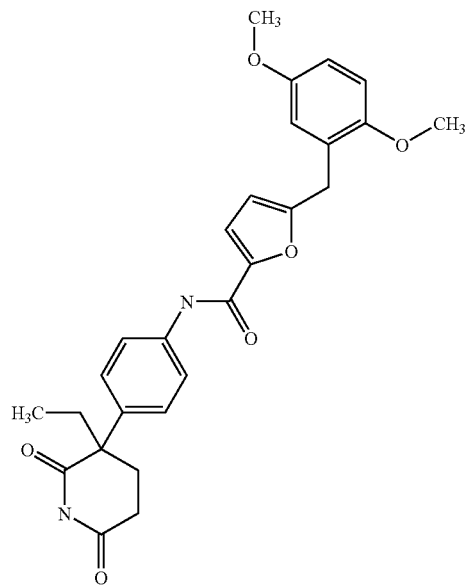
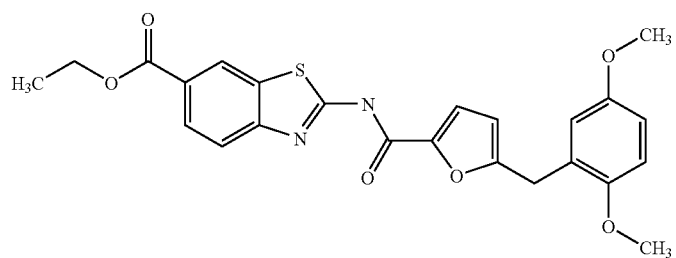
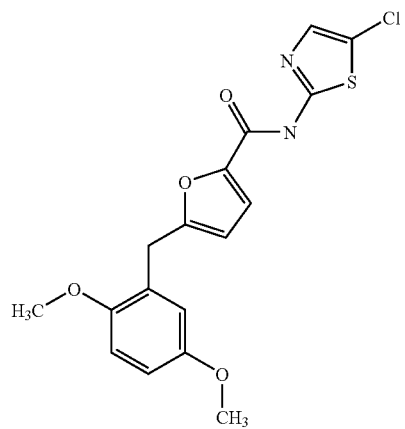

-continued
MOLSTRUCTURE
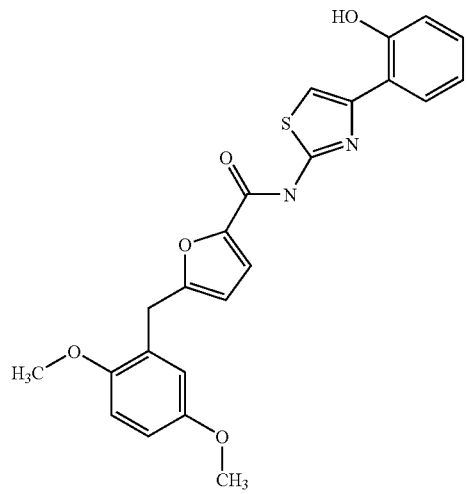
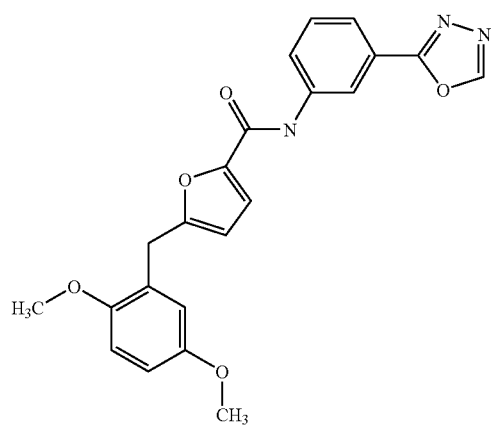
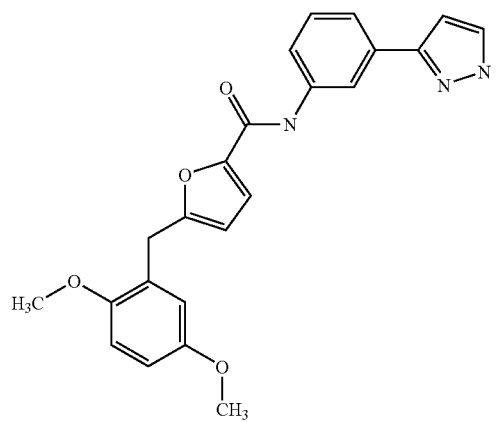

| MOLSTRUCTURE |
| --- |
| 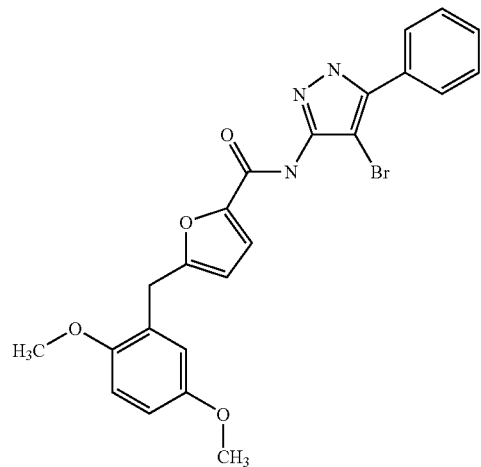 |
| 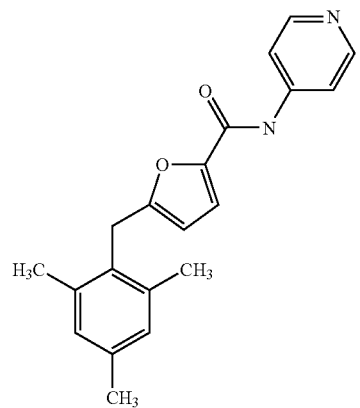 |
| 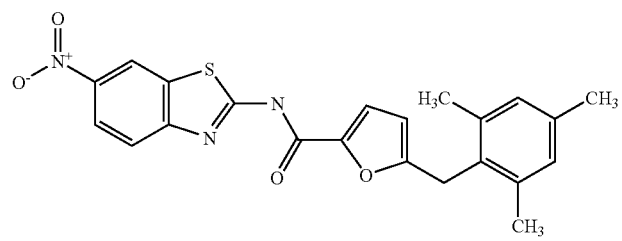 |
| 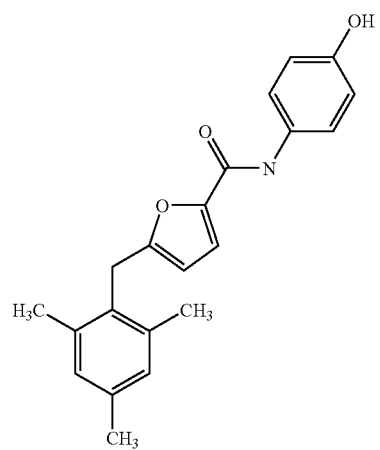 |

-continued
MOLSTRUCTURE
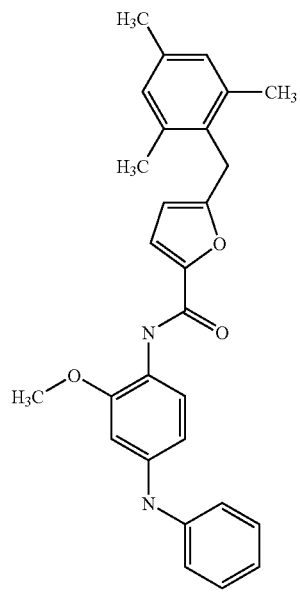
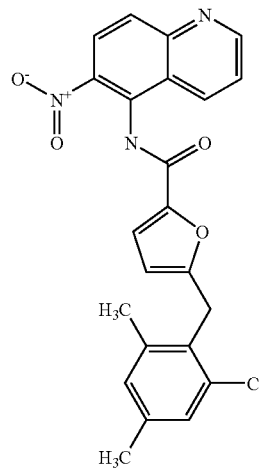
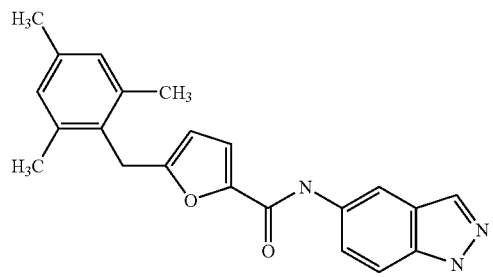

| MOLSTRUCTURE |
| --- |
| 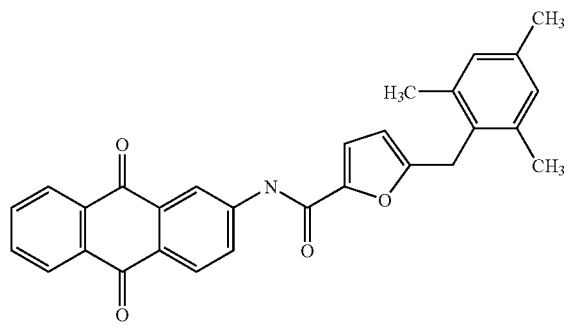 |
| 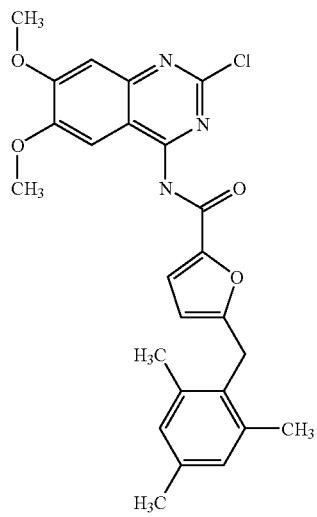 |
| 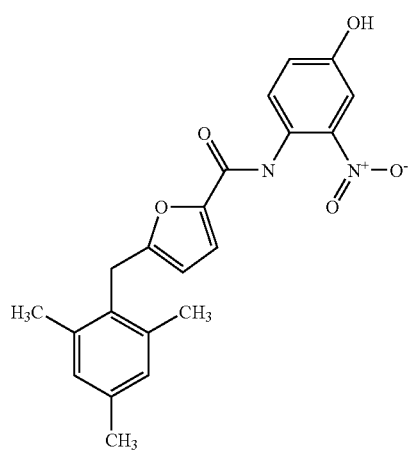 |

-continued
MOLSTRUCTURE
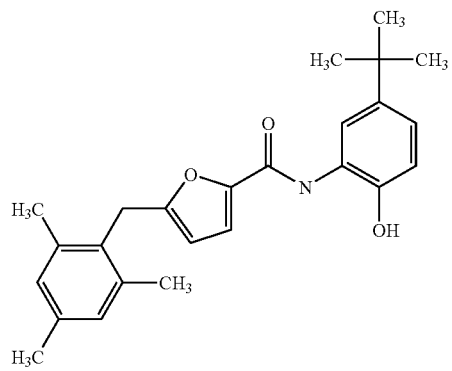
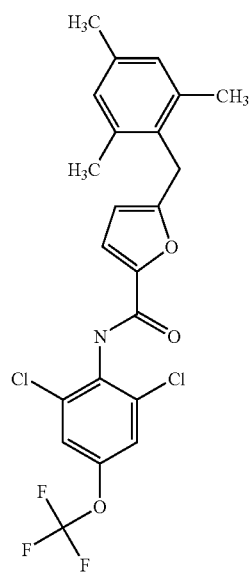
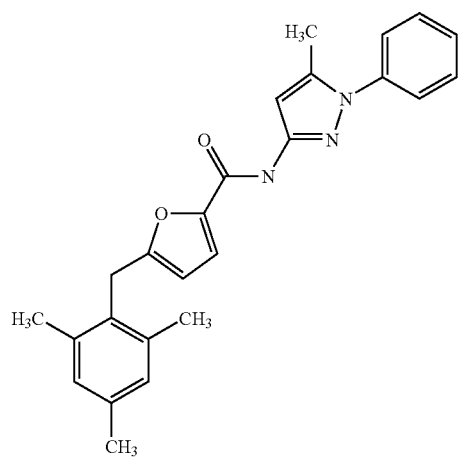

-continued
MOLSTRUCTURE
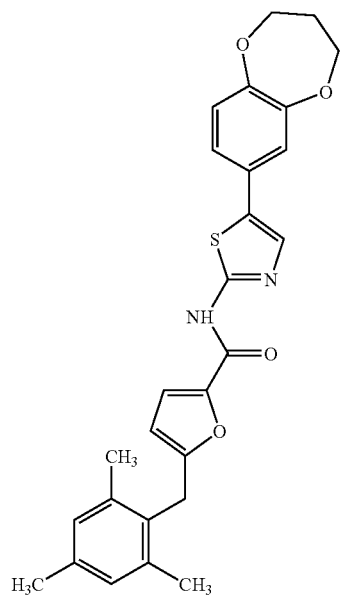
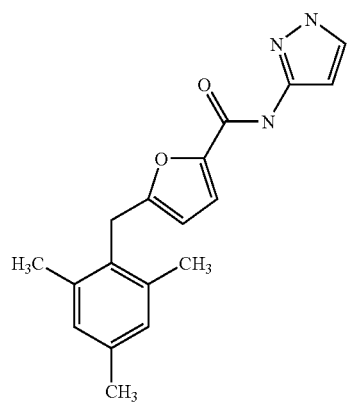
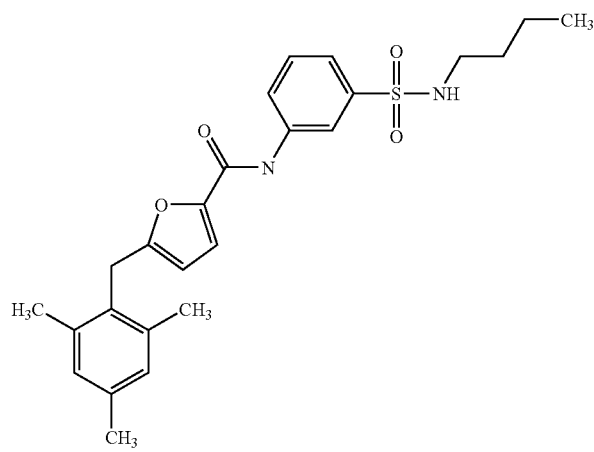

| MOLSTRUCTURE |
|---|
| 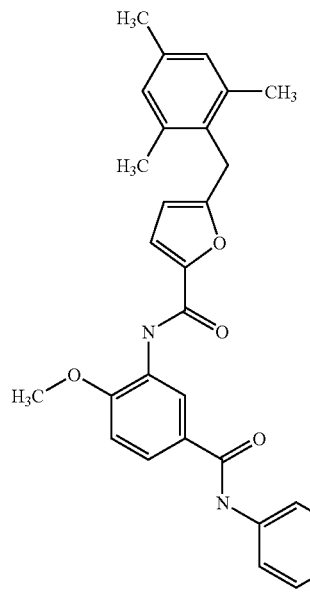 |
| 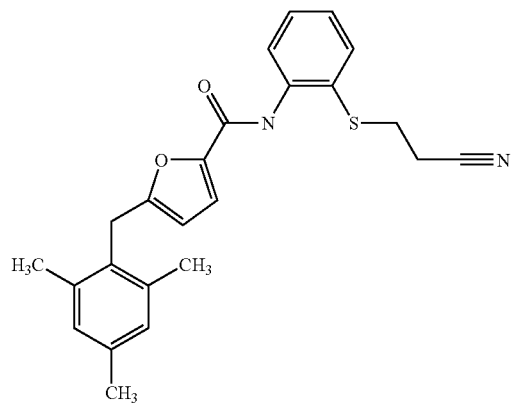 |
| 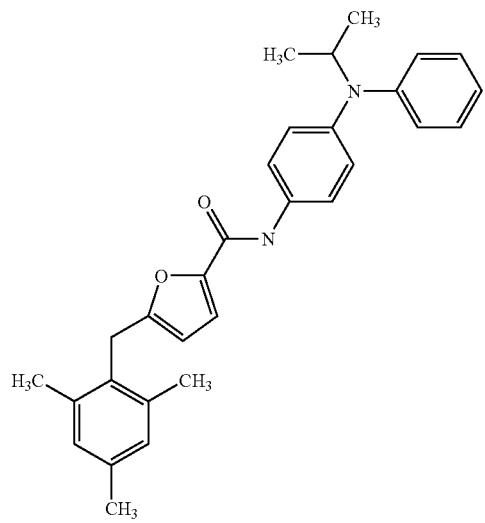 |

-continued
MOLSTRUCTURE
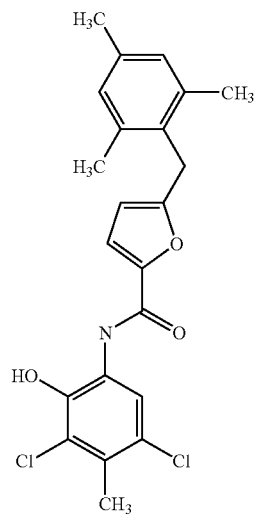
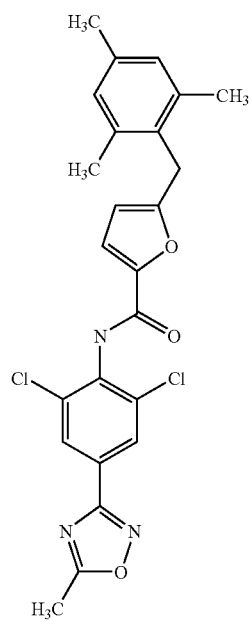

-continued
MOLSTRUCTURE
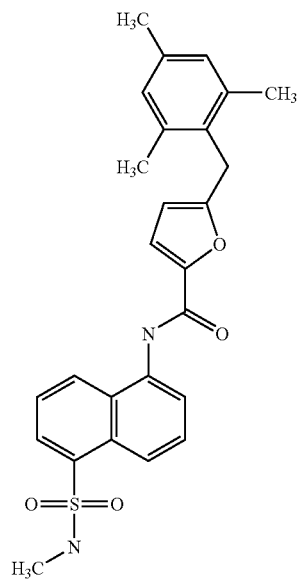
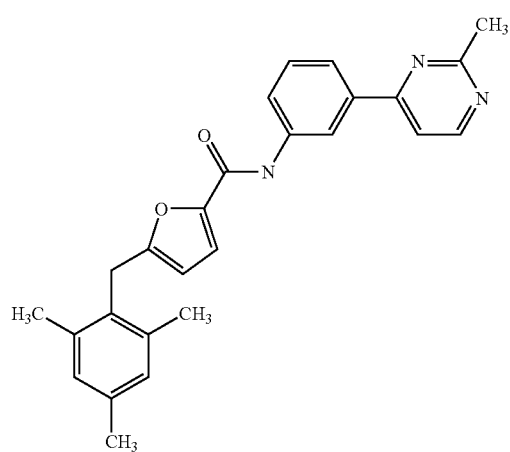
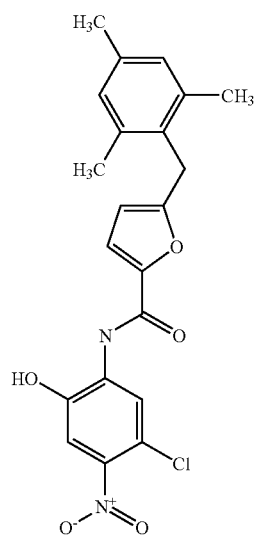

MOLSTRUCTURE
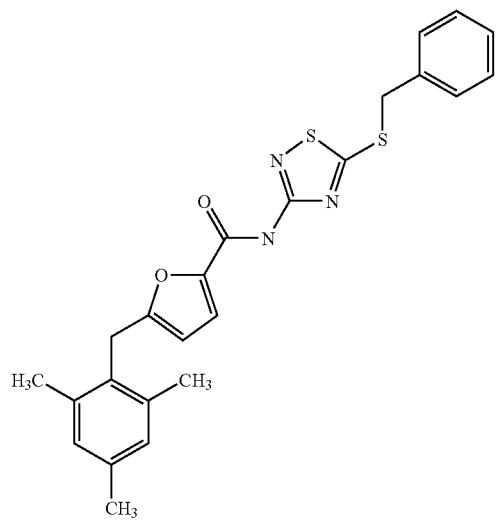
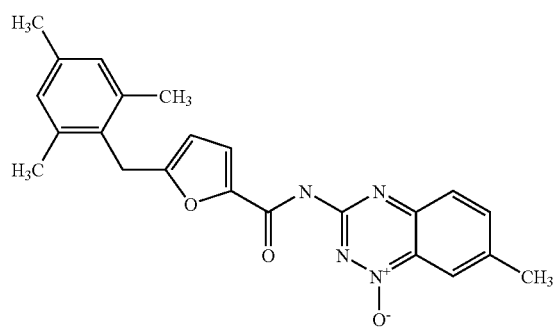
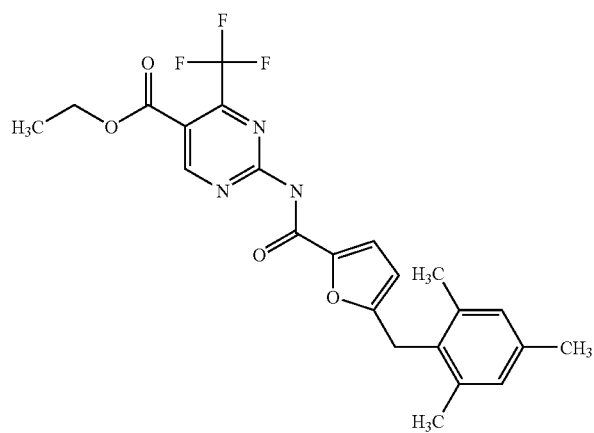

-continued
MOLSTRUCTURE
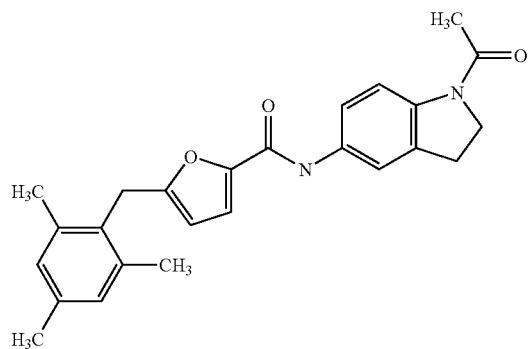
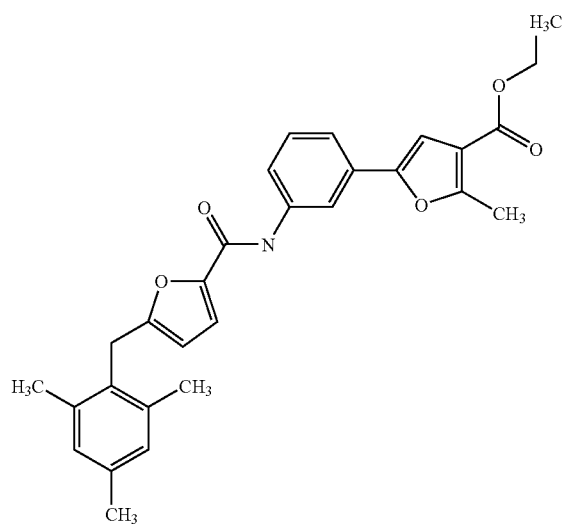
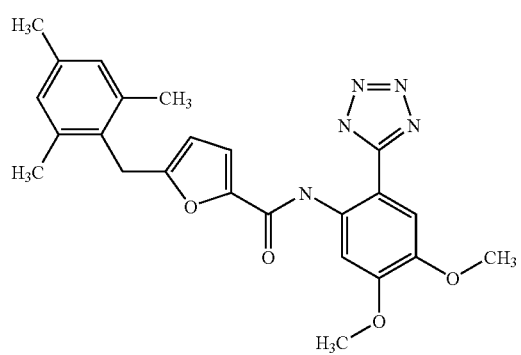

| MOLSTRUCTURE |
|---|
| 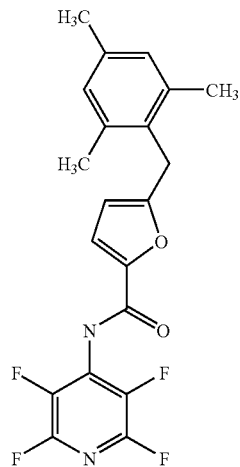 |
| 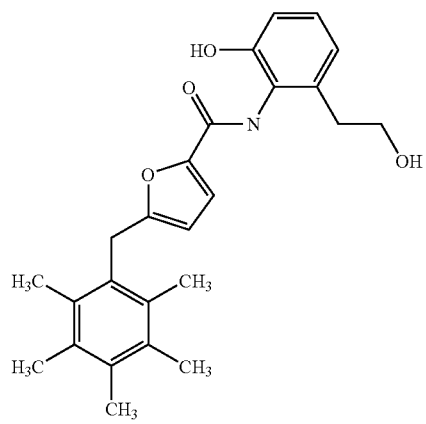 |
| 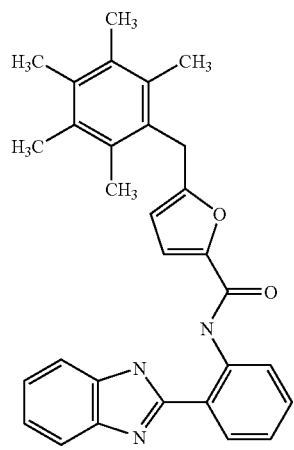 |

-continued
| MOLSTRUCTURE |
|---|
| 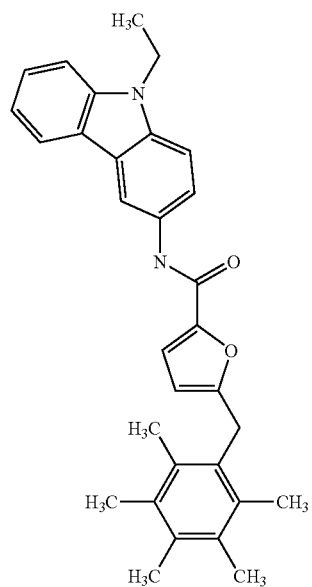 |
| 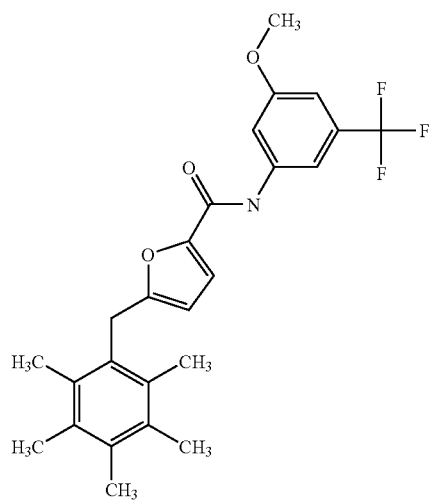 |

| MOLSTRUCTURE |
| --- |
| 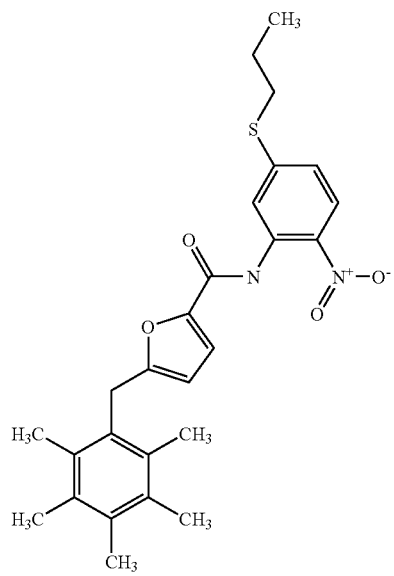 |
| 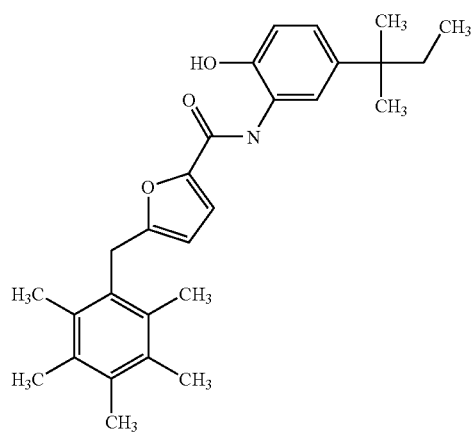 |
| 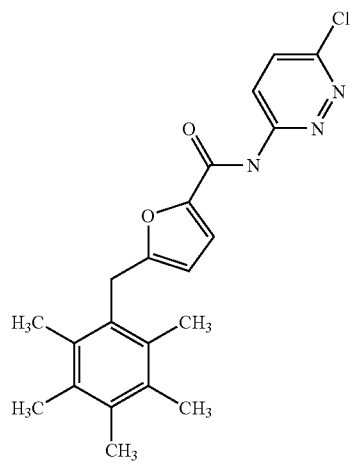 |

-continued
MOLSTRUCTURE
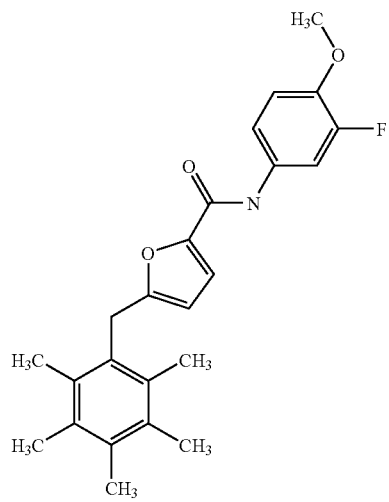
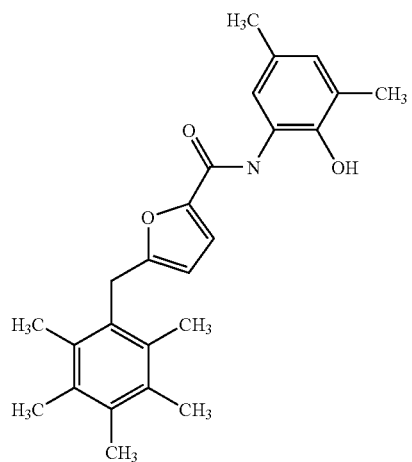
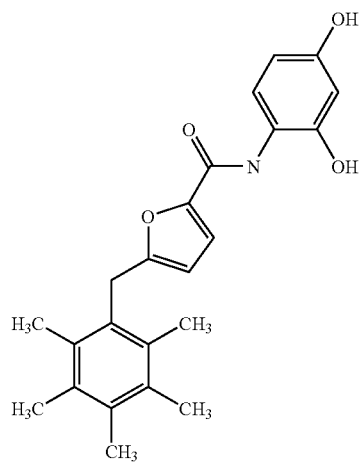

-continued
MOLSTRUCTURE
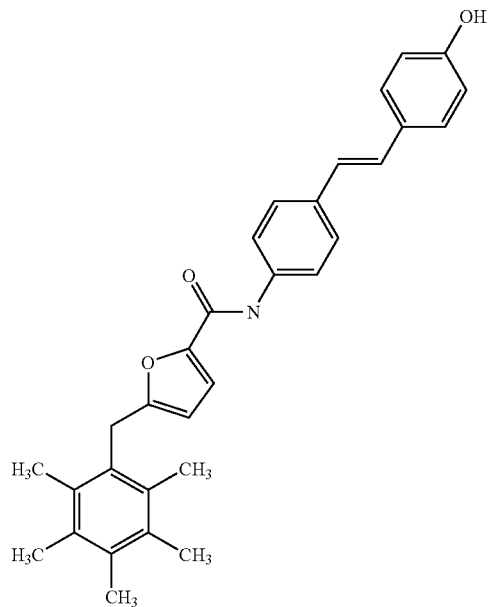
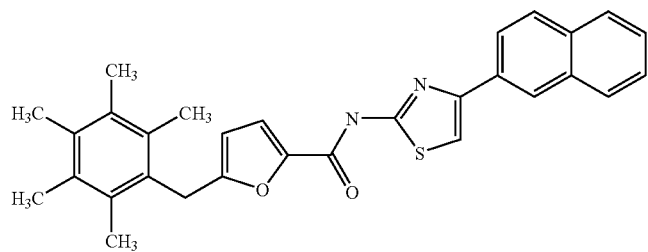
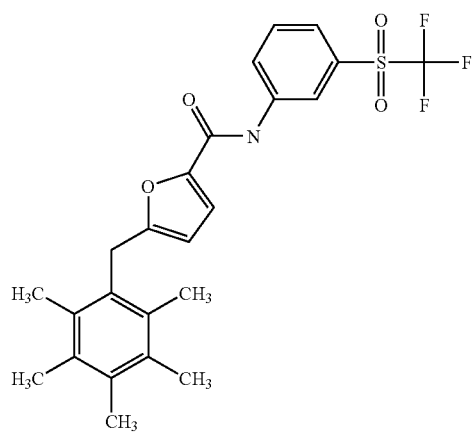
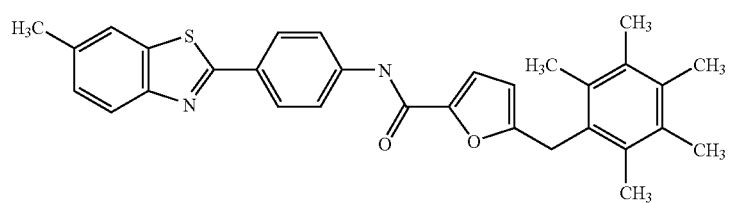

| MOLSTRUCTURE |
|---|
| 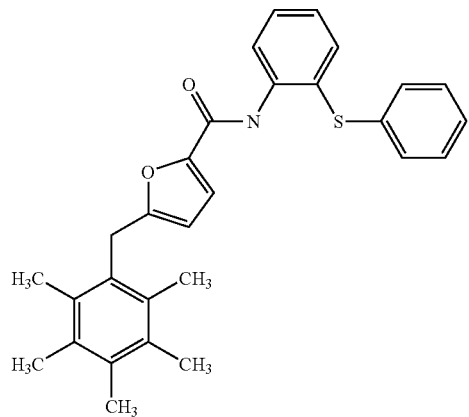 |
| 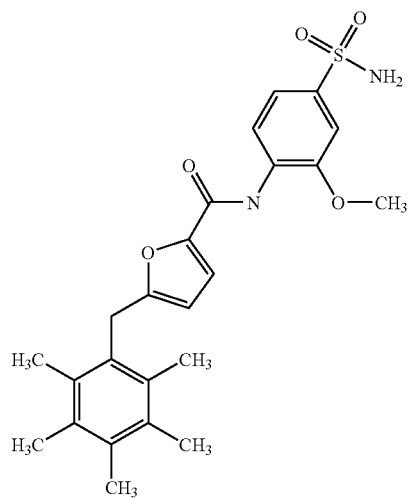 |
| 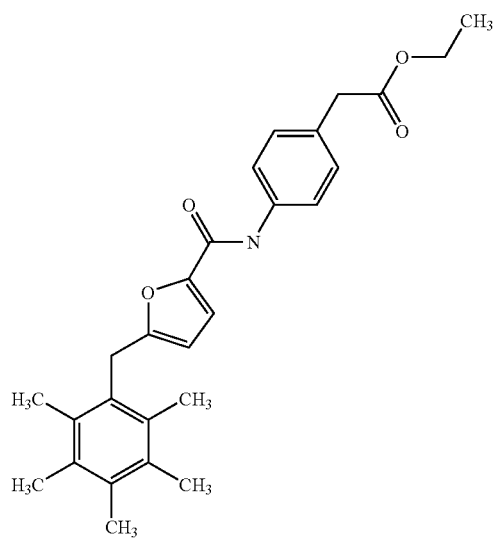 |

| MOLSTRUCTURE |
|---|
| 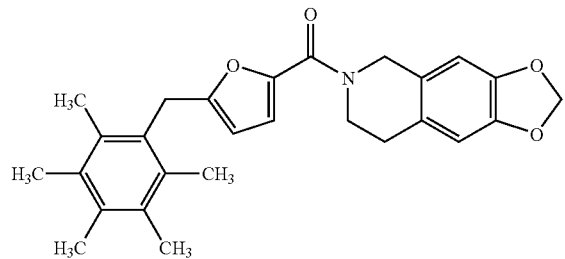 |
| 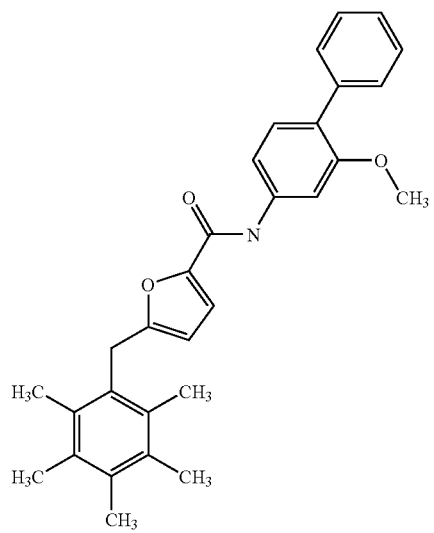 |
| 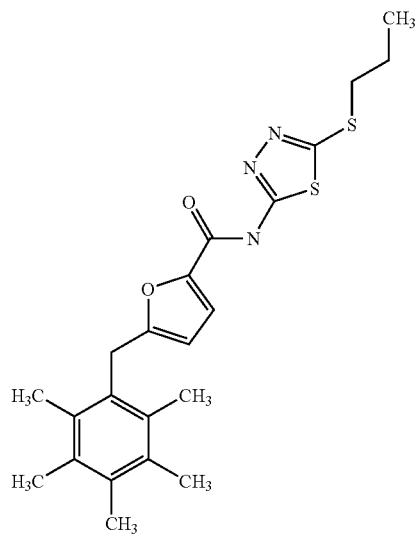 |

-continued
MOLSTRUCTURE
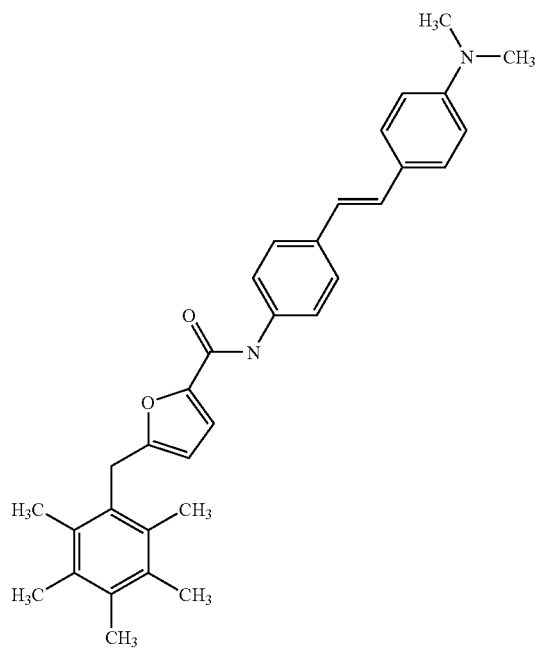
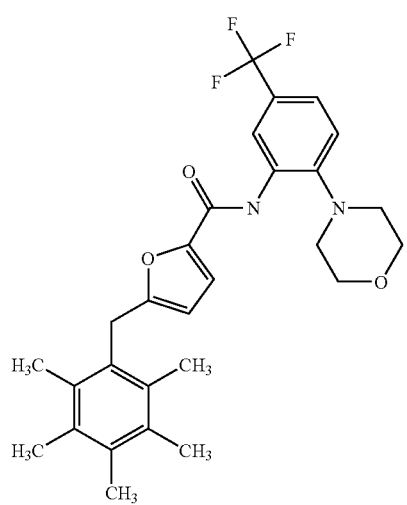

-continued
| MOLSTRUCTURE |
|---|
| 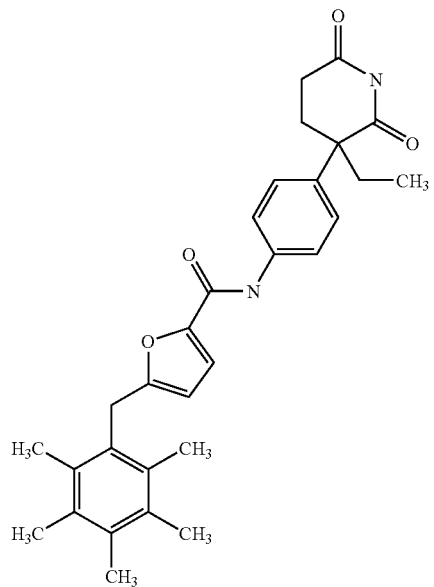 |
| 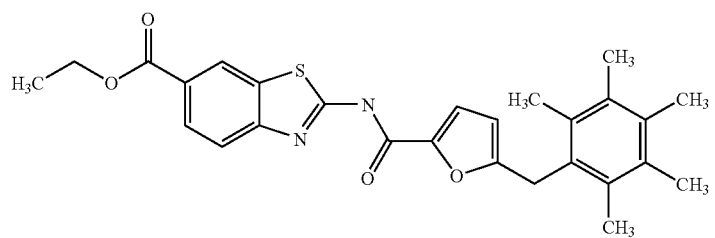 |
| 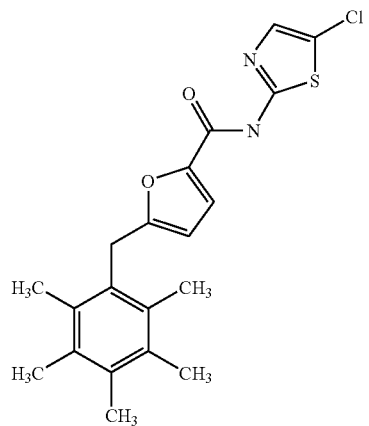 |

-continued
| MOLSTRUCTURE |
|---|
| 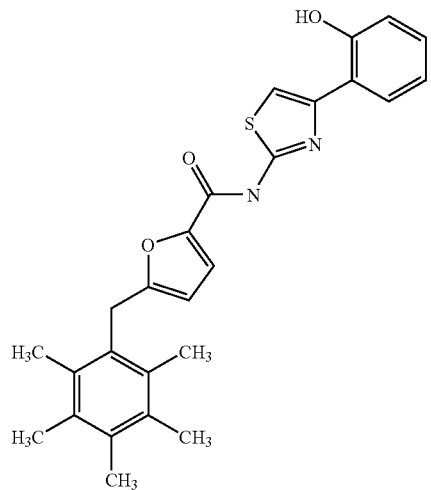 |
| 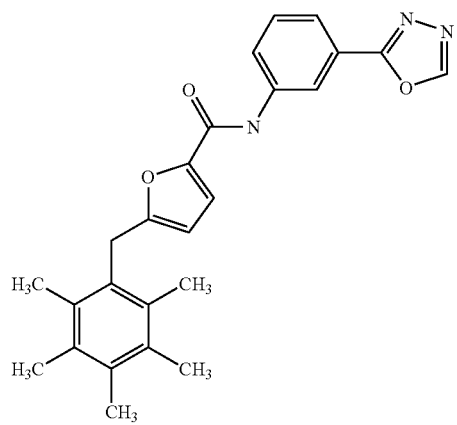 |
| 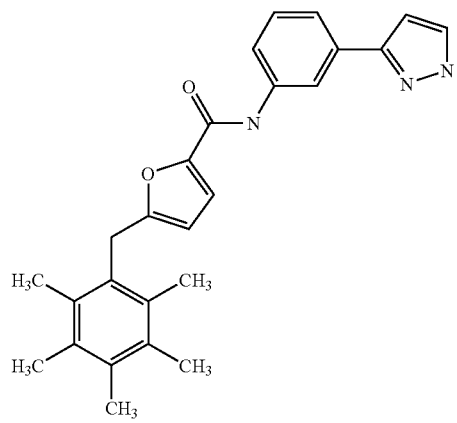 |

-continued
| MOLSTRUCTURE |
| --- |
| 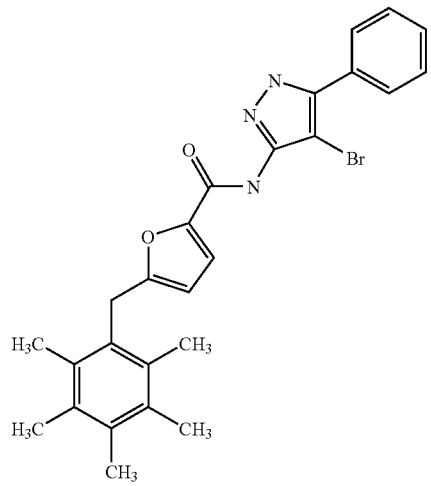 |
| 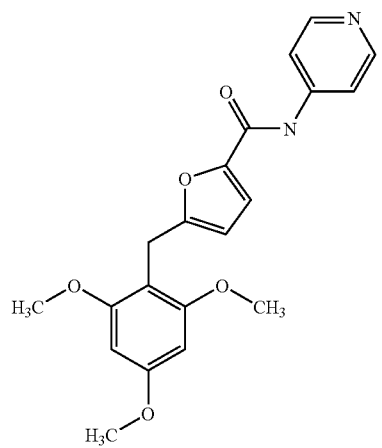 |
| 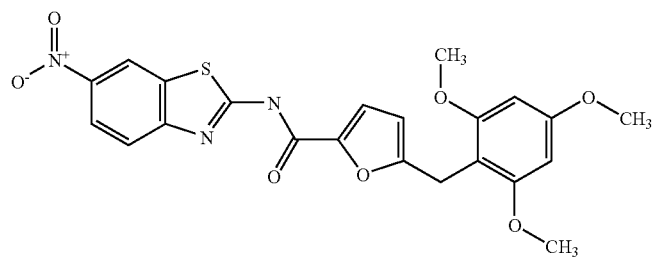 |

-continued
MOLSTRUCTURE
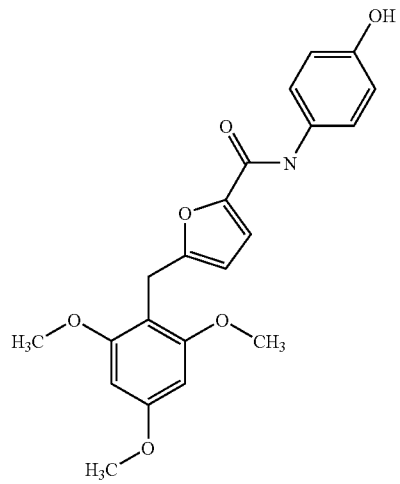
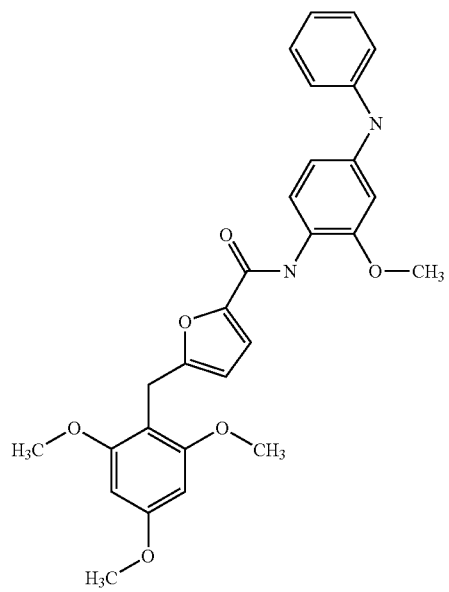
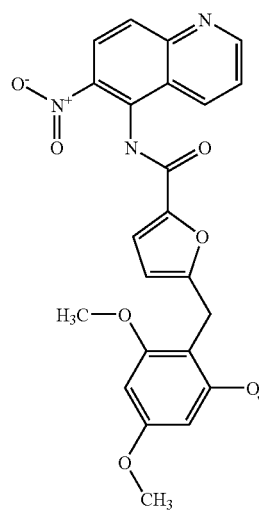

| MOLSTRUCTURE |
|---|
| 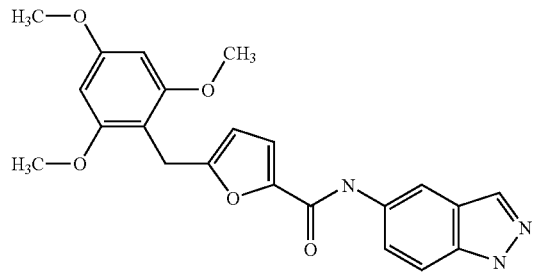 |
| 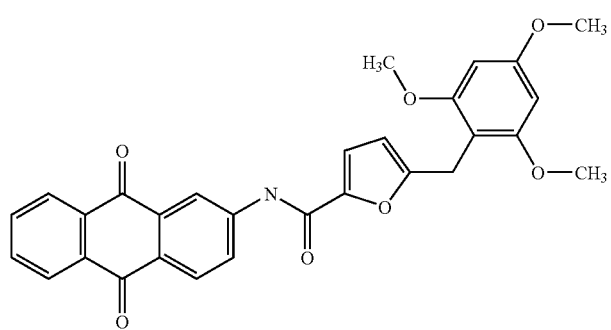 |
| 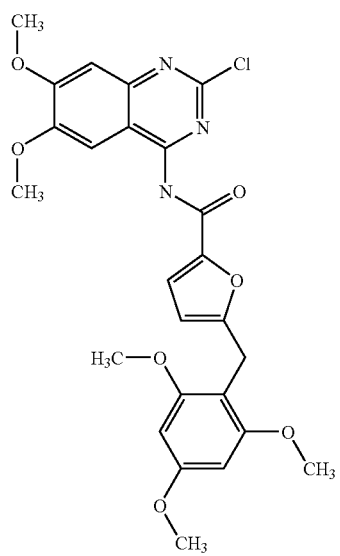 |

| MOLSTRUCTURE |
| --- |
| 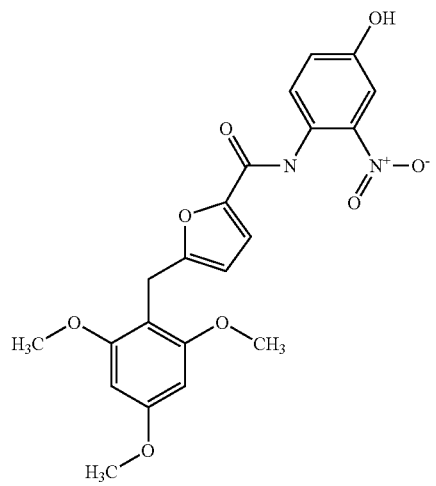 |
| 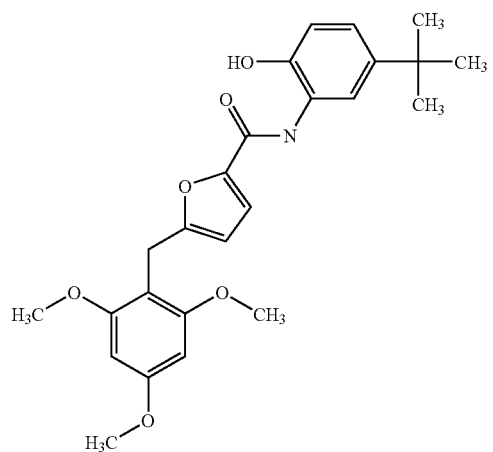 |
| 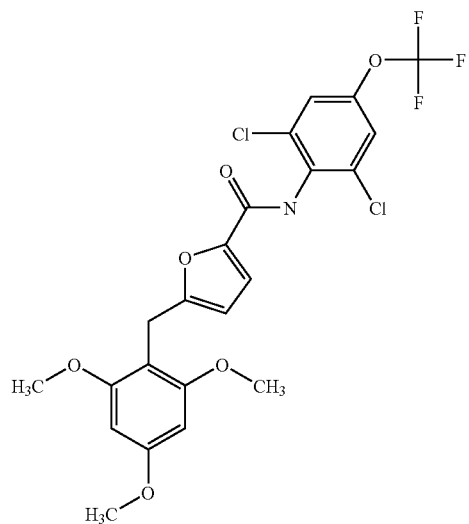 |

-continued
| MOLSTRUCTURE |
| --- |
| 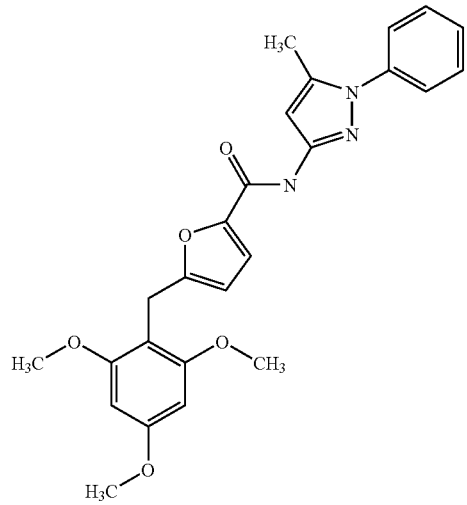 |
| 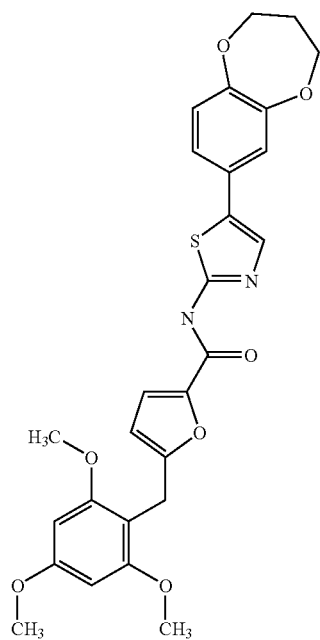 |
| 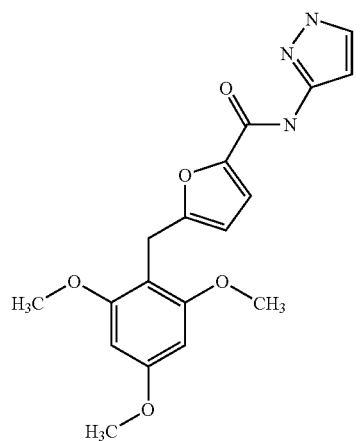 |

| 1221 | 1222 |
-continued
MOLSTRUCTURE
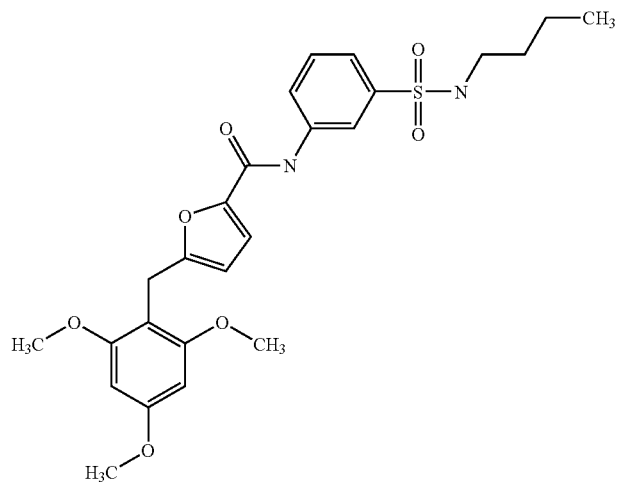
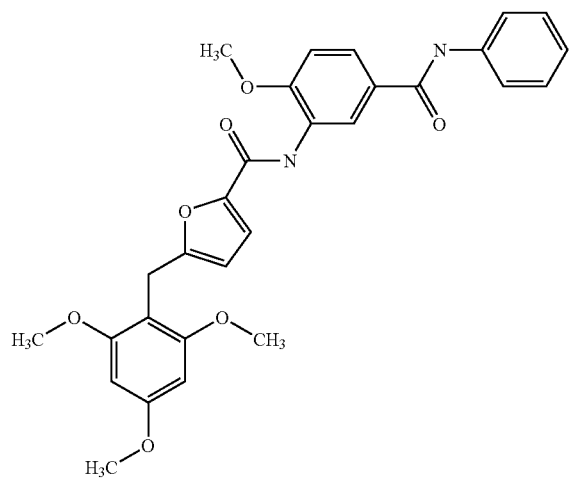
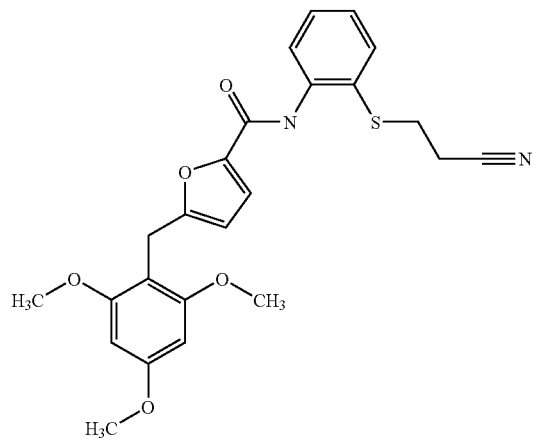

-continued
| MOLSTRUCTURE |
|---|
| 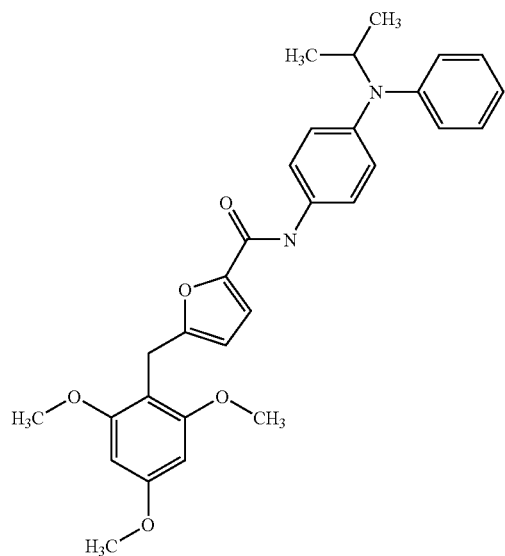 |
| 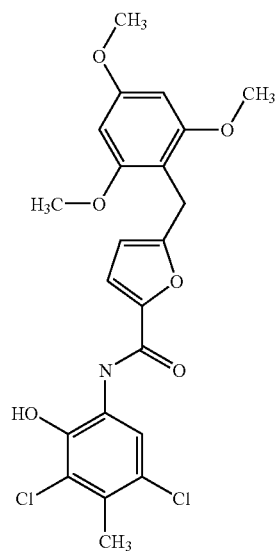 |

| MOLSTRUCTURE |
|---|
| 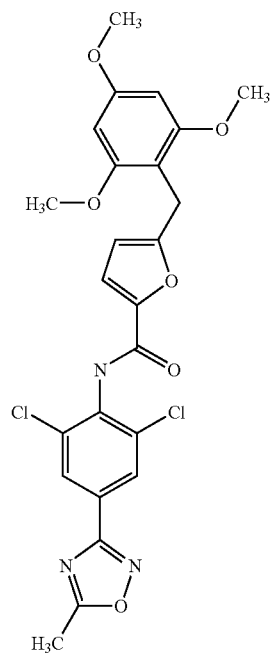 |
| 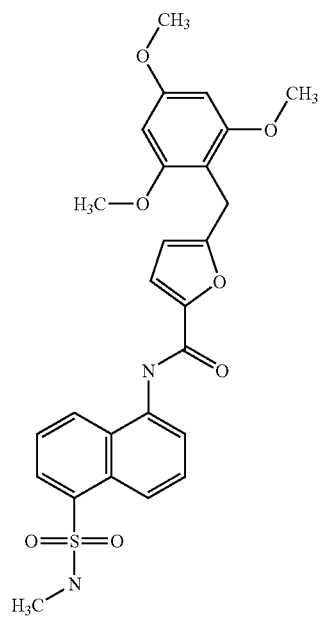 |

-continued
MOLSTRUCTURE
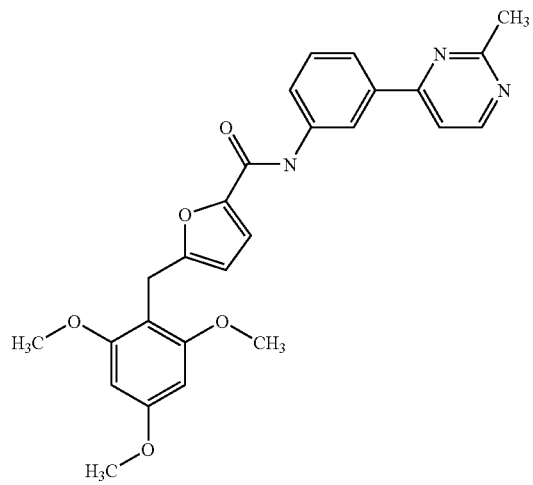
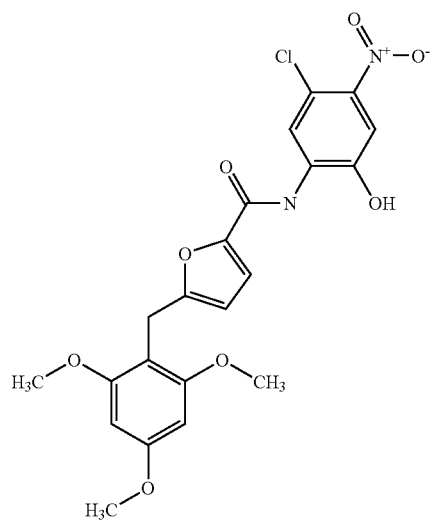
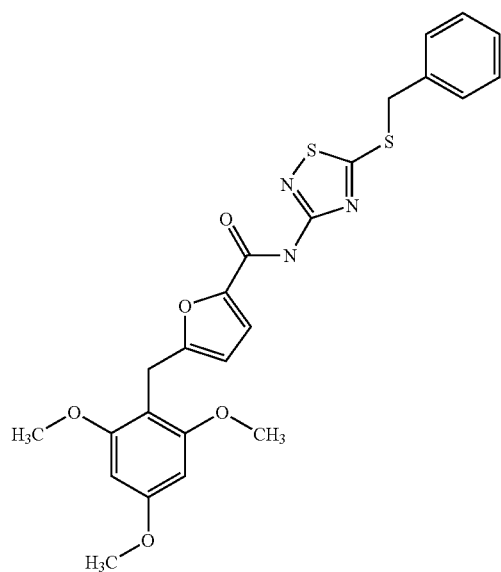

| MOLSTRUCTURE |
|---|
| 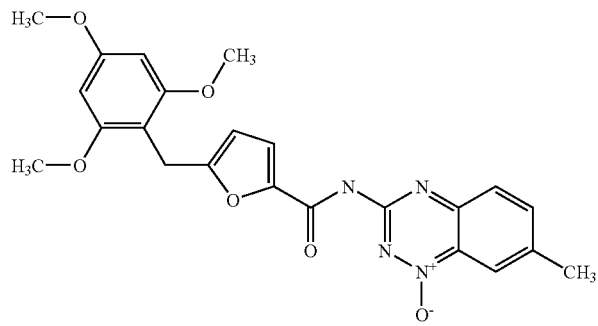 |
| 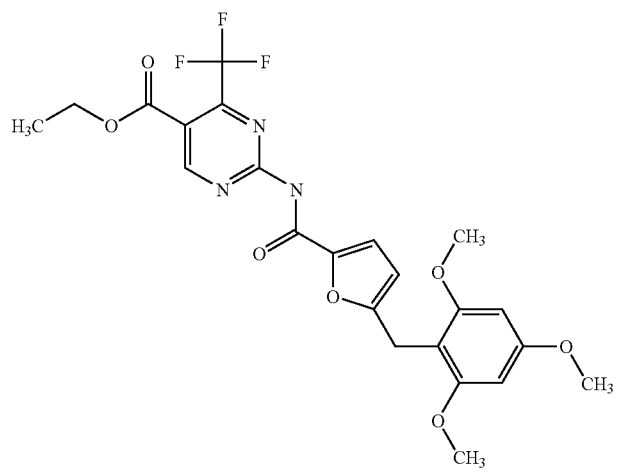 |
| 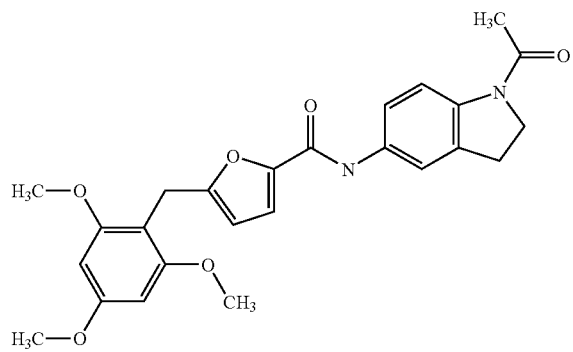 |

-continued
MOLSTRUCTURE
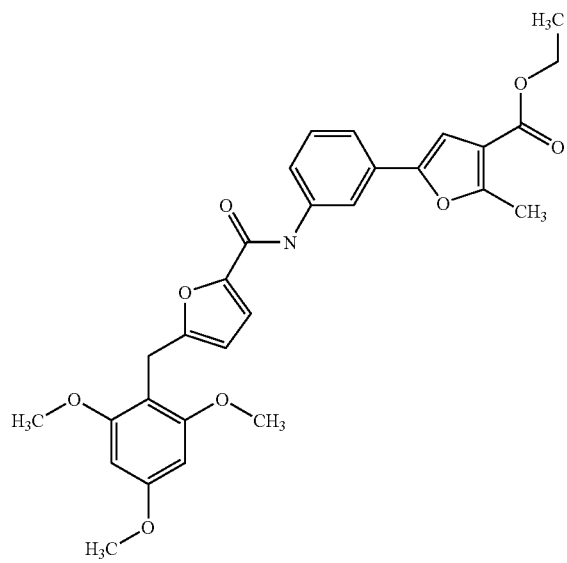
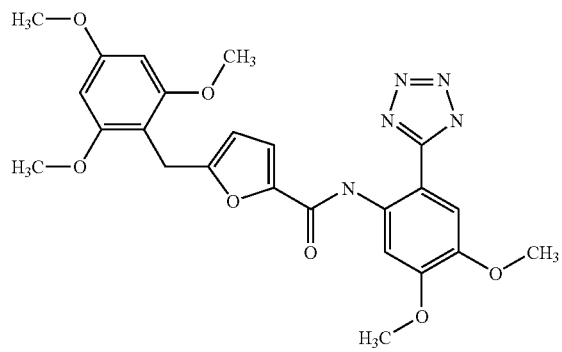
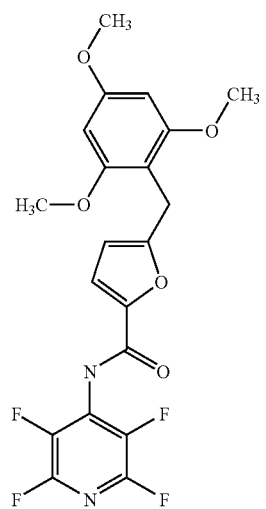

-continued
| MOLSTRUCTURE |
|---|
| 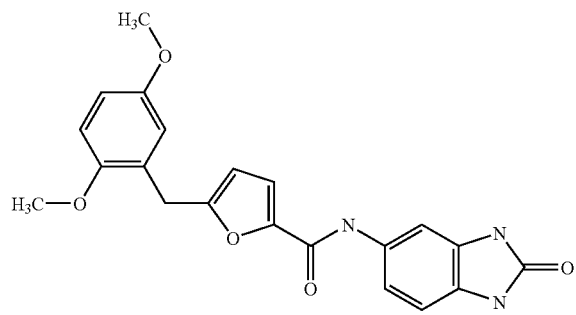 |
| 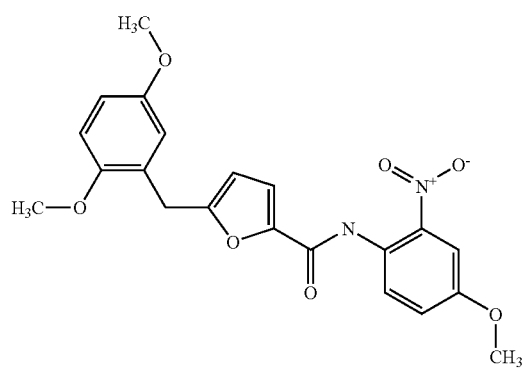 |
| 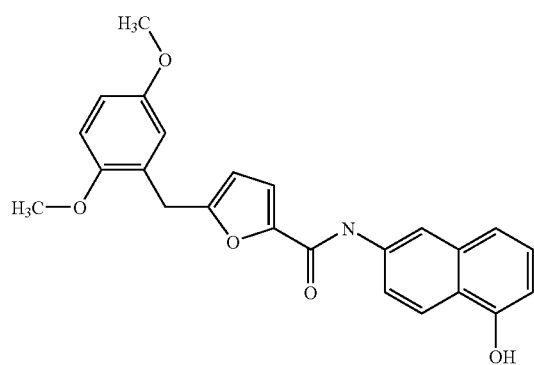 |
| 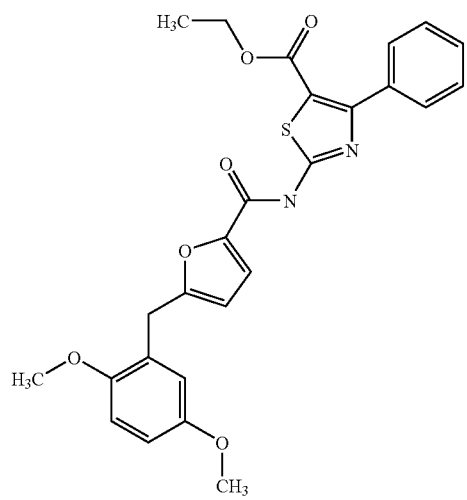 |

-continued
| MOLSTRUCTURE |
|---|
| 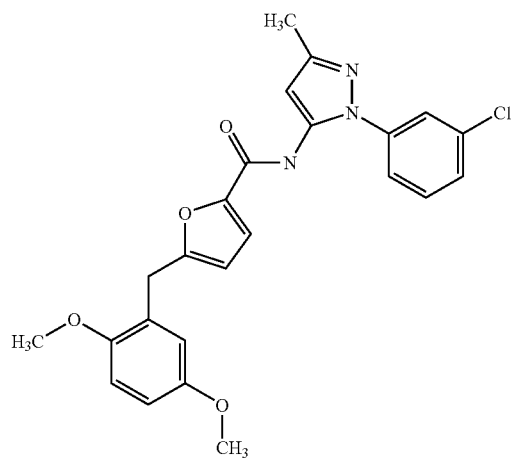 |
| 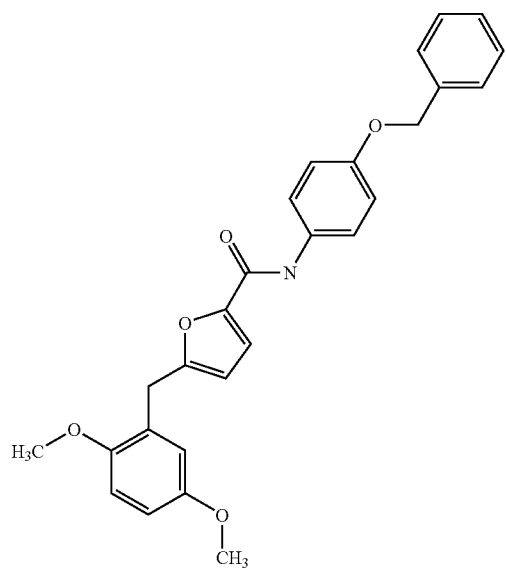 |
| 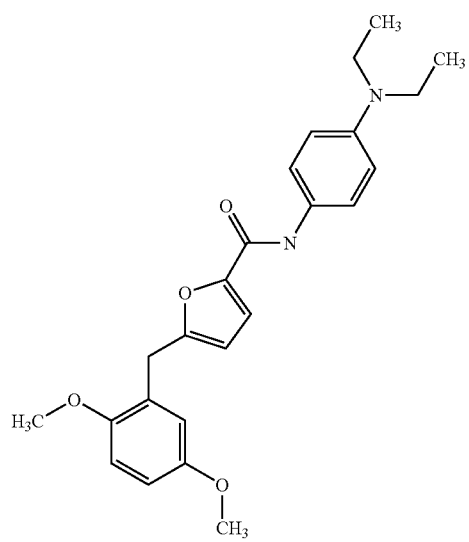 |

-continued
| MOLSTRUCTURE |
|---|
| 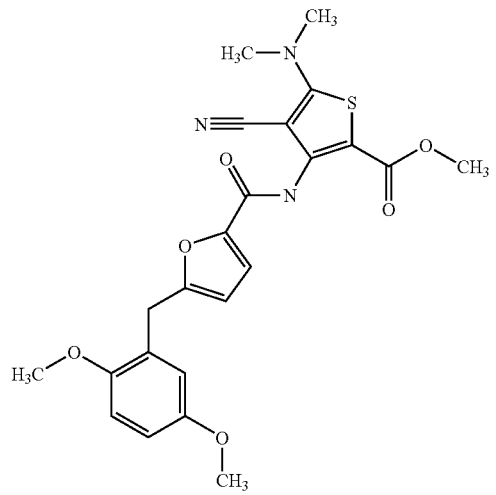 |
| 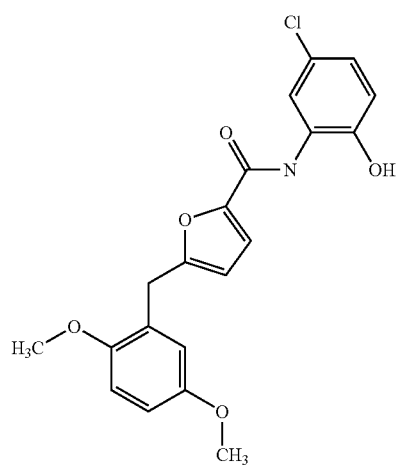 |
| 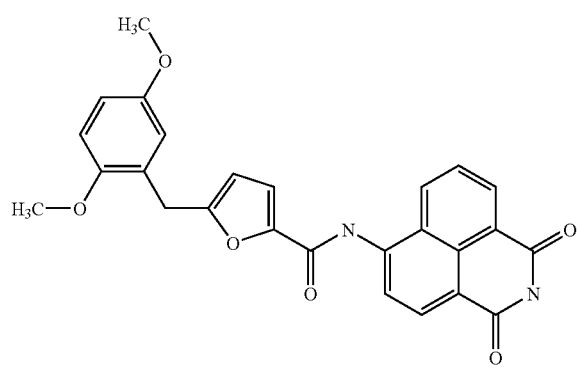 |
| 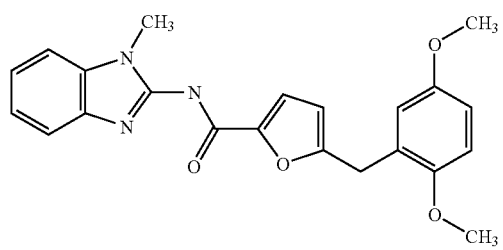 |

-continued
MOLSTRUCTURE
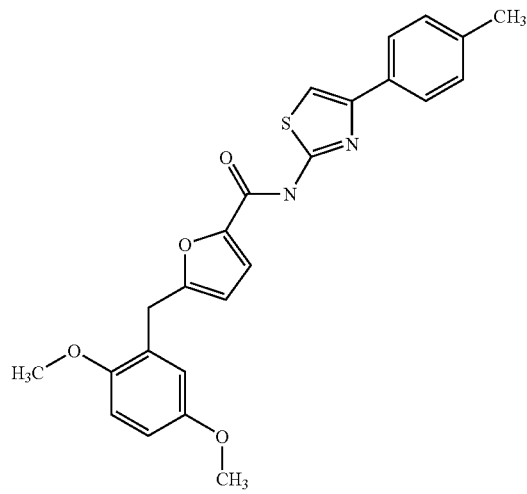
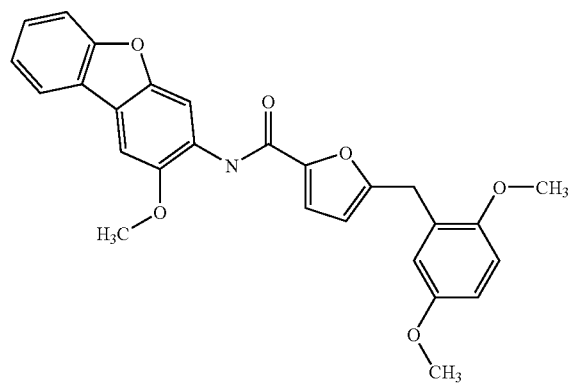
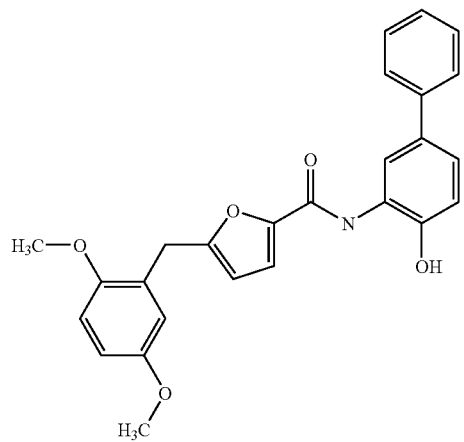

-continued
MOLSTRUCTURE
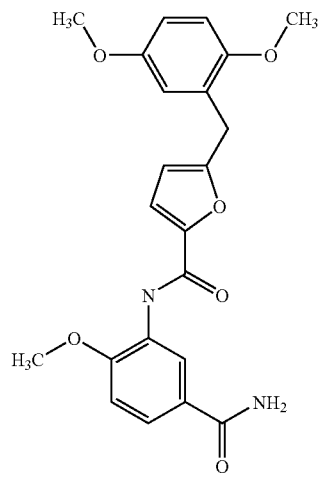
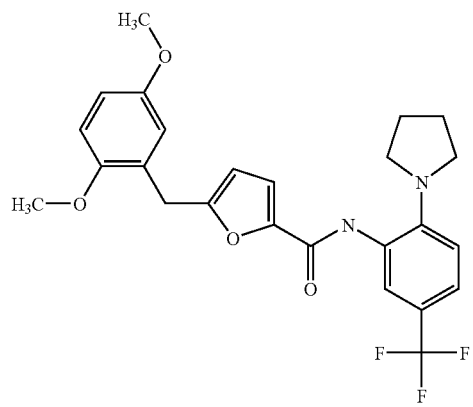
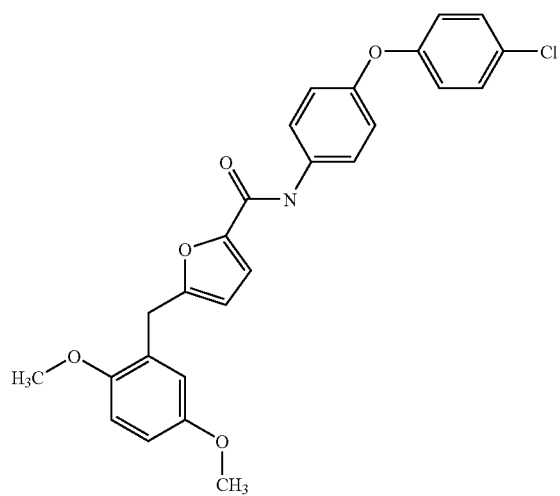

-continued
| MOLSTRUCTURE |
|---|
| 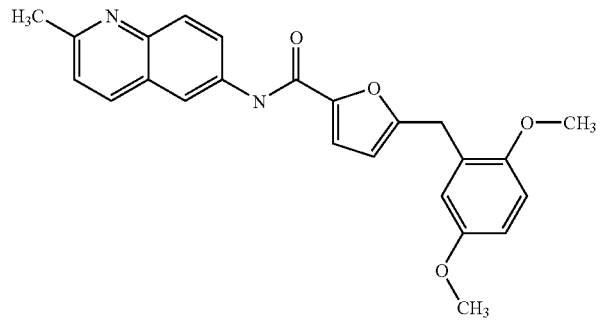 |
| 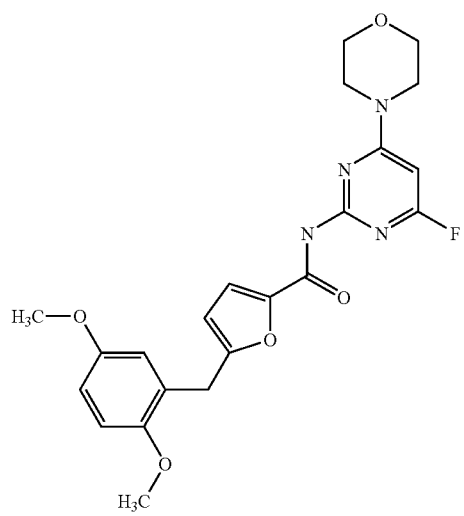 |
| 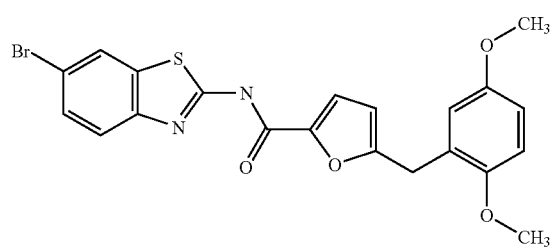 |

-continued
MOLSTRUCTURE
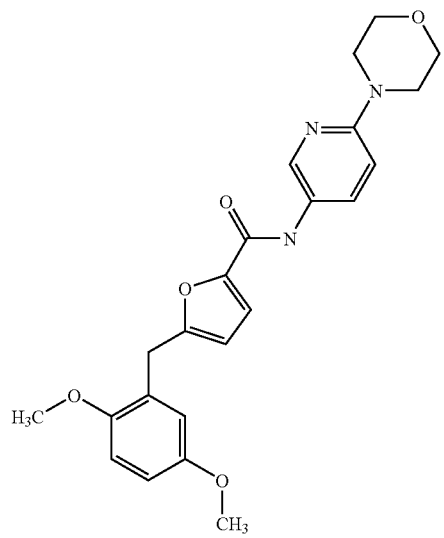
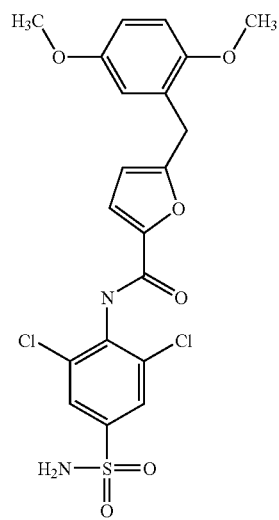
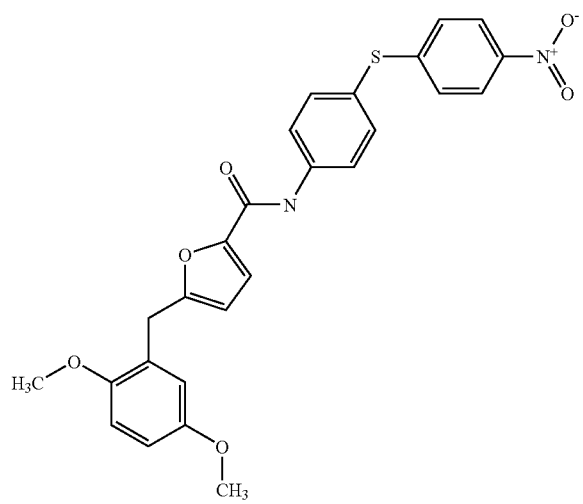

-continued
MOLSTRUCTURE
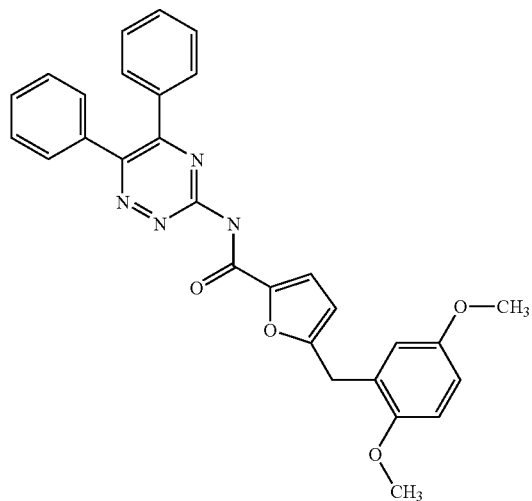
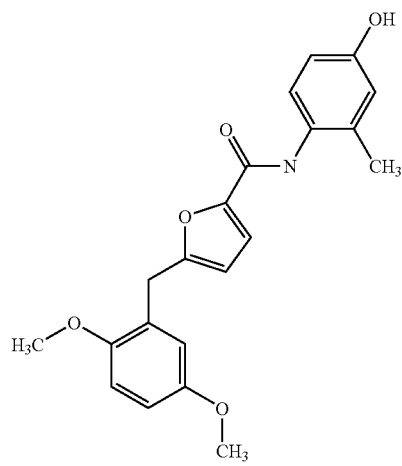
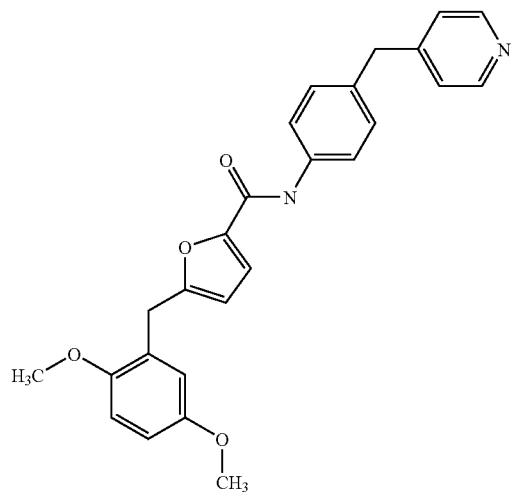

| MOLSTRUCTURE |
|---|
| 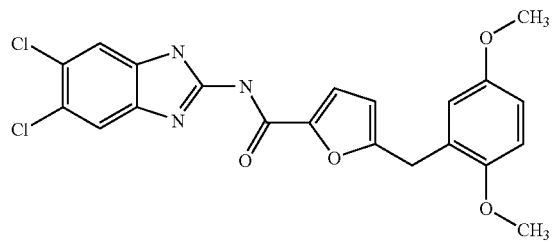 |
| 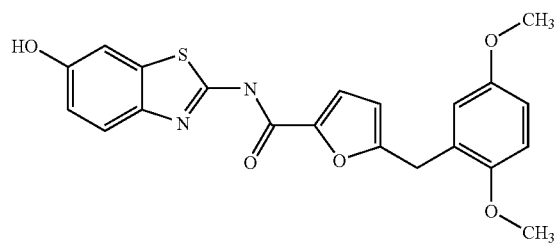 |
| 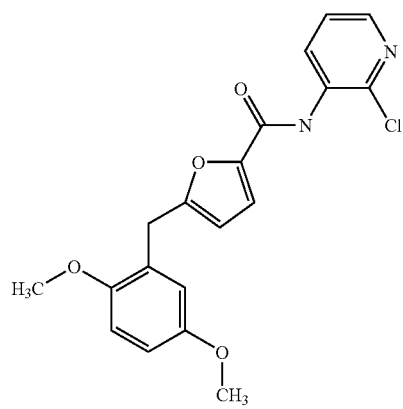 |
| 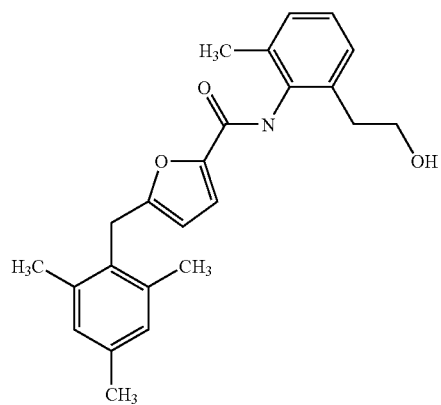 |

| MOLSTRUCTURE |
|---|
| 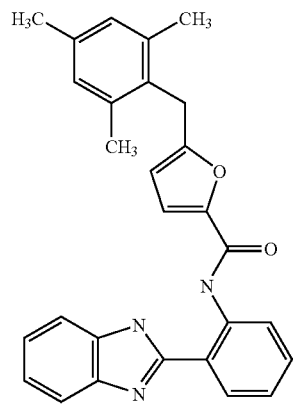 |
| 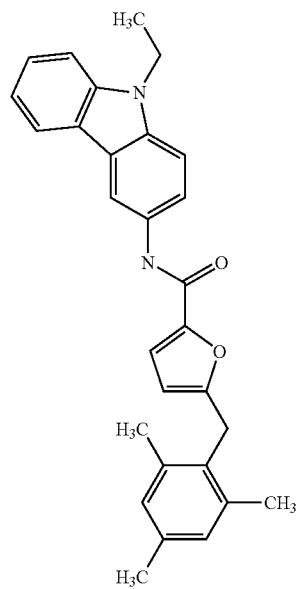 |
| 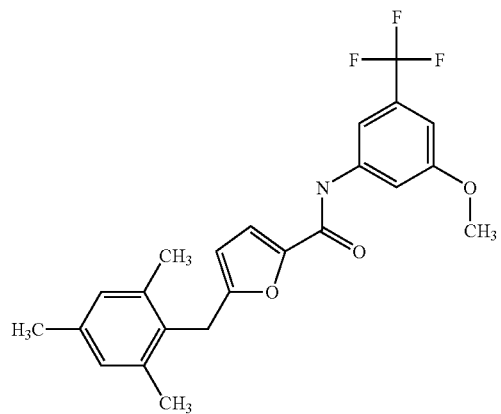 |

-continued
MOLSTRUCTURE
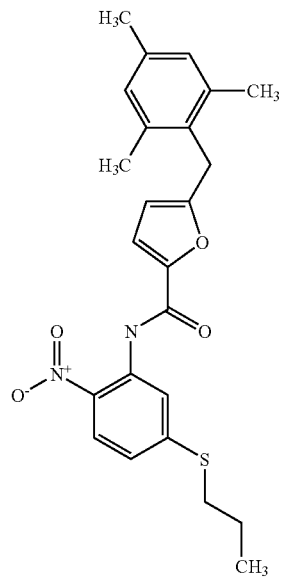
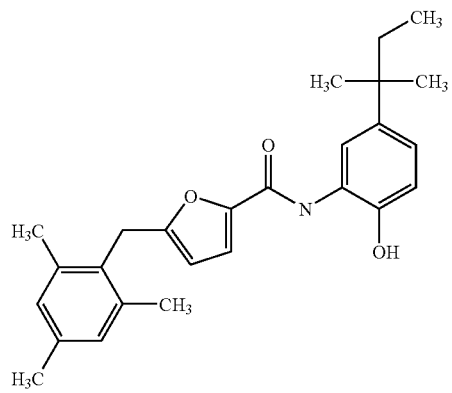
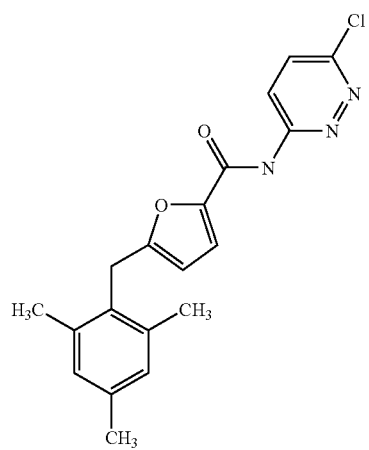

| MOLSTRUCTURE |
|---|
| 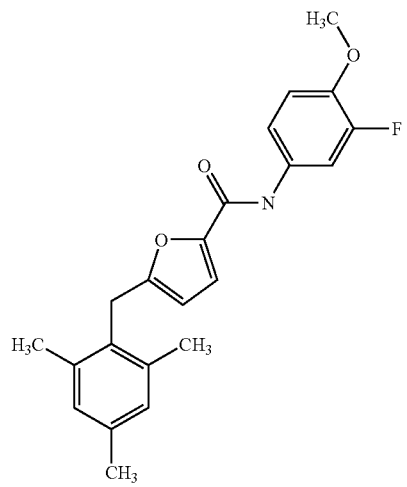 |
| 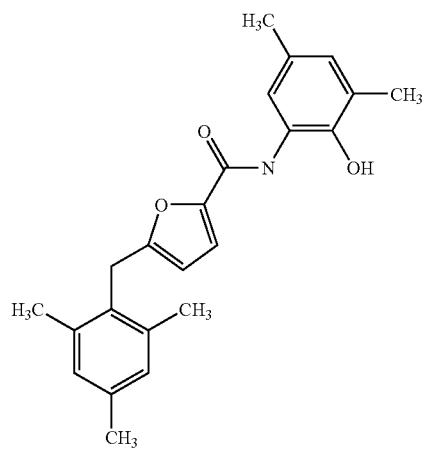 |
| 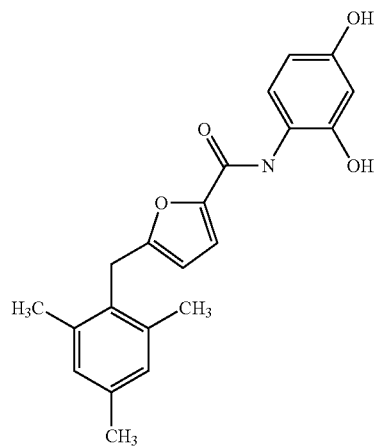 |

| MOLSTRUCTURE |
|---|
| 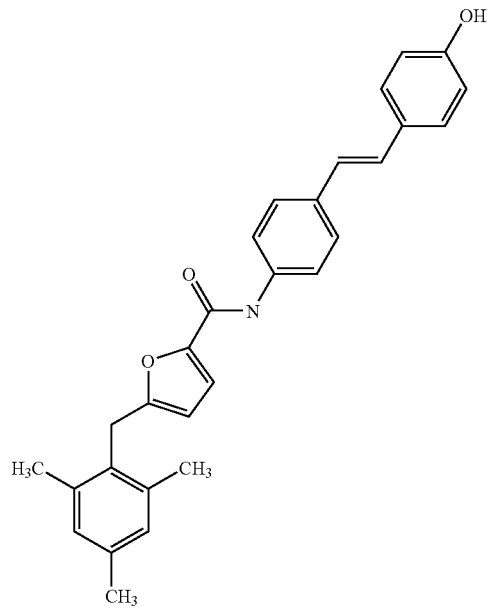 |
| 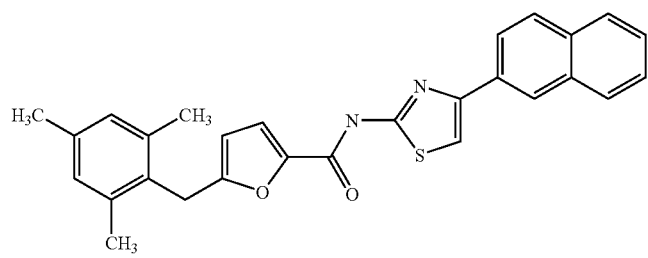 |
| 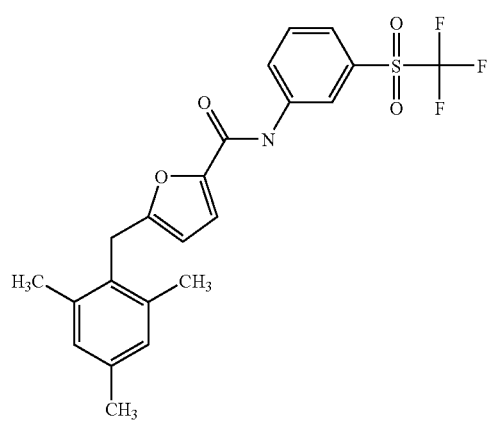 |
|  |

| MOLSTRUCTURE |
|---|
| 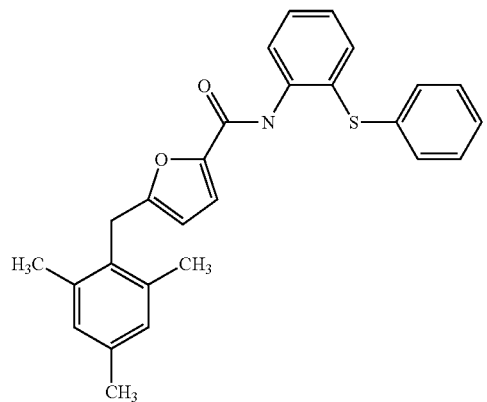 |
| 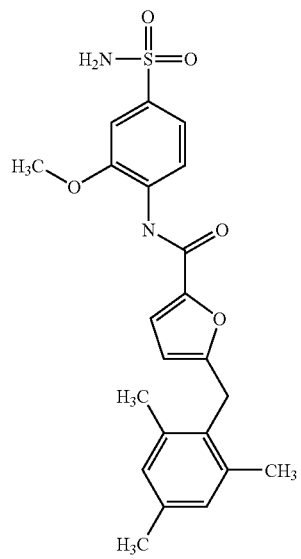 |
| 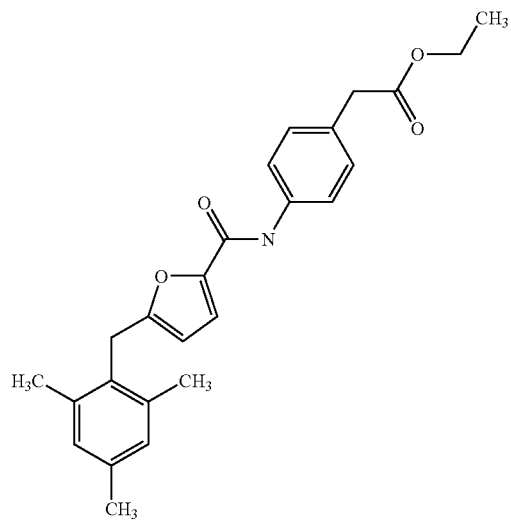 |

| MOLSTRUCTURE |
|---|
| 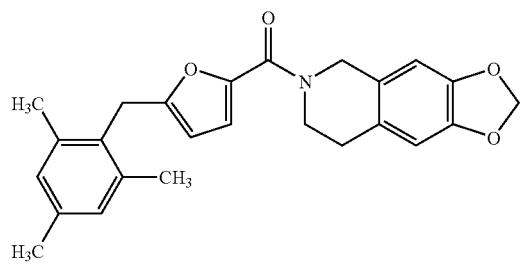 |
| 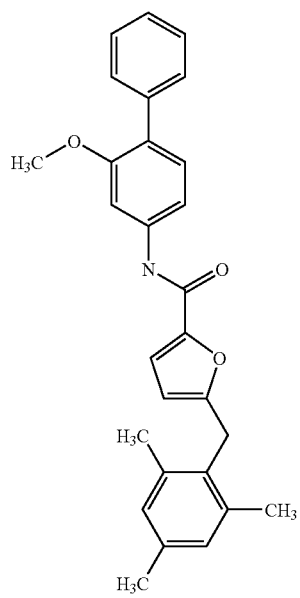 |
| 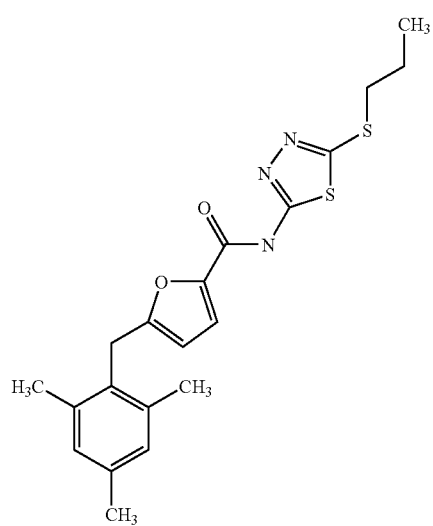 |

-continued
MOLSTRUCTURE
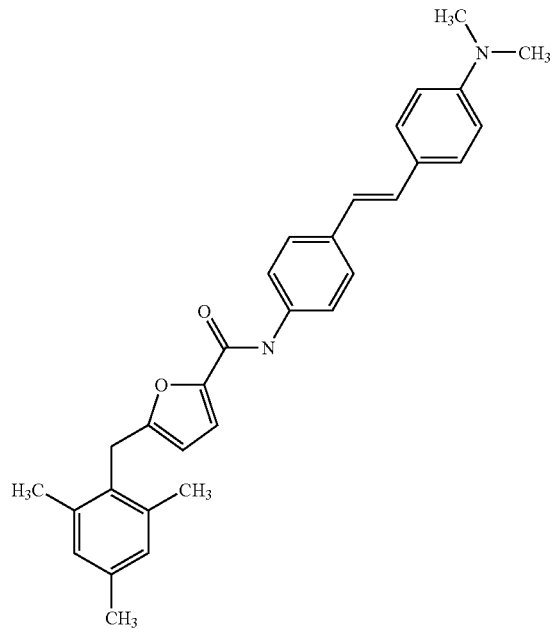
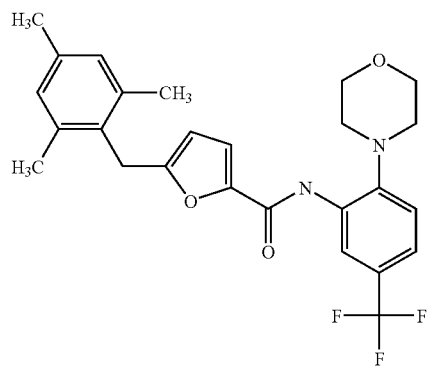
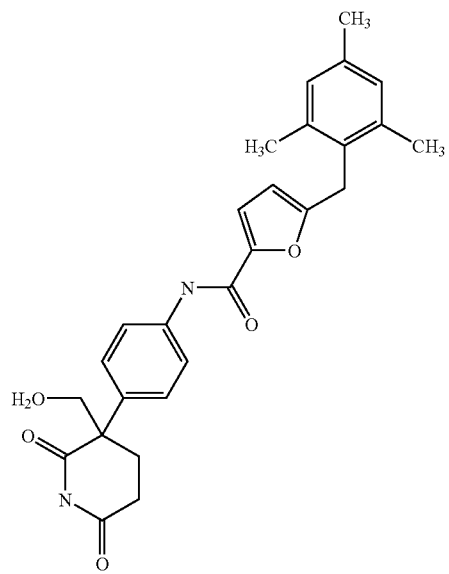

-continued
MOLSTRUCTURE
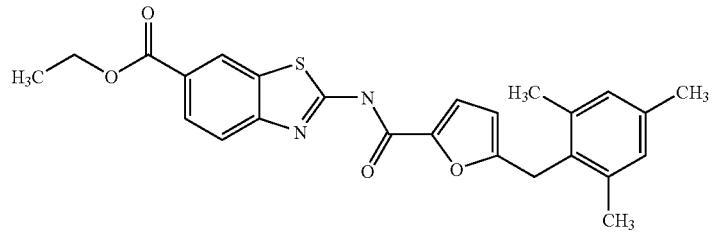
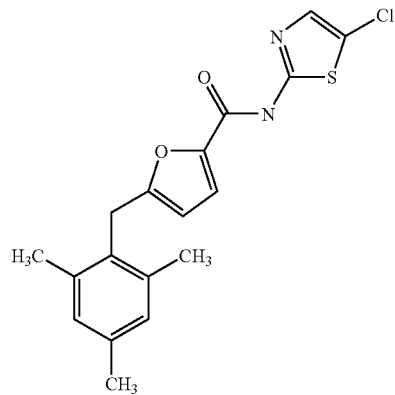
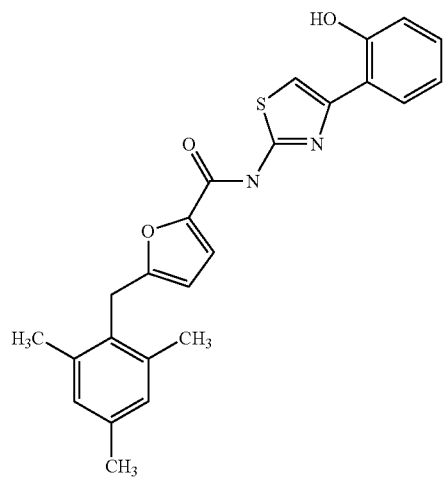
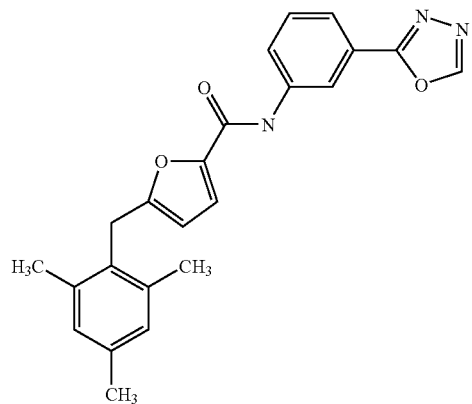

-continued
MOLSTRUCTURE
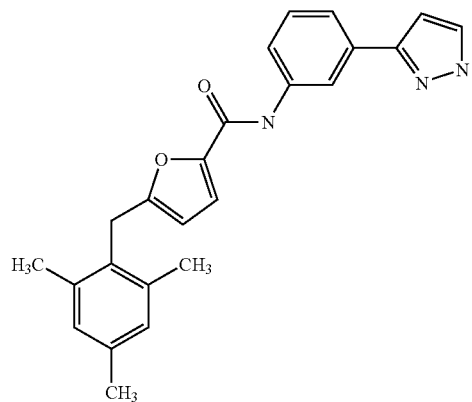
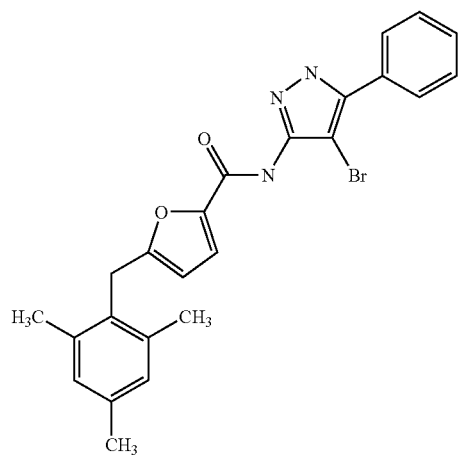
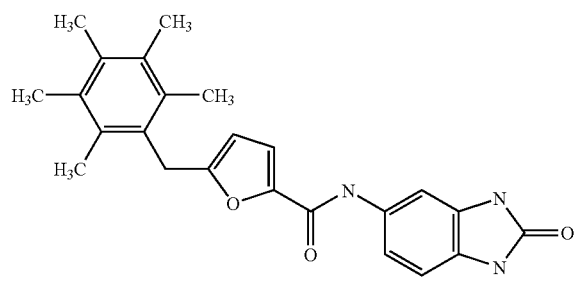

-continued
| MOLSTRUCTURE |
|---|
| 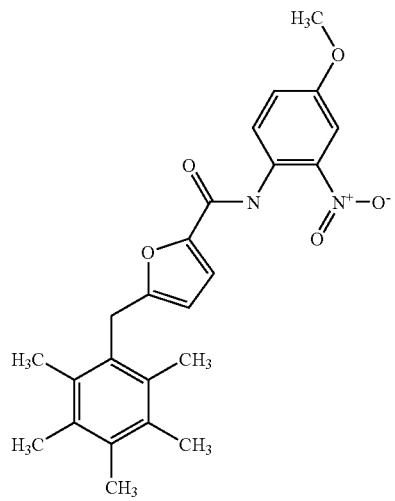 |
| 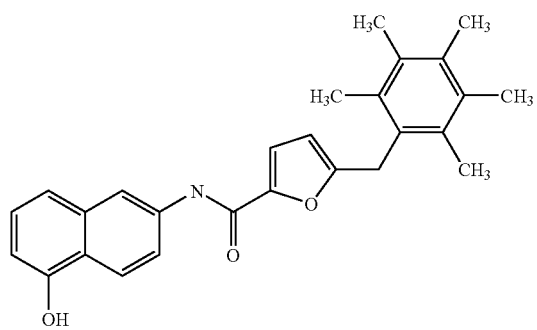 |
| 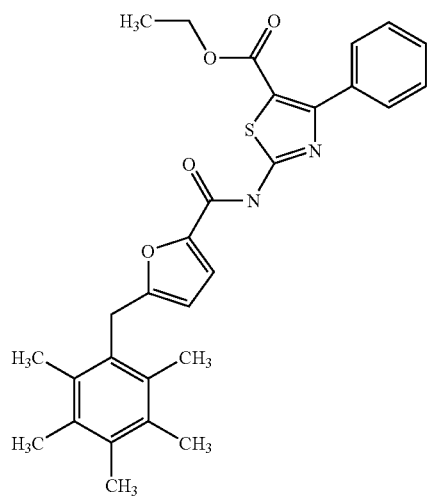 |

-continued
MOLSTRUCTURE
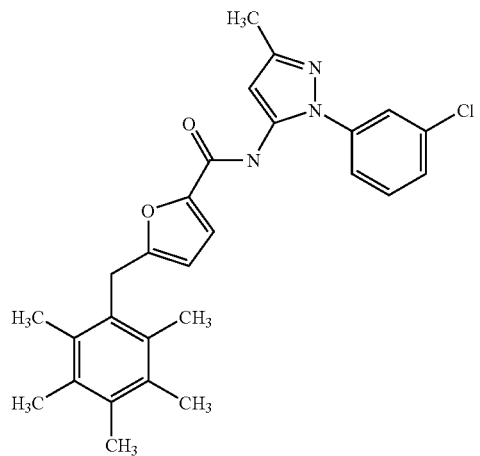
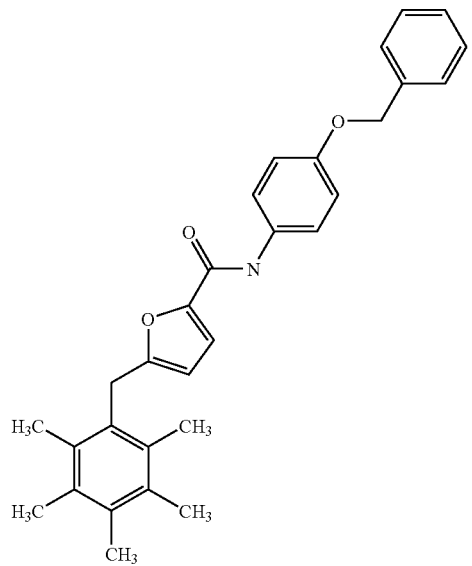
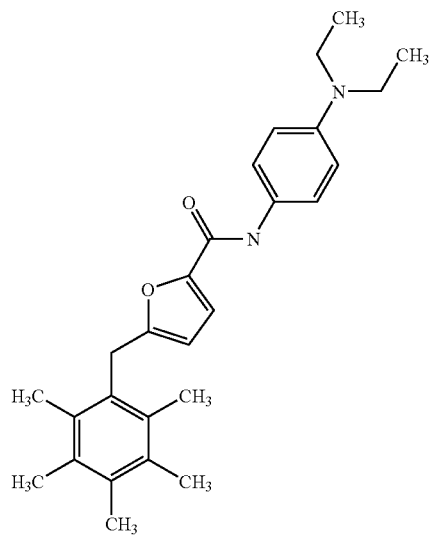

| MOLSTRUCTURE |
|---|
| 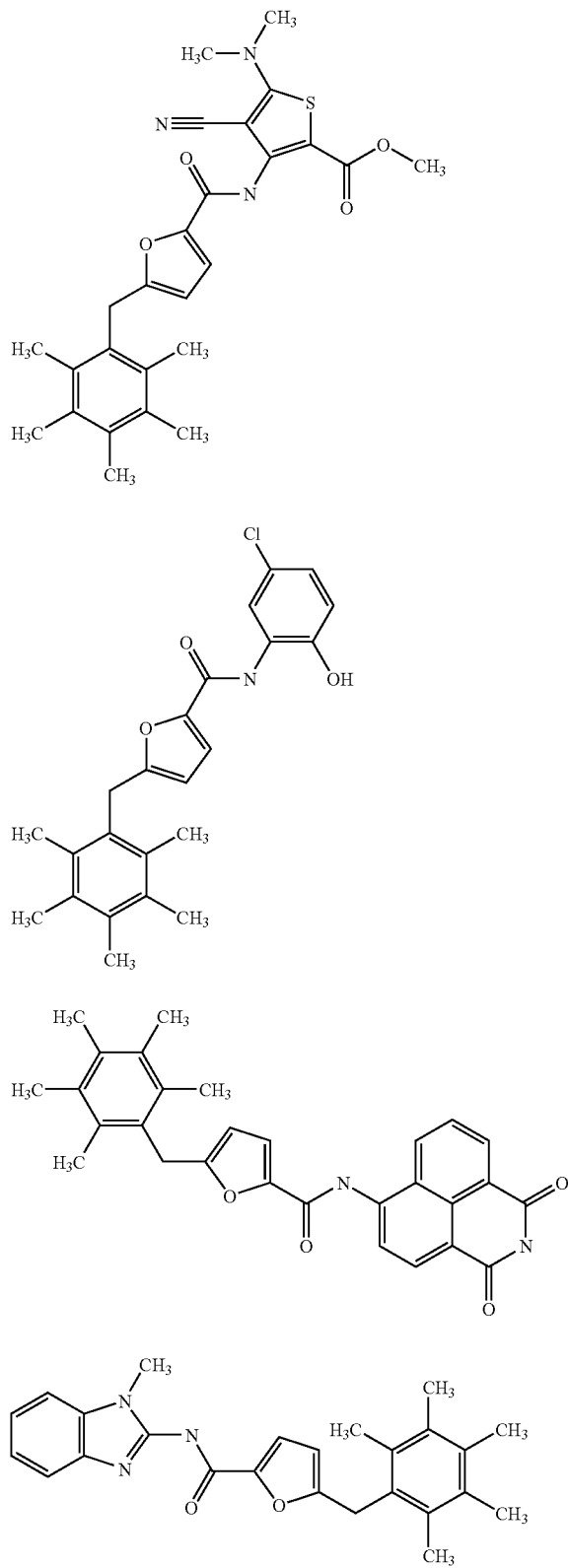 |

MOLSTRUCTURE
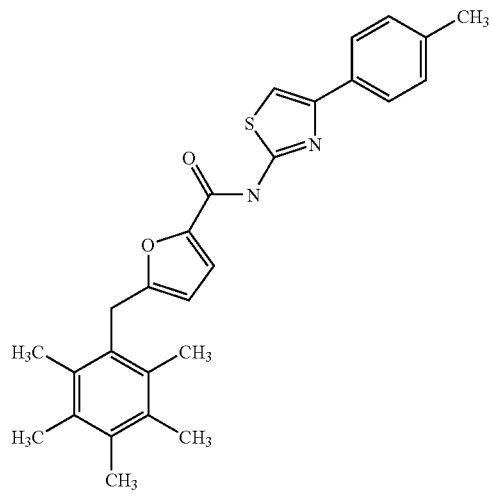
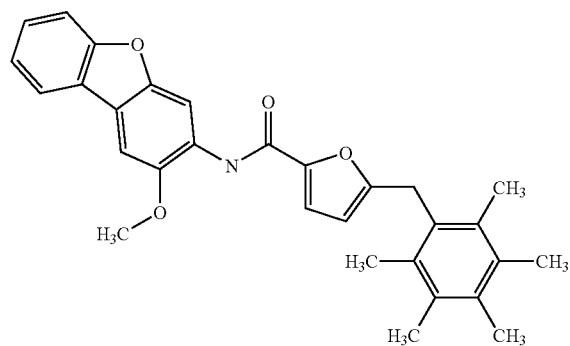
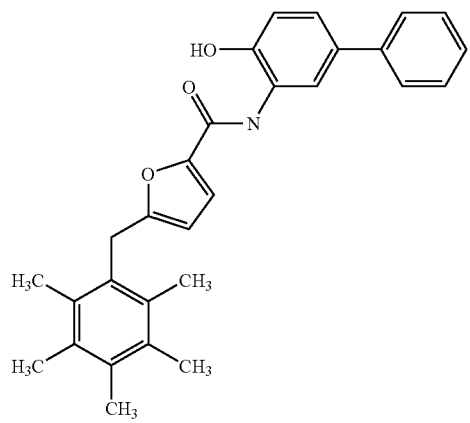

-continued
MOLSTRUCTURE
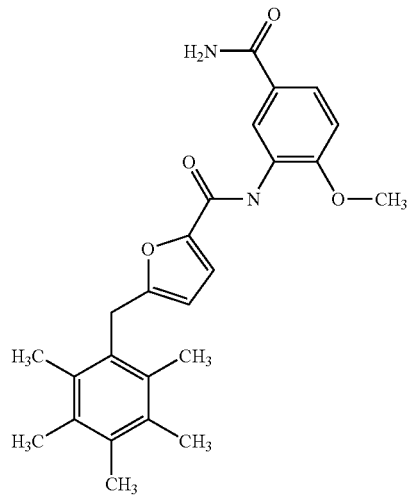
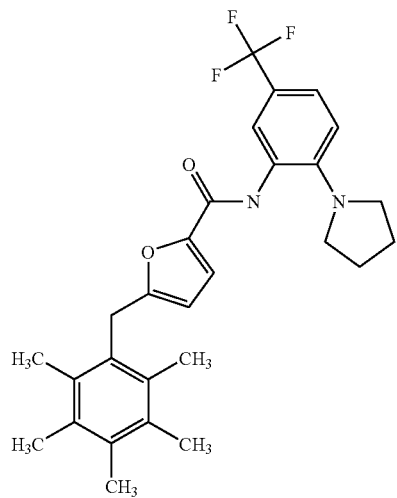
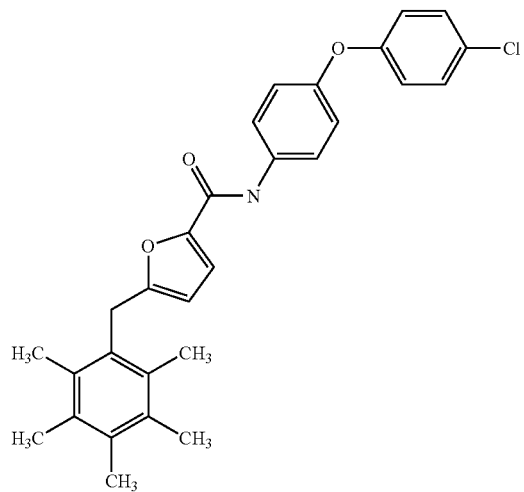

-continued
MOLSTRUCTURE
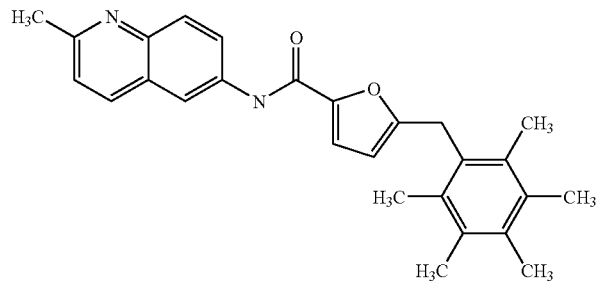
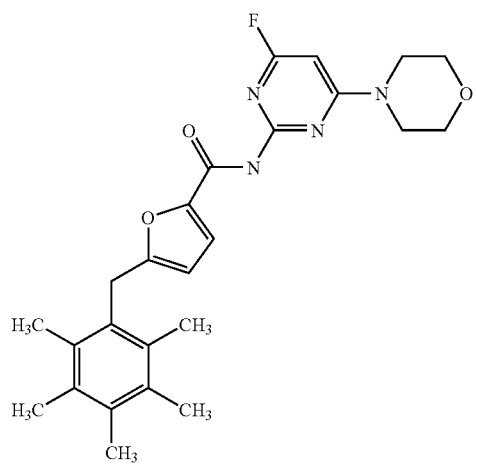
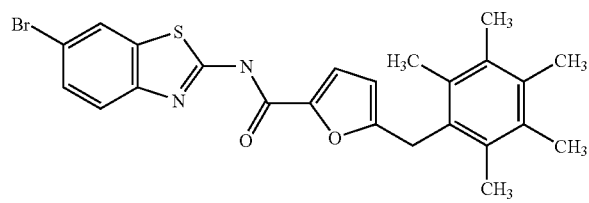
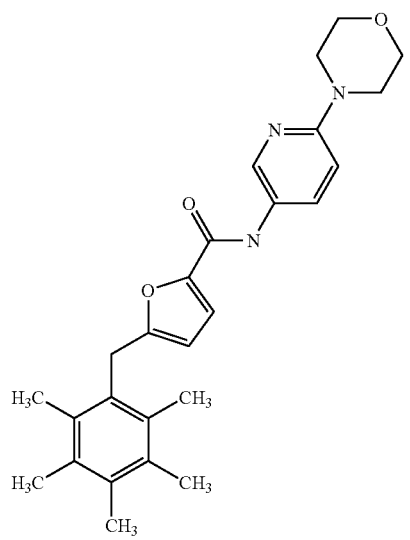

| MOLSTRUCTURE |
|---|
| 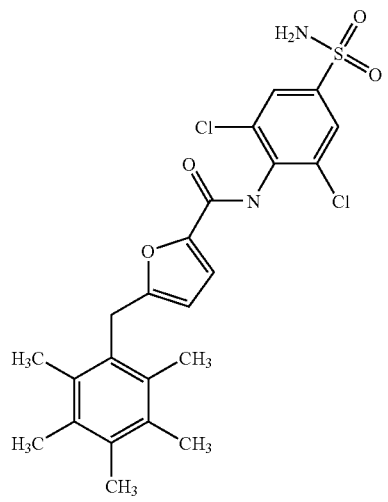 |
| 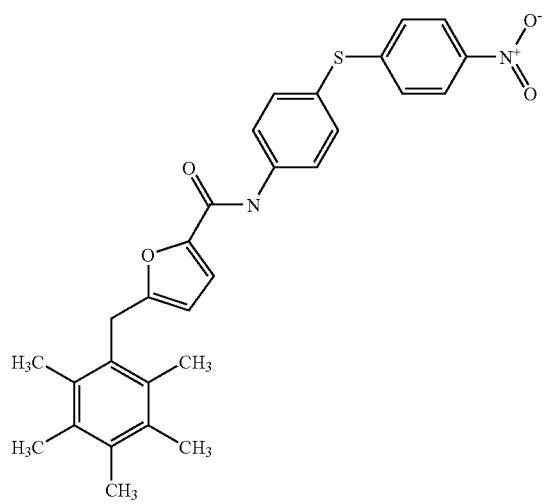 |
| 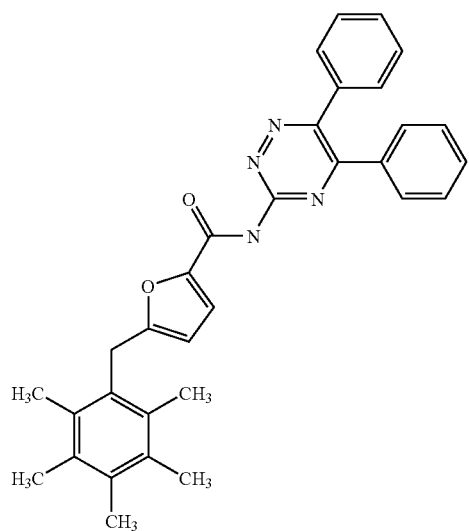 |

| MOLSTRUCTURE |
|---|
| 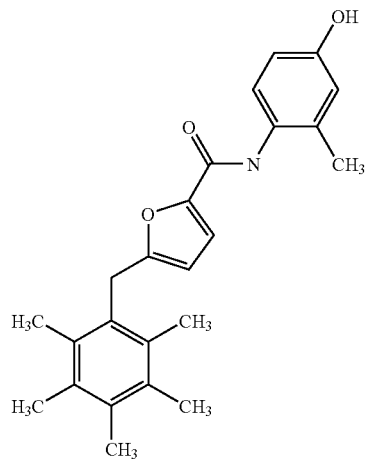 |
| 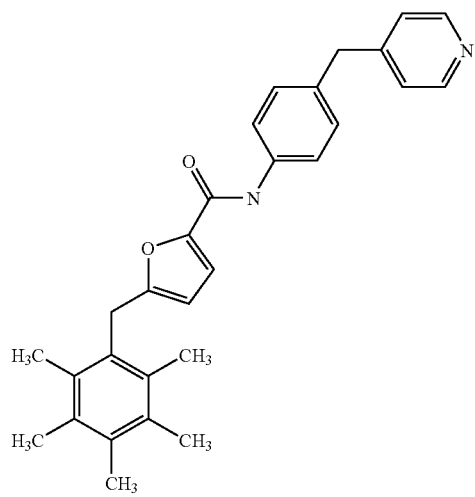 |
| 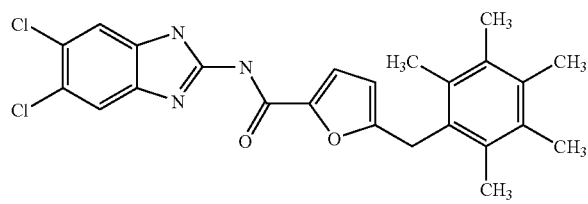 |
| 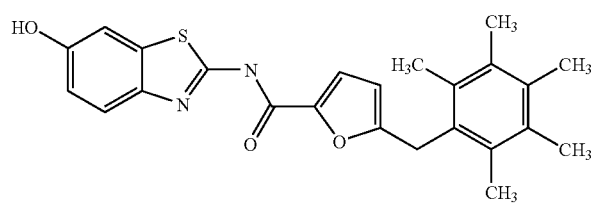 |

-continued
MOLSTRUCTURE
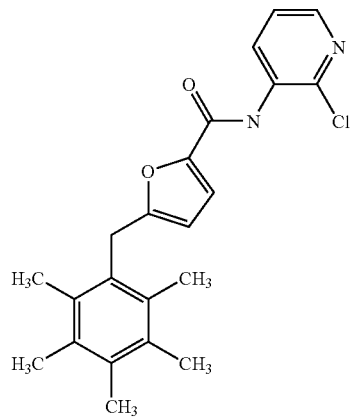
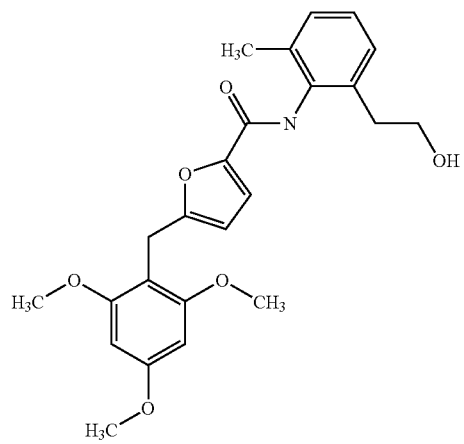
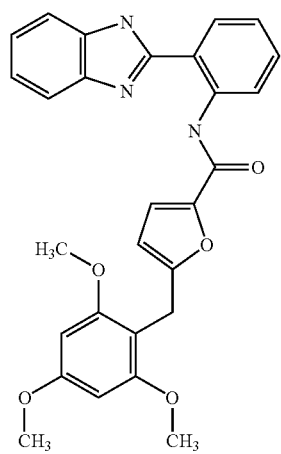

-continued
MOLSTRUCTURE
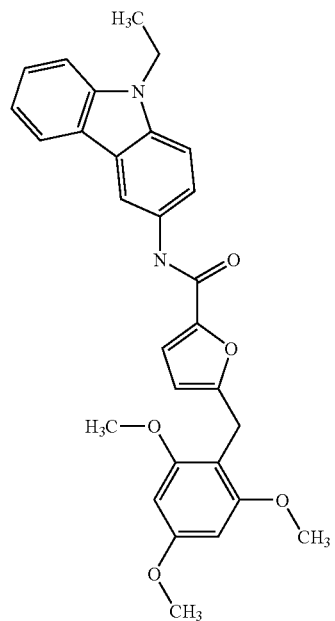
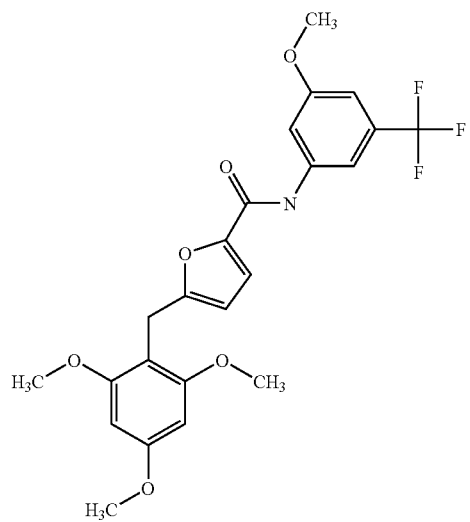

-continued
| MOLSTRUCTURE |
|---|
| 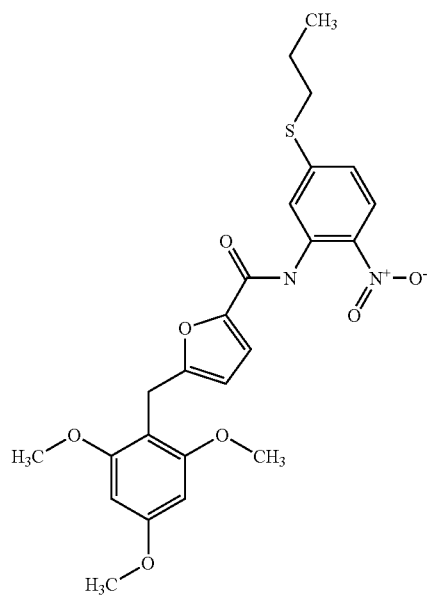 |
| 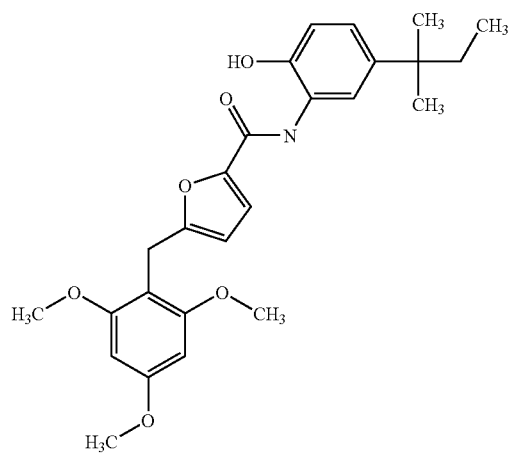 |
| 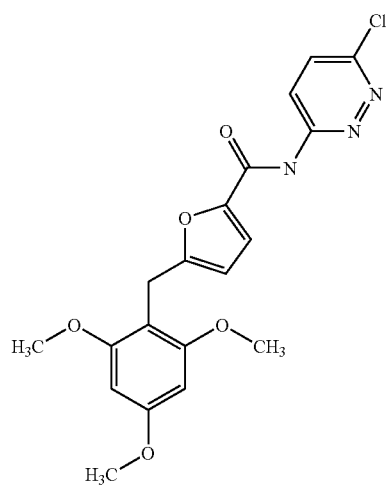 |

-continued
MOLSTRUCTURE
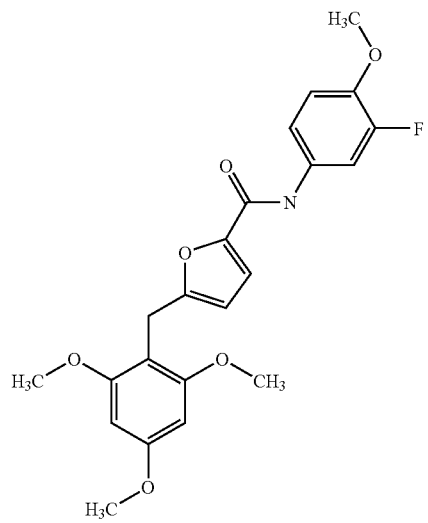
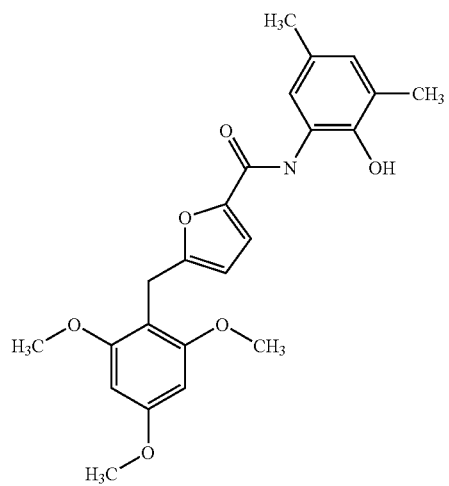
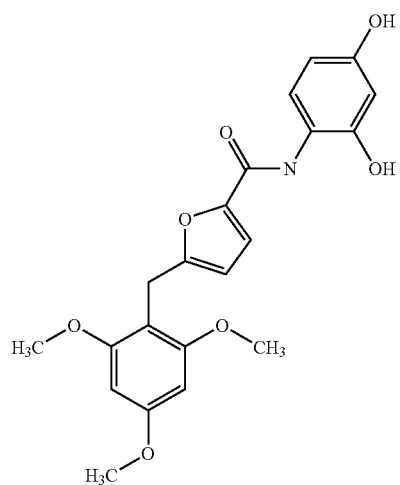

MOLSTRUCTURE
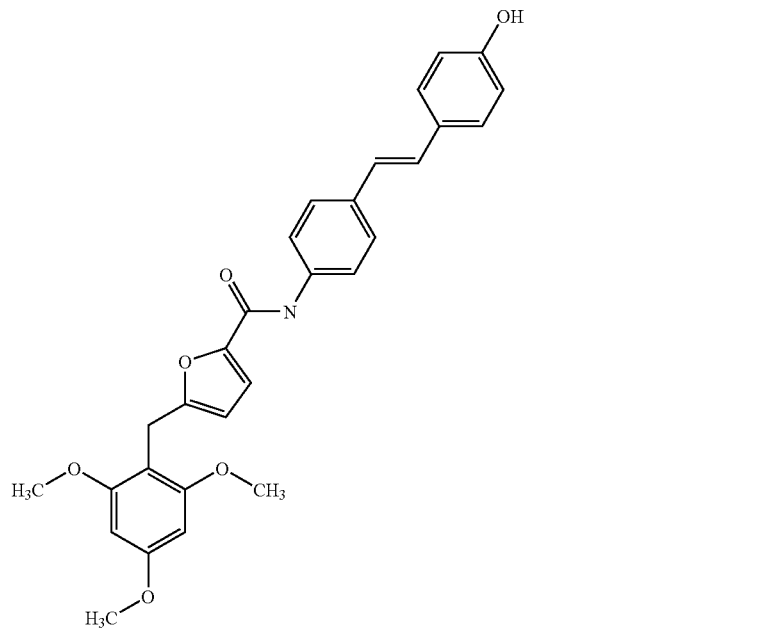
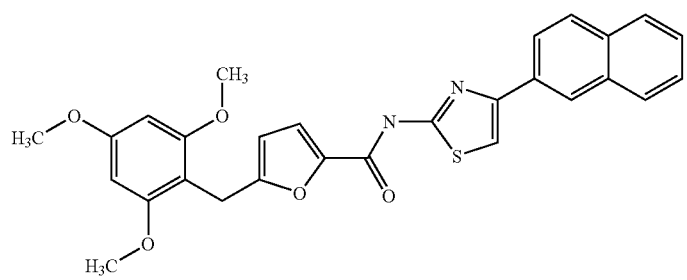
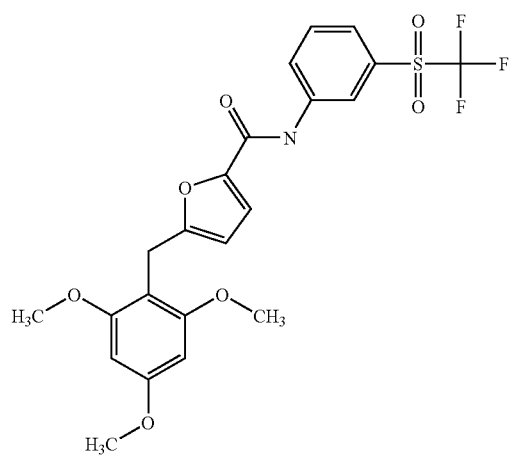
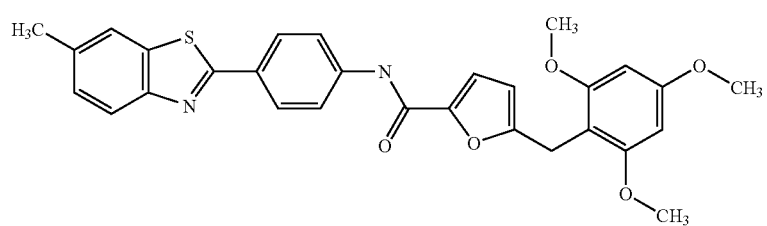

| MOLSTRUCTURE |
| --- |
| 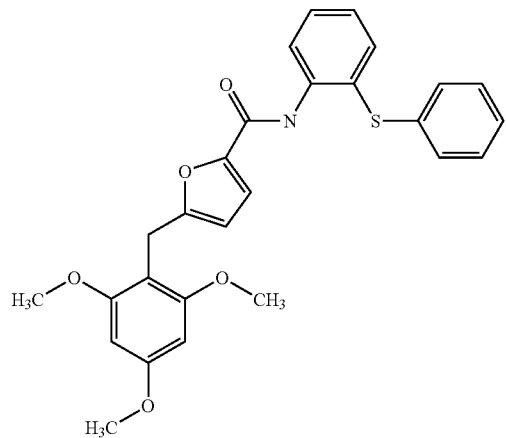 |
| 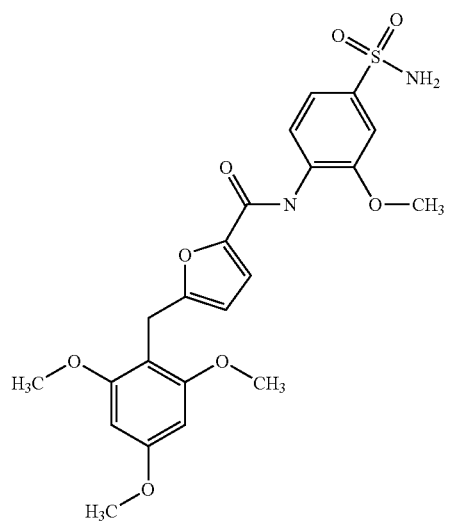 |
| 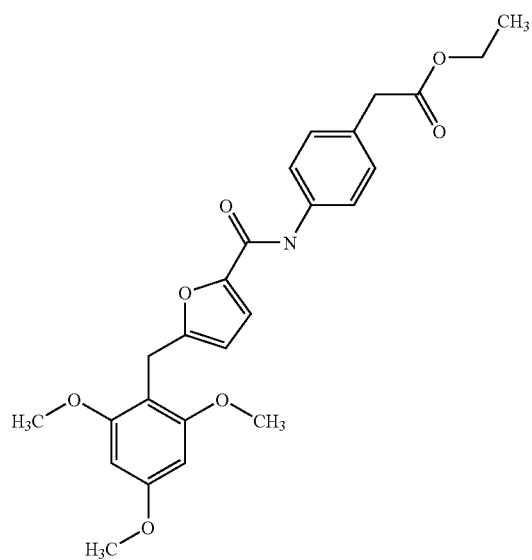 |

MOLSTRUCTURE
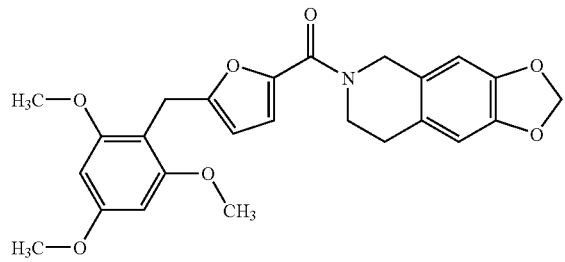
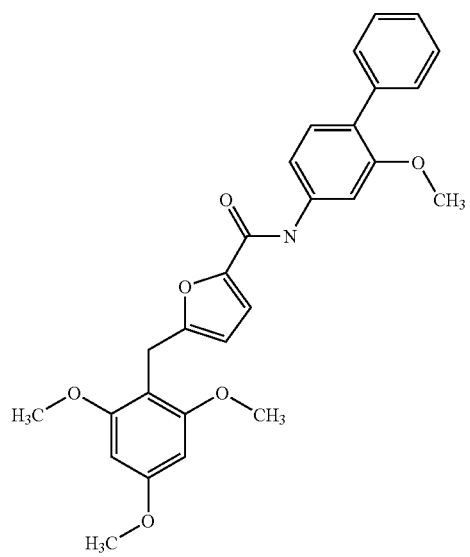
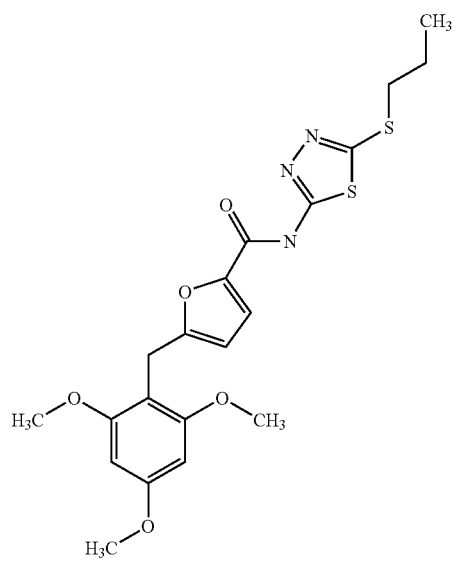

-continued
MOLSTRUCTURE
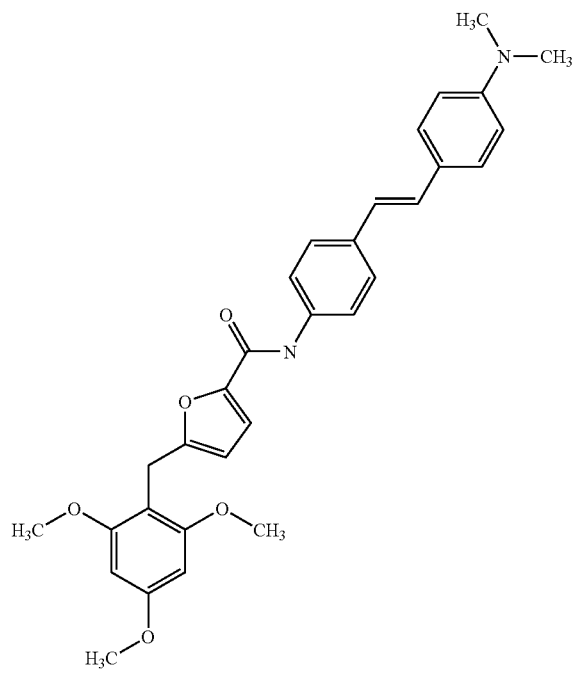
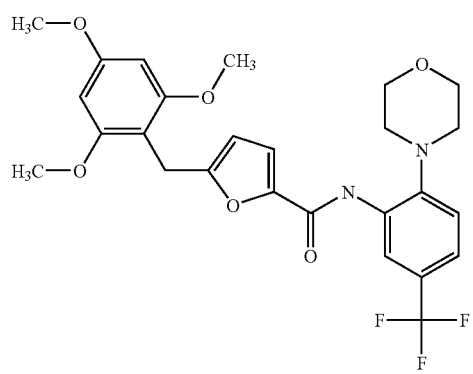

| MOLSTRUCTURE |
| --- |
| 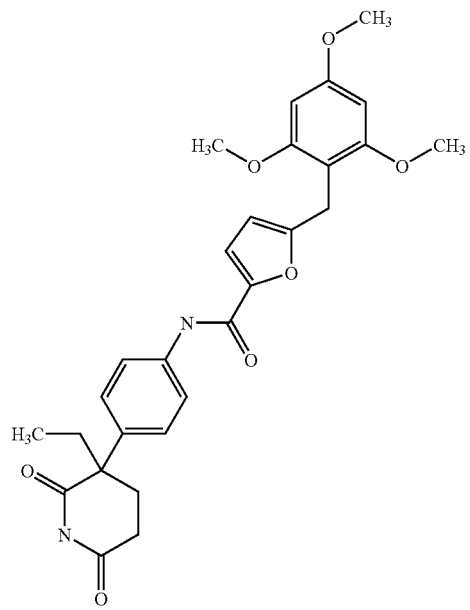 |
| 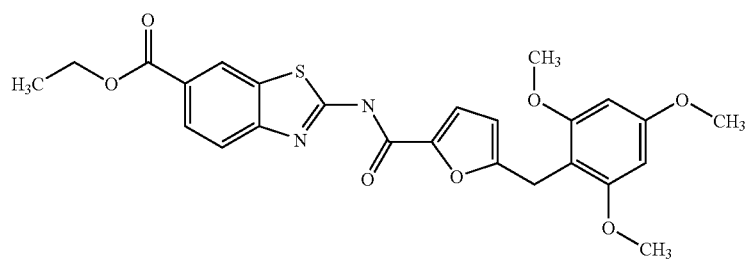 |
| 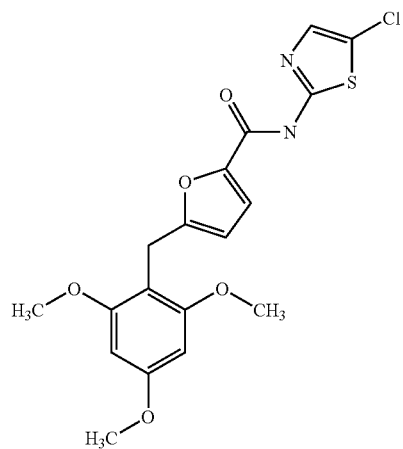 |

| MOLSTRUCTURE |
| --- |
| 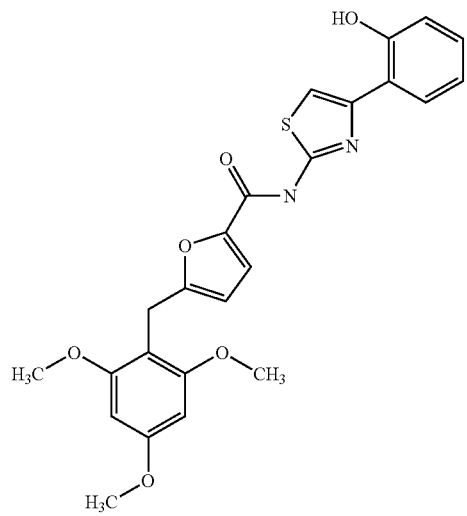 |
| 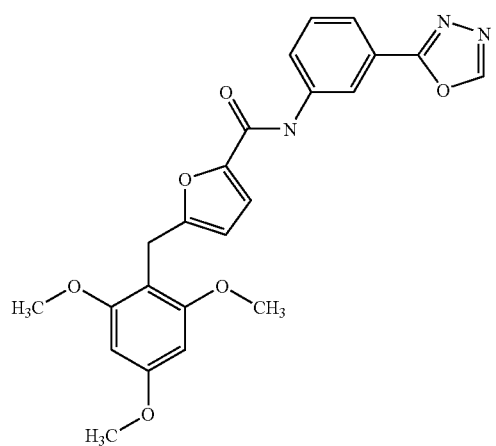 |
| 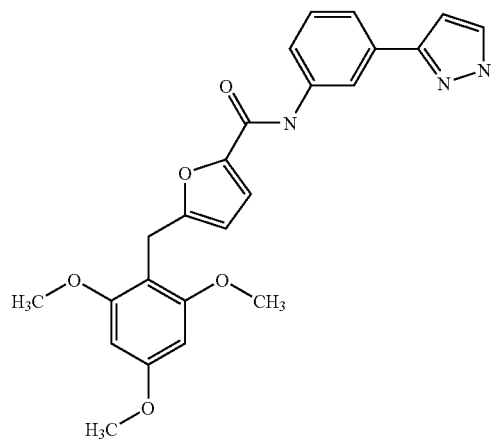 |

-continued
MOLSTRUCTURE
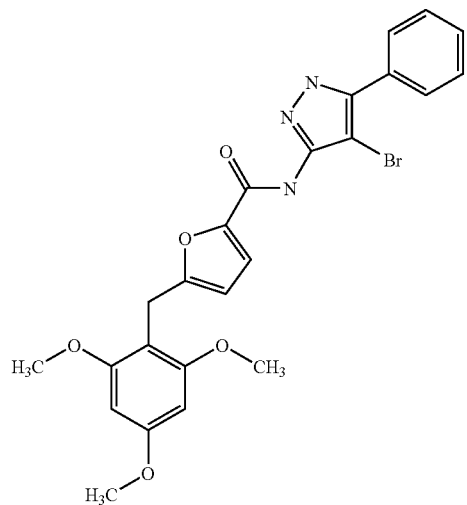
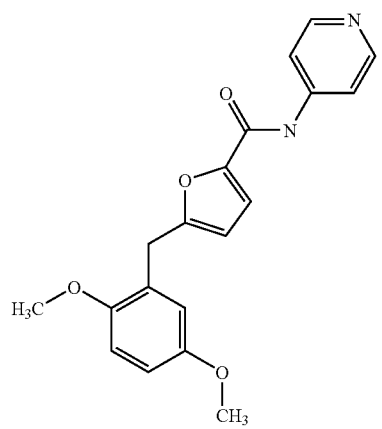
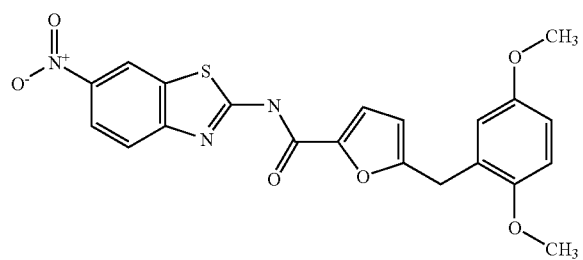

-continued
MOLSTRUCTURE
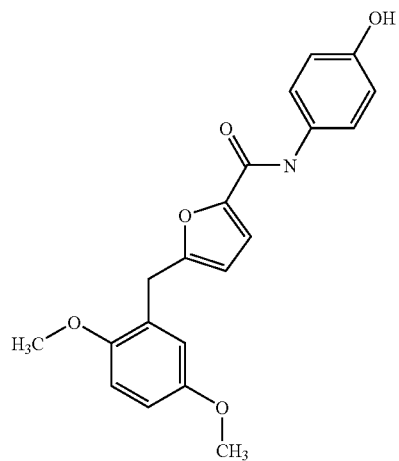
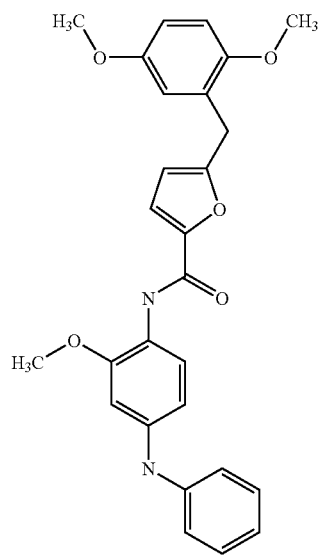
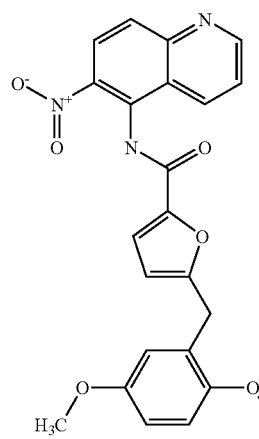

| MOLSTRUCTURE |
| --- |
| 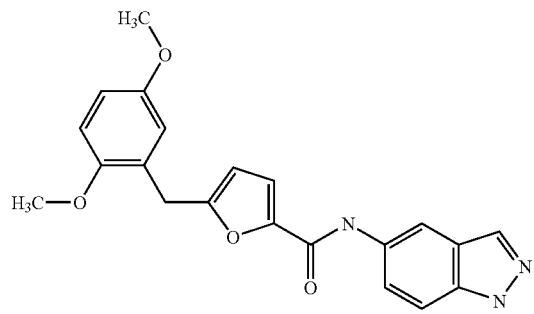 |
| 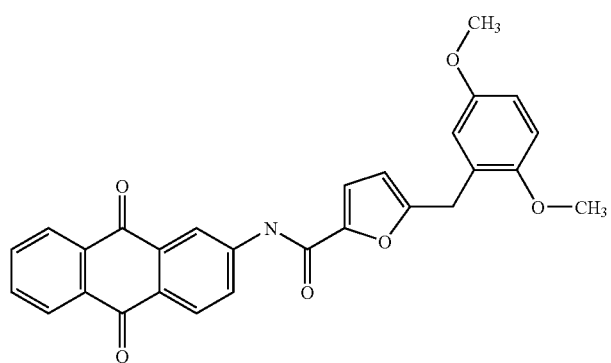 |
| 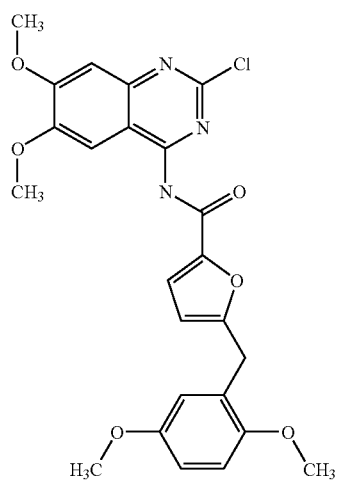 |

| MOLSTRUCTURE |
|---|
| 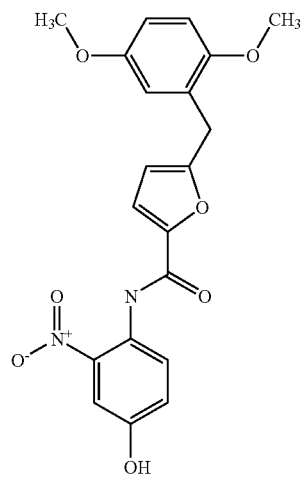 |
| 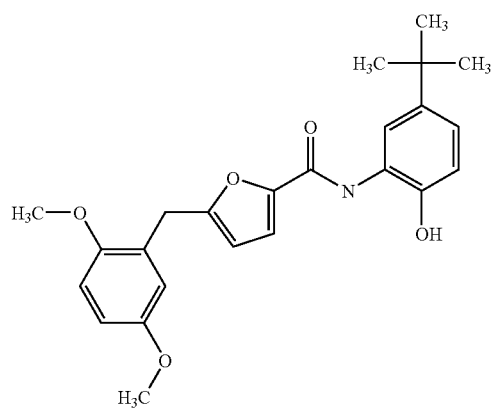 |
| 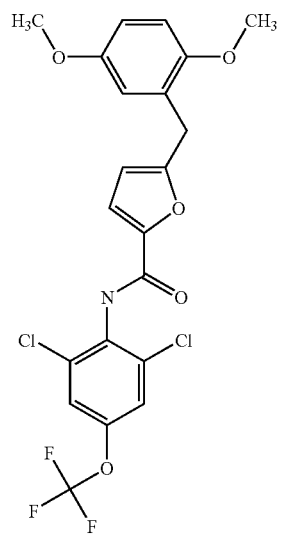 |

| MOLSTRUCTURE |
|---|
| 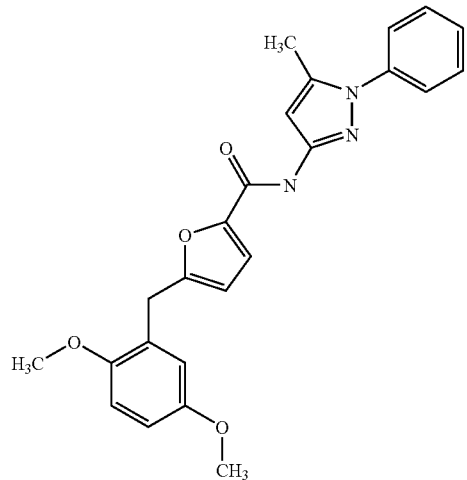 |
| 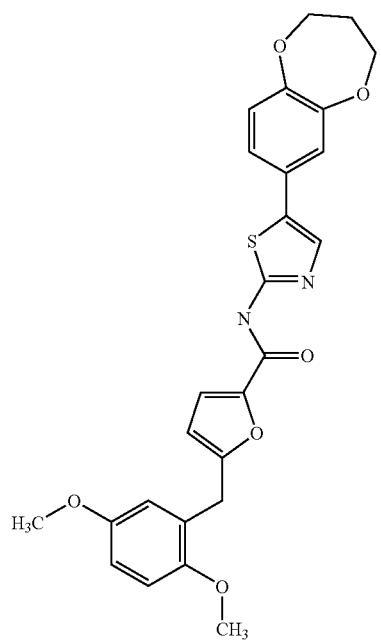 |
| 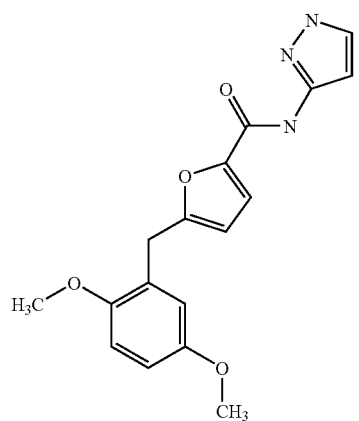 |

| MOLSTRUCTURE |
|---|
| 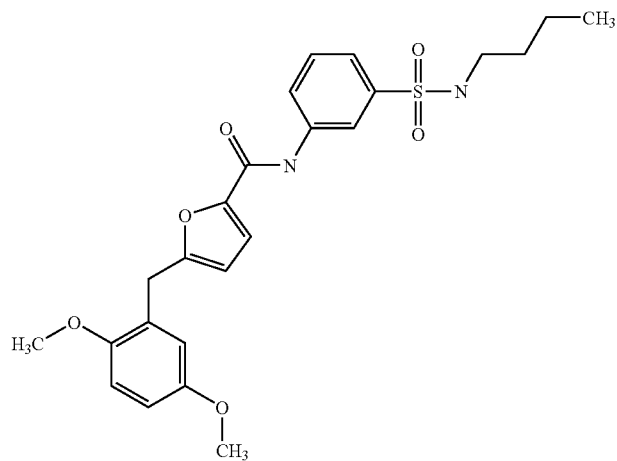 |
| 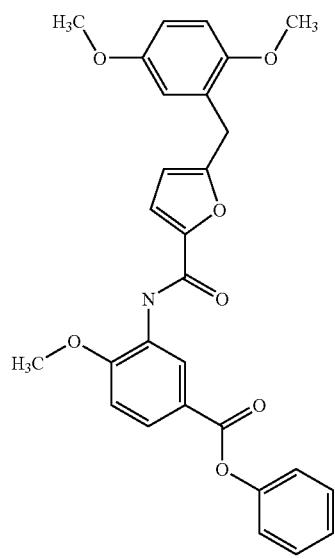 |
| 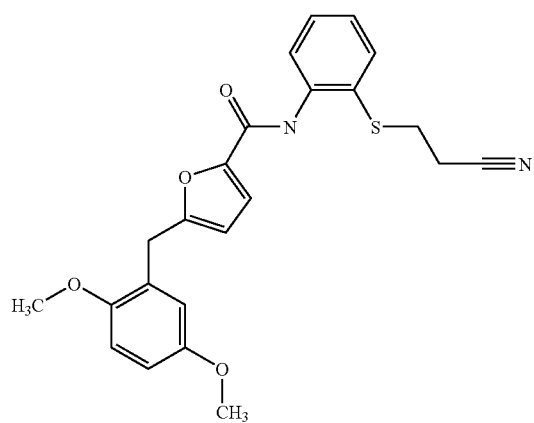 |

-continued
MOLSTRUCTURE
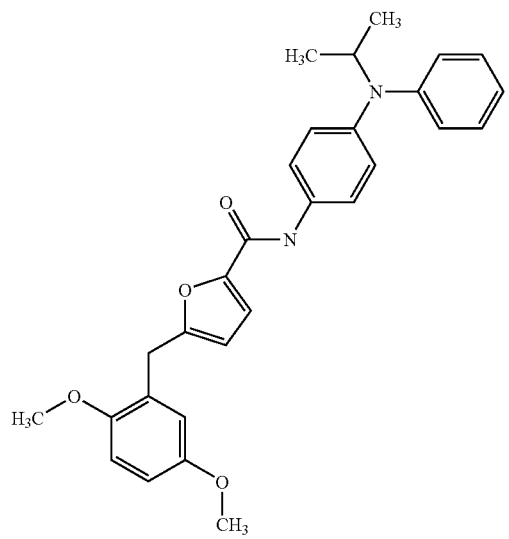
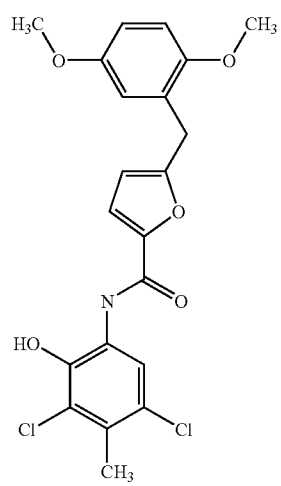
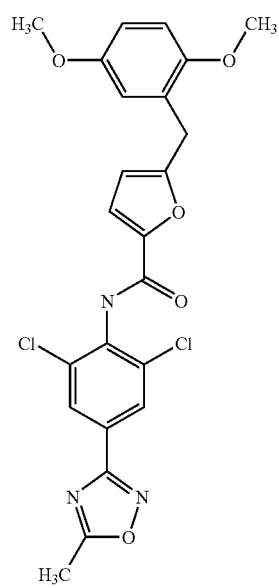

-continued
MOLSTRUCTURE
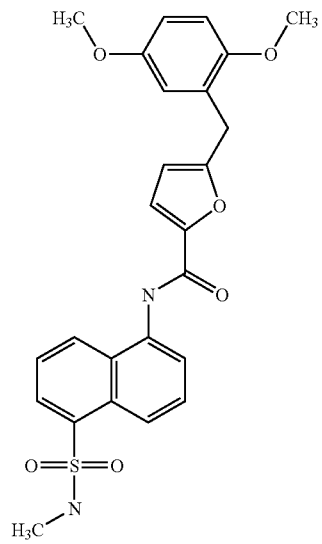
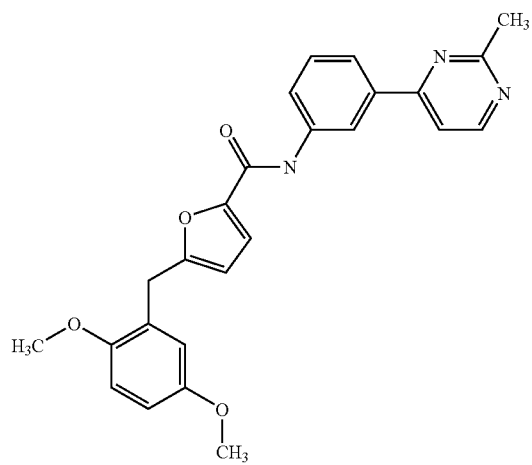
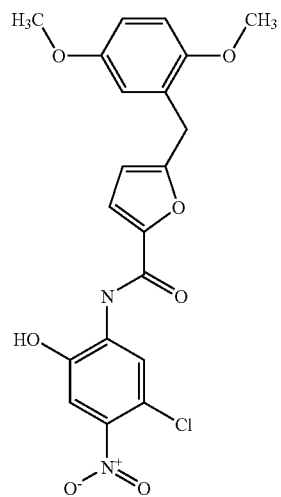

-continued
| MOLSTRUCTURE |
|---|
| 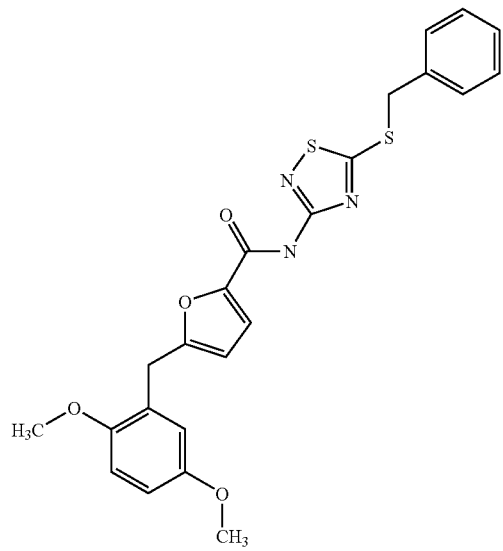 |
| 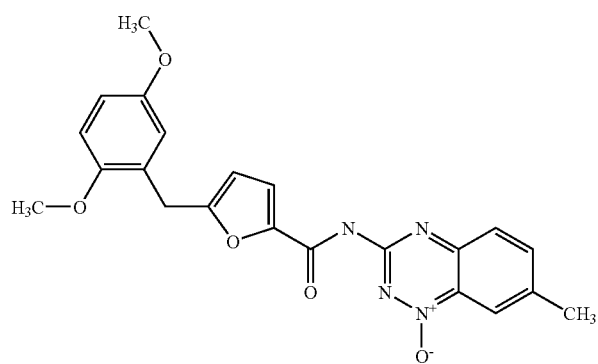 |
| 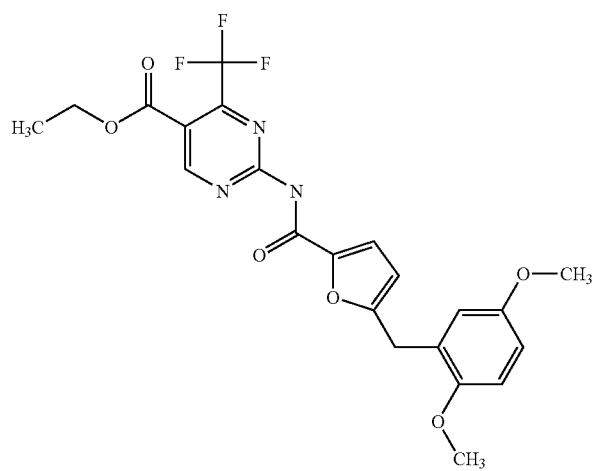 |

-continued
MOLSTRUCTURE
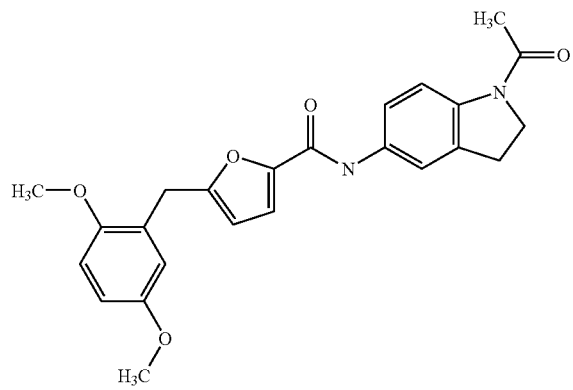
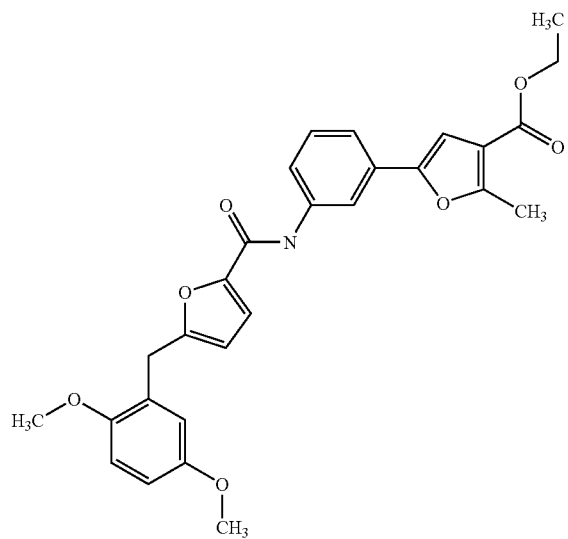
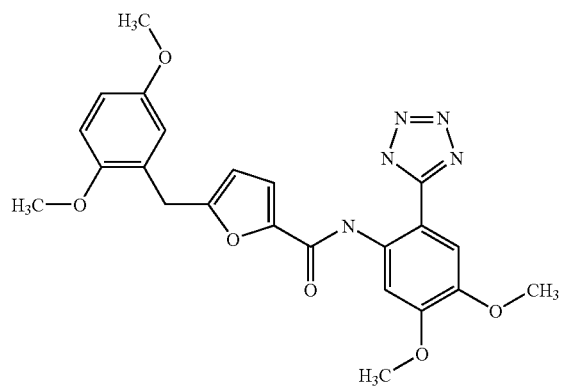

-continued
MOLSTRUCTURE
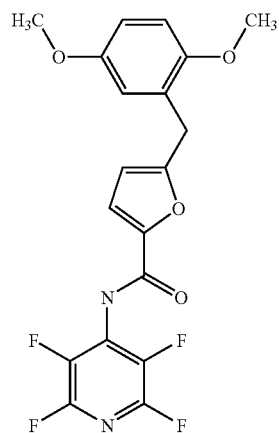
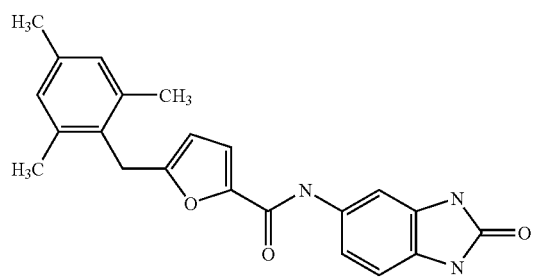
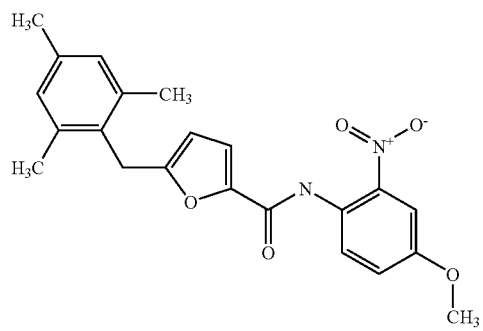
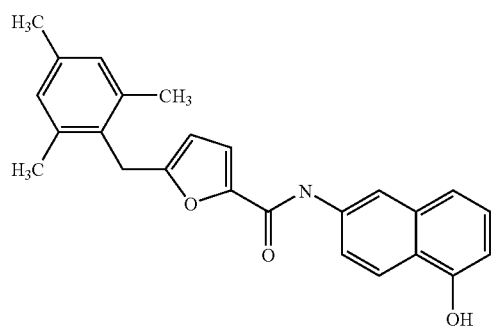

-continued
| MOLSTRUCTURE |
| --- |
| 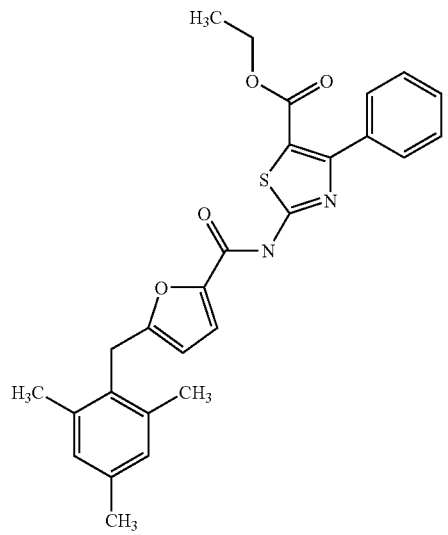 |
| 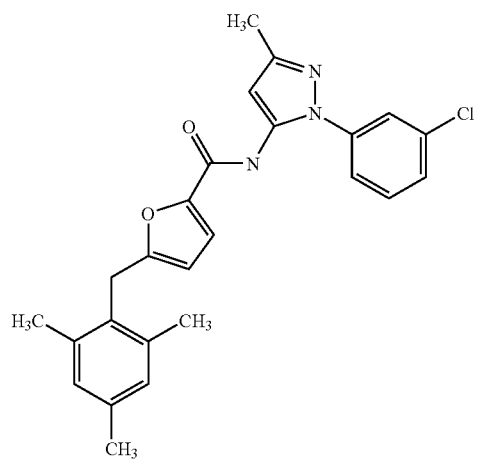 |
| 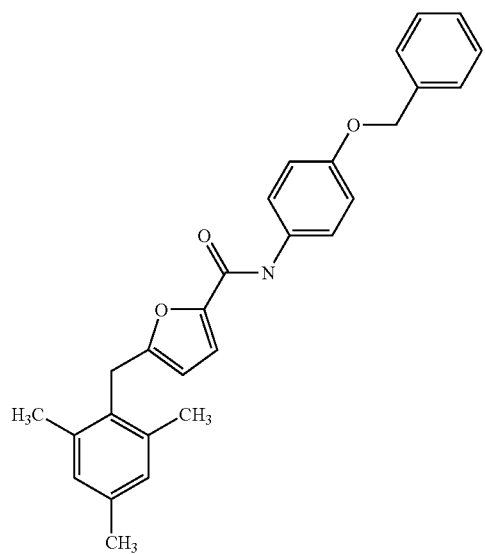 |

-continued
MOLSTRUCTURE
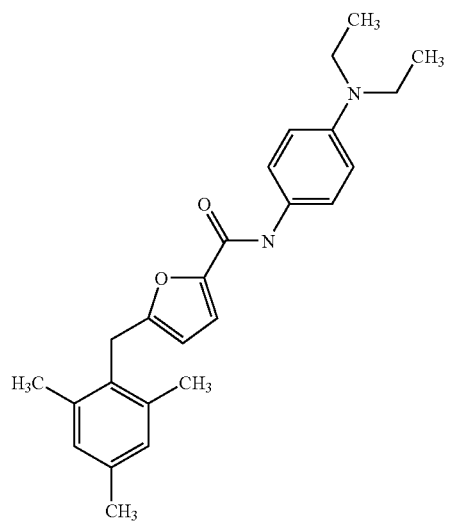
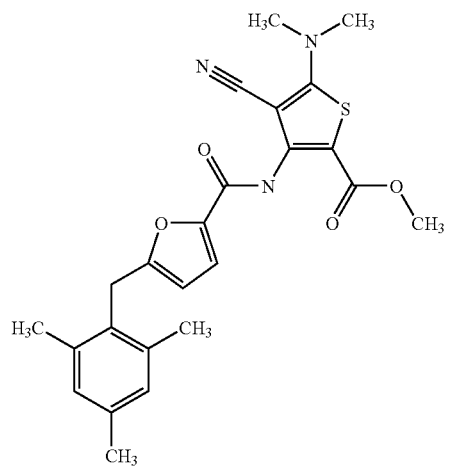
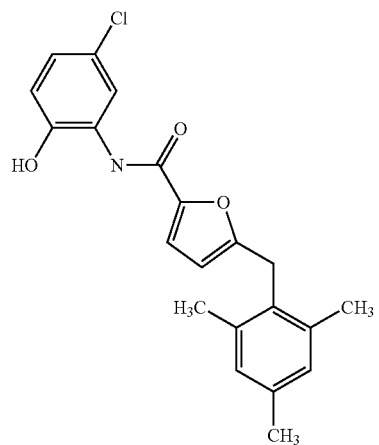

| MOLSTRUCTURE |
|---|
| 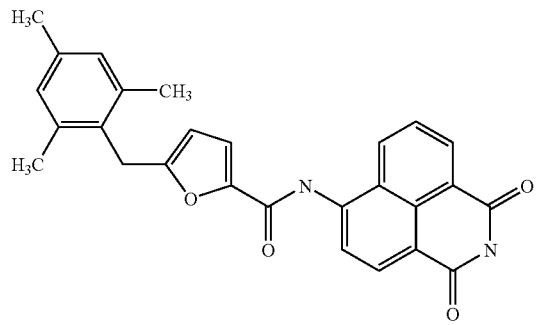 |
| 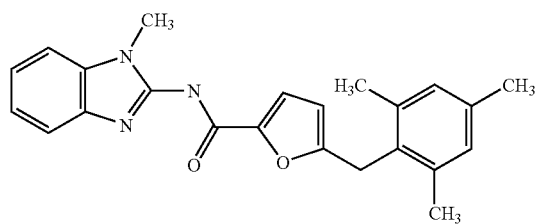 |
| 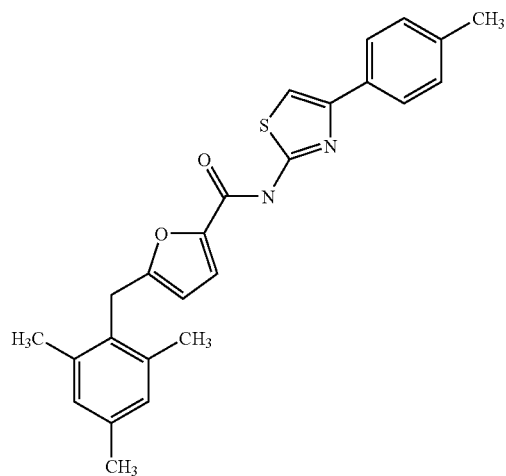 |
| 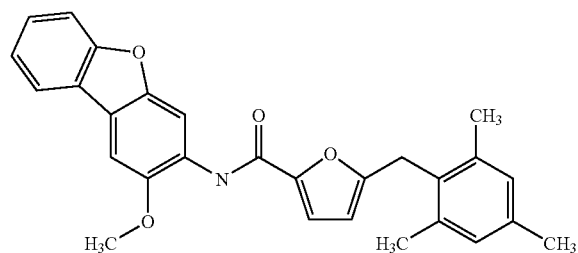 |

| MOLSTRUCTURE |
| --- |
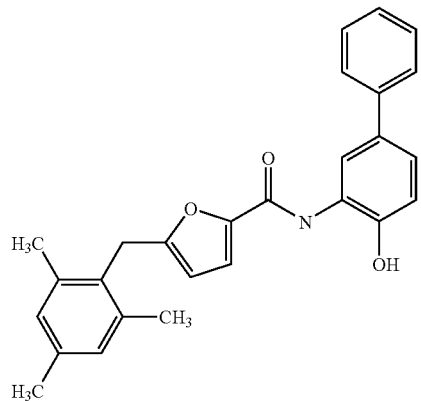
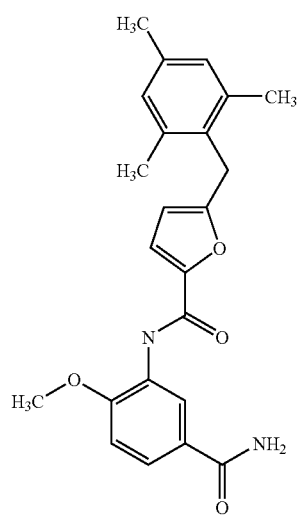
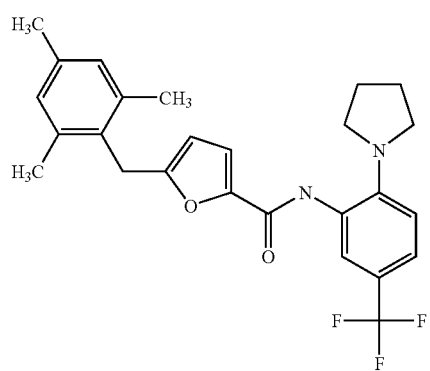

-continued
MOLSTRUCTURE
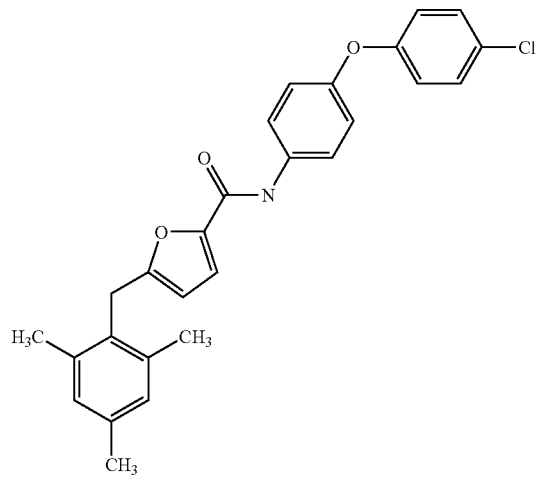
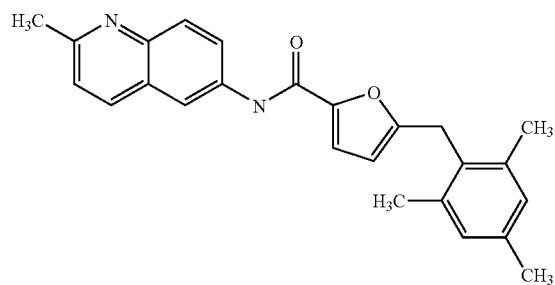
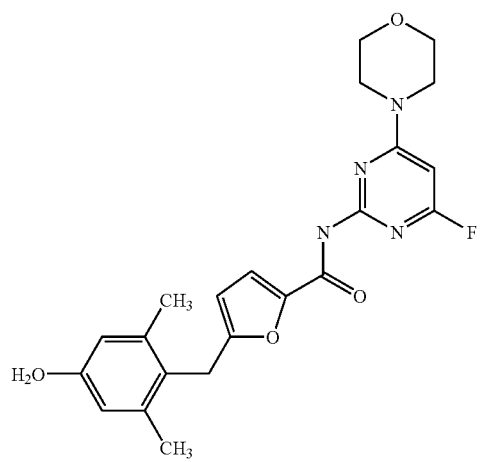
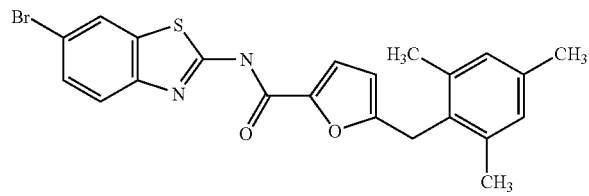

-continued
MOLSTRUCTURE
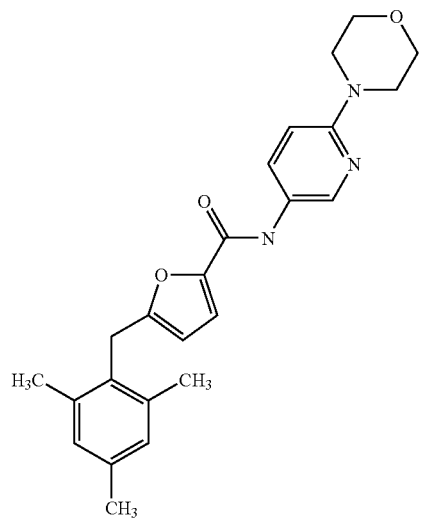
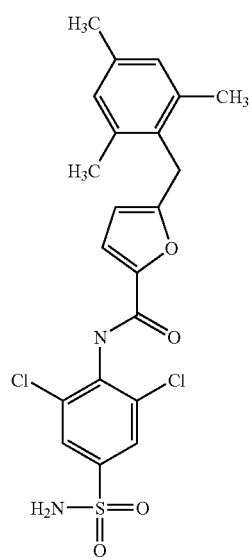
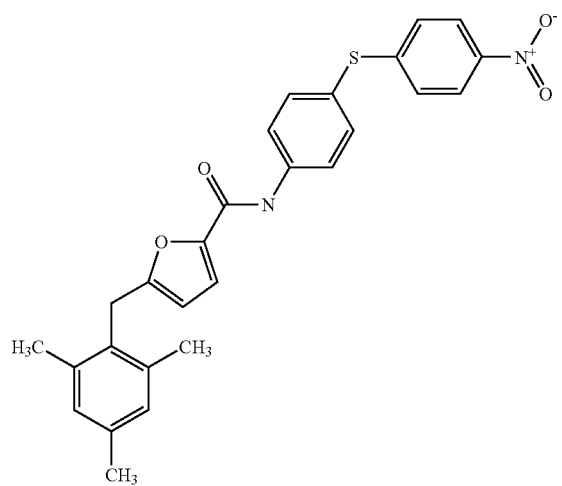

-continued
MOLSTRUCTURE
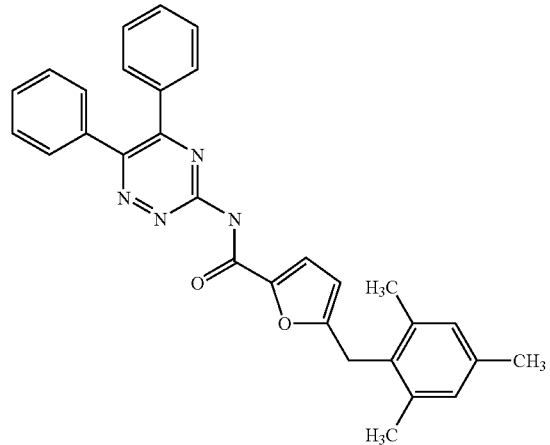
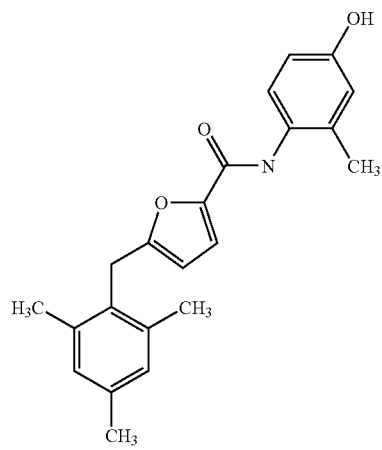
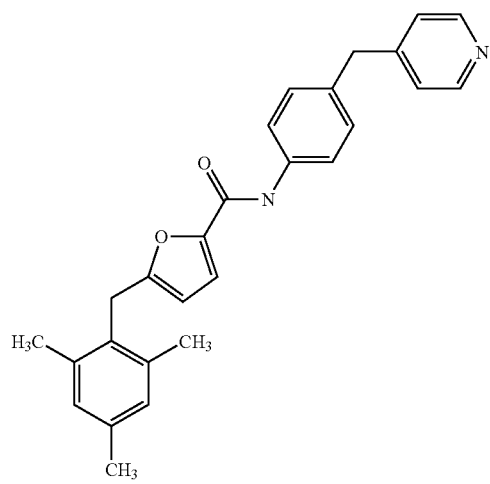
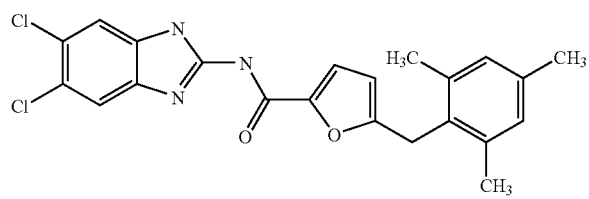

| MOLSTRUCTURE |
|---|
| 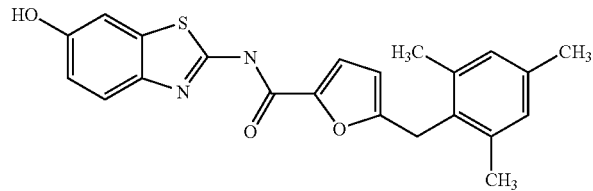 |
| 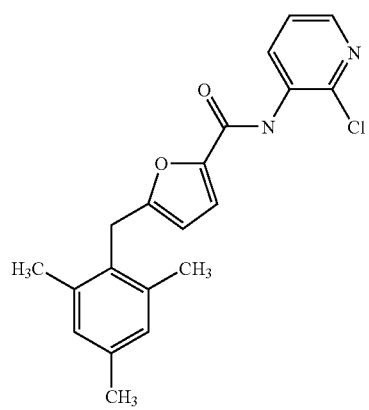 |
| MOLSTRUCTURE |
|---|
| 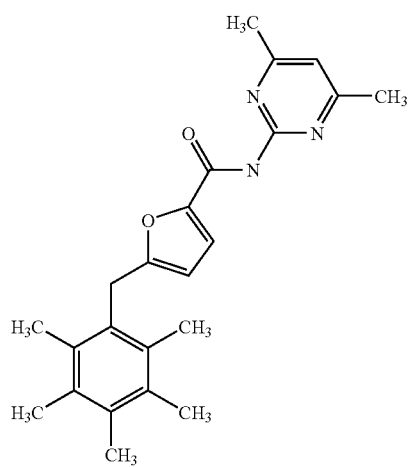 |

-continued
| MOLSTRUCTURE |
|---|
| 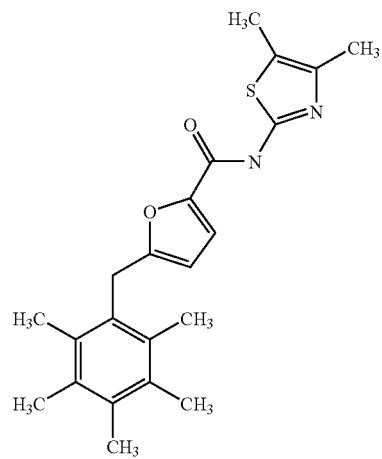 |
| 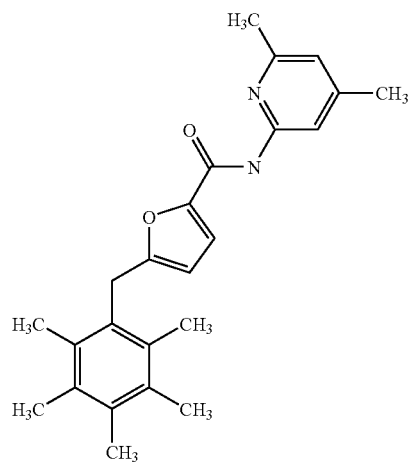 |
| 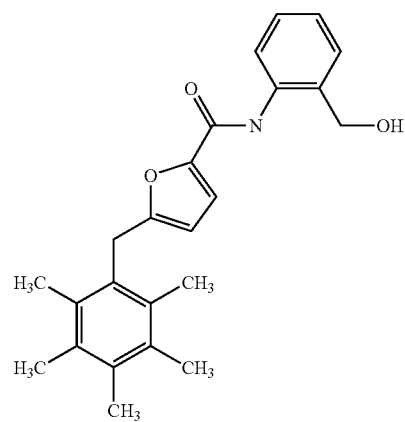 |

| MOLSTRUCTURE |
|---|
| 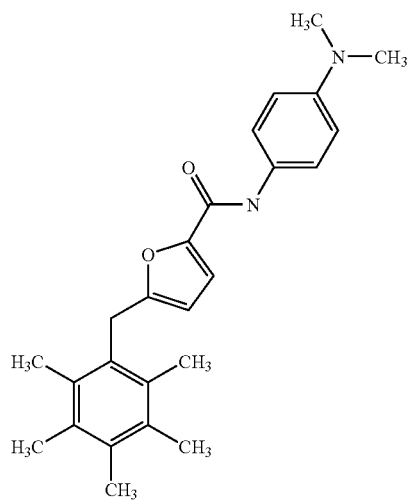 |
| 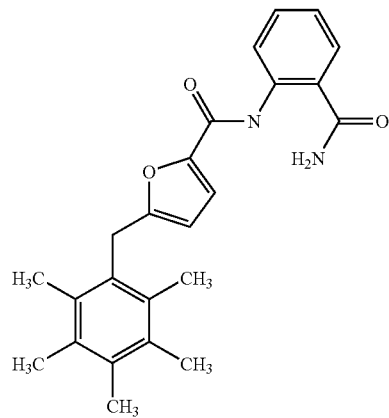 |
| 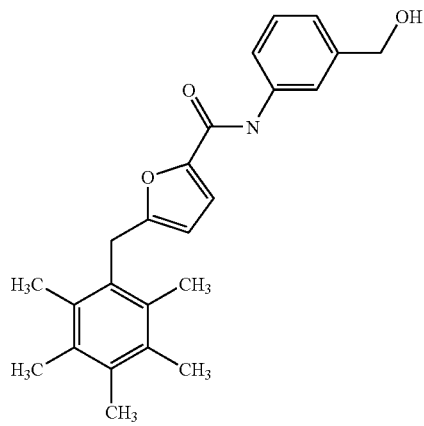 |

-continued
| MOLSTRUCTURE |
|---|
| 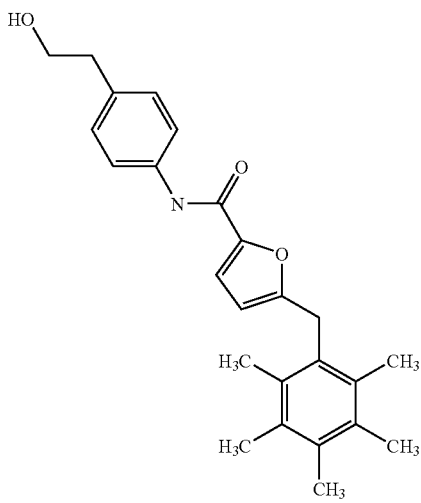 |
| 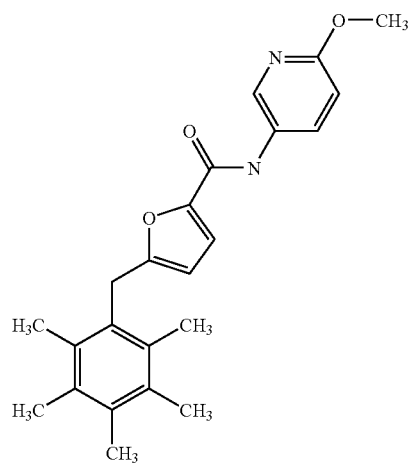 |
| 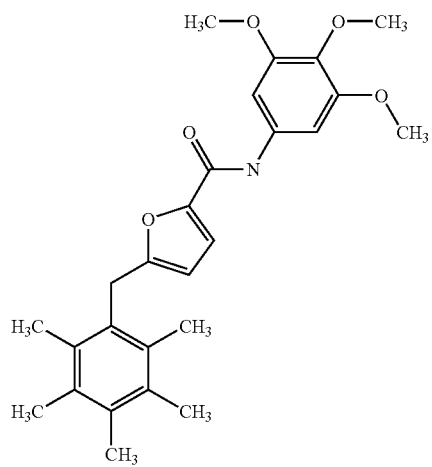 |

| MOLSTRUCTURE |
|---|
| 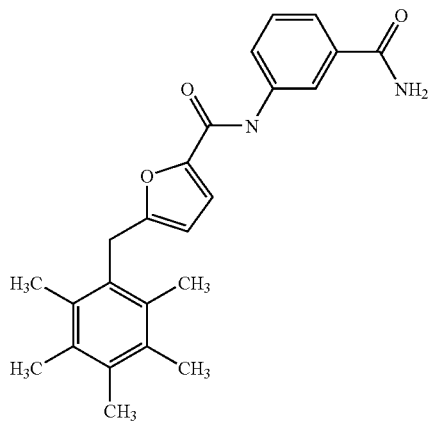 |
| 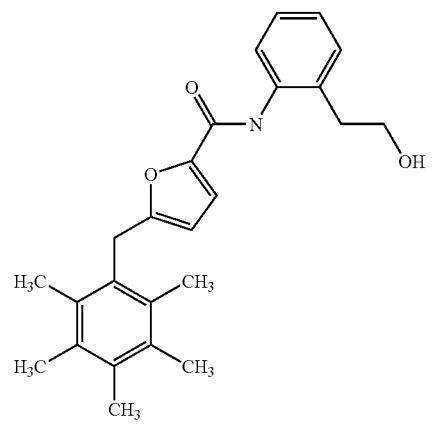 |
| 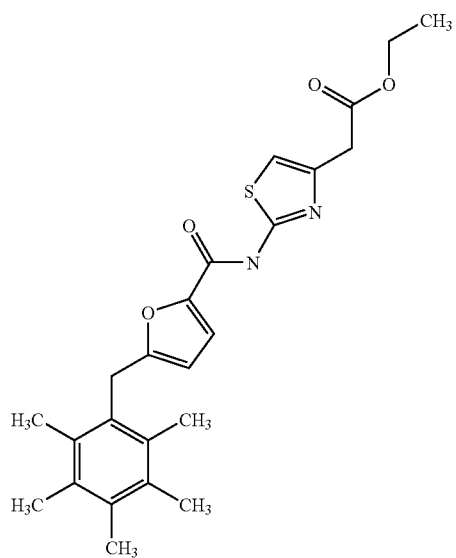 |

-continued
| MOLSTRUCTURE |
|---|
| 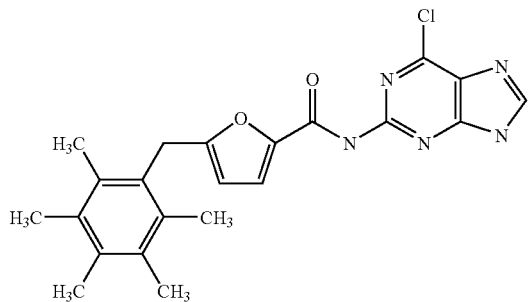 |
| 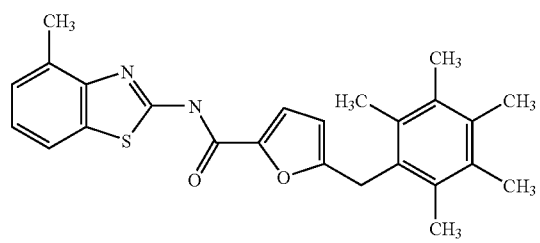 |
| 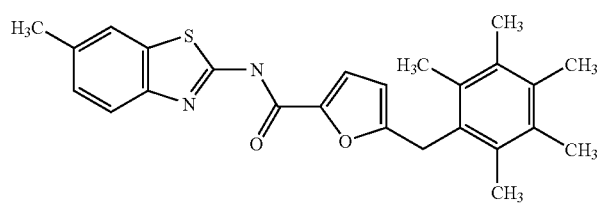 |
| 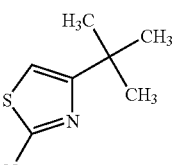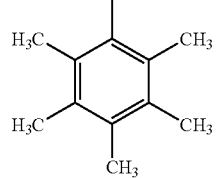 |
| 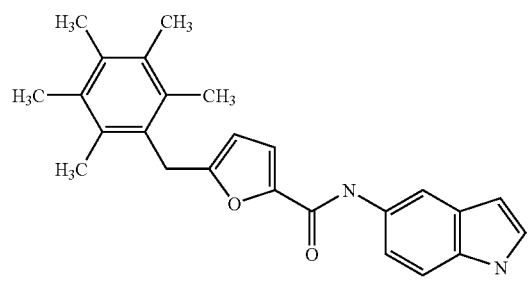 |

-continued
| MOLSTRUCTURE |
|---|
| 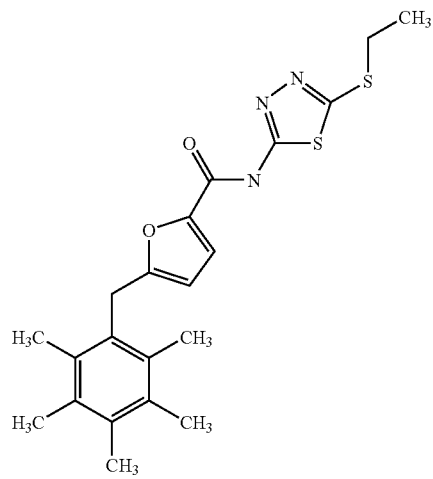 |
| 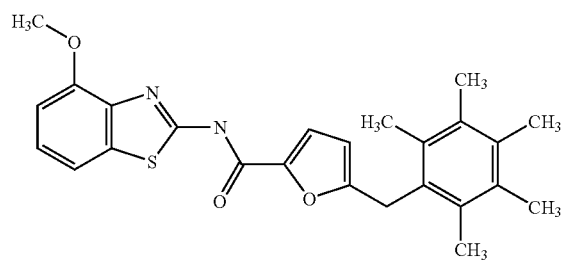 |
| 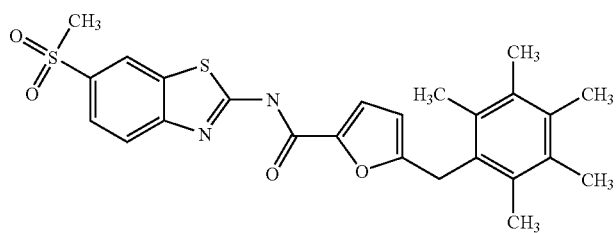 |
| 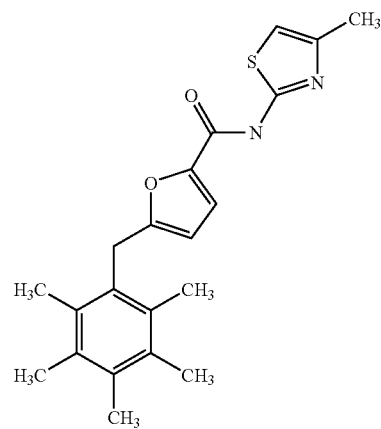 |

-continued
MOLSTRUCTURE
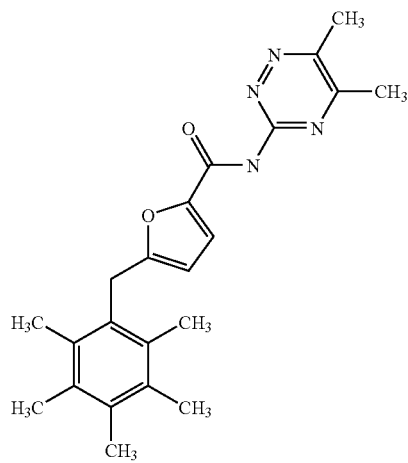
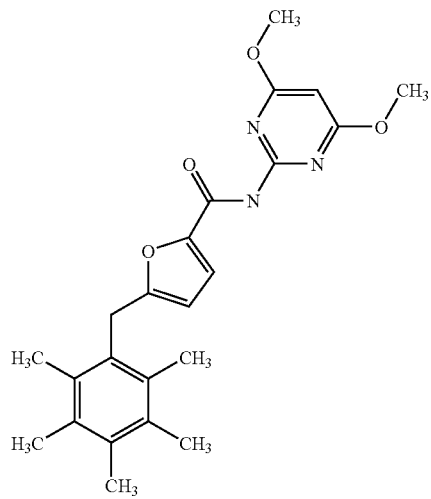
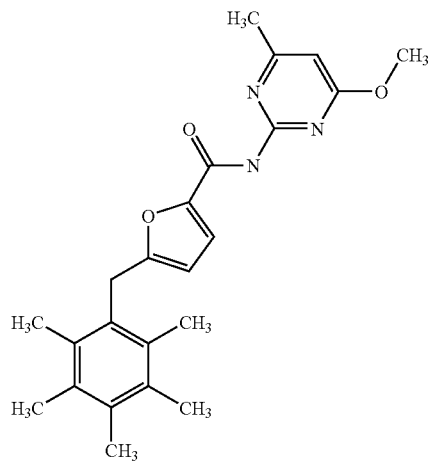

-continued
| MOLSTRUCTURE |
| --- |
| 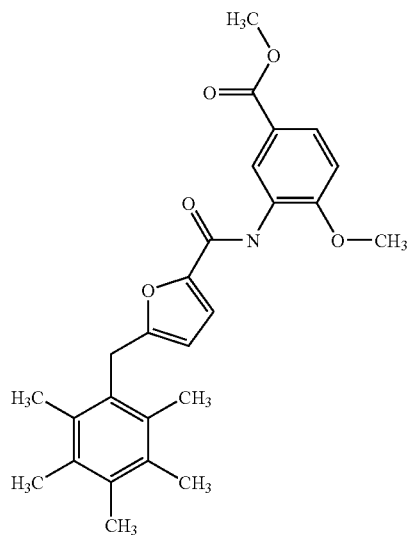 |
| 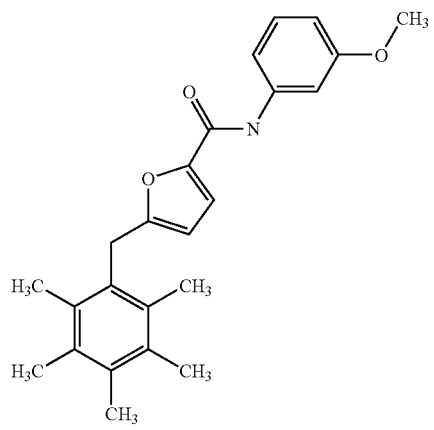 |
| 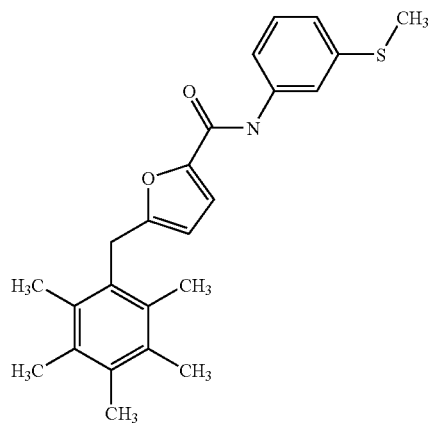 |

| MOLSTRUCTURE |
| --- |
| 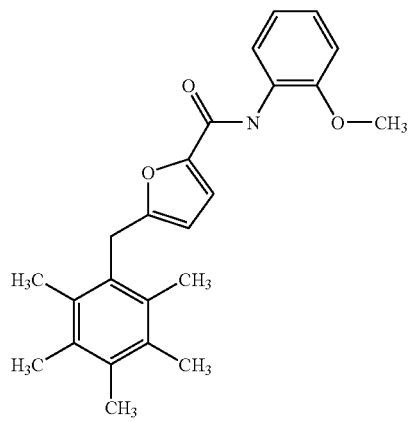 |
| 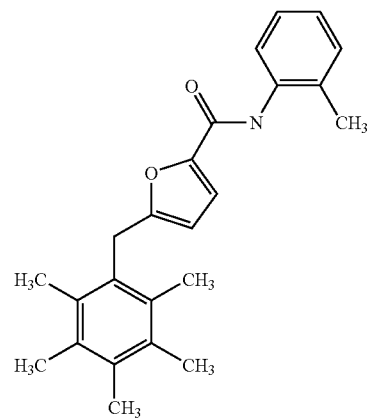 |
| 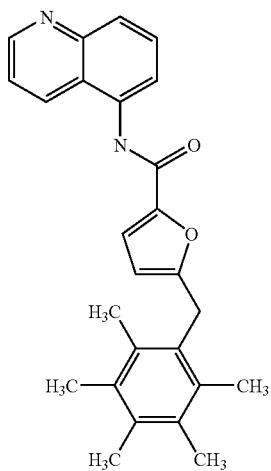 |

-continued
MOLSTRUCTURE
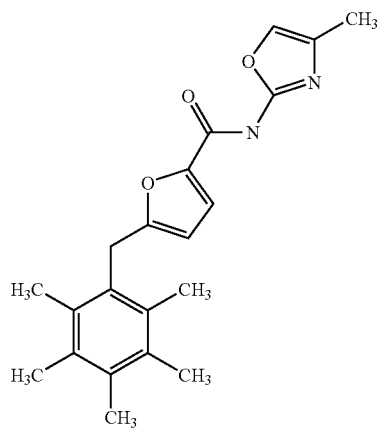
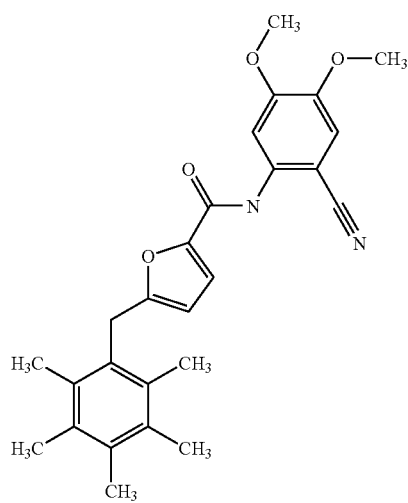
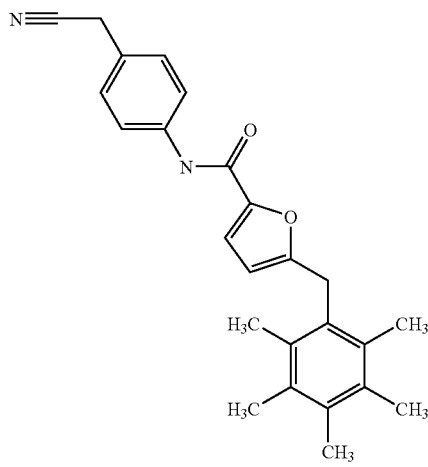

-continued
MOLSTRUCTURE
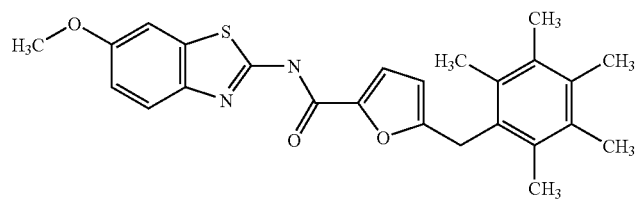
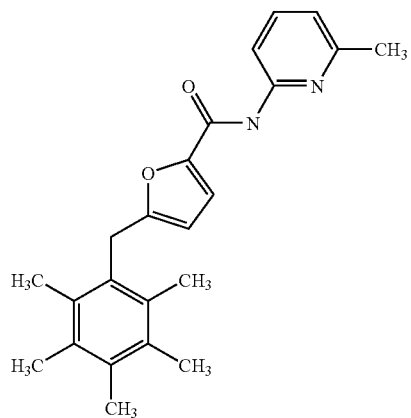
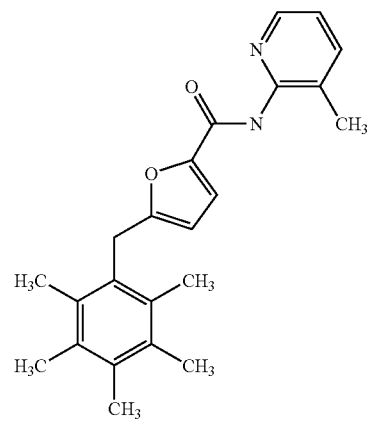
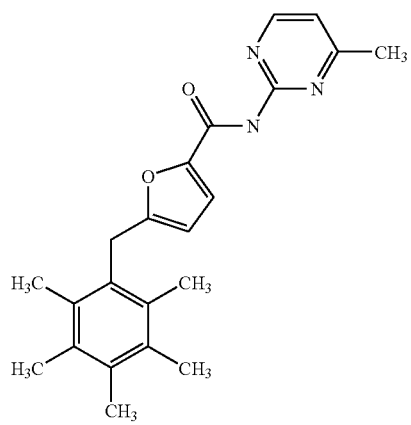

| MOLSTRUCTURE |
|---|
| 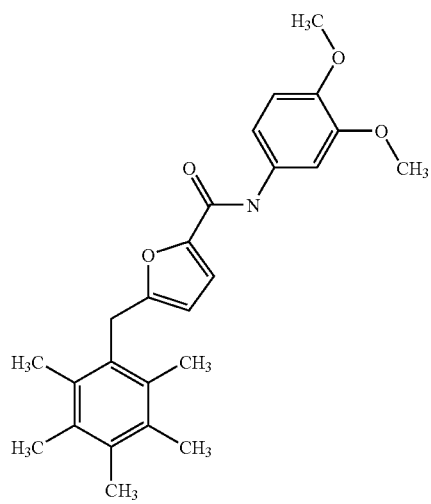 |
| 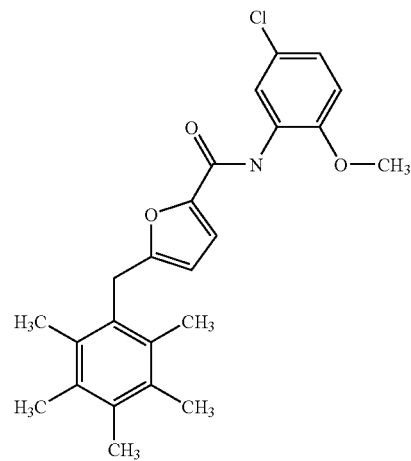 |
| 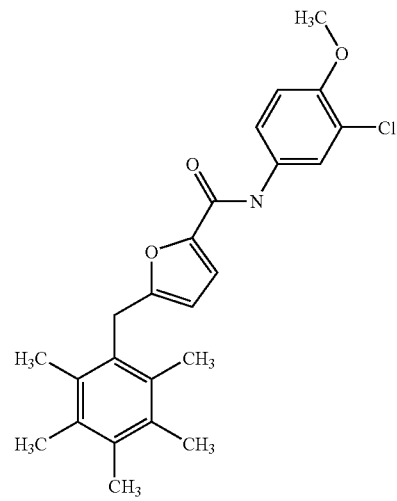 |

-continued
| MOLSTRUCTURE |
|---|
| 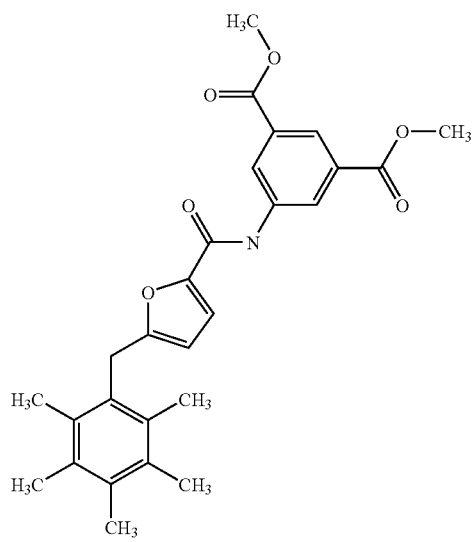 |
| 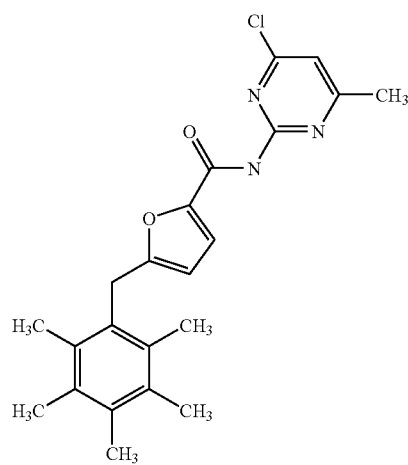 |
| 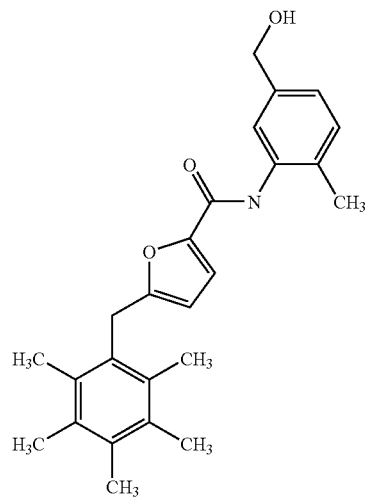 |

| MOLSTRUCTURE |
|---|
| 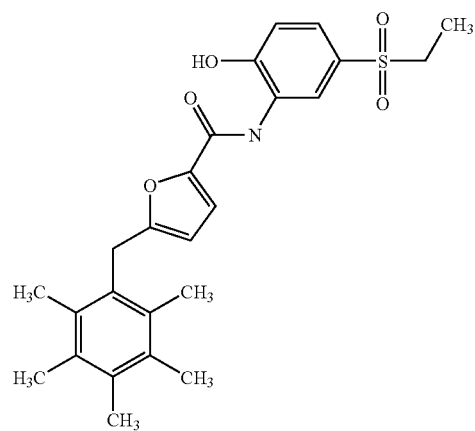 |
| 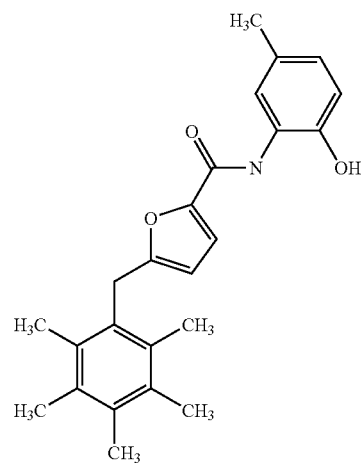 |
| 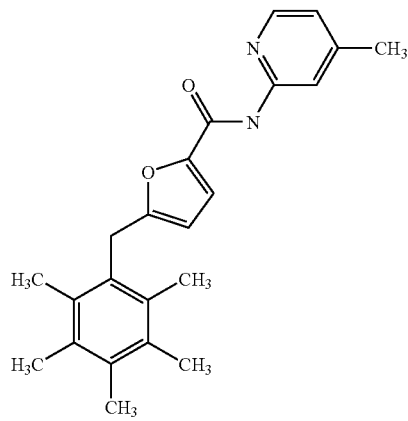 |

| MOLSTRUCTURE |
|---|
| 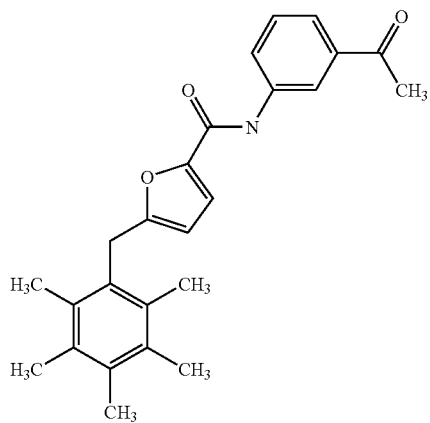 |
| 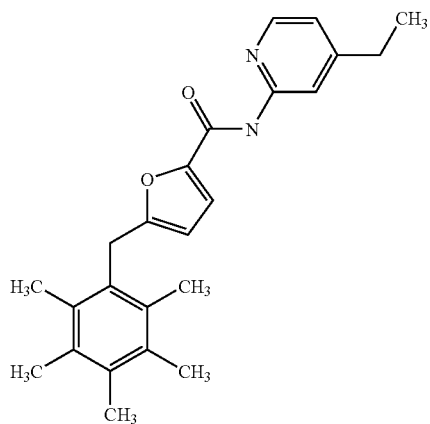 |
| 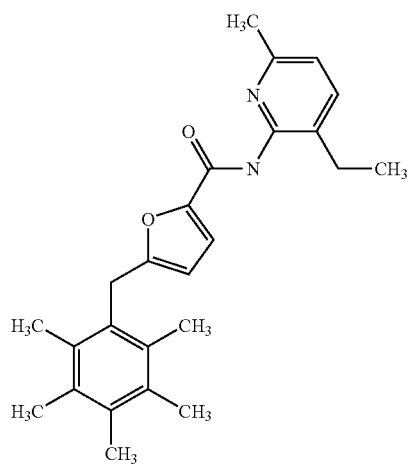 |

-continued
| MOLSTRUCTURE |
|---|
| 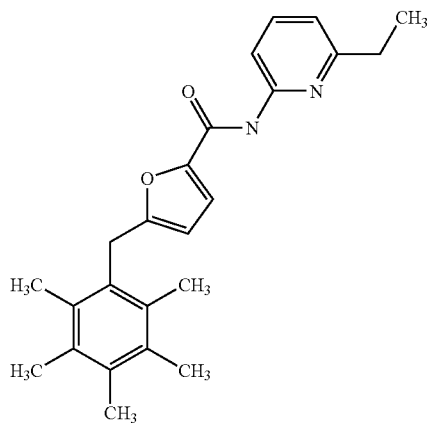 |
| 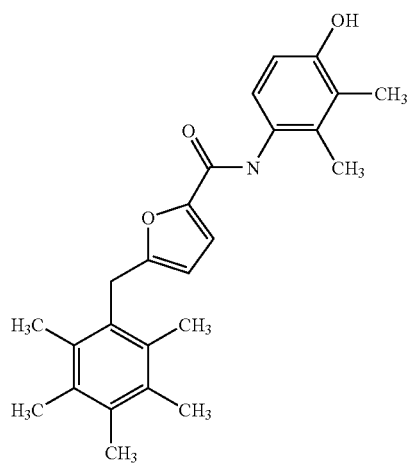 |
| 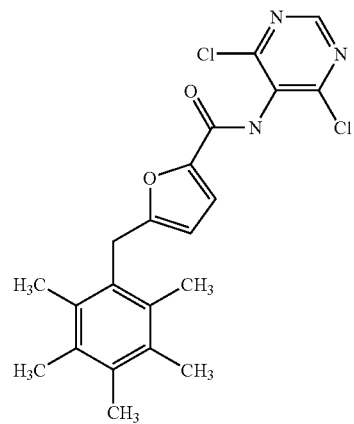 |

-continued
| MOLSTRUCTURE |
|---|
| 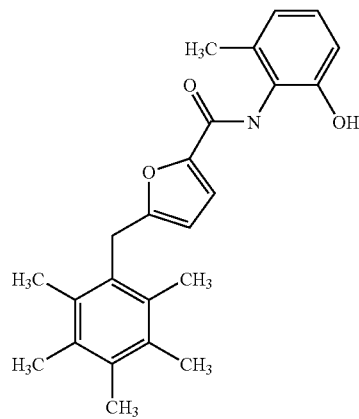 |
| 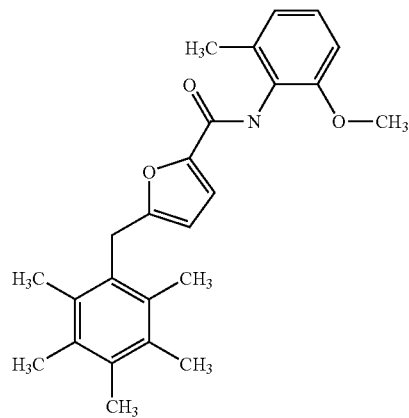 |
| 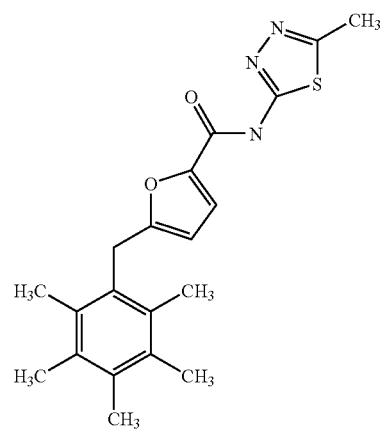 |

-continued
| MOLSTRUCTURE |
|---|
| 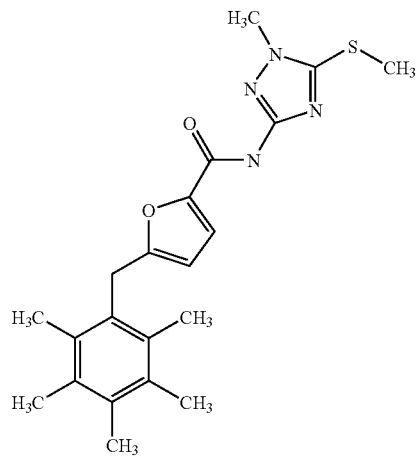 |
| 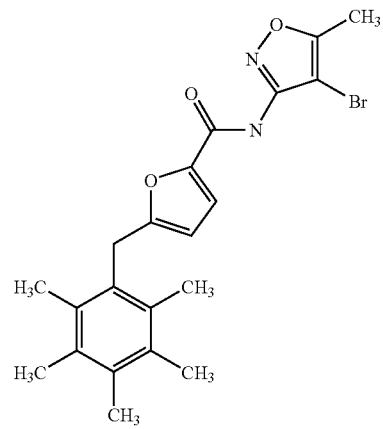 |
| 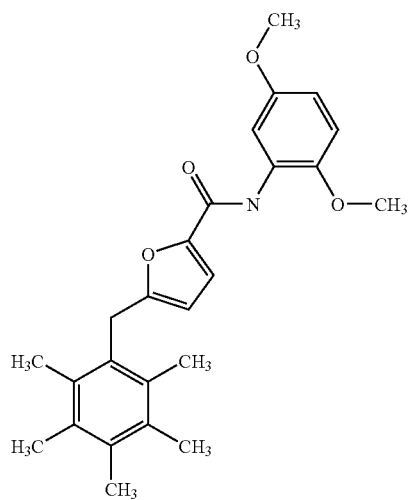 |

| MOLSTRUCTURE |
|---|
| 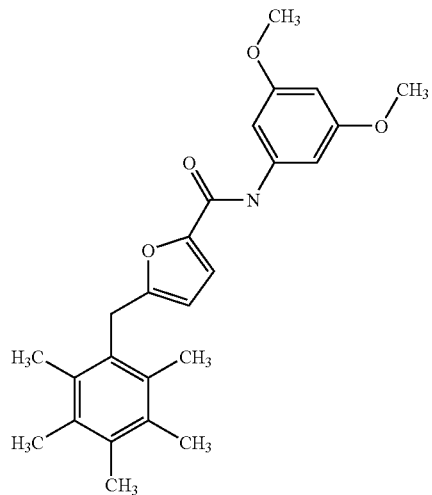 |
| 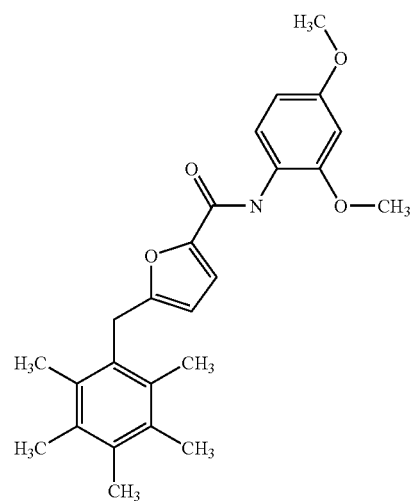 |
| 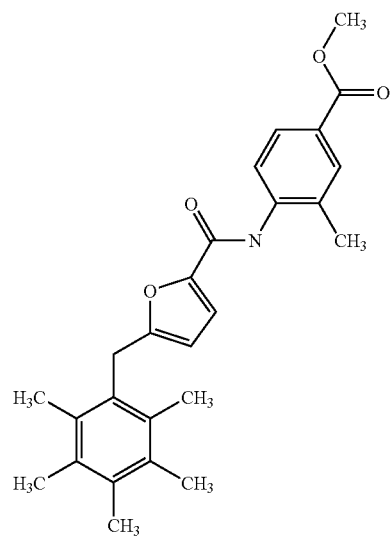 |

-continued
| MOLSTRUCTURE |
| --- |
| 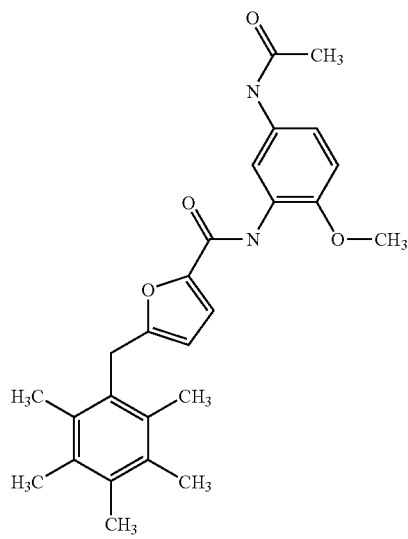 |
| 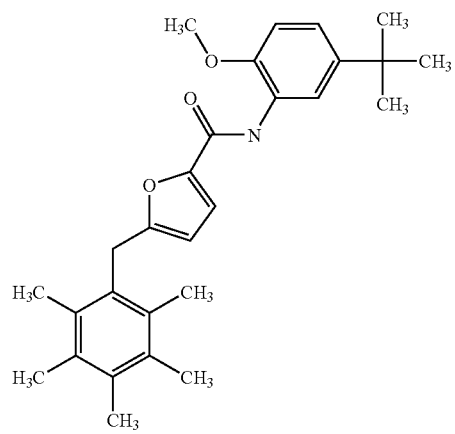 |
| 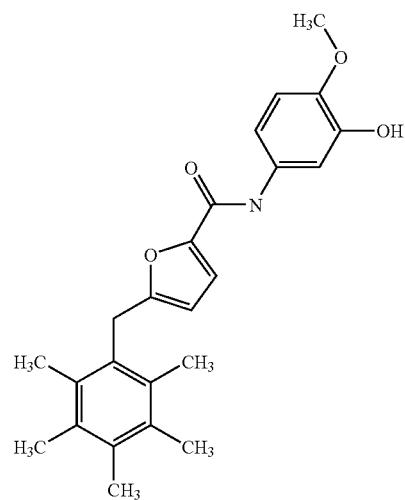 |

-continued
MOLSTRUCTURE
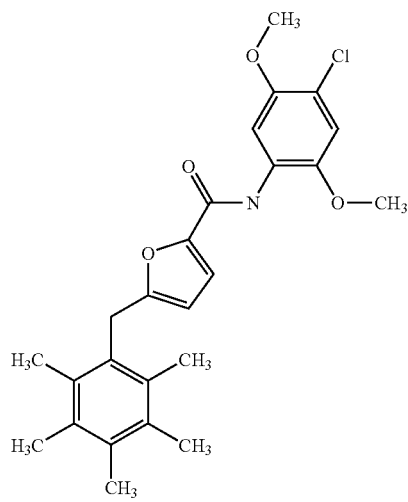
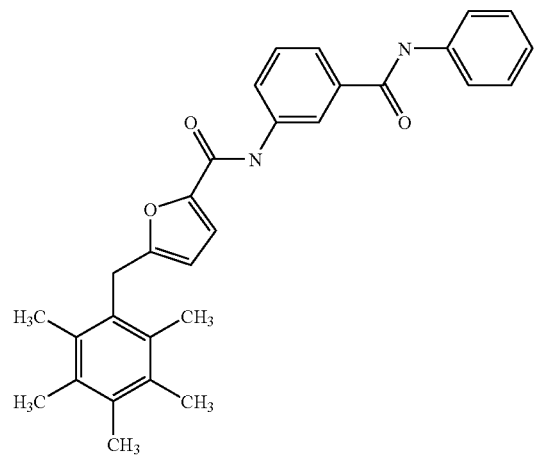
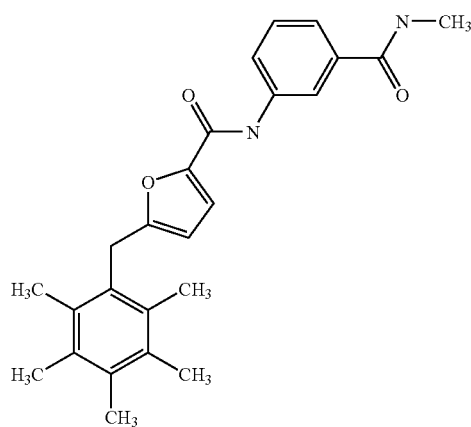

| MOLSTRUCTURE |
| --- |
| 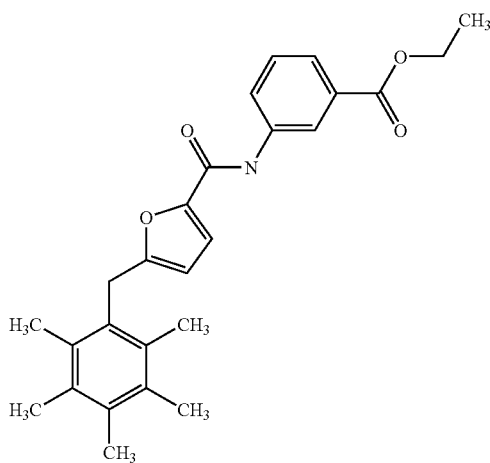 |
| 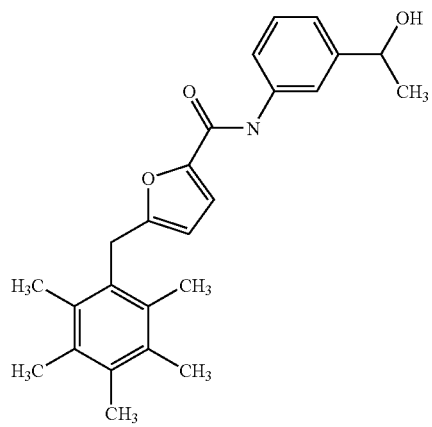 |
| 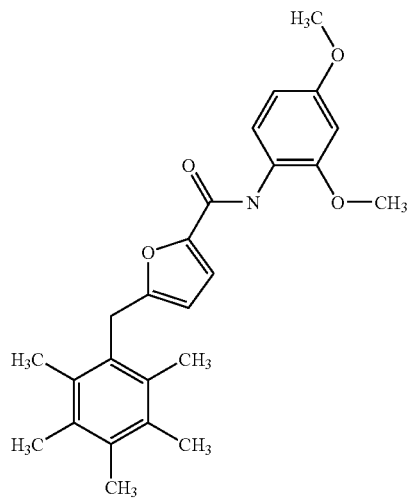 |

-continued
MOLSTRUCTURE
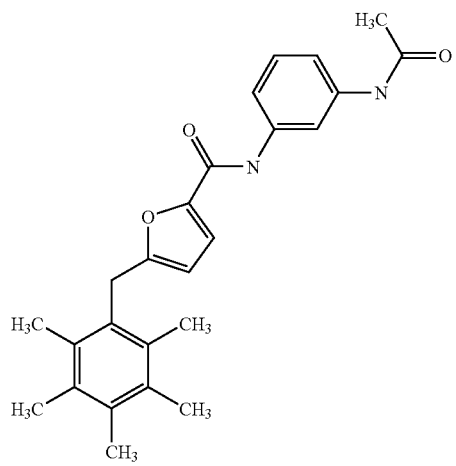
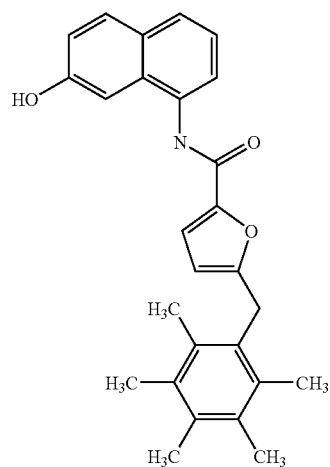
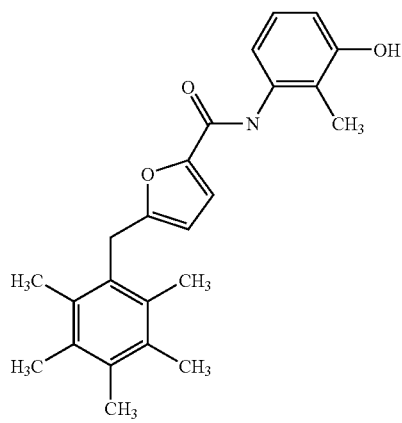

-continued
| MOLSTRUCTURE |
|---|
| 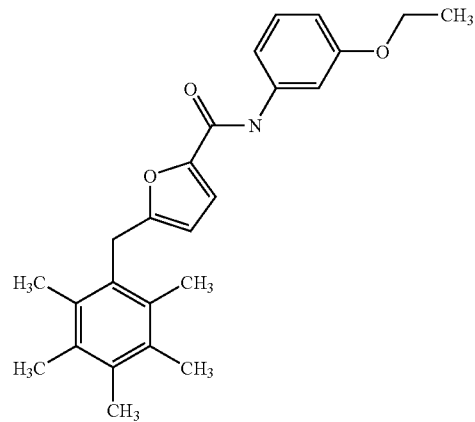 |
| 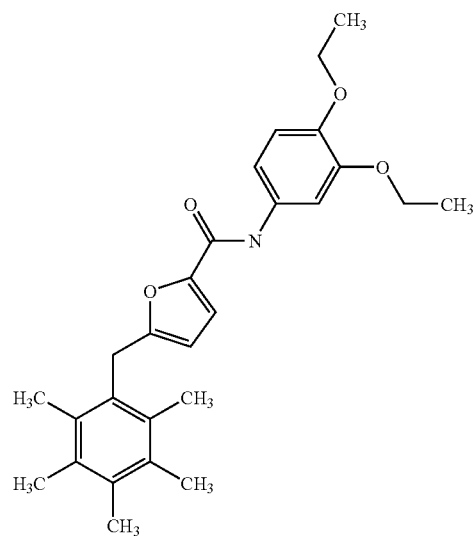 |
| 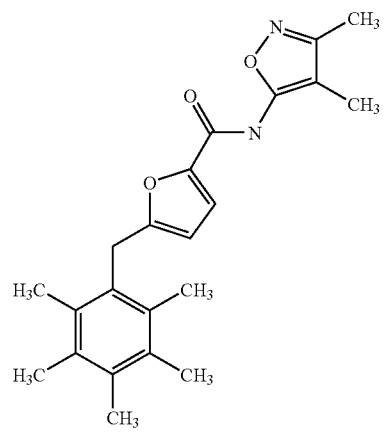 |

| MOLSTRUCTURE |
|---|
| 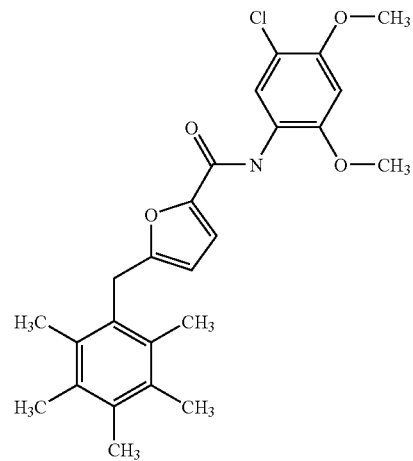 |
| 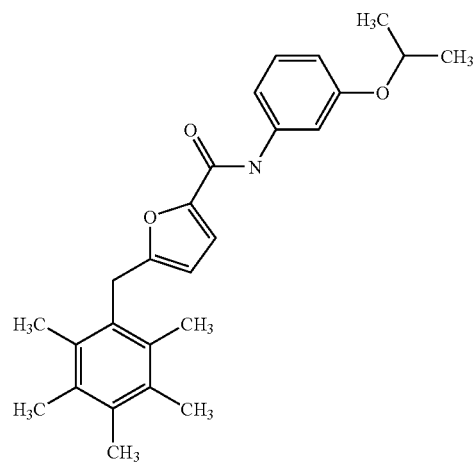 |
| 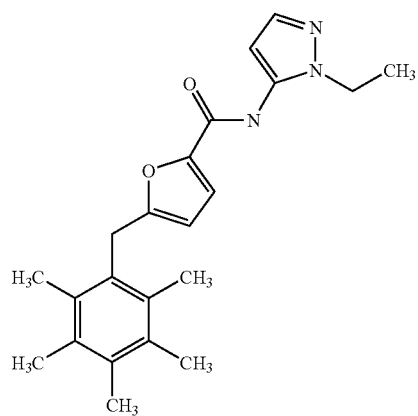 |

-continued
| MOLSTRUCTURE |
|---|
| 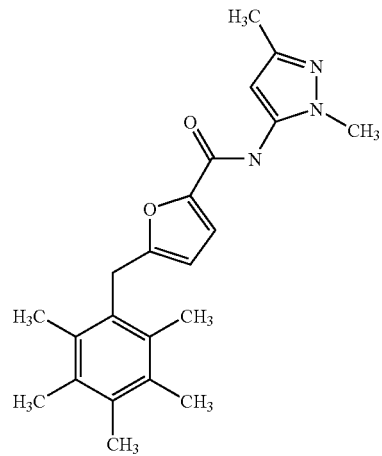 |
| 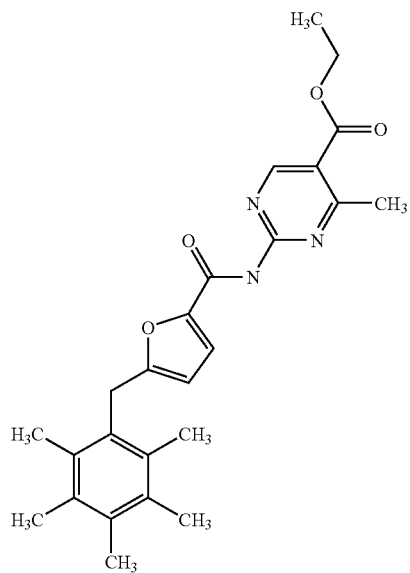 |
| 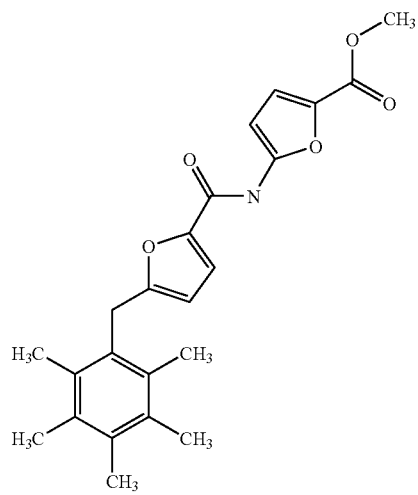 |

| MOLSTRUCTURE |
|---|
| 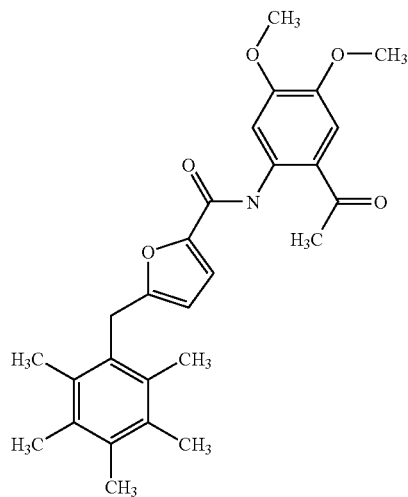 |
| 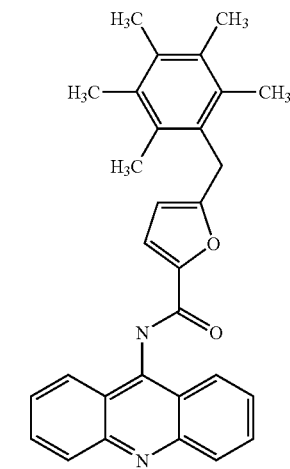 |
| 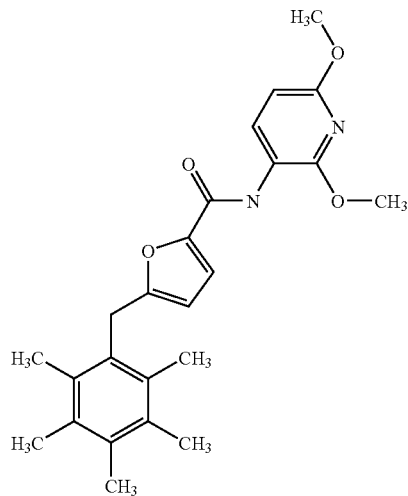 |

| MOLSTRUCTURE |
|---|
| 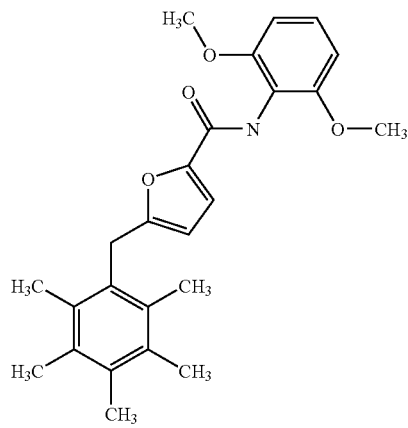 |
| 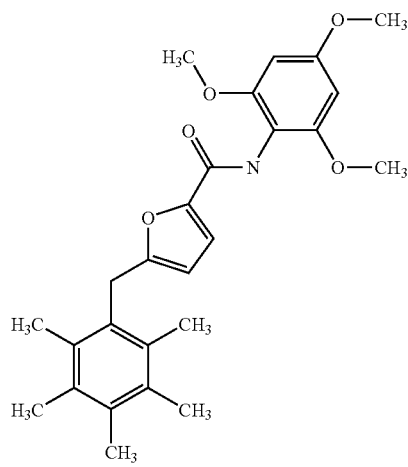 |
| 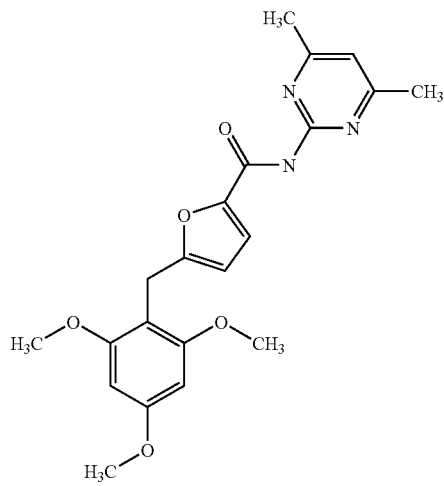 |

| MOLSTRUCTURE |
|---|
| 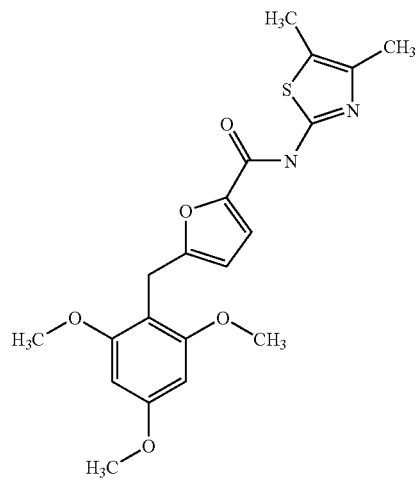 |
| 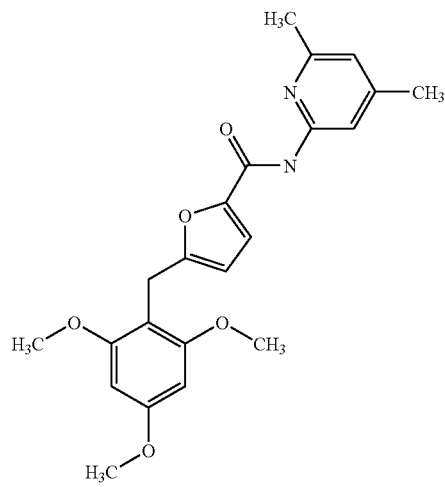 |
| 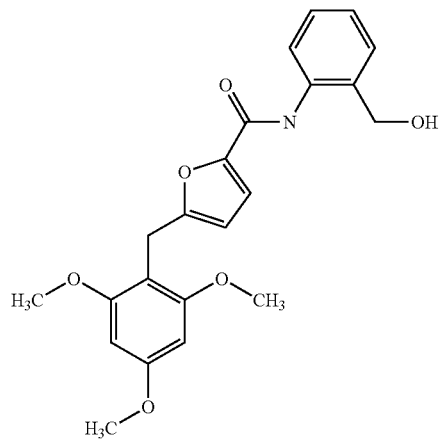 |

-continued
| MOLSTRUCTURE |
| --- |
| 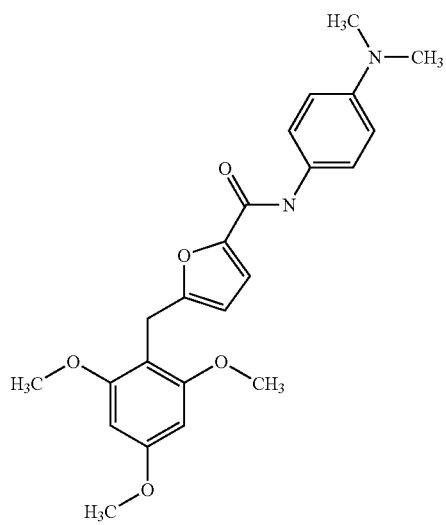 |
| 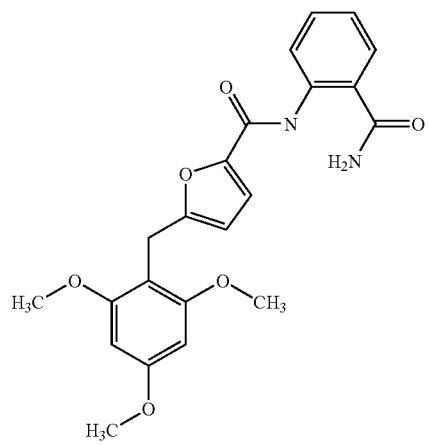 |
| 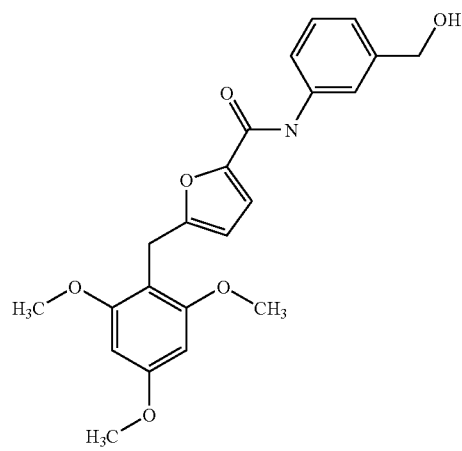 |

-continued
| MOLSTRUCTURE |
|---|
| 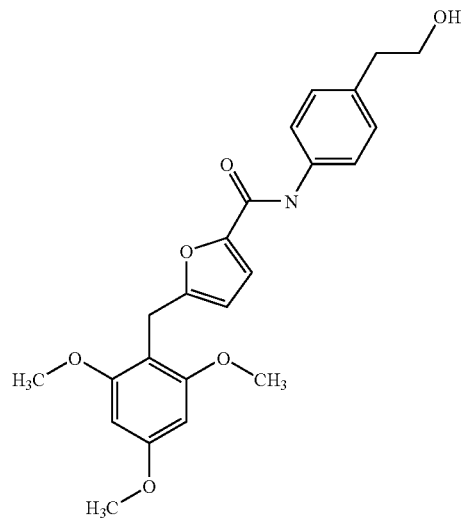 |
| 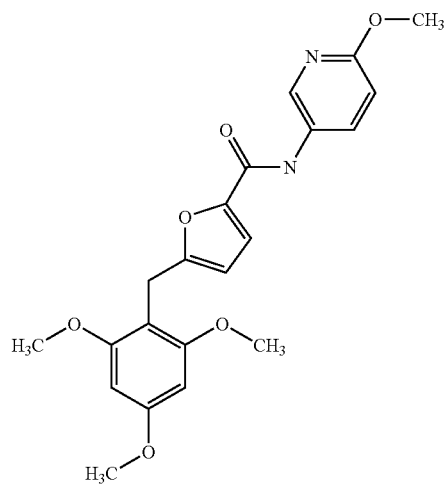 |
| 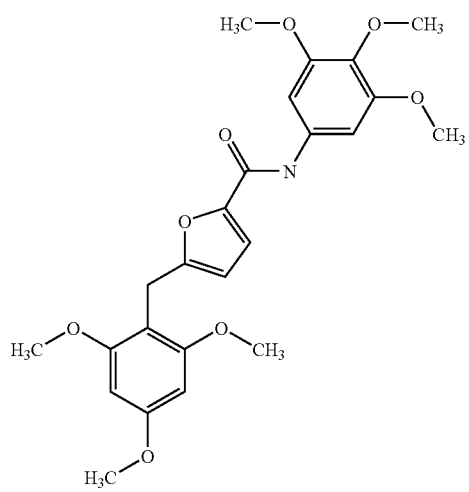 |

| MOLSTRUCTURE |
|---|
| 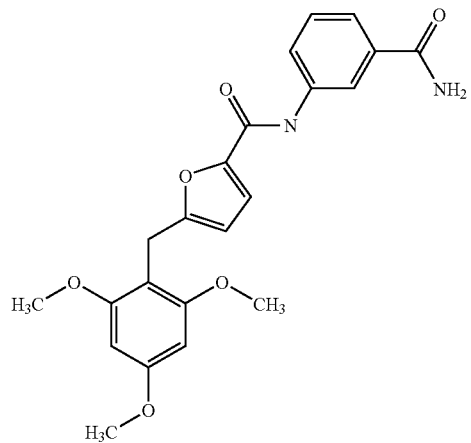 |
| 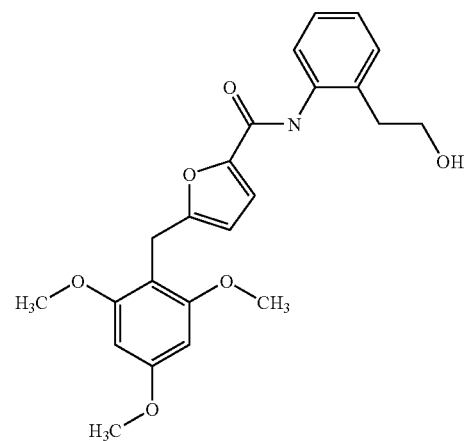 |
| 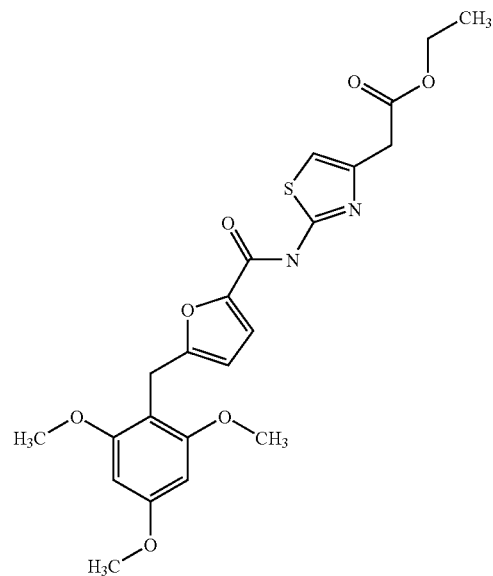 |

| MOLSTRUCTURE |
|---|
| 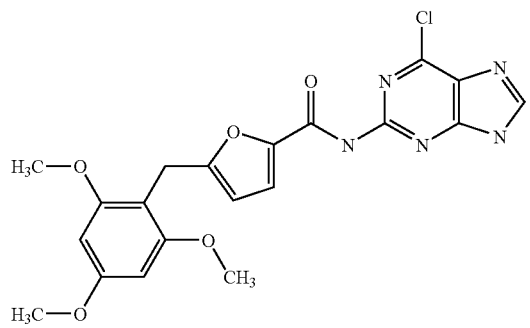 |
| 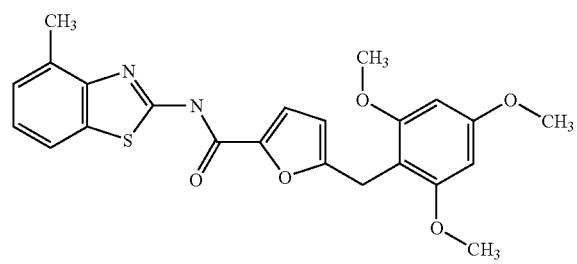 |
| 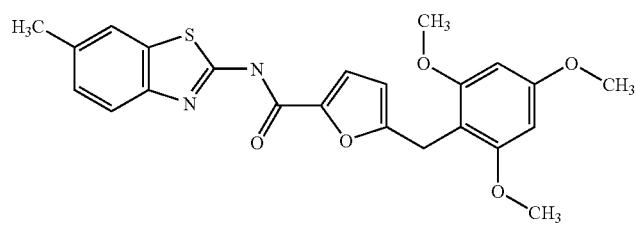 |
| 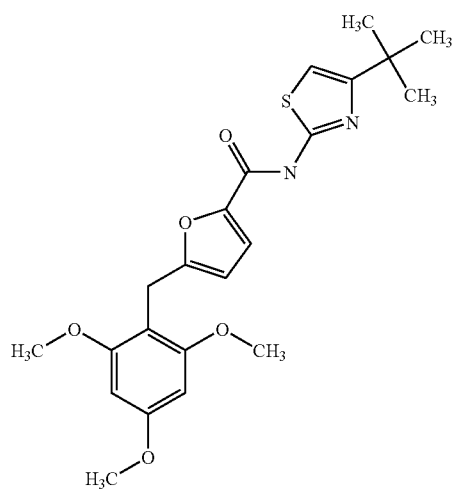 |

-continued
| MOLSTRUCTURE |
|---|
| 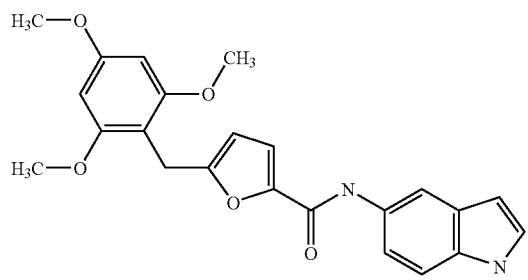 |
| 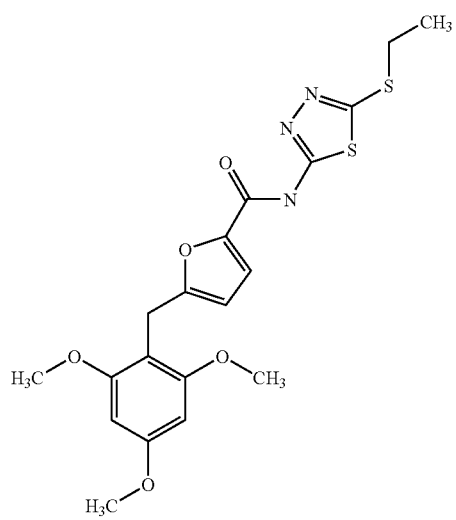 |
| 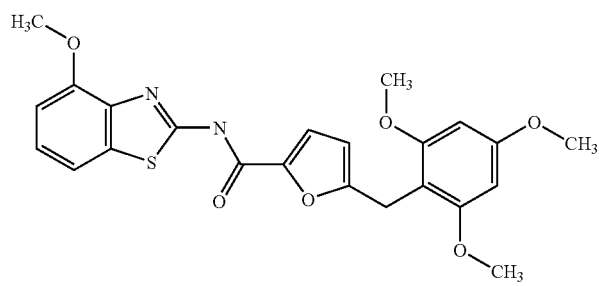 |
| 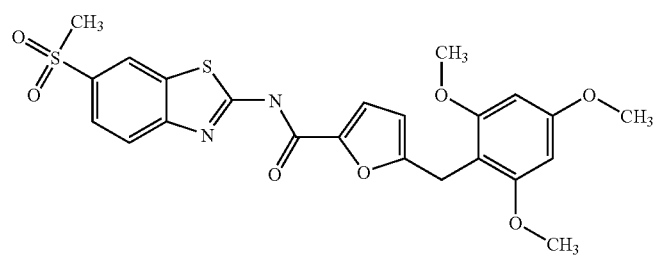 |

-continued
| MOLSTRUCTURE |
|---|
| 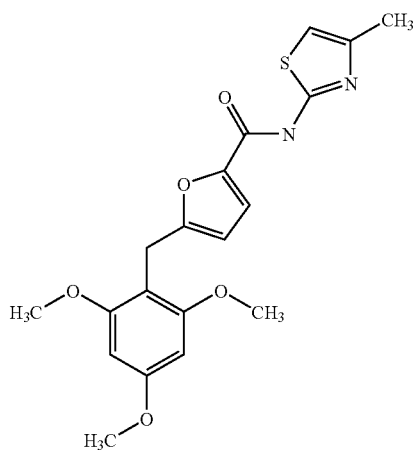 |
| 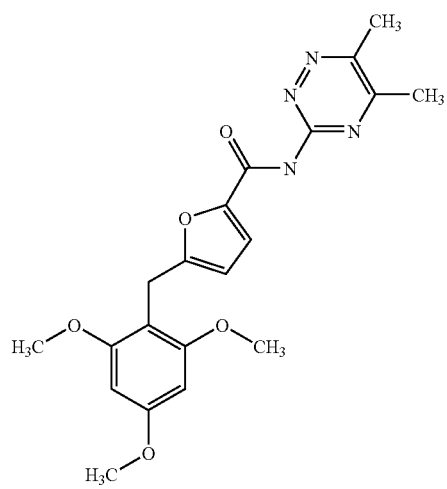 |
| 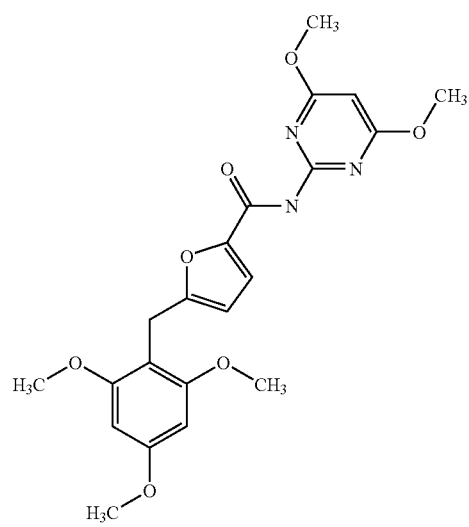 |

| MOLSTRUCTURE |
| --- |
| 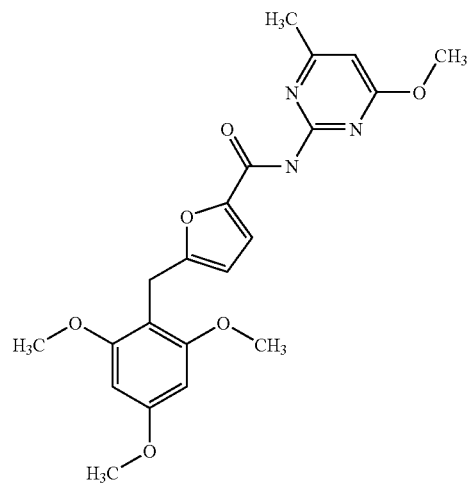 |
| 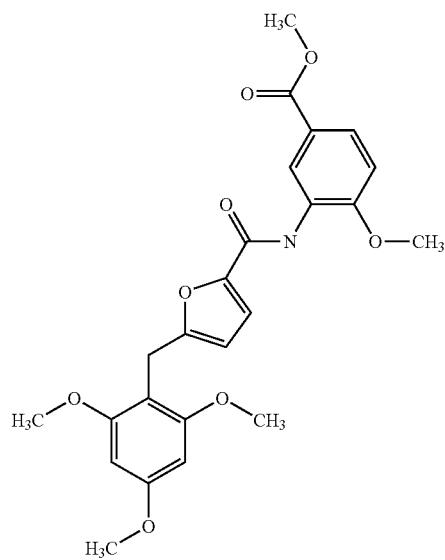 |
| 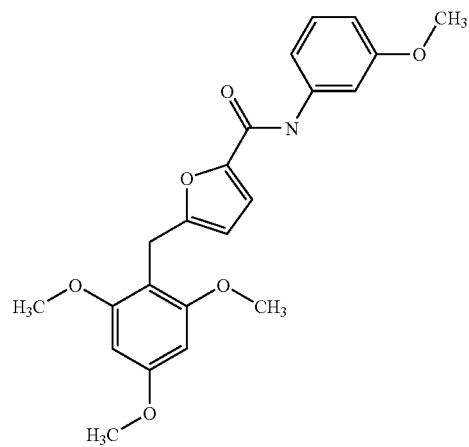 |

-continued
| MOLSTRUCTURE |
|---|
| 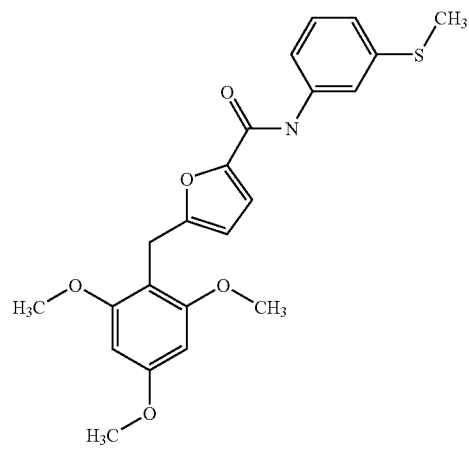 |
| 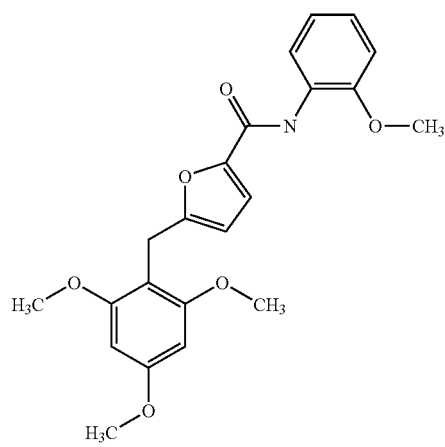 |
| 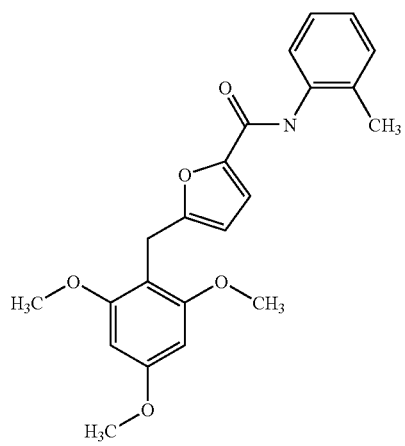 |

| MOLSTRUCTURE |
|---|
| 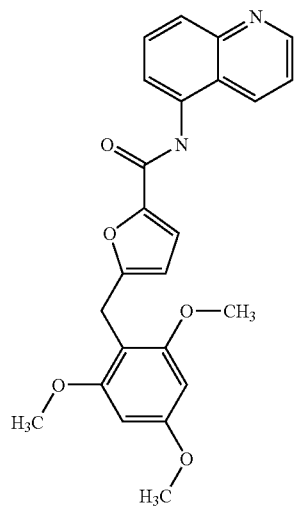 |
| 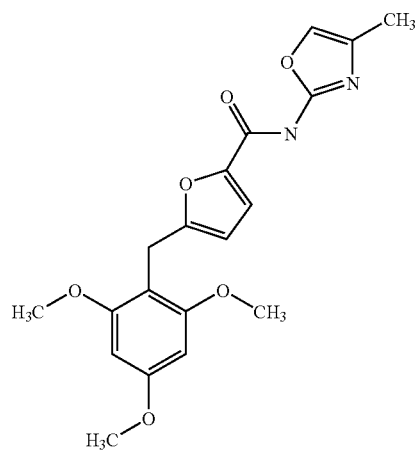 |
| 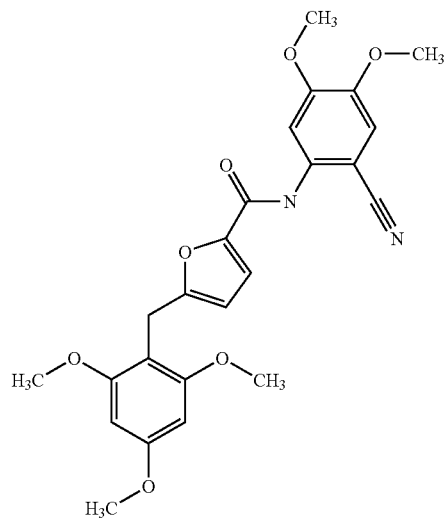 |

-continued
| MOLSTRUCTURE |
| --- |
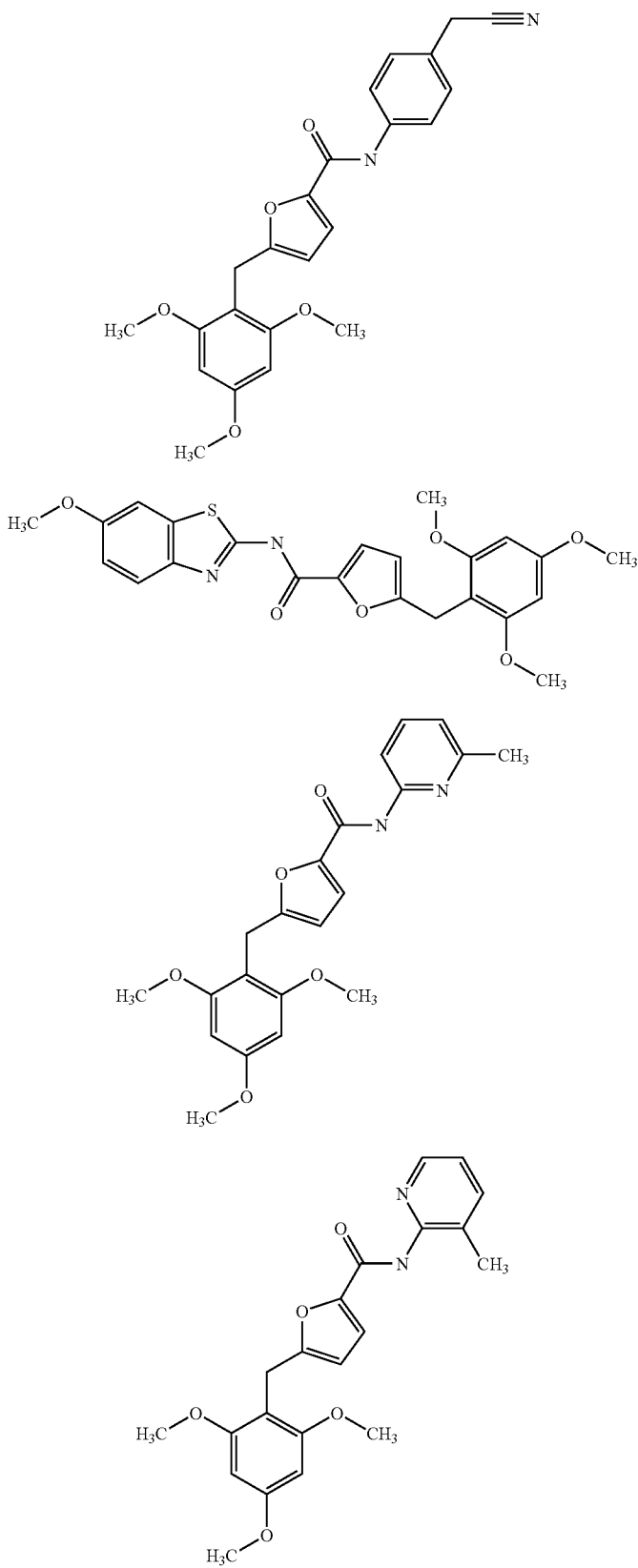

-continued
MOLSTRUCTURE
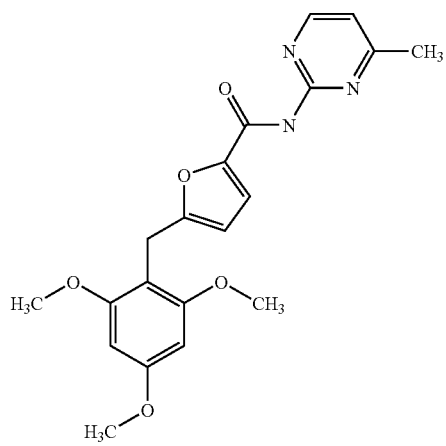
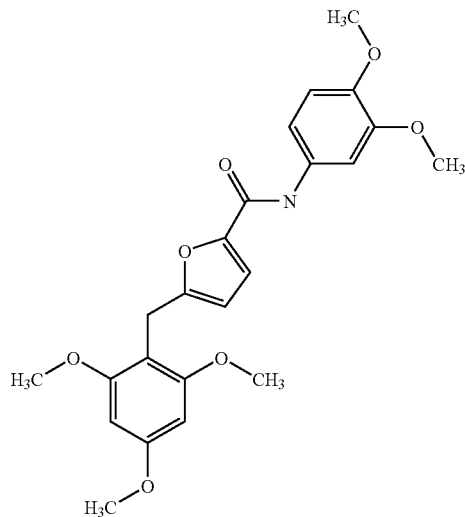
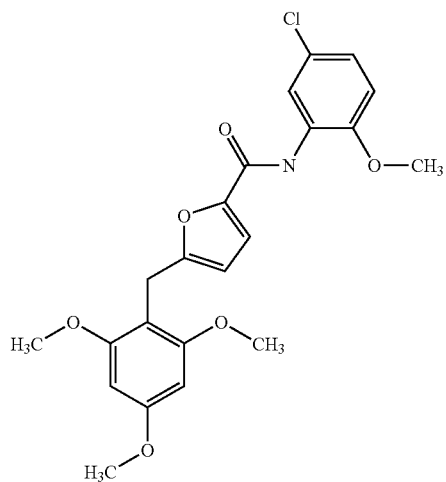

-continued
MOLSTRUCTURE
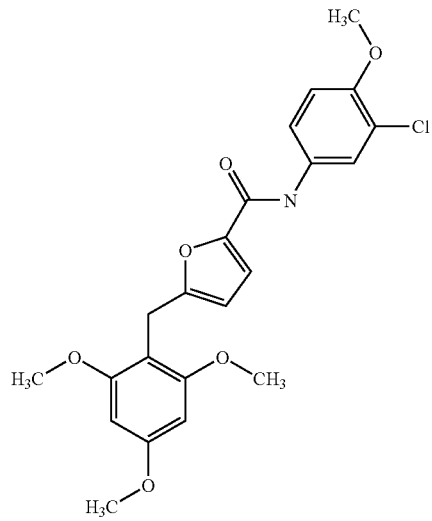
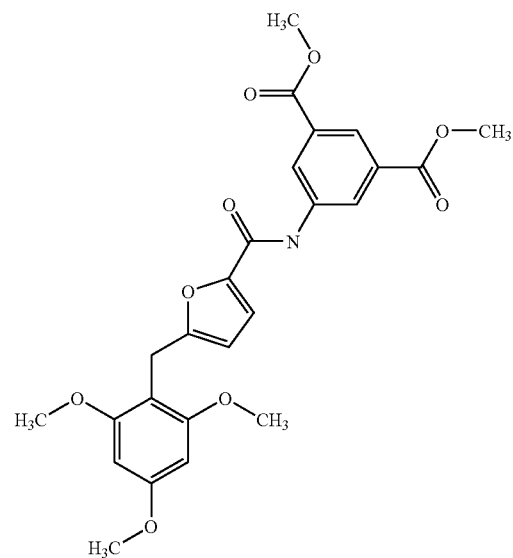
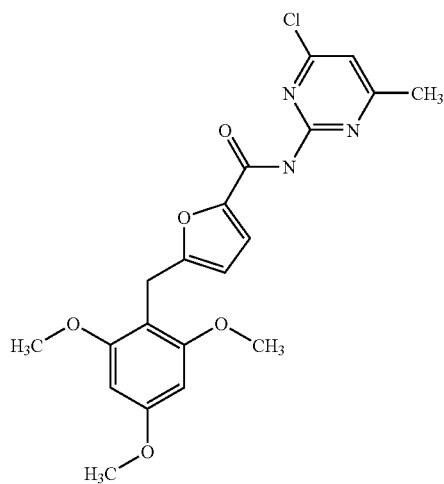

| MOLSTRUCTURE |
| --- |
| 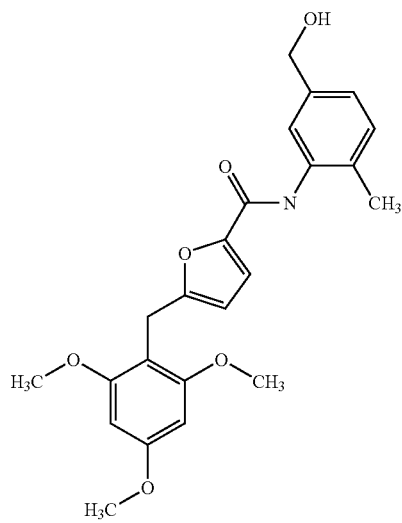 |
| 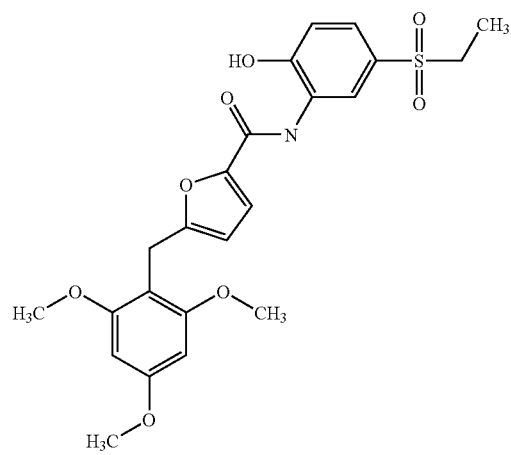 |
| 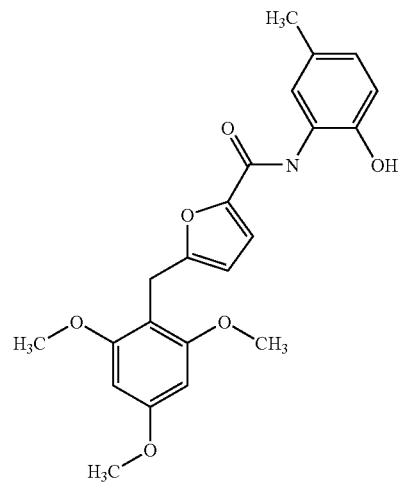 |

| MOLSTRUCTURE |
|---|
| 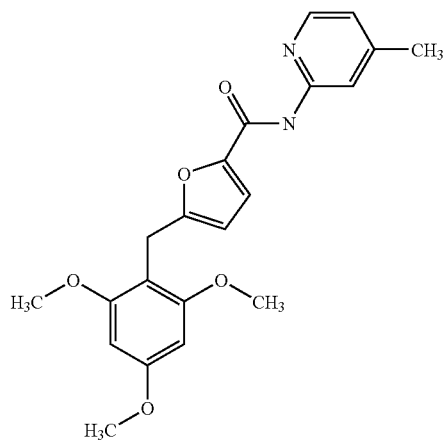 |
| 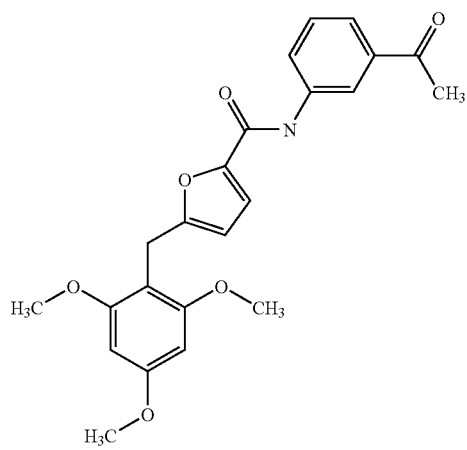 |
| 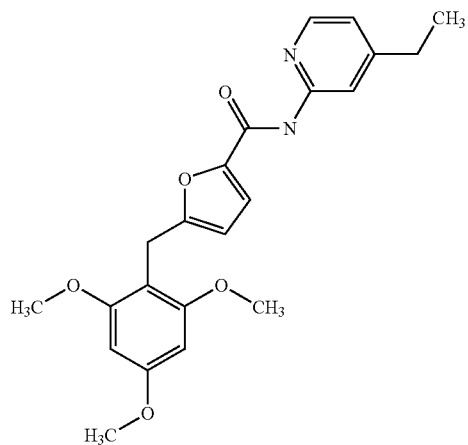 |

| MOLSTRUCTURE |
|---|
| 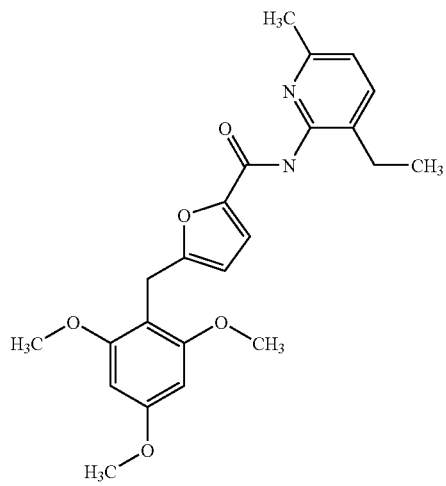 |
| 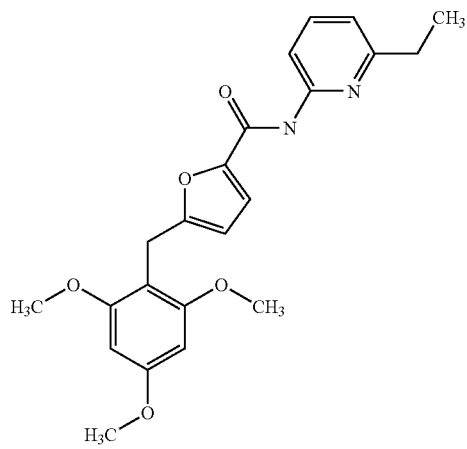 |
| 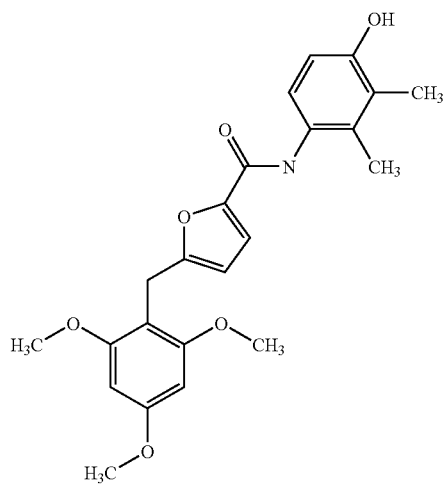 |

-continued
MOLSTRUCTURE
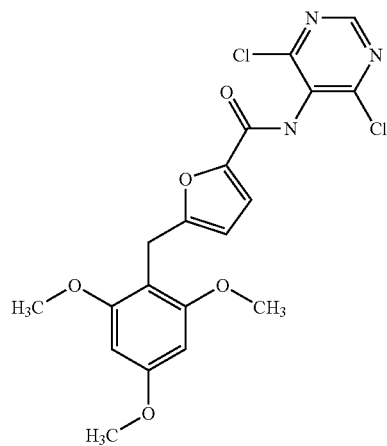
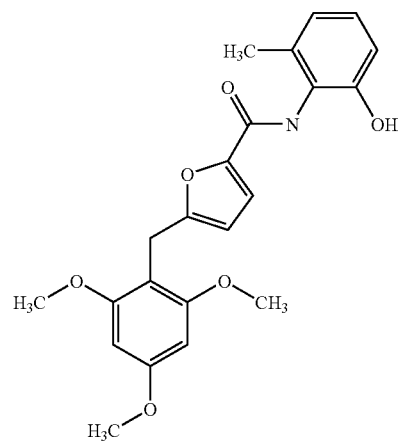
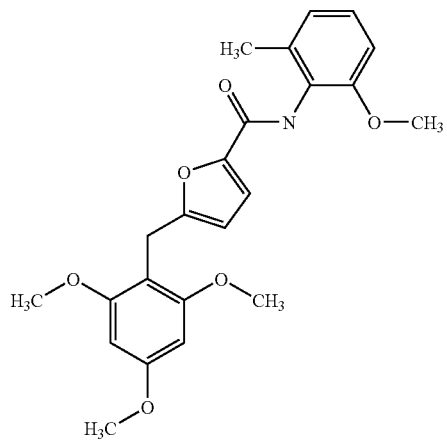

| MOLSTRUCTURE |
| --- |
| 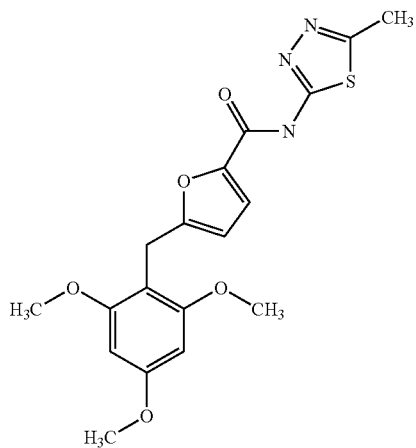 |
| 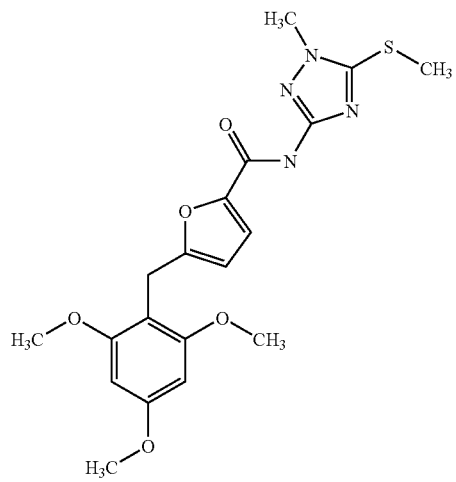 |
| 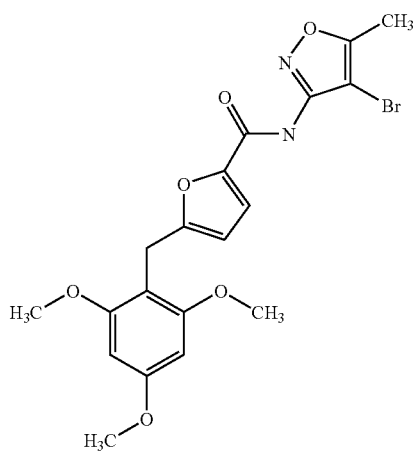 |

-continued
MOLSTRUCTURE
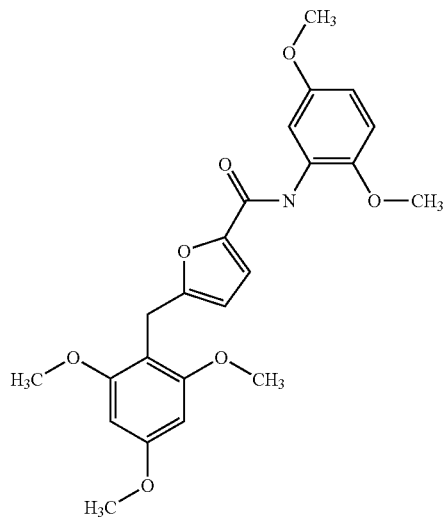
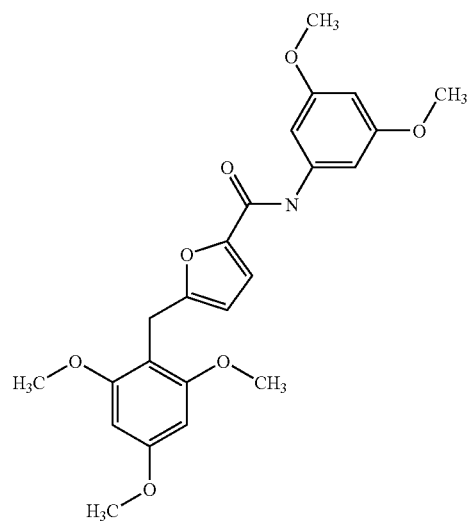
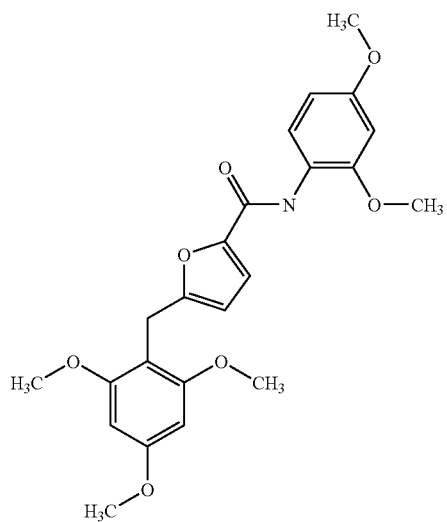

-continued
MOLSTRUCTURE
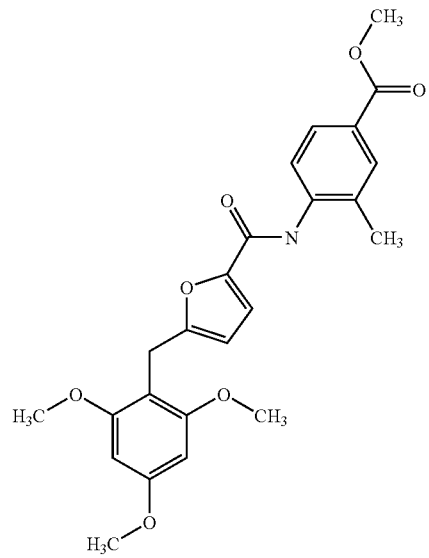
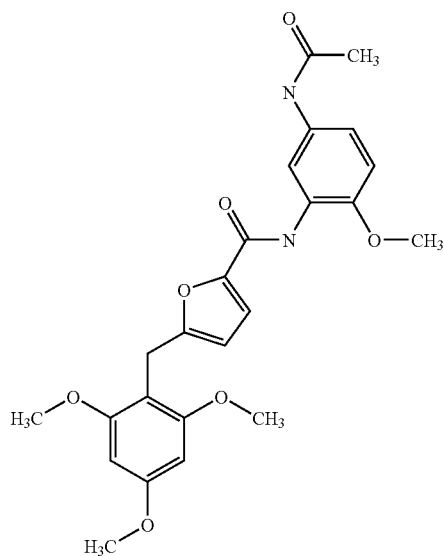
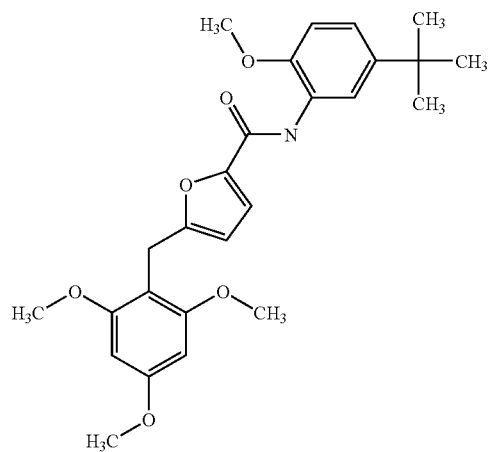

-continued
MOLSTRUCTURE
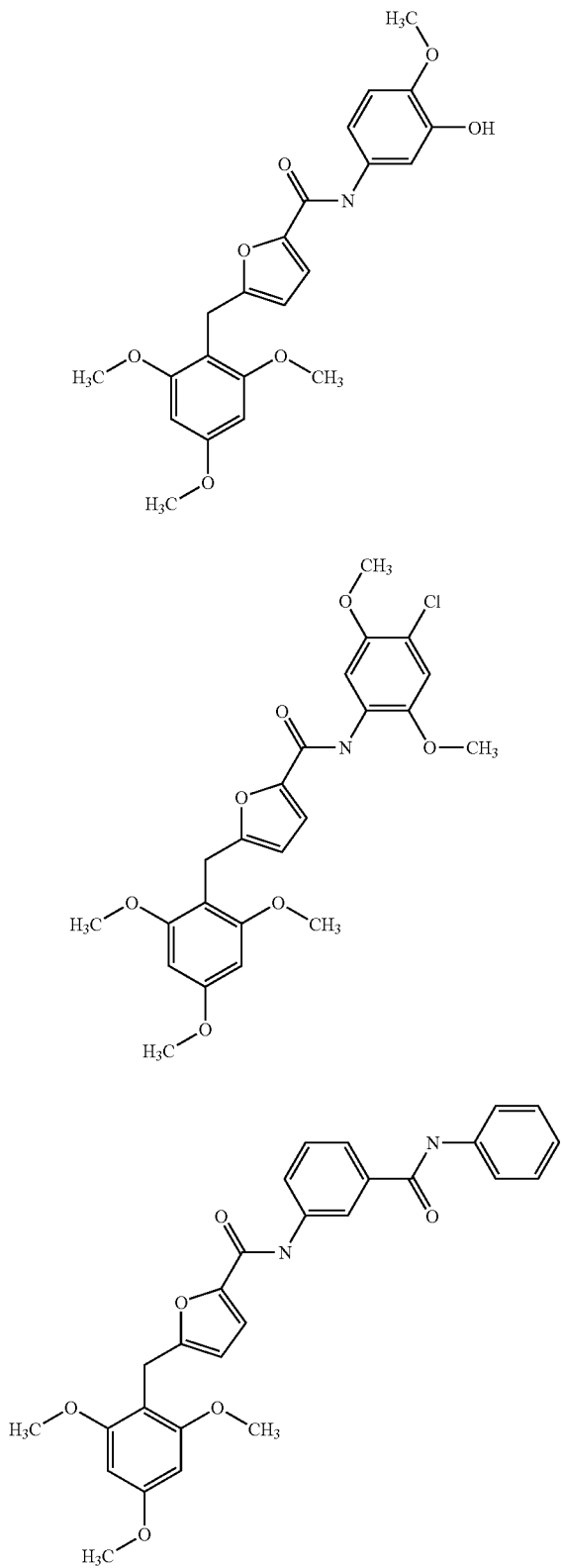

-continued
MOLSTRUCTURE
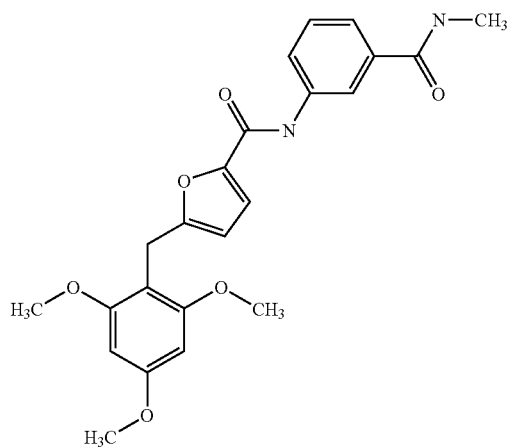
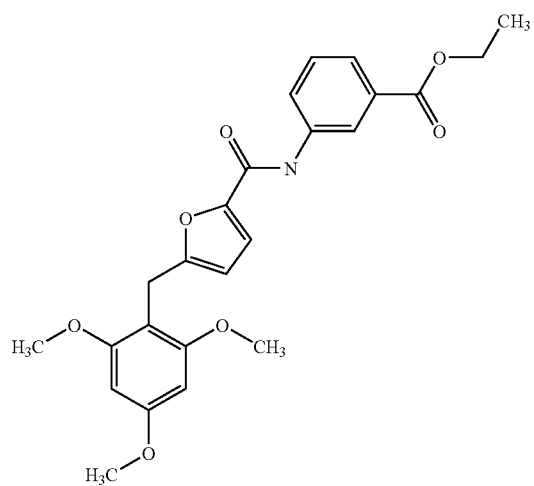
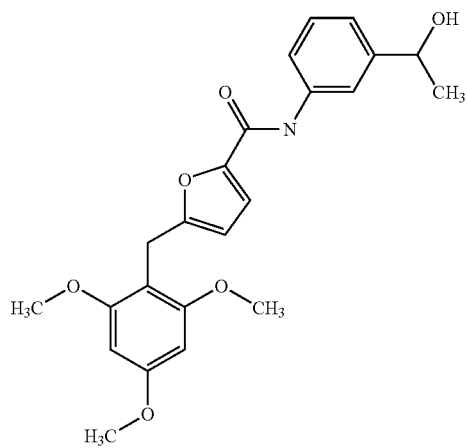

| MOLSTRUCTURE |
|---|
| 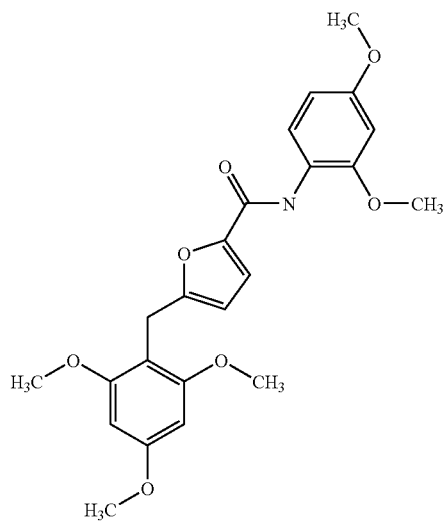 |
| 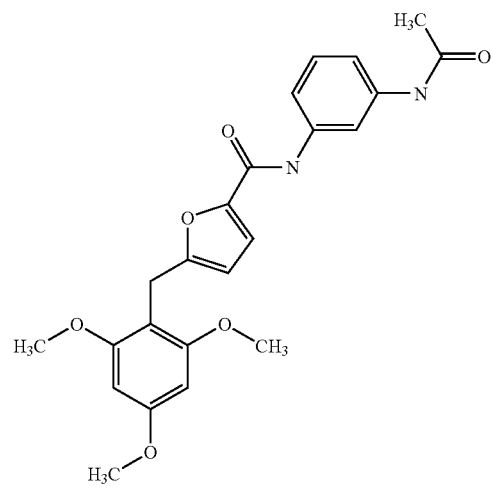 |
| 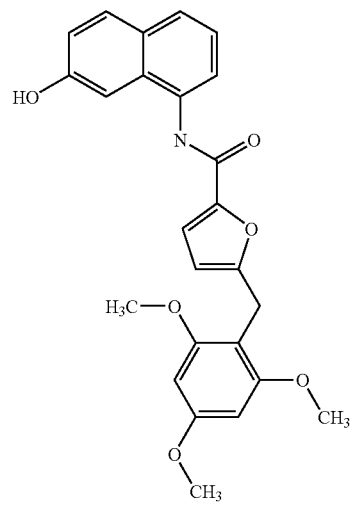 |

| MOLSTRUCTURE |
| --- |
| 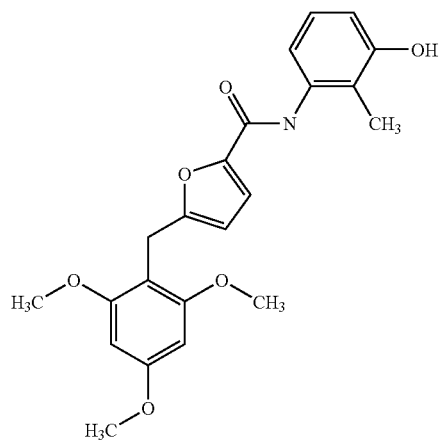 |
| 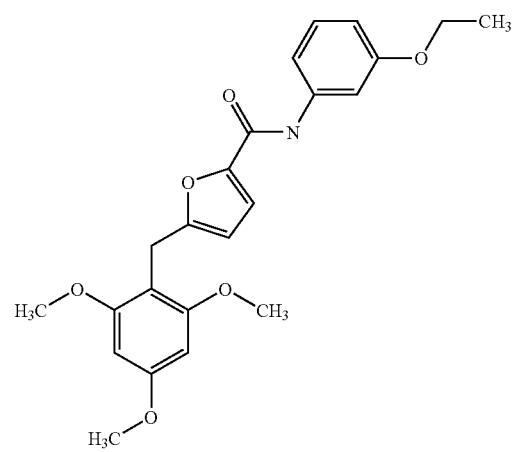 |
| 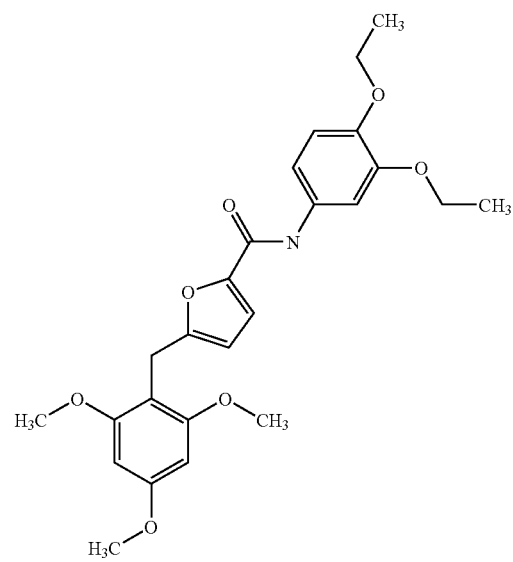 |

| MOLSTRUCTURE |
|---|
| 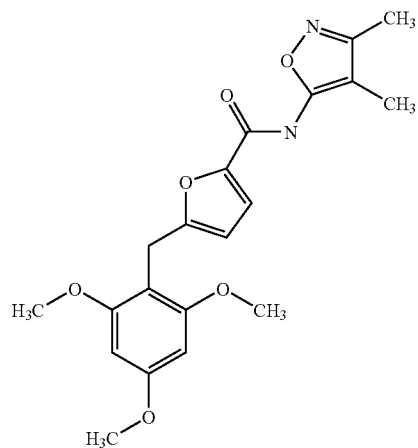 |
| 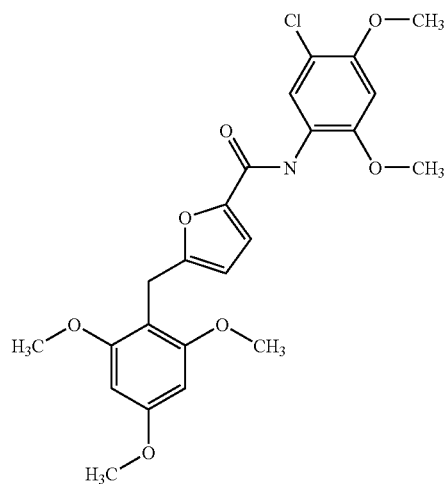 |
| 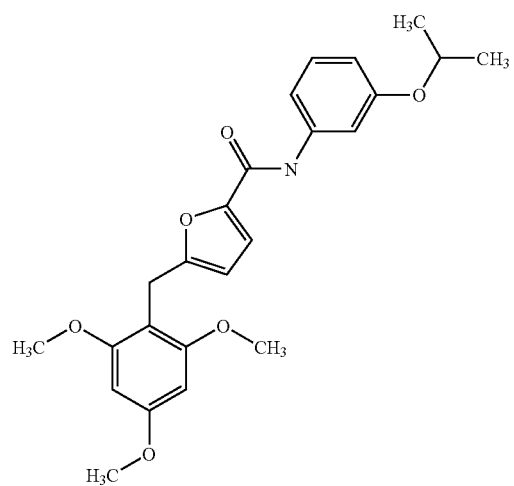 |

| MOLSTRUCTURE |
|---|
| 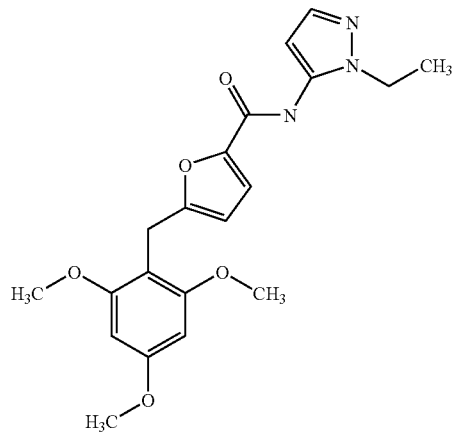 |
| 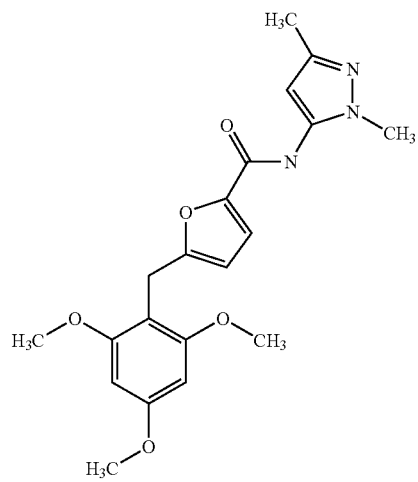 |
| 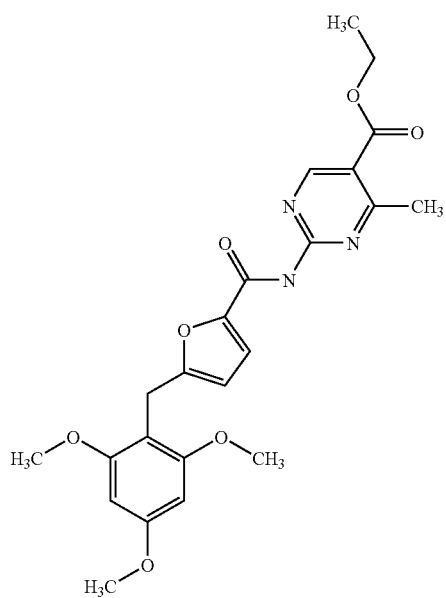 |

-continued
MOLSTRUCTURE
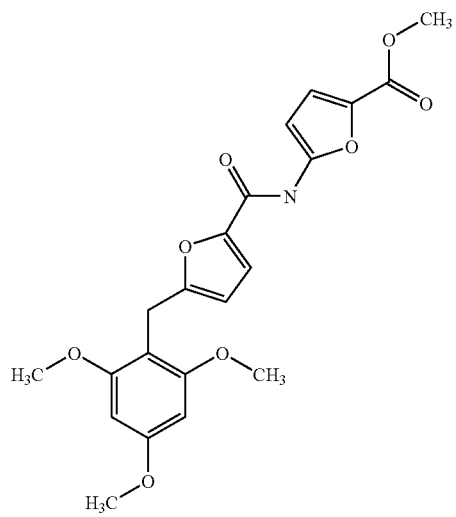
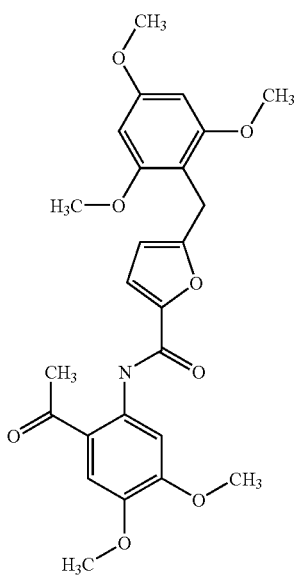
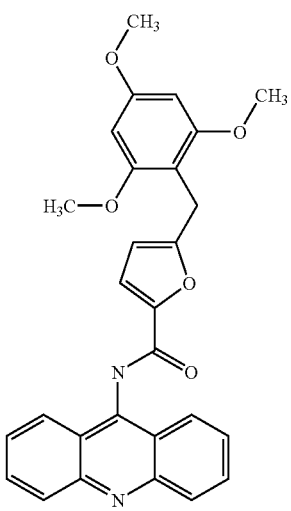

| MOLSTRUCTURE |
| --- |
| 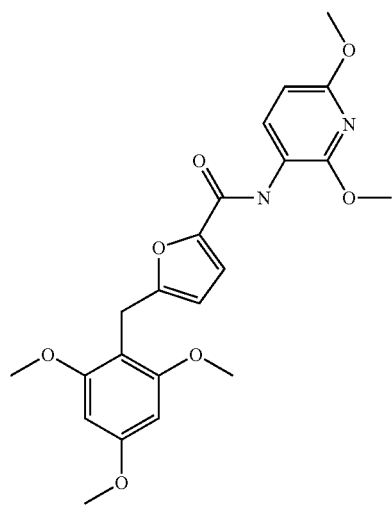 |
| 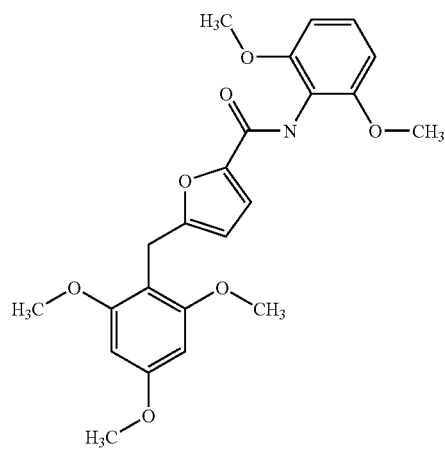 |
| 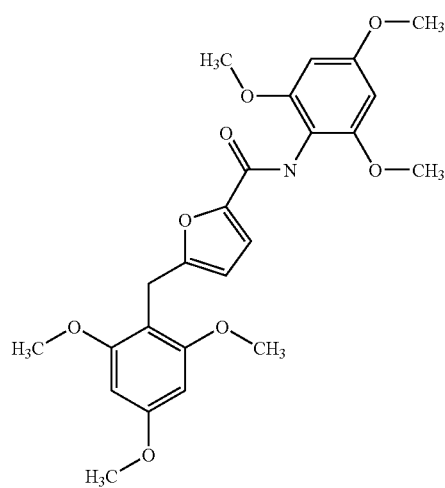 |

| MOLSTRUCTURE |
|---|
| 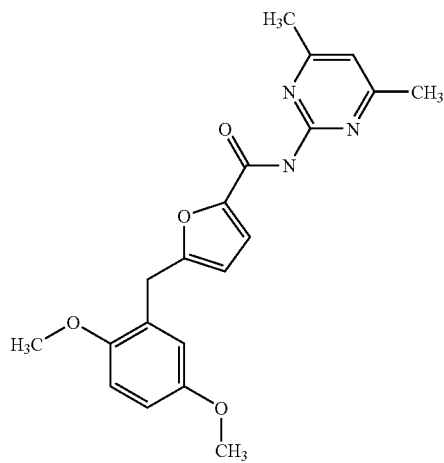 |
| 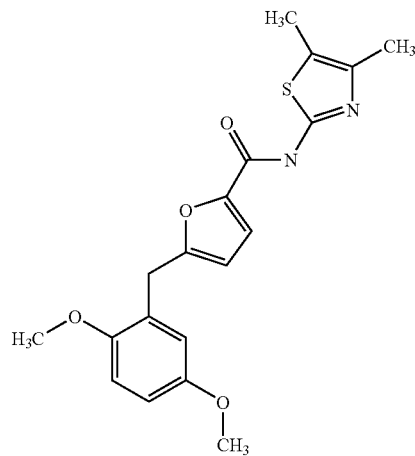 |
| 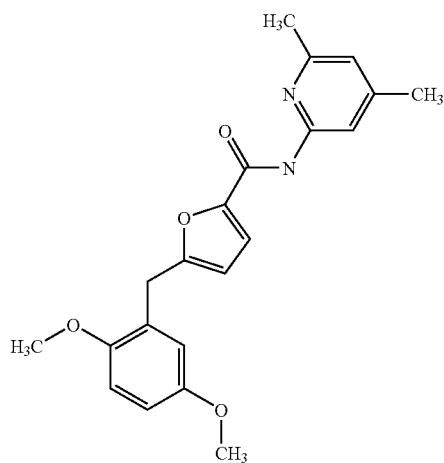 |

| MOLSTRUCTURE |
|---|
| 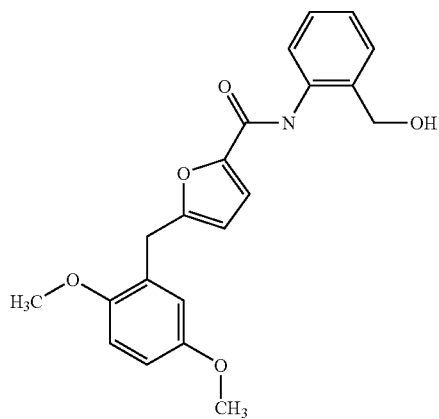 |
| 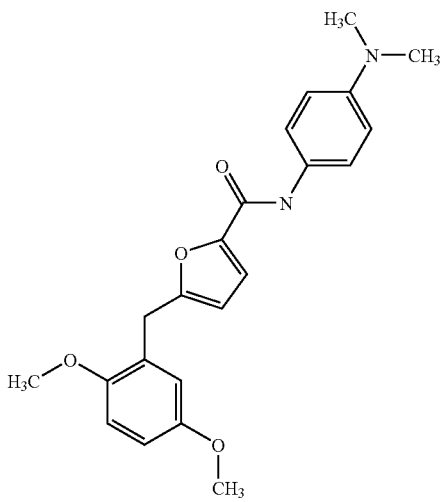 |
| 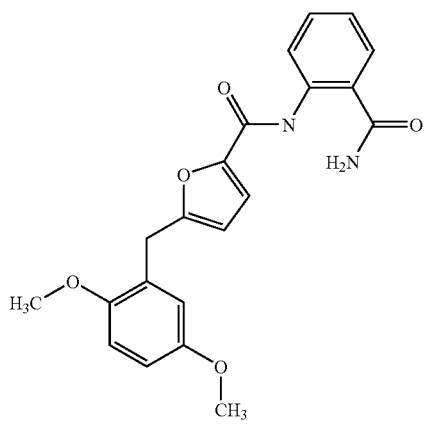 |

| MOLSTRUCTURE |
|---|
| 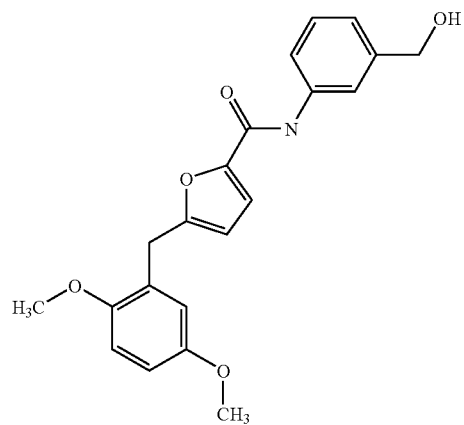 |
| 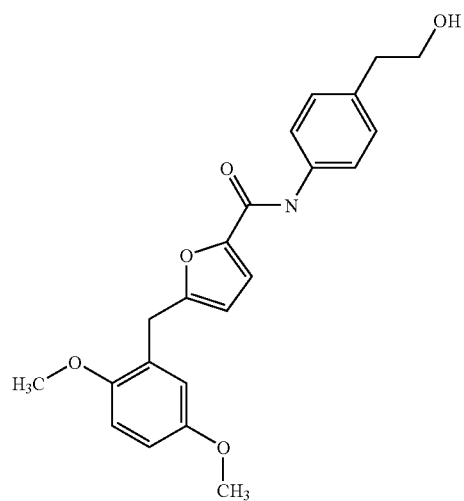 |
| 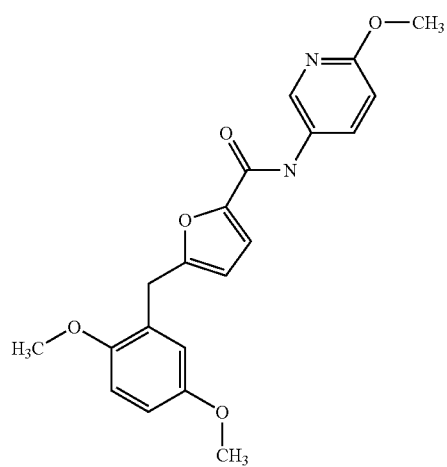 |

-continued
| MOLSTRUCTURE |
| --- |
| 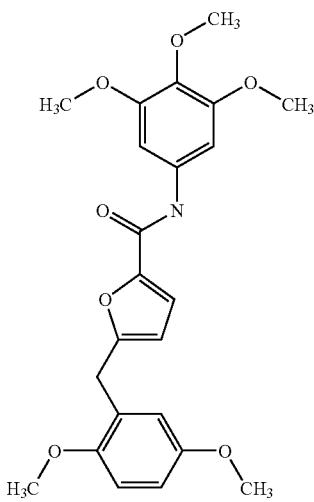 |
| 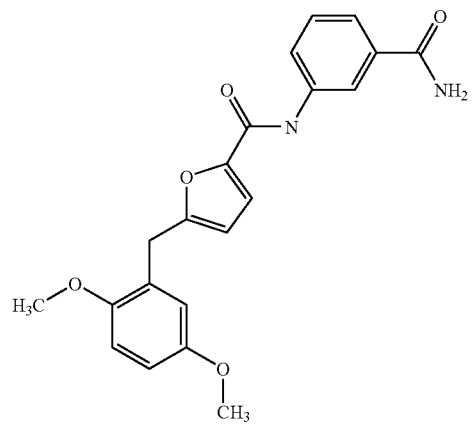 |
| 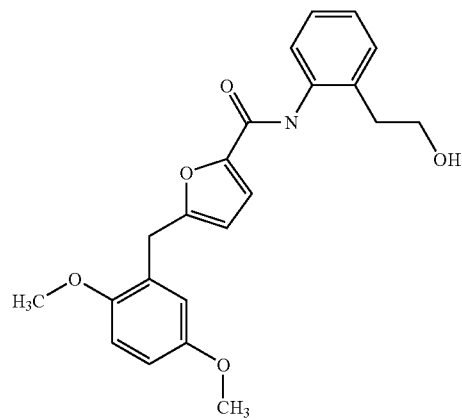 |

MOLSTRUCTURE
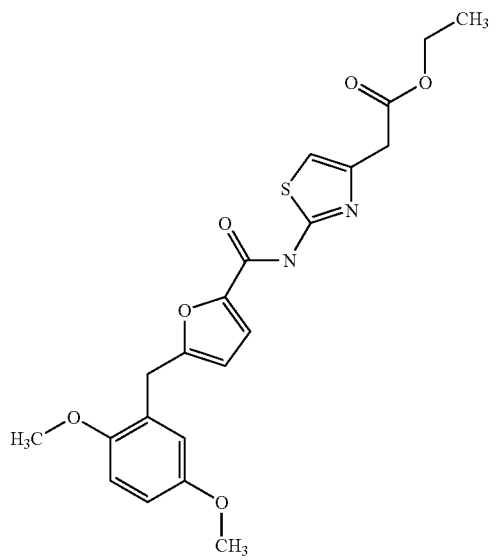
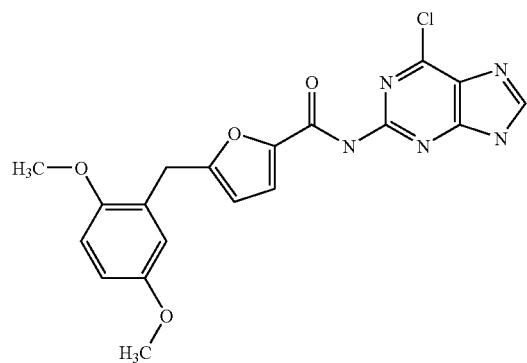
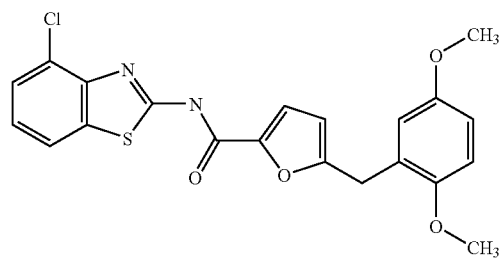
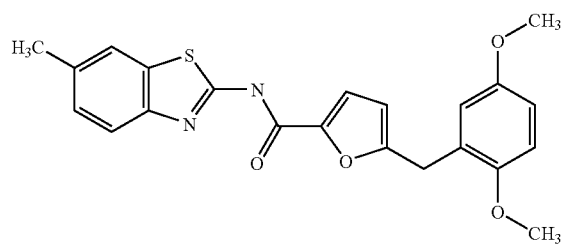

-continued
MOLSTRUCTURE
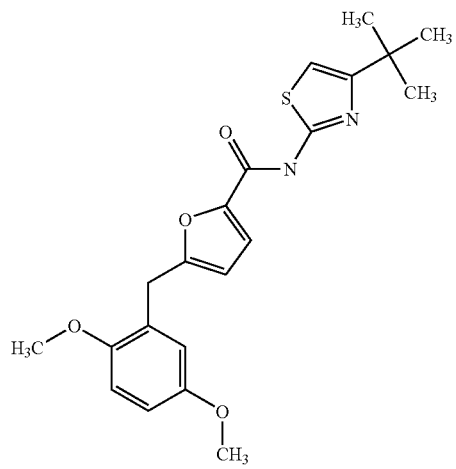
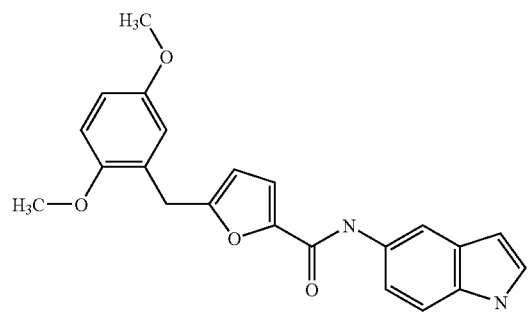
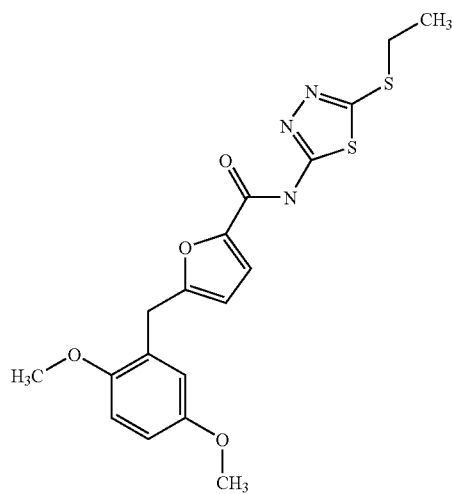
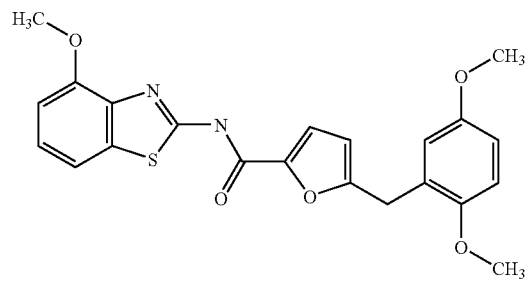

-continued
| MOLSTRUCTURE |
|---|
| 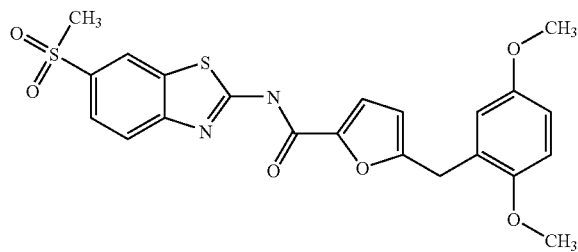 |
| 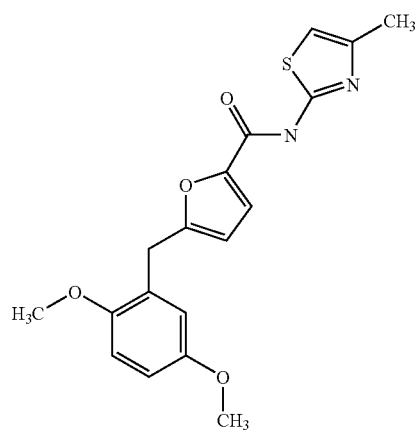 |
| 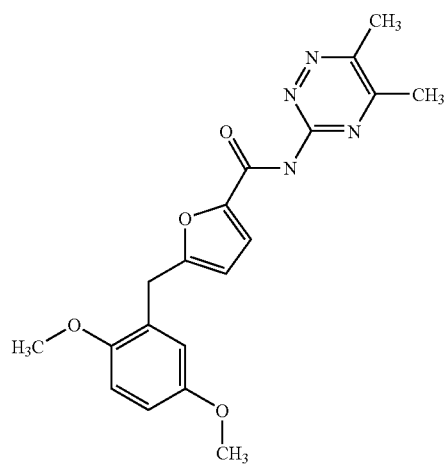 |

-continued
| MOLSTRUCTURE |
|---|
| 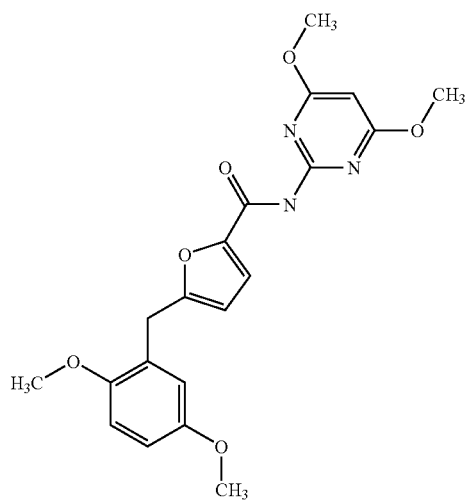 |
| 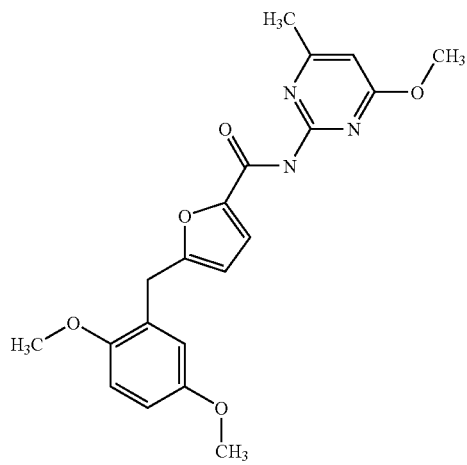 |
| 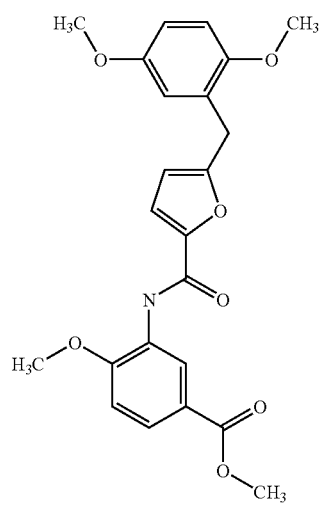 |

-continued
MOLSTRUCTURE
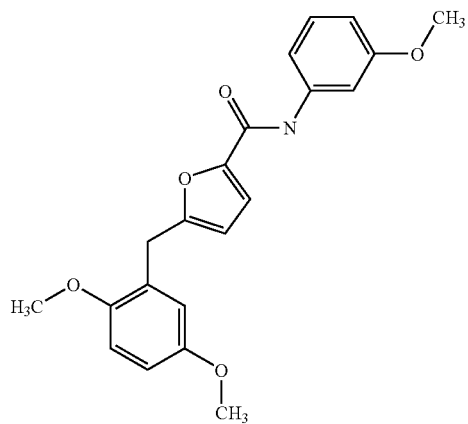
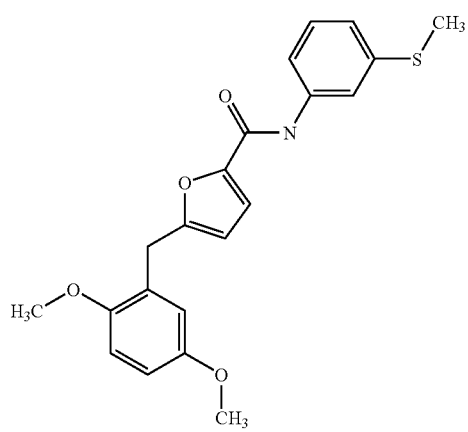
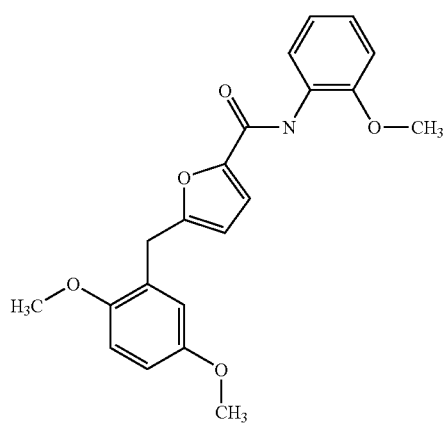

-continued
| MOLSTRUCTURE |
|---|
| 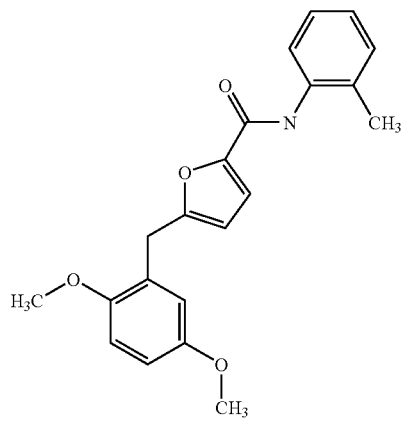 |
| 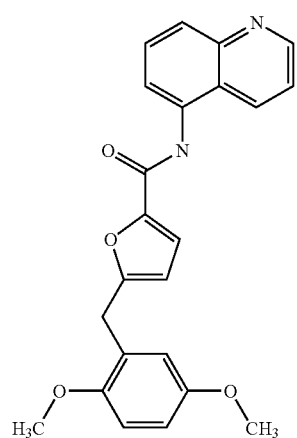 |
| 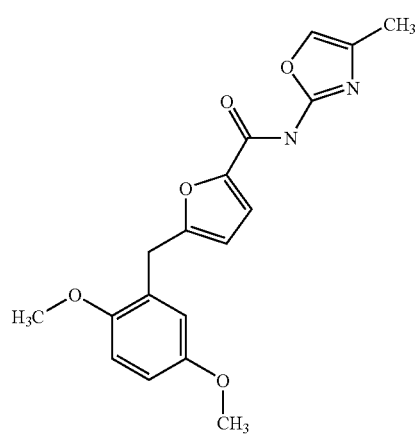 |

| MOLSTRUCTURE |
|---|
| 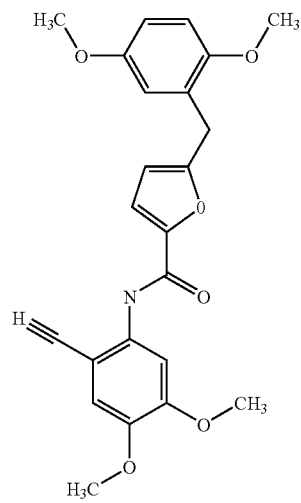 |
| 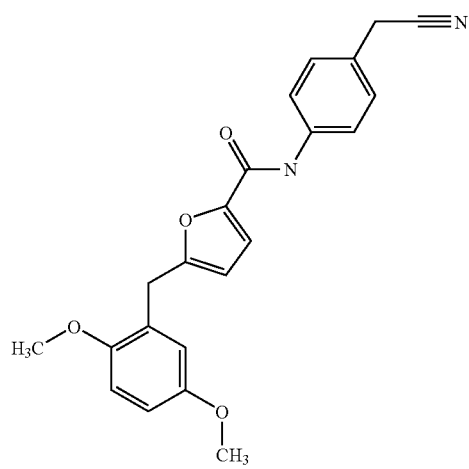 |
| 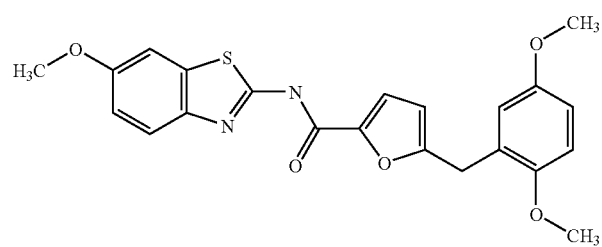 |

-continued
| MOLSTRUCTURE |
|---|
| 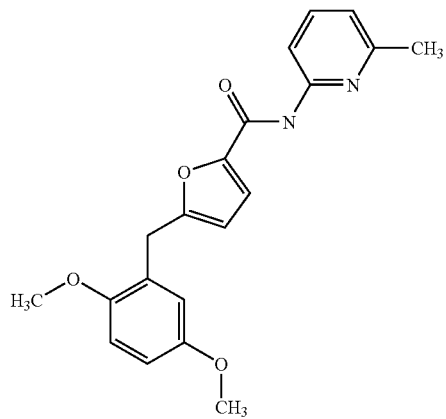 |
| 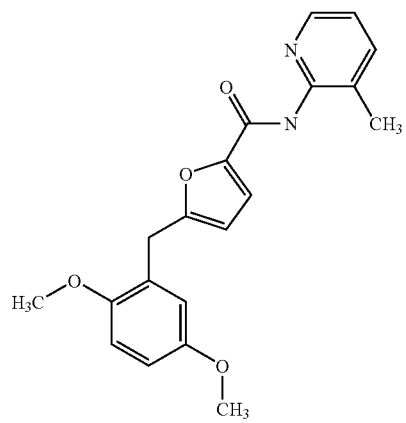 |
| 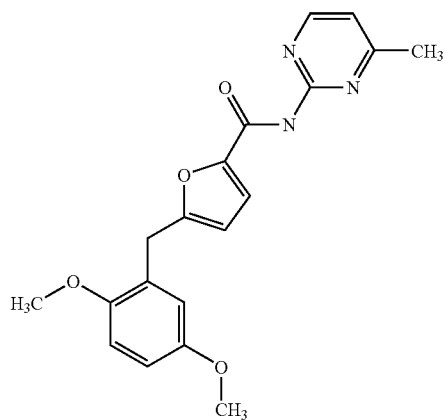 |

-continued
MOLSTRUCTURE
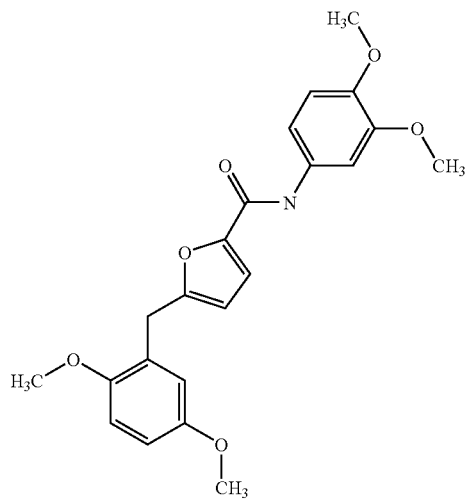
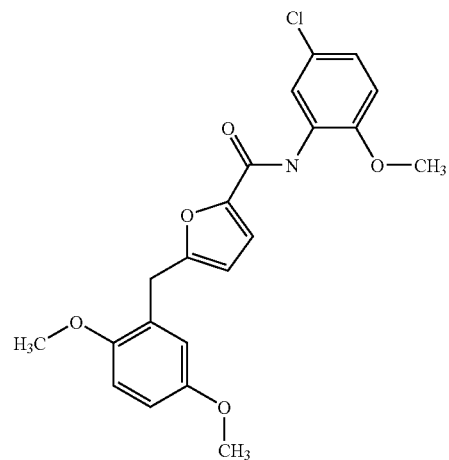
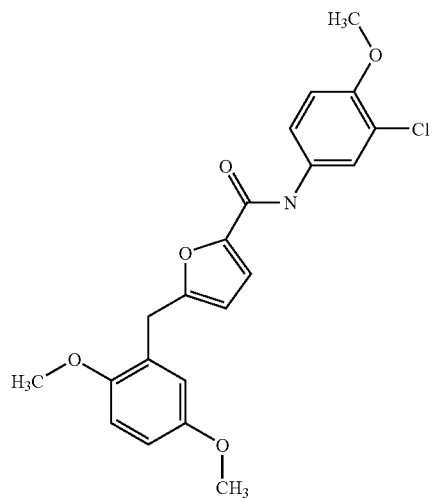

-continued
| MOLSTRUCTURE |
|---|
| 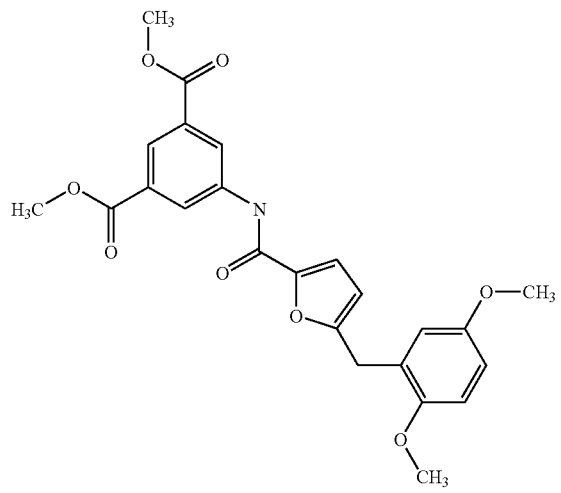 |
| 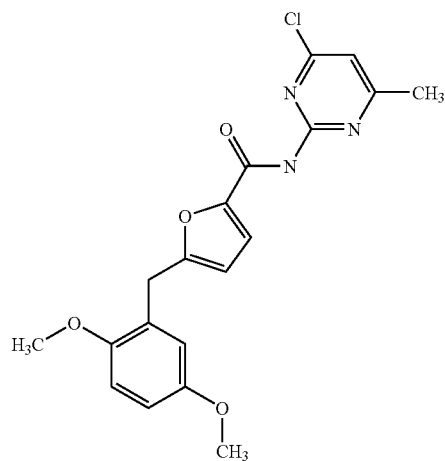 |
| 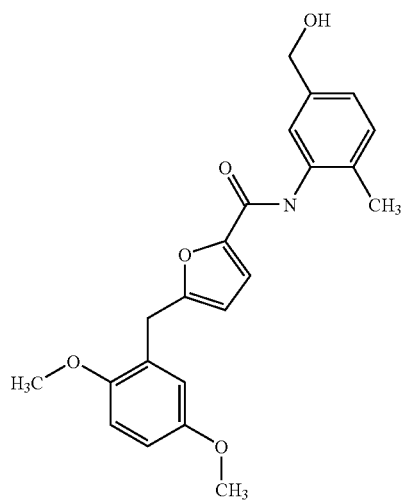 |

-continued
MOLSTRUCTURE
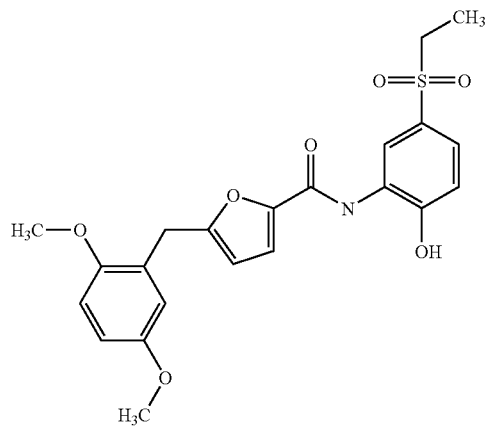

-continued
MOLSTRUCTURE
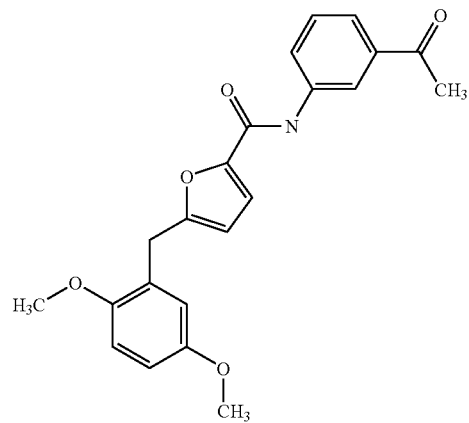
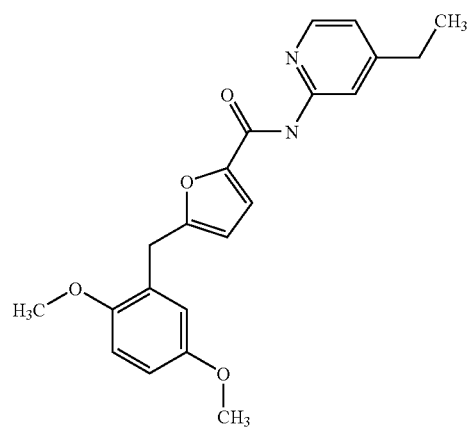
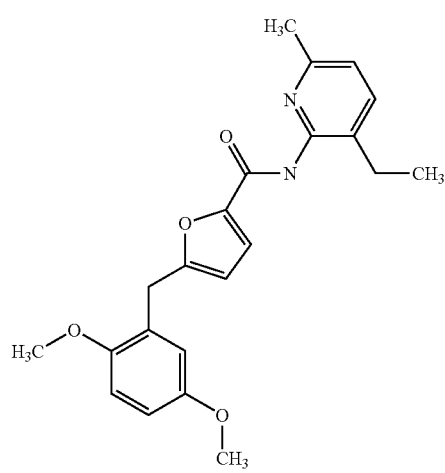

| MOLSTRUCTURE |
|---|
| 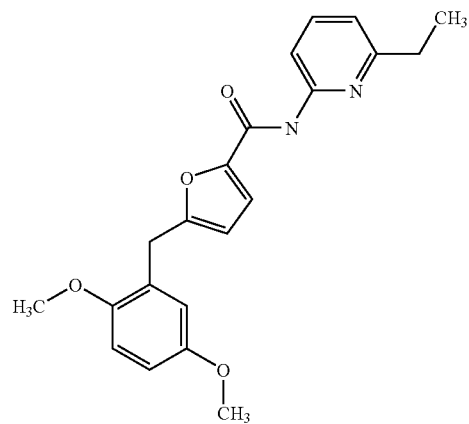 |
| 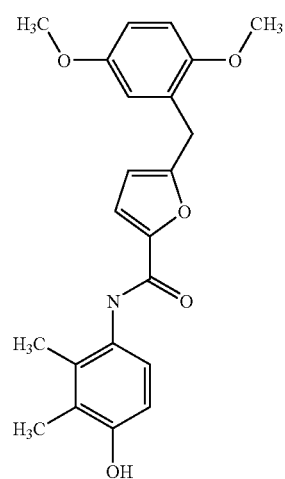 |
| 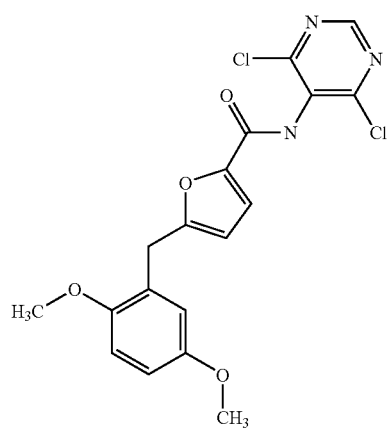 |

-continued
MOLSTRUCTURE
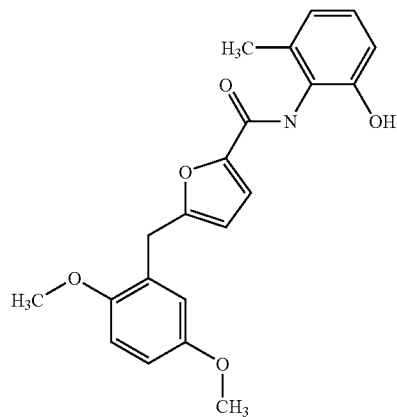
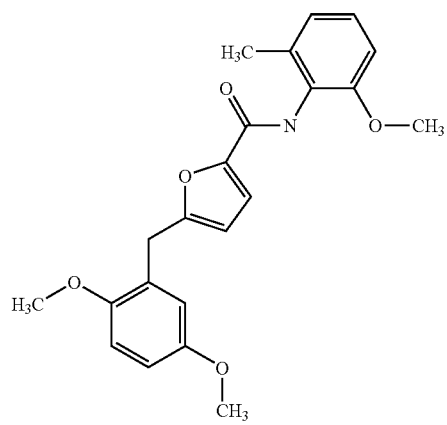
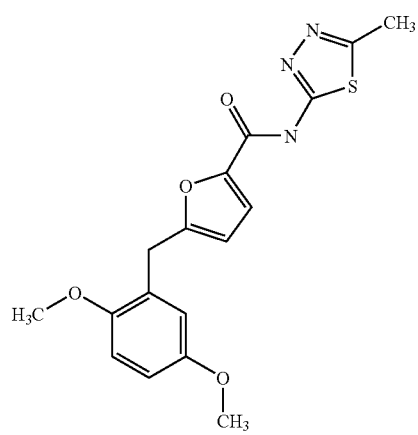

| MOLSTRUCTURE |
|---|
| 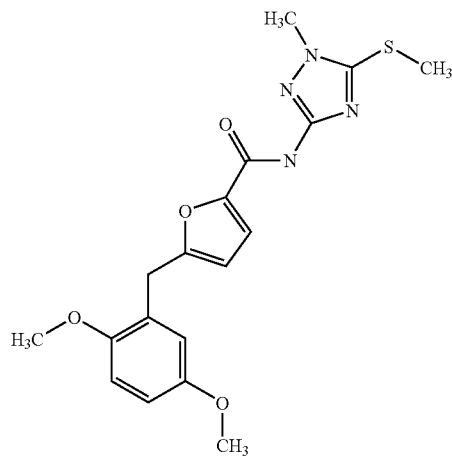 |
| 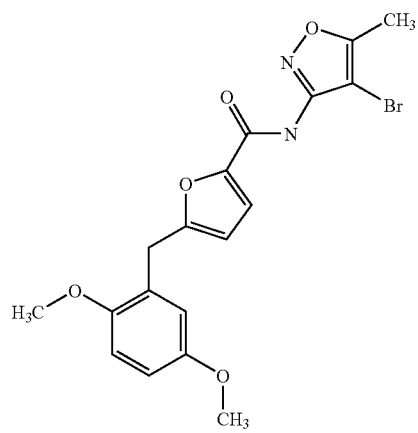 |
| 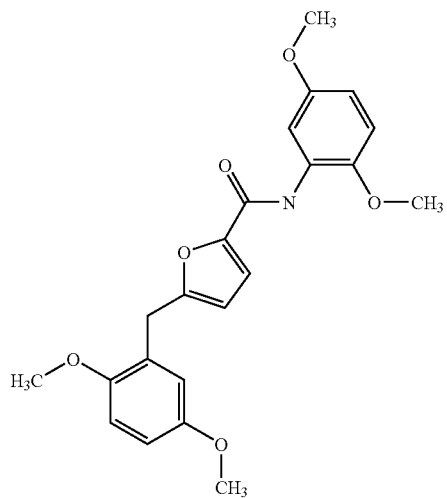 |

-continued
| MOLSTRUCTURE |
|---|
| 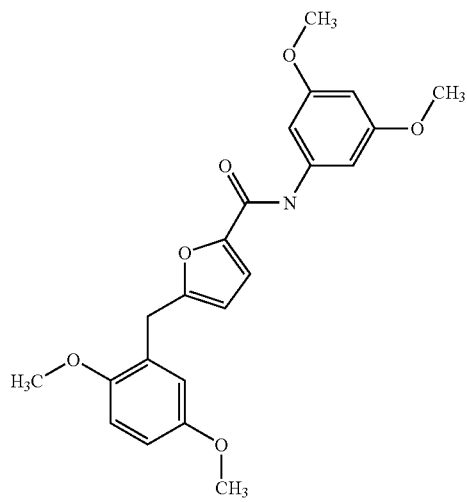 |
| 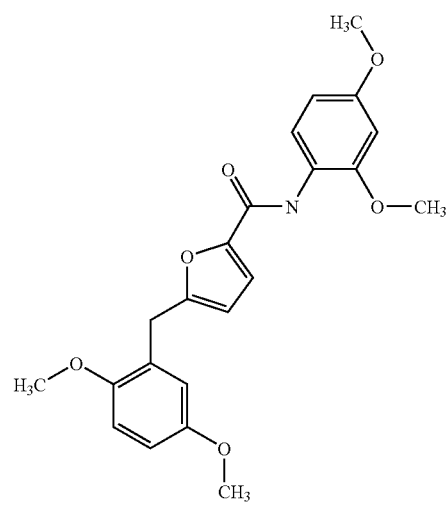 |
| 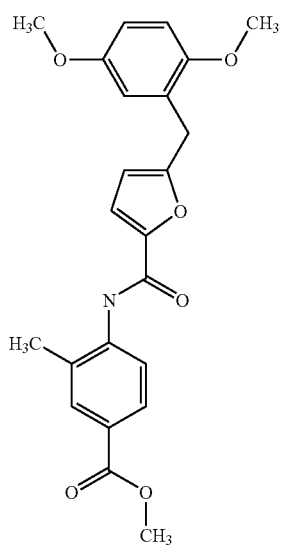 |

| MOLSTRUCTURE |
| --- |
| 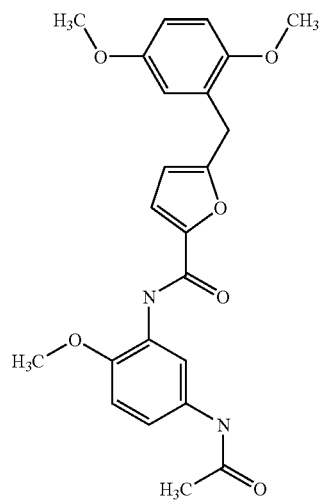 |
| 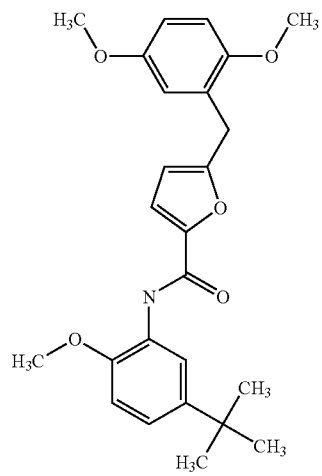 |
| 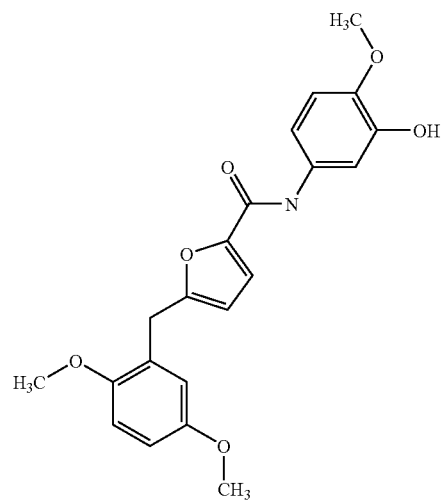 |

| MOLSTRUCTURE |
|---|
| 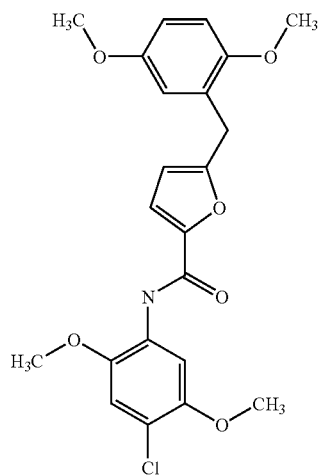 |
| 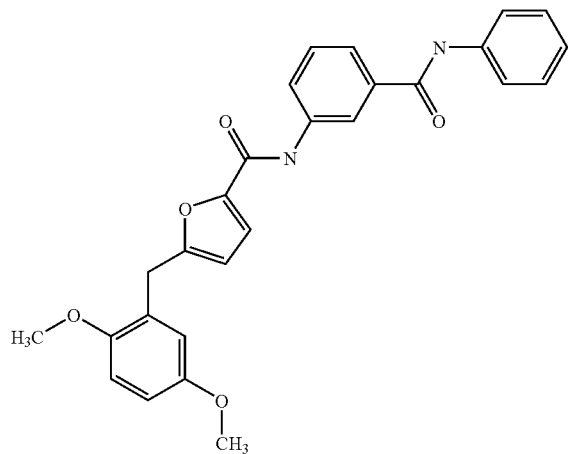 |
| 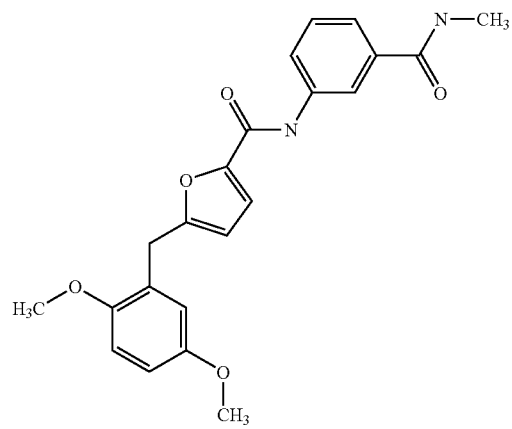 |

| MOLSTRUCTURE |
|---|
| 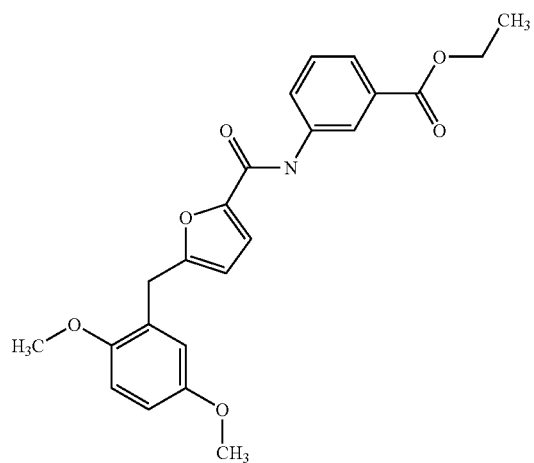 |
| 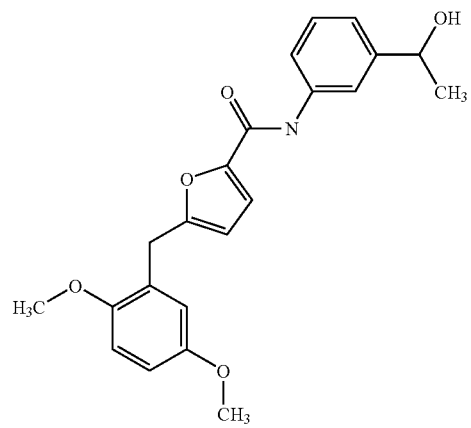 |
| 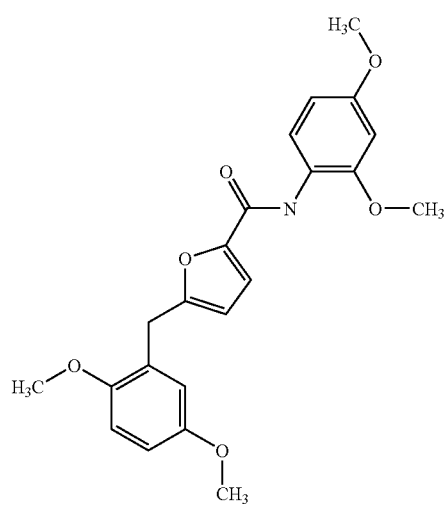 |

-continued
| MOLSTRUCTURE |
| --- |
| 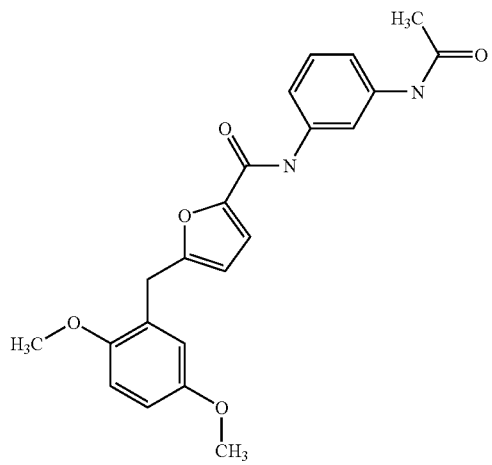 |
| 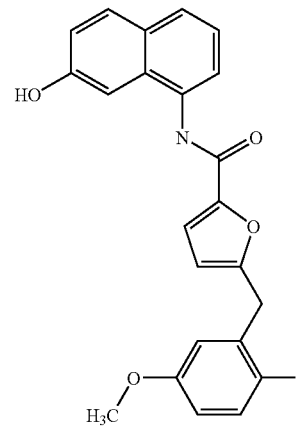 |
| 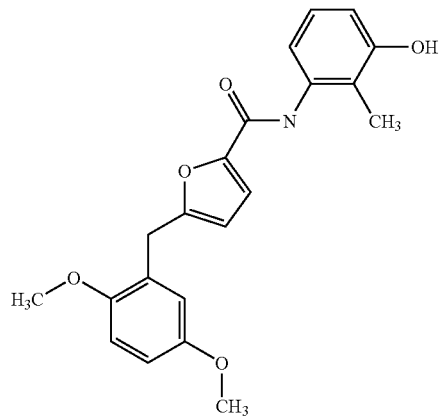 |

| 1503 | 1504 |
|---|---|
-continued
| MOLSTRUCTURE |
|---|
| 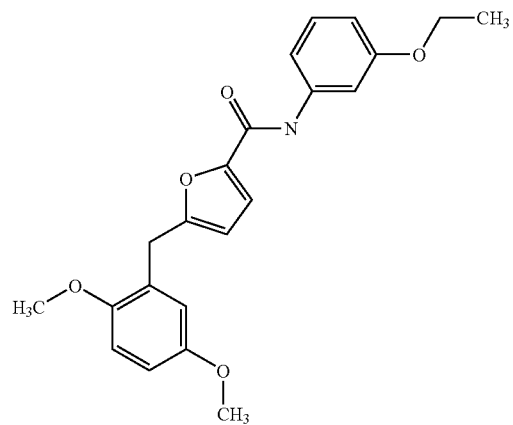 |
| 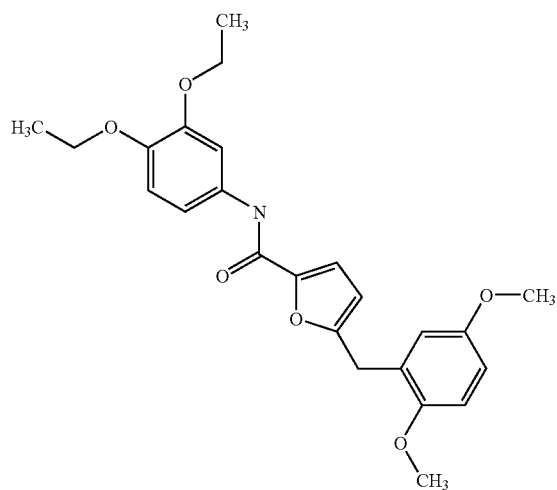 |
| 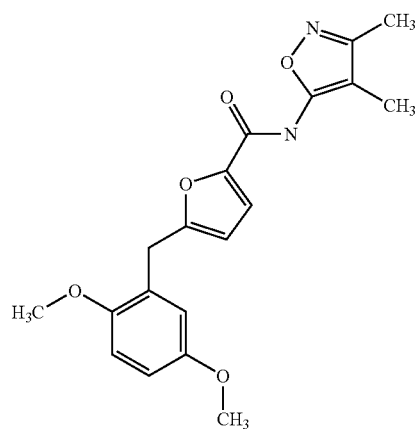 |

-continued
| MOLSTRUCTURE |
| --- |
| 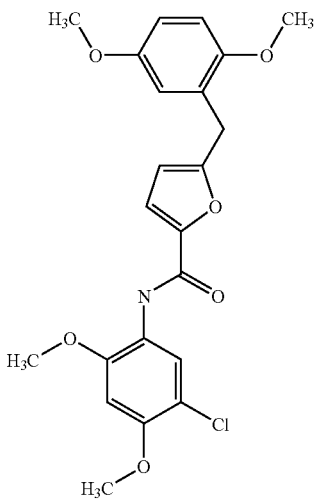 |
| 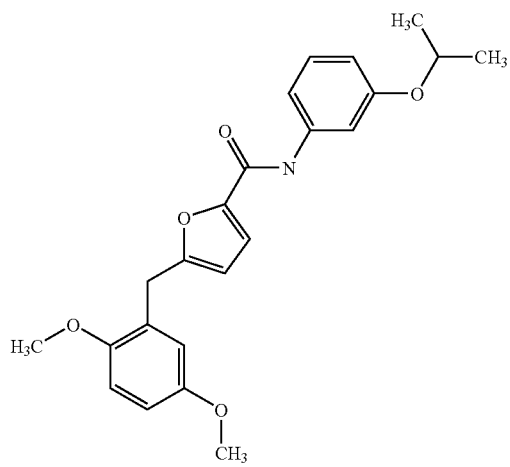 |
| 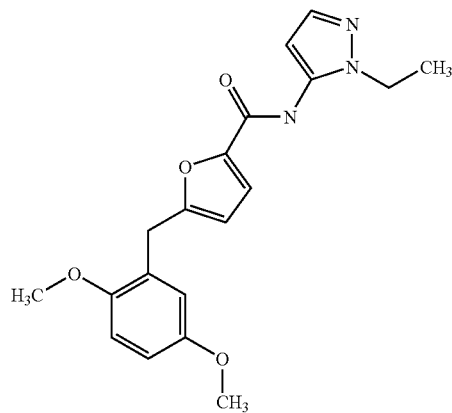 |

| MOLSTRUCTURE |
|---|
| 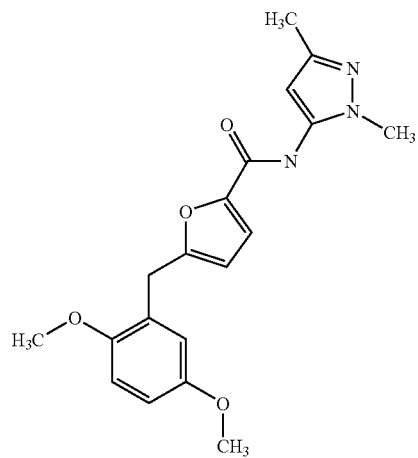 |
| 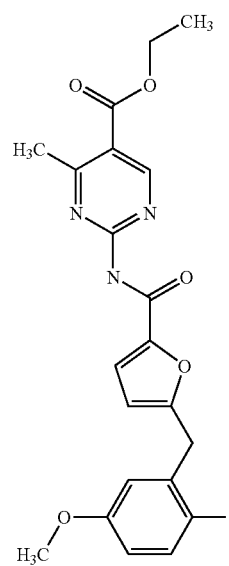 |
| 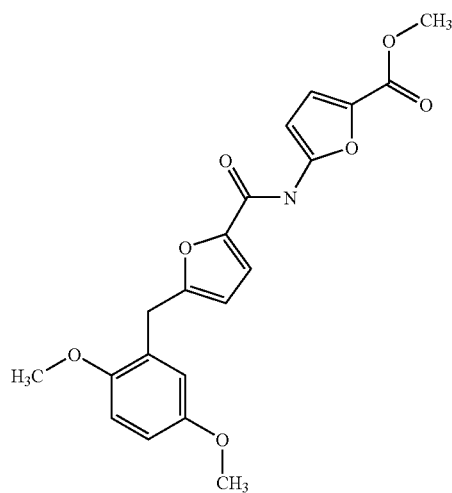 |

| MOLSTRUCTURE |
|---|
| 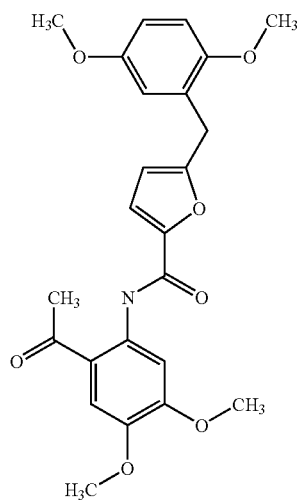 |
| 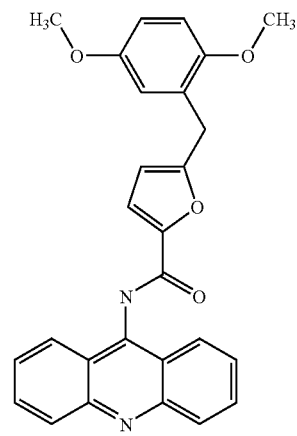 |
| 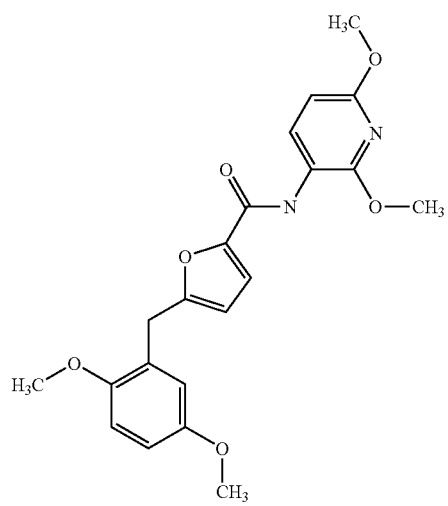 |

| MOLSTRUCTURE |
|---|
| 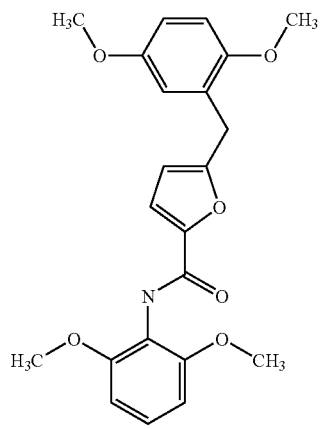 |
| 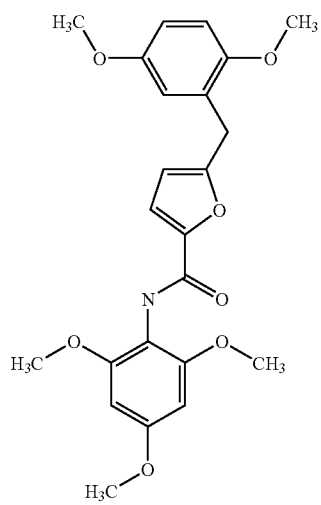 |
| 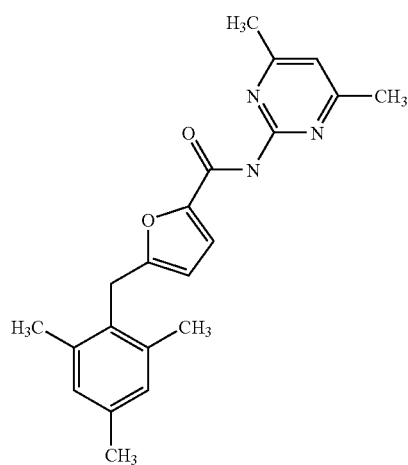 |

-continued
MOLSTRUCTURE
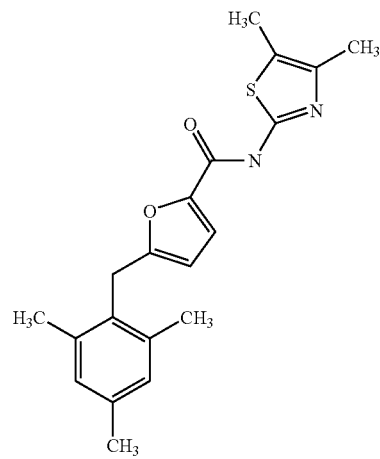
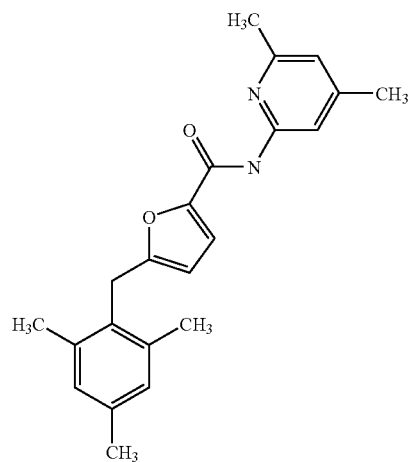
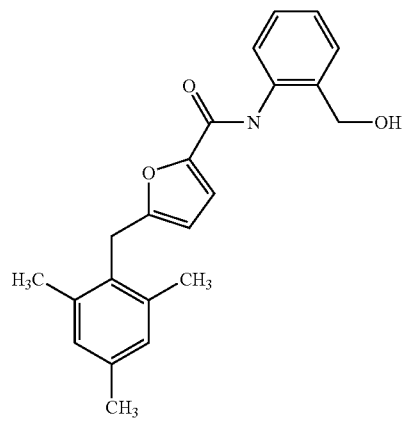

-continued
| MOLSTRUCTURE |
| --- |
| 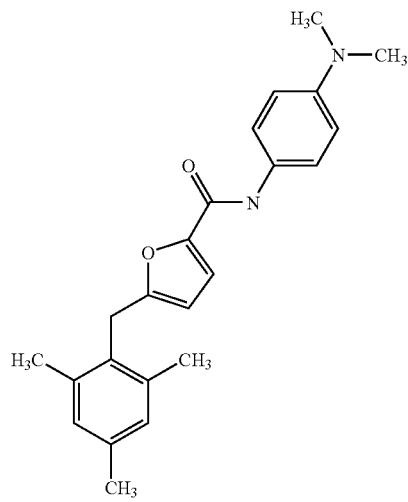 |
| 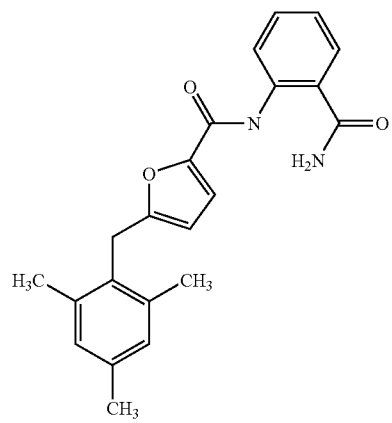 |
| 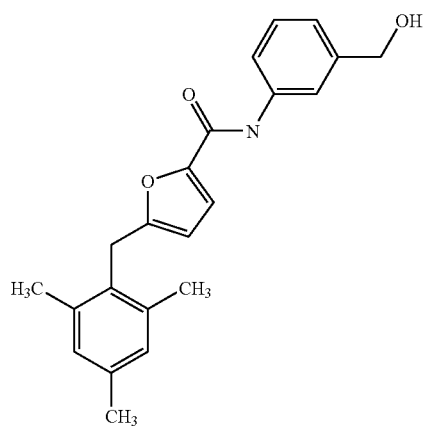 |

-continued
| MOLSTRUCTURE |
|---|
| 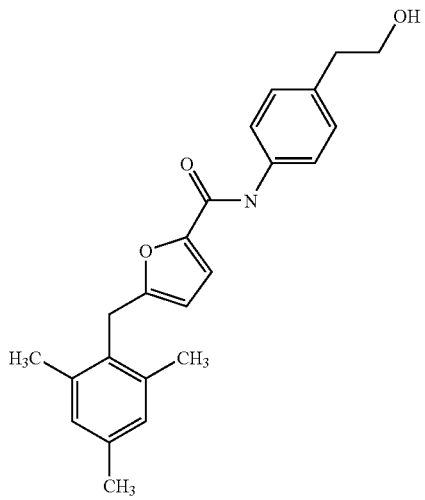 |
| 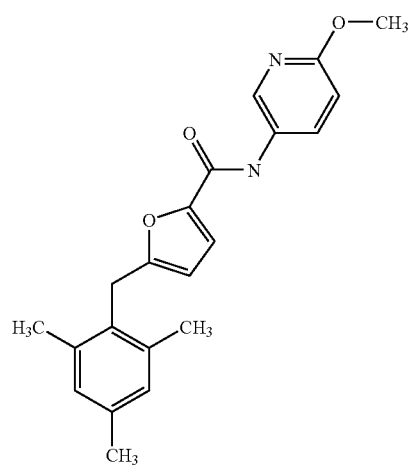 |
| 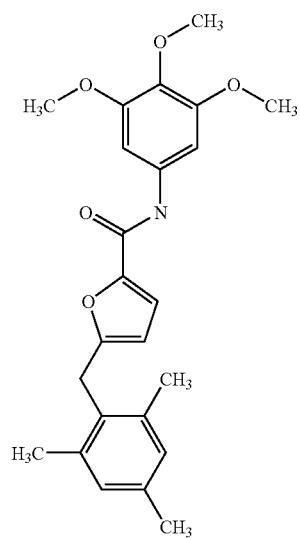 |

| MOLSTRUCTURE |
| --- |
| 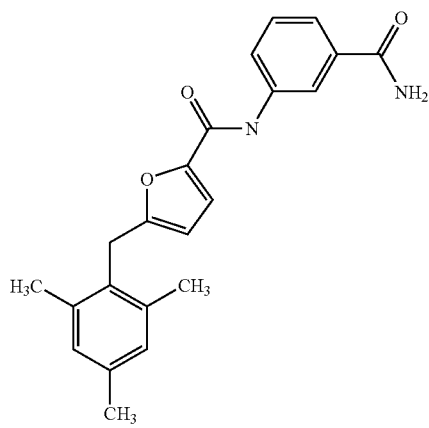 |
| 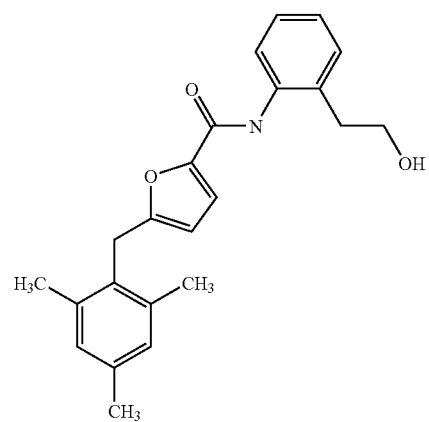 |
| 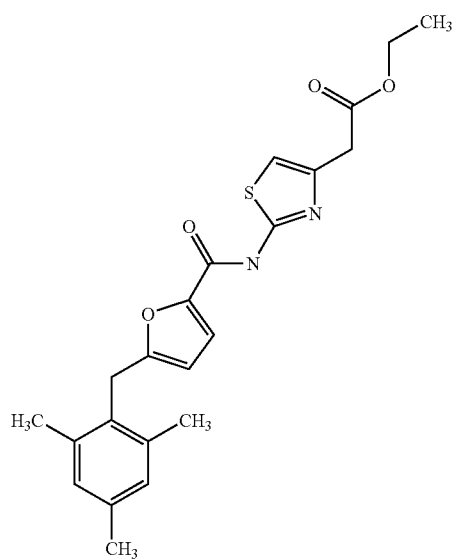 |

-continued
| MOLSTRUCTURE |
| --- |
| 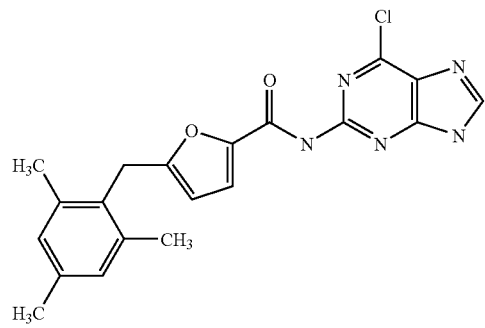 |
| 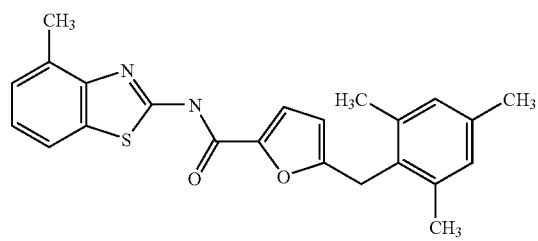 |
| 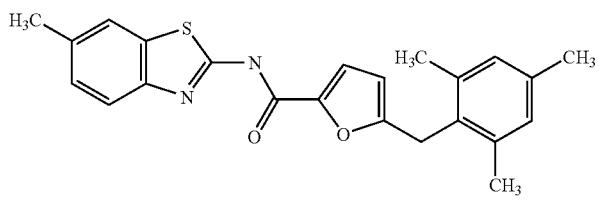 |
| 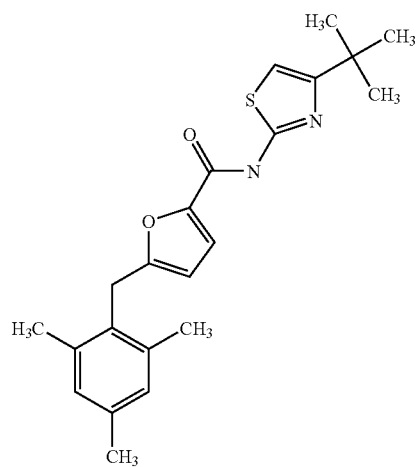 |
| 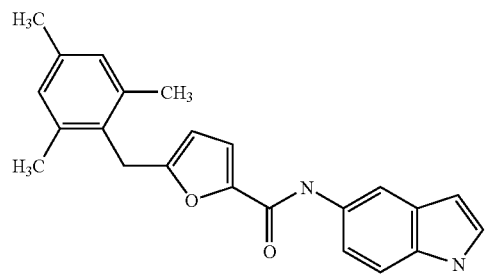 |

| MOLSTRUCTURE |
|---|
| 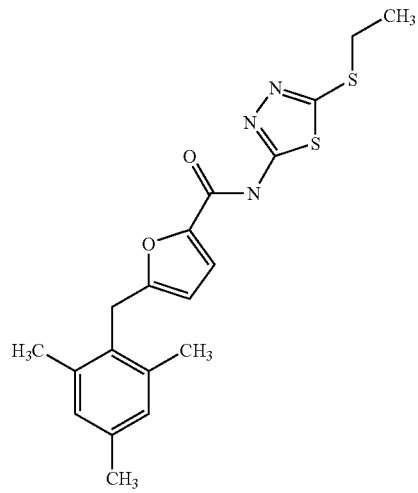 |
| 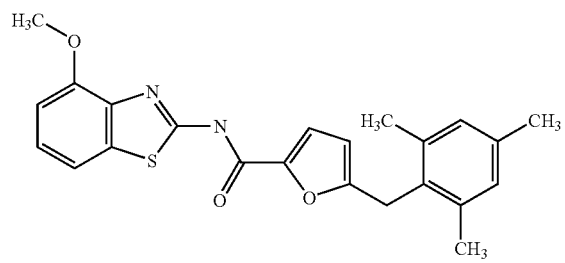 |
| 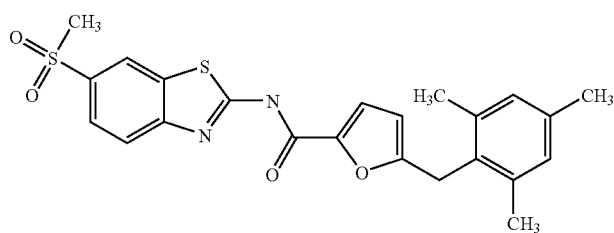 |
| 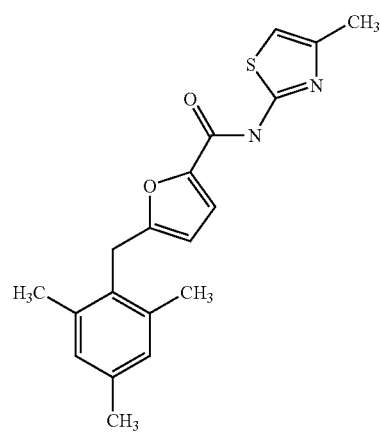 |

-continued
| MOLSTRUCTURE |
| --- |
| 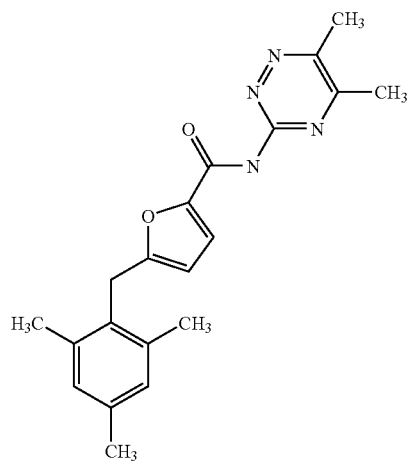 |
| 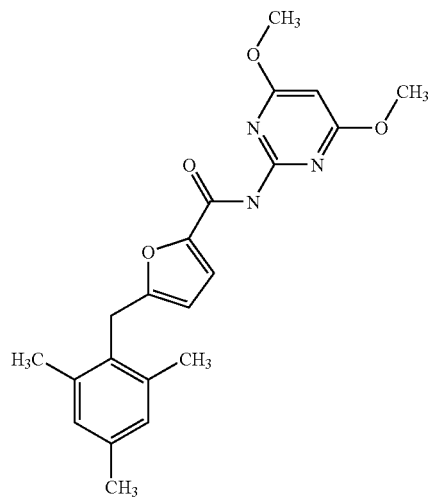 |
| 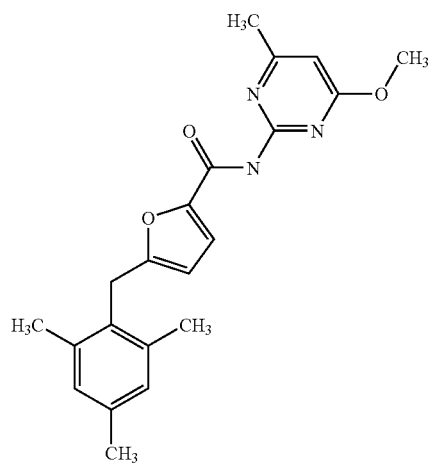 |

-continued
| MOLSTRUCTURE |
|---|
| 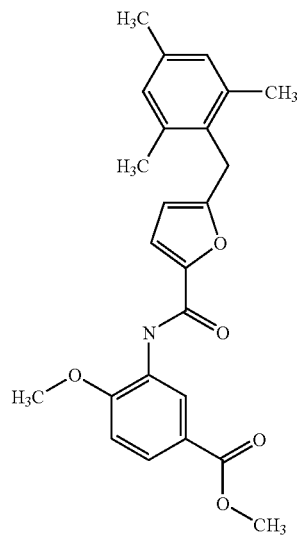 |
| 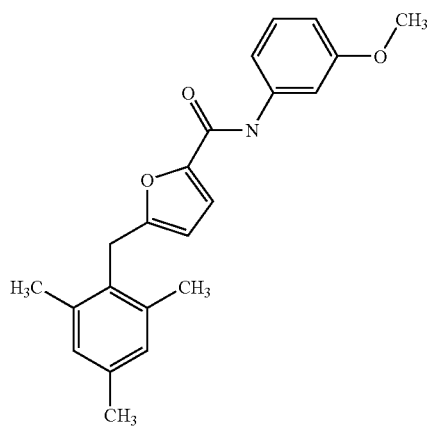 |
| 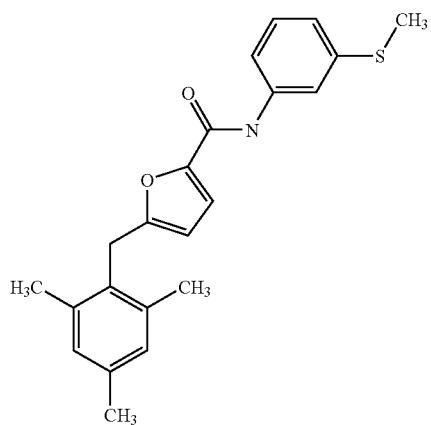 |

| MOLSTRUCTURE |
|---|
| 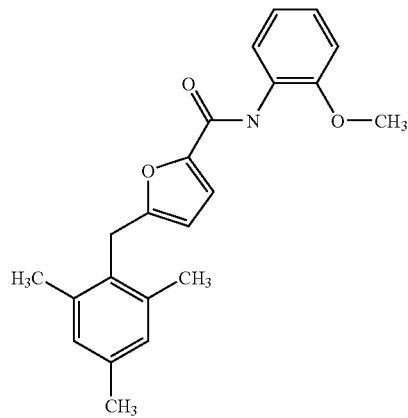 |
| 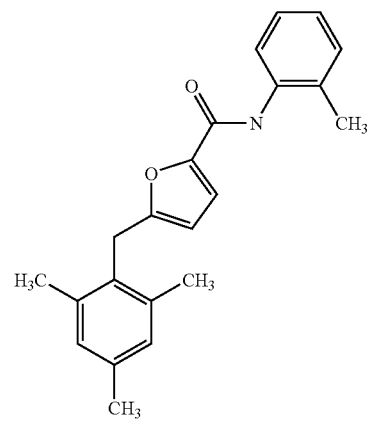 |
| 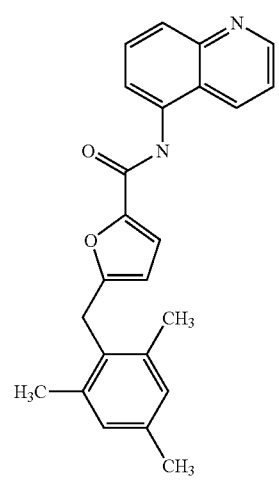 |

| MOLSTRUCTURE |
|---|
| 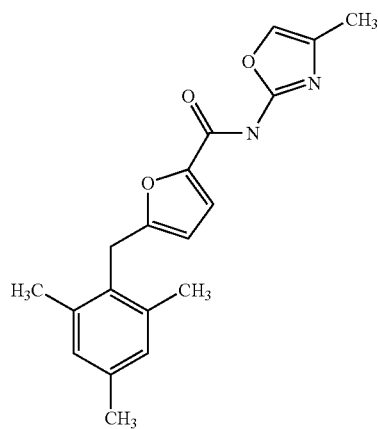 |
| 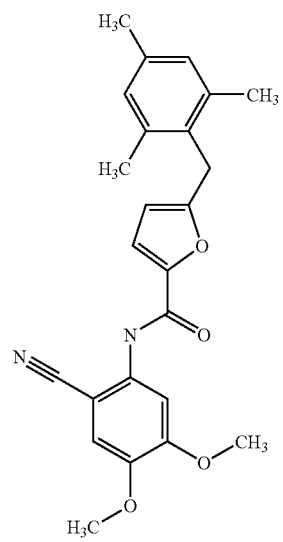 |
| 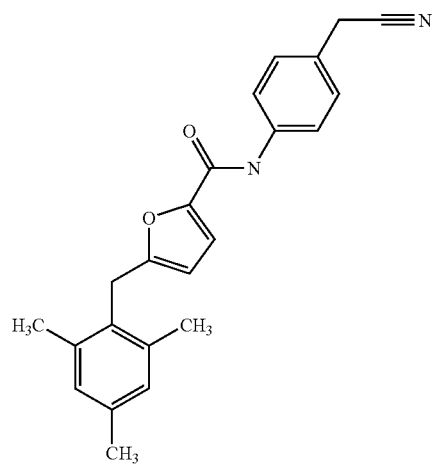 |

1533 1534
-continued
MOLSTRUCTURE
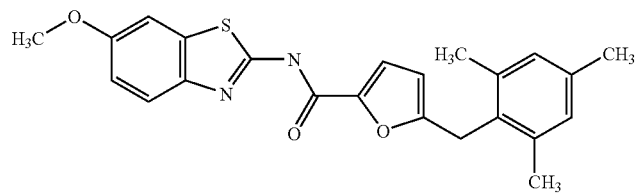
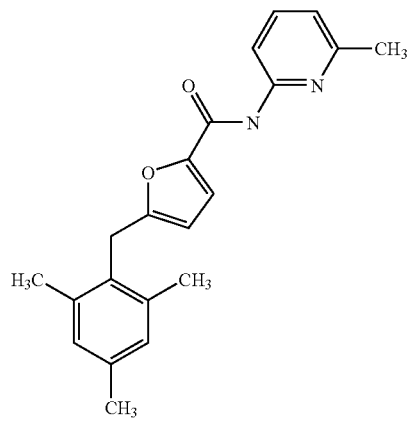
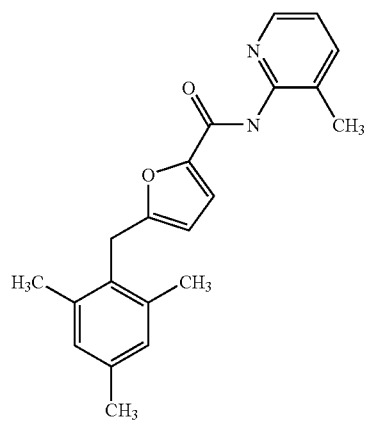
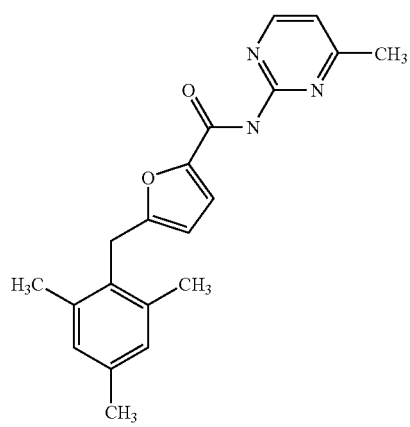

| MOLSTRUCTURE |
| --- |
| 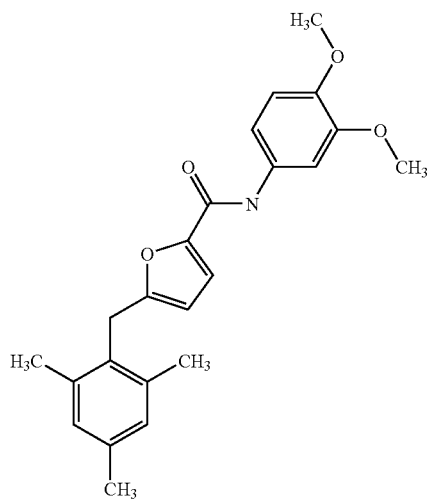 |
| 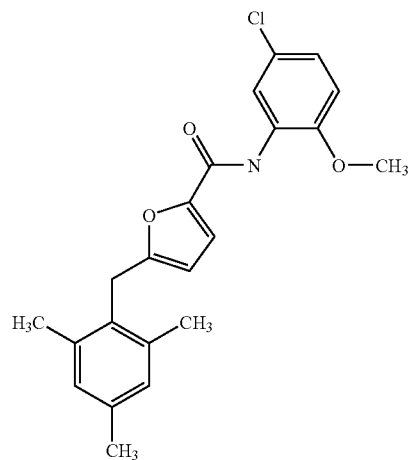 |
| 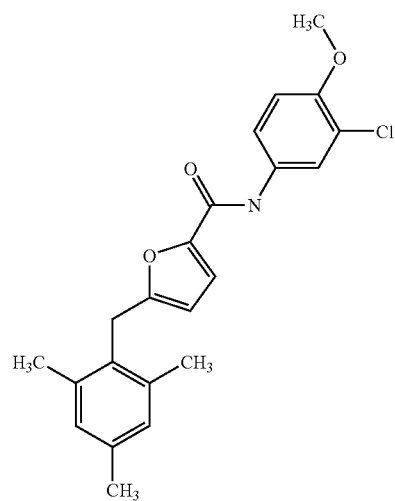 |

| MOLSTRUCTURE |
|---|
| 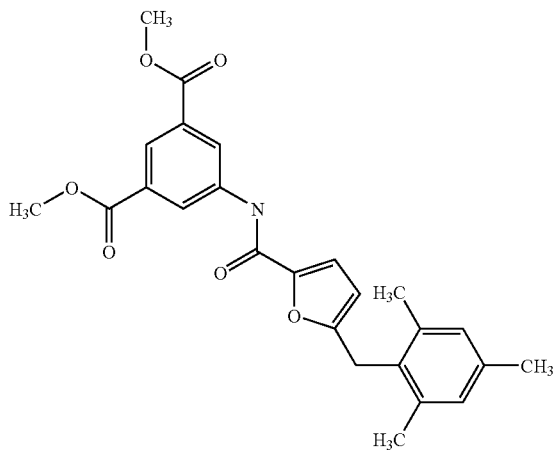 |
| 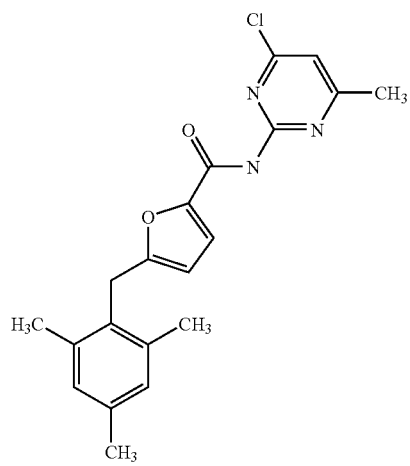 |
| 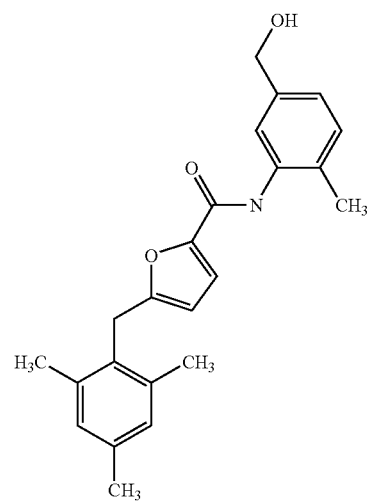 |

-continued
| MOLSTRUCTURE |
| --- |
| 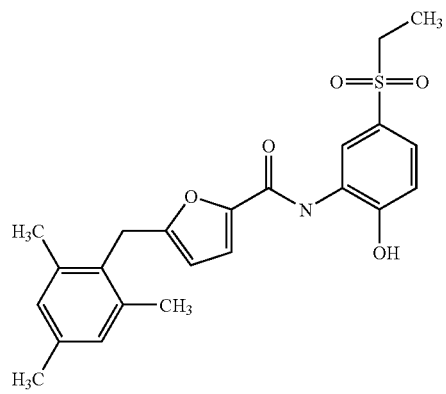 |
| 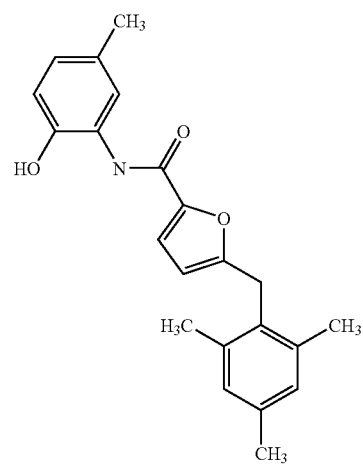 |
| 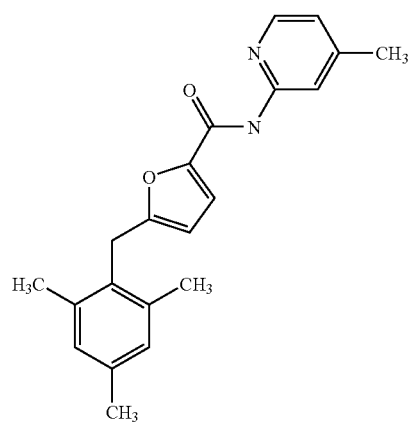 |

| MOLSTRUCTURE |
|---|
| 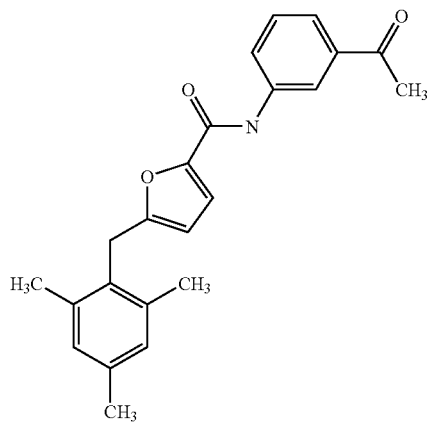 |
| 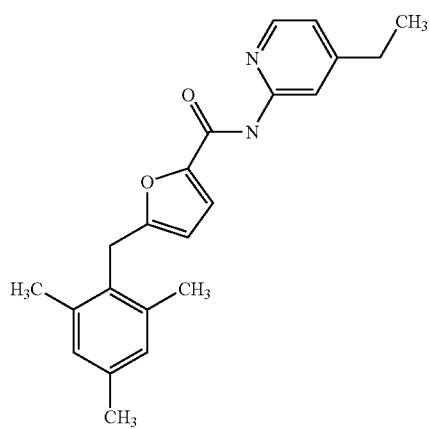 |
| 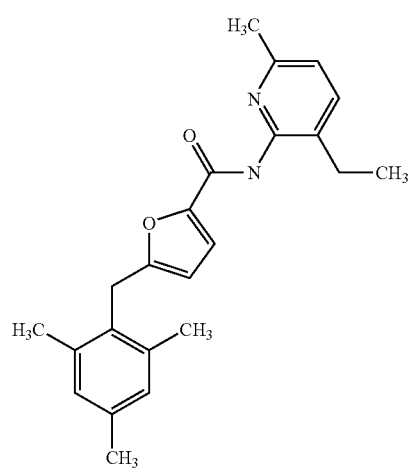 |

| MOLSTRUCTURE |
|---|
| 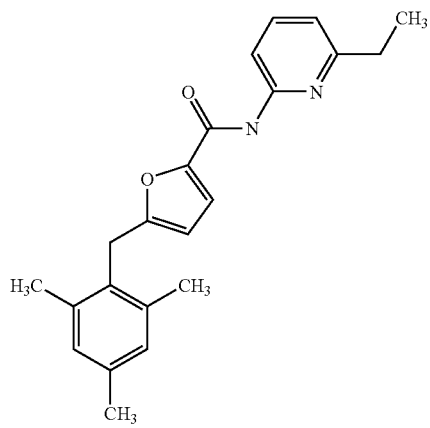 |
| 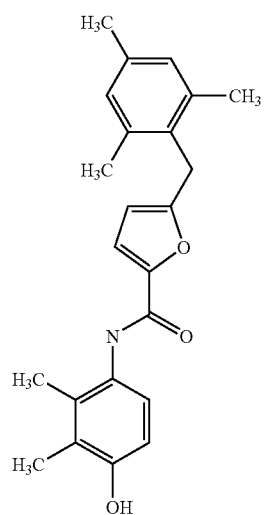 |
| 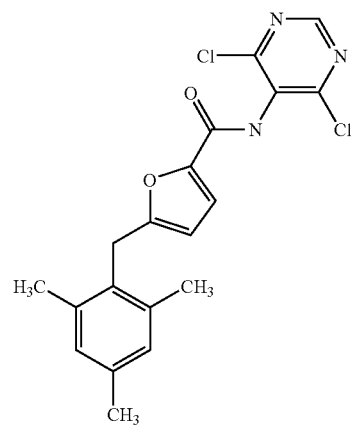 |

| MOLSTRUCTURE |
|---|
| 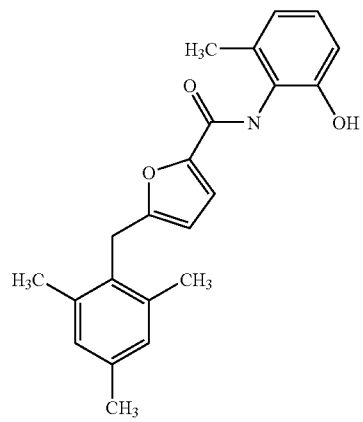 |
| 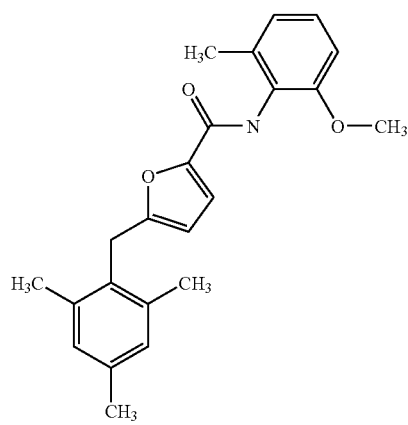 |
| 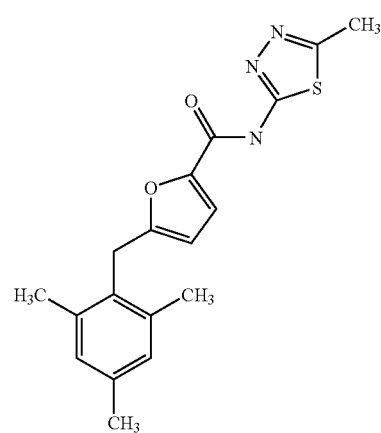 |

-continued
MOLSTRUCTURE
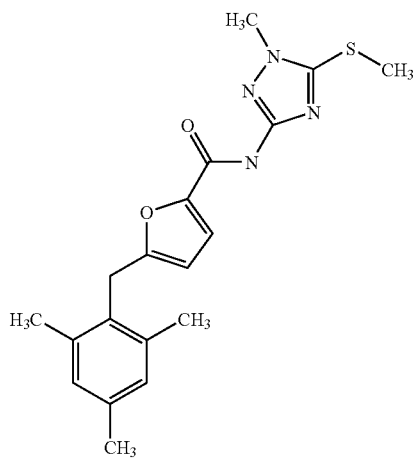
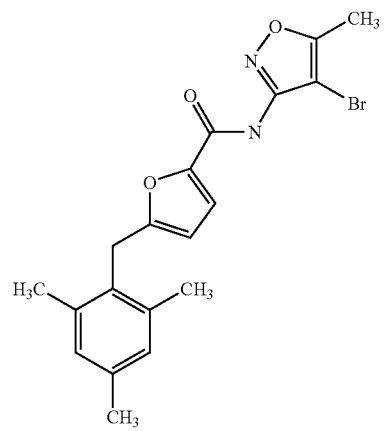
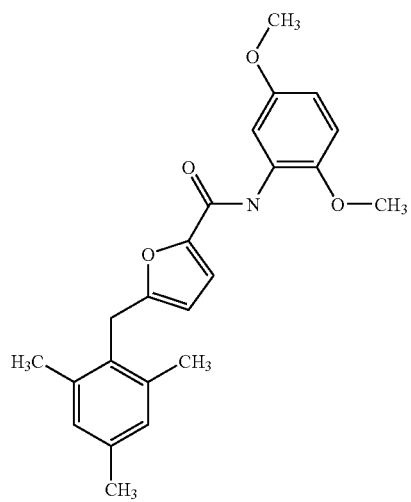

-continued
| MOLSTRUCTURE |
|---|
| 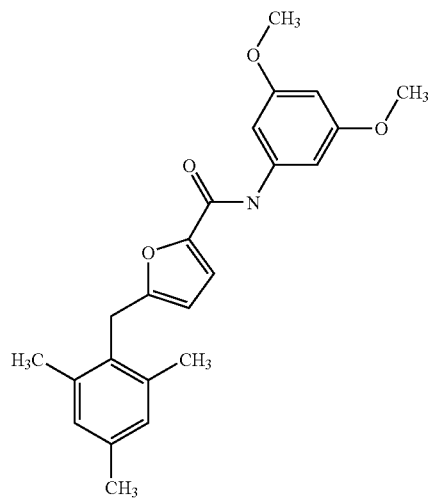 |
| 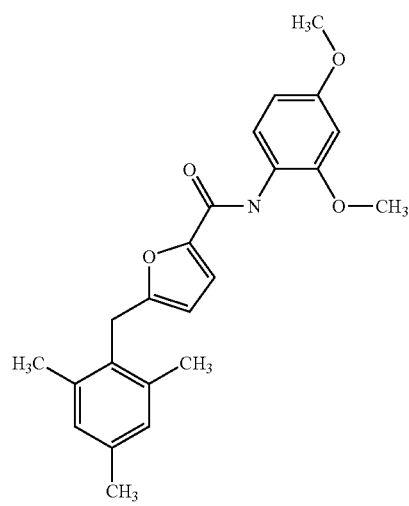 |
| 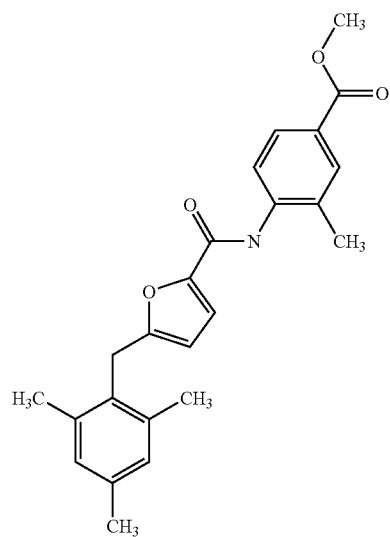 |

-continued
| MOLSTRUCTURE |
|---|
| 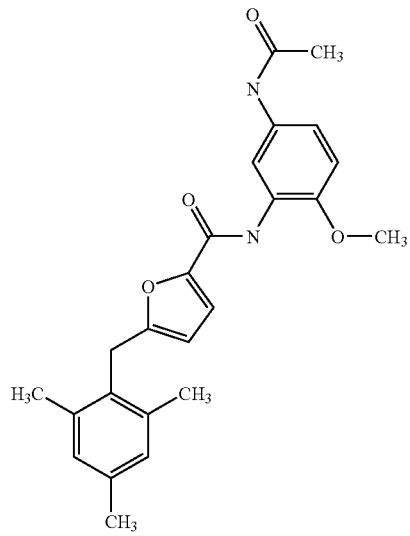 |
| 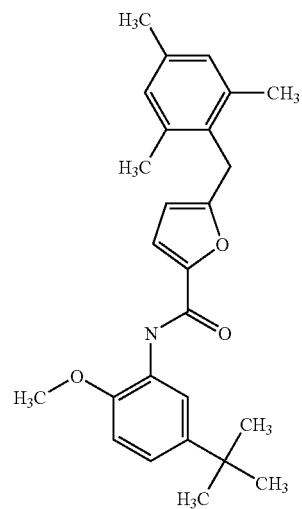 |
| 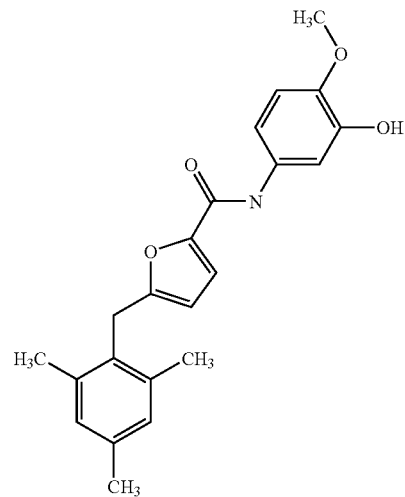 |

-continued
| MOLSTRUCTURE |
| --- |
| 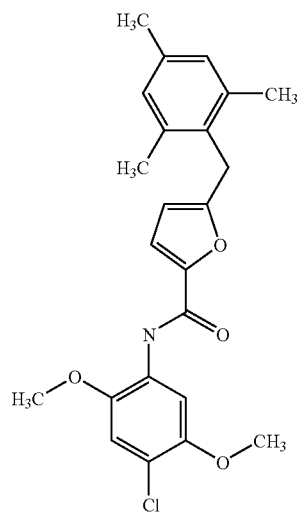 |
| 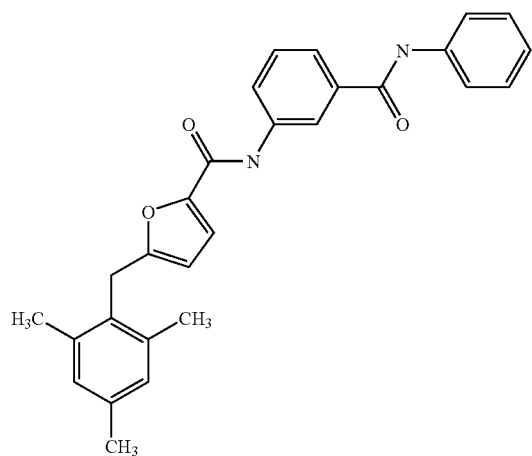 |
| 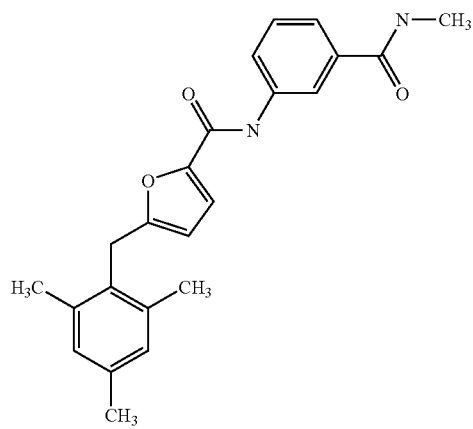 |

-continued
| MOLSTRUCTURE |
| --- |
| 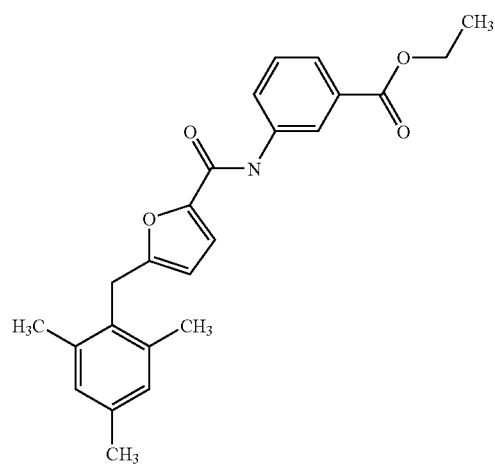 |
| 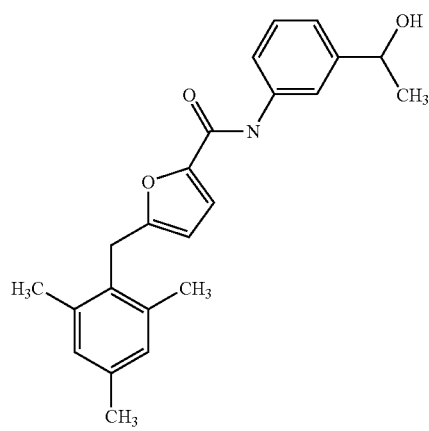 |
| 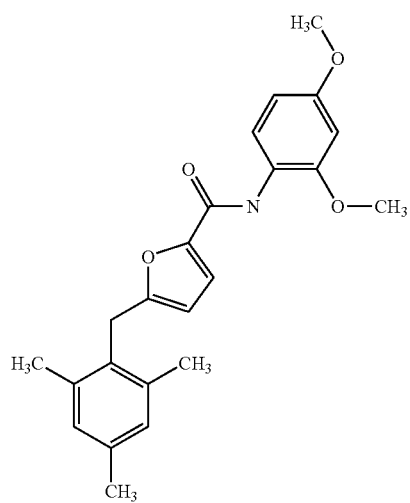 |

| MOLSTRUCTURE |
|---|
| 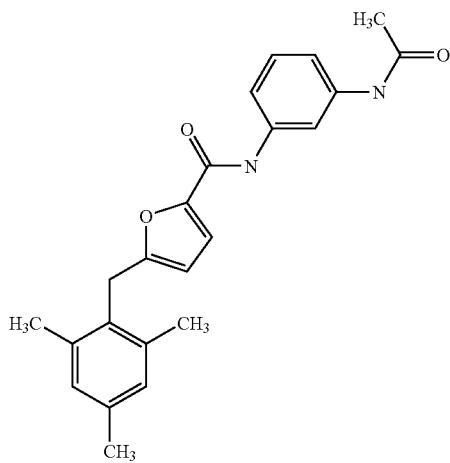 |
| 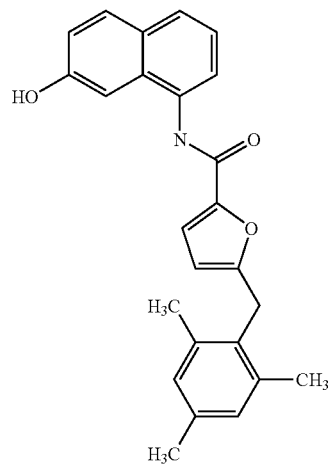 |
| 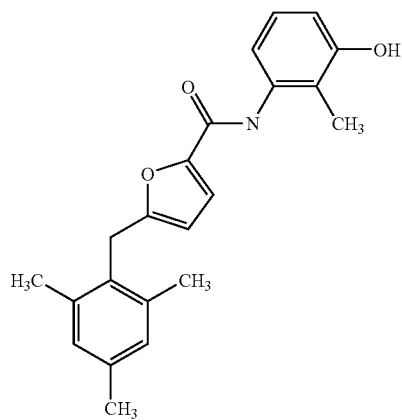 |

-continued
MOLSTRUCTURE
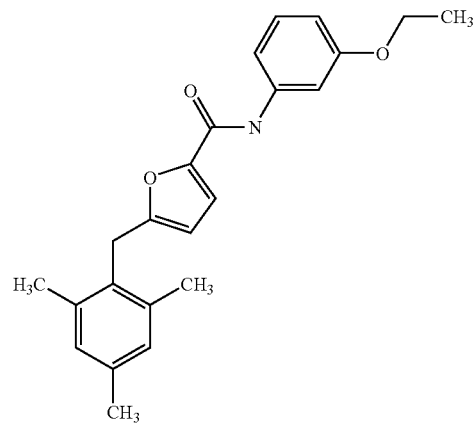
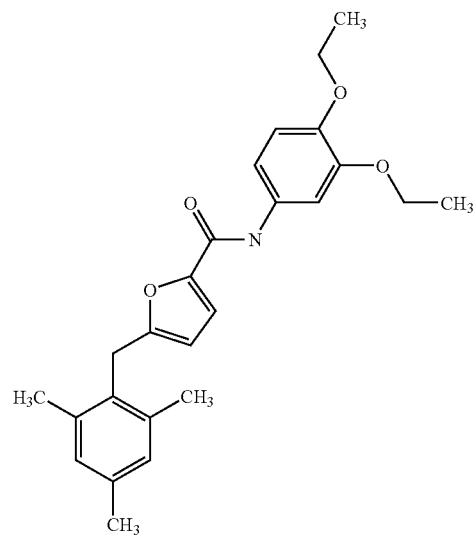
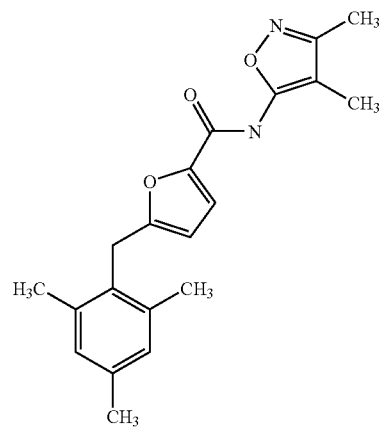

-continued
| MOLSTRUCTURE |
|---|
| 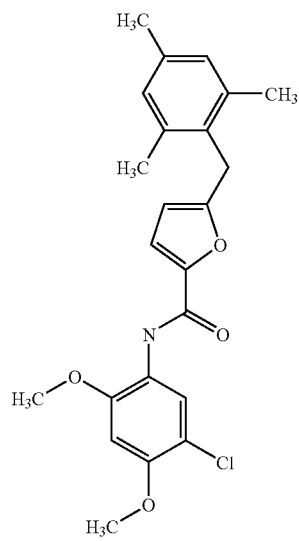 |
| 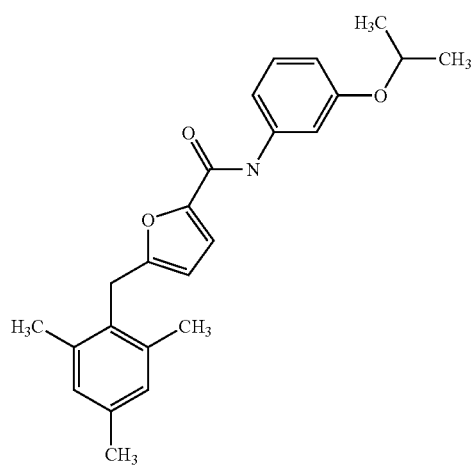 |
| 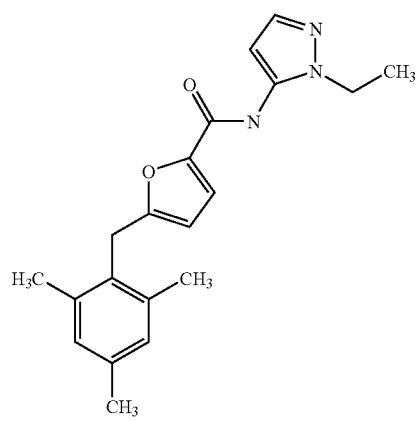 |

-continued
| MOLSTRUCTURE |
|---|
| 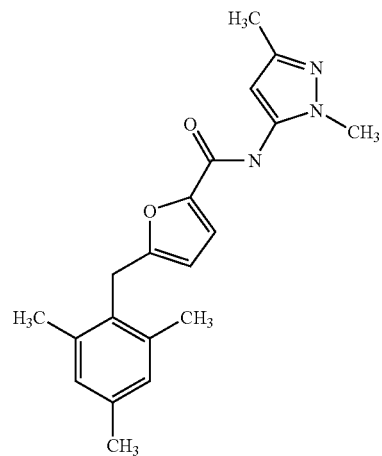 |
| 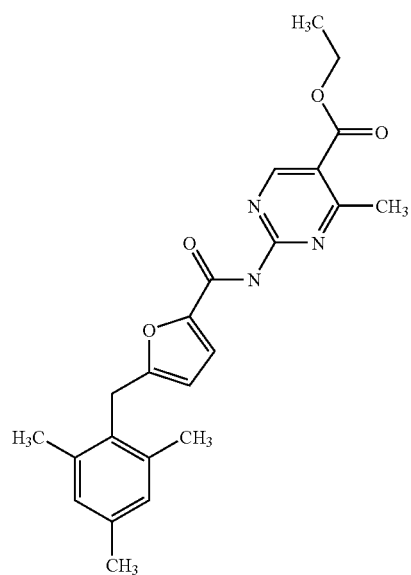 |
| 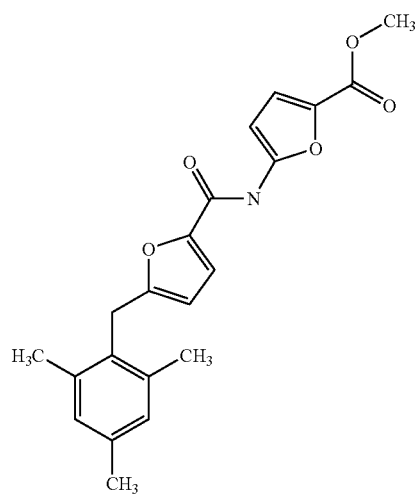 |

-continued
MOLSTRUCTURE
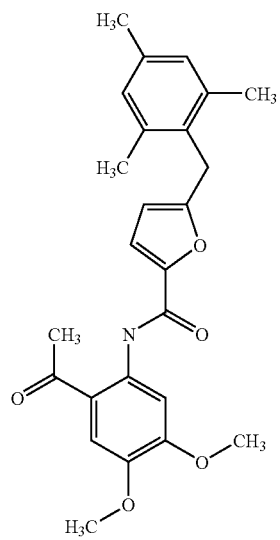
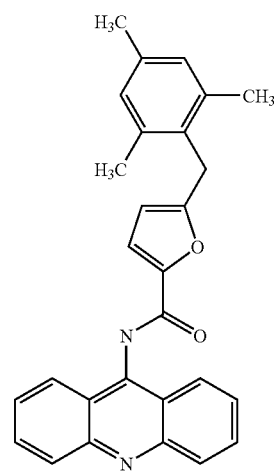
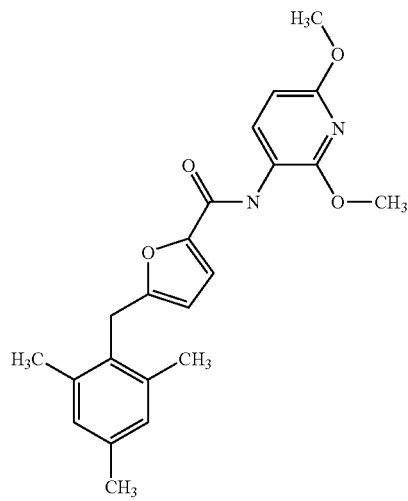

| MOLSTRUCTURE |
| --- |
| 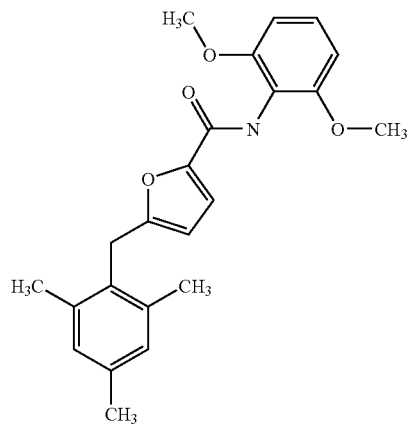 |
| 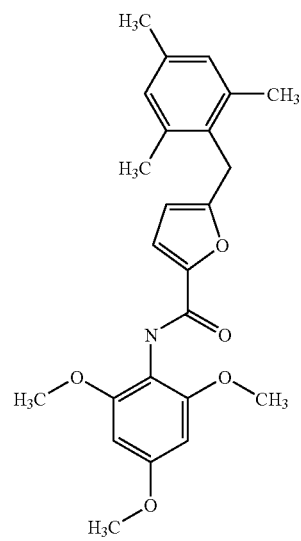 |
| 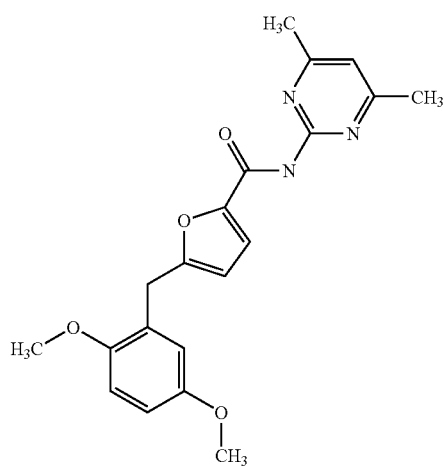 |

-continued
MOLSTRUCTURE
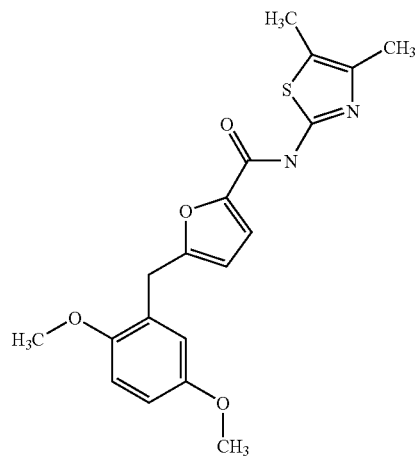
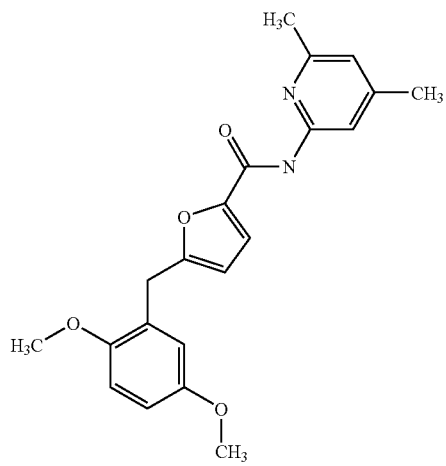
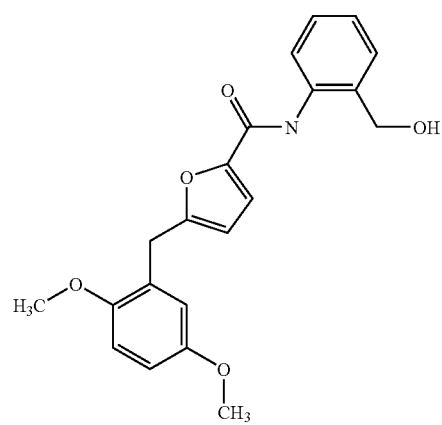

| MOLSTRUCTURE |
| --- |
| 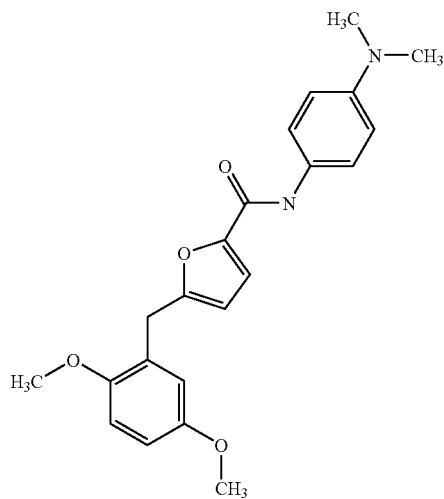 |
| 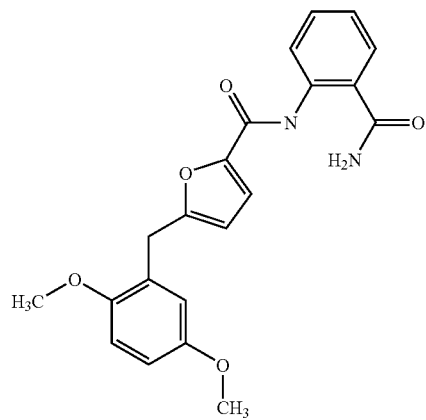 |
| 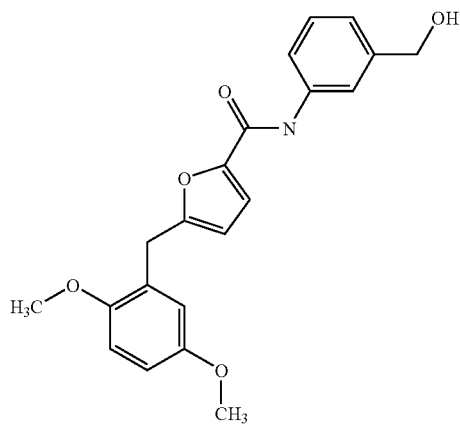 |

-continued
MOLSTRUCTURE
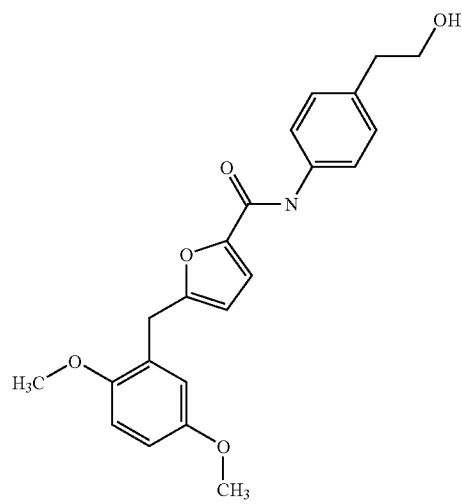
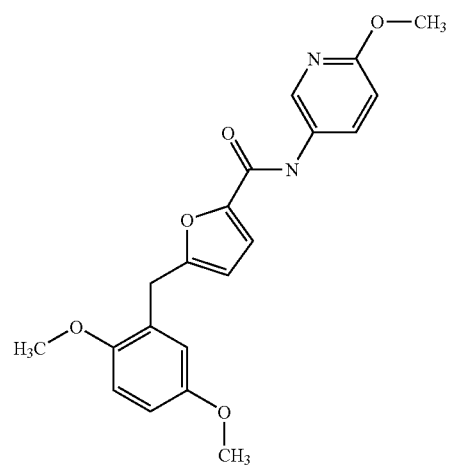
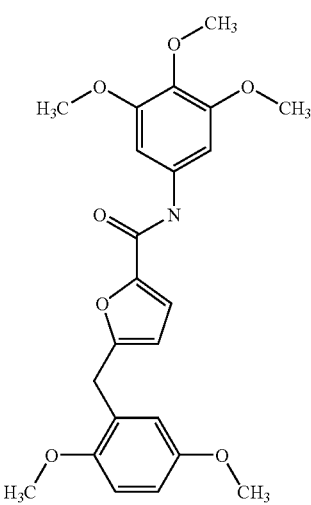

-continued
| MOLSTRUCTURE |
|---|
| 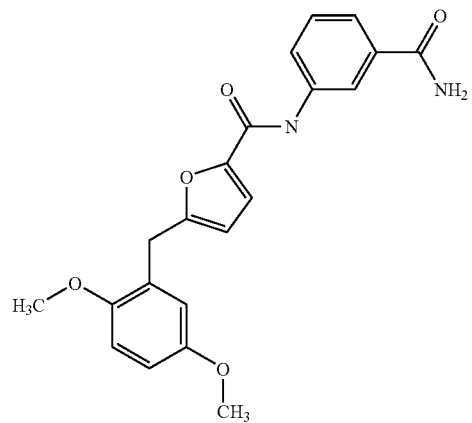 |
| 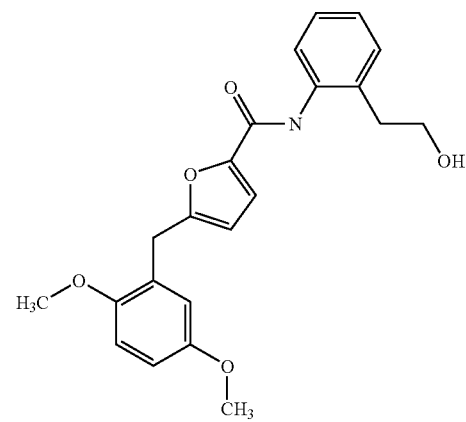 |
| 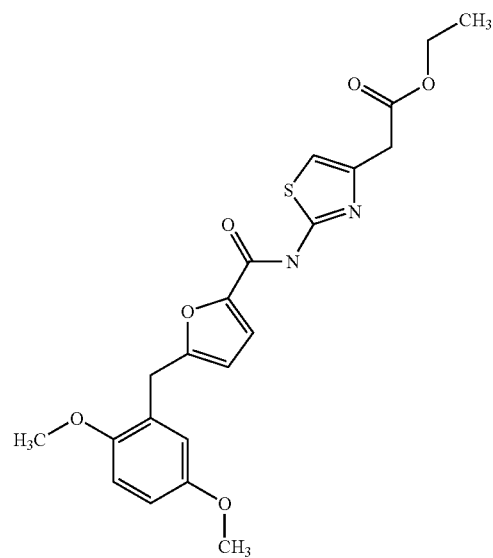 |

| MOLSTRUCTURE |
|---|
| 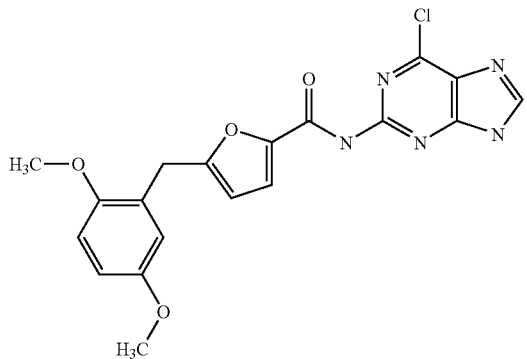 |
| 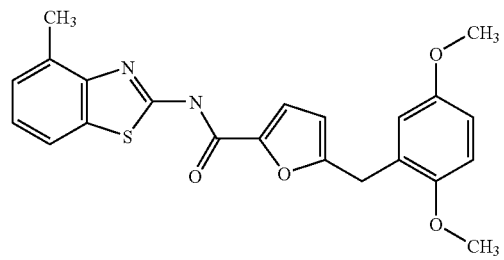 |
| 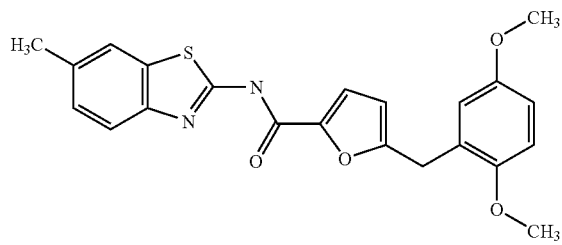 |
| 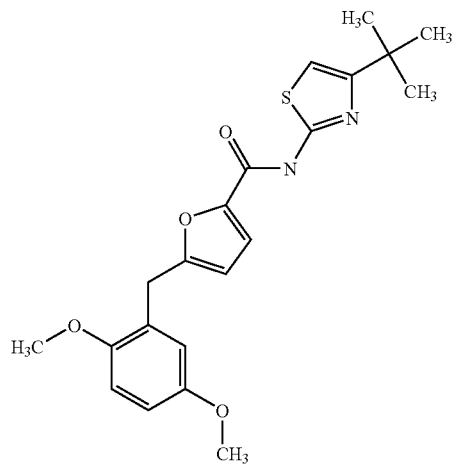 |

| MOLSTRUCTURE |
|---|
| 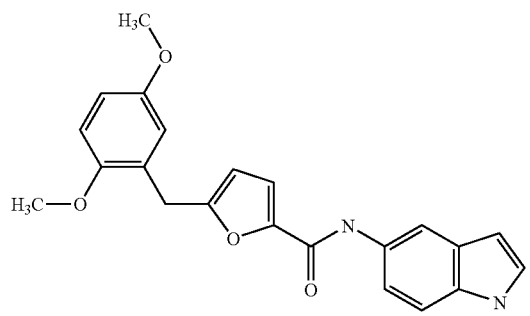 |
| 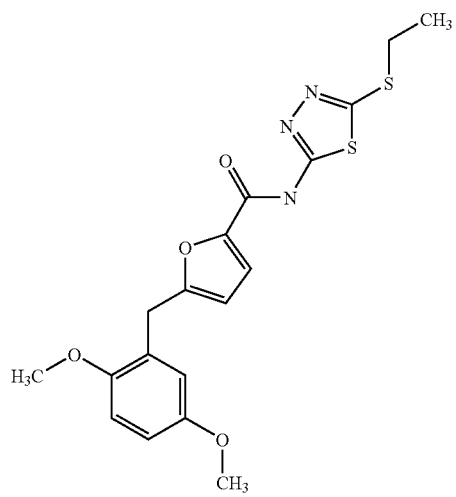 |
| 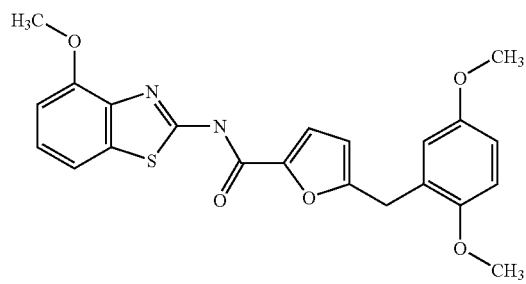 |
| 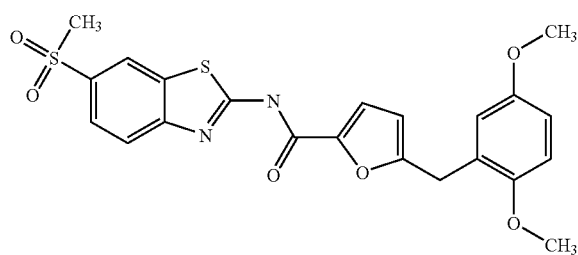 |

-continued
| MOLSTRUCTURE |
| --- |
| 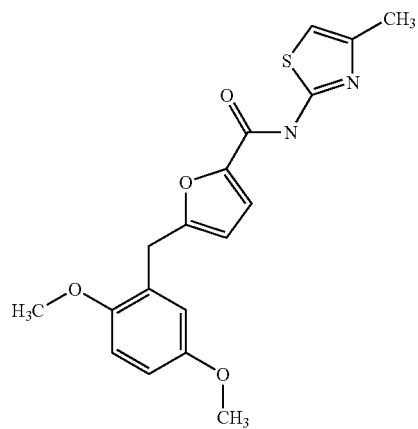 |
| 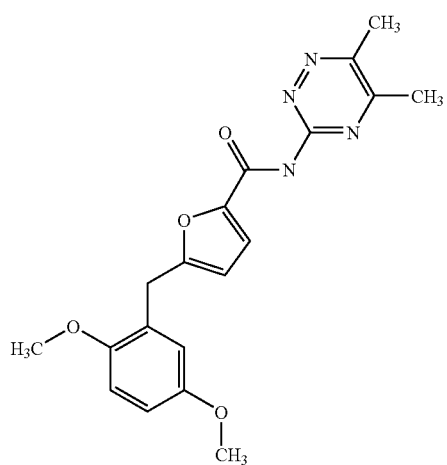 |
| 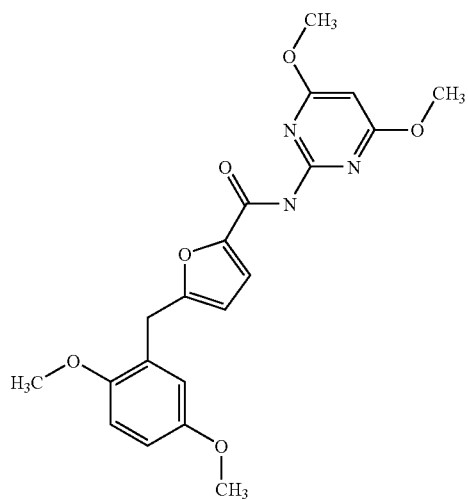 |

-continued
| MOLSTRUCTURE |
|---|
| 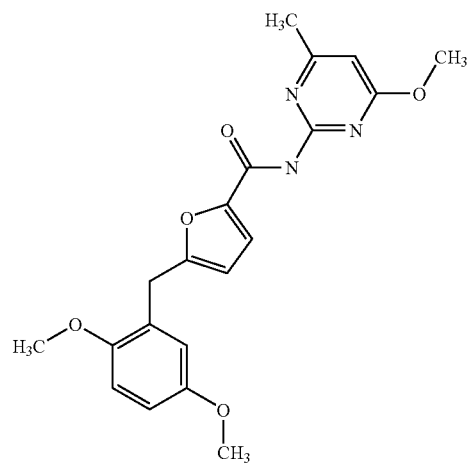 |
| 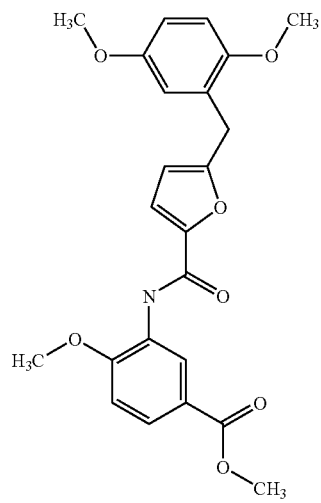 |
| 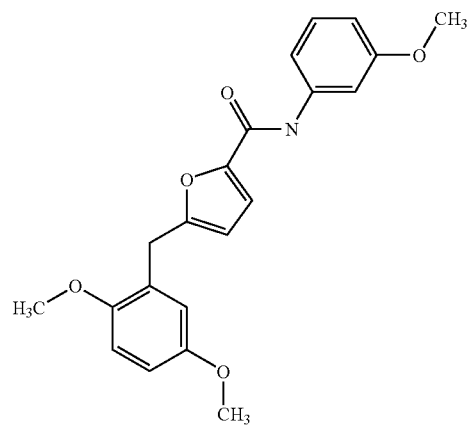 |

-continued
| MOLSTRUCTURE |
| --- |
| 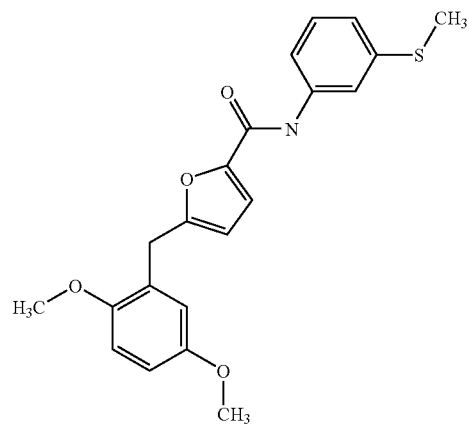 |
| 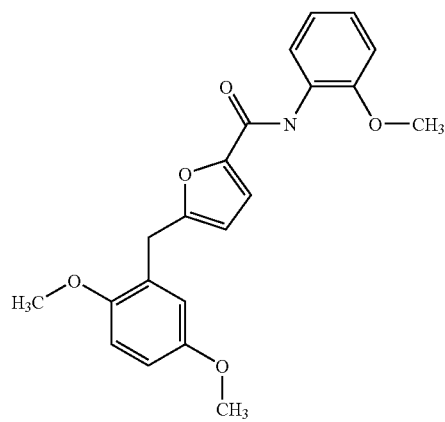 |
| 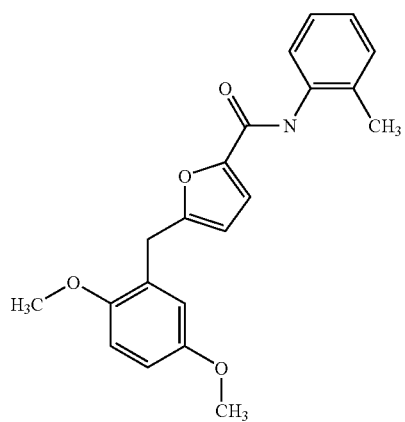 |

| MOLSTRUCTURE |
| --- |
| 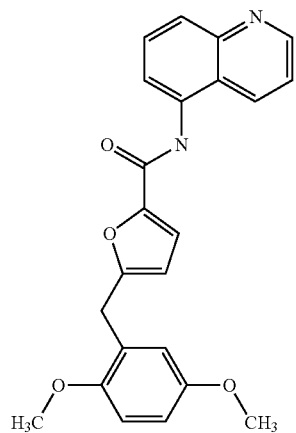 |
| 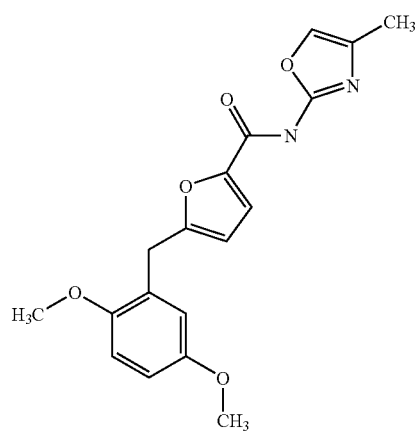 |
| 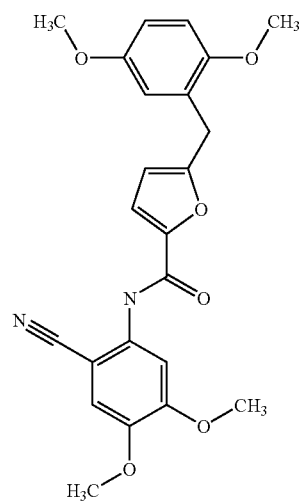 |

-continued
| MOLSTRUCTURE |
|---|
| 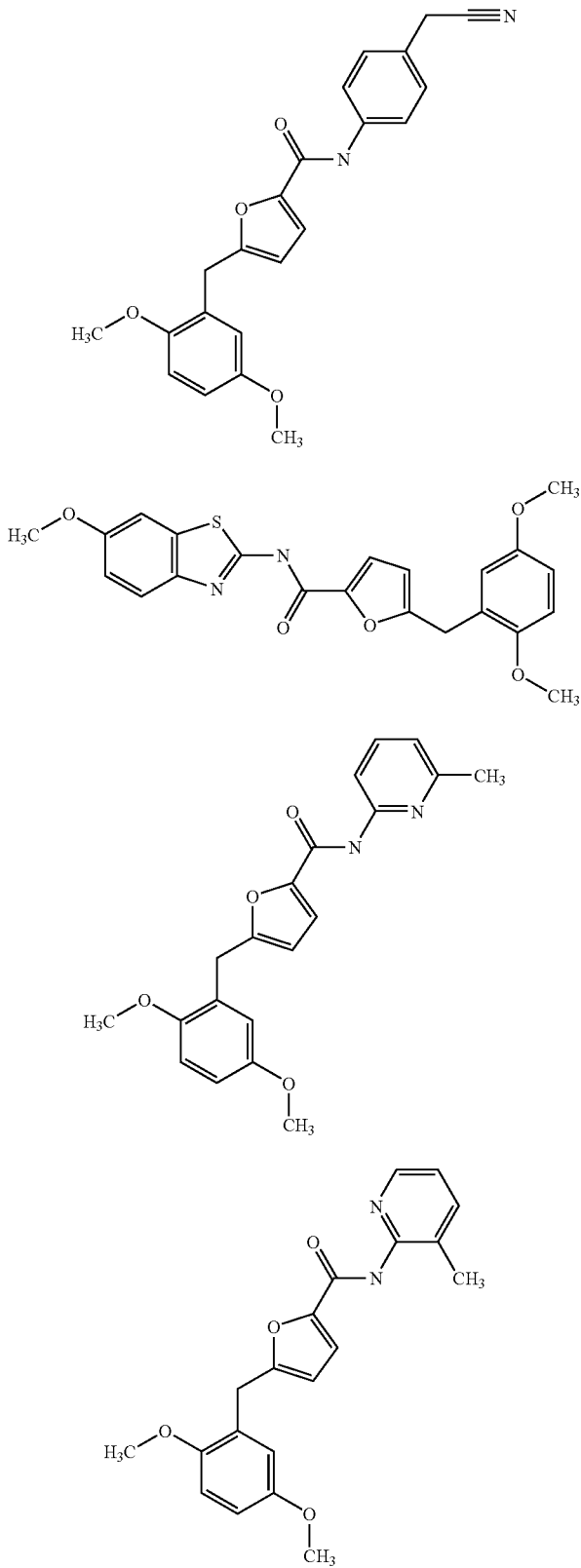 |

| MOLSTRUCTURE |
|---|
| 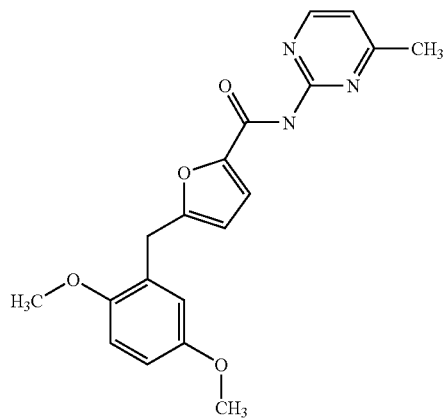 |
| 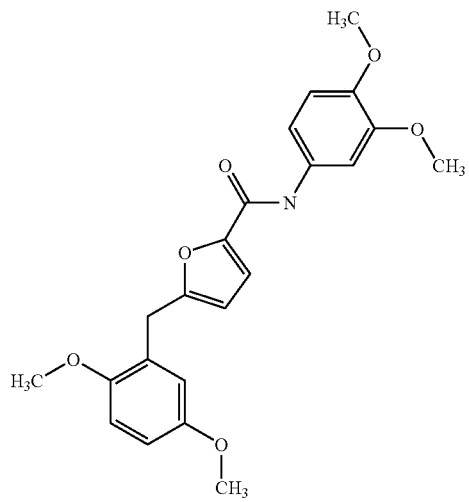 |
| 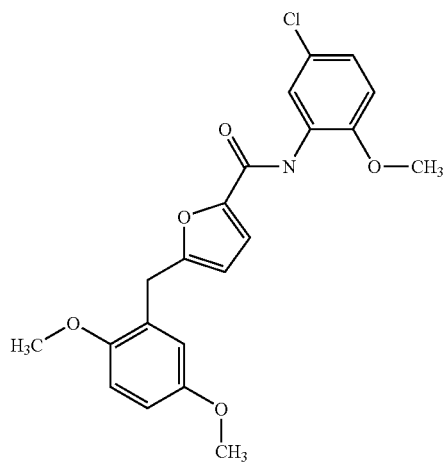 |

| MOLSTRUCTURE |
|---|
| 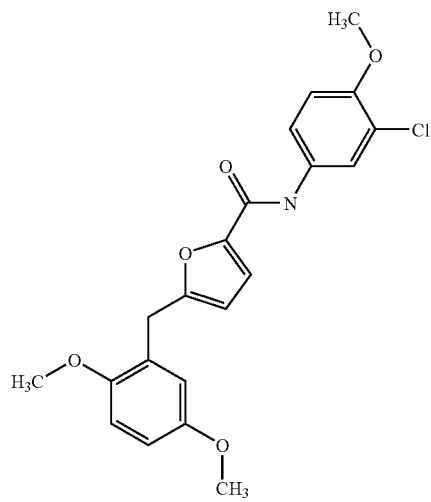 |
| 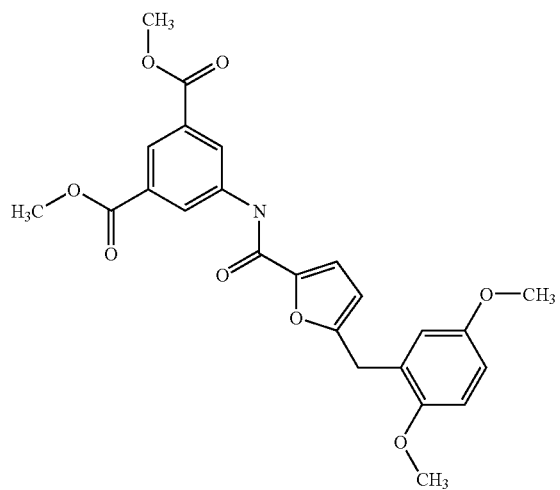 |
| 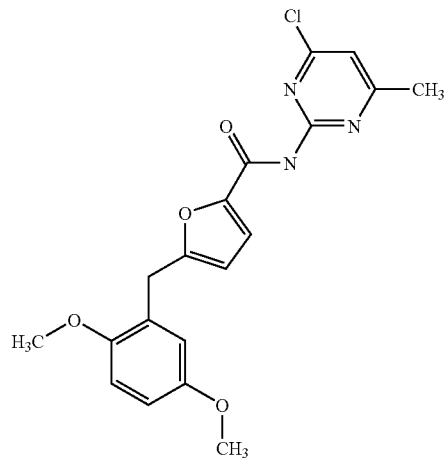 |

-continued
| MOLSTRUCTURE |
|---|
| 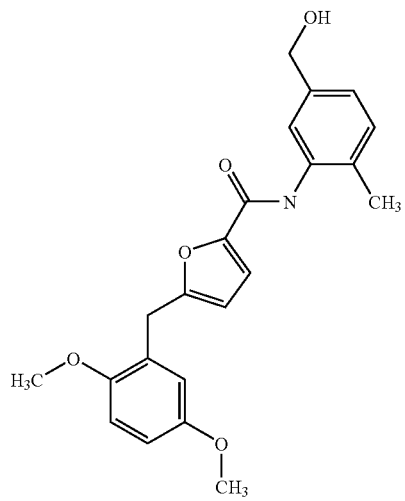 |
| 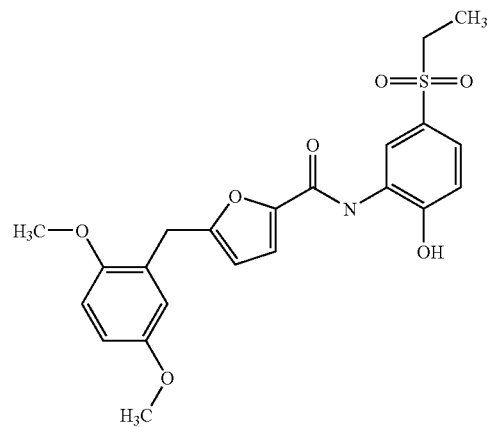 |
| 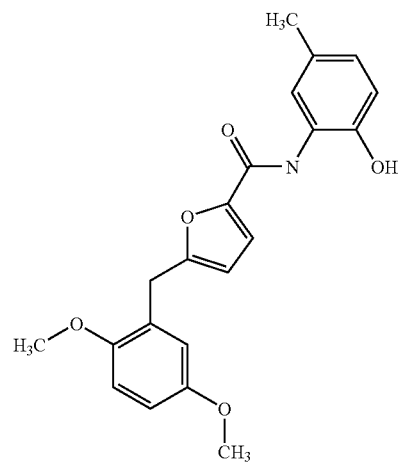 |

| MOLSTRUCTURE |
|---|
| 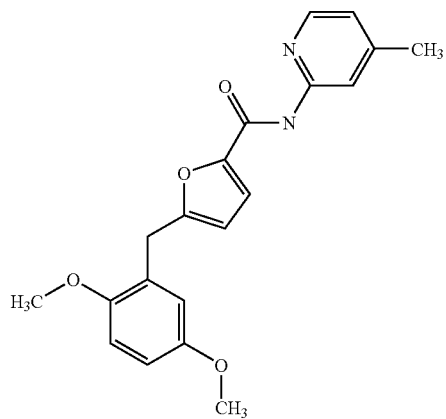 |
| 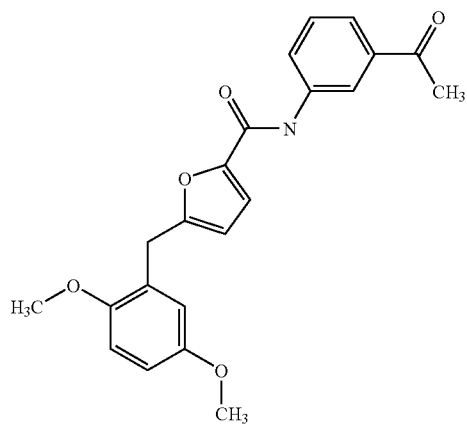 |
| 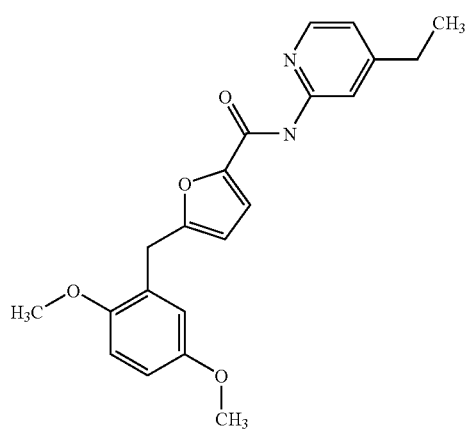 |

-continued
| MOLSTRUCTURE |
|---|
| 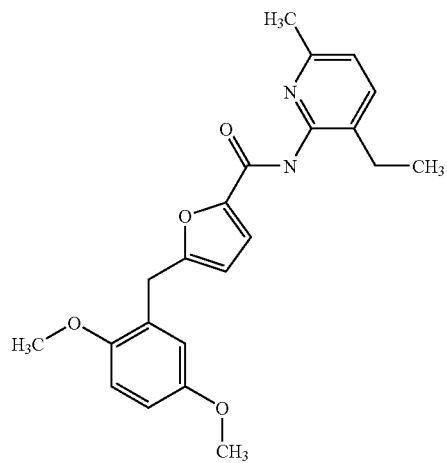 |
| 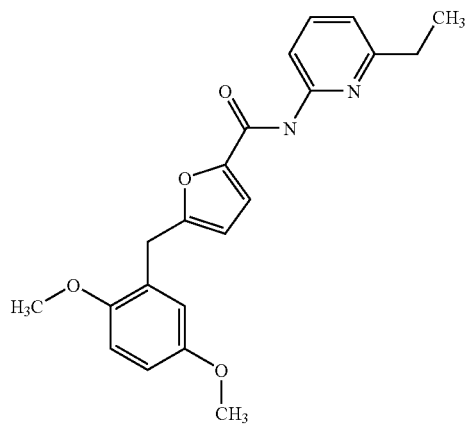 |
| 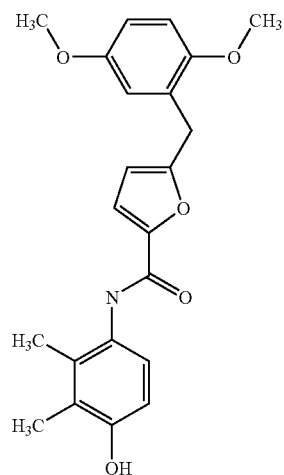 |

-continued
MOLSTRUCTURE
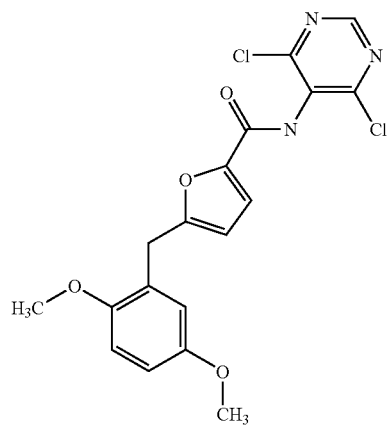
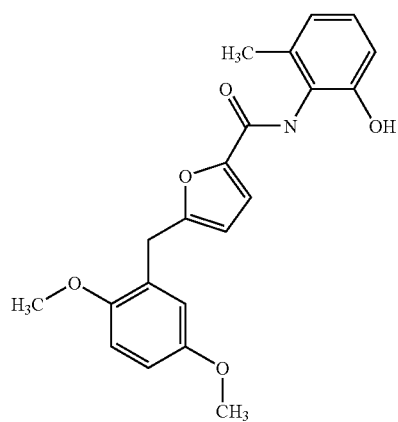
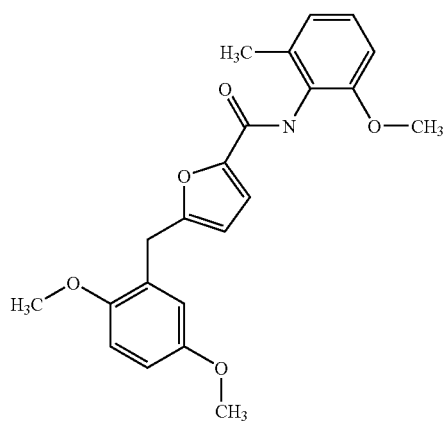

-continued
| MOLSTRUCTURE |
|---|
| 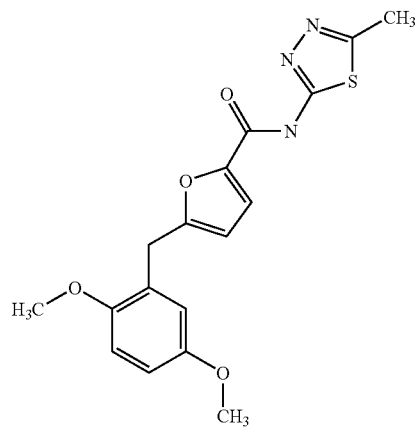 |
| 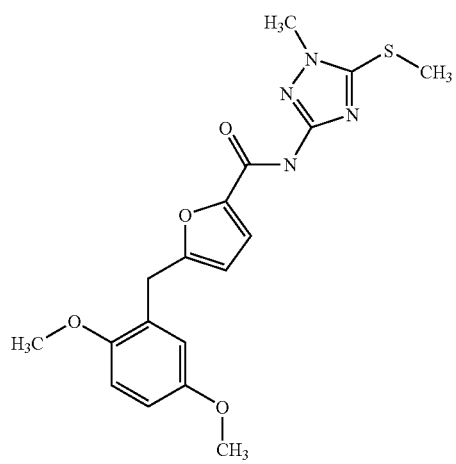 |
| 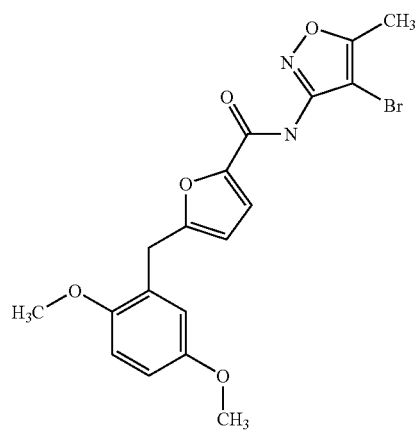 |

| MOLSTRUCTURE |
|---|
| 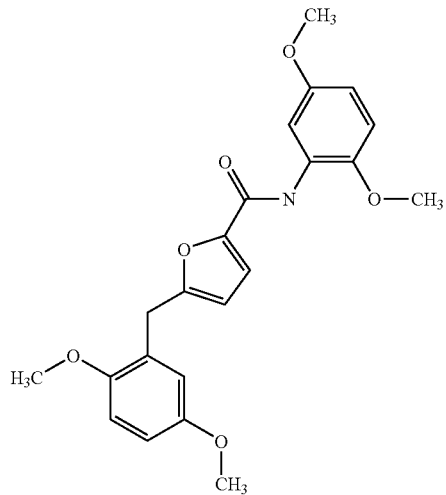 |
| 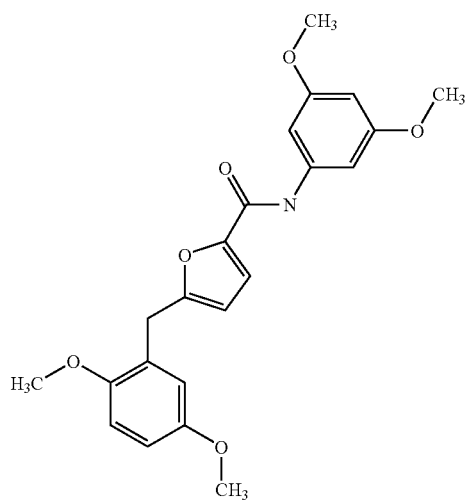 |
| 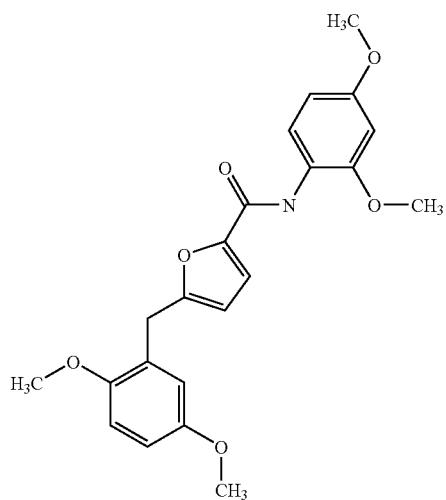 |

-continued
| MOLSTRUCTURE |
|---|
| 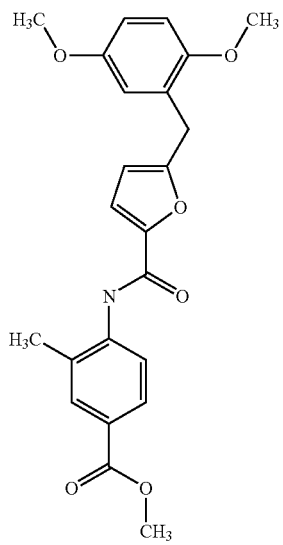 |
| 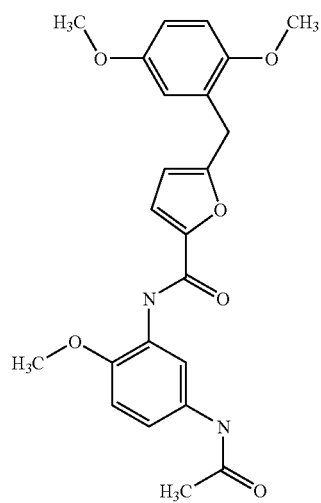 |
| 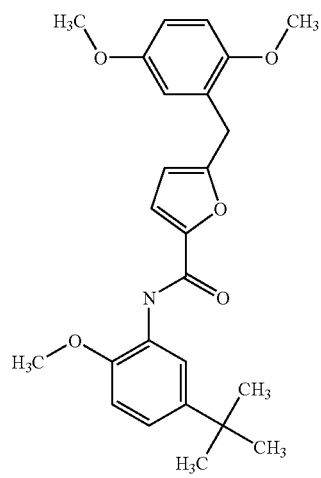 |

-continued
| MOLSTRUCTURE |
|---|
| 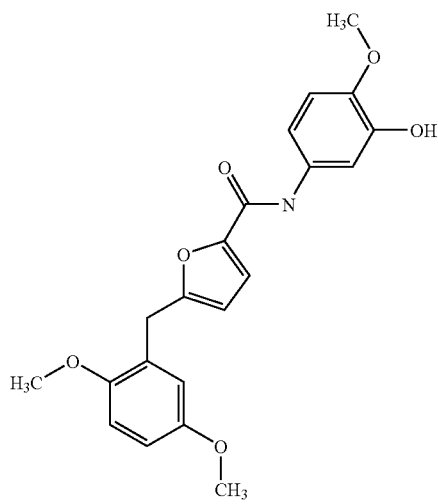 |
| 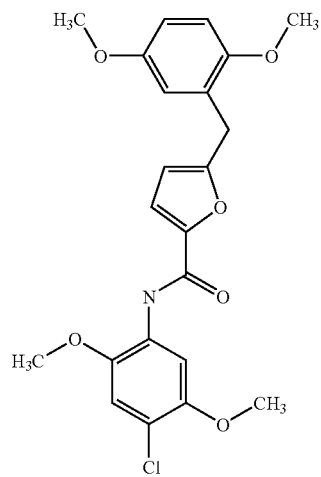 |
| 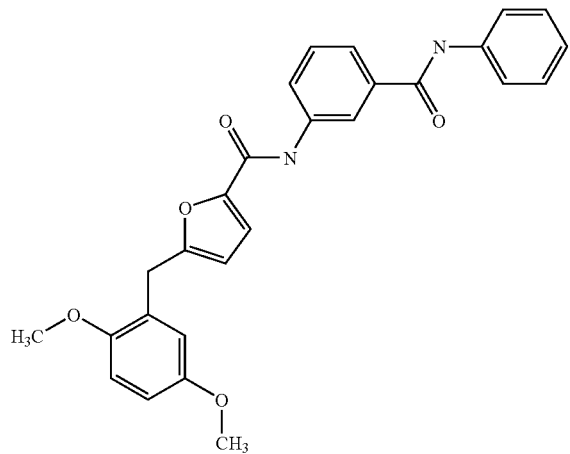 |

-continued
MOLSTRUCTURE
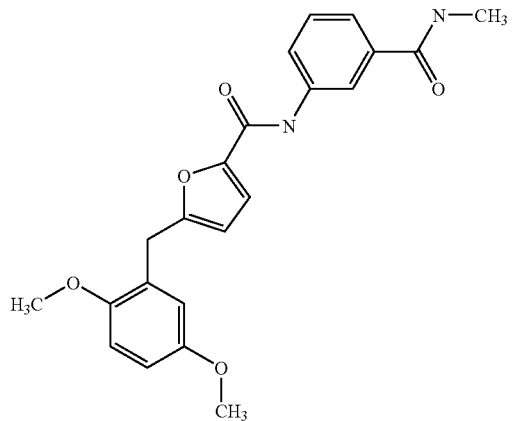
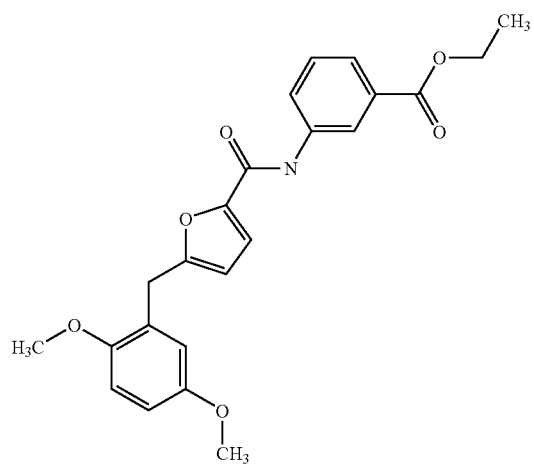
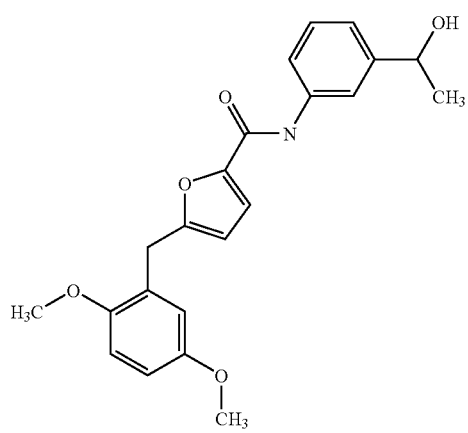

-continued
| MOLSTRUCTURE |
|---|
| 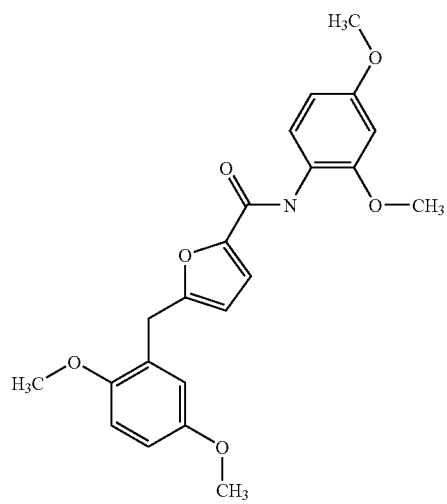 |
| 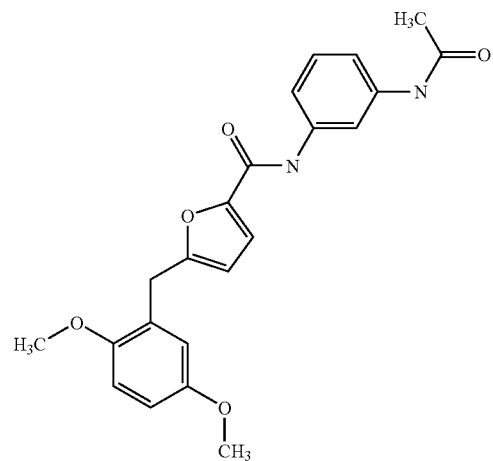 |
| 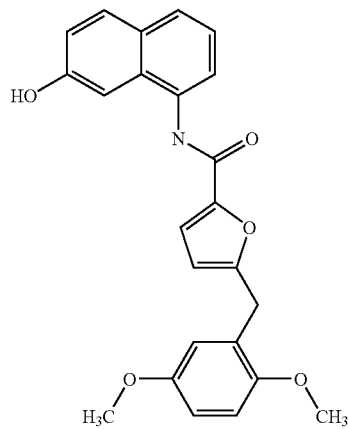 |

| MOLSTRUCTURE |
|---|
| 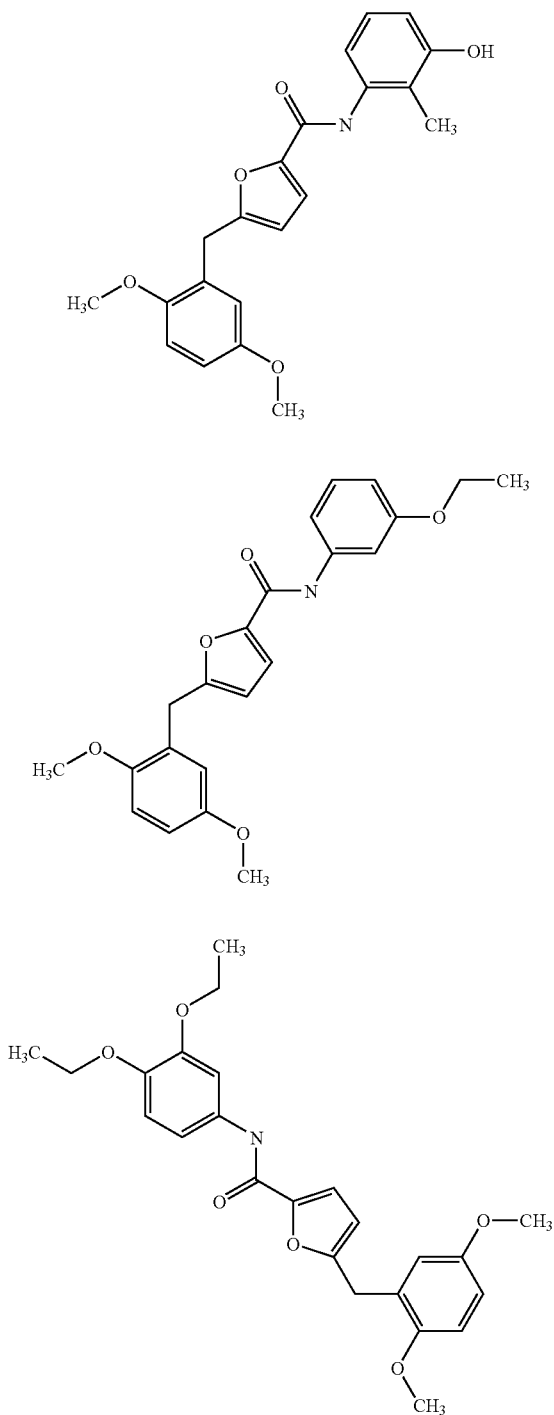 |

-continued
| MOLSTRUCTURE |
|---|
| 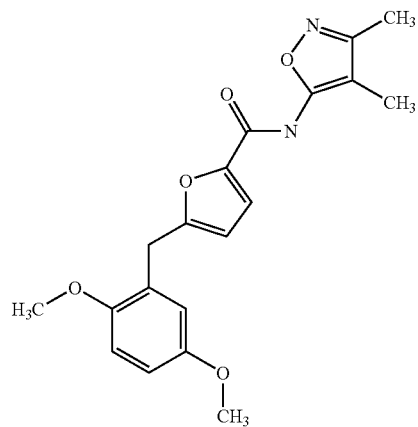 |
| 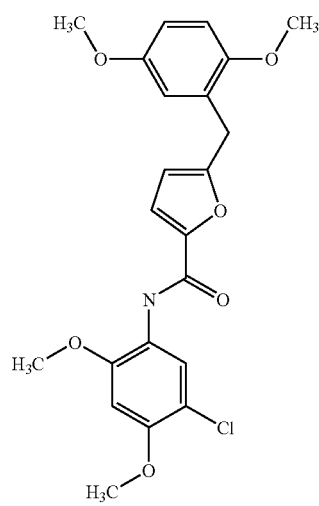 |
| 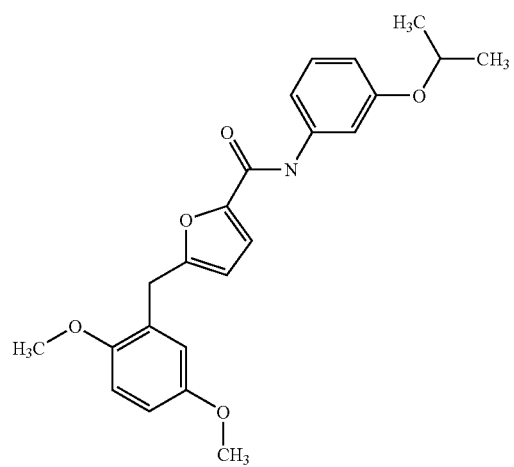 |

-continued
| MOLSTRUCTURE |
| --- |
| 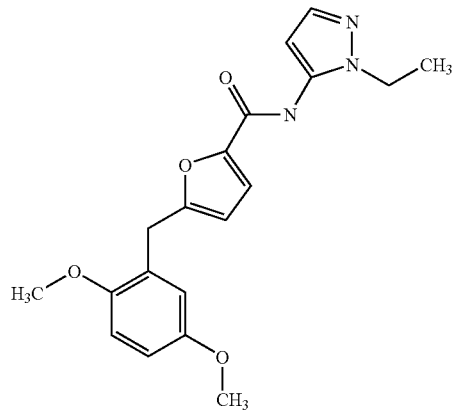 |
| 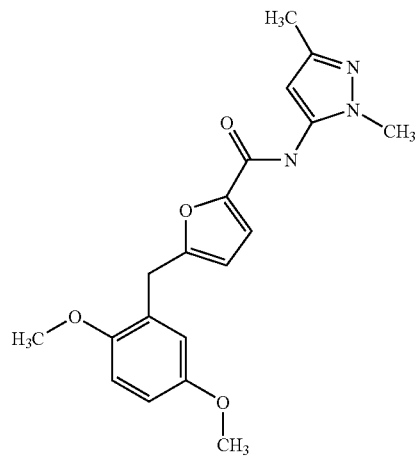 |
| 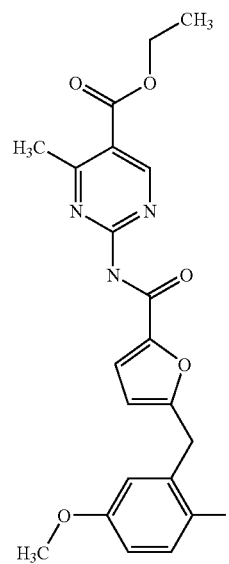 |

| MOLSTRUCTURE |
|---|
| 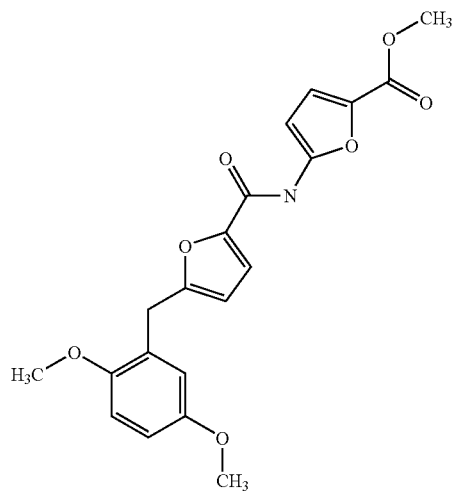 |
| 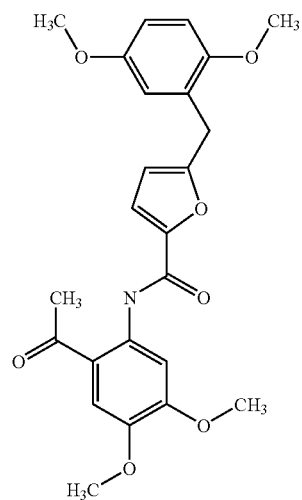 |
| 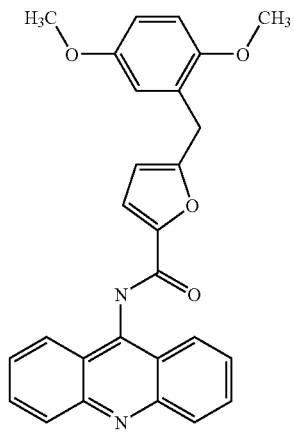 |

| MOLSTRUCTURE |
|---|
| 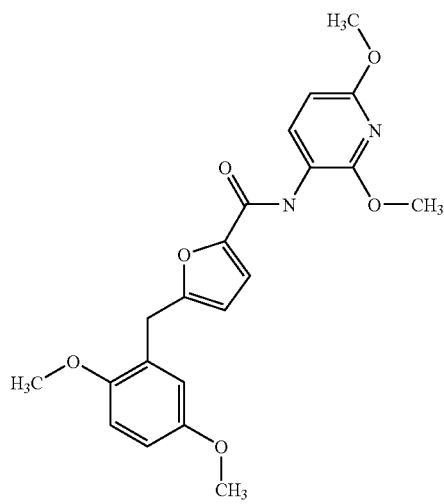 |
| 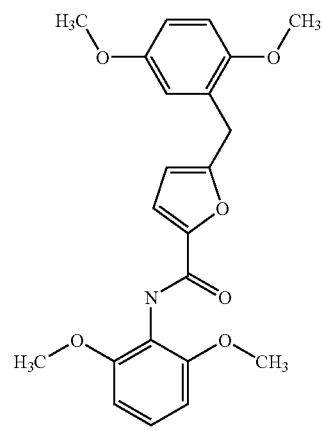 |
| 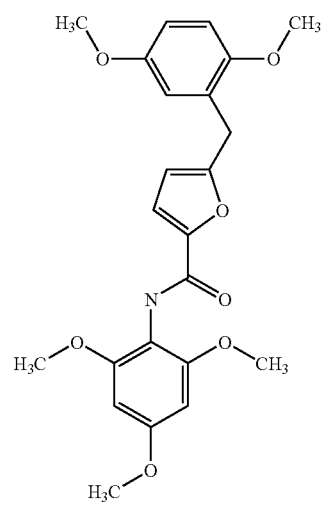 |

-continued
| MOLSTRUCTURE |
| --- |
| 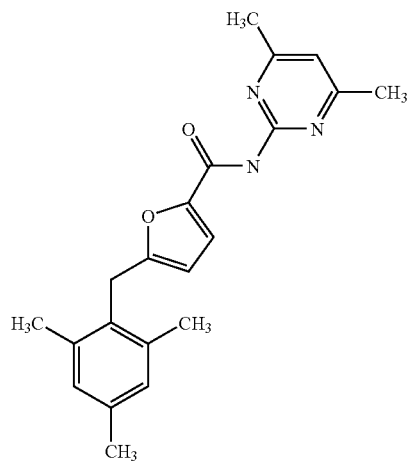 |
| 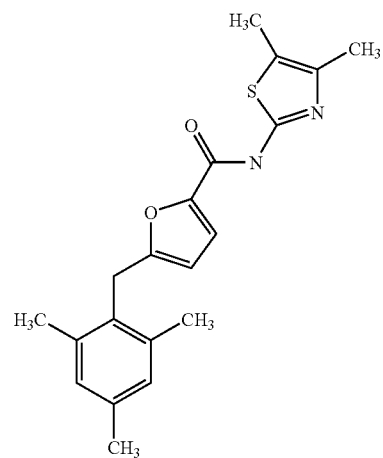 |
| 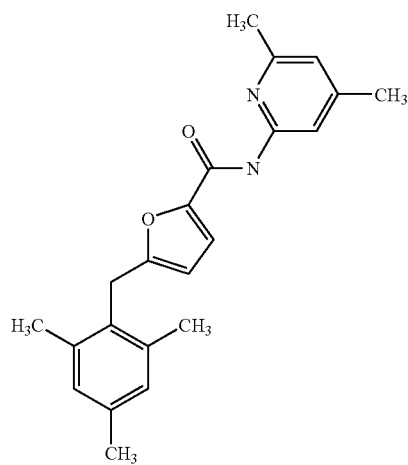 |

-continued
| MOLSTRUCTURE |
|---|
| 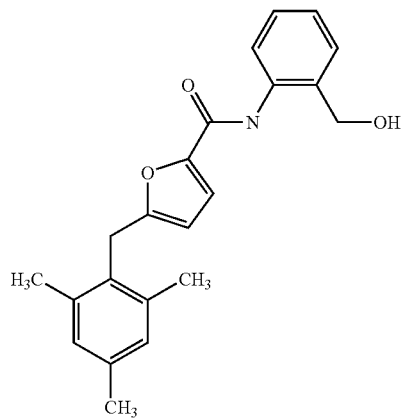 |
| 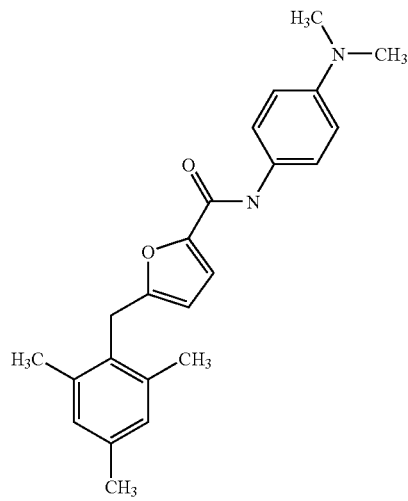 |
| 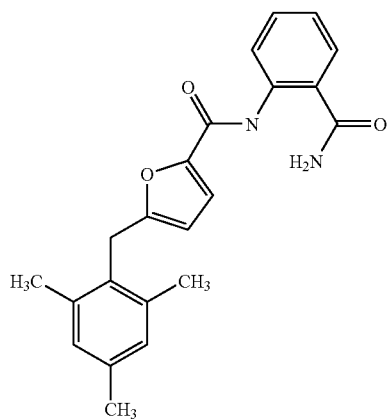 |

| MOLSTRUCTURE |
| --- |
| 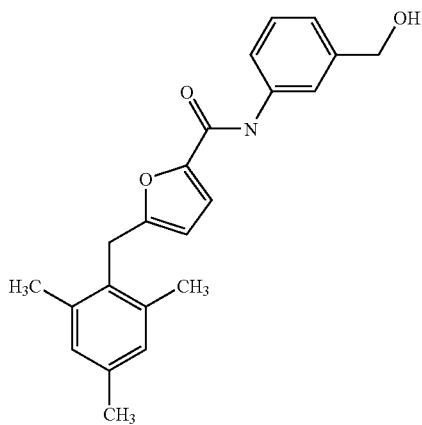 |
| 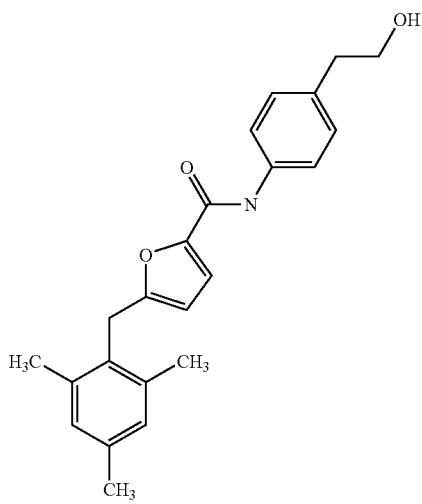 |
| 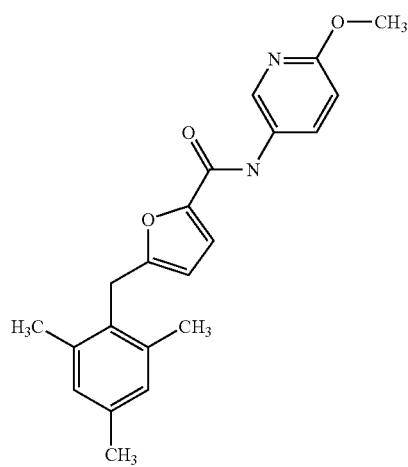 |

-continued
| MOLSTRUCTURE |
| --- |
| 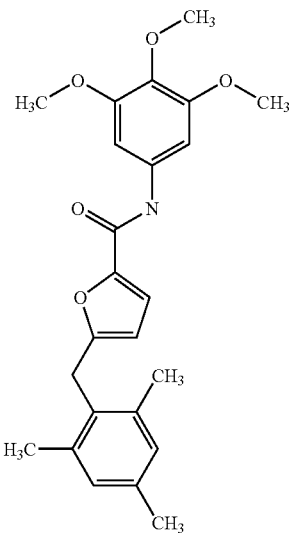 |
| 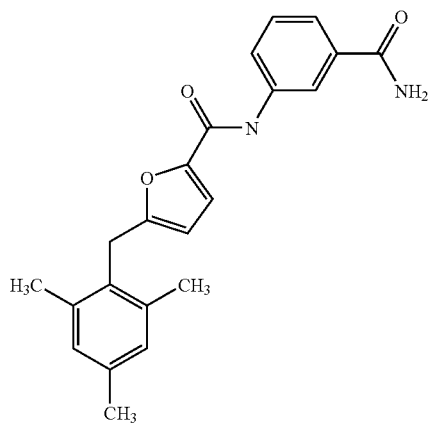 |
| 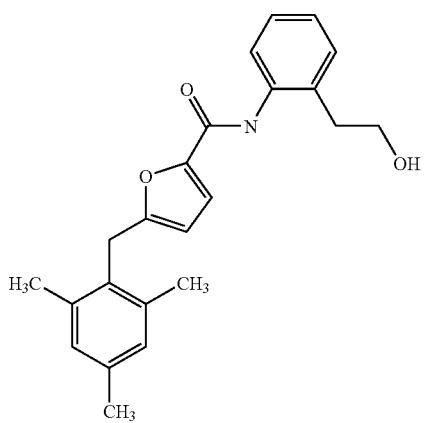 |

-continued
| MOLSTRUCTURE |
| --- |
| 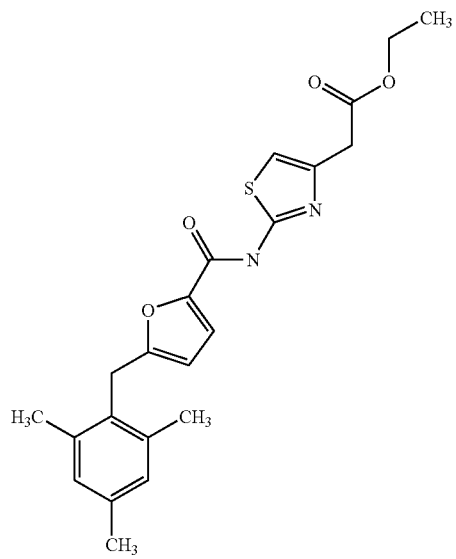 |
| 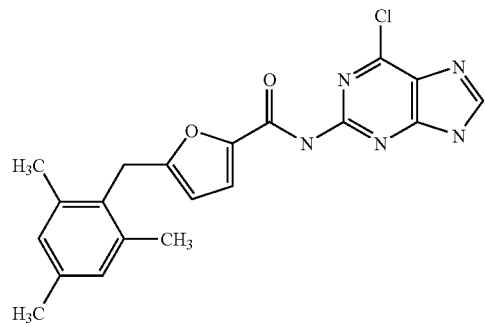 |
| 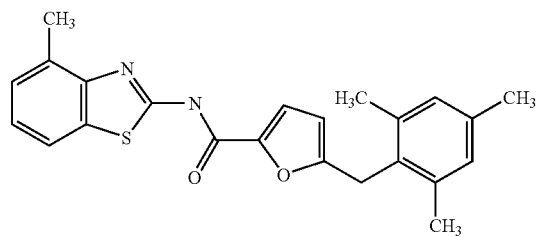 |
| 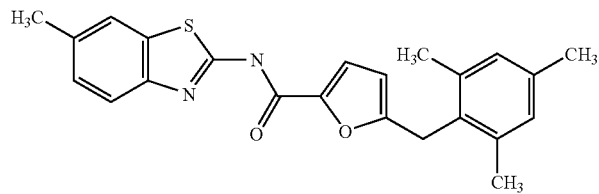 |

| MOLSTRUCTURE |
|---|
| 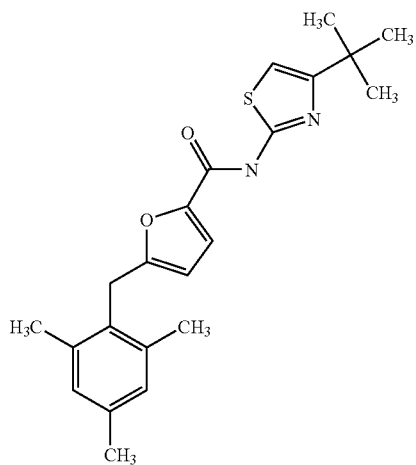 |
| 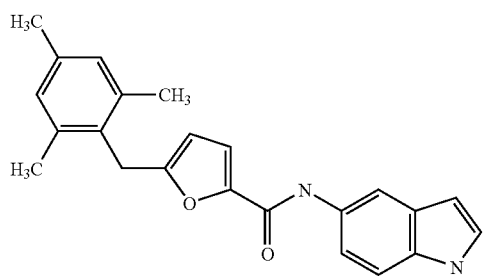 |
| 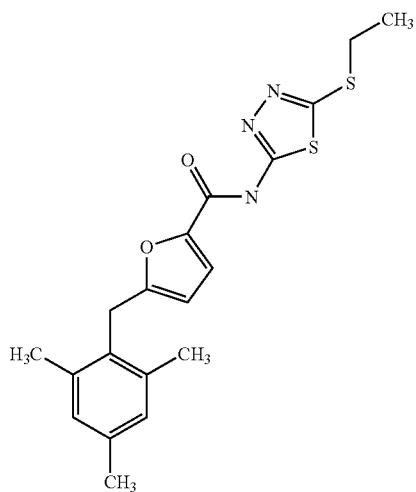 |
| 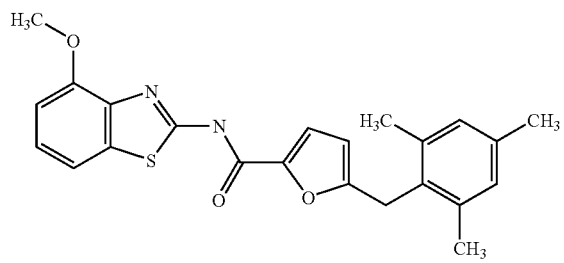 |

-continued
MOLSTRUCTURE
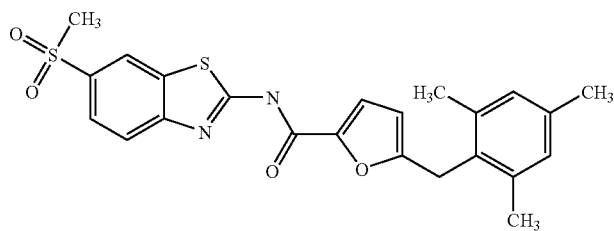
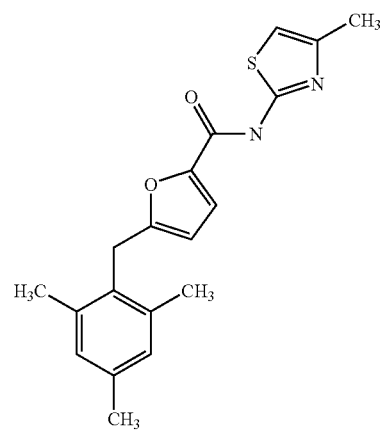
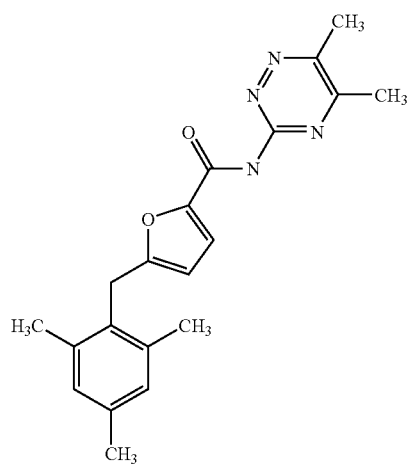

-continued
| MOLSTRUCTURE |
|---|
| 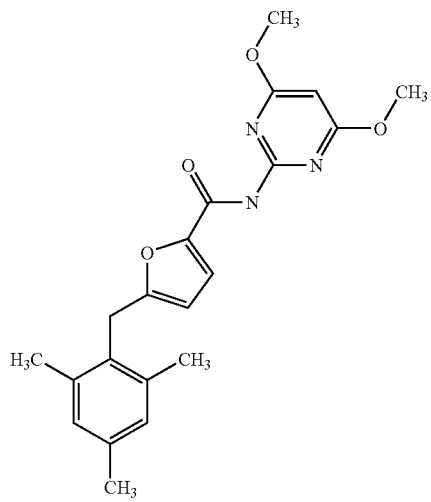 |
| 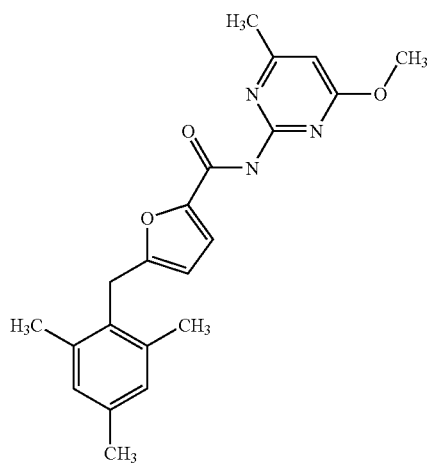 |
| 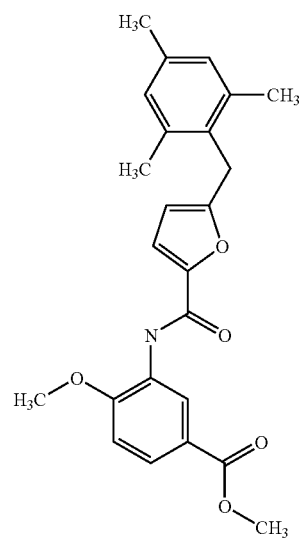 |

-continued
| MOLSTRUCTURE |
|---|
| 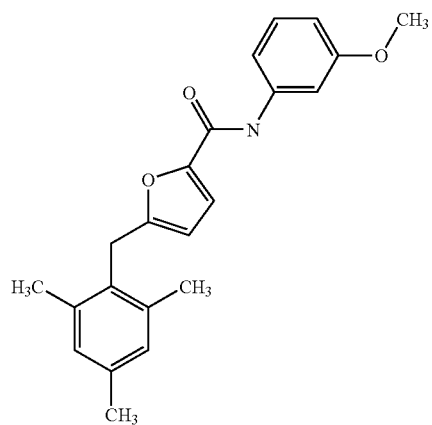 |
| 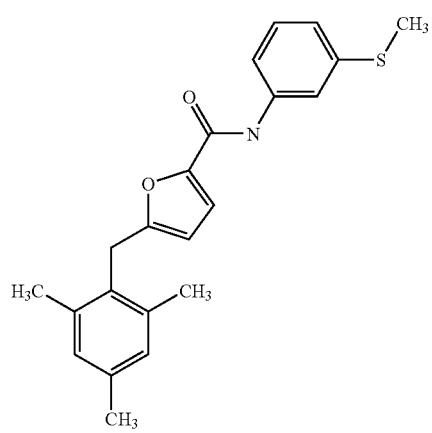 |
| 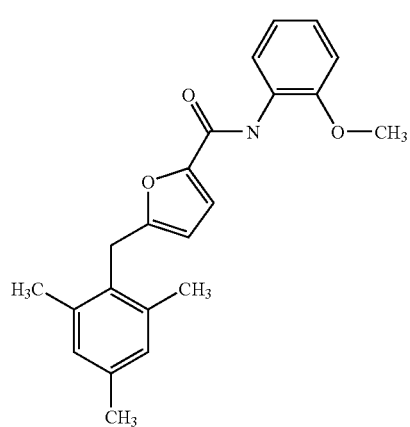 |

-continued
| MOLSTRUCTURE |
|---|
| 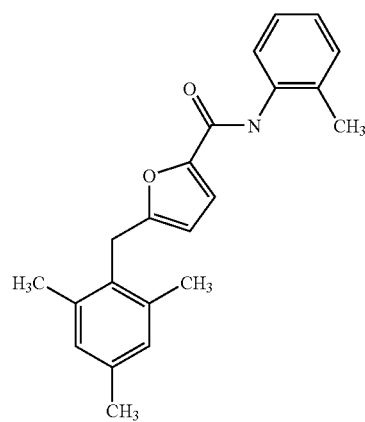 |
| 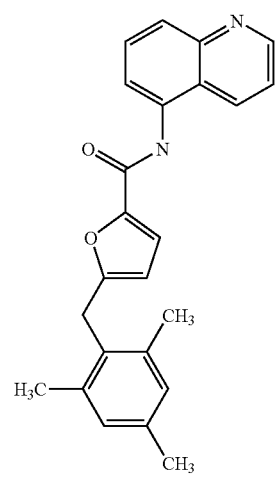 |
| 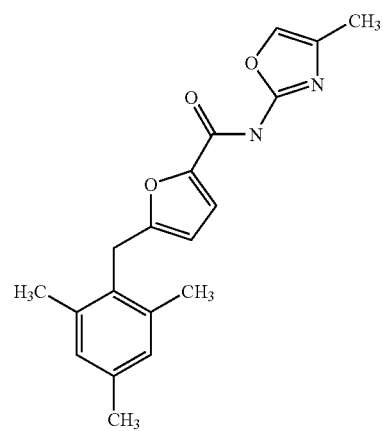 |

| MOLSTRUCTURE |
|---|
| 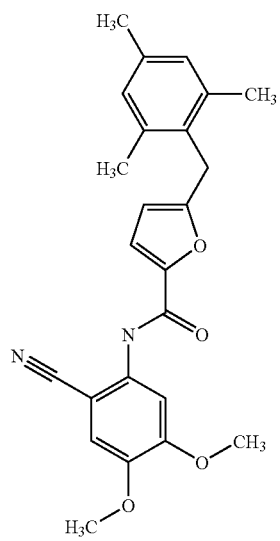 |
| 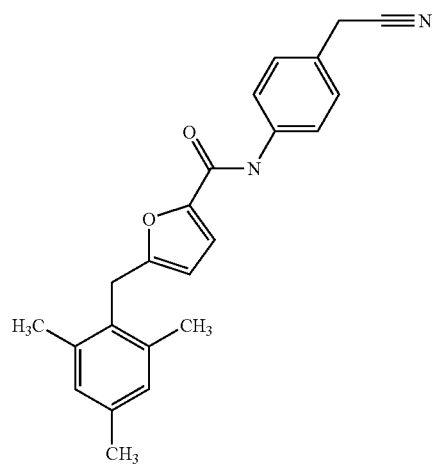 |
| 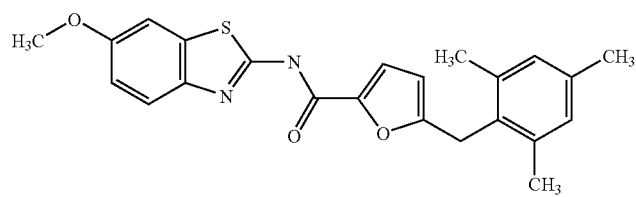 |

-continued
| MOLSTRUCTURE |
|---|
| 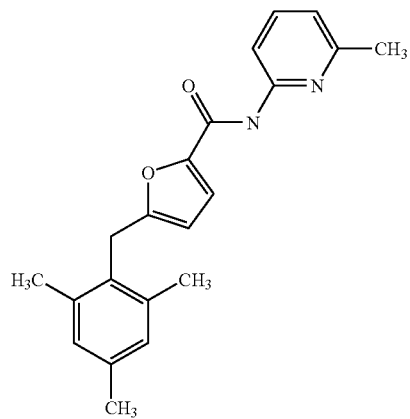 |
| 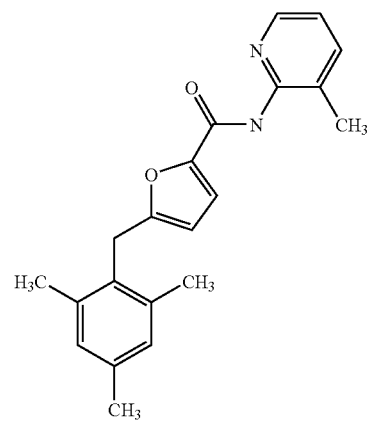 |
| 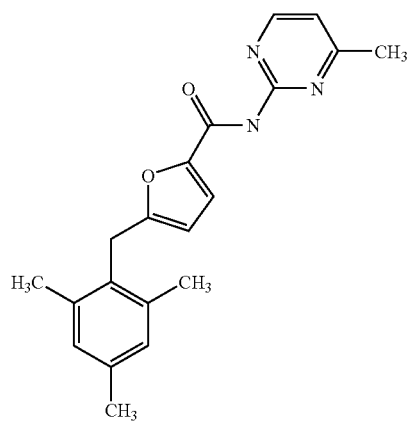 |

-continued
MOLSTRUCTURE
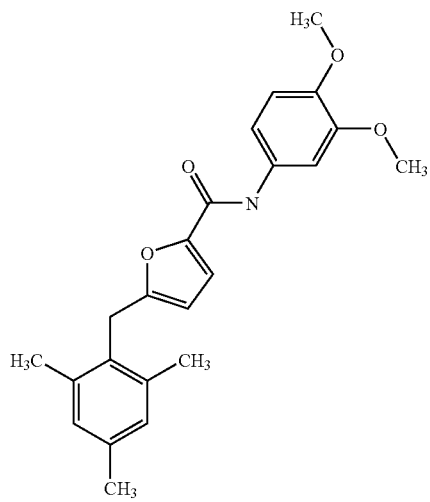
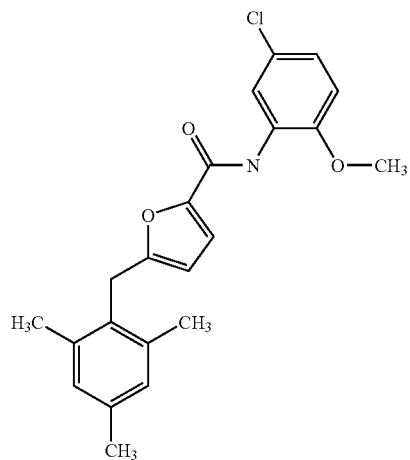
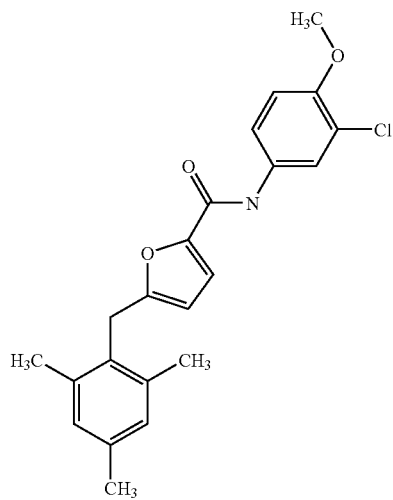

-continued
| MOLSTRUCTURE |
|---|
| 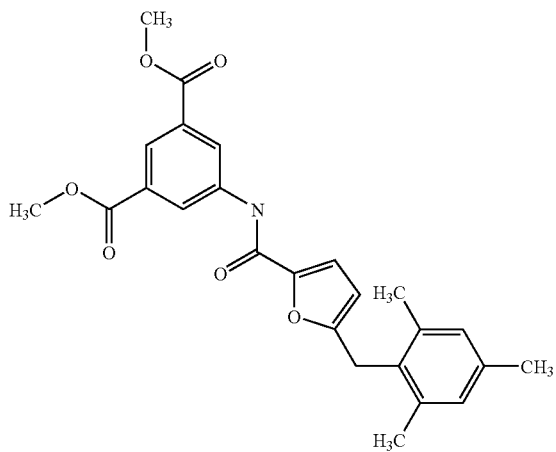 |
| 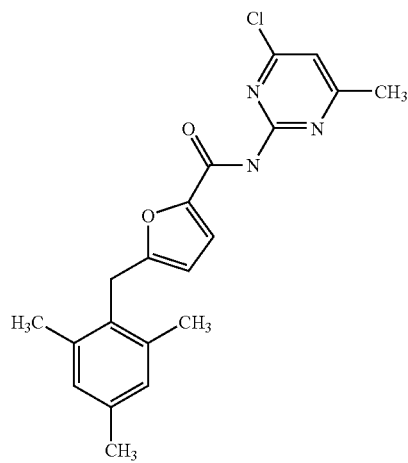 |
| 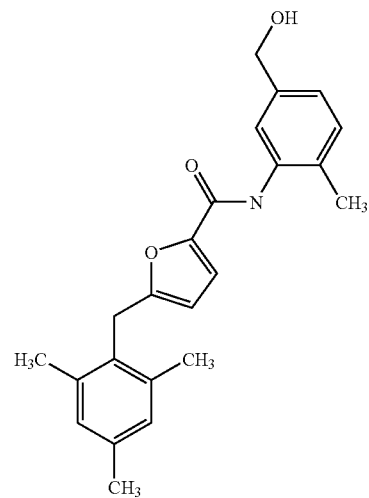 |

-continued
| MOLSTRUCTURE |
|---|
| 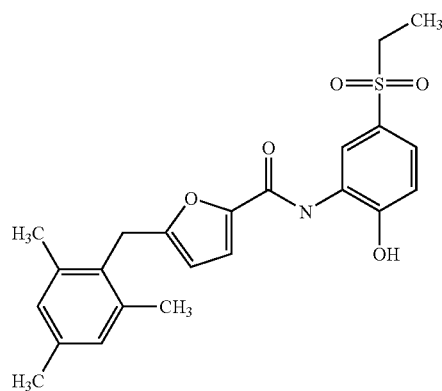 |
| 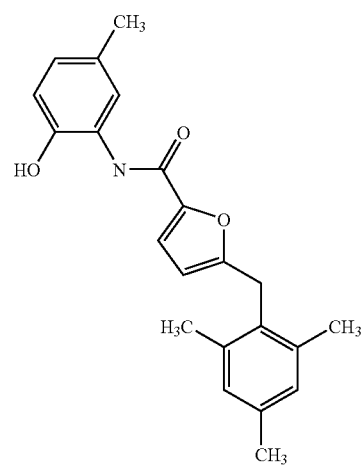 |
| 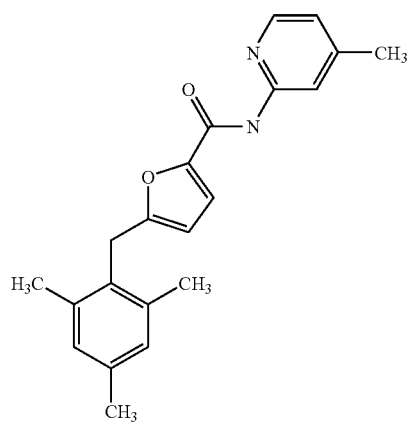 |

-continued
| MOLSTRUCTURE |
|---|
| 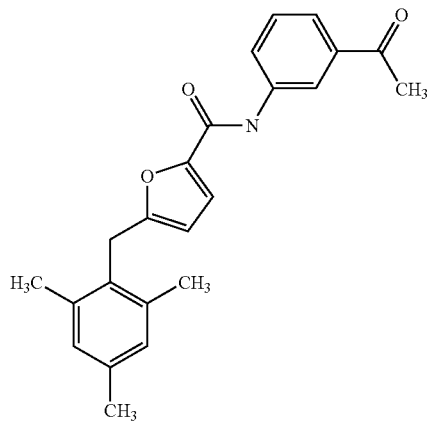 |
| 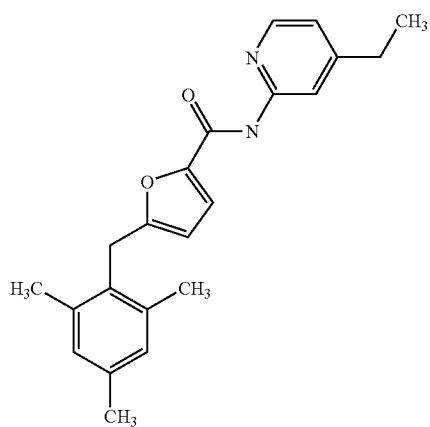 |
| 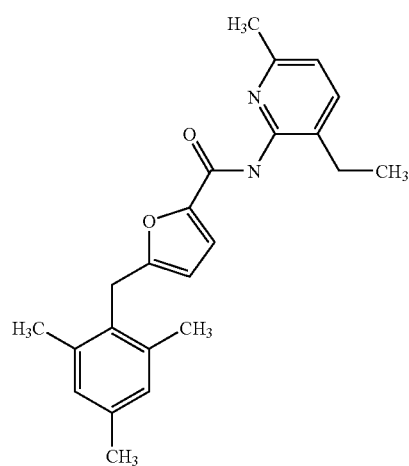 |

-continued
| MOLSTRUCTURE |
|---|
| 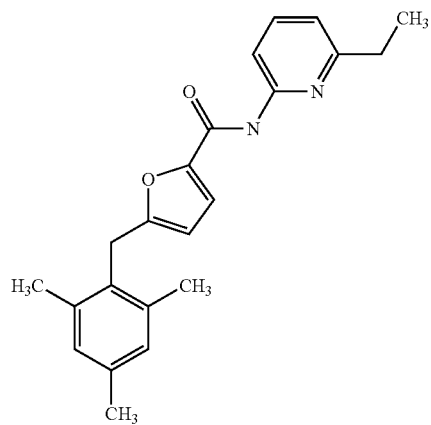 |
| 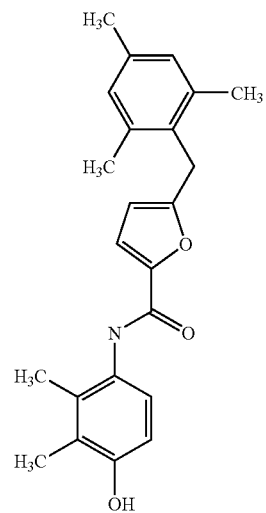 |
| 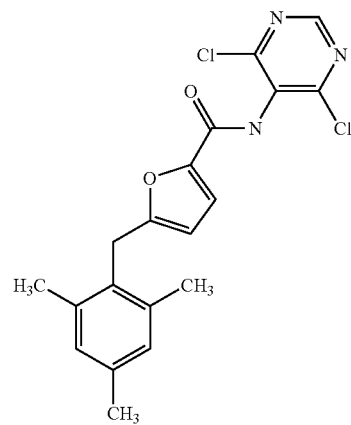 |

-continued
| MOLSTRUCTURE |
|---|
| 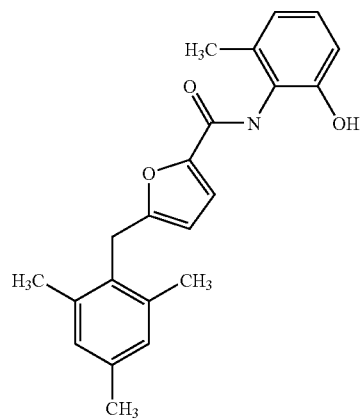 |
| 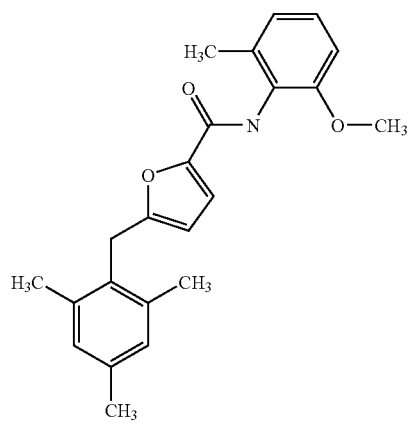 |
| 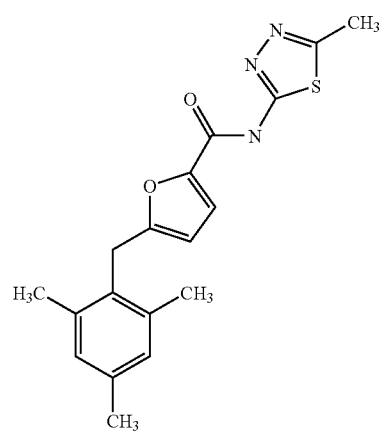 |

| MOLSTRUCTURE |
| --- |
| 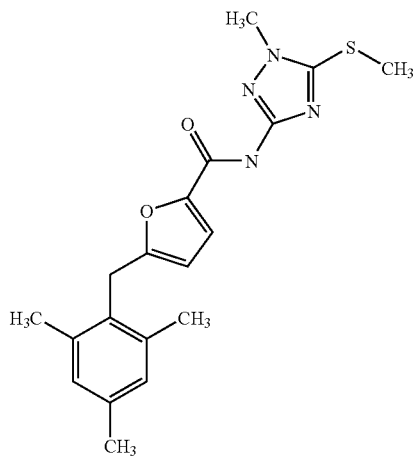 |
| 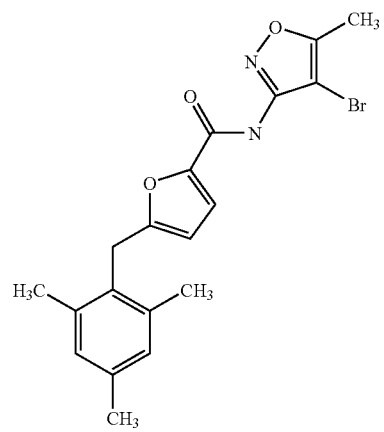 |
| 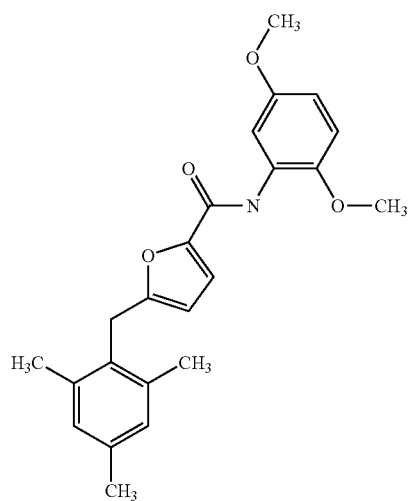 |

-continued
| MOLSTRUCTURE |
|---|
| 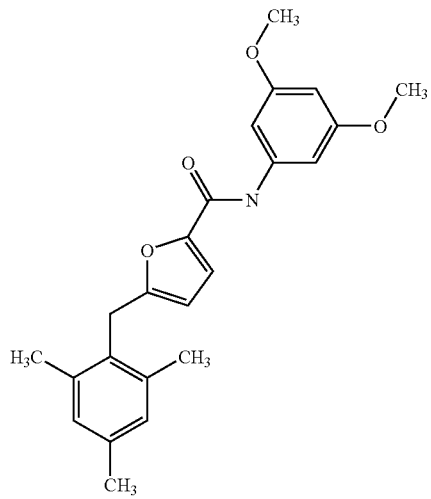 |
| 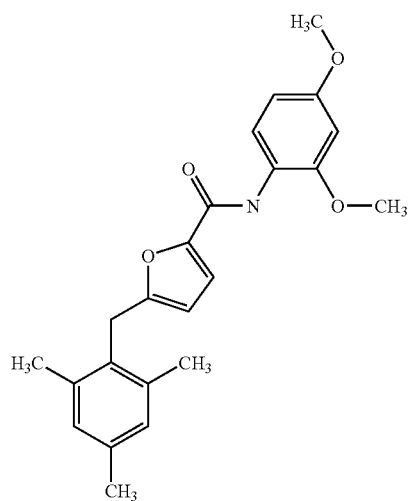 |
| 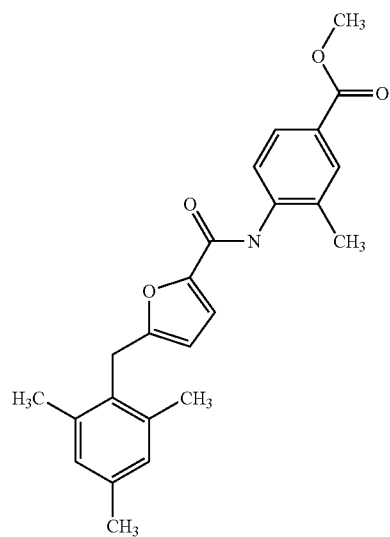 |

-continued
| MOLSTRUCTURE |
|---|
| 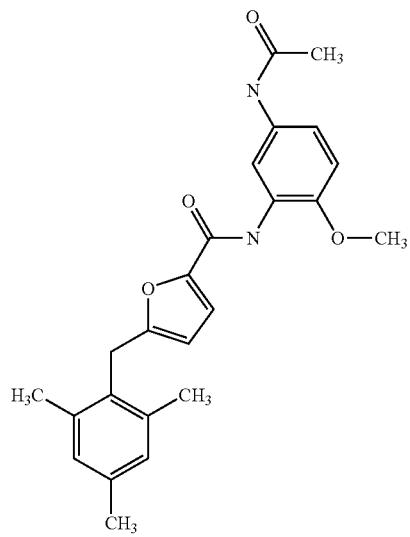 |
| 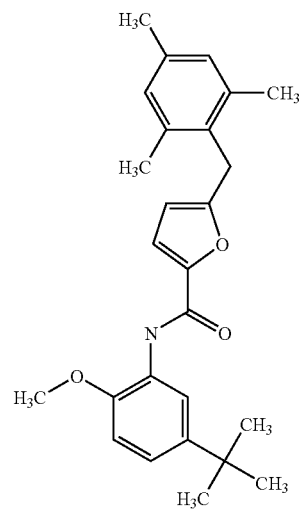 |
| 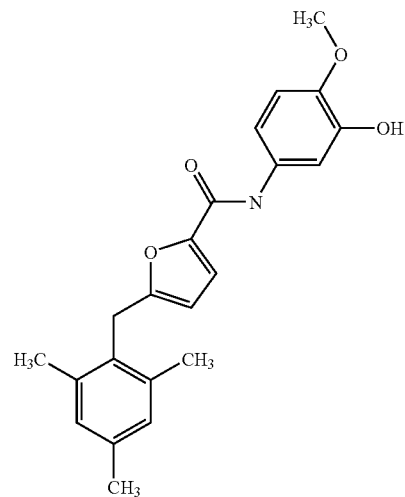 |

-continued
| MOLSTRUCTURE |
|---|
| 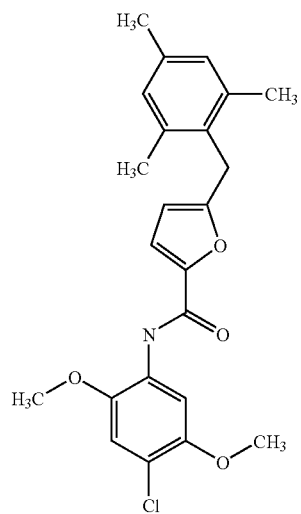 |
| 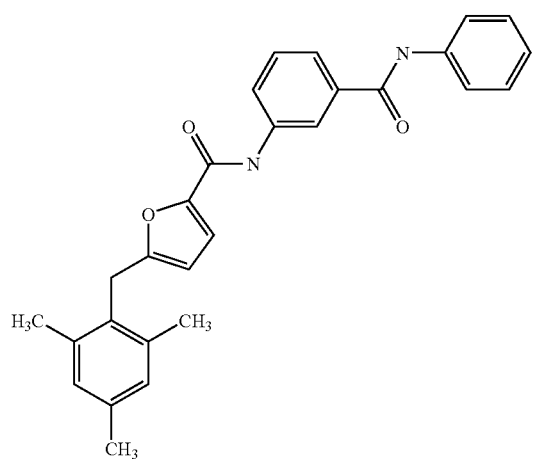 |
| 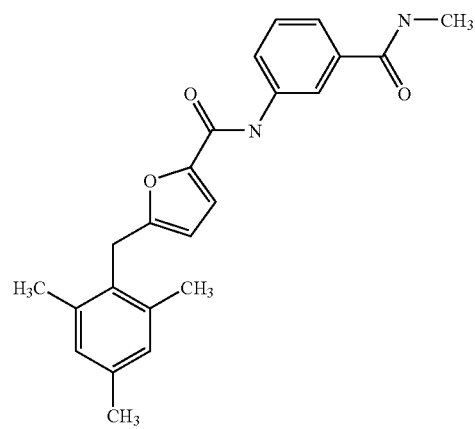 |

| MOLSTRUCTURE |
| --- |
| 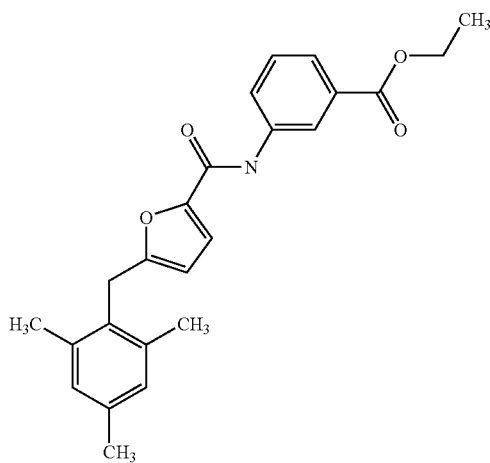 |
| 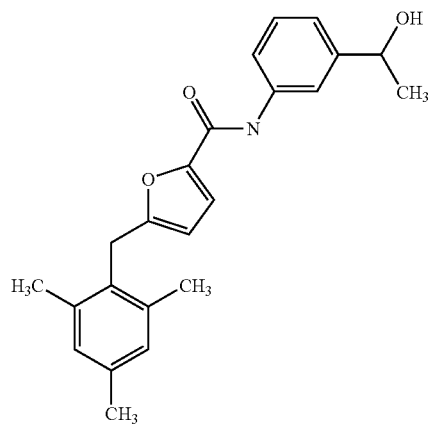 |
| 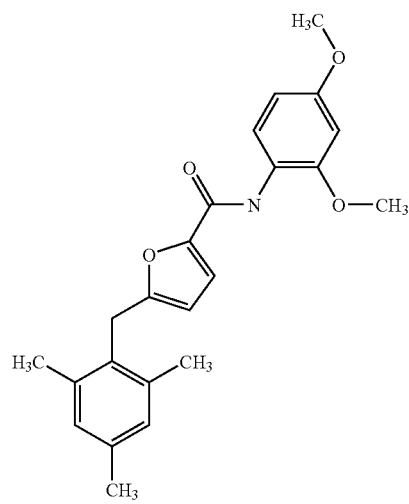 |

| MOLSTRUCTURE |
| --- |
| 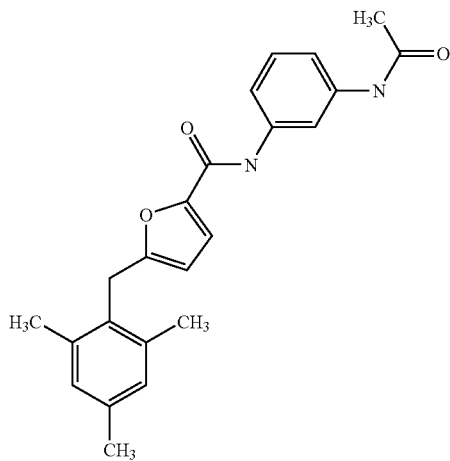 |
| 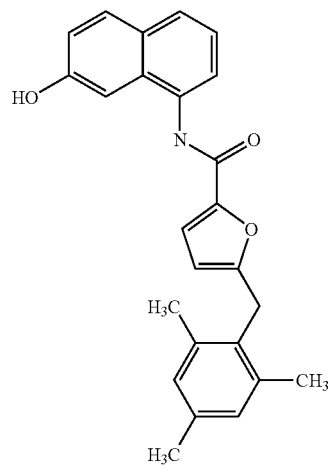 |
| 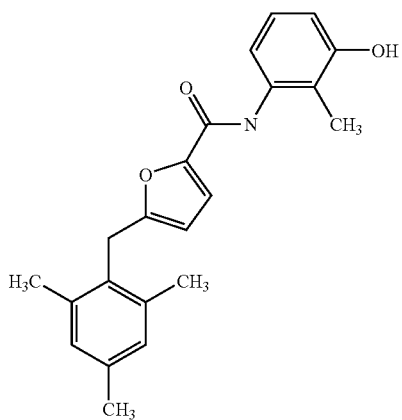 |

-continued
| MOLSTRUCTURE |
|---|
| 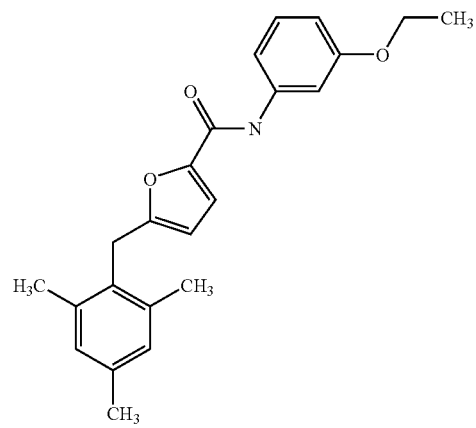 |
| 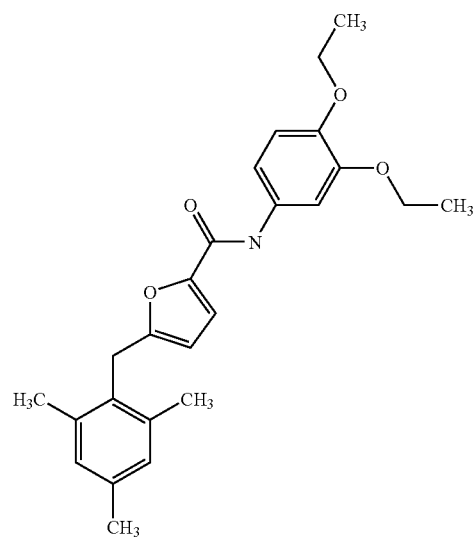 |
| 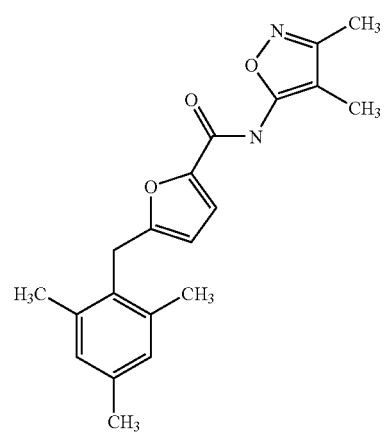 |

-continued
MOLSTRUCTURE
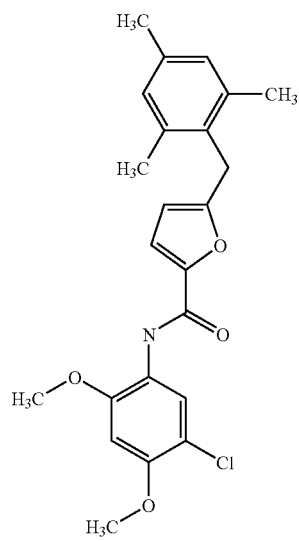
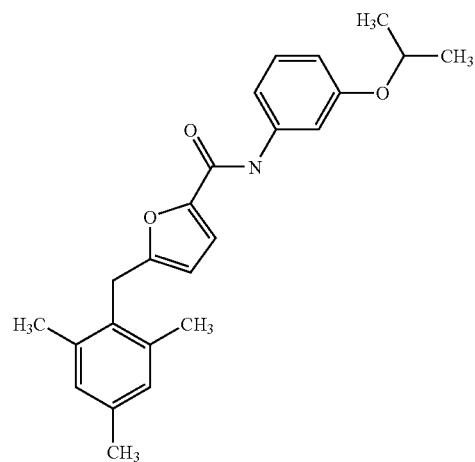
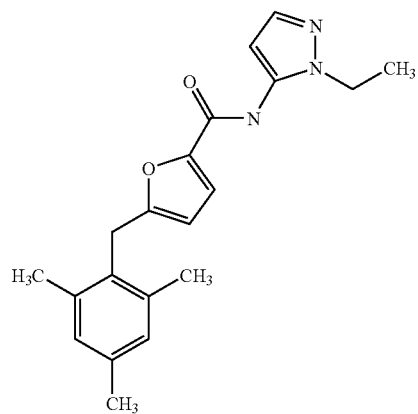

-continued
MOLSTRUCTURE
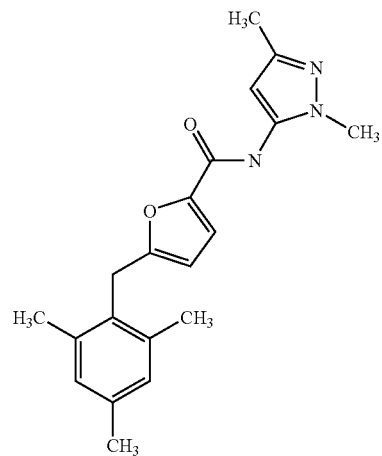
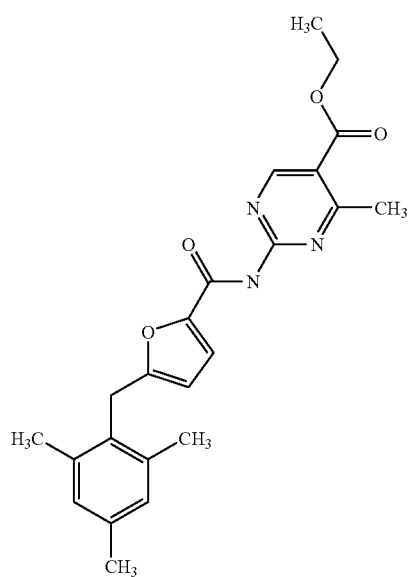
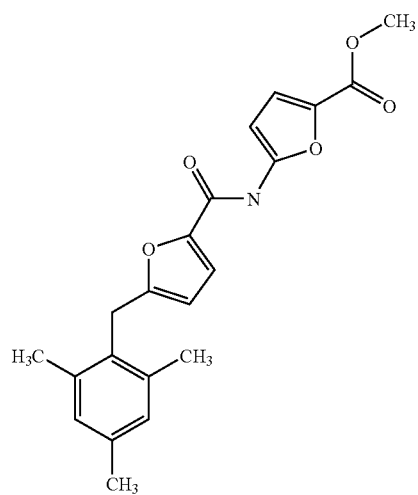

-continued
MOLSTRUCTURE
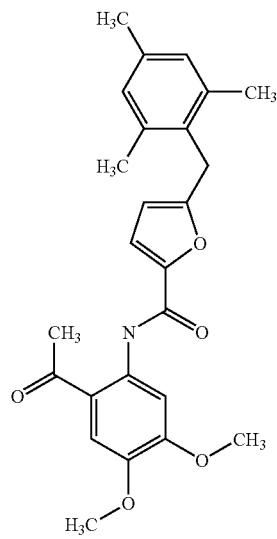
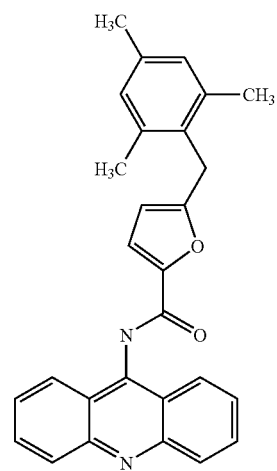
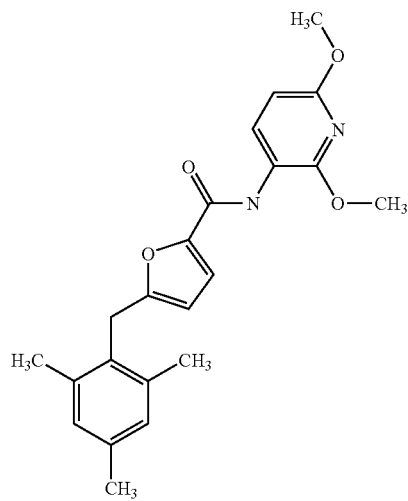

-continued
| MOLSTRUCTURE |
|---|
| 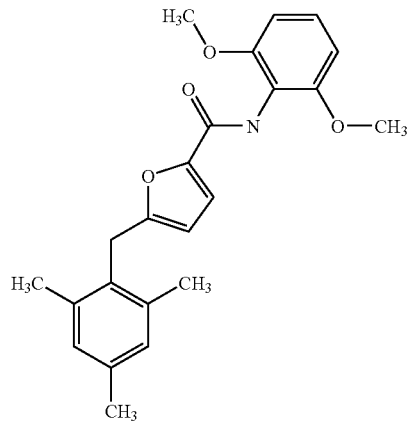 |
| 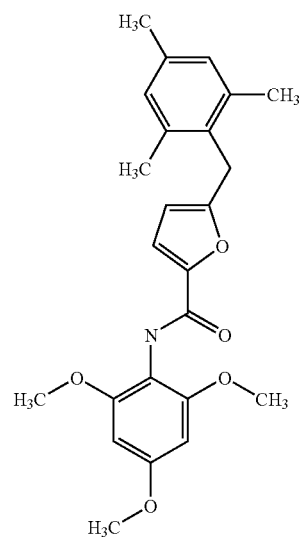 |
| MOLSTRUCTURE |
|---|
| 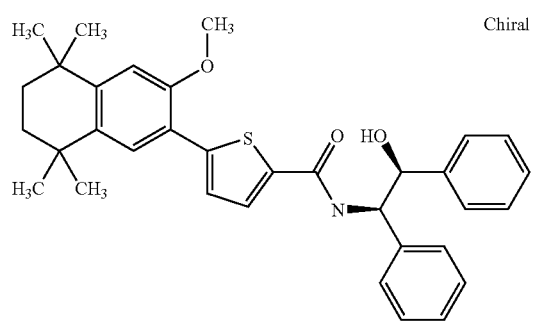 |

| MOLSTRUCTURE |
|---|
| 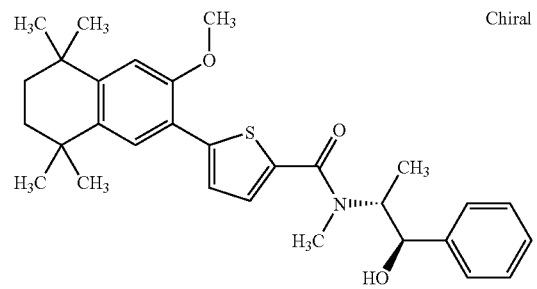 |
| 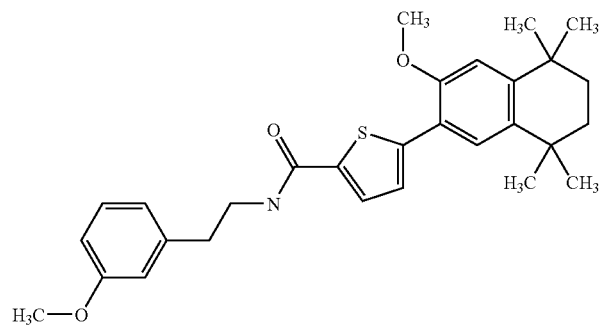 |
| 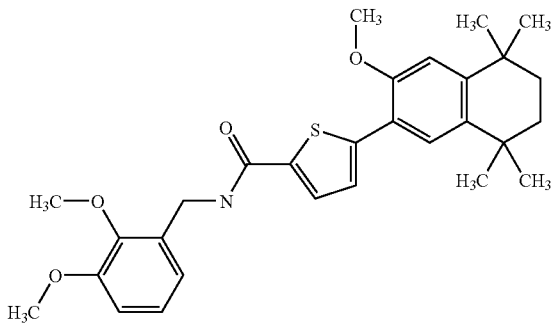 |
| 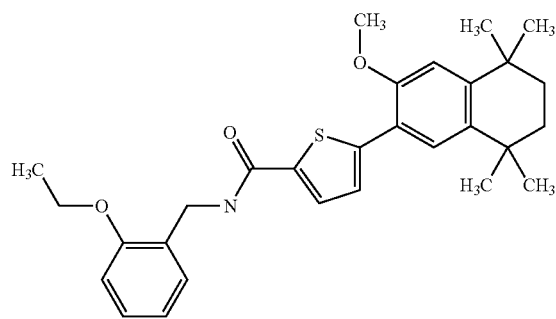 |

| MOLSTRUCTURE |
|---|
| 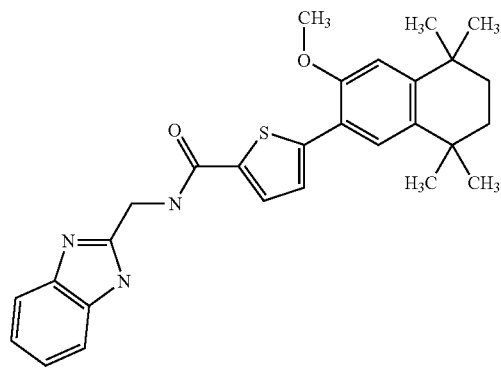 |
| 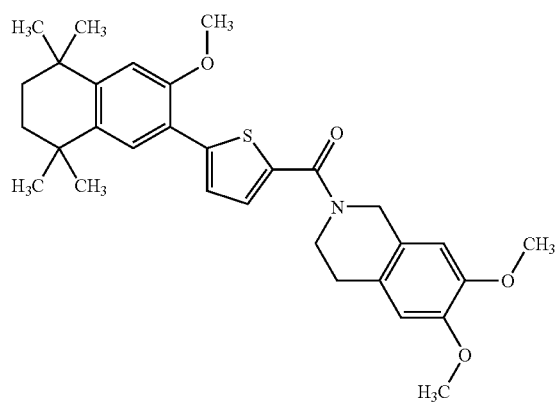 |
| 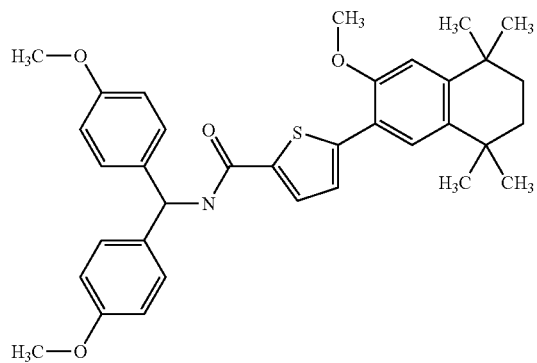 |
| 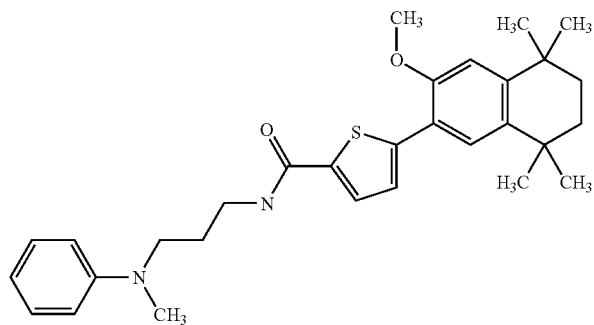 |

-continued
| MOLSTRUCTURE |
|---|
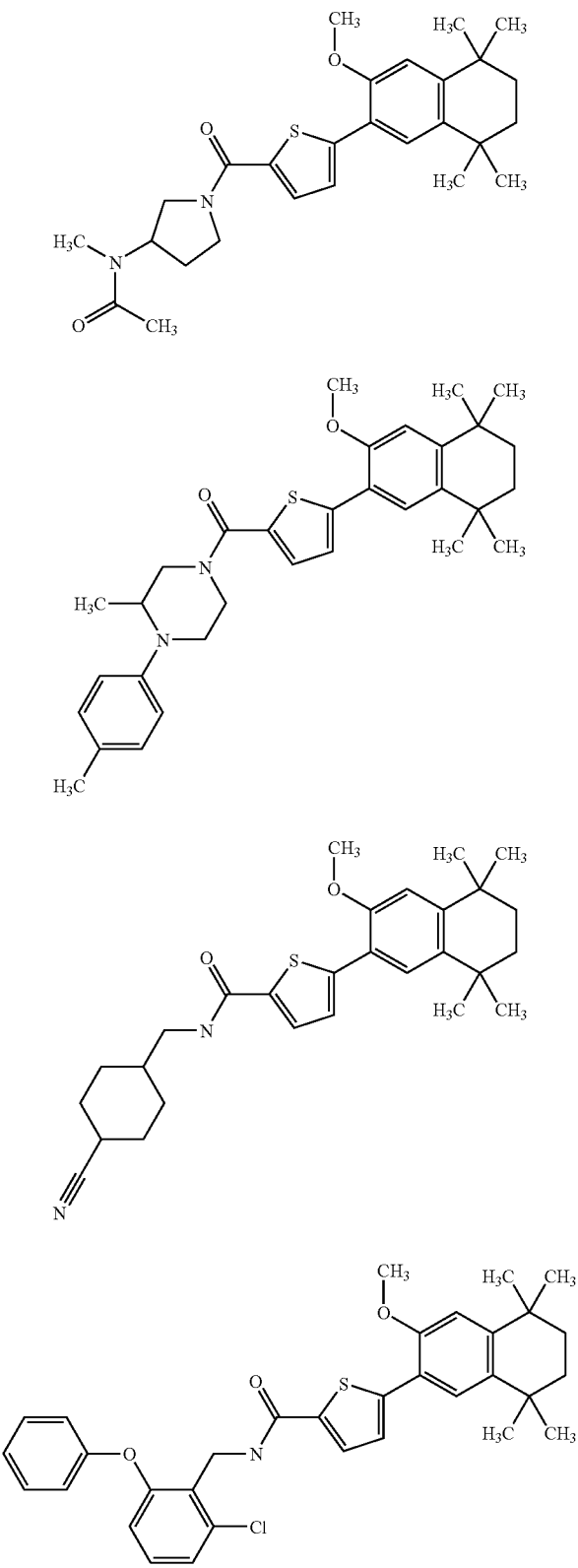

-continued
MOLSTRUCTURE
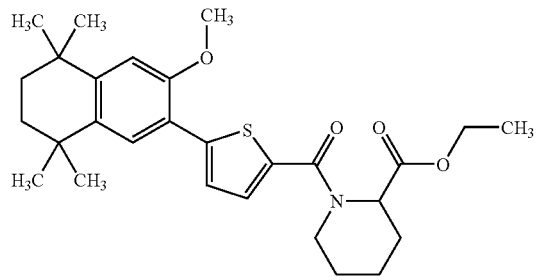
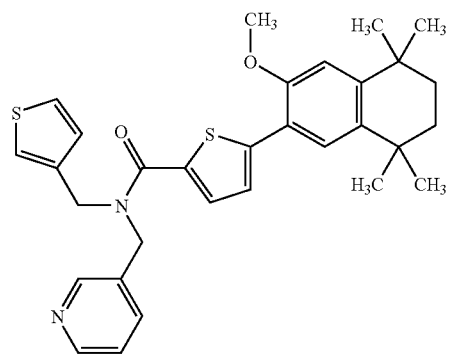
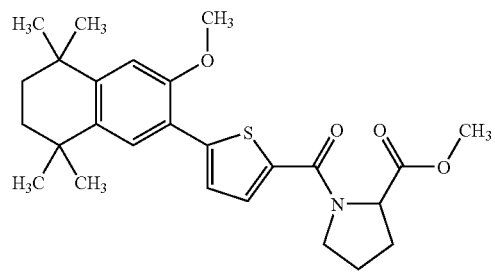
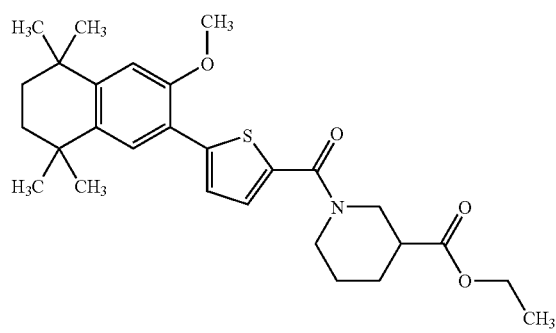
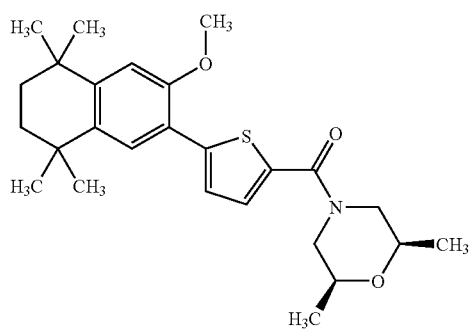

| MOLSTRUCTURE |
|---|
| 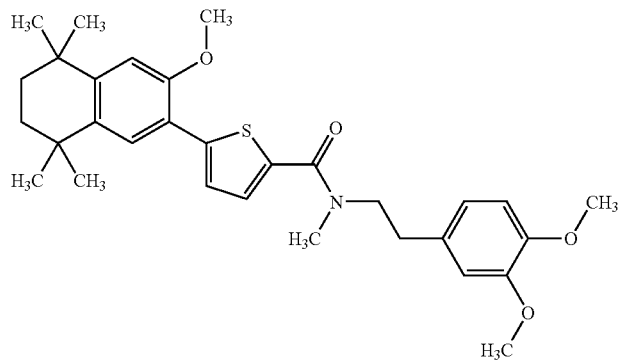 |
| 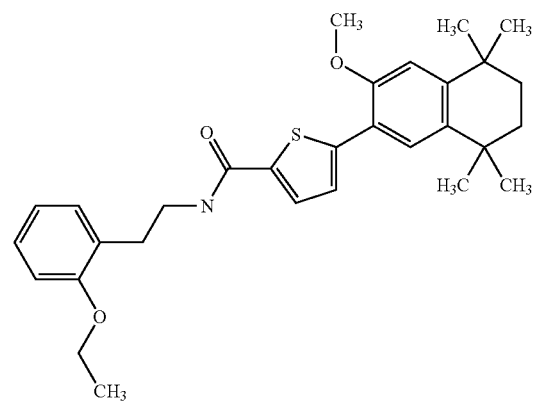 |
| 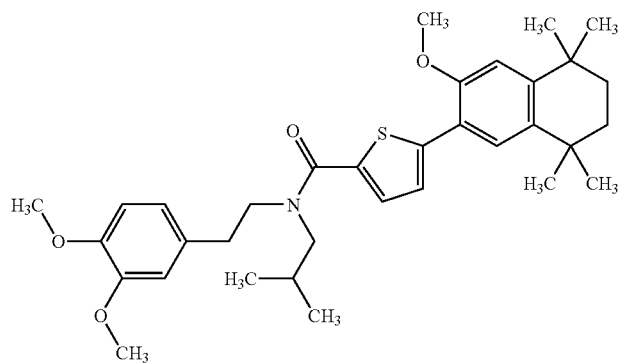 |

-continued
MOLSTRUCTURE
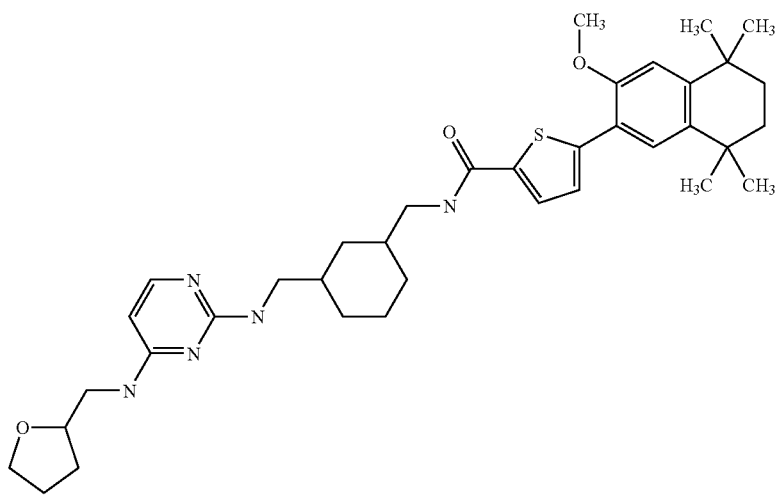
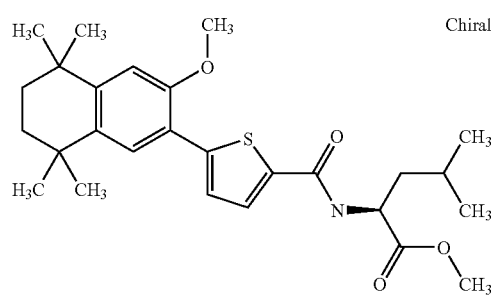
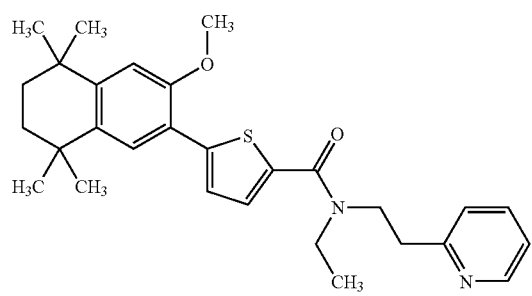
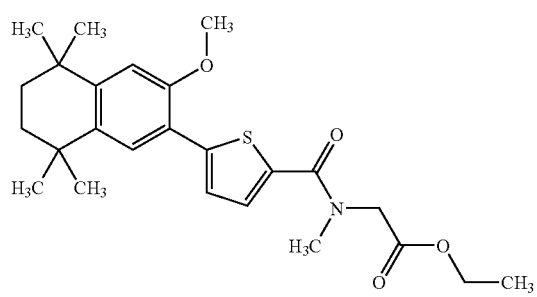

| MOLSTRUCTURE |
|---|
| 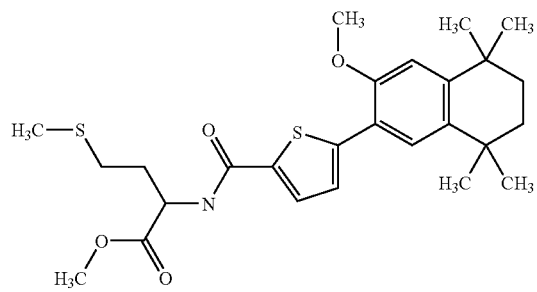 |
| 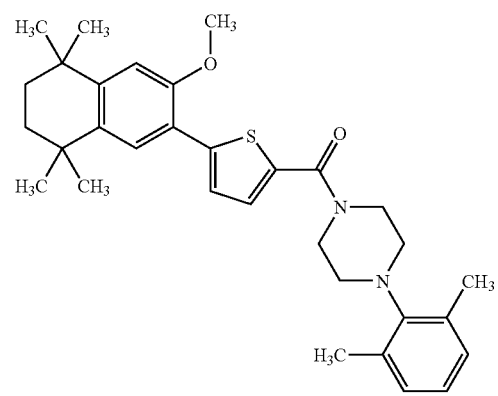 |
| 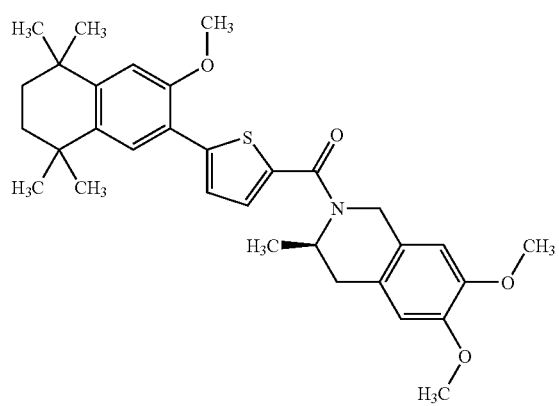 |
| 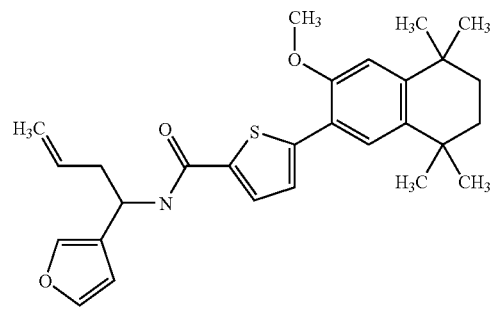 |

| MOLSTRUCTURE |
|---|
| 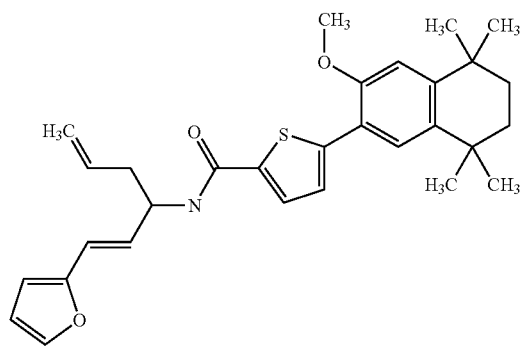 |
| 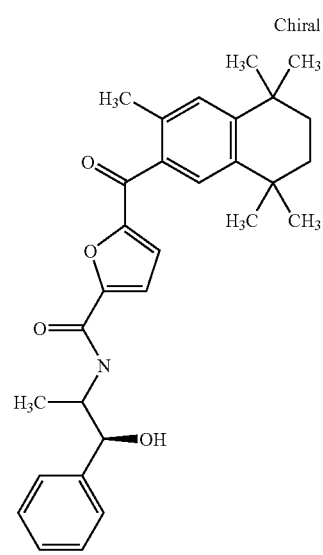 |
| 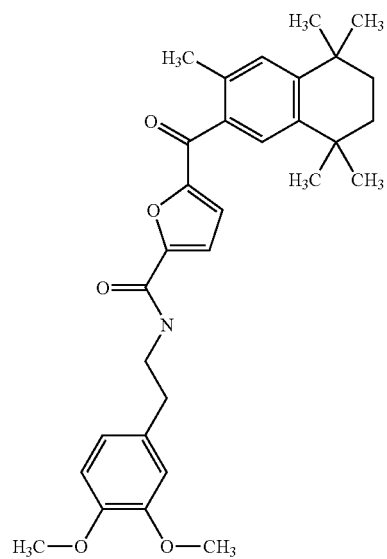 |

-continued
| MOLSTRUCTURE |
|---|
| 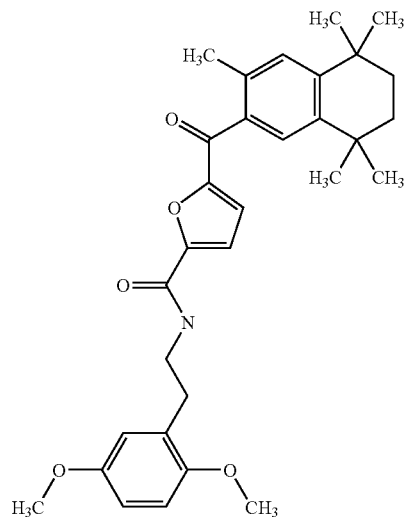 |
| 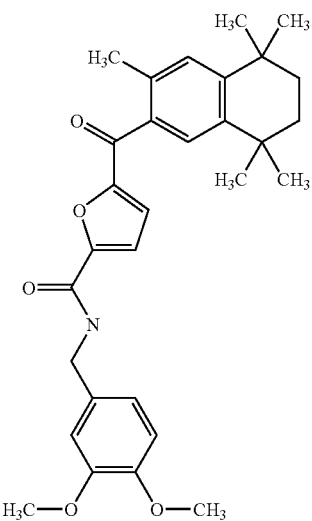 |
| 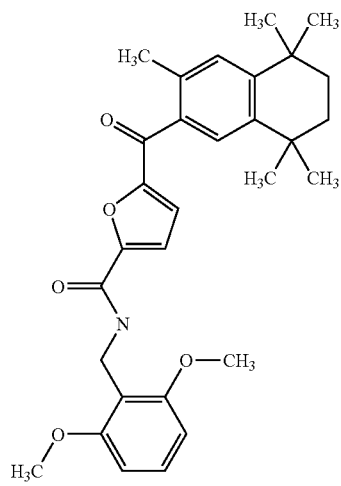 |

-continued
MOLSTRUCTURE
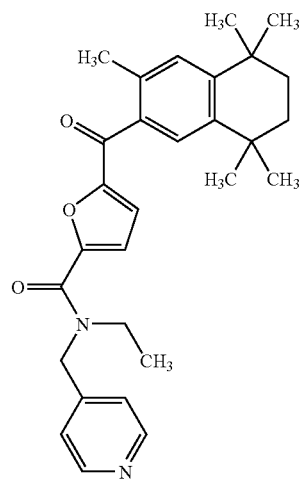
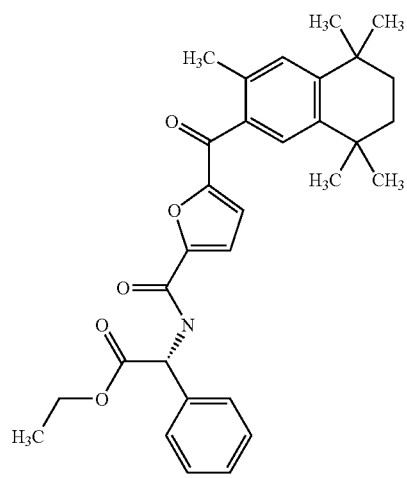
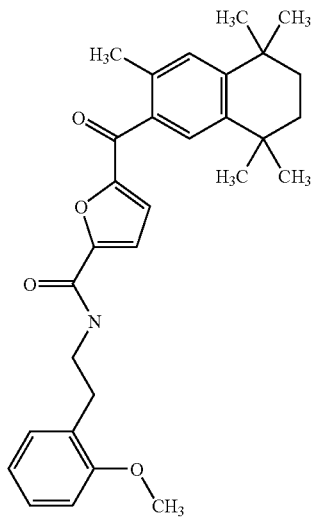

| MOLSTRUCTURE |
|---|
| 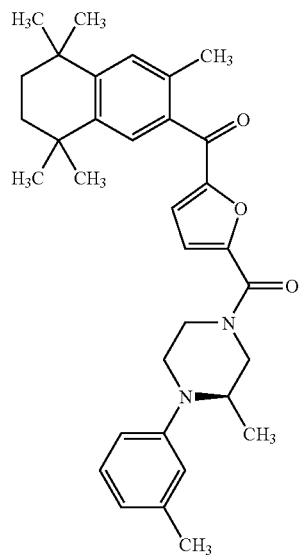 |
| 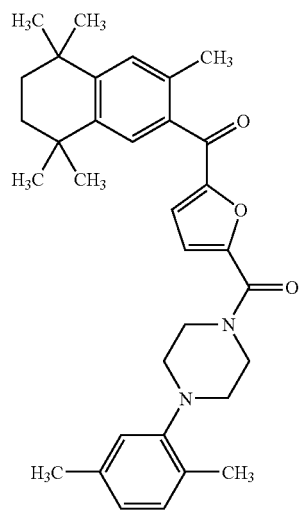 |

-continued
MOLSTRUCTURE
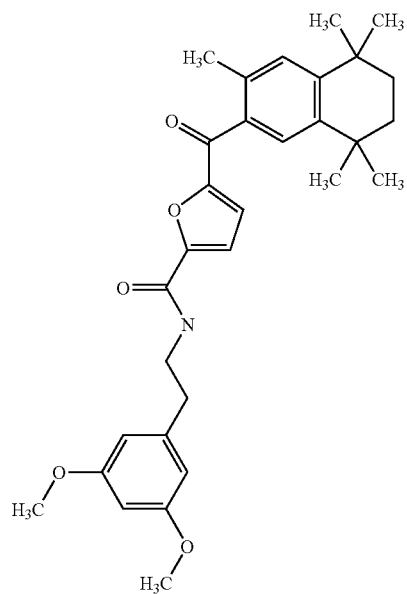
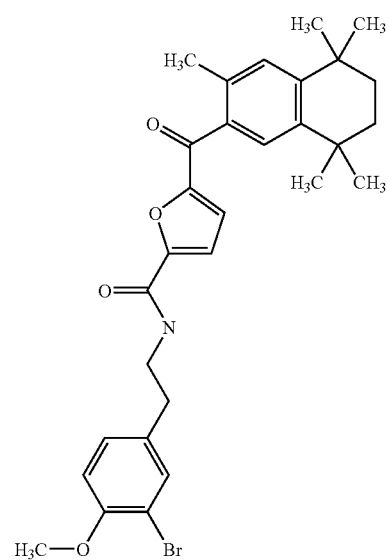

-continued
MOLSTRUCTURE
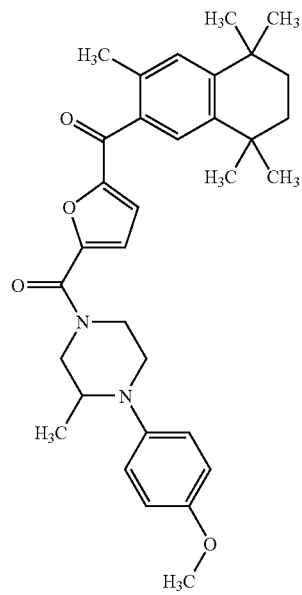
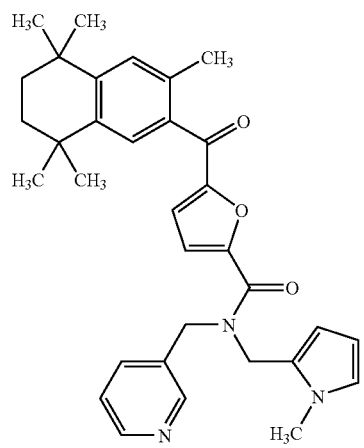
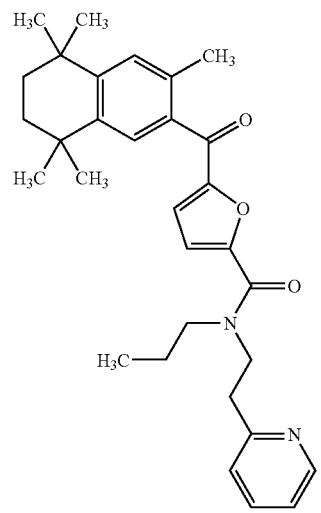

| MOLSTRUCTURE |
| --- |
| 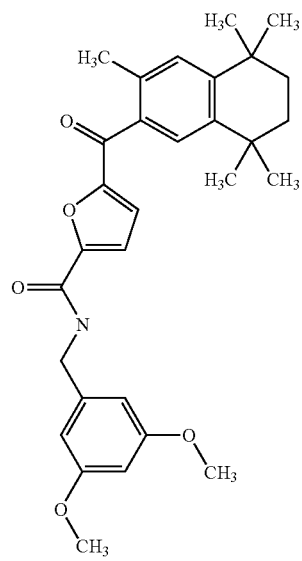 |
| 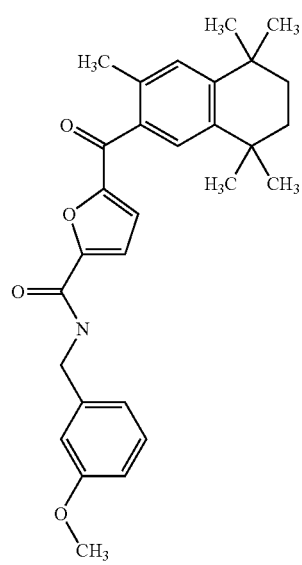 |

-continued
| MOLSTRUCTURE |
|---|
| 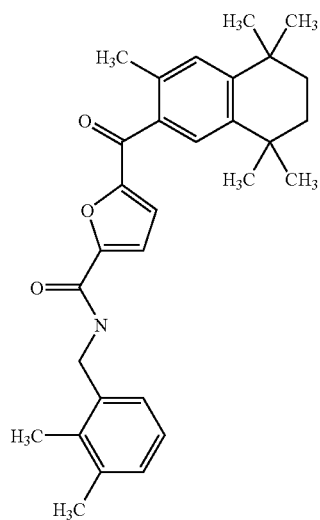 |
| 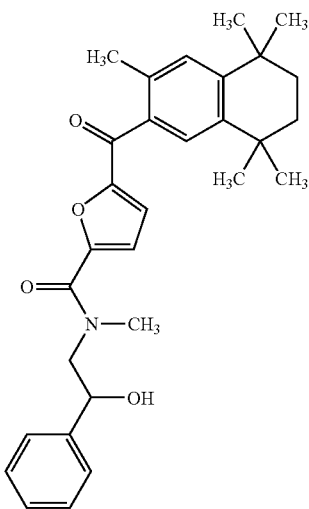 |
| 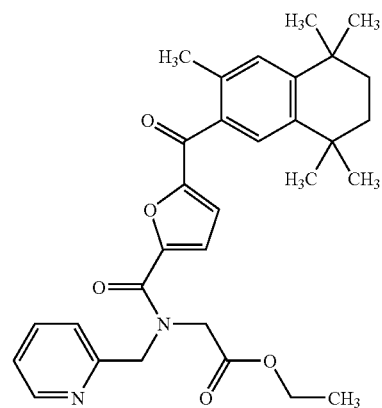 |

-continued
MOLSTRUCTURE
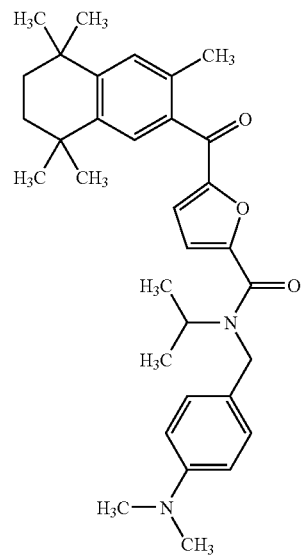
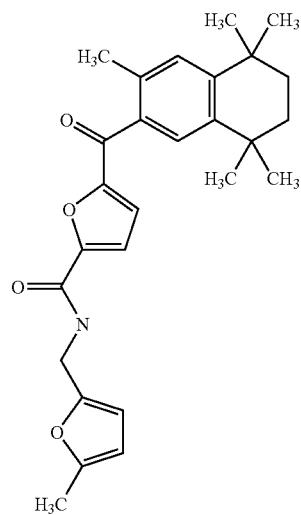
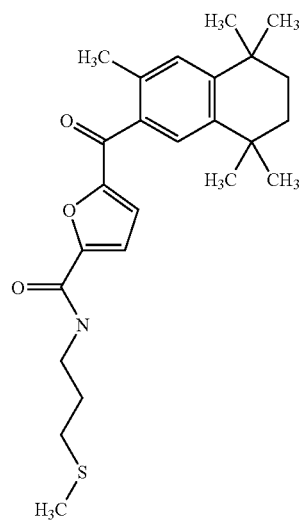

-continued
MOLSTRUCTURE
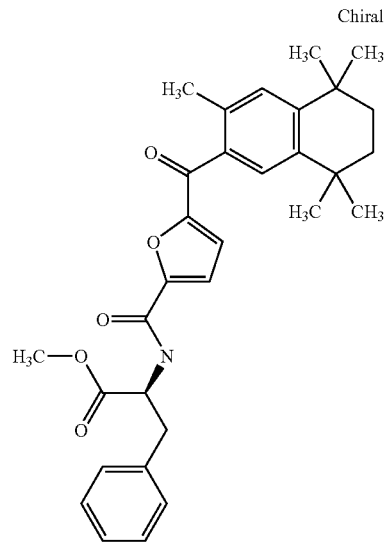
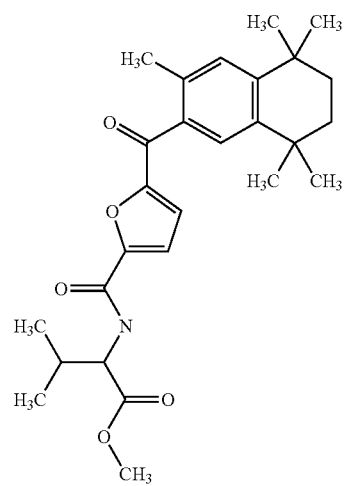
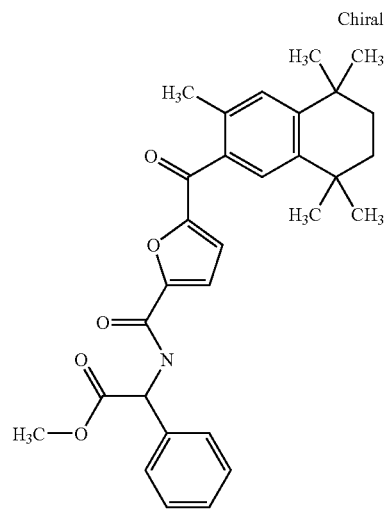

-continued
MOLSTRUCTURE
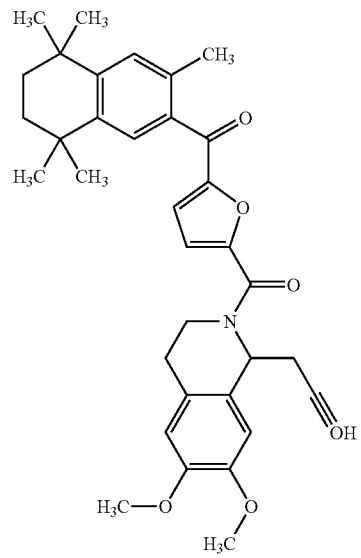
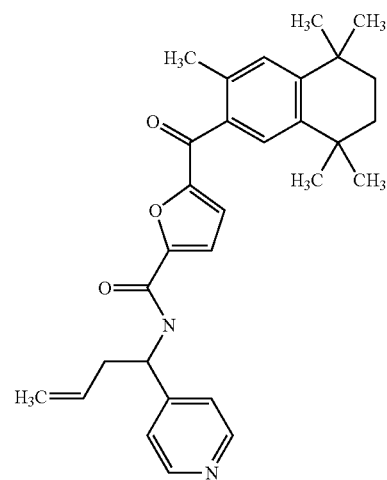
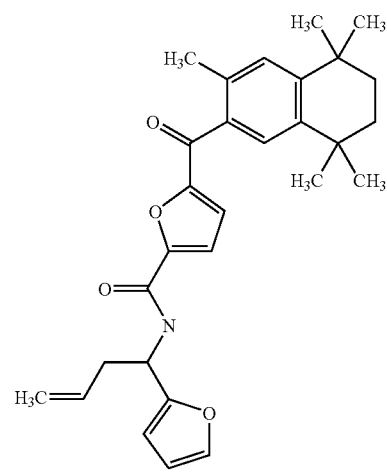

-continued
MOLSTRUCTURE
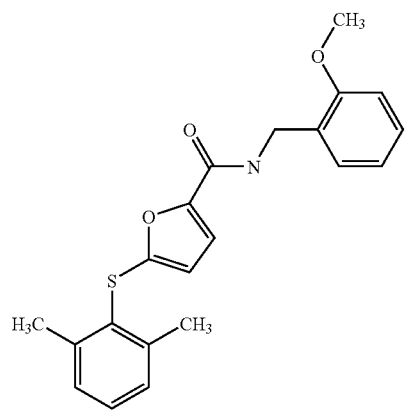
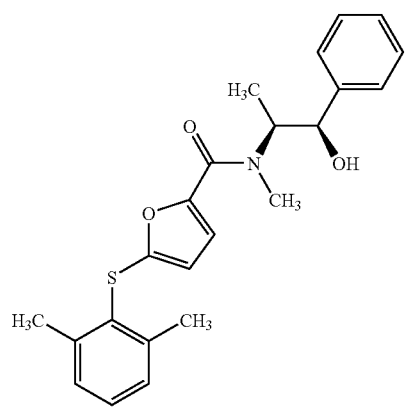
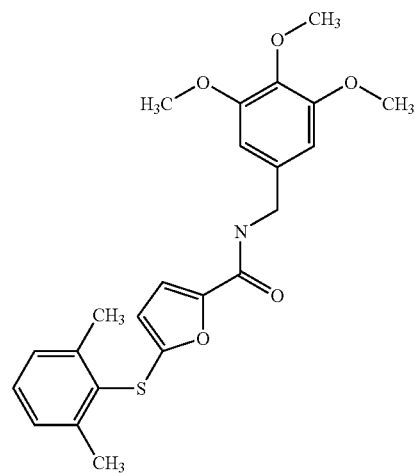

-continued
MOLSTRUCTURE
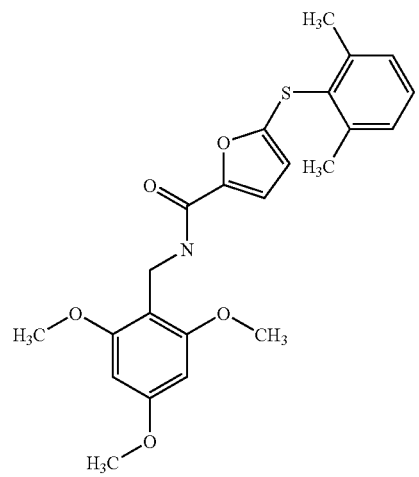
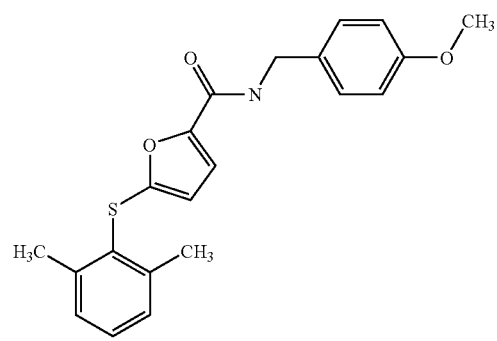
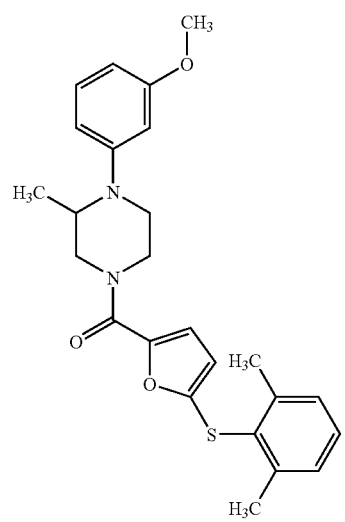

| MOLSTRUCTURE |
|---|
| 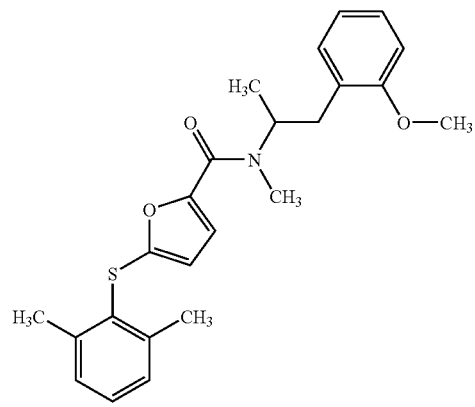 |
| 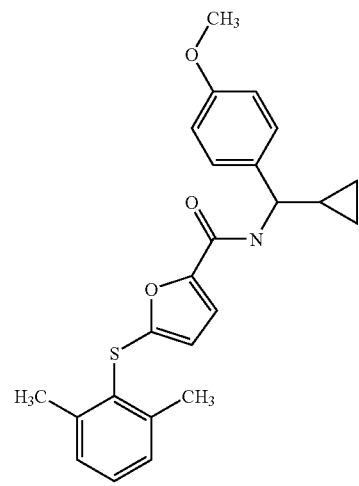 |
| 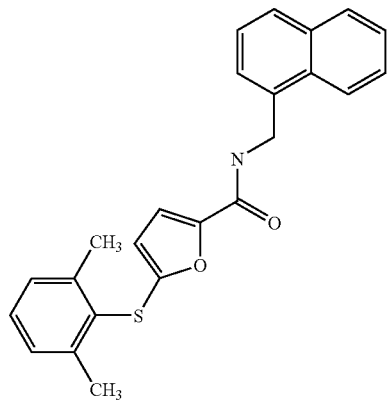 |

-continued
MOLSTRUCTURE
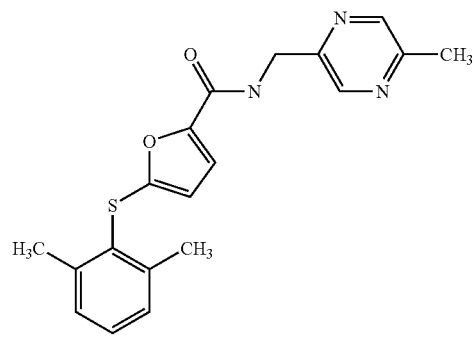
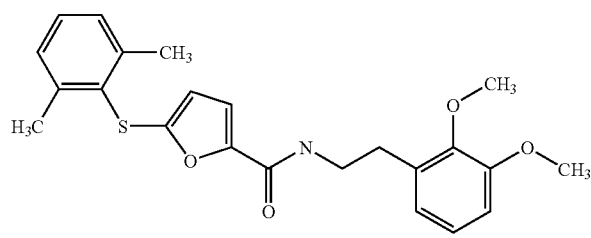
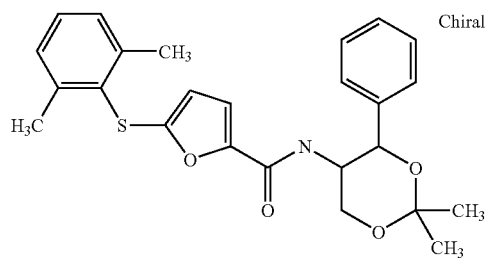
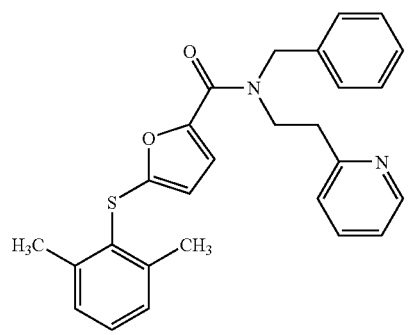

| MOLSTRUCTURE |
|---|
| 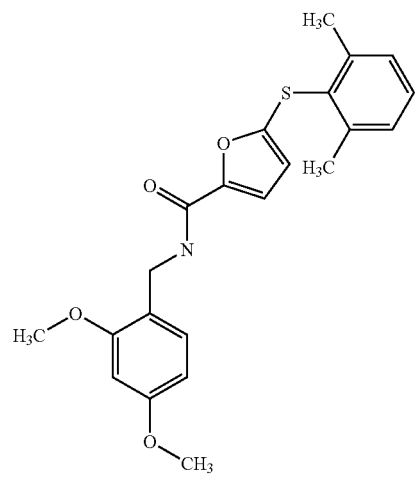 |
| 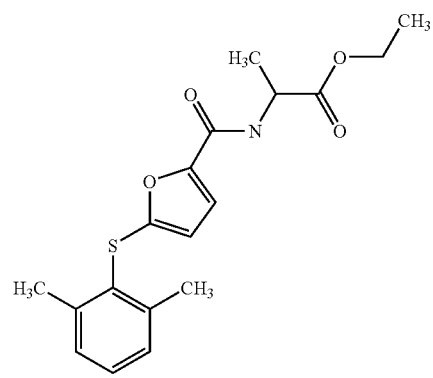 |
| 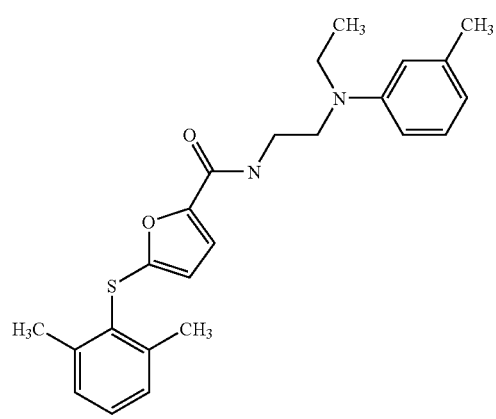 |

-continued
| MOLSTRUCTURE |
|---|
| 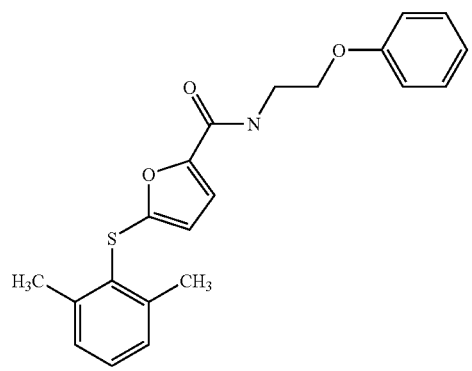 |
| 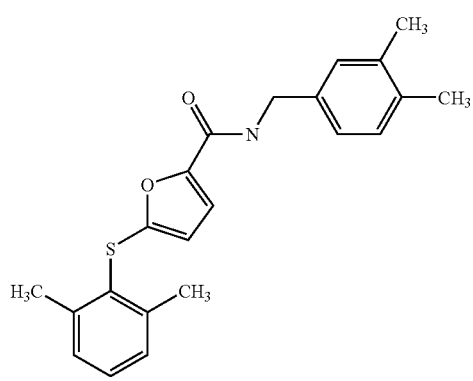 |
| 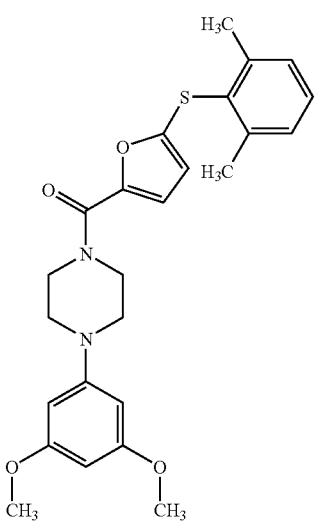 |
| 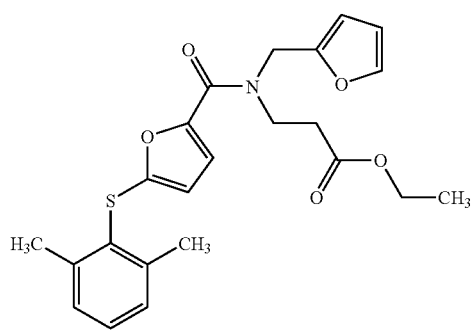 |

-continued
| MOLSTRUCTURE |
| --- |
| 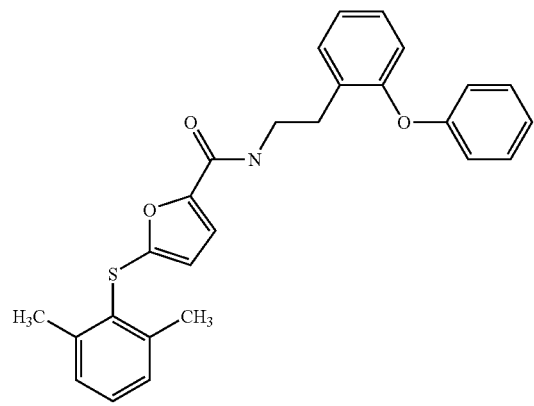 |
| 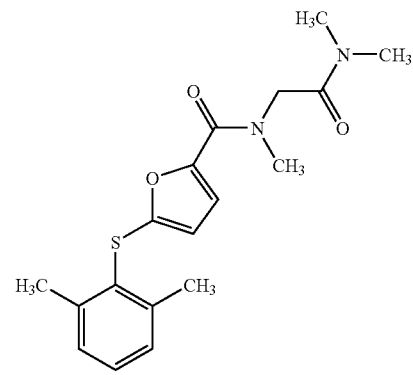 |
| 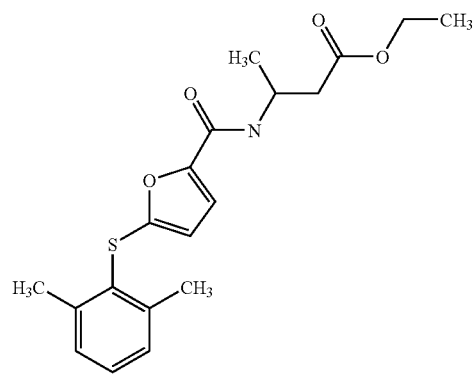 |
| 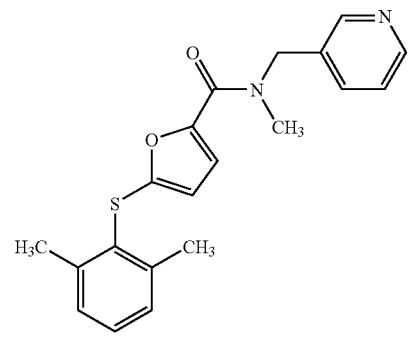 |

-continued
MOLSTRUCTURE
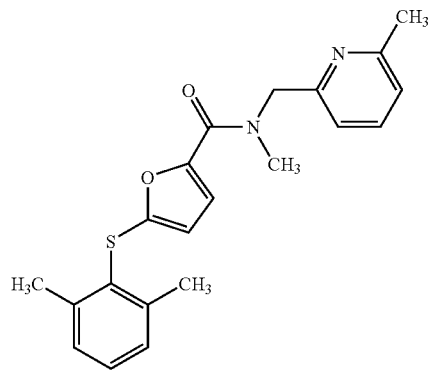
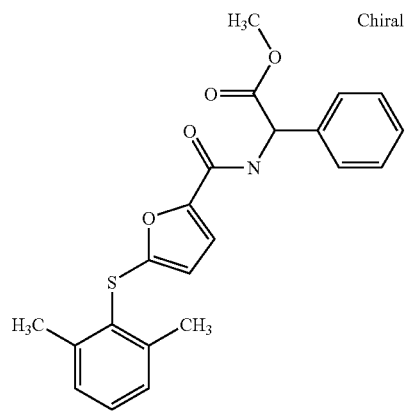
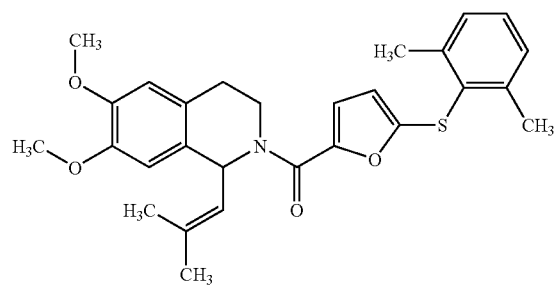
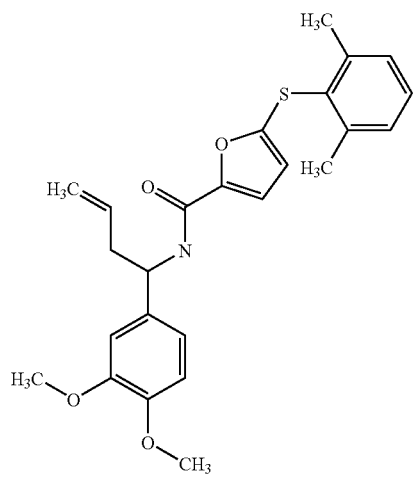

| MOLSTRUCTURE |
|---|
| 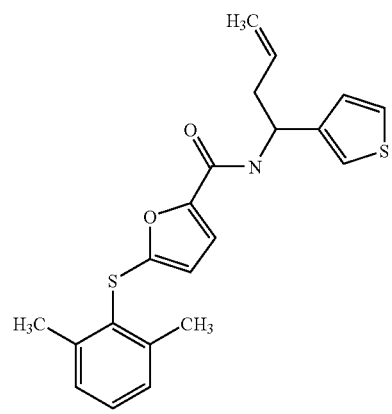 |
| 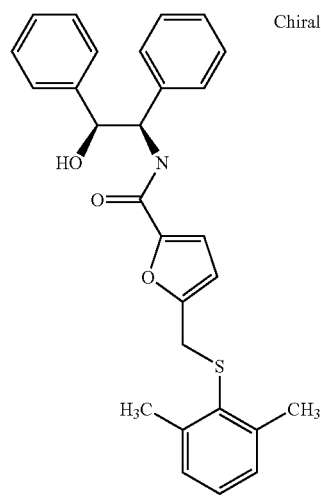 |
| 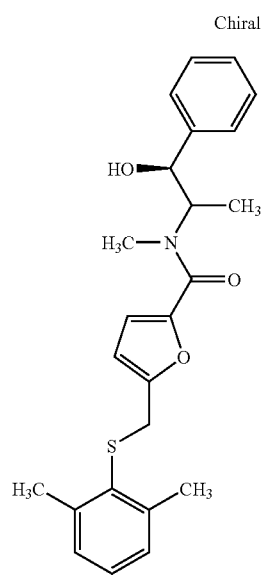 |

-continued
MOLSTRUCTURE
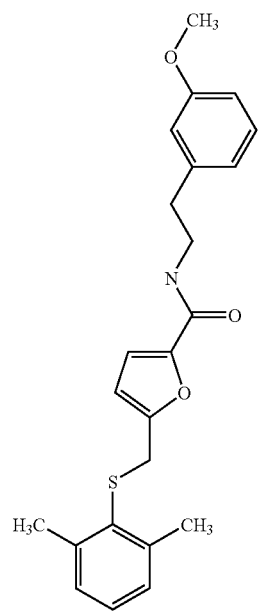
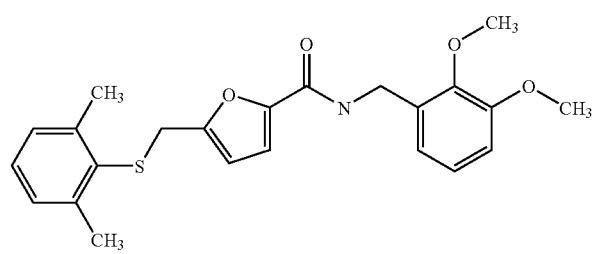
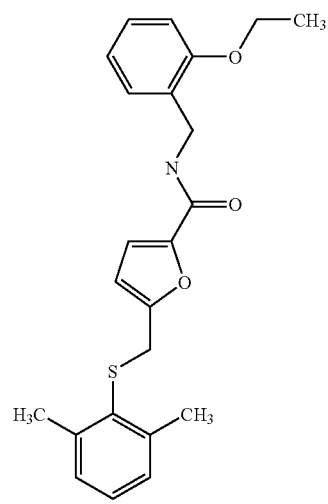

-continued
MOLSTRUCTURE
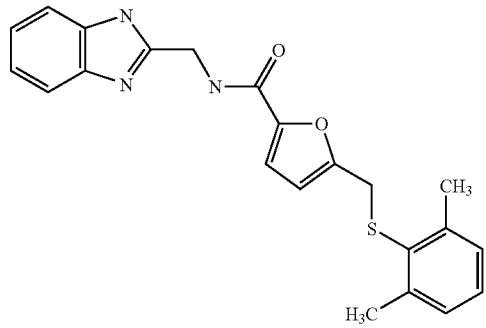
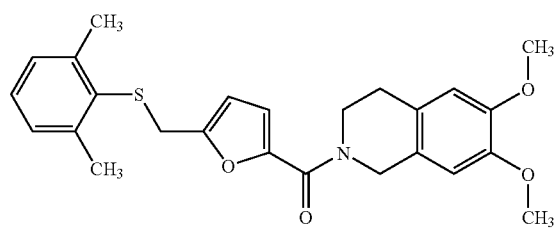
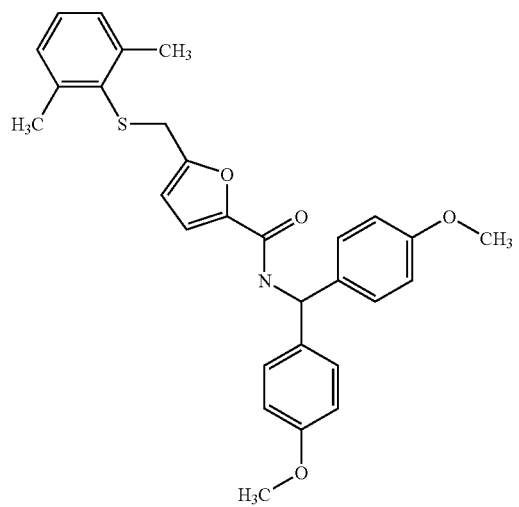

| MOLSTRUCTURE |
| --- |
| 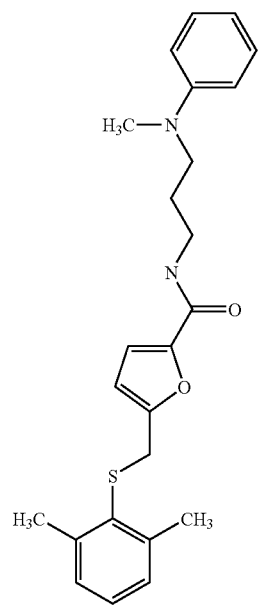 |
| 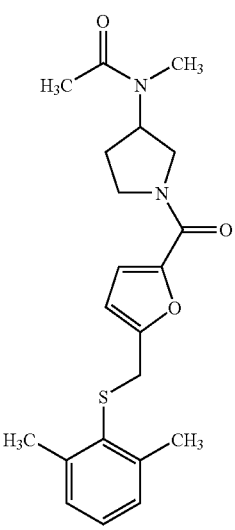 |

-continued
MOLSTRUCTURE
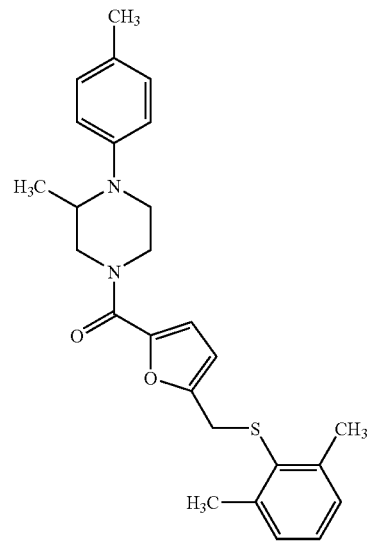
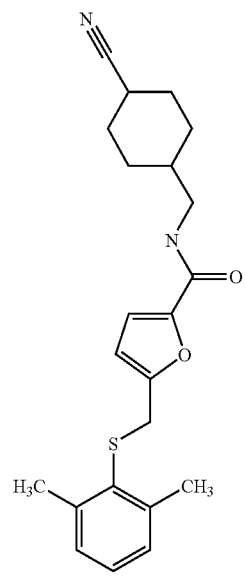
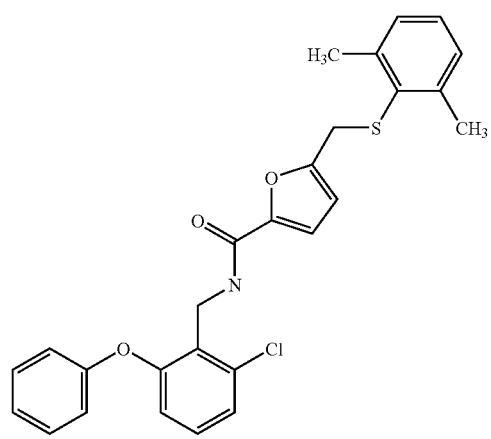

-continued
MOLSTRUCTURE
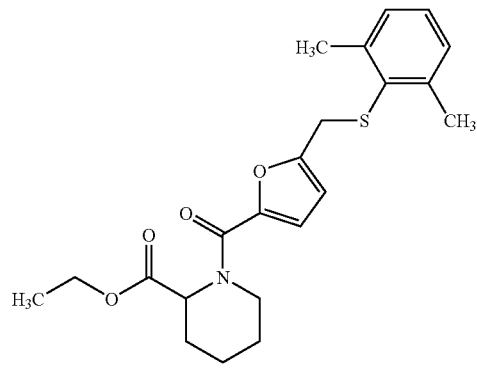
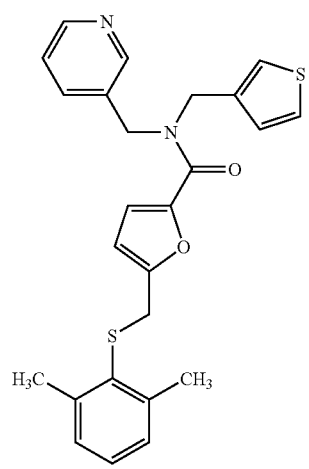
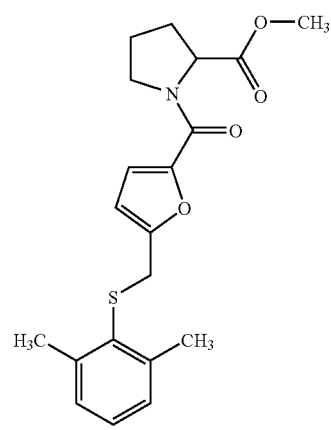

-continued
MOLSTRUCTURE
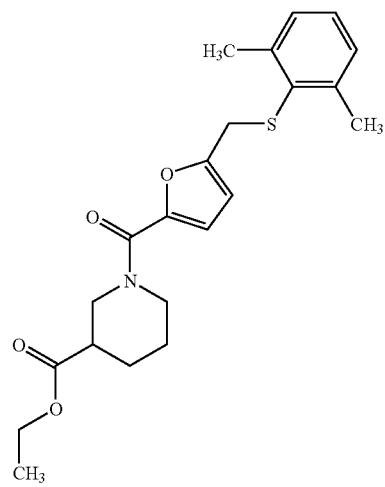
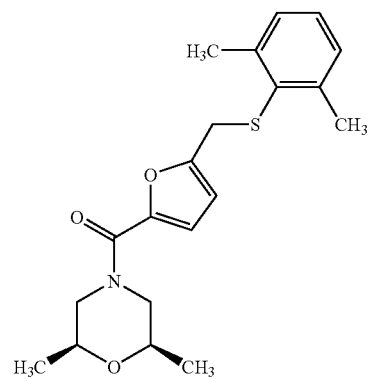
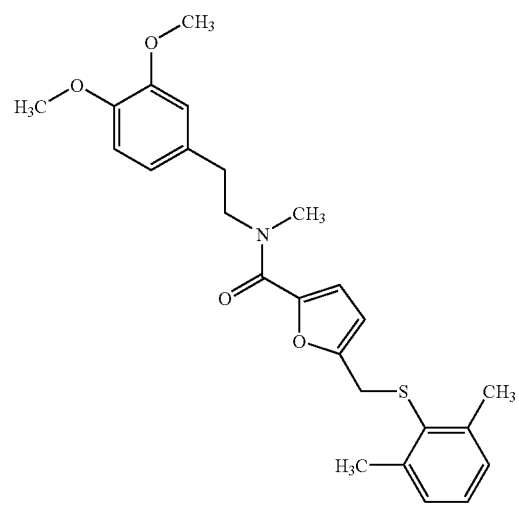

-continued
| MOLSTRUCTURE |
|---|
| 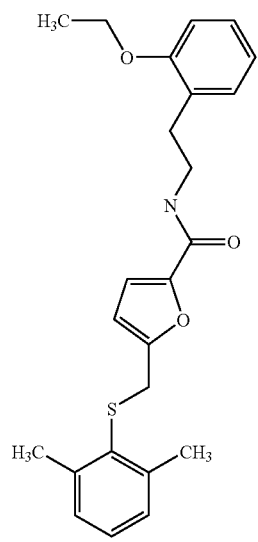 |
| 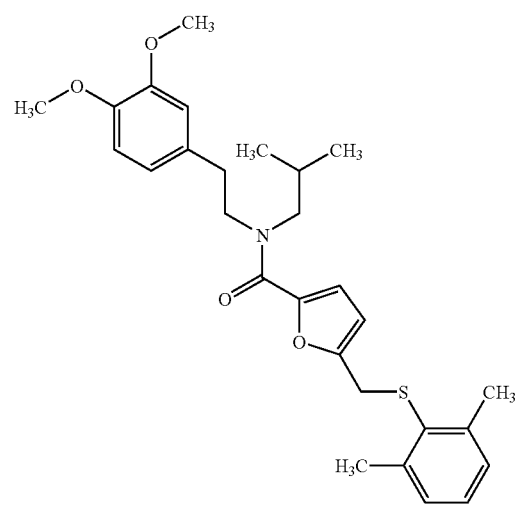 |

-continued
MOLSTRUCTURE
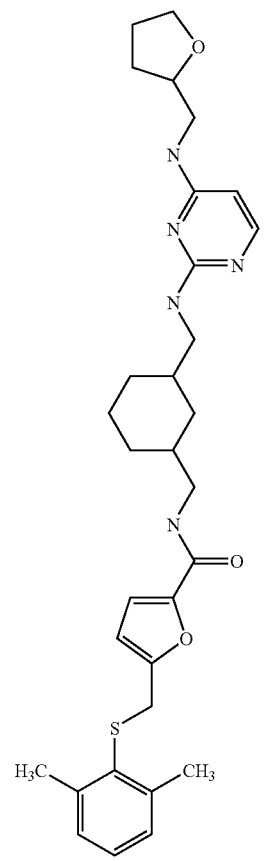
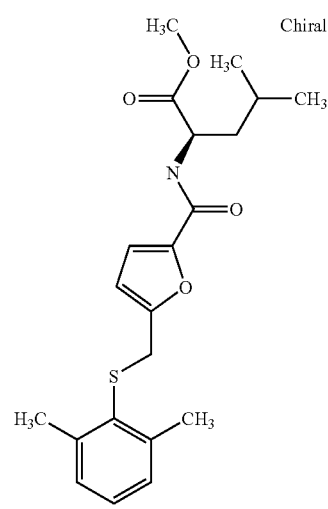

-continued
| MOLSTRUCTURE |
| --- |
| 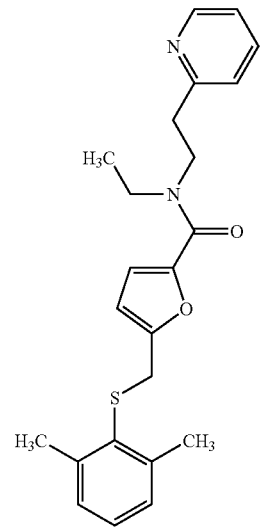 |
| 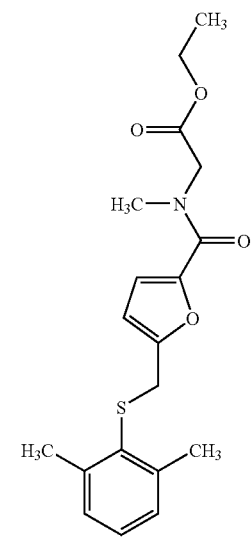 |
| 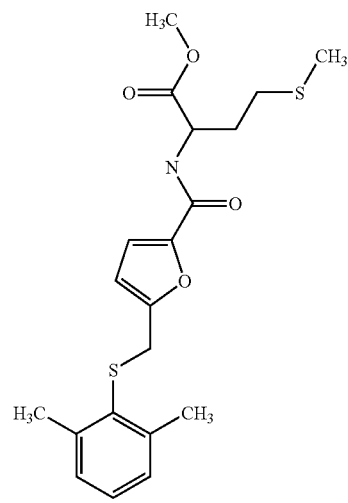 |

-continued
MOLSTRUCTURE
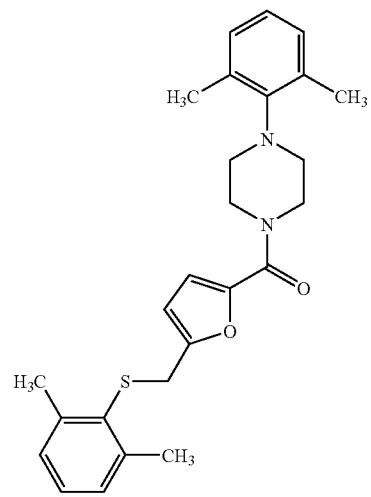
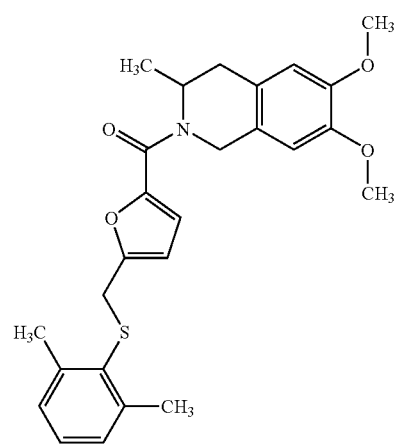
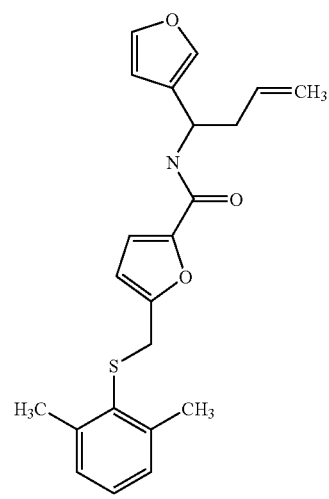

-continued
MOLSTRUCTURE
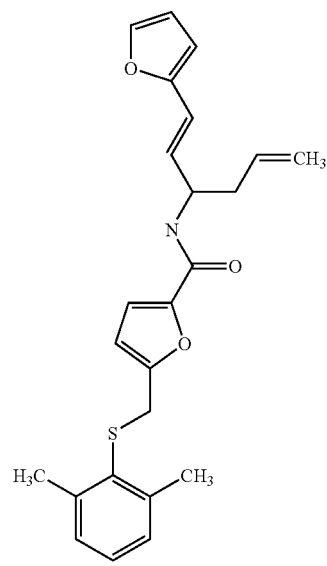
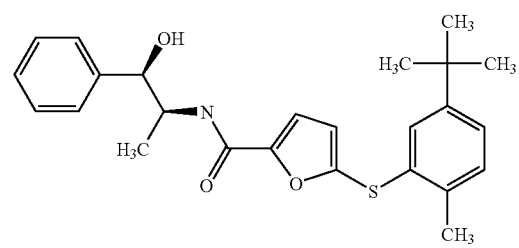
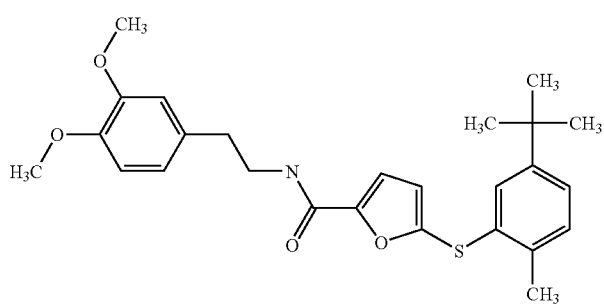
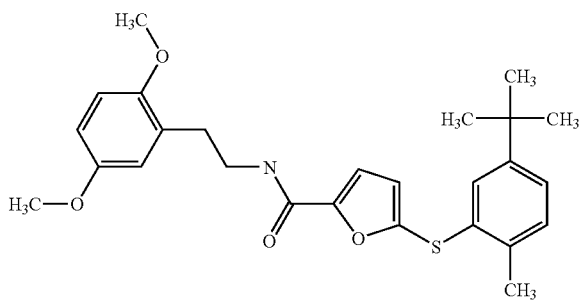

-continued
MOLSTRUCTURE
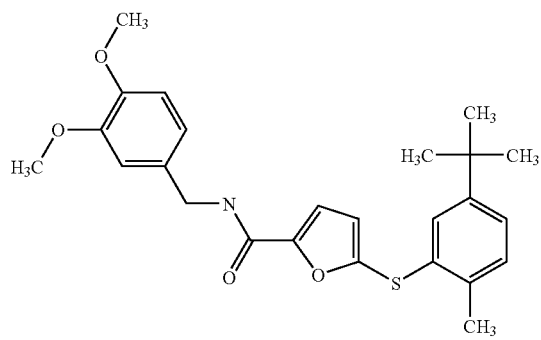
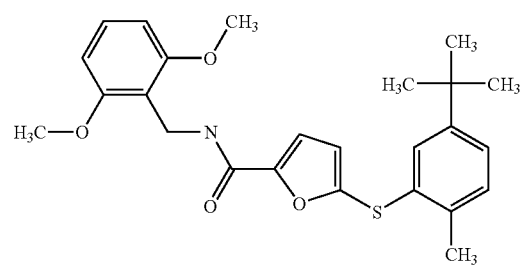
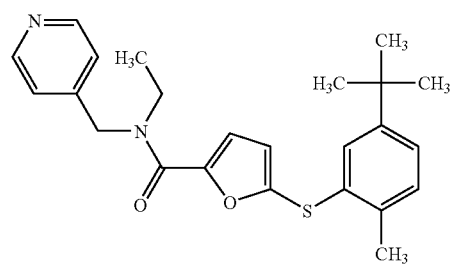
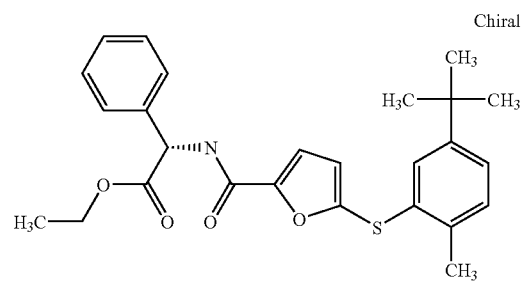
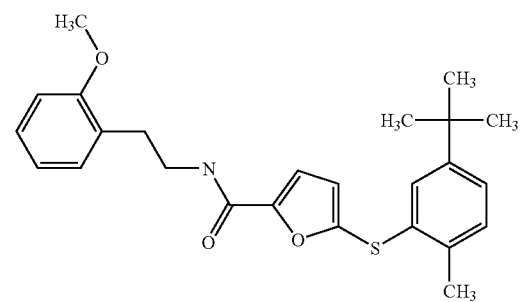

| MOLSTRUCTURE |
|---|
| 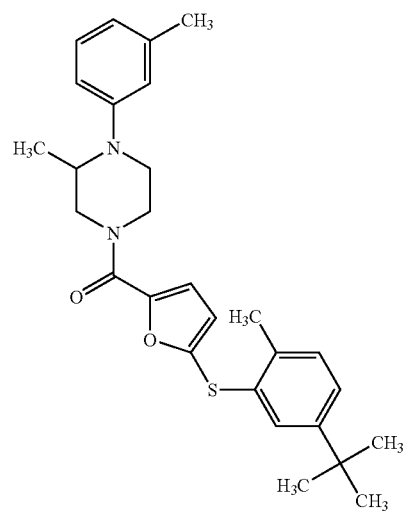 |
| 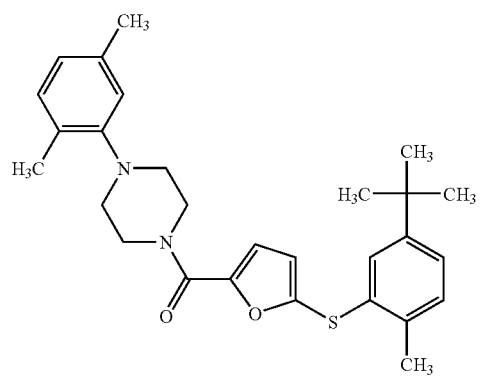 |
| 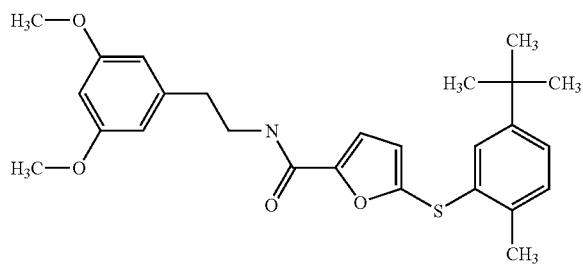 |
| 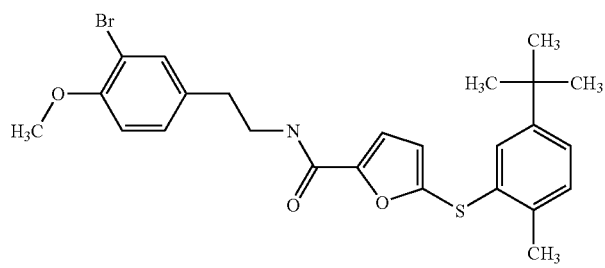 |

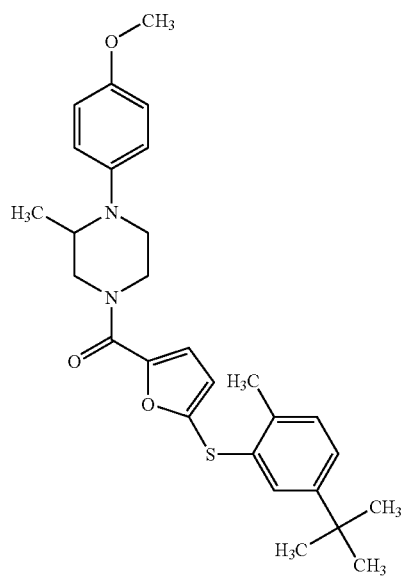
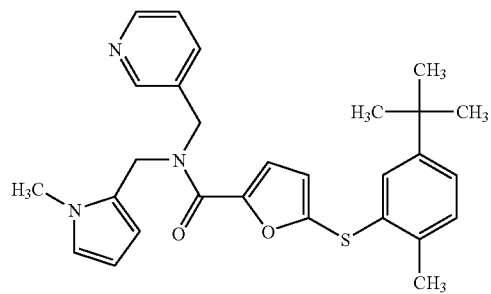
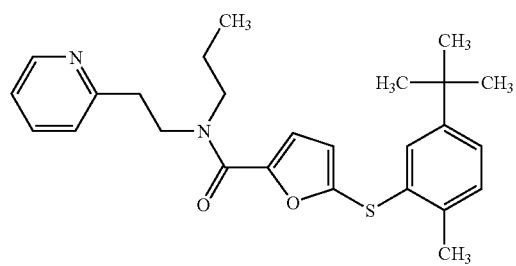
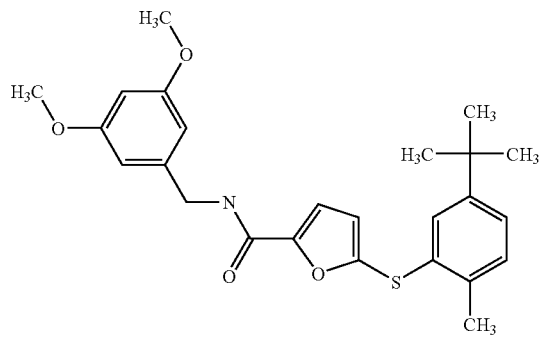

-continued
| MOLSTRUCTURE |
|---|
| 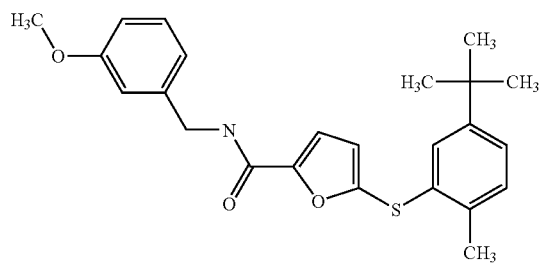 |
| 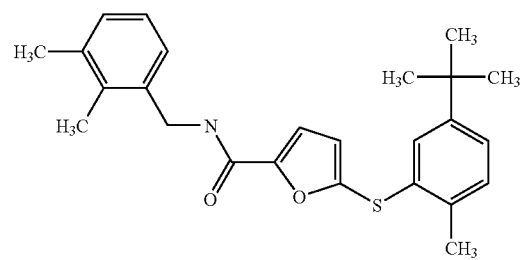 |
| 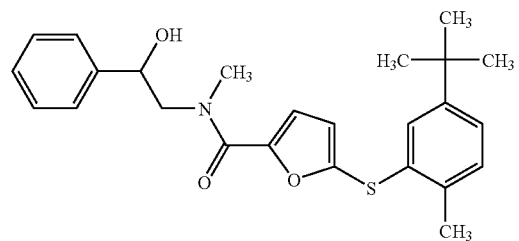 |
| 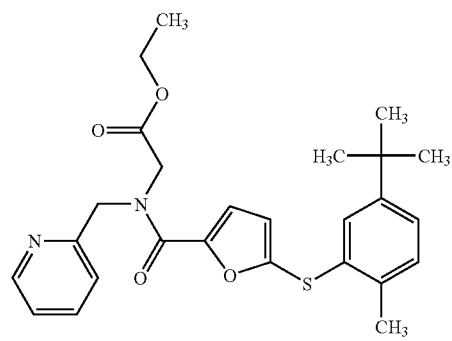 |
| 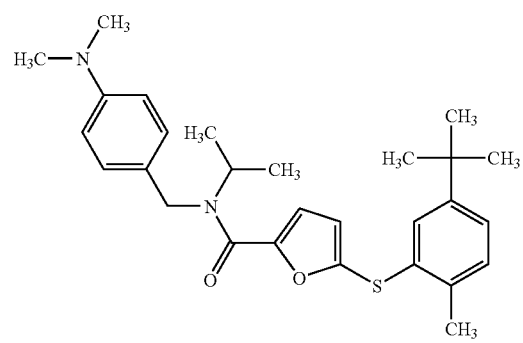 |

-continued
MOLSTRUCTURE
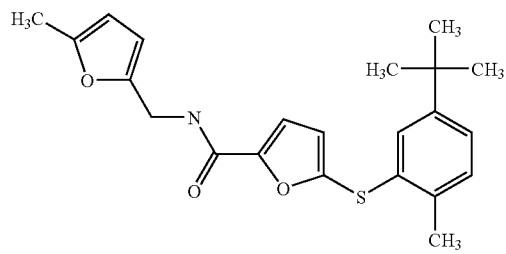
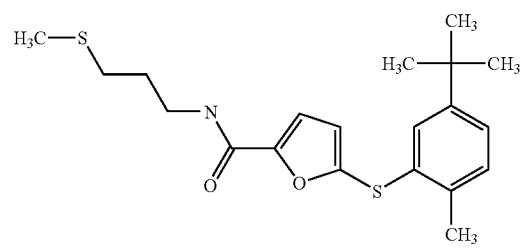
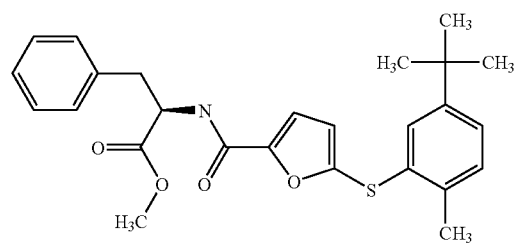
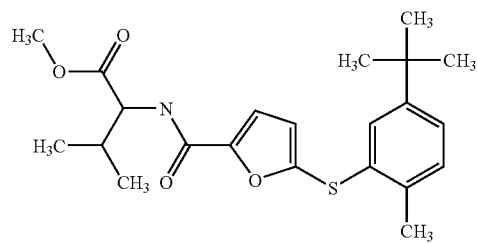
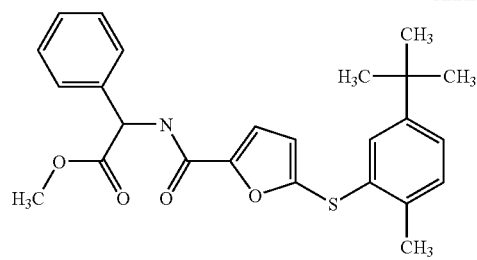

-continued
MOLSTRUCTURE
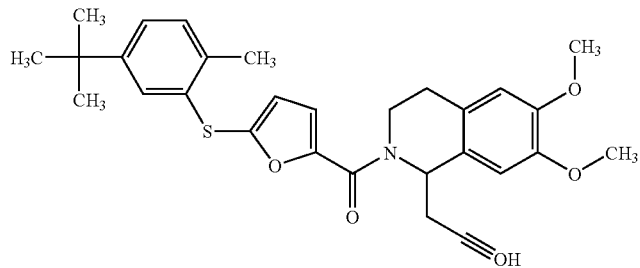
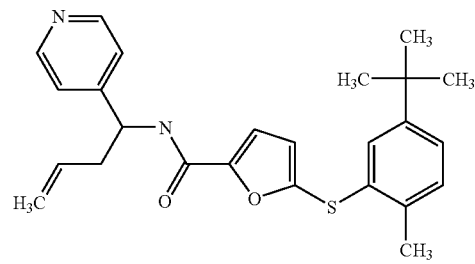
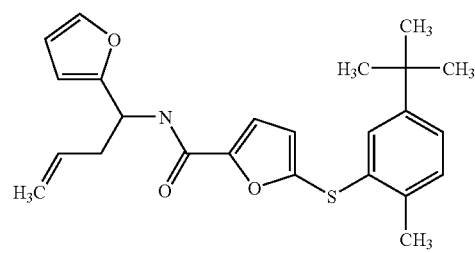
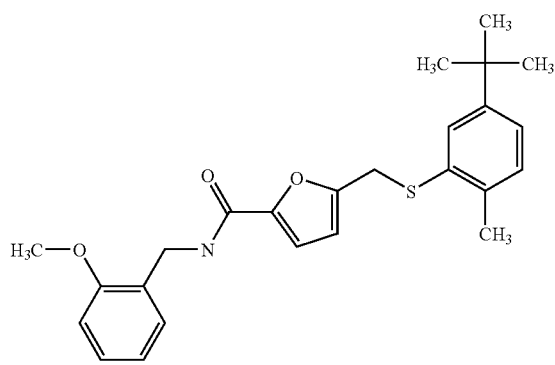
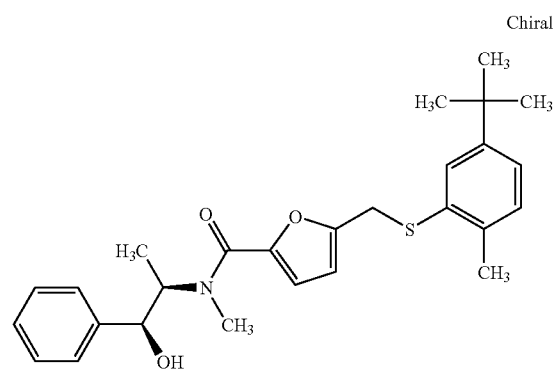

-continued
MOLSTRUCTURE
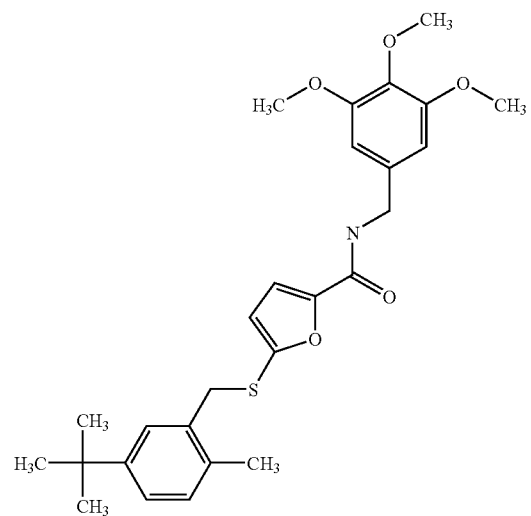
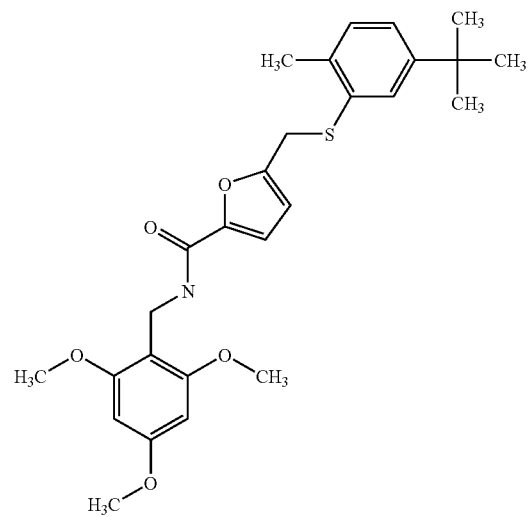
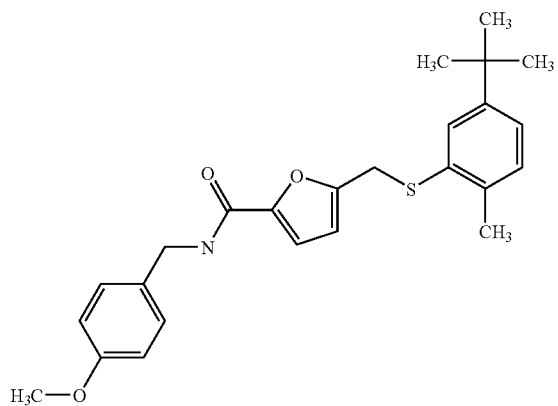

-continued
MOLSTRUCTURE
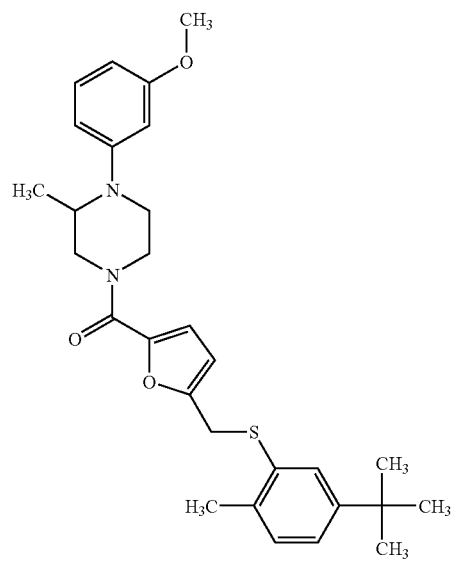
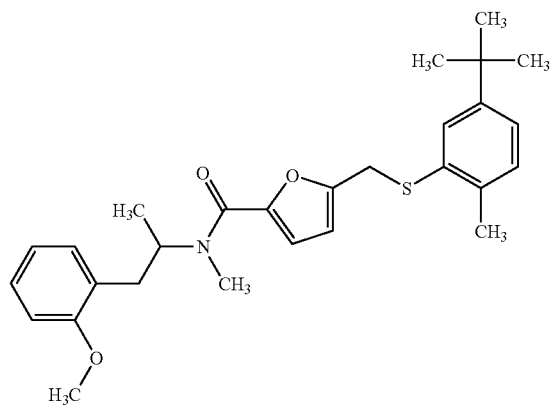
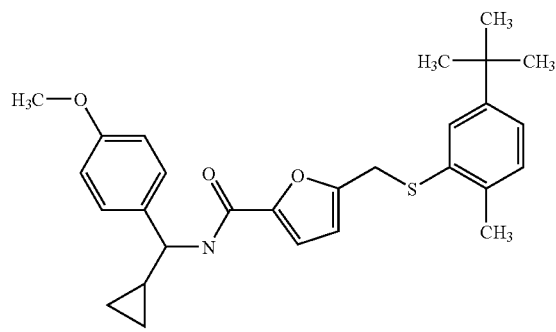

-continued
MOLSTRUCTURE
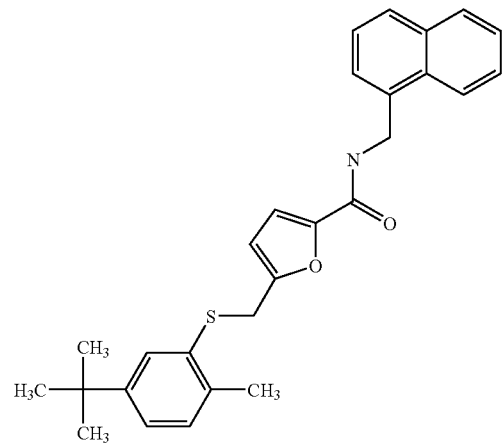
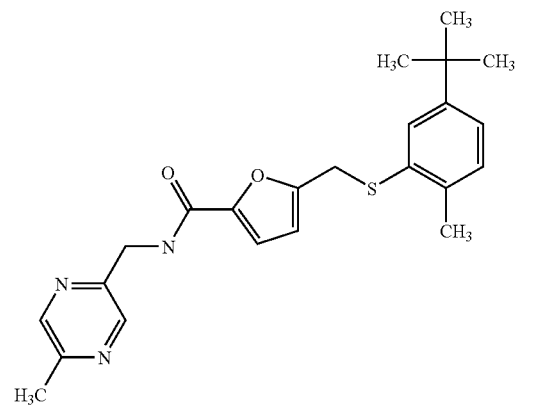
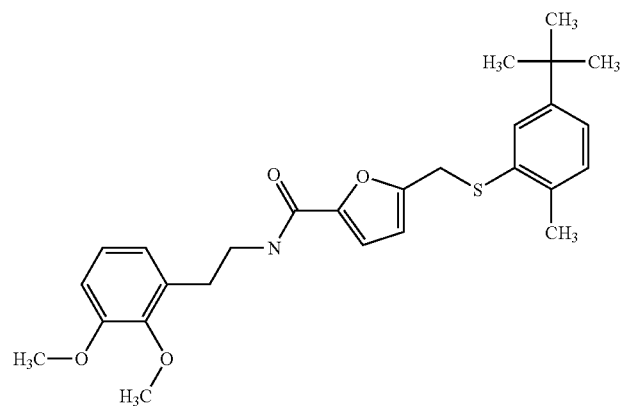
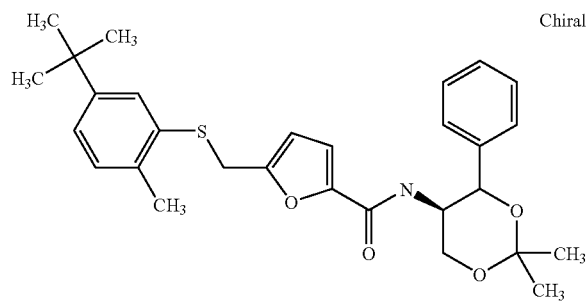

-continued
| MOLSTRUCTURE |
|---|
| 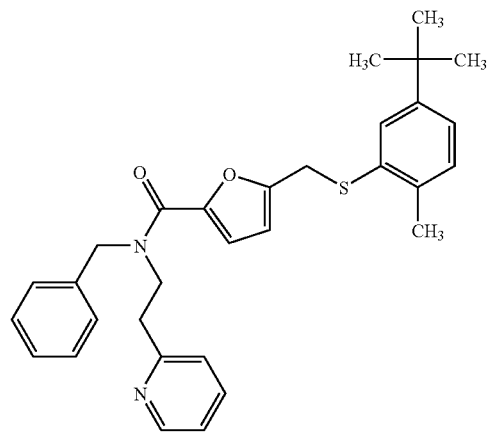 |
| 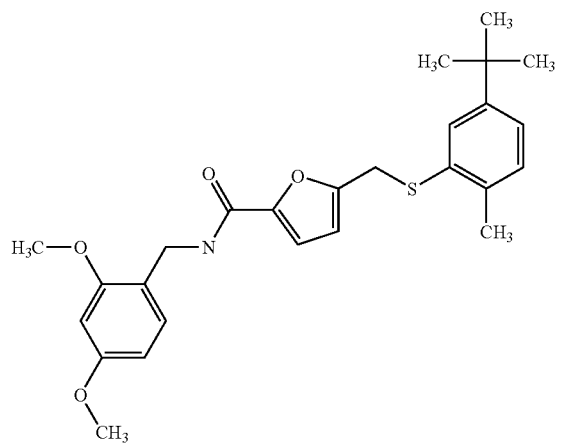 |
| 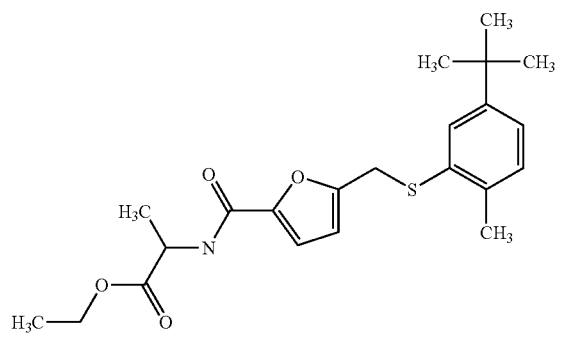 |

-continued
MOLSTRUCTURE
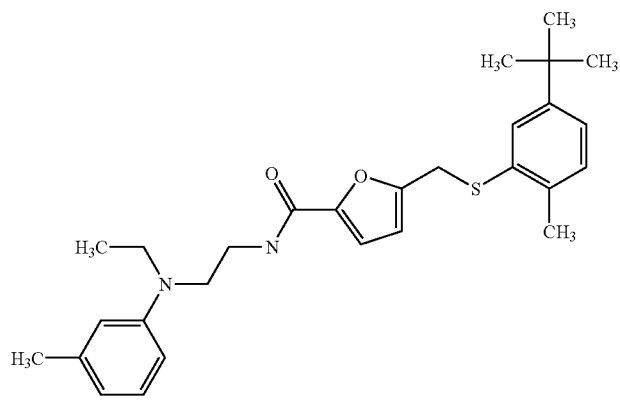
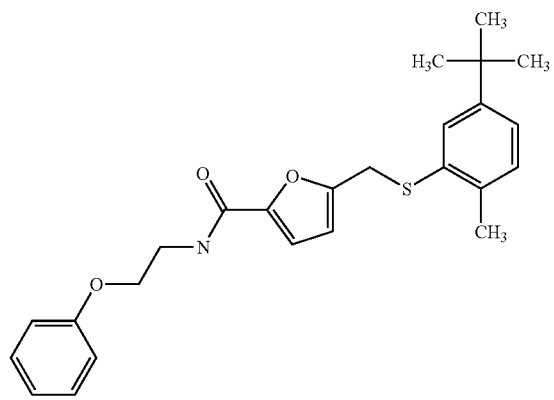
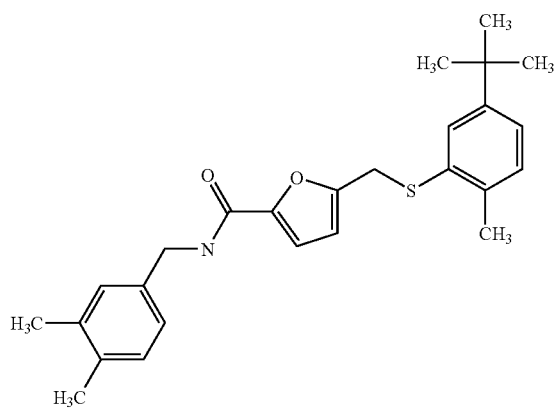

| MOLSTRUCTURE |
|---|
| 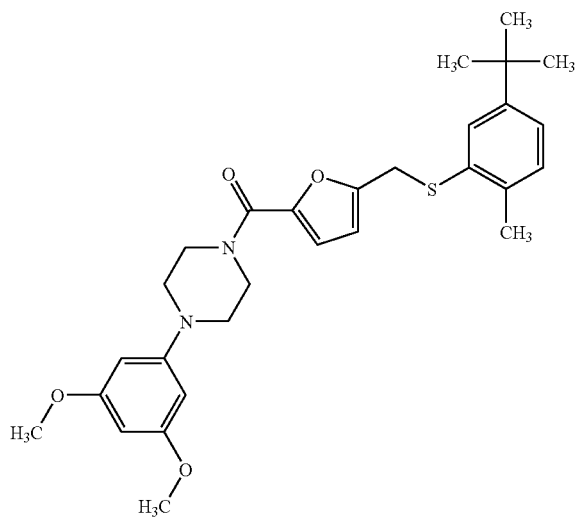 |
| 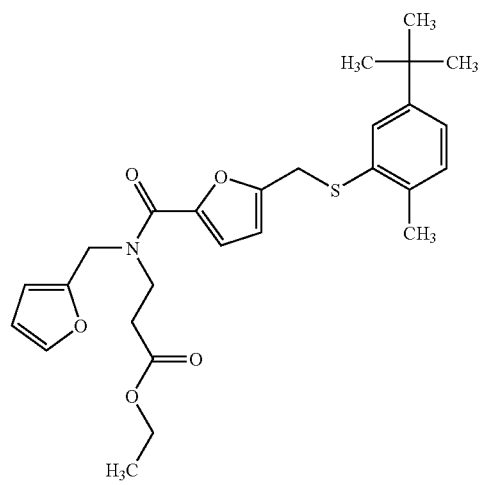 |
| 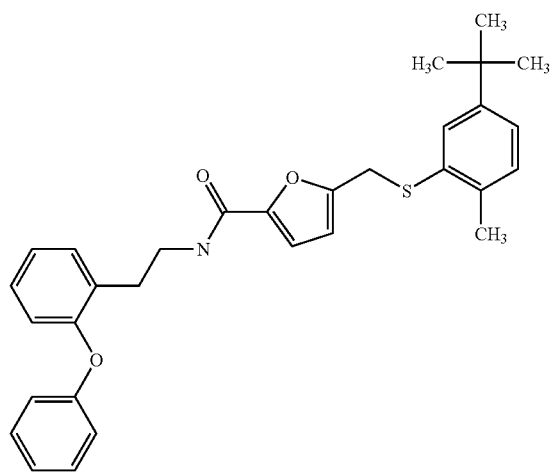 |

-continued
MOLSTRUCTURE
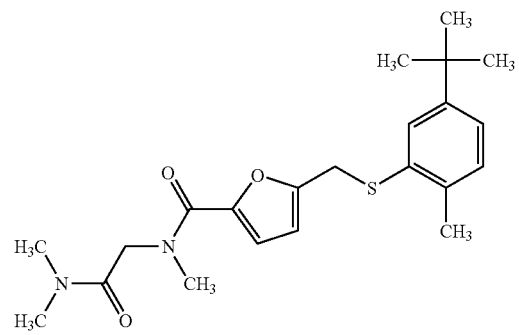
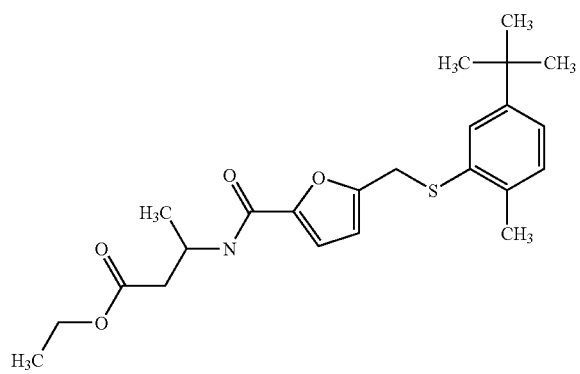
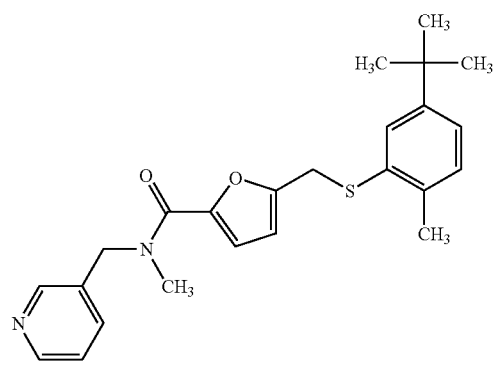
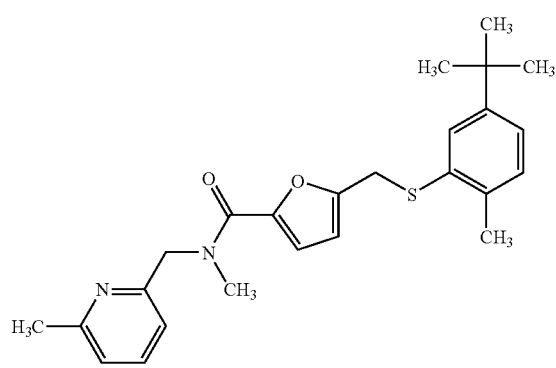

| MOLSTRUCTURE |
|---|
| 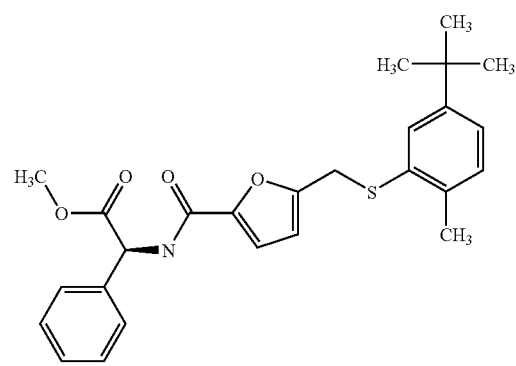 |
| 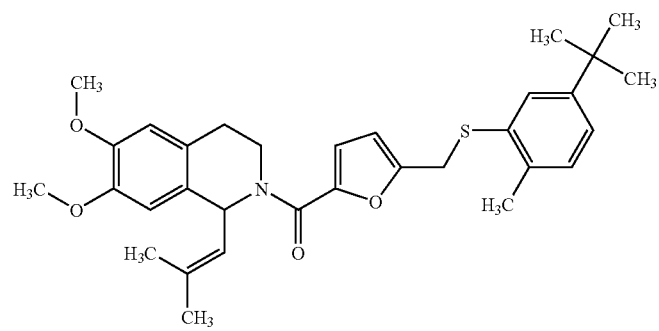 |
| 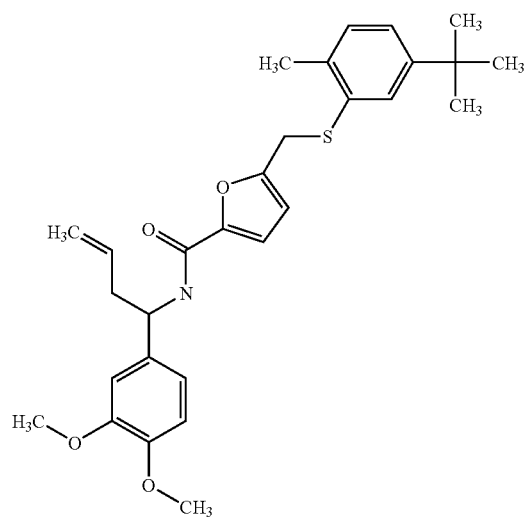 |

| MOLSTRUCTURE |
|---|
| 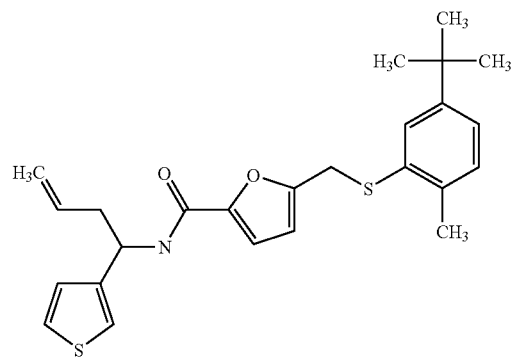 |
| 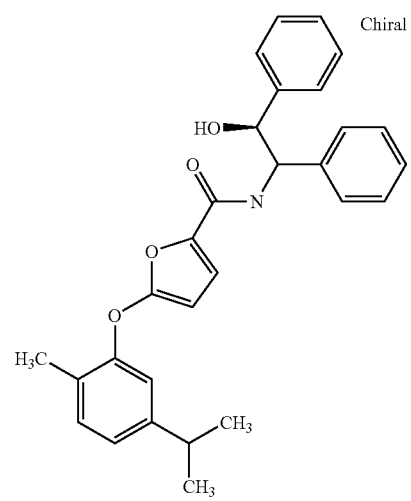 |
| 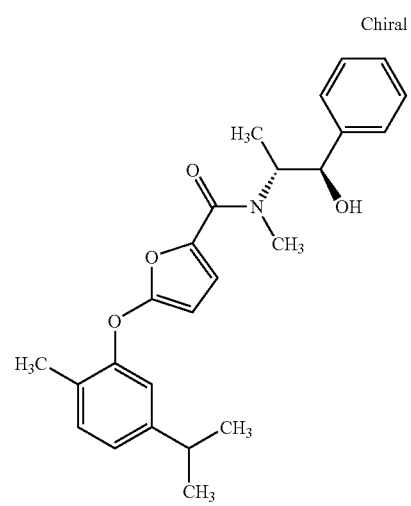 |

| MOLSTRUCTURE |
|---|
| 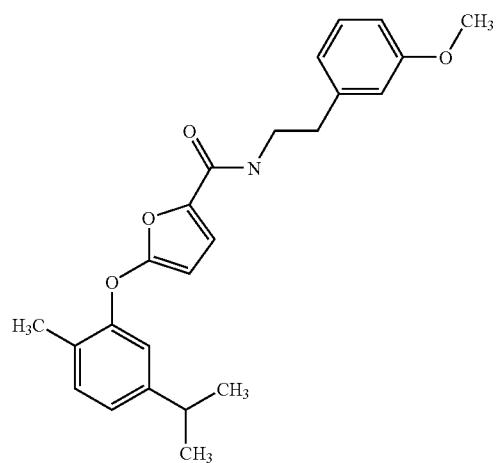 |
| 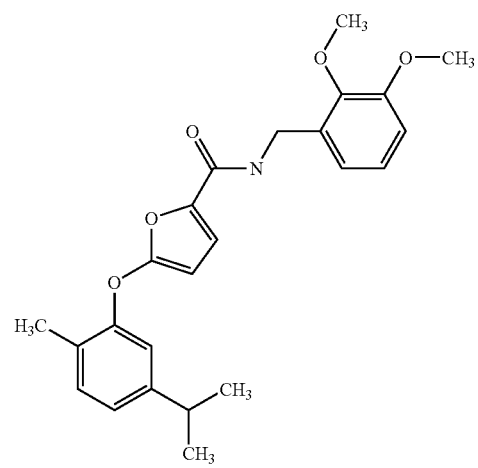 |
| 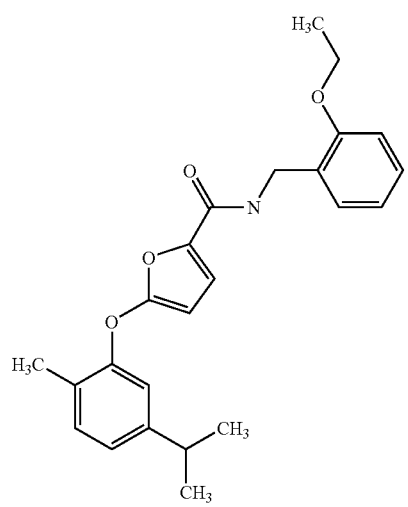 |

| MOLSTRUCTURE |
|---|
| 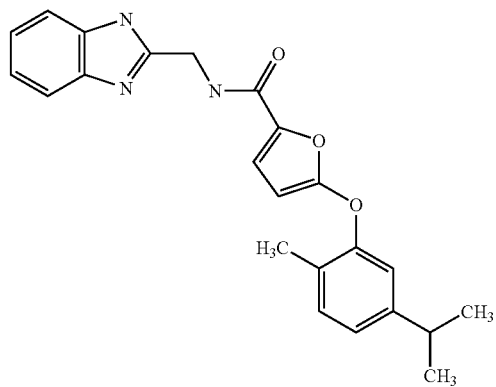 |
| 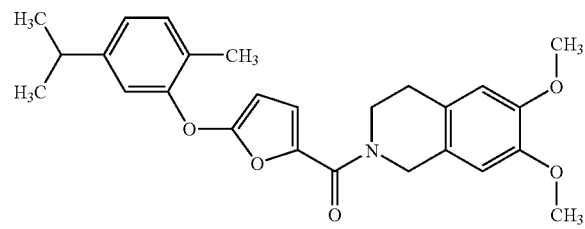 |
| 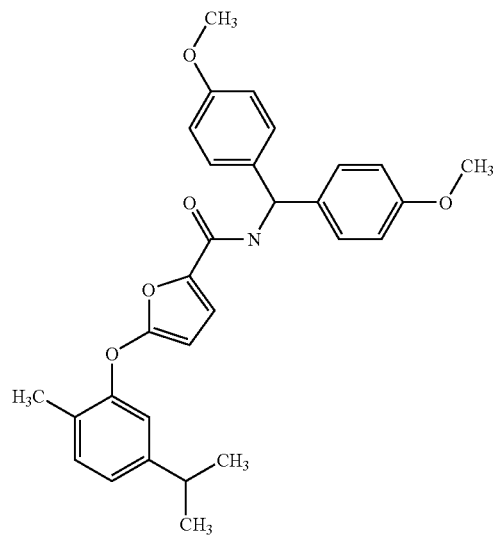 |

-continued
MOLSTRUCTURE
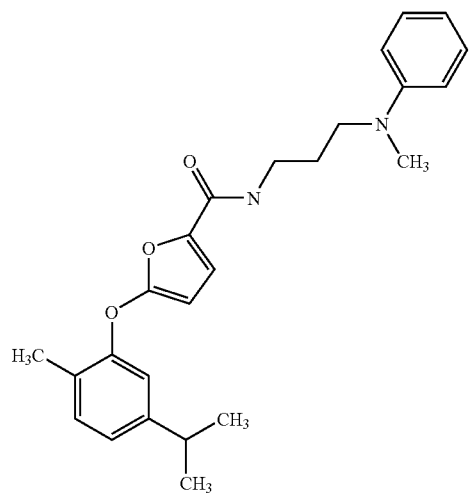
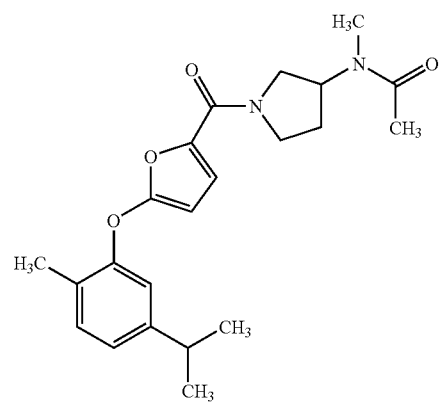
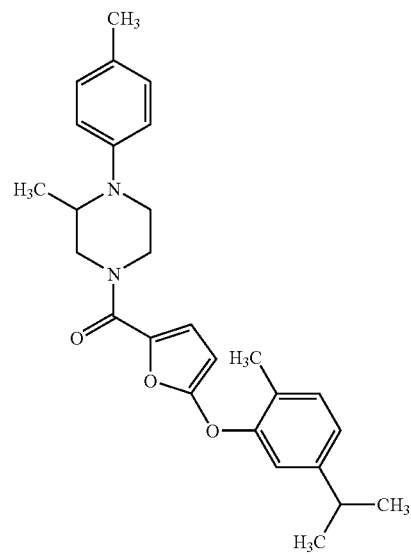

| MOLSTRUCTURE |
|---|
| 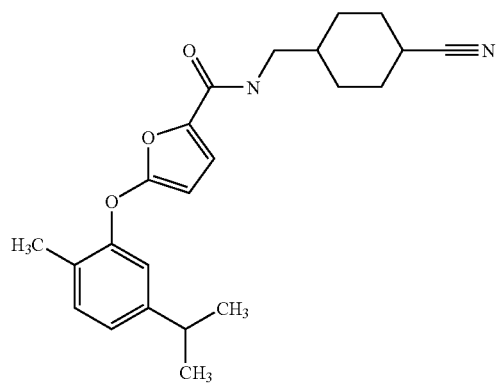 |
| 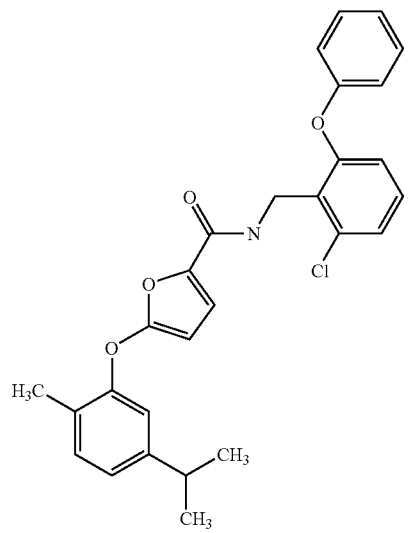 |
| 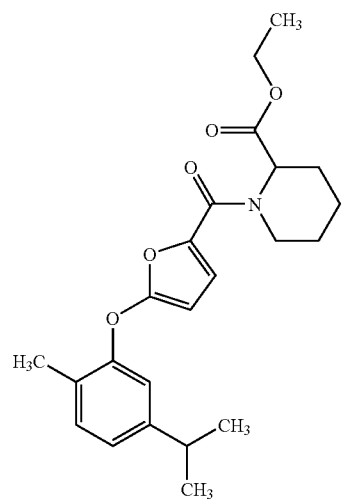 |

-continued
MOLSTRUCTURE
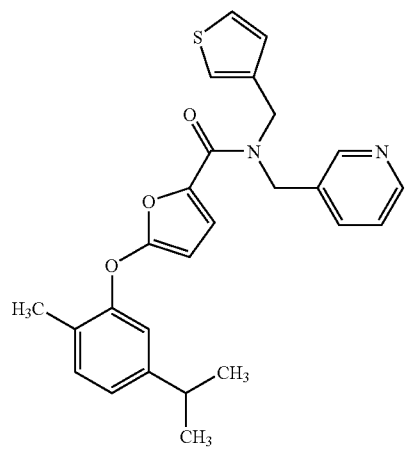
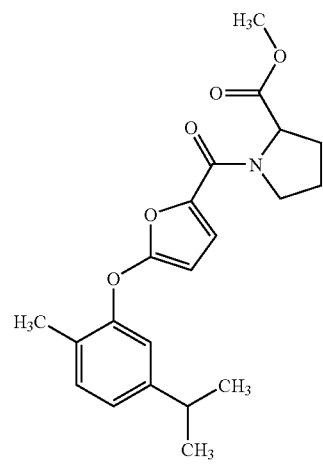
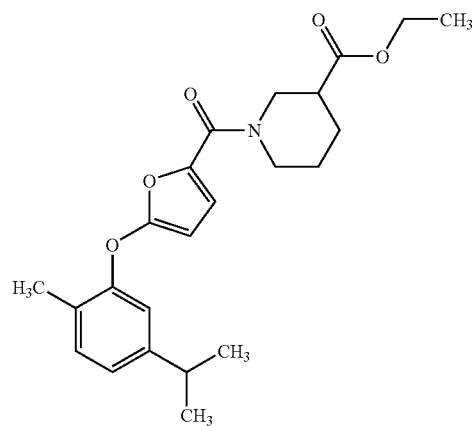

-continued
MOLSTRUCTURE
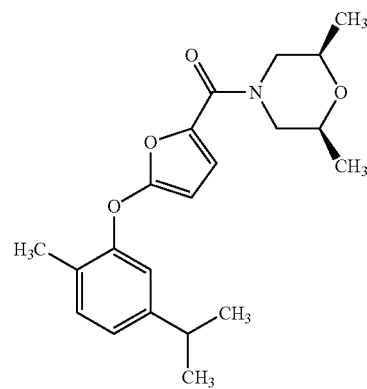
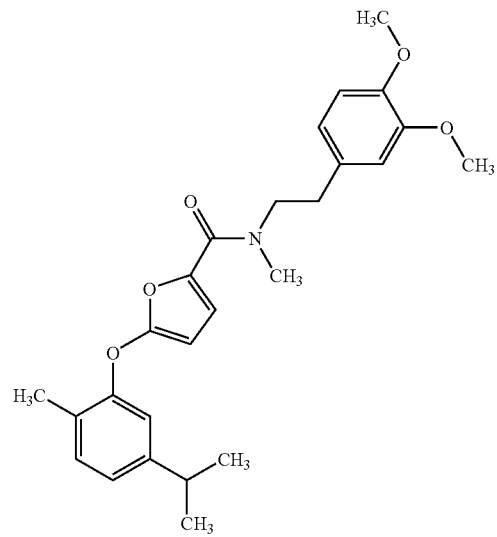
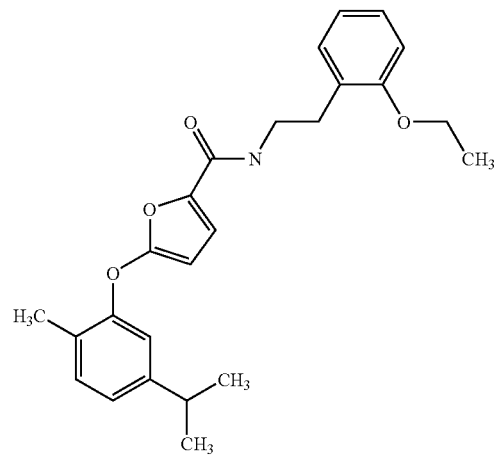

-continued
| MOLSTRUCTURE |
| --- |
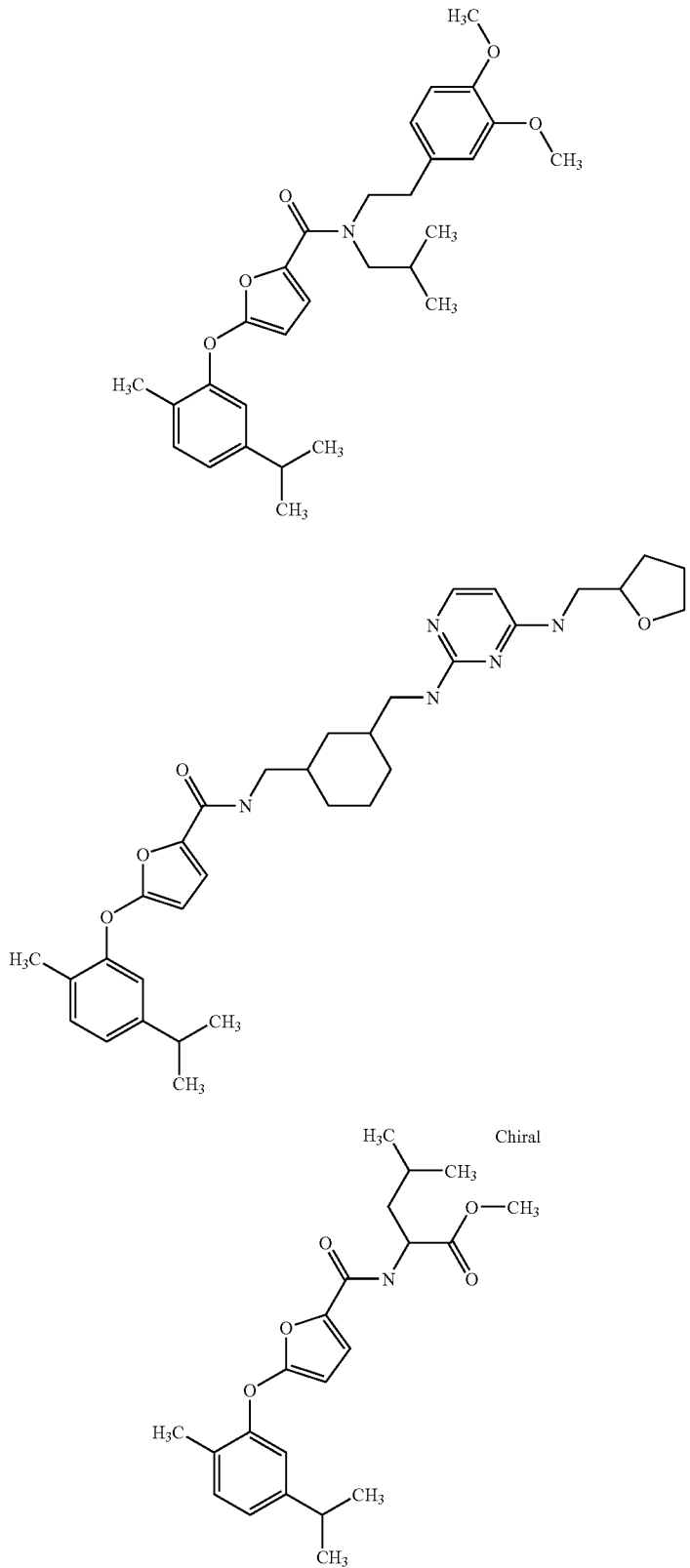

| MOLSTRUCTURE |
|---|
| 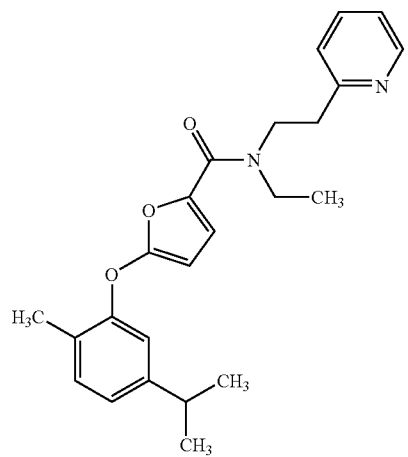 |
| 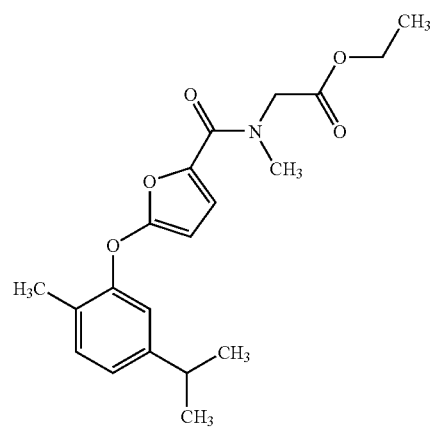 |
| 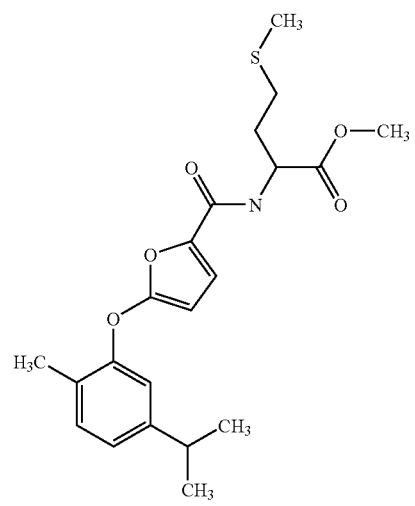 |

-continued
MOLSTRUCTURE
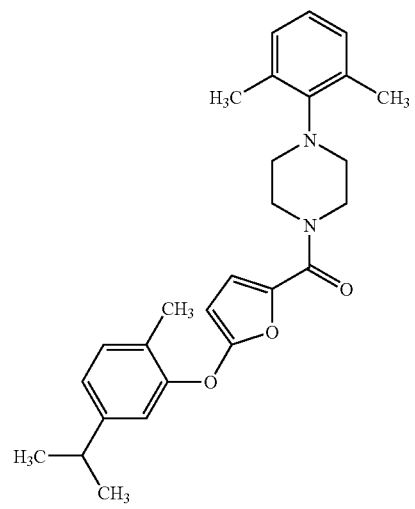
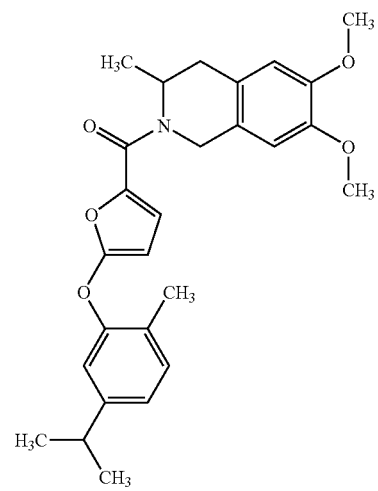
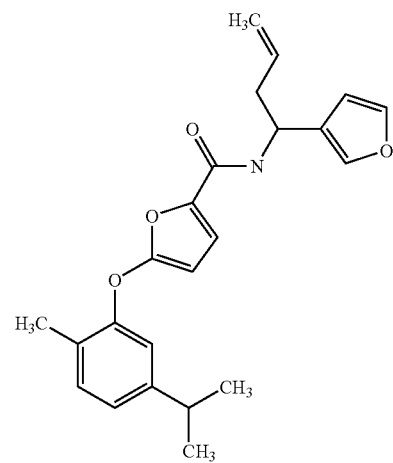

-continued
MOLSTRUCTURE
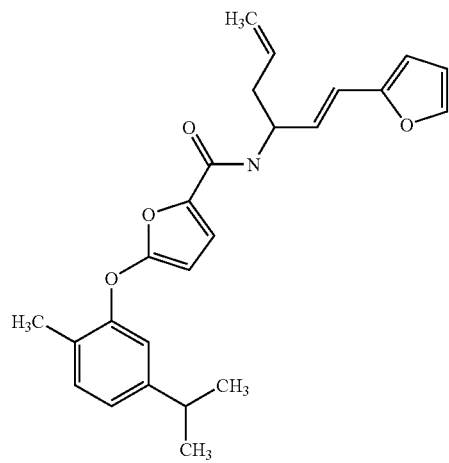
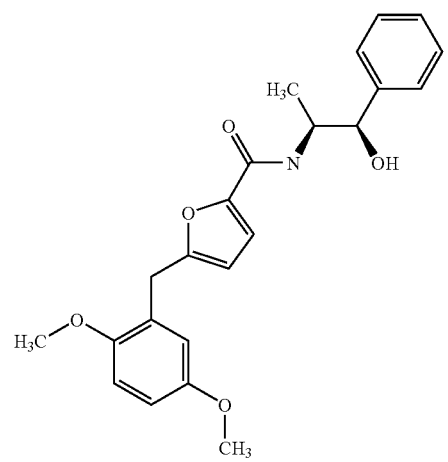
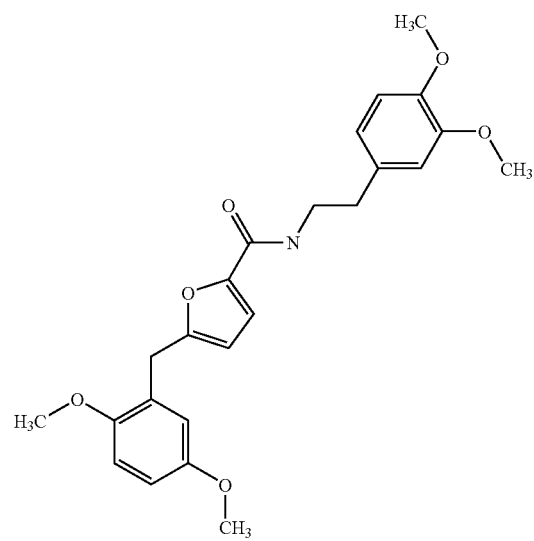

-continued
MOLSTRUCTURE
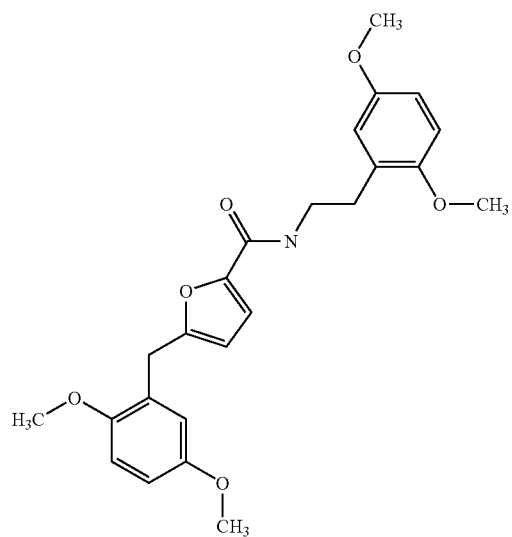
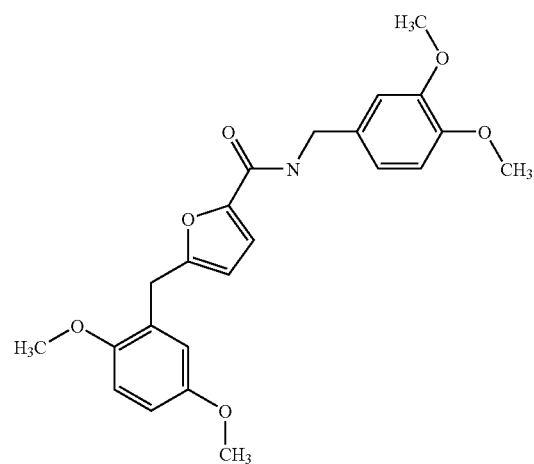
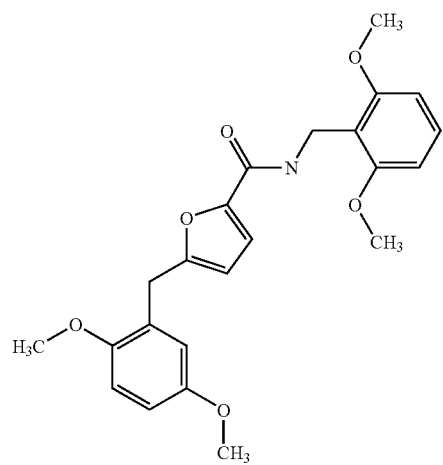

| MOLSTRUCTURE |
|---|
| 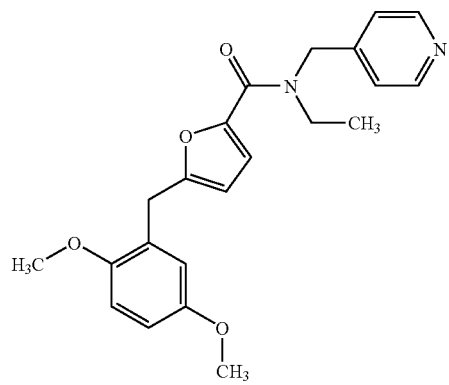 |
| 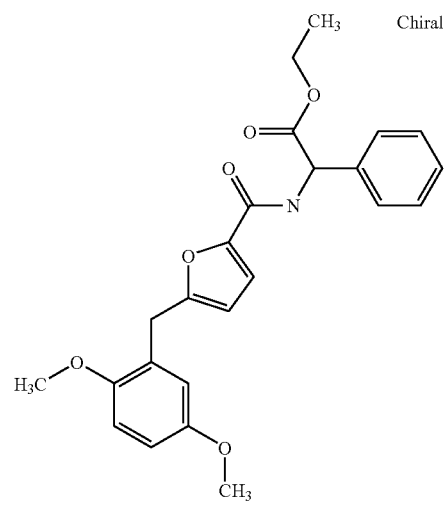 |
| 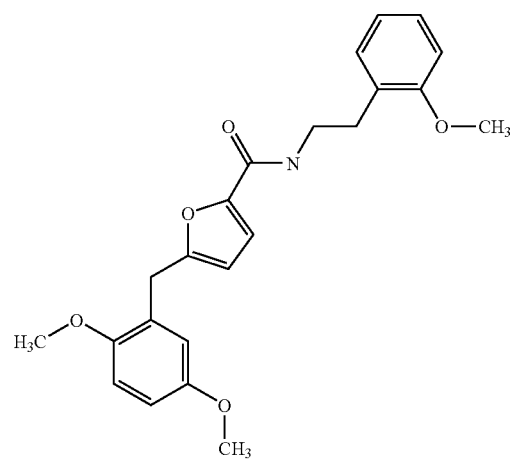 |

-continued
| MOLSTRUCTURE |
|---|
| 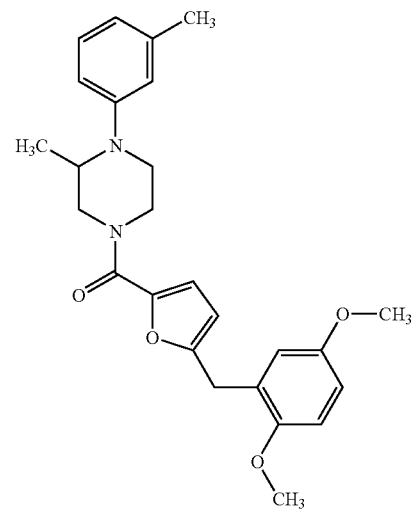 |
| 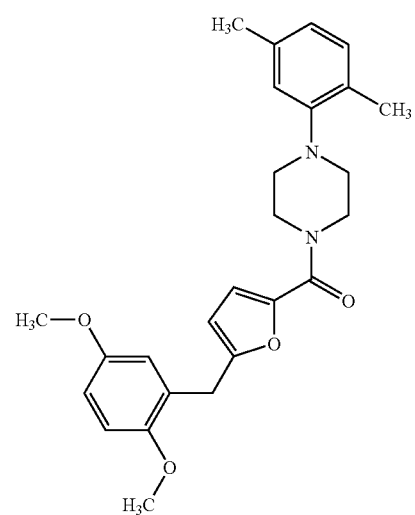 |
| 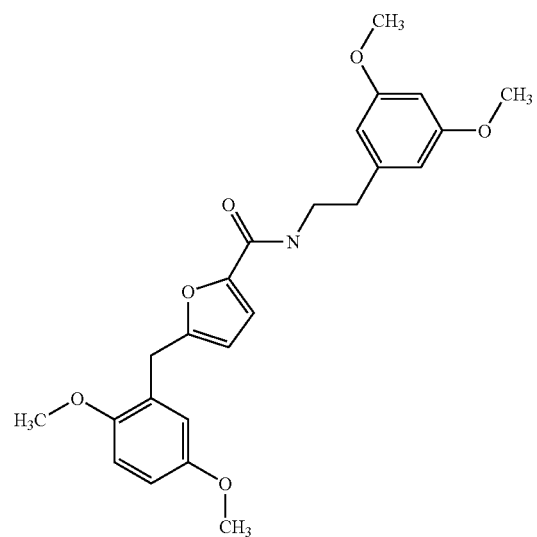 |

-continued
MOLSTRUCTURE
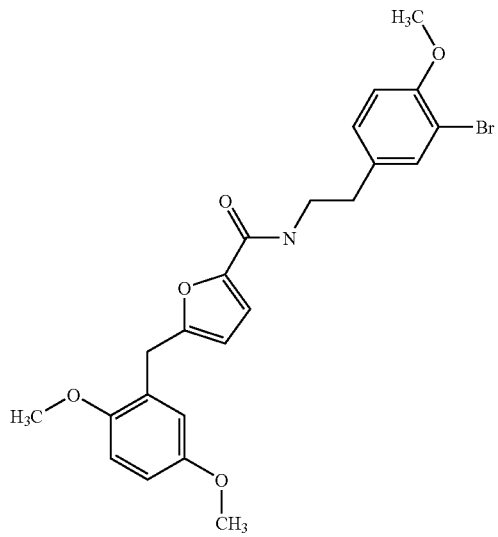
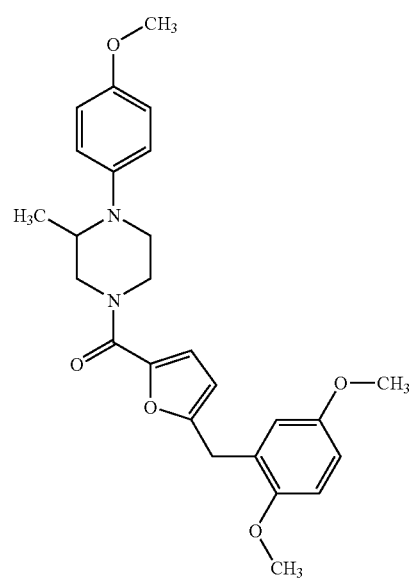
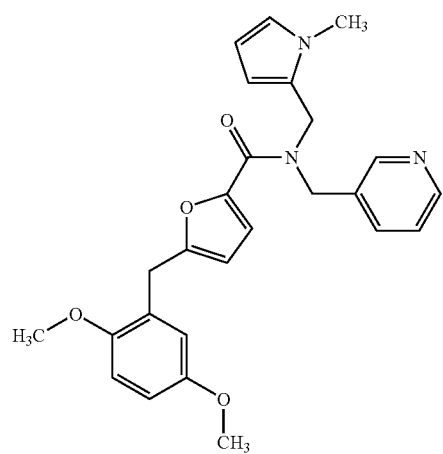

| MOLSTRUCTURE |
|---|
| 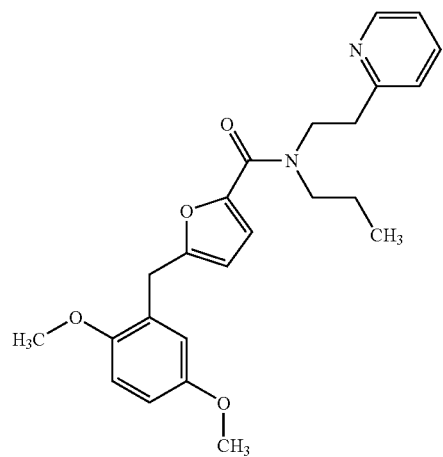 |
| 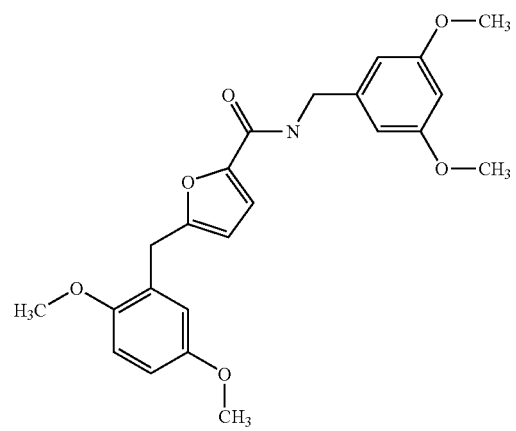 |
| 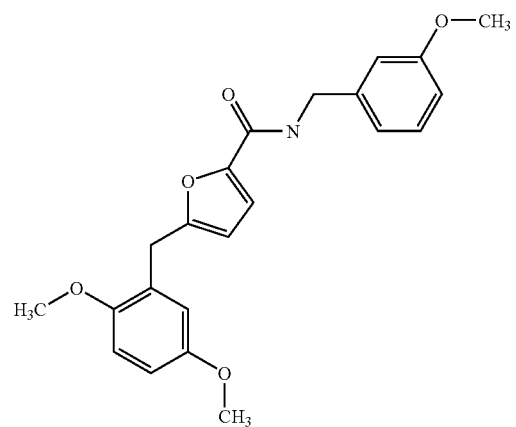 |

| MOLSTRUCTURE |
| --- |
| 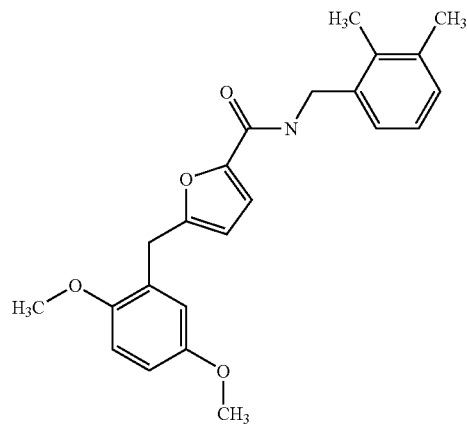 |
| 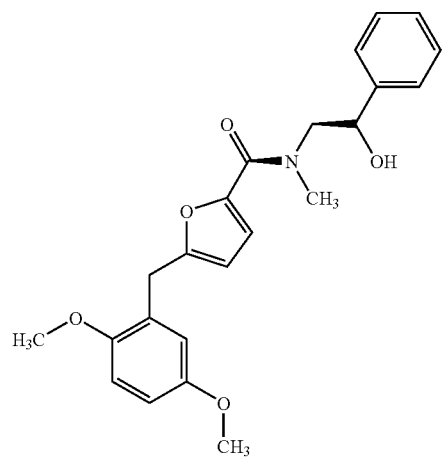 |
| 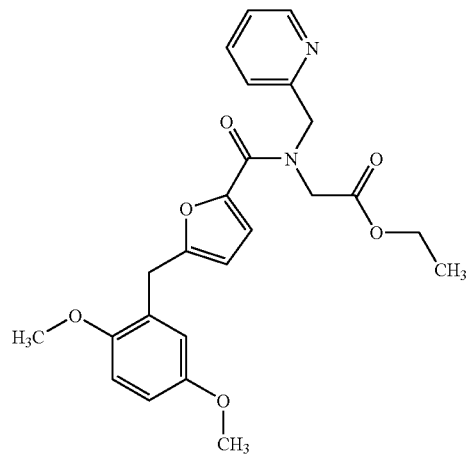 |

-continued
| MOLSTRUCTURE |
|---|
| 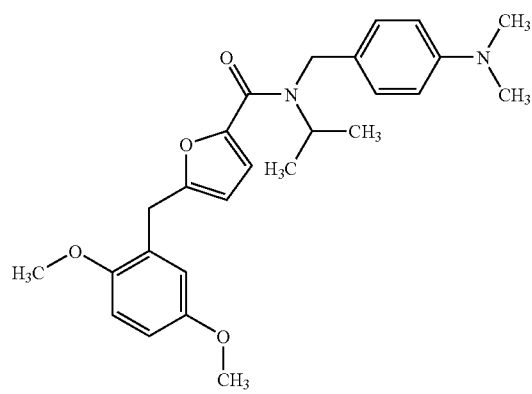 |
| 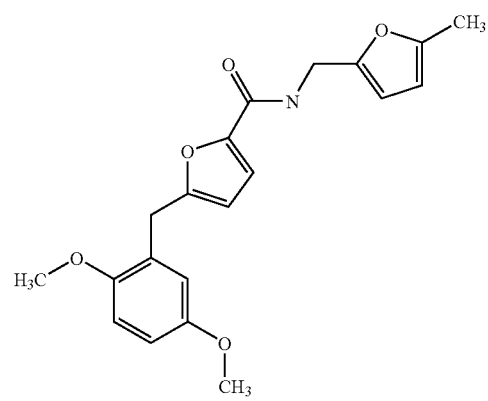 |
| 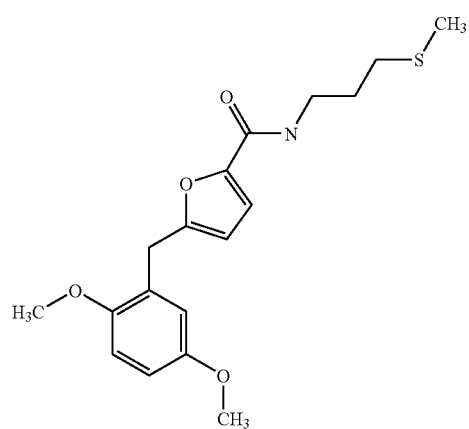 |

-continued
MOLSTRUCTURE
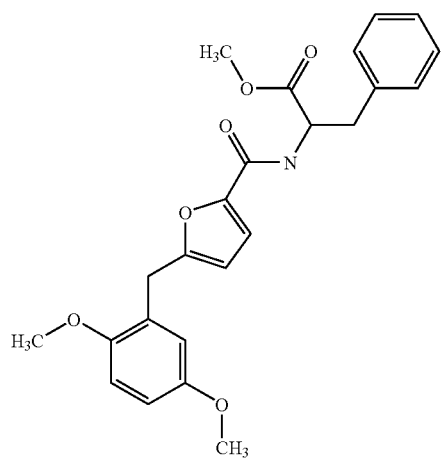
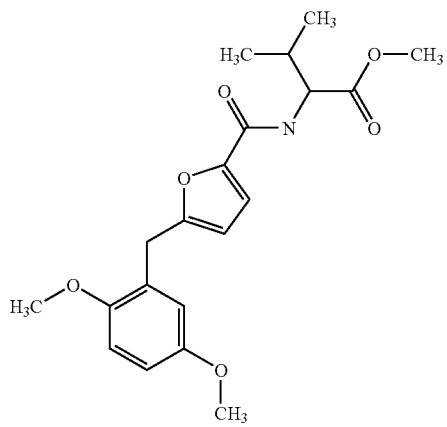
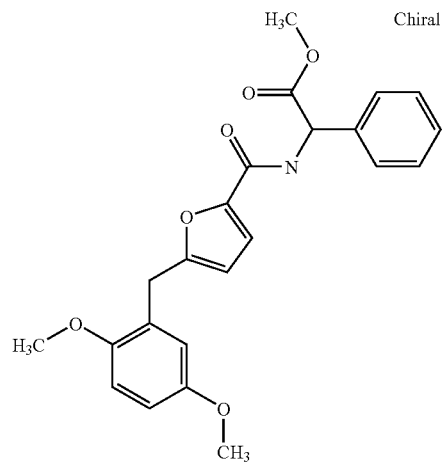

| MOLSTRUCTURE |
| --- |
| 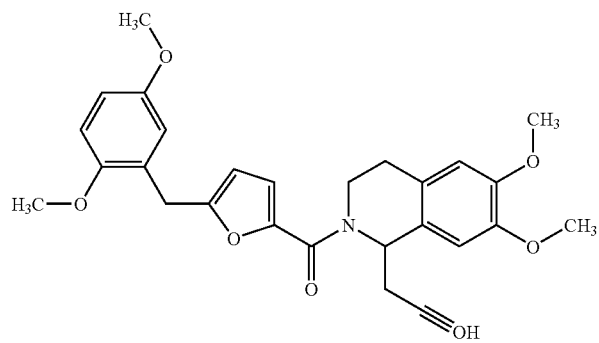 |
| 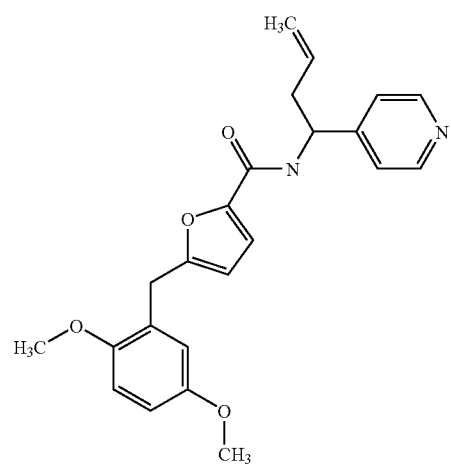 |
| 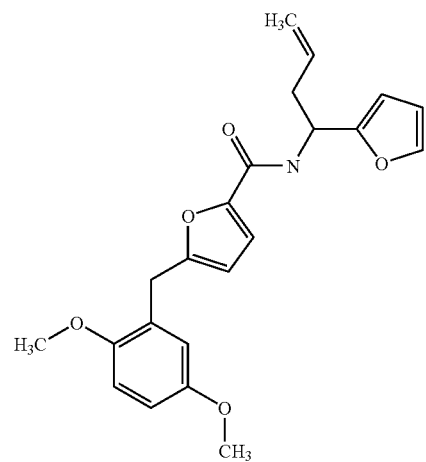 |

-continued
MOLSTRUCTURE
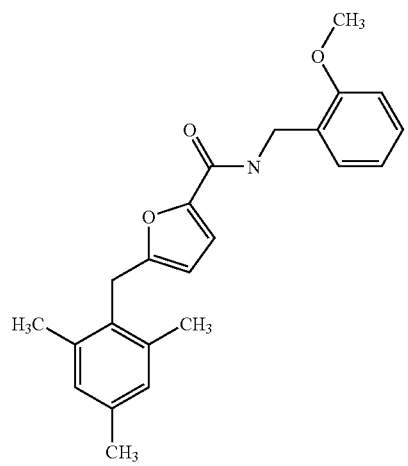
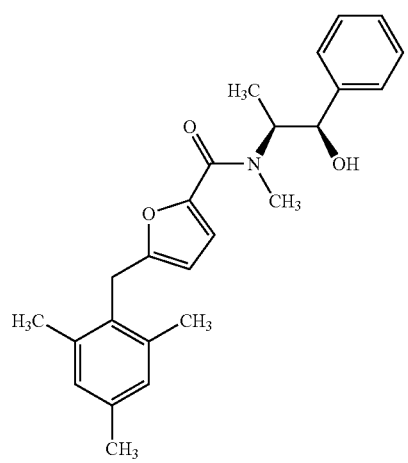
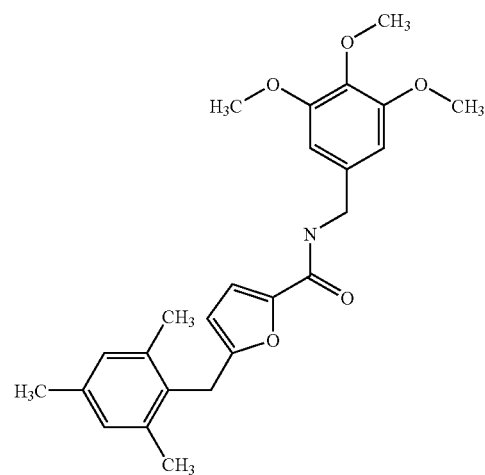

-continued
MOLSTRUCTURE
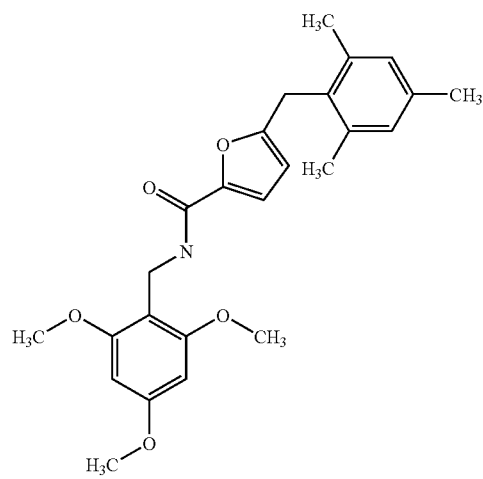
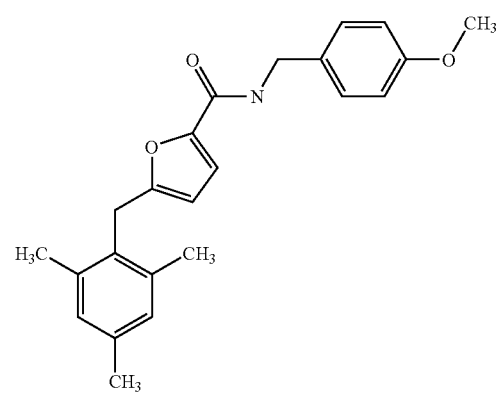
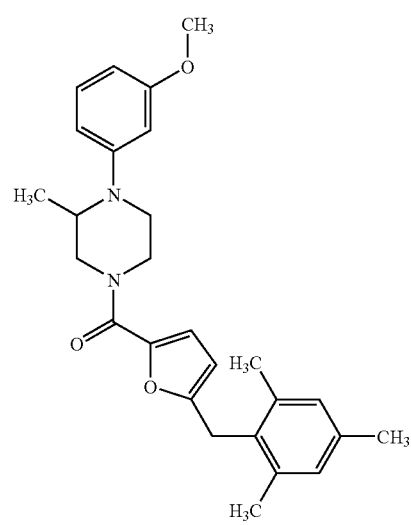

-continued
MOLSTRUCTURE
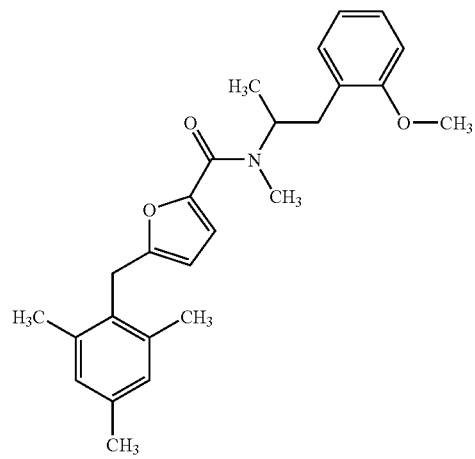
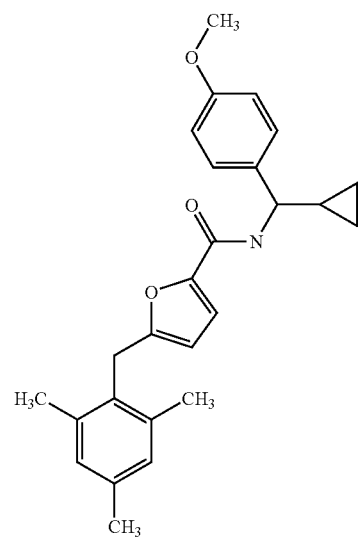
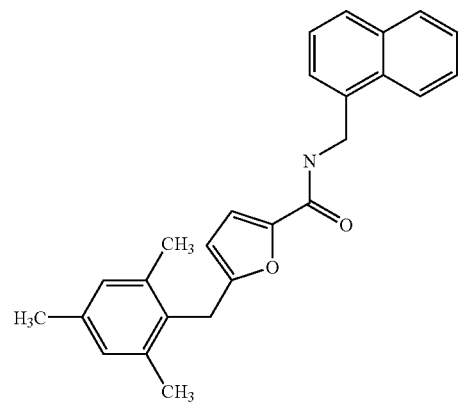

-continued
| MOLSTRUCTURE |
|---|
| 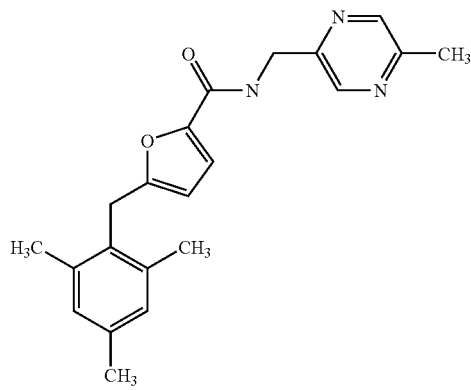 |
| 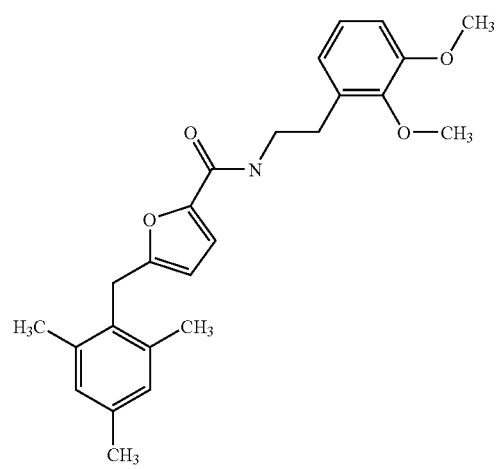 |
| 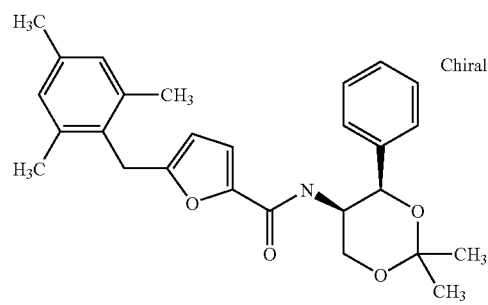 |
| 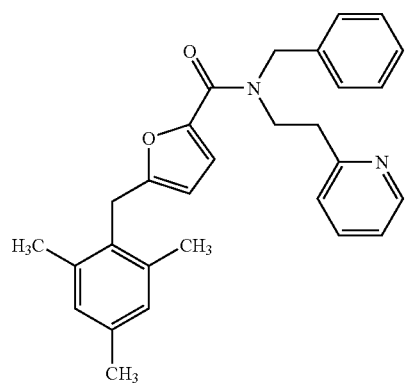 |

| MOLSTRUCTURE |
|---|
| 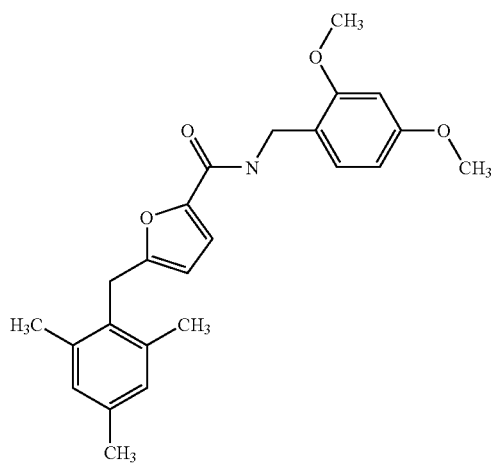 |
| 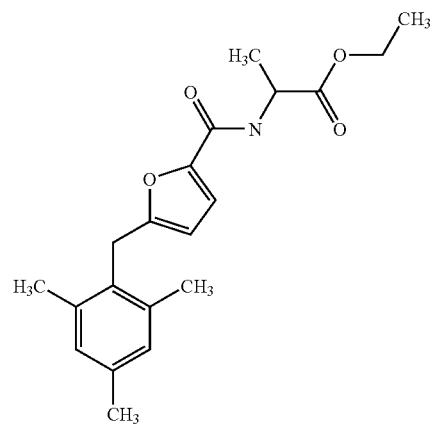 |
| 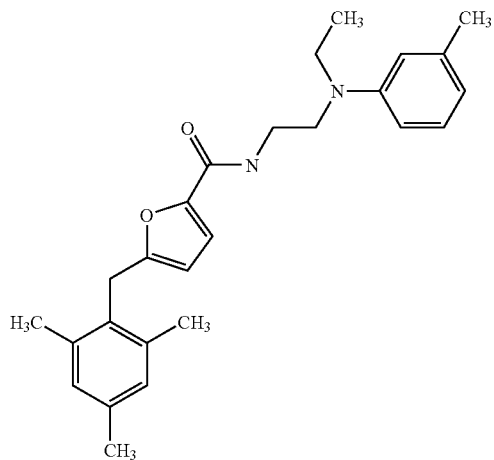 |

-continued
MOLSTRUCTURE
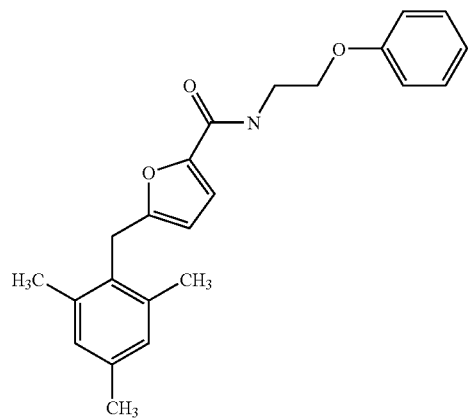
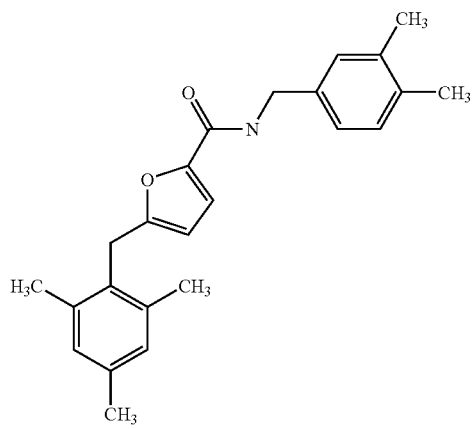
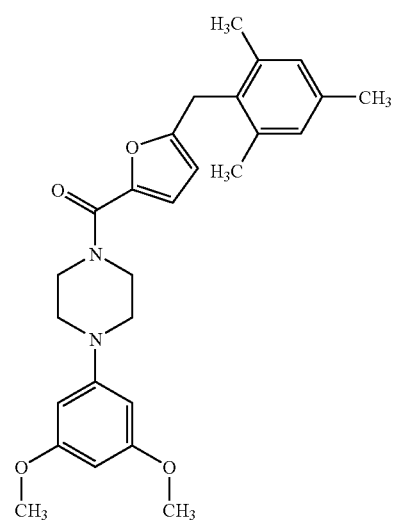

-continued
| MOLSTRUCTURE |
|---|
| 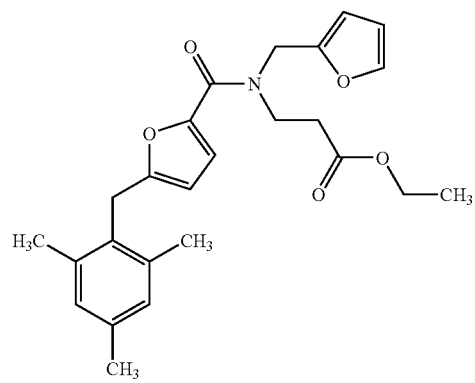 |
| 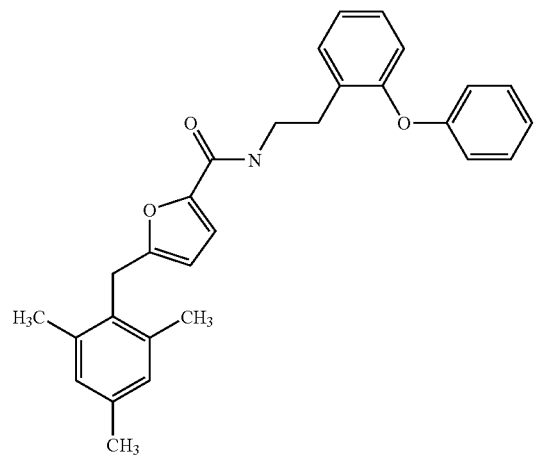 |
| 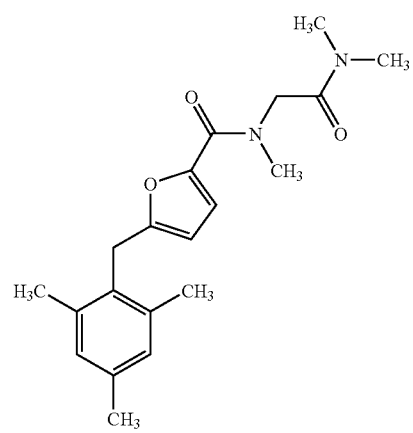 |

| MOLSTRUCTURE |
|---|
| 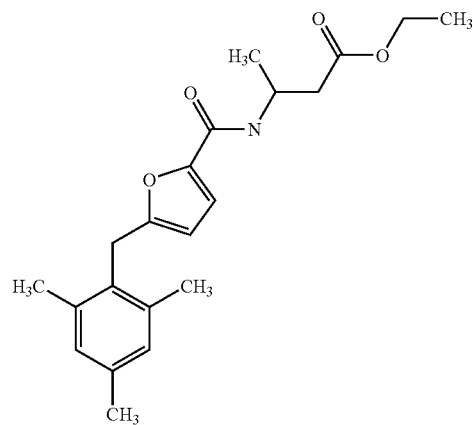 |
| 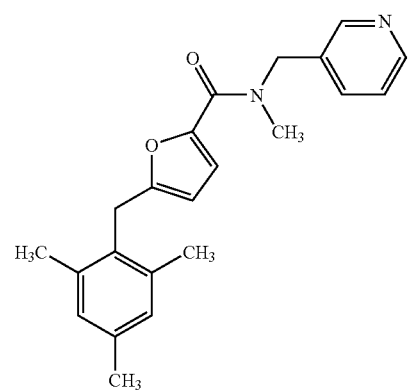 |
| 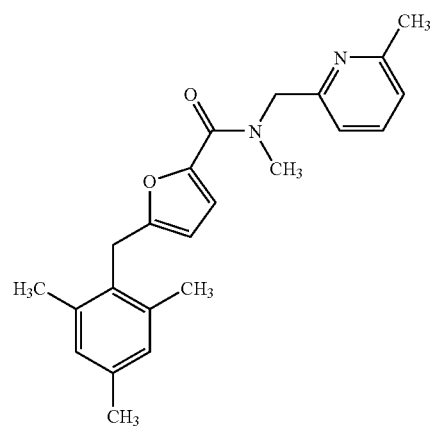 |

| MOLSTRUCTURE |
|---|
| 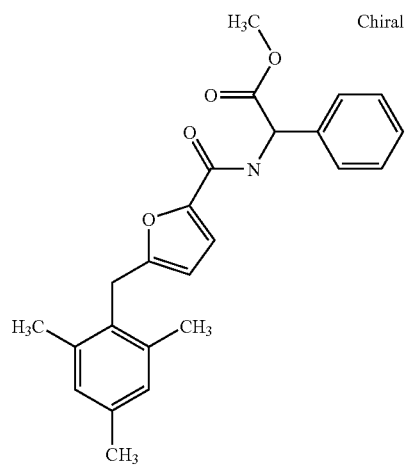 |
| 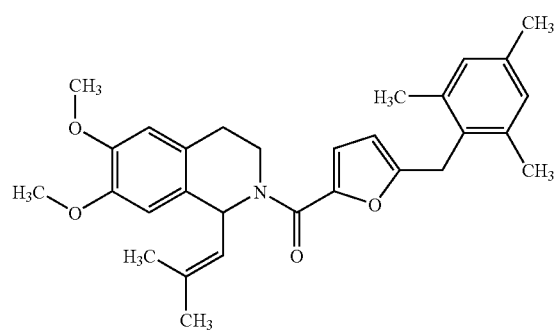 |
| 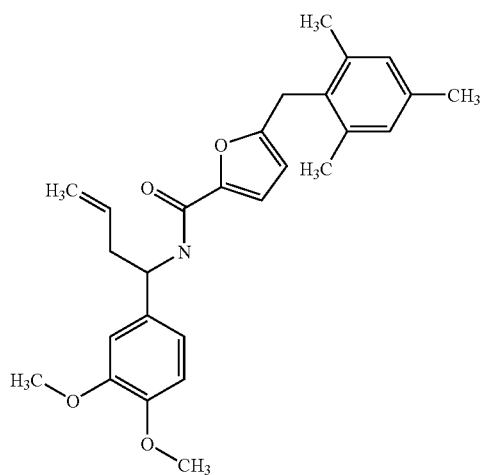 |

-continued
| MOLSTRUCTURE |
|---|
| 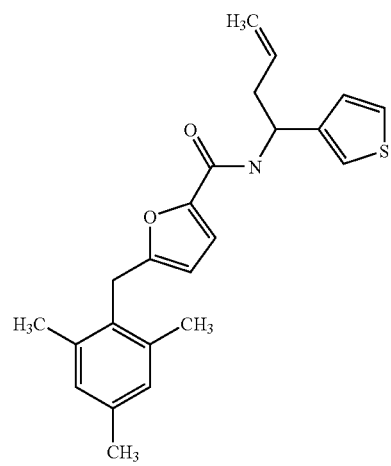 |
| 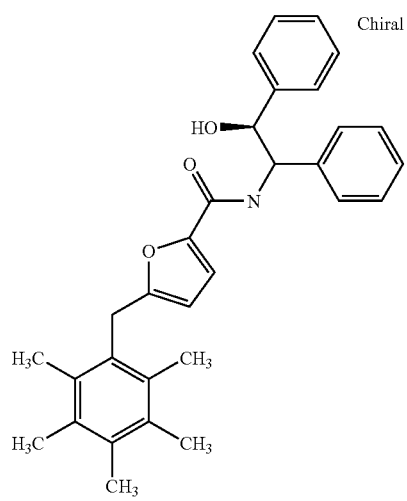 |
| 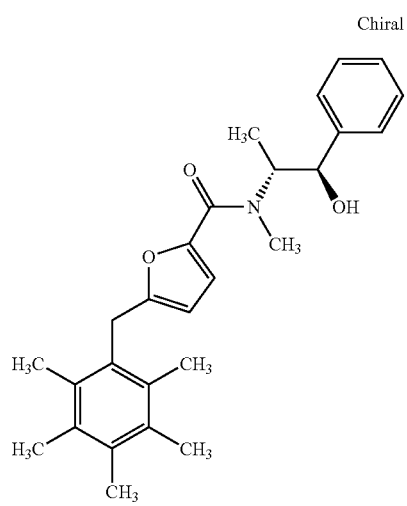 |

| MOLSTRUCTURE |
|---|
| 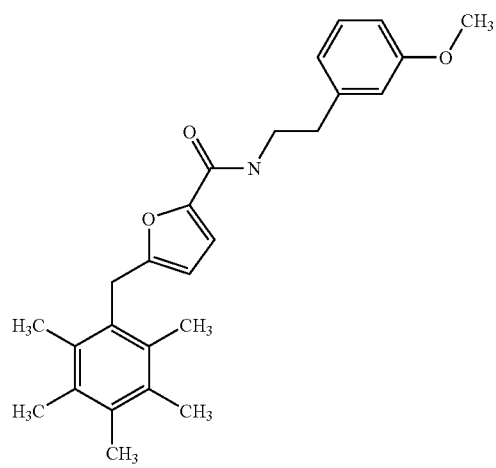 |
| 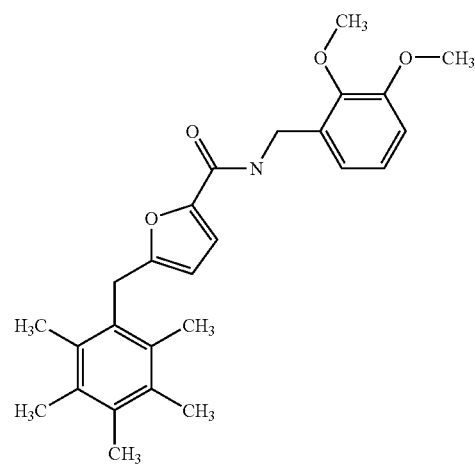 |
| 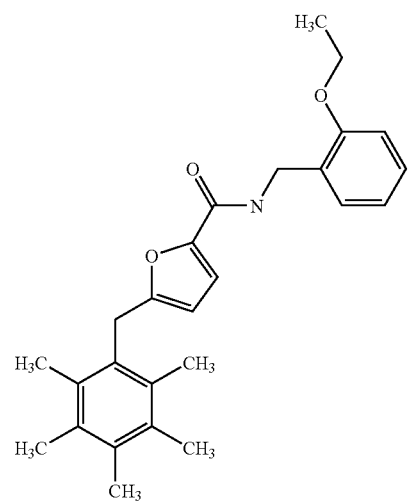 |

-continued
MOLSTRUCTURE
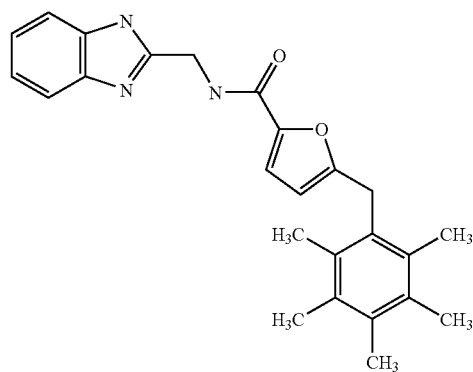
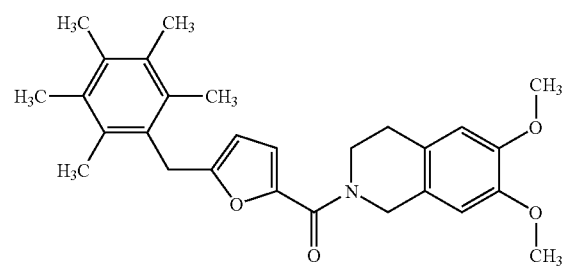
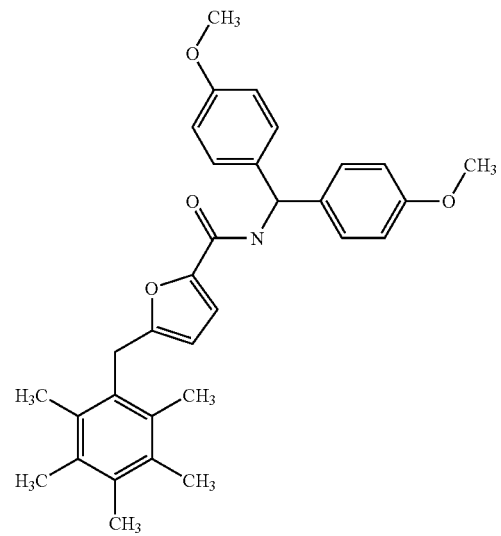

-continued
MOLSTRUCTURE
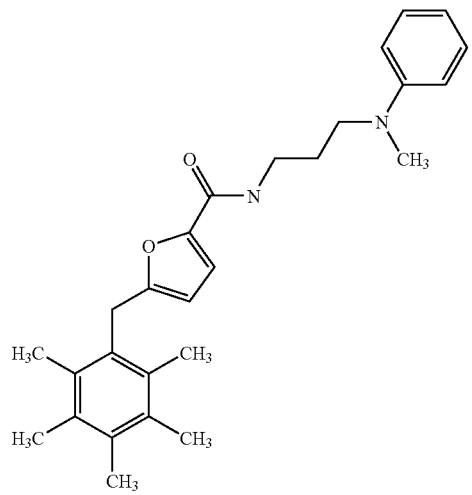
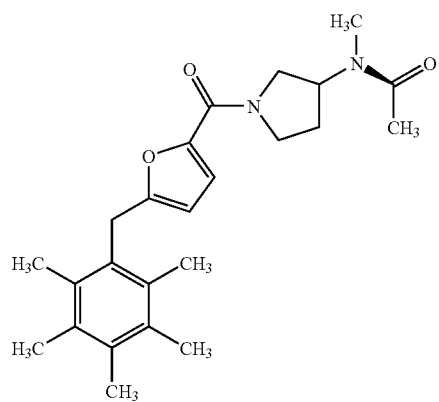
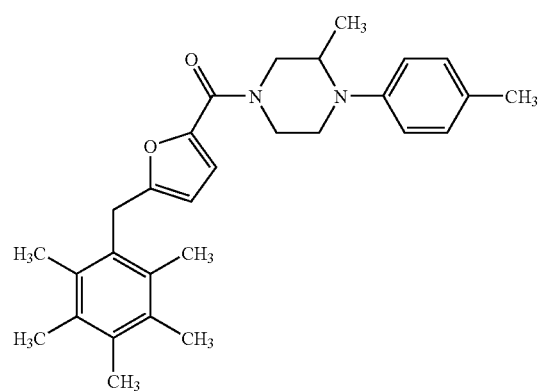

-continued
MOLSTRUCTURE
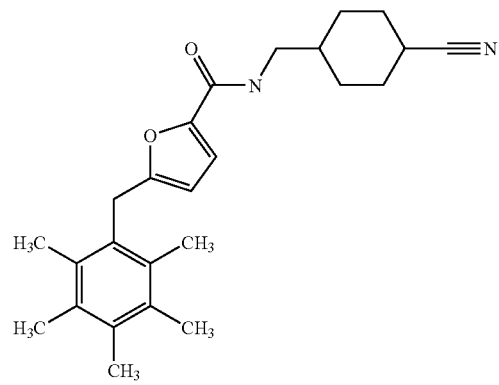
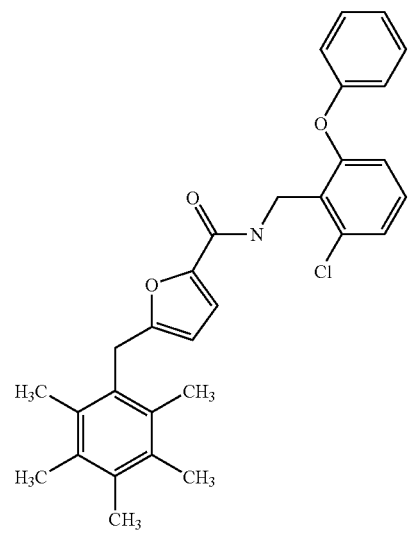
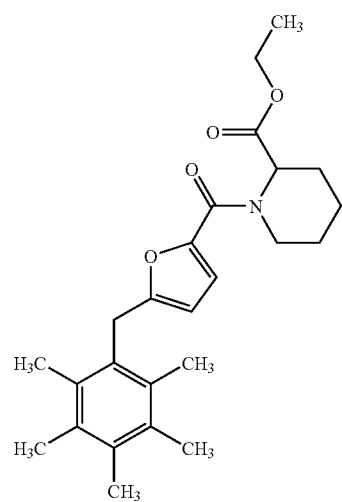

-continued
MOLSTRUCTURE
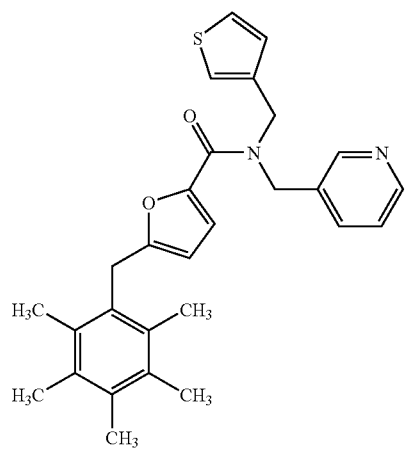
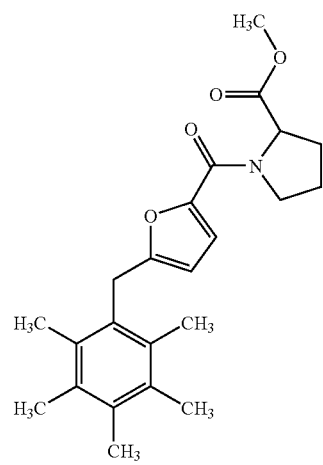
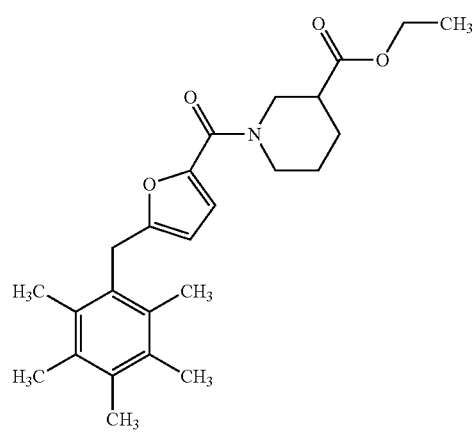

-continued
MOLSTRUCTURE
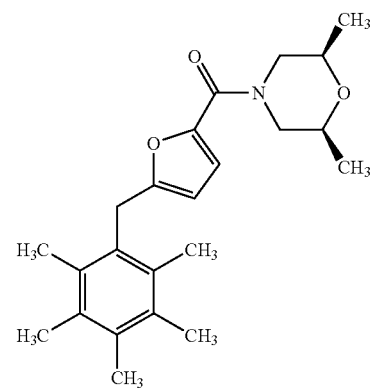
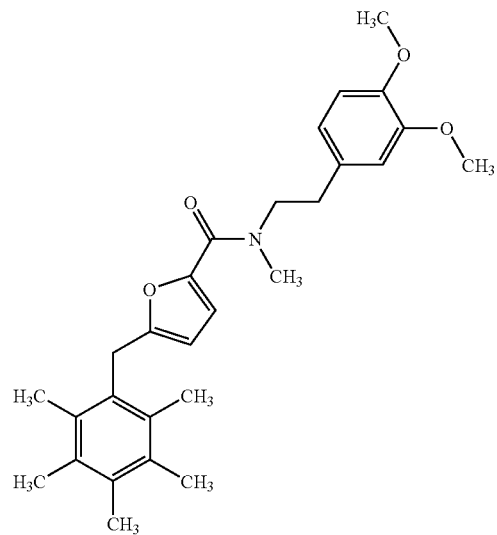
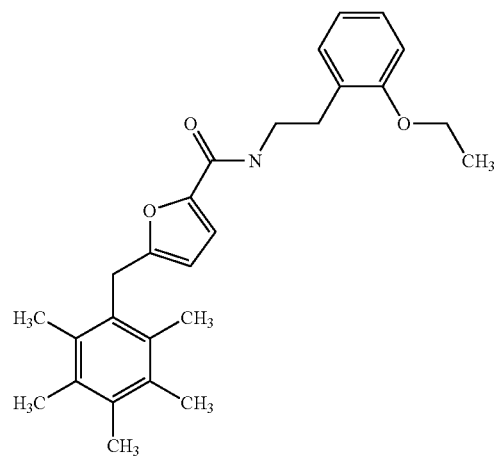

-continued
| MOLSTRUCTURE |
|---|
| 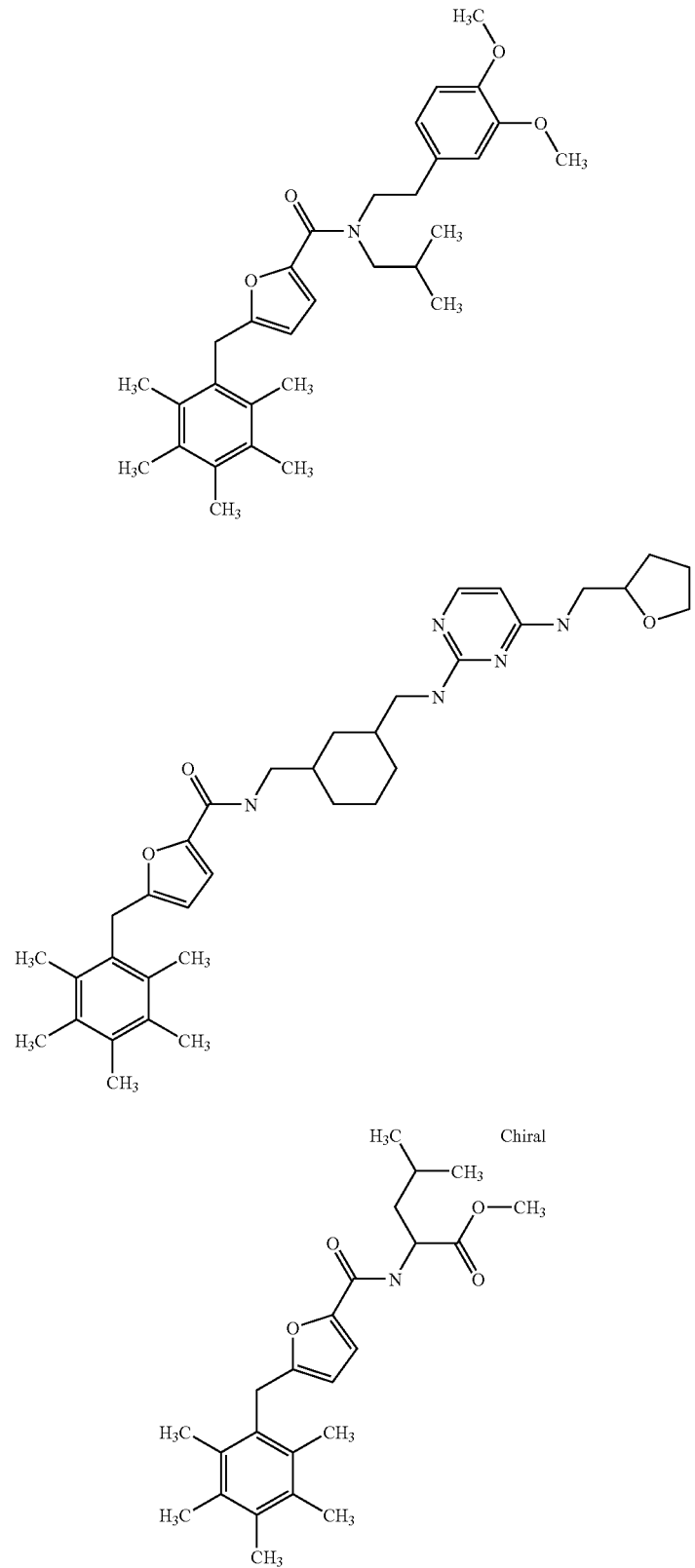 |

-continued
| MOLSTRUCTURE |
|---|
| 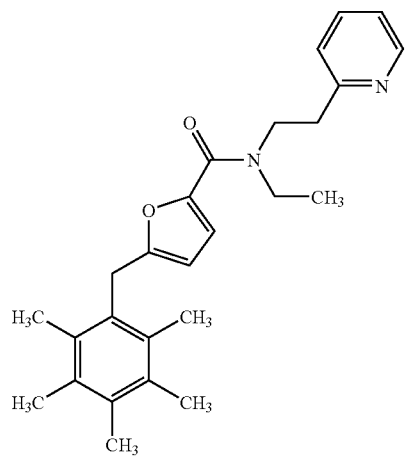 |
| 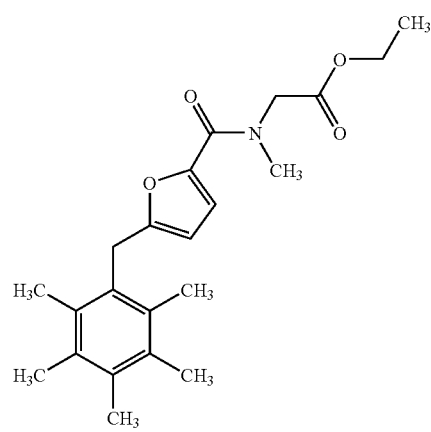 |
| 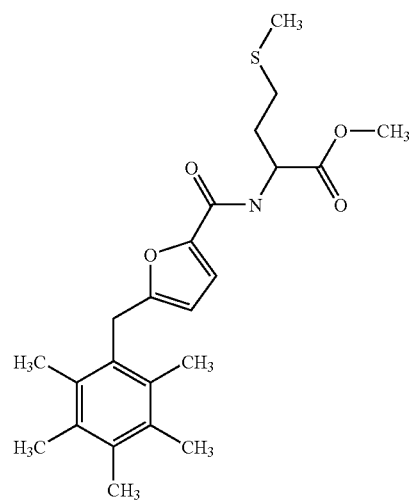 |

-continued
MOLSTRUCTURE
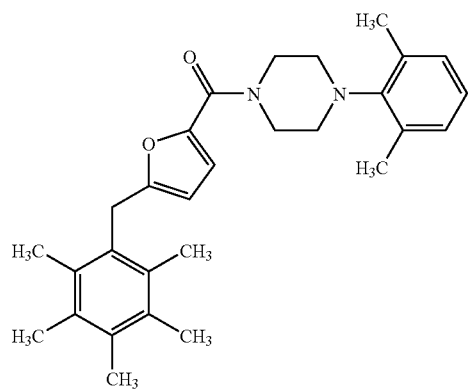
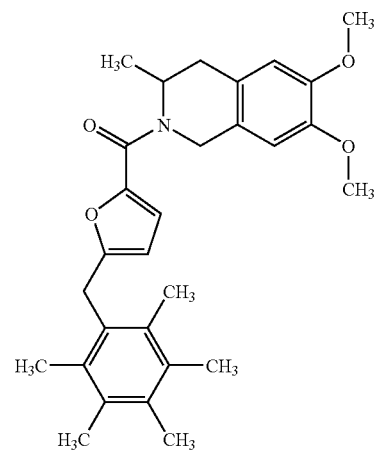
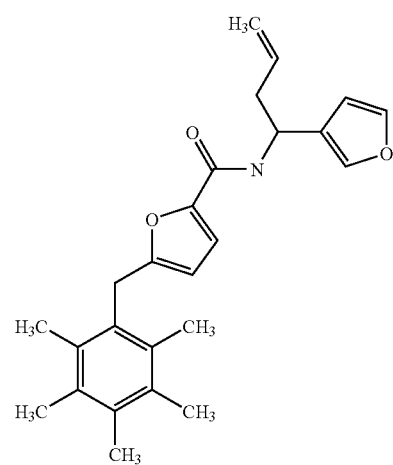

-continued
MOLSTRUCTURE
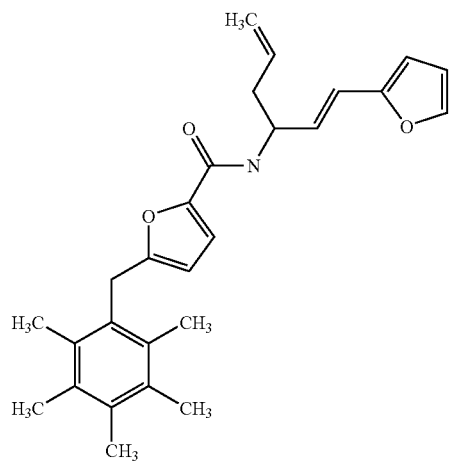
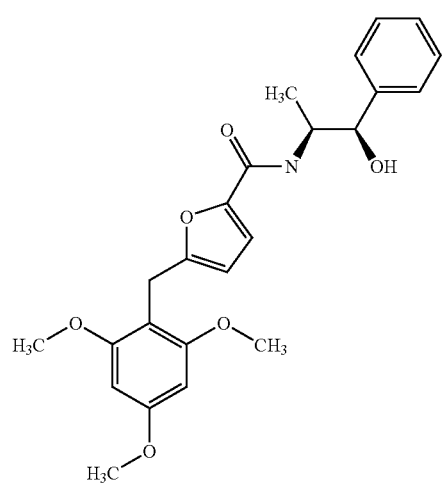
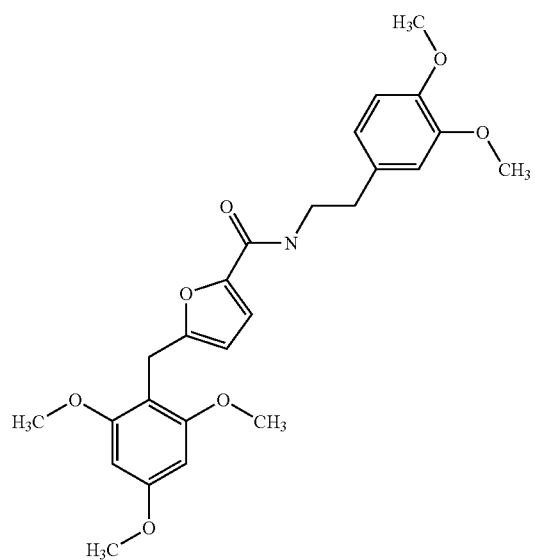

| MOLSTRUCTURE |
|---|
| 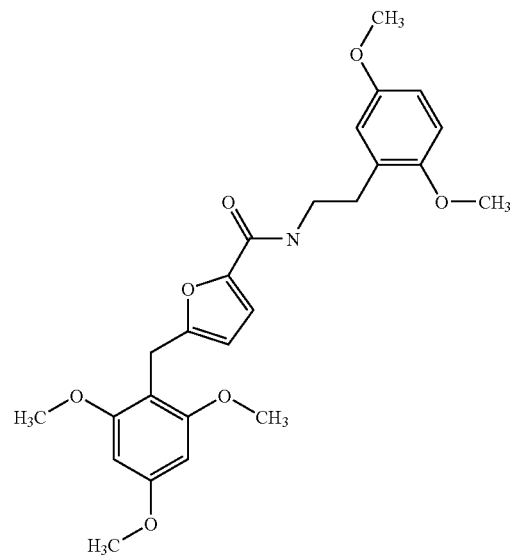 |
| 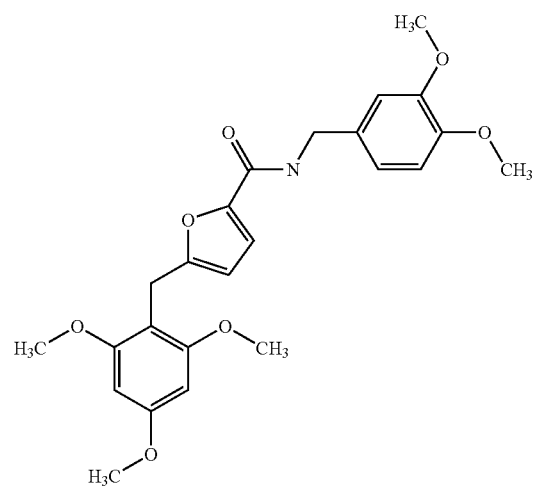 |
| 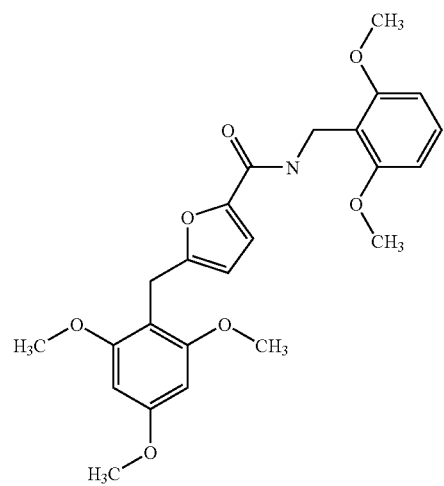 |

-continued
MOLSTRUCTURE
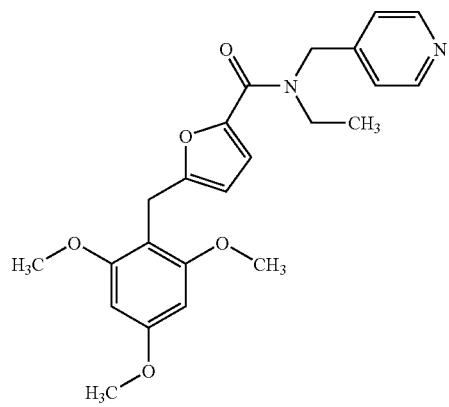
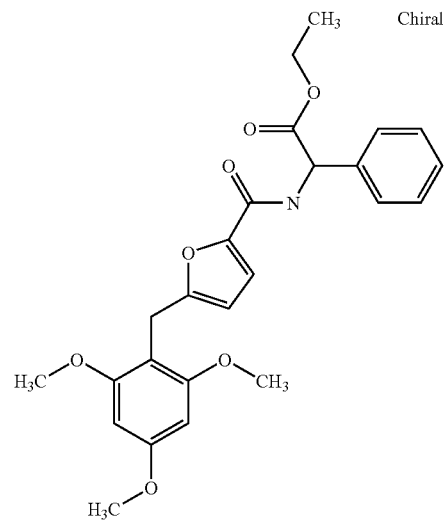
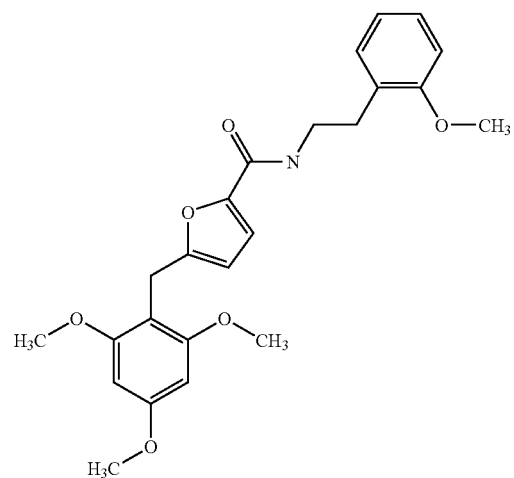

| MOLSTRUCTURE |
| --- |
| 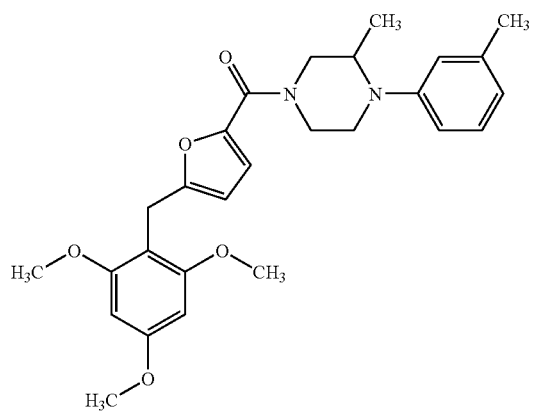 |
| 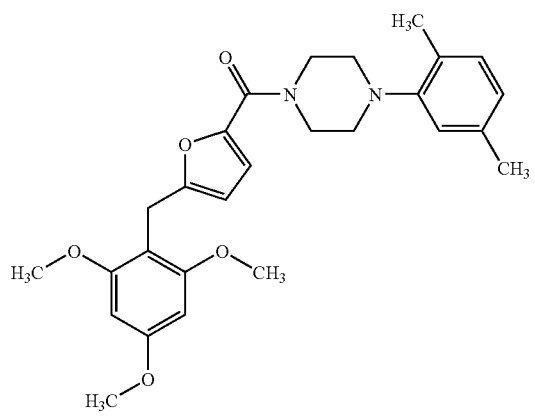 |
| 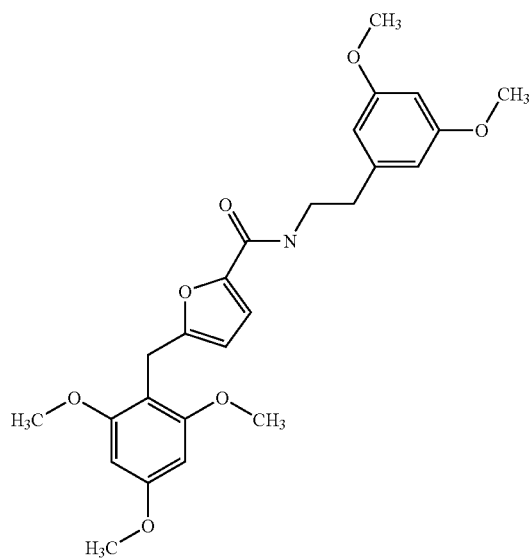 |

| MOLSTRUCTURE |
|---|
| 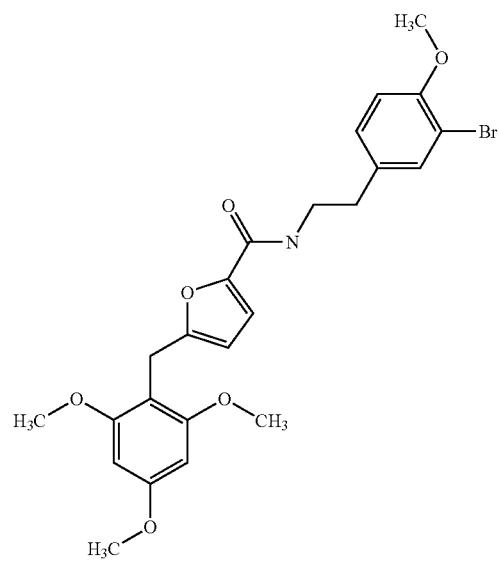 |
| 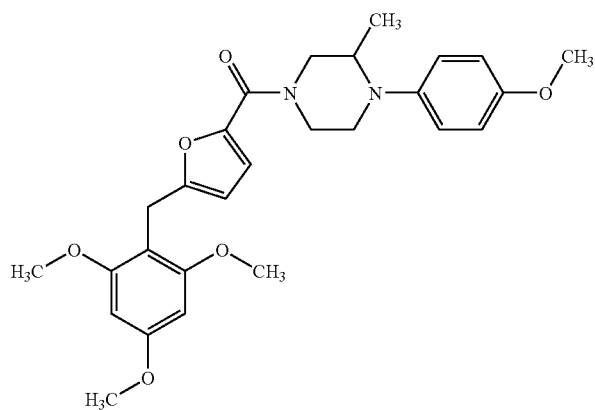 |
| 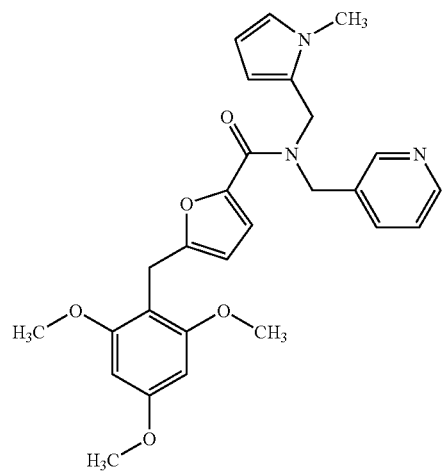 |

| MOLSTRUCTURE |
|---|
| 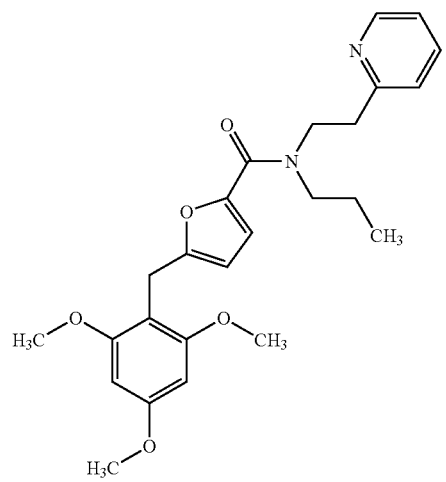 |
| 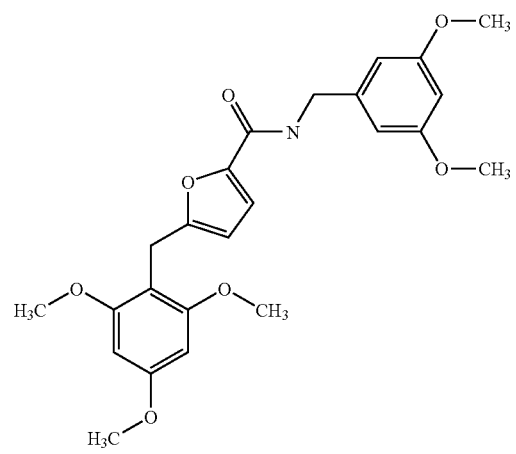 |
| 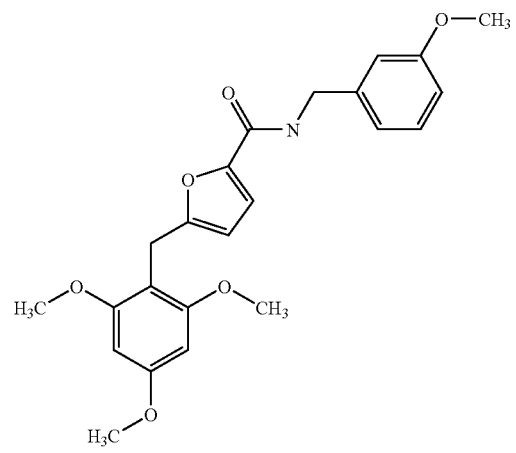 |

-continued
MOLSTRUCTURE
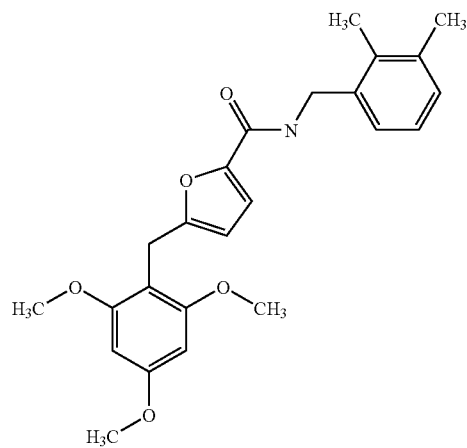
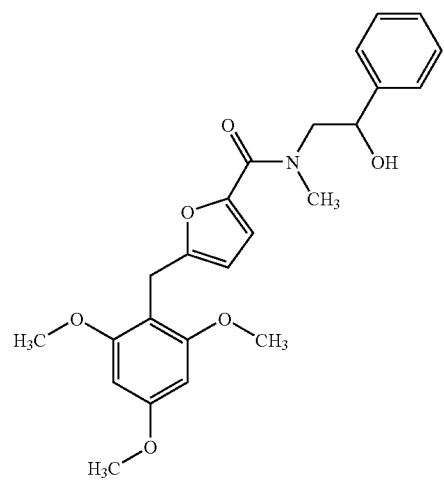
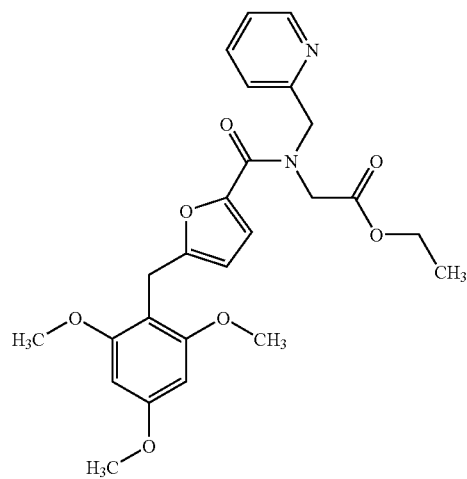

-continued
MOLSTRUCTURE
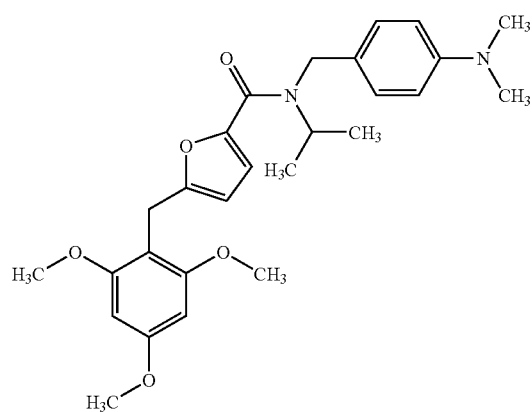
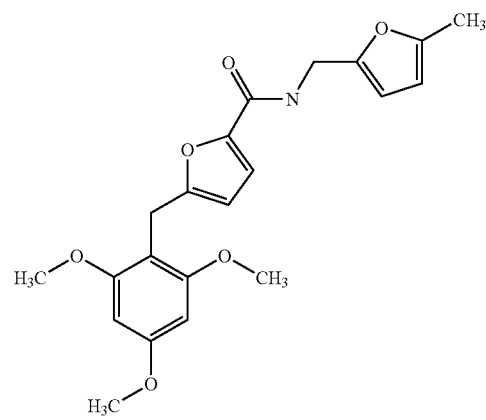
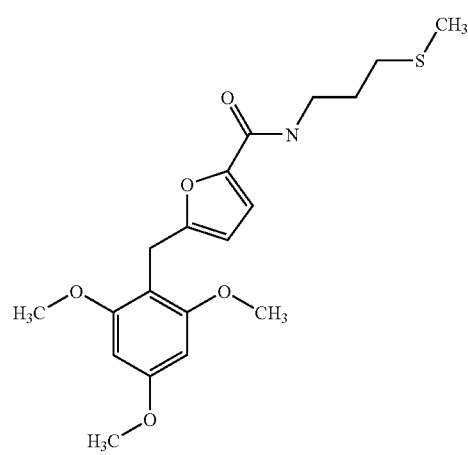

-continued
MOLSTRUCTURE
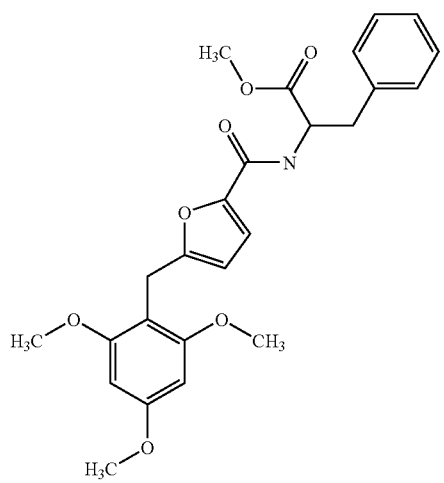
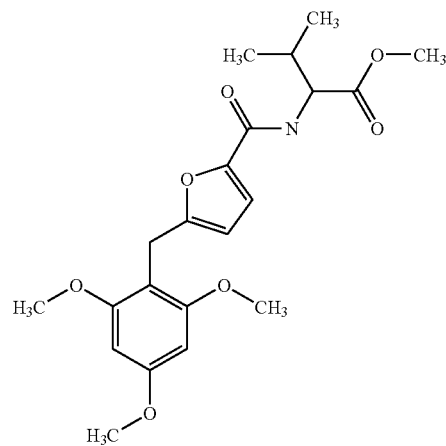
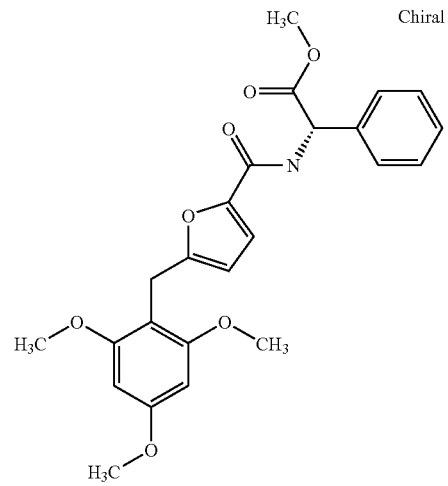

-continued
| MOLSTRUCTURE |
| --- |
| 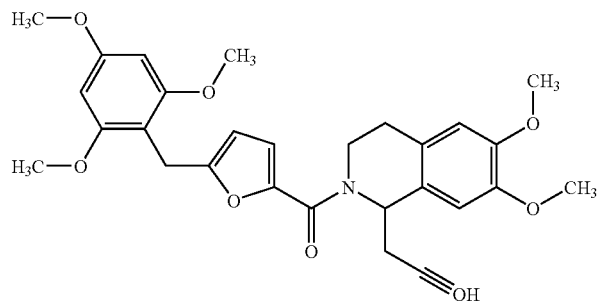 |
| 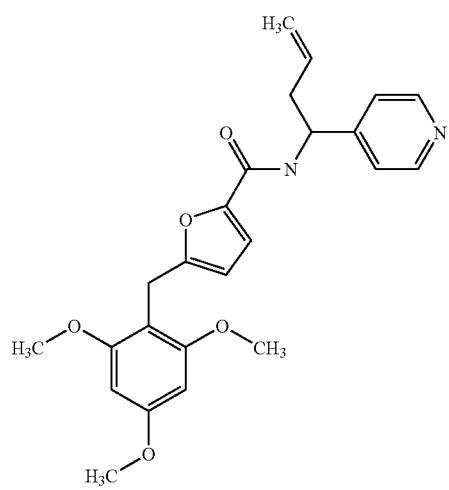 |
| 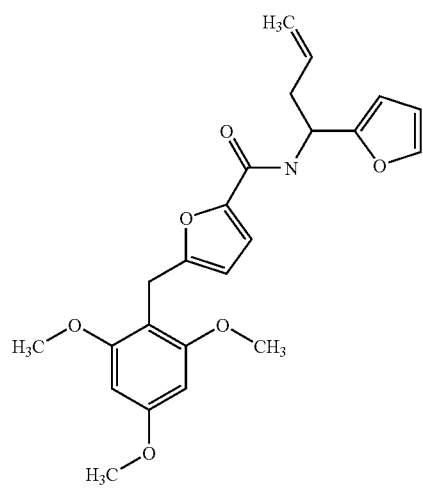 |
| 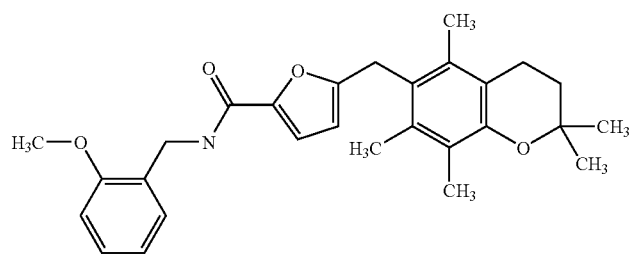 |

-continued
| MOLSTRUCTURE |
|---|
| 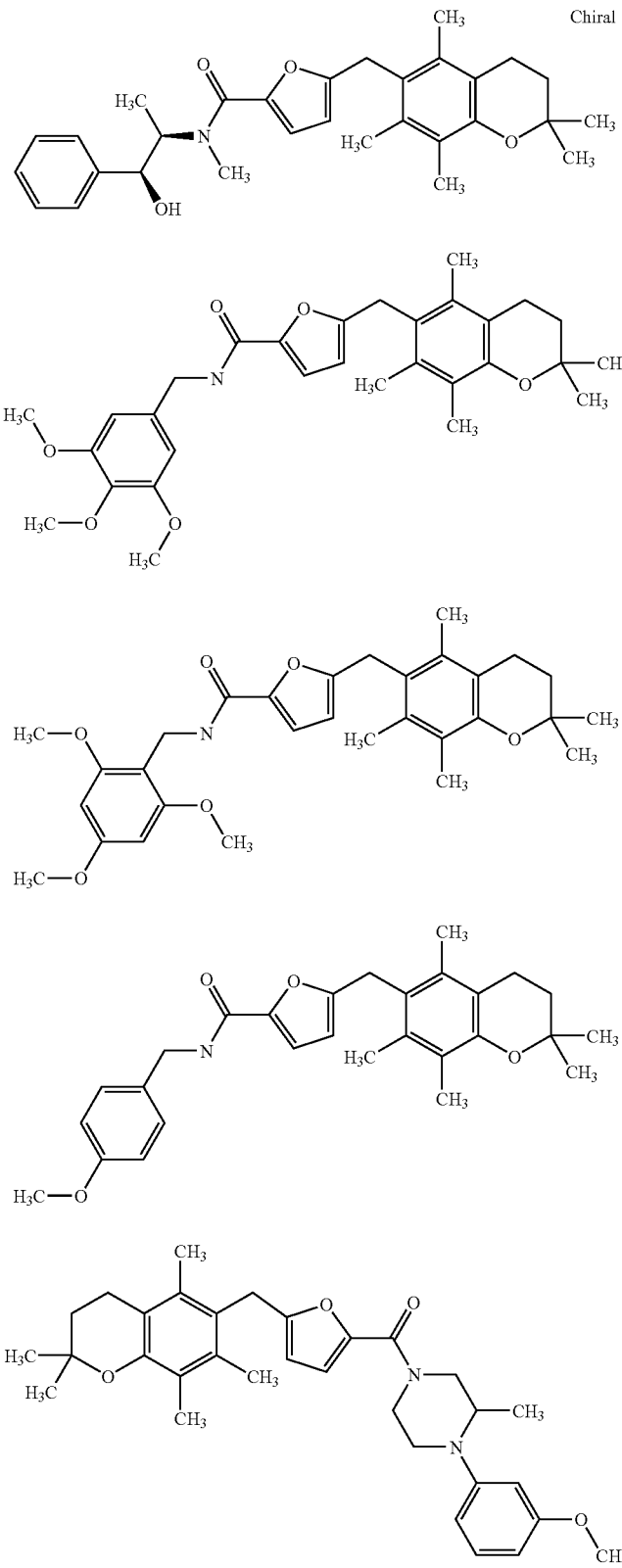 |

-continued
MOLSTRUCTURE
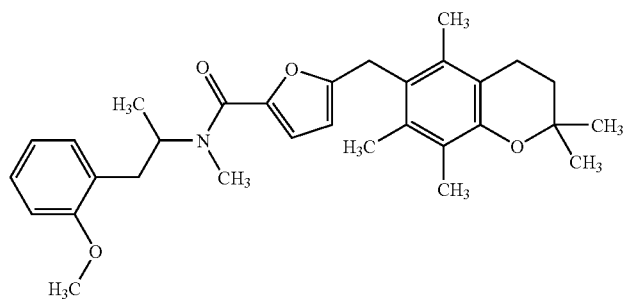
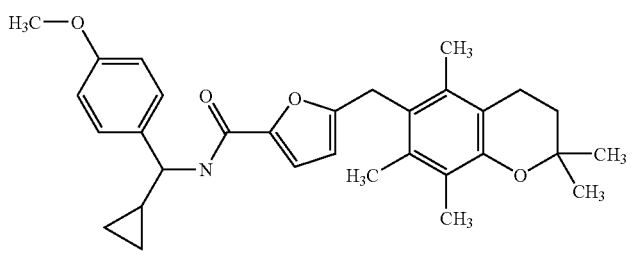
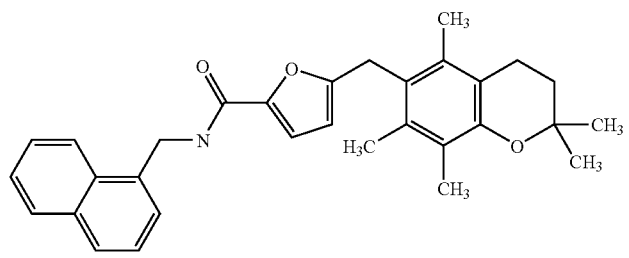
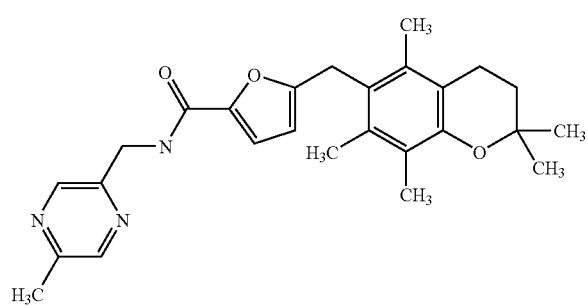
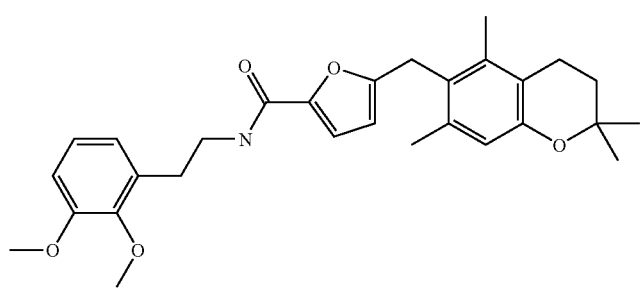

-continued
| MOLSTRUCTURE |
|---|
| 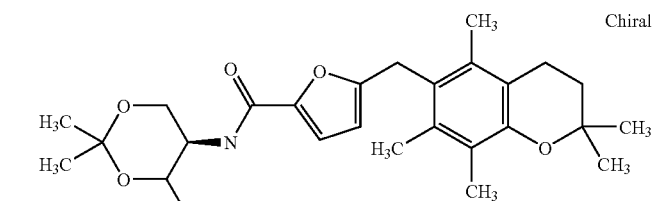 |
| 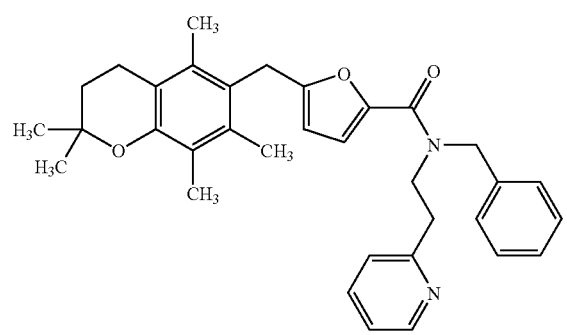 |
| 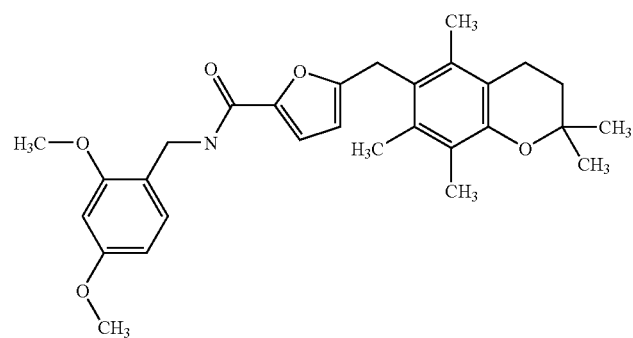 |
| 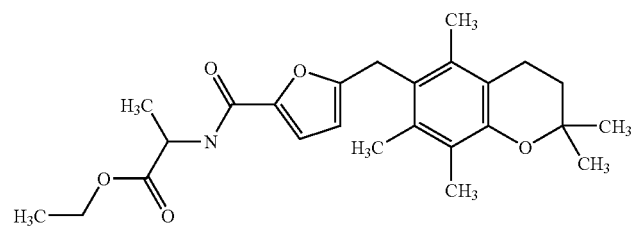 |
| 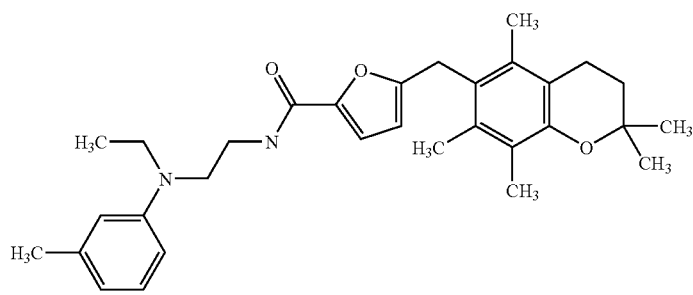 |

| MOLSTRUCTURE |
|---|
| 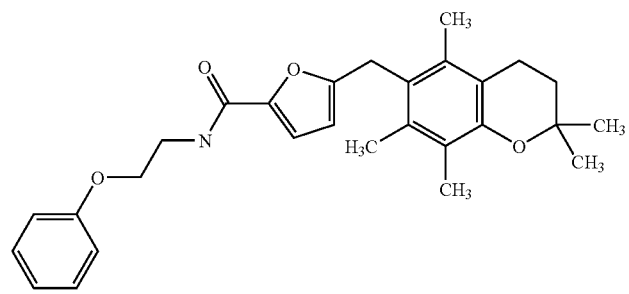 |
| 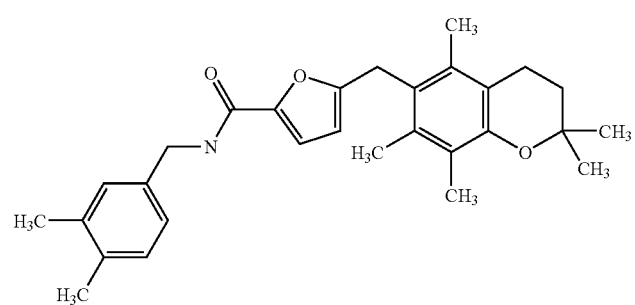 |
| 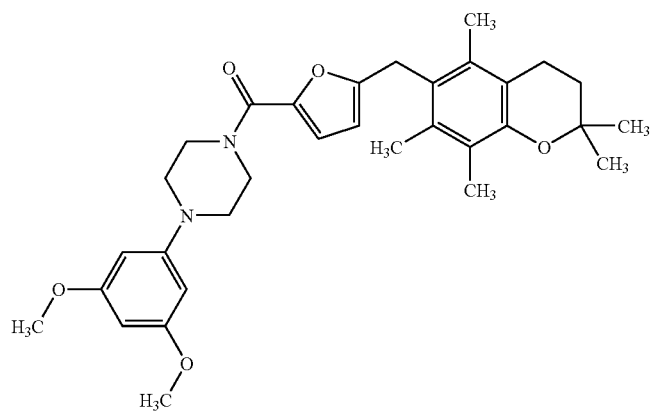 |
| 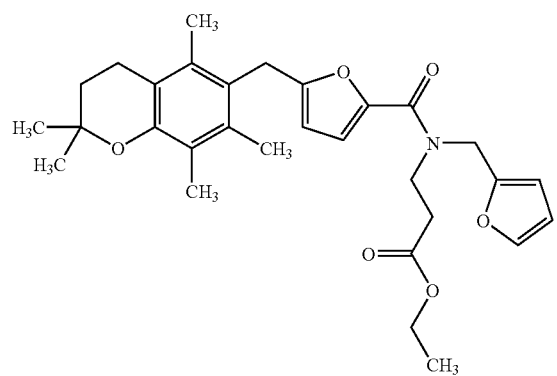 |

-continued
| MOLSTRUCTURE |
|---|
| 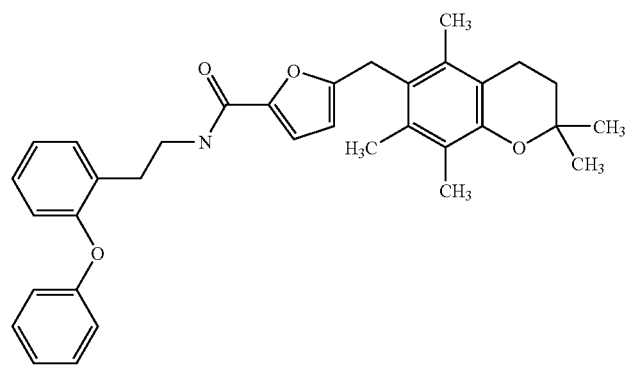 |
| 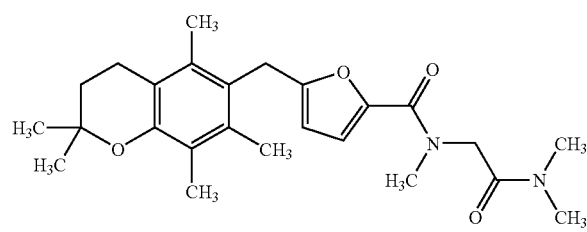 |
| 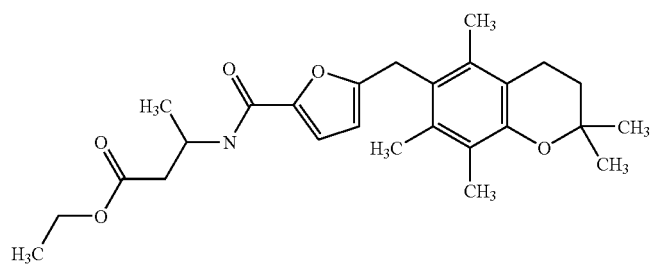 |
| 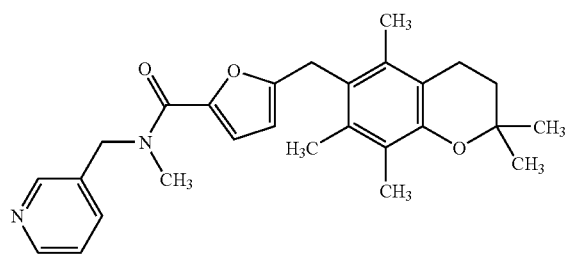 |
| 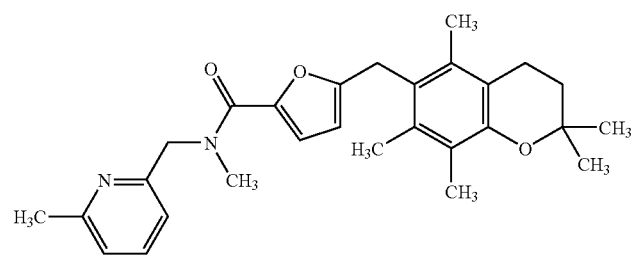 |

-continued
| MOLSTRUCTURE |
|---|
| 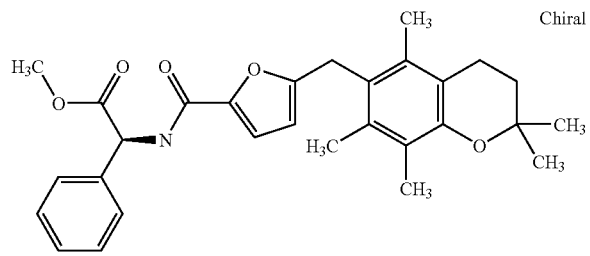 |
| 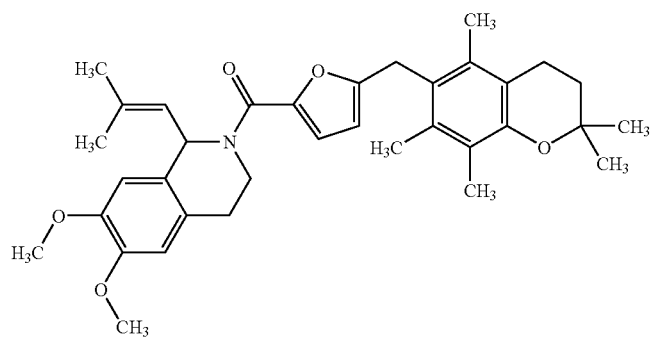 |
| 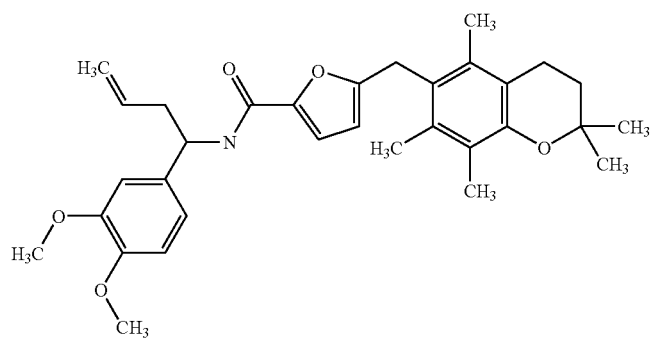 |
| 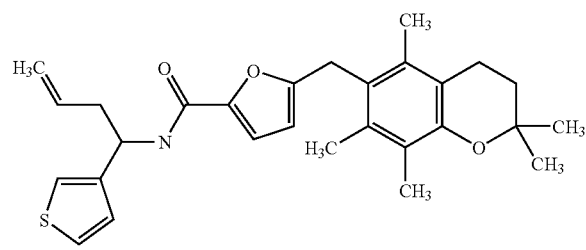 |
| 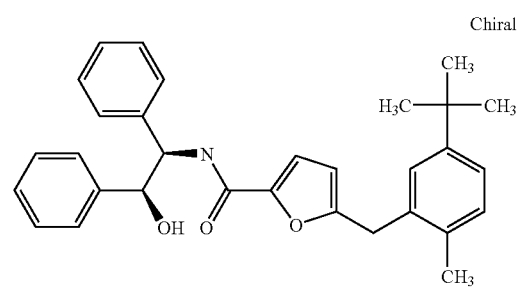 |

| MOLSTRUCTURE |
|---|
| 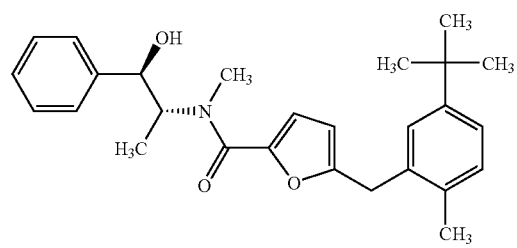 |
| 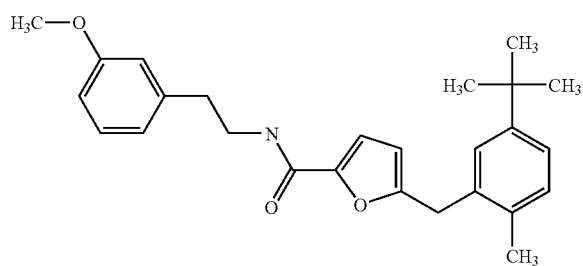 |
| 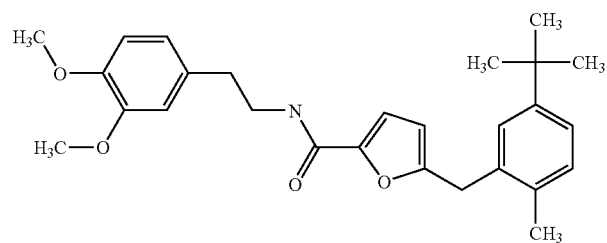 |
| 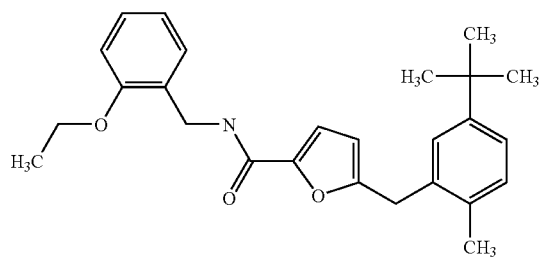 |
| 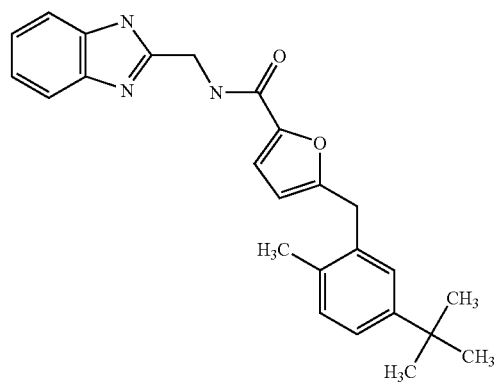 |

-continued
MOLSTRUCTURE
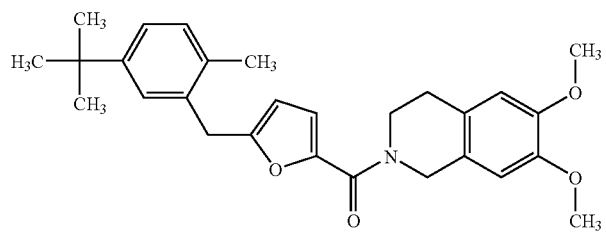
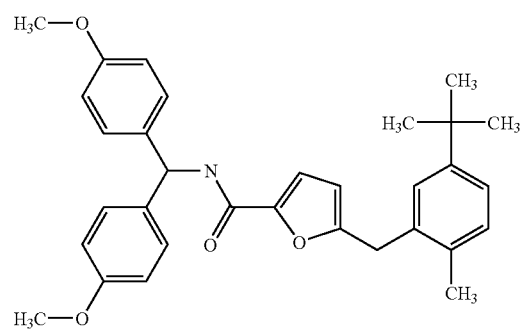
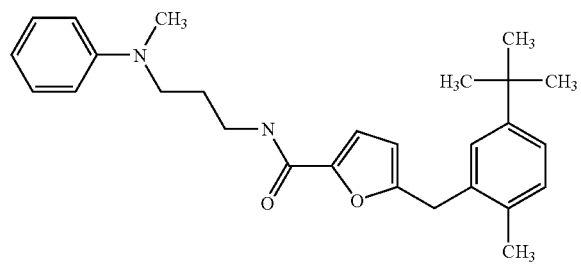
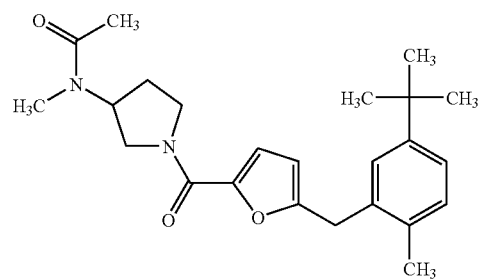

| MOLSTRUCTURE |
|---|
| 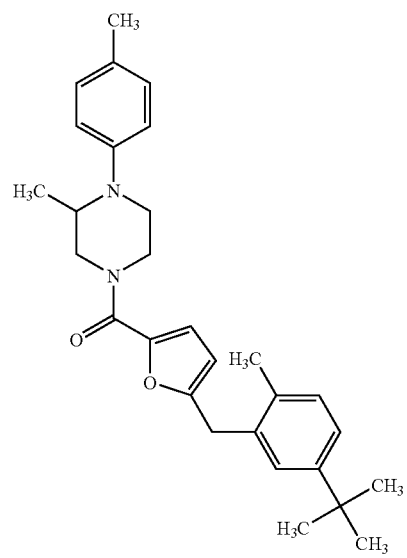 |
| 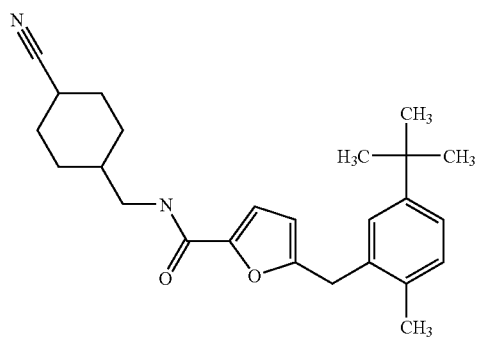 |
| 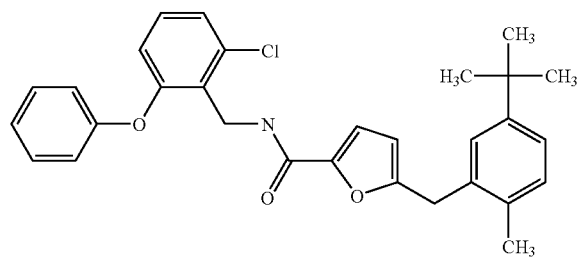 |
| 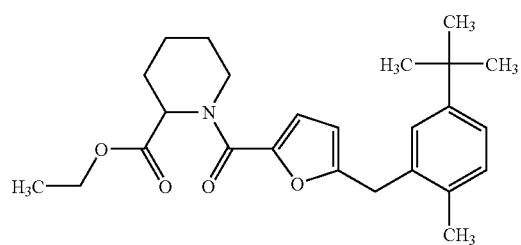 |

-continued
MOLSTRUCTURE
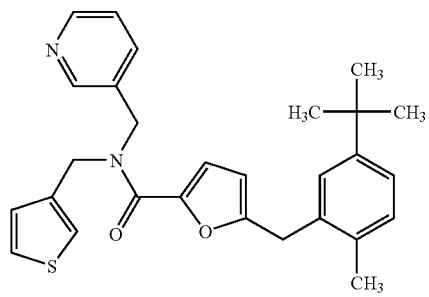
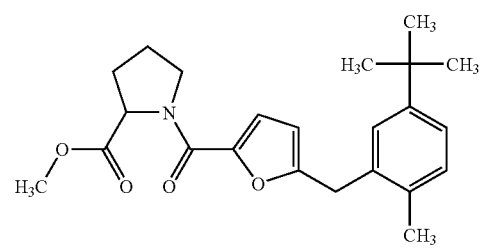
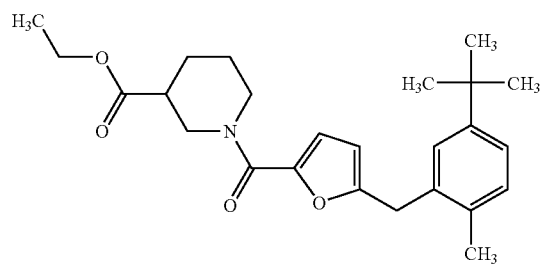
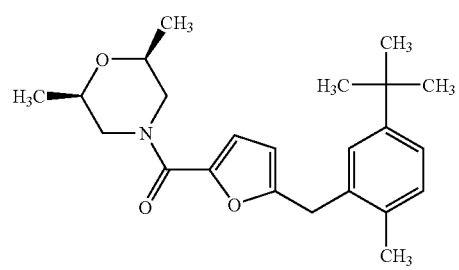
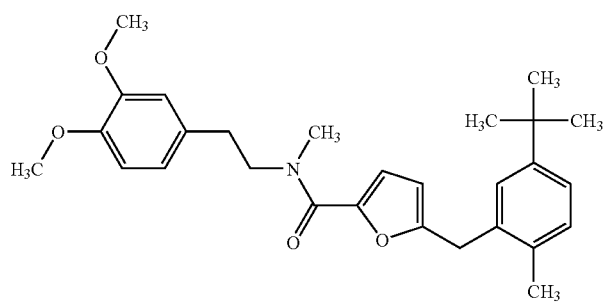

| MOLSTRUCTURE |
|---|
| 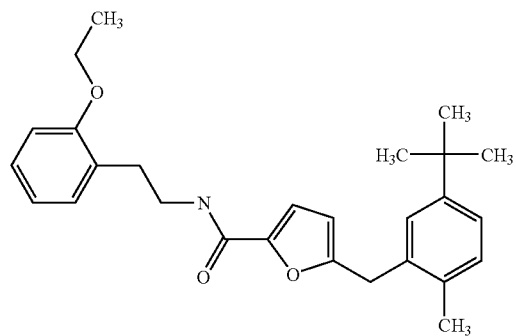 |
| 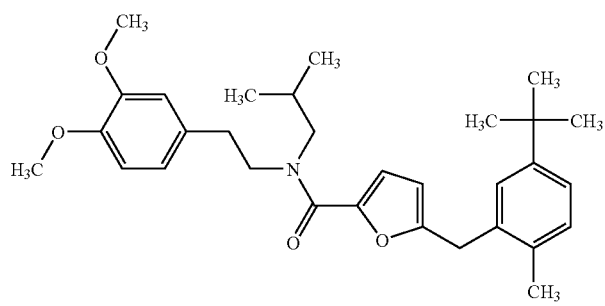 |
| 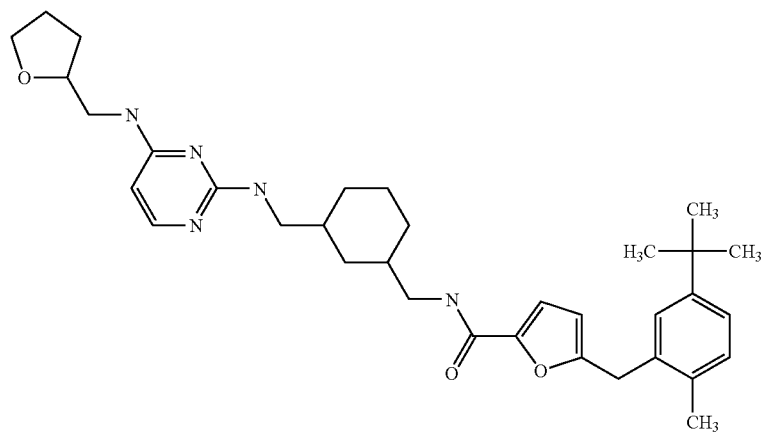 |
| 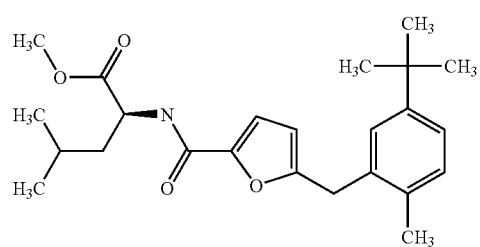 |

-continued
| MOLSTRUCTURE |
|---|
| 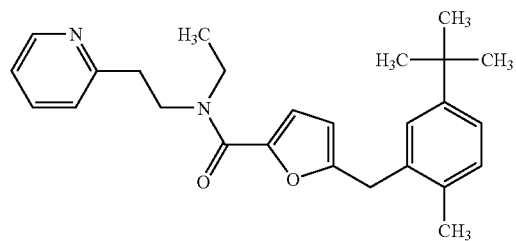 |
| 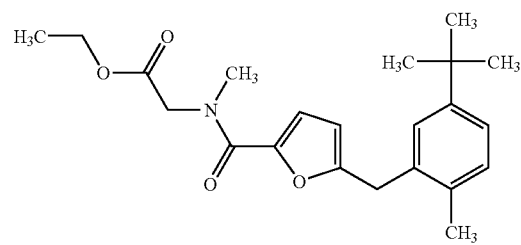 |
| 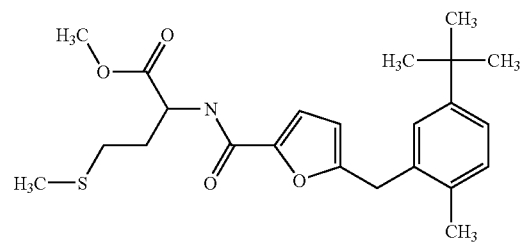 |
| 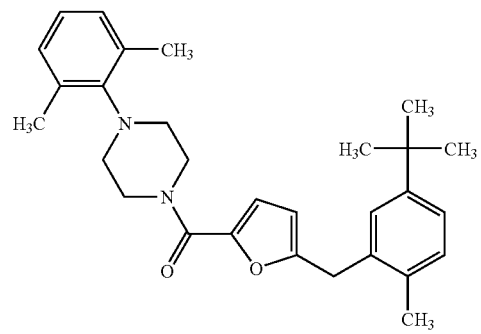 |
| 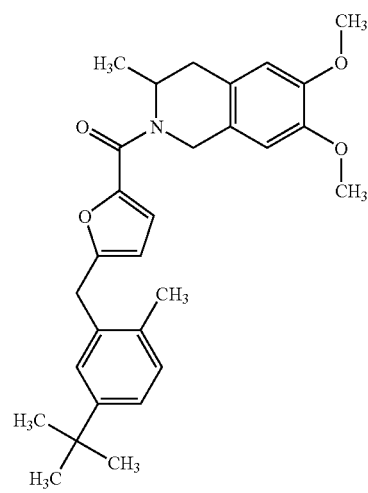 |

-continued
MOLSTRUCTURE
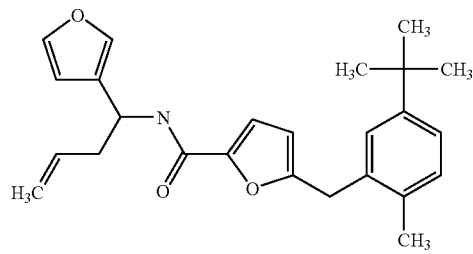
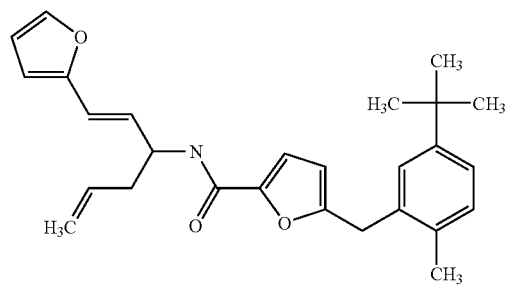
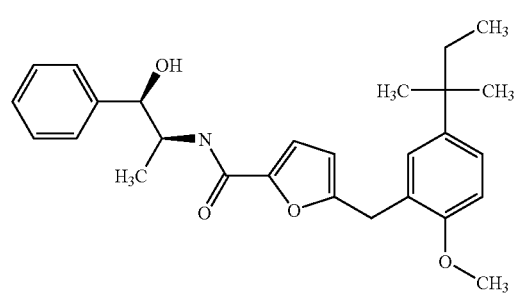
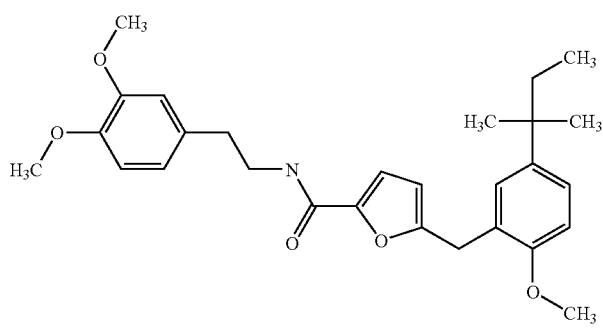
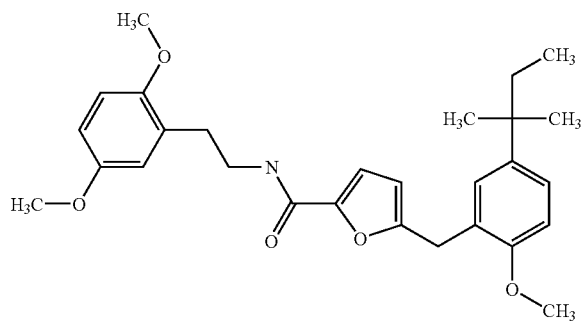

-continued
MOLSTRUCTURE
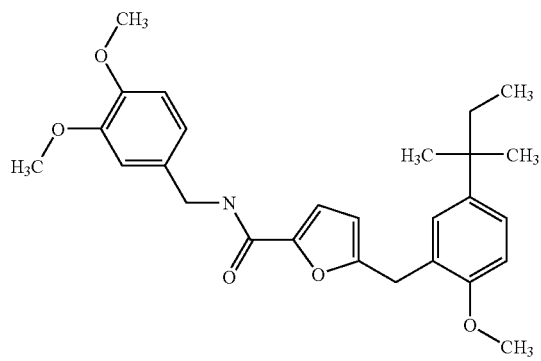
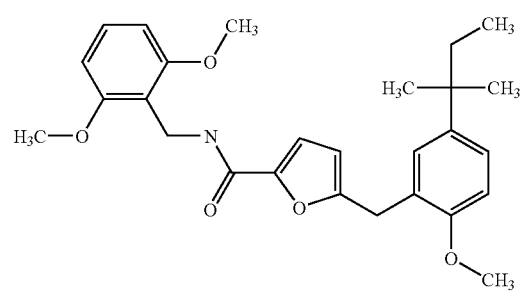
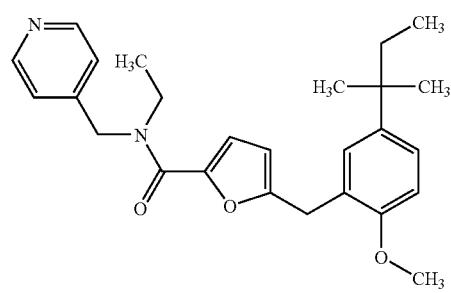
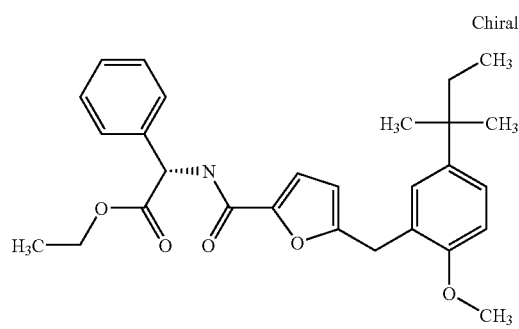

| MOLSTRUCTURE |
|---|
| 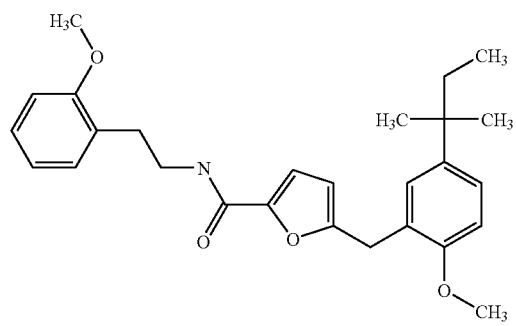 |

-continued
| MOLSTRUCTURE |
|---|
| 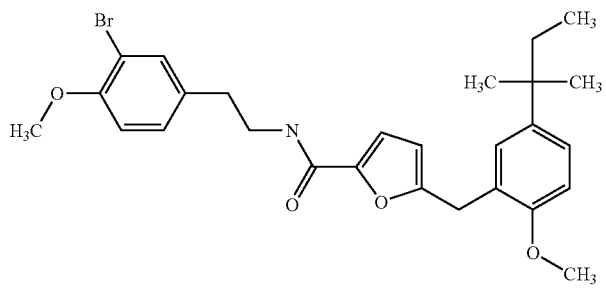 |
| 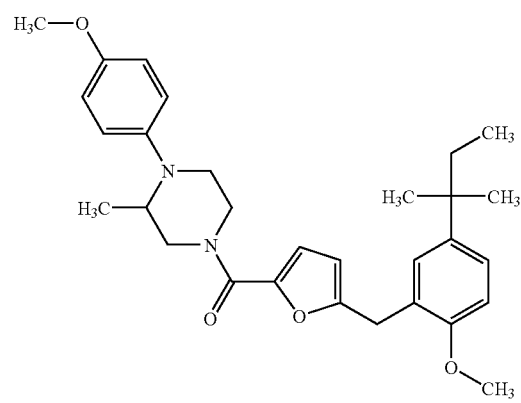 |
| 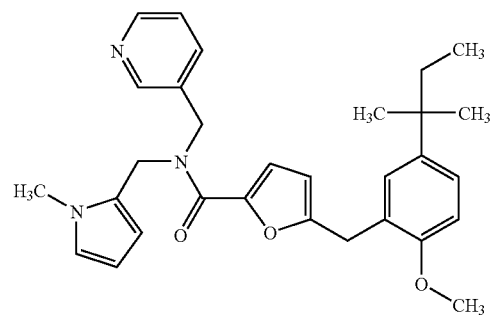 |
| 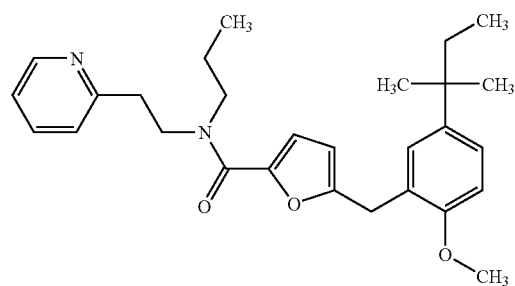 |

-continued
MOLSTRUCTURE
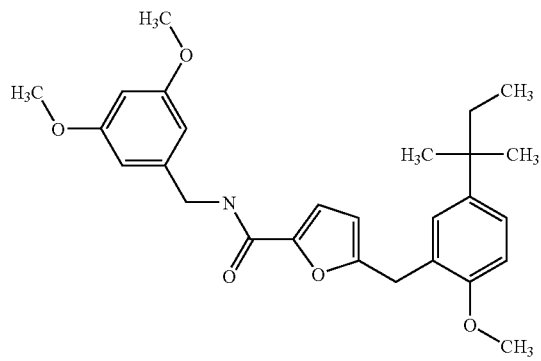
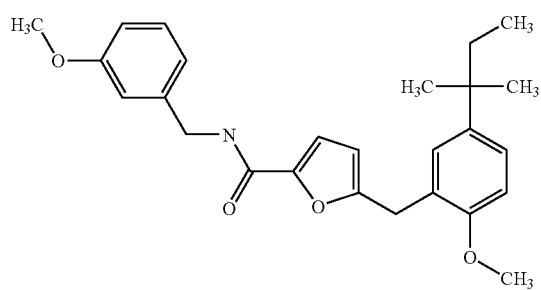
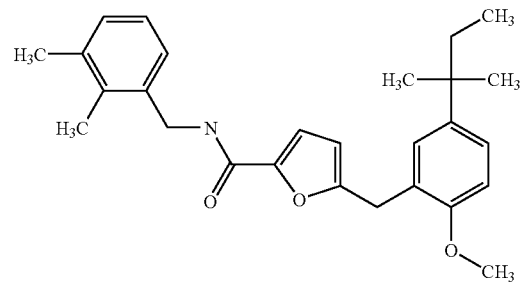
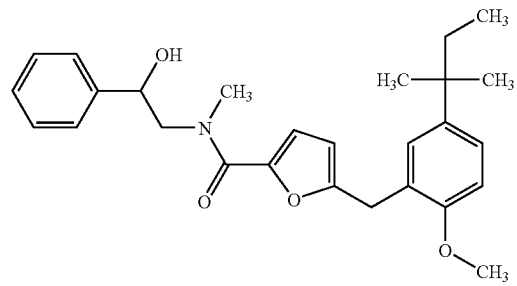

| MOLSTRUCTURE |
| --- |
| 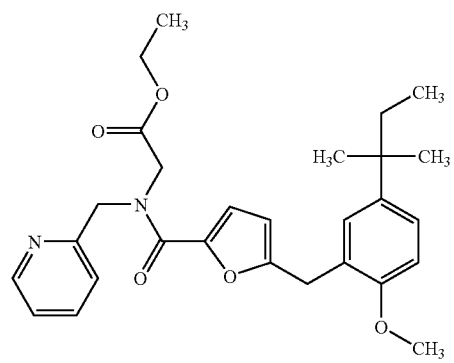 |
| 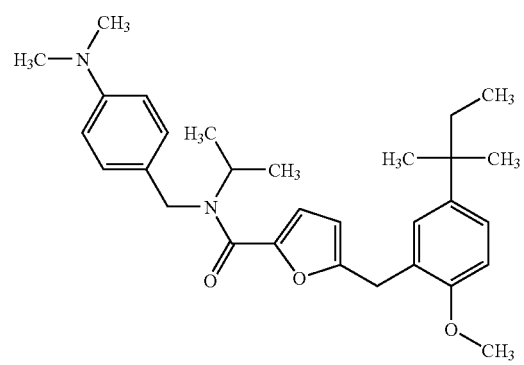 |
| 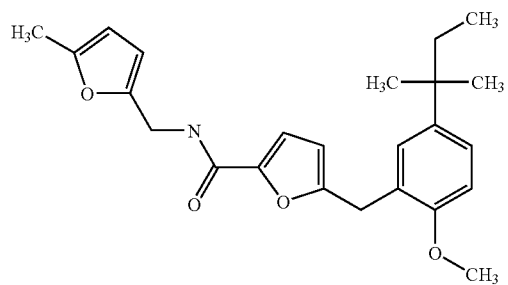 |
| 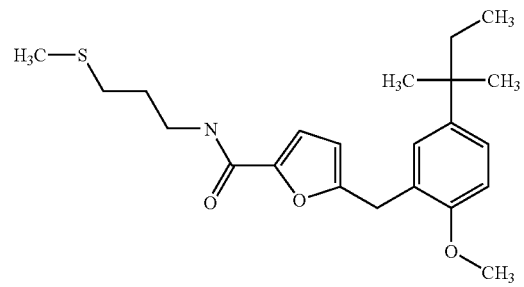 |

| MOLSTRUCTURE |
|---|
| 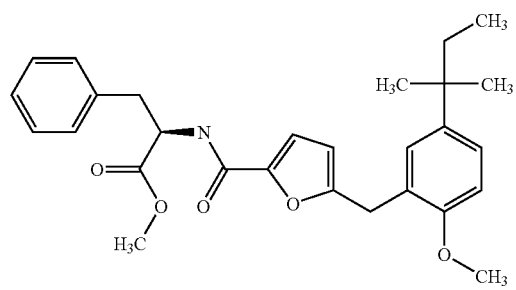 |
| 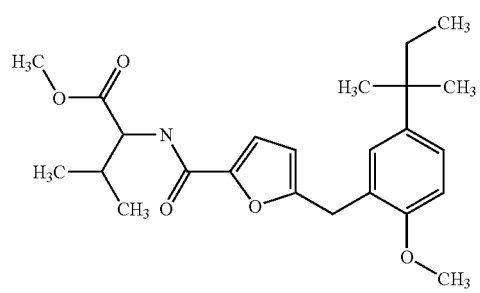 |
| 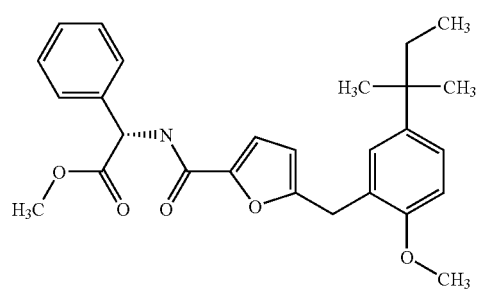 |
| 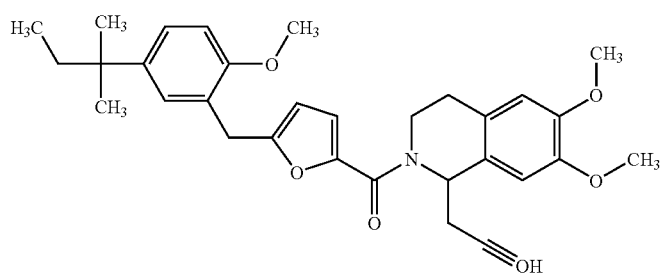 |
| 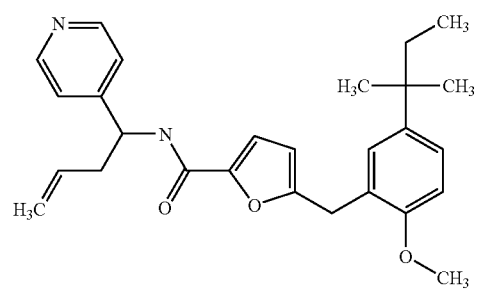 |

| MOLSTRUCTURE |
|---|
| 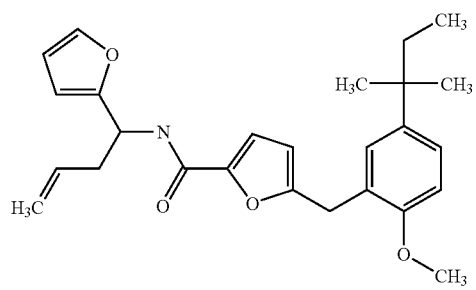 |
| 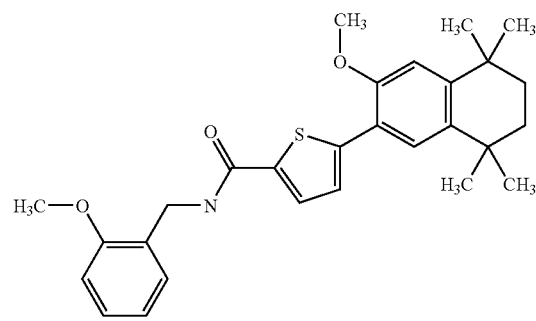 |
| 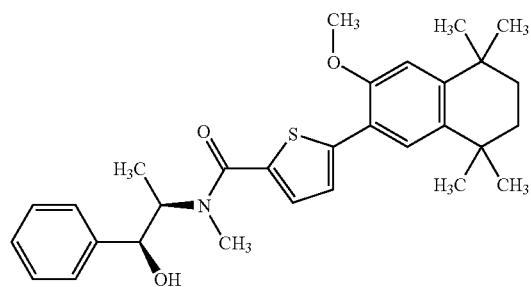 |
| 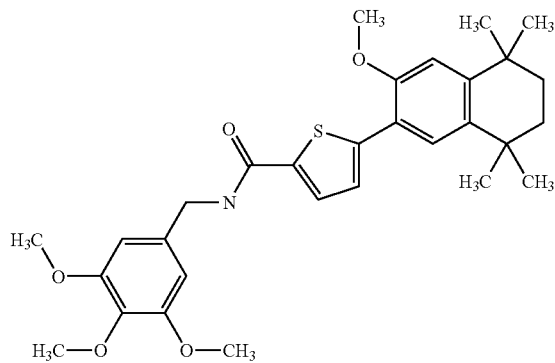 |

-continued
MOLSTRUCTURE
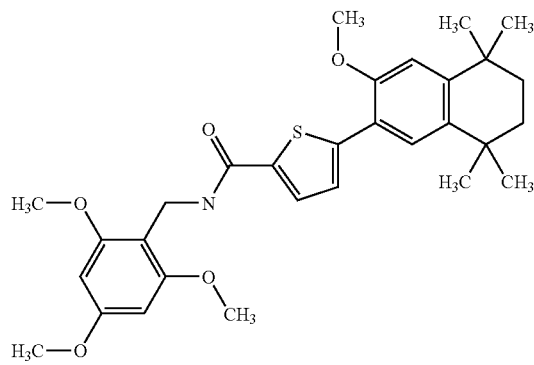
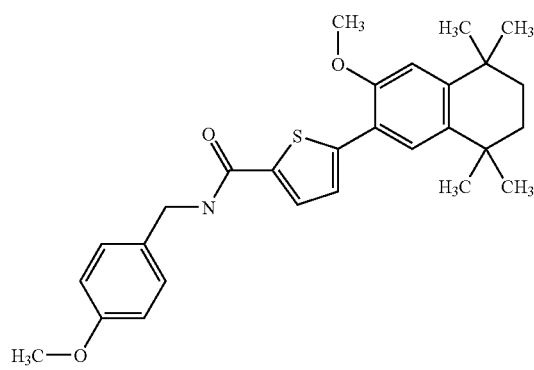
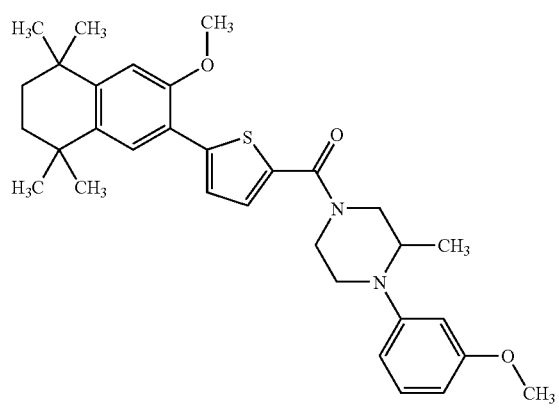
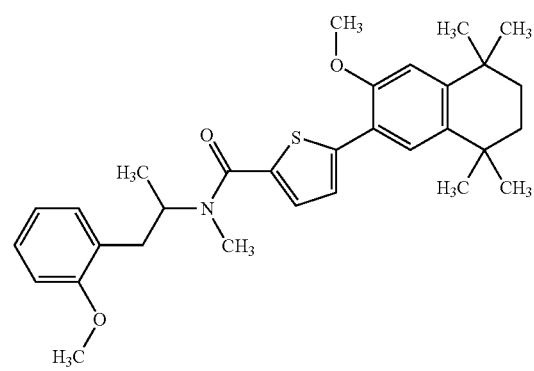

-continued
MOLSTRUCTURE
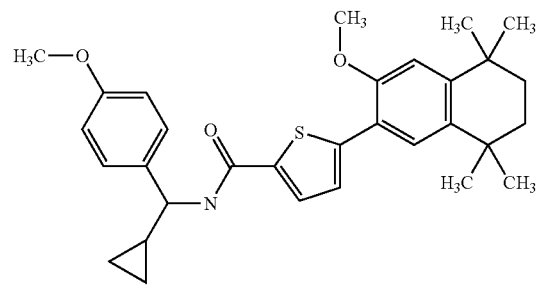
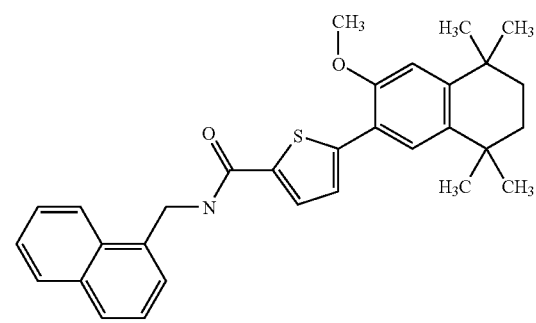
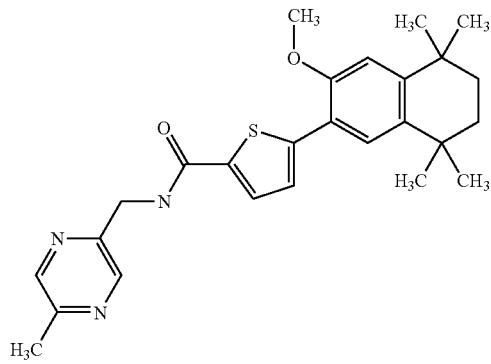
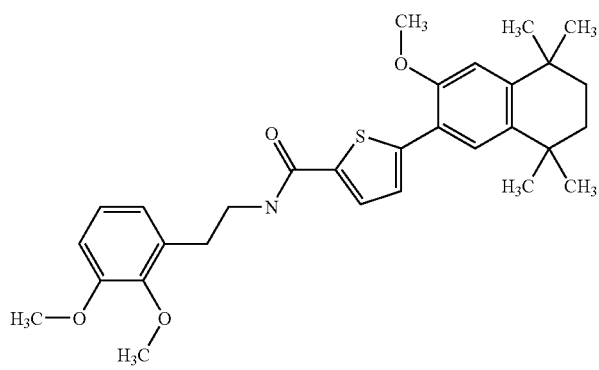

| MOLSTRUCTURE |
|---|
| 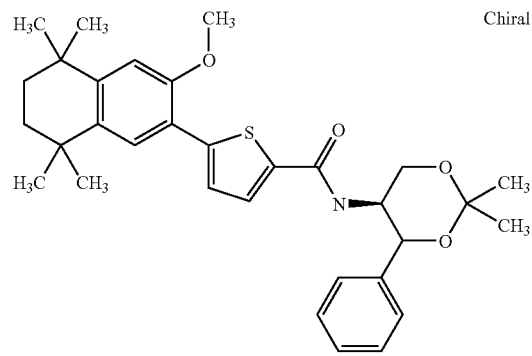 |
| 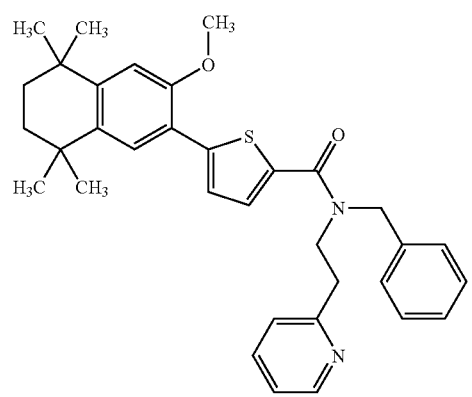 |
| 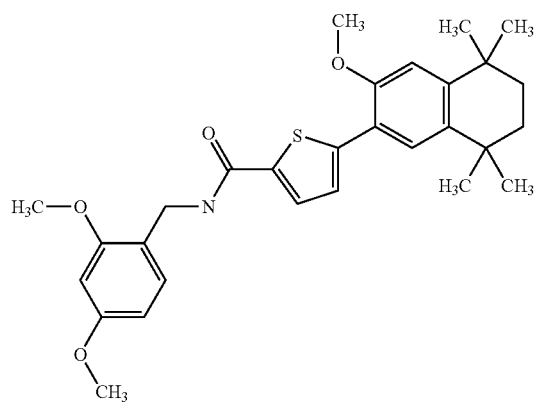 |
| 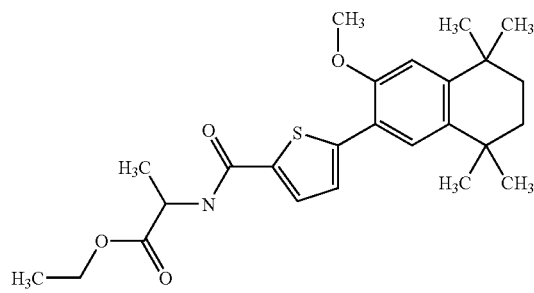 |

-continued
| MOLSTRUCTURE |
|---|
| 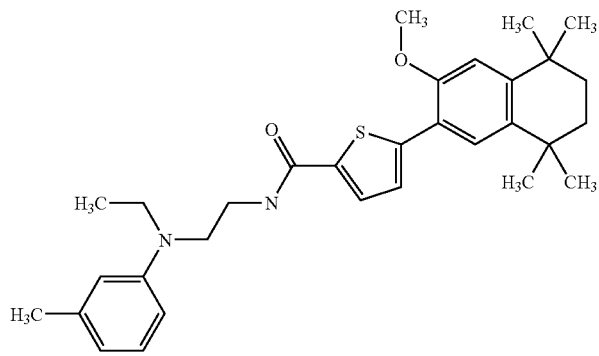 |
| 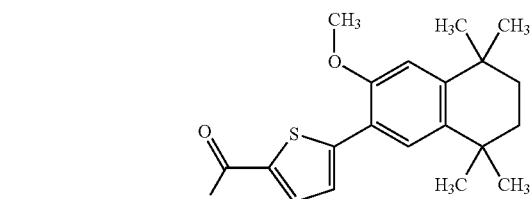 |
| 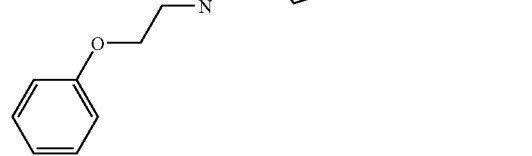 |
| 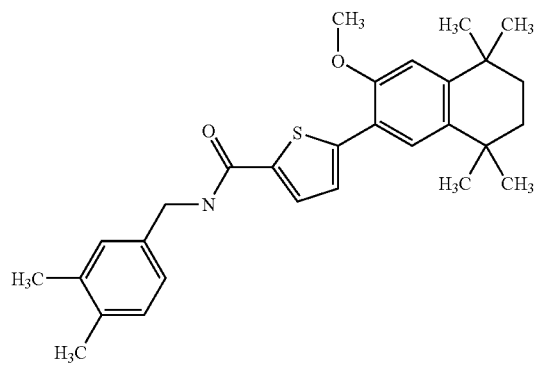 |

-continued
| MOLSTRUCTURE |
|---|
| 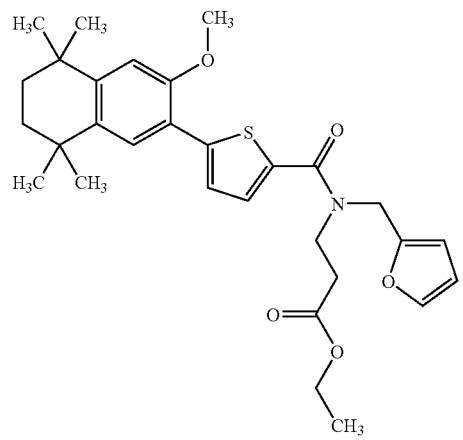 |
| 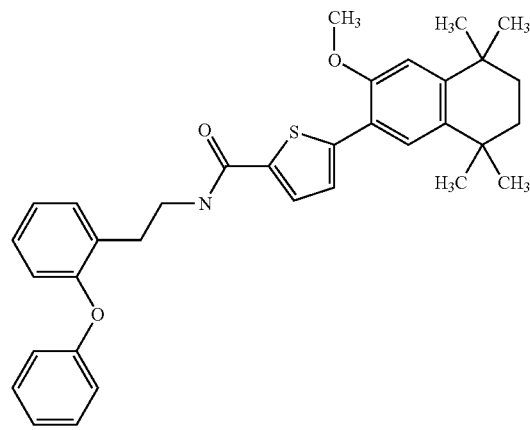 |
| 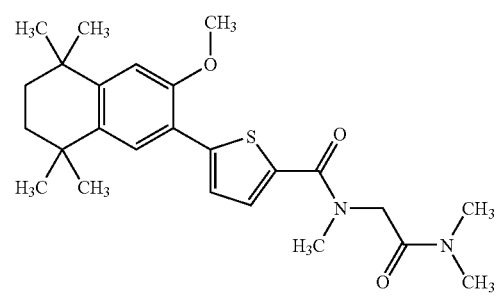 |
| 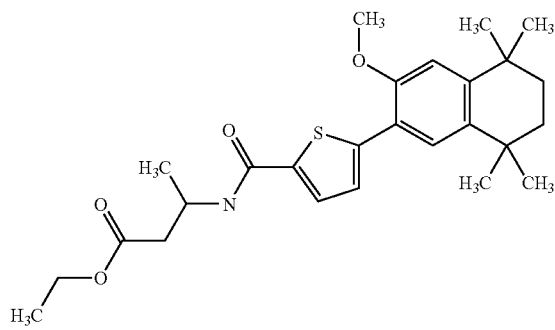 |

-continued
MOLSTRUCTURE
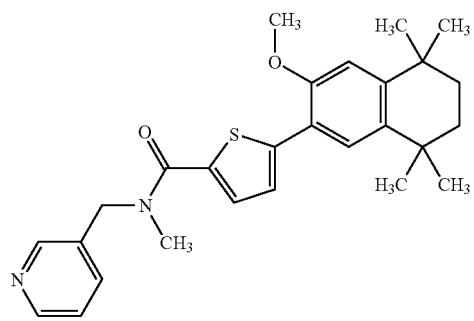
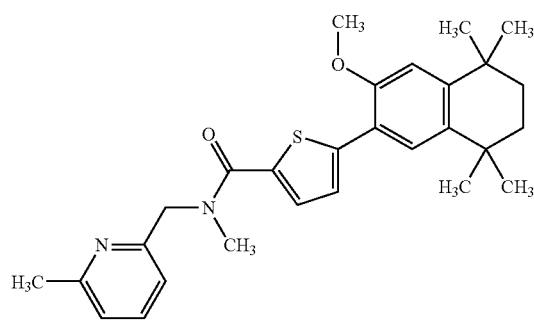
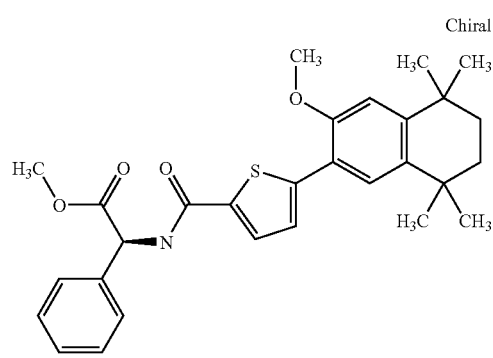
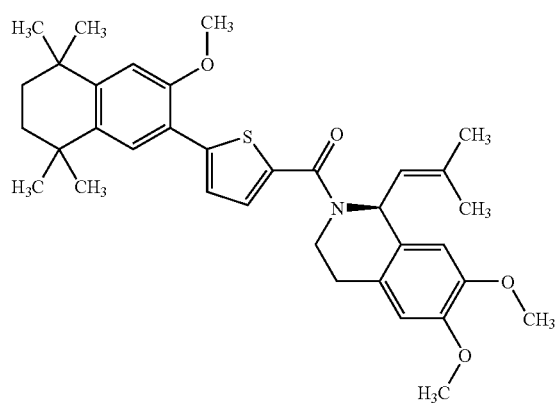

-continued
MOLSTRUCTURE
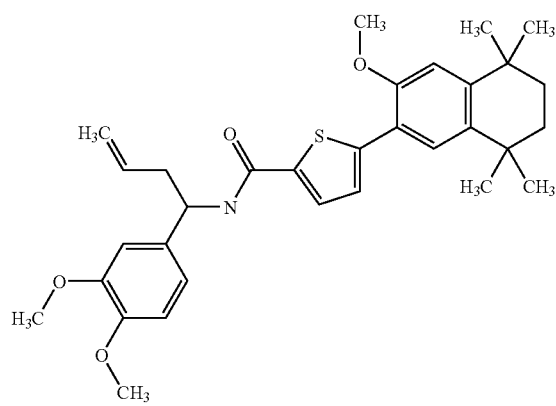
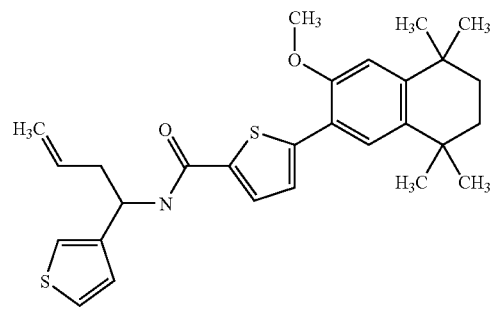
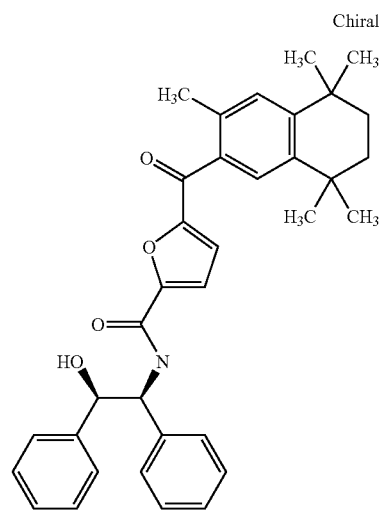

-continued
MOLSTRUCTURE
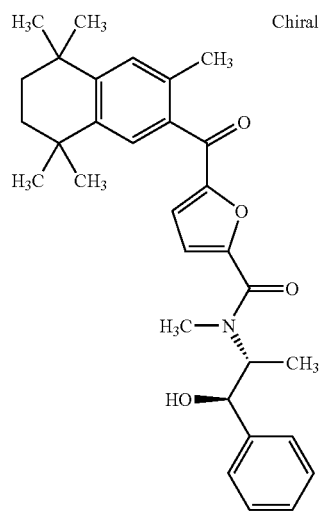
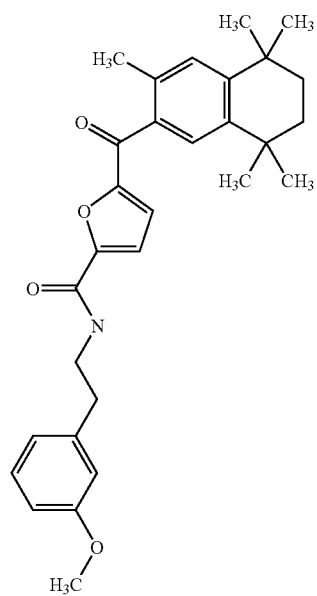

| -continued |
|---|
| MOLSTRUCTURE |
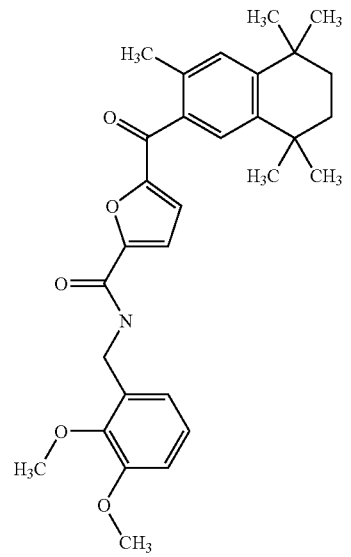
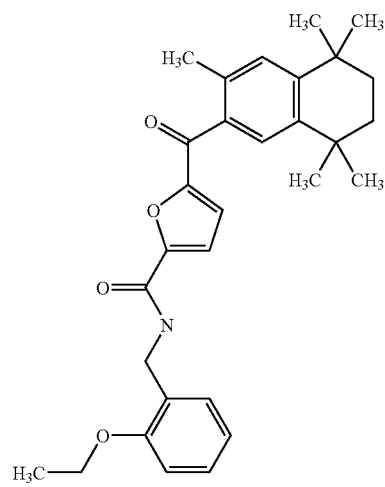
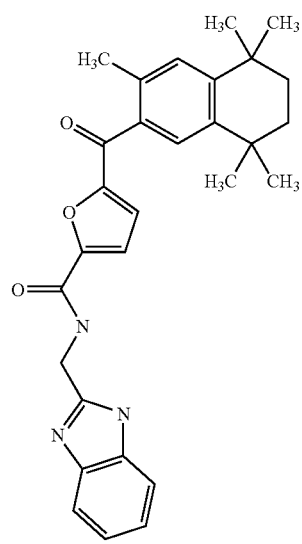

-continued
| MOLSTRUCTURE |
|---|
| 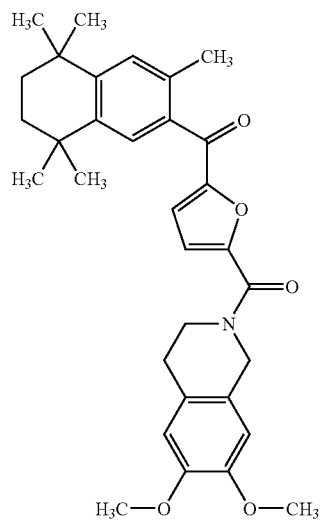 |
| 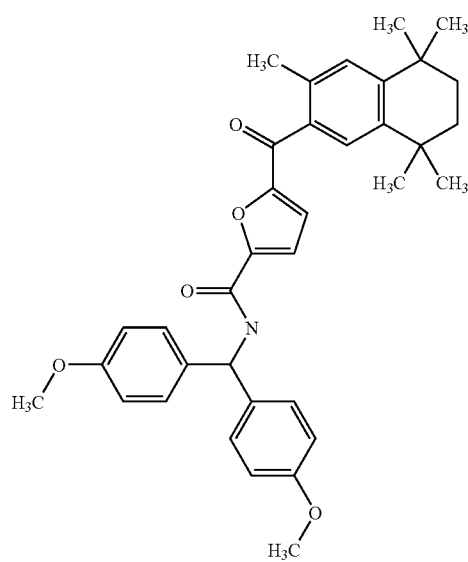 |

-continued
MOLSTRUCTURE
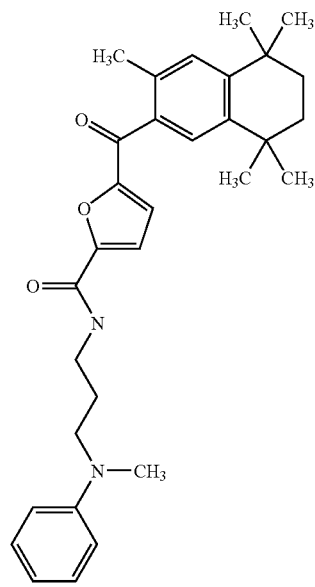
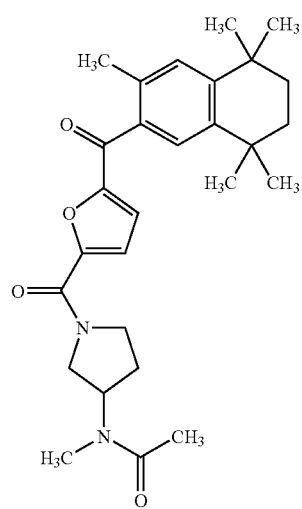

-continued
MOLSTRUCTURE
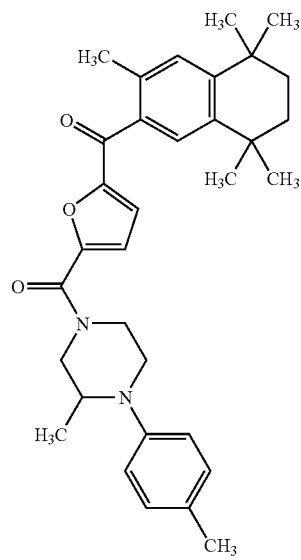
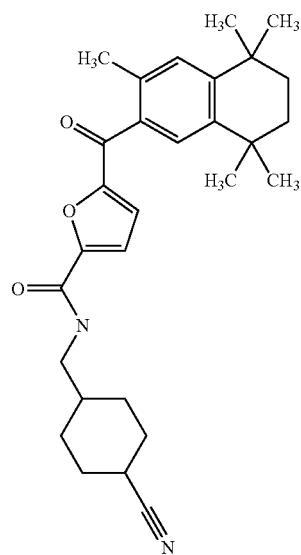

-continued
MOLSTRUCTURE
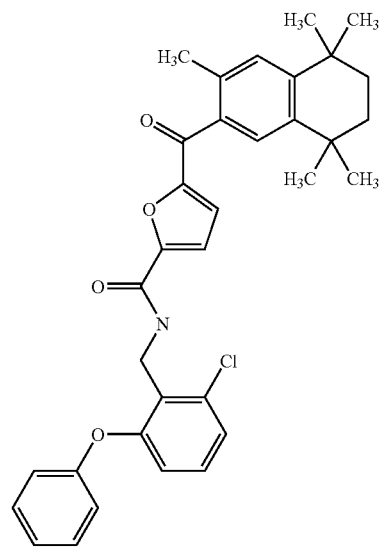
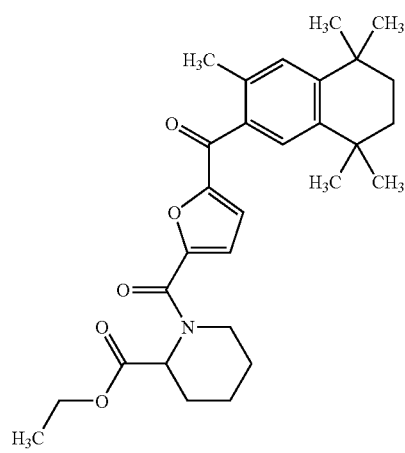
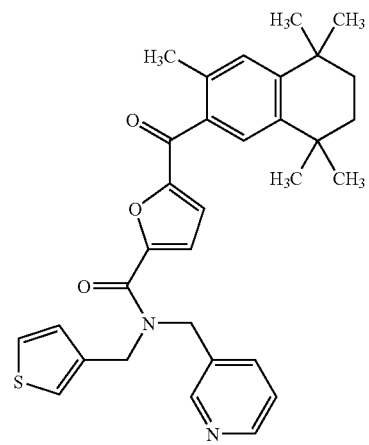

-continued
MOLSTRUCTURE
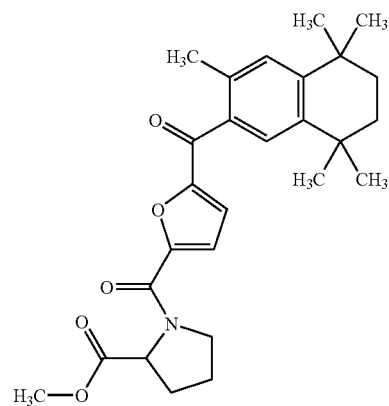
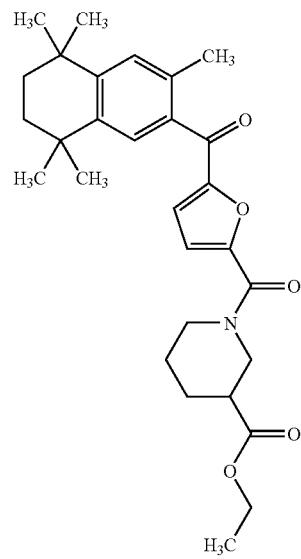
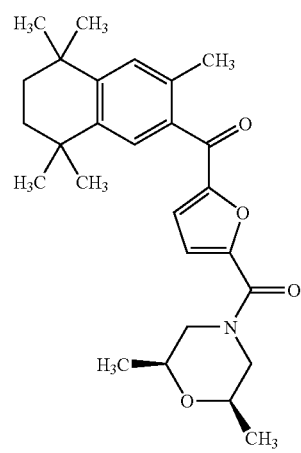

| MOLSTRUCTURE |
| --- |
| 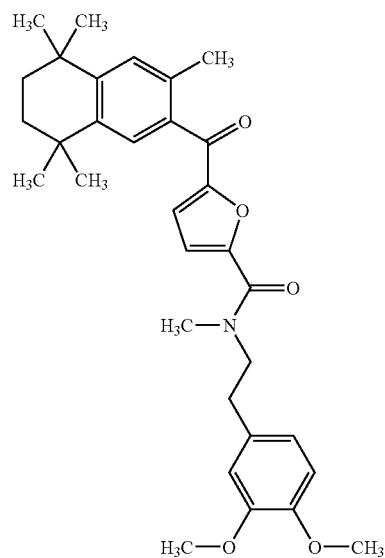 |
| 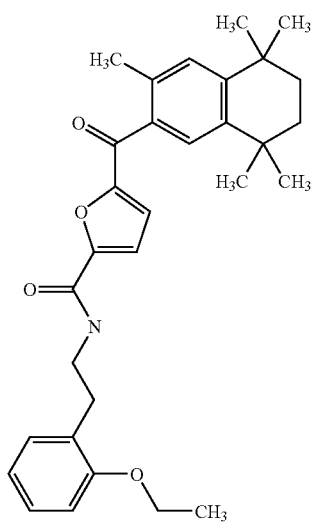 |

-continued
| MOLSTRUCTURE |
| --- |
| 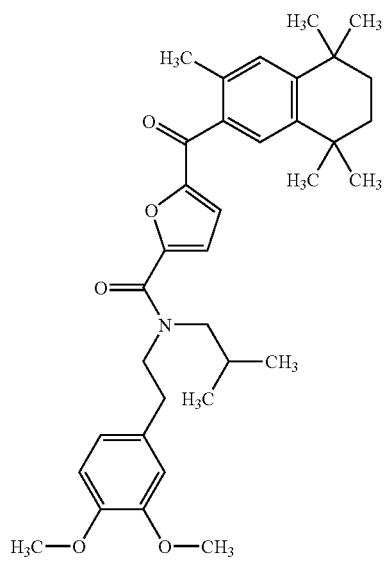 |
| 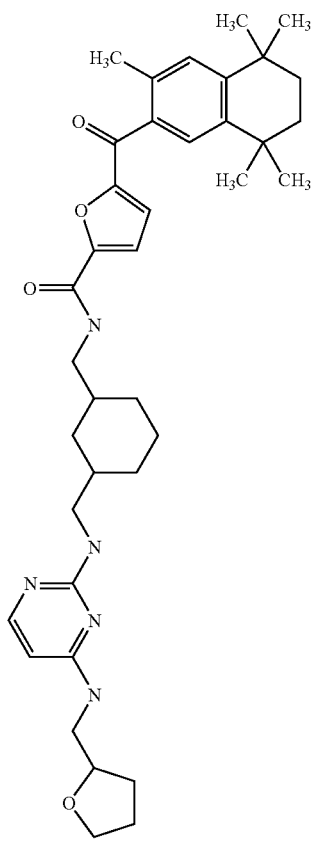 |

-continued
| MOLSTRUCTURE |
|---|
| 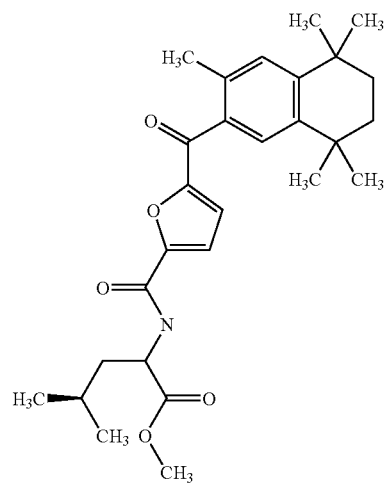 |
| 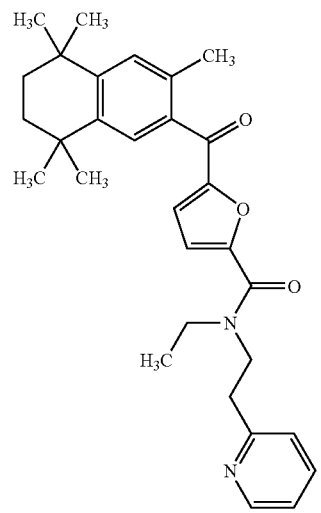 |
| 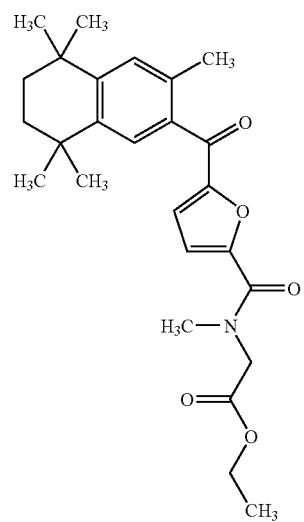 |

-continued
| MOLSTRUCTURE |
|---|
| 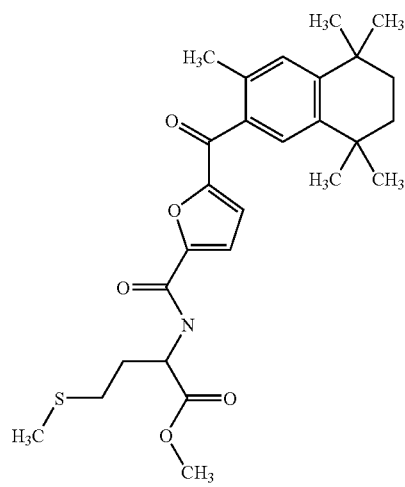 |
| 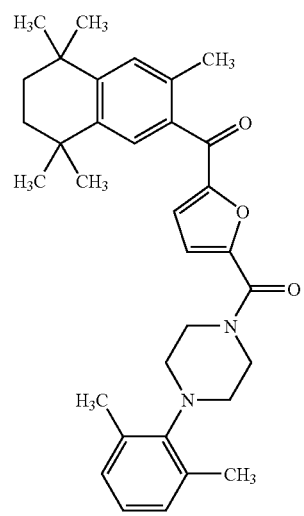 |
| 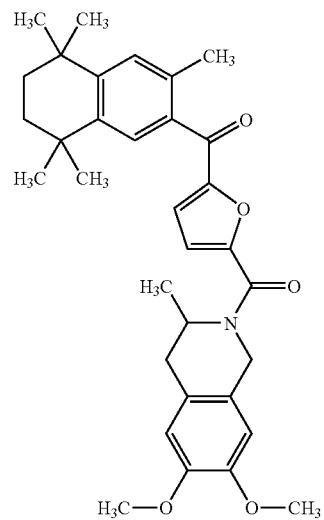 |

| MOLSTRUCTURE |
| --- |
| 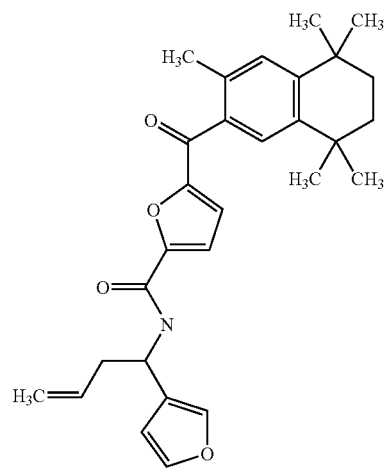 |
| 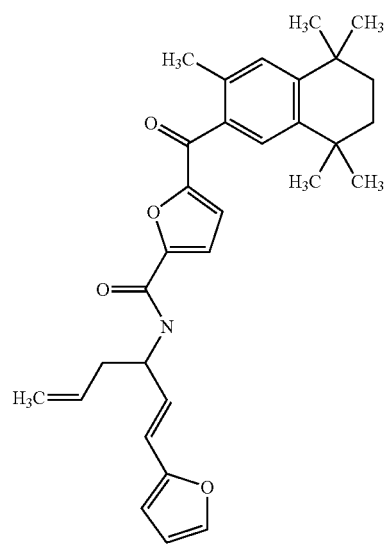 |
| 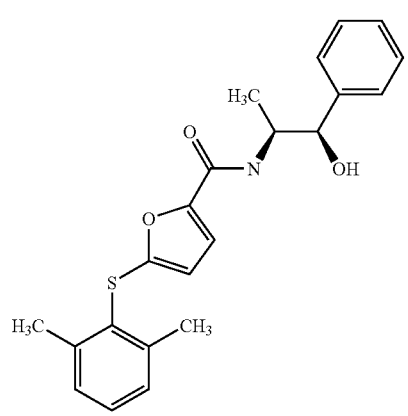 |

1963　　　　　　　　　　　　　　　　　　　　　　　　1964
-continued
| MOLSTRUCTURE |
| --- |
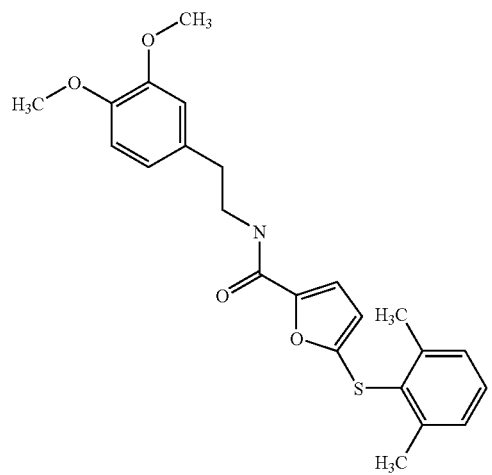
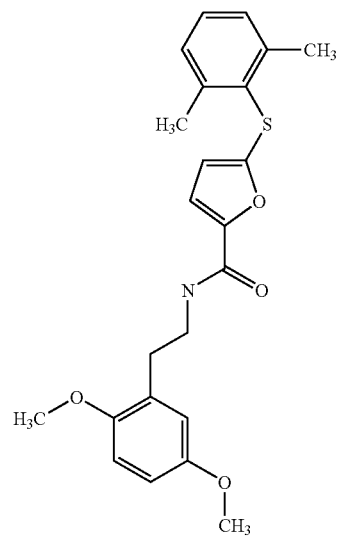
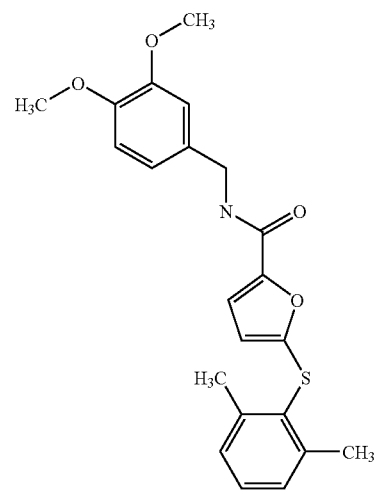

-continued
| MOLSTRUCTURE |
|---|
| 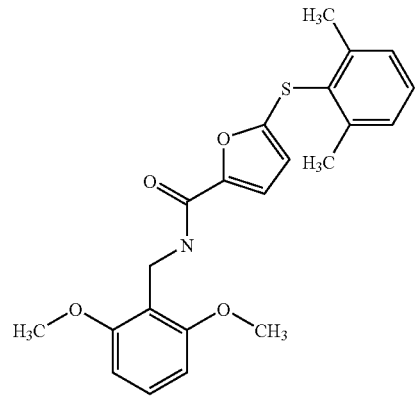 |
| 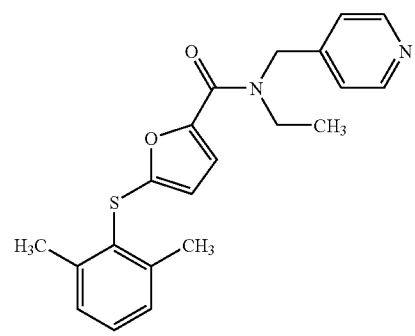 |
| 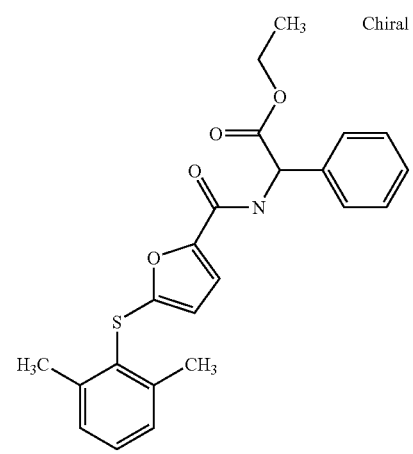 |
| 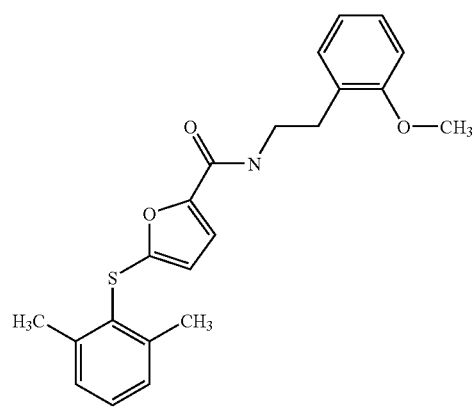 |

-continued
MOLSTRUCTURE
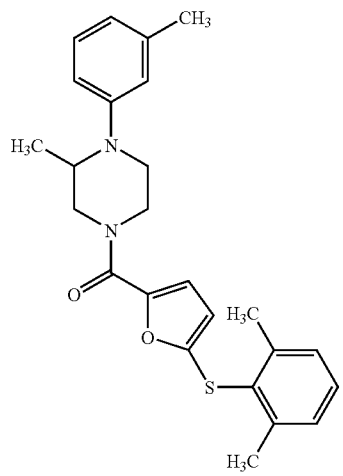
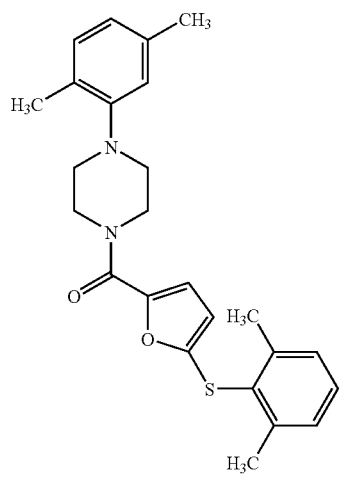
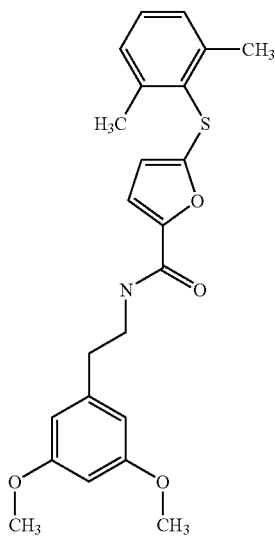

-continued
| MOLSTRUCTURE |
|---|
| 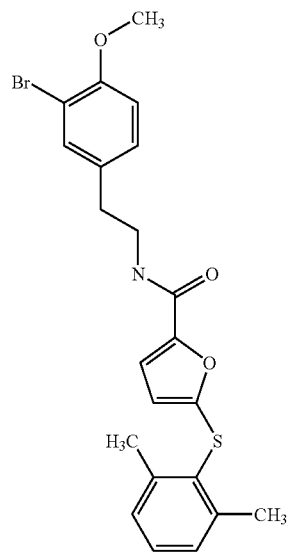 |
| 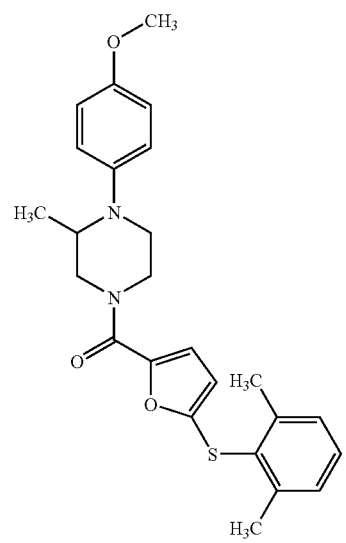 |
| 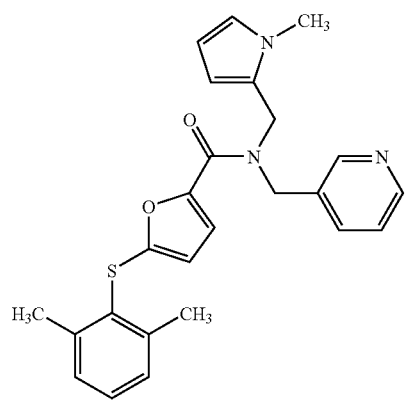 |

-continued
MOLSTRUCTURE
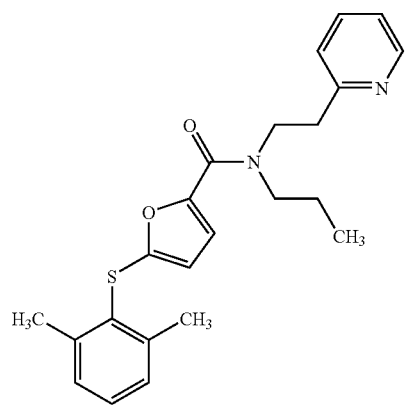
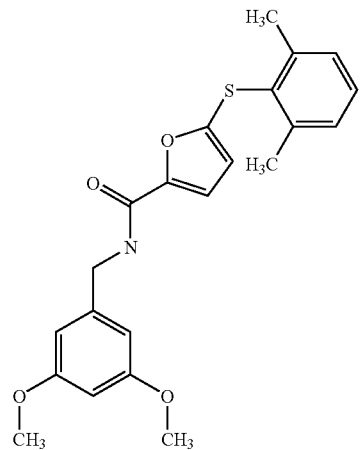
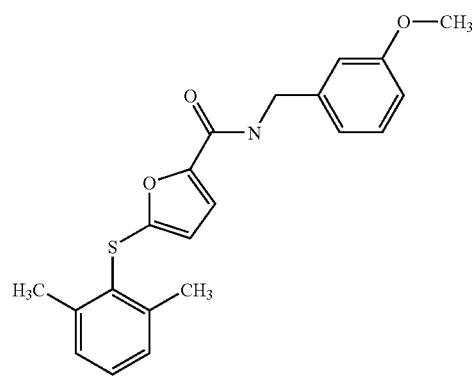

| -continued |
|---|
| MOLSTRUCTURE |
| 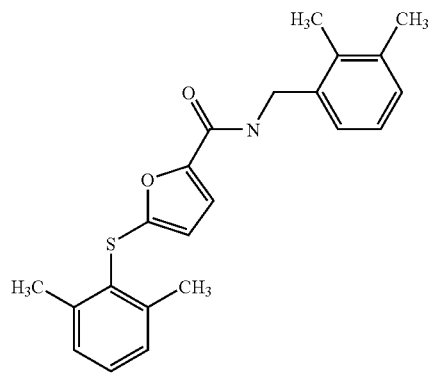 |
| 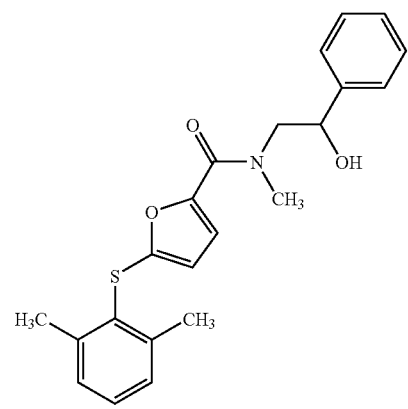 |
| 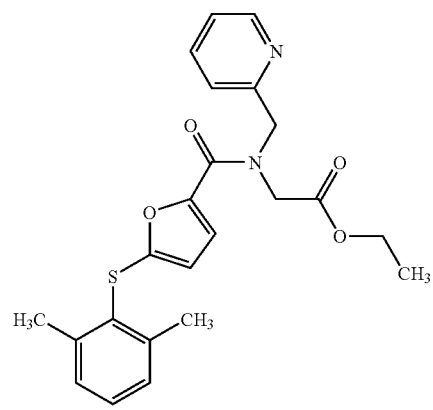 |
| 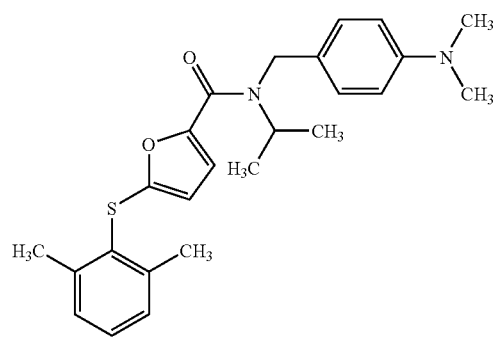 |

| MOLSTRUCTURE |
| --- |
| 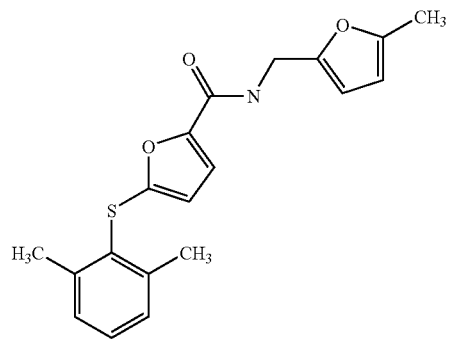 |
| 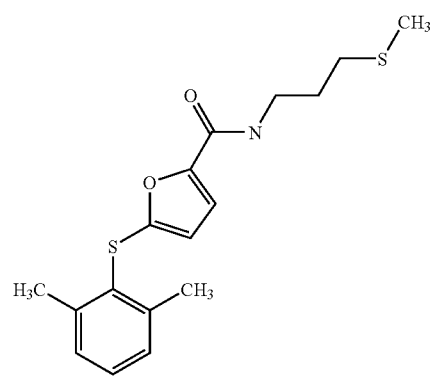 |
| 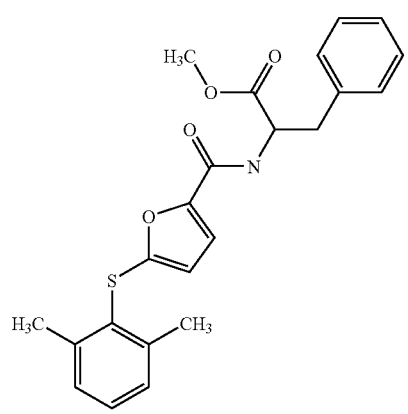 |
| 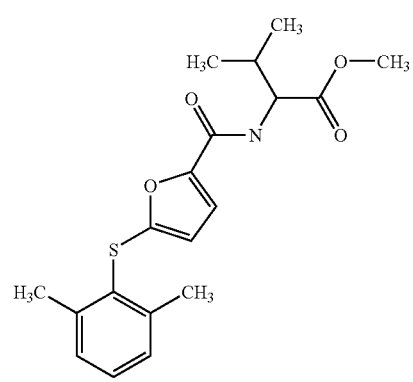 |

-continued
| MOLSTRUCTURE |
|---|
| 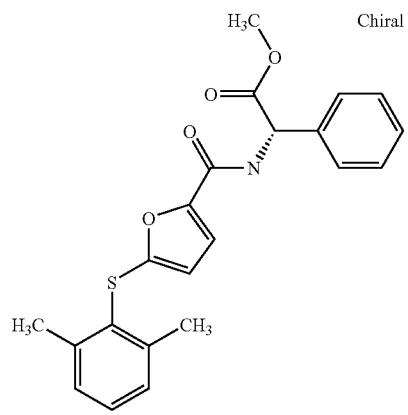 |
| 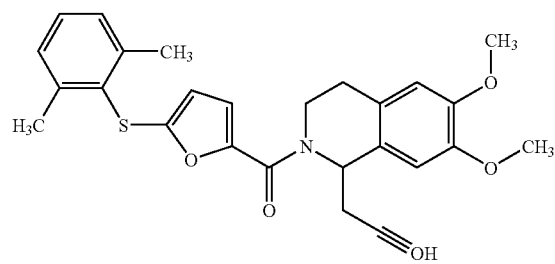 |
| 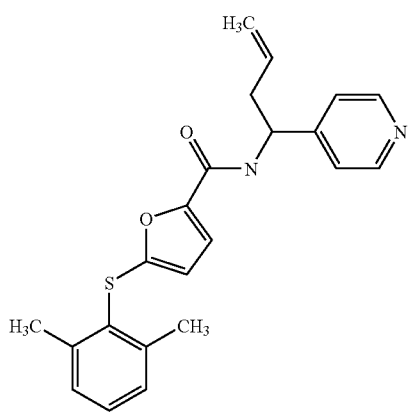 |
| 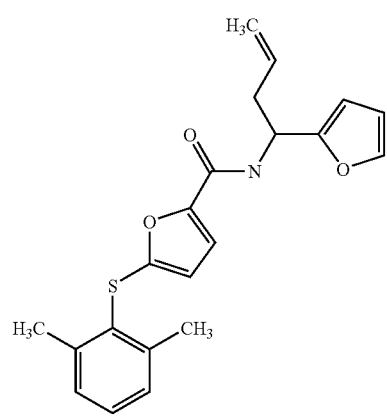 |

-continued
| MOLSTRUCTURE |
|---|
| 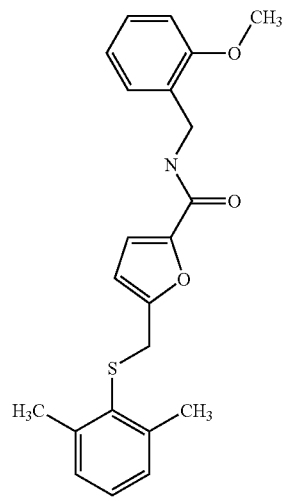 |
| 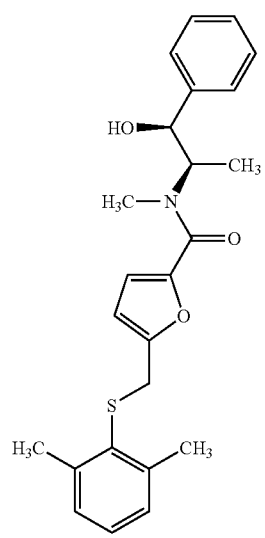 |
| 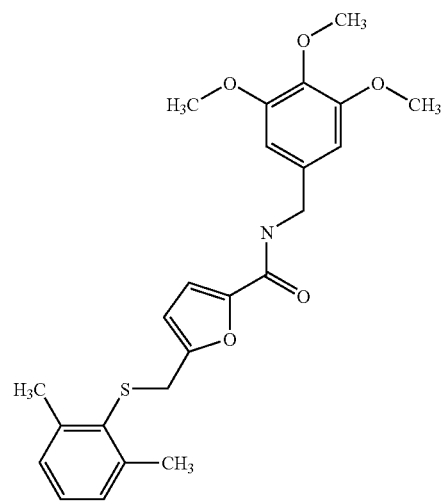 |

| MOLSTRUCTURE |
|---|
| 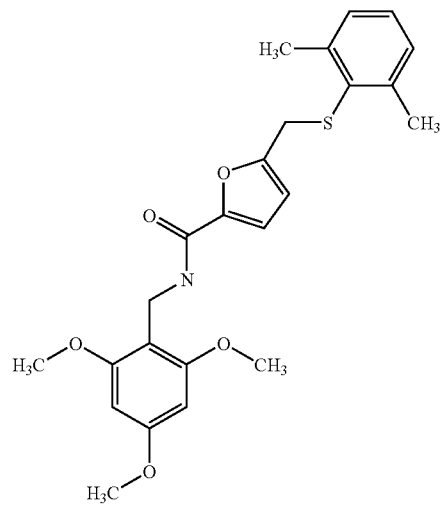 |
| 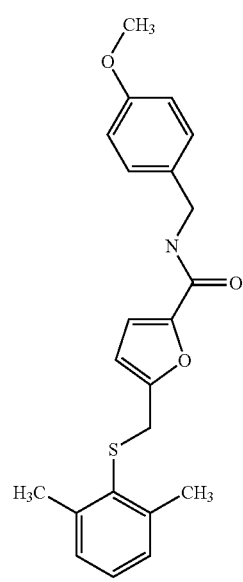 |

| MOLSTRUCTURE |
| --- |
| 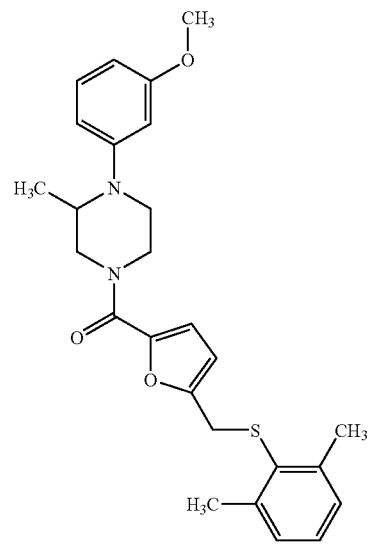 |
| 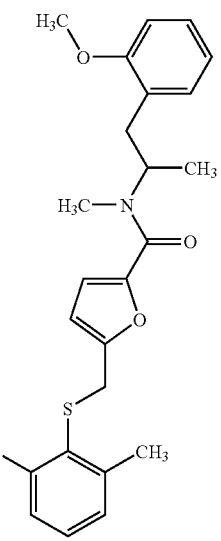 |
| 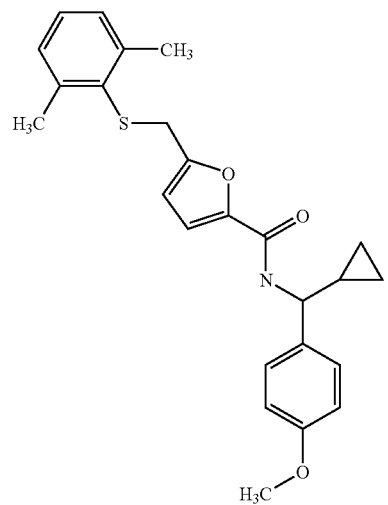 |

-continued
MOLSTRUCTURE
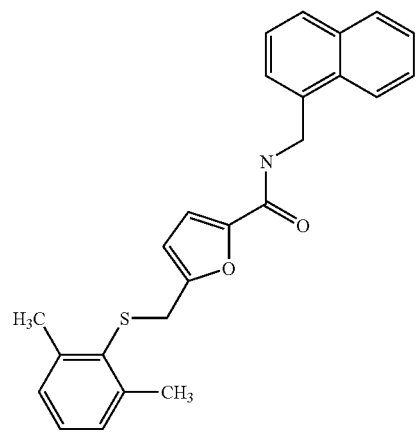
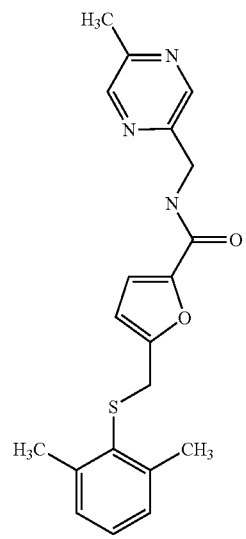
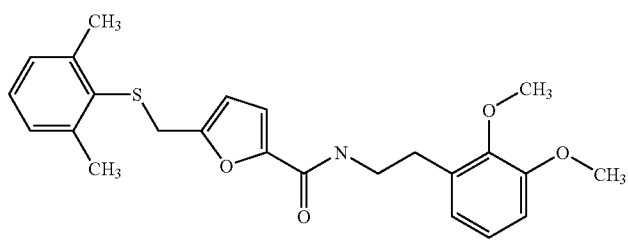
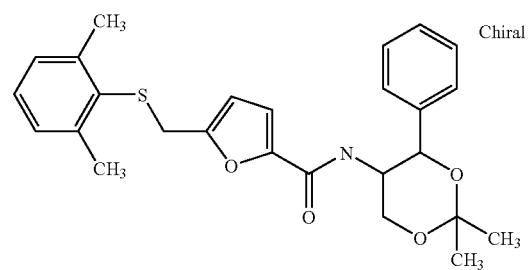

-continued
MOLSTRUCTURE
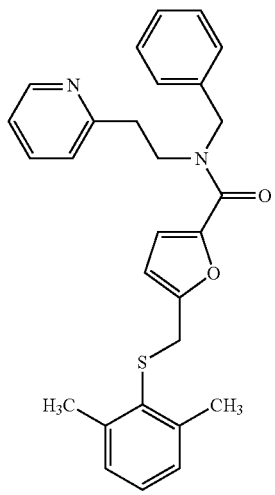
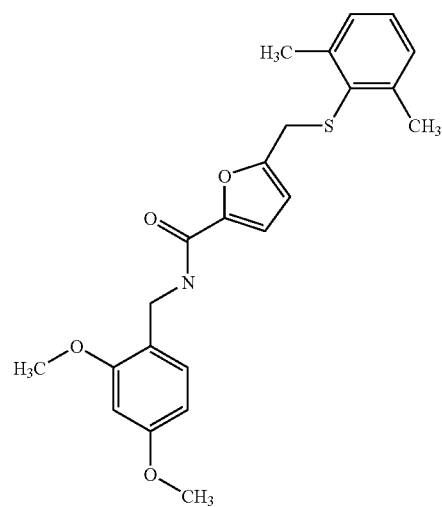
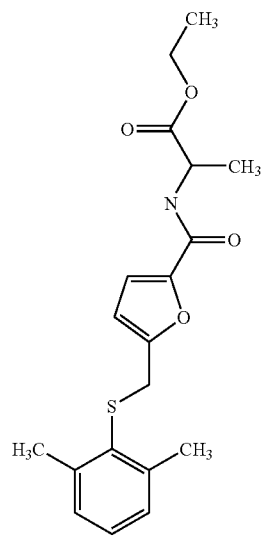

| -continued |
|---|
| MOLSTRUCTURE |
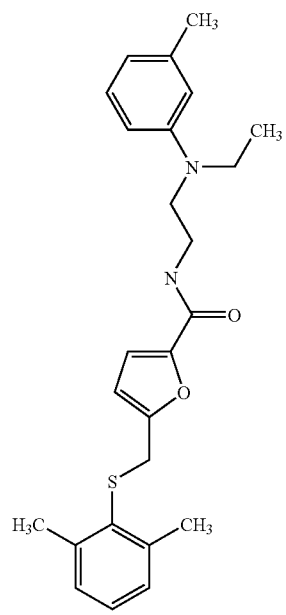
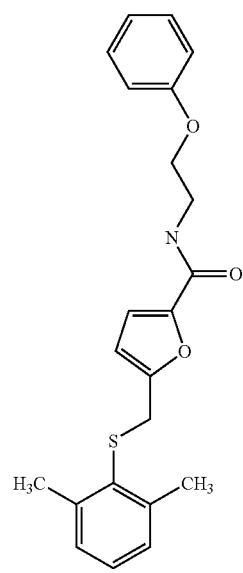

| MOLSTRUCTURE |
| --- |
| 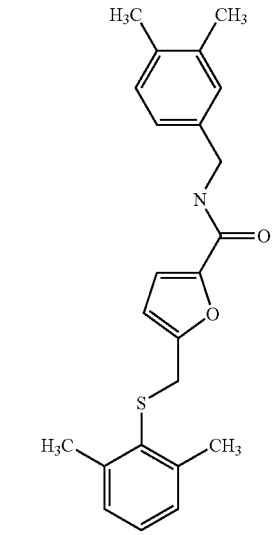 |
| 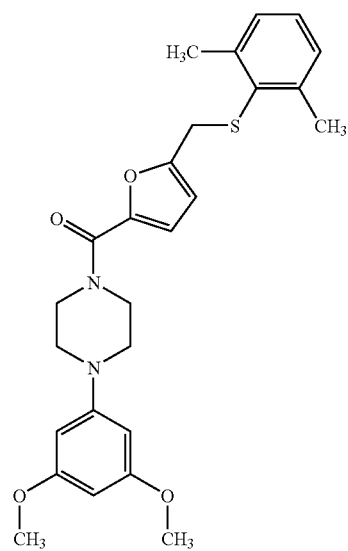 |
| 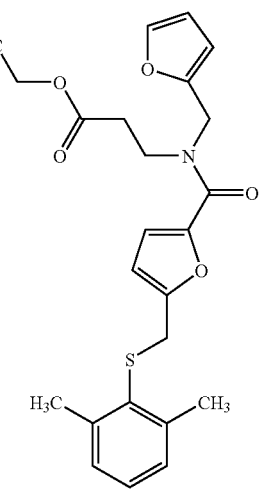 |

| MOLSTRUCTURE |
| --- |
| 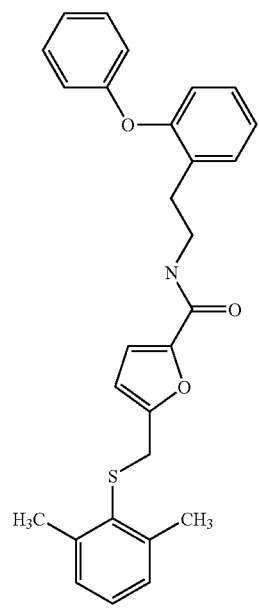 |
| 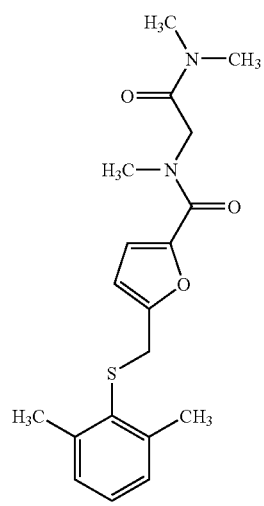 |

| MOLSTRUCTURE |
| --- |
| 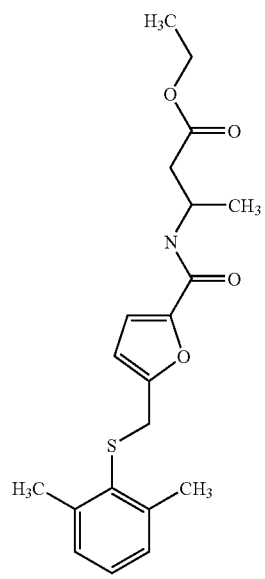 |
| 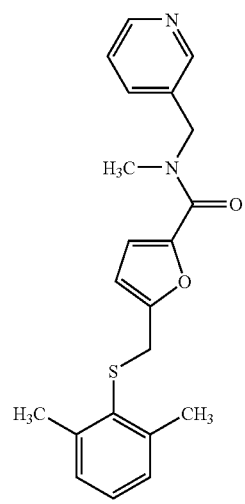 |

| MOLSTRUCTURE |
|---|
| 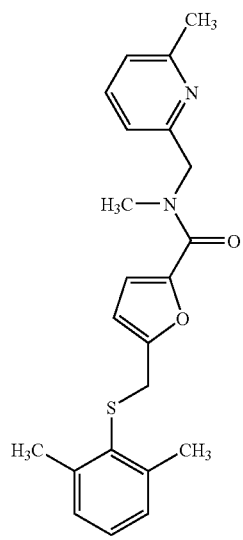 |
| 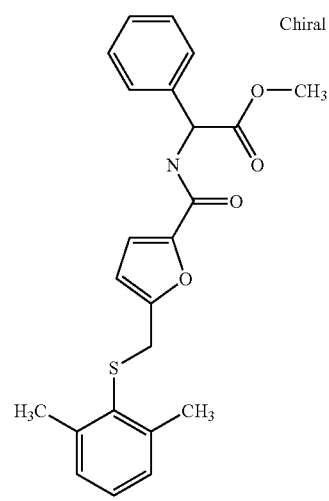 |
| 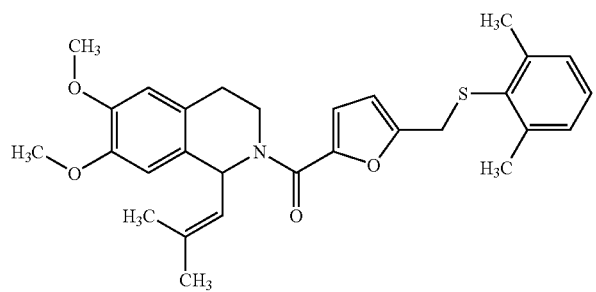 |

-continued
| MOLSTRUCTURE |
|---|
| 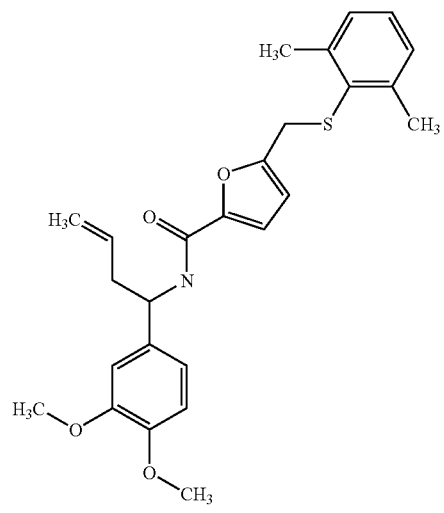 |
| 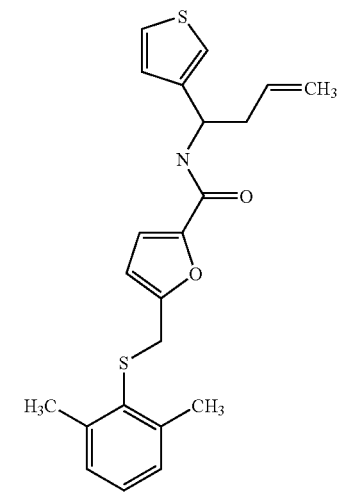 |
| 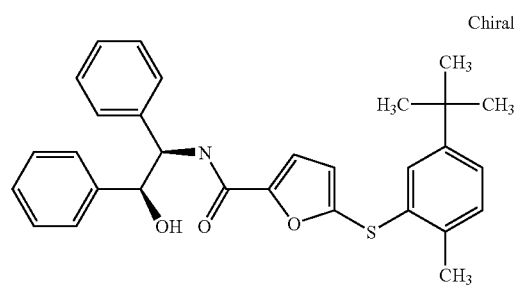 |
| 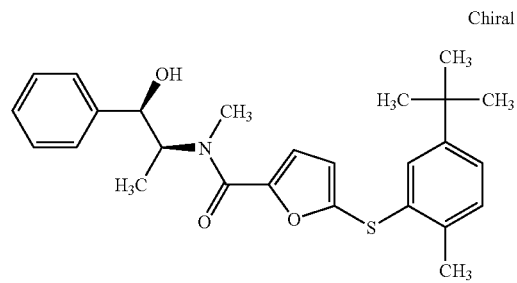 |

-continued
MOLSTRUCTURE
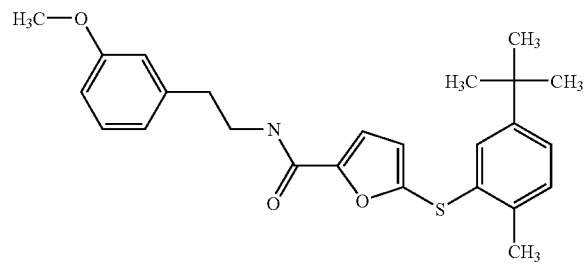
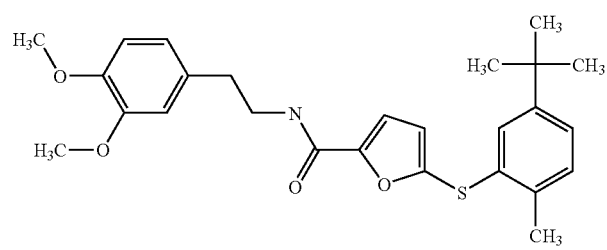
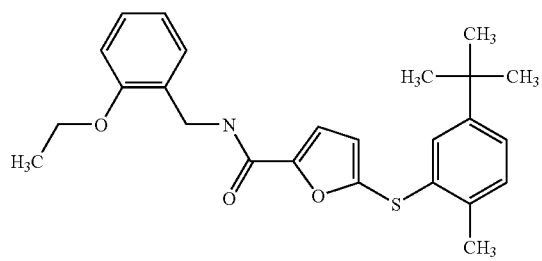
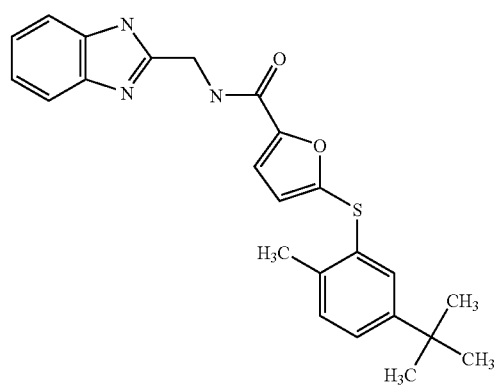
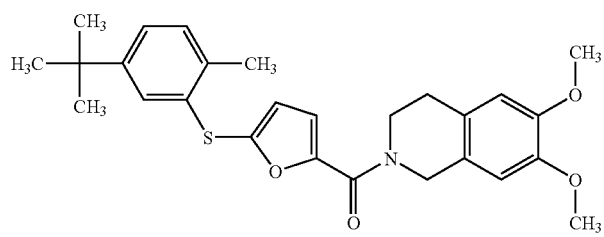

| MOLSTRUCTURE |
|---|
| 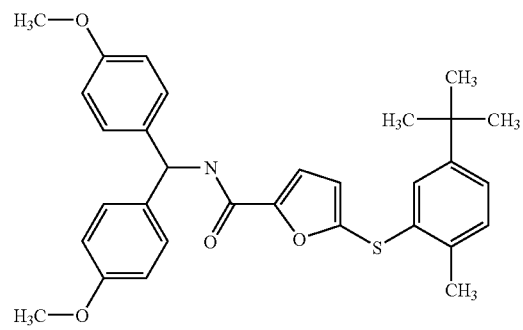 |
| 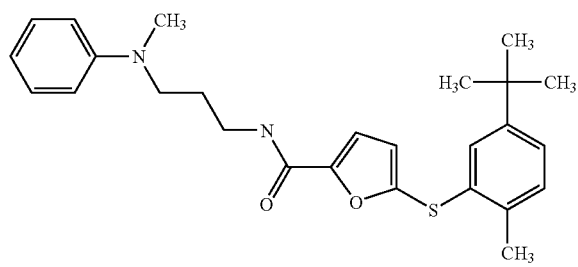 |
| 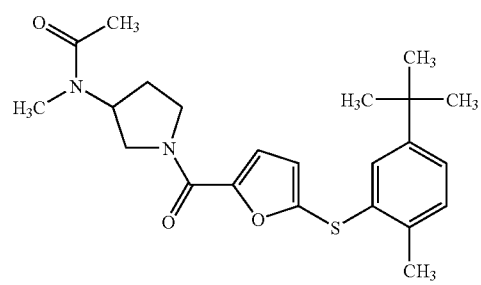 |
| 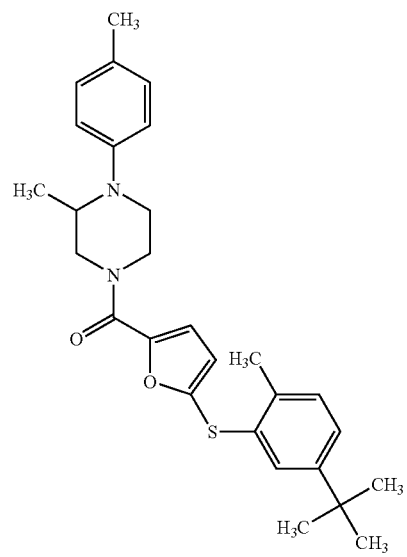 |

| MOLSTRUCTURE |
|---|
| 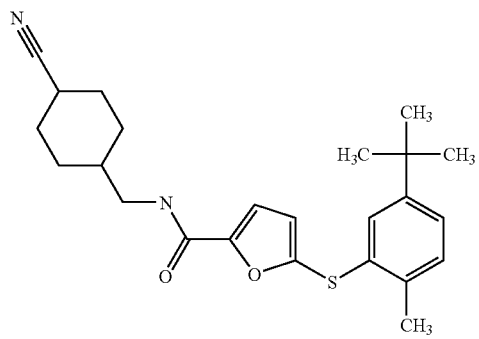 |
| 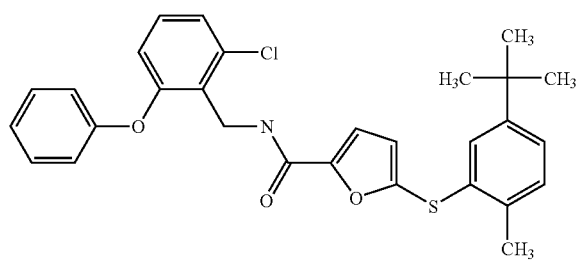 |
| 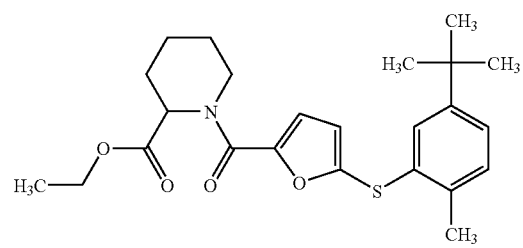 |
| 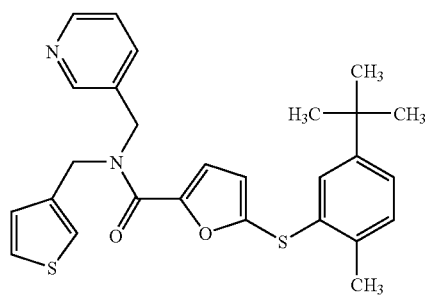 |
| 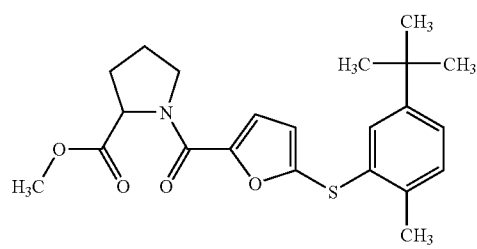 |

-continued
MOLSTRUCTURE
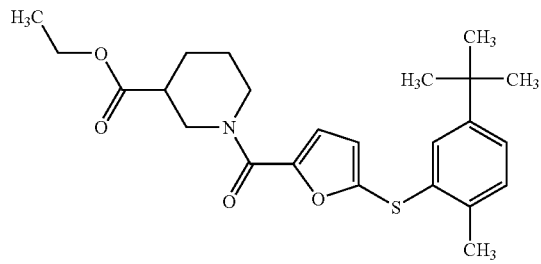
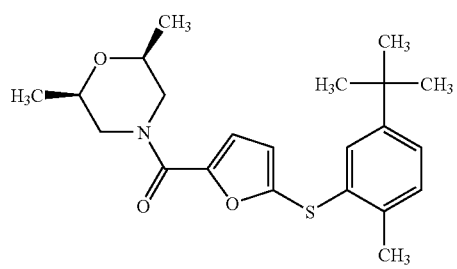
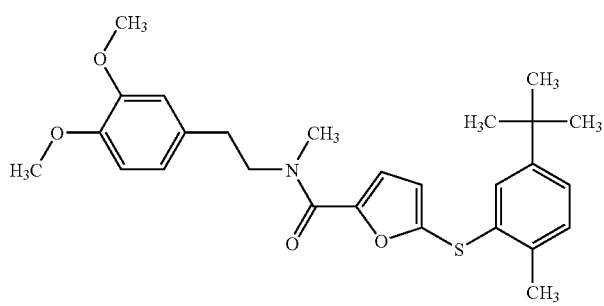
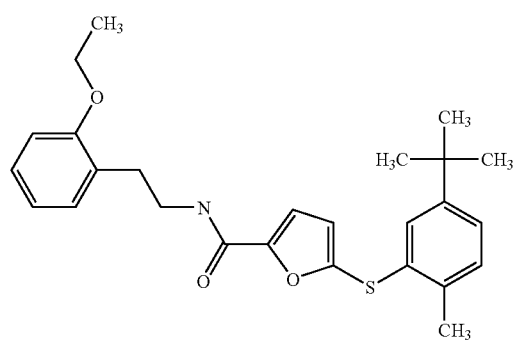
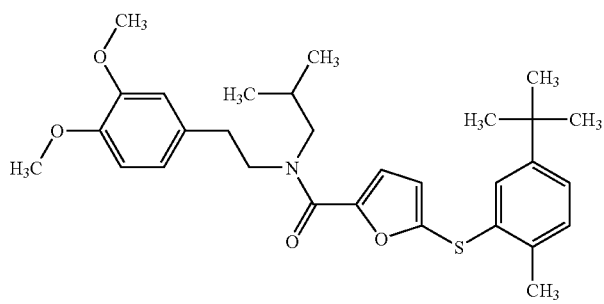

-continued
MOLSTRUCTURE
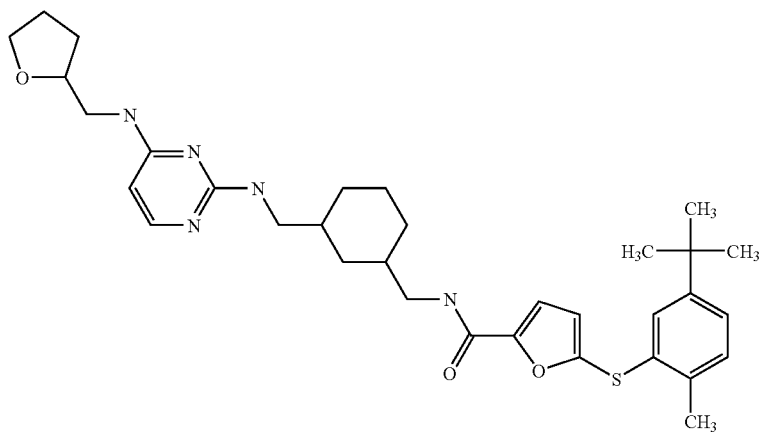
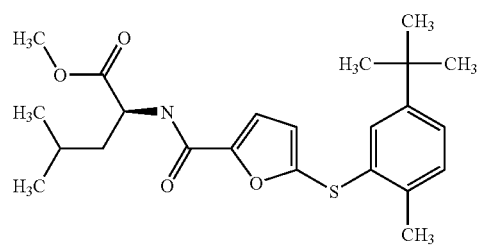
Chiral
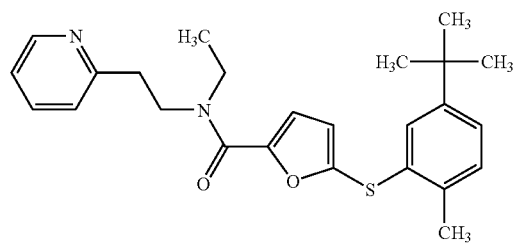
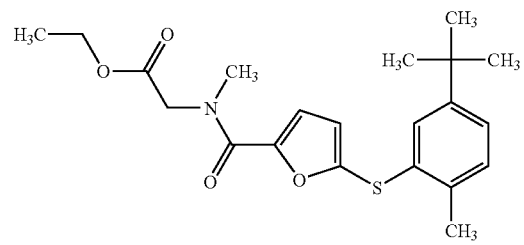
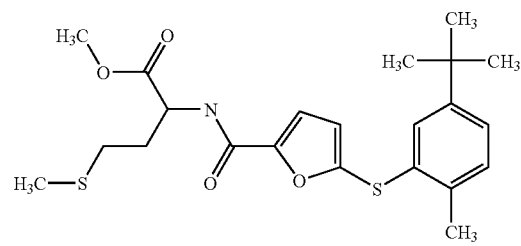

-continued
MOLSTRUCTURE
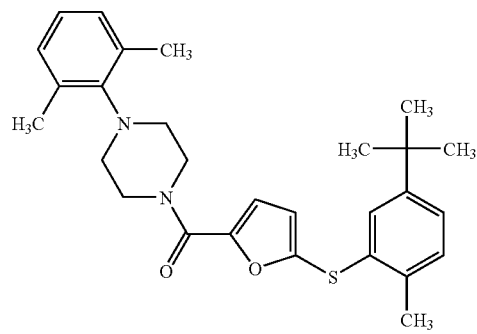
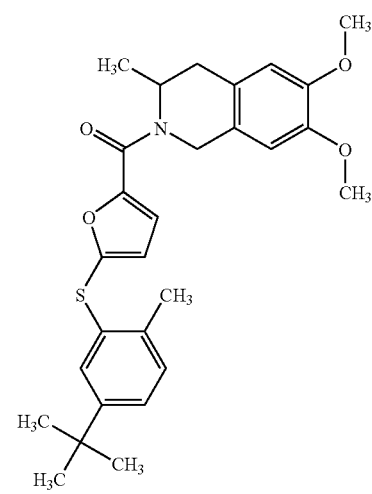
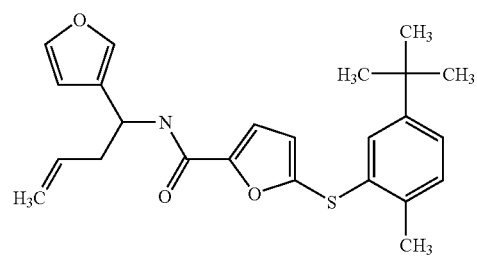
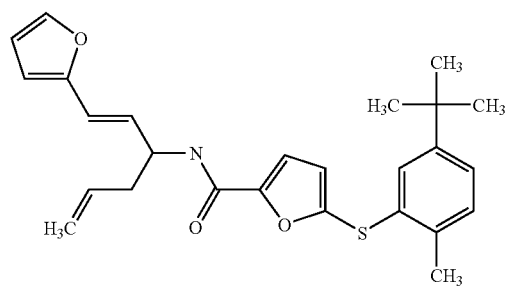

| MOLSTRUCTURE |
| --- |
| 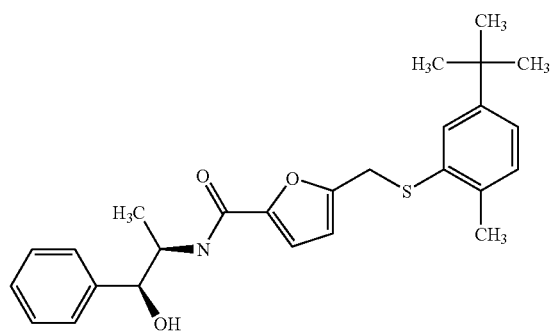 |
| 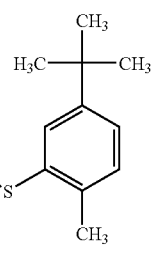 |
| 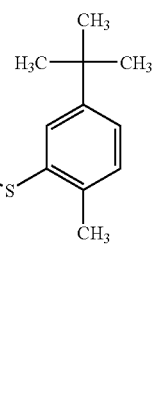 |

-continued
MOLSTRUCTURE
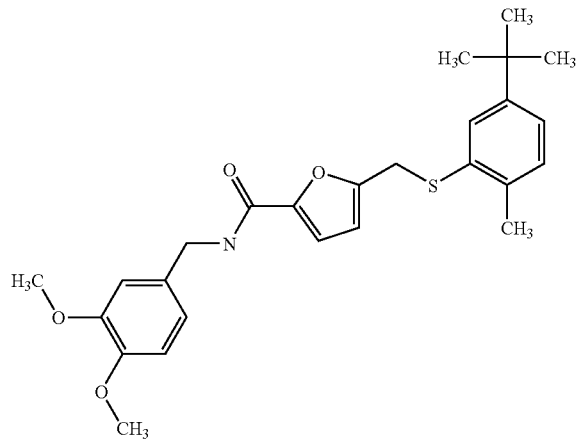
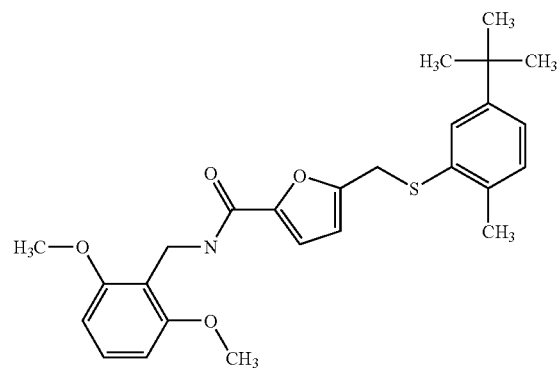
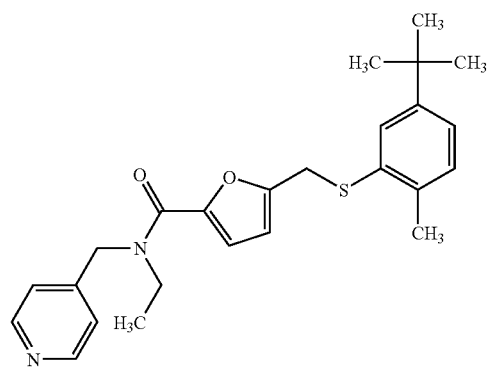
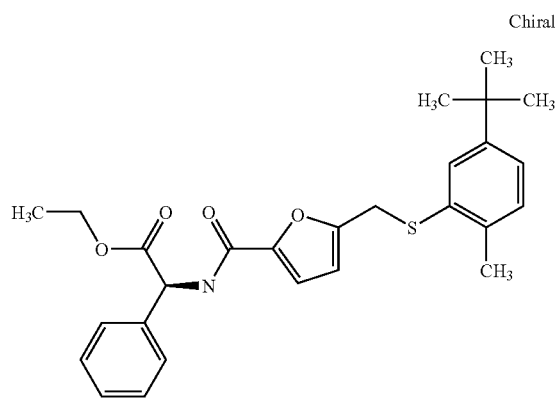

2017 2018
-continued
| MOLSTRUCTURE |
| --- |
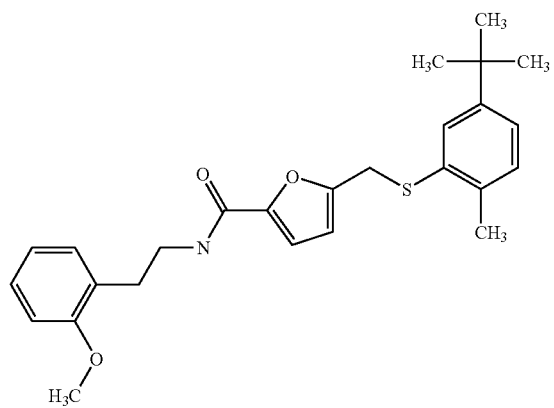
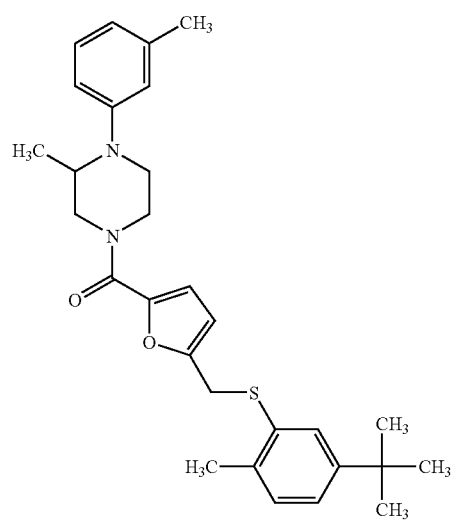
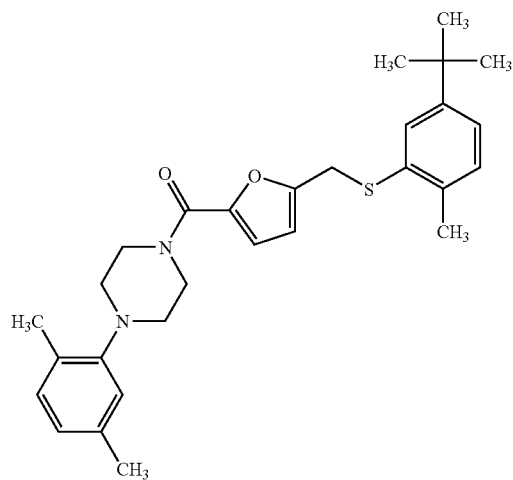

2019
-continued
| MOLSTRUCTURE |
| --- |
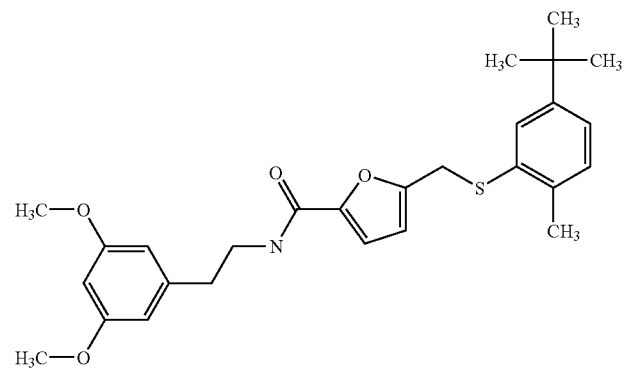
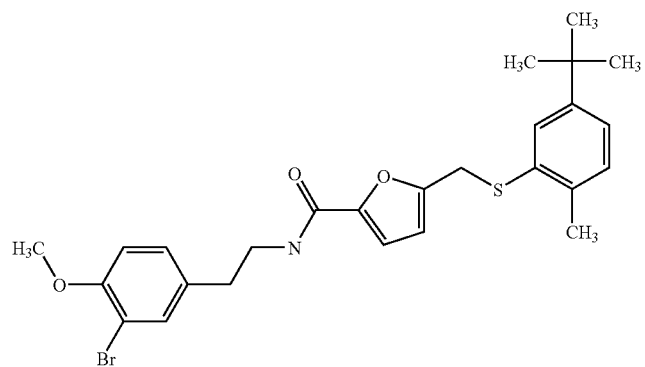
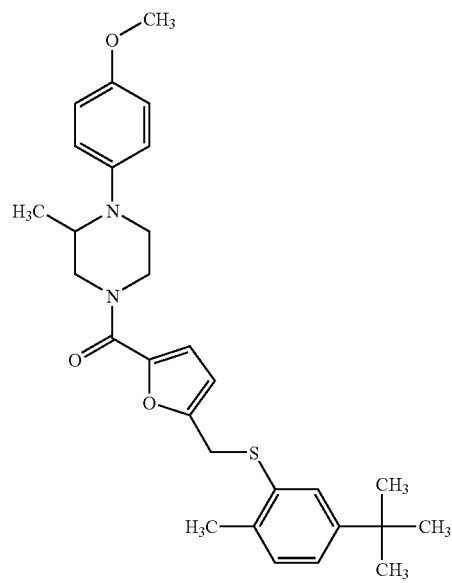

-continued
| MOLSTRUCTURE |
| --- |
| 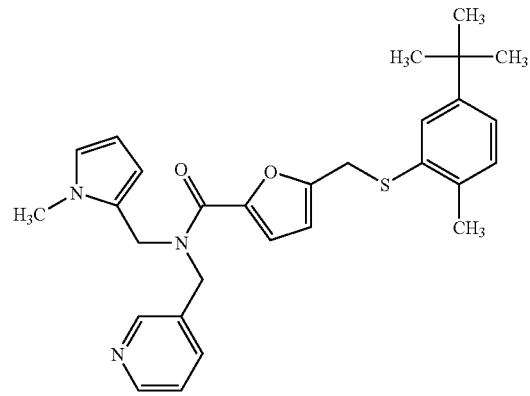 |
| 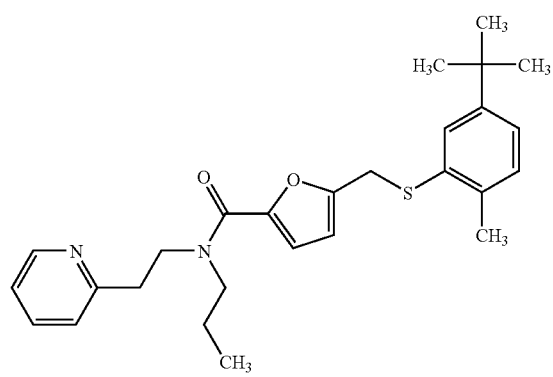 |
| 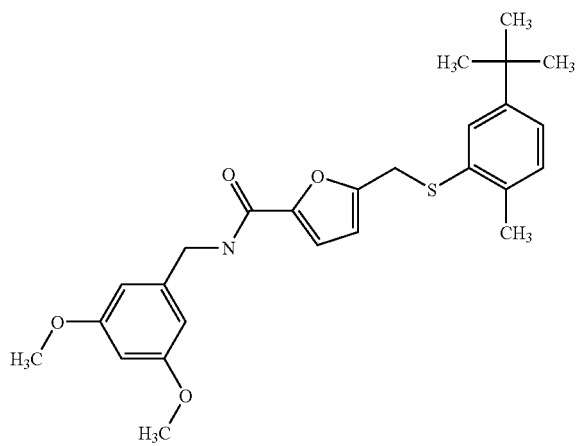 |
| 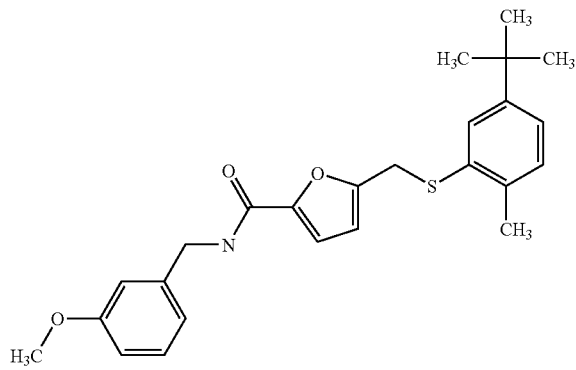 |

| MOLSTRUCTURE |
|---|
| 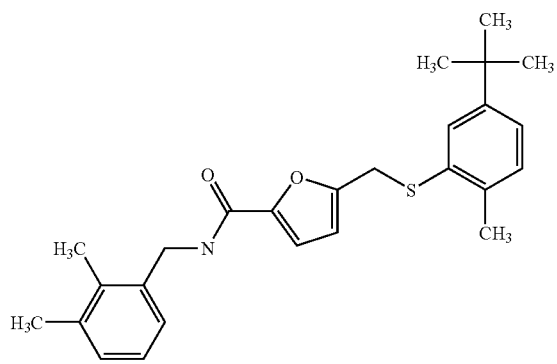 |
| 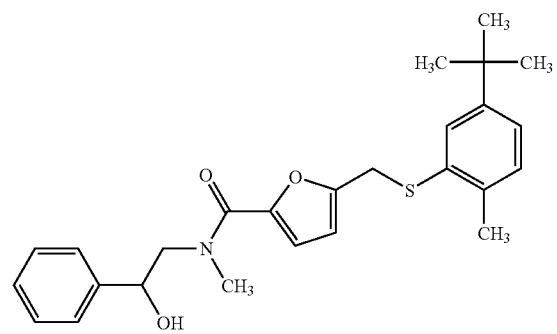 |
| 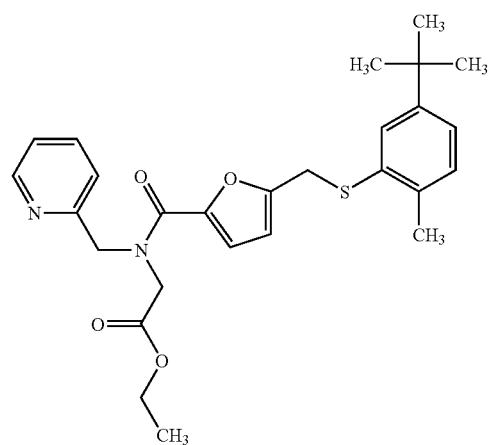 |

| MOLSTRUCTURE |
|---|
| 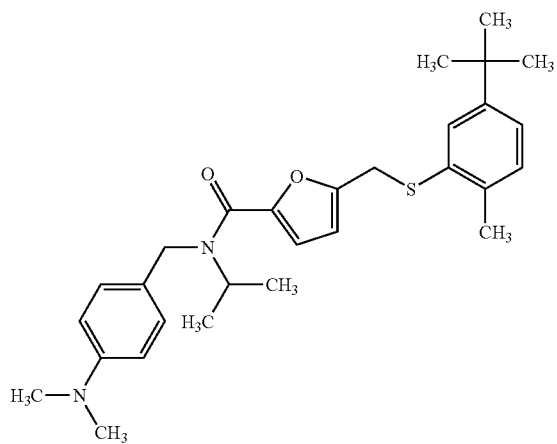 |
| 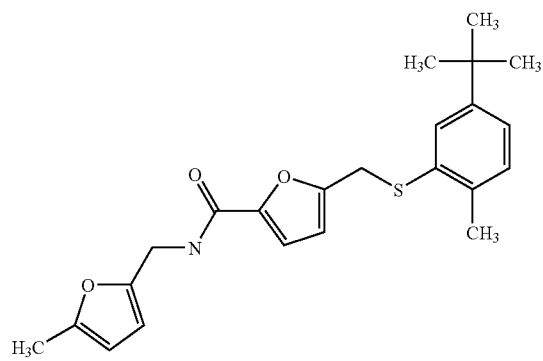 |
| 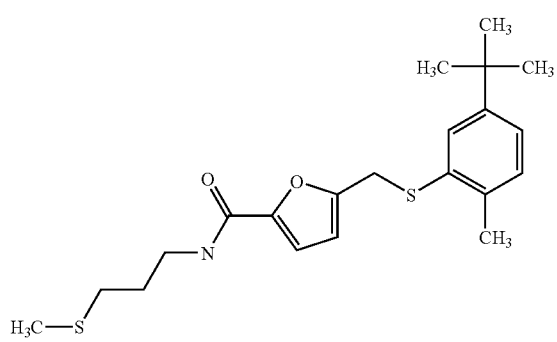 |
| 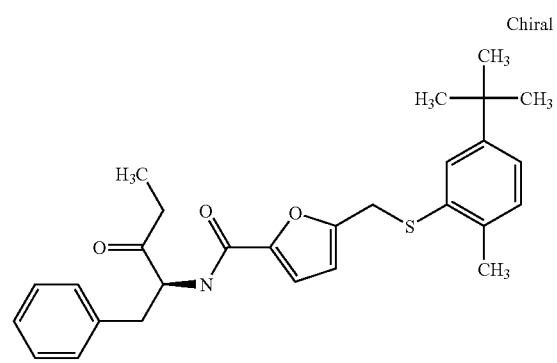 |

-continued
| MOLSTRUCTURE |
|---|
| 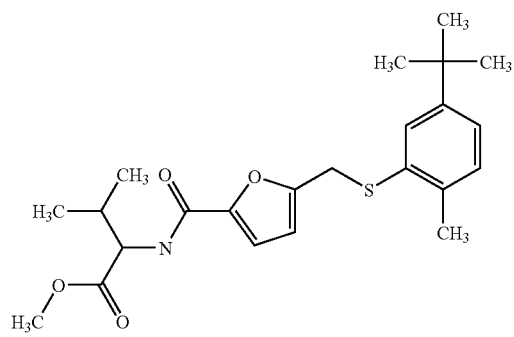 |
| 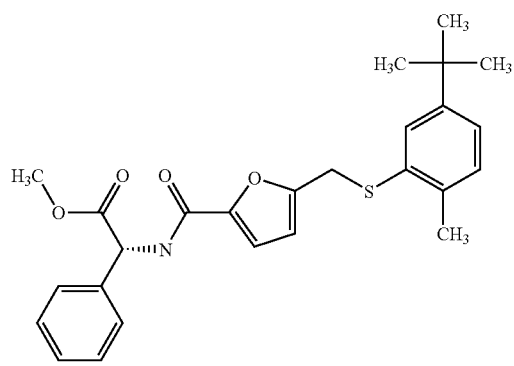 |
| 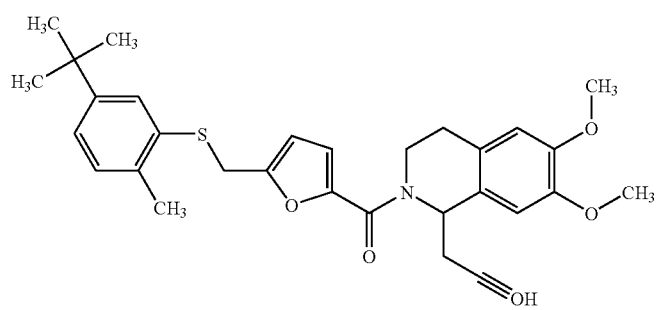 |
| 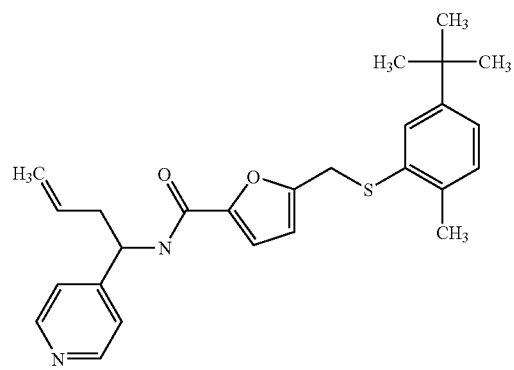 |

| MOLSTRUCTURE |
|---|
| 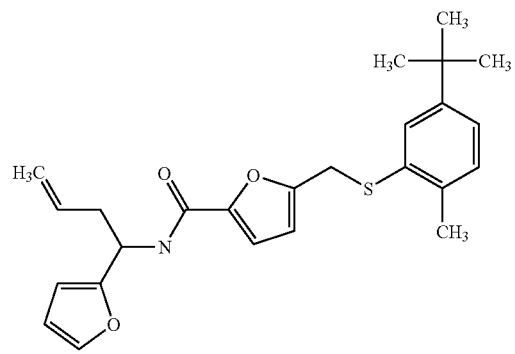 |
| 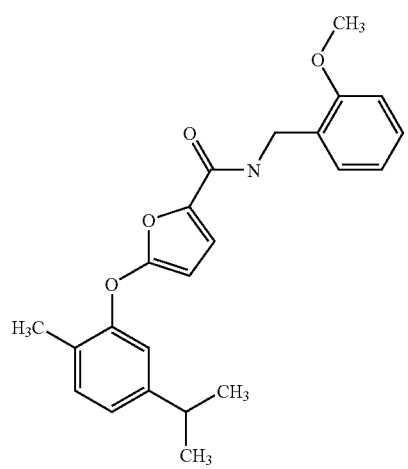 |
| 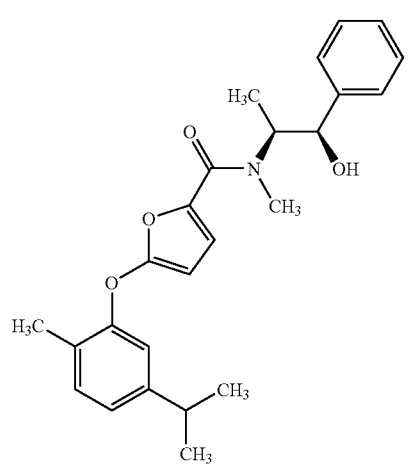 |

| MOLSTRUCTURE |
|---|
| 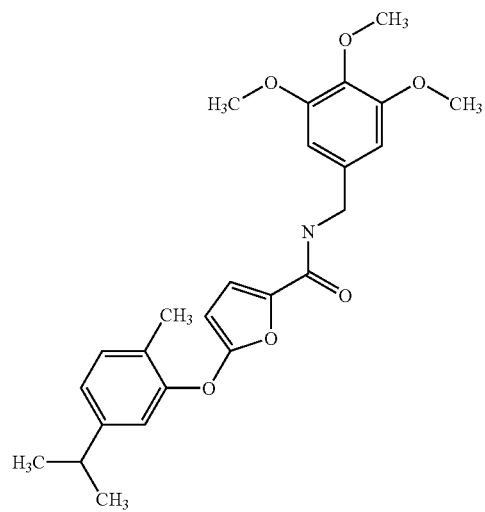 |
| 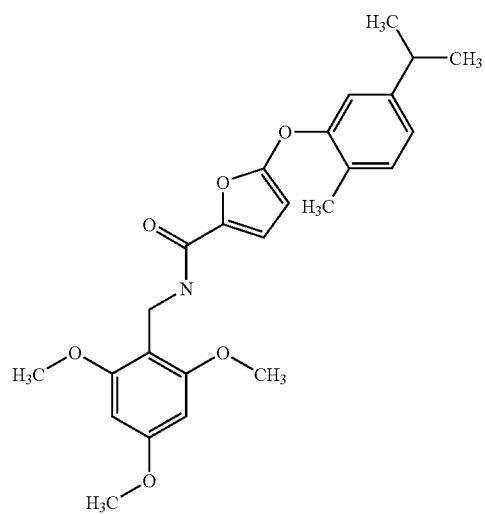 |
| 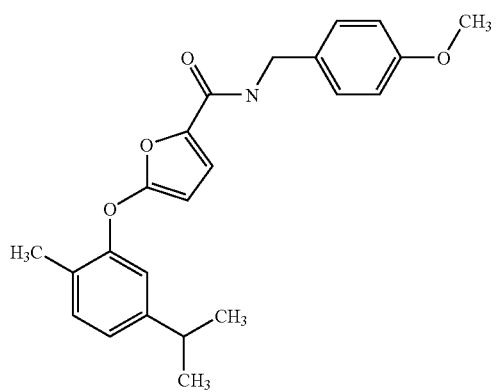 |

-continued
| MOLSTRUCTURE |
| --- |
| 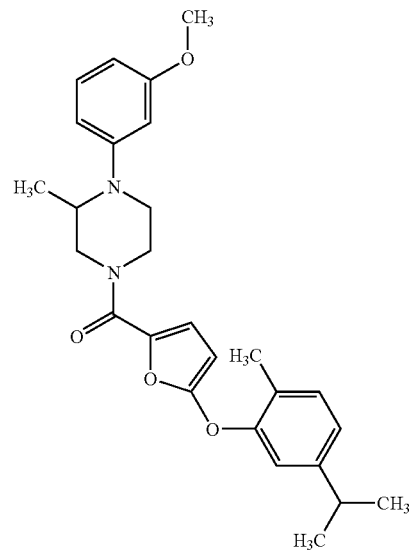 |
| 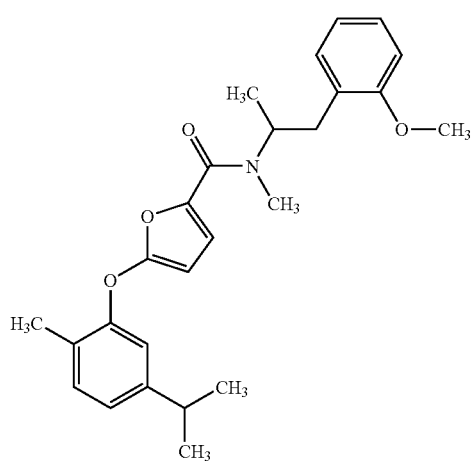 |
| 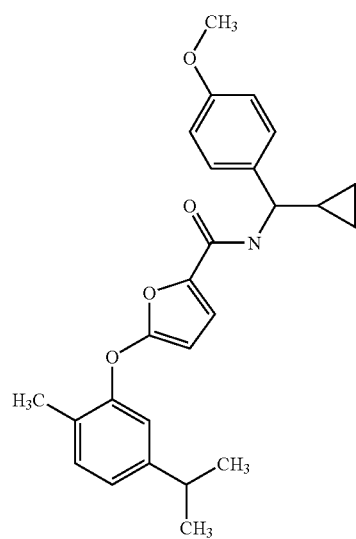 |

| MOLSTRUCTURE |
|---|
| 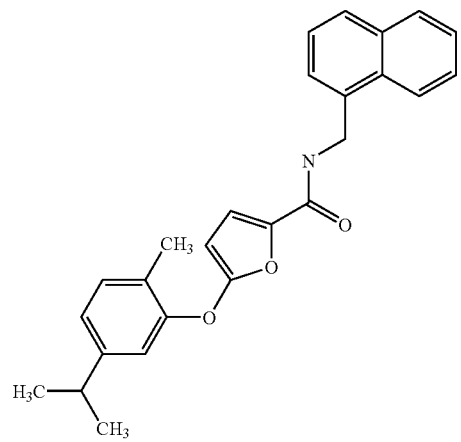 |
| 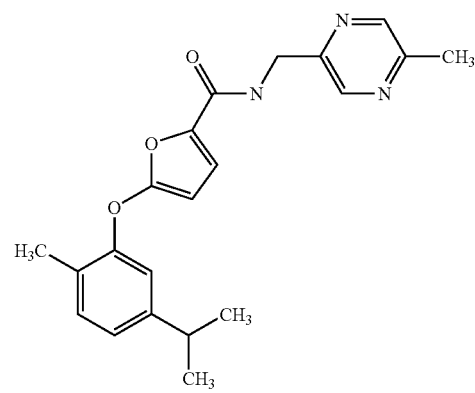 |
| 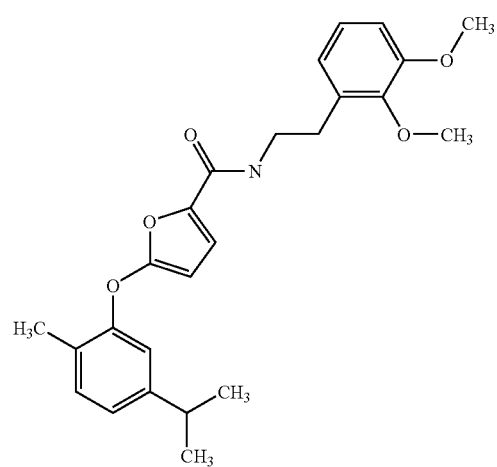 |
| 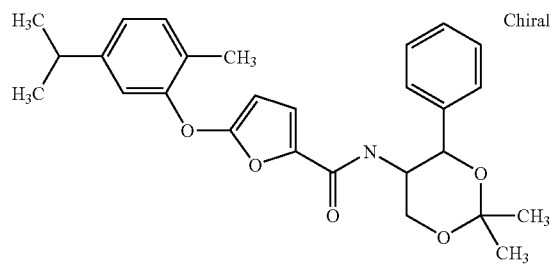 |

-continued
MOLSTRUCTURE
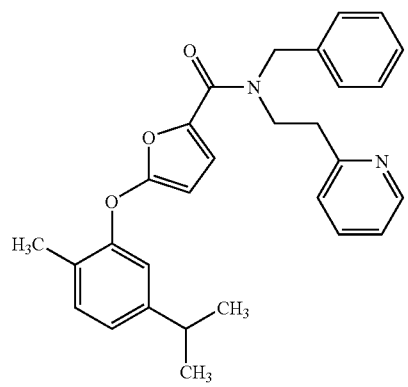
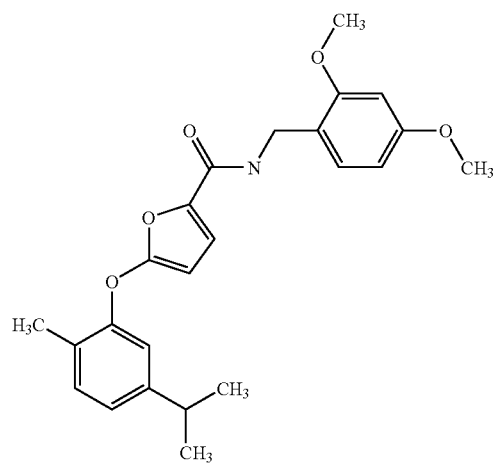
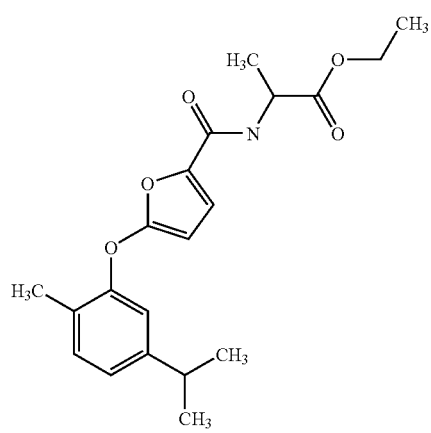

-continued
| MOLSTRUCTURE |
|---|
| 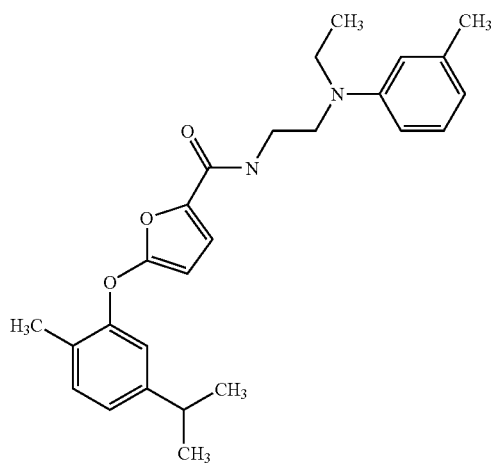 |
| 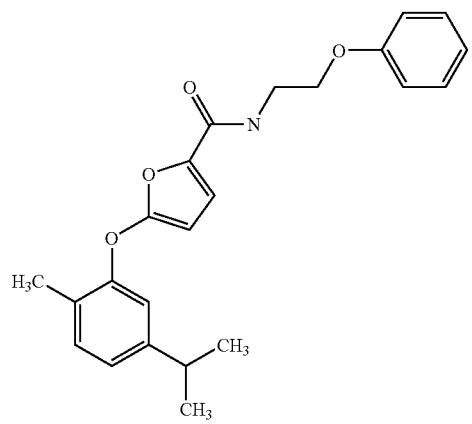 |
| 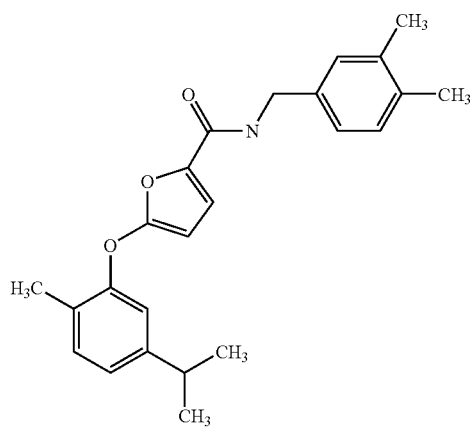 |

-continued
| MOLSTRUCTURE |
| --- |
| 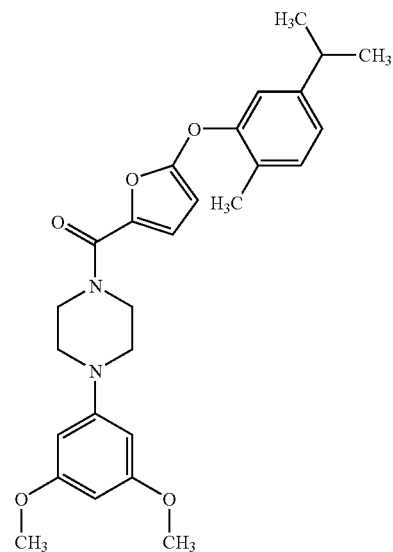 |
| 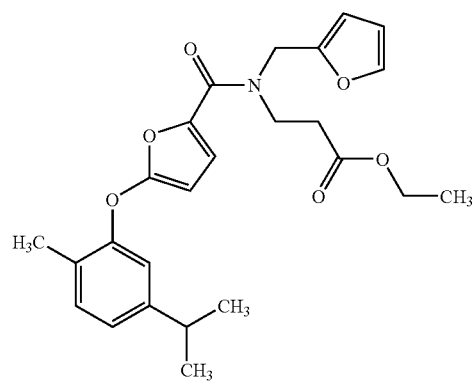 |
| 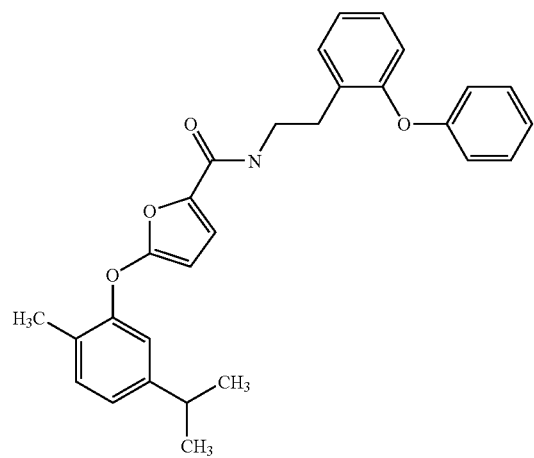 |

| MOLSTRUCTURE |
| --- |
| 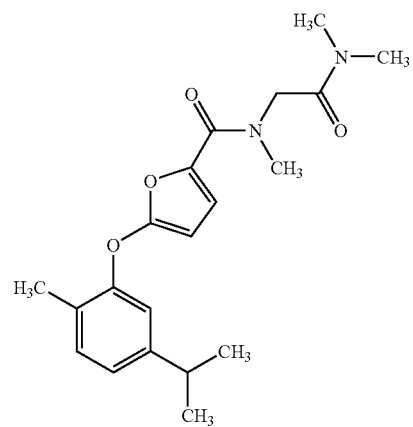 |
| 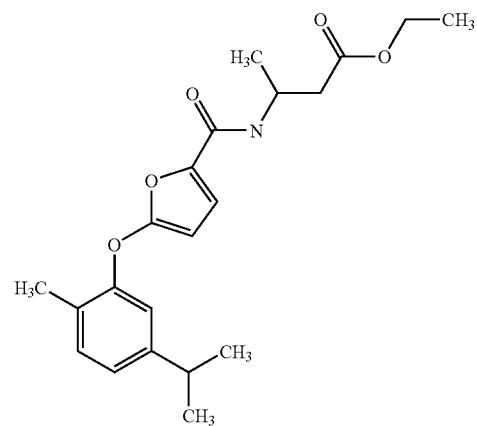 |
| 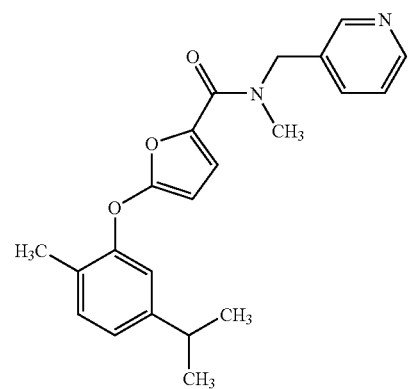 |

| MOLSTRUCTURE |
|---|
| 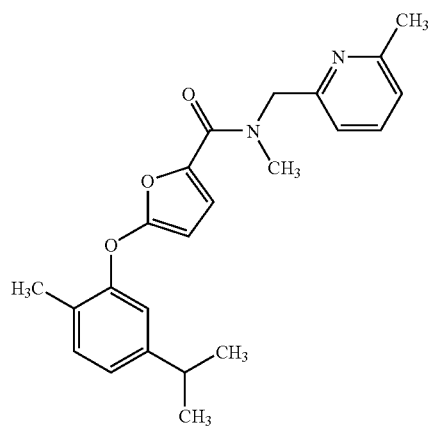 |
| 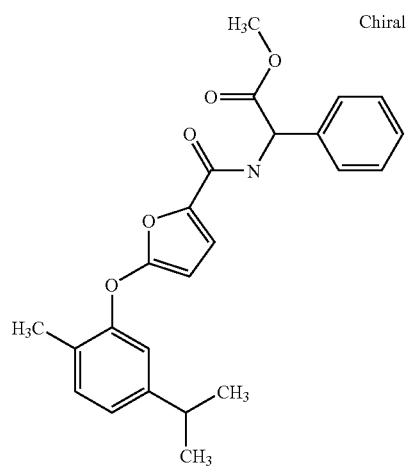 |
| 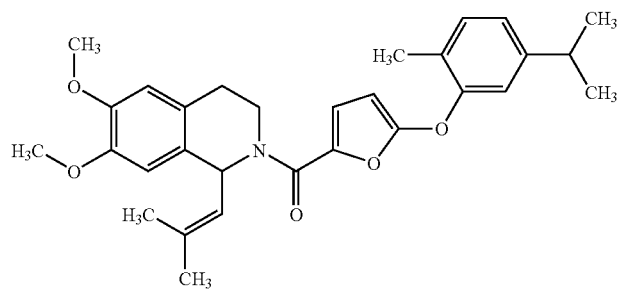 |

| MOLSTRUCTURE |
|---|
| 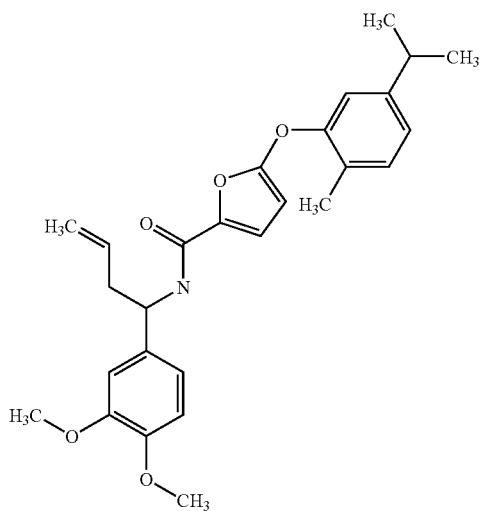 |
| 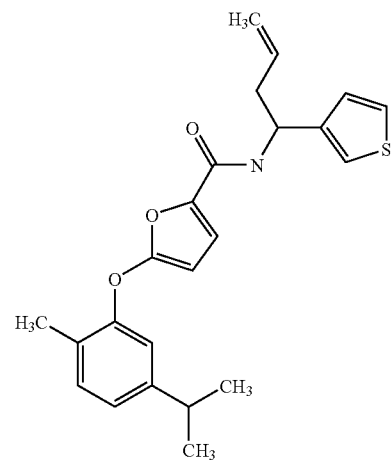 |
| 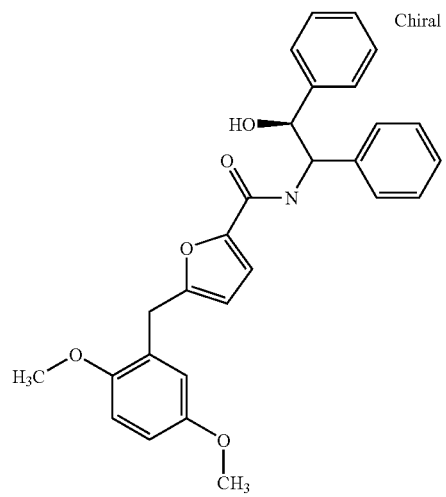 |

| MOLSTRUCTURE |
|---|
| 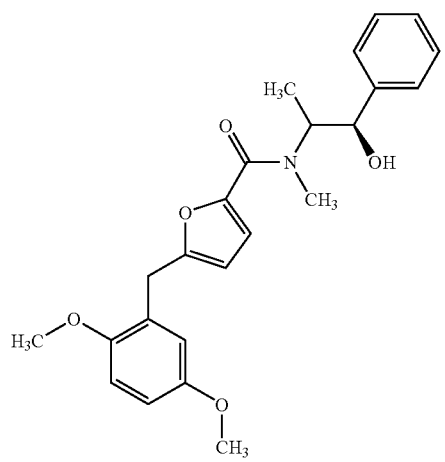 |
| 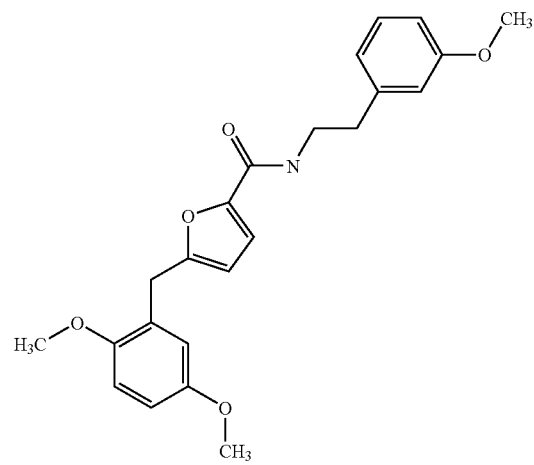 |
| 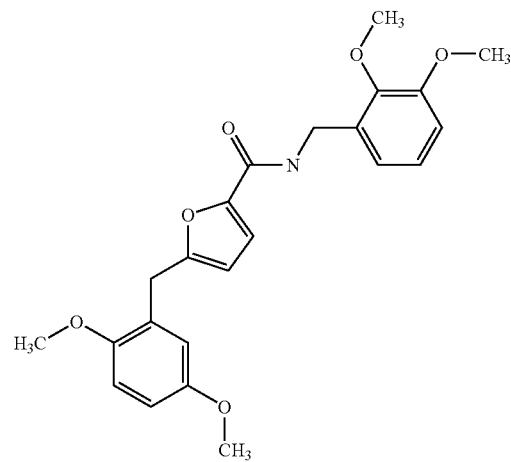 |

-continued
| MOLSTRUCTURE |
|---|
| 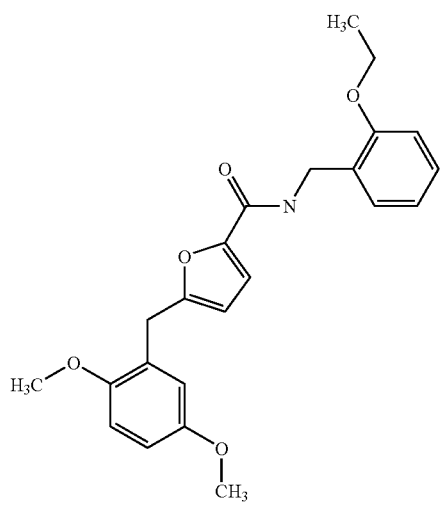 |
| 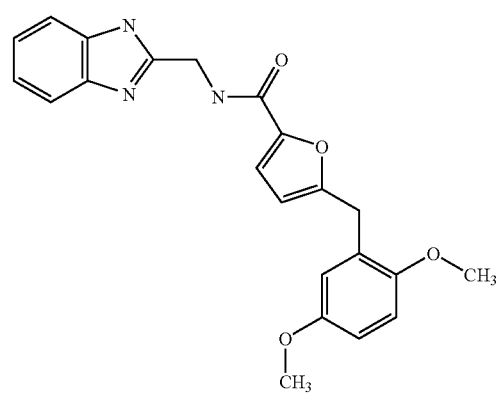 |
| 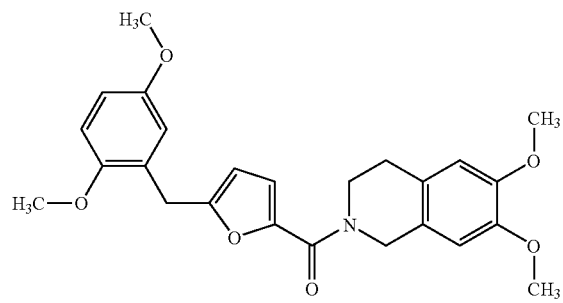 |

| MOLSTRUCTURE |
|---|
| 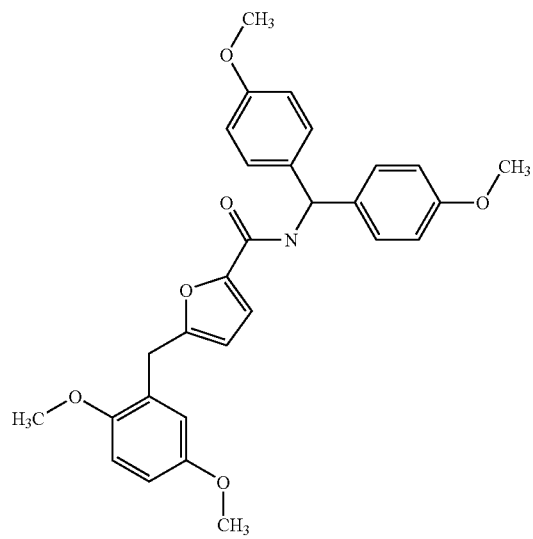 |
| 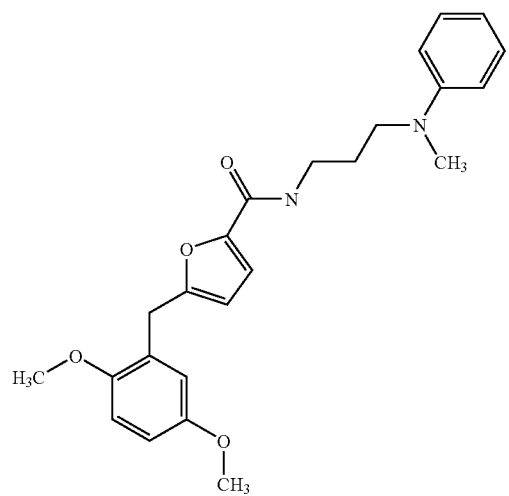 |
| 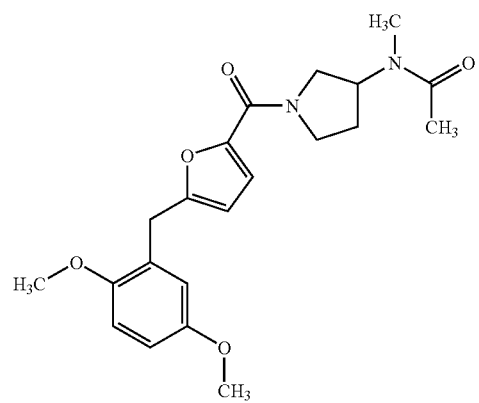 |

-continued
MOLSTRUCTURE
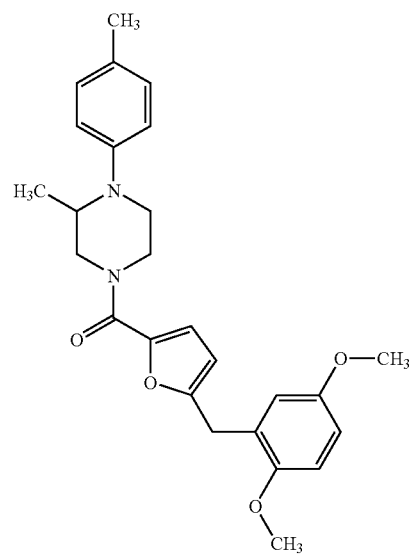
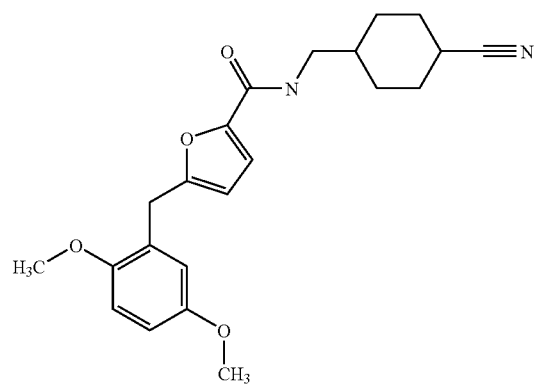
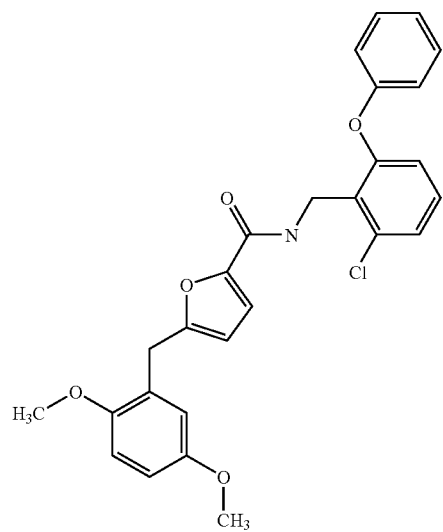

-continued
| MOLSTRUCTURE |
| --- |
| 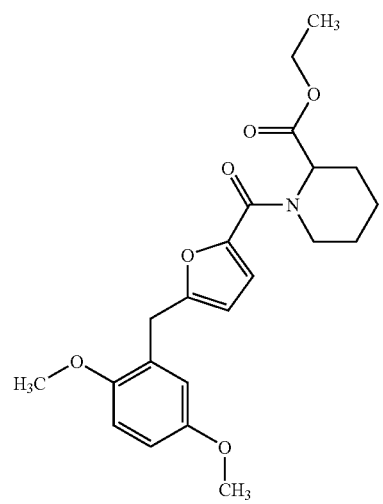 |
| 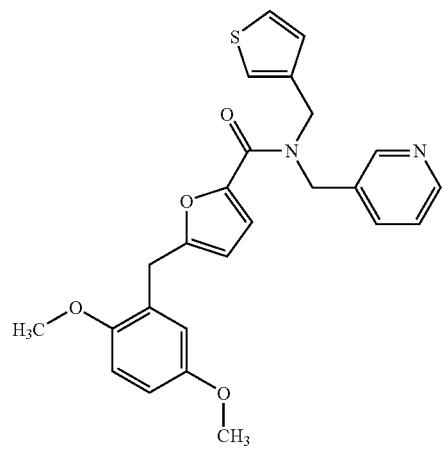 |
| 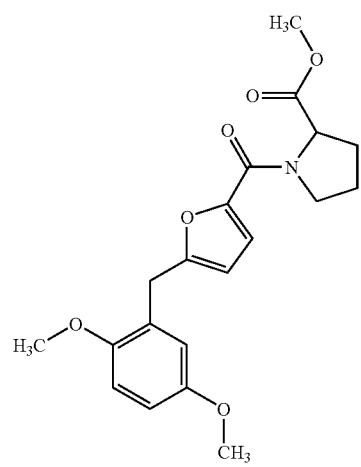 |

-continued
MOLSTRUCTURE
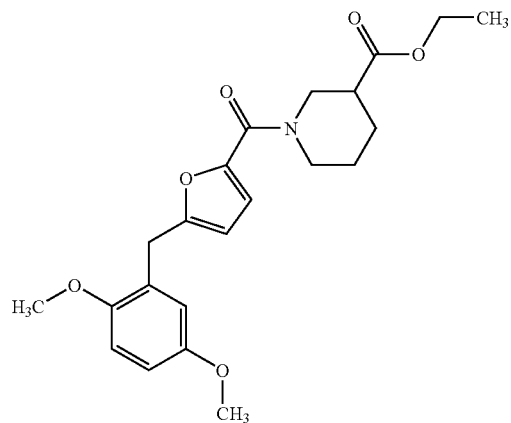
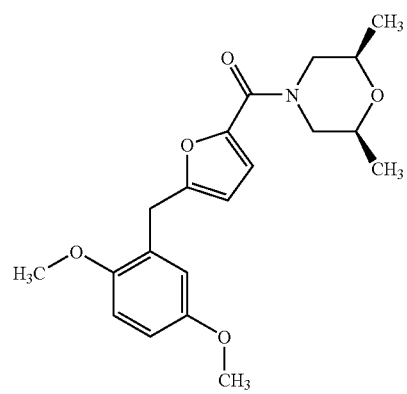
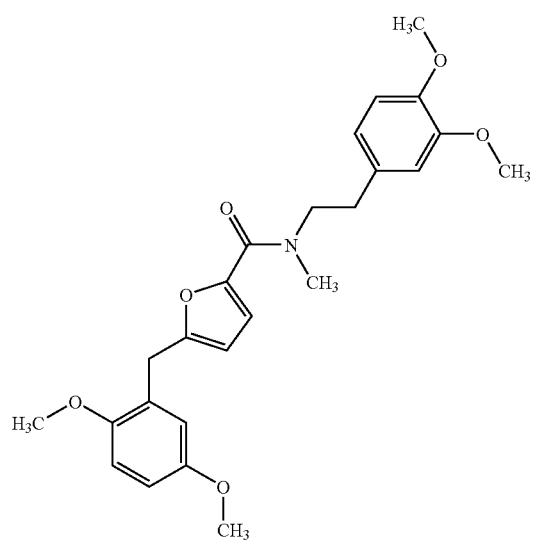

-continued
| MOLSTRUCTURE |
| --- |
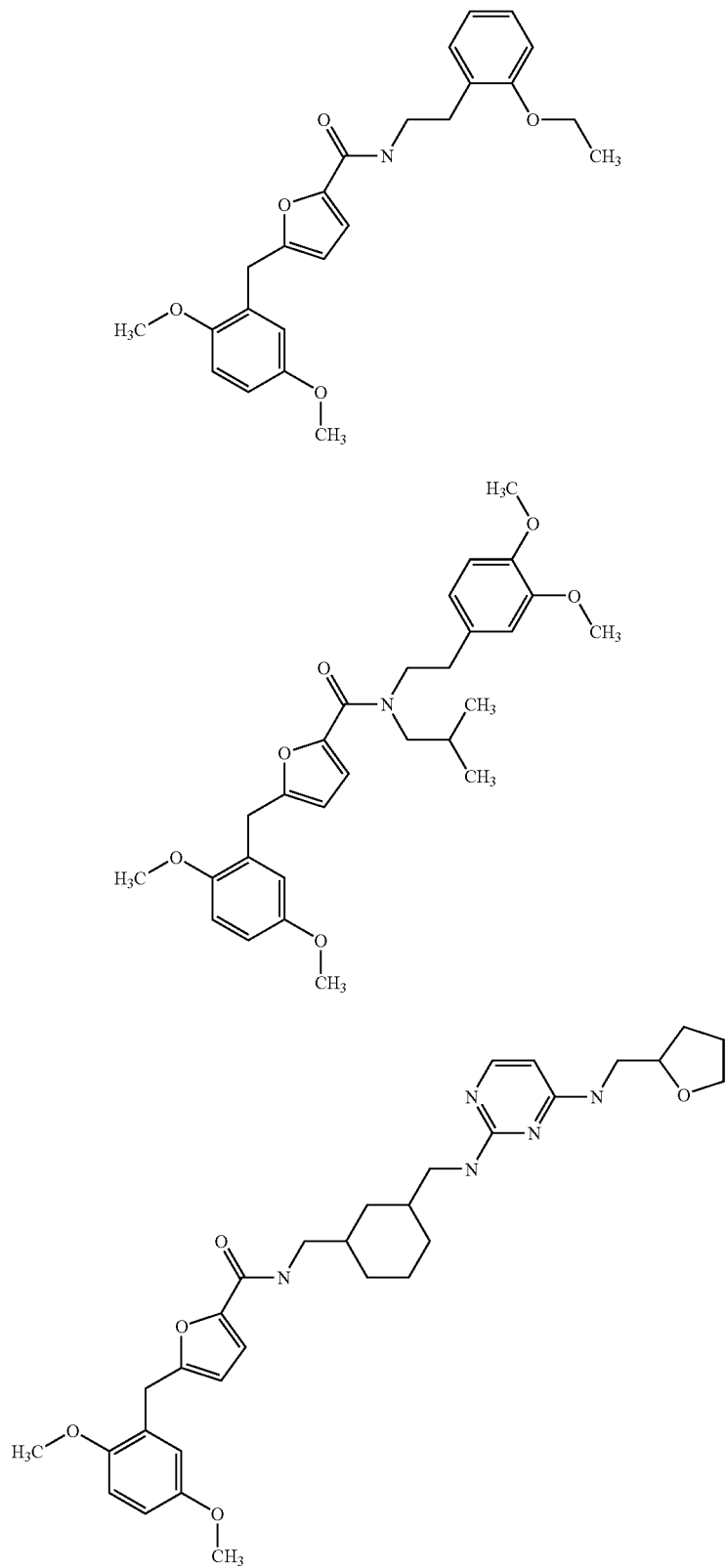

-continued
| MOLSTRUCTURE |
|---|
| 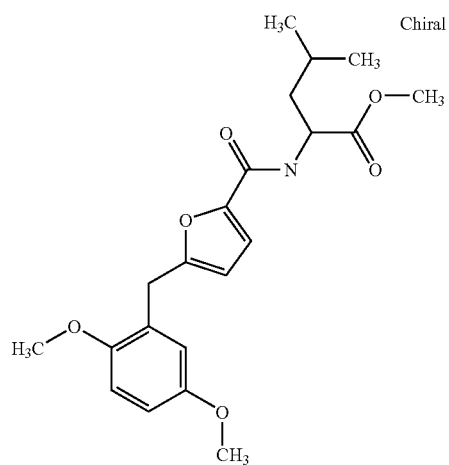 |
| 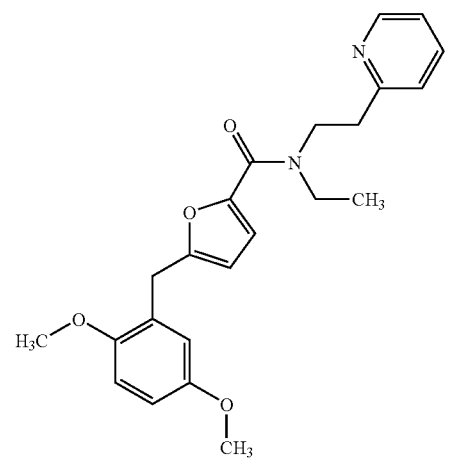 |
| 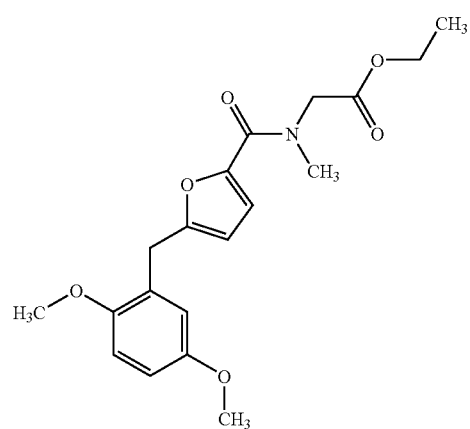 |

| MOLSTRUCTURE |
|---|
| 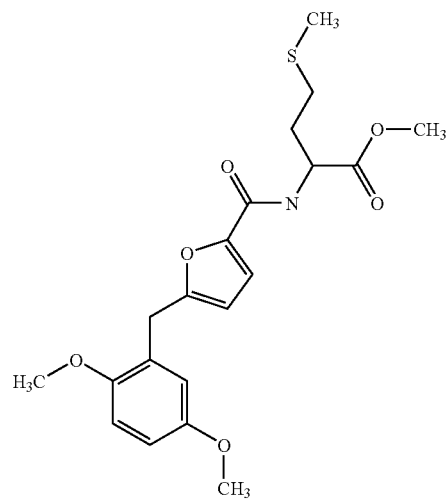 |
| 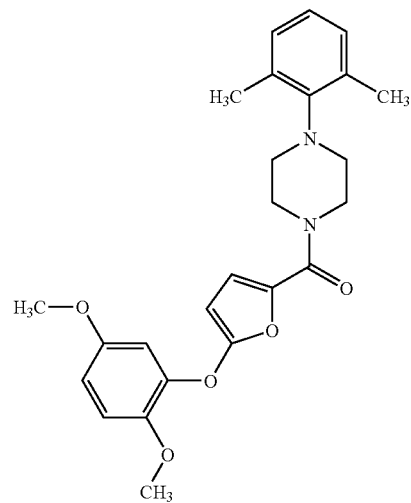 |
| 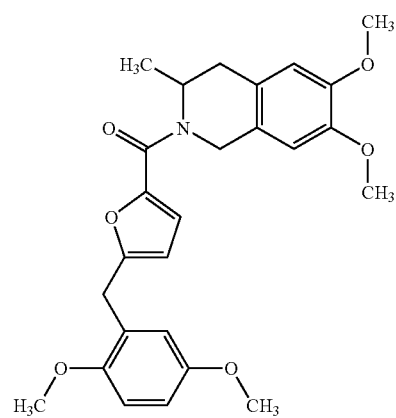 |

| MOLSTRUCTURE |
| --- |
| 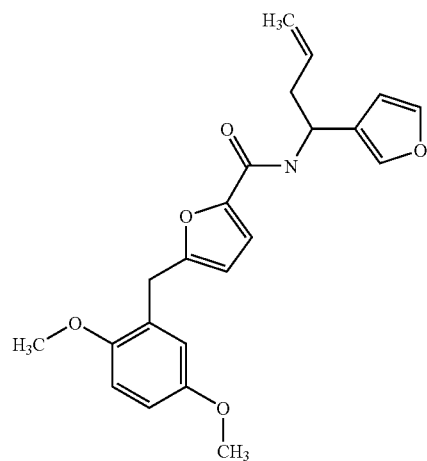 |
| 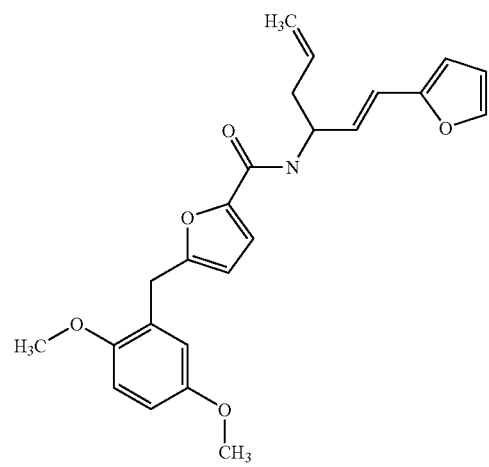 |
| 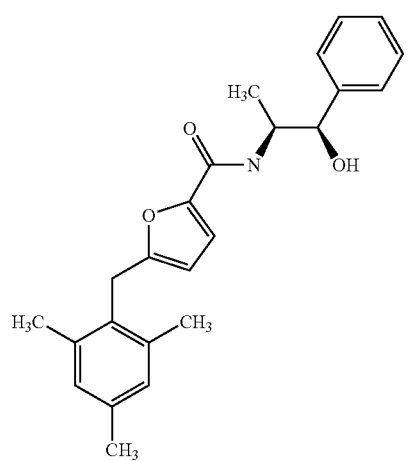 |

-continued
| MOLSTRUCTURE |
| --- |
| 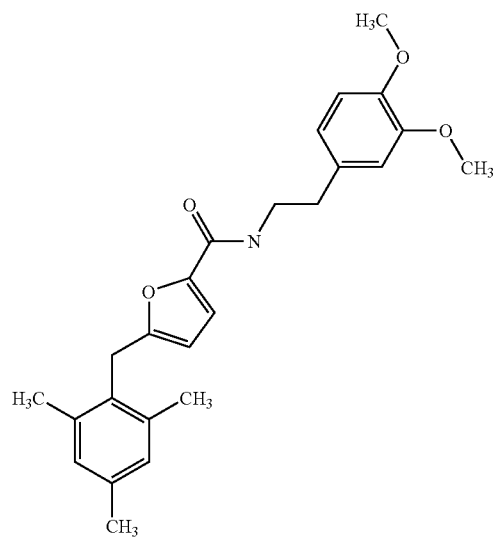 |
| 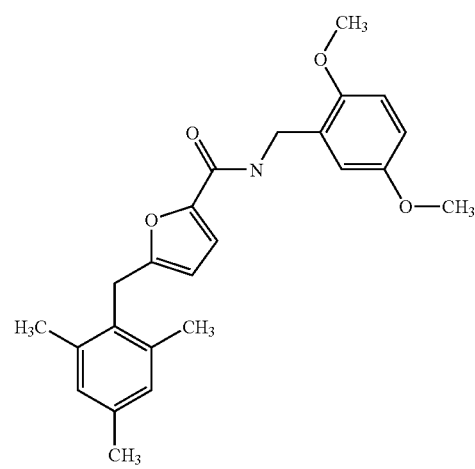 |
| 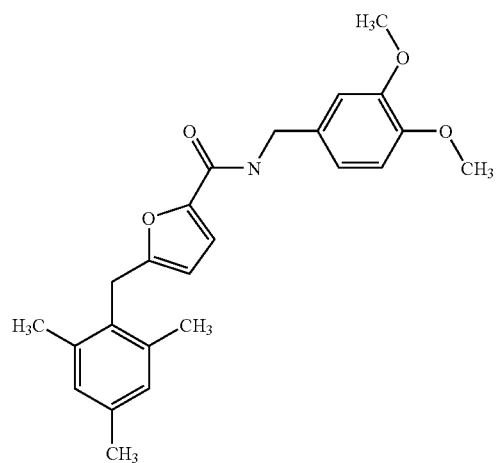 |

| MOLSTRUCTURE |
|---|
| 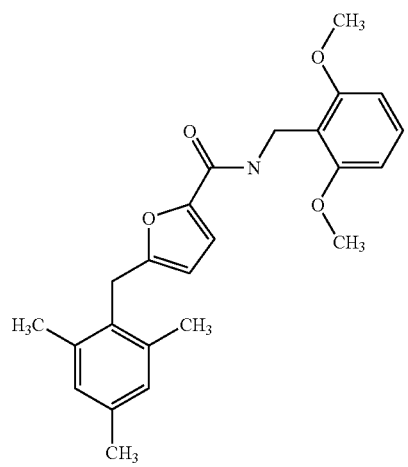 |
| 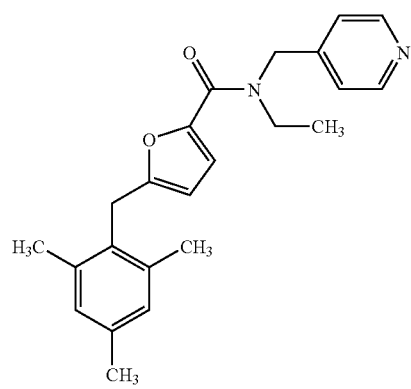 |
| 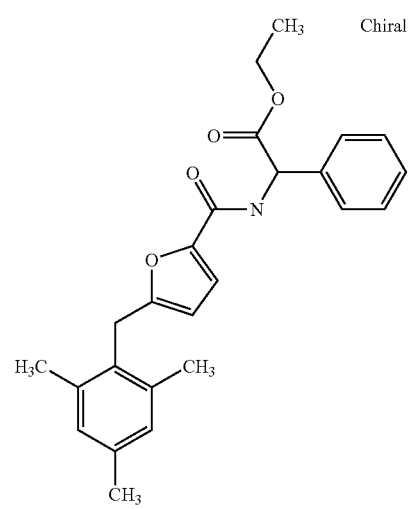 |

-continued
MOLSTRUCTURE
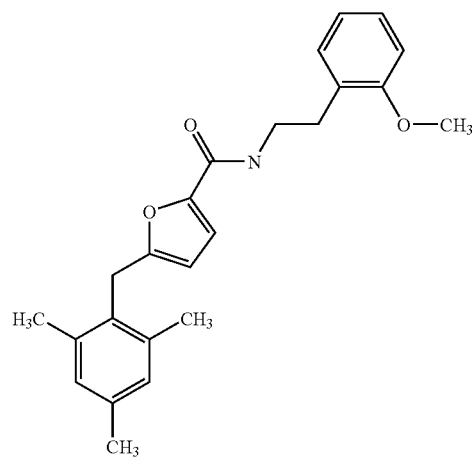
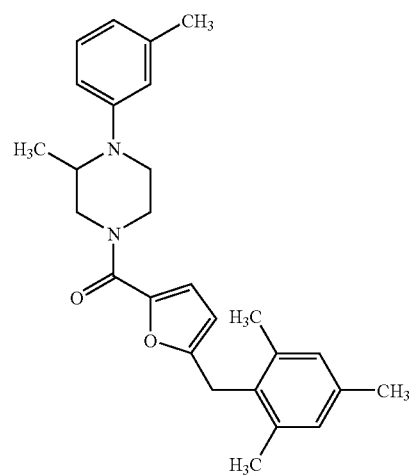
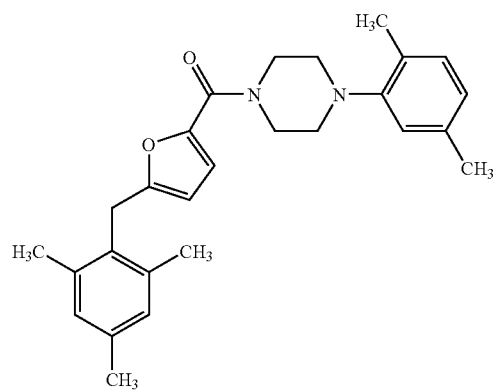

| MOLSTRUCTURE |
|---|
| 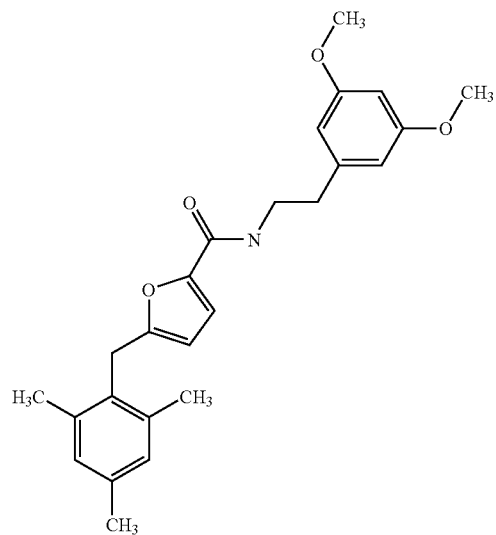 |
| 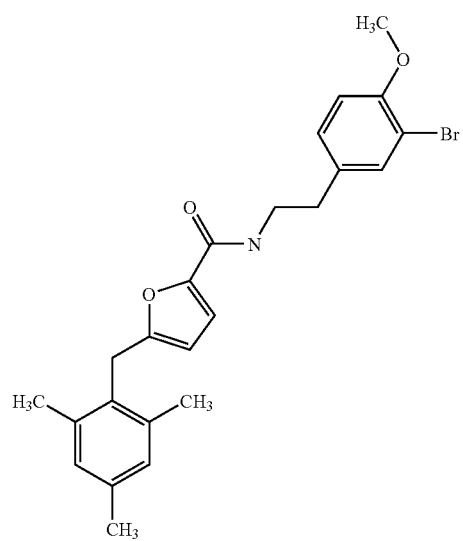 |

-continued
MOLSTRUCTURE
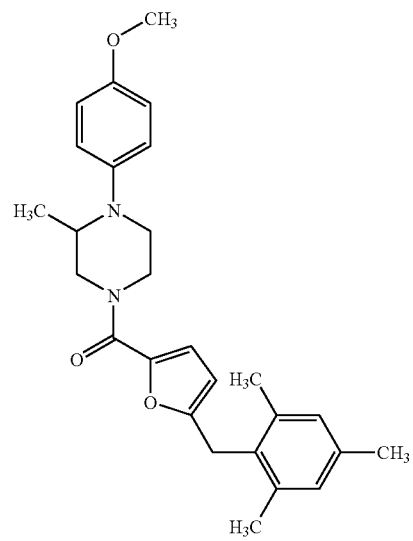
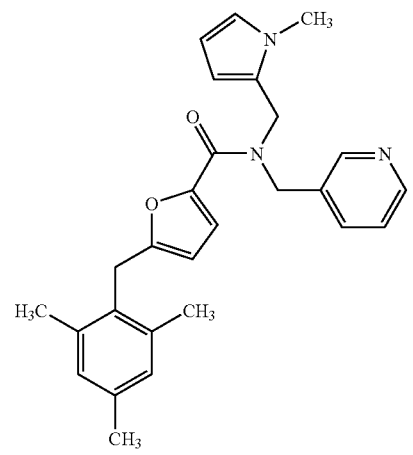
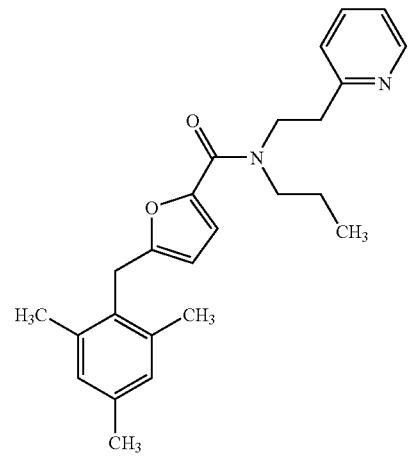

| MOLSTRUCTURE |
|---|
| 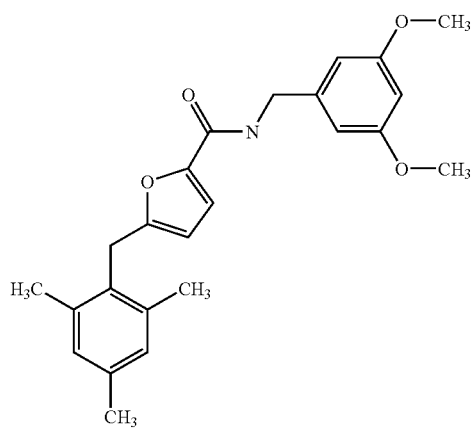 |
| 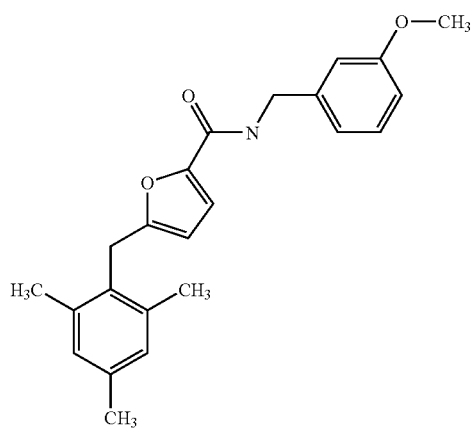 |
| 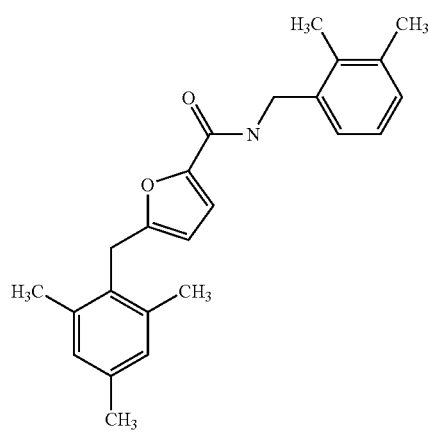 |

-continued
MOLSTRUCTURE
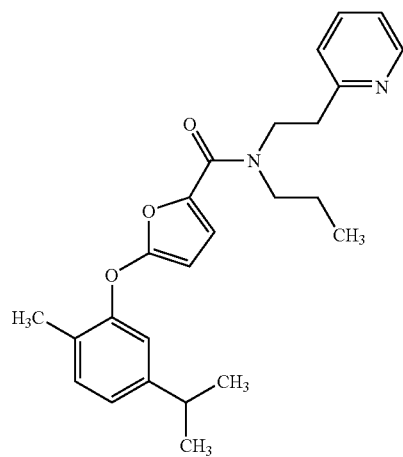
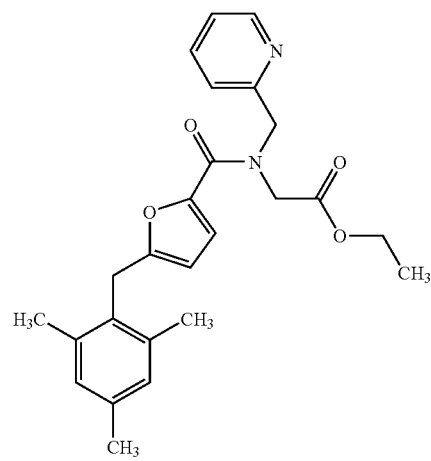
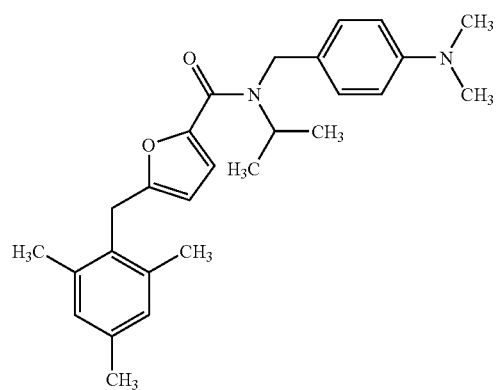

| MOLSTRUCTURE |
|---|
| 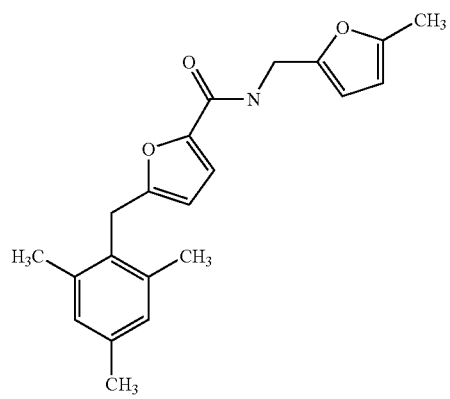 |
| 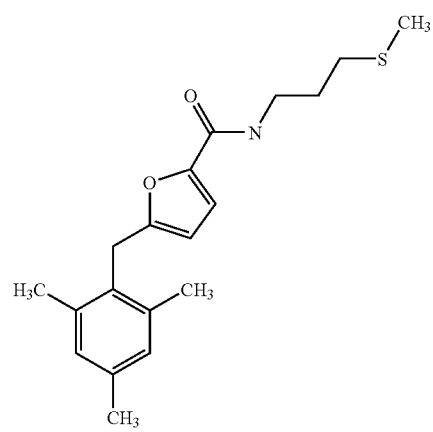 |
| 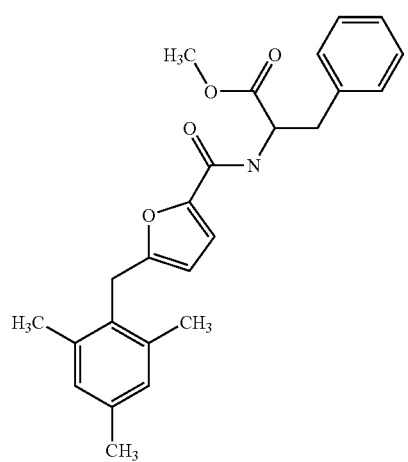 |

| MOLSTRUCTURE |
|---|
| 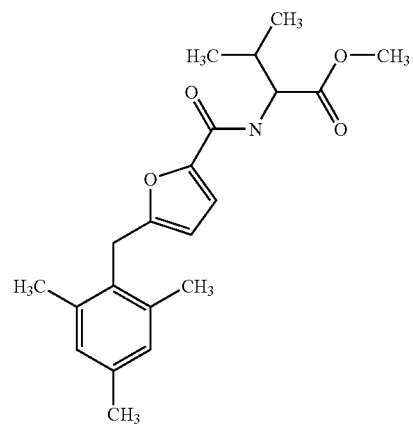 |
| 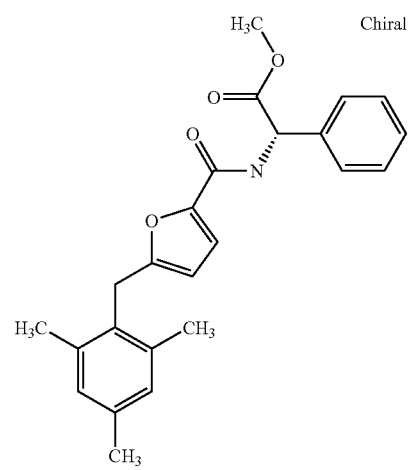 |
| 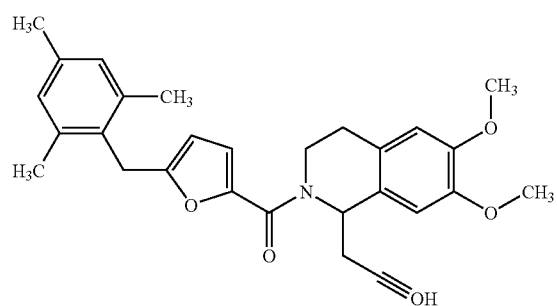 |

| MOLSTRUCTURE |
|---|
| 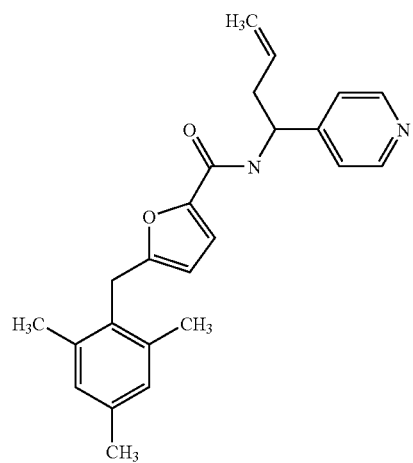 |
| 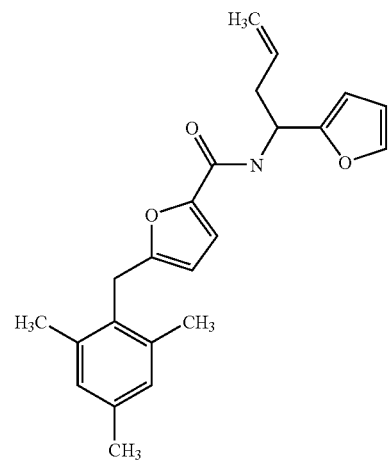 |
| 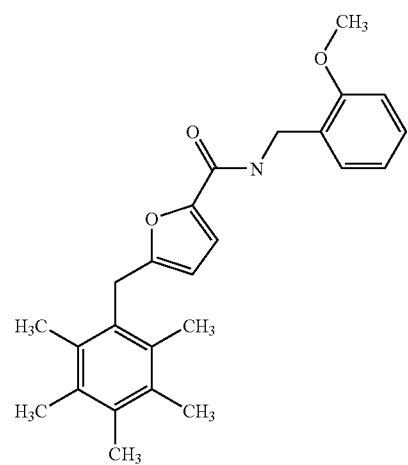 |

| MOLSTRUCTURE |
|---|
| 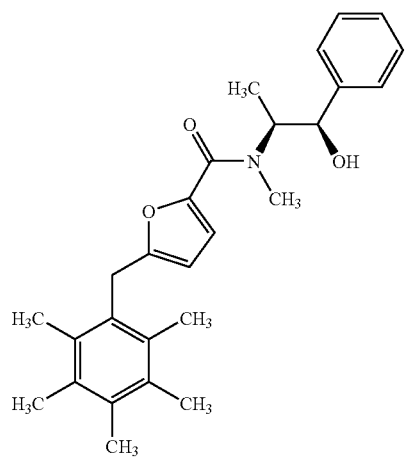 |
| 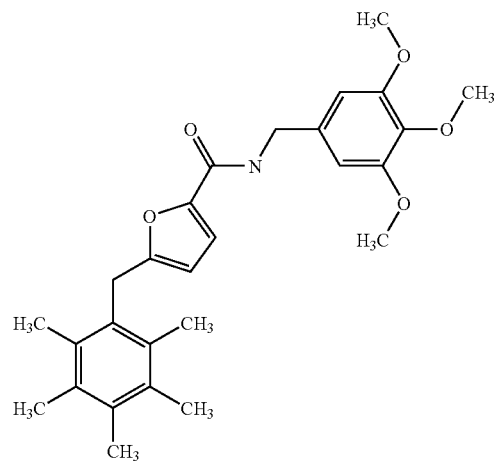 |
| 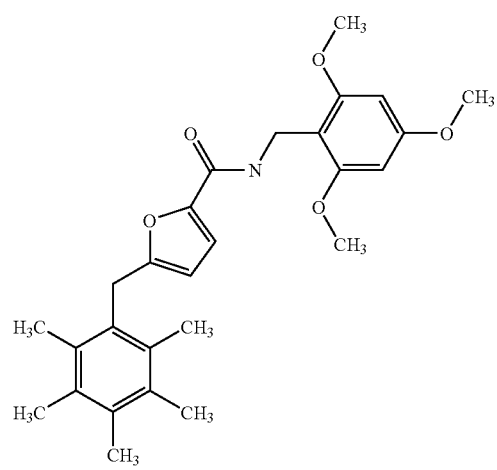 |

-continued
MOLSTRUCTURE
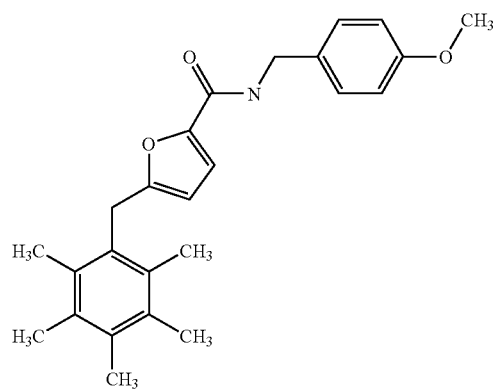
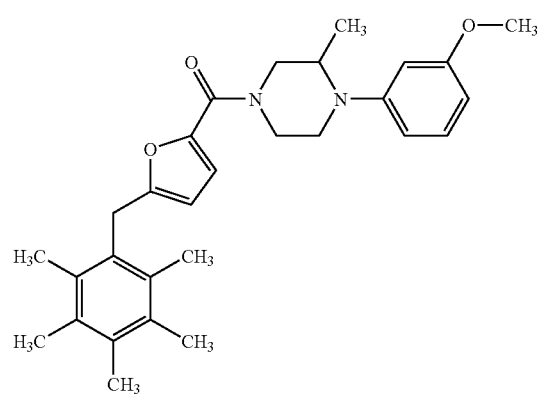
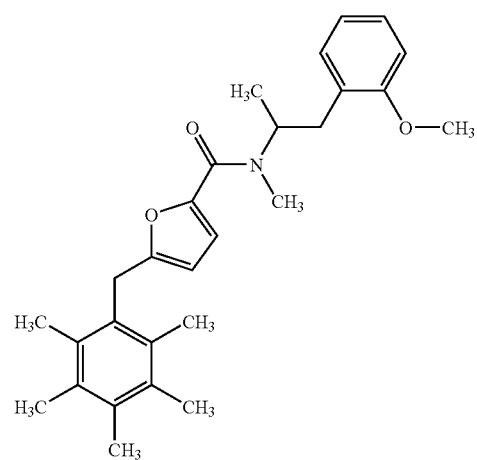

| MOLSTRUCTURE |
|---|
| 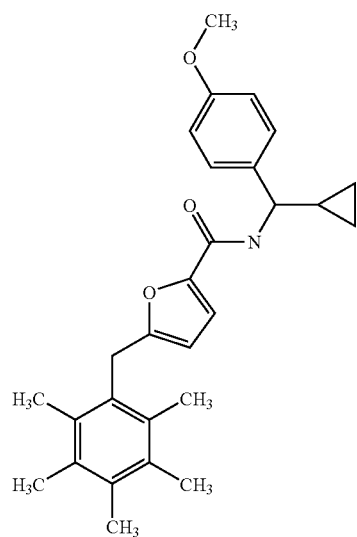 |
| 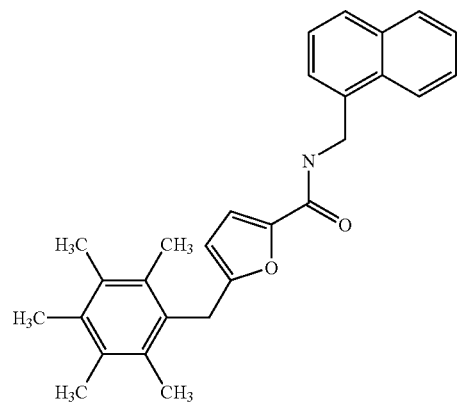 |
| 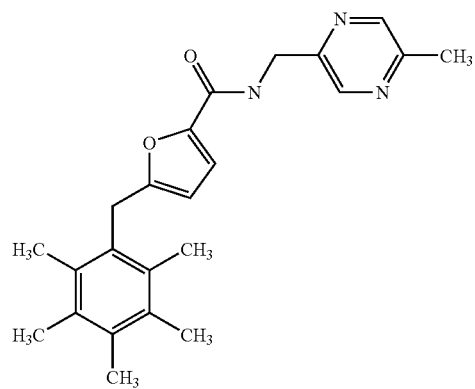 |

| MOLSTRUCTURE |
|---|
| 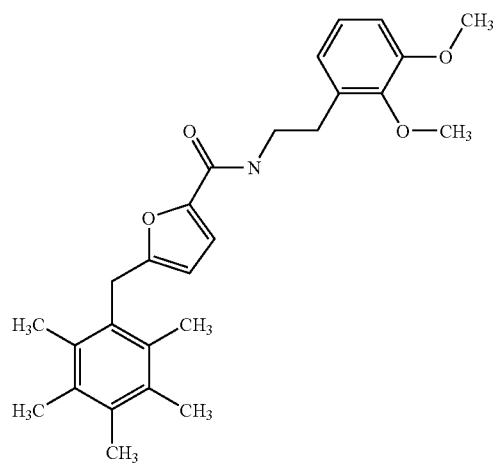 |
| 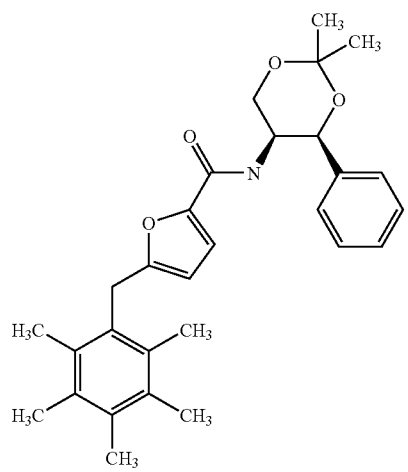 |
| 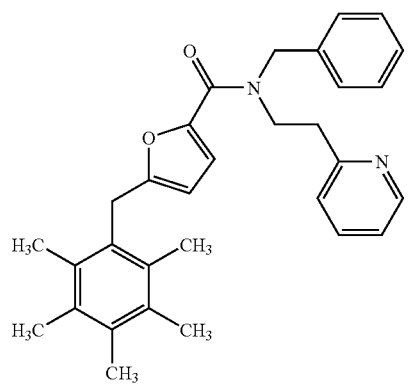 |

-continued
MOLSTRUCTURE
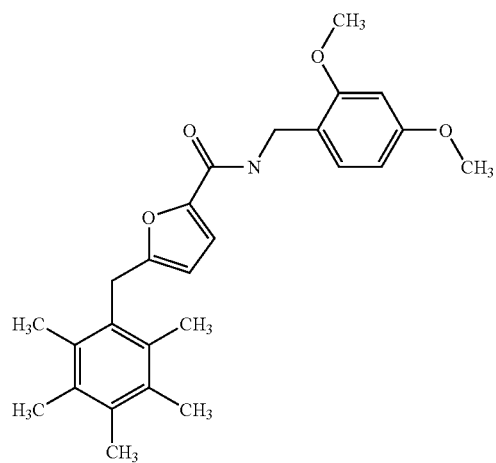
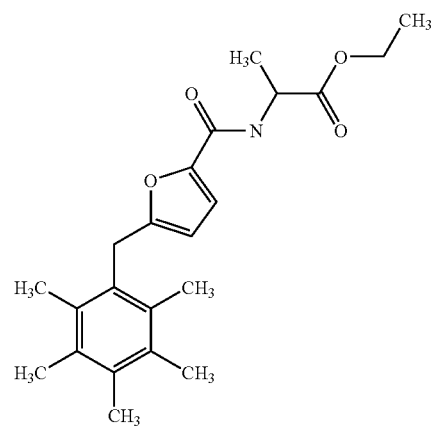
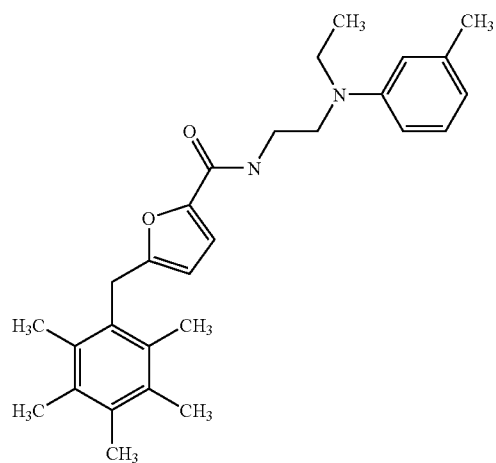

-continued
MOLSTRUCTURE
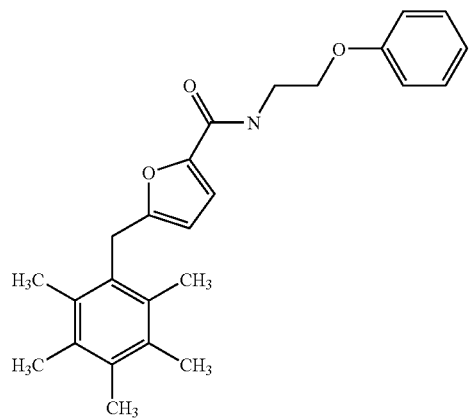
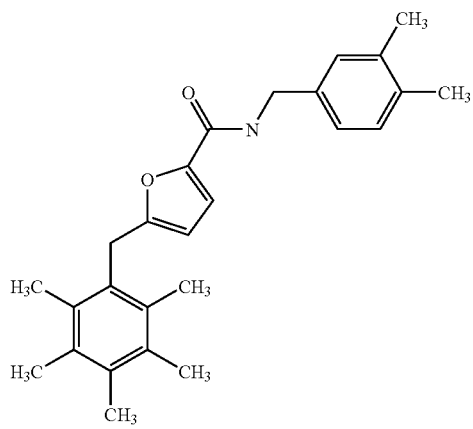
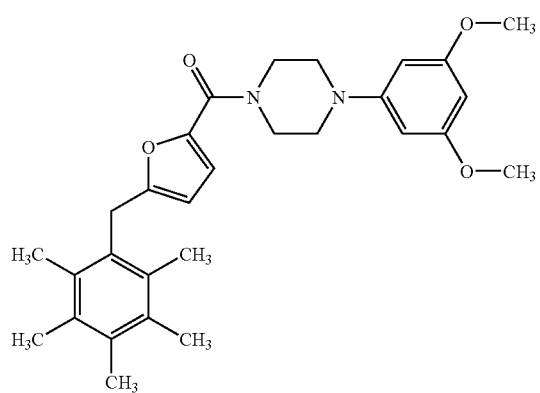

2101 -continued
| MOLSTRUCTURE |
|---|
| 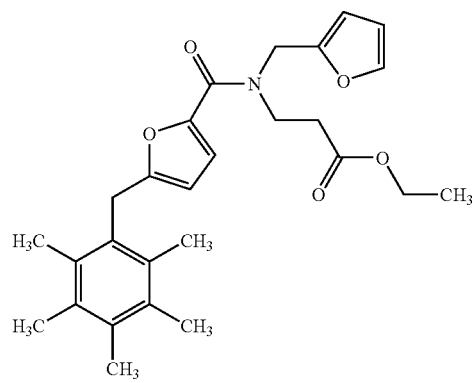 |
| 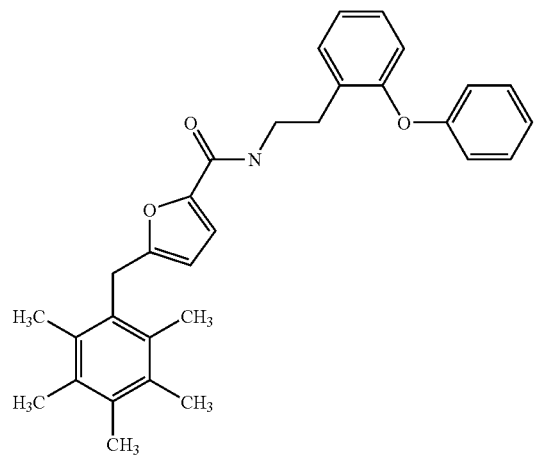 |
| 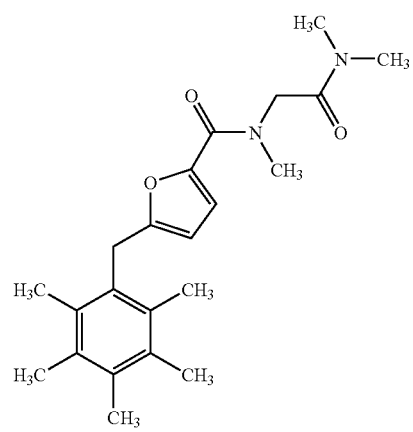 |

| MOLSTRUCTURE |
|---|
| 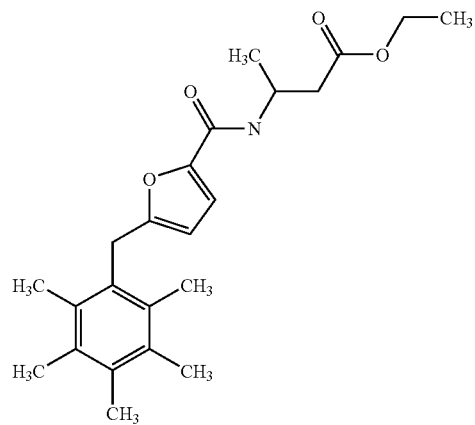 |
| 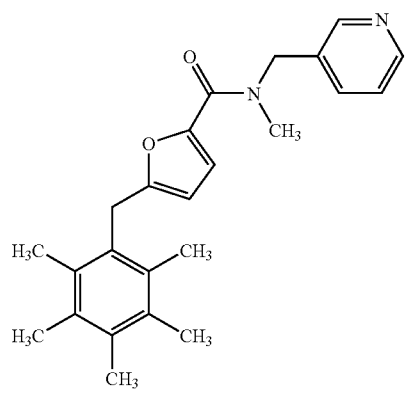 |
| 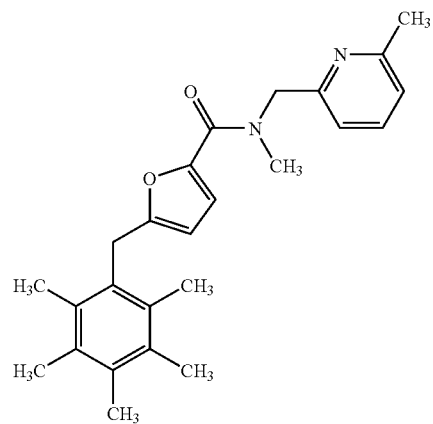 |

| MOLSTRUCTURE |
|---|
| 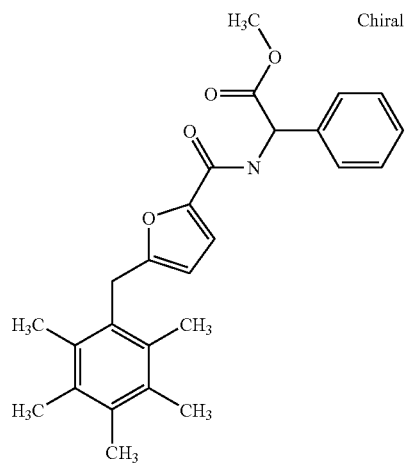 |
| 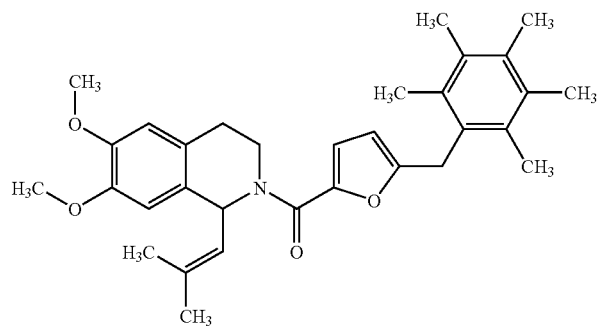 |
| 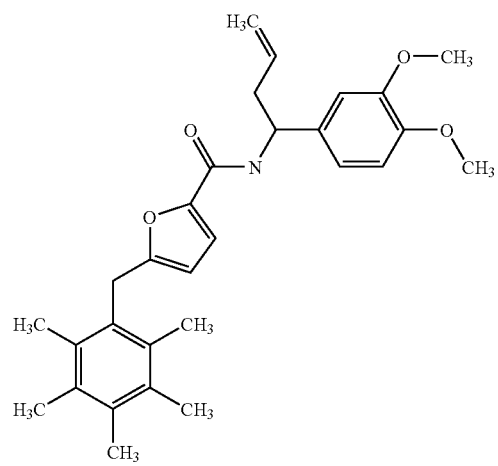 |

-continued
MOLSTRUCTURE
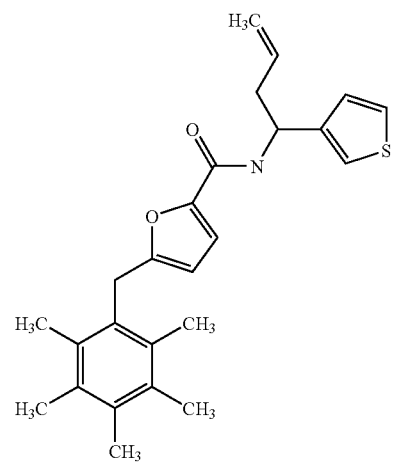
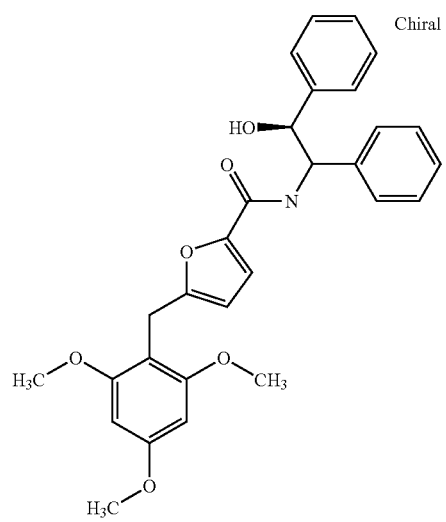
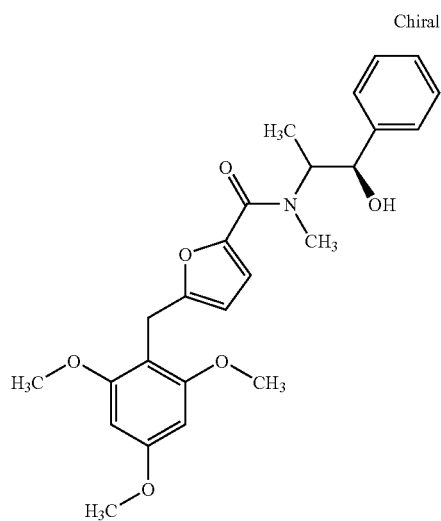

| MOLSTRUCTURE |
|---|
| 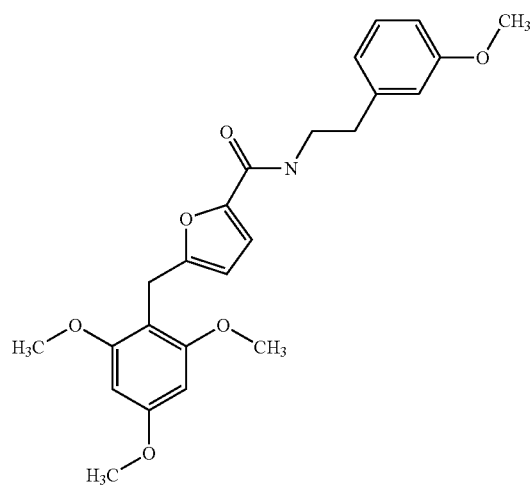 |
| 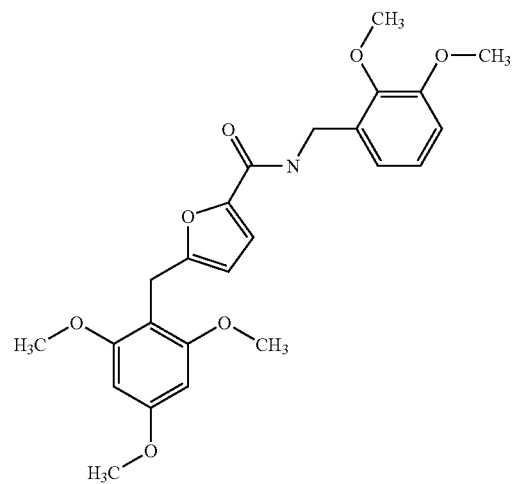 |
| 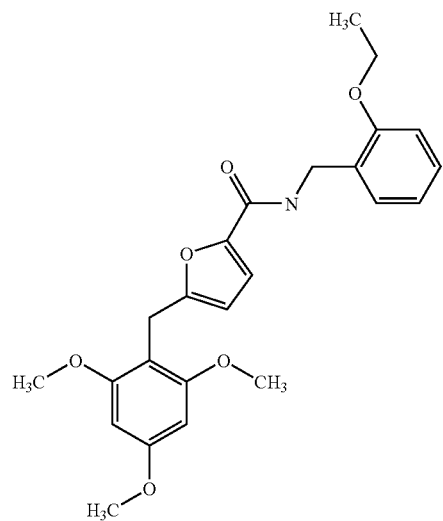 |

| MOLSTRUCTURE |
|---|
| 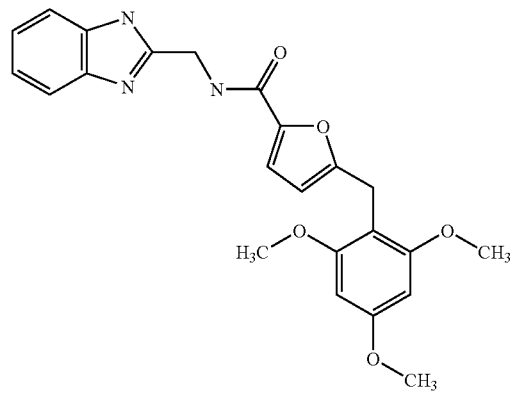 |
| 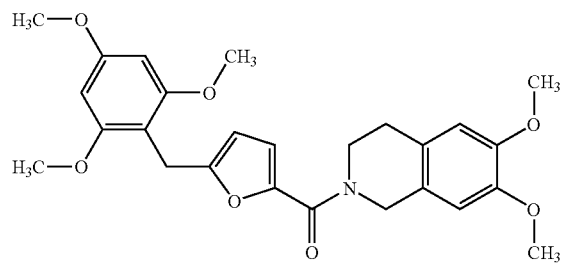 |
| 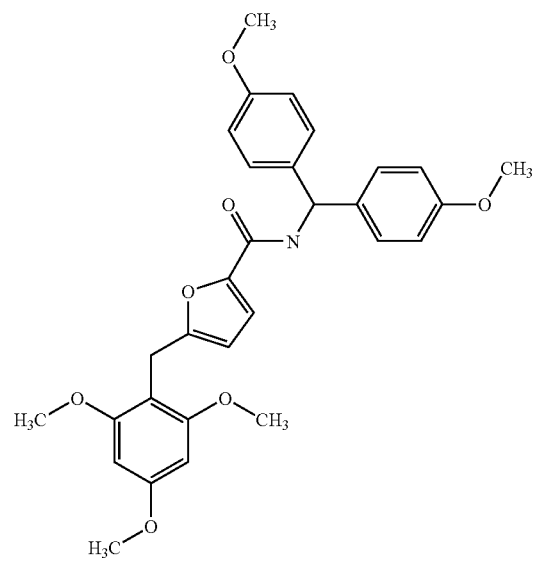 |

| MOLSTRUCTURE |
|---|
| 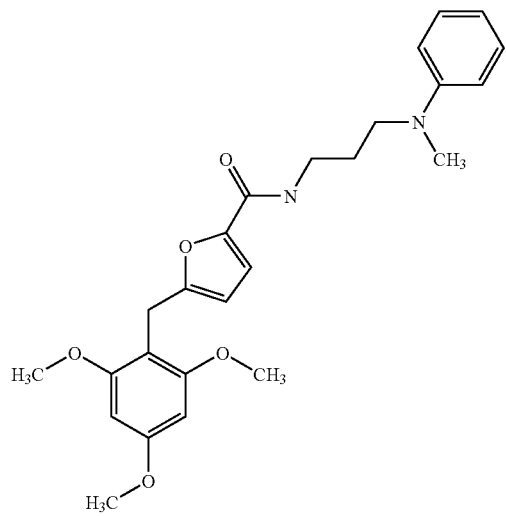 |
| 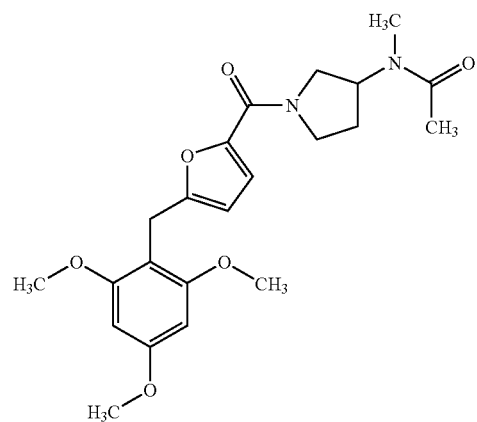 |
| 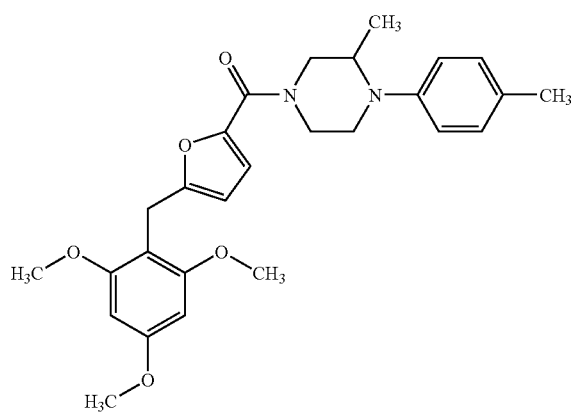 |

-continued
MOLSTRUCTURE
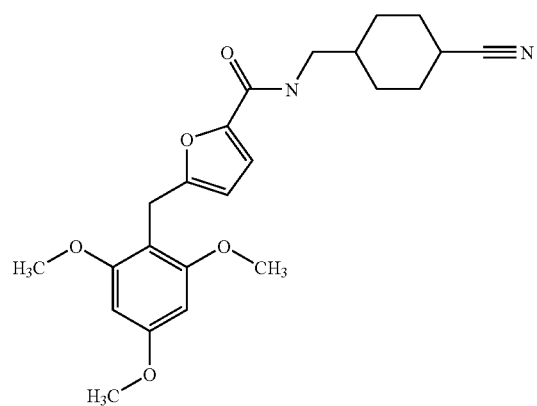
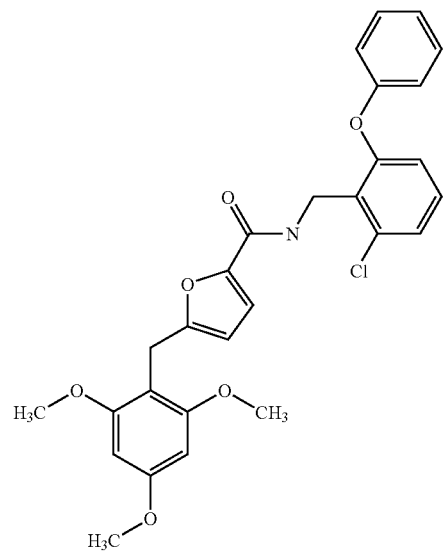
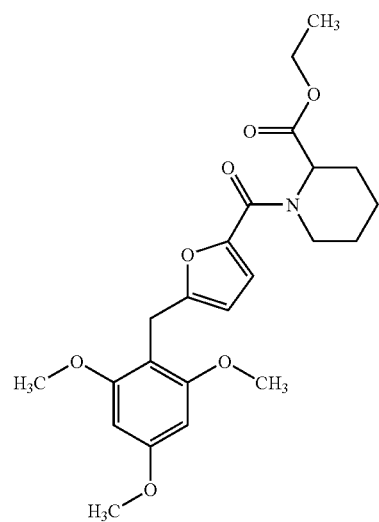

| MOLSTRUCTURE |
|---|
| 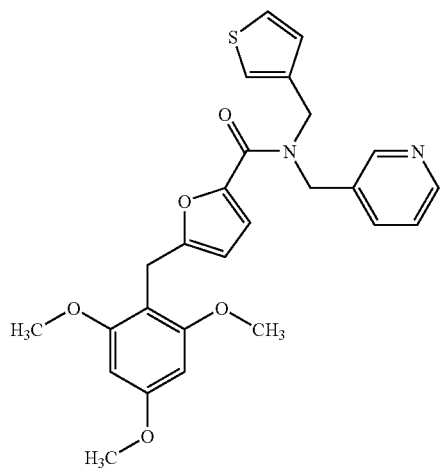 |
| 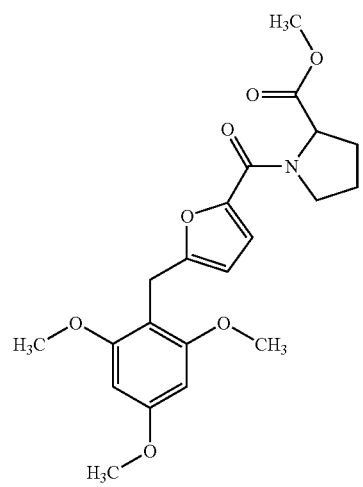 |
| 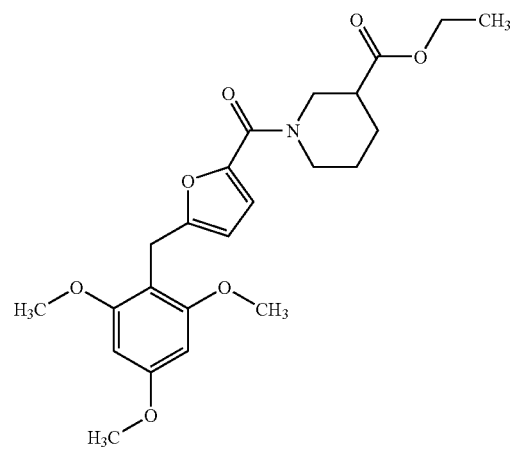 |

-continued
MOLSTRUCTURE
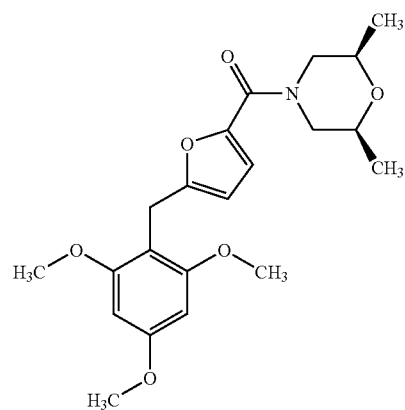
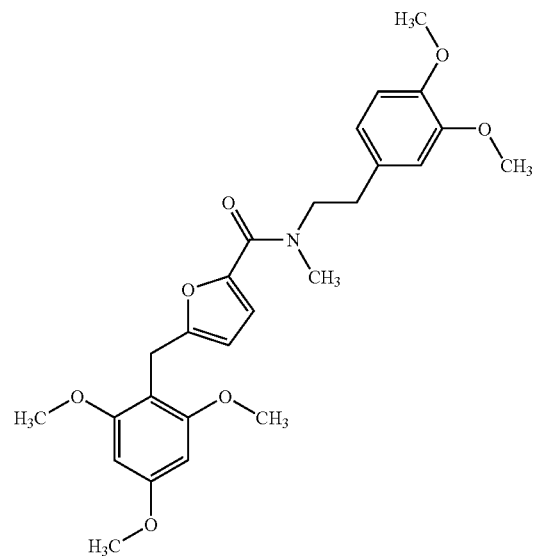
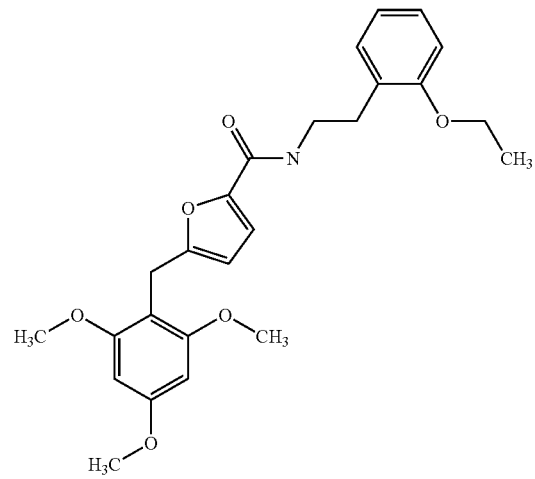

| MOLSTRUCTURE |
|---|
| 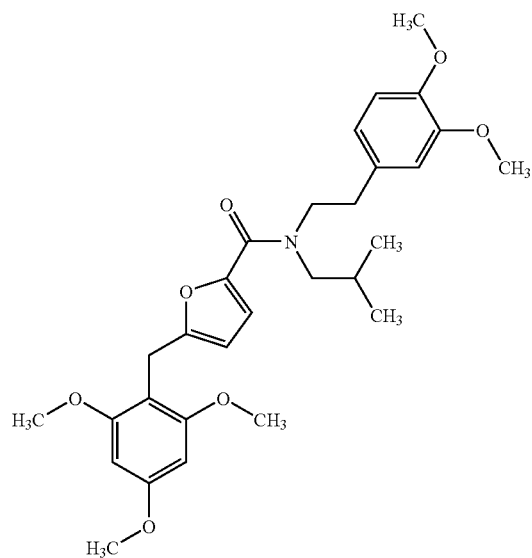 |
| 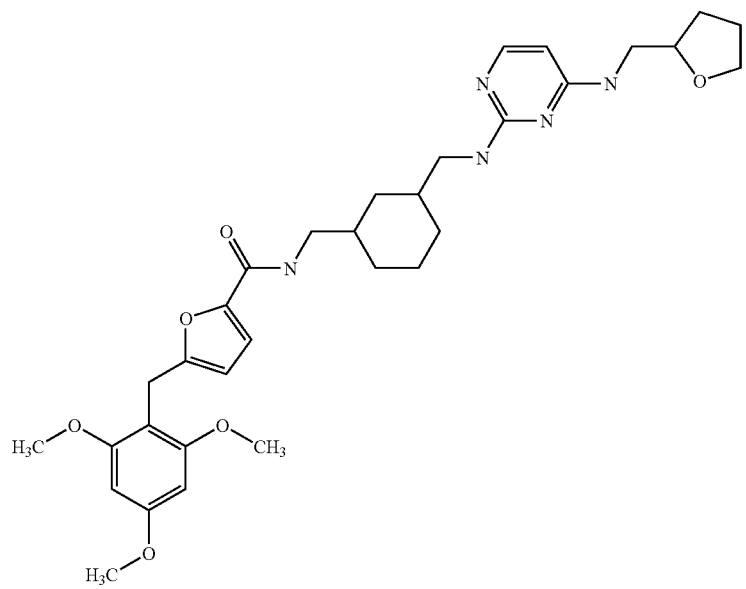 |

| MOLSTRUCTURE |
|---|
| 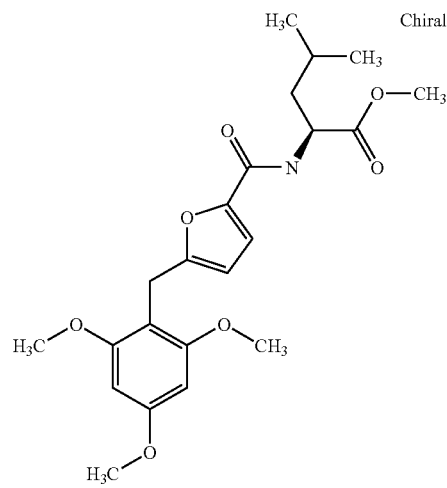 |
| 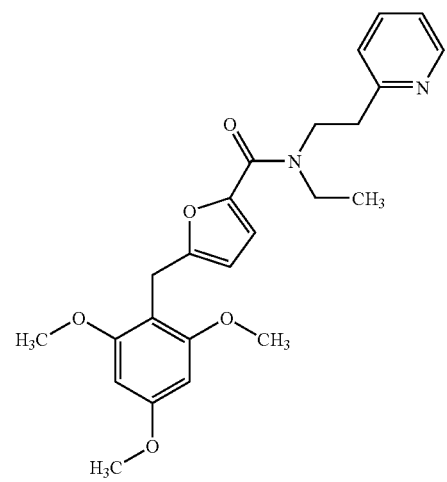 |
| 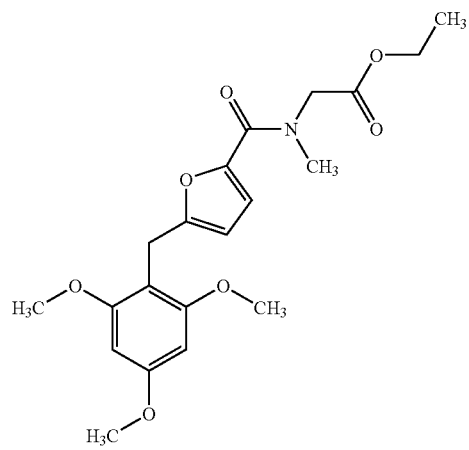 |

| MOLSTRUCTURE |
|---|
| 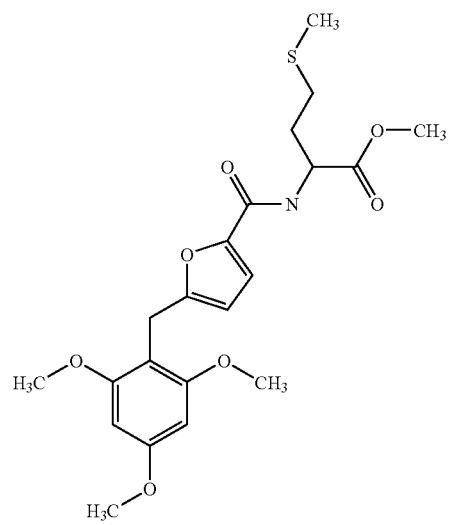 |
| 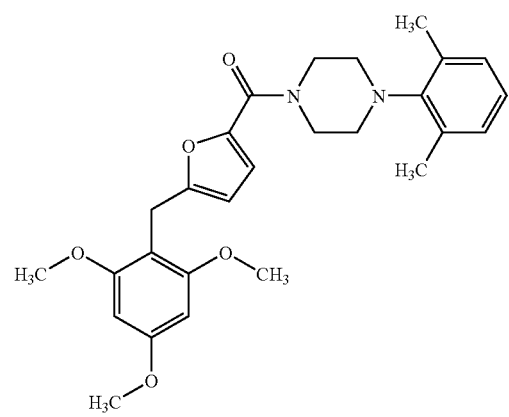 |
| 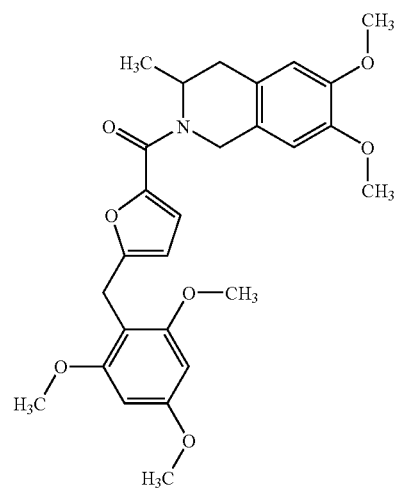 |

-continued
| MOLSTRUCTURE |
|---|
| 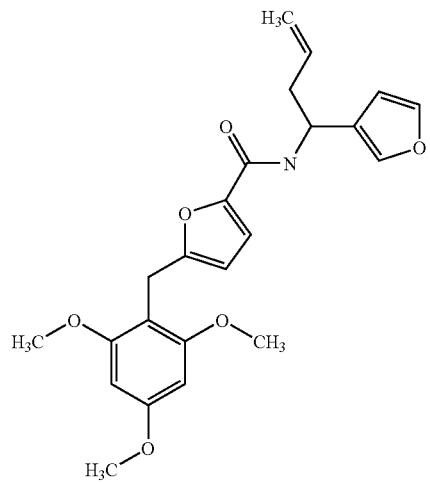 |
| 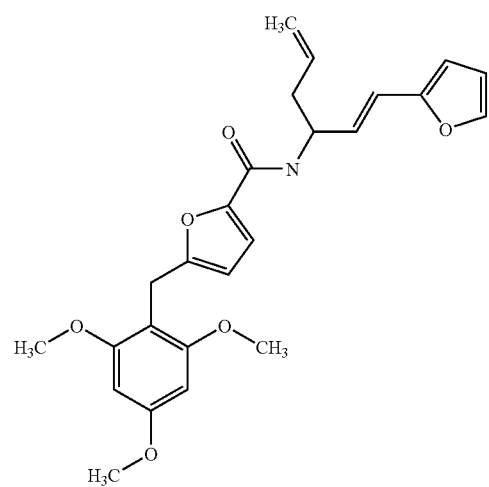 |
| 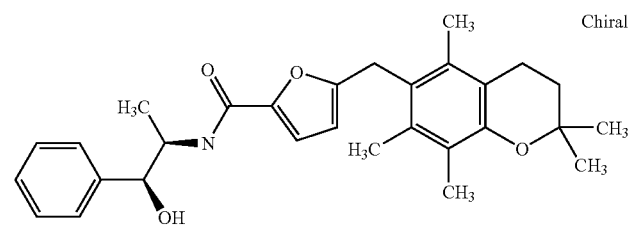 |
| 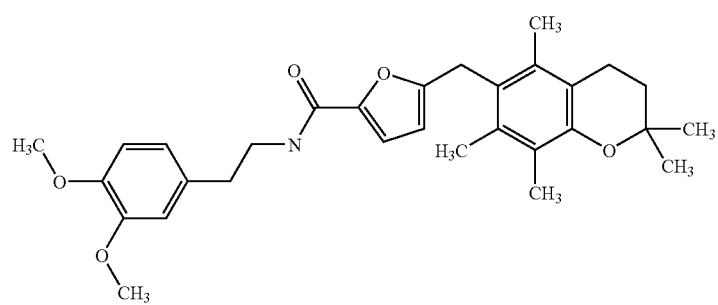 |

| MOLSTRUCTURE |
|---|
| 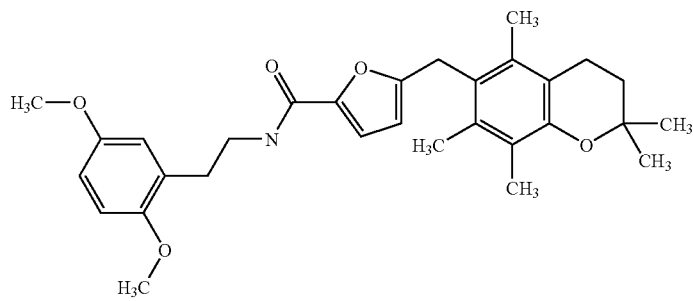 |
| 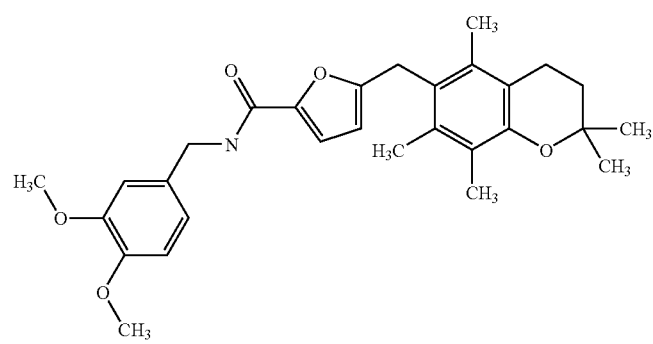 |
| 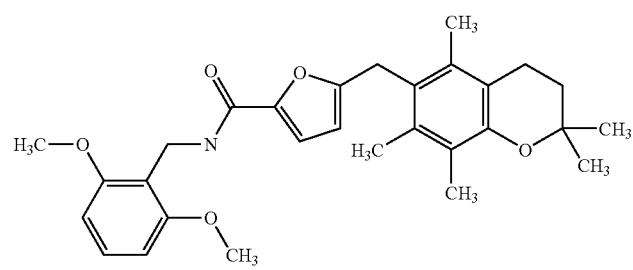 |
| 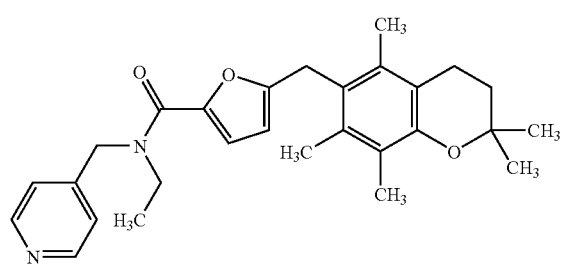 |
| 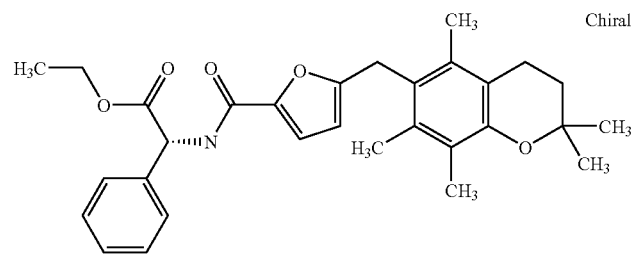 |

-continued
MOLSTRUCTURE
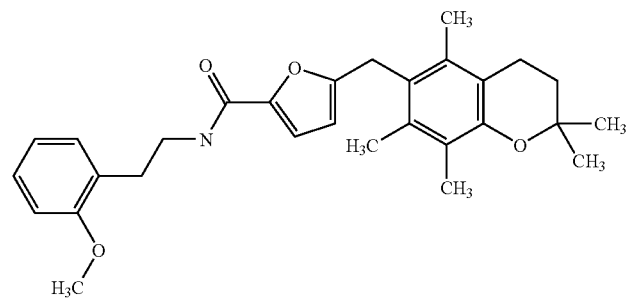
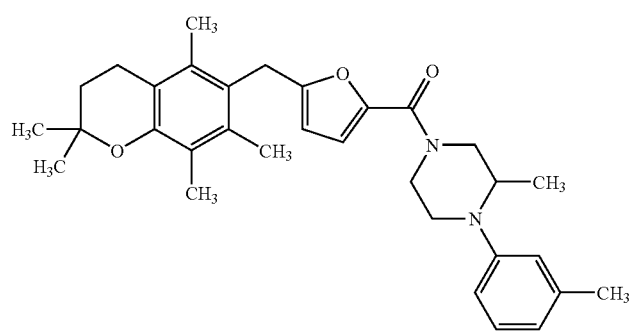
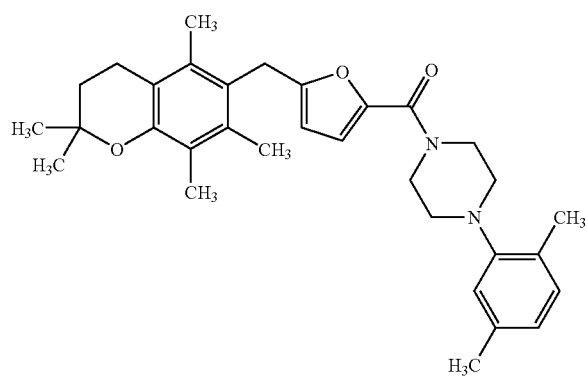
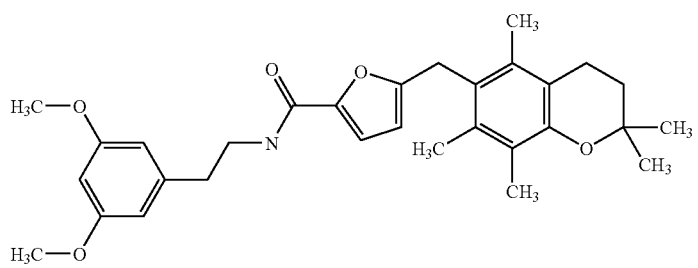
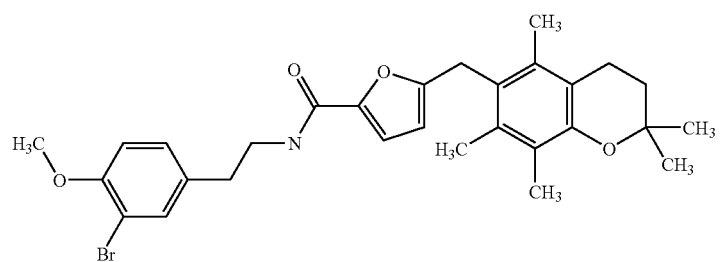

-continued
MOLSTRUCTURE
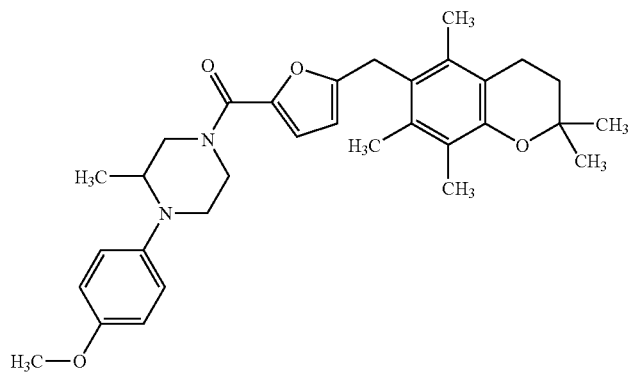
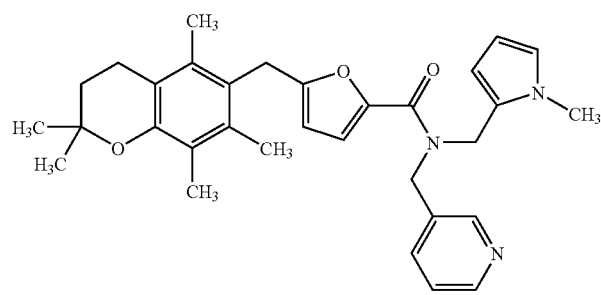
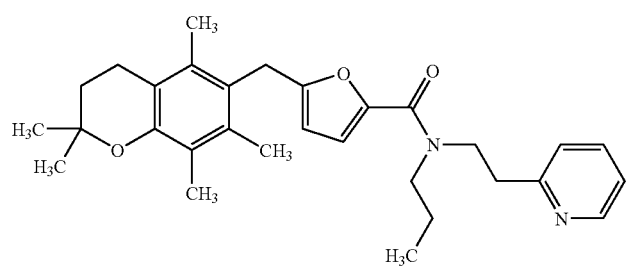
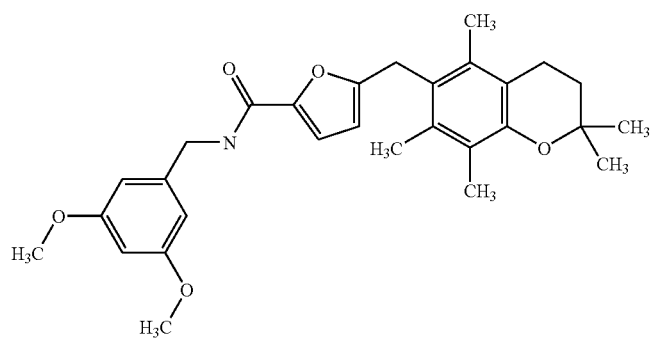
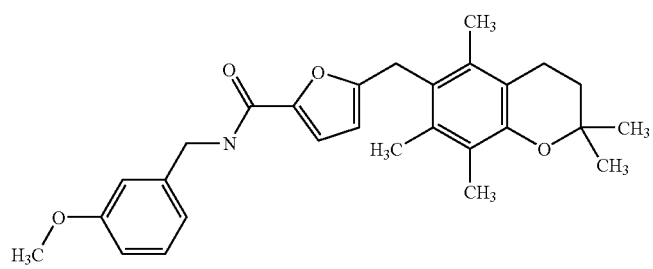

-continued
| MOLSTRUCTURE |
| --- |
| 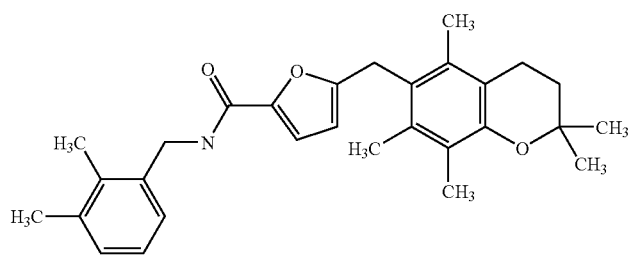 |
| 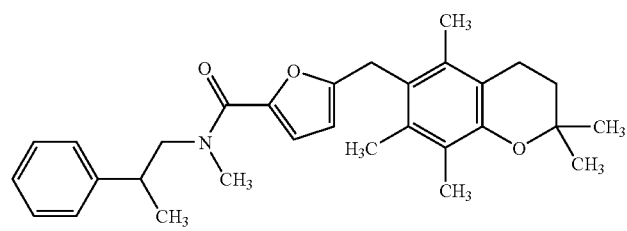 |
| 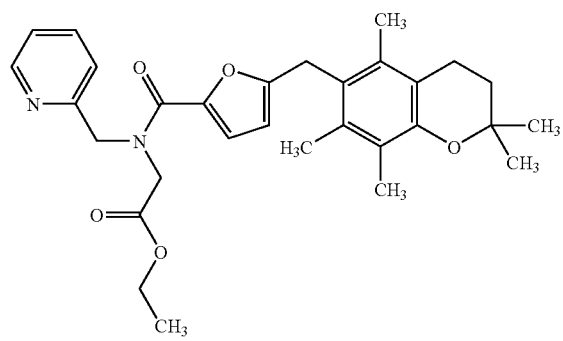 |
| 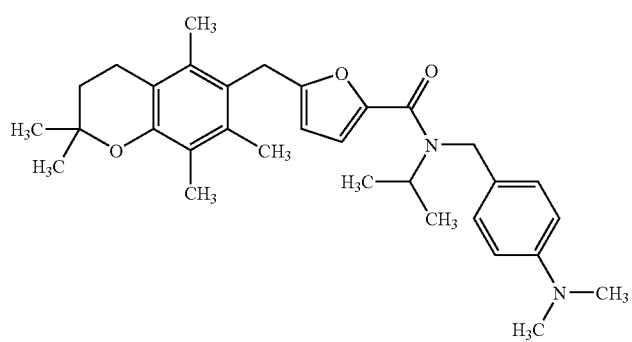 |
| 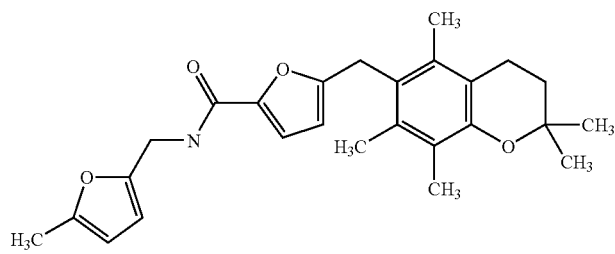 |

-continued
| MOLSTRUCTURE |
|---|
| 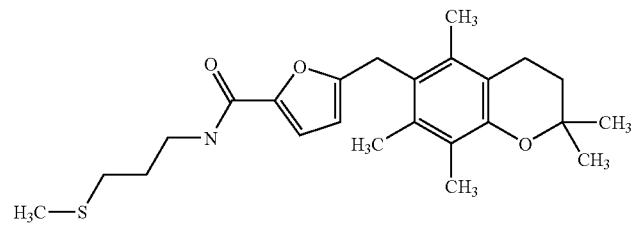 |
| 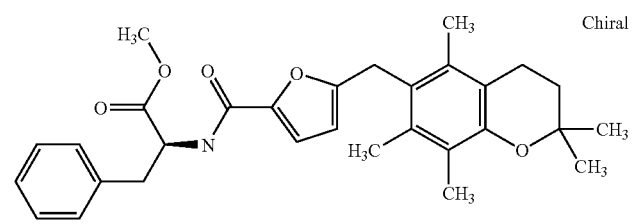 Chiral |
| 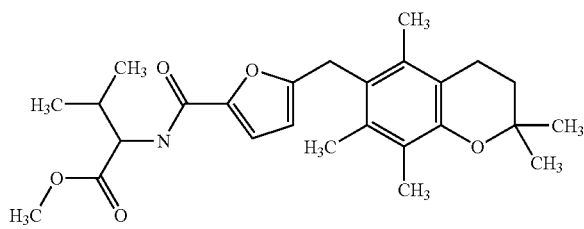 |
| 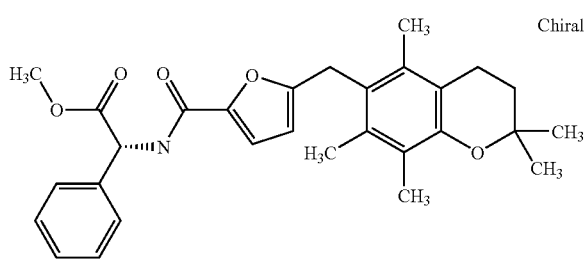 Chiral |
| 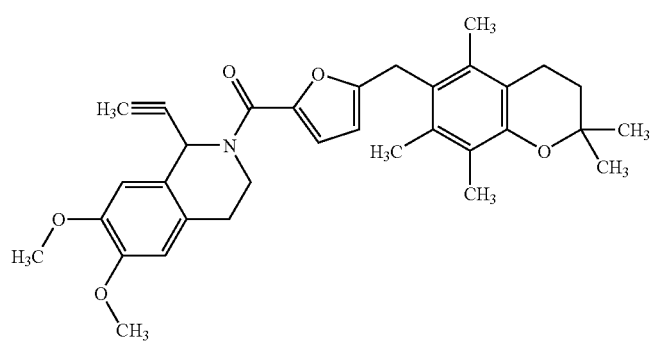 |
| 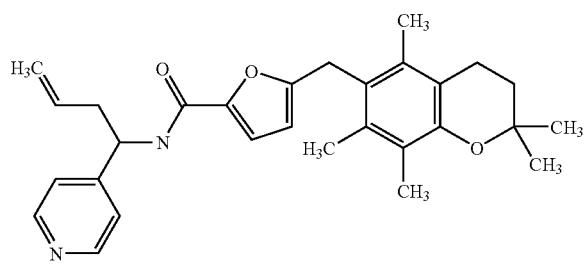 |

-continued
MOLSTRUCTURE
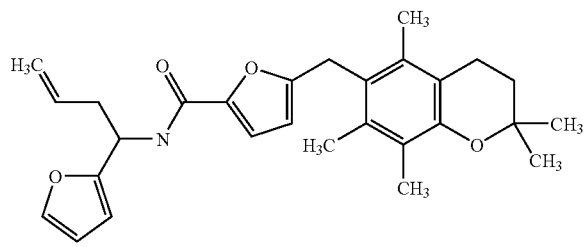
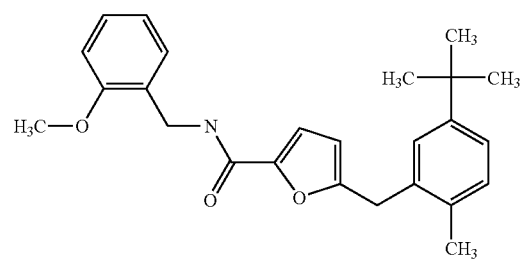
Chiral
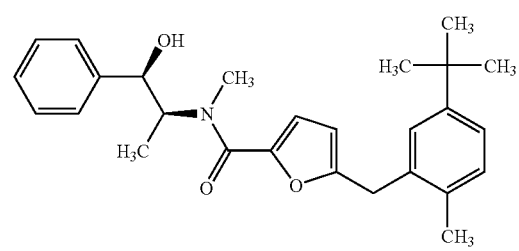
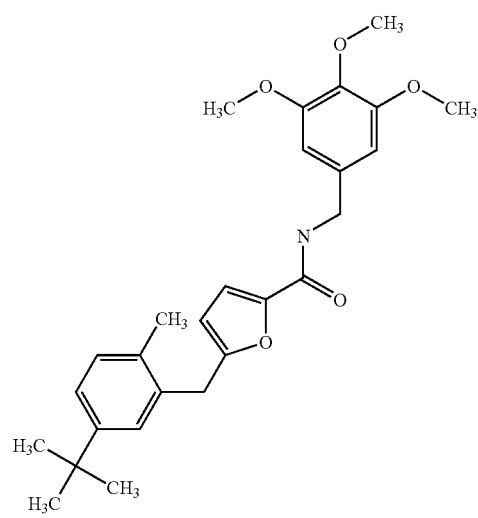

| MOLSTRUCTURE |
| --- |
| 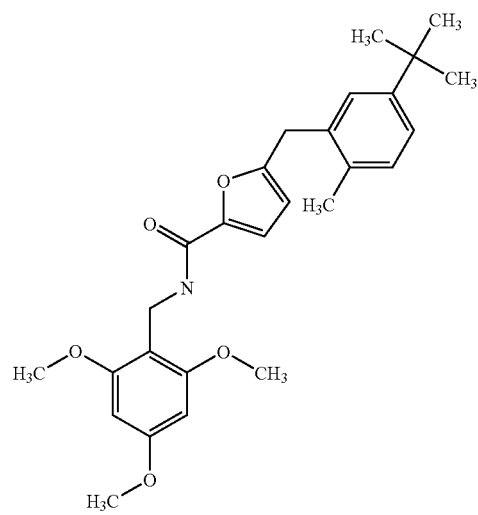 |
| 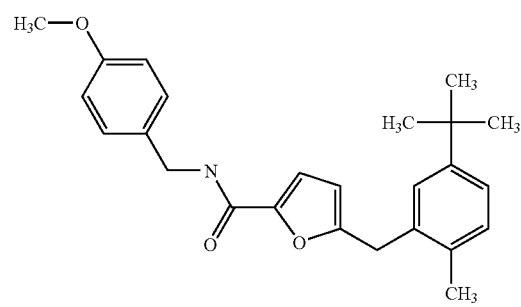 |
| 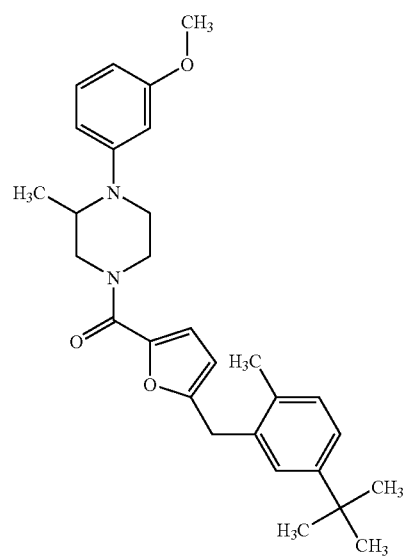 |

-continued
MOLSTRUCTURE
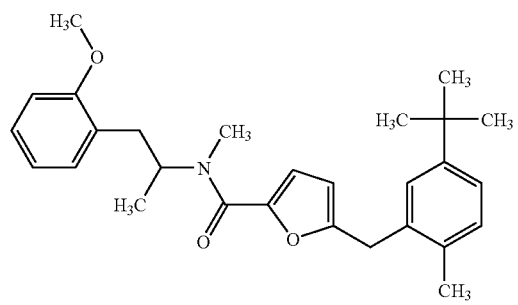
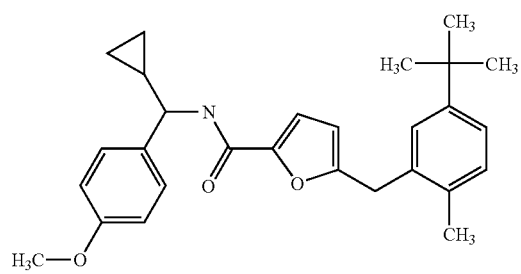
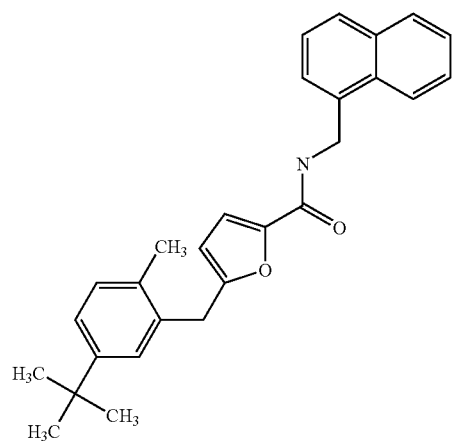
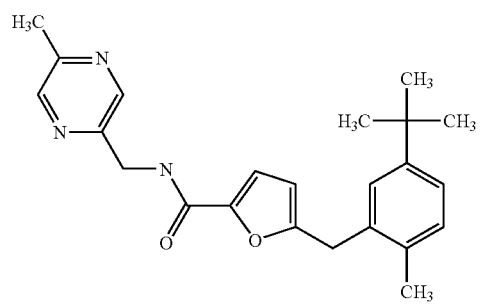

-continued
| MOLSTRUCTURE |
|---|
| 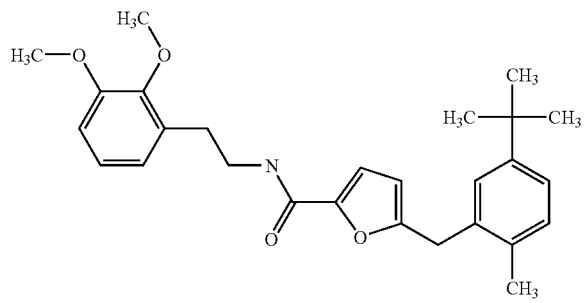 |
| 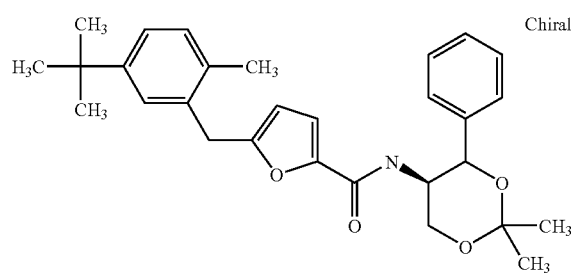 |
| 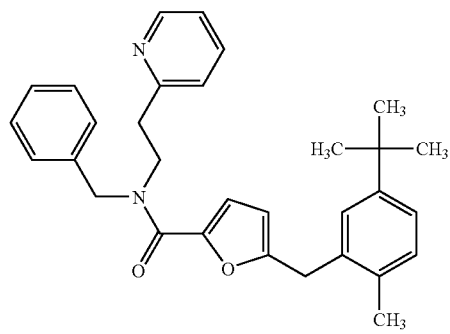 |
| 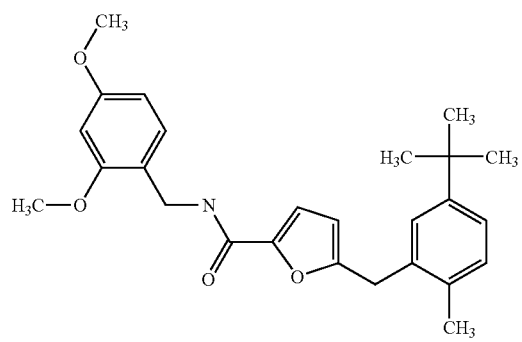 |
| 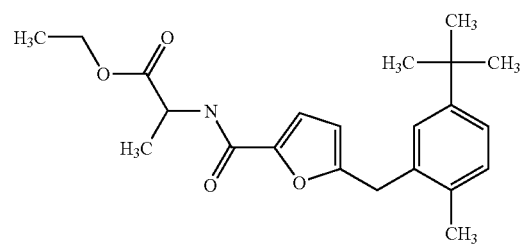 |

-continued
| MOLSTRUCTURE |
|---|
| 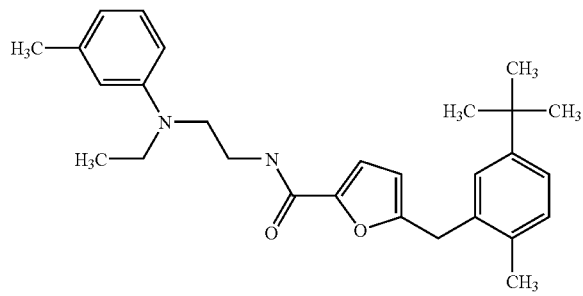 |
| 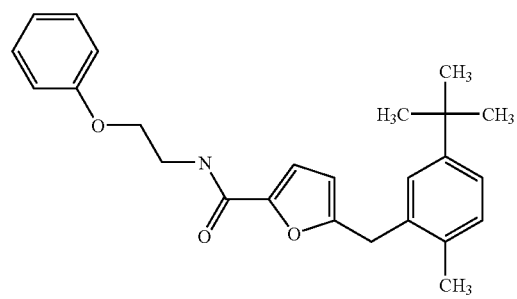 |
| 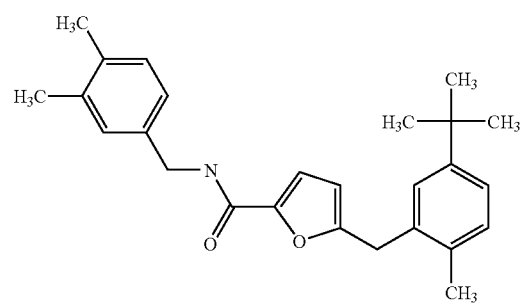 |
| 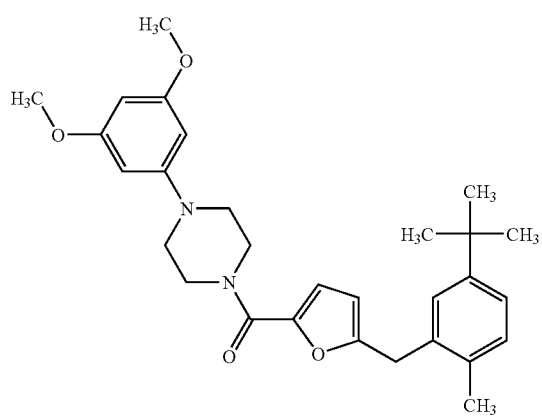 |

-continued
MOLSTRUCTURE
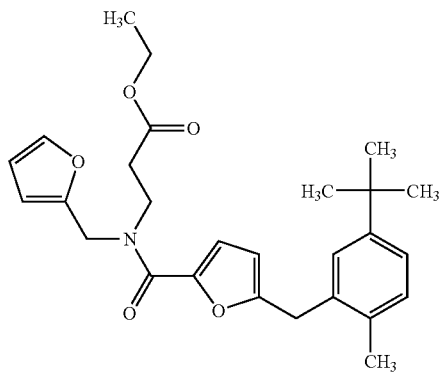
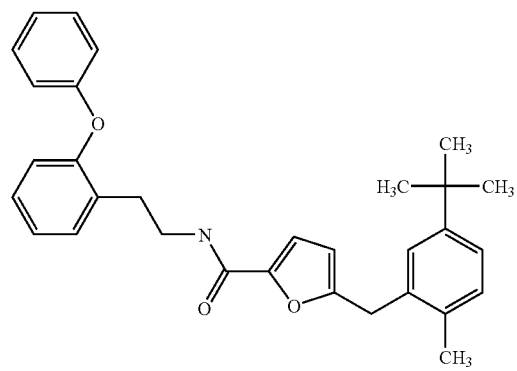
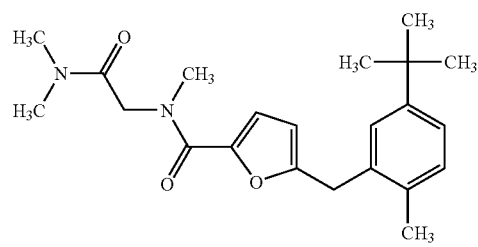
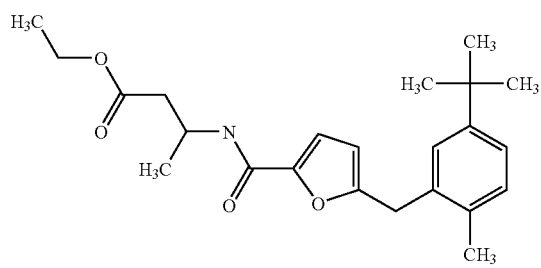
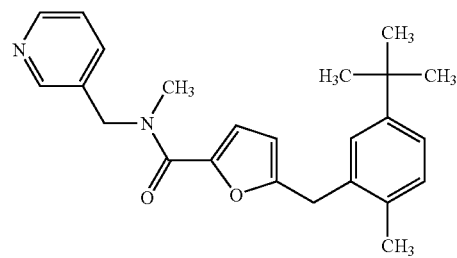

| MOLSTRUCTURE |
|---|
| 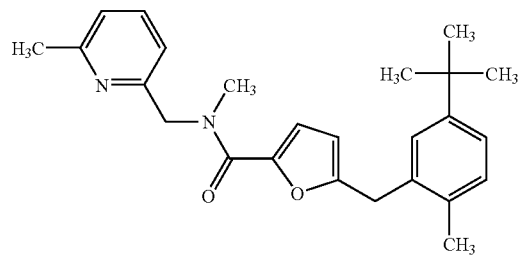 |
| 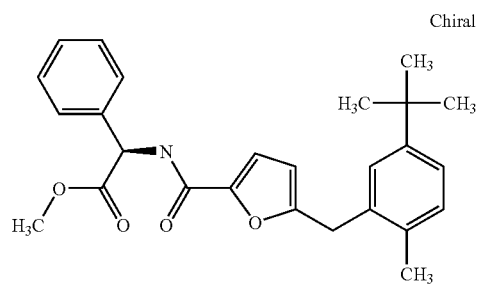 |
| 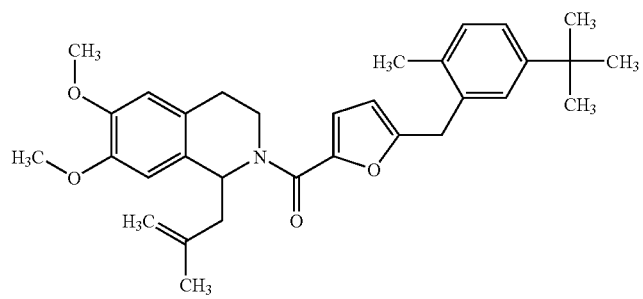 |
| 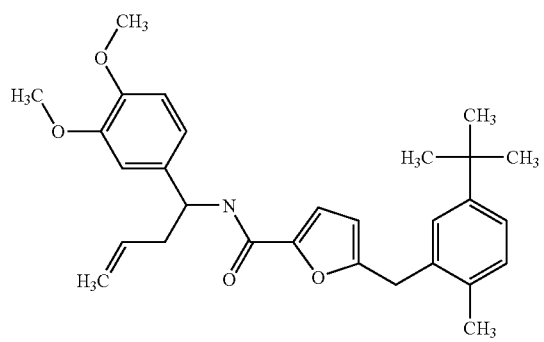 |
| 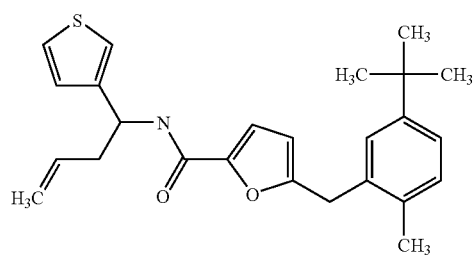 |

-continued
MOLSTRUCTURE
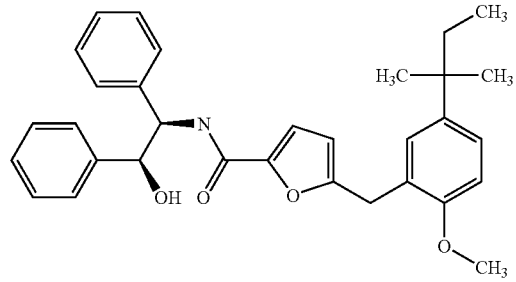
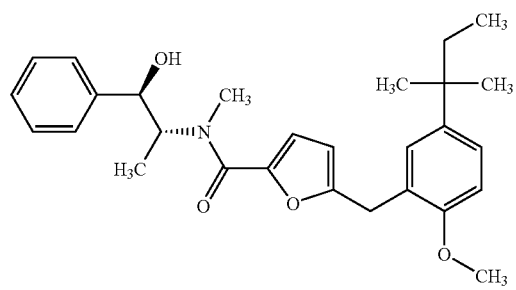
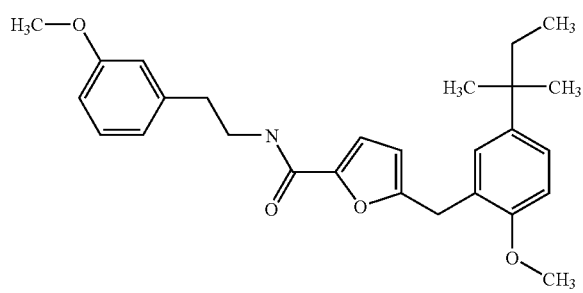
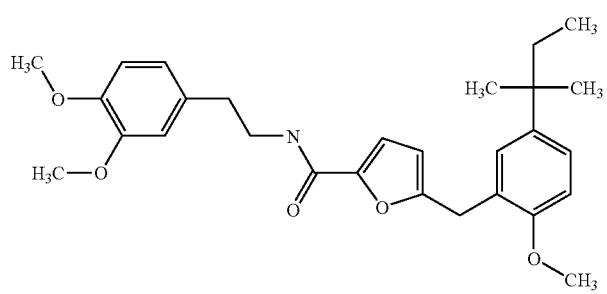
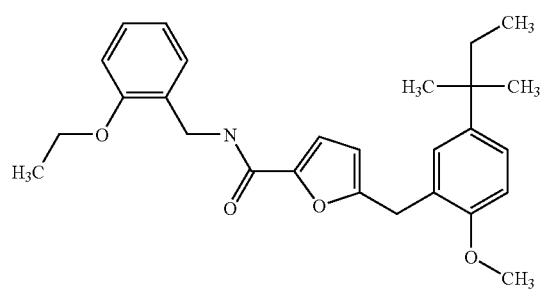

-continued
MOLSTRUCTURE
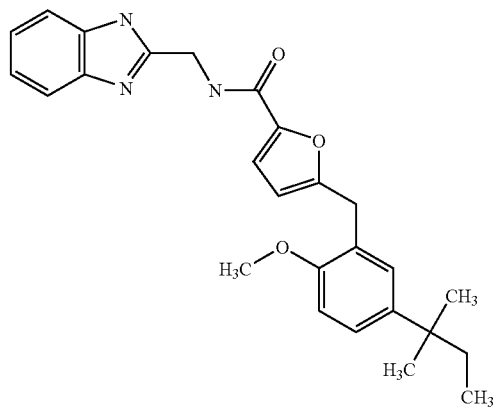
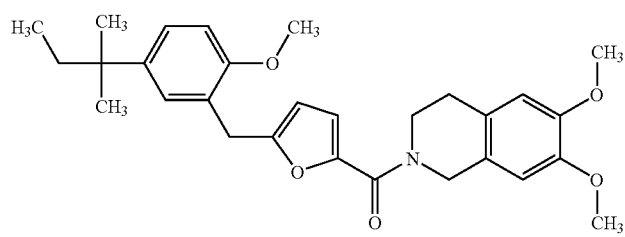
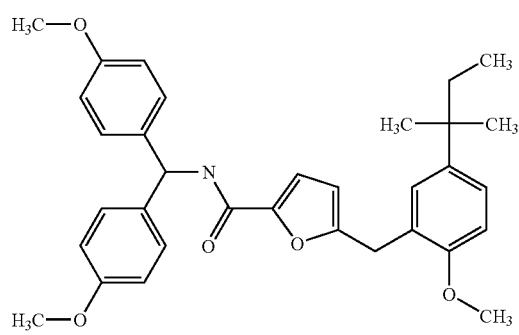
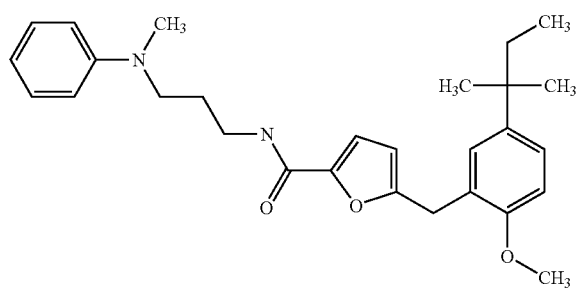
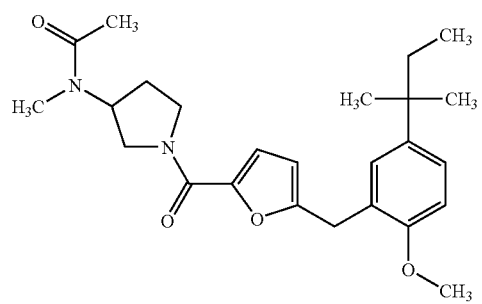

| MOLSTRUCTURE |
|---|
| 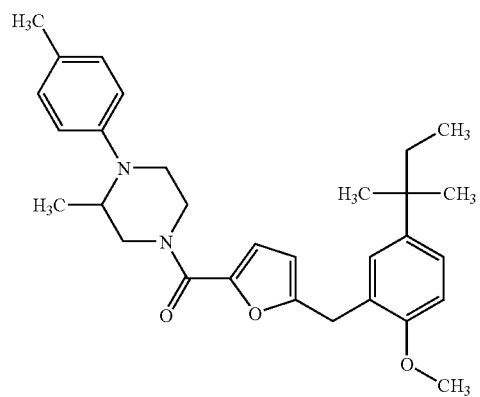 |
| 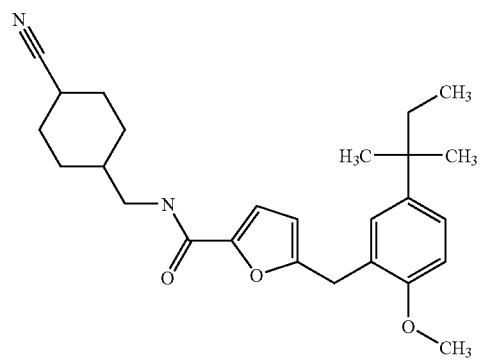 |
| 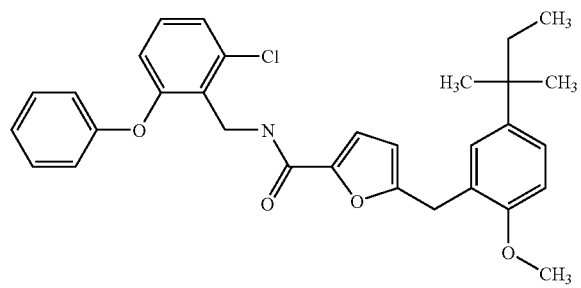 |
| 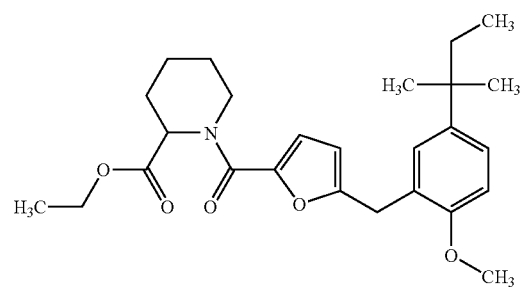 |

-continued
| MOLSTRUCTURE |
|---|
| 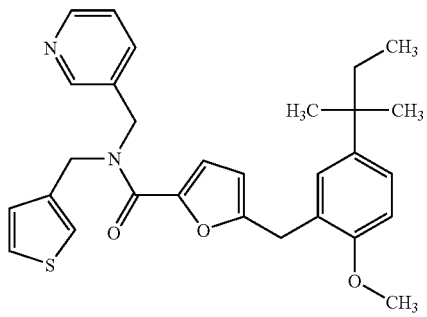 |
| 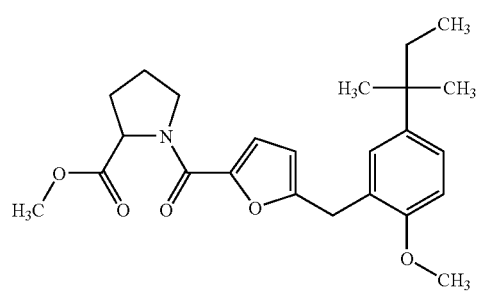 |
| 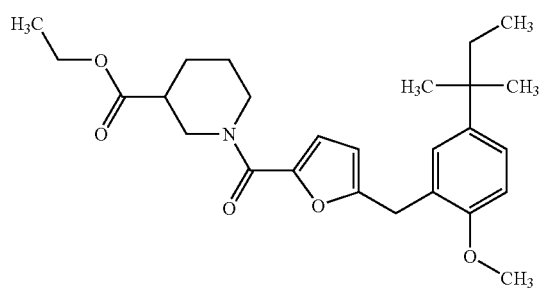 |
| 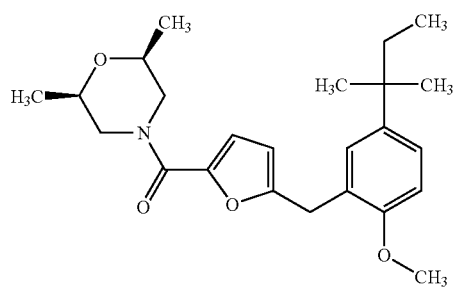 |
| 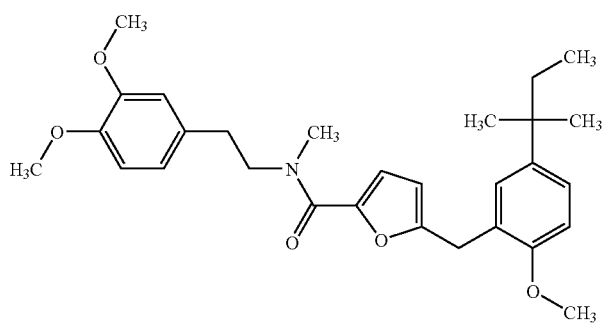 |

-continued
| MOLSTRUCTURE |
|---|
| 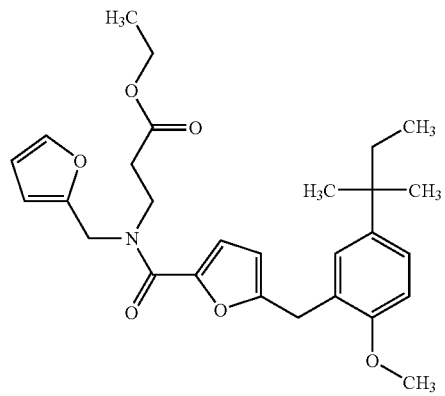 |
| 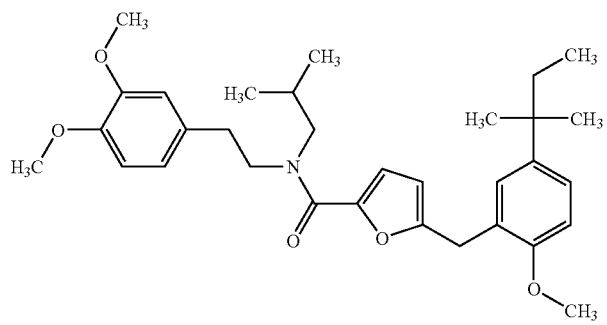 |
| 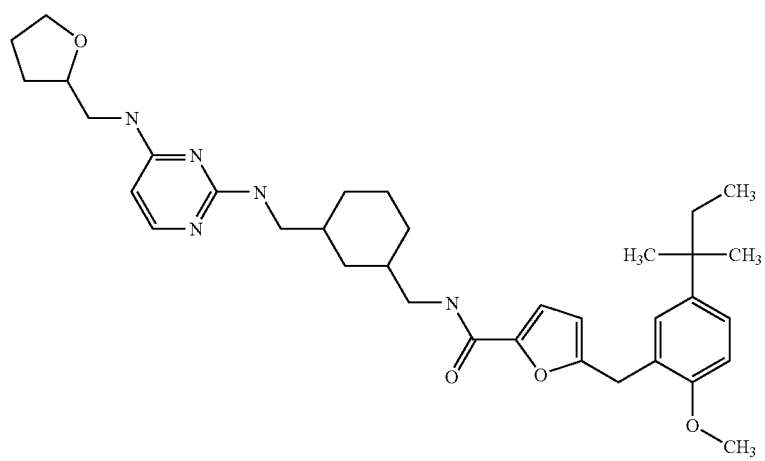 |
| Chiral<br />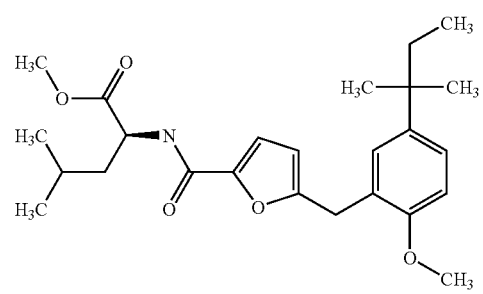 |

-continued
MOLSTRUCTURE
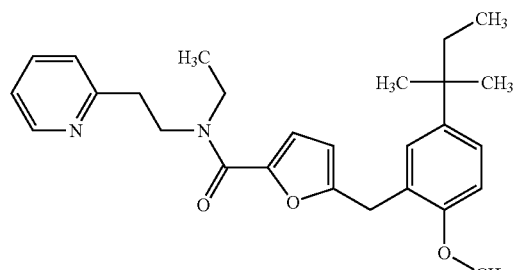
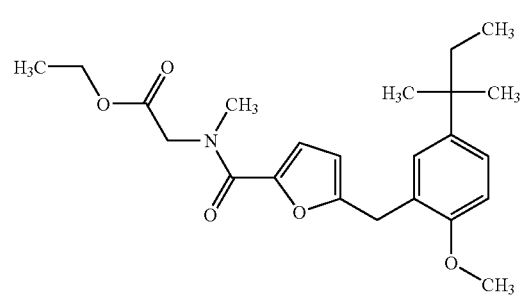
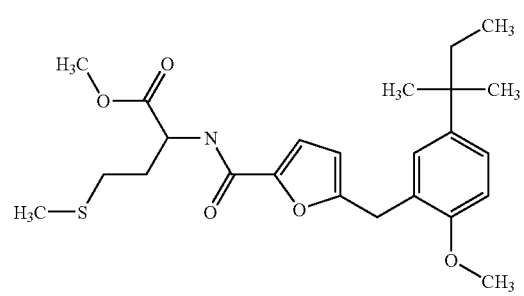
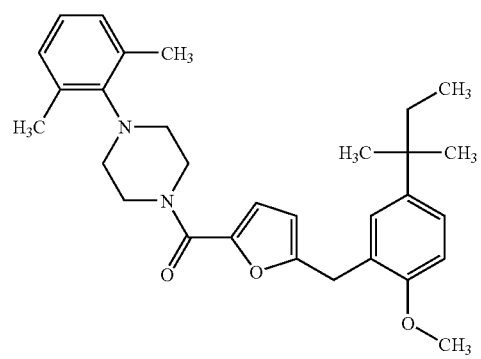

| MOLSTRUCTURE |
|---|
| 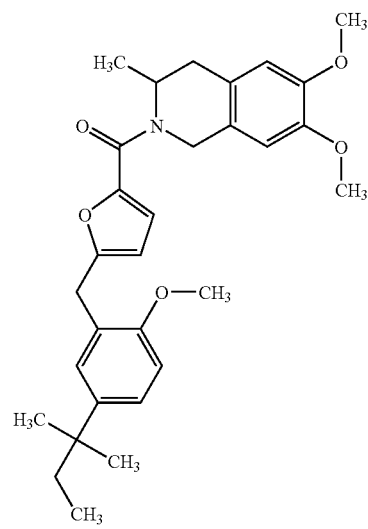 |
| 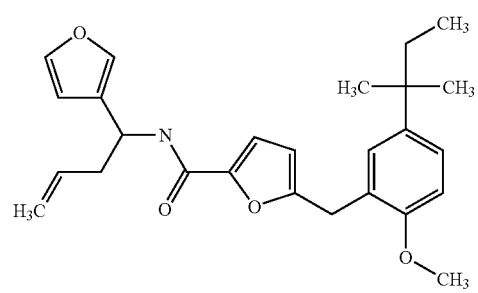 |
| 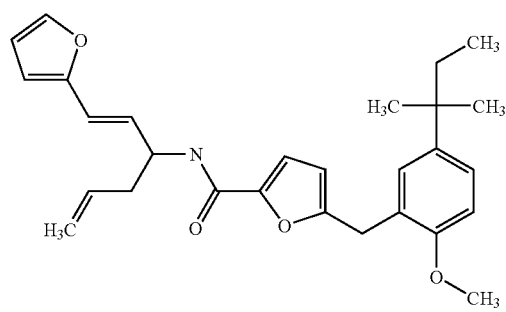 |
| 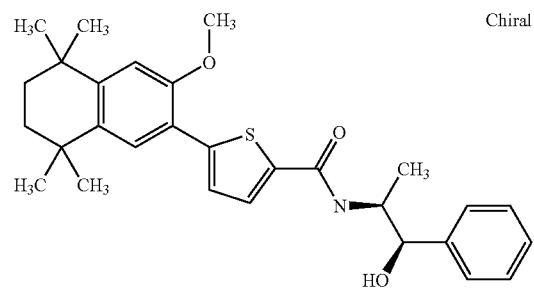 |

-continued
| MOLSTRUCTURE |
|---|
| 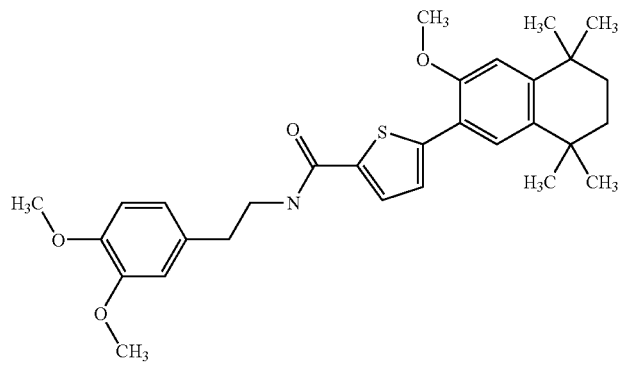 |
| 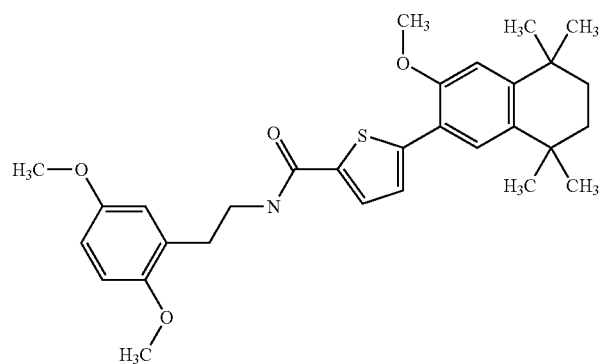 |
| 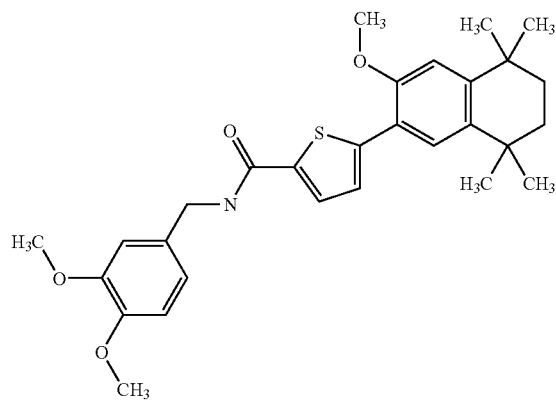 |
| 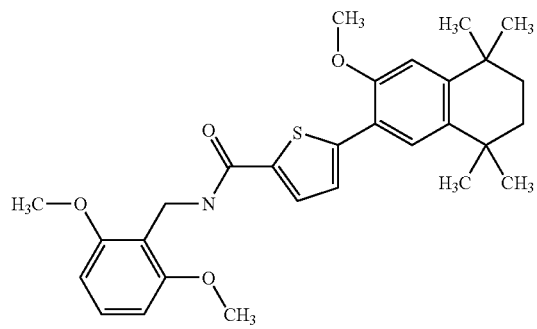 |

-continued
MOLSTRUCTURE
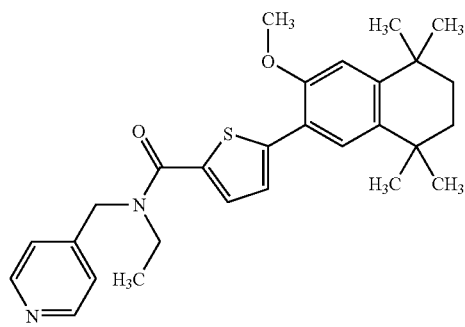
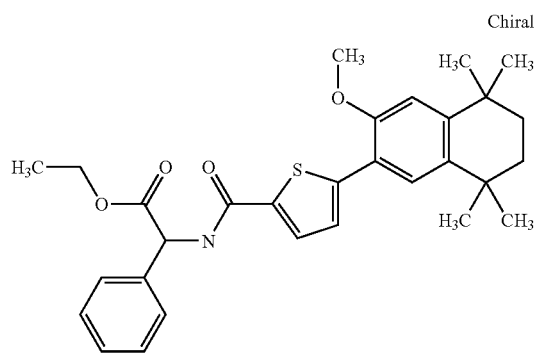
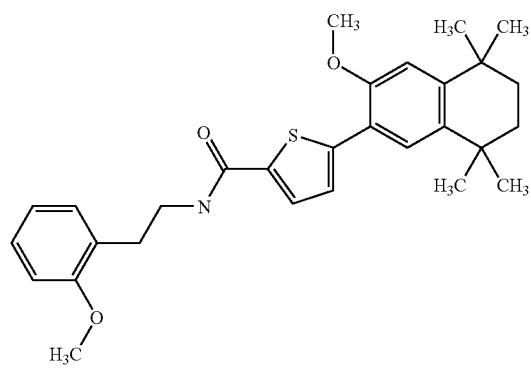
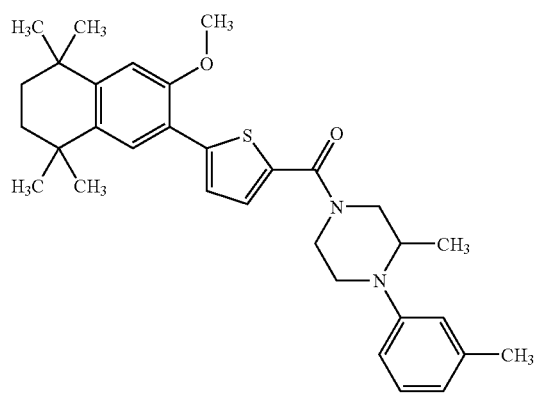

-continued
MOLSTRUCTURE
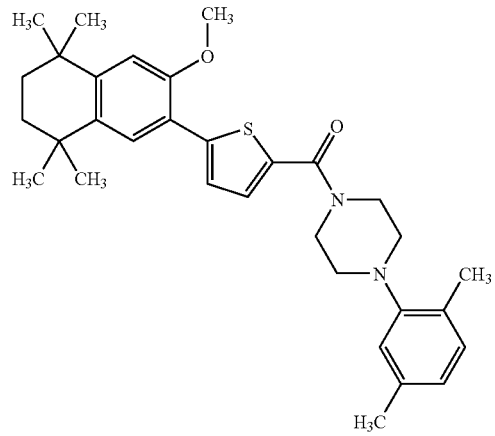
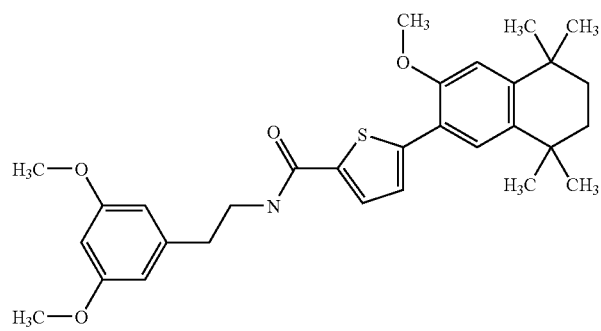
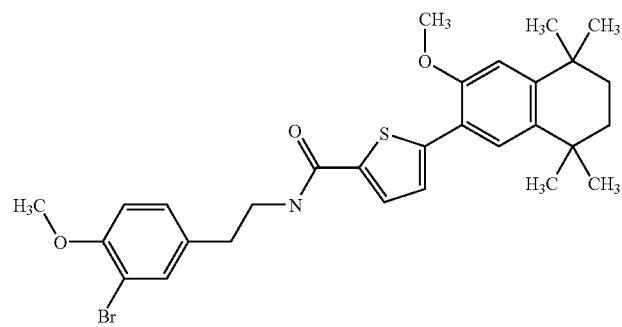
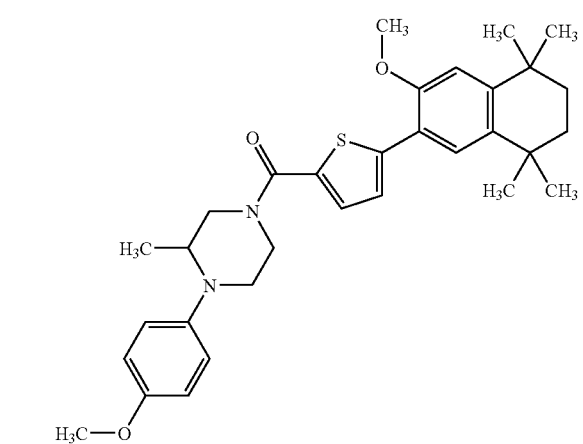

| MOLSTRUCTURE |
|---|
| 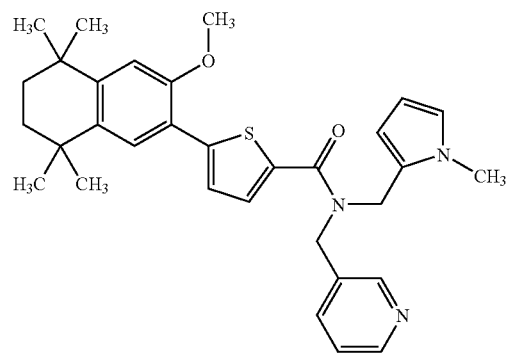 |
| 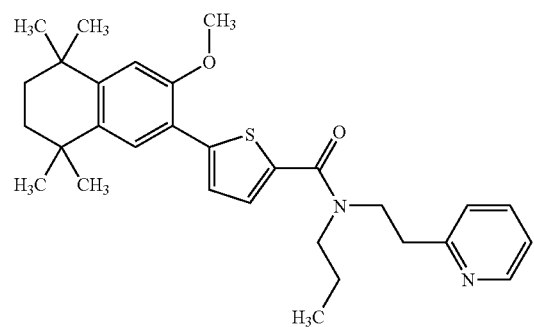 |
| 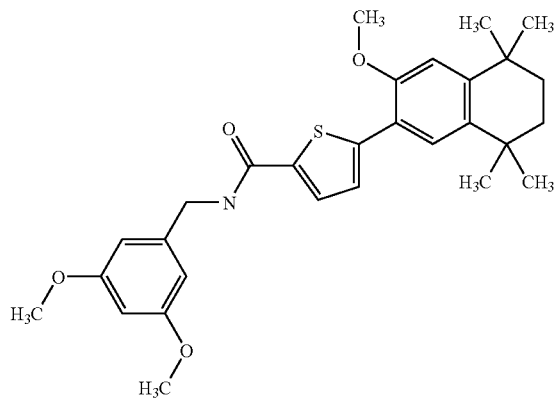 |
| 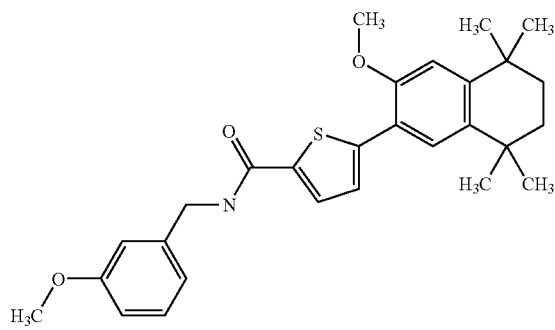 |

| MOLSTRUCTURE |
|---|
| 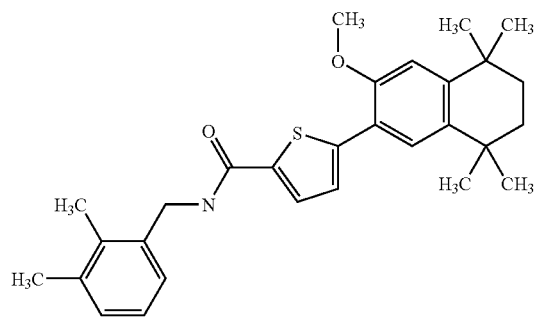 |
| 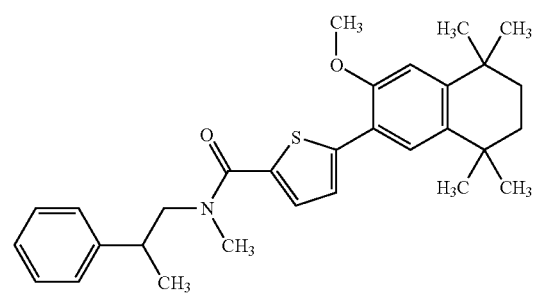 |
| 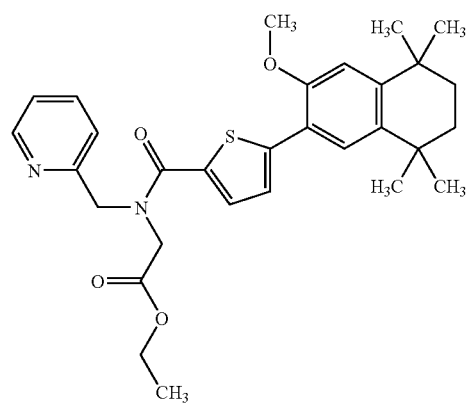 |
| 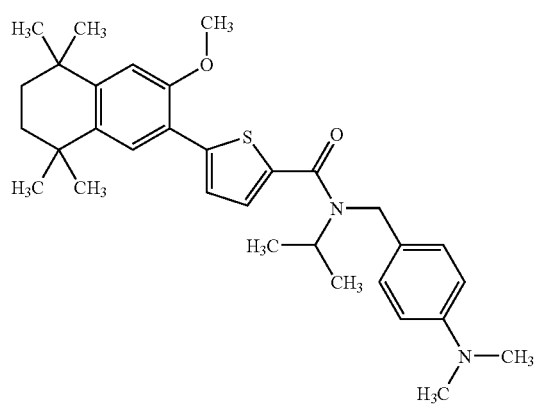 |

-continued
MOLSTRUCTURE
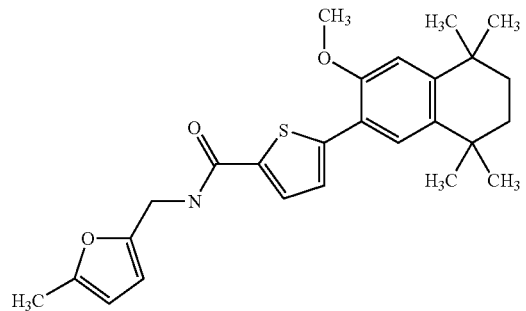
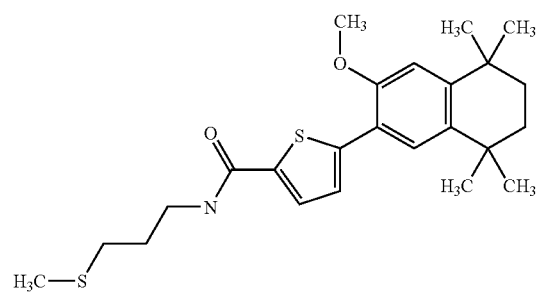
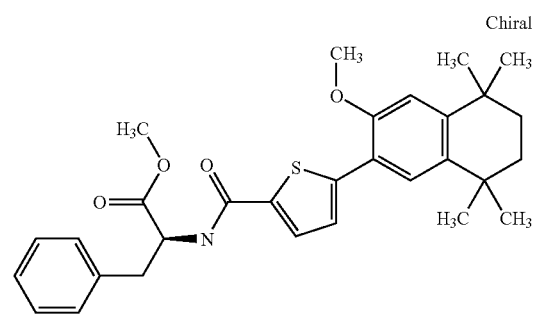
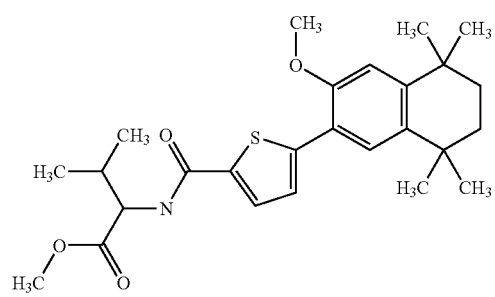
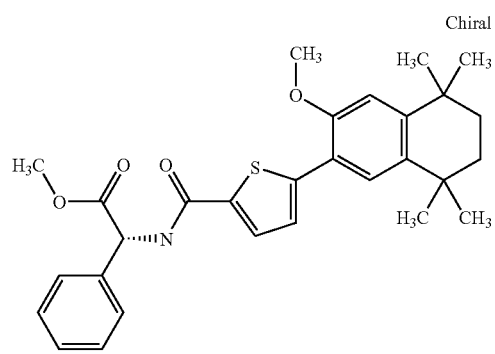

-continued
| MOLSTRUCTURE |
|---|
| 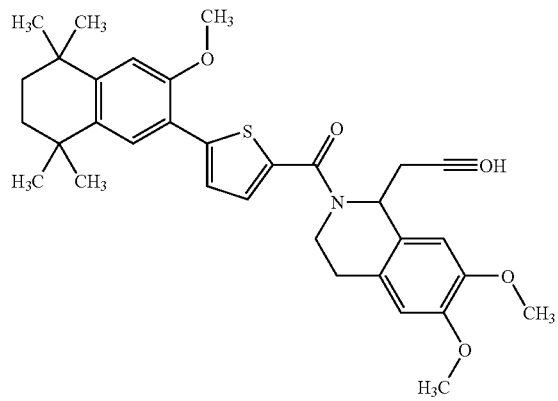 |
| 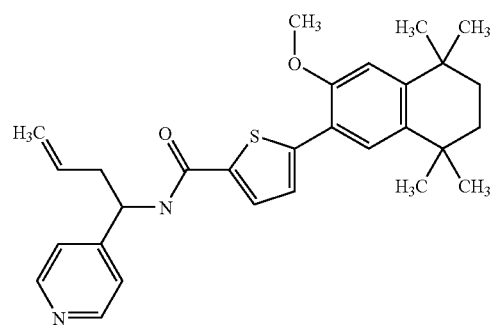 |
| 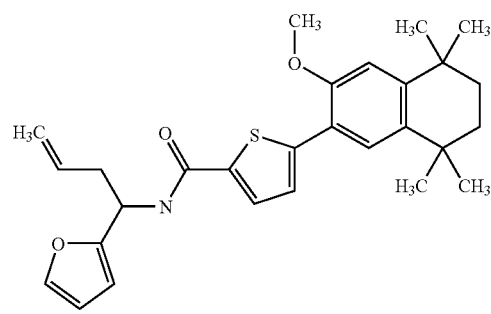 |
| 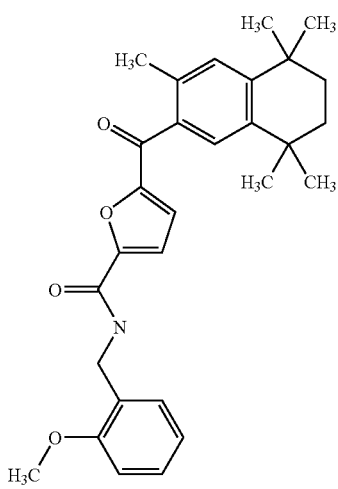 |

-continued
MOLSTRUCTURE
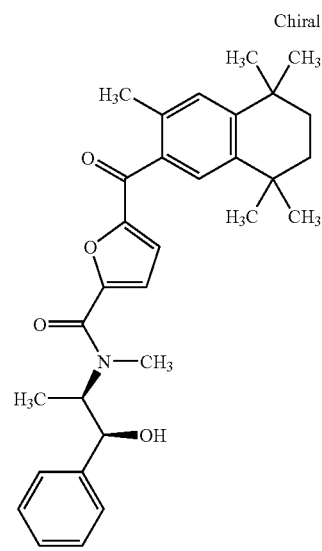
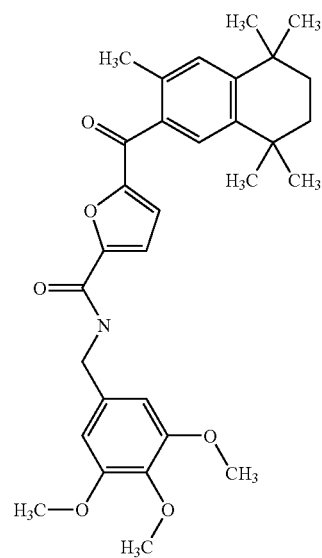

-continued
| MOLSTRUCTURE |
|---|
| 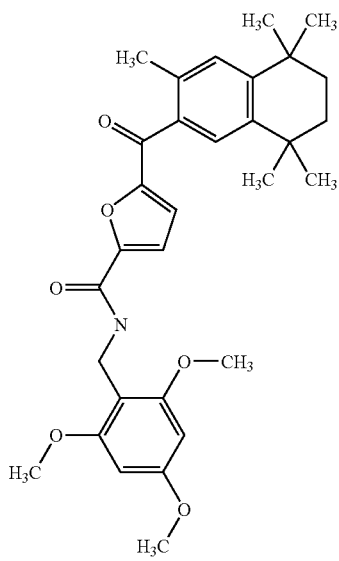 |
| 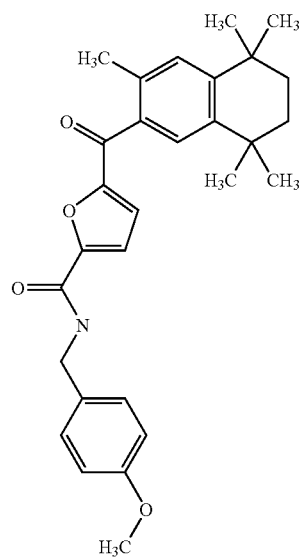 |

-continued
MOLSTRUCTURE
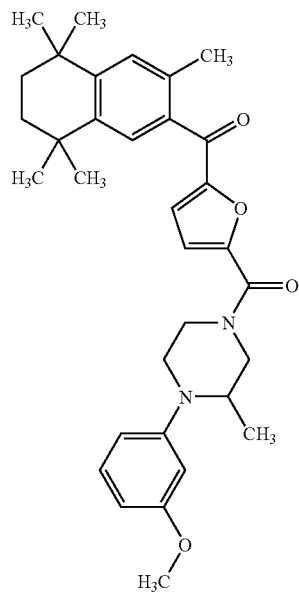
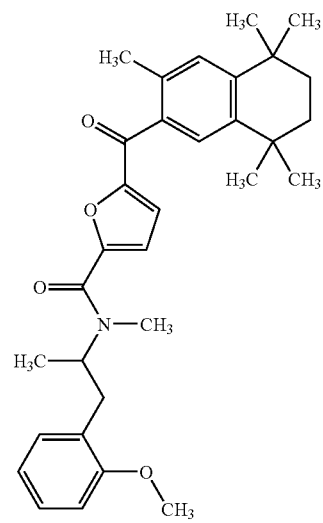
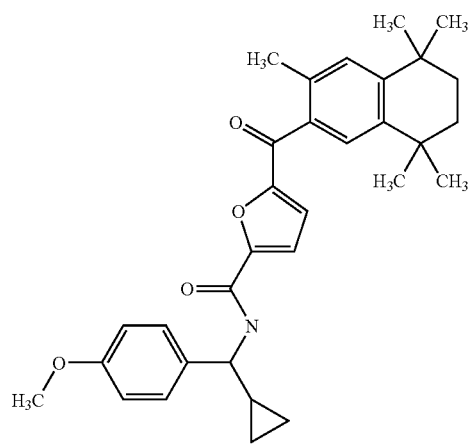

| MOLSTRUCTURE |
|---|
| 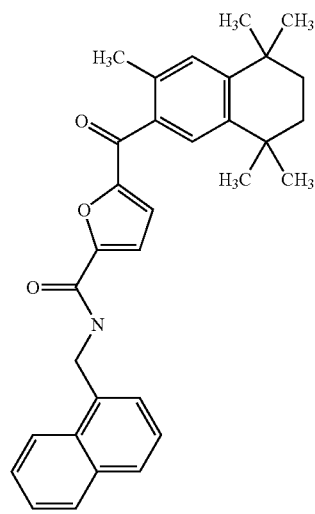 |
| 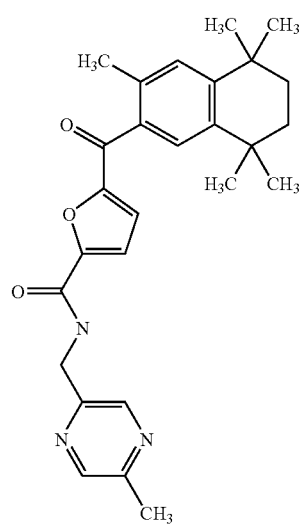 |

-continued
MOLSTRUCTURE
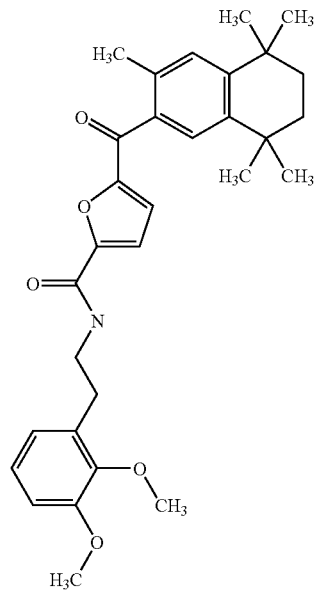
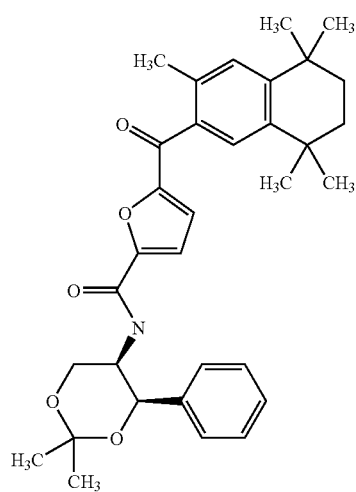
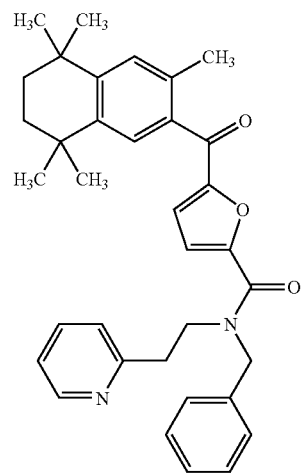

| MOLSTRUCTURE |
|---|
| 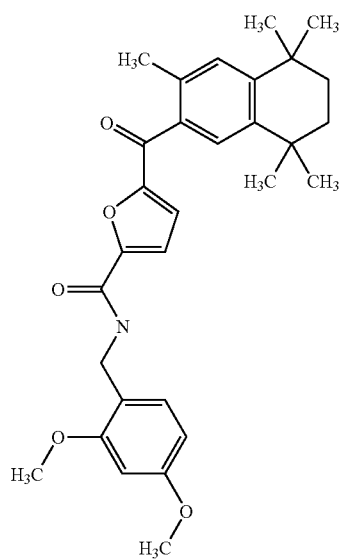 |
| 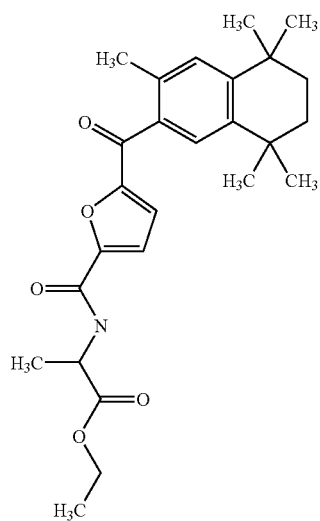 |

-continued
MOLSTRUCTURE
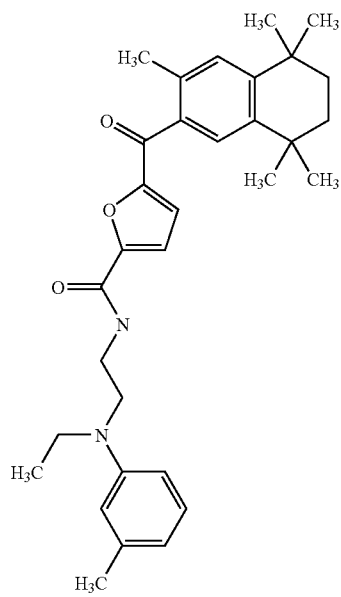
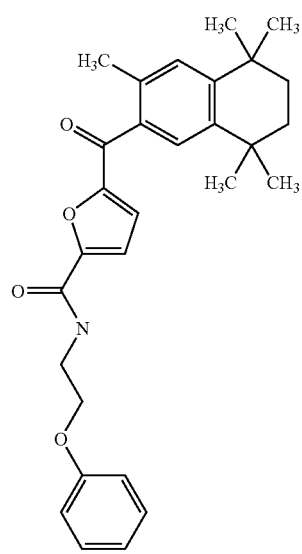

-continued
MOLSTRUCTURE
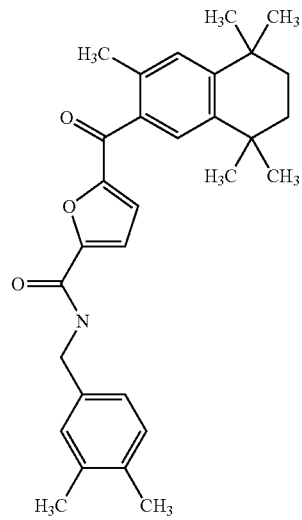
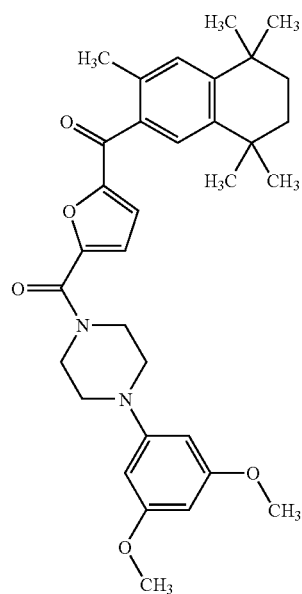
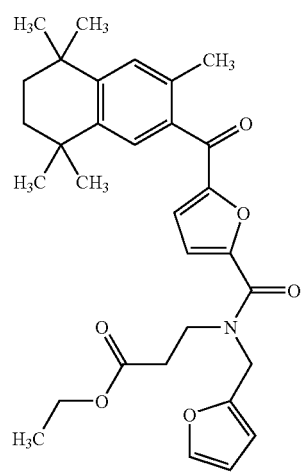

| MOLSTRUCTURE |
|---|
| 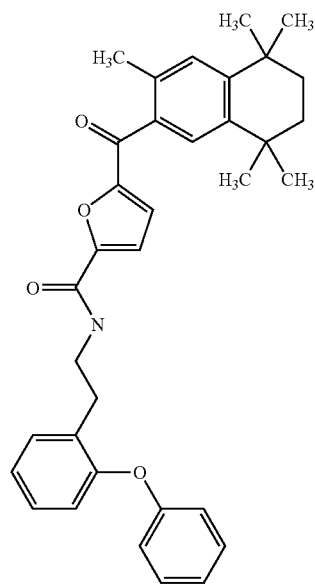 |
| 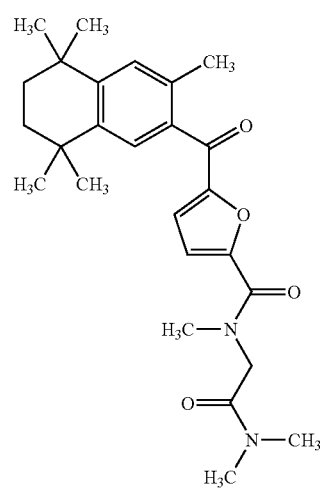 |

-continued
MOLSTRUCTURE
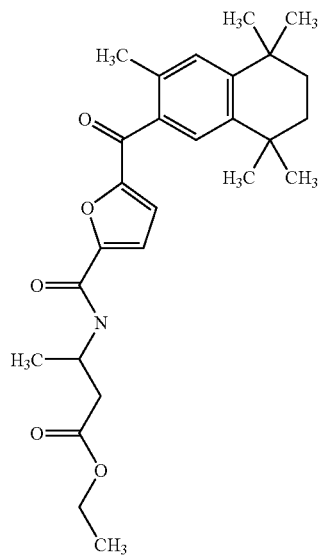
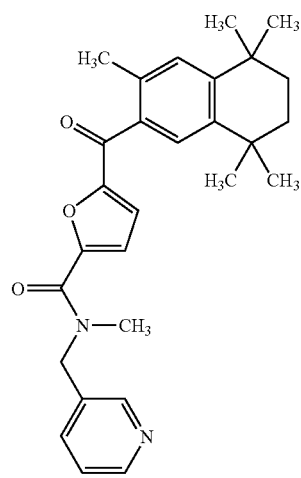
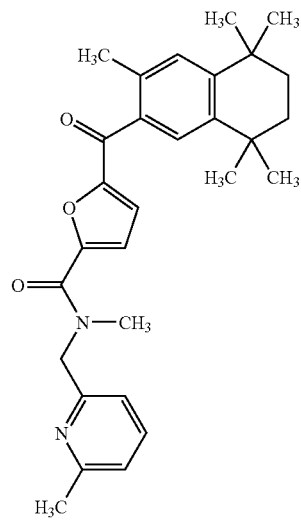

| MOLSTRUCTURE |
|---|
| 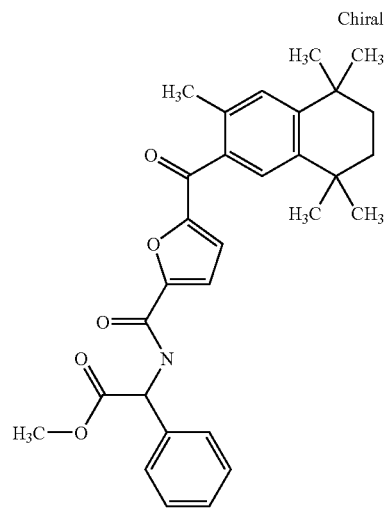 |
| 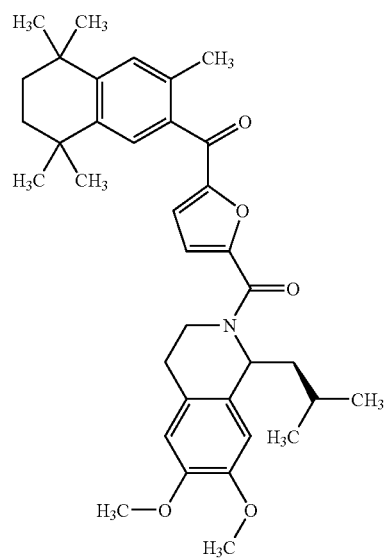 |
| 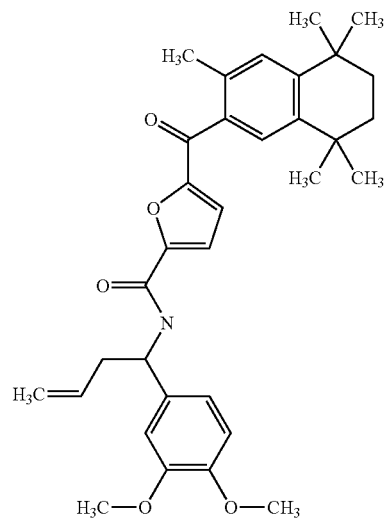 |

| MOLSTRUCTURE |
|---|
| 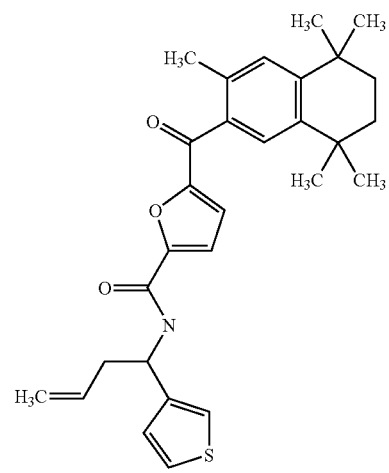 |
| 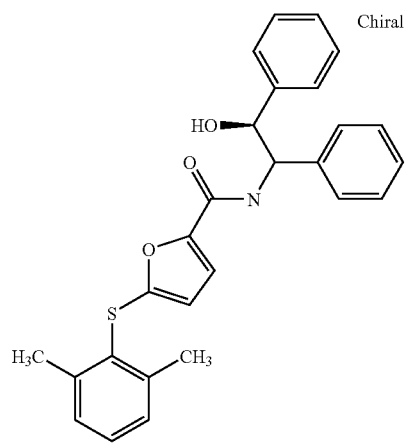 |
| 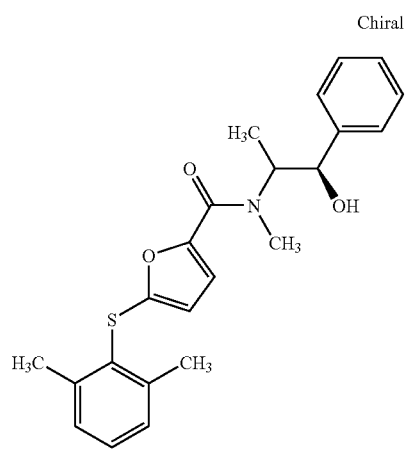 |

| MOLSTRUCTURE |
|---|
| 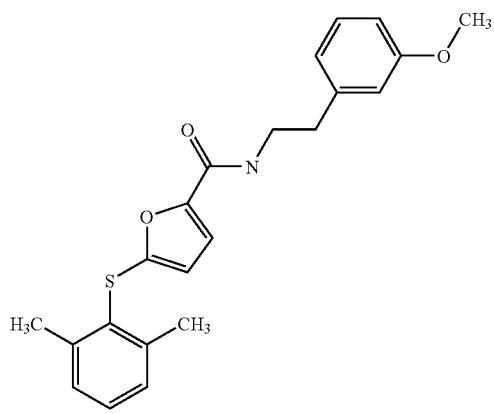 |
| 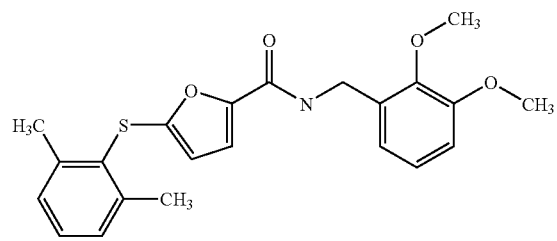 |
| 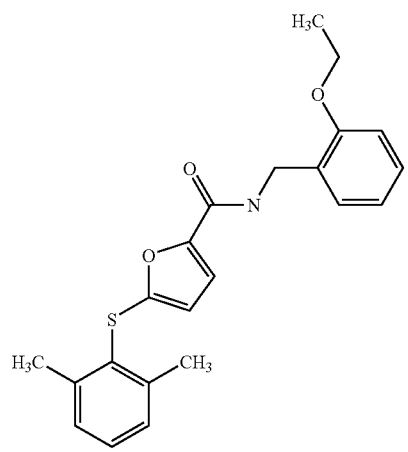 |
| 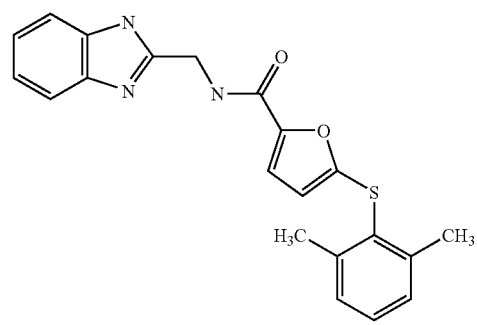 |

| MOLSTRUCTURE |
|---|
| 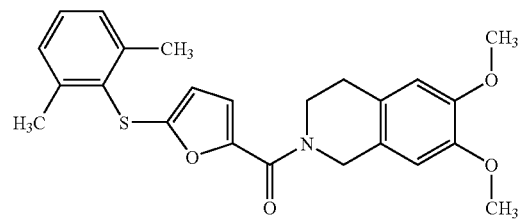 |
| 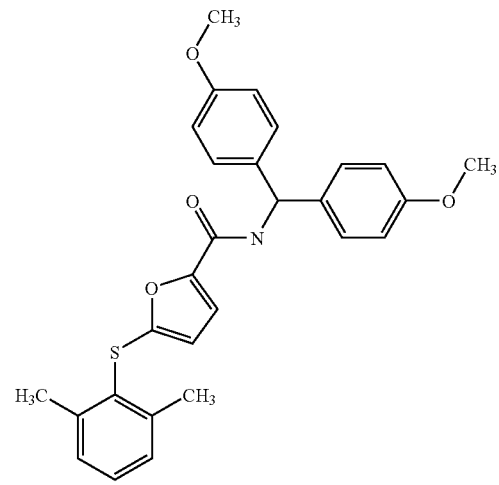 |
| 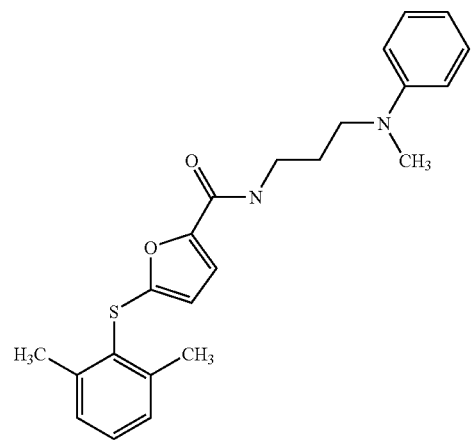 |
| 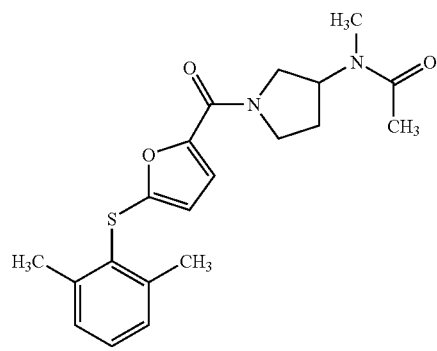 |

-continued
MOLSTRUCTURE
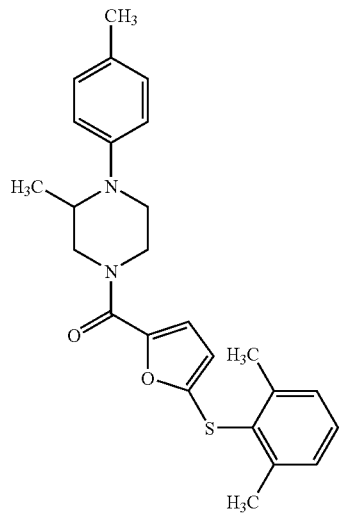
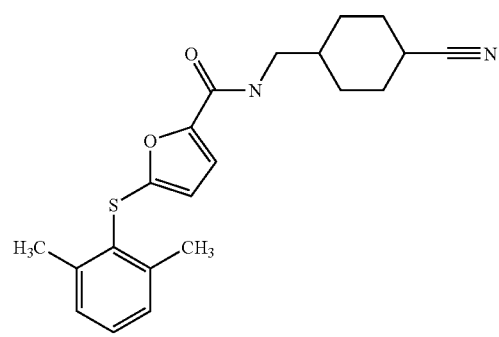
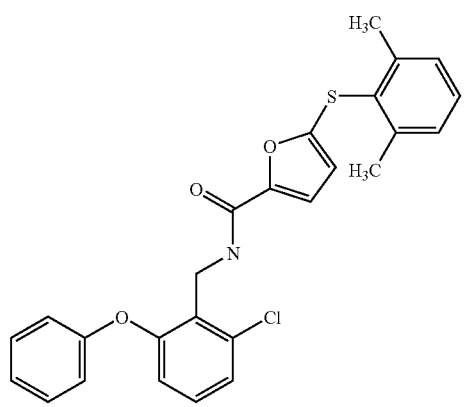
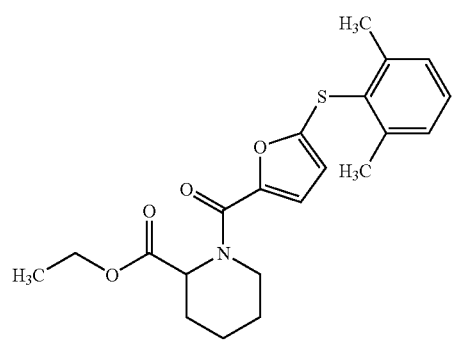

-continued
MOLSTRUCTURE
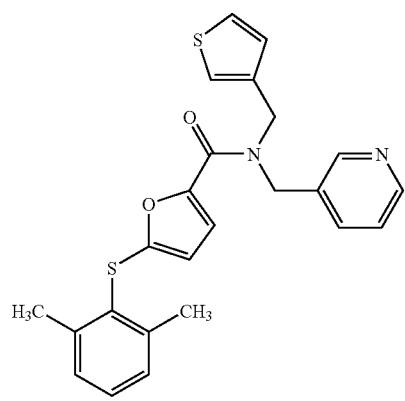
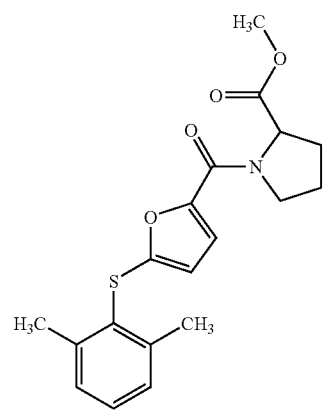
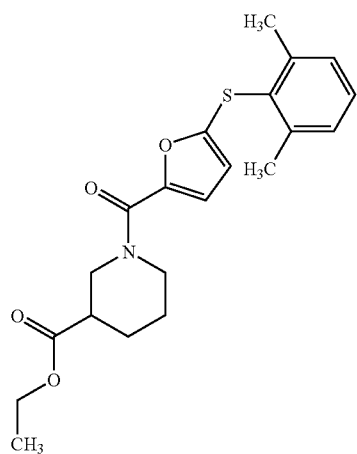

-continued
MOLSTRUCTURE
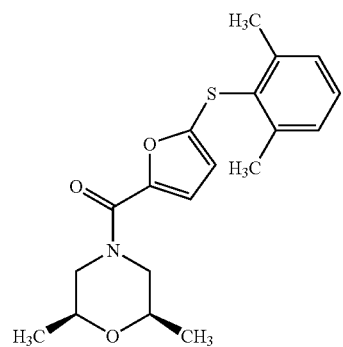
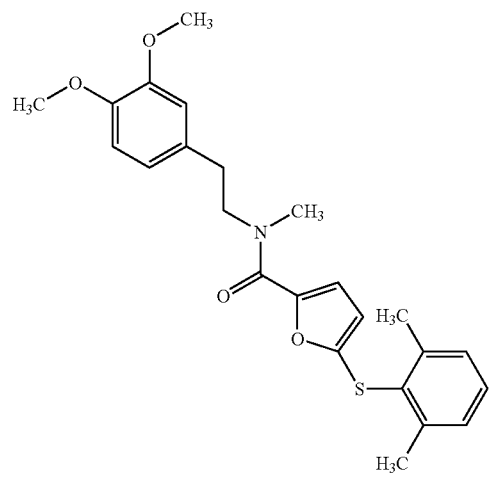
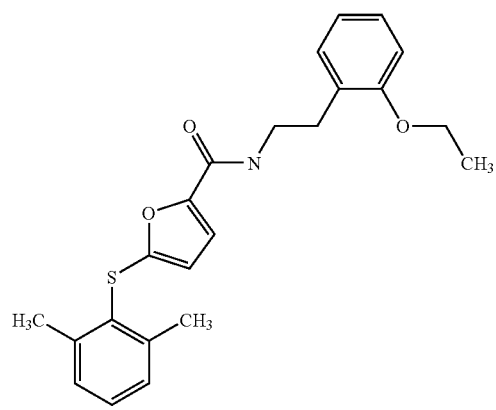

-continued
MOLSTRUCTURE
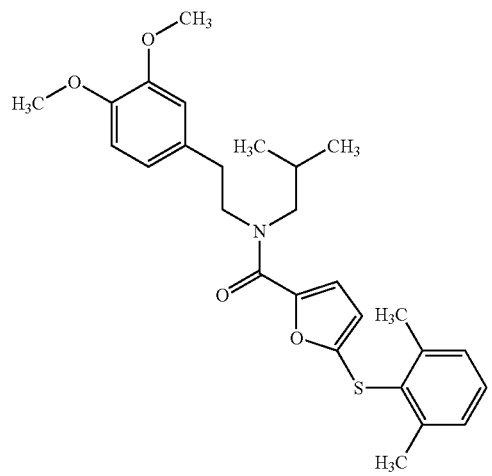
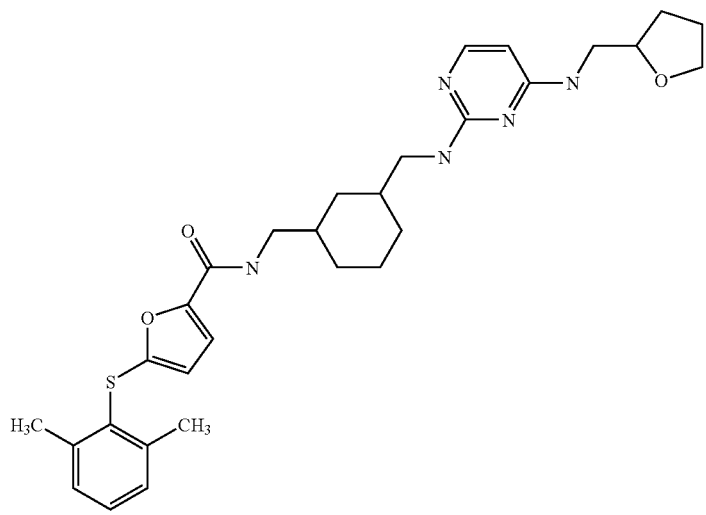
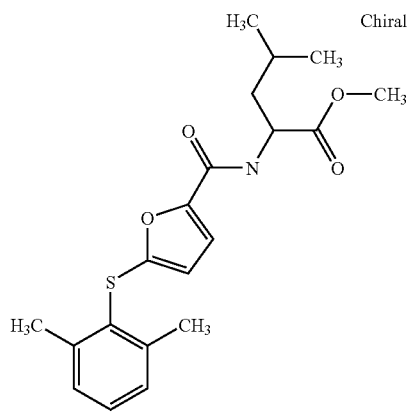

MOLSTRUCTURE
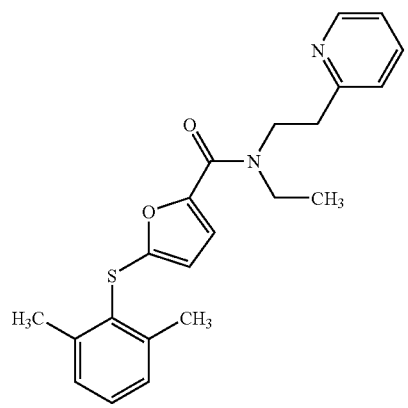
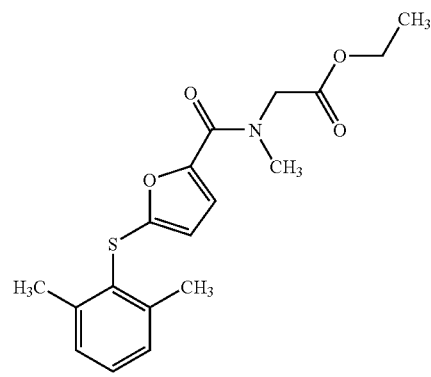
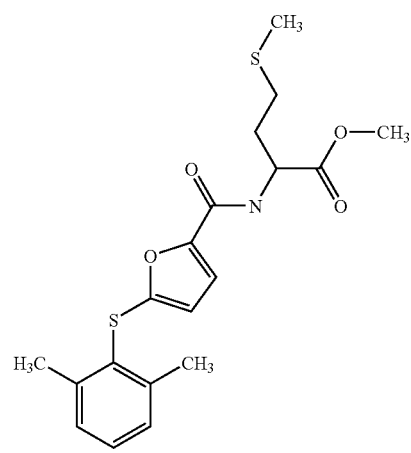

-continued
MOLSTRUCTURE
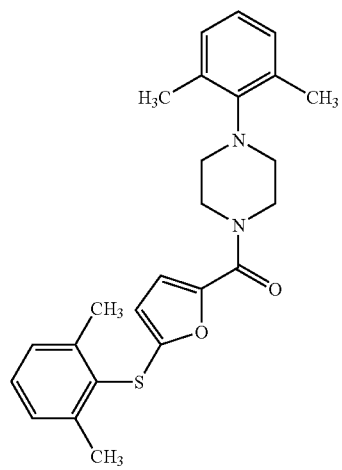
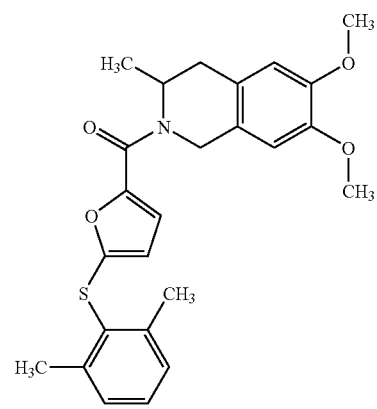
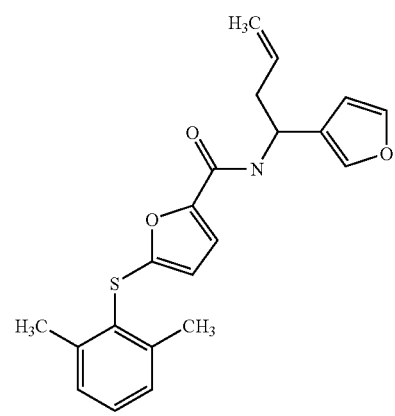

-continued
MOLSTRUCTURE
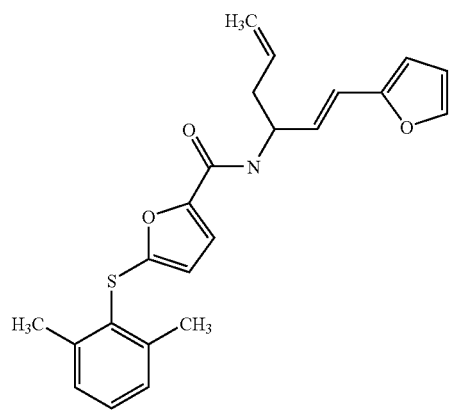
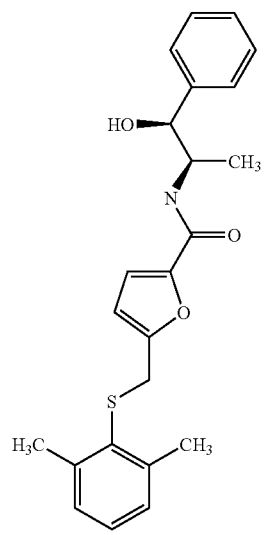
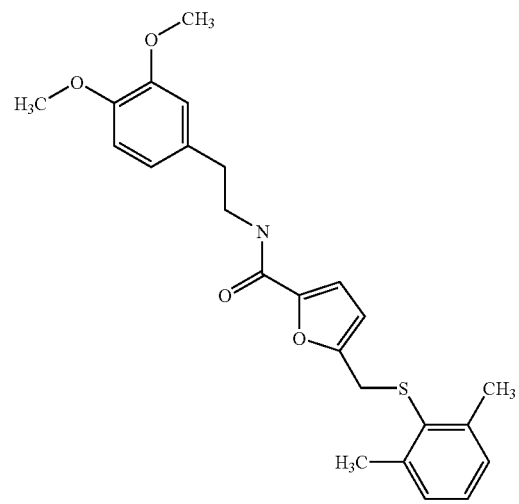

-continued
| MOLSTRUCTURE |
|---|
| 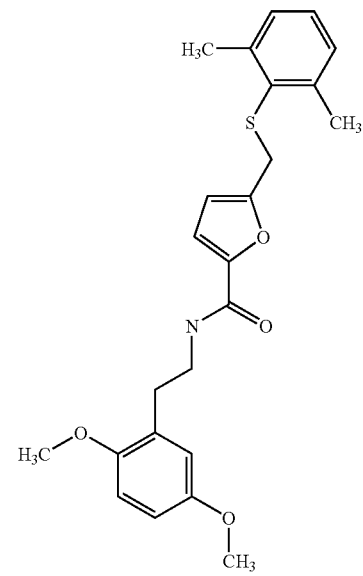 |
| 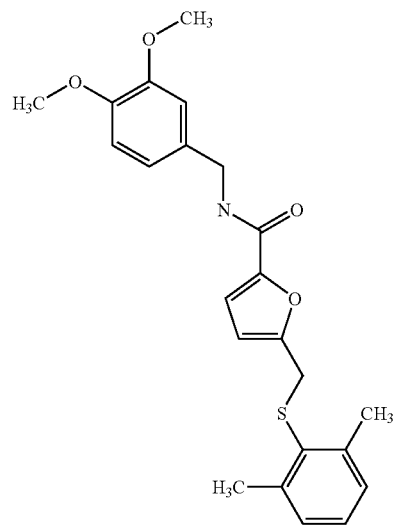 |
| 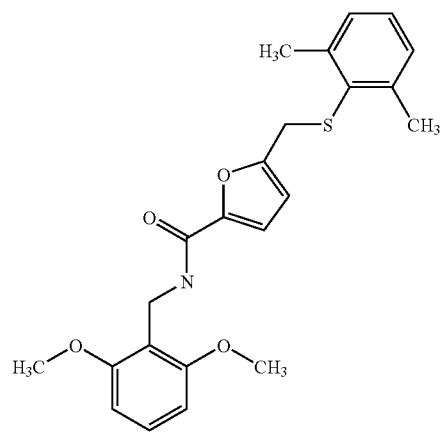 |

MOLSTRUCTURE
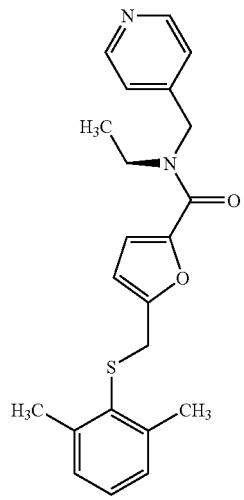
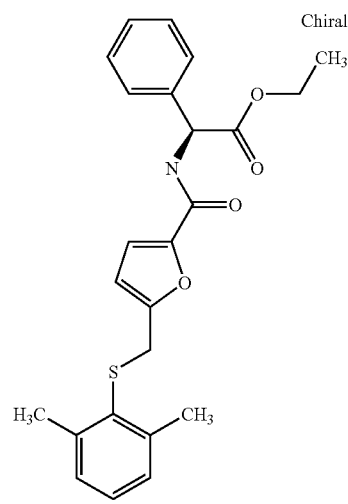
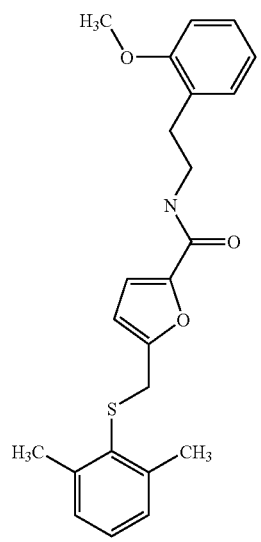

-continued
MOLSTRUCTURE
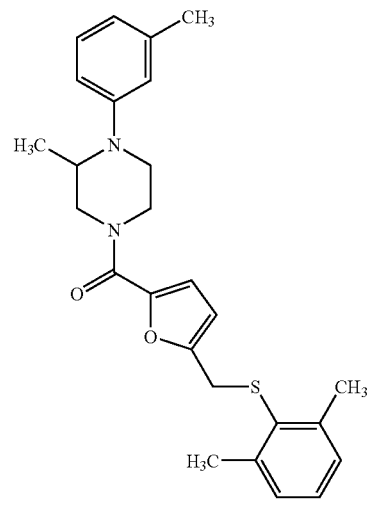
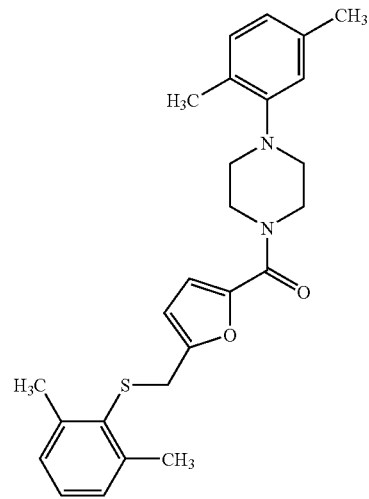
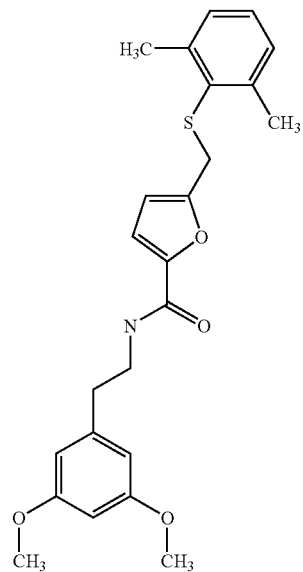

-continued
MOLSTRUCTURE
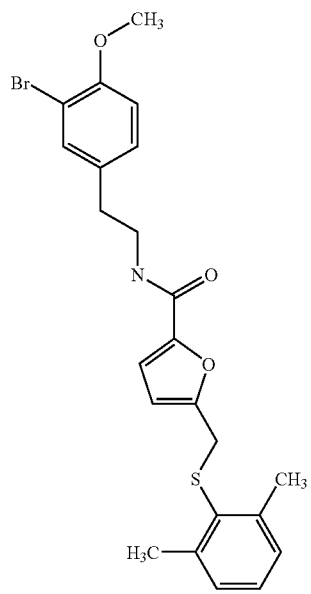
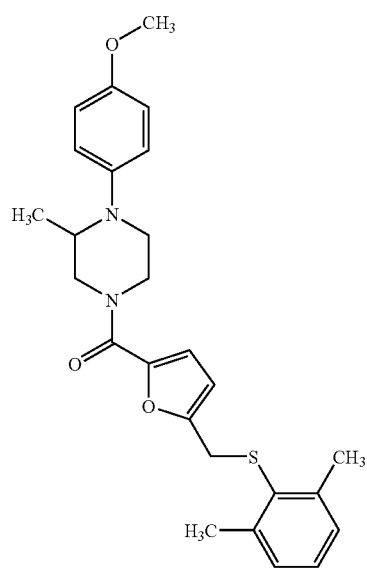

-continued
MOLSTRUCTURE
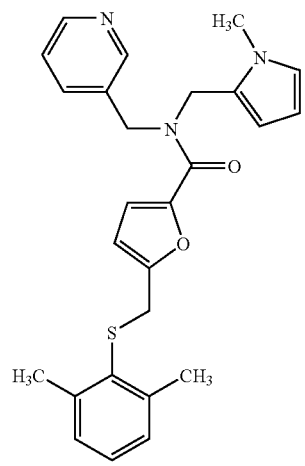
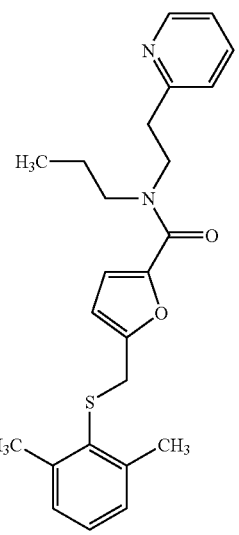
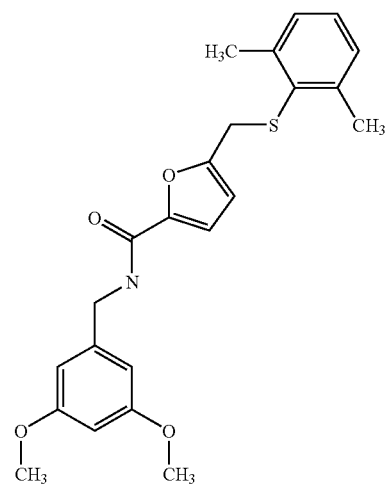

-continued
| MOLSTRUCTURE |
| --- |
| 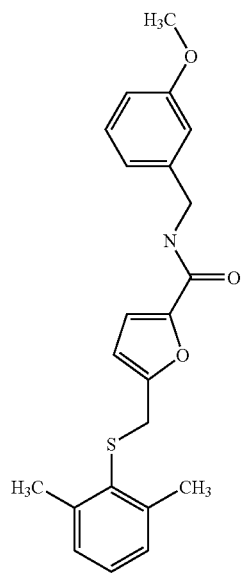 |
| 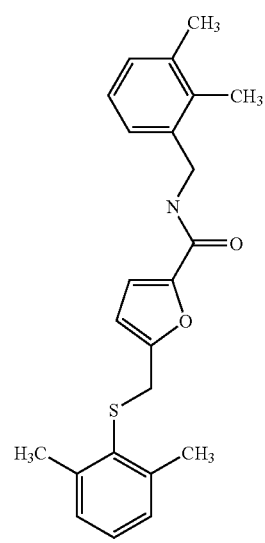 |

-continued
MOLSTRUCTURE
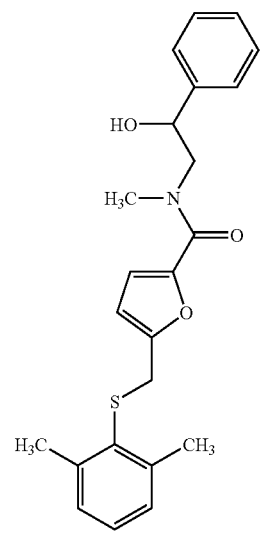
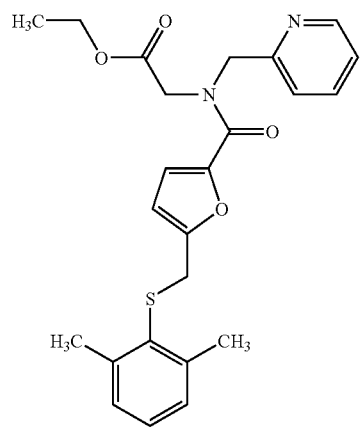
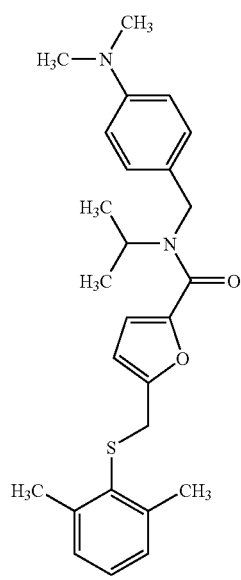

| MOLSTRUCTURE |
|---|
| 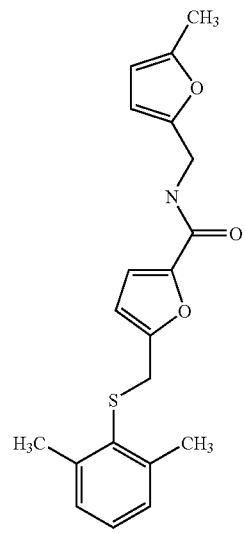 |
| 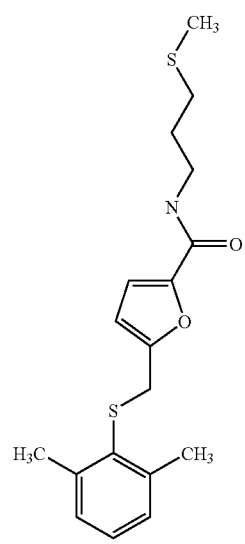 |
| 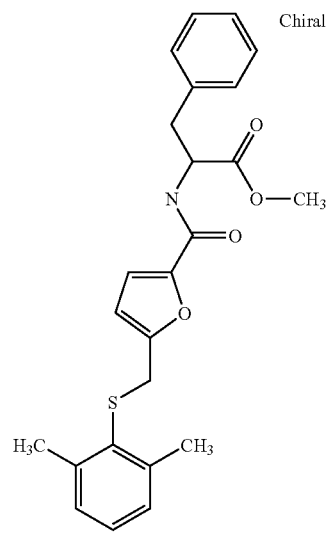 |

-continued
MOLSTRUCTURE
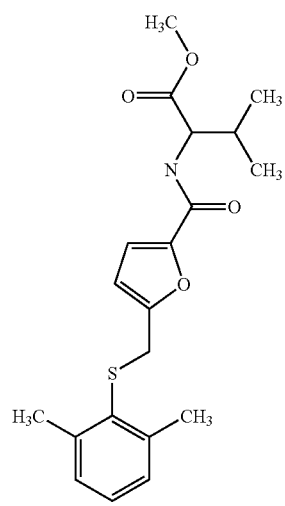
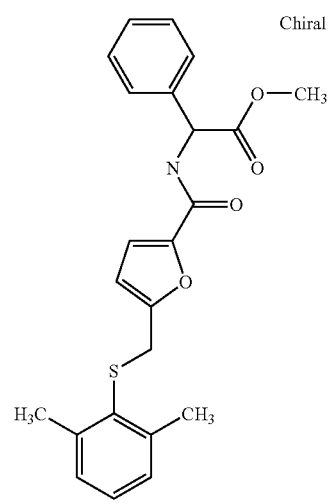
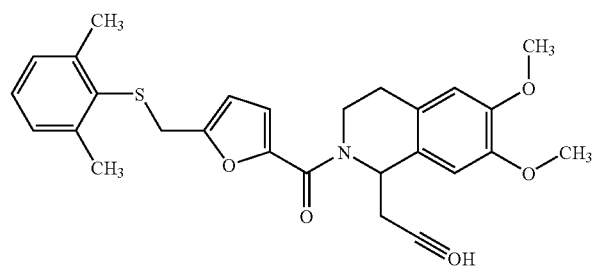

-continued
MOLSTRUCTURE
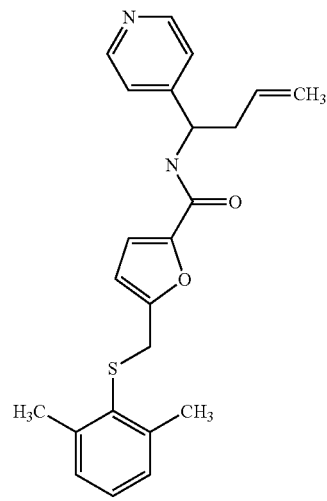
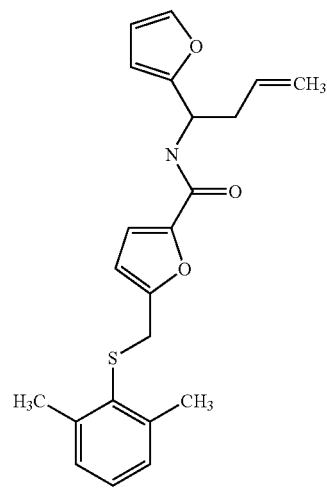
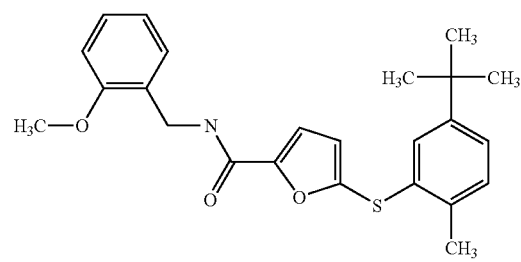
Chiral
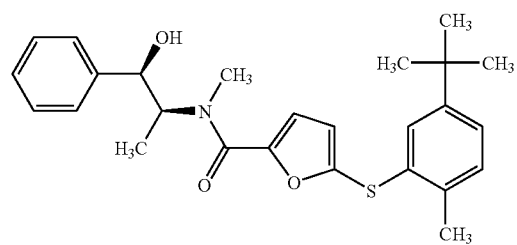

| MOLSTRUCTURE |
|---|
| 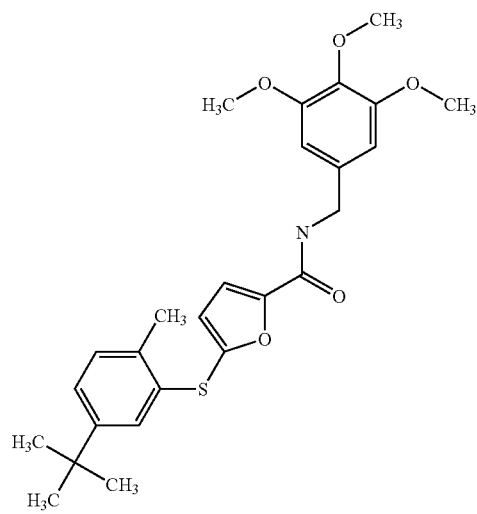 |
| 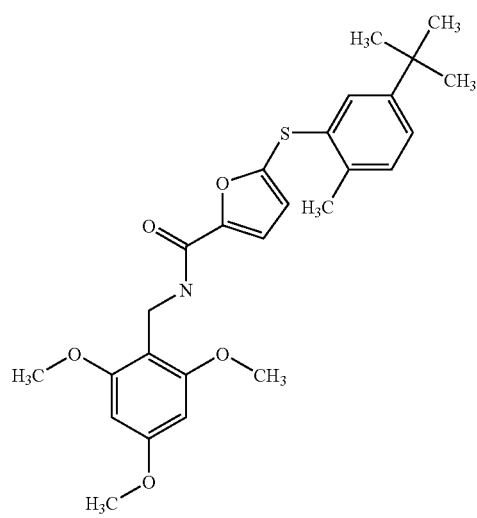 |
| 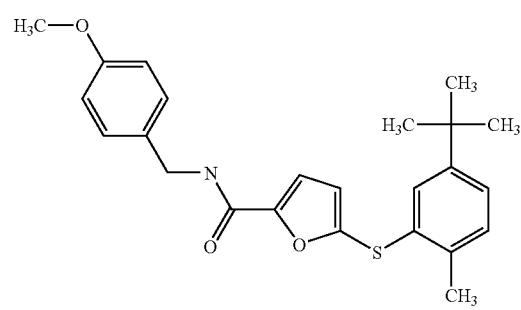 |

-continued
MOLSTRUCTURE
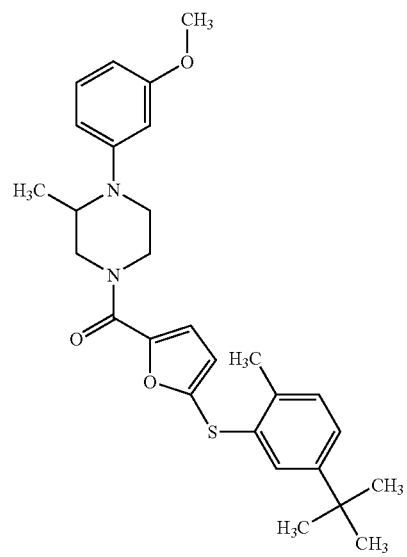
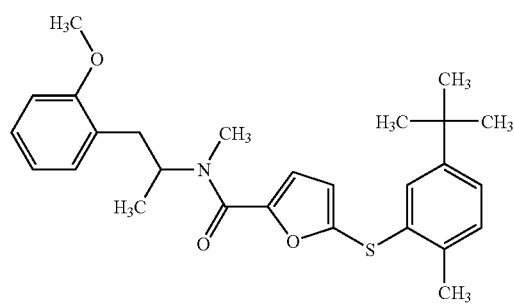
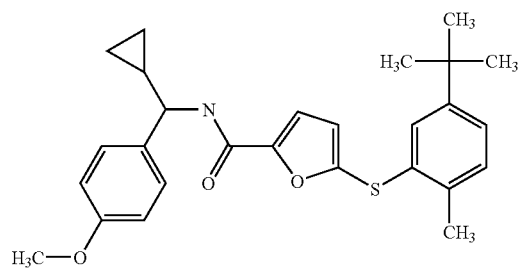
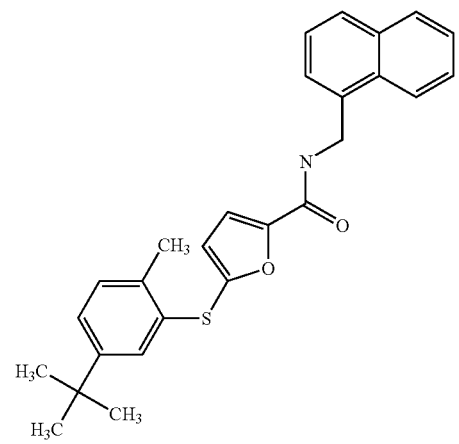

-continued
| MOLSTRUCTURE |
|---|
| 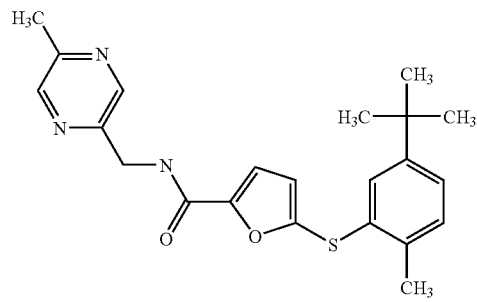 |
| 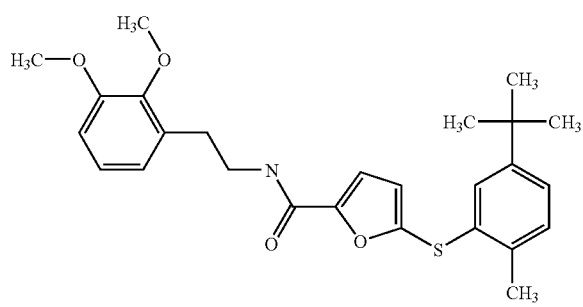 |
| 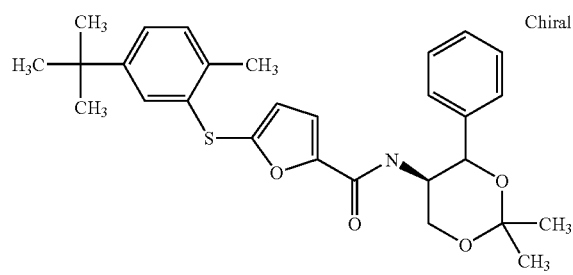 |
| 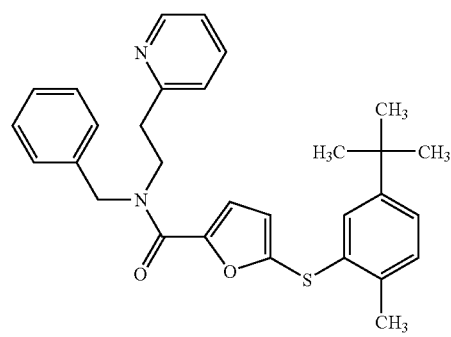 |
| 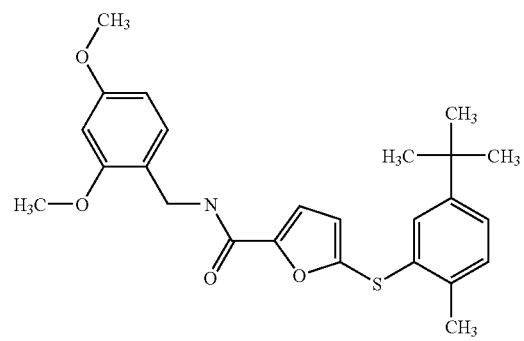 |

-continued
| MOLSTRUCTURE |
|---|
| 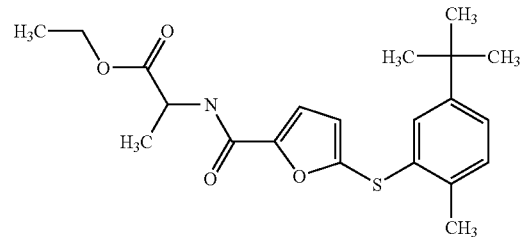 |
| 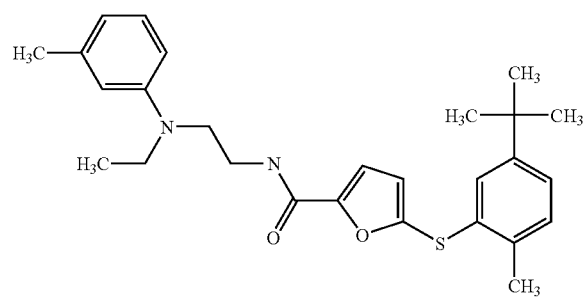 |
| 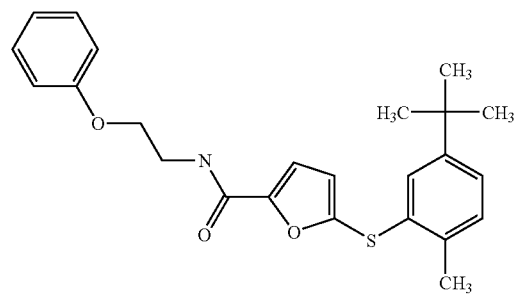 |
| 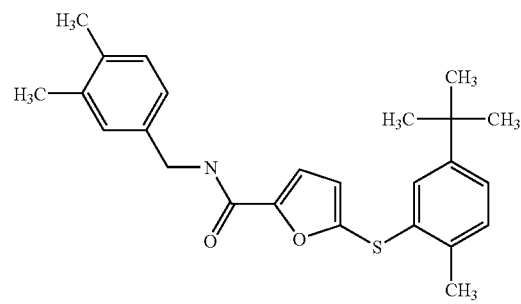 |
| 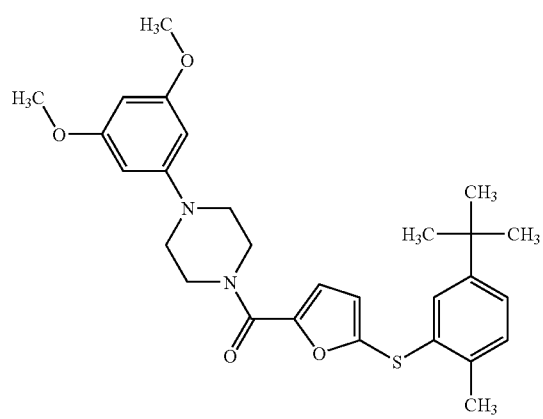 |

-continued
MOLSTRUCTURE
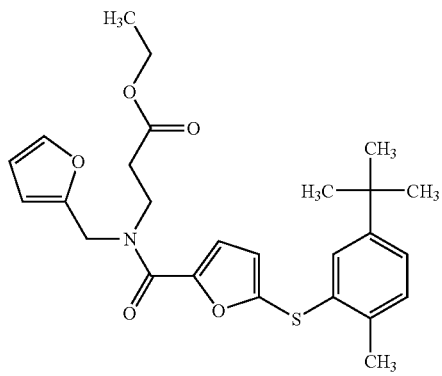
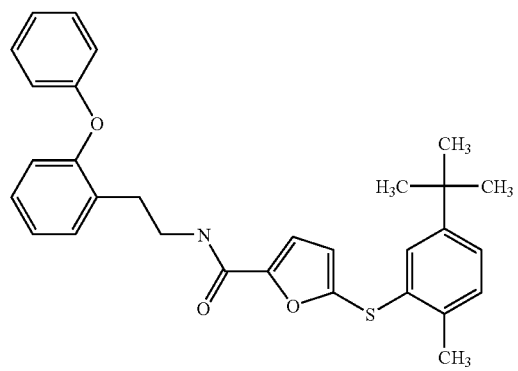
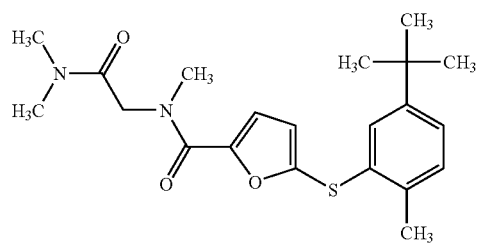
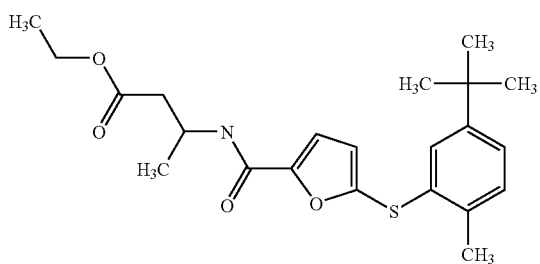
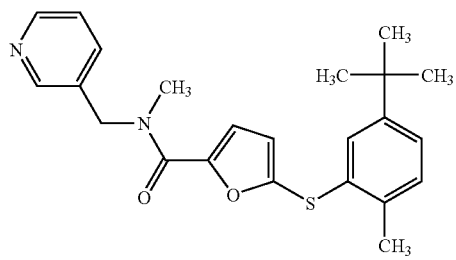

-continued
| MOLSTRUCTURE |
|---|
| 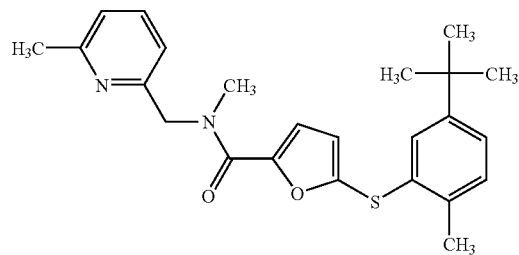 |
| 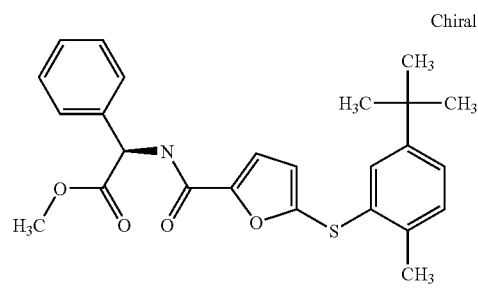 |
| 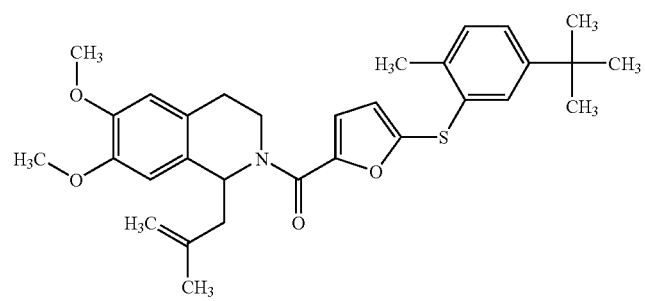 |
| 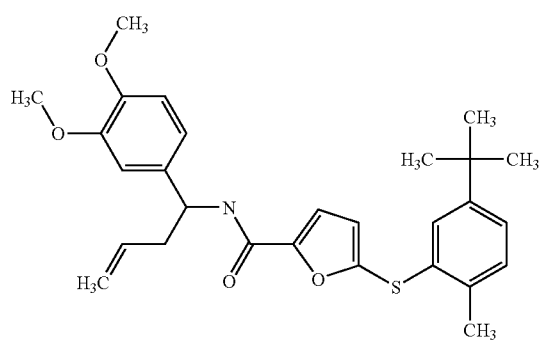 |
| 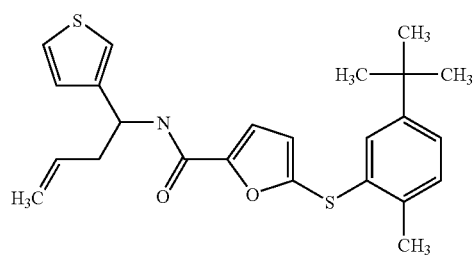 |

-continued
MOLSTRUCTURE
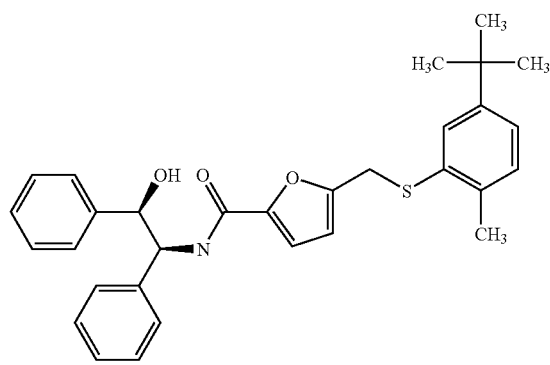
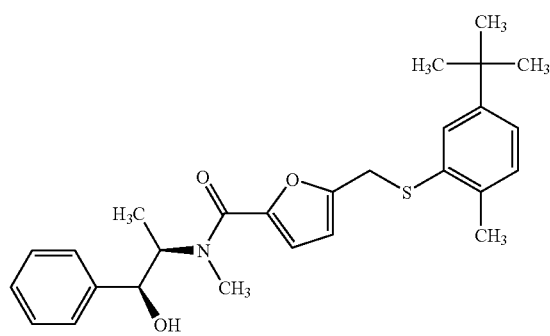
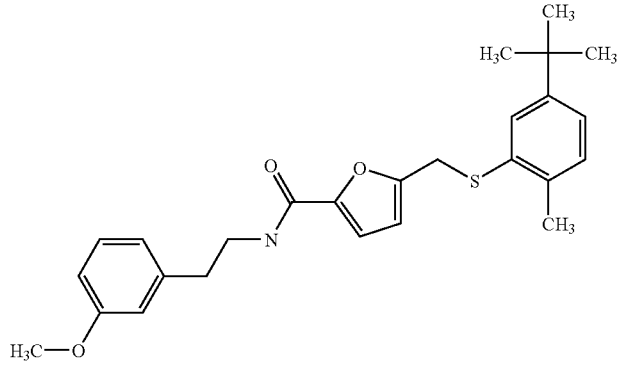
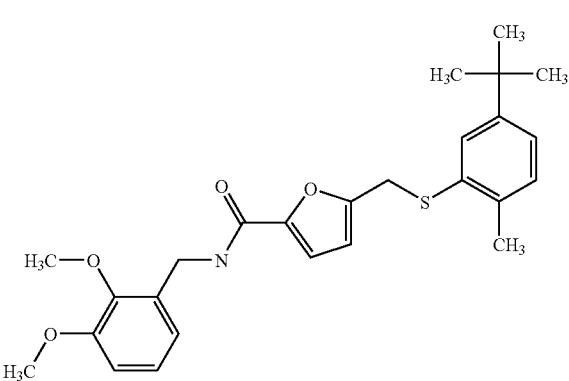

| MOLSTRUCTURE |
|---|
| 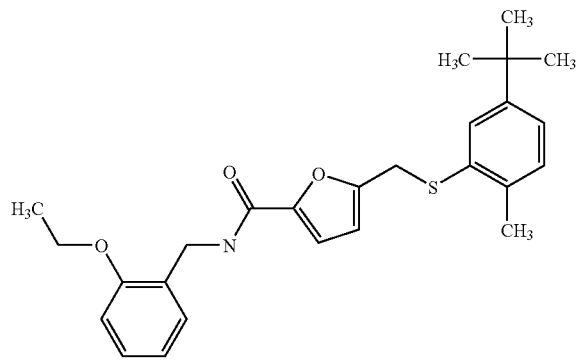 |
| 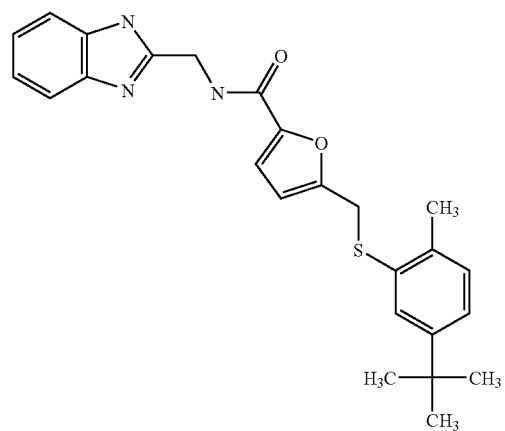 |
| 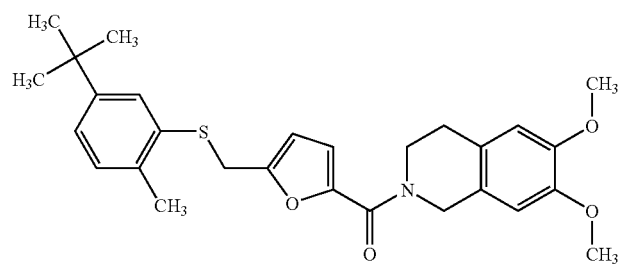 |
|  |

| MOLSTRUCTURE |
|---|
| 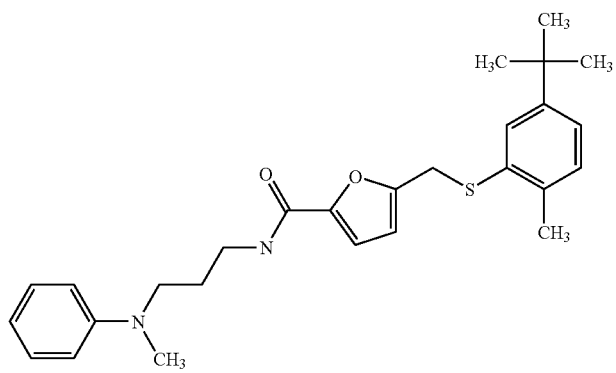 |
| 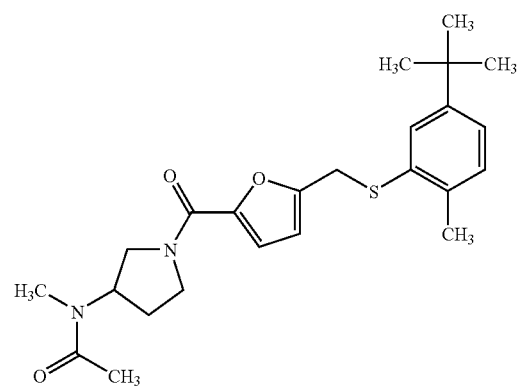 |
| 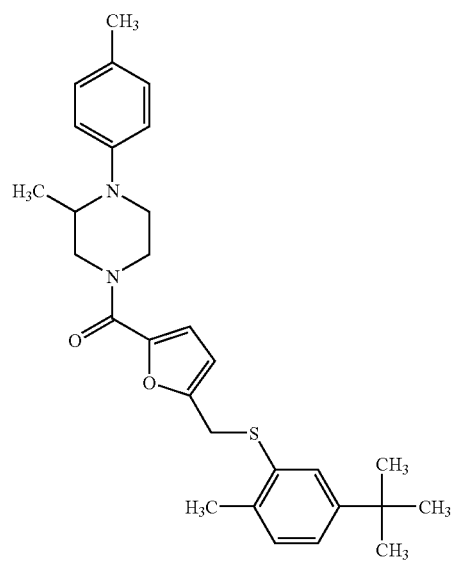 |

-continued
MOLSTRUCTURE
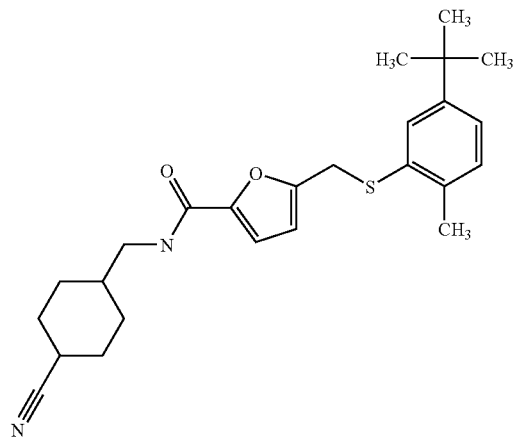
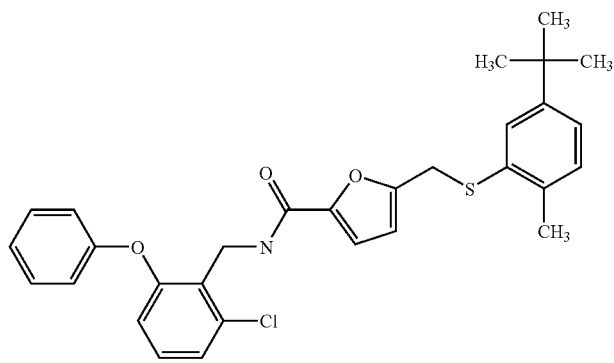
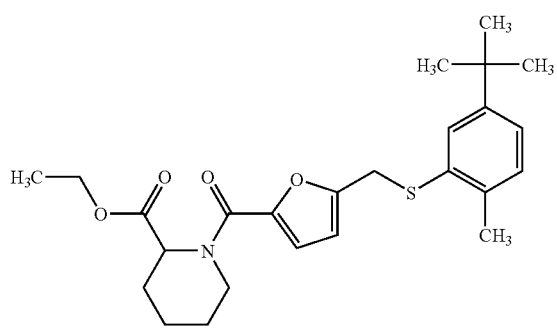
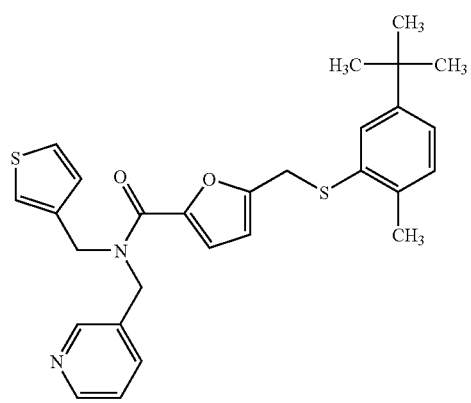

-continued
| MOLSTRUCTURE |
|---|
| 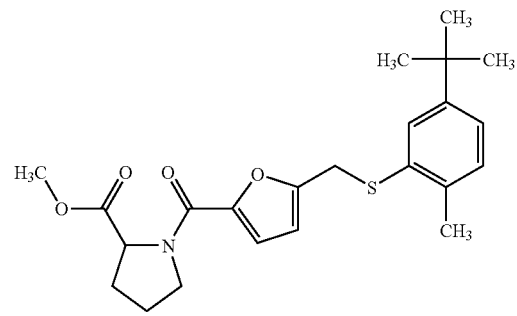 |
| 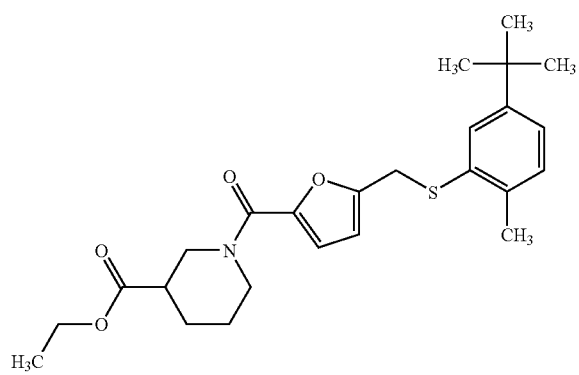 |
| 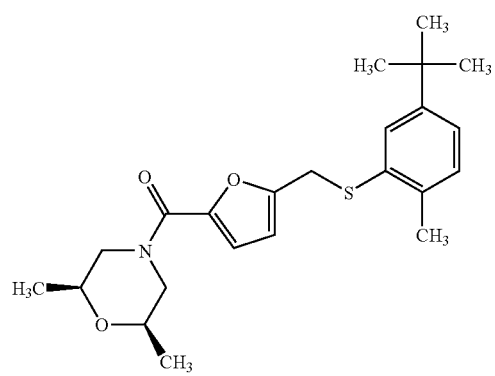 |
| 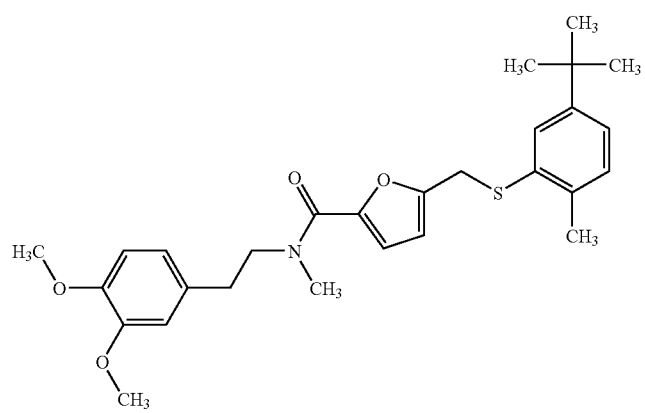 |

-continued
| MOLSTRUCTURE |
|---|
| 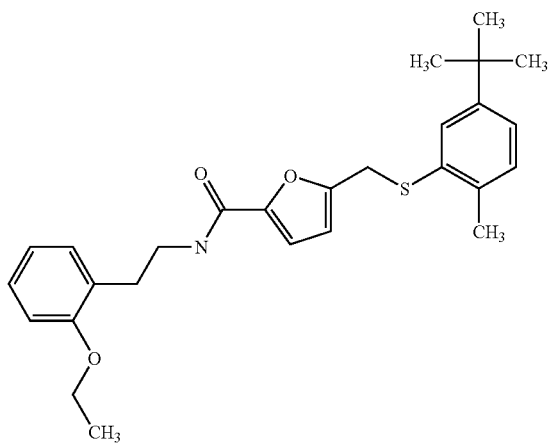 |
| 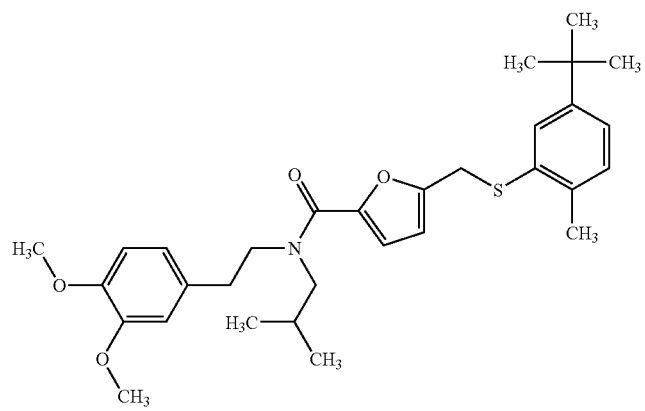 |
| 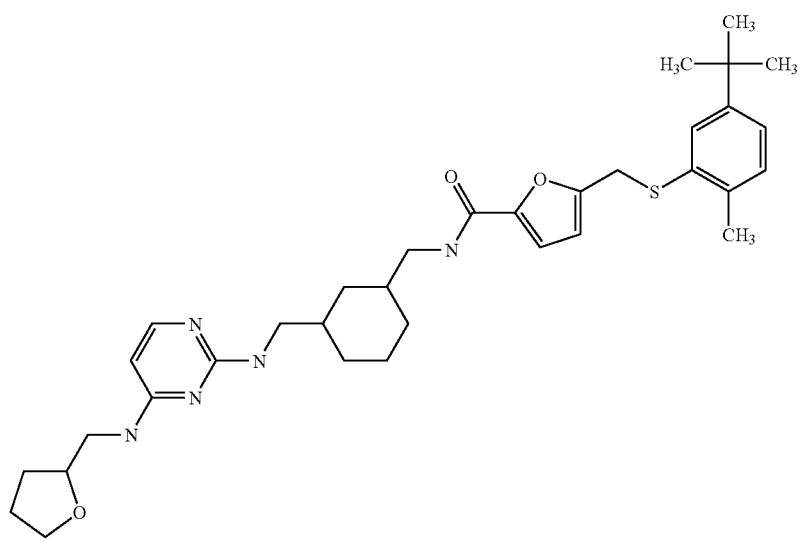 |

-continued
MOLSTRUCTURE
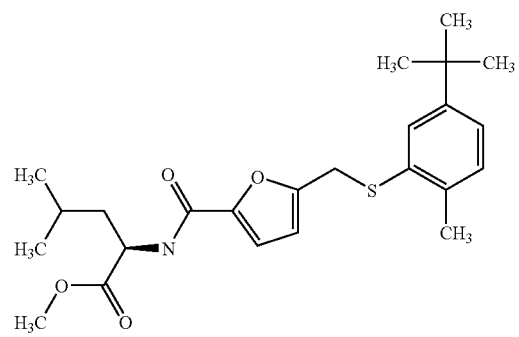
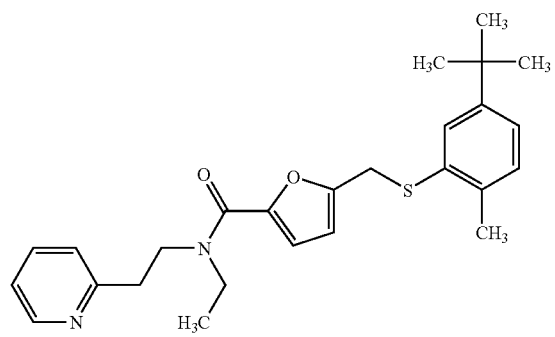
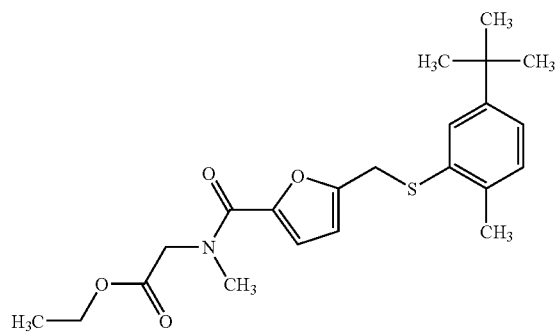
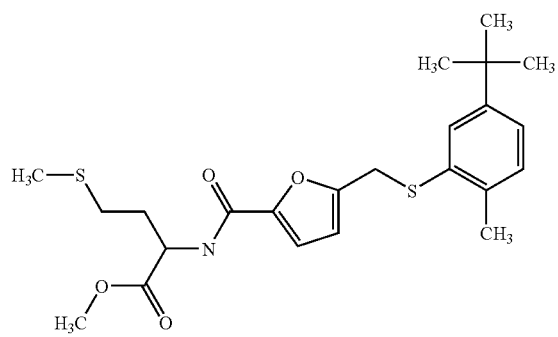

| MOLSTRUCTURE |
| --- |
| 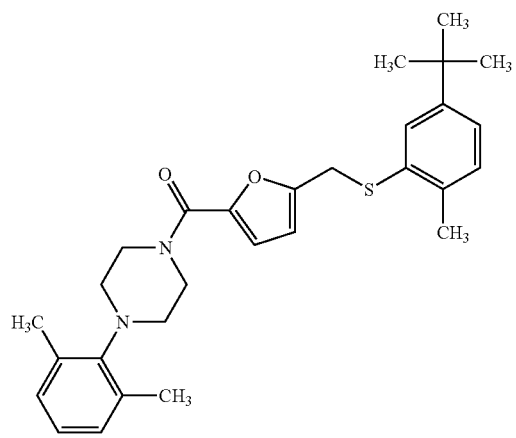 |
| 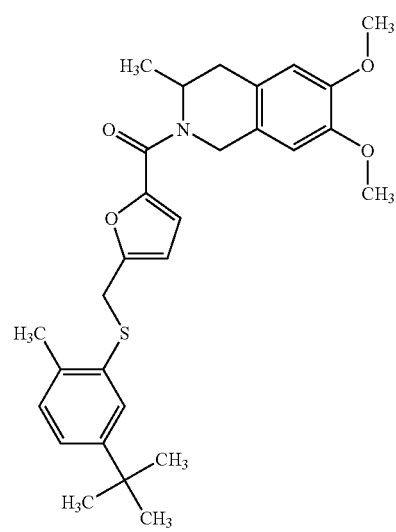 |
| 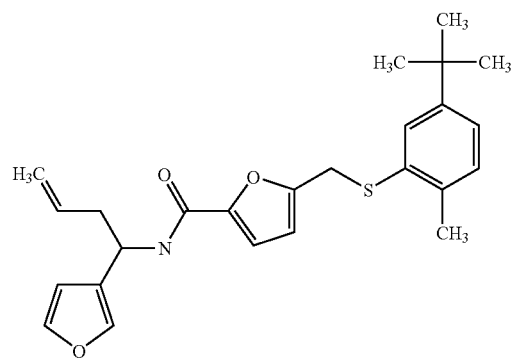 |

-continued
MOLSTRUCTURE
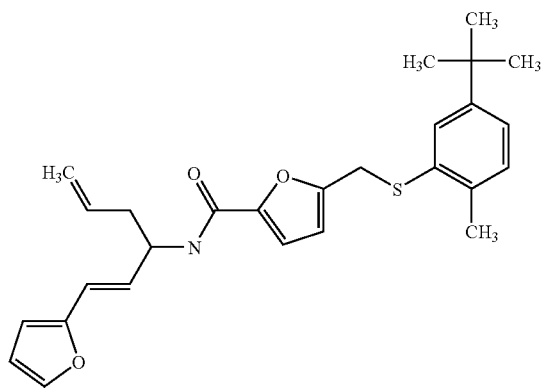
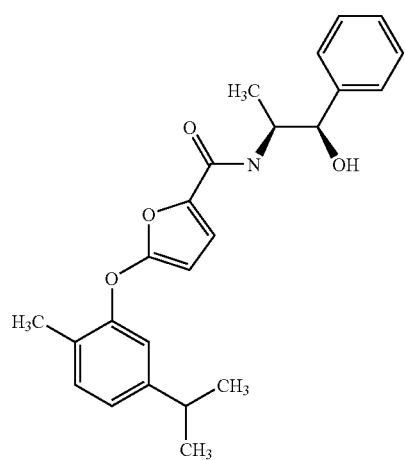
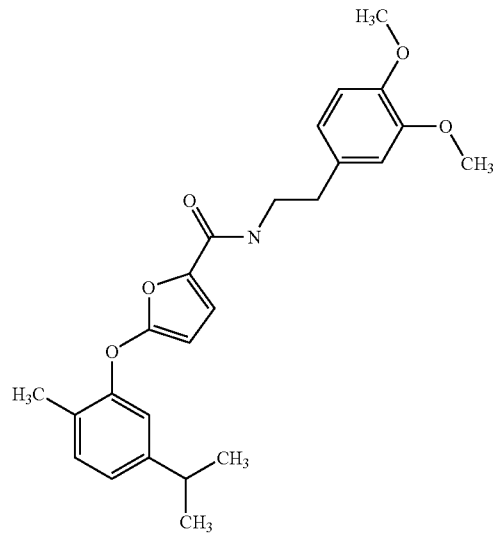

| MOLSTRUCTURE |
|---|
| 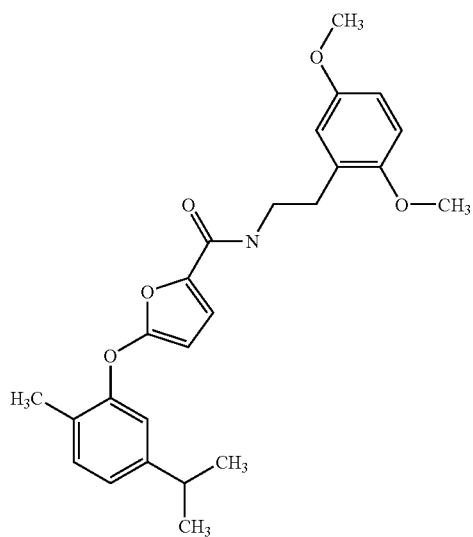 |
| 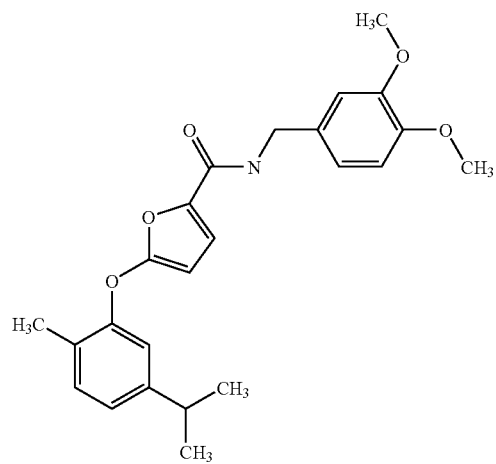 |
| 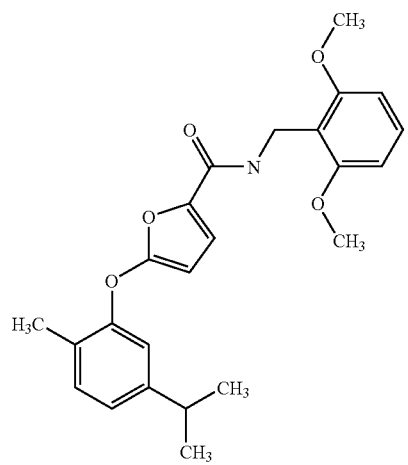 |

-continued
| MOLSTRUCTURE |
|---|
| 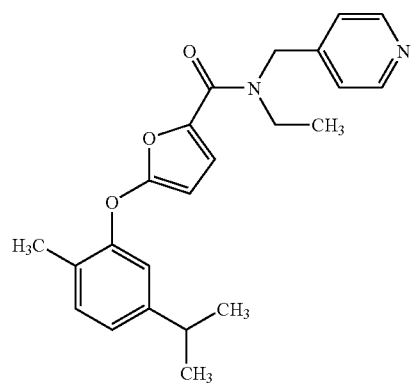 |
| 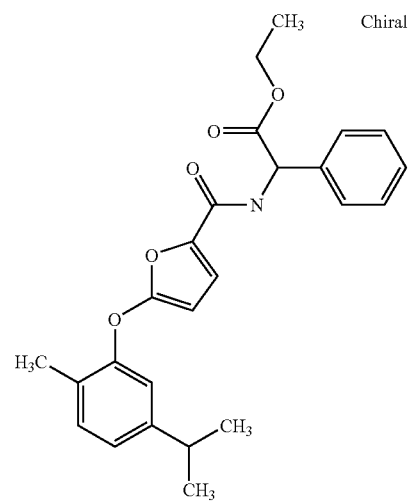 |
| 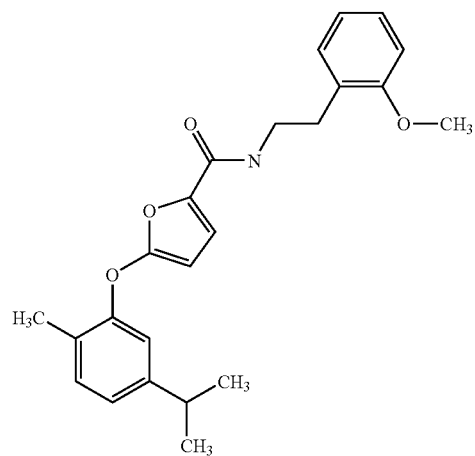 |

| MOLSTRUCTURE |
|---|
| 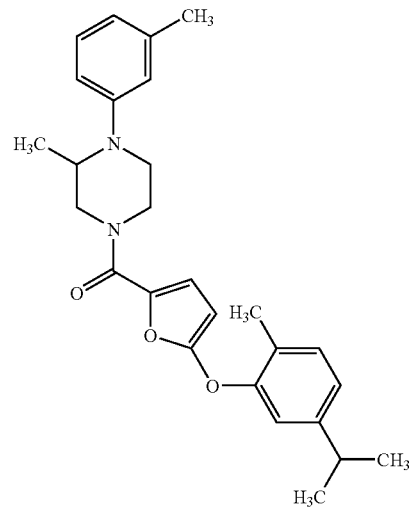 |
| 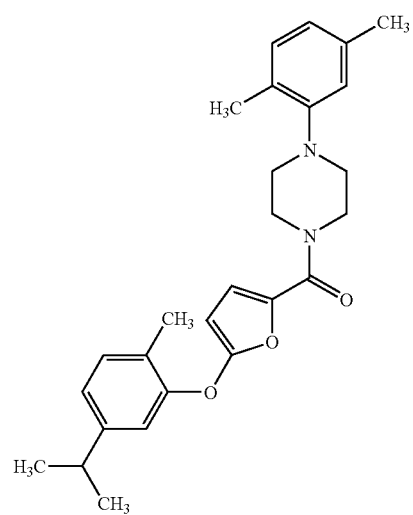 |
| 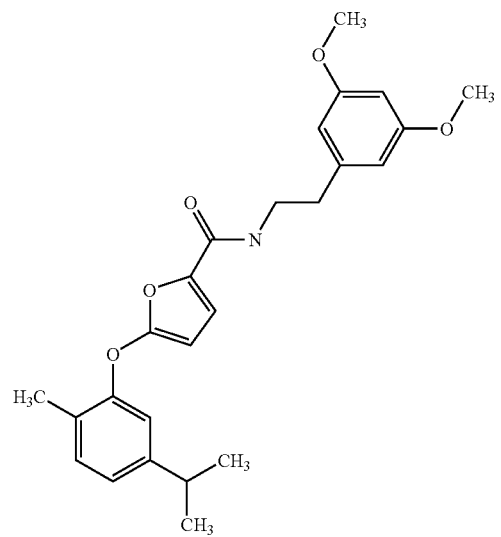 |

-continued
MOLSTRUCTURE
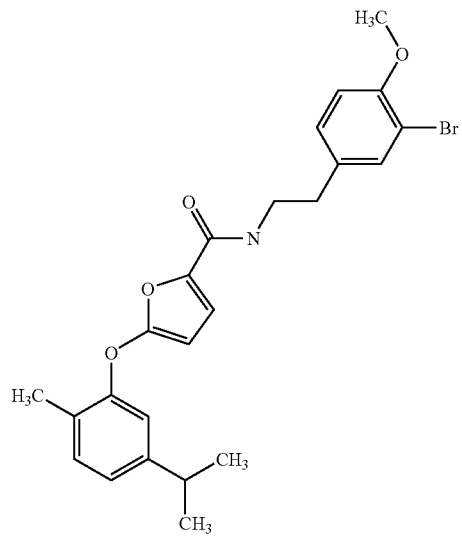
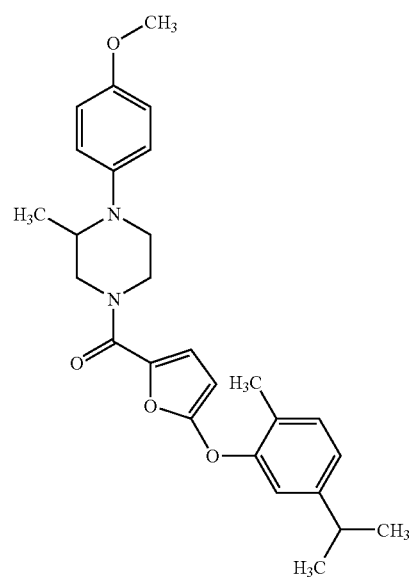
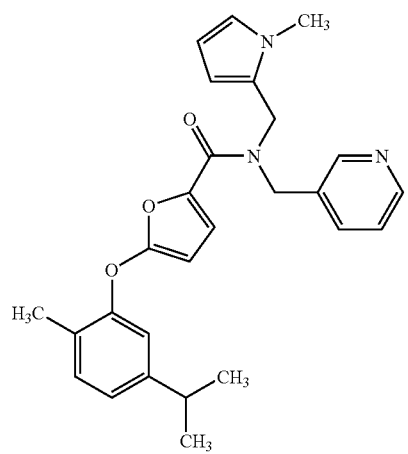

-continued
| MOLSTRUCTURE |
|---|
| 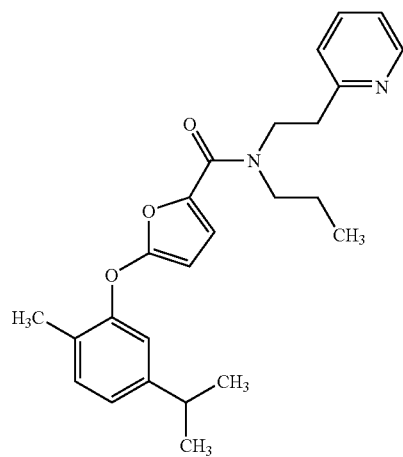 |
| 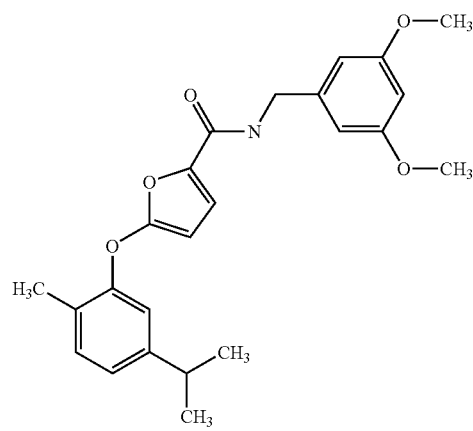 |
| 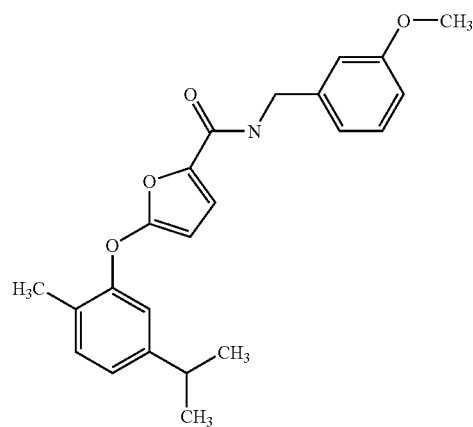 |

| MOLSTRUCTURE |
|---|
| 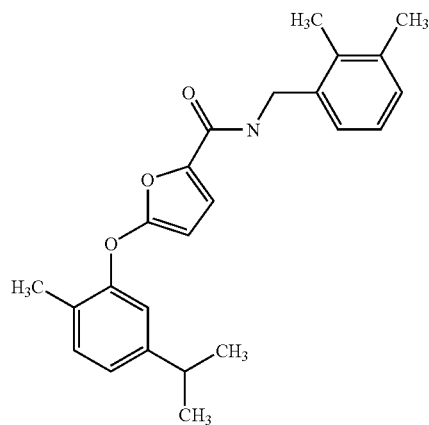 |
| 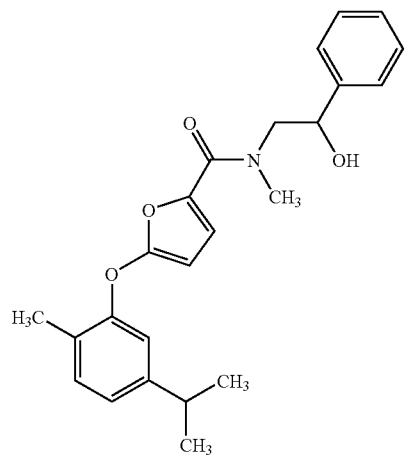 |
| 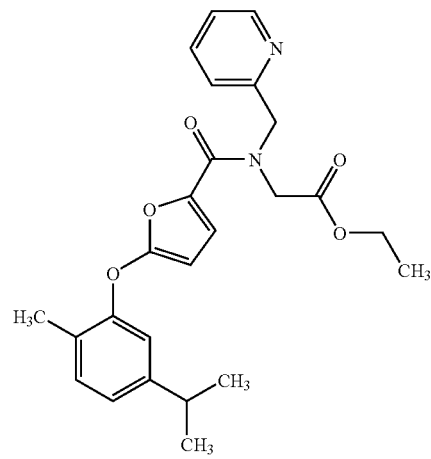 |

| MOLSTRUCTURE |
|---|
| 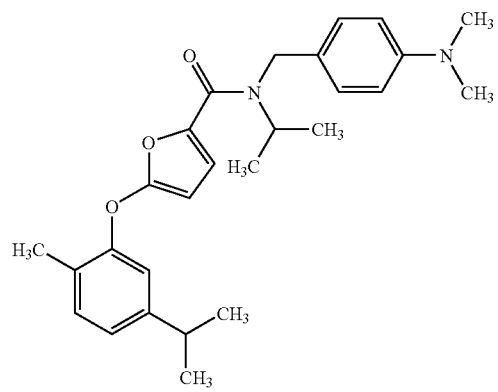 |
| 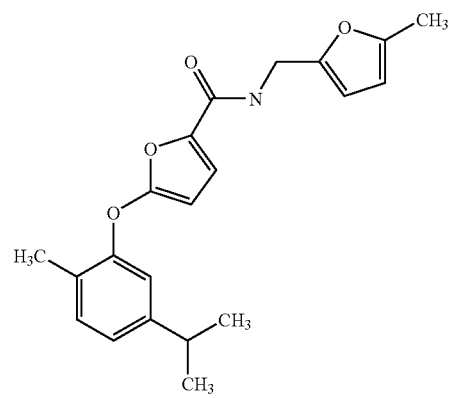 |
| 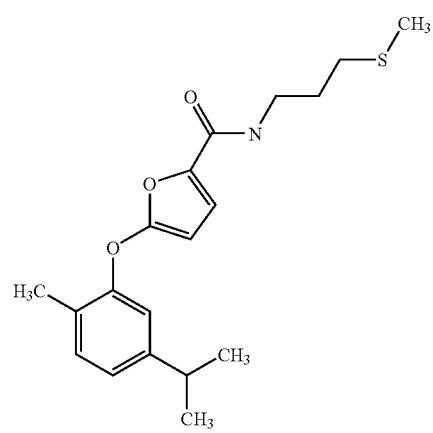 |

| MOLSTRUCTURE |
|---|
| 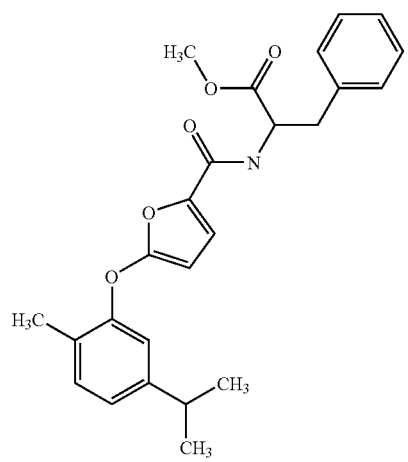 |
| 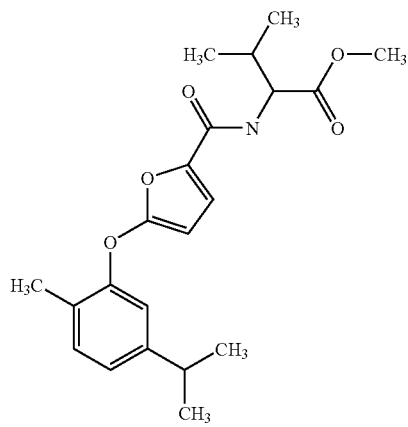 |
| 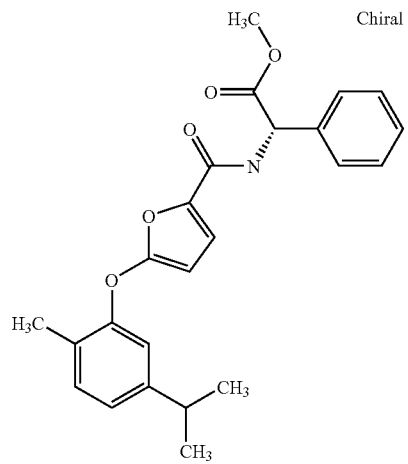 |

| MOLSTRUCTURE |
|---|
| 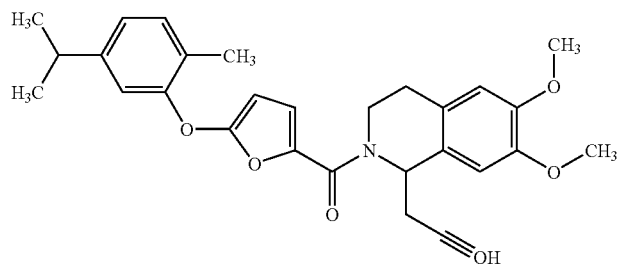 |
| 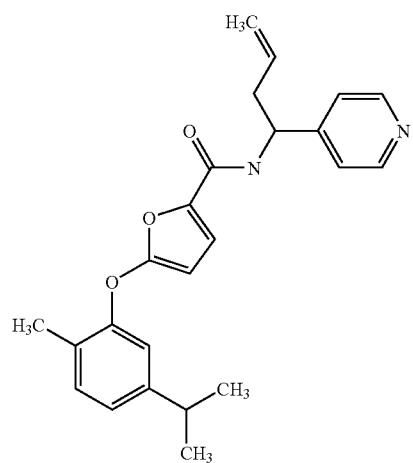 |
| 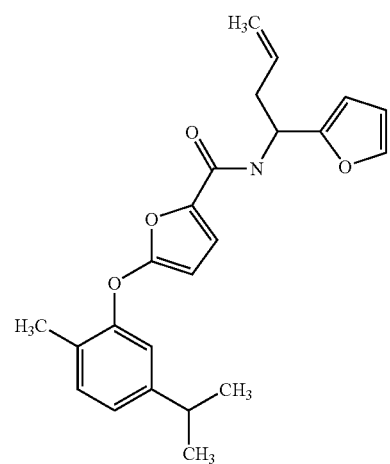 |

| MOLSTRUCTURE |
|---|
| 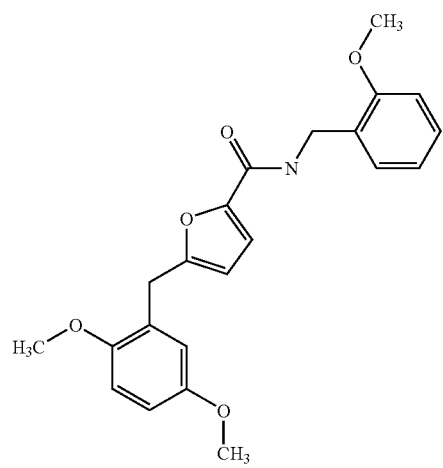 |
| 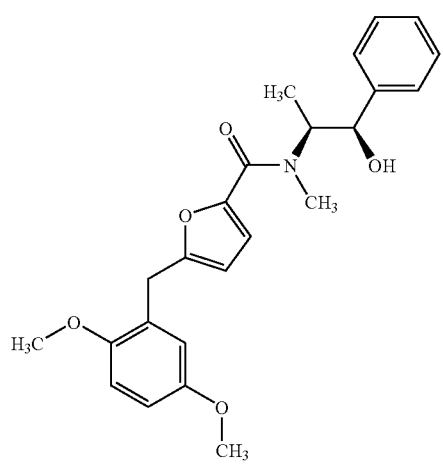 |
| 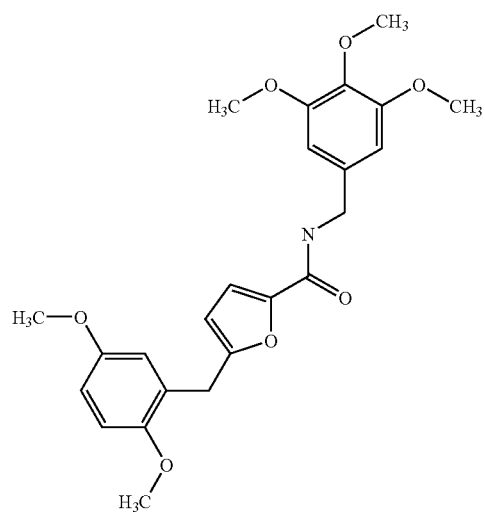 |

-continued
MOLSTRUCTURE
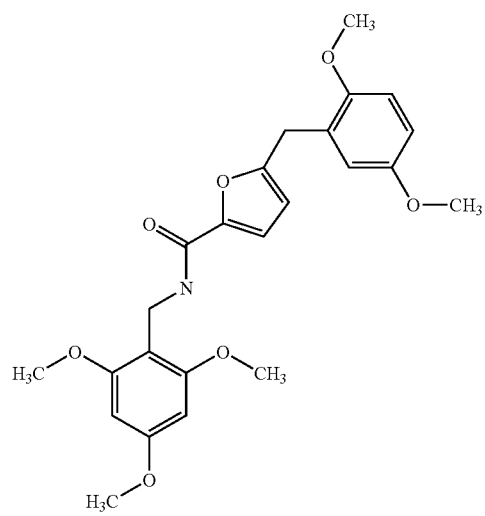
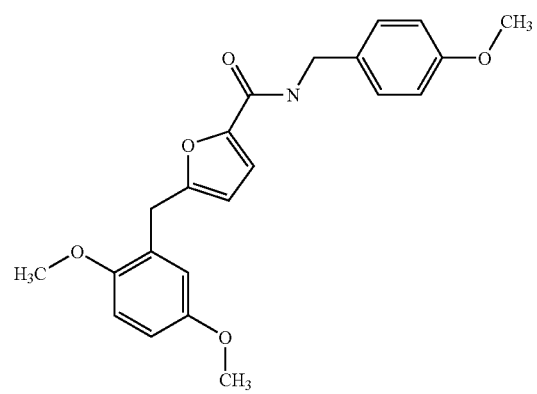
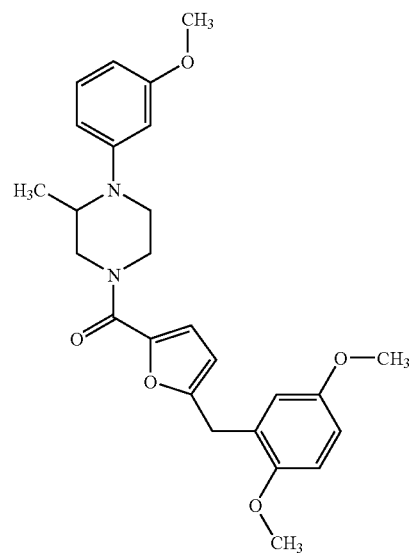

| MOLSTRUCTURE |
|---|
| 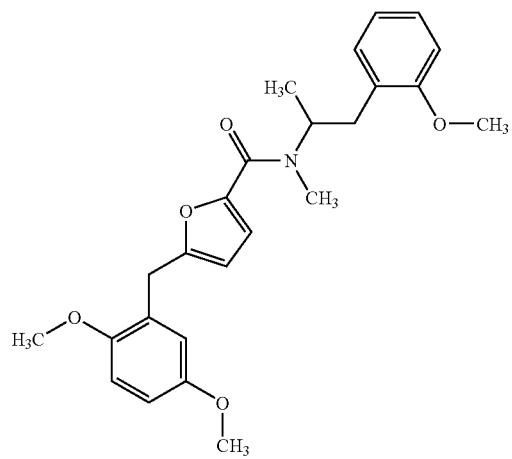 |
| 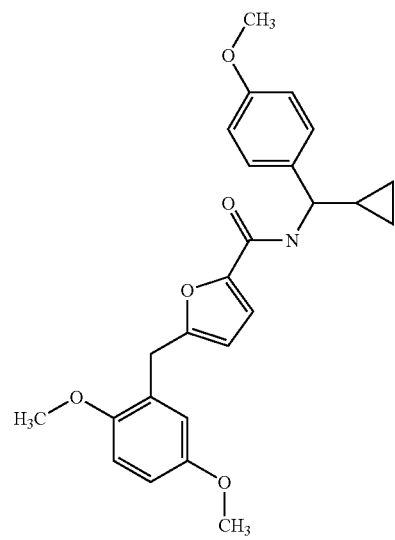 |
| 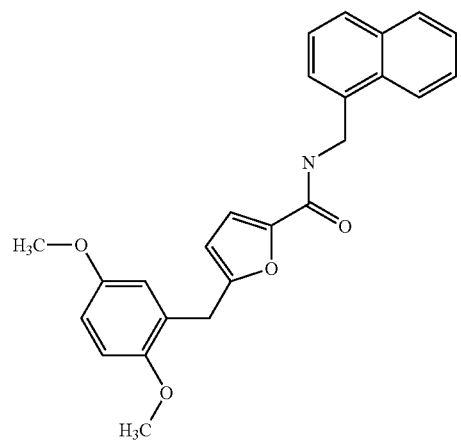 |

MOLSTRUCTURE
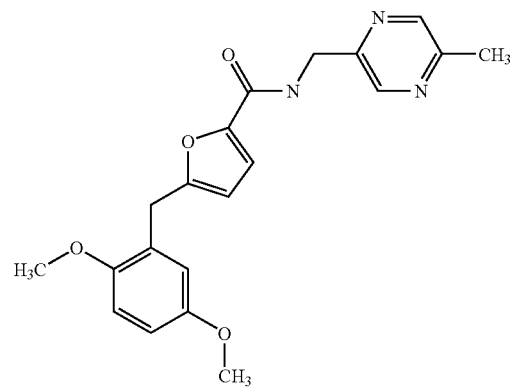
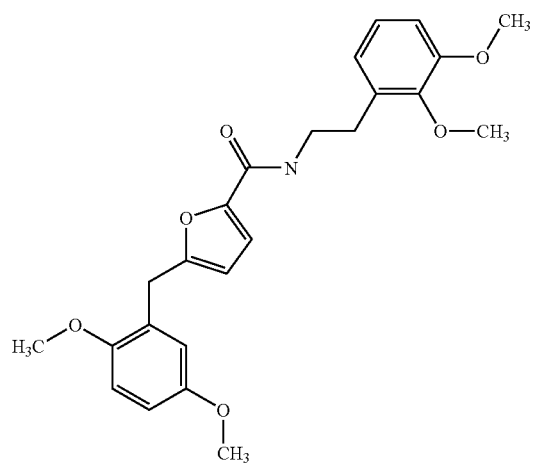
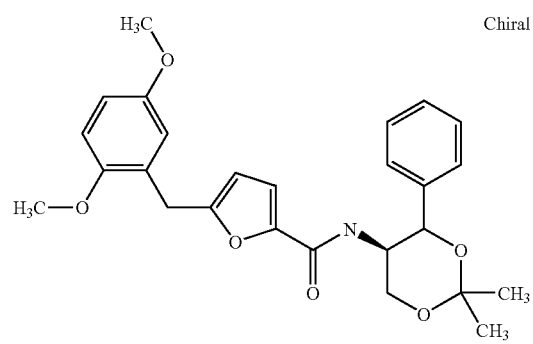
Chiral
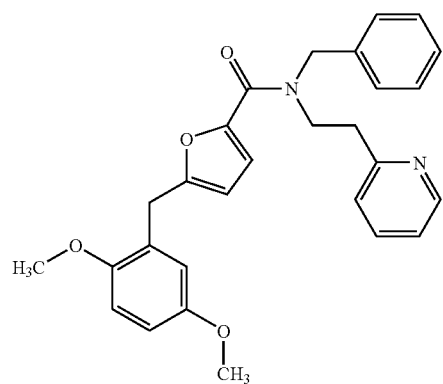

| MOLSTRUCTURE |
|---|
| 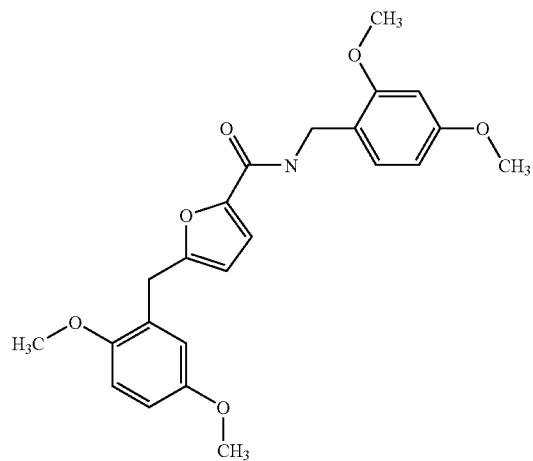 |
| 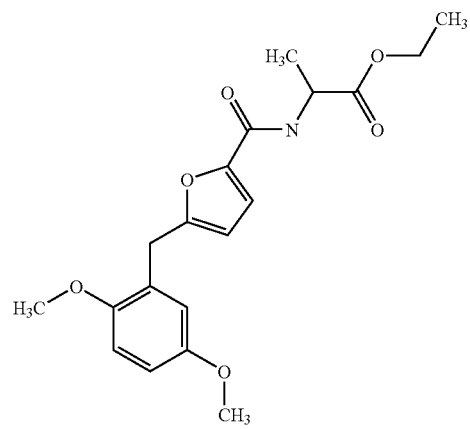 |
| 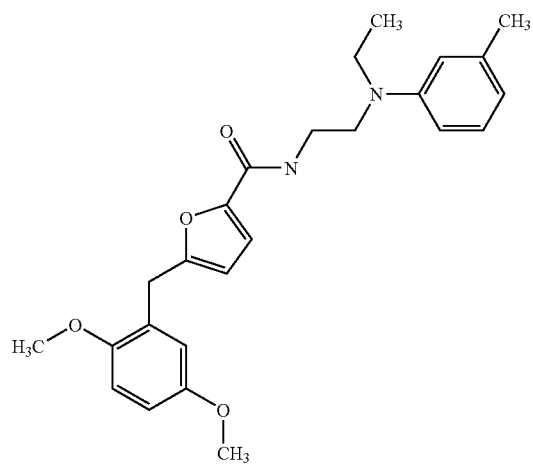 |

-continued
MOLSTRUCTURE
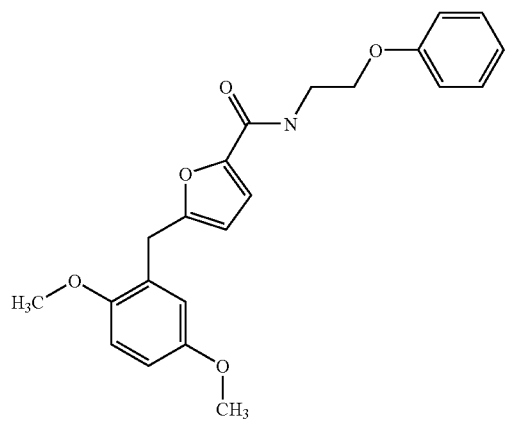
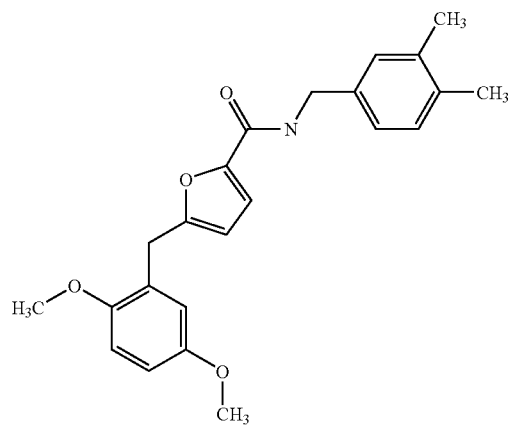
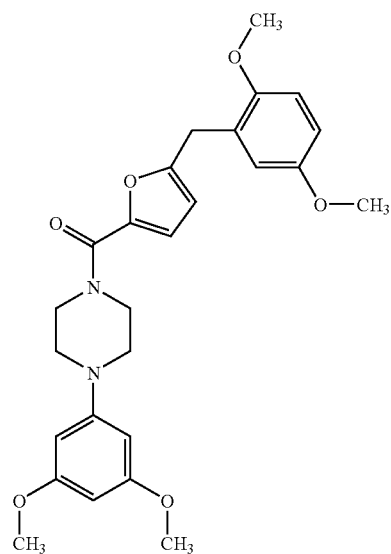

| MOLSTRUCTURE |
| --- |
| 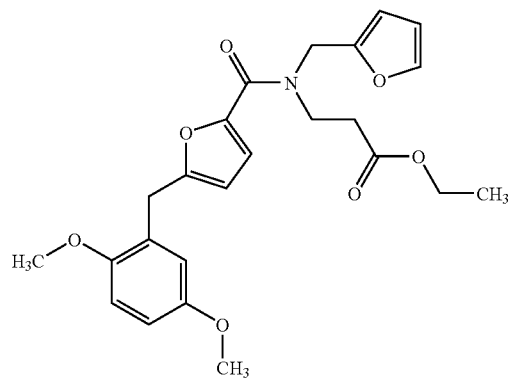 |
| 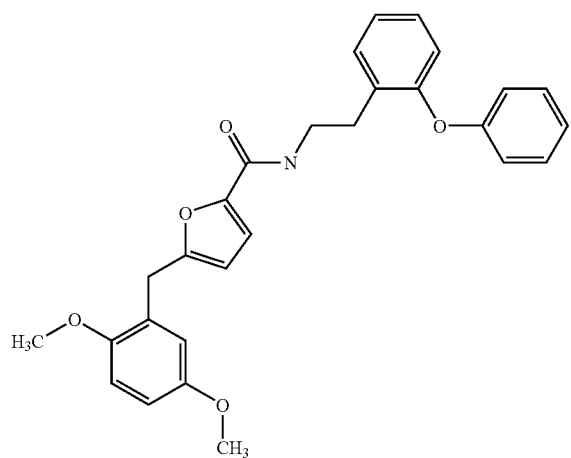 |
| 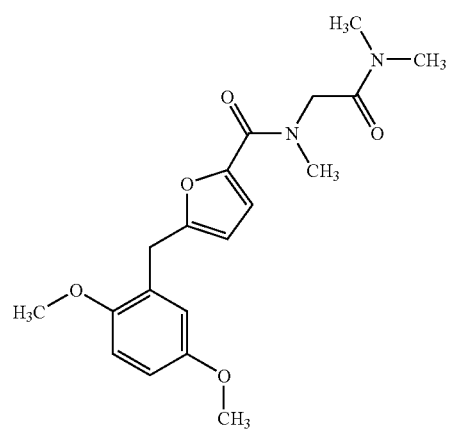 |

| MOLSTRUCTURE |
|---|
| 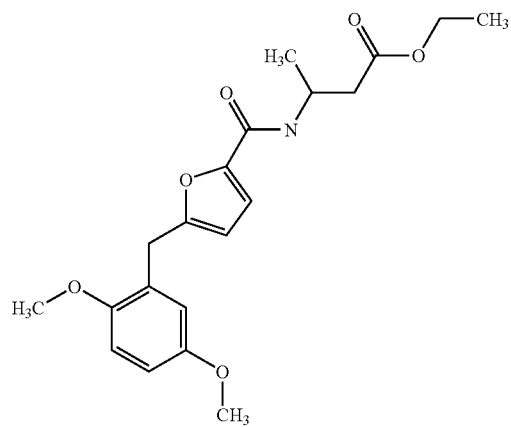 |
| 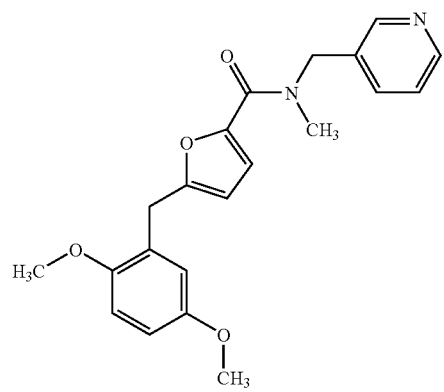 |
| 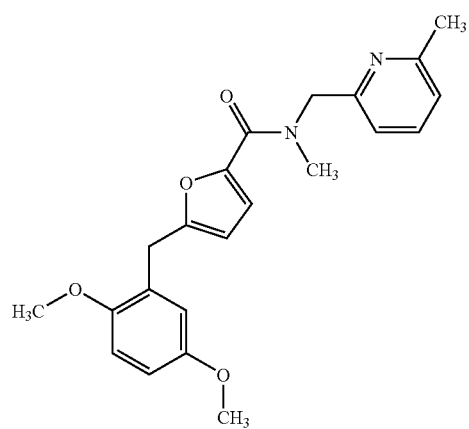 |

| MOLSTRUCTURE |
|---|
| 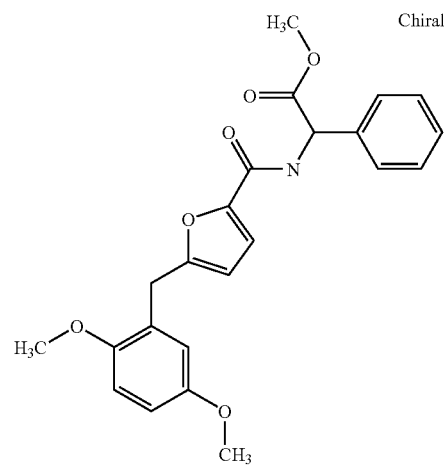 |
| 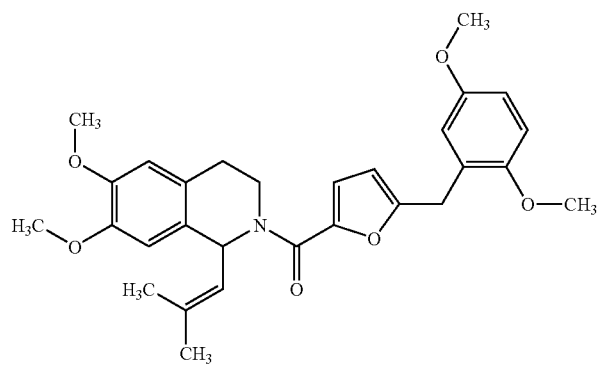 |
| 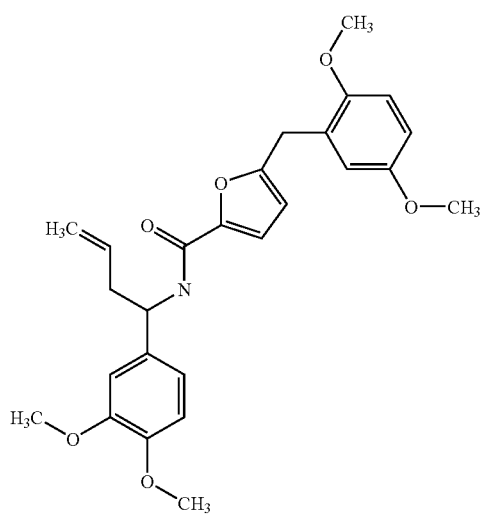 |

-continued
MOLSTRUCTURE
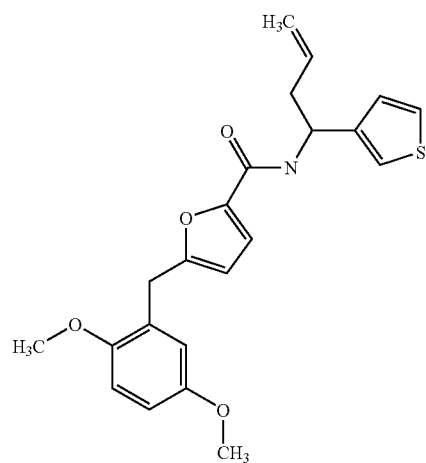
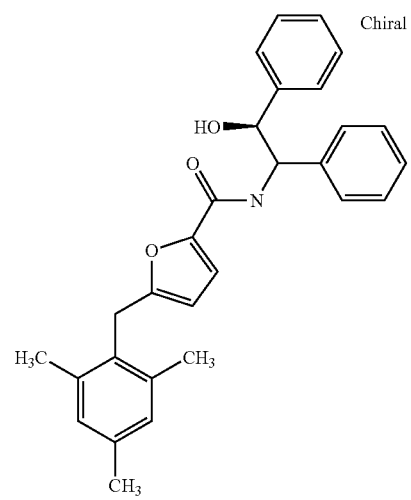
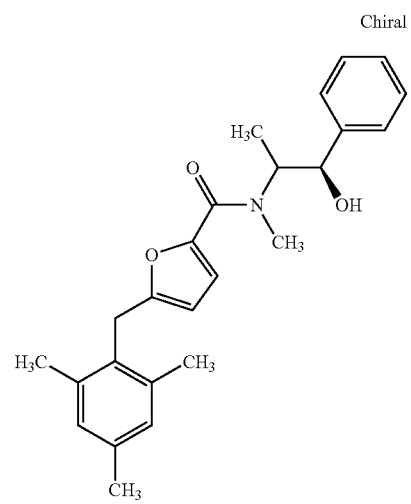

| MOLSTRUCTURE |
|---|
| 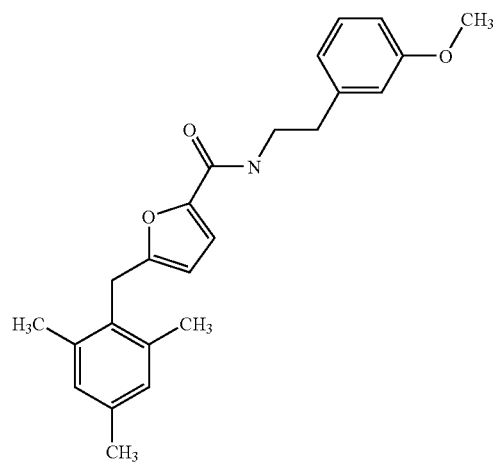 |
| 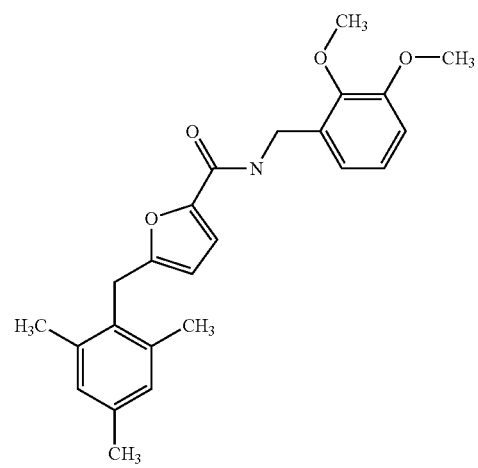 |
| 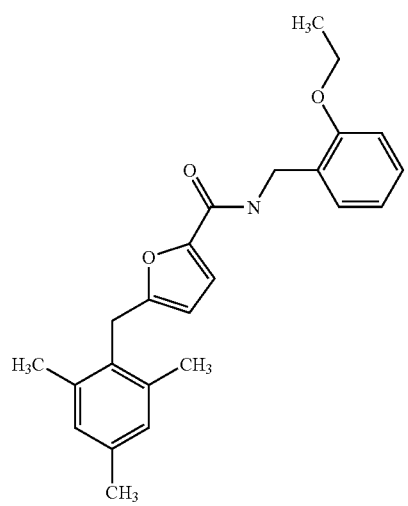 |

-continued
MOLSTRUCTURE
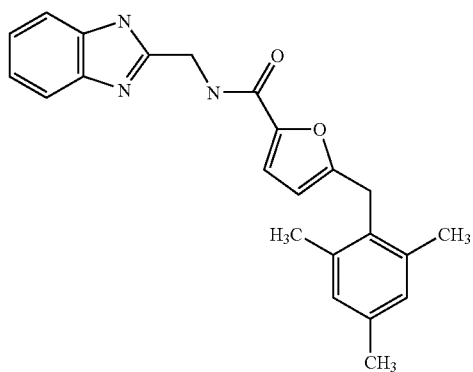
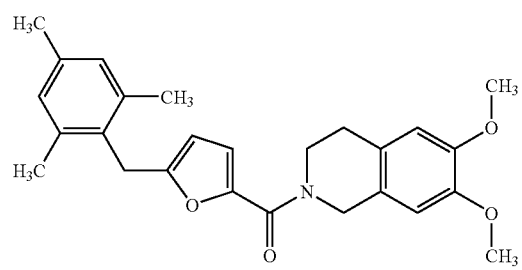
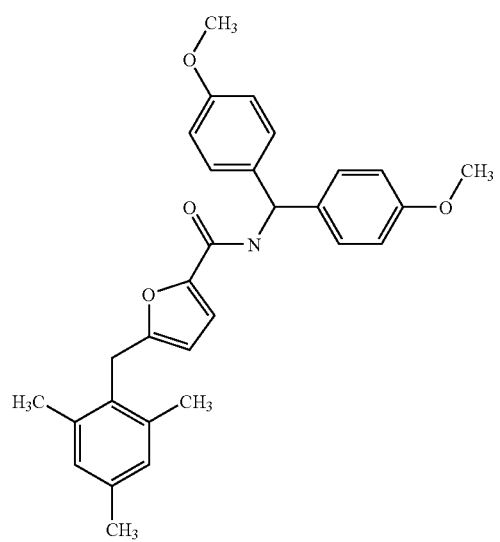

-continued
MOLSTRUCTURE
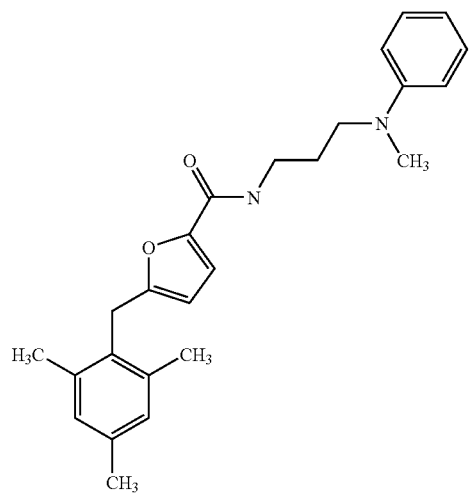
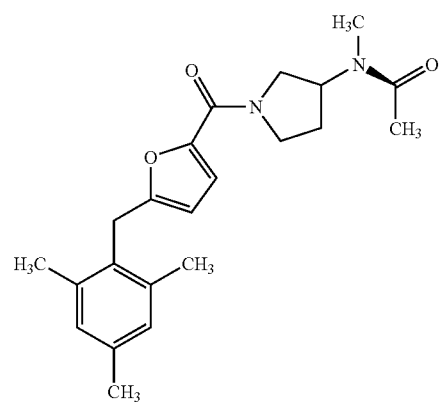
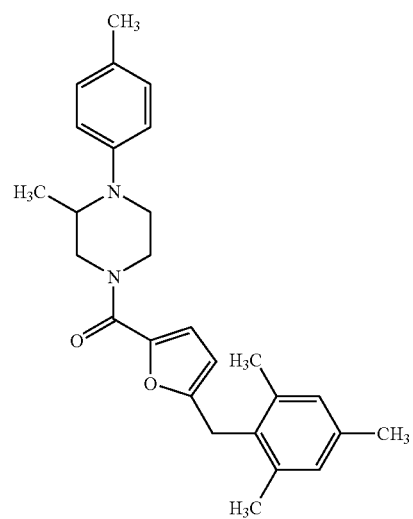

-continued
MOLSTRUCTURE
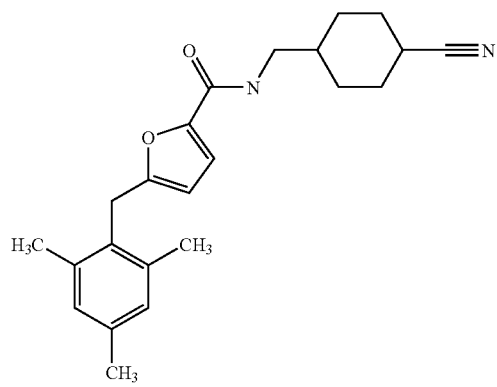
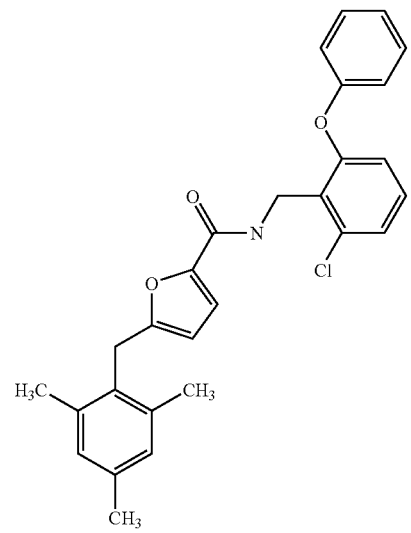
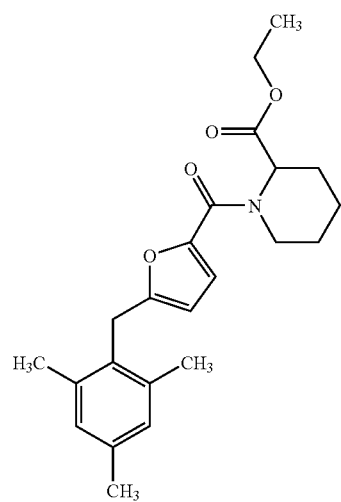

| MOLSTRUCTURE |
|---|
| 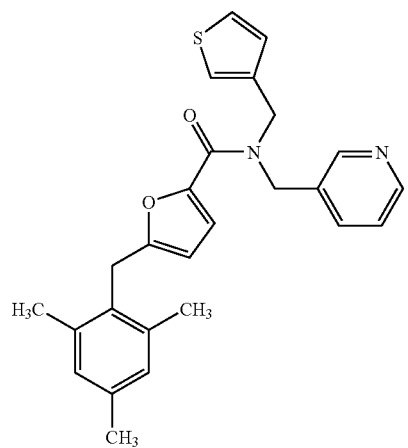 |
| 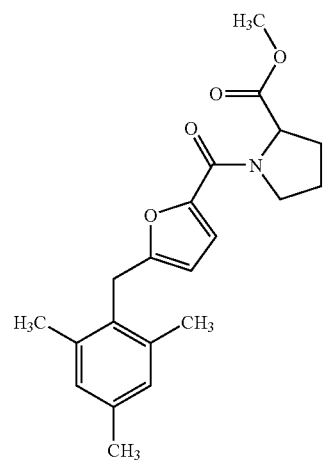 |
| 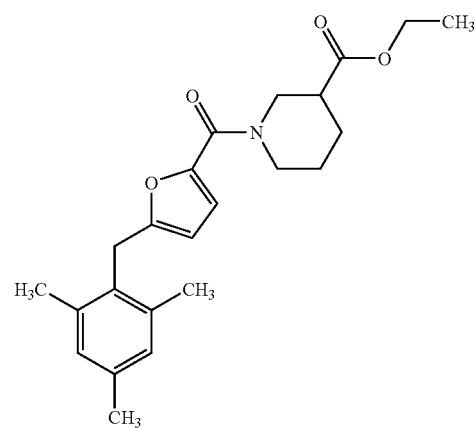 |

-continued
MOLSTRUCTURE
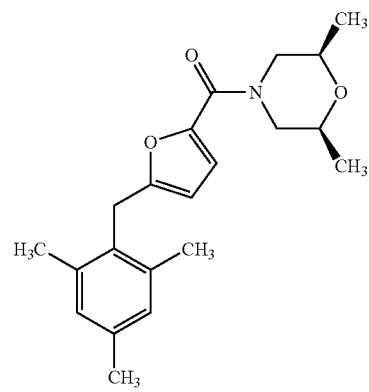
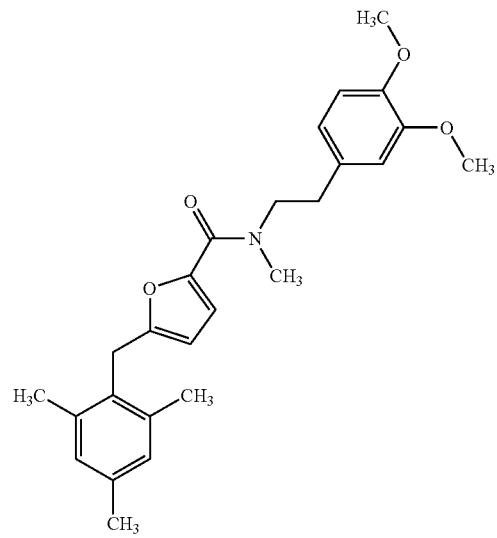
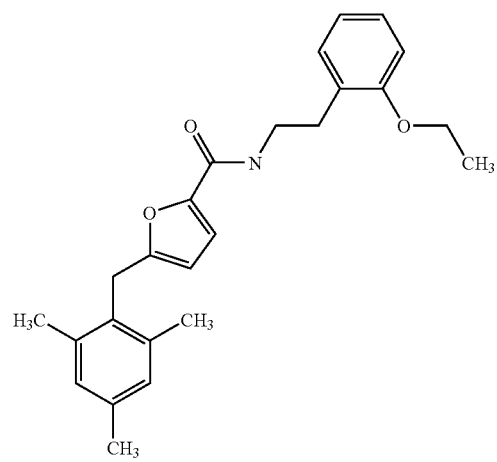

| MOLSTRUCTURE |
|---|
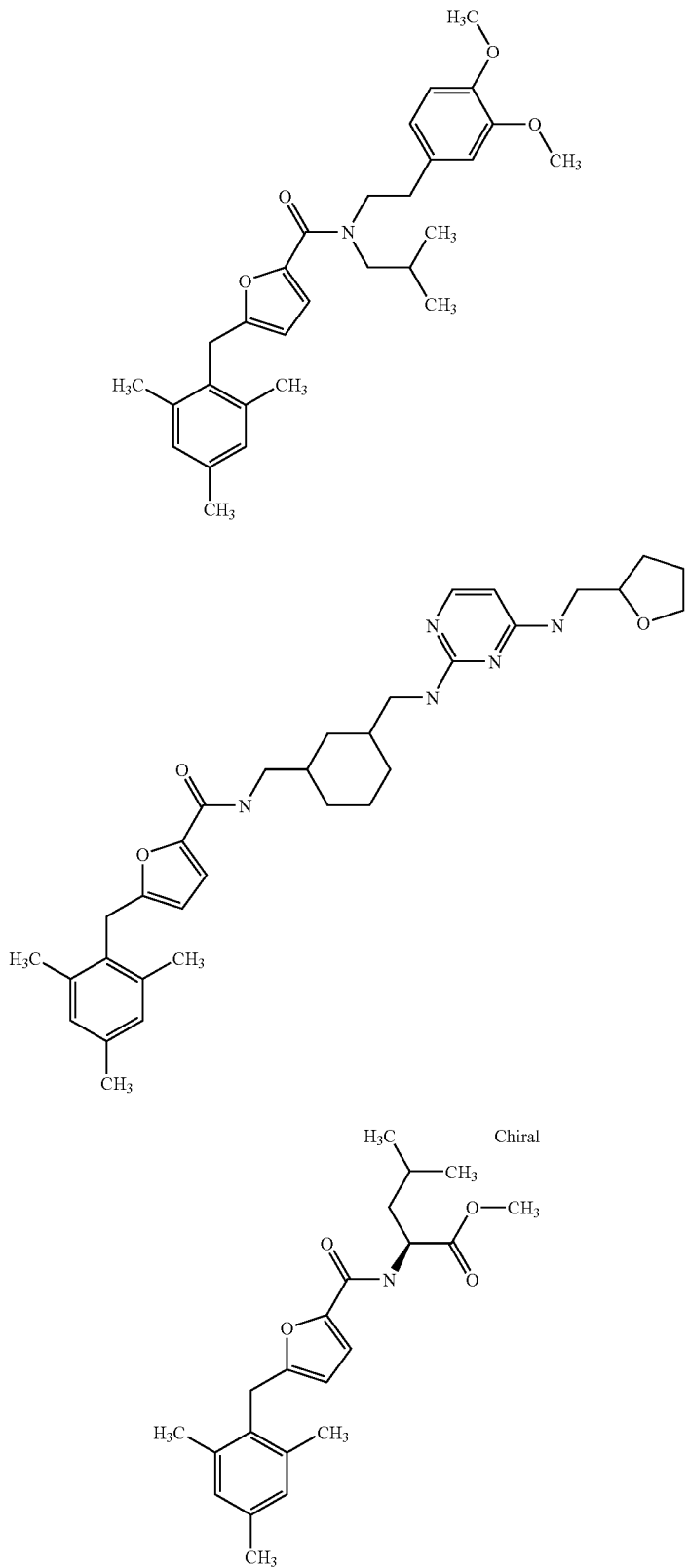

| MOLSTRUCTURE |
|---|
| 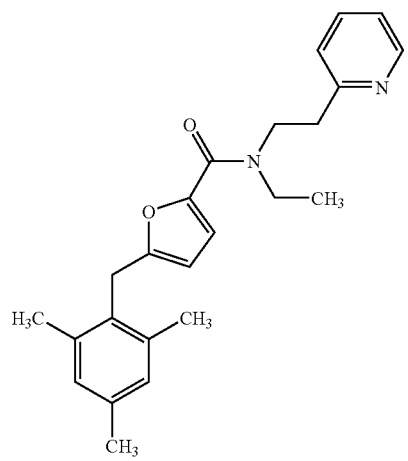 |
| 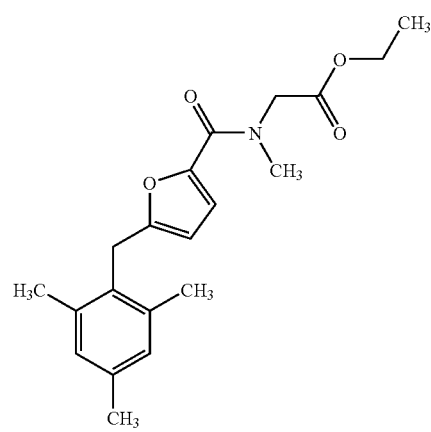 |
| 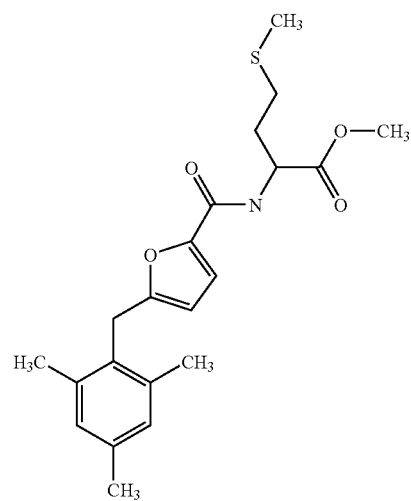 |

| MOLSTRUCTURE |
|---|
| 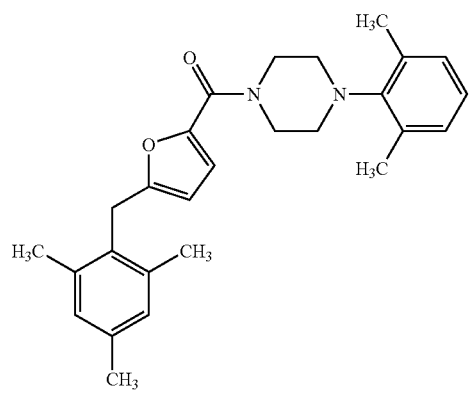 |
| 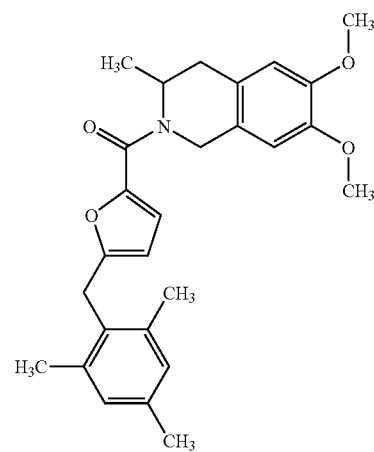 |
| 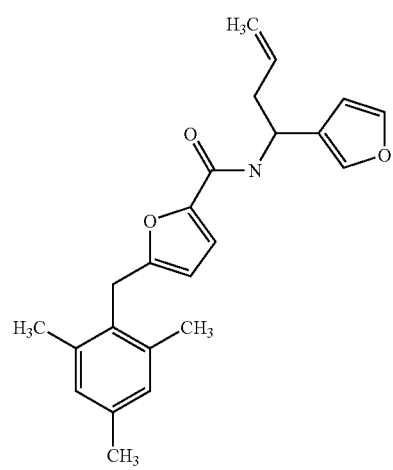 |

-continued
MOLSTRUCTURE
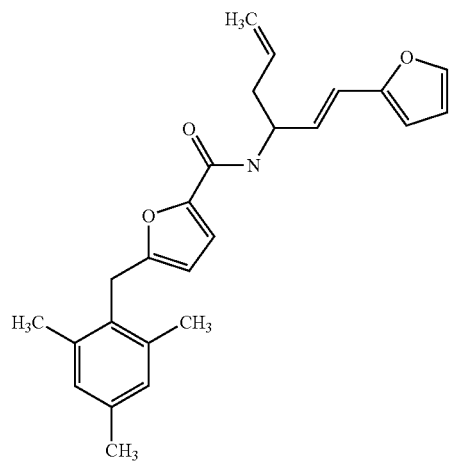
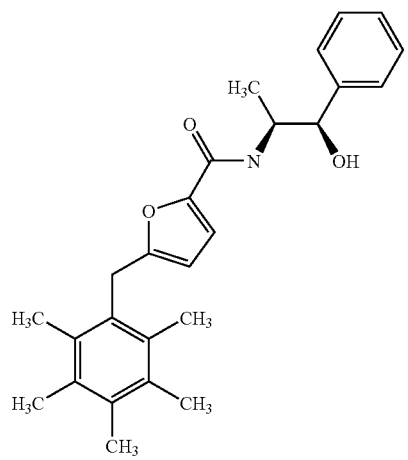
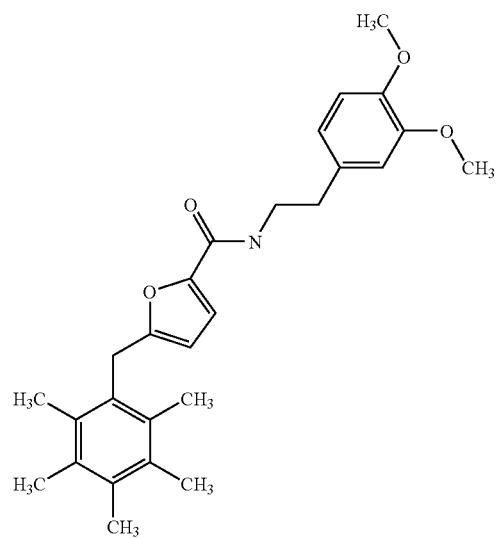

| MOLSTRUCTURE |
|---|
| 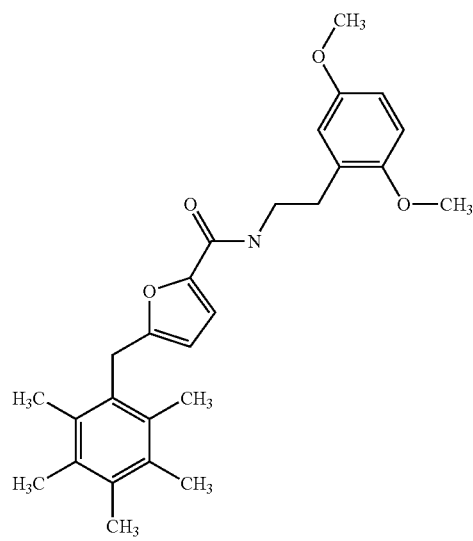 |
| 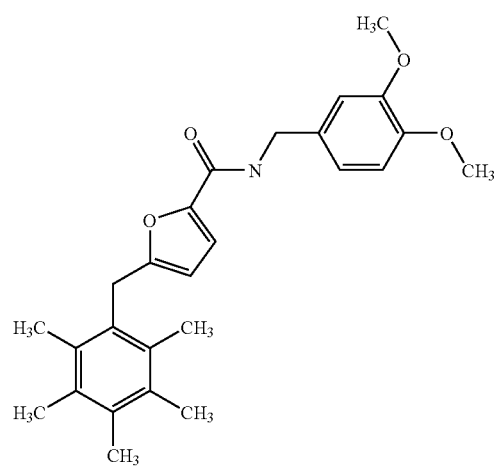 |
| 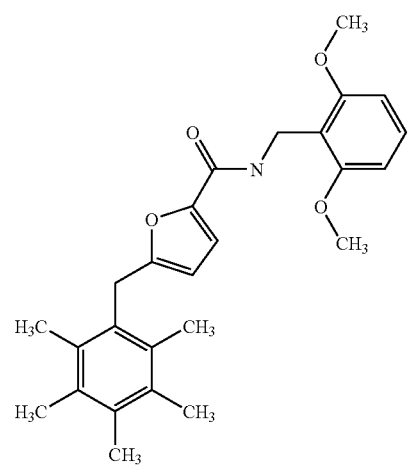 |

-continued
MOLSTRUCTURE
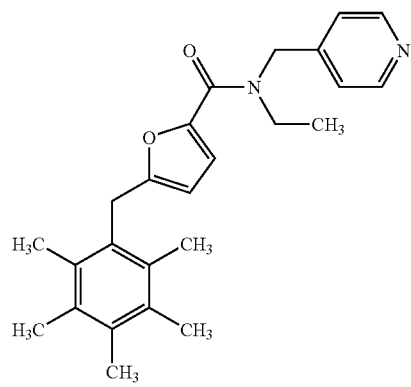
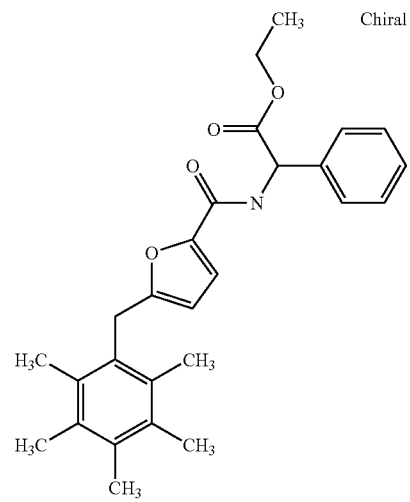
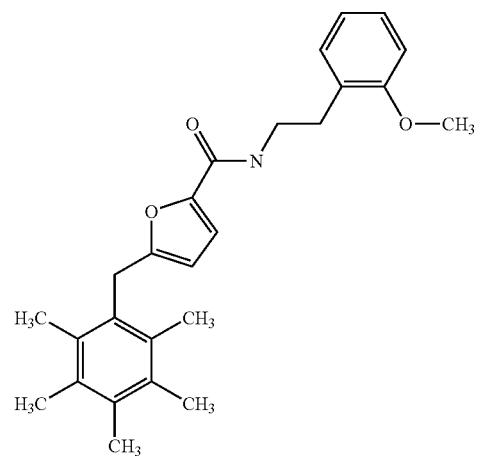

| MOLSTRUCTURE |
| --- |
| 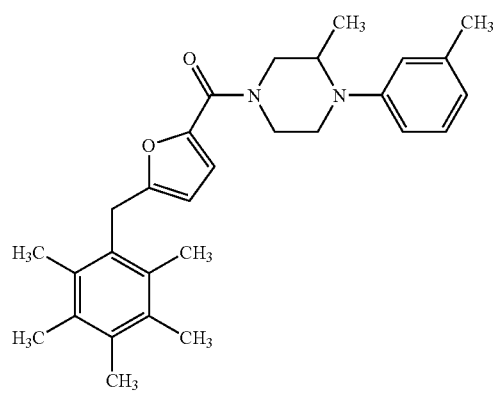 |
| 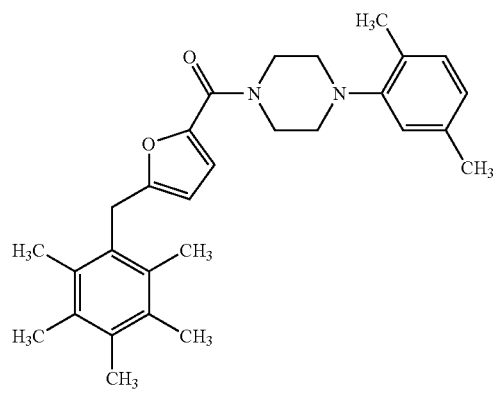 |
| 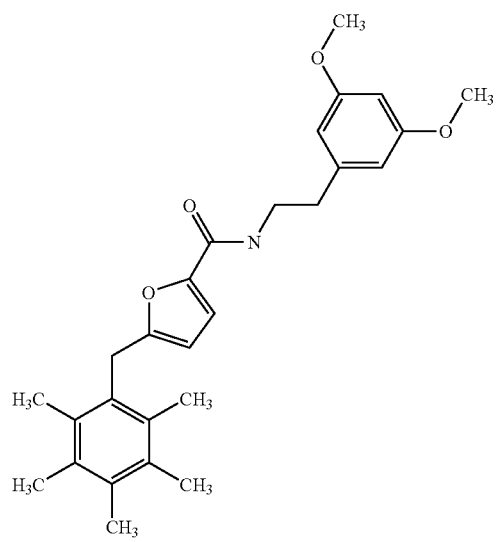 |

| MOLSTRUCTURE |
|---|
| 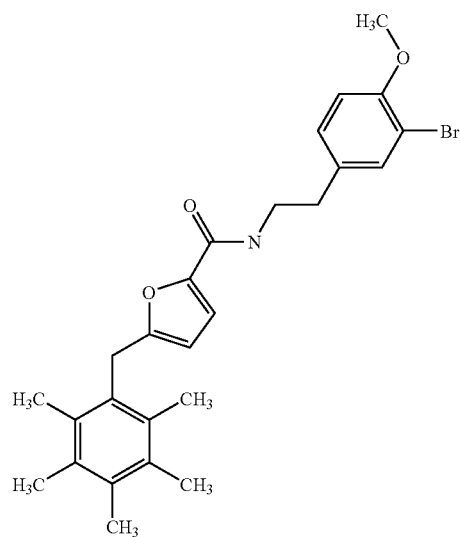 |
| 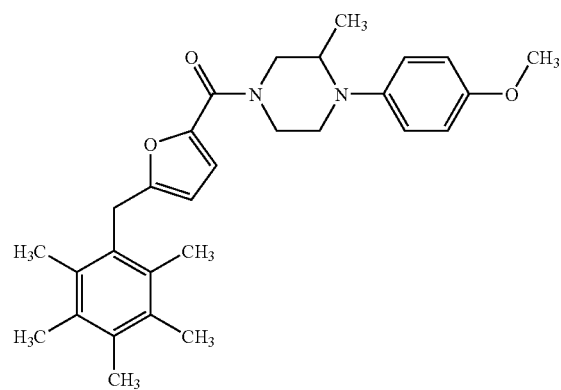 |
| 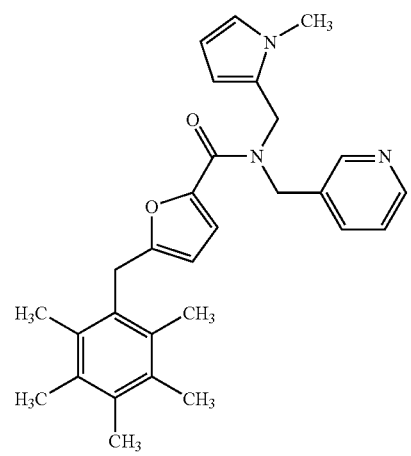 |

| MOLSTRUCTURE |
|---|
| 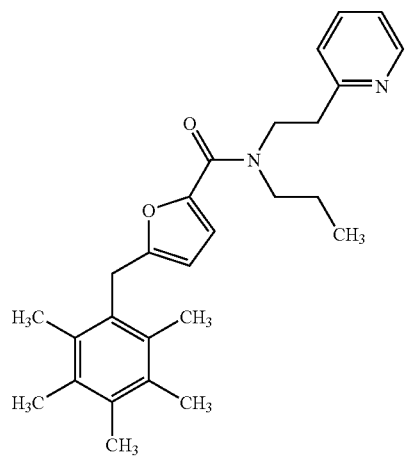 |
| 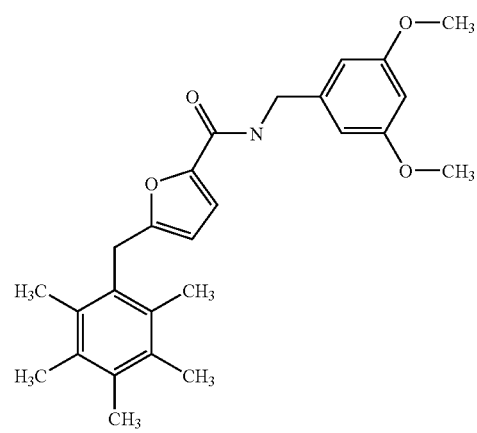 |
| 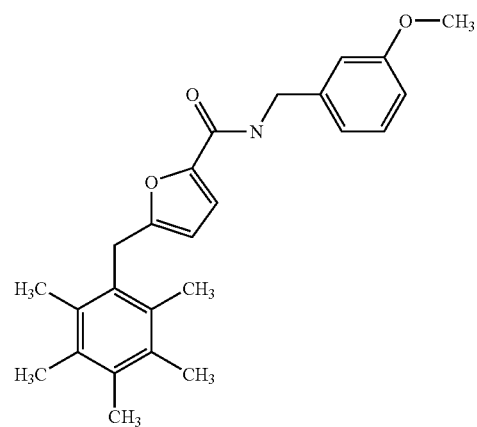 |

-continued
| MOLSTRUCTURE |
|---|
| 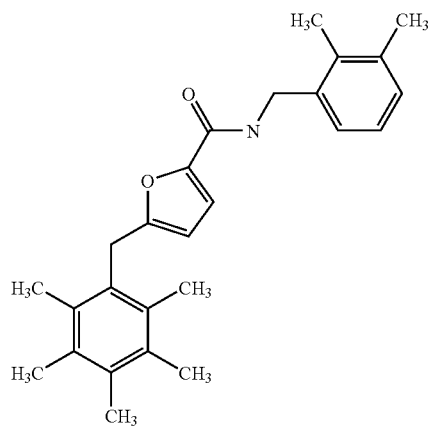 |
| 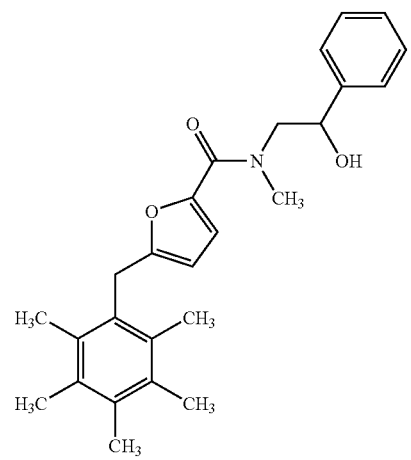 |
| 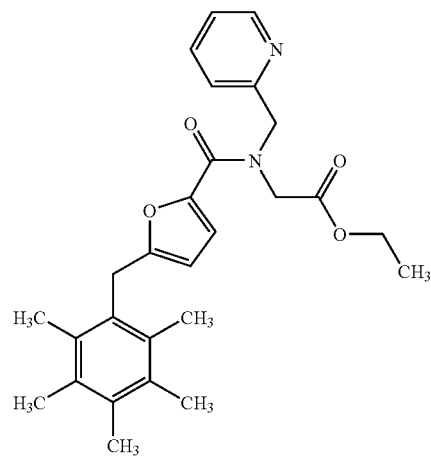 |

| MOLSTRUCTURE |
|---|
| 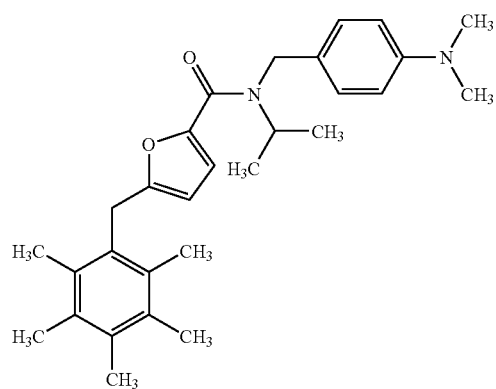 |
| 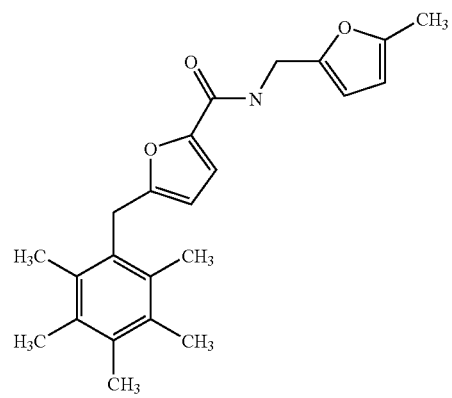 |
| 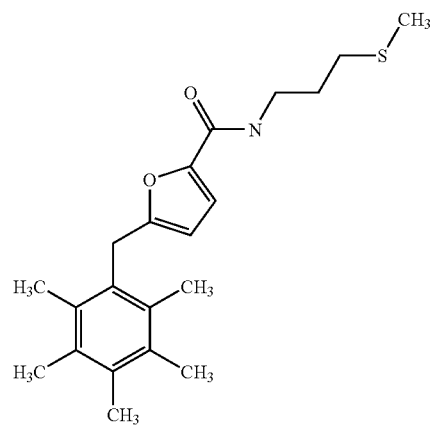 |

| MOLSTRUCTURE |
|---|
| 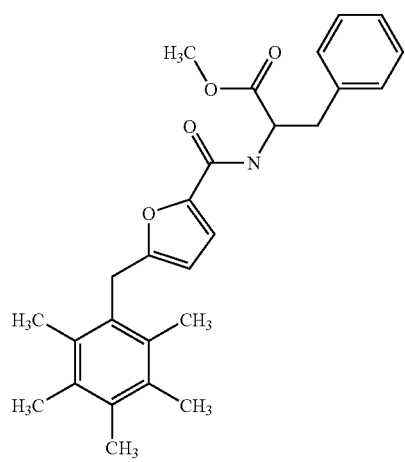 |
| 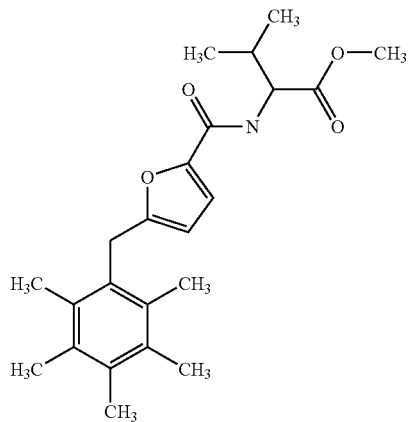 |
| 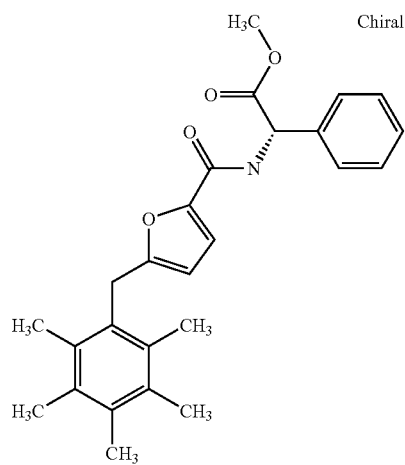 |

-continued
MOLSTRUCTURE
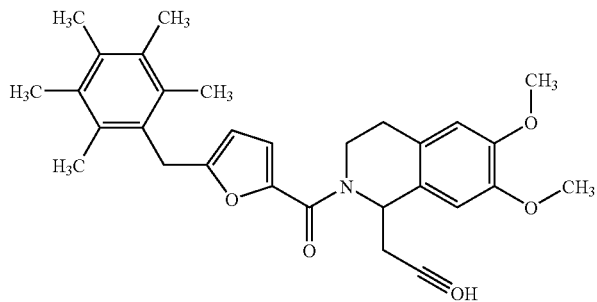
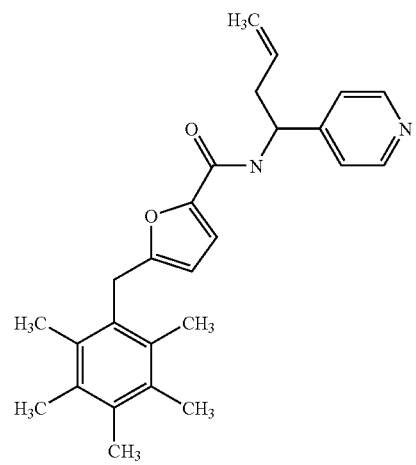
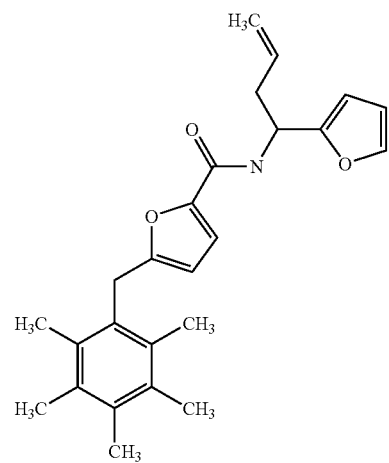

-continued
MOLSTRUCTURE
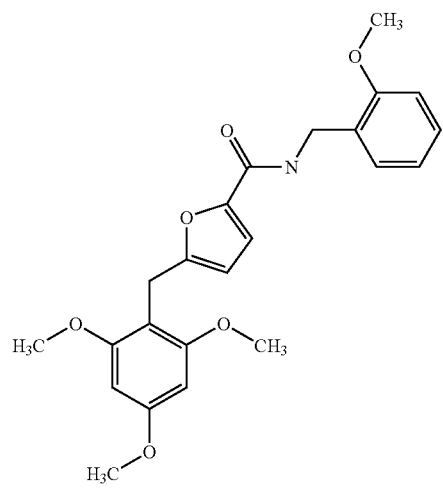
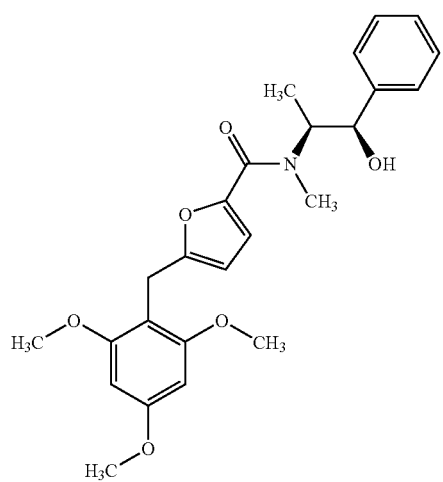
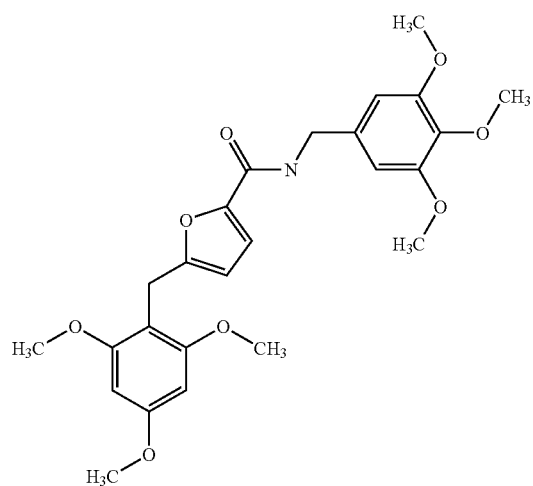

-continued
MOLSTRUCTURE
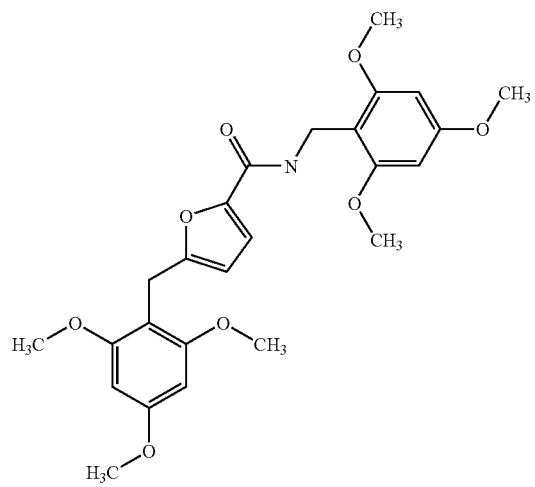
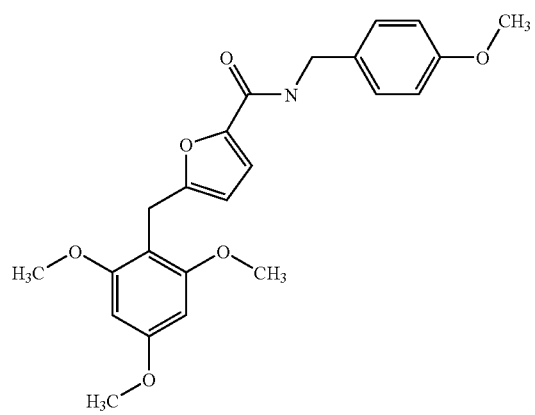
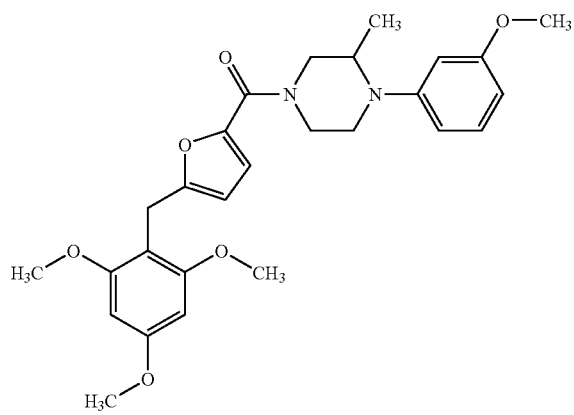

-continued
MOLSTRUCTURE
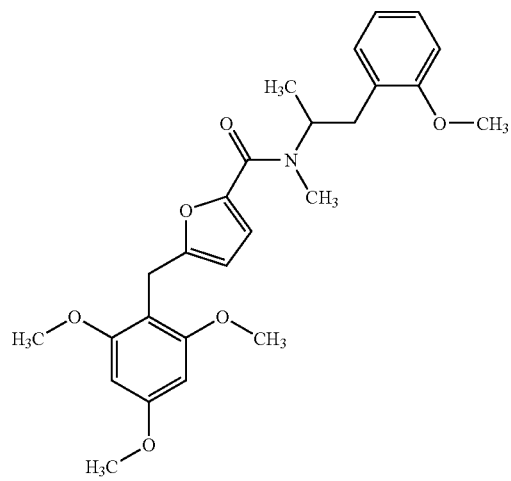
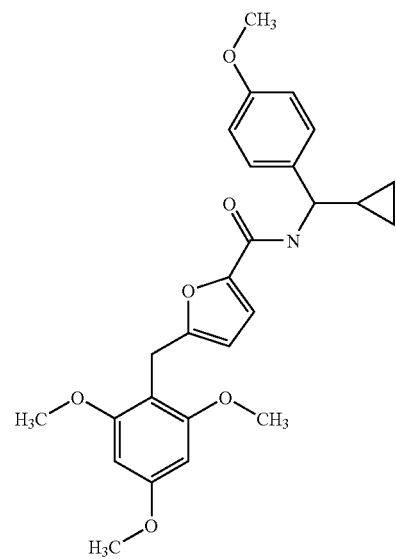
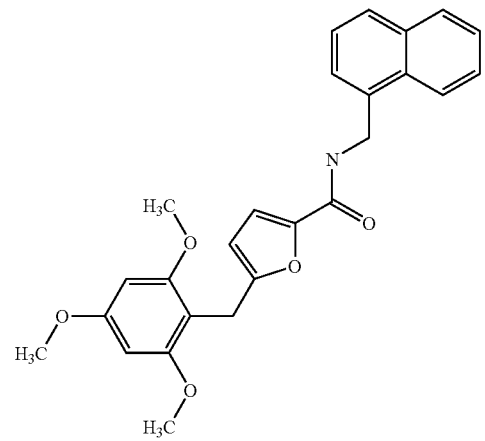

| MOLSTRUCTURE |
|---|
| 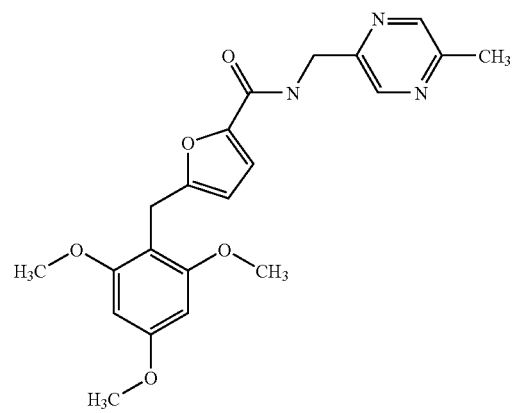 |
| 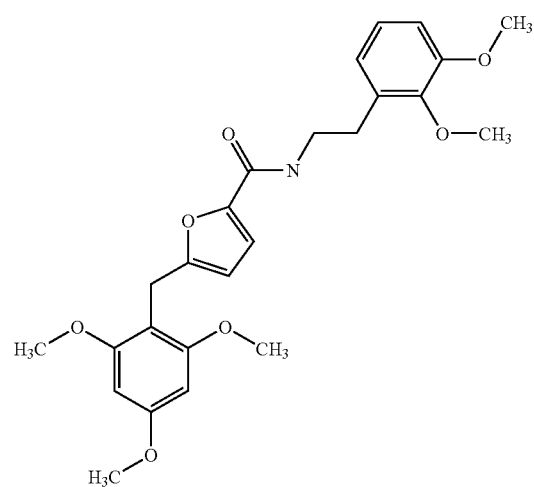 |
| 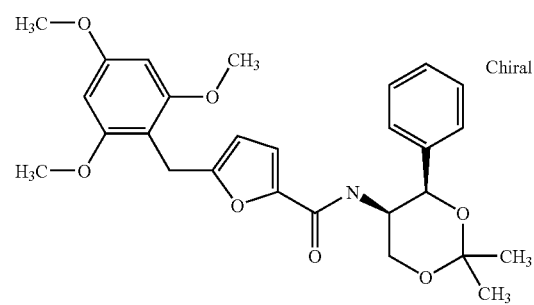 |

| MOLSTRUCTURE |
|---|
| 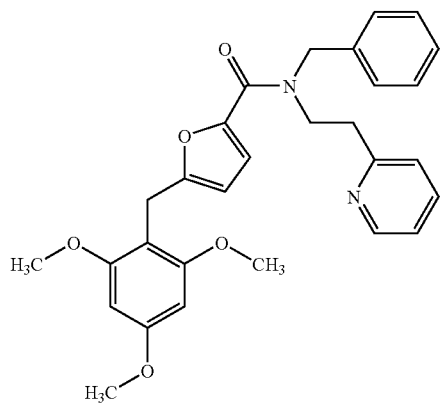 |
| 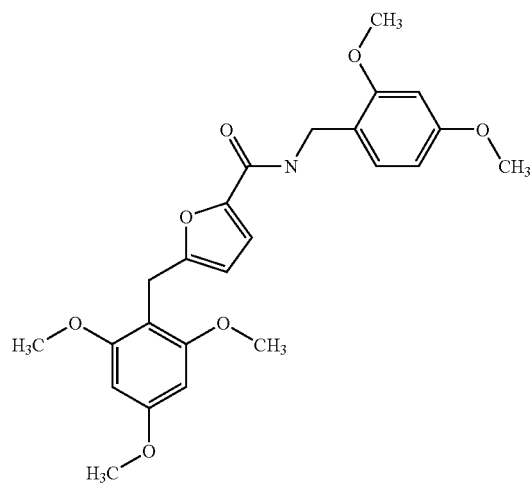 |
| 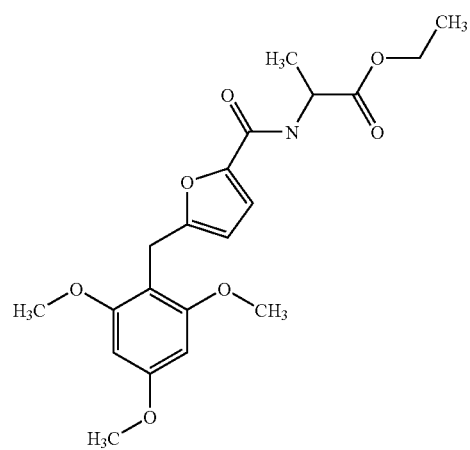 |

| MOLSTRUCTURE |
|---|
| 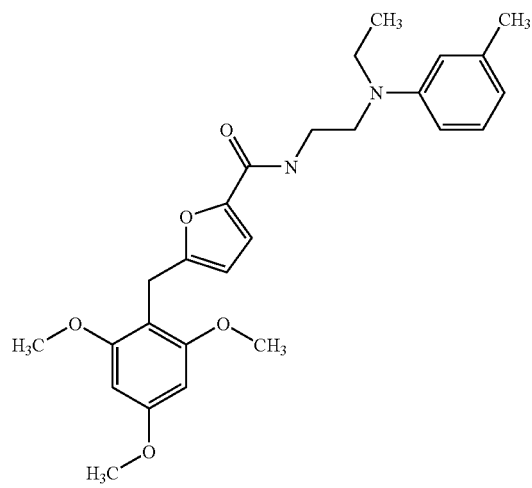 |
| 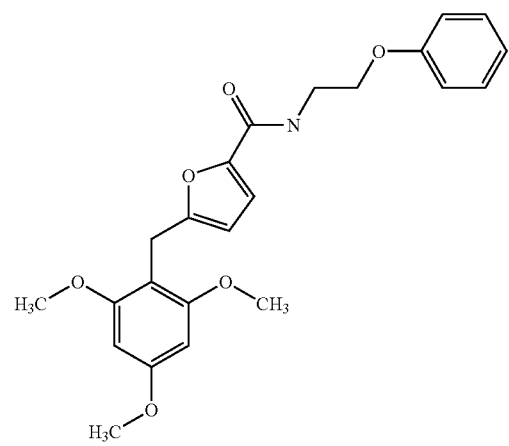 |
| 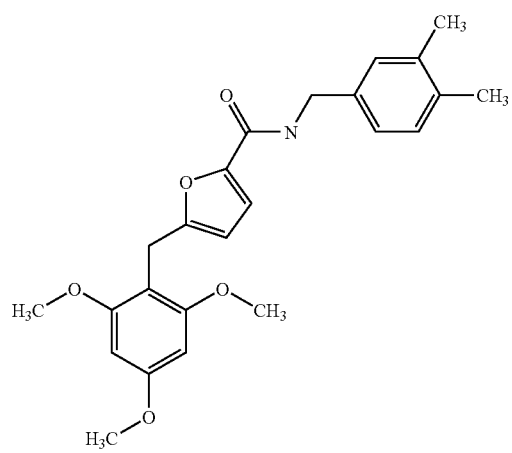 |

-continued
MOLSTRUCTURE
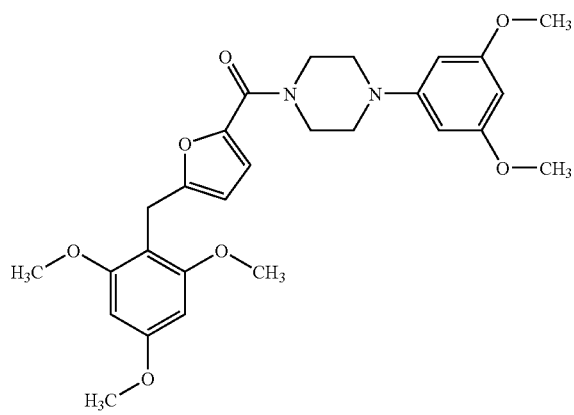
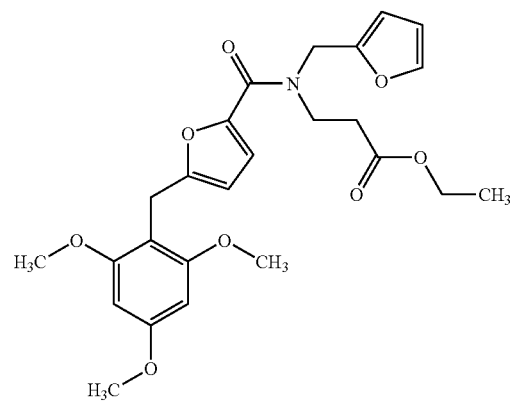
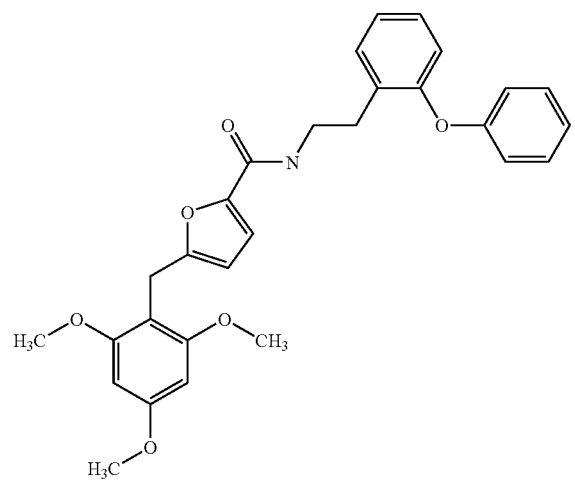

| MOLSTRUCTURE |
|---|
| 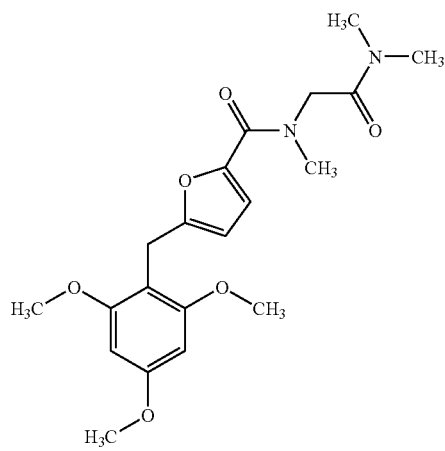 |
| 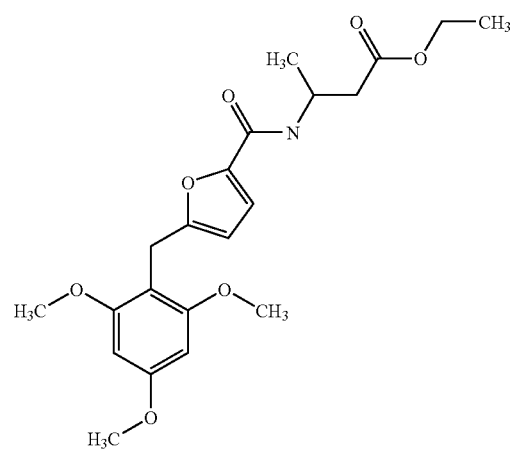 |
| 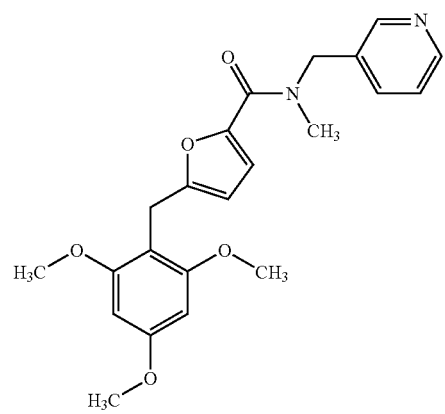 |

| MOLSTRUCTURE |
|---|
| 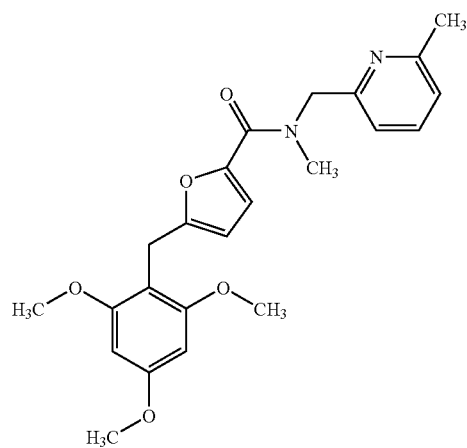 |
| 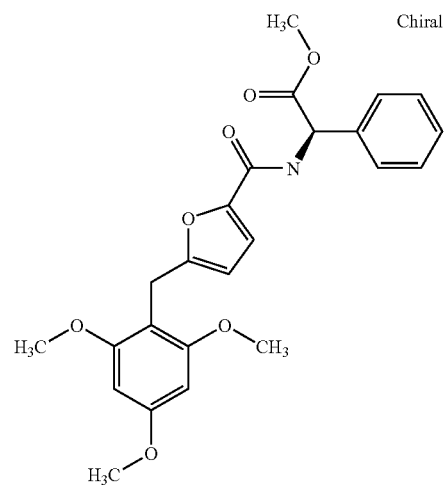 |
| 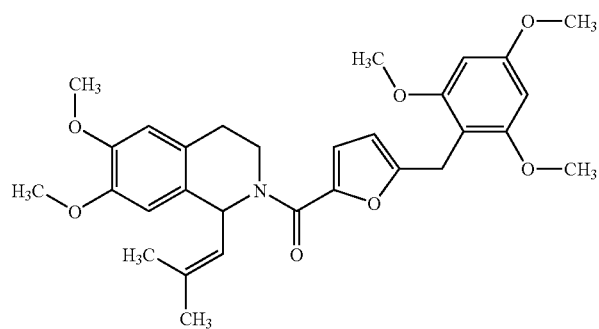 |

MOLSTRUCTURE
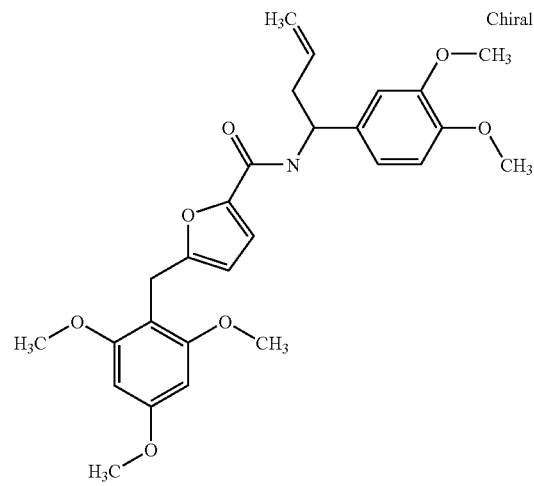
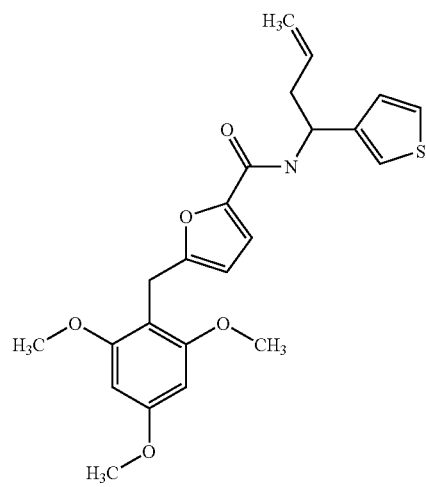
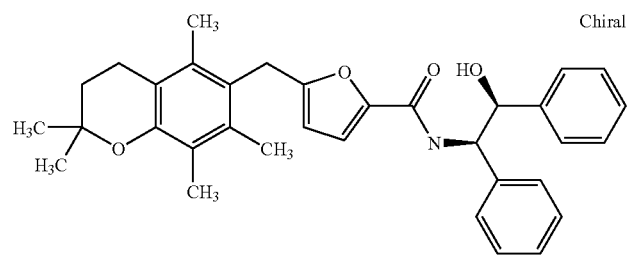
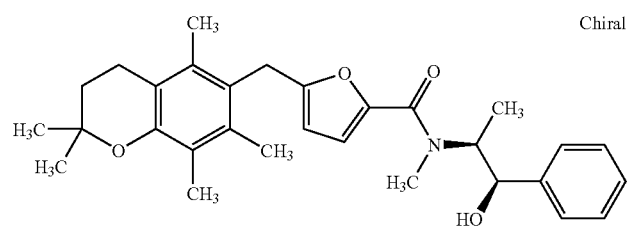

-continued
MOLSTRUCTURE
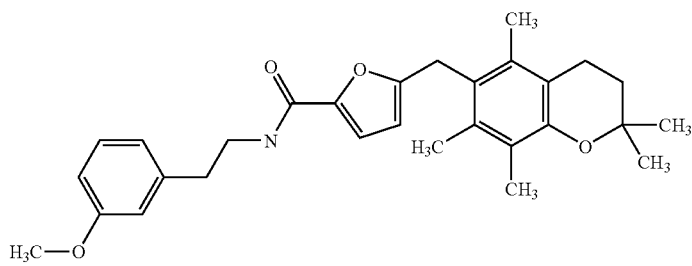
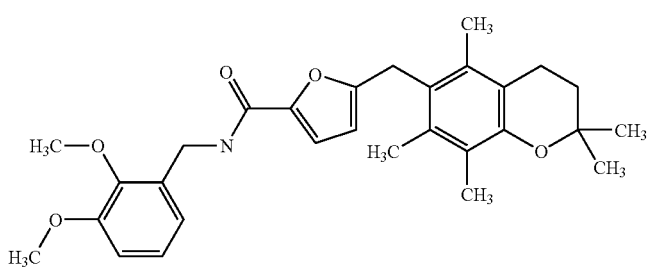
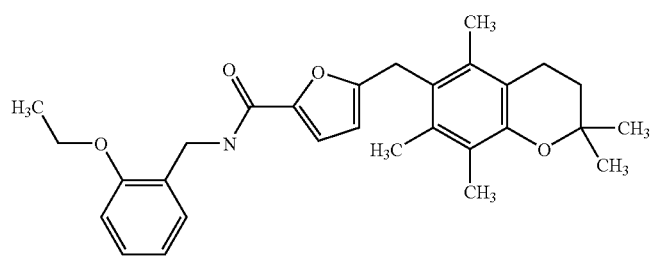
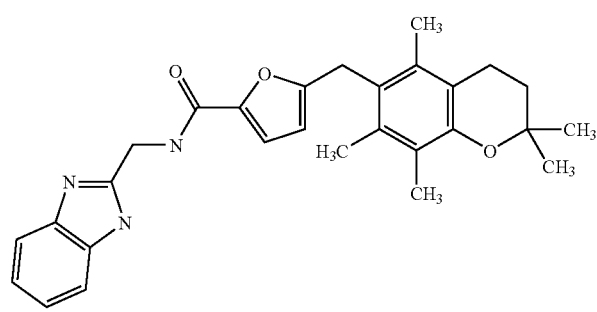
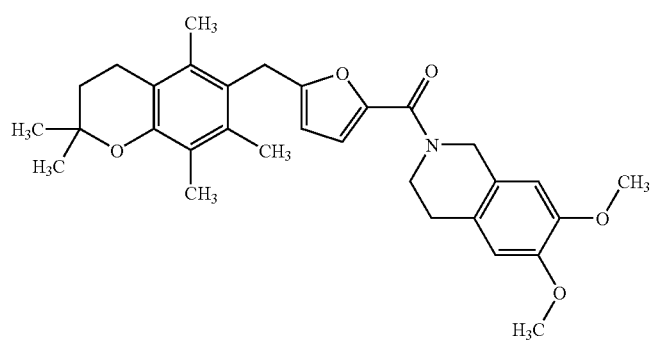

-continued
MOLSTRUCTURE
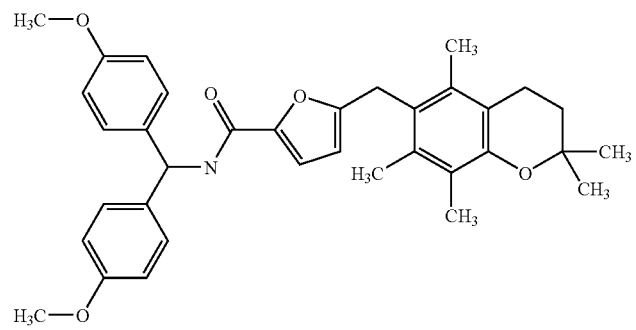
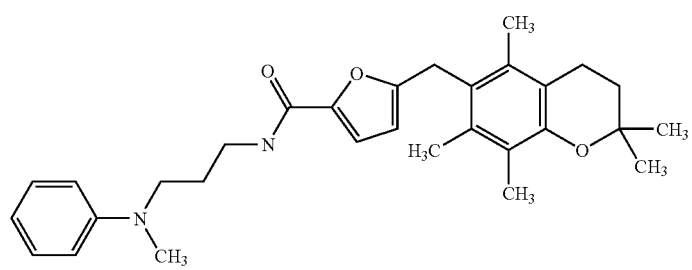
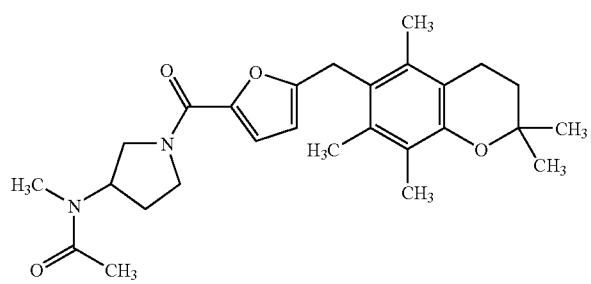
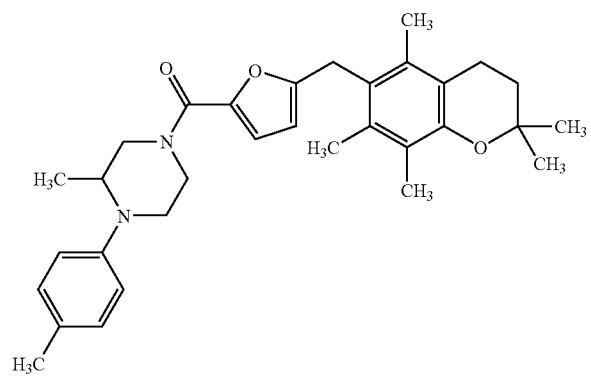

-continued
MOLSTRUCTURE
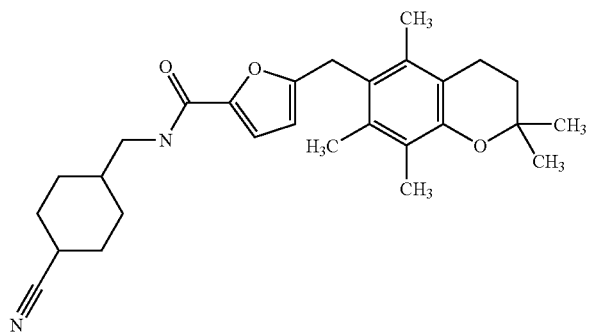
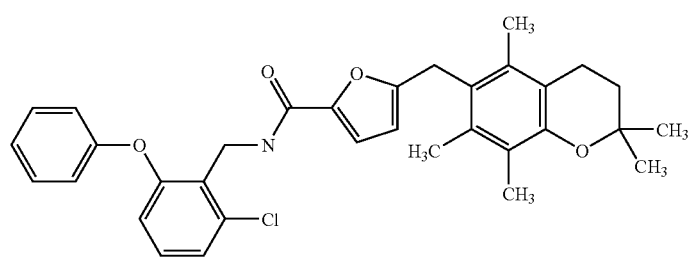
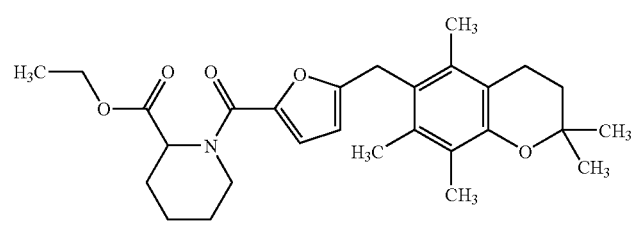
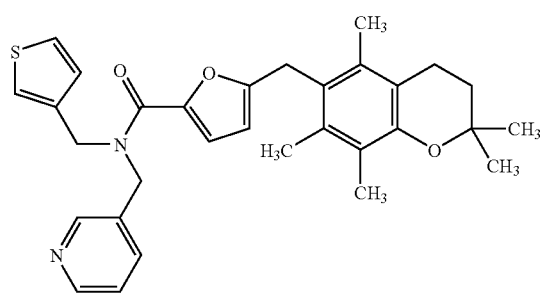
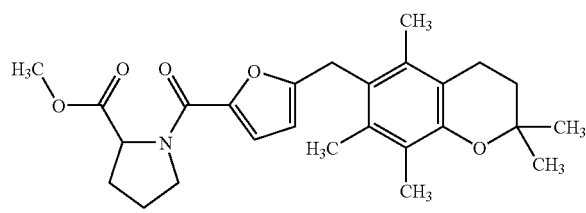

-continued
MOLSTRUCTURE
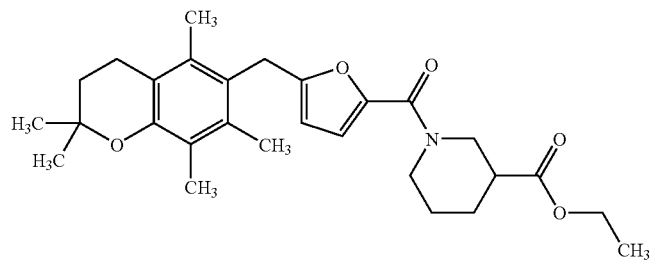
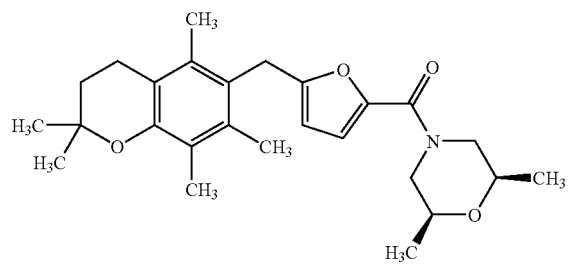
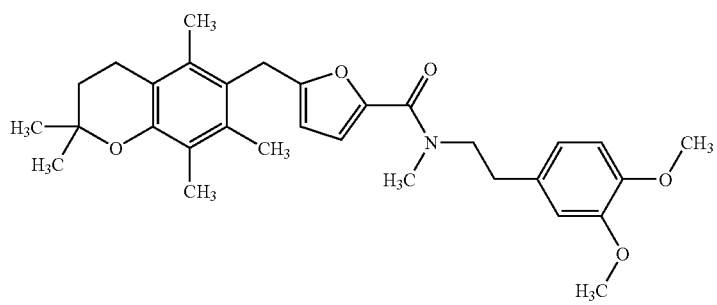
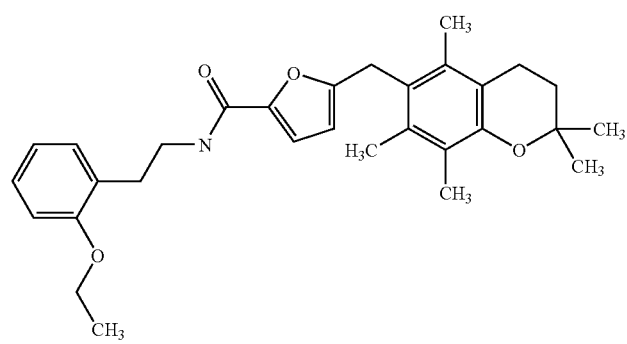
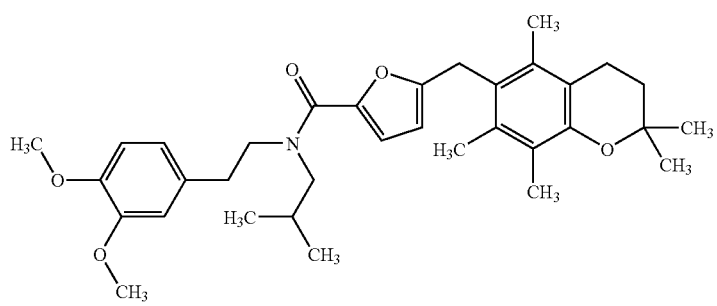

MOLSTRUCTURE
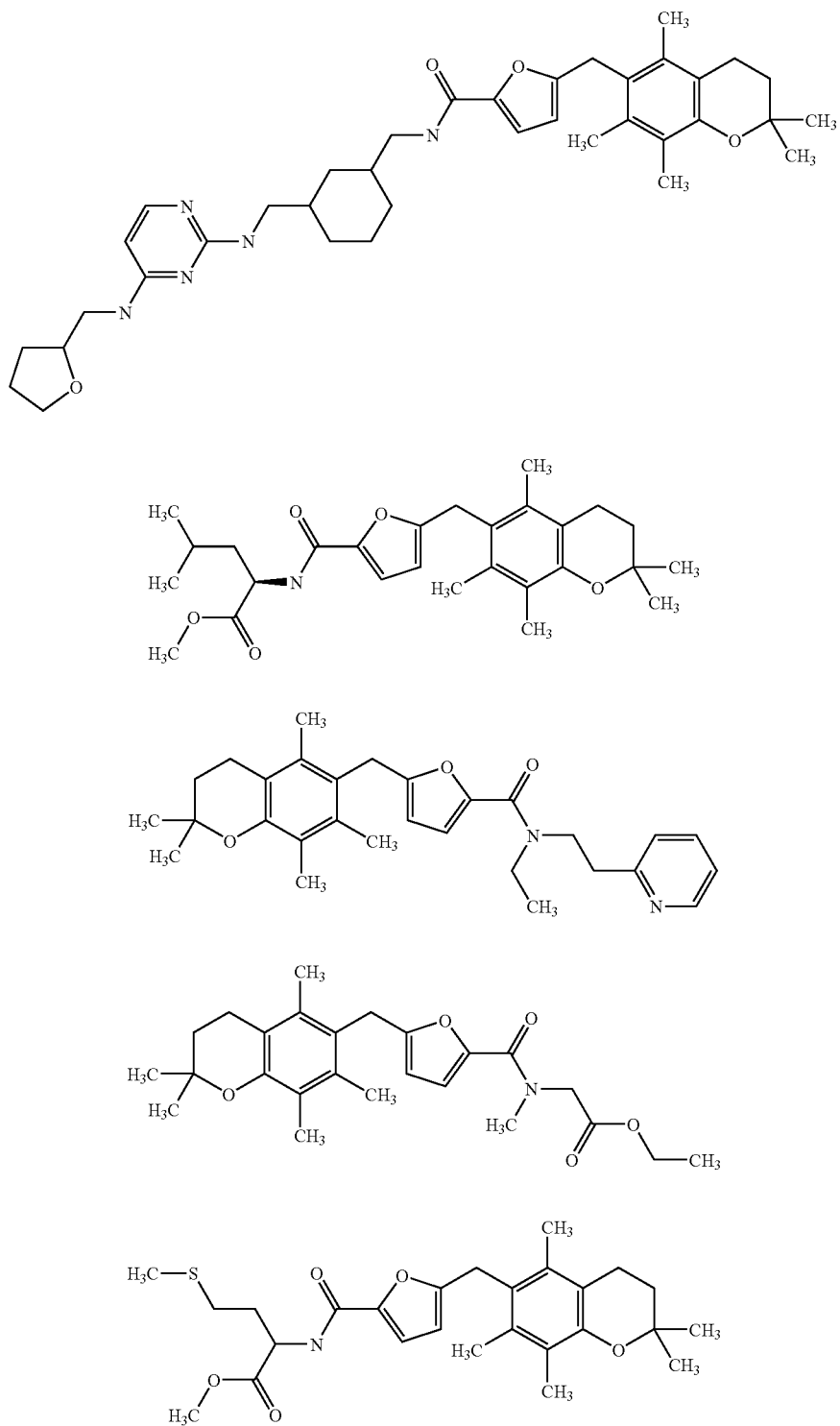

-continued
MOLSTRUCTURE
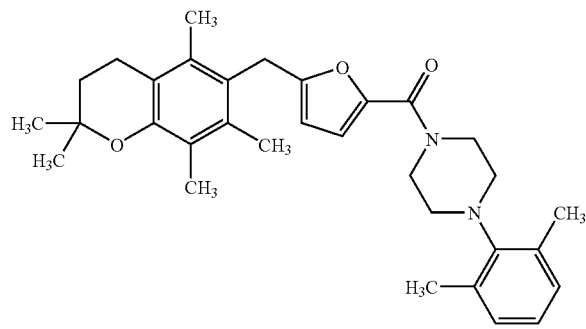
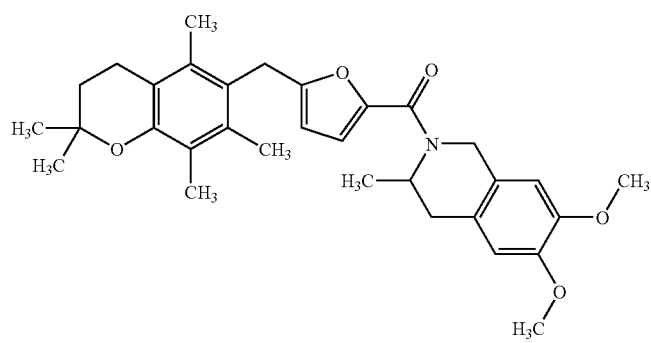
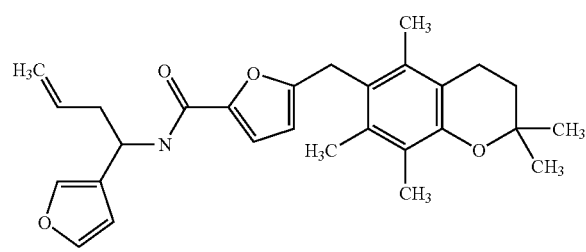
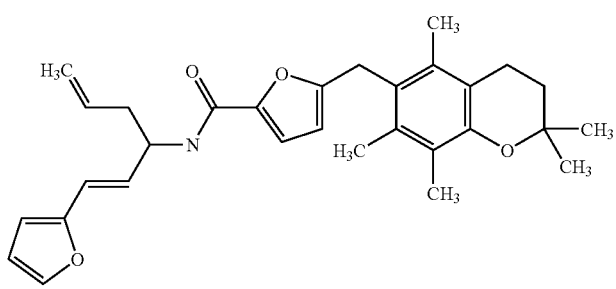
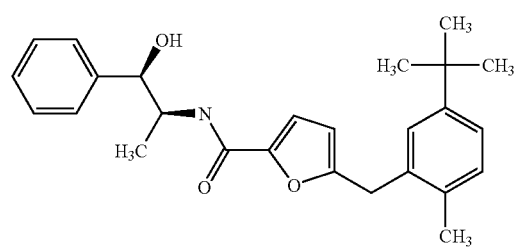

| MOLSTRUCTURE |
|---|
| 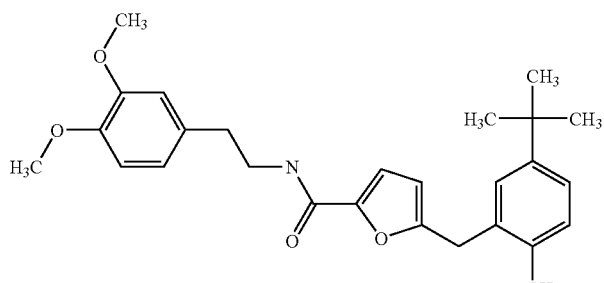 |
| 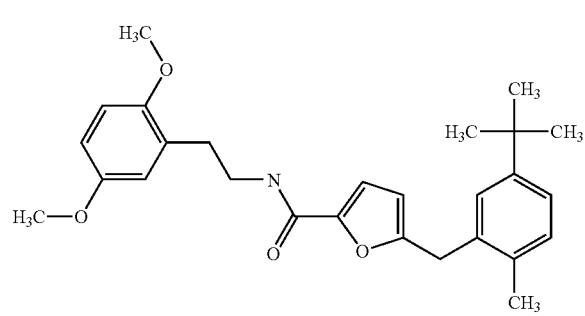 |
| 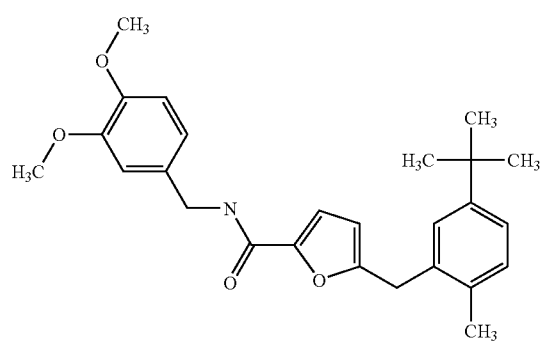 |
| 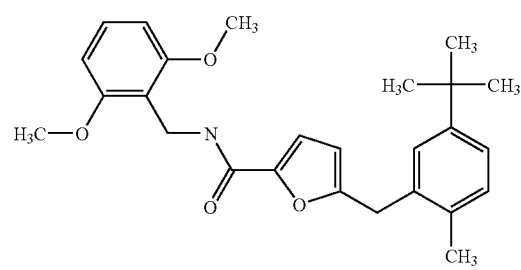 |
| 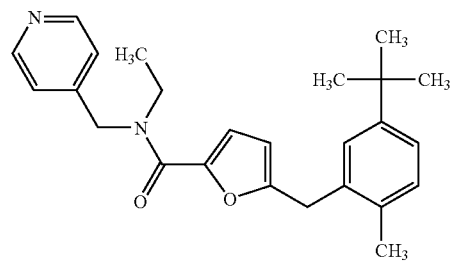 |

-continued
MOLSTRUCTURE
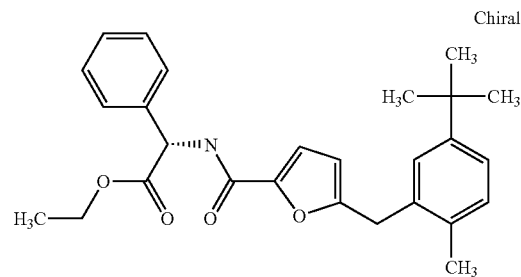
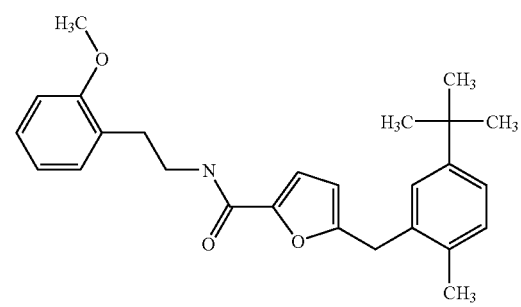
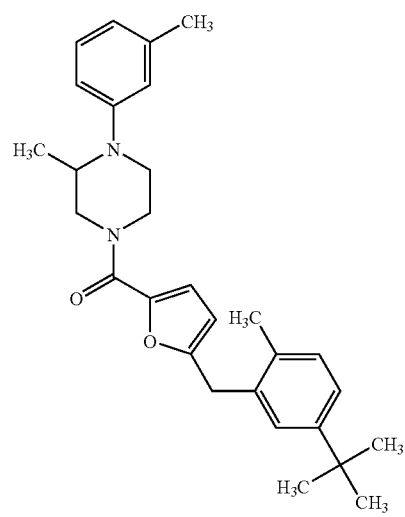
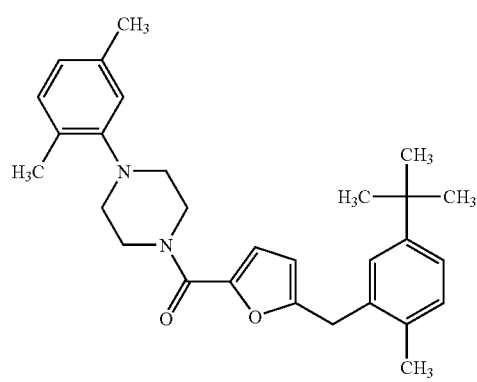

| MOLSTRUCTURE |
|---|
| 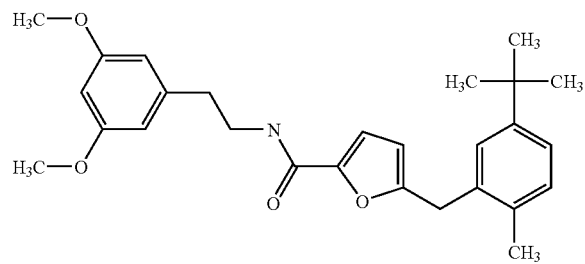 |
| 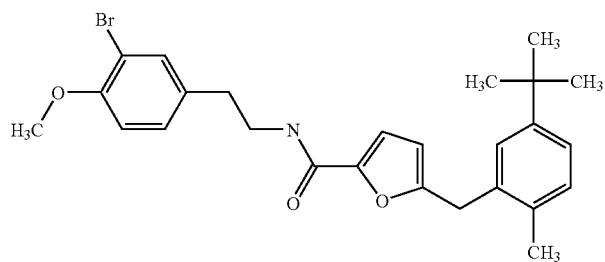 |
| 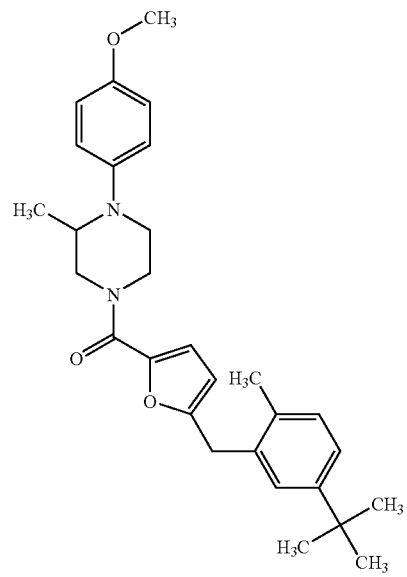 |
| 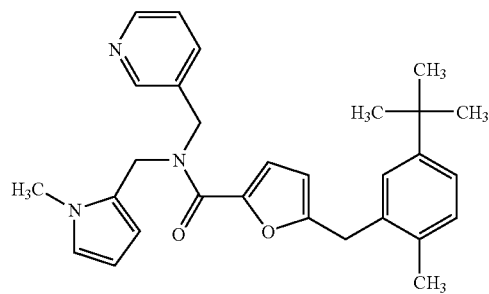 |

-continued
MOLSTRUCTURE
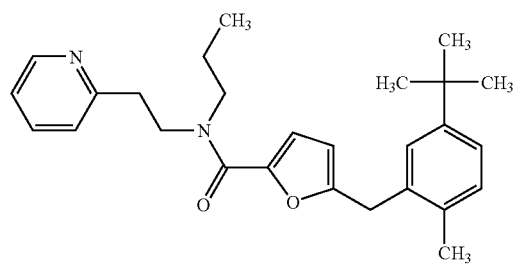
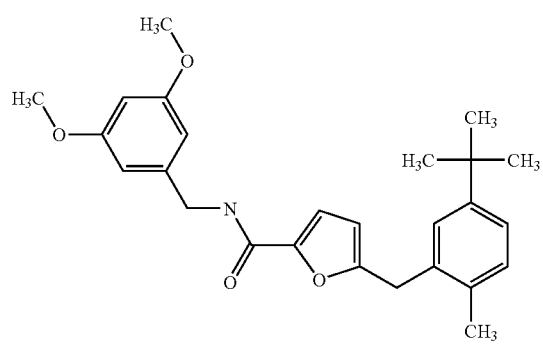
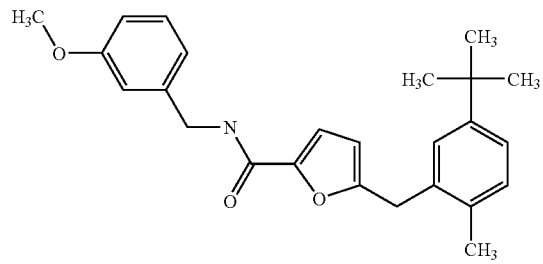
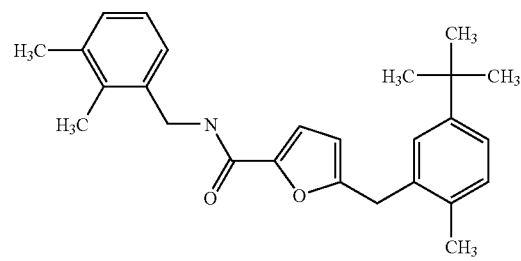
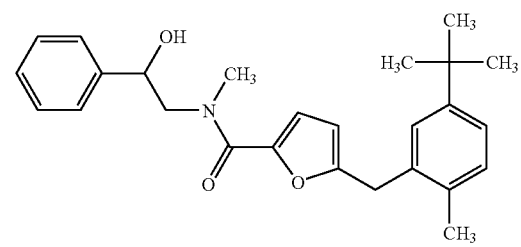

| MOLSTRUCTURE |
|---|
| 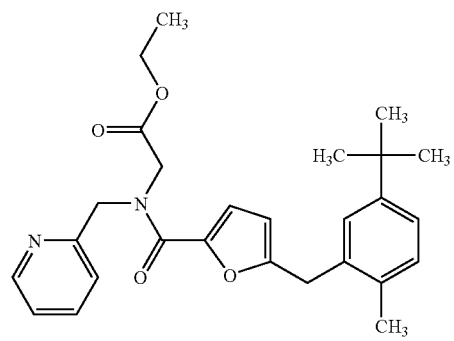 |
| 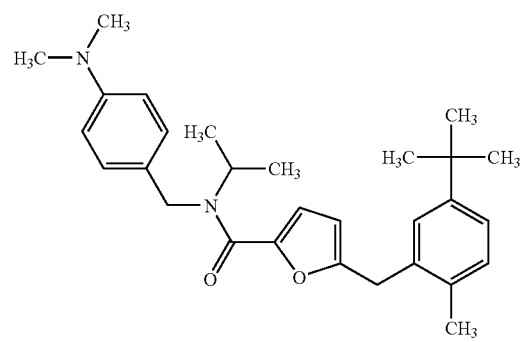 |
| 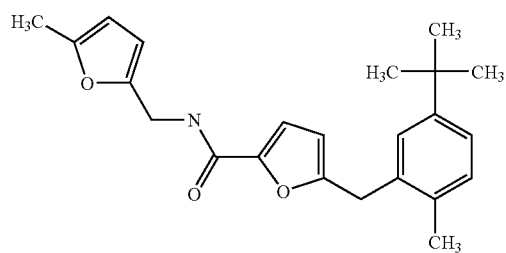 |
| 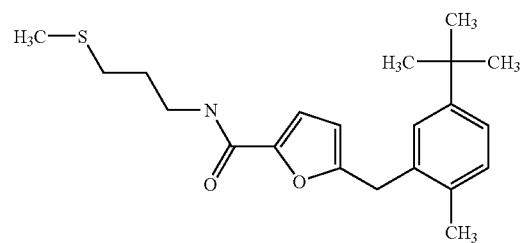 |
| 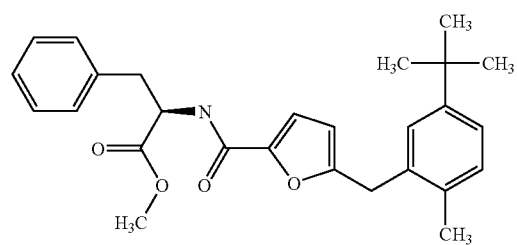 |

-continued
MOLSTRUCTURE
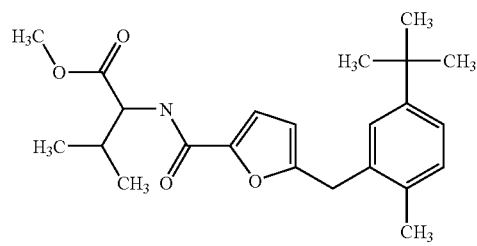
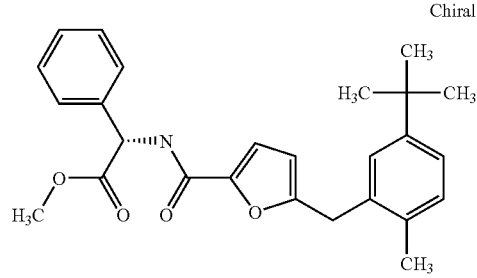
Chiral
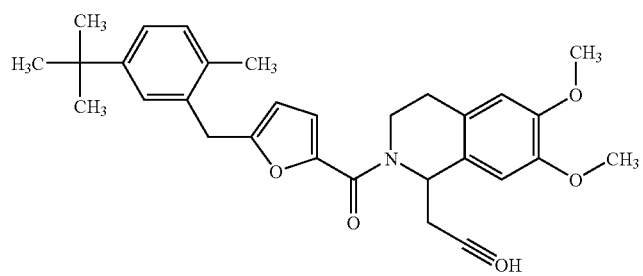
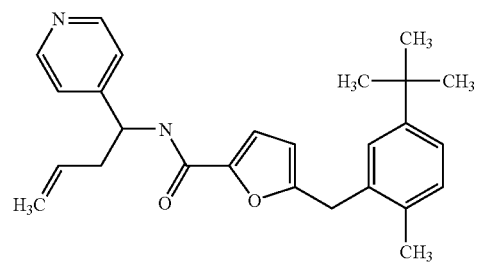
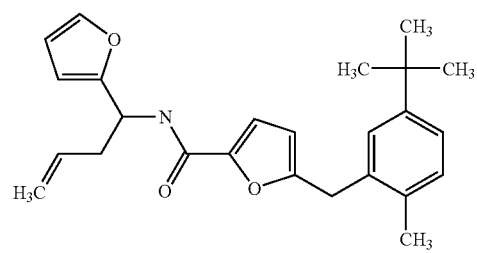

| MOLSTRUCTURE |
|---|
| 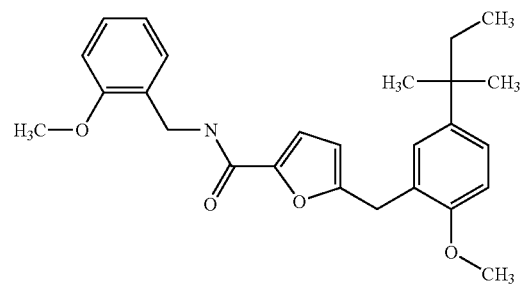 |
| 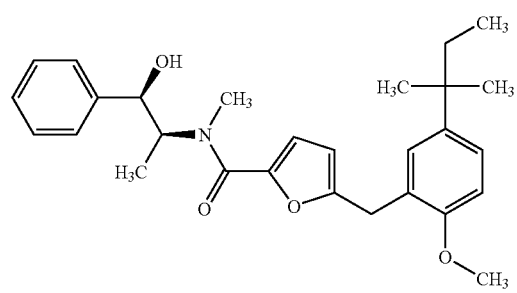 |
| 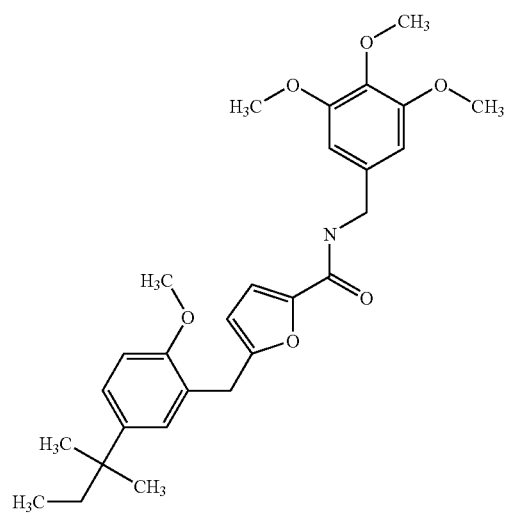 |

| -continued |
|---|
| MOLSTRUCTURE |
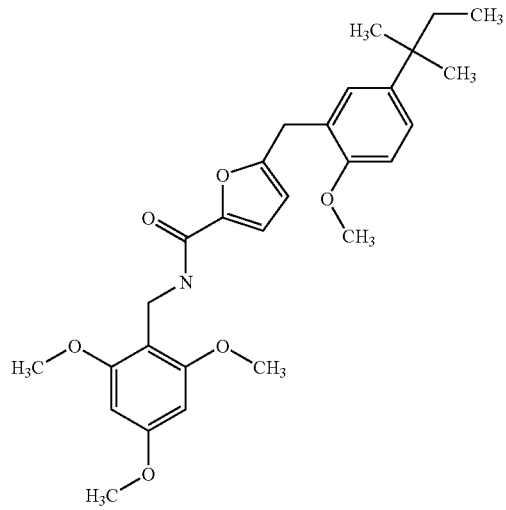
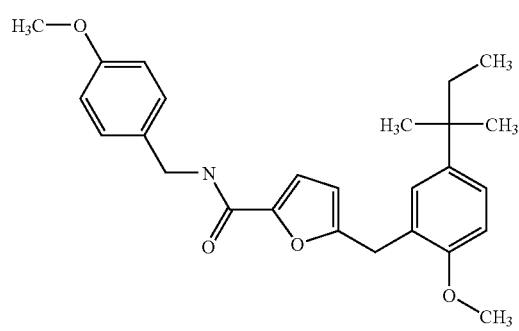
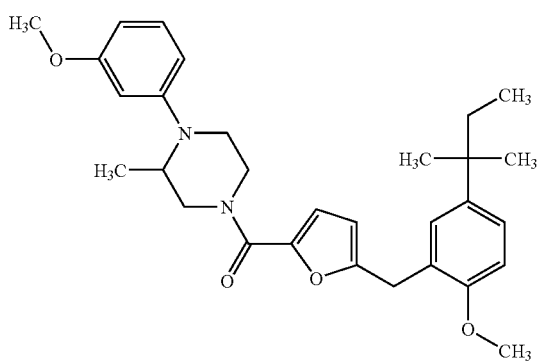
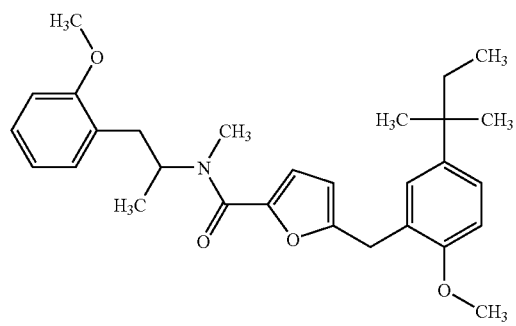

| MOLSTRUCTURE |
|---|
| 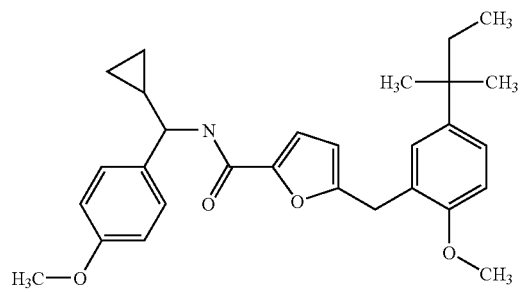 |
| 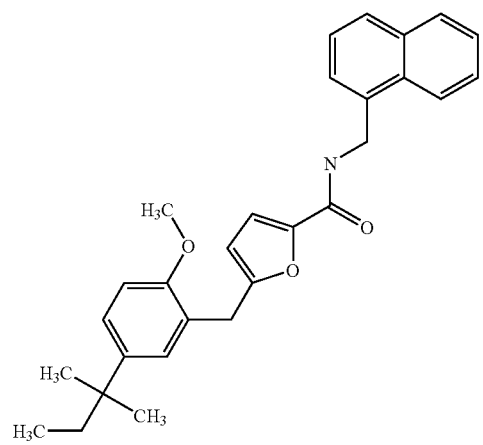 |
| 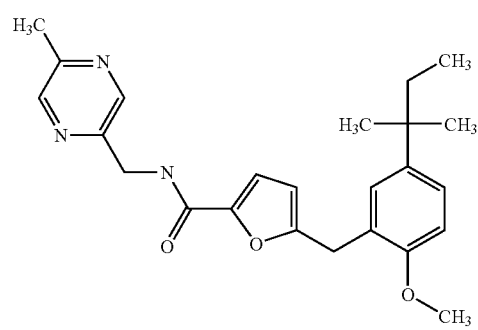 |
| 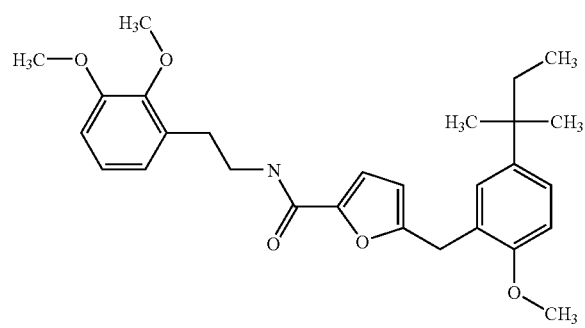 |

| MOLSTRUCTURE |
| --- |
| 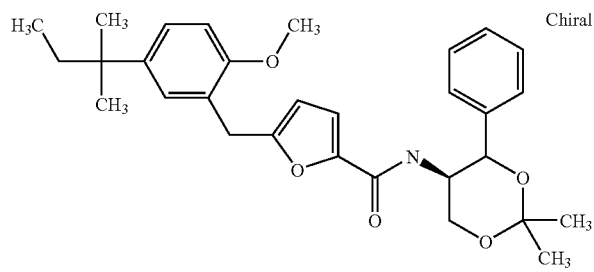 |
| 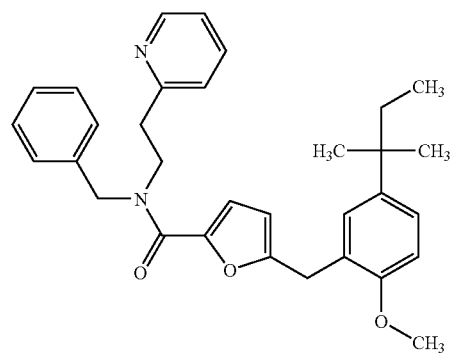 |
| 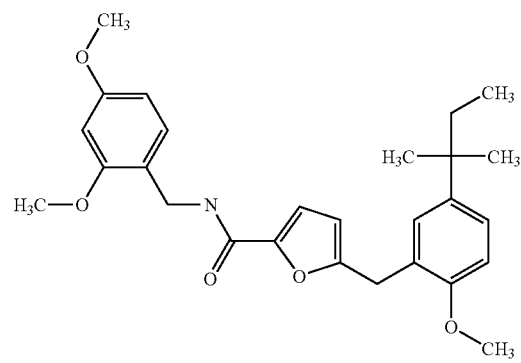 |
| 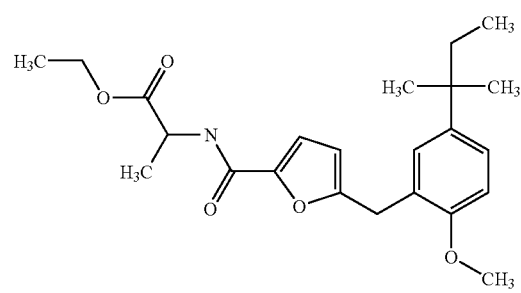 |

| MOLSTRUCTURE |
| --- |
| 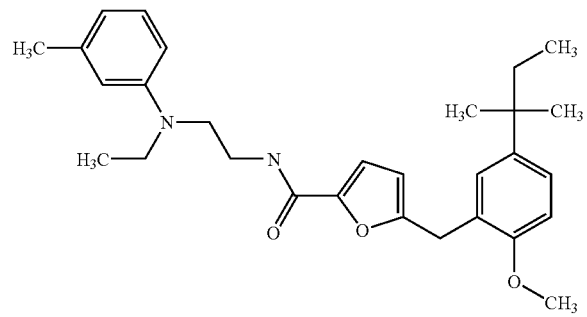 |
| 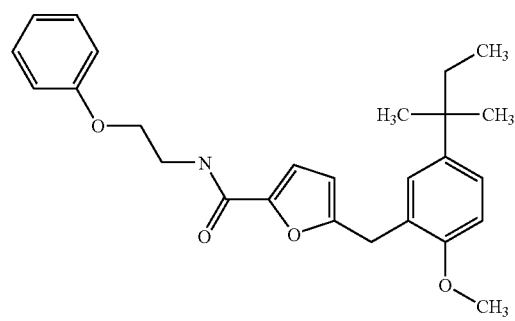 |
| 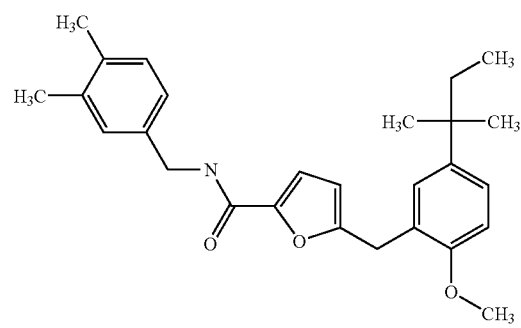 |
| 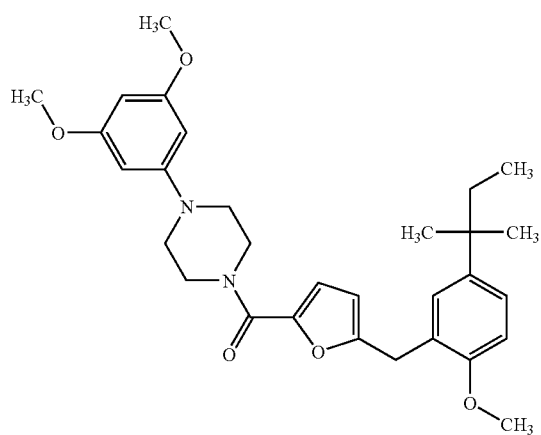 |

| MOLSTRUCTURE |
| --- |
| 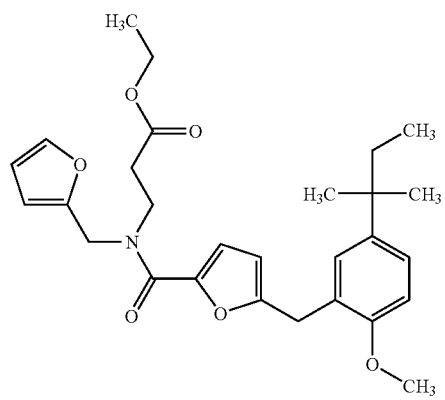 |
| 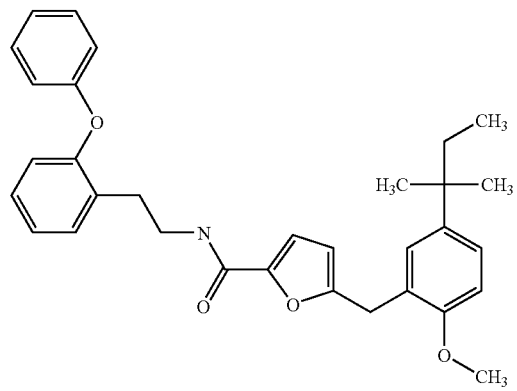 |
| 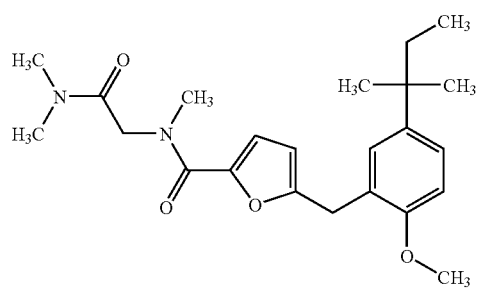 |
| 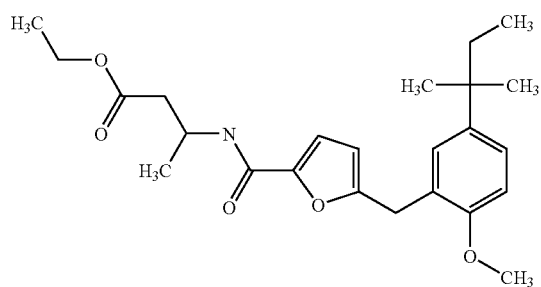 |

-continued
| MOLSTRUCTURE |
| --- |
| 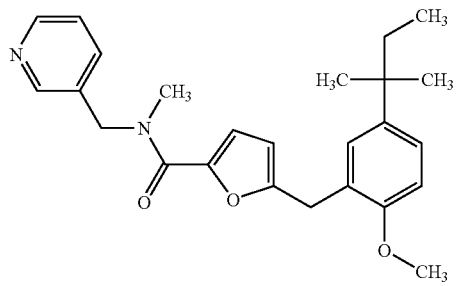 |
| 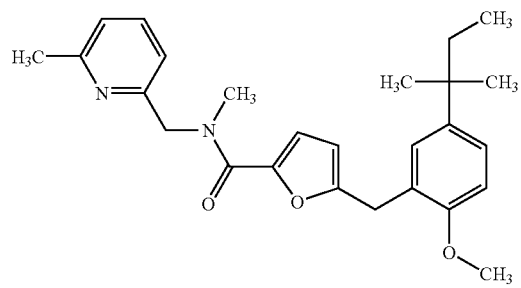 |
| Chiral<br />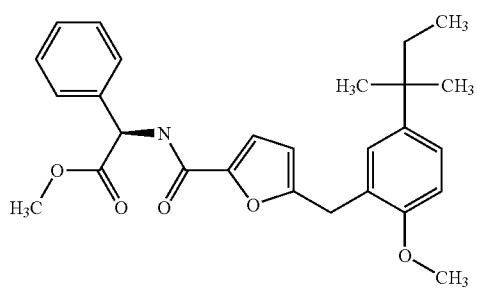 |
| 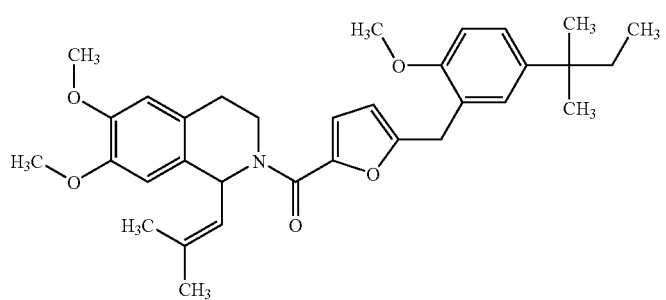 |
| 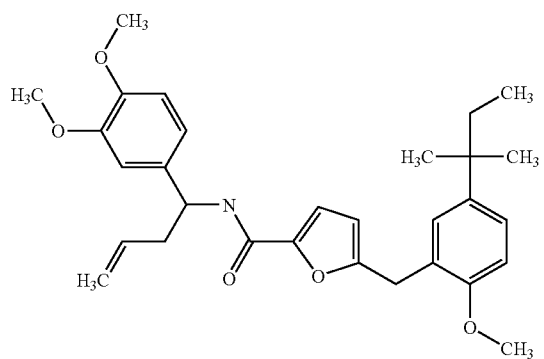 |

| MOLSTRUCTURE |
|---|
| 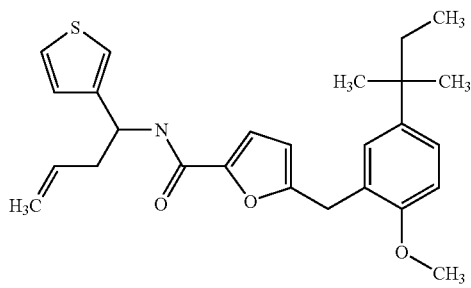 |
| 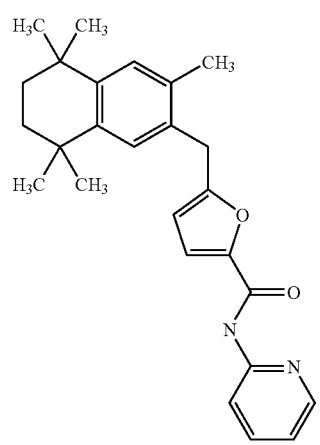 |
| 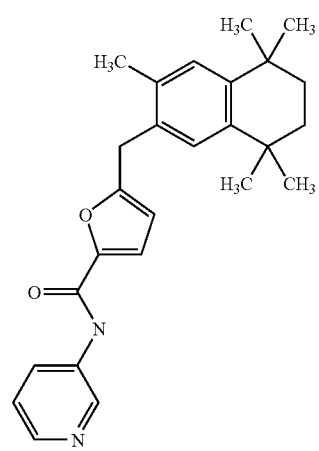 |
| MOLSTRUCTURE |
|---|
| 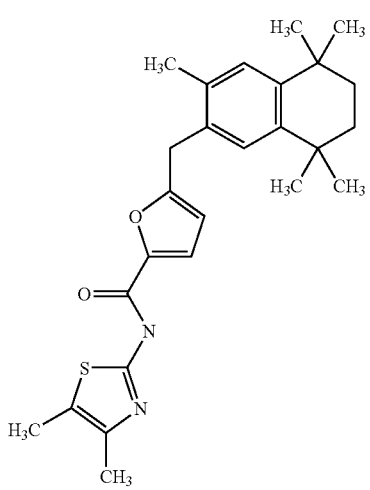 |
| 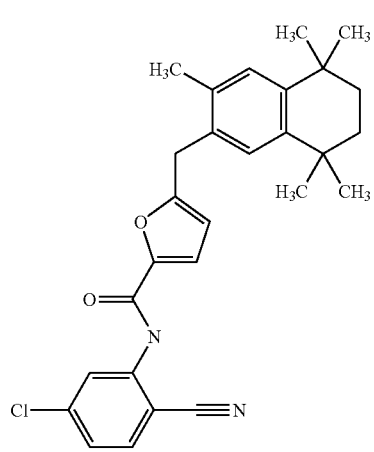 |

| 2409 | 2410 |
|---|---|
| -continued | -continued |
| MOLSTRUCTURE | MOLSTRUCTURE |
| 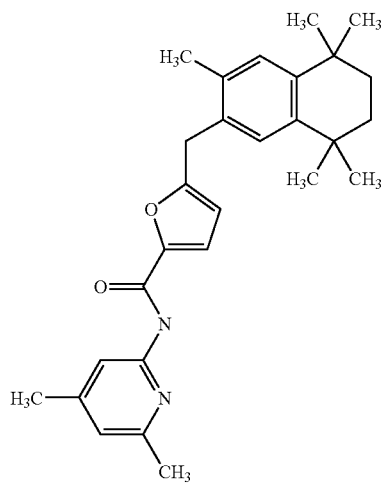 | 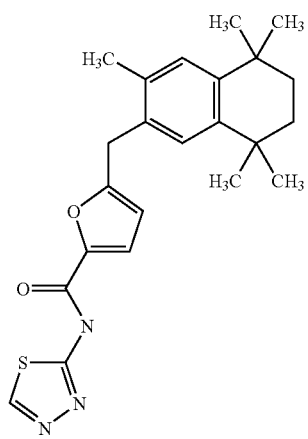 |
| 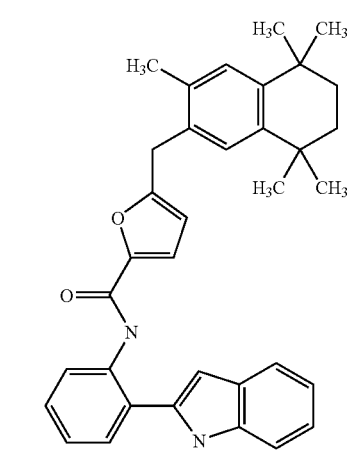 | 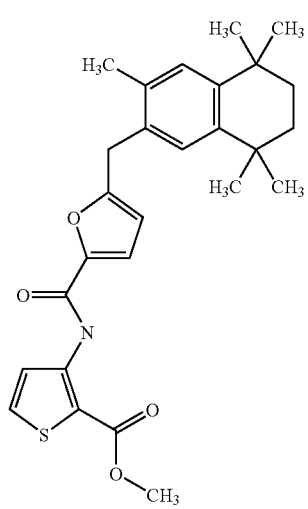 |
| 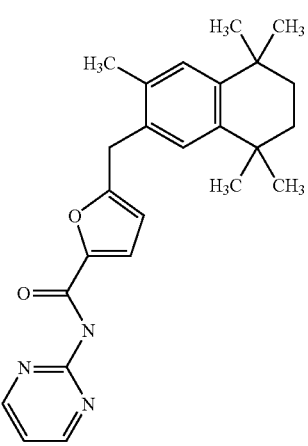 | 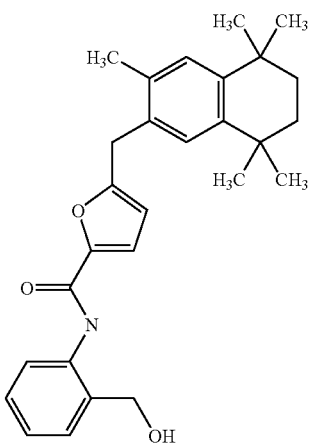 |

| 2411 | 2412 |
|---|---|
| -continued | -continued |
| MOLSTRUCTURE | MOLSTRUCTURE |
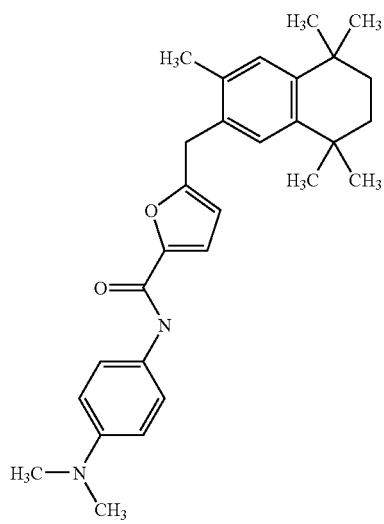
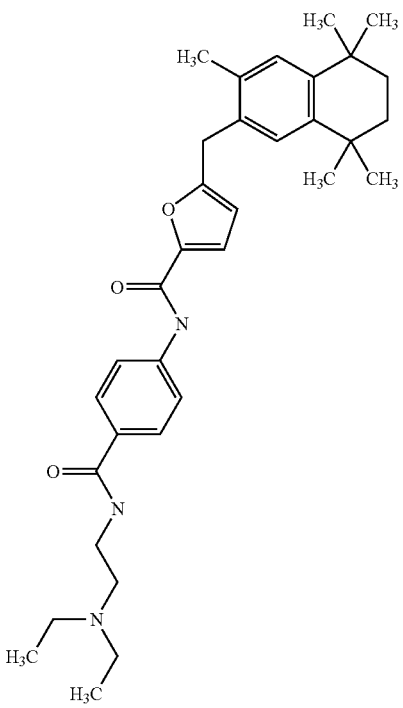

| 2413 | 2414 |
|---|---|
| -continued | -continued |
| MOLSTRUCTURE | MOLSTRUCTURE |
| 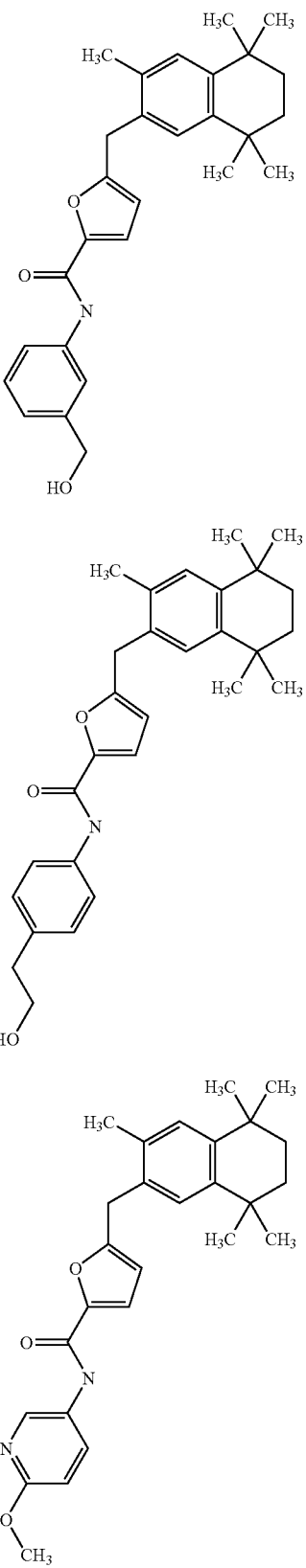 | 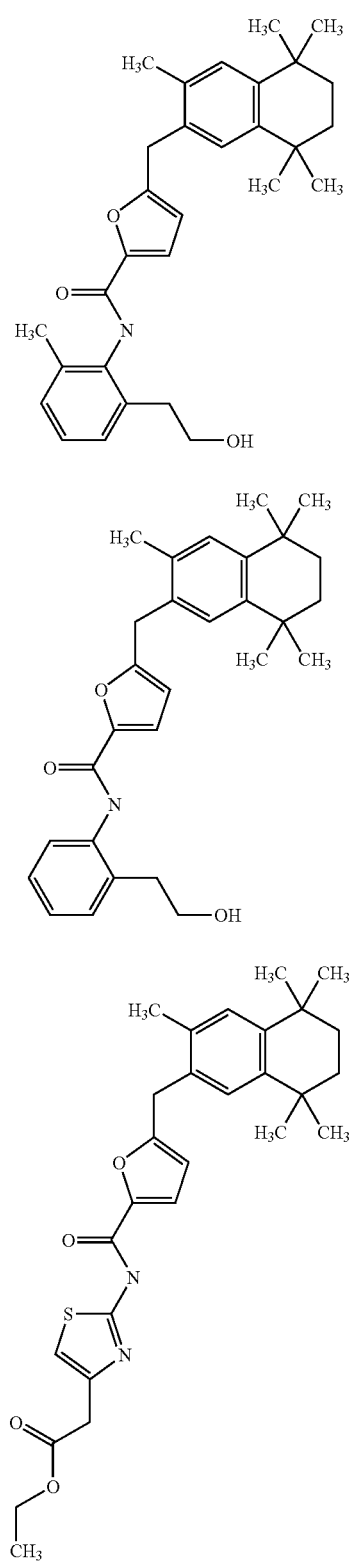 |

| 2415 | 2416 |
|---|---|
| -continued | -continued |
| MOLSTRUCTURE | MOLSTRUCTURE |
| 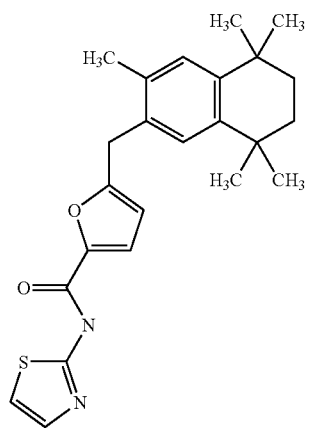 | 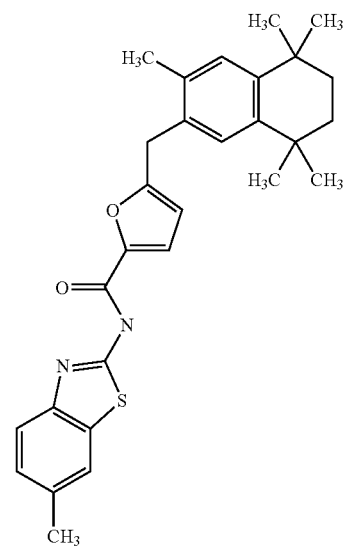 |
| 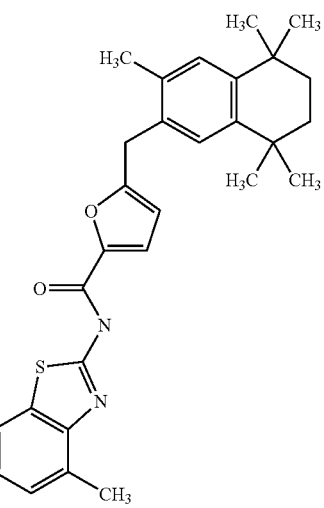 | |
| 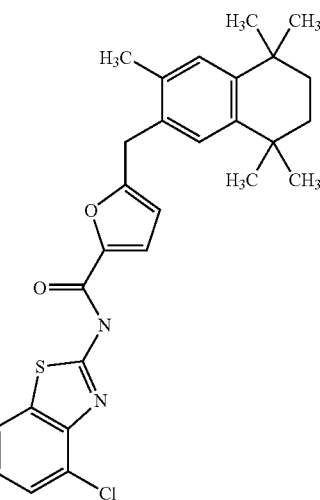 | 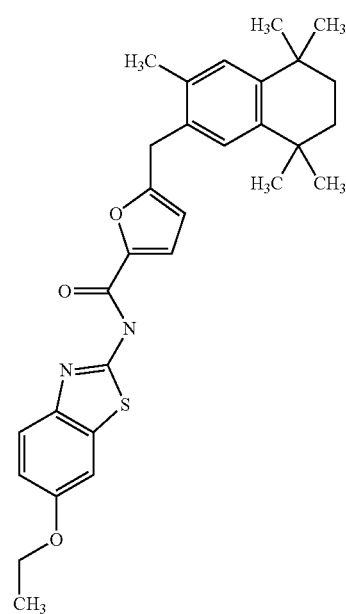 |

| 2417 | 2418 |
|---|---|
| -continued | -continued |
| MOLSTRUCTURE | MOLSTRUCTURE |
| 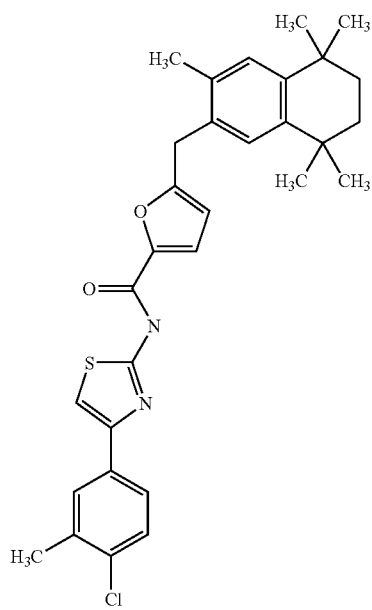 | 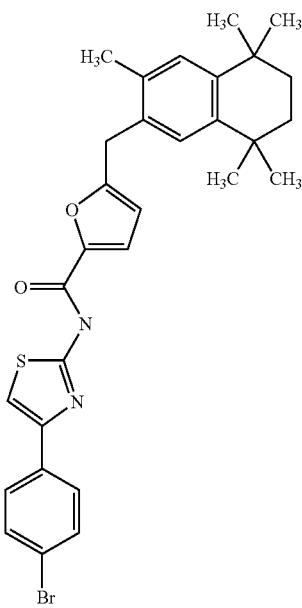 |
| 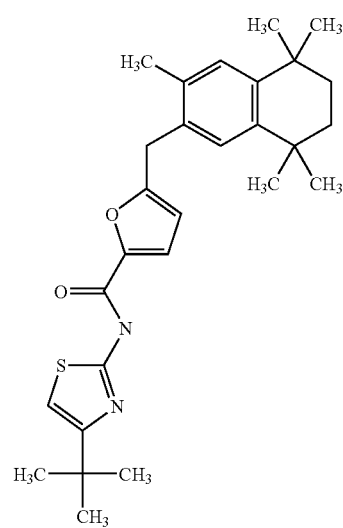 | 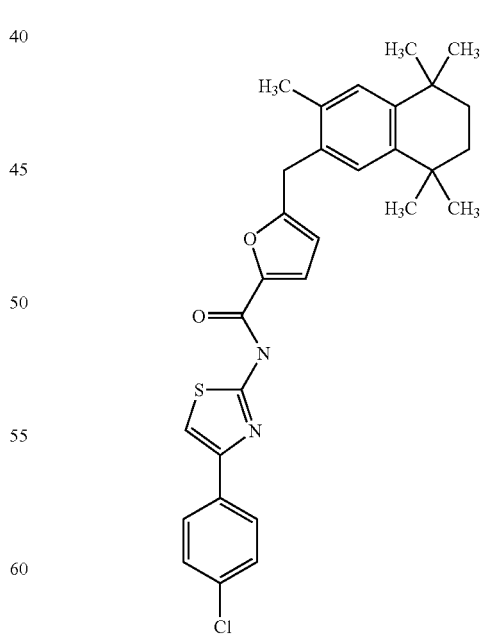 |

| 2419 | 2420 |
|---|---|
| -continued | -continued |
| MOLSTRUCTURE | MOLSTRUCTURE |
| 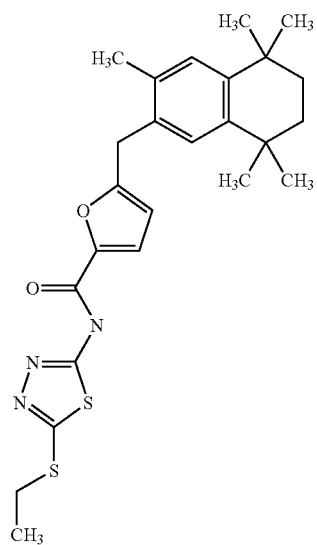 | 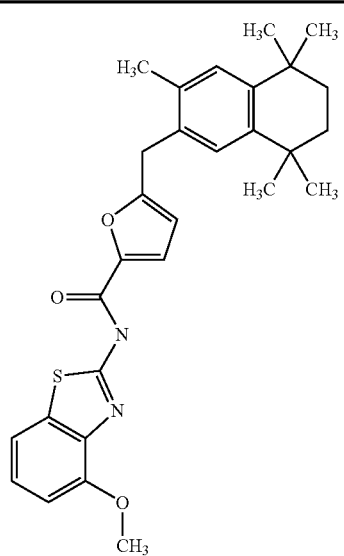 |
| 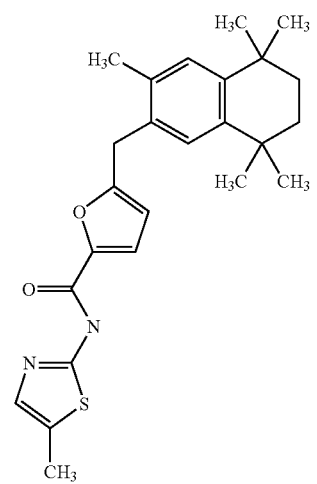 | 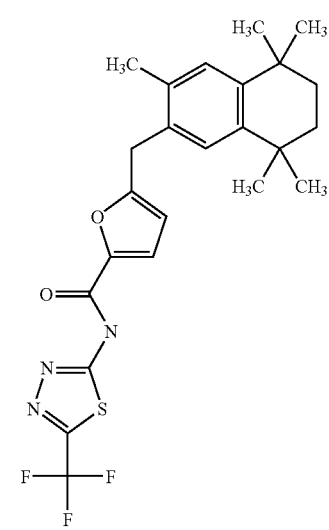 |
| 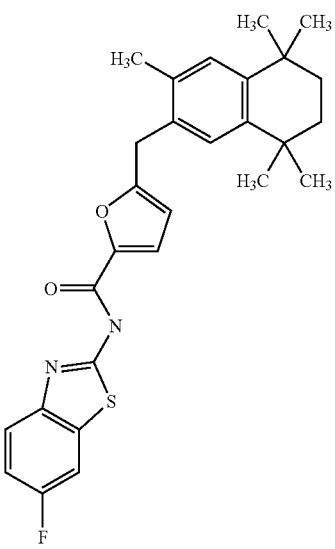 | 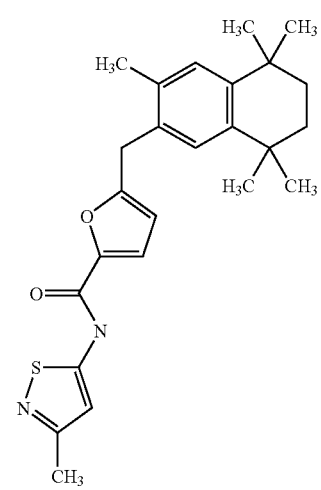 |

| 2421 | 2422 |
|---|---|
| -continued | -continued |
| MOLSTRUCTURE | MOLSTRUCTURE |
| 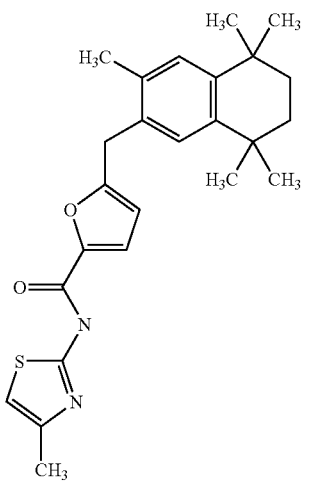 | 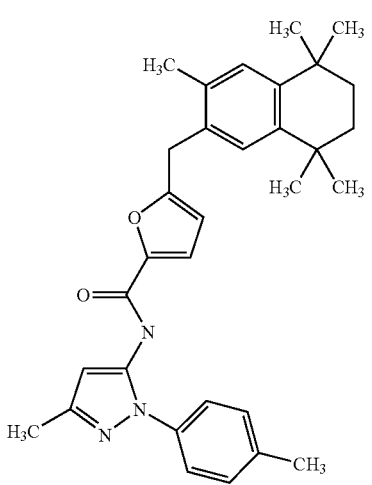 |
| 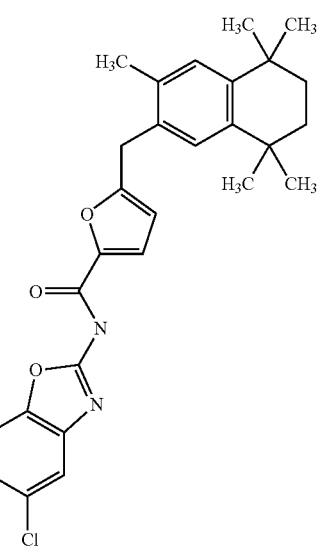 | 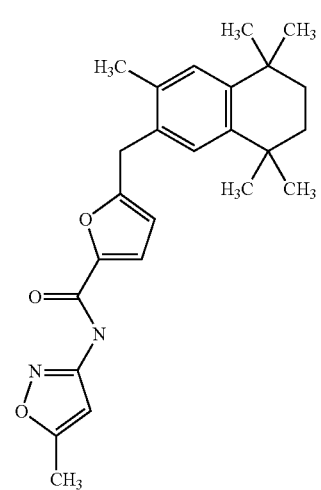 |
| 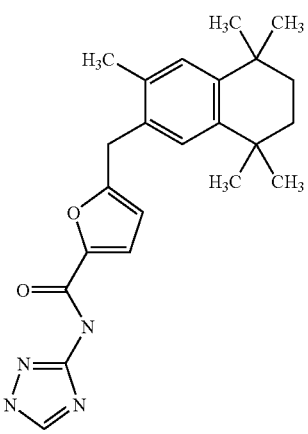 | 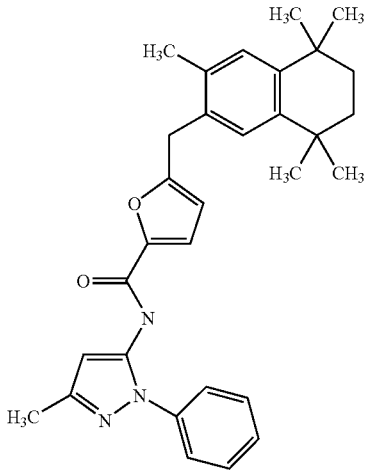 |

| 2423 | 2424 |
|---|---|
| -continued | -continued |
| MOLSTRUCTURE | MOLSTRUCTURE |
| 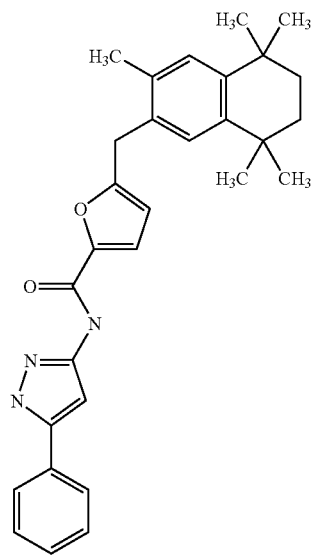 | 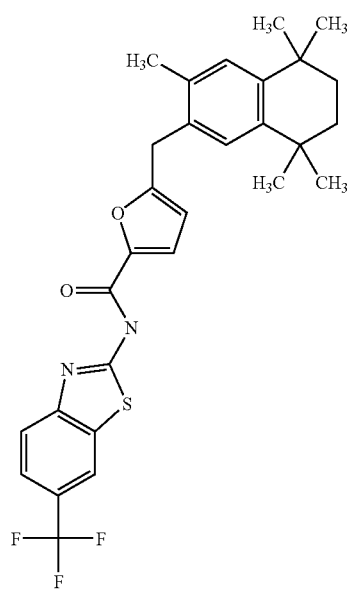 |
| 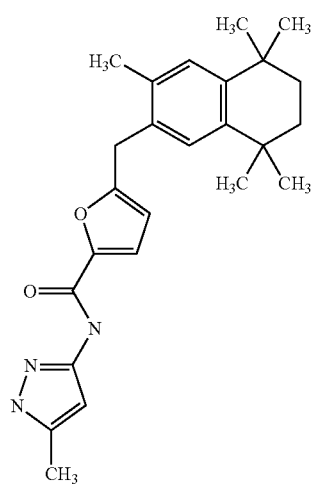 | |
| 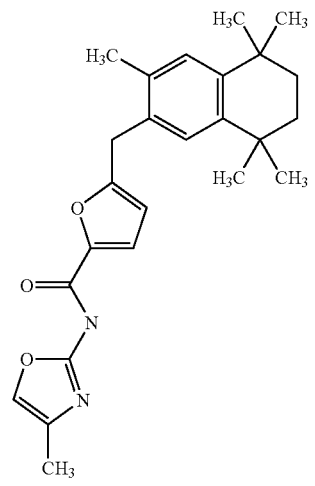 | 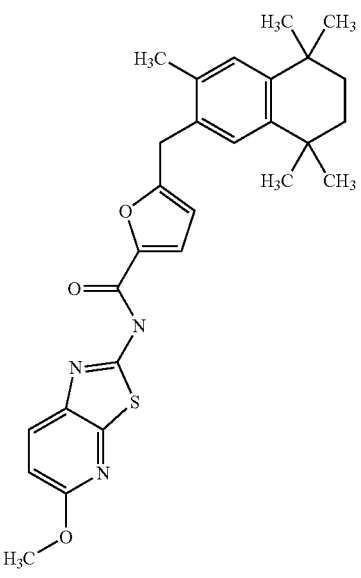 |

| 2425 | 2426 |
|---|---|
| -continued | -continued |
| MOLSTRUCTURE | MOLSTRUCTURE |
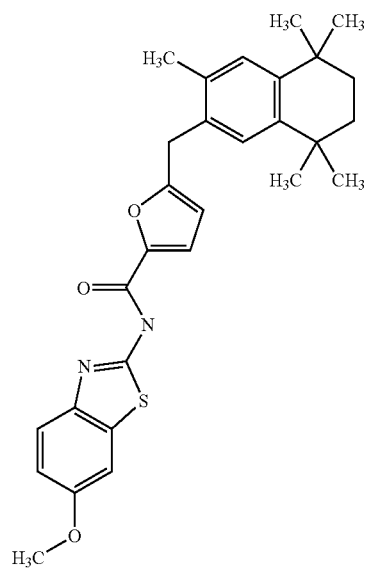
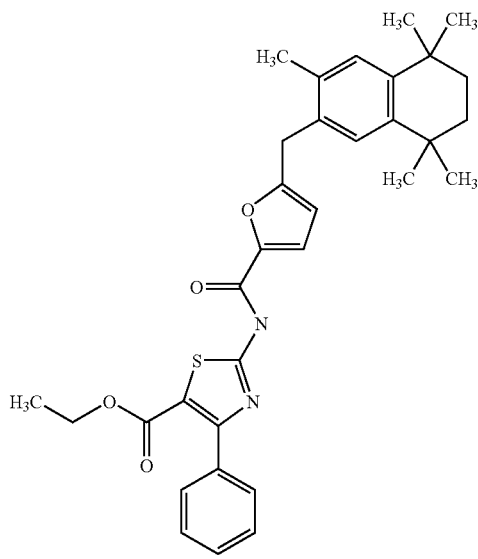
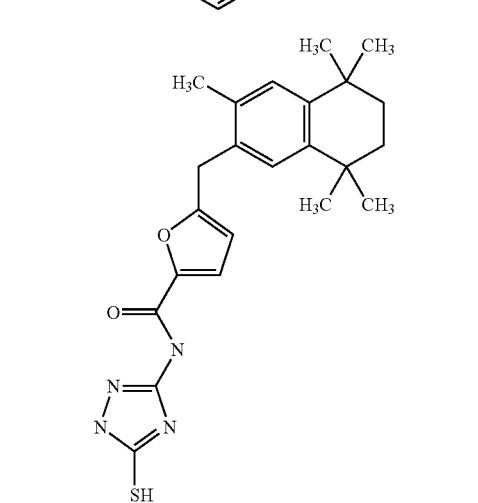
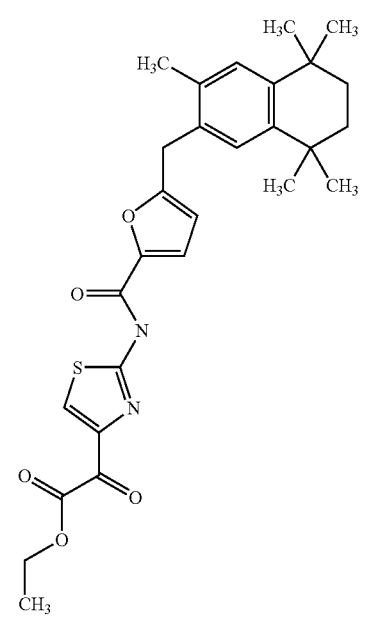
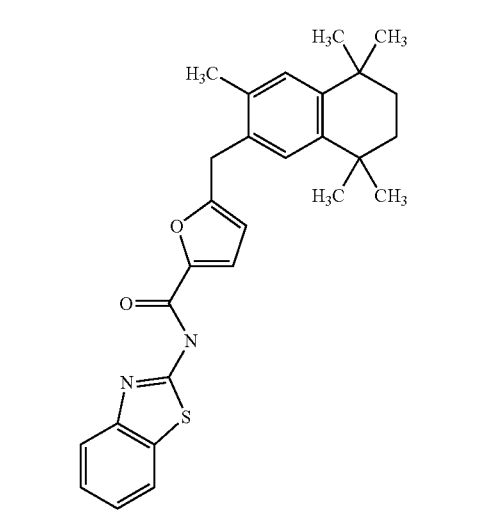

| 2427 | 2428 |
|---|---|
| -continued | -continued |
| MOLSTRUCTURE | MOLSTRUCTURE |
| 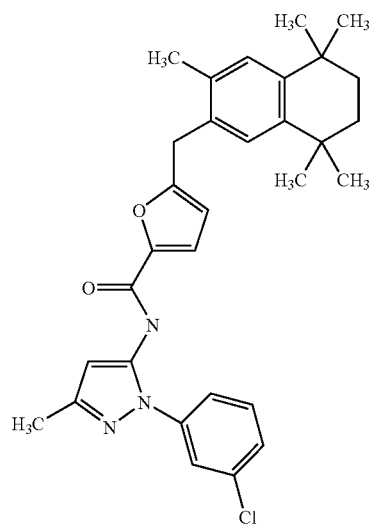 | 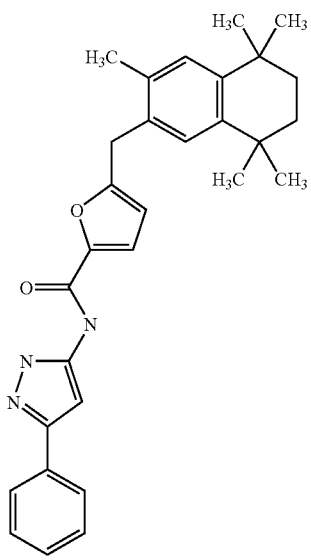 |
| 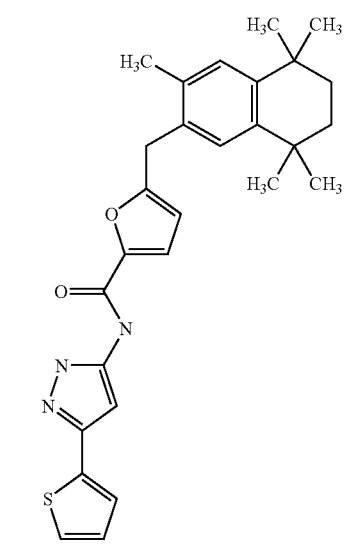 | 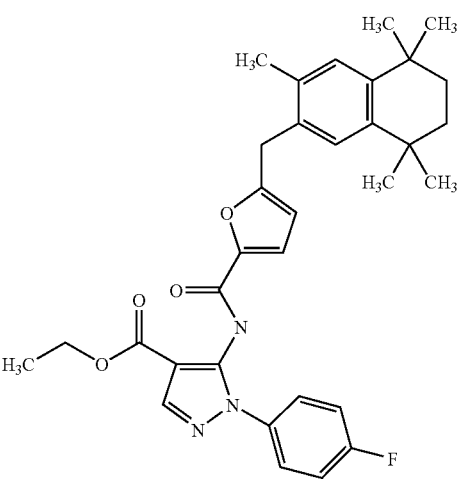 |
|  | 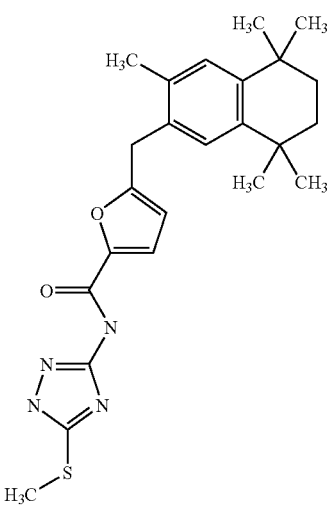 |

| 2429 | 2430 |
|---|---|
| -continued | -continued |
| MOLSTRUCTURE | MOLSTRUCTURE |
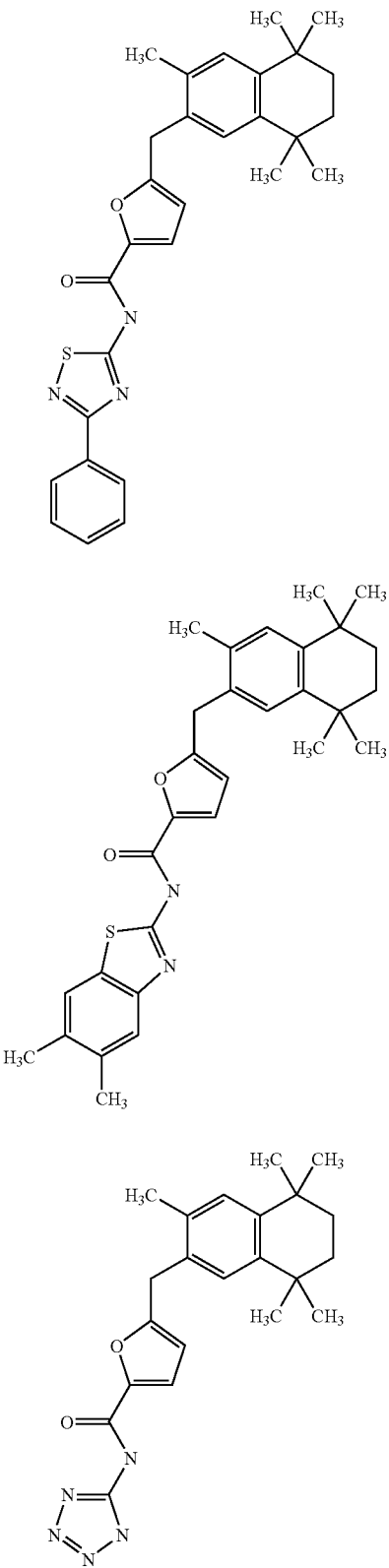
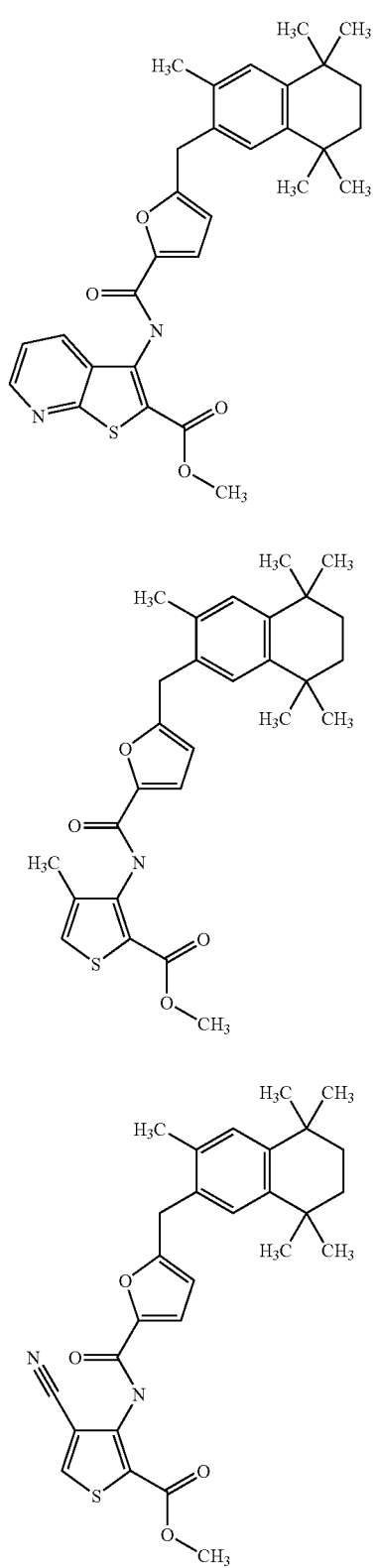

US 7,101,878 B1
| 2431 | 2432 |
|---|---|
| -continued | -continued |
| MOLSTRUCTURE | MOLSTRUCTURE |
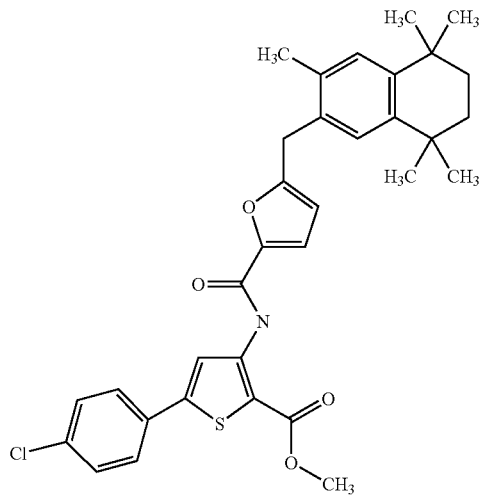
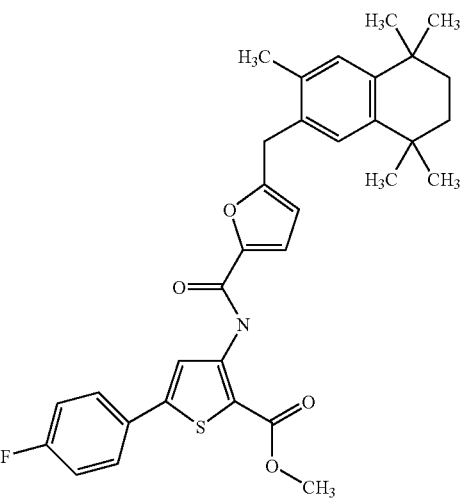
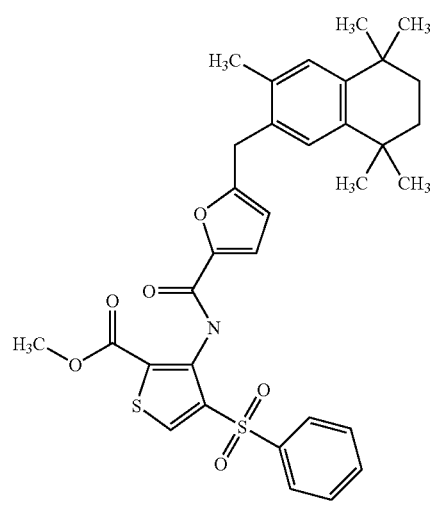
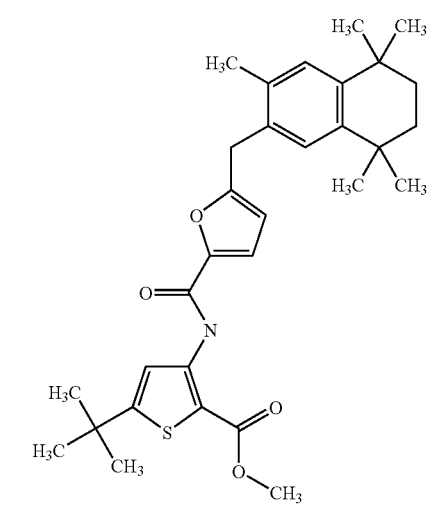
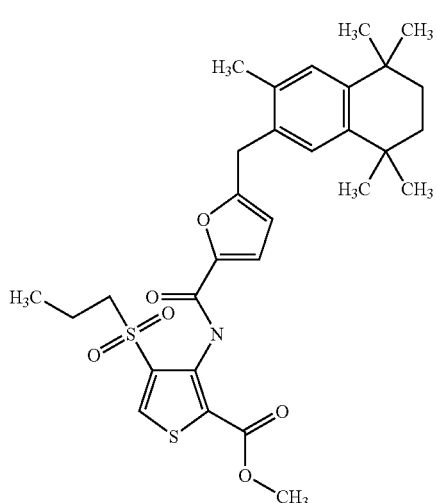
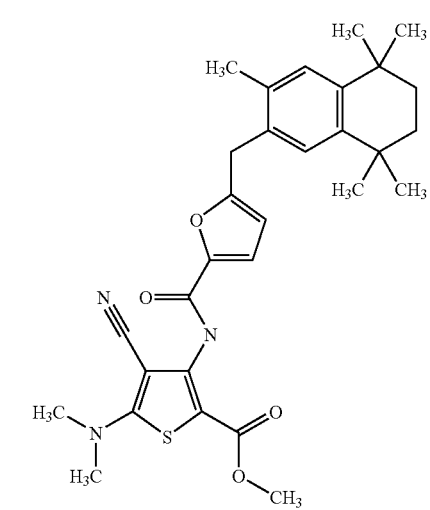

| 2433 | 2434 |
|---|---|
| -continued | -continued |
| MOLSTRUCTURE | MOLSTRUCTURE |
| 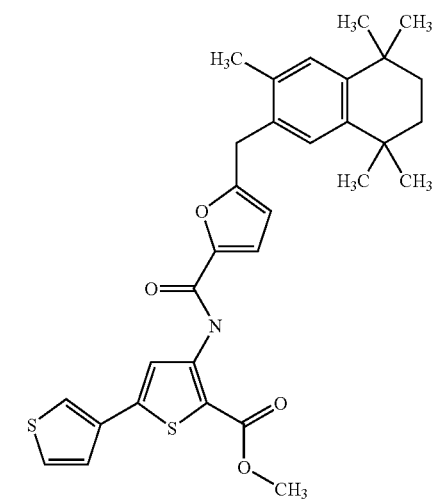 | 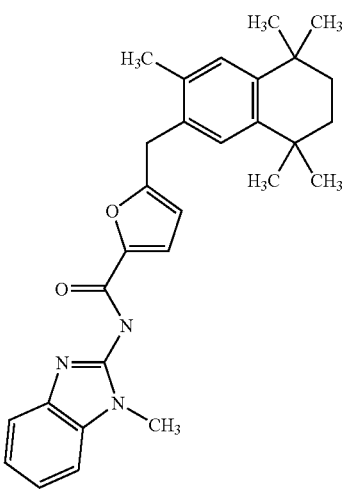 |
| 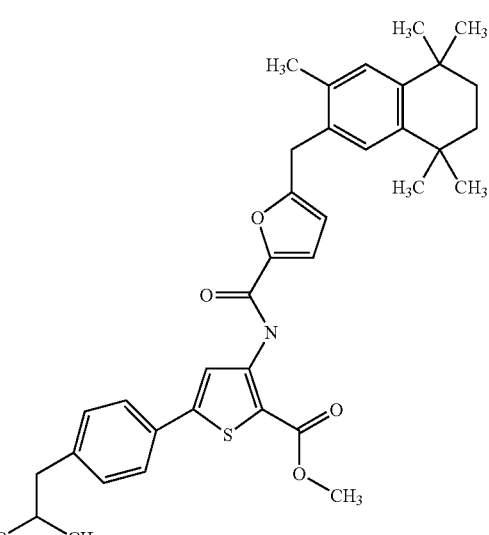 | 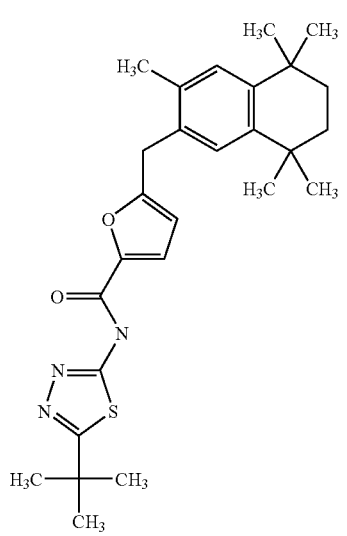 |
| 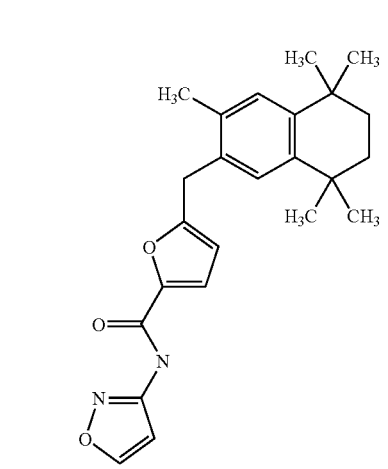 | 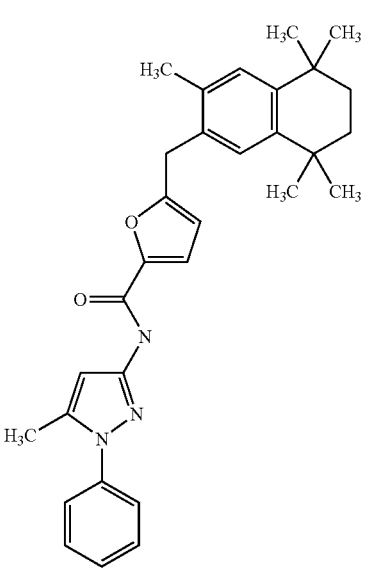 |

| 2435 | 2436 |
|---|---|
| -continued | -continued |
| MOLSTRUCTURE | MOLSTRUCTURE |
| 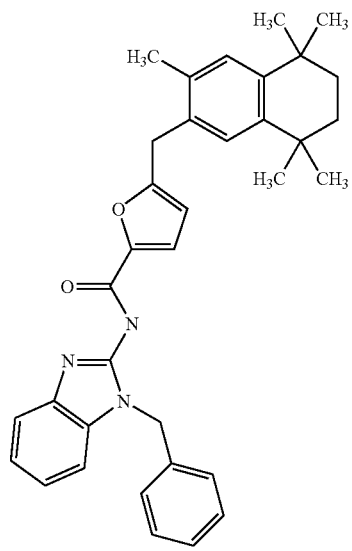 | 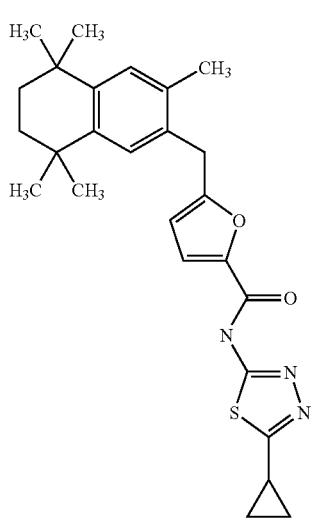 |
| 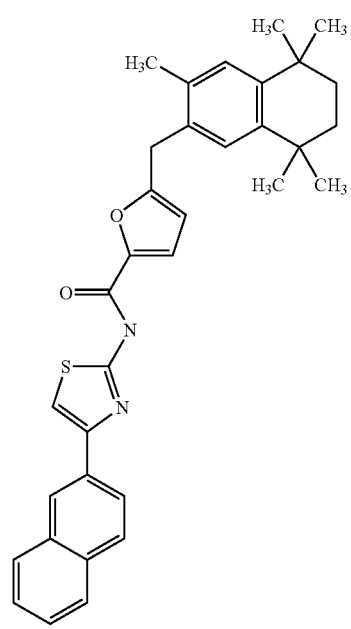 | 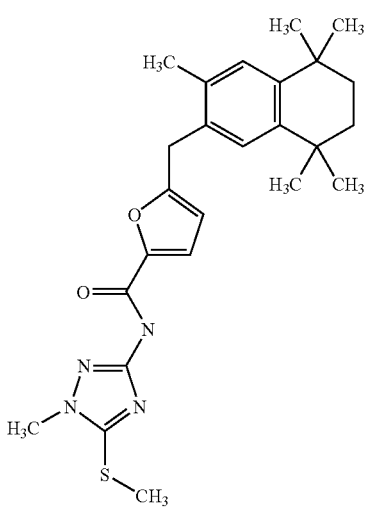 |

| 2437 | 2438 |
|---|---|
| -continued | -continued |
| MOLSTRUCTURE | MOLSTRUCTURE |
| 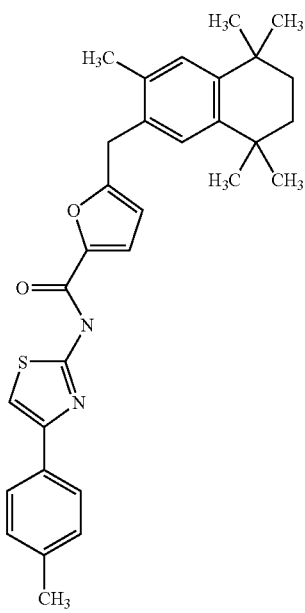 | 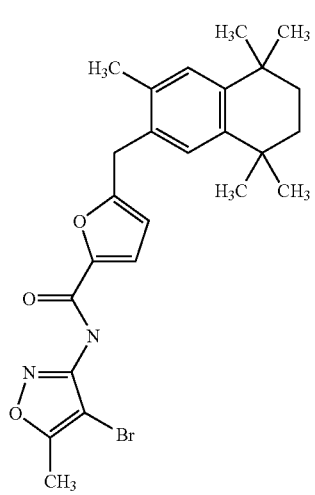 |
| 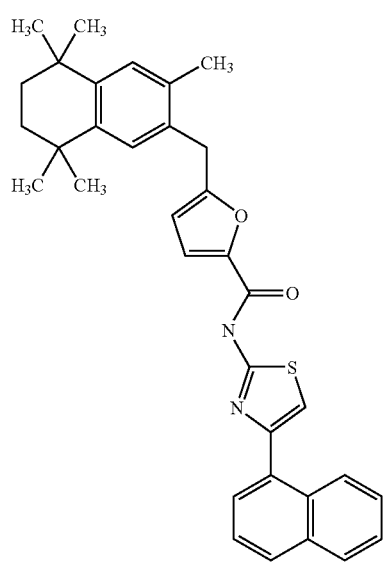 | 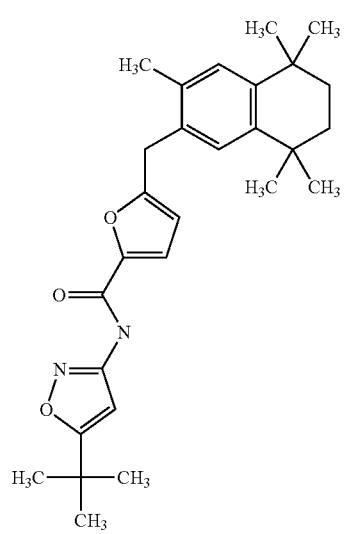 |

| 2439 | 2440 |
|---|---|
| -continued | -continued |
| MOLSTRUCTURE | MOLSTRUCTURE |
| 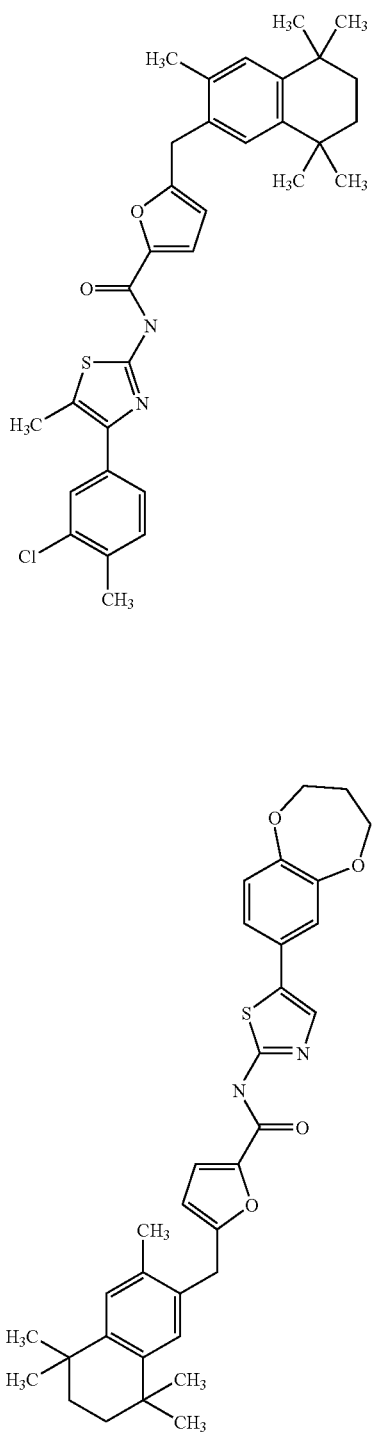 | 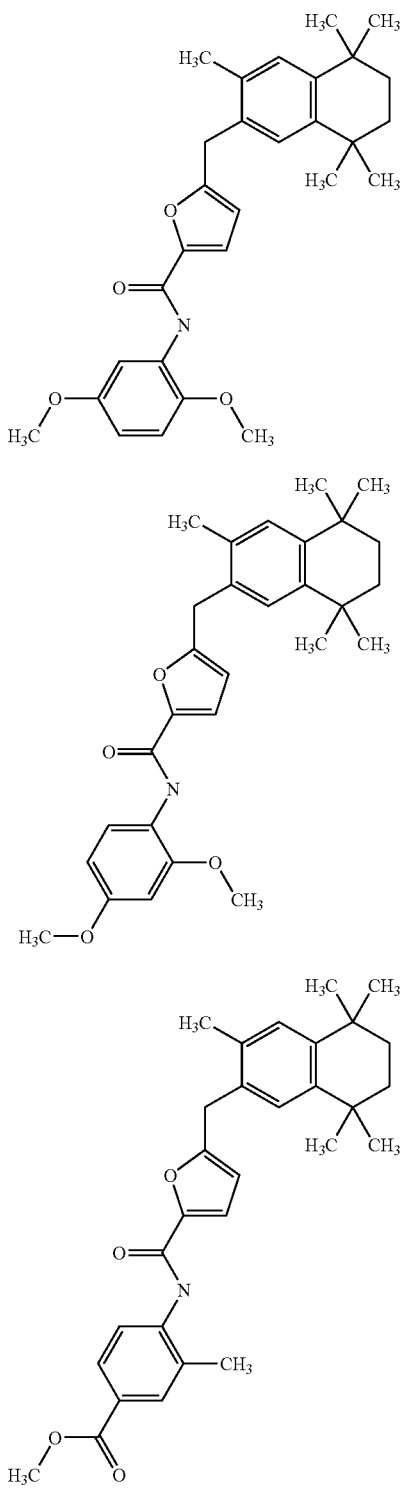 |

| 2441 | 2442 |
|---|---|
| -continued | -continued |
| MOLSTRUCTURE | MOLSTRUCTURE |
| 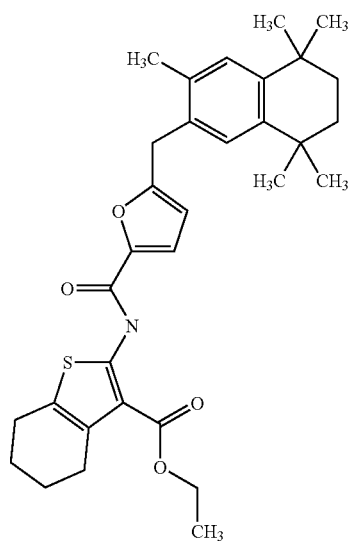 | 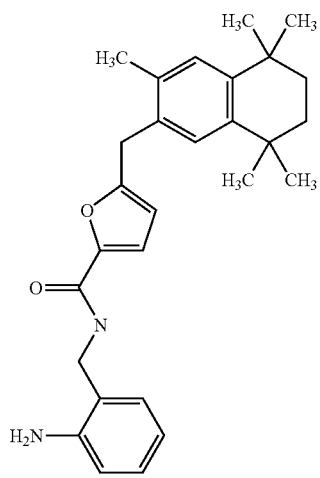 |
| 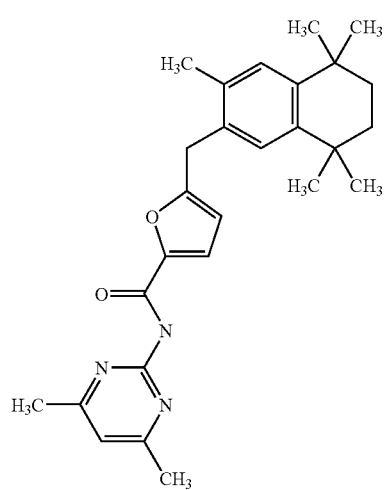 | 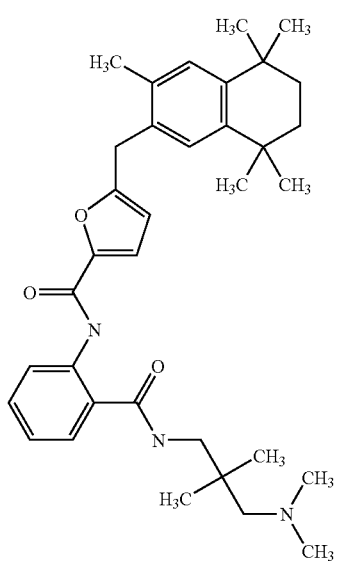 |
| 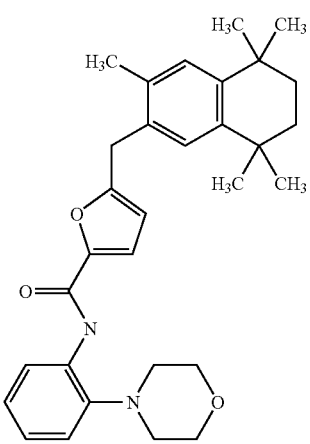 | 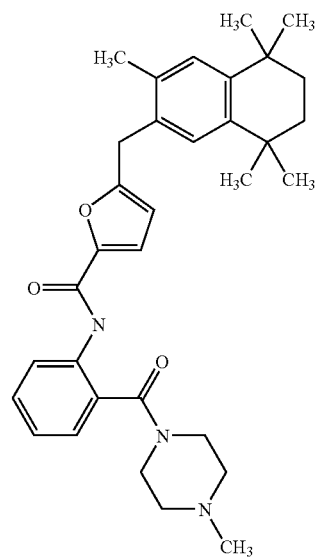 |

| 2443 | 2444 |
|---|---|
| -continued | -continued |
| MOLSTRUCTURE | MOLSTRUCTURE |
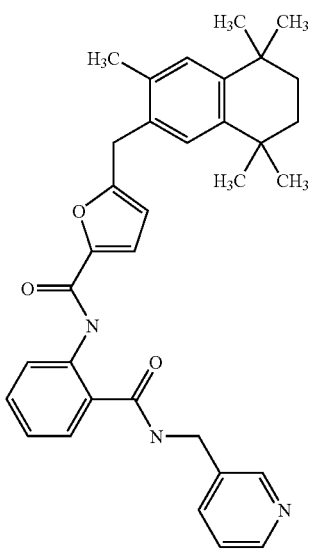
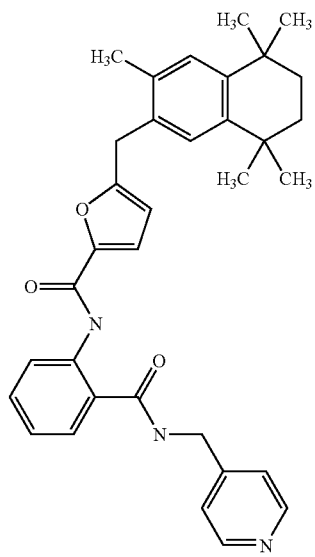
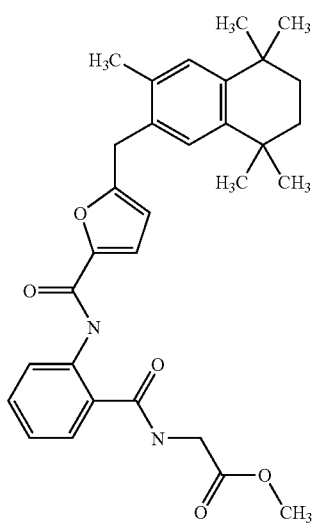
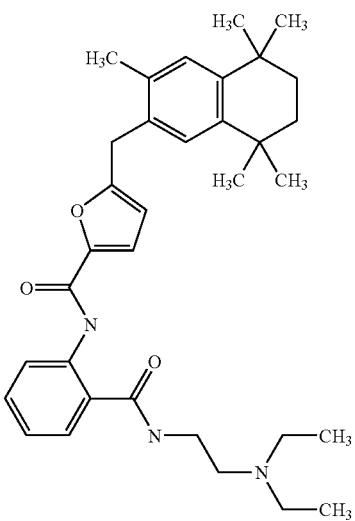

| 2445 | 2446 |
|---|---|
| -continued | -continued |
| MOLSTRUCTURE | MOLSTRUCTURE |
| 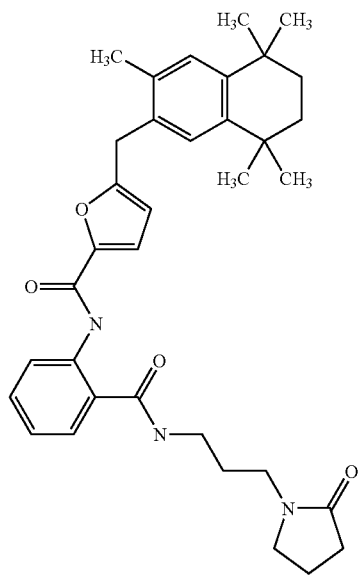 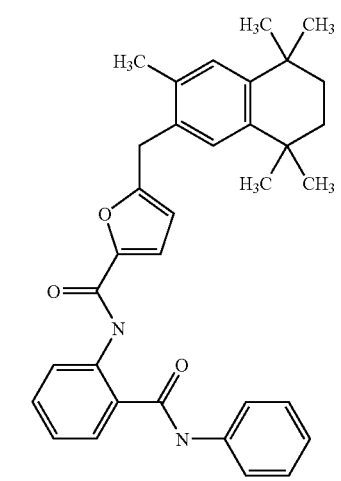 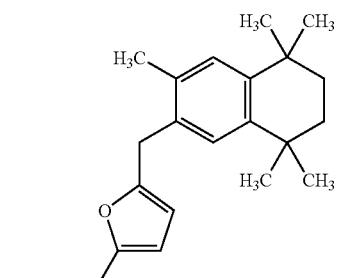 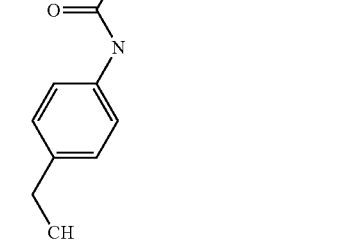 | 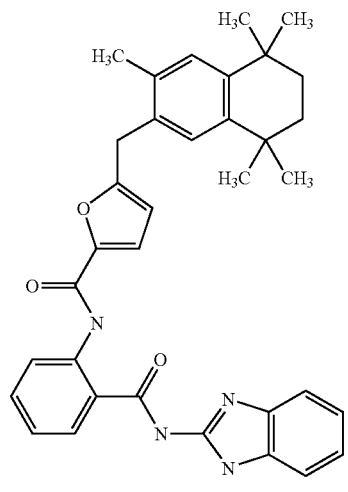 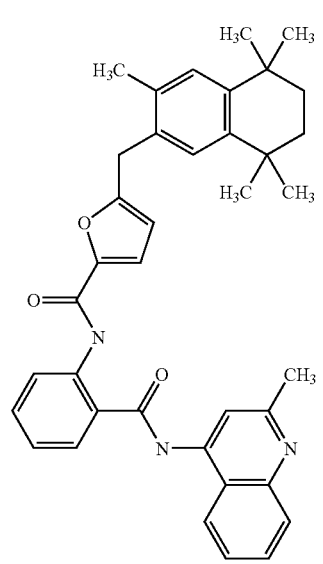 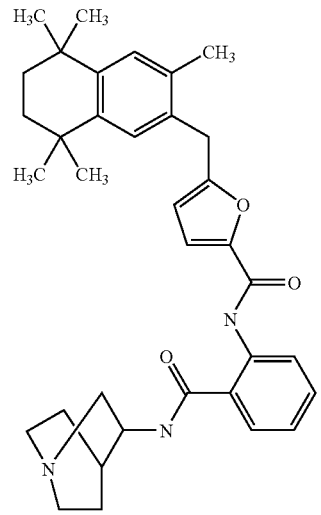 |

| 2447 | 2448 |
|---|---|
| -continued | -continued |
| MOLSTRUCTURE | MOLSTRUCTURE |
| 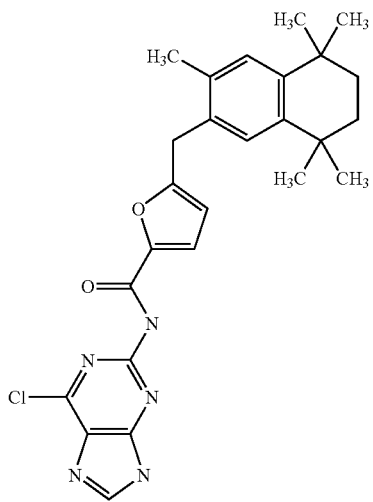 | 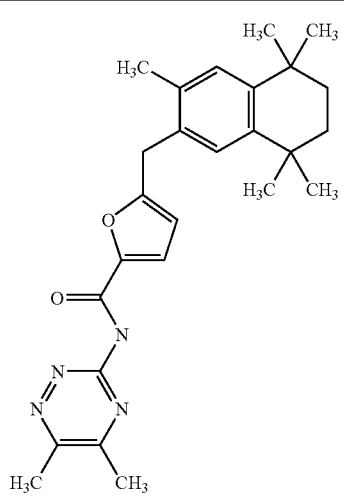 |
| 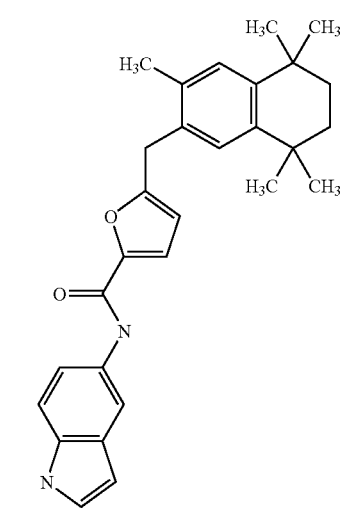 | 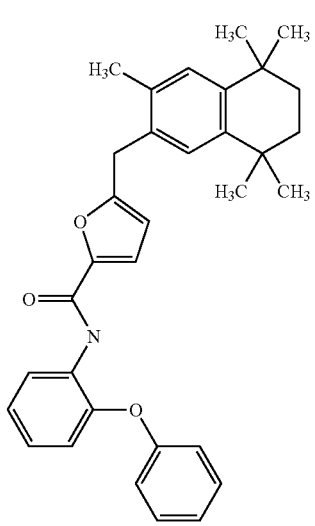 |
| 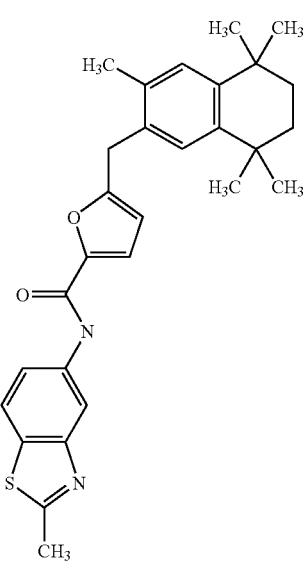 | 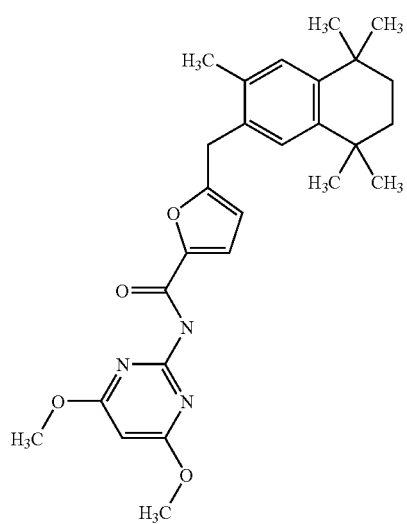 |

| 2449 | 2450 |
|---|---|
| -continued | -continued |
| MOLSTRUCTURE | MOLSTRUCTURE |
| 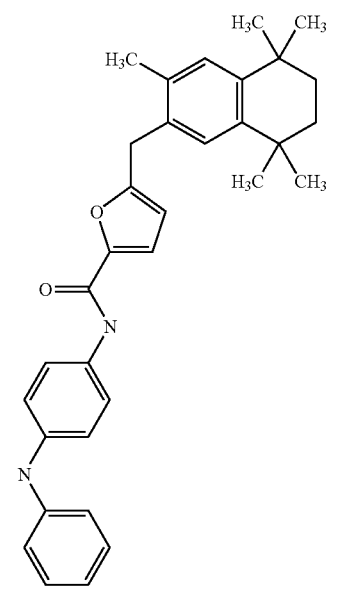 | 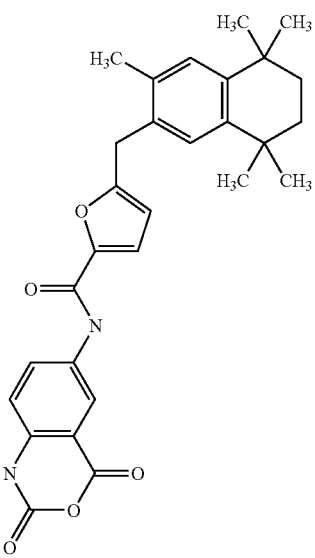 |
| 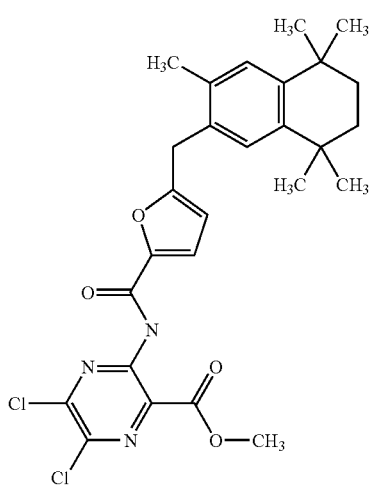 | 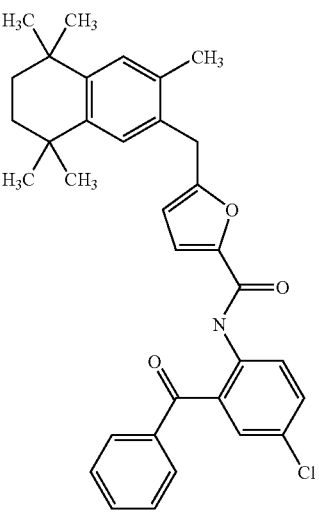 |
| | 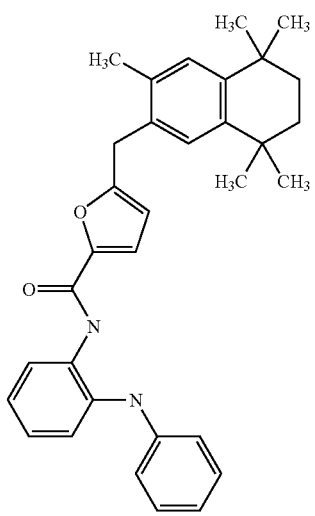 |

| 2451 | 2452 |
|---|---|
| -continued | -continued |
| MOLSTRUCTURE | MOLSTRUCTURE |
| 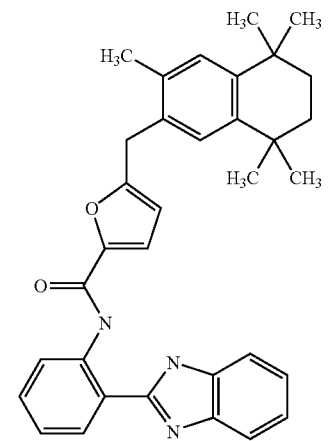 | 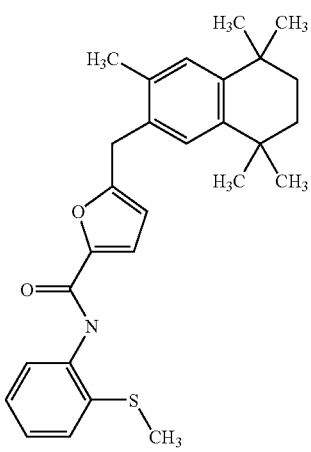 |
| 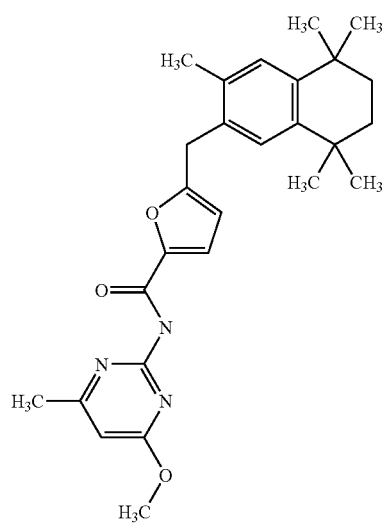 | 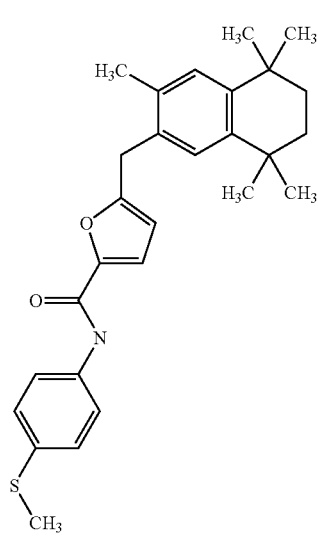 |
| 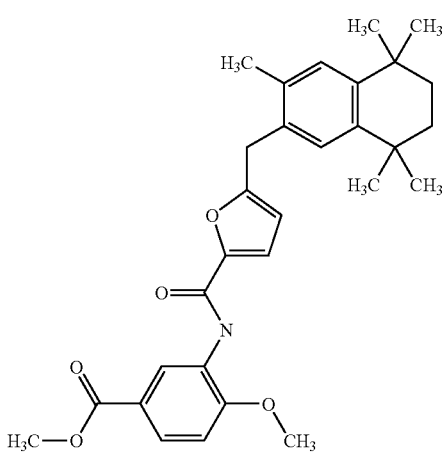 | 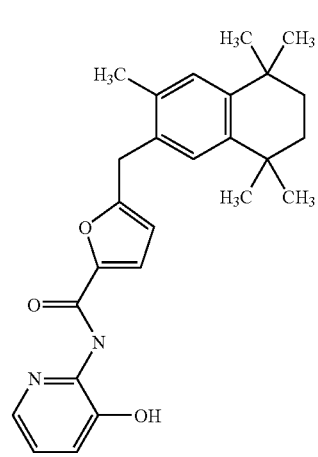 |

| 2453 | 2454 |
|---|---|
| -continued | -continued |
| MOLSTRUCTURE | MOLSTRUCTURE |
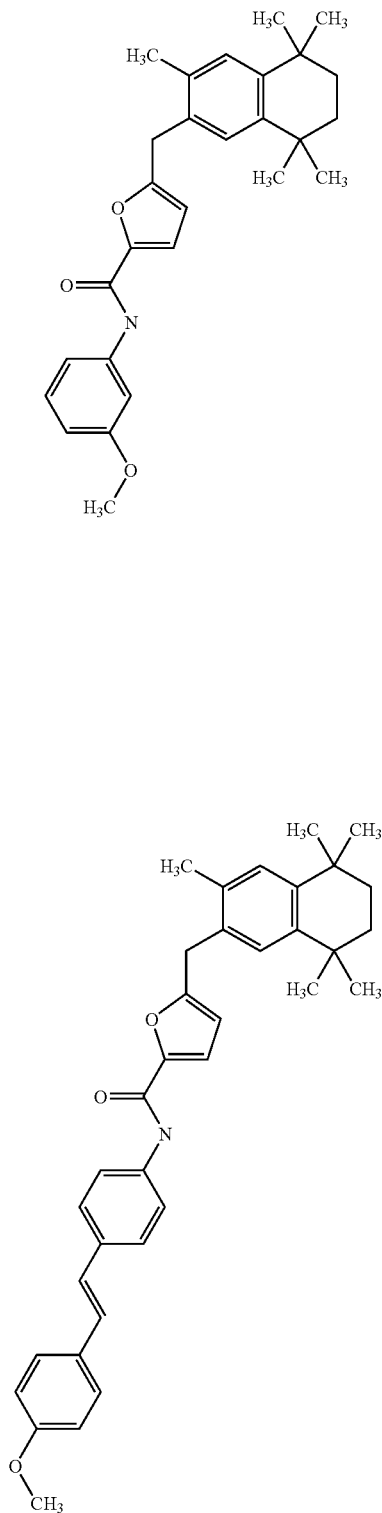
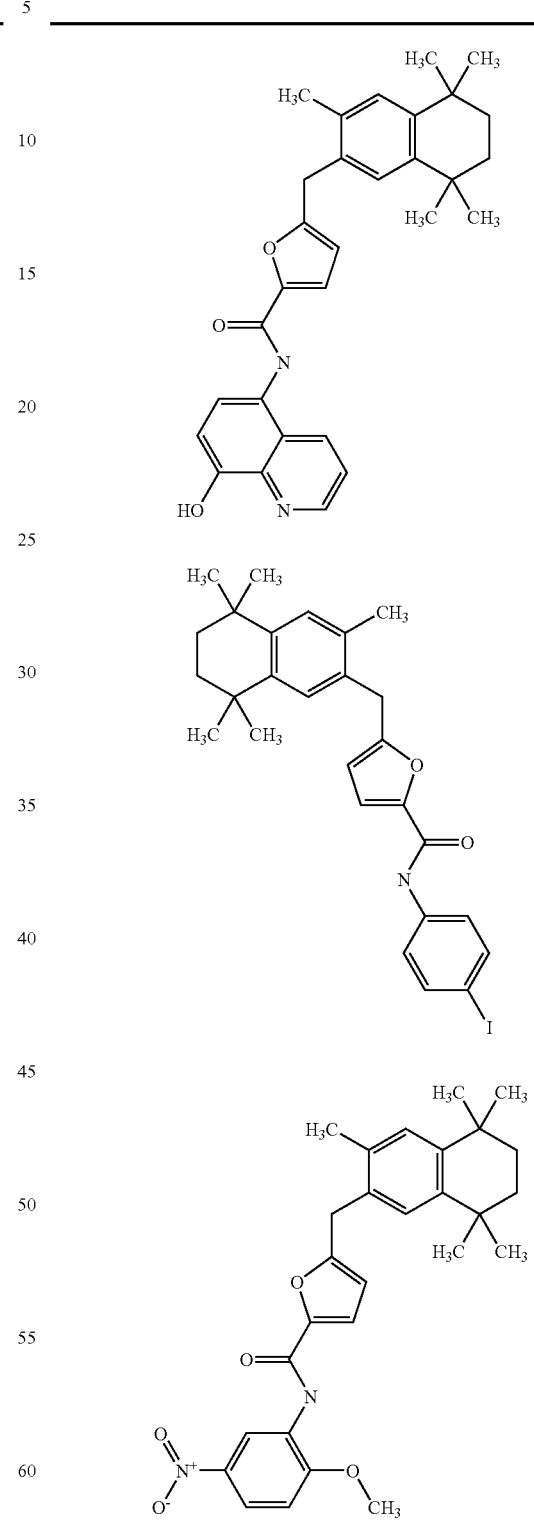

| 2455 | 2456 |
|---|---|
| -continued | -continued |
| MOLSTRUCTURE | MOLSTRUCTURE |
| 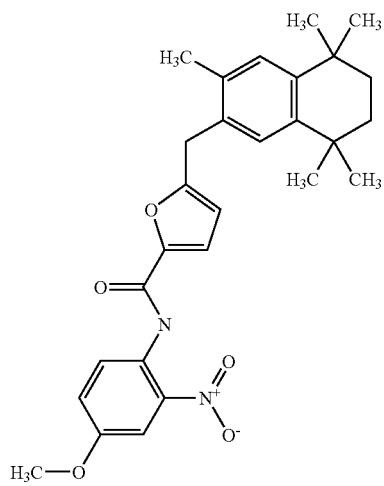 | 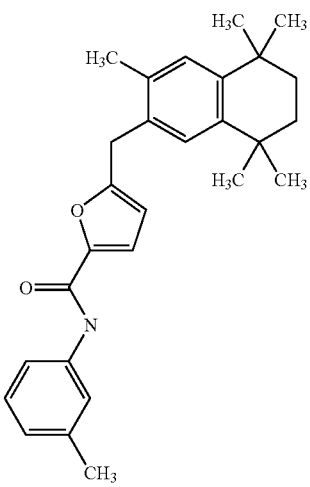 |
| 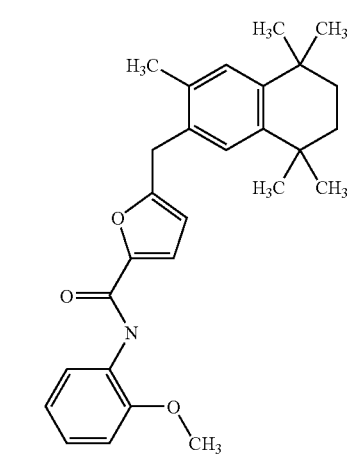 | 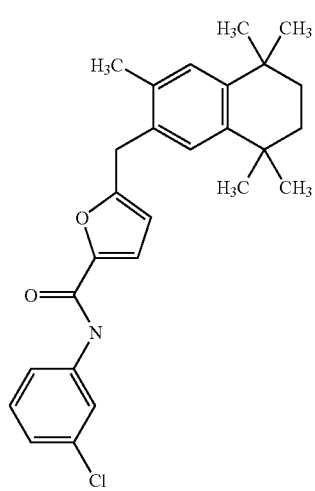 |
| 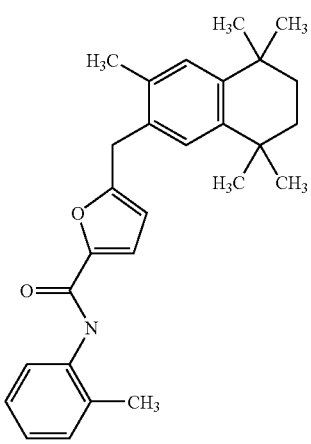 | 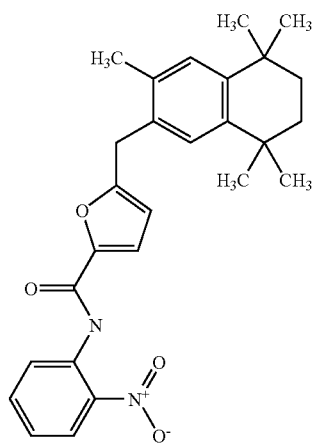 |

| 2457 | 2458 |
|---|---|
| -continued | -continued |
| MOLSTRUCTURE | MOLSTRUCTURE |
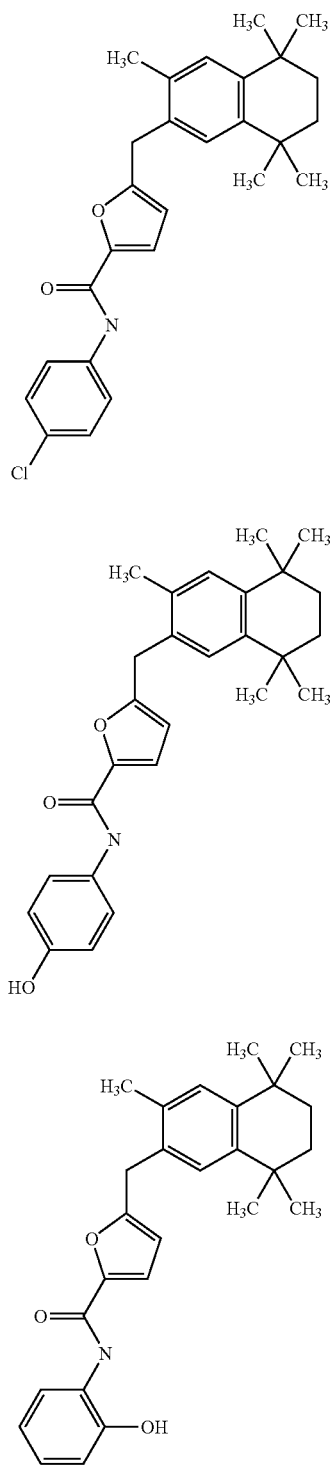

| 2459 | 2460 |
|---|---|
| -continued | -continued |
| MOLSTRUCTURE | MOLSTRUCTURE |
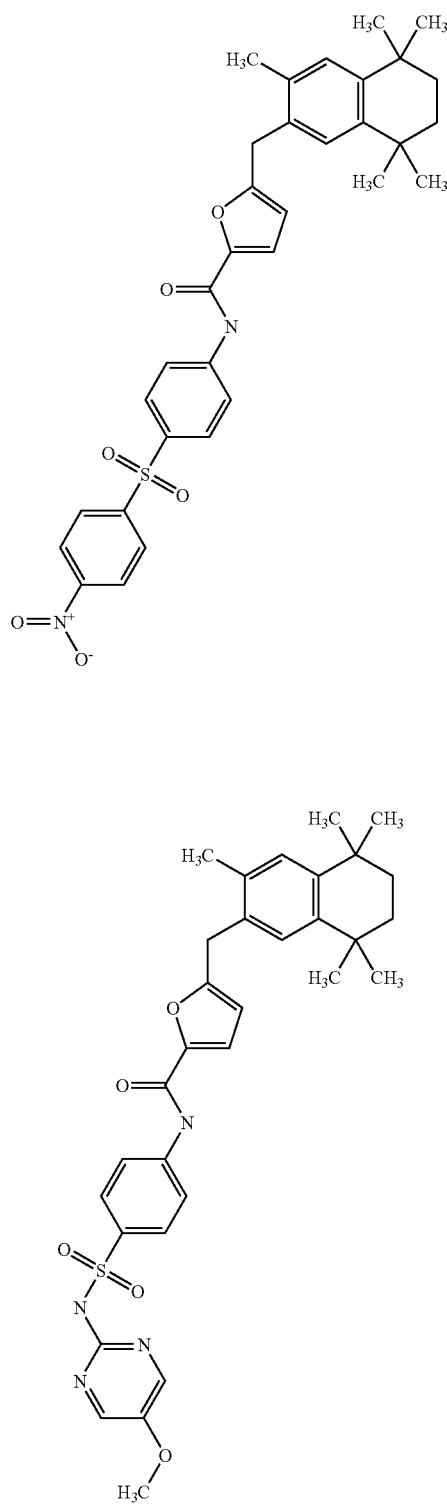
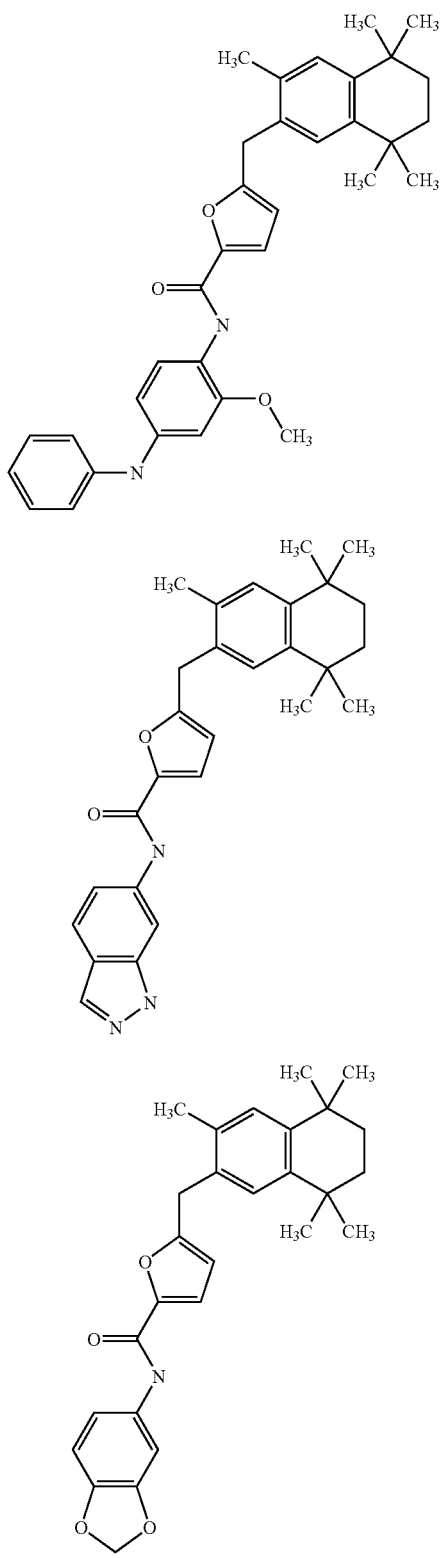

| 2461 | 2462 |
|---|---|
| -continued | -continued |
| MOLSTRUCTURE | MOLSTRUCTURE |
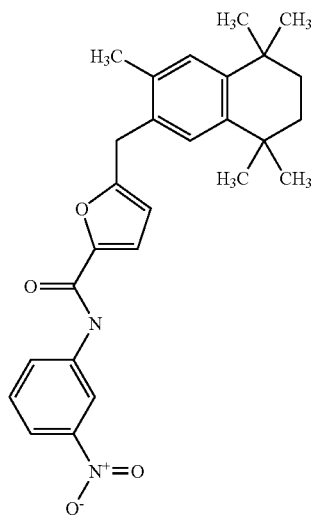
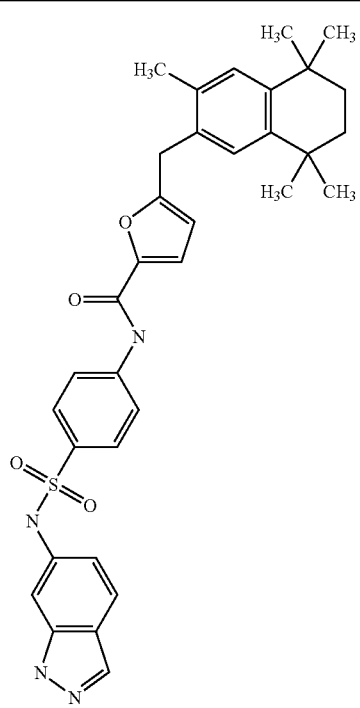
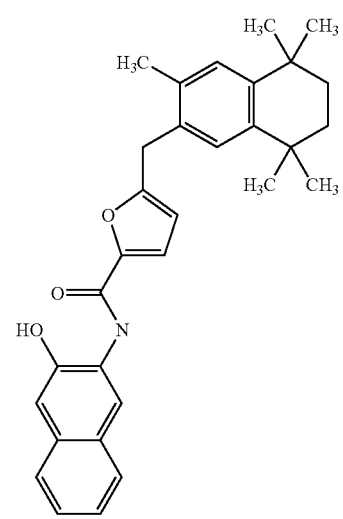
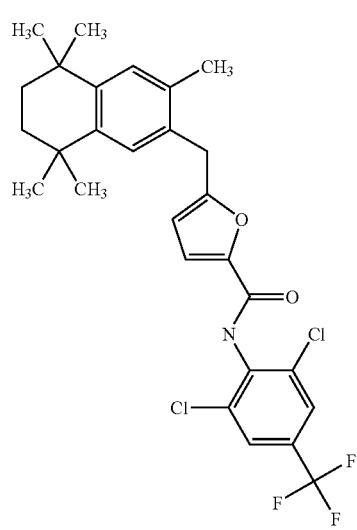
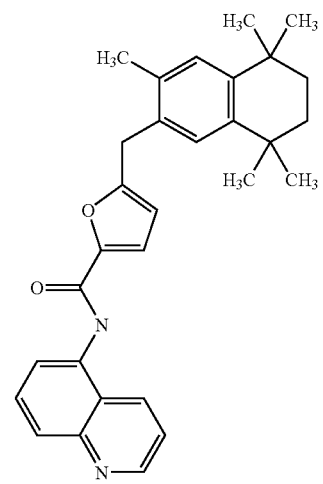

| 2463 | 2464 |
|---|---|
| -continued | -continued |
| MOLSTRUCTURE | MOLSTRUCTURE |
| 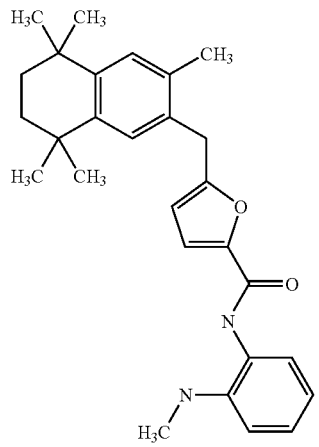 | 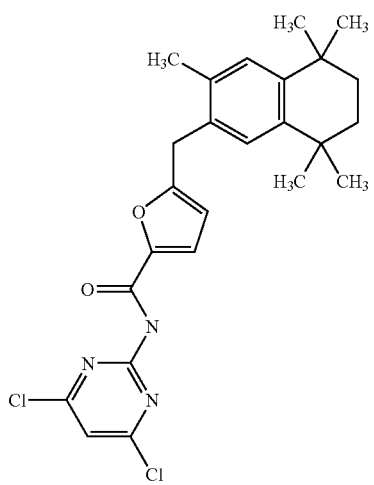 |
| 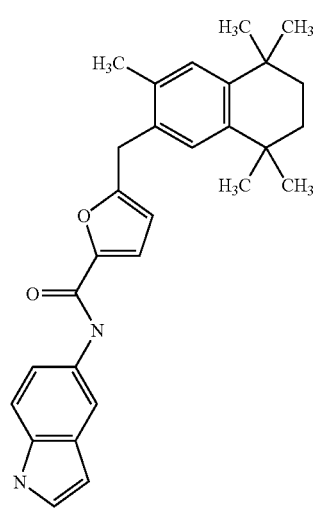 | 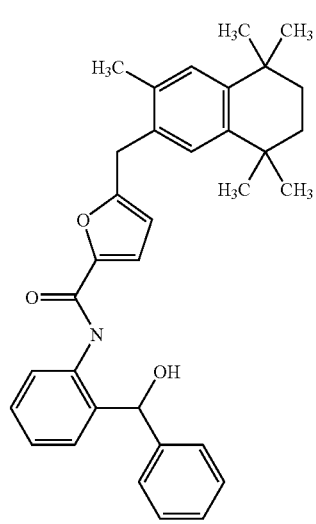 |
| 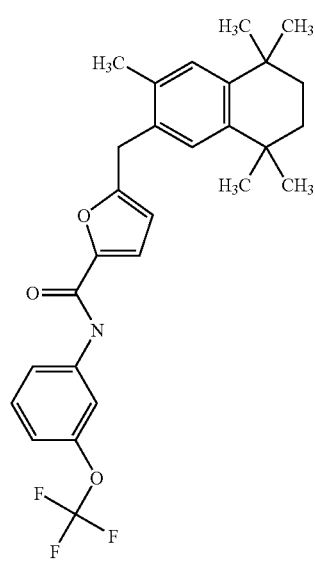 | 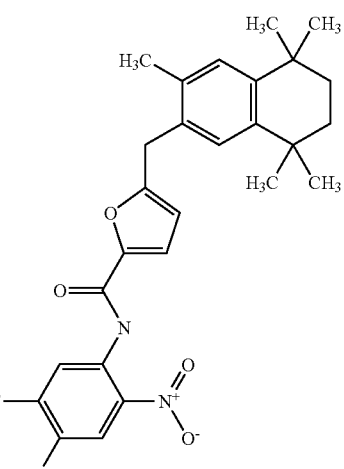 |

| 2465 | 2466 |
|---|---|
| -continued | -continued |
| MOLSTRUCTURE | MOLSTRUCTURE |
| 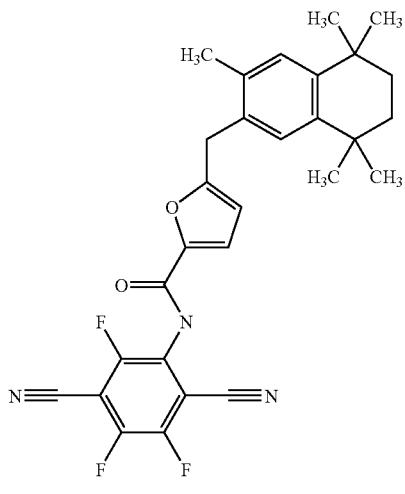 | 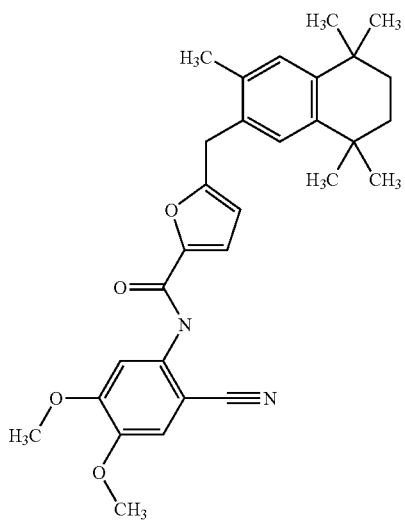 |
| 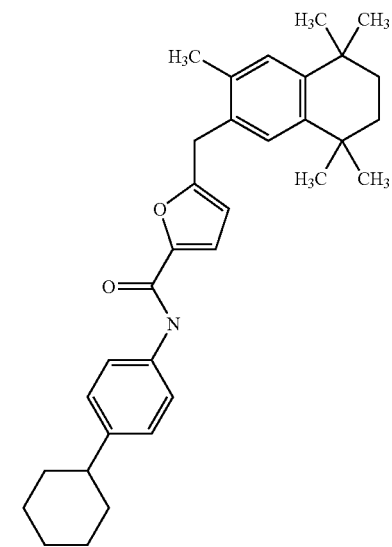 | 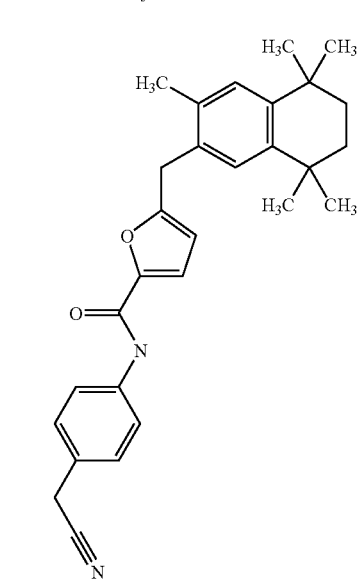 |
| 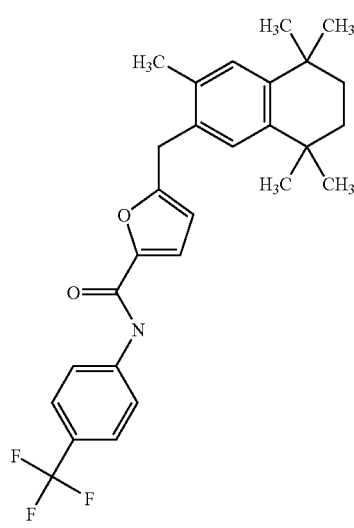 | 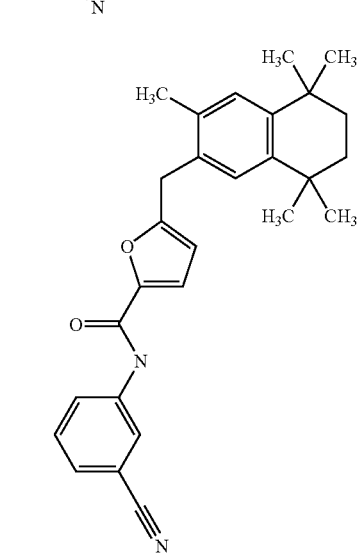 |

| 2467 | 2468 |
|---|---|
| -continued | -continued |
| MOLSTRUCTURE | MOLSTRUCTURE |
| 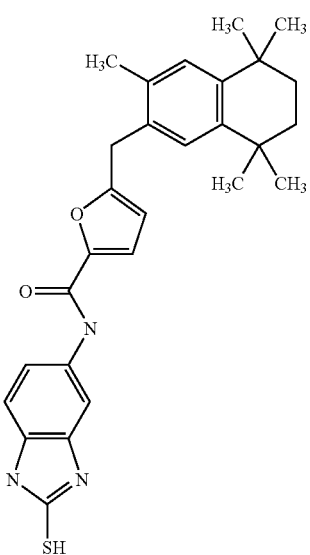 | 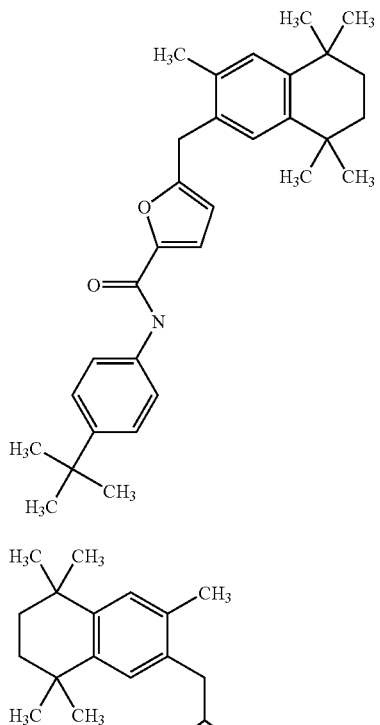 |
| 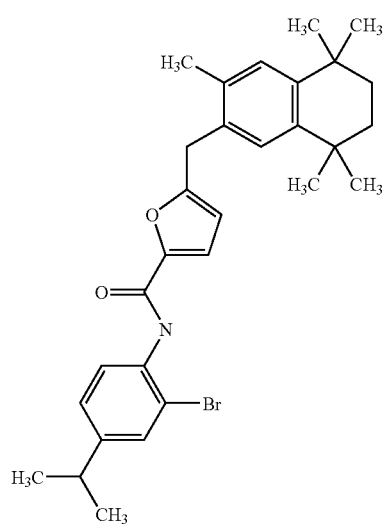 | 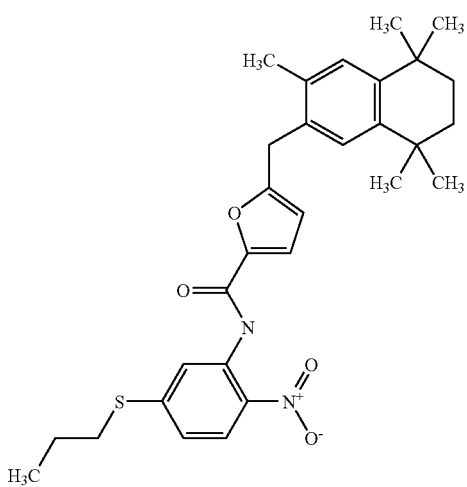 |

| 2469 | 2470 |
|---|---|
| -continued | -continued |
| MOLSTRUCTURE | MOLSTRUCTURE |
| 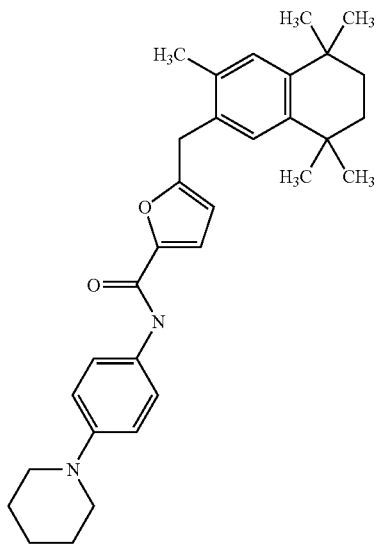 | 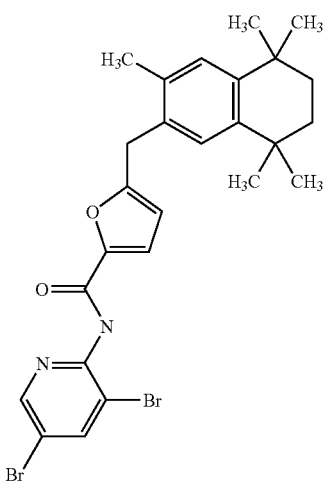 |
| 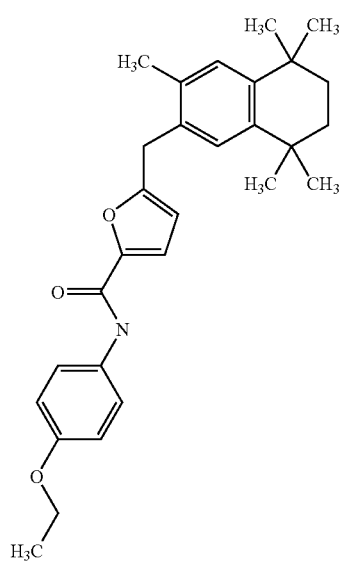 | 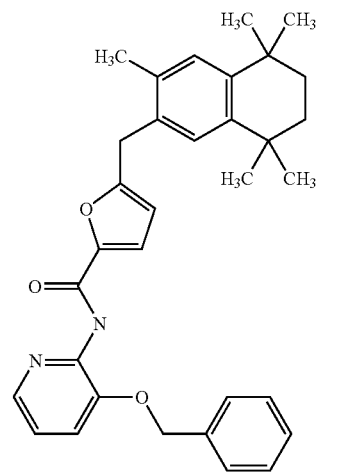 |
| 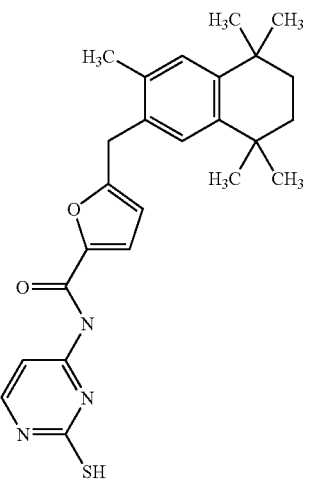 | 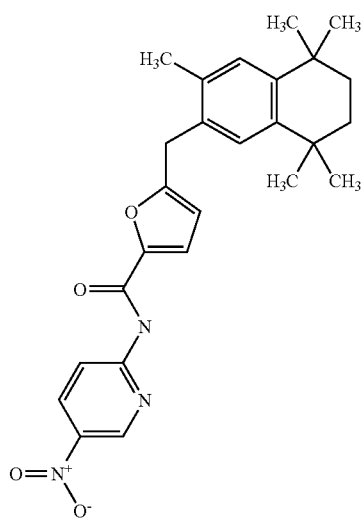 |

| 2471 | 2472 |
|---|---|
| -continued | -continued |
| MOLSTRUCTURE | MOLSTRUCTURE |
| 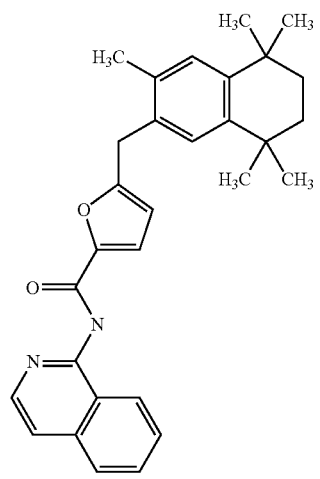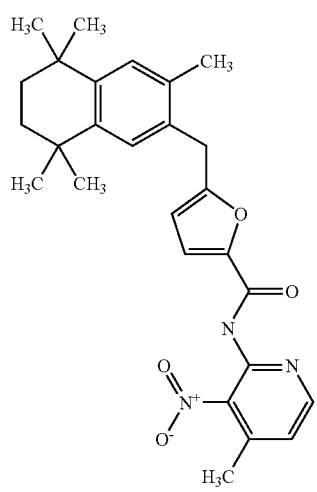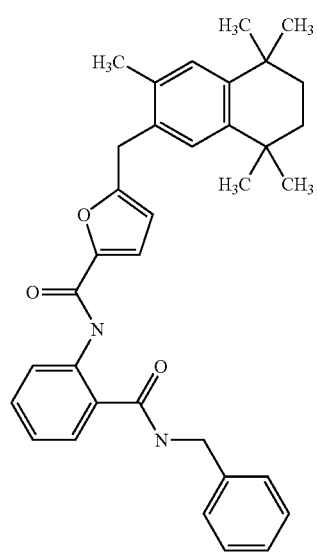 | 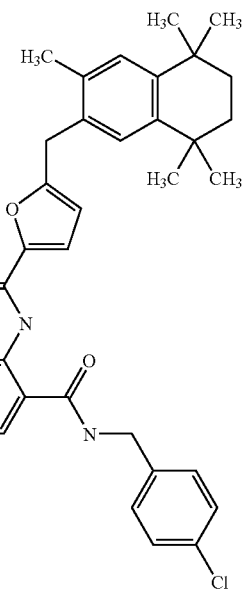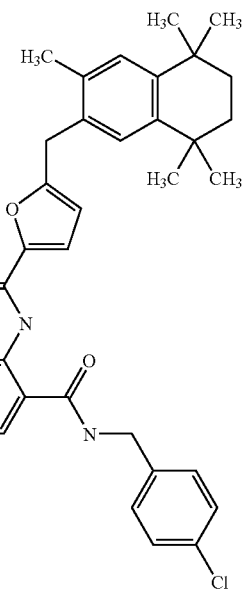 |

| 2473 | 2474 |
|---|---|
| -continued | -continued |
| MOLSTRUCTURE | MOLSTRUCTURE |
| 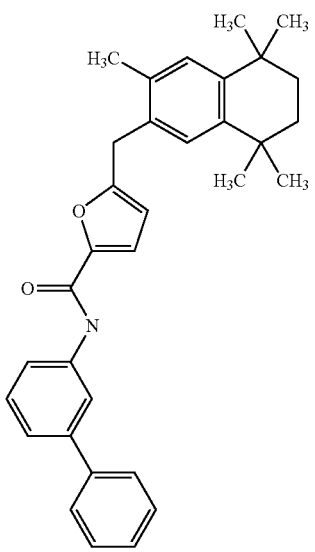 | 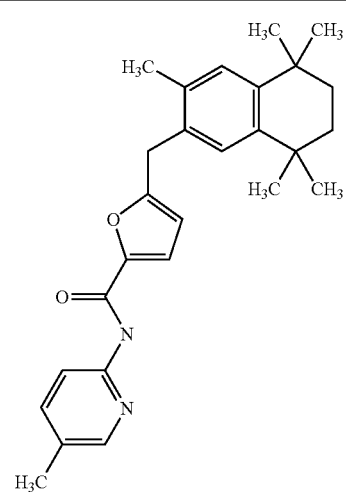 |
| 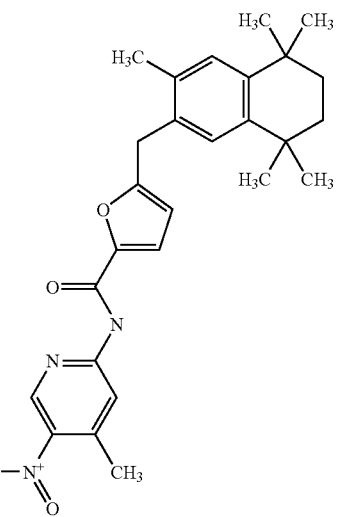 | 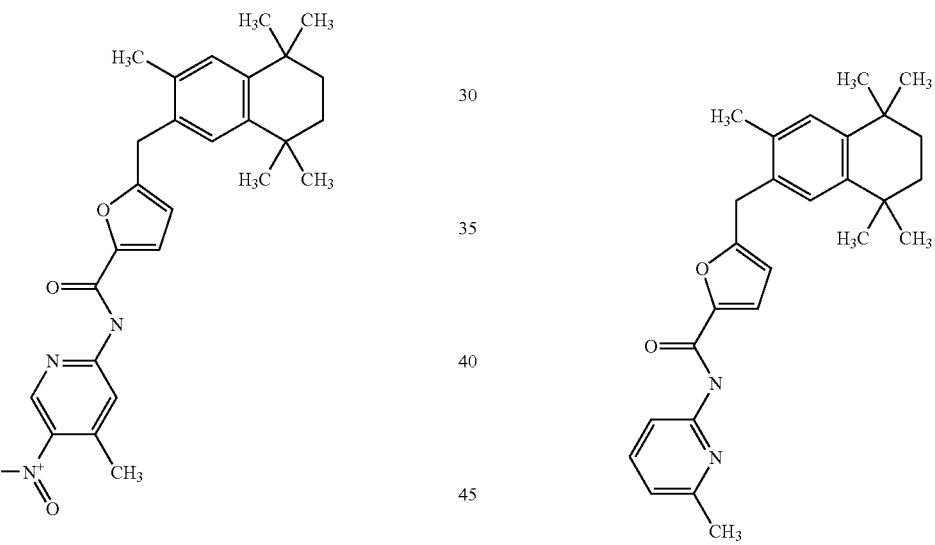 |
| 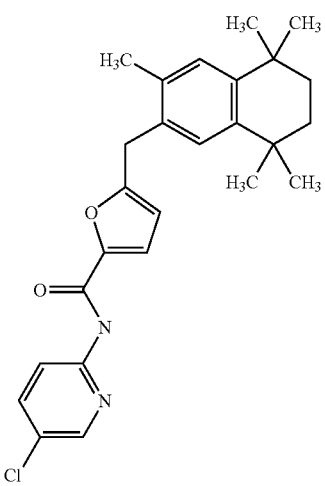 | 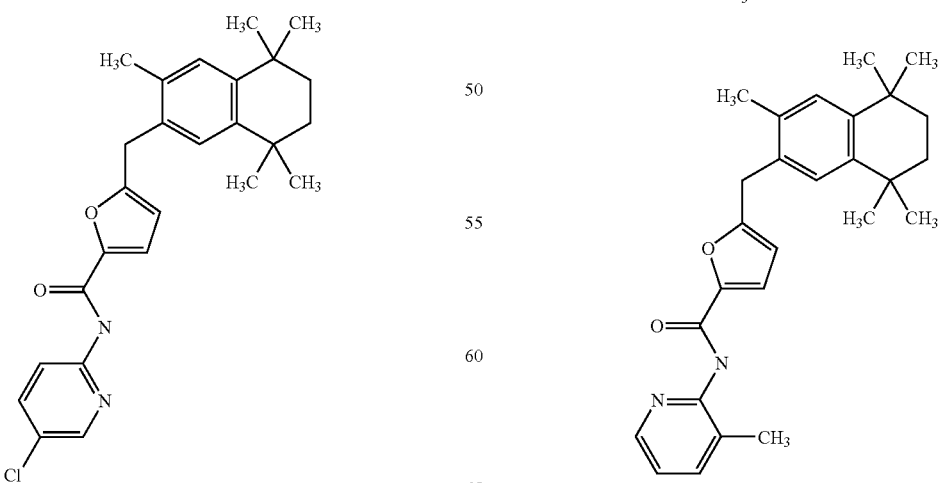 |

| 2475 | 2476 |
|---|---|
| -continued | -continued |
| MOLSTRUCTURE | MOLSTRUCTURE |
| 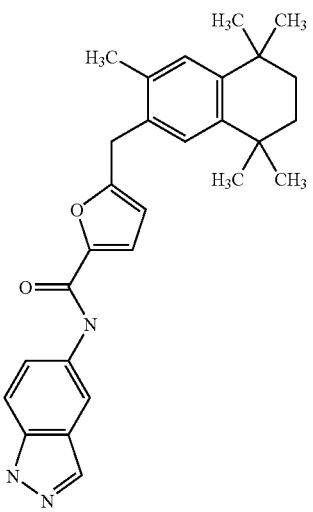<br>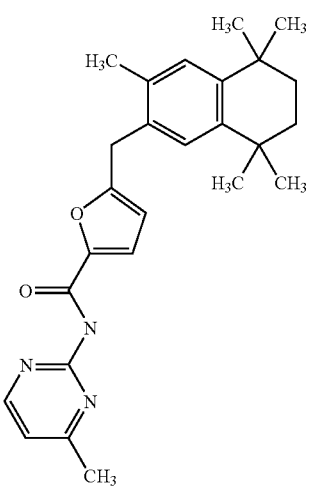<br>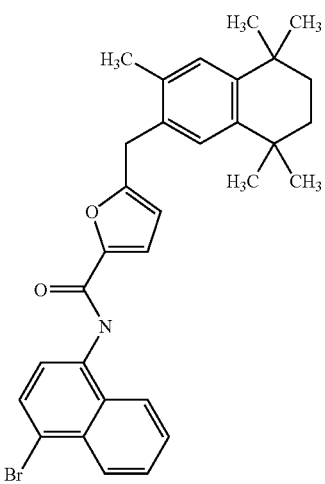 | 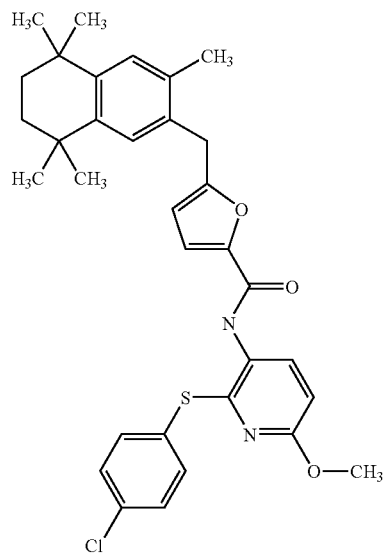<br>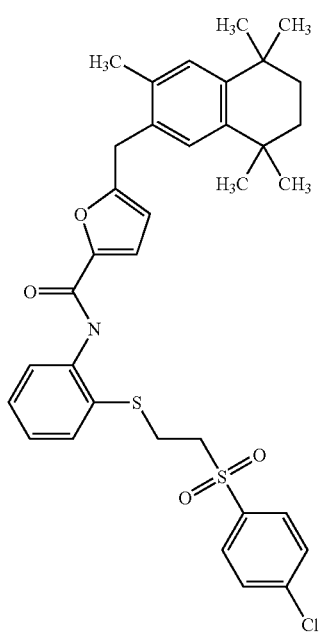 |

| 2477 | 2478 |
|---|---|
| -continued | -continued |
| MOLSTRUCTURE | MOLSTRUCTURE |
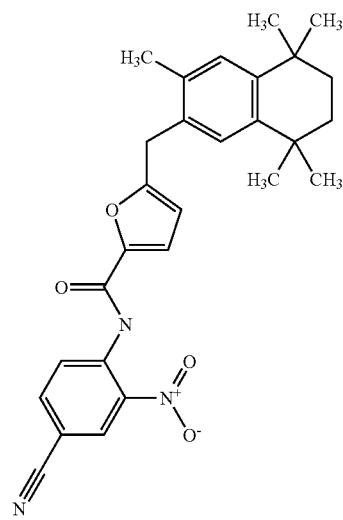
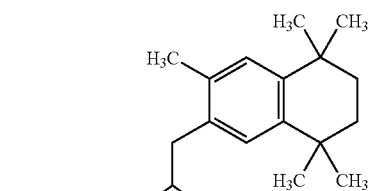
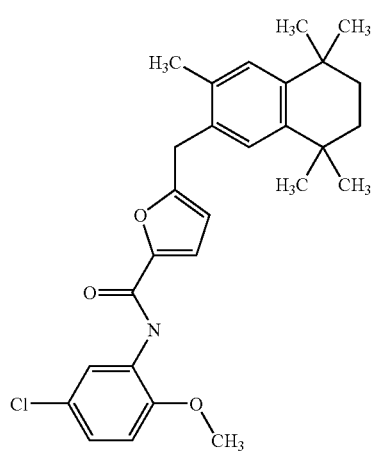
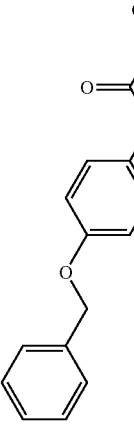
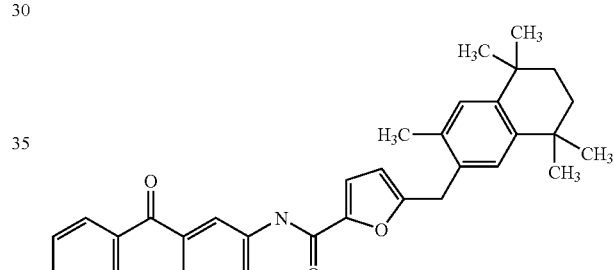
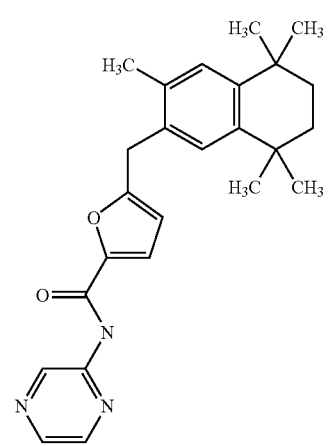
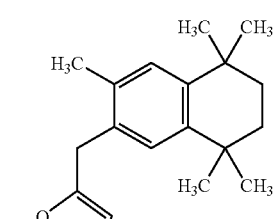
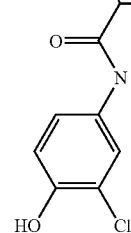

| 2479 | 2480 |
|---|---|
| -continued | -continued |
| MOLSTRUCTURE | MOLSTRUCTURE |
| 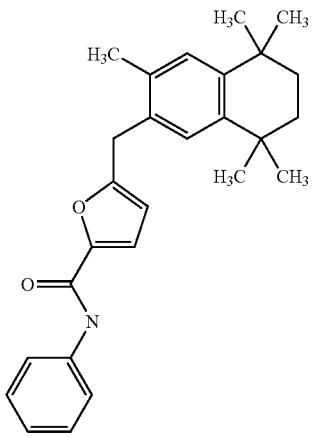 | 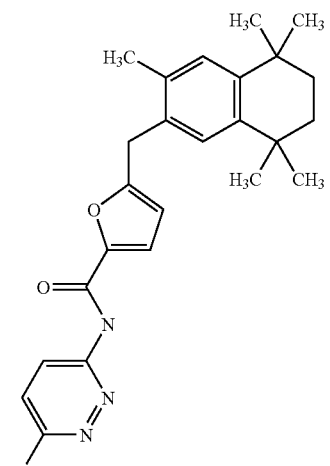 |
| 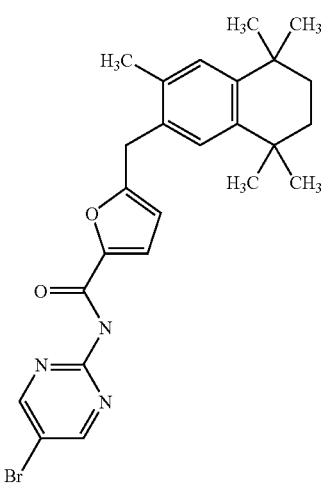 | 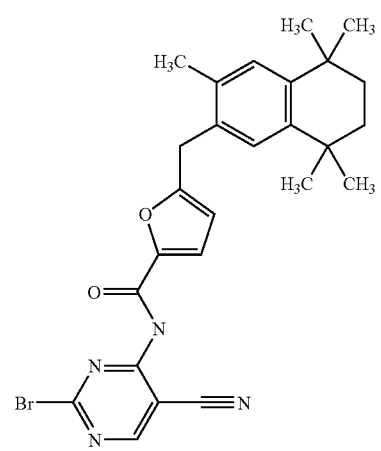 |
| 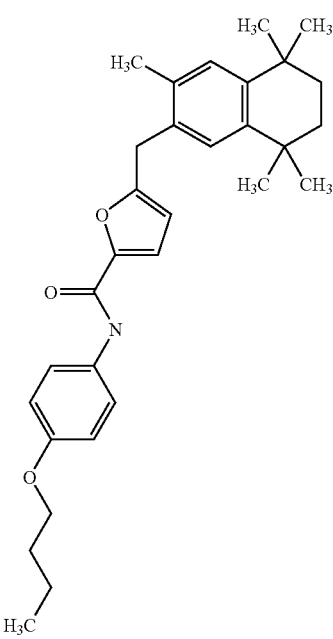 | 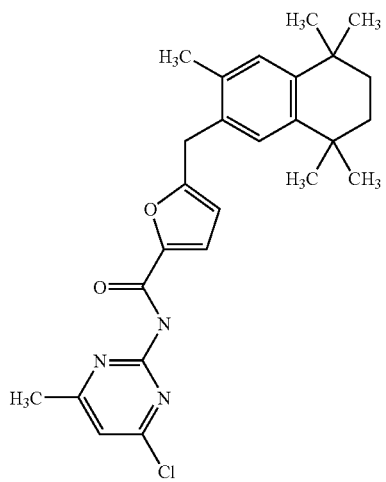 |

| 2481 | 2482 |
|---|---|
| -continued | -continued |
| MOLSTRUCTURE | MOLSTRUCTURE |
| 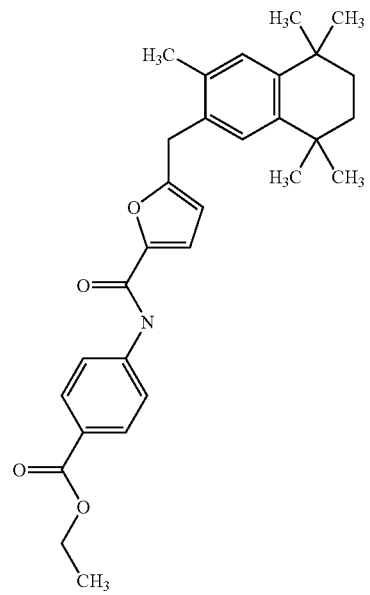 | 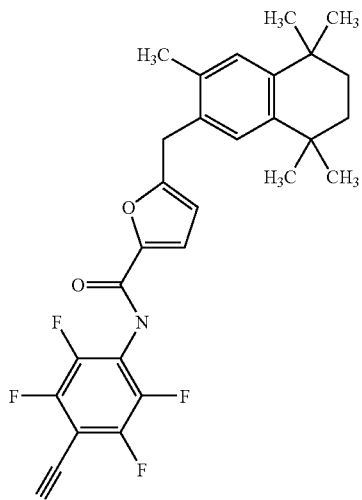 |
| 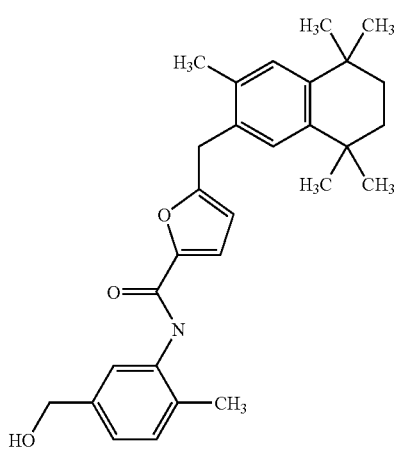 | 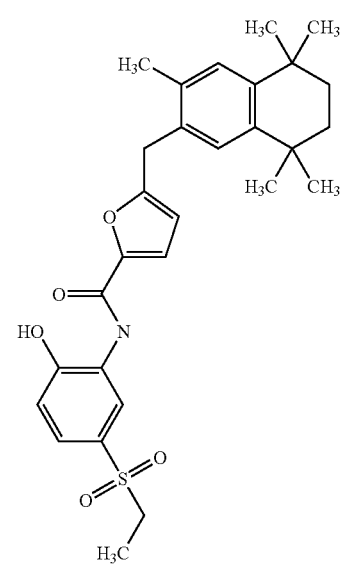 |
| 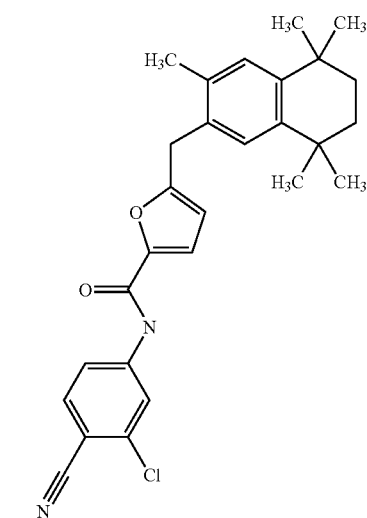 | 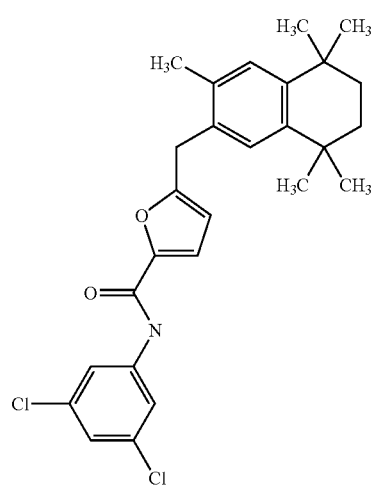 |

| 2483 | 2484 |
|---|---|
| -continued | -continued |
| MOLSTRUCTURE | MOLSTRUCTURE |
| 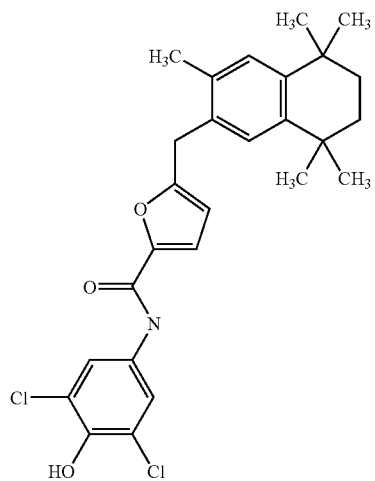 | 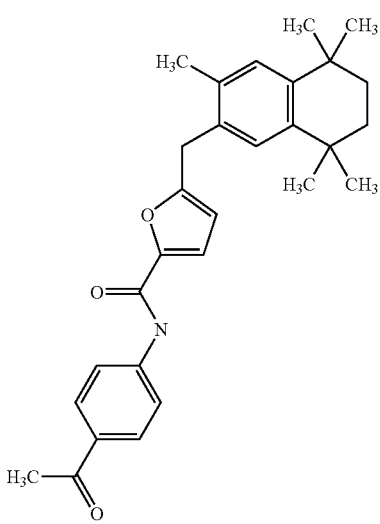 |
| 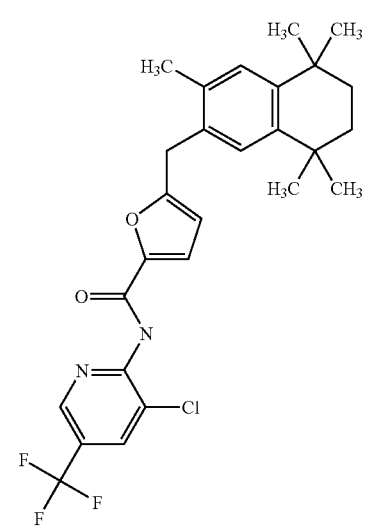 | 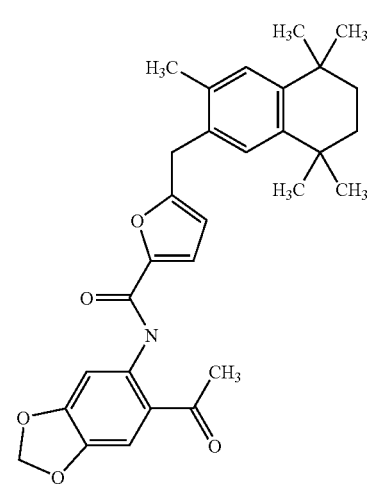 |
| 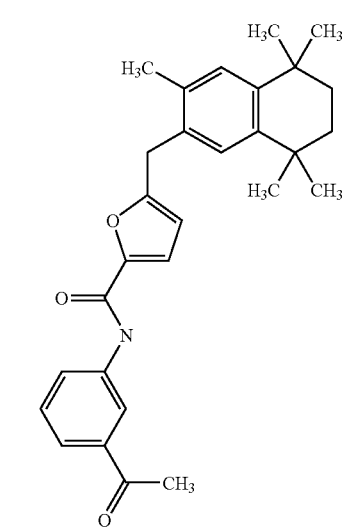 | 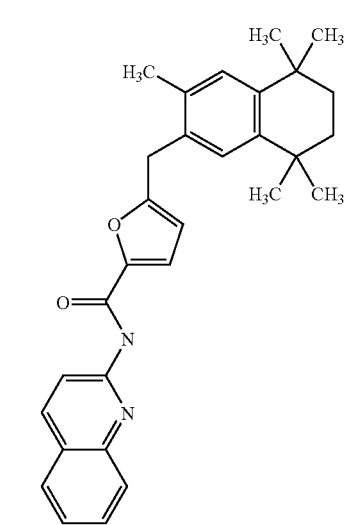 |

| 2485 | 2486 |
|---|---|
| -continued | -continued |
| MOLSTRUCTURE | MOLSTRUCTURE |
| 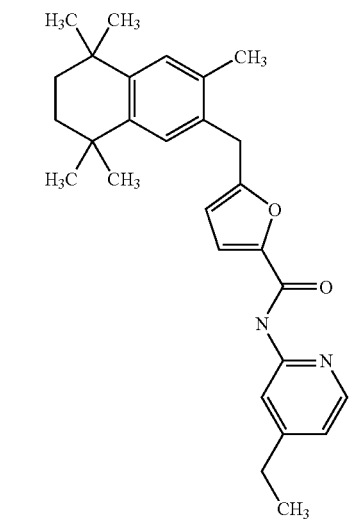 | 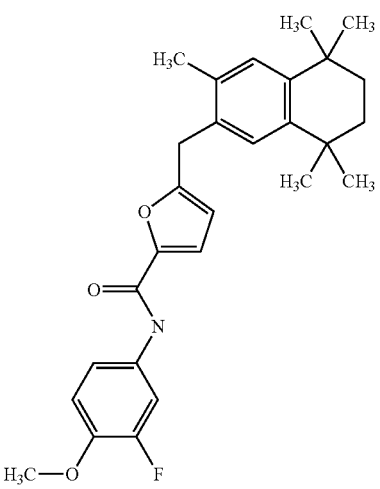 |
| 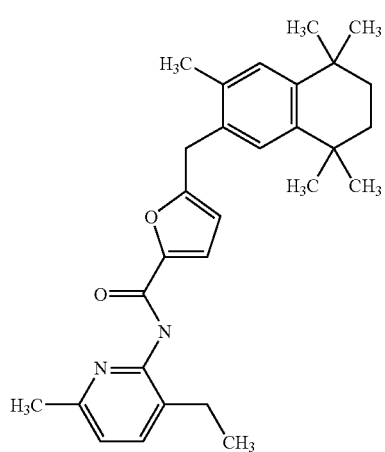 | 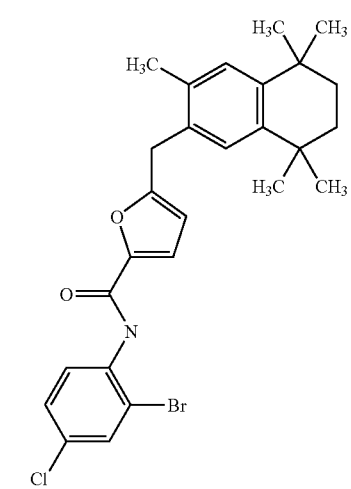 |
| 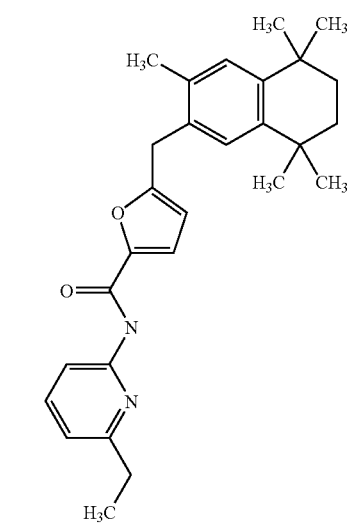 | 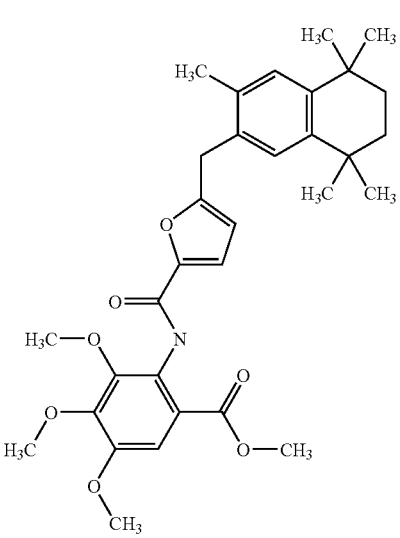 |

| 2487 | 2488 |
|---|---|
| -continued | -continued |
| MOLSTRUCTURE | MOLSTRUCTURE |
| 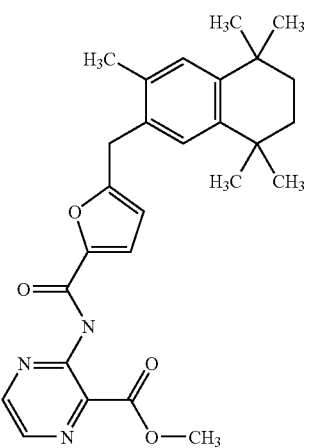 | 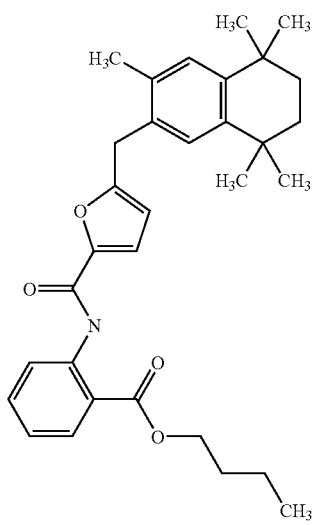 |
| 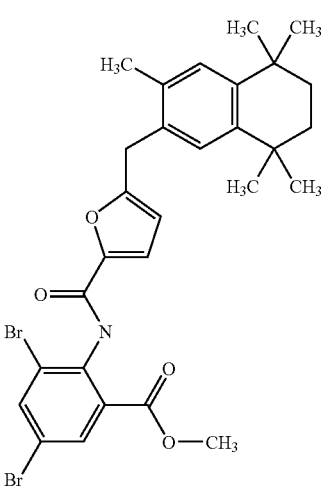 | 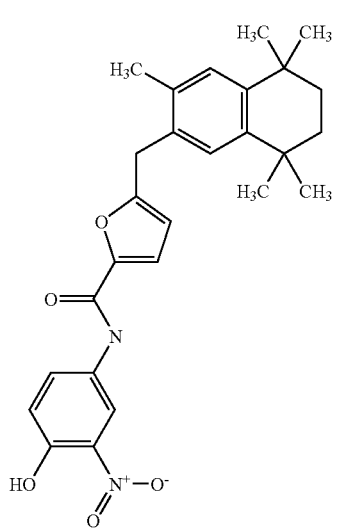 |
| 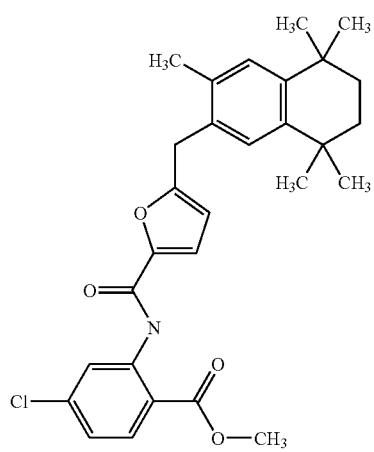 | 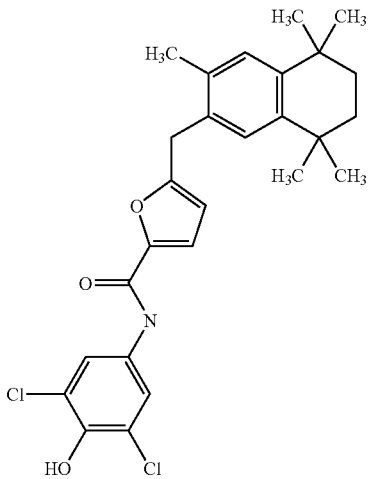 |

| 2489 | 2490 |
|---|---|
| -continued | -continued |
| MOLSTRUCTURE | MOLSTRUCTURE |
| 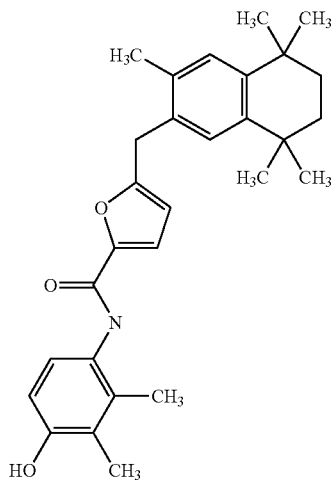 | 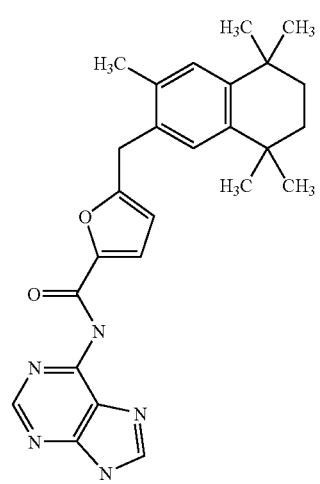 |
| 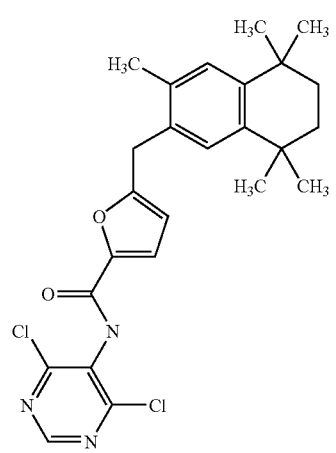 | 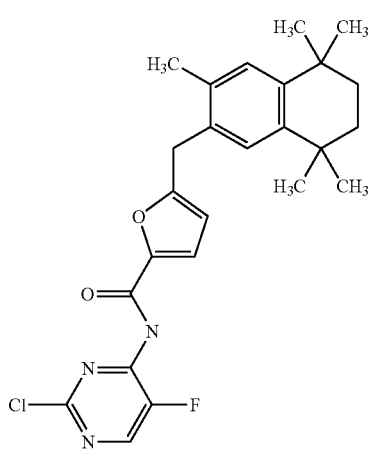 |
| 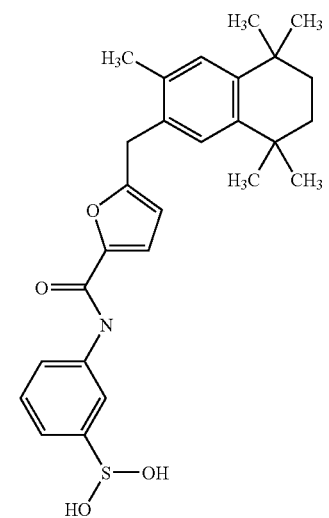 | 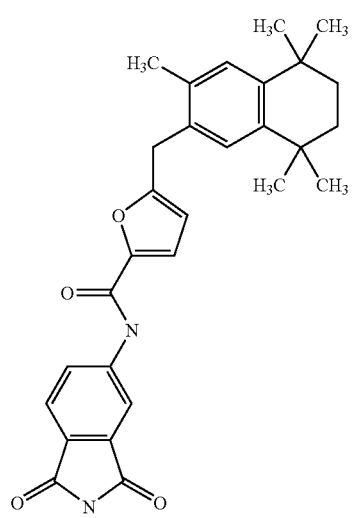 |

| 2491 | 2492 |
|---|---|
| -continued | -continued |
| MOLSTRUCTURE | MOLSTRUCTURE |
| 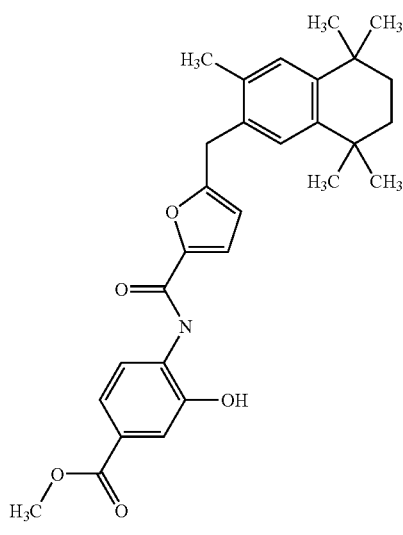 | 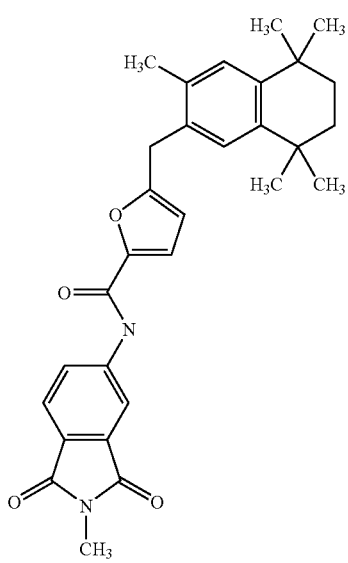 |
| 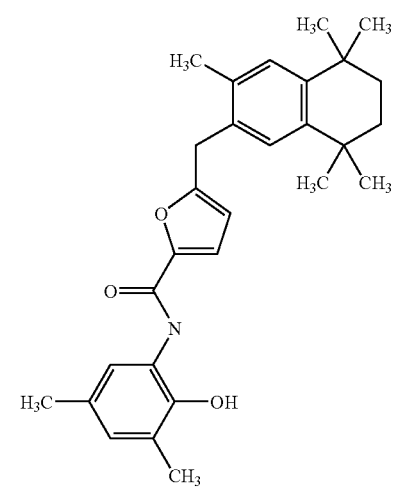 | 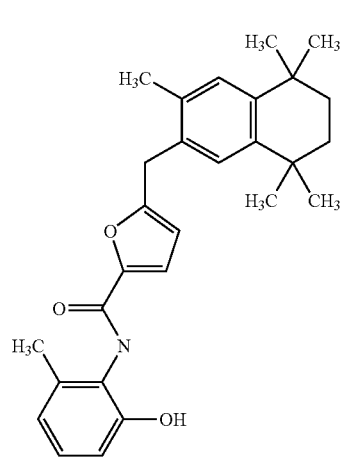 |
| 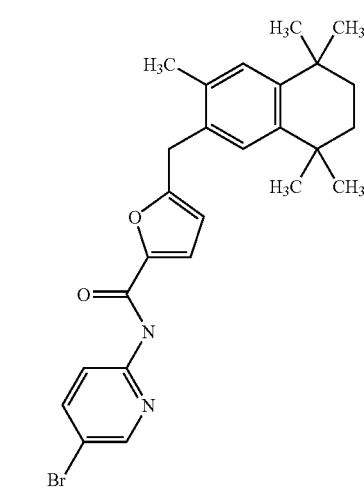 | 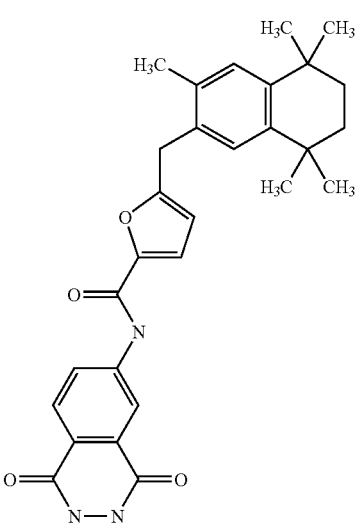 |

| 2493 | 2494 |
|---|---|
| -continued | -continued |
| MOLSTRUCTURE | MOLSTRUCTURE |
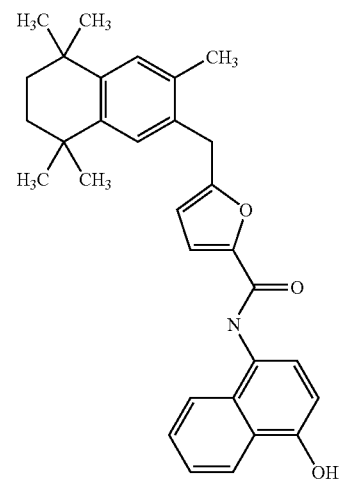
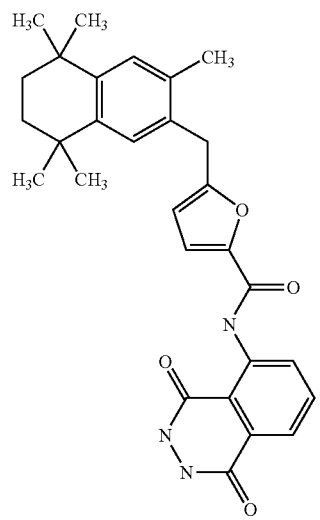
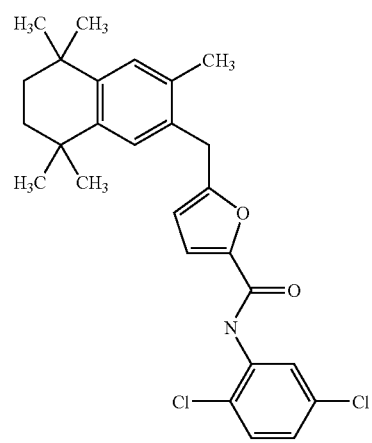
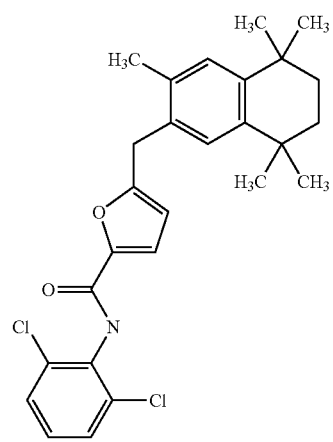
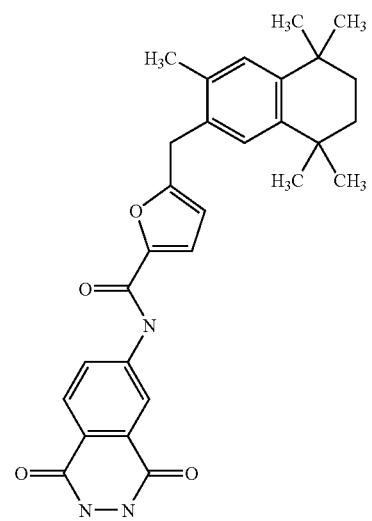
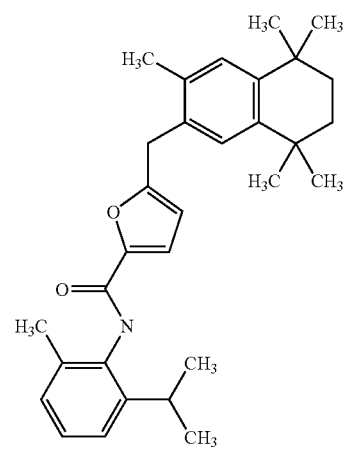

| 2495 | 2496 |
|---|---|
| -continued | -continued |
| MOLSTRUCTURE | MOLSTRUCTURE |
| 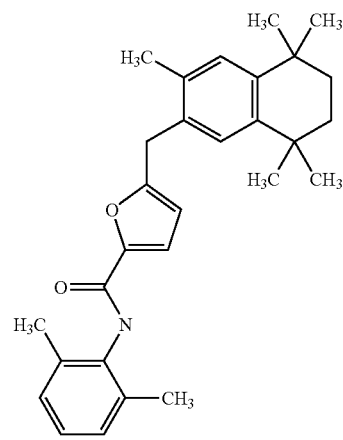 | 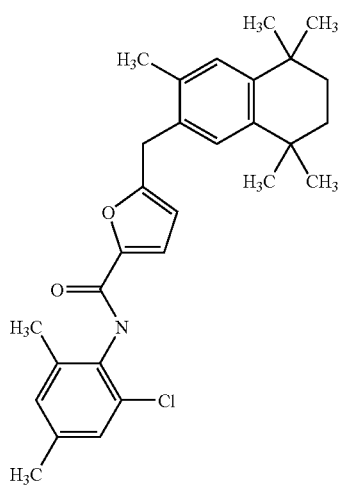 |
| 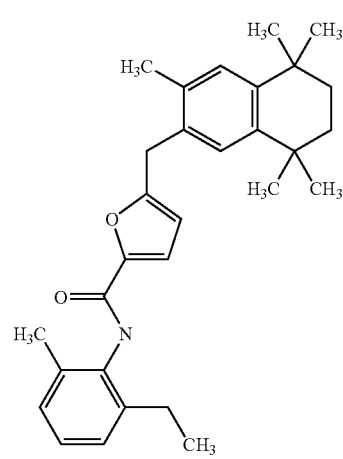 | 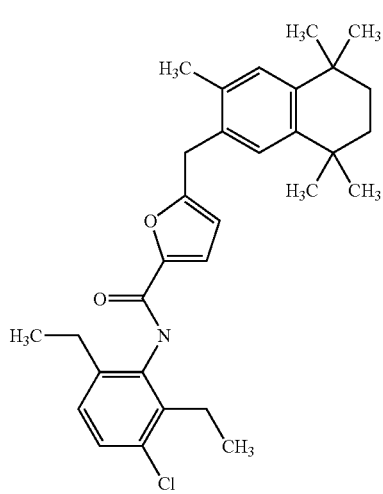 |
| 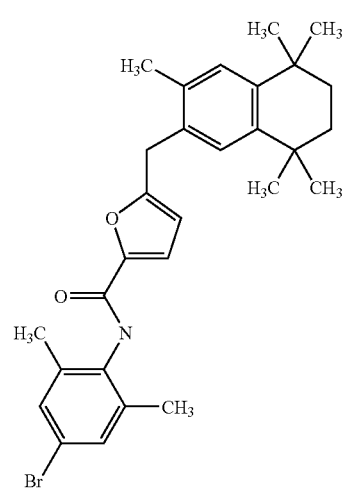 | 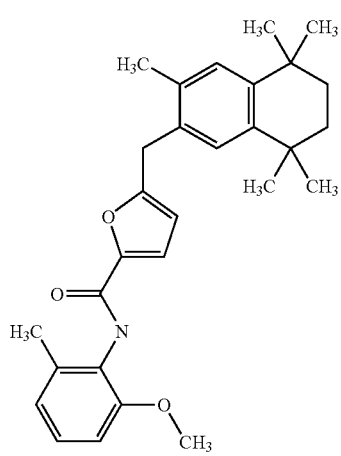 |

| 2497 | 2498 |
|---|---|
| -continued | -continued |
| MOLSTRUCTURE | MOLSTRUCTURE |
| 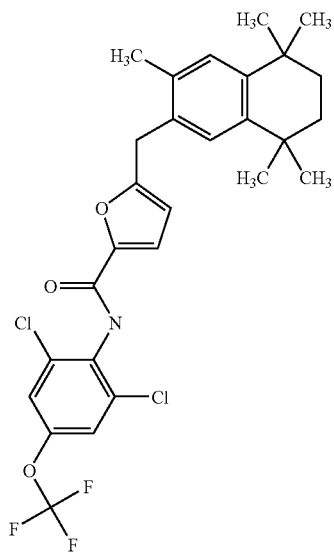 | 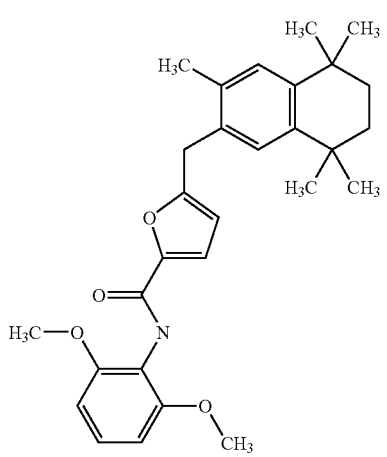 |
| 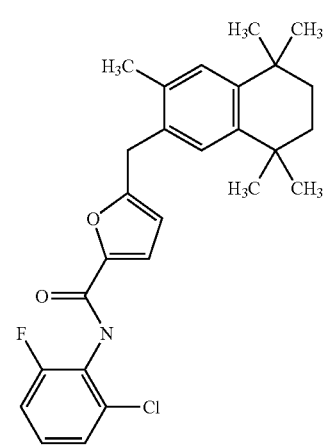 | 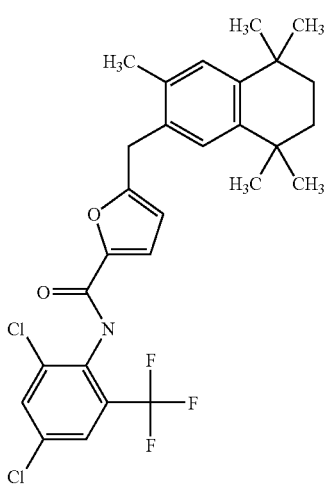 |
| 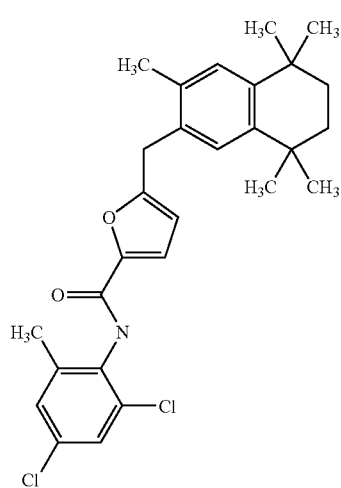 | 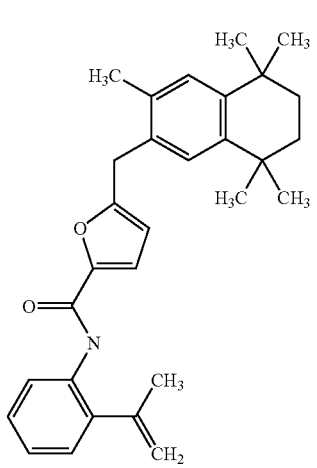 |

| 2499 | 2500 |
|---|---|
| -continued | -continued |
| MOLSTRUCTURE | MOLSTRUCTURE |
| 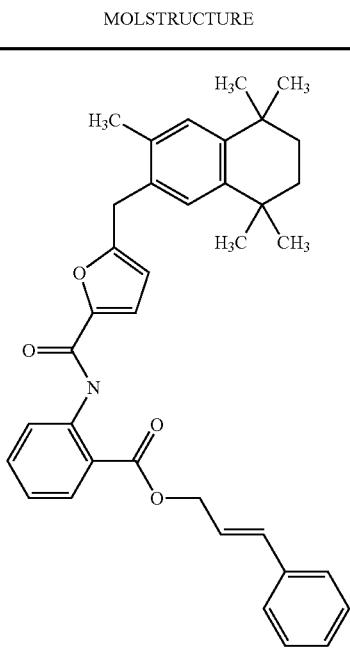 | 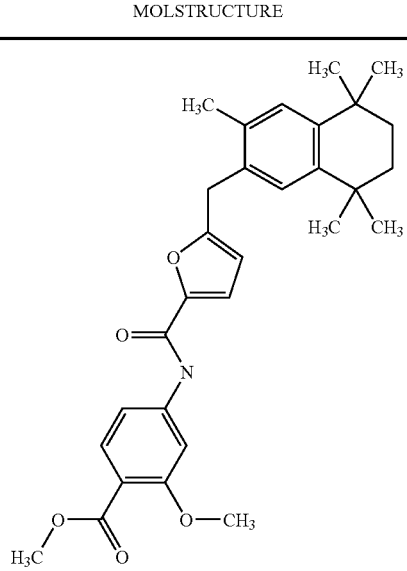 |
| 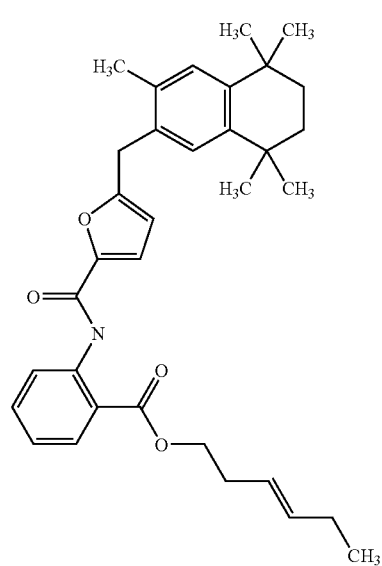 | 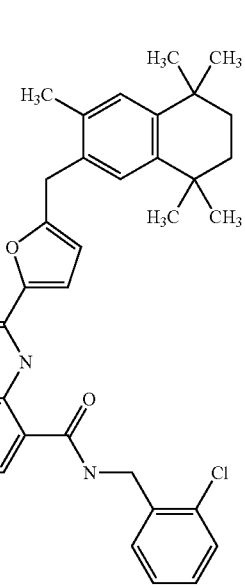 |

| 2501 | 2502 |
|---|---|
| -continued | -continued |
| MOLSTRUCTURE | MOLSTRUCTURE |
| 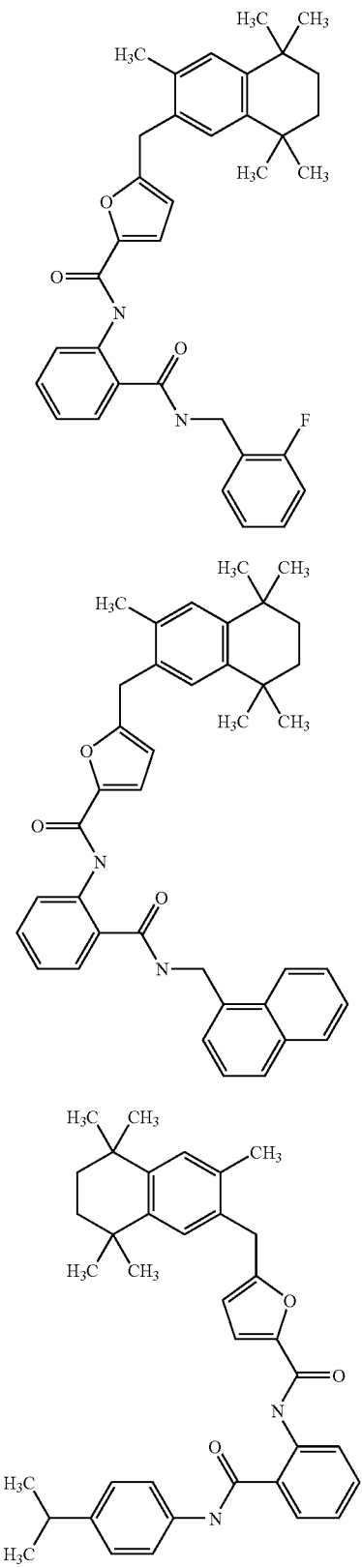 | 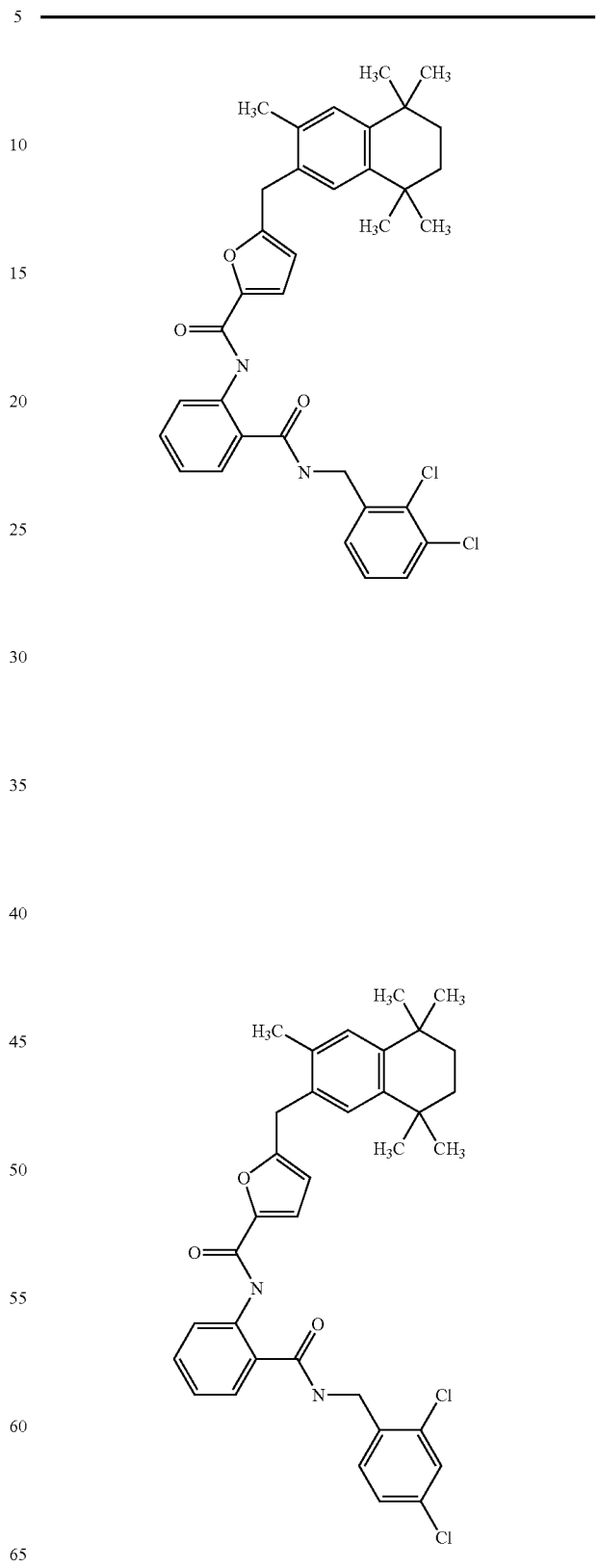 |

| 2503 | 2504 |
|---|---|
| -continued | -continued |
| MOLSTRUCTURE | MOLSTRUCTURE |
| 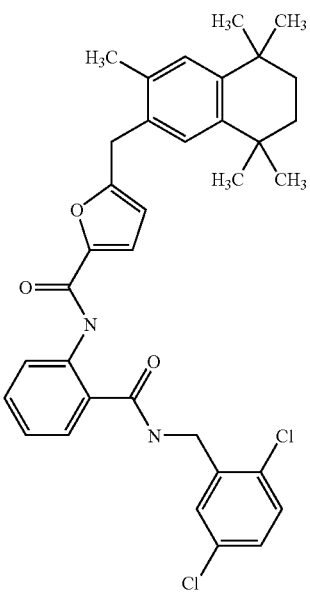 | 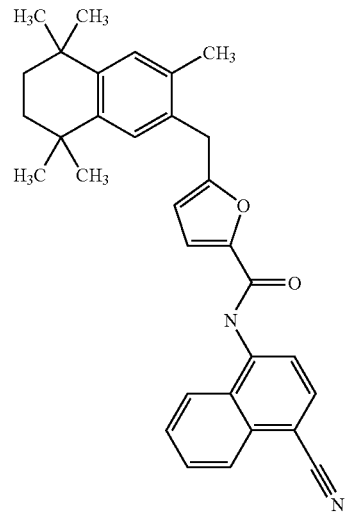 |
| 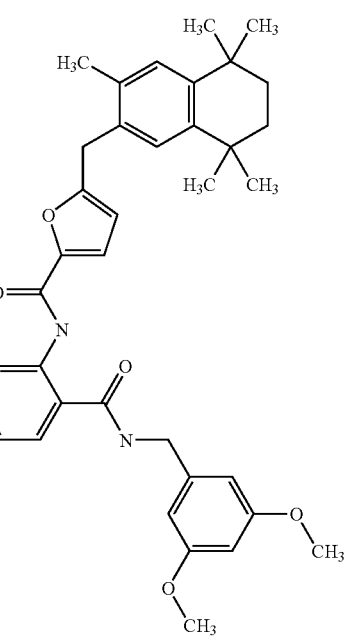 | |
What is claimed is:
1. A compound having a formula selected from the group consisting of:
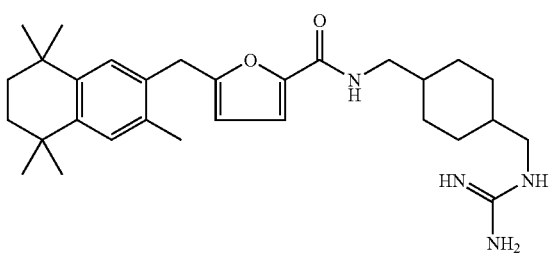
and
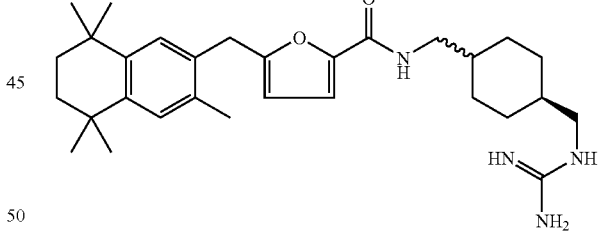
or a pharmaceutically acceptable salt thereof.
2. A compound having a formula selected from the group consisting of:
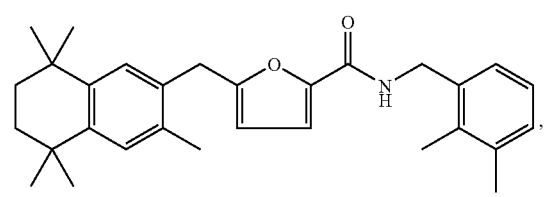

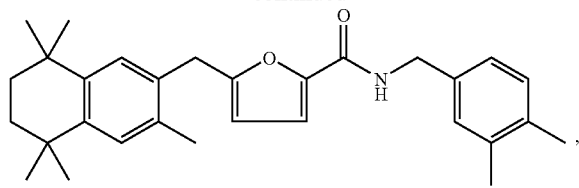

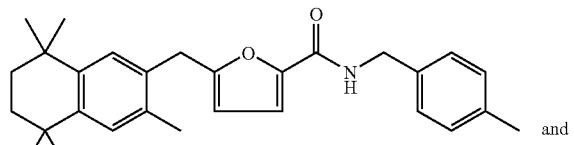
and

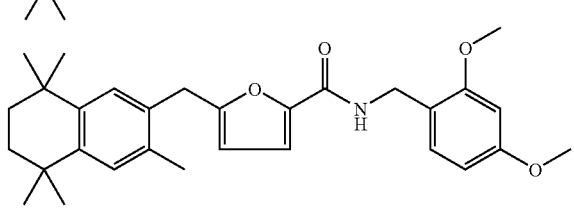

or a pharmaceutically acceptable salt thereof.

3. A compound having the formula:

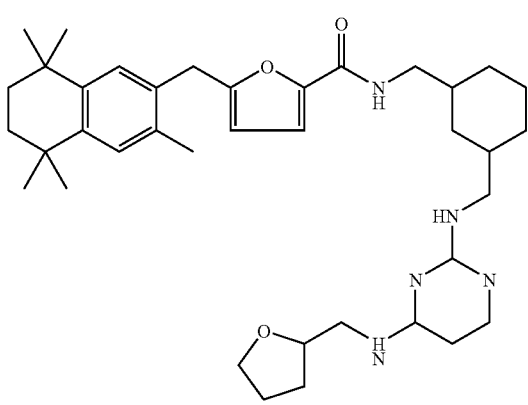

or a pharmaceutically acceptable salt thereof.

4. A compound having a formula selected from the group consisting of:

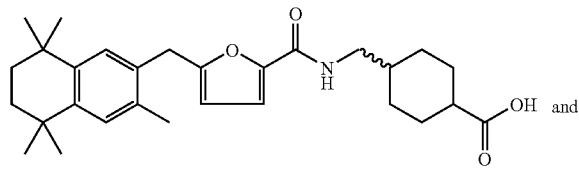
and

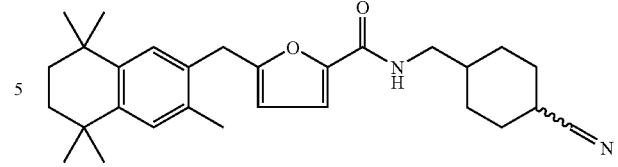

or a pharmaceutically acceptable salt thereof.

5. A compound having the formula:

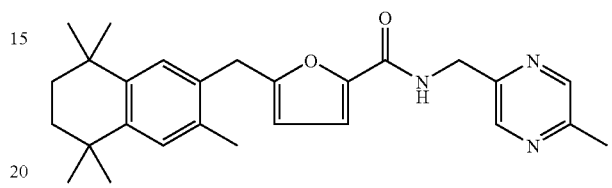

or a pharmaceutically acceptable salt thereof.

6. A compound having a formula selected from the group consisting of:

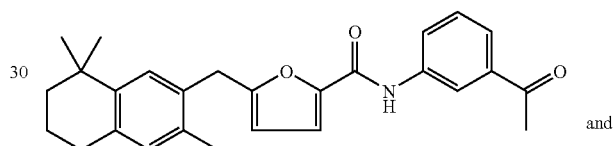
and

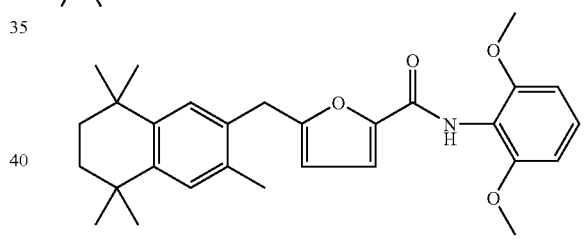

or a pharmaceutically acceptable salt thereof.

7. A pharmaceutical composition comprising: a therapeutically effective amount of a compound or pharmaceutically acceptable salt thereof as defined in any one of claims 1–6; and a pharmaceutically acceptable carrier or diluent.

8. A method for regulating the secretion of gonadotropins in mammals, comprising administering a therapeutically effective amount of a compound or pharmaceutically acceptable salt thereof as defined in any one of claims 1–6.

* * * * *